US012048749B2

(12) United States Patent
Burnett et al.

(10) Patent No.: US 12,048,749 B2
(45) **Date of Patent: *Jul. 30, 2024**

(54) C40-, C28-, AND C-32-LINKED RAPAMYCIN ANALOGS AS mTOR INHIBITORS

(71) Applicant: Revolution Medicines, Inc., Redwood City, CA (US)

(72) Inventors: G. Leslie Burnett, Redwood City, CA (US); James Bradley Aggen, Redwood City, CA (US); Jennifer Pitzen, Redwood City, CA (US)

(73) Assignee: REVOLUTION MEDICINES, INC., Redwood City, CA (US)

( * ) Notice: Subject to any disclaimer, the term of this patent is extended or adjusted under 35 U.S.C. 154(b) by 27 days.

This patent is subject to a terminal disclaimer.

(21) Appl. No.: 17/733,755

(22) Filed: Apr. 29, 2022

(65) Prior Publication Data

US 2023/0055672 A1 Feb. 23, 2023

Related U.S. Application Data

(63) Continuation of application No. 17/083,172, filed on Oct. 28, 2020, now Pat. No. 11,364,300, which is a continuation of application No. 16/398,011, filed on Apr. 29, 2019, now abandoned.

(60) Provisional application No. 62/665,435, filed on May 1, 2018, provisional application No. 62/752,874, filed on Oct. 30, 2018, provisional application No. 62/836,036, filed on Apr. 18, 2019.

(51) Int. Cl.

| | |
|---|---|
| *A61P 35/00* | (2006.01) |
| *A61K 31/436* | (2006.01) |
| *A61K 31/519* | (2006.01) |
| *A61K 31/553* | (2006.01) |
| *A61K 47/54* | (2017.01) |

(52) U.S. Cl.

CPC .......... *A61K 47/545* (2017.08); *A61K 31/436* (2013.01); *A61K 31/519* (2013.01); *A61K 31/553* (2013.01)

(58) Field of Classification Search

CPC ..... A61P 35/00; A61K 31/436; A61K 31/519; A61K 31/553

See application file for complete search history.

(56) References Cited

U.S. PATENT DOCUMENTS

| | | | |
|---|---|---|---|
| 3,929,992 | A | 12/1975 | Sehgal et al. |
| 4,316,885 | A | 2/1982 | Rakhit |
| 4,650,803 | A | 3/1987 | Stella et al. |
| 4,861,760 | A | 8/1989 | Mazuel et al. |
| 4,911,920 | A | 3/1990 | Jani et al. |
| 5,023,263 | A | 6/1991 | Von Burg |
| 5,023,264 | A | 6/1991 | Caufield et al. |
| 5,100,883 | A | 3/1992 | Schiehser |
| 5,102,876 | A | 4/1992 | Caufield |
| 5,118,677 | A | 6/1992 | Caufield |
| 5,118,678 | A | 6/1992 | Kao et al. |
| 5,120,726 | A | 6/1992 | Failli et al. |
| 5,120,842 | A | 6/1992 | Failli et al. |
| 5,130,307 | A | 7/1992 | Failli et al. |
| 5,151,413 | A | 9/1992 | Caufield et al. |
| 5,162,333 | A | 11/1992 | Failli et al. |
| 5,177,203 | A | 1/1993 | Failli et al. |
| 5,212,162 | A | 5/1993 | Missel et al. |
| 5,221,670 | A | 6/1993 | Caufield |
| 5,233,036 | A | 8/1993 | Hughes |
| 5,252,579 | A | 10/1993 | Skotnicki et al. |
| 5,256,790 | A | 10/1993 | Nelson |
| 5,258,389 | A | 11/1993 | Goulet et al. |
| 5,260,300 | A | 11/1993 | Hu |
| 5,262,423 | A | 11/1993 | Kao |
| 5,262,564 | A | 11/1993 | Kun et al. |
| 5,302,584 | A | 4/1994 | Kao et al. |
| 5,344,833 | A | 9/1994 | Hughes |
| 5,362,718 | A | 11/1994 | Skotnicki et al. |
| 5,373,014 | A | 12/1994 | Failli et al. |
| 5,378,836 | A | 1/1995 | Kao et al. |
| 5,385,908 | A | 1/1995 | Nelson et al. |
| 5,385,909 | A | 1/1995 | Nelson et al. |
| 5,385,910 | A | 1/1995 | Ocain et al. |
| 5,389,639 | A | 2/1995 | Failli et al. |
| 5,391,730 | A | 2/1995 | Skotnicki et al. |
| 5,403,841 | A | 4/1995 | Lang et al. |
| 5,411,967 | A | 5/1995 | Kao et al. |
| 5,434,260 | A | 7/1995 | Skotnicki et al. |
| 5,463,048 | A | 10/1995 | Skotnicki et al. |
| 5,480,988 | A | 1/1996 | Failli et al. |
| 5,480,989 | A | 1/1996 | Kao et al. |
| 5,489,680 | A | 2/1996 | Failli et al. |

(Continued)

FOREIGN PATENT DOCUMENTS

| | | |
|---|---|---|
| CN | 1132512 A | 10/1996 |
| CN | 106188093 A | 12/2016 |

(Continued)

OTHER PUBLICATIONS

Al-Muhammed et al., In-vivo studies on dexamethasone sodium phosphate liposomes, J Microencapsul, May-Jun. 1996, pp. 293-306, vol. 13, No. 3.

Apsel et al. Targeted polypharmacology: discovery of dual inhibitors of tyrosine and phosphoinositide kinases, Nature Chemical Biology, Nov. 2008, e-published Oct. 12, 2008, pp. 691-699, vol. 4, No. 11.

Ayral-Kaloustian Hybrid inhibitors of phosphatidylinositol 3-kinase (PI3K) and the mammalian target of rapamycin (mTOR): design, synthesis, and superior antitumor activity of novel wortmannin-rapamycin conjugates, J Med Chem, Jan. 2010, pp. 452-459, vol. 53, No. 1.

(Continued)

*Primary Examiner* — Bruck Kifle

(74) *Attorney, Agent, or Firm* — Cooley LLP

(57) ABSTRACT

The present disclosure relates to mTOR inhibitors. Specifically, the embodiments are directed to compounds and compositions inhibiting mTOR, methods of treating diseases mediated by mTOR, and methods of synthesizing these compounds.

10 Claims, No Drawings

Specification includes a Sequence Listing.

(56) References Cited

U.S. PATENT DOCUMENTS

| | | | |
|---|---|---|---|
| 5,491,231 | A | 2/1996 | Nelson et al. |
| 5,504,091 | A | 4/1996 | Molnar-Kimber et al. |
| 5,527,907 | A | 6/1996 | Or et al. |
| 5,563,145 | A | 10/1996 | Failli et al. |
| 5,583,139 | A | 12/1996 | Or et al. |
| 5,665,772 | A | 9/1997 | Cottens et al. |
| 5,741,677 | A | 4/1998 | Kozlowski et al. |
| 5,780,462 | A | 7/1998 | Lee et al. |
| 5,985,890 | A | 11/1999 | Cottens et al. |
| 6,200,985 | B1 | 3/2001 | Cottens et al. |
| 6,277,983 | B1 | 8/2001 | Shaw et al. |
| 6,323,201 | B1 | 11/2001 | Carson et al. |
| 6,342,507 | B1 | 1/2002 | Naicker et al. |
| 6,358,969 | B1 | 3/2002 | Shelley et al. |
| 6,562,819 | B2 | 5/2003 | Carson et al. |
| 6,720,344 | B2 | 4/2004 | Kerwin et al. |
| 7,074,804 | B2 | 7/2006 | Zhu et al. |
| 7,160,867 | B2 | 1/2007 | Abel et al. |
| 7,241,771 | B2 | 7/2007 | Zhu |
| 7,429,596 | B2 | 9/2008 | Tanaka et al. |
| 7,585,868 | B2 | 9/2009 | Knight et al. |
| 8,101,602 | B2 | 1/2012 | Menear et al. |
| 8,410,131 | B2 | 4/2013 | Lane et al. |
| 8,492,405 | B2 | 7/2013 | Tsuneo et al. |
| 8,604,032 | B2 | 12/2013 | Ren et al. |
| 8,642,604 | B2 | 2/2014 | Knight et al. |
| 8,697,709 | B2 | 4/2014 | Dar et al. |
| 8,785,454 | B2 | 7/2014 | Ren et al. |
| 8,980,899 | B2 | 3/2015 | Korennykh et al. |
| 9,321,772 | B2 | 4/2016 | Dar et al. |
| 9,358,229 | B2 | 6/2016 | Vannucchi et al. |
| 9,493,467 | B2 | 11/2016 | Knight et al. |
| 9,512,125 | B2 | 12/2016 | Shokat et al. |
| 9,603,891 | B2 | 3/2017 | Bae et al. |
| 9,629,843 | B2 | 4/2017 | Shokat et al. |
| 10,117,945 | B2 | 11/2018 | Shokat et al. |
| 10,160,767 | B2 | 12/2018 | Zhong |
| 10,980,889 | B1 | 4/2021 | Pitzen et al. |
| 11,364,300 | B2 | 6/2022 | Pitzen et al. |
| 11,685,749 | B2 | 6/2023 | Semko et al. |
| 2004/0235762 | A1 | 11/2004 | Abel et al. |
| 2005/0085472 | A1 | 4/2005 | Tanaka et al. |
| 2005/0101624 | A1 | 5/2005 | Betts et al. |
| 2005/0192311 | A1 | 9/2005 | Isozaki et al. |
| 2008/0249123 | A1 | 10/2008 | Gu et al. |
| 2009/0074831 | A1 | 3/2009 | Falotico et al. |
| 2009/0124638 | A1 | 5/2009 | Shokat et al. |
| 2009/0181988 | A1 | 7/2009 | Tanaka et al. |
| 2009/0131631 | A1 | 10/2009 | Krafft et al. |
| 2009/0253733 | A1 | 10/2009 | Rhodes et al. |
| 2009/0270426 | A1 | 10/2009 | Knight et al. |
| 2009/0274739 | A1 | 11/2009 | Marks et al. |
| 2009/0292118 | A1 | 11/2009 | Lee et al. |
| 2009/0312319 | A1 | 12/2009 | Ren et al. |
| 2010/0009963 | A1 | 1/2010 | Knight et al. |
| 2010/0190749 | A1 | 7/2010 | Ren et al. |
| 2010/0190980 | A1 | 7/2010 | Umemiya |
| 2011/0046165 | A1 | 2/2011 | Ren et al. |
| 2011/0098241 | A1 | 4/2011 | Sun et al. |
| 2011/0124641 | A1 | 5/2011 | Ren et al. |
| 2011/0144134 | A1 | 6/2011 | Shokat et al. |
| 2011/0172228 | A1 | 7/2011 | Ren et al. |
| 2011/0224223 | A1 | 9/2011 | Shokat et al. |
| 2011/0269779 | A1 | 11/2011 | Wilson et al. |
| 2011/0281866 | A1 | 11/2011 | Ren et al. |
| 2011/0301144 | A1 | 12/2011 | Knight et al. |
| 2012/0065154 | A1 | 3/2012 | Tanaka et al. |
| 2012/0065426 | A1 | 3/2012 | Watanabe et al. |
| 2012/0294930 | A1 | 11/2012 | Ren et al. |
| 2012/0322814 | A1 | 12/2012 | Korennykh et al. |
| 2012/0329776 | A1 | 12/2012 | Ren et al. |
| 2013/0289271 | A1 | 10/2013 | Perrin-Ninkovic et al. |
| 2014/0066462 | A1 | 3/2014 | Pearce et al. |
| 2014/0288096 | A1 | 9/2014 | Knight et al. |
| 2015/0031881 | A1 | 1/2015 | Tanaka et al. |
| 2015/0368297 | A1 | 12/2015 | Bae et al. |
| 2016/0000789 | A1 | 1/2016 | Shokat et al. |
| 2016/0168151 | A1 | 6/2016 | Tanaka et al. |
| 2016/0279108 | A1 | 9/2016 | Forrest et al. |
| 2016/0354377 | A1 | 12/2016 | Dar et al. |
| 2017/0246305 | A1 | 8/2017 | Shokat et al. |
| 2019/0284146 | A1 | 9/2019 | Yan et al. |
| 2019/0336609 | A1 | 11/2019 | Pitzen et al. |
| 2021/0094975 | A1 | 4/2021 | Aggen et al. |
| 2021/0338824 | A1 | 11/2021 | Pitzen et al. |
| 2022/0340596 | A1 | 10/2022 | Semko et al. |
| 2023/0093861 | A1 | 3/2023 | Aggen et al. |

FOREIGN PATENT DOCUMENTS

| | | | |
|---|---|---|---|
| EP | 0088593 | A2 | 9/1983 |
| EP | 0467606 | A1 | 1/1992 |
| EP | 1 916 006 | A1 | 4/2008 |
| ES | 2258763 | T3 | 9/2006 |
| GB | 1459571 | A | 12/1976 |
| JP | H 0249775 | A | 2/1990 |
| JP | H-04112877 | A | 4/1992 |
| JP | H-04-230389 | A | 8/1992 |
| JP | 2004-161716 | A | 6/2004 |
| JP | 2008-273976 | A | 11/2008 |
| JP | 2009-513222 | A | 4/2009 |
| JP | 2012-528165 | A | 11/2012 |
| JP | 2016-500112 | A | 1/2016 |
| JP | 2017531624 | A | 10/2017 |
| RU | 2152946 | C1 | 7/2000 |
| RU | 2 322 981 | C2 | 4/2008 |
| RU | 2487711 | C2 | 7/2013 |
| WO | WO 92/05179 | A1 | 4/1992 |
| WO | WO 93/11130 | A1 | 6/1993 |
| WO | WO 94/02136 | A1 | 2/1994 |
| WO | WO 94/02485 | A1 | 2/1994 |
| WO | WO-1994004540 | A1 | 3/1994 |
| WO | WO 94/09010 | A1 | 4/1994 |
| WO | WO 94/11380 | A1 | 5/1994 |
| WO | WO 94/25072 | A1 | 11/1994 |
| WO | WO 95/04738 | A1 | 2/1995 |
| WO | WO 95/14023 | A1 | 5/1995 |
| WO | WO 95/16691 | A1 | 6/1995 |
| WO | WO 96/041807 | A1 | 12/1996 |
| WO | WO 99/36553 | A2 | 7/1999 |
| WO | WO 01/014387 | A1 | 3/2001 |
| WO | WO 2004/024719 | A1 | 3/2004 |
| WO | WO 2004/101583 | A1 | 11/2004 |
| WO | WO 2005/007085 | A2 | 1/2005 |
| WO | WO 2005/007085 | A3 | 1/2005 |
| WO | WO 2005/105760 | A1 | 11/2005 |
| WO | WO 2006/009518 | A1 | 1/2006 |
| WO | WO 2006/068760 | A2 | 6/2006 |
| WO | WO 2006/068760 | A3 | 6/2006 |
| WO | WO-2006069038 | A1 | 6/2006 |
| WO | WO 2006/116727 | A2 | 11/2006 |
| WO | WO 2007/061737 | A2 | 5/2007 |
| WO | WO-2007057457 | A2 | 5/2007 |
| WO | WO 2007/068462 | A2 | 6/2007 |
| WO | WO 2007/114926 | A2 | 10/2007 |
| WO | WO 2007/114926 | A3 | 10/2007 |
| WO | WO 2007/121453 | A2 | 10/2007 |
| WO | WO 2007/121453 | A3 | 10/2007 |
| WO | WO 2008/046641 | A2 | 4/2008 |
| WO | WO 2008/046641 | A3 | 4/2008 |
| WO | WO 2008/047821 | A1 | 4/2008 |
| WO | WO 2008/065887 | A1 | 6/2008 |
| WO | WO 2008/115974 | A2 | 9/2008 |
| WO | WO 2008/127226 | A2 | 10/2008 |
| WO | WO 2008/127226 | A3 | 10/2008 |
| WO | WO 2009/046436 | A1 | 4/2009 |
| WO | WO 2009/088986 | A1 | 7/2009 |
| WO | WO 2009/088990 | A1 | 7/2009 |
| WO | WO 2009/089262 | A1 | 7/2009 |
| WO | WO 2009/122176 | A2 | 10/2009 |
| WO | WO 2009/131631 | A1 | 10/2009 |
| WO | WO 2010/006072 | A2 | 1/2010 |
| WO | WO 2010/006072 | A3 | 1/2010 |
| WO | WO 2010/006086 | A2 | 1/2010 |

(56) References Cited

FOREIGN PATENT DOCUMENTS

| | | | |
|---|---|---|---|
| WO | WO 2010/006086 | A3 | 1/2010 |
| WO | WO 2010/025406 | A1 | 3/2010 |
| WO | WO 2010/036380 | A1 | 4/2010 |
| WO | WO 2010/044885 | A2 | 4/2010 |
| WO | WO 2010/051042 | A1 | 5/2010 |
| WO | WO 2010/051043 | A1 | 5/2010 |
| WO | WO 2010/138487 | A1 | 12/2010 |
| WO | WO 2011/022439 | A1 | 2/2011 |
| WO | WO 2011/022440 | A2 | 2/2011 |
| WO | WO 2011/047384 | A2 | 4/2011 |
| WO | WO 2011/047384 | A9 | 4/2011 |
| WO | WO 2012/017449 | A1 | 2/2012 |
| WO | WO 2012/066502 | A1 | 5/2012 |
| WO | WO 2012/103959 | A1 | 8/2012 |
| WO | WO 2012/103960 | A1 | 8/2012 |
| WO | WO 2012/151562 | A1 | 11/2012 |
| WO | WO 2012/154695 | A2 | 11/2012 |
| WO | WO 2012/154695 | A3 | 11/2012 |
| WO | WO 2013/077921 | A2 | 5/2013 |
| WO | WO 2013/077921 | A3 | 5/2013 |
| WO | WO 2013/077921 | A9 | 5/2013 |
| WO | WO 2014/082286 | A1 | 6/2014 |
| WO | WO-2015066371 | A1 | 5/2015 |
| WO | WO-WO2015066371 | A1 | 5/2015 |
| WO | WO 2015/095755 | A1 | 6/2015 |
| WO | WO 2015/184983 | A1 | 12/2015 |
| WO | WO 2016/040806 | A1 | 3/2016 |
| WO | WO 2016/100116 | A1 | 6/2016 |
| WO | WO 2017/044720 | A1 | 3/2017 |
| WO | WO 2017/121444 | A1 | 7/2017 |
| WO | WO 2018/204416 | A1 | 11/2018 |
| WO | WO 2019/064182 | A1 | 4/2019 |
| WO | WO 2019/212990 | A1 | 11/2019 |
| WO | WO 2019/212991 | A1 | 11/2019 |
| WO | WO-2020160711 | A1 | 8/2020 |
| WO | WO-2021257736 | A1 | 12/2021 |
| WO | WO-2022216900 | A2 | 10/2022 |

OTHER PUBLICATIONS

Banerjee, Poly(ethylene glycol)-Prodrug Conjugates: Concept, Design, and Applications, J Drug Delivery, May 7, 2012, 17 pages.
CAS Registry No. 53123-88-9, accessed Feb. 27, 2018, 2 pages.
Choi, Structure of the FKBP12-rapamycin complex interacting with the binding domain of human FRAP, Science, Jul. 1996, pp. 239-242, vol. 273, No. 5272.
Chonn et al., Recent advances in liposomal drug-delivery systems, Curr Opin Biotechnol, Dec., pp. 698-708, vol. 6, No. 6.
Dowling et al. mTORC1-mediated cell proliferation, but not cell growth, controlled by the 4E-BPs, Science, May 28, 2010, pp. 1172-1176, vol. 328, No. 5982.
Drachman et al, Antibody-drug conjugates: the chemistry behind empowering antibodies to fight cancer, Hematology Am Soc Hematol Educ Program, 2013. pp. 306-310.
Eyles et al., Oral delivery and fate of poly(lactic acid) microsphere-encapsulated interferon in rats, J Pharm Pharmacol, Jul. 1997, pp. 669-674, vol. 49, No. 7.
Feldman et al. Active-site inhibitors of mTOR target rapamycin-resistant outputs of mTORC1 and mTORC2, PLoS Biol, Feb. 10, 2009, e38, vol. 7, No. 2.
Flygare et al. Antibody-drug conjugates for the treatment of cancer, Chem Biol Drug Des, Jan. 2013, 113-121, vol. 81, No. 1.
Galat, Functional diversity and pharmacological profiles of the FKBPs and their complexes with small natural ligands, Cell Mol Life Sci., Sep. 2013, pp. 3243-3275, vol. 70, No. 18.
Gao et al., Controlled release of a contraceptive steroid from biodegradable and injectable gel formulations: in vitro evaluation, Pharm Res., Jun. 1995, pp. 857-863, vol. 12, No. 6.
Hackam et al., Translation of Research Evidence From Animals to Humans, JAMA, Oct. 11, 2006, pp. 1731-1732, vol. 296, No. 14.
Hara et al., Raptor, a binding partner of target of rapamycin (TOR), mediates TOR action, Cell, Jul. 26, 2002, pp. 177-189., vol. 110, No. 2.
Hsieh et al. The translational landscape of mTOR signalling steers cancer initiation and metastasis, Nature, Feb. 22, 2012, 55-61, vol. 485, No. 7396.
Hsieh et al. Genetic dissection of the oncogenic mTOR pathway reveals druggable addiction to translational control via 4EBP-el F4E, Cancer Cell, Mar. 16, 2010, pp. 249-261, vol. 17, No. 3.
Hughes et al., The isolation, synthesis and characterization of an isomeric form of rapamycin, Tetrahedron Letters, Aug. 11, 1992, pp. 4739-4742 vol. 33, Issue 33.
Infante et al. Abstract C252: A phase 1, dose-escalation study of MLN0128, an investigational oral mammalian target of rapamycin complex 1/2 (mTORC1/2) catalytic inhibitor, in patients (pts) with advanced non-hematologic malignancies. Mol. Cancer Ther. 2013.
European Patent Office, International Search Report for PCT Application No. PCT/US2018/030531, Aug. 28, 2018, 16 pages.
United States Patent and Trademark Office, International Search Report for PCT Application No. PCT/US2015/049693, Dec. 14, 2015, 3 pages.
European Patent Office, International Search Report For PCT Application No. PCT/US2019/029738, Jun. 26, 2019, 4 pages.
European Patent Office, International Search Report for PCT Application No. PCT/US2019/029737, Sep. 23, 2019, 12 pages.
Jacinto, et al. Mammalian TOR complex 2 controls the actin cytoskeleton and is rapamycin insensitive, Nat Cell Biol, Nov. 2004, e-published Oct. 3, 2004, 1122-1128, vol. 6, No. 11.
Jordan, Tamoxifen: A Most Unlikely Pioneering Medicine, Nature Reviews: Drug Discovery, Mar. 2003, pp. 205-213, vol. 2.
Kallen et al., X-ray Crystal Structure of 28-O-Methylrapamycin complexed with FKBP12: Is the Cyclohexyl Moiety Part of the Effector Domain of Rapamycin, J. Am. Chem. Soc., 1996, pp. 5857-5861, vol. 118.
Kim et al. mTOR interacts with raptor to form a nutrient-sensitive complex that signals to the cell growth machinery, Cell, Jul. 26, 2002, pp. 163-175, vol. 110, No. 2.
Kolb et al, Click Chemistry: Diverse Chemical Function from a Few Good Reactions, Angewandte Chemie International Edition, Jun. 1, 2001, pp. 2004-2021, vol. 40, No. 11.
Lamming, et al., Rapamycin-induced insulin resistance is mediated by mTORC2 loss and uncoupled from longevity, Science, Mar. 30, 2012, pp. 1638-1643, vol. 335, No. 6076.
Liu et al., Discovery of 1-(4-(4-propionylpiperazin-1-yl)-3-(trifluoromethyl)phenyl)-9-(quinolin-3-yl)benzo[h][1,6]naphthyridin-2(1H)-one as a highly potent, selective mammalian target of rapamycin (mTOR) inhibitor for the treatment of cancer, J Med Chem., Oct. 14, 2010, pp. 7146-7155, vol. 53, No. 19.
Luengo et al., Manipulation of the Rapamycin Effector Domain. Selective Nucleophilic Substitution of the C7 Methoxy Group, Org. Chem. 1994, pp. 6512-6513, vol. 59, No. 22.
Masuda, et al., “Synthesis of Alkoxy-, (Alkylthio)-, Phenoxy-, and (Phenylthio)pyrazines and their Olfactive Properties,” J. Agric. Food Chem., 1986, 34(2), pp. 377-381.
McCormick et al. TOR and ageing: a complex pathway for a complex process, Philas Trans R Soc Land B Biol Sci, Jan. 12, 2011, pp. 17-27, vol. 366, No. 1561.
Moni et al., Synthesis of rapamycin glycoconjugates via a CuAAC-based approach, Tetrahedron Letters, Dec. 18, 2013, pp. 6999-7003, vol. 54, Issue 51.
Naing et al., Safety, tolerability, pharmacokinetics and pharmacodynamics of AZD8055 in advanced solid tumours and lymphoma, Br J Cancer, Sep. 25, 2012, pp. 1093-1099, vol. 107, No. 7.
Neasta et al., mTOR complex 1: a key player in neuroadaptations induced by drugs of abuse, J Neurochem, Jul. 2014, e-published Apr. 19, 2014, pp. 172-184, vol. 130, No. 2.
Nelson et al., Manipulation of the C(22)-C(27) Region of Rapamycin: Stability Issues and Biological Implications, Bioorganic & Medicinal Chemistry Letters, 1999, pp. 295-300, vol. 9, No. 2.
Nowak et al., Discovery of potent and selective inhibitors of the mammalian target of rapamycin (mTOR) kinase, J Med Chem., Nov. 26, 2009, pp. 7081-7089, vol. 52, No. 22.

(56) References Cited

OTHER PUBLICATIONS

O'Donnell et al., Phase I pharmacokinetic and pharmacodynamic study of the oral mammalian target of rapamycin inhibitor everolimus in patients with advanced solid tumors, J Clin Onco, (Apr. 1, 2008, e-published Mar. 10, 2008), pp. 1588-1595, vol. 26, No. 10.
O'Reilly et al., mTOR inhibition induces upstream receptor tyrosine kinase signaling and activates Akt, Cancer Res., Feb. 1, 2006, pp. 1500-1508, vol. 66, No. 3.
Ostro et al., Use of liposomes as injectable-drug delivery systems, Am J Hosp Pharm. Aug. 1989, pp. 1576-1587, vol. 46, No. 8.
Rao, Recent developments of collagen-based materials for medical applications and drug delivery systems, J Biomater Sci Polym Ed., 1995, pp. 623-645, vol. 7, No. 7.
Rhodes et al., Characterization of an Akt kinase inhibitor with potent pharmacodynamic and antitumor activity, Cancer Res, Apr. 1, 2008, pp. 2366-2374, vol. 68, No. 7.
Rodrik-Outmezguine, et al. Overcoming mTOR resistance mutations with a new-generation mTOR inhibitor, Nature, Jun. 9, 2016, pp. 272-278, vol. 534, No. 7606.
Rodrik-Outmezguine, et al., mTOR kinase inhibition causes feedback-dependent biphasic regulation of AKT signaling, Cancer Discovery, Aug. 2011, e-published Jun. 17, 2011, pp. 248-259, vol. 1, No. 3.
Ruggero et al., The translation factor eIF-4E promotes tumor formation and cooperates with c-Myc in lymphomagenesis, Nat Med, May 2004, e-published Apr. 18, 2004, pp. 484-486, vol. 10, No. 5.
Sarbassov et al., Prolonged rapamycin treatment inhibits mTORC2 assembly and Akt/PKB, Mol Cell, Apr. 21, 2006, pp. 159-168, vol. 22, No. 2.
Sarbassov, et al., Rictor, a novel binding partner of mTOR, defines a rapamycin-insensitive and raptor-independent pathway that regulates the cytoskeleton, Curr Biol., Jul. 27, 2004, 1296-1302, vol. 14, No. 14.
Shu et al., Synthesis of I-125 labeled photoaffinity rapamycin analogs, Journal of Labelled Compounds and Radiopharmaceuticals, 1996, pp. 227-237, vol. 38, No. 3.
Strom et al., Structural identification of SAR-943 metabolites generated by human liver microsomes in vitro using mass spectrometry in combination with analysis of fragmentation patters, J. Mass. Spectrom, 2011, pp. 615-624, vol. 46.
Su et al., Pretreatment epidermal growth factor receptor (EGFR) T790M mutation predicts shorter EGFR tyrosine kinase inhibitor response duration in patients with non-small-cell lung cancer, J Clin Oncol, Feb. 1, 2012, pp. 433-440, vol. 30, No. 4.
Thoreen et al., An ATP-competitive mammalian target of rapamycin inhibitor reveals rapamycin-resistant functions of mTORC1, J Biol Chem, Mar. 20, 2009, e-published Jan. 15, 2009, pp. 8023-8032, vol. 281, No. 12.
Umeda et al., A photocleavable rapamycin conjugate for spatiotemporal control of small GTPase activity, J Am Chem Soc., Jan. 12, 2011, e-published Dec. 13, 2010, pp. 12-14, vol. 133, No. 1.
Wood et al., A unique structure for epidermal growth factor receptor bound to GW572016 (Lapatinib): relationships among protein conformation, inhibitor off-rate, and receptor activity in tumor cells, Cancer Res, Sep. 15, 2004, pp. 6652-6659, vol. 64, No. 18.
United Statews Patent and Trademark Office, Written Opinion for PCT Application No. PCT/US2015/049693, Dec. 14, 2015, 7 pages.
Xie et al., Design, Synthesis and Biological Evaluation of Novel Rapamycin Benzothiazole Hybrids as mTOR Targeted Anti-cancer Agents, Chem Pharm Bull, 2016, pp. 346-355, vol. 64, No. 4.
Xie et al., Synthesis of Rapamycin Derivatives Containing the Triazole Moiety Used as Potential mTOR-Targeted Anticancer Agents, Arch Pharm, Jun. 2016 , pp. 428-441, vol. 349, No. 6.
Xu et al., The combination of RAD001 and NVP-BEZ235 exerts synergistic anticancer activity against non-small cell lung cancer in vitro and in vivo, PLoS One, Jun. 14, 2011, vol. 6, No. 6.
Yang et al., mTOR kinase structure, mechanism and regulation, Nature, May 1, 2013, pp. 217-223, vol. 497, No. 7448.
Yamanishi Y. et al., "Syntheses of trimethylpyrazines and their antibacterial properties," Yakugaku Zasshi, 1967, 87(1), pp. 105-107.
Zeng et al., mTORC1 couples immune signals and metabolic programming to establish T(reg)-cell function, Nature, Jun. 30, 2013, pp. 485-490, vol. 7459.
Chou, "Drug Combination Studies and Their Synergy Quantification Using the Chou-Talalay Method." Cancer Research (2010); 70(2): 440-446. Published OnlineFirst Jan. 12, 2010.
Fundamentals of Medical Prevention. Educational and Methodological Manual for Students and Cadets of Professional Development Cycles of State Professional Educational Institutions. Novosibirsk, 2016, UDC 614.2-084, BBC 51.1(2)2, pp. 13-21, Available online https://rcmpnso.ru/profila/m_mater/docs/osnovi_med_pomoshi.pdf?ysclid=I5wi7xgplo450927514. (Machine Translation).
International Search Report and Written Opinion in PCT/US2022/023778, mailed Nov. 25, 2022, 1-18.
Kümmerer , K., et al., "Pharmaceuticals in the Environment," Annual Review of Environment and Resources (2010); vol. 35, pp. 57-75. Epub Aug. 18, 2010.
Mashkovsky, MD et al., Medicaments, 14th edition, vol. 1. Moscow., 2001, p. 11.
Sanchez-Martinez, Conception, "Cyclin dependent kinase (CDK) inhibitors as anticancer drugs", Bioorganic & Medicinal Chemistry Letters, Pergamon, Amsterdam, NL, 25(17), Jun. 6, 2015, pp. 3420-3435.
Anonymous, "Scientific Discussion," EMEA, 2015, pp. 1-49.
Awad, M.M. et al., "Acquired Resistance to KRASG12C Inhibition in Cancer," The New England Journal of Medicine, Jun. 24, 2021, vol. 384, pp. 2382-2393.
Burnett L G., "Discovery of RMC-5552: A selective bi-steric inhibitor of mTORC1 that suppresses 4EBP1 phosphorylation, for the treatment of mTORC1-activated tumors including RAS pathway escape", In: Proceedings of the American Association for Cancer Research Annual Meeting 2021; Apr. 10-15, 2021 and May 17-21, 25 pages, Retrieved from: <https://s3-US-west-2.amazonaws.com/rvmdpubs.revmed.com/2021/04+ND10+RMC-5552.pdf>.
Campanero, M. et al., "Therapeutic drug monitoring for sirolimus in whole blood of organ transplants by high-performance liquid chromatography with ultraviolet detection," Journal of Chromotography, 2004, vol. 1031, pp. 265-273.
Chou, "Drug Combination Studies and Their Synergy Quantification Using the Chou-Talalay Method." Cancer Research, Jan. 12, 2010, vol. 70, No. 2, pp. 440-446.
Christensen, J., "The KRASG12C Inhibitor, MRTX849, Provides Insight Toward Therapeutic Susceptibility of KRAS Mutant Cancer," Presentation at AACR-NCI-EORTC International Conference, Oct. 26-30, 2019, 30 pages, audio and visual available at https://webcast.aacr.org/console/player/41715?mediaType=audio&.
ClinicalTrials.gov, "Combination Study of RMC-4630 and Sotorasib for NSCLC Subjects With KRASG12C Mutation After Failure of Prior Standard Therapies," NCT No. NCT05054725, last updated Apr. 3, 2023, 9 pages.
ClinicalTrials.gov, "Dose Escalation and Dose Expansion Study of RMC-6291 Monotherapy in Subjects with Advanced KRASG12C Mutant Solid Tumors," NCT No. NCT05462717, last updated Sep. 6, 2023, 7 pages.
ClinicalTrials.gov, "Dose Escalation of RMC-4630 Monotherapy in Relapsed/Refractory Solid Tumors," NCT No. NCT03634982, last updated Sep. 1, 2022, 8 pages.
ClinicalTrials.gov, "Dose Escalation of RMC-5552 Monotherapy in Relapsed/Refractory Solid Tumors," NCT No. NCT04774952, last updated Mar. 7, 2023, 8 pages.
ClinicalTrials.gov, "Evaluation of RMC-6236 in Subjects with Advanced Solid Tumors Harboring Specific Mutations in KRAS," NCT No. NCT05379985, last updated Dec. 27, 2022, 7 pages.
ClinicalTrials.gov, "History of Changes for Study: NCT04774952; Dose Escalation of RMC-5552 Monotherapy in Relapsed/Refractory Solid Tumors," NCT No. NCT04774952, earliest publication date of Feb. 25, 2023, 4 pages.
ClinicalTrials.gov, "Sotorasib Activity in Subjects With Advanced Solid Tumors With KRAS p.G12C Mutation (CodeBreak 101)," NCT No. NCT04185883, last updated Sep. 14, 2023, 14 pages.

(56) References Cited

OTHER PUBLICATIONS

Database Registry [Online], CAS Registry No. 1237826-20-8 (Aug. 23, 2010), 1 page.
Database Registry [Online], CAS Registry No. 153984-91-9 (Mar. 30, 1994), 1 page.
Dhaon, M. et al., "Synthesis, isolation, and characterization of ABT-578 equilibrium isomers," Tetrahedron Letters, Dec. 22, 2006, vol. 48, pp. 1059-1062.
European Search Report in EP Application No. 23164819.7, mailed Sep. 28, 2023, 18 pages.
Feldman, ME et al, "New inhibitors of the PI3K-Akt-mTOR pathway: insights into mTOR signaling from a new generation of Tor kinase domain inhibitors (TORKinibs)," Phosphoinositide 3-kinase in Health and Disease, 2011, vol. 2, pp. 241-262.
Guo et al., "High-throughput screening using patient-derived tumor xenografts to predict clinical trial drug response," Nature Medicine, Oct. 19, 2015, vol. 21, No. 11, pp. 1318-1325.
Il'Ichev, Y. et al., "Degradation of rapamycin and its ring-opened isomer: role of base catalysis," Arkivoc, May 6, 2007, vol. 12, pp. 110-131.
International Preliminary Report on Patentability for International Application No. PCT/US2022/023778 dated Oct. 19, 2023, 11 pages.
International Search Report and Written Opinion for PCT Application No. PCT/US2023/067503 dated Jul. 19, 2023, 15 pages.
Katritzky, A.R., et al., "QSAR modeling, synthesis and bioassay of diverse leukemia RPMI-8226 cell line active agents," Eur J Med Chem., Nov. 1, 2010, vol. 45, No. 11, pp. 5183-5199.
Katritzky, A.R., et al., "Tautomerism in drug discovery," Journal of computer-aided molecular design, Jun. 2010, vol. 24 (6-7), pp. 475-484.
Kummerer, K. "Pharmaceuticals in the Environment", Annual Review of Environment and Resources, Nov. 21, 2010, vol. 35, pp. 57-75.
Lee, BJ et al., "Selective inhibitors of mTORC1 activate 4EBP1 and suppress tumor growth," Nat Chem Biol., Oct. 2021, vol. 17, No. 10, pp. 1065-1074.
Leungo, J. et al., "Studies on Selective Reductions of Rapamycin," Tetrahedron Letters, Aug. 29, 1994, vol. 35, No. 35, pp. 6469-6472.
Mashkovsky, M.D., "Medicaments (Doctor's Manual)", 14th Edition, 2001, vol. 1, Moscow pp. 11; 6 pages.
Nelson, F.C. et al., "A Novel Ring Contraction of Rapamycin," Tetrahedron Letters, 1994, vol. 35, No. 41, pp. 7557-7560.
Ohbayashi, Y., et al., "Topical steroid injection for refractory oral chronic graft-versus-host disease" Rinsho Ketsueki—The Japanese Journal of Clinical Hematology, Nov. 1, 2007, vol. 48, No. 11, pp. 1508-1510.
Pokrovsky, V.I., "Small Medical Encyclopedia," Medicine, 1996, V5, pp. 90-96, and English translation of relevant portion, 12 pages.
Prior, I. et al., "The Frequency of Ras Mutations in Cancer," Cancer Research, 2020, vol. 80, pp. 2969-2974.
Revolution Medicines, Inc., "Targeting KRASG12C(ON) and Potential Application to Overcoming Drug Resistance in RAS-Addicted Tumors," RAS-Targeted Drug Development, Sep. 22, 2021, 16 pages.
Revolution Medicines, Inc., "The Bi-steric mTORC1-Selective Inhibitor RMC-5552 in Tumors with Activation of mTOR Signaling: Preclinical Activity in Combination with RAS(ON) Inhibitors in RAS-Addicted Tumors, and Initial Clinical Findings from a Single Agent Phase 1/1b Study," 2022 ASCO Annual Meeting, Jun. 3-7, 2002, Chicago, IL, Abstract No. 3098, 1 page.
Ricciutelli, M. et al., "Evaluation of rapamycin chemical stability in volatile-organic solvents by HPLC," Journal of Pharmaceutical and Biomedical Analysis, Mar. 20, 2006, vol. 41, pp. 1070-1074.
Sanchez-Martinez, Conception, "Cyclin dependent kinase (CDK) inhibitors as anticancer drugs", Bioorganic & Medicinal Chemistry Letters, Jun. 6, 2-15, vol. 25, No. 17,pp. 3420-3435.
Sobhani, H. et al., "A Reversed Phase High Performance Liquid Chromatographic Method for Determination of Rapamycin," Iranian Journal of Pharmaceutical Research, Feb. 2013, vol. 12 (supplement), pp. 77-81.
Tallarida, R.J., "Quantitative methods for assessing drug synergism," Genes and cancer, Nov. 2011, vol. 2, No. 11, pp. 1003-1008.
Tanaka, N. et al., "Clinical Acquired Resistance to KRASG12C Inhibition through a Novel KRAS Switch-II Pocket Mutation and Polyclonal Alterations Converging on RAS-MAPK Reactivation," AACR Cancer Discovery, Aug. 2021, vol. 11, No. 8, pp. 1913-1922.
Vengerovskiy, A. I., "Pharmacological incompatibility", Bulletin of Siberian Medicine (2003); 2(3): 49-56; 16 pages (English translation of Russian Office Action for Russian Application No. 2013107378/13(010962) attached).
Viale, PH., "The American Cancer Society's Facts & Figures: 2020 Edition," Journal of the Advanced Practitioner in Oncology, Mar. 2020, vol. 11, No. 2, pp. 135-136.
Wagner, R. et al., "Rapamycin analogs with reduced systemic exposure," Bioorganic Medicinal Chemistry Letters, Sep. 26, 2005, vol. 15, pp. 5340-5343.
Wyeth Laboratories, Rapamune® (sirolimus) Oral Solution Tablets, 37 pages, retrieved from https://www.accessdata.fda.gov/drugsatfda_docs/label/2007/021083s030,021110s038lbl.pdf.
Yohannes, D. et al., "Degradation of Rapamycin Retrieval of Major Intact Subunits," Tetraheron Letters, Jan. 1, 1992, vol. 33, No. 49, pp. 7469-7472.

SEQUENCE LISTING

```
<160> NUMBER OF SEQ ID NOS: 5

<210> SEQ ID NO 1
<211> LENGTH: 2549
<212> TYPE: PRT
<213> ORGANISM: Homo sapiens

<400> SEQUENCE: 1

Met Leu Gly Thr Gly Pro Ala Ala Ala Thr Thr Ala Ala Thr Thr Ser
1               5                   10                  15

Ser Asn Val Ser Val Leu Gln Gln Phe Ala Ser Gly Leu Lys Ser Arg
            20                  25                  30

Asn Glu Glu Thr Arg Ala Lys Ala Ala Lys Glu Leu Gln His Tyr Val
        35                  40                  45

Thr Met Glu Leu Arg Glu Met Ser Gln Glu Glu Ser Thr Arg Phe Tyr
    50                  55                  60

Asp Gln Leu Asn His His Ile Phe Glu Leu Val Ser Ser Ser Asp Ala
65                  70                  75                  80

Asn Glu Arg Lys Gly Gly Ile Leu Ala Ile Ala Ser Leu Ile Gly Val
                85                  90                  95

Glu Gly Gly Asn Ala Thr Arg Ile Gly Arg Phe Ala Asn Tyr Leu Arg
            100                 105                 110

Asn Leu Leu Pro Ser Asn Asp Pro Val Val Met Glu Met Ala Ser Lys
        115                 120                 125

Ala Ile Gly Arg Leu Ala Met Ala Gly Asp Thr Phe Thr Ala Glu Tyr
    130                 135                 140
```

-continued

```
Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175

Ile Ser Val Pro Thr Phe Phe Phe Gln Gln Val Gln Pro Phe Phe Asp
            180                 185                 190

Asn Ile Phe Val Ala Val Trp Asp Pro Lys Gln Ala Ile Arg Glu Gly
        195                 200                 205

Ala Val Ala Ala Leu Arg Ala Cys Leu Ile Leu Thr Thr Gln Arg Glu
    210                 215                 220

Pro Lys Glu Met Gln Lys Pro Gln Trp Tyr Arg His Thr Phe Glu Glu
225                 230                 235                 240

Ala Glu Lys Gly Phe Asp Glu Thr Leu Ala Lys Glu Lys Gly Met Asn
                245                 250                 255

Arg Asp Asp Arg Ile His Gly Ala Leu Leu Ile Leu Asn Glu Leu Val
            260                 265                 270

Arg Ile Ser Ser Met Glu Gly Glu Arg Leu Arg Glu Glu Met Glu Glu
        275                 280                 285

Ile Thr Gln Gln Gln Leu Val His Asp Lys Tyr Cys Lys Asp Leu Met
    290                 295                 300

Gly Phe Gly Thr Lys Pro Arg His Ile Thr Pro Phe Thr Ser Phe Gln
305                 310                 315                 320

Ala Val Gln Pro Gln Gln Ser Asn Ala Leu Val Gly Leu Leu Gly Tyr
                325                 330                 335

Ser Ser His Gln Gly Leu Met Gly Phe Gly Thr Ser Pro Ser Pro Ala
            340                 345                 350

Lys Ser Thr Leu Val Glu Ser Arg Cys Cys Arg Asp Leu Met Glu Glu
        355                 360                 365

Lys Phe Asp Gln Val Cys Gln Trp Val Leu Lys Cys Arg Asn Ser Lys
    370                 375                 380

Asn Ser Leu Ile Gln Met Thr Ile Leu Asn Leu Leu Pro Arg Leu Ala
385                 390                 395                 400

Ala Phe Arg Pro Ser Ala Phe Thr Asp Thr Gln Tyr Leu Gln Asp Thr
                405                 410                 415

Met Asn His Val Leu Ser Cys Val Lys Lys Glu Lys Glu Arg Thr Ala
            420                 425                 430

Ala Phe Gln Ala Leu Gly Leu Leu Ser Val Ala Val Arg Ser Glu Phe
        435                 440                 445

Lys Val Tyr Leu Pro Arg Val Leu Asp Ile Ile Arg Ala Ala Leu Pro
    450                 455                 460

Pro Lys Asp Phe Ala His Lys Arg Gln Lys Ala Met Gln Val Asp Ala
465                 470                 475                 480

Thr Val Phe Thr Cys Ile Ser Met Leu Ala Arg Ala Met Gly Pro Gly
                485                 490                 495

Ile Gln Gln Asp Ile Lys Glu Leu Leu Glu Pro Met Leu Ala Val Gly
            500                 505                 510

Leu Ser Pro Ala Leu Thr Ala Val Leu Tyr Asp Leu Ser Arg Gln Ile
        515                 520                 525

Pro Gln Leu Lys Lys Asp Ile Gln Asp Gly Leu Leu Lys Met Leu Ser
    530                 535                 540

Leu Val Leu Met His Lys Pro Leu Arg His Pro Gly Met Pro Lys Gly
545                 550                 555                 560
```

-continued

Leu Ala His Gln Leu Ala Ser Pro Gly Leu Thr Thr Leu Pro Glu Ala
565 570 575

Ser Asp Val Gly Ser Ile Thr Leu Ala Leu Arg Thr Leu Gly Ser Phe
580 585 590

Glu Phe Glu Gly His Ser Leu Thr Gln Phe Val Arg His Cys Ala Asp
595 600 605

His Phe Leu Asn Ser Glu His Lys Glu Ile Arg Met Glu Ala Ala Arg
610 615 620

Thr Cys Ser Arg Leu Leu Thr Pro Ser Ile His Leu Ile Ser Gly His
625 630 635 640

Ala His Val Val Ser Gln Thr Ala Val Gln Val Val Ala Asp Val Leu
645 650 655

Ser Lys Leu Leu Val Val Gly Ile Thr Asp Pro Asp Pro Asp Ile Arg
660 665 670

Tyr Cys Val Leu Ala Ser Leu Asp Glu Arg Phe Asp Ala His Leu Ala
675 680 685

Gln Ala Glu Asn Leu Gln Ala Leu Phe Val Ala Leu Asn Asp Gln Val
690 695 700

Phe Glu Ile Arg Glu Leu Ala Ile Cys Thr Val Gly Arg Leu Ser Ser
705 710 715 720

Met Asn Pro Ala Phe Val Met Pro Phe Leu Arg Lys Met Leu Ile Gln
725 730 735

Ile Leu Thr Glu Leu Glu His Ser Gly Ile Gly Arg Ile Lys Glu Gln
740 745 750

Ser Ala Arg Met Leu Gly His Leu Val Ser Asn Ala Pro Arg Leu Ile
755 760 765

Arg Pro Tyr Met Glu Pro Ile Leu Lys Ala Leu Ile Leu Lys Leu Lys
770 775 780

Asp Pro Asp Pro Asp Pro Asn Pro Gly Val Ile Asn Asn Val Leu Ala
785 790 795 800

Thr Ile Gly Glu Leu Ala Gln Val Ser Gly Leu Glu Met Arg Lys Trp
805 810 815

Val Asp Glu Leu Phe Ile Ile Ile Met Asp Met Leu Gln Asp Ser Ser
820 825 830

Leu Leu Ala Lys Arg Gln Val Ala Leu Trp Thr Leu Gly Gln Leu Val
835 840 845

Ala Ser Thr Gly Tyr Val Val Glu Pro Tyr Arg Lys Tyr Pro Thr Leu
850 855 860

Leu Glu Val Leu Leu Asn Phe Leu Lys Thr Glu Gln Asn Gln Gly Thr
865 870 875 880

Arg Arg Glu Ala Ile Arg Val Leu Gly Leu Leu Gly Ala Leu Asp Pro
885 890 895

Tyr Lys His Lys Val Asn Ile Gly Met Ile Asp Gln Ser Arg Asp Ala
900 905 910

Ser Ala Val Ser Leu Ser Glu Ser Lys Ser Ser Gln Asp Ser Ser Asp
915 920 925

Tyr Ser Thr Ser Glu Met Leu Val Asn Met Gly Asn Leu Pro Leu Asp
930 935 940

Glu Phe Tyr Pro Ala Val Ser Met Val Ala Leu Met Arg Ile Phe Arg
945 950 955 960

Asp Gln Ser Leu Ser His His His Thr Met Val Val Gln Ala Ile Thr
965 970 975

-continued

```
Phe Ile Phe Lys Ser Leu Gly Leu Lys Cys Val Gln Phe Leu Pro Gln
            980                 985                 990

Val Met Pro Thr Phe Leu Asn Val  Ile Arg Val Cys Asp  Gly Ala Ile
        995                 1000                1005

Arg Glu  Phe Leu Phe Gln Gln  Leu Gly Met Leu Val  Ser Phe Val
    1010                 1015                 1020

Lys Ser  His Ile Arg Pro Tyr  Met Asp Glu Ile Val  Thr Leu Met
    1025                 1030                 1035

Arg Glu  Phe Trp Val Met Asn  Thr Ser Ile Gln Ser  Thr Ile Ile
    1040                 1045                 1050

Leu Leu  Ile Glu Gln Ile Val  Val Ala Leu Gly Gly  Glu Phe Lys
    1055                 1060                 1065

Leu Tyr  Leu Pro Gln Leu Ile  Pro His Met Leu Arg  Val Phe Met
    1070                 1075                 1080

His Asp  Asn Ser Pro Gly Arg  Ile Val Ser Ile Lys  Leu Leu Ala
    1085                 1090                 1095

Ala Ile  Gln Leu Phe Gly Ala  Asn Leu Asp Asp Tyr  Leu His Leu
    1100                 1105                 1110

Leu Leu  Pro Pro Ile Val Lys  Leu Phe Asp Ala Pro  Glu Ala Pro
    1115                 1120                 1125

Leu Pro  Ser Arg Lys Ala Ala  Leu Glu Thr Val Asp  Arg Leu Thr
    1130                 1135                 1140

Glu Ser  Leu Asp Phe Thr Asp  Tyr Ala Ser Arg Ile  Ile His Pro
    1145                 1150                 1155

Ile Val  Arg Thr Leu Asp Gln  Ser Pro Glu Leu Arg  Ser Thr Ala
    1160                 1165                 1170

Met Asp  Thr Leu Ser Ser Leu  Val Phe Gln Leu Gly  Lys Lys Tyr
    1175                 1180                 1185

Gln Ile  Phe Ile Pro Met Val  Asn Lys Val Leu Val  Arg His Arg
    1190                 1195                 1200

Ile Asn  His Gln Arg Tyr Asp  Val Leu Ile Cys Arg  Ile Val Lys
    1205                 1210                 1215

Gly Tyr  Thr Leu Ala Asp Glu  Glu Glu Asp Pro Leu  Ile Tyr Gln
    1220                 1225                 1230

His Arg  Met Leu Arg Ser Gly  Gln Gly Asp Ala Leu  Ala Ser Gly
    1235                 1240                 1245

Pro Val  Glu Thr Gly Pro Met  Lys Lys Leu His Val  Ser Thr Ile
    1250                 1255                 1260

Asn Leu  Gln Lys Ala Trp Gly  Ala Ala Arg Arg Val  Ser Lys Asp
    1265                 1270                 1275

Asp Trp  Leu Glu Trp Leu Arg  Arg Leu Ser Leu Glu  Leu Leu Lys
    1280                 1285                 1290

Asp Ser  Ser Ser Pro Ser Leu  Arg Ser Cys Trp Ala  Leu Ala Gln
    1295                 1300                 1305

Ala Tyr  Asn Pro Met Ala Arg  Asp Leu Phe Asn Ala  Ala Phe Val
    1310                 1315                 1320

Ser Cys  Trp Ser Glu Leu Asn  Glu Asp Gln Gln Asp  Glu Leu Ile
    1325                 1330                 1335

Arg Ser  Ile Glu Leu Ala Leu  Thr Ser Gln Asp Ile  Ala Glu Val
    1340                 1345                 1350

Thr Gln  Thr Leu Leu Asn Leu  Ala Glu Phe Met Glu  His Ser Asp
    1355                 1360                 1365
```

Lys Gly Pro Leu Pro Leu Arg Asp Asp Asn Gly Ile Val Leu Leu
1370 1375 1380

Gly Glu Arg Ala Ala Lys Cys Arg Ala Tyr Ala Lys Ala Leu His
1385 1390 1395

Tyr Lys Glu Leu Glu Phe Gln Lys Gly Pro Thr Pro Ala Ile Leu
1400 1405 1410

Glu Ser Leu Ile Ser Ile Asn Asn Lys Leu Gln Gln Pro Glu Ala
1415 1420 1425

Ala Ala Gly Val Leu Glu Tyr Ala Met Lys His Phe Gly Glu Leu
1430 1435 1440

Glu Ile Gln Ala Thr Trp Tyr Glu Lys Leu His Glu Trp Glu Asp
1445 1450 1455

Ala Leu Val Ala Tyr Asp Lys Lys Met Asp Thr Asn Lys Asp Asp
1460 1465 1470

Pro Glu Leu Met Leu Gly Arg Met Arg Cys Leu Glu Ala Leu Gly
1475 1480 1485

Glu Trp Gly Gln Leu His Gln Gln Cys Cys Glu Lys Trp Thr Leu
1490 1495 1500

Val Asn Asp Glu Thr Gln Ala Lys Met Ala Arg Met Ala Ala Ala
1505 1510 1515

Ala Ala Trp Gly Leu Gly Gln Trp Asp Ser Met Glu Glu Tyr Thr
1520 1525 1530

Cys Met Ile Pro Arg Asp Thr His Asp Gly Ala Phe Tyr Arg Ala
1535 1540 1545

Val Leu Ala Leu His Gln Asp Leu Phe Ser Leu Ala Gln Gln Cys
1550 1555 1560

Ile Asp Lys Ala Arg Asp Leu Leu Asp Ala Glu Leu Thr Ala Met
1565 1570 1575

Ala Gly Glu Ser Tyr Ser Arg Ala Tyr Gly Ala Met Val Ser Cys
1580 1585 1590

His Met Leu Ser Glu Leu Glu Glu Val Ile Gln Tyr Lys Leu Val
1595 1600 1605

Pro Glu Arg Arg Glu Ile Ile Arg Gln Ile Trp Trp Glu Arg Leu
1610 1615 1620

Gln Gly Cys Gln Arg Ile Val Glu Asp Trp Gln Lys Ile Leu Met
1625 1630 1635

Val Arg Ser Leu Val Val Ser Pro His Glu Asp Met Arg Thr Trp
1640 1645 1650

Leu Lys Tyr Ala Ser Leu Cys Gly Lys Ser Gly Arg Leu Ala Leu
1655 1660 1665

Ala His Lys Thr Leu Val Leu Leu Leu Gly Val Asp Pro Ser Arg
1670 1675 1680

Gln Leu Asp His Pro Leu Pro Thr Val His Pro Gln Val Thr Tyr
1685 1690 1695

Ala Tyr Met Lys Asn Met Trp Lys Ser Ala Arg Lys Ile Asp Ala
1700 1705 1710

Phe Gln His Met Gln His Phe Val Gln Thr Met Gln Gln Gln Ala
1715 1720 1725

Gln His Ala Ile Ala Thr Glu Asp Gln Gln His Lys Gln Glu Leu
1730 1735 1740

His Lys Leu Met Ala Arg Cys Phe Leu Lys Leu Gly Glu Trp Gln
1745 1750 1755

-continued

```
Leu Asn  Leu Gln Gly Ile Asn  Glu Ser Thr Ile Pro  Lys Val Leu
    1760                 1765                 1770

Gln Tyr  Tyr Ser Ala Ala Thr  Glu His Asp Arg Ser  Trp Tyr Lys
    1775                 1780                 1785

Ala Trp  His Ala Trp Ala Val  Met Asn Phe Glu Ala  Val Leu His
    1790                 1795                 1800

Tyr Lys  His Gln Asn Gln Ala  Arg Asp Glu Lys Lys  Lys Leu Arg
    1805                 1810                 1815

His Ala  Ser Gly Ala Asn Ile  Thr Asn Ala Thr Thr  Ala Ala Thr
    1820                 1825                 1830

Thr Ala  Ala Thr Ala Thr Thr  Thr Ala Ser Thr Glu  Gly Ser Asn
    1835                 1840                 1845

Ser Glu  Ser Glu Ala Glu Ser  Thr Glu Asn Ser Pro  Thr Pro Ser
    1850                 1855                 1860

Pro Leu  Gln Lys Lys Val Thr  Glu Asp Leu Ser Lys  Thr Leu Leu
    1865                 1870                 1875

Met Tyr  Thr Val Pro Ala Val  Gln Gly Phe Phe Arg  Ser Ile Ser
    1880                 1885                 1890

Leu Ser  Arg Gly Asn Asn Leu  Gln Asp Thr Leu Arg  Val Leu Thr
    1895                 1900                 1905

Leu Trp  Phe Asp Tyr Gly His  Trp Pro Asp Val Asn  Glu Ala Leu
    1910                 1915                 1920

Val Glu  Gly Val Lys Ala Ile  Gln Ile Asp Thr Trp  Leu Gln Val
    1925                 1930                 1935

Ile Pro  Gln Leu Ile Ala Arg  Ile Asp Thr Pro Arg  Pro Leu Val
    1940                 1945                 1950

Gly Arg  Leu Ile His Gln Leu  Leu Thr Asp Ile Gly  Arg Tyr His
    1955                 1960                 1965

Pro Gln  Ala Leu Ile Tyr Pro  Leu Thr Val Ala Ser  Lys Ser Thr
    1970                 1975                 1980

Thr Thr  Ala Arg His Asn Ala  Ala Asn Lys Ile Leu  Lys Asn Met
    1985                 1990                 1995

Cys Glu  His Ser Asn Thr Leu  Val Gln Gln Ala Met  Met Val Ser
    2000                 2005                 2010

Glu Glu  Leu Ile Arg Val Ala  Ile Leu Trp His Glu  Met Trp His
    2015                 2020                 2025

Glu Gly  Leu Glu Glu Ala Ser  Arg Leu Tyr Phe Gly  Glu Arg Asn
    2030                 2035                 2040

Val Lys  Gly Met Phe Glu Val  Leu Glu Pro Leu His  Ala Met Met
    2045                 2050                 2055

Glu Arg  Gly Pro Gln Thr Leu  Lys Glu Thr Ser Phe  Asn Gln Ala
    2060                 2065                 2070

Tyr Gly  Arg Asp Leu Met Glu  Ala Gln Glu Trp Cys  Arg Lys Tyr
    2075                 2080                 2085

Met Lys  Ser Gly Asn Val Lys  Asp Leu Thr Gln Ala  Trp Asp Leu
    2090                 2095                 2100

Tyr Tyr  His Val Phe Arg Arg  Ile Ser Lys Gln Leu  Pro Gln Leu
    2105                 2110                 2115

Thr Ser  Leu Glu Leu Gln Tyr  Val Ser Pro Lys Leu  Leu Met Cys
    2120                 2125                 2130

Arg Asp  Leu Glu Leu Ala Val  Pro Gly Thr Tyr Asp  Pro Asn Gln
    2135                 2140                 2145
```

-continued

```
Pro Ile  Ile Arg Ile Gln Ser  Ile Ala Pro Ser Leu  Gln Val Ile
    2150                 2155                 2160

Thr Ser  Lys Gln Arg Pro Arg  Lys Leu Thr Leu Met  Gly Ser Asn
    2165                 2170                 2175

Gly His  Glu Phe Val Phe Leu  Leu Lys Gly His Glu  Asp Leu Arg
    2180                 2185                 2190

Gln Asp  Glu Arg Val Met Gln  Leu Phe Gly Leu Val  Asn Thr Leu
    2195                 2200                 2205

Leu Ala  Asn Asp Pro Thr Ser  Leu Arg Lys Asn Leu  Ser Ile Gln
    2210                 2215                 2220

Arg Tyr  Ala Val Ile Pro Leu  Ser Thr Asn Ser Gly  Leu Ile Gly
    2225                 2230                 2235

Trp Val  Pro His Cys Asp Thr  Leu His Ala Leu Ile  Arg Asp Tyr
    2240                 2245                 2250

Arg Glu  Lys Lys Lys Ile Leu  Leu Asn Ile Glu His  Arg Ile Met
    2255                 2260                 2265

Leu Arg  Met Ala Pro Asp Tyr  Asp His Leu Thr Leu  Met Gln Lys
    2270                 2275                 2280

Val Glu  Val Phe Glu His Ala  Val Asn Asn Thr Ala  Gly Asp Asp
    2285                 2290                 2295

Leu Ala  Lys Leu Leu Trp Leu  Lys Ser Pro Ser Ser  Glu Val Trp
    2300                 2305                 2310

Phe Asp  Arg Arg Thr Asn Tyr  Thr Arg Ser Leu Ala  Val Met Ser
    2315                 2320                 2325

Met Val  Gly Tyr Ile Leu Gly  Leu Gly Asp Arg His  Pro Ser Asn
    2330                 2335                 2340

Leu Met  Leu Asp Arg Leu Ser  Gly Lys Ile Leu His  Ile Asp Phe
    2345                 2350                 2355

Gly Asp  Cys Phe Glu Val Ala  Met Thr Arg Glu Lys  Phe Pro Glu
    2360                 2365                 2370

Lys Ile  Pro Phe Arg Leu Thr  Arg Met Leu Thr Asn  Ala Met Glu
    2375                 2380                 2385

Val Thr  Gly Leu Asp Gly Asn  Tyr Arg Ile Thr Cys  His Thr Val
    2390                 2395                 2400

Met Glu  Val Leu Arg Glu His  Lys Asp Ser Val Met  Ala Val Leu
    2405                 2410                 2415

Glu Ala  Phe Val Tyr Asp Pro  Leu Leu Asn Trp Arg  Leu Met Asp
    2420                 2425                 2430

Thr Asn  Thr Lys Gly Asn Lys  Arg Ser Arg Thr Arg  Thr Asp Ser
    2435                 2440                 2445

Tyr Ser  Ala Gly Gln Ser Val  Glu Ile Leu Asp Gly  Val Glu Leu
    2450                 2455                 2460

Gly Glu  Pro Ala His Lys Lys  Thr Gly Thr Thr Val  Pro Glu Ser
    2465                 2470                 2475

Ile His  Ser Phe Ile Gly Asp  Gly Leu Val Lys Pro  Glu Ala Leu
    2480                 2485                 2490

Asn Lys  Lys Ala Ile Gln Ile  Ile Asn Arg Val Arg  Asp Lys Leu
    2495                 2500                 2505

Thr Gly  Arg Asp Phe Ser His  Asp Asp Thr Leu Asp  Val Pro Thr
    2510                 2515                 2520

Gln Val  Glu Leu Leu Ile Lys  Gln Ala Thr Ser His  Glu Asn Leu
    2525                 2530                 2535
```

```
Cys Gln  Cys Tyr Ile Gly Trp  Cys Pro Phe Trp
    2540                 2545


<210> SEQ ID NO 2
<211> LENGTH: 8733
<212> TYPE: DNA
<213> ORGANISM: Homo sapiens

<400> SEQUENCE: 2

gctcccggct tagaggacag cggggaaggc gggcggtggg gcagggggcc tgaagcggcg     60

gtaccggtgc tggcggcggc agctgaggcc ttggccgaag ccgcgcgaac ctcagggcaa    120

gatgcttgga accggacctg ccgccgccac caccgctgcc accacatcta gcaatgtgag    180

cgtcctgcag cagtttgcca gtggcctaaa gagccggaat gaggaaacca gggccaaagc    240

cgccaaggag ctccagcact atgtcaccat ggaactccga gagatgagtc aagaggagtc    300

tactcgcttc tatgaccaac tgaaccatca catttttgaa ttggtttcca gctcagatgc    360

caatgagagg aaaggtggca tcttggccat agctagcctc ataggagtgg aaggtgggaa    420

tgccacccga attggcagat ttgccaacta tcttcggaac ctcctcccct ccaatgaccc    480

agttgtcatg gaaatggcat ccaaggccat tggccgtctt gccatggcag gggacacttt    540

taccgctgag tacgtggaat ttgaggtgaa gcgagccctg gaatggctgg gtgctgaccg    600

caatgagggc cggagacatg cagctgtcct ggttctccgt gagctggcca tcagcgtccc    660

taccttcttc ttccagcaag tgcaaccctt ctttgacaac atttttgtgg ccgtgtggga    720

ccccaaacag gccatccgtg agggagctgt agccgccctt cgtgcctgtc tgattctcac    780

aacccagcgt gagccgaagg agatgcagaa gcctcagtgg tacaggcaca catttgaaga    840

agcagagaag ggatttgatg agaccttggc caaagagaag ggcatgaatc gggatgatcg    900

gatccatgga gccttgttga tccttaacga gctggtccga atcagcagca tggaggggaga    960

gcgtctgaga gaagaaatgg aagaaatcac acagcagcag ctggtacacg acaagtactg   1020

caaagatctc atgggcttcg gaacaaaacc tcgtcacatt accccccttca ccagtttcca   1080

ggctgtacag ccccagcagt caaatgcctt ggtggggctg ctggggtaca gctctcacca   1140

aggcctcatg ggatttggga cctcccccag tccagctaag tccaccctgg tggagagccg   1200

gtgttgcaga gacttgatgg aggagaaatt tgatcaggtg tgccagtggg tgctgaaatg   1260

caggaatagc aagaactcgc tgatccaaat gacaatcctt aatttgttgc cccgcttggc   1320

tgcattccga ccttctgcct tcacagatac ccagtatctc caagatacca tgaaccatgt   1380

cctaagctgt gtcaagaagg agaaggaacg tacagcggcc ttccaagccc tggggctact   1440

ttctgtggct gtgaggtctg agtttaaggt ctatttgcct cgcgtgctgg acatcatccg   1500

agcggccctg cccccaaagg acttcgccca taagaggcag aaggcaatgc aggtggatgc   1560

cacagtcttc acttgcatca gcatgctggc tcgagcaatg ggccaggca tccagcagga    1620

tatcaaggag ctgctggagc ccatgctggc agtgggacta agccctgccc tcactgcagt   1680

gctctacgac ctgagccgtc agattccaca gctaaagaag gacattcaag atgggctact   1740

gaaaatgctg tccctggtcc ttatgcacaa accccttcgc cacccaggca tgcccaaggg   1800

cctggcccat cagctggcct ctcctggcct cacgaccctc cctgaggcca gcgatgtggg   1860

cagcatcact cttgccctcc gaacgcttgg cagctttgaa tttgaaggcc actctctgac   1920

ccaatttgtt cgccactgtg cggatcattt cctgaacagt gagcacaagg agatccgcat   1980

ggaggctgcc cgcacctgct cccgcctgct cacaccctcc atccacctca tcagtggcca   2040
```

-continued

```
tgctcatgtg gttagccaga ccgcagtgca agtggtggca gatgtgctta gcaaactgct   2100
cgtagttggg ataacagatc ctgaccctga cattcgctac tgtgtcttgg cgtccctgga   2160
cgagcgcttt gatgcacacc tggcccaggc ggagaacttg caggccttgt ttgtggctct   2220
gaatgaccag gtgtttgaga tccgggagct ggccatctgc actgtgggcc gactcagtag   2280
catgaaccct gcctttgtca tgcctttcct gcgcaagatg ctcatccaga ttttgacaga   2340
gttggagcac agtgggattg gaagaatcaa agagcagagt gcccgcatgc tggggcacct   2400
ggtctccaat gccccccgac tcatccgccc ctacatggag cctattctga aggcattaat   2460
tttgaaactg aaagatccag accctgatcc aaacccaggt gtgatcaata atgtcctggc   2520
aacaatagga gaattggcac aggttagtgg cctggaaatg aggaaatggg ttgatgaact   2580
ttttattatc atcatggaca tgctccagga ttcctctttg ttggccaaaa ggcaggtggc   2640
tctgtggacc ctgggacagt tggtggccag cactggctat gtagtagagc cctacaggaa   2700
gtaccctact ttgcttgagg tgctactgaa ttttctgaag actgagcaga accagggtac   2760
acgcagagag gccatccgtg tgttagggct tttaggggct ttggatcctt acaagcacaa   2820
agtgaacatt ggcatgatag accagtcccg ggatgcctct gctgtcagcc tgtcagaatc   2880
caagtcaagt caggattcct ctgactatag cactagtgaa atgctggtca acatgggaaa   2940
cttgcctctg gatgagttct acccagctgt gtccatggtg gccctgatgc ggatcttccg   3000
agaccagtca ctctctcatc atcacaccat ggttgtccag gccatcacct tcatcttcaa   3060
gtccctggga ctcaaatgtg tgcagttcct gccccaggtc atgcccacgt tccttaacgt   3120
cattcgagtc tgtgatgggg ccatccggga atttttgttc cagcagctgg gaatgttggt   3180
gtcctttgtg aagagccaca tcagacctta tatggatgaa atagtcaccc tcatgagaga   3240
attctgggtc atgaacacct caattcagag cacgatcatt cttctcattg agcaaattgt   3300
ggtagctctt gggggtgaat ttaagctcta cctgccccag ctgatcccac acatgctgcg   3360
tgtcttcatg catgacaaca gcccaggccg cattgtctct atcaagttac tggctgcaat   3420
ccagctgttt ggcgccaacc tggatgacta cctgcattta ctgctgcctc ctattgttaa   3480
gttgtttgat gcccctgaag ctccactgcc atctcgaaag gcagcgctag agactgtgga   3540
ccgcctgacg gagtccctgg atttcactga ctatgcctcc cggatcattc accctattgt   3600
tcgaacactg gaccagagcc cagaactgcg ctccacagcc atggacacgc tgtcttcact   3660
tgtttttcag ctggggaaga agtaccaaat tttcattcca atggtgaata aagttctggt   3720
gcgacaccga atcaatcatc agcgctatga tgtgctcatc tgcagaattg tcaagggata   3780
cacacttgct gatgaagagg aggatccttt gatttaccag catcggatgc ttaggagtgg   3840
ccaaggggat gcattggcta gtggaccagt ggaaacagga cccatgaaga aactgcacgt   3900
cagcaccatc aacctccaaa aggcctgggg cgctgccagg agggtctcca aagatgactg   3960
gctggaatgg ctgagacggc tgagcctgga gctgctgaag gactcatcat cgccctccct   4020
gcgctcctgc tgggccctgg cacaggccta caacccgatg gccagggatc tcttcaatgc   4080
tgcatttgtg tcctgctggt ctgaactgaa tgaagatcaa caggatgagc tcatcagaag   4140
catcgagttg gccctcacct cacaagacat cgctgaagtc acacagaccc tcttaaactt   4200
ggctgaattc atggaacaca gtgacaaggg cccccctgcca ctgagagatg acaatggcat   4260
tgttctgctg ggtgagagag ctgccaagtg ccgagcatat gccaaagcac tacactacaa   4320
agaactggag ttccagaaag gccccacccc tgccattcta gaatctctca tcagcattaa   4380
taataagcta cagcagccgg aggcagcggc cggagtgtta gaatatgcca tgaaacactt   4440
```

-continued

```
tggagagctg gagatccagg ctacctggta tgagaaactg cacgagtggg aggatgccct   4500
tgtggcctat gacaagaaaa tggacaccaa caaggacgac ccagagctga tgctgggccg   4560
catgcgctgc ctcgaggcct tgggggaatg gggtcaactc caccagcagt gctgtgaaaa   4620
gtggaccctg gttaatgatg agacccaagc caagatggcc cggatggctg ctgcagctgc   4680
atggggttta ggtcagtggg acagcatgga agaatacacc tgtatgatcc ctcgggacac   4740
ccatgatggg gcattttata gagctgtgct ggcactgcat caggacctct tctccttggc   4800
acaacagtgc attgacaagg ccagggacct gctggatgct gaattaactg cgatggcagg   4860
agagagttac agtcgggcat atggggccat ggtttcttgc cacatgctgt ccgagctgga   4920
ggaggttatc cagtacaaac ttgtccccga gcgacgagag atcatccgcc agatctggtg   4980
ggagagactg cagggctgcc agcgtatcgt agaggactgg cagaaaatcc ttatggtgcg   5040
gtcccttgtg gtcagccctc atgaagacat gagaacctgg ctcaagtatg caagcctgtg   5100
cggcaagagt ggcaggctgg ctcttgctca taaaacttta gtgttgctcc tgggagttga   5160
tccgtctcgg caacttgacc atcctctgcc aacagttcac cctcaggtga cctatgccta   5220
catgaaaaac atgtggaaga gtgcccgcaa gatcgatgcc ttccagcaca tgcagcattt   5280
tgtccagacc atgcagcaac aggcccagca tgccatcgct actgaggacc agcagcataa   5340
gcaggaactg cacaagctca tggcccgatg cttcctgaaa cttggagagt ggcagctgaa   5400
tctacagggc atcaatgaga gcacaatccc caaagtgctg cagtactaca gcgccgccac   5460
agagcacgac cgcagctggt acaaggcctg gcatgcgtgg gcagtgatga acttcgaagc   5520
tgtgctacac tacaaacatc agaaccaagc ccgcgatgag aagaagaaac tgcgtcatgc   5580
cagcggggcc aacatcacca acgccaccac tgccgccacc acggccgcca ctgccaccac   5640
cactgccagc accgagggca gcaacagtga gagcgaggcc gagagcaccg agaacagccc   5700
caccccatcg ccgctgcaga agaaggtcac tgaggatctg tccaaaaccc tcctgatgta   5760
cacggtgcct gccgtccagg gcttcttccg ttccatctcc ttgtcacgag gcaacaacct   5820
ccaggataca ctcagagttc tcaccttatg gtttgattat ggtcactggc cagatgtcaa   5880
tgaggcctta gtggaggggg tgaaagccat ccagattgat acctggctac aggttatacc   5940
tcagctcatt gcaagaattg atacgcccag acccttggtg ggacgtctca ttcaccagct   6000
tctcacagac attggtcggt accaccccca ggccctcatc tacccactga cagtggcttc   6060
taagtctacc acgacagccc ggcacaatgc agccaacaag attctgaaga acatgtgtga   6120
gcacagcaac accctggtcc agcaggccat gatggtgagc gaggagctga tccgagtggc   6180
catcctctgg catgagatgt ggcatgaagg cctggaagag gcatctcgtt tgtactttgg   6240
ggaaaggaac gtgaaaggca tgtttgaggt gctggagccc ttgcatgcta tgatggaacg   6300
gggcccccag actctgaagg aaacatcctt taatcaggcc tatggtcgag atttaatgga   6360
ggcccaagag tggtgcagga agtacatgaa atcagggaat gtcaaggacc tcacccaagc   6420
ctgggacctc tattatcatg tgttccgacg aatctcaaag cagctgcctc agctcacatc   6480
cttagagctg caatatgttt ccccaaaact tctgatgtgc cgggaccttg aattggctgt   6540
gccaggaaca tatgacccca accagccaat cattcgcatt cagtccatag caccgtcttt   6600
gcaagtcatc acatccaagc agaggccccg gaaattgaca cttatgggca gcaacggaca   6660
tgagtttgtt ttccttctaa aaggccatga agatctgcgc caggatgagc gtgtgatgca   6720
gctcttcggc ctggttaaca cccttctggc caatgaccca acatctcttc ggaaaaacct   6780
```

```
cagcatccag agatacgctg tcatcccttt atcgaccaac tcgggcctca ttggctgggt   6840
tccccactgt gacacactgc acgccctcat ccgggactac agggagaaga agaagatcct   6900
tctcaacatc gagcatcgca tcatgttgcg gatggctccg gactatgacc acttgactct   6960
gatgcagaag gtggaggtgt ttgagcatgc cgtcaataat acagctgggg acgacctggc   7020
caagctgctg tggctgaaaa gccccagctc cgaggtgtgg tttgaccgaa gaaccaatta   7080
tacccgttct ttagcggtca tgtcaatggt tgggtatatt ttaggcctgg gagatagaca   7140
cccatccaac ctgatgctgg accgtctgag tgggaagatc ctgcacattg actttgggga   7200
ctgctttgag gttgctatga cccgagagaa gtttccagag aagattccat ttagactaac   7260
aagaatgttg accaatgcta tggaggttac aggcctggat ggcaactaca gaatcacatg   7320
ccacacagtg atggaggtgc tgcgagagca caaggacagt gtcatggccg tgctggaagc   7380
ctttgtctat gaccccttgc tgaactggag gctgatggac acaaatacca aaggcaacaa   7440
gcgatcccga acgaggacgg attcctactc tgctggccag tcagtcgaaa ttttggacgg   7500
tgtggaactt ggagagccag cccataagaa aacggggacc acagtgccag aatctattca   7560
ttctttcatt ggagacggtt tggtgaaacc agaggcccta aataagaaag ctatccagat   7620
tattaacagg gttcgagata agctcactgg tcgggacttc tctcatgatg acactttgga   7680
tgttccaacg caagttgagc tgctcatcaa acaagcgaca tcccatgaaa acctctgcca   7740
gtgctatatt ggctggtgcc ctttctggta actggaggcc cagatgtgcc catcacgttt   7800
tttctgaggc ttttgtactt tagtaaatgc ttccactaaa ctgaaaccat ggtgagaaag   7860
tttgactttg ttaaatattt tgaaatgtaa atgaaaagaa ctactgtata ttaaaagttg   7920
gtttgaacca actttctagc tgctgttgaa gaatatattg tcagaaacac aaggcttgat   7980
ttggttccca ggacagtgaa acatagtaat accacgtaaa tcaagccatt cattttgggg   8040
aacagaagat ccataacttt agaaatacgg gttttgactt aactcacaag agaactcatc   8100
ataagtactt gctgatggaa gaatgaccta gttgctcctc tcaacatggg tacagcaaac   8160
tcagcacagc caagaagcct caggtcgtgg agaacatgga ttaggatcct agactgtaaa   8220
gacacagaag atgctgacct cacccctgcc acctatccca agacctcact ggtctgtgga   8280
cagcagcaga aatgtttgca agataggcca aaatgagtac aaaaggtctg tcttccatca   8340
gacccagtga tgctgcgact cacacgcttc aattcaagac ctgaccgcta gtagggaggt   8400
ttattcagat cgctggcagc ctcggctgag cagatgcaca gaggggatca ctgtgcagtg   8460
ggaccaccct cactggcctt ctgcagcagg gttctgggat gttttcagtg gtcaaaatac   8520
tctgtttaga gcaagggctc agaaaacaga aatactgtca tggaggtgct gaacacaggg   8580
aaggtctggt acatattgga aattatgagc agaacaaata ctcaactaaa tgcacaaagt   8640
ataaagtgta gccatgtcta gacaccatgt tgtatcagaa taatttttgt gccaataaat   8700
gacatcagaa ttttaaacat atgtaaaaaa aaa                                 8733
```

<210> SEQ ID NO 3
<211> LENGTH: 108
<212> TYPE: PRT
<213> ORGANISM: Homo sapiens

<400> SEQUENCE: 3

```
Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30
```

Asp Gly Lys Lys Phe Asp Ser Ser Arg Asp Arg Asn Lys Pro Phe Lys
35 40 45

Phe Met Leu Gly Lys Gln Glu Val Ile Arg Gly Trp Glu Glu Gly Val
50 55 60

Ala Gln Met Ser Val Gly Gln Arg Ala Lys Leu Thr Ile Ser Pro Asp
65 70 75 80

Tyr Ala Tyr Gly Ala Thr Gly His Pro Gly Ile Ile Pro Pro His Ala
85 90 95

Thr Leu Val Phe Asp Val Glu Leu Leu Lys Leu Glu
100 105

<210> SEQ ID NO 4
<211> LENGTH: 118
<212> TYPE: PRT
<213> ORGANISM: Homo sapiens

<400> SEQUENCE: 4

Met Ser Gly Gly Ser Ser Cys Ser Gln Thr Pro Ser Arg Ala Ile Pro
1 5 10 15

Ala Thr Arg Arg Val Val Leu Gly Asp Gly Val Gln Leu Pro Pro Gly
20 25 30

Asp Tyr Ser Thr Thr Pro Gly Gly Thr Leu Phe Ser Thr Thr Pro Gly
35 40 45

Gly Thr Arg Ile Ile Tyr Asp Arg Lys Phe Leu Met Glu Cys Arg Asn
50 55 60

Ser Pro Val Thr Lys Thr Pro Pro Arg Asp Leu Pro Thr Ile Pro Gly
65 70 75 80

Val Thr Ser Pro Ser Ser Asp Glu Pro Pro Met Glu Ala Ser Gln Ser
85 90 95

His Leu Arg Asn Ser Pro Glu Asp Lys Arg Ala Gly Gly Glu Glu Ser
100 105 110

Gln Phe Glu Met Asp Ile
115

<210> SEQ ID NO 5
<211> LENGTH: 480
<212> TYPE: PRT
<213> ORGANISM: Homo sapiens

<400> SEQUENCE: 5

Met Ser Asp Val Ala Ile Val Lys Glu Gly Trp Leu His Lys Arg Gly
1 5 10 15

Glu Tyr Ile Lys Thr Trp Arg Pro Arg Tyr Phe Leu Leu Lys Asn Asp
20 25 30

Gly Thr Phe Ile Gly Tyr Lys Glu Arg Pro Gln Asp Val Asp Gln Arg
35 40 45

Glu Ala Pro Leu Asn Asn Phe Ser Val Ala Gln Cys Gln Leu Met Lys
50 55 60

Thr Glu Arg Pro Arg Pro Asn Thr Phe Ile Ile Arg Cys Leu Gln Trp
65 70 75 80

Thr Thr Val Ile Glu Arg Thr Phe His Val Glu Thr Pro Glu Glu Arg
85 90 95

Glu Glu Trp Thr Thr Ala Ile Gln Thr Val Ala Asp Gly Leu Lys Lys
100 105 110

Gln Glu Glu Glu Glu Met Asp Phe Arg Ser Gly Ser Pro Ser Asp Asn
115 120 125

-continued

```
Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
        435                 440                 445

Ile Thr Pro Pro Asp Gln Asp Asp Ser Met Glu Cys Val Asp Ser Glu
    450                 455                 460

Arg Arg Pro His Phe Pro Gln Phe Ser Tyr Ser Ala Ser Gly Thr Ala
465                 470                 475                 480
```

C40-, C28-, AND C-32-LINKED RAPAMYCIN ANALOGS AS mTOR INHIBITORS

CROSS REFERENCE TO RELATED APPLICATIONS

This application is a continuation of U.S. application Ser. No. 17/083,172, filed Oct. 28, 2020, which is a continuation of U.S. Application Ser. No. 16/398,011, filed Apr. 29, 2019, which claims the benefit of U.S. Provisional Application No. 62/665,435, filed May 1, 2018 and U.S. Provisional Application No. 62/752,874, filed Oct. 30, 2018 and U.S. Provisional Application No. 62/836,036, filed Apr. 18, 2019, the contents of which are incorporated herein by reference in their entireties.

REFERENCE TO A SEQUENCE LISTING

The Sequence Listing associated with this application is provided in text format in lieu of a paper copy, and is hereby incorporated by reference into the specification. The name of the text file containing the Sequence Listing is REME 008 06US SeqList ST25.txt. The text file is about 40 Kilo Bytes, was created on Apr. 29, 2022, and is being submitted electronically via EFS-Web.

FIELD OF THE DISCLOSURE

The present disclosure relates to mTOR inhibitors. Specifically, the embodiments are directed to compounds and compositions inhibiting mTOR, methods of treating diseases mediated by mTOR, and methods of synthesizing these compounds.

BACKGROUND OF THE DISCLOSURE

The mammalian target of rapamycin (mTOR) is a serine-threonine kinase related to the lipid kinases of the phosphoinositide 3-kinase (PI3K) family. mTOR exists in two complexes, mTORC1 and mTORC2, which are differentially regulated, have distinct substrate specificities, and are differentially sensitive to rapamycin. mTORC1 integrates signals from growth factor receptors with cellular nutritional status and controls the level of cap-dependent mRNA translation by modulating the activity of key translational components such as the cap-binding protein and oncogene eIF4E.

mTOR signaling has been deciphered in increasing detail. The differing pharmacology of inhibitors of mTOR has been particularly informative. The first reported inhibitor of mTOR, Rapamycin is now understood to be an incomplete inhibitor of mTORC1. Rapamycin is a selective mTORC1 inhibitor through the binding to the FK506 Rapamycin Binding (FRB) domain of mTOR kinase with the aid of FK506 binding protein 12 (FKBP12). The FRB domain of mTOR is accessible in the mTORC1 complex, but less so in the mTORC2 complex. Interestingly, the potency of inhibitory activities against downstream substrates of mTORC1 by the treatment of Rapamycin is known to be diverse among the mTORC1 substrates. For example, Rapamycin strongly inhibits phosphorylation of the mTORC1 substrate S6K and, indirectly, phosphorylation of the downstream ribosomal protein S6 which control ribosomal biogenesis. On the other hand, Rapamycin shows only partial inhibitory activity against phosphorylation of 4E-BP1, a major regulator of eIF4E which controls the initiation of CAP-dependent translation. As a result, more complete inhibitors of mTORC1 signaling are of interest.

A second class of “ATP-site” inhibitors of mTOR kinase were reported. This class of mTOR inhibitors will be referred to as TORi (ATP site TOR inhibitor). The molecules compete with ATP, the substrate for the kinase reaction, in the active site of the mTOR kinase (and are therefore also mTOR active site inhibitors). As a result, these molecules inhibit downstream phosphorylation of a broader range of substrates.

Although mTOR inhibition may have the effect of blocking 4E-BP1 phosphorylation, these agents may also inhibit mTORC2, which leads to a block of Akt activation due to inhibition of phosphorylation of Akt S473.

Disclosed herein, inter alia, are mTOR inhibitors. In some embodiments, compounds disclosed herein are more selective inhibitors of mTORC1 versus mTORC2. In some embodiments, compounds disclosed herein are more selective inhibitors of mTORC2 versus mTORC1. In some embodiments, compounds disclosed herein exhibit no selectivity difference between mTORC1 and mTORC2.

SUMMARY OF THE DISCLOSURE

The present disclosure relates to compounds capable of inhibiting the activity of mTOR. The present disclosure further provides a process for the preparation of compounds of the present disclosure, pharmaceutical preparations comprising such compounds and methods of using such compounds and compositions in the management of diseases or disorders mediated by mTOR.

The present disclosure provides a compound of Formula Ic:

(Ic)

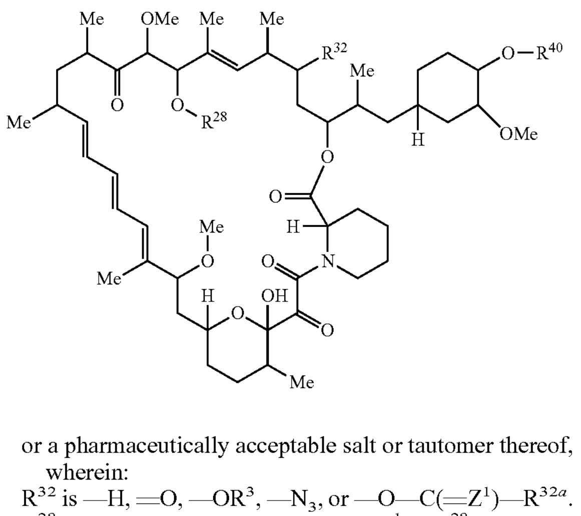

or a pharmaceutically acceptable salt or tautomer thereof, wherein:

$R^{32}$ is —H, =O, —$OR^3$, —$N_3$, or —O—C(=$Z^1$)—$R^{32a}$.

$R^{28}$ is —H, ($C_1$-$C_6$)alkyl, or —C(=$Z^1$)—$R^{28a}$.

$R^{40}$ is —H or —C(=$Z^1$)—$R^{40a}$;

wherein when $R^{28}$ and $R^{40}$ are H, then $R^{32}$ is not =O;

each $Z^1$ is independently O or S;

$R^{28a}$, $R^{32a}$, and $R^{40a}$ are independently -$A^1$-$L^1$-$A^2$-B; -$A^1$-$A^2$-B; -$L^2$-$A^1$-$L^1$-$A^2$-$L^3$-B; —O—($C_1$-$C_6$)alkyl; or —O—($C_6$-$C_{10}$)aryl; wherein the aryl of —O—($C_6$-$C_{10}$)aryl is unsubstituted or substituted with 1-5 substituents selected from —$NO_2$ and halogen;

$A^1$ and $A^2$ are independently absent or are independently selected from

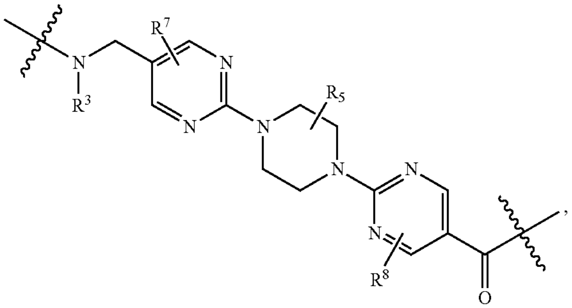,
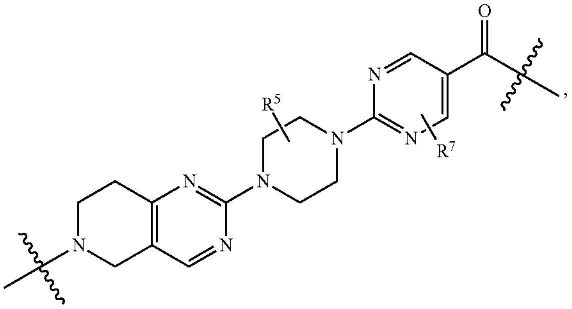,
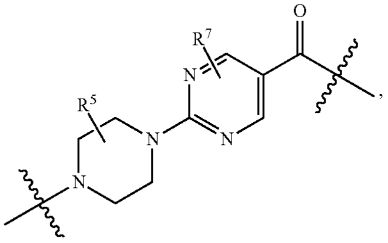,
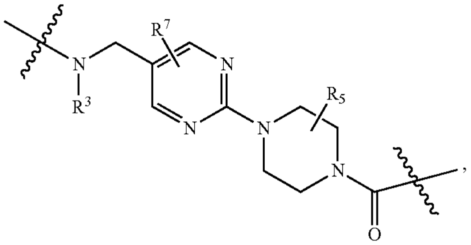,
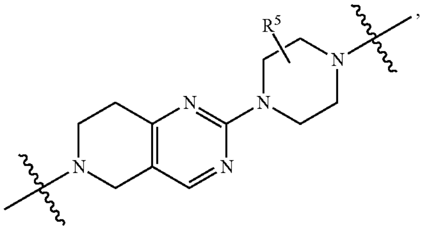,
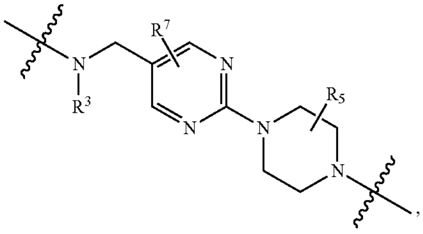,
-continued
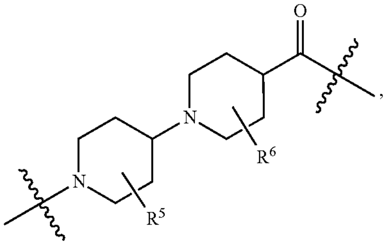,
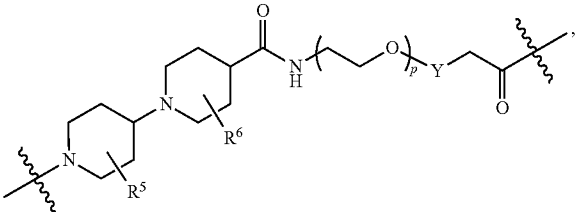,
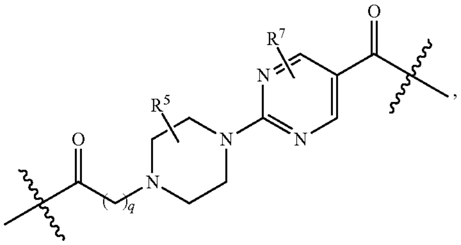,
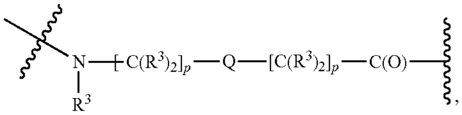,
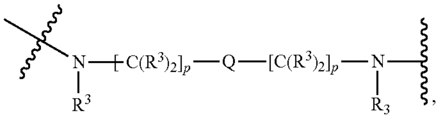,
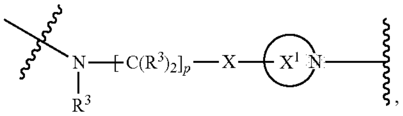,
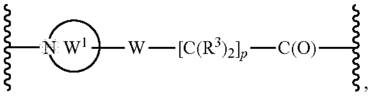,
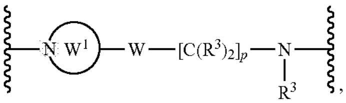,
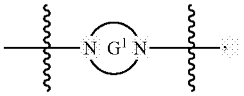,
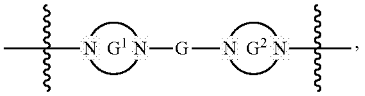,
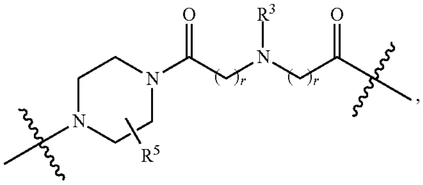, -continued

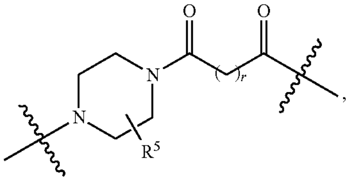,

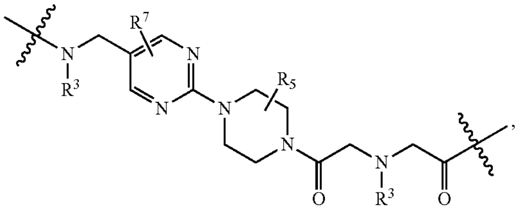,

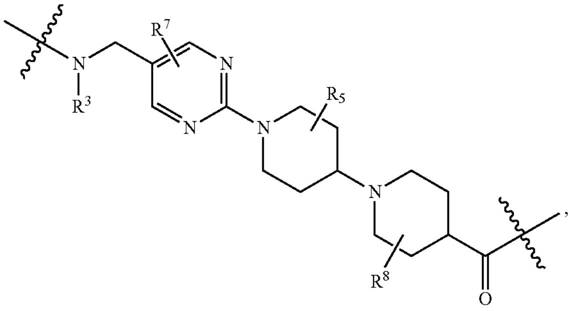,

-continued and 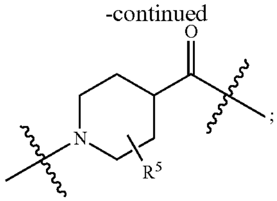;

wherein the bond on the left side of $A^1$, as drawn, is bound to —C(=$Z^1$)— or $L^2$; and wherein the bond on the right side of the $A^2$ moiety, as drawn, is bound to B or $L^3$;

each Q is independently 1 to 3 rings selected from arylene, cycloalkylene, heteroarylene, and heterocyclylene;

each X is independently absent or 1 to 2 rings selected from arylene, cycloalkylene, heteroarylene, and heterocyclylene;

each $X^1$ is independently a heteroarylene or heterocyclylene ring;

each W is independently absent or 1 to 2 rings selected from arylene, cycloalkylene, heteroarylene, and heterocyclylene;

each $W^1$ is independently a heteroarylene or heterocyclylene ring;

each G is independently absent or a ring selected from arylene, cycloalkylene, heteroarylene, and heterocyclylene;

each $G^1$ and $G^2$ are independently heteroarylene or heterocyclylene ring;

each $L^1$ is independently selected from

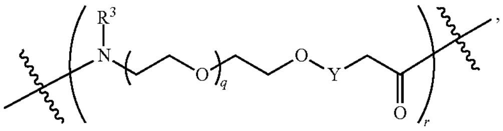,

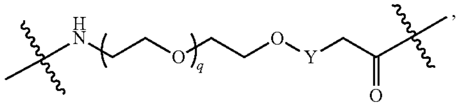,

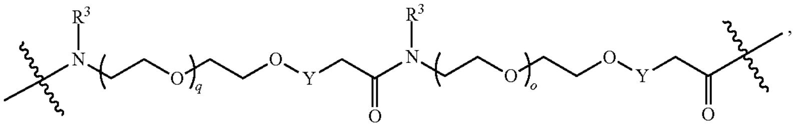,

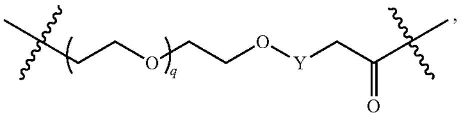,

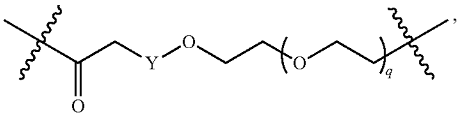,

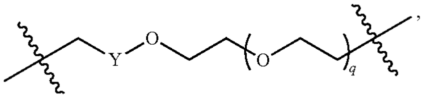,

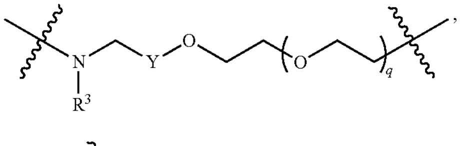,

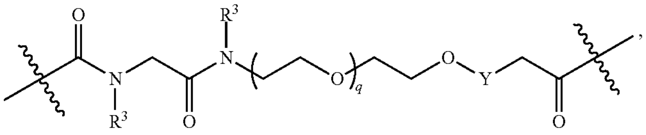,

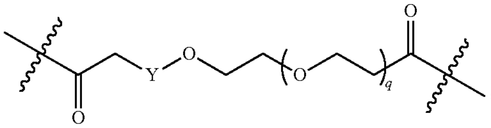, and

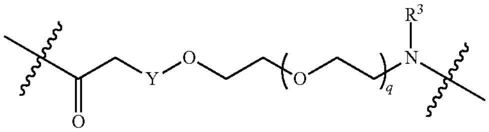;

-continued
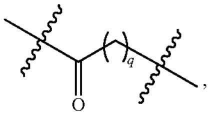
and
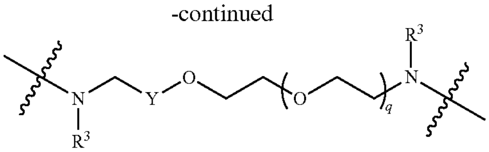
;
$L^2$ and $L^3$ are independently absent or are independently selected from
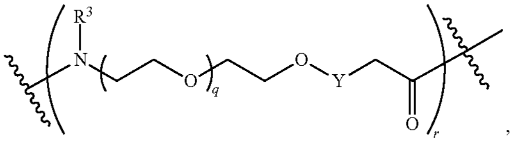
,
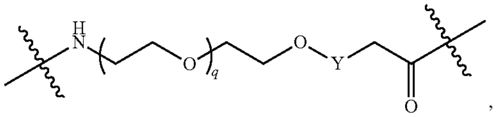
,
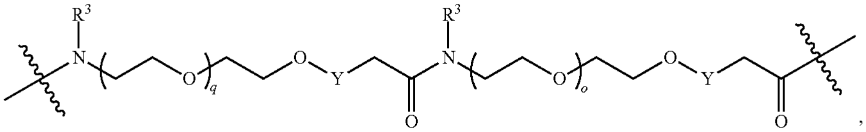
,
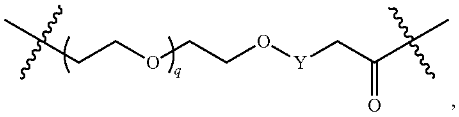
,
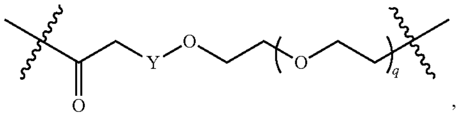
,
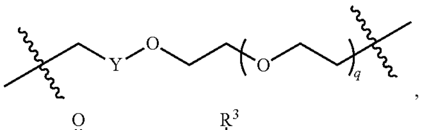
,
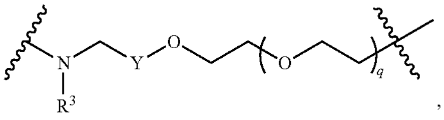
,
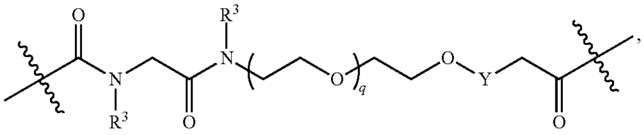
,
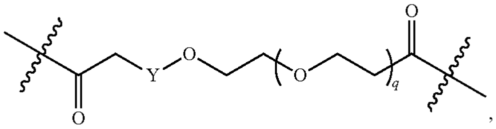
, and
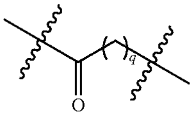
;
each B is independently selected from
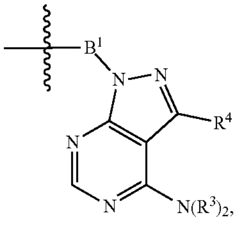
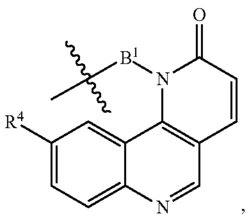
,
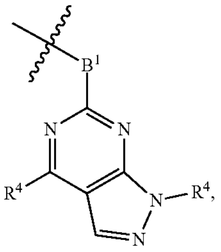
-continued
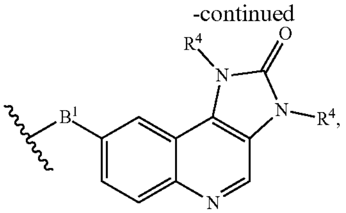
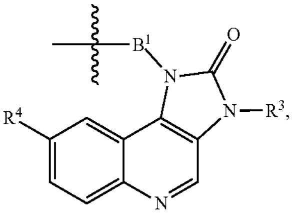
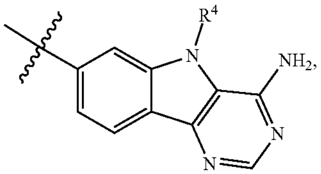

-continued
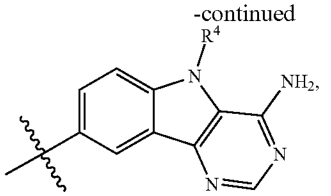
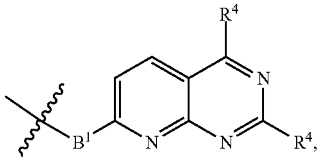
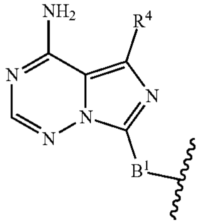
and
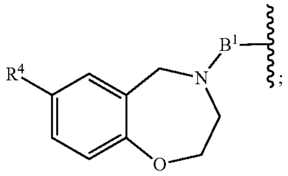
each $B^1$ is independently selected from
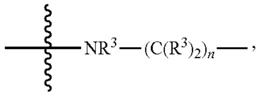
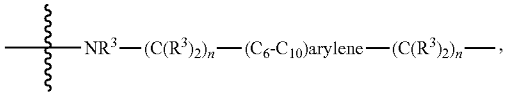
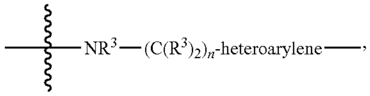
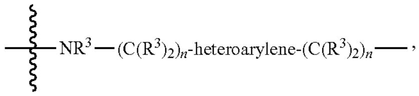
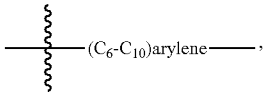
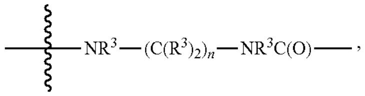
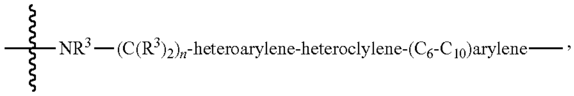
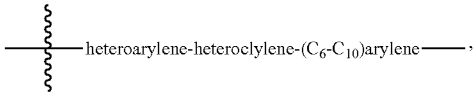
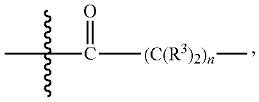
-continued
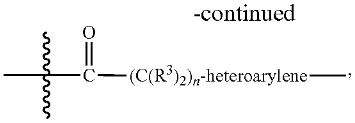
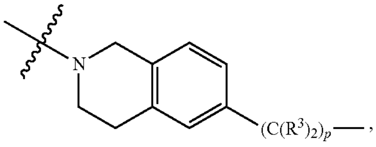
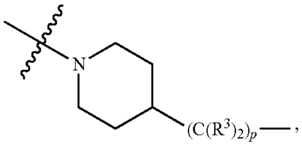
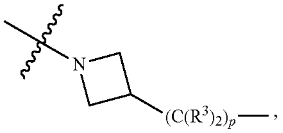
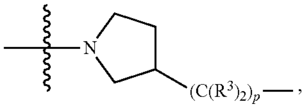
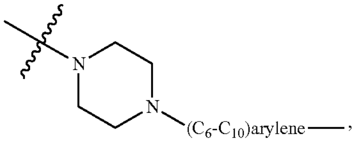
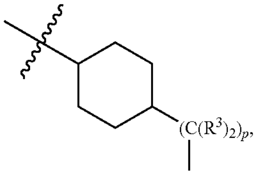
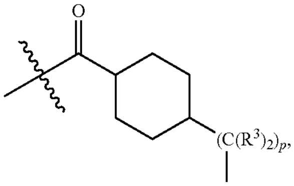
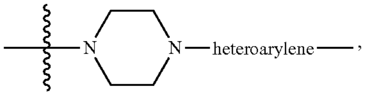
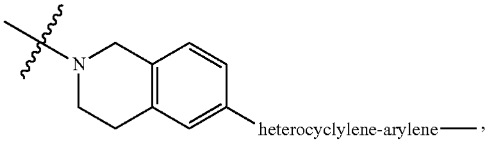
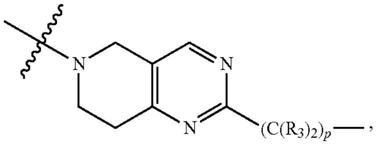
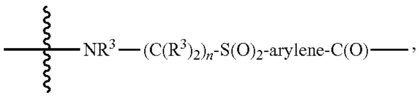
and
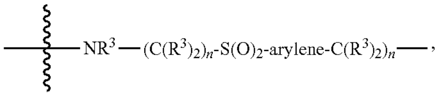

-continued wherein the  bond on the left side of $B^1$, as drawn, is bound to $A^2$, $L^3$, or $L^1$; and wherein the heteroarylene, heterocyclylene, and arylene are each independently optionally substituted with alkyl, hydroxyalkyl, haloalkyl, alkoxy, halogen, or hydroxyl;

each $R^3$ is independently H or $(C_1\text{-}C_6)$alkyl;

each $R^4$ is independently H, $(C_1\text{-}C_6)$alkyl, halogen, 5-12 membered heteroaryl, 5-12 membered heterocyclyl, $(C_6\text{-}C_{10})$aryl, wherein the heteroaryl, heterocyclyl, and aryl are each independently optionally substituted with —$N(R^3)_2$, —$OR^3$, halogen, $(C_1\text{-}C_6)$alkyl, —$(C_1\text{-}C_6)$alkylene-heteroaryl, —$(C_1\text{-}C_6)$alkylene-CN, —C(O)$NR^3$-heteroaryl, or —C(O)$NR^3$-heterocyclyl;

each $R^5$ is independently H, $(C_1\text{-}C_6)$alkyl, —C(O)$OR^3$, or —$N(R^3)_2$, wherein the alkyl of $(C_1\text{-}C_6)$alkyl is each independently optionally substituted with —$N(R^3)_2$ or —$OR^3$;

each $R^6$ is independently H, $(C_1\text{-}C_6)$alkyl, —C(O)$OR^3$, or —$N(R^3)_2$, wherein the alkyl of $(C_1\text{-}C_6)$alkyl is each independently optionally substituted with —$N(R^3)_2$ or —$OR^3$;

each $R^7$ is independently H, $(C_1\text{-}C_6)$alkyl, —C(O)$OR^3$, or —$N(R^3)_2$, wherein the alkyl of $(C_1\text{-}C_6)$alkyl is each independently optionally substituted with —$N(R^3)_2$ or —$OR^3$;

each $R^8$ is independently H, $(C_1\text{-}C_6)$alkyl, —C(O)$OR^3$, or —$N(R^3)_2$, wherein the alkyl of $(C_1\text{-}C_6)$alkyl is each independently optionally substituted with —$N(R^3)_2$ or —$OR^3$;

each Y is independently —$C(R^3)_2$ or a bond;

each n is independently an integer from one to 12;

each o is independently an integer from zero to 30;

each p is independently an integer from zero to 12;

each q is independently an integer from zero to 30; and each r is independently an integer from one to 6.

The present disclosure provides a compound of Formula Ia:

(Ia)

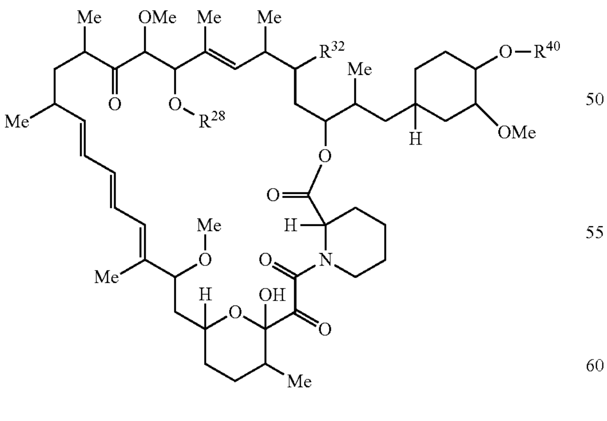

or a pharmaceutically acceptable salt or tautomer thereof, wherein:

$R^{32}$ is —H, =O, —$OR^3$, —$N_3$, or —O—C(=$Z^1$)—$R^{32a}$.

$R^{28}$ is —H, $(C_1\text{-}C_6)$alkyl, or —C(=$Z^1$)—$R^{28a}$.

$R^{40}$ is —H or —C(=$Z^1$)—$R^{41a}$;

wherein when $R^{28}$ and $R^{40}$ are H, then $R^{32}$ is not =O;

each $Z^1$ is independently O or S;

$R^{28a}$, $R^{32a}$, and $R^{40a}$ are independently -$A^1$-$L^1$-$A^2$-B; -$A^1$-$A^2$-B; -$L^2$-$A^1$-$L^1$-$A^2$-$L^3$-B; —O—$(C_1\text{-}C_6)$alkyl; or —O—$(C_6\text{-}C_{10})$aryl; wherein the aryl of —O—$(C_6\text{-}C_{10})$aryl is unsubstituted or substituted with 1-5 substituents selected from —$NO_2$ and halogen;

$A^1$ and $A^2$ are independently absent or are independently selected from

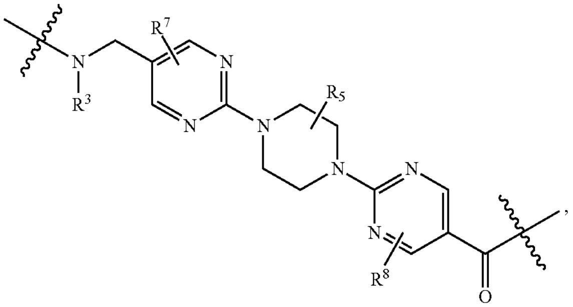

,

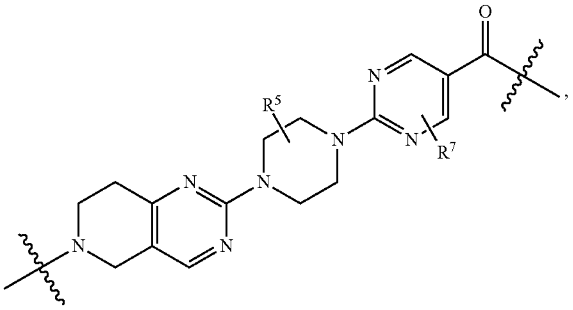

,

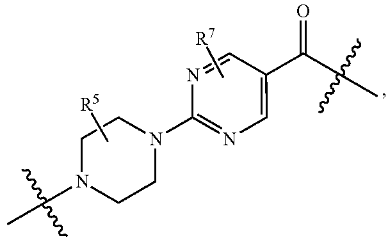

,

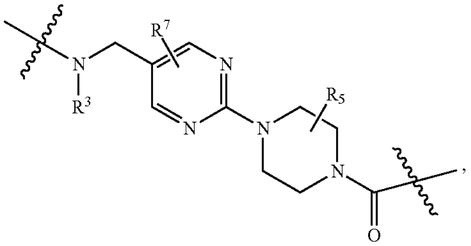

,

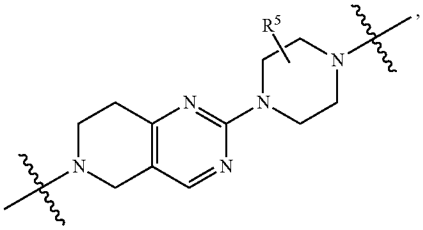

,

-continued

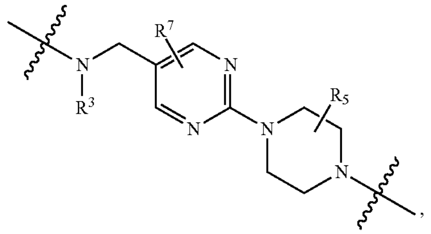

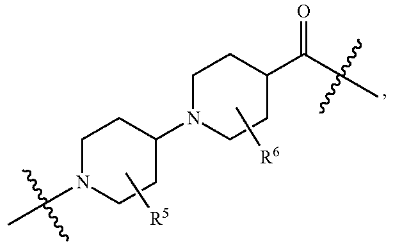

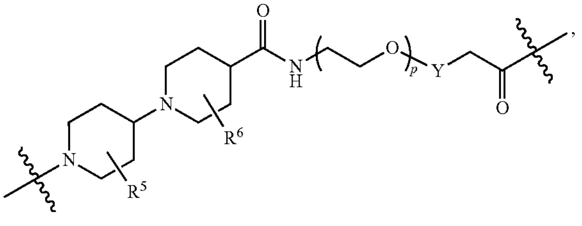

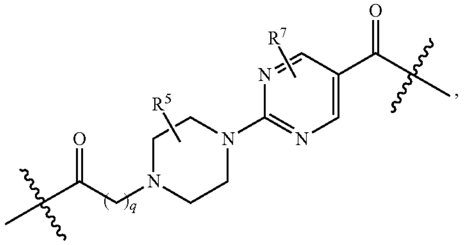

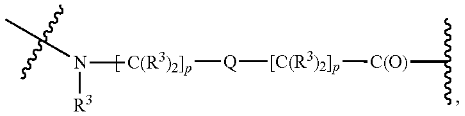

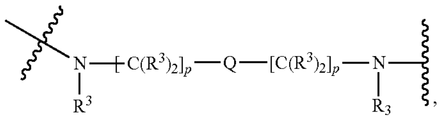

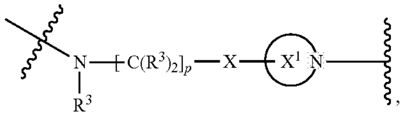

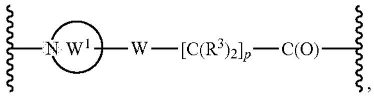

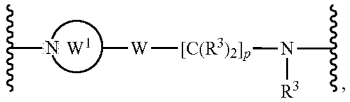

-continued

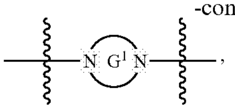

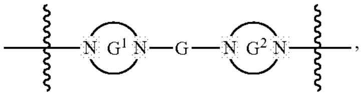

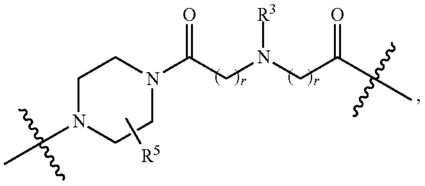

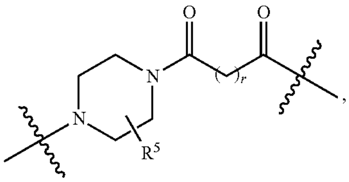

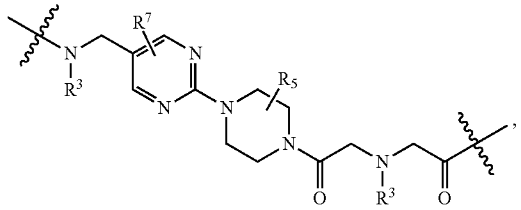

and

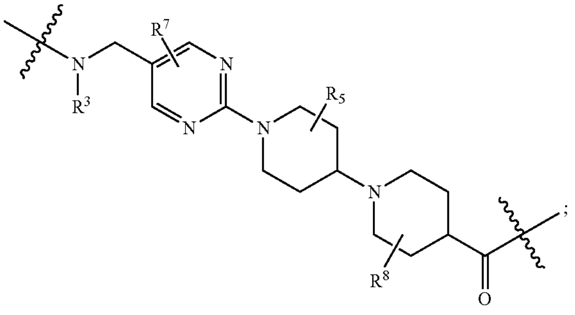

wherein the bond on the left side of $A^1$, as drawn, is bound to —C(=$Z^1$)— or $L^2$; and wherein the bond on the right side of the $A^2$ moiety, as drawn, is bound to B or $L^3$;

each Q is independently 1 to 3 rings selected from arylene, cycloalkylene, heteroarylene, and heterocyclylene;

each X is independently absent or 1 to 2 rings selected from arylene, cycloalkylene, heteroarylene, and heterocyclylene;

each $X^1$ independently is a heteroarylene or heterocyclylene ring;

each W is independently absent or 1 to 2 rings selected from arylene, cycloalkylene, heteroarylene, and heterocyclylene;

each $W^1$ independently is a heteroarylene or heterocyclylene ring;

each G is independently absent or a ring selected from arylene, cycloalkylene, heteroarylene, and heterocyclylene;

each $G^1$ and $G^2$ are independently heteroarylene or heterocyclylene ring;

each $L^1$ is independently selected from
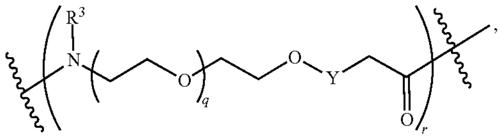,
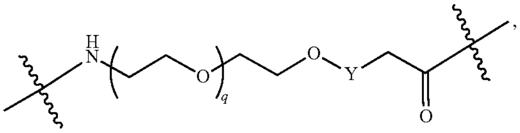,
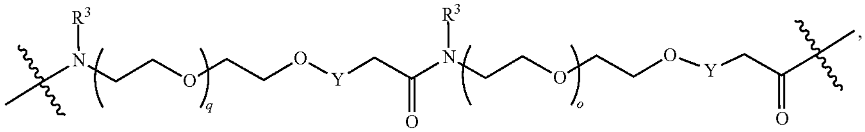,
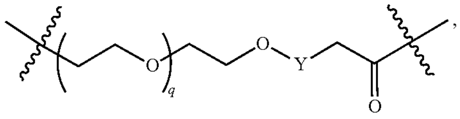,
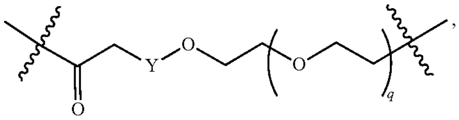,
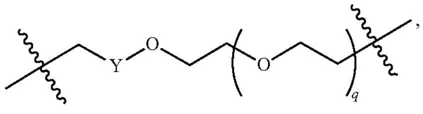,
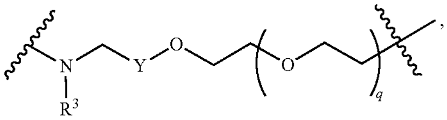,
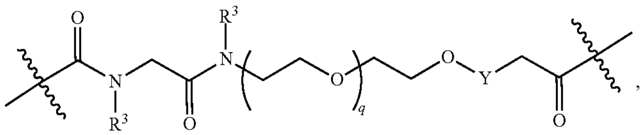,
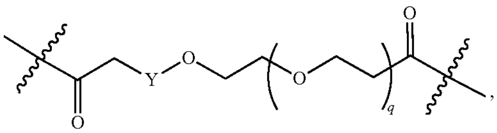,
and 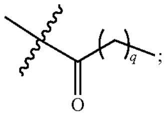;
$L^2$ and $L^3$ are independently absent or are independently selected from
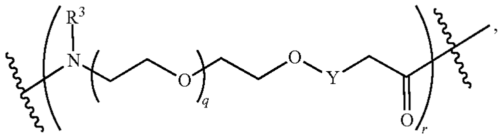,
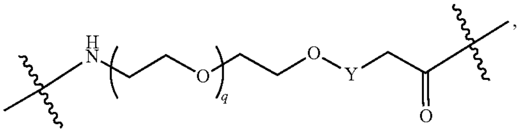,
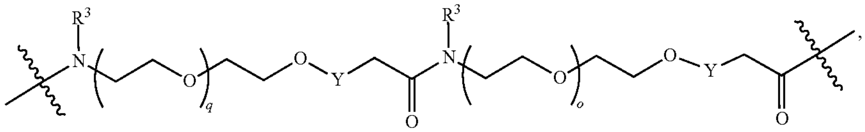,
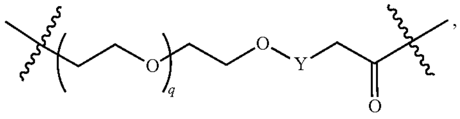,
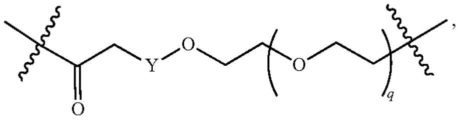,
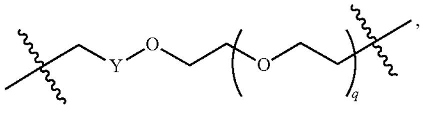,
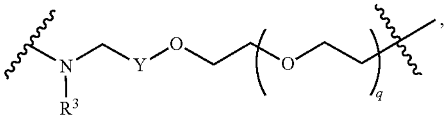,
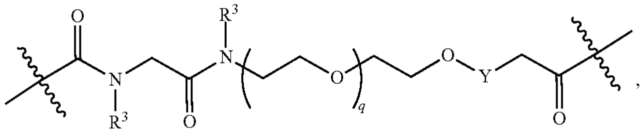,
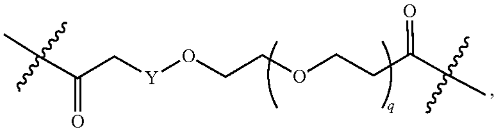,
and 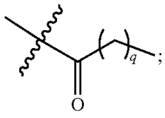;

each B is independently selected from
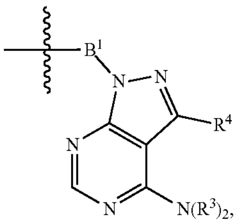
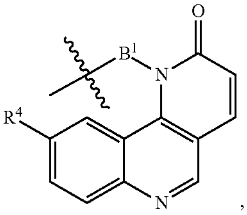
,
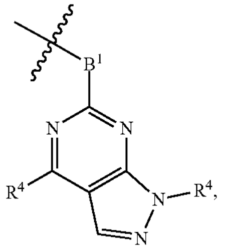
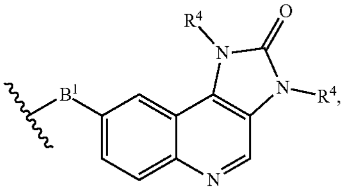
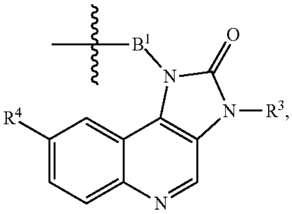
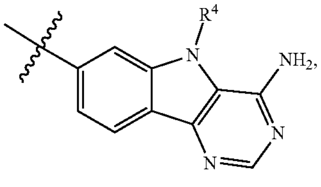
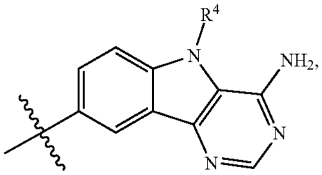
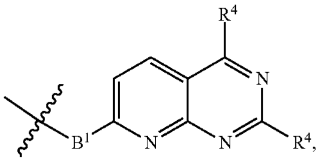
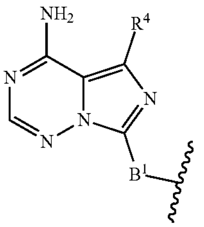
and
-continued
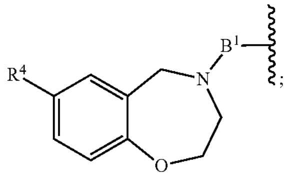
each $B^1$ is independently selected from
$-NR^3-(C(R^3)_2)_n-$,
$-NR^3-(C(R^3)_2)_n-(C_6-C_{10})arylene-(C(R^3)_2)_n-$,
$-NR^3-(C(R^3)_2)_n$-heteroarylene-,
$-(C_6-C_{10})arylene$, $-NR^3-(C(R^3)_2)_n-NR^3C(O)-$,
$-NR^3-(C(R^3)_2)_n$-heteroarylene-heterocyclylene-$(C_6-C_{10})$arylene-,
-heteroarylene-heterocyclylene-$(C_6-C_{10})$arylene-,
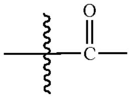
$-(C(R^3)_2)_p-$,
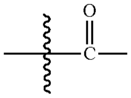
$-(C(R^3)_2)_p$-heteroarylene-,
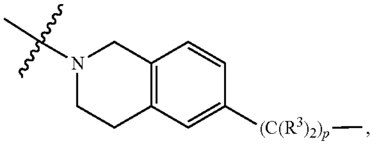
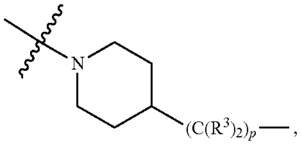
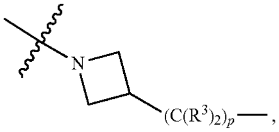
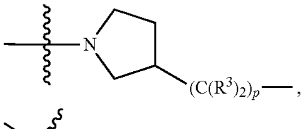
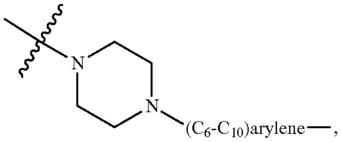

-continued

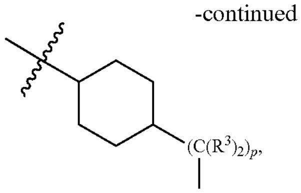

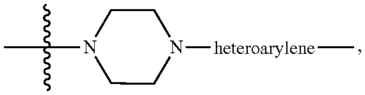,

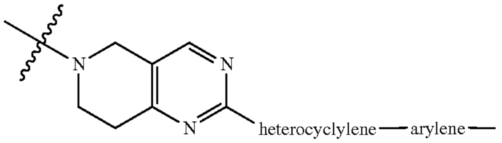

and 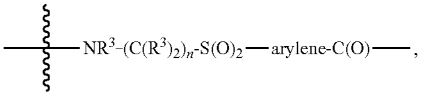, wherein the 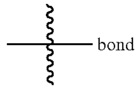 bond on the left side of $B^1$, as drawn, is bound to $A^2$, L, or L; and wherein the heteroarylene, heterocyclylene, and arylene are each independently optionally substituted with alkyl, hydroxyalkyl, haloalkyl, alkoxy, halogen, or hydroxyl;

each $R^3$ is independently H or $(C_1\text{-}C_6)$alkyl;

each $R^4$ is independently H, $(C_1\text{-}C_6)$alkyl, halogen, 5-12 membered heteroaryl, 5-12 membered heterocyclyl, $(C_6\text{-}C_{10})$aryl, wherein the heteroaryl, heterocyclyl, and aryl are each independently optionally substituted with $—N(R^3)_2$, $—OR^3$, halogen, $(C_1\text{-}C_6)$alkyl, $—(C_1\text{-}C_6)$alkylene-heteroaryl, $—(C_1\text{-}C_6)$alkylene-CN, $—C(O)NR^3$-heteroaryl, or $—C(O)NR^3$-heterocyclyl;

each $R^5$ is independently H, $(C_1\text{-}C_6)$alkyl, $—C(O)OR^3$, or $—N(R^3)_2$, wherein the alkyl of $(C_1\text{-}C_6)$alkyl is each independently optionally substituted with $—N(R^3)_2$ or $—OR^3$;

each $R^6$ is independently H, $(C_1\text{-}C_6)$alkyl, $—C(O)OR^3$, or $—N(R^3)_2$, wherein the alkyl of $(C_1\text{-}C_6)$alkyl is each independently optionally substituted with $—N(R^3)_2$ or $—OR^3$;

each $R^7$ is independently H, $(C_1\text{-}C_6)$alkyl, $—C(O)OR^3$, or $—N(R^3)_2$, wherein the alkyl of $(C_1\text{-}C_6)$alkyl is each independently optionally substituted with $—N(R^3)_2$ or $—OR^3$;

each $R^8$ is independently H, $(C_1\text{-}C_6)$alkyl, $—C(O)OR^3$, or $—N(R^3)_2$, wherein the alkyl of $(C_1\text{-}C_6)$alkyl is each independently optionally substituted with $—N(R^3)_2$ or $—OR^3$;

each Y is independently $—C(R^3)_2$ or a bond;

each n is independently an integer from one to 12;

each o is independently an integer from zero to 30;

each p is independently an integer from zero to 12;

each q is independently an integer from zero to 30; and each r is independently an integer from one to 6.

The present disclosure provides a compound of Formula I:

(I)

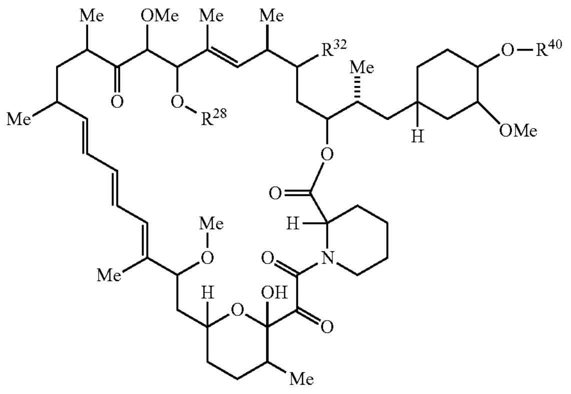

or pharmaceutically acceptable salt or tautomer thereof, wherein:

$R^{32}$ is —H, =O, or $—OR^3$;

$R^{28}$ is —H or $—C(=Z^1)—R^{28a}$;

$R^{40}$ is —H or $—C(=Z^1)—R^{41a}$;

wherein at least one of $R^{28}$ and $R^{40}$ is not H;

$Z^1$ is independently O or S;

$R^{28a}$ and $R^{40a}$ are independently $-A^1\text{-}L^1\text{-}A^2\text{-}B$; $-A^1\text{-}A^2\text{-}B$; $-L^2\text{-}A^1\text{-}L^1\text{-}A^2\text{-}L^3\text{-}B$; $—O—(C_1\text{-}C_6)$alkyl; or $—O—(C_6\text{-}C_{10})$aryl; wherein the aryl of $—O—(C_6\text{-}C_{10})$aryl is unsubstituted or substituted with 1-5 substituents selected from $—NO_2$ and halogen;

$A^1$ and $A^2$ are independently absent or are independently selected from

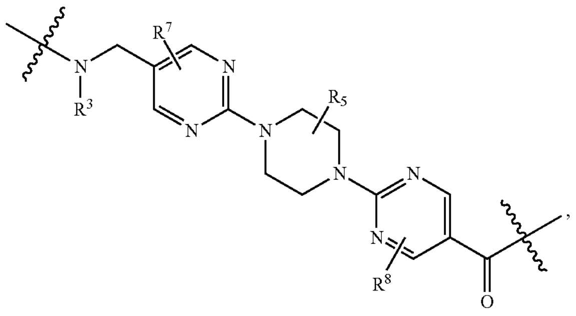,

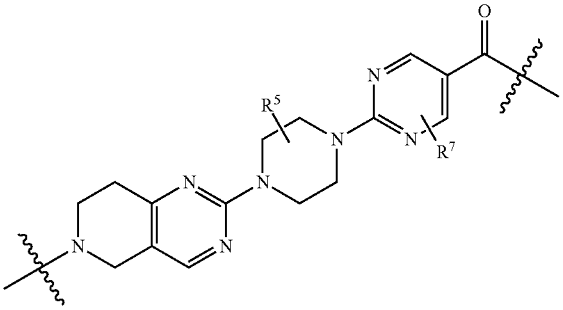,

-continued
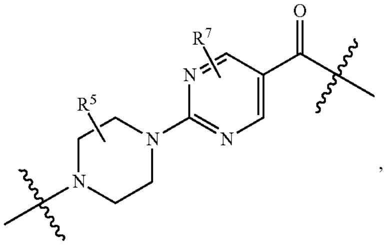,
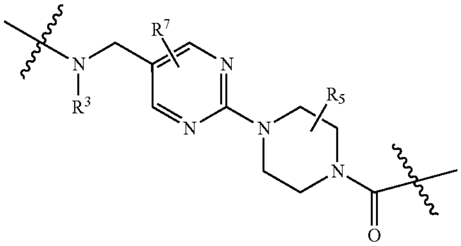,
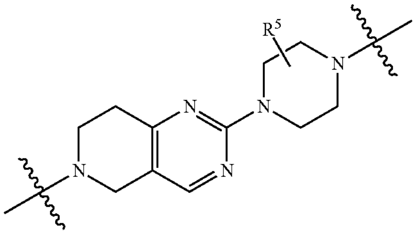,
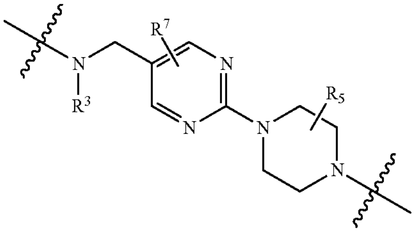,
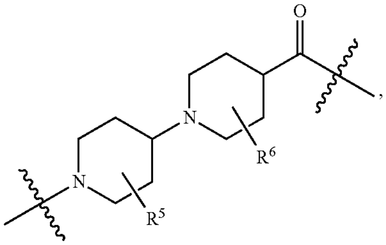,
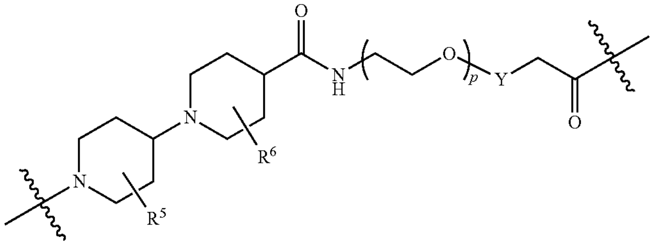,
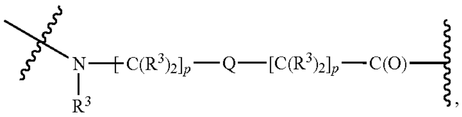,
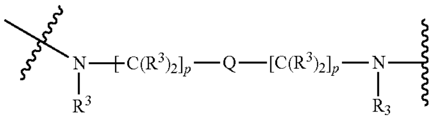,
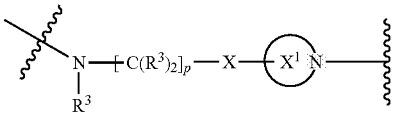,
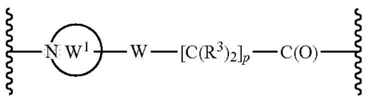,
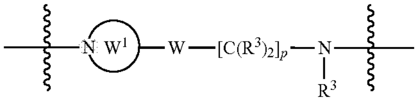,
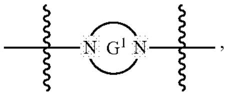,
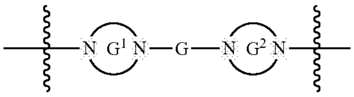,
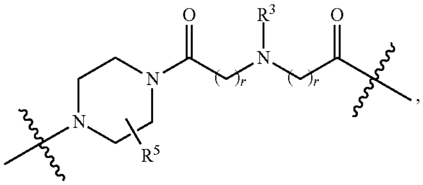,
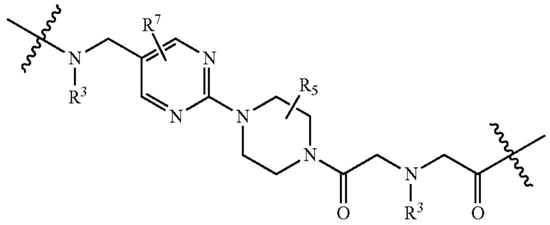,
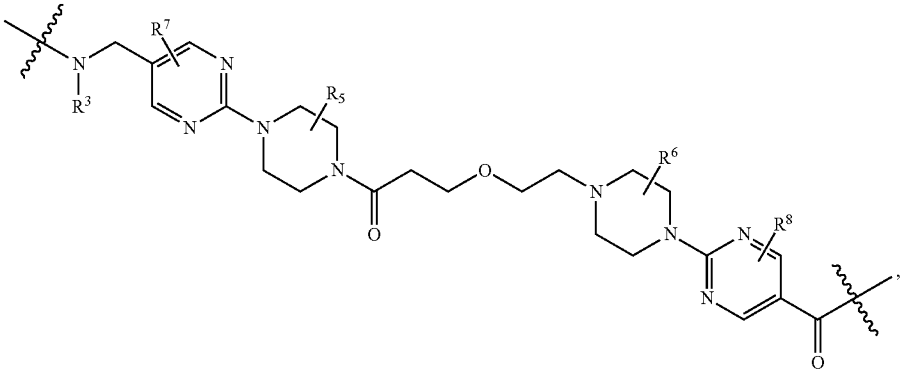, -continued

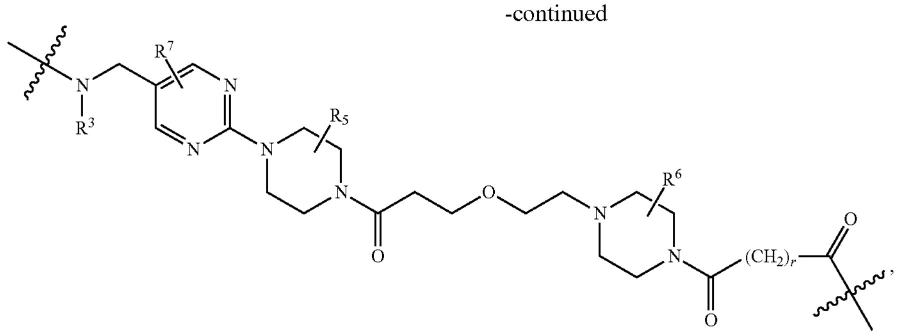

,

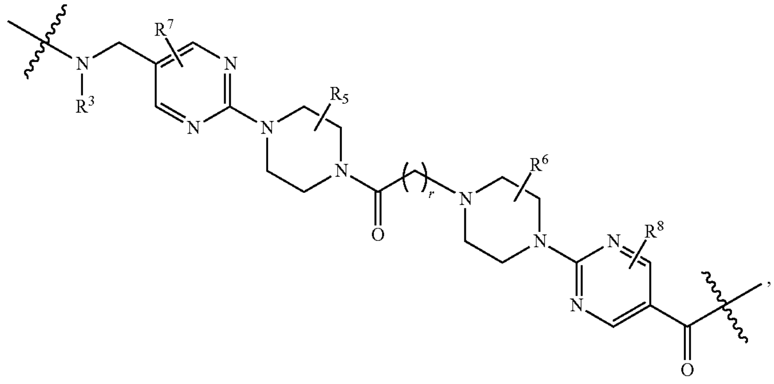

, and

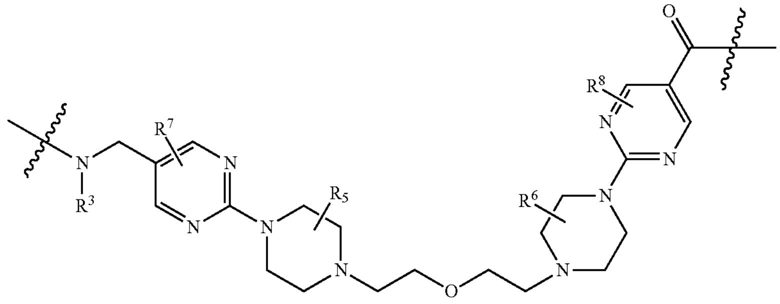

;

wherein the bond on the left side of $A^1$, as drawn, is bound to —C(=$Z^1$)— or $L^2$; and wherein the bond on the right side of the $A^2$ moiety, as drawn, is bound to B or $L^3$;

each Q is independently 1 to 3 rings selected from arylene, cycloalkylene, heteroarylene, and heterocyclylene;

each X is independently absent or 1 to 2 rings selected from arylene, cycloalkylene, heteroarylene, and heterocyclylene;

each $X^1$ is independently a heteroarylene or heterocyclylene ring;

each W is independently absent or 1 to 2 rings selected from arylene, cycloalkylene, heteroarylene, and heterocyclylene;

each $W^1$ independently is a heteroarylene or heterocyclylene ring;

each G is independently absent or a ring selected from arylene, cycloalkylene, heteroarylene, and heterocyclylene;

each $G^1$ and $G^2$ are independently heteroarylene or heterocyclylene ring;

each $L^1$ is independently selected from

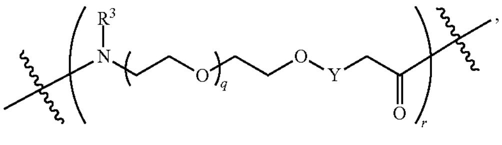

,

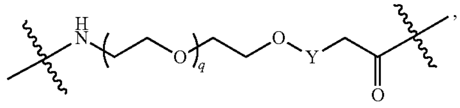

,

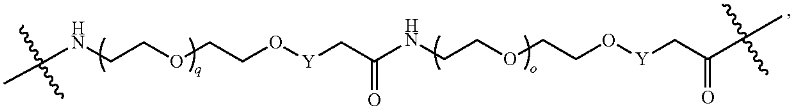

,

-continued
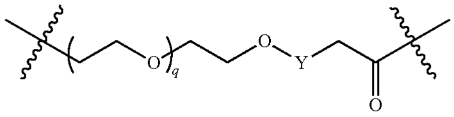,
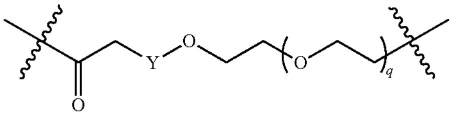,
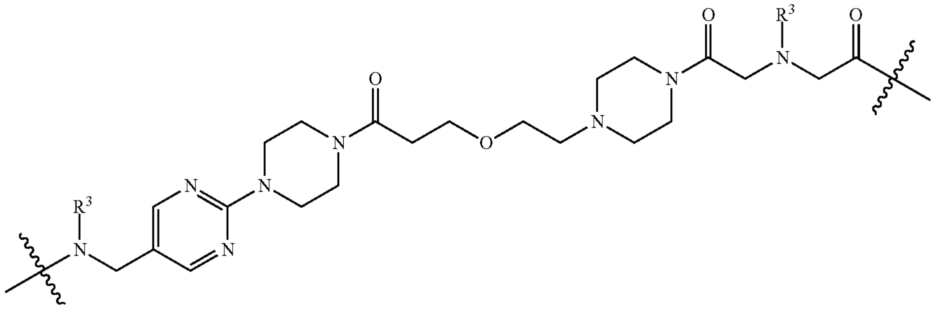,
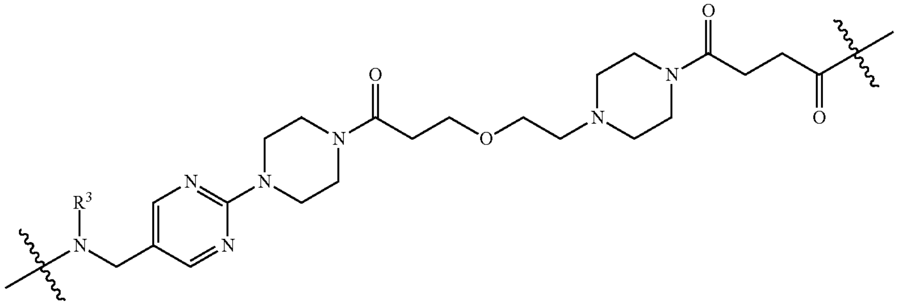,
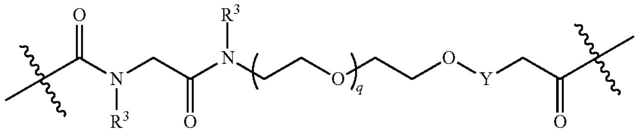,
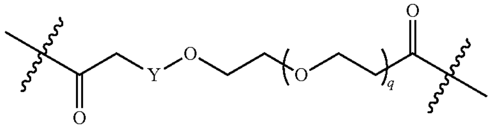, and 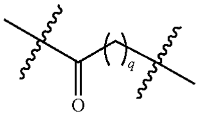;
$L^2$ and $L^3$ are independently absent or are independently selected from
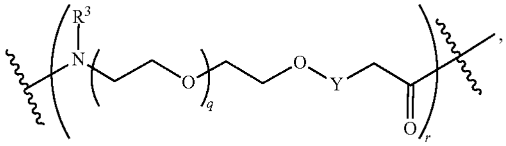,
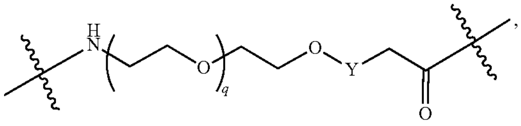,
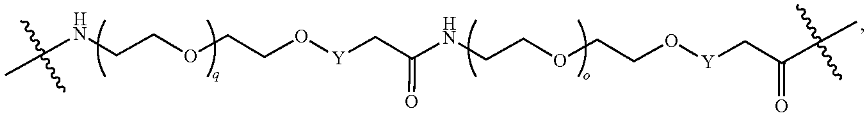,
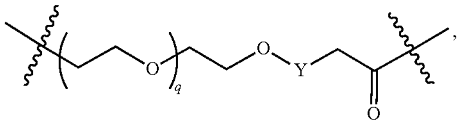,
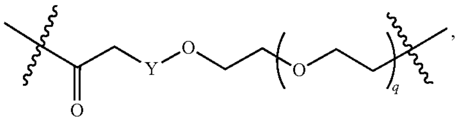, -continued
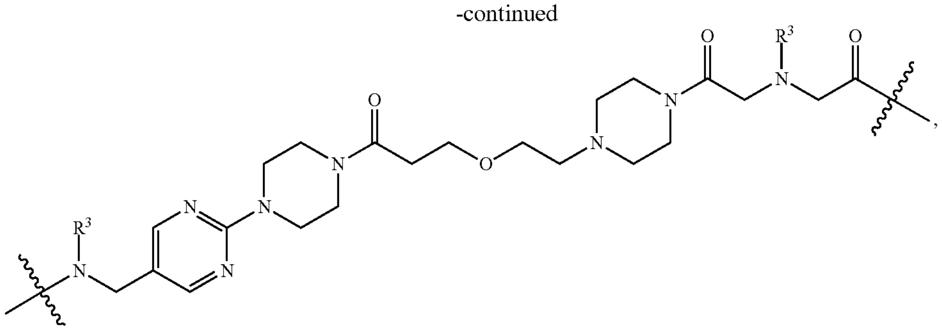
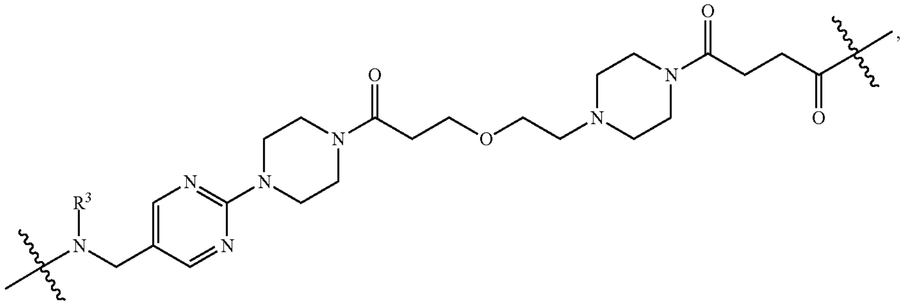
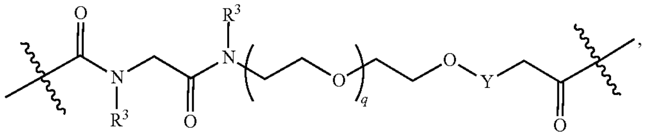
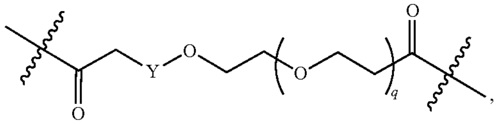
and
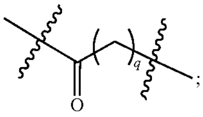
each B is independently selected from
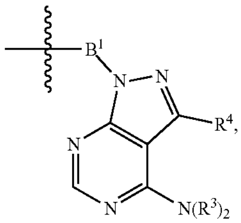
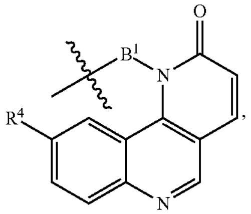
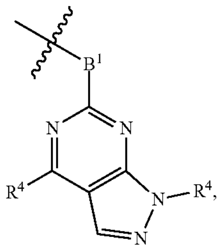
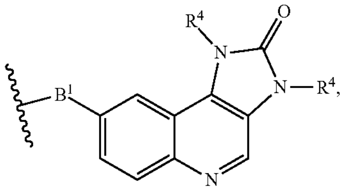
-continued
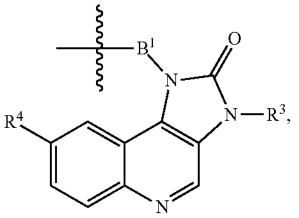
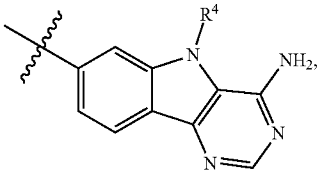
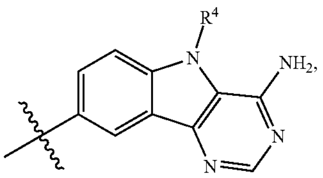
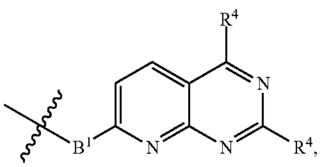

-continued

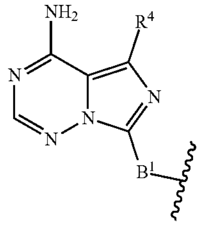

and

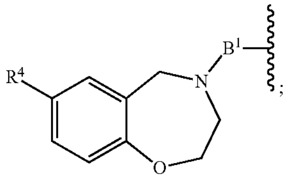

each $B^1$ is independently selected from

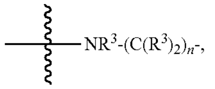

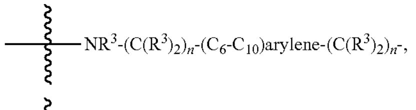

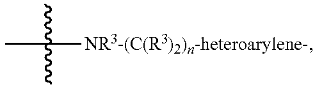

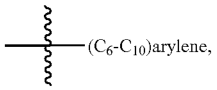

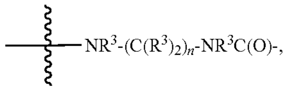

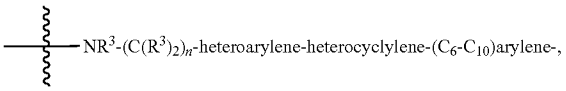

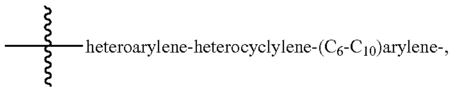

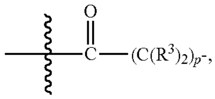

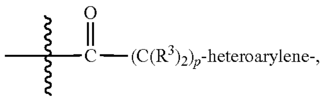

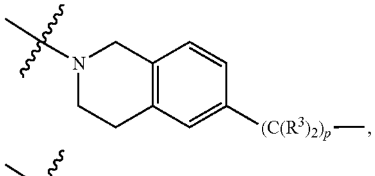

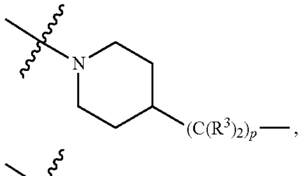

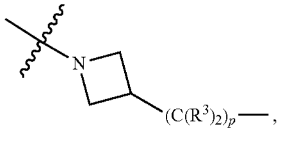

-continued

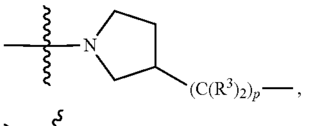

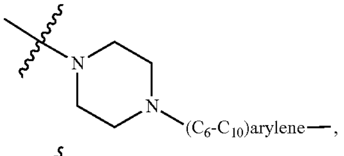

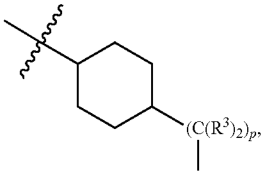

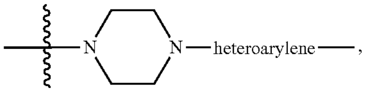

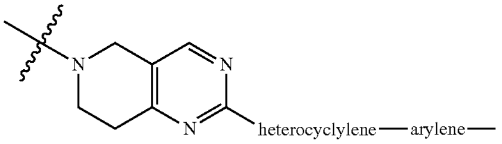

and 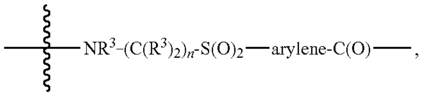

wherein the 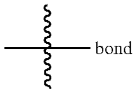 bond on the left side of $B^1$, as drawn, is bound to $A^2$, $L^3$, or $L^1$; and wherein the heteroarylene, heterocyclylene, and arylene are each independently optionally substituted with alkyl, hydroxyalkyl, haloalkyl, alkoxy, halogen, or hydroxyl;

each $R^3$ is independently H or $(C_1$-$C_6)$alkyl;

each $R^4$ is independently H, $(C_1$-$C_6)$alkyl, halogen, 5-12 membered heteroaryl, 5-12 membered heterocyclyl, $(C_6$-$C_{10})$aryl, wherein the heteroaryl, heterocyclyl, and aryl are each independently optionally substituted with —$N(R^3)_2$, —$OR^3$, halogen, $(C_1$-$C_6)$alkyl, —$(C_1$-$C_6)$alkylene-heteroaryl, —$(C_1$-$C_6)$alkylene-CN, —C(O)$NR^3$-heteroaryl, or —C(O)$NR^3$-heterocyclyl;

each $R^5$ is independently H, $(C_1$-$C_6)$alkyl, —C(O)$OR^3$, or —$N(R^3)_2$, wherein the alkyl of $(C_1$-$C_6)$alkyl is optionally substituted with —$N(R^3)_2$ or —$OR^3$;

each $R^6$ is independently H, $(C_1$-$C_6)$alkyl, —C(O)$OR^3$, or —$N(R^3)_2$, wherein the alkyl is of $(C_1$-$C_6)$alkyl optionally substituted with —$N(R^3)_2$ or —$OR^3$;

each $R^7$ is independently H, $(C_1$-$C_6)$alkyl, —C(O)$OR^3$, or —$N(R^3)_2$, wherein the alkyl of $(C_1$-$C_6)$alkyl is optionally substituted with —$N(R^3)_2$ or —$OR^3$;

each $R^8$ is independently H, $(C_1$-$C_6)$alkyl, —C(O)$OR^3$, or —$N(R^3)_2$, wherein the alkyl of $(C_1$-$C_6)$alkyl is optionally substituted with —$N(R^3)_2$ or —$OR^3$;

each Y is independently —$C(R^3)_2$ or a bond;

each n is independently an integer from one to 12;

each o is independently an integer from zero to 30;

each p is independently an integer from zero to 12;

each q is independently an integer from zero to 30; and each r is independently an integer from one to 6.

The present disclosure provides a compound of Formula II:

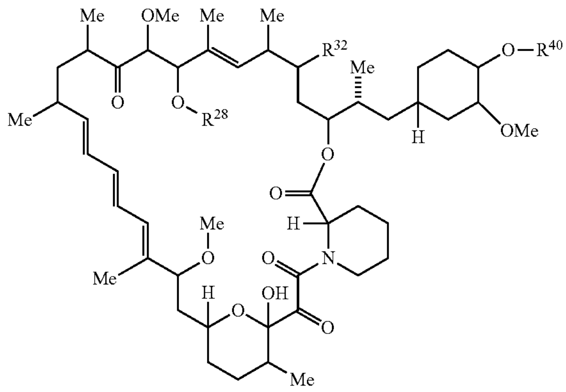

(II)

or a pharmaceutically acceptable salt or tautomer thereof, wherein:

$R^{32}$ is —H, =O or —$OR^3$;

$R^{28}$ is —H or —C(=$Z^1$)—$R^{28a}$;

$R^{40}$ is —H or —C(=$Z^1$)—$R^{41a}$;

wherein at least one of $R^{28}$ and $R^{40}$ is not H;

$Z^1$ is independently O or S;

$R^{28a}$ and $R^{40a}$ are independently -$A^1$-$L^1$-$A^2$-B; -$A^1$-$A^2$-B; —O—($C_1$-$C_6$)alkyl; or —O—($C_6$-$C_{10}$)aryl; wherein the aryl of —O—($C_6$-$C_{10}$)aryl is unsubstituted or substituted with 1-5 substituents selected from —$NO_2$ and halogen;

$A^1$ and $A^2$ are independently absent or are independently selected from

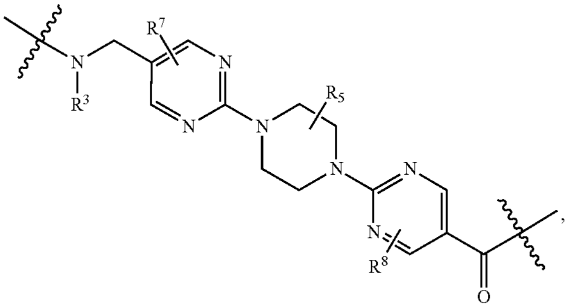

,

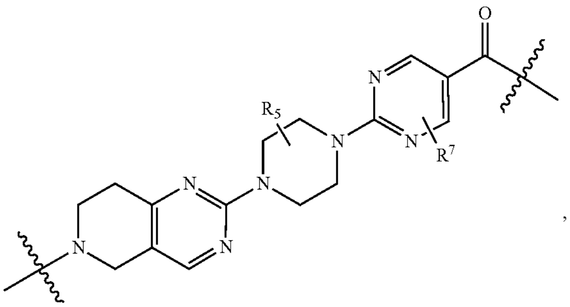

,

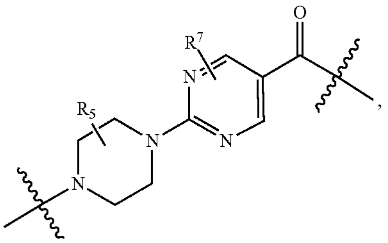

,

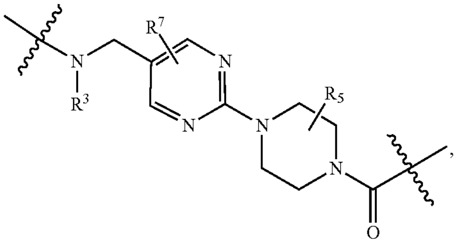

,

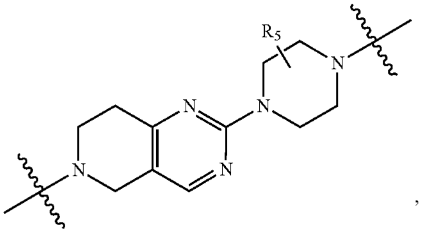

,

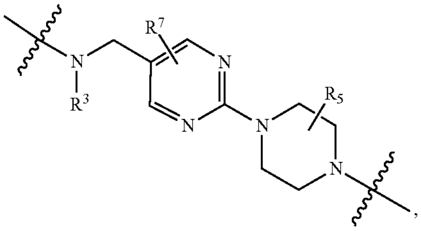

,

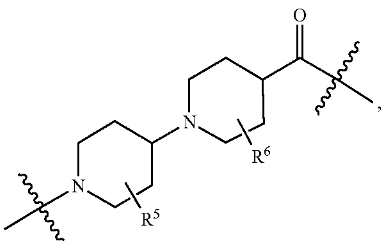

,

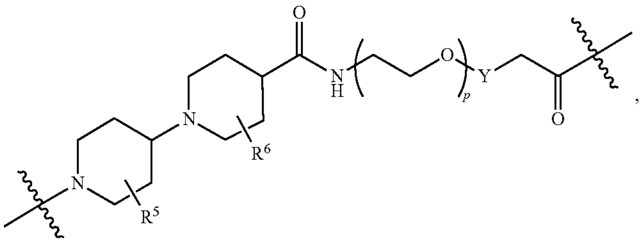

,

-continued
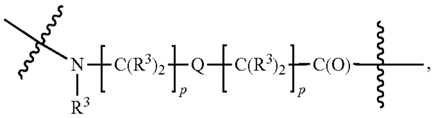,
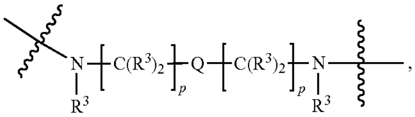,
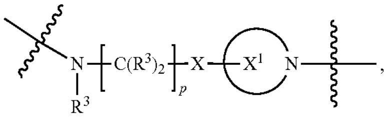,
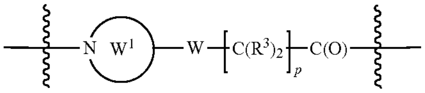
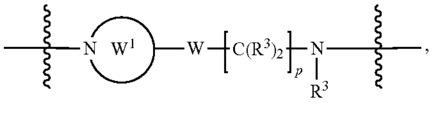,
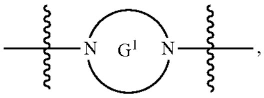,
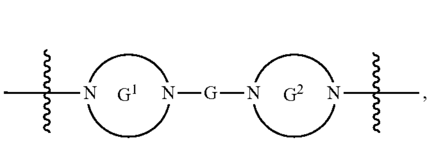,
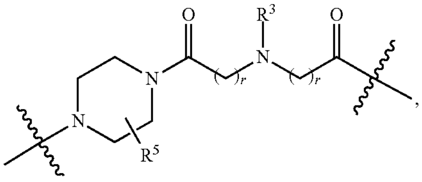,
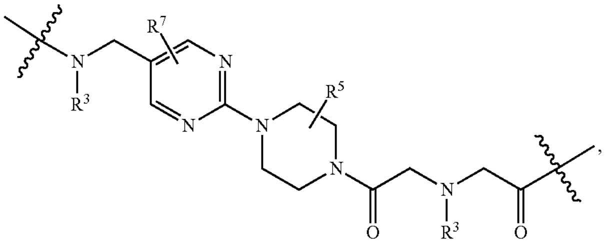,
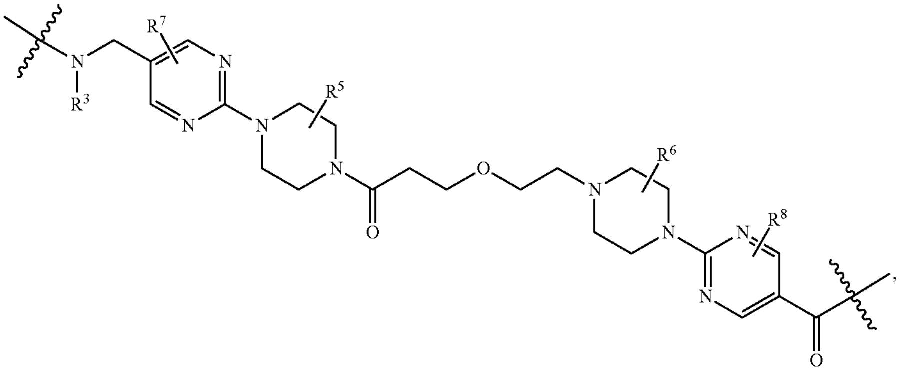,
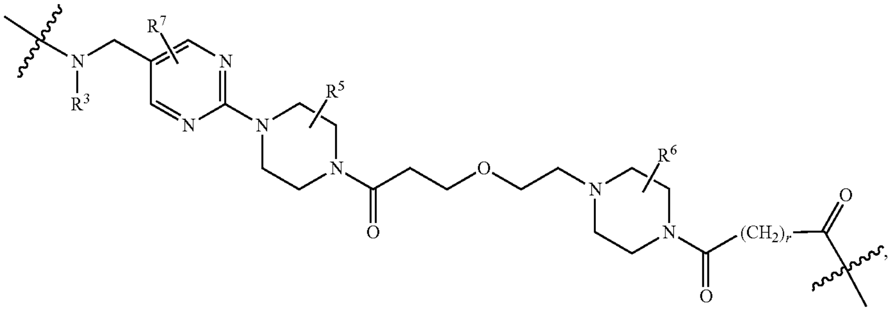, -continued

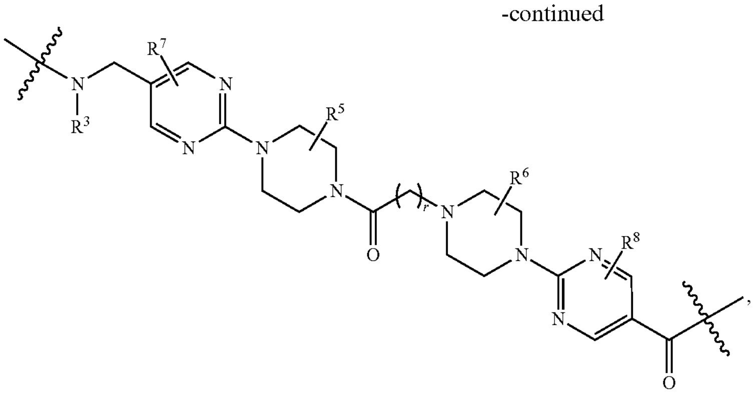

and

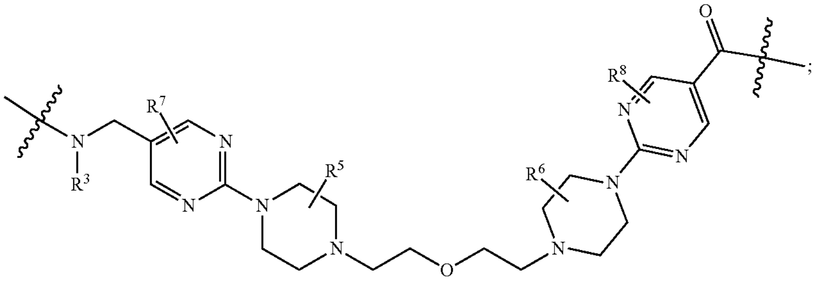

;

wherein the bond on the left side of $A^1$, as drawn, is bound to —C(=$Z^1$)—; and wherein the bond on the right side of the $A^2$ moiety, as drawn, is bound to B;

each Q is independently 1 to 3 rings selected from arylene, cycloalkylene, heteroarylene, and heterocyclylene;

each X is independently absent or 1 to 2 rings selected from arylene, cycloalkylene, heteroarylene, and heterocyclylene;

each $X^1$ is independently a heteroarylene or heterocyclylene ring;

each W is independently absent or 1 to 2 rings selected from arylene, cycloalkylene, heteroarylene, and heterocyclylene;

each $W^1$ is independently a heteroarylene or heterocyclylene ring;

each G is independently absent or a ring selected from arylene, cycloalkylene, heteroarylene, and heterocyclylene;

each $G^1$ and $G^2$ are independently heteroarylene or heterocyclylene ring;

each $L^1$ is independently selected from

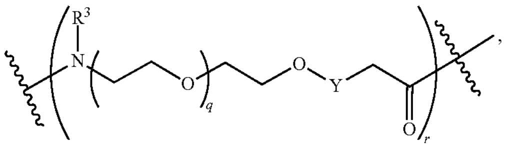

,

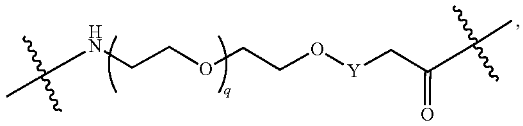

,

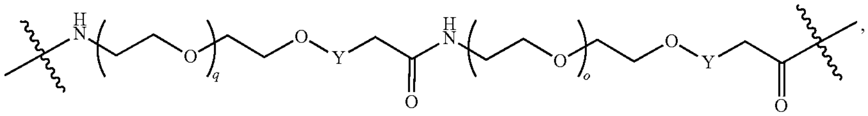

,

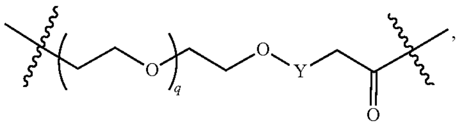

,

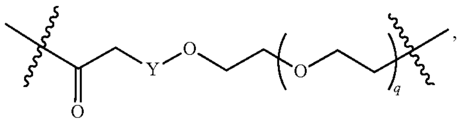

,

-continued
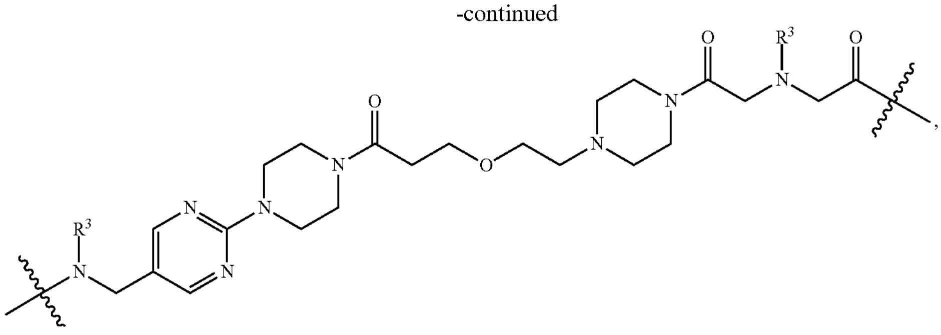
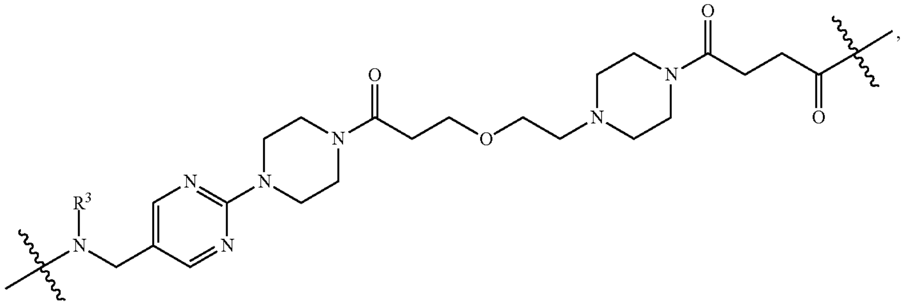
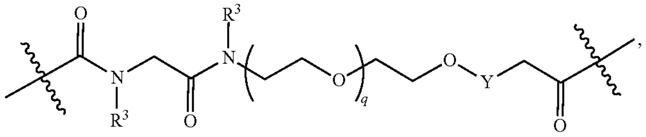
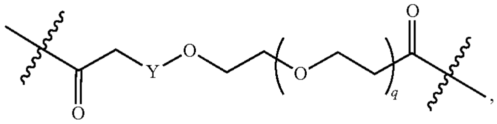
and
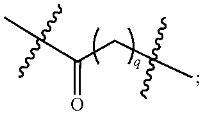
;
each B is independently selected from
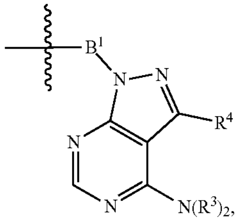
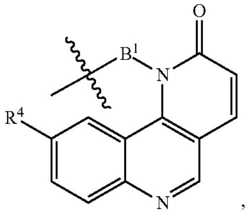
,
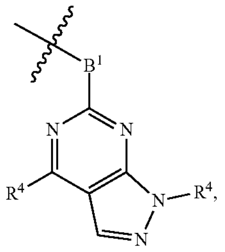
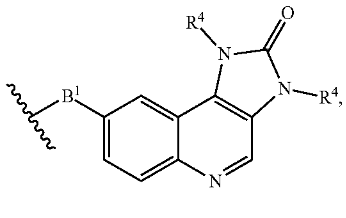
-continued
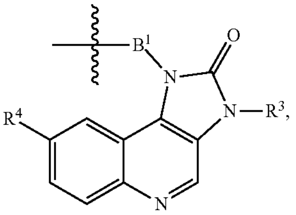
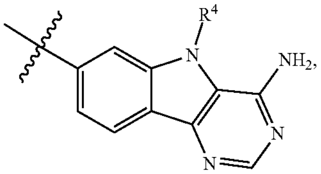
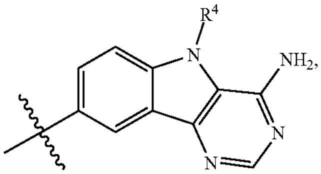
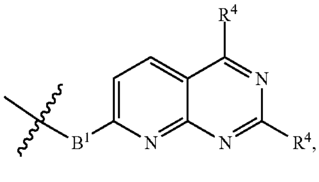

-continued

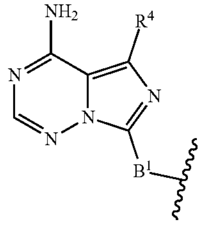

and

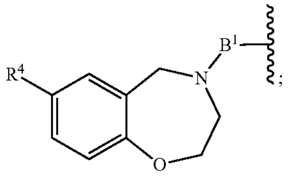

each $B^1$ is independently selected from

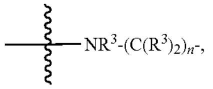

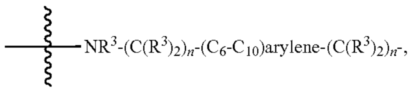

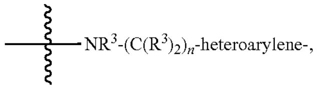

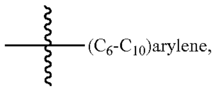

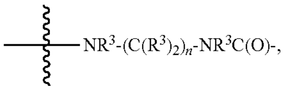

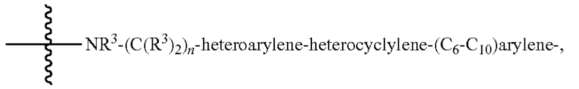

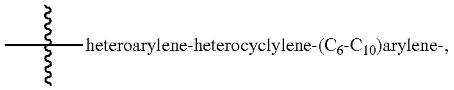

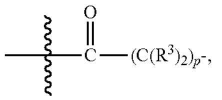

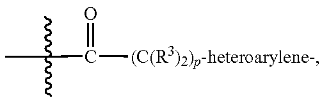

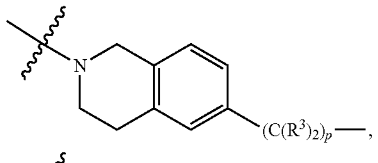

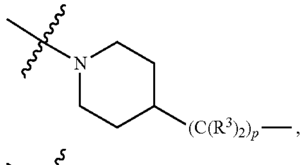

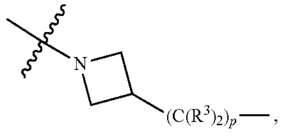

-continued

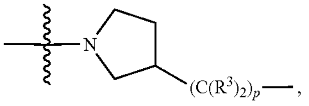

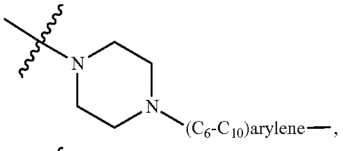

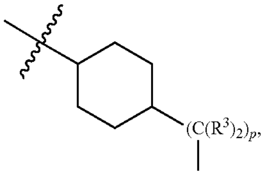

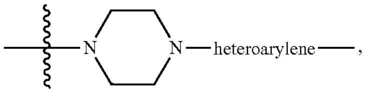

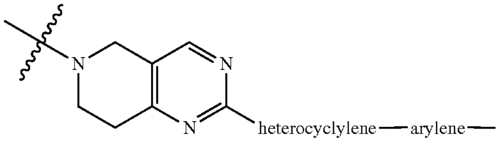

and

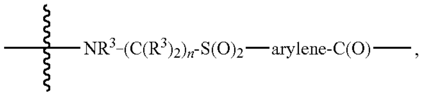

wherein the

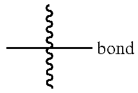

bond on the left side of $B^1$, as drawn, is bound to $A^2$ or $L^1$; and wherein the heteroarylene, heterocyclylene, and arylene are each independently optionally substituted with alkyl, hydroxyalkyl, haloalkyl, alkoxy, halogen, or hydroxyl;

each $R^3$ is independently H or $(C_1\text{-}C_6)$alkyl;

each $R^4$ is independently H, $(C_1\text{-}C_6)$alkyl, halogen, 5-12 membered heteroaryl, 5-12 membered heterocyclyl, $(C_6\text{-}C_{10})$aryl, wherein the heteroaryl, heterocyclyl, and aryl are each independently optionally substituted with —$N(R^3)_2$, —$OR^3$, halogen, $(C_1\text{-}C_6)$alkyl, —$(C_1\text{-}C_6)$alkylene-heteroaryl, —$(C_1\text{-}C_6)$alkylene-CN, —C(O)$NR^3$-heteroaryl, or —C(O)$NR^3$-heterocyclyl;

each $R^5$ is independently H, $(C_1\text{-}C_6)$alkyl, —C(O)$OR^3$, or —$N(R^3)_2$, wherein the alkyl of $(C_1\text{-}C_6)$alkyl is optionally substituted with —$N(R^3)_2$ or —$OR^3$;

each $R^6$ is independently H, $(C_1\text{-}C_6)$alkyl, —C(O)$OR^3$, or —$N(R^3)_2$, wherein the alkyl of $(C_1\text{-}C_6)$alkyl is optionally substituted with —$N(R^3)_2$ or —$OR^3$;

each $R^7$ is independently H, $(C_1\text{-}C_6)$alkyl, —C(O)$OR^3$, or —$N(R^3)_2$, wherein the alkyl of $(C_1\text{-}C_6)$alkyl is optionally substituted with —$N(R^3)_2$ or —$OR^3$;

each $R^8$ is independently H, $(C_1\text{-}C_6)$alkyl, —C(O)$OR^3$, or —$N(R^3)_2$, wherein the alkyl of $(C_1\text{-}C_6)$alkyl is optionally substituted with —$N(R^3)_2$ or —$OR^3$;

each Y is independently $C(R^3)_2$ or a bond;

each n is independently an integer from one to 12;

each o is independently an integer from zero to 30;

each p is independently an integer from zero to 12;

each q is independently an integer from zero to 30; and each r is independently an integer from one to 6.

In some embodiments, a compound of Formula I or II is represented by the structure of Formula I-28:

(I-28)

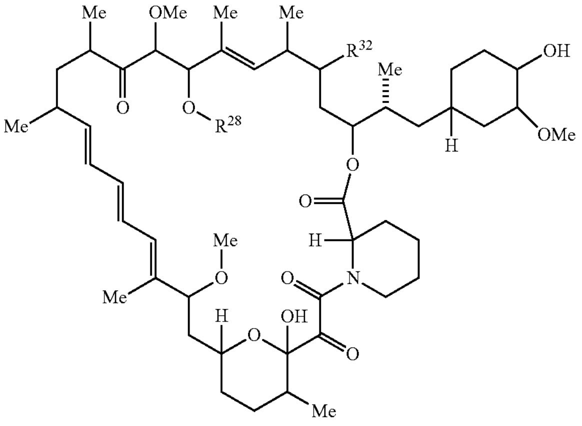

or a pharmaceutically acceptable salt or tautomer thereof.

In some embodiments, a compound of Formula Ia, Ic, I, or II is represented by the structure of Formula I-28b:

(I-28b)

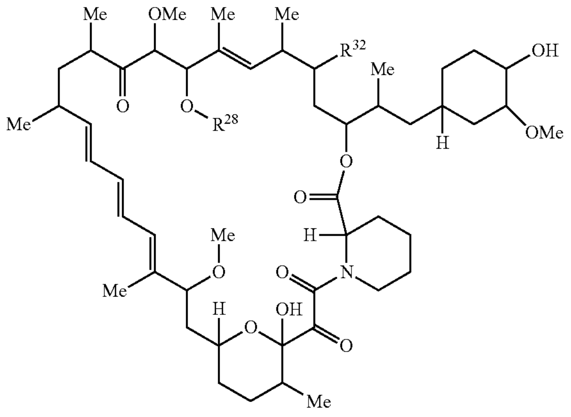

or a pharmaceutically acceptable salt or a tautomer thereof.

In some embodiments, a compound of Formula I or II is represented by the structure of Formula I-40:

(I-40)

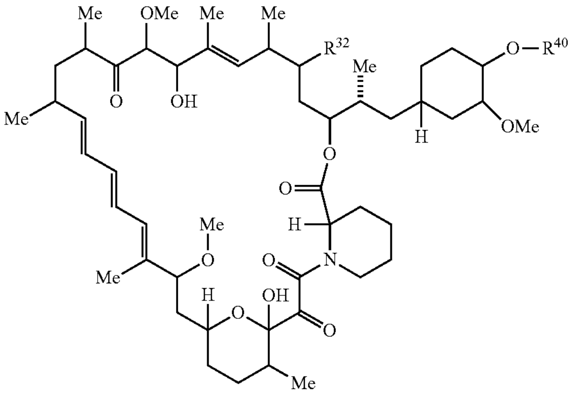

or a pharmaceutically acceptable salt or tautomer thereof.

In some embodiments, a compound of Formula Ia, Ic, I or II is represented by the structure of Formula I-40b:

(I-40b)

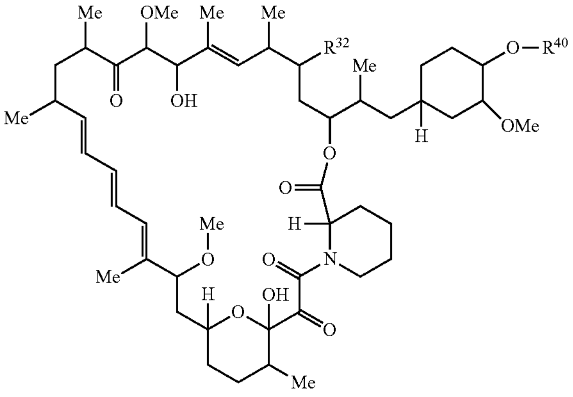

or a pharmaceutically acceptable salt or a tautomer thereof.

In some embodiments, a compound of Formula ta, Ic, I or II is represented by the structure of Formula I-32b.

(I-32b)

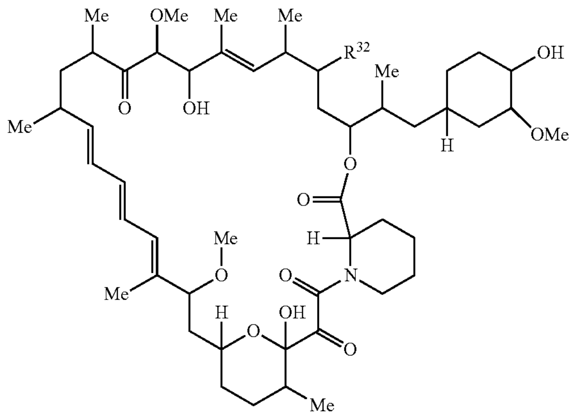

or a pharmaceutically acceptable salt or a tautomer thereof.

The present disclosure provides a method of treating a disease or disorder mediated by mTOR comprising administering to the subject suffering from or susceptible to developing a disease or disorder mediated by mTOR a therapeutically effective amount of one or more disclosed compounds. The present disclosure provides a method of preventing a disease or disorder mediated by mTOR comprising administering to the subject suffering from or susceptible to developing a disease or disorder mediated by mTOR a therapeutically effective amount of one or more disclosed compounds. The present disclosure provides a method of reducing the risk of a disease or disorder mediated by mTOR comprising administering to the subject suffering from or susceptible to developing a disease or disorder mediated by mTOR a therapeutically effective amount of one or more disclosed compounds.

Another aspect of the present disclosure is directed to a pharmaceutical composition comprising a compound of Formula I, Ia, Ib, Ic, II, or IIb, or a pharmaceutically acceptable salt or tautomer of any of the foregoing, and a pharmaceutically acceptable carrier. The pharmaceutically acceptable carrier can further comprise an excipient, diluent, or surfactant. The pharmaceutical composition can be effective for treating, preventing, or reducing the risk of a disease or disorder mediated by mTOR in a subject in need thereof.

Another aspect of the present disclosure relates to a compound of Formula I, Ia, Ib, Ic, II, or IIb, or a pharmaceutically acceptable salt or tautomer of any of the foregoing, for use in treating, preventing, or reducing the risk of a disease or disorder mediated by mTOR in a subject in need thereof.

Another aspect of the present disclosure relates to the use of a compound of Formula I, Ia, Ib, Ic, II, or IIb, or a pharmaceutically acceptable salt or tautomer of any of the foregoing, in the manufacture of a medicament for in treating, preventing, or reducing the risk of a disease or disorder mediated by mTOR in a subject in need thereof.

The present disclosure also provides compounds that are useful in inhibiting mTOR.

DETAILED DESCRIPTION OF THE DISCLOSURE

The present disclosure relates to mTOR inhibitors. Specifically, the embodiments are directed to compounds and compositions inhibiting mTOR, methods of treating diseases mediated by mTOR, and methods of synthesizing these compounds.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also may include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Terms

The articles "a" and "an" are used in this disclosure and refers to one or more than one (i.e., to at least one) of the grammatical object of the article, unless indicated otherwise. By way of example, "an element" may mean one element or more than one element, unless indicated otherwise.

The term "or" means "and/or" unless indicated otherwise. The term "and/or" means either "and" or "or", or both, unless indicated otherwise.

The term "optionally substituted" unless otherwise specified means that a group may be unsubstituted or substituted by one or more (e.g., 0, 1, 2, 3, 4, or 5 or more, or any range derivable therein) of the substituents listed for that group in which said substituents may be the same or different. In an embodiment, an optionally substituted group has 1 substituent. In another embodiment an optionally substituted group has 2 substituents. In another embodiment an optionally substituted group has 3 substituents. In another embodiment an optionally substituted group has 4 substituents. In another embodiment an optionally substituted group has 5 substituents.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene," by itself or as part of another substituent, means, unless otherwise stated, a divalent radical derived from an alkyl. Typically, an alkyl (or alkylene) group will have from 1 to 24 carbon atoms, such as those groups having 10 or fewer carbon atoms.

The term "alkenyl" means an aliphatic hydrocarbon group containing a carbon-carbon double bond and which may be straight or branched having about 2 to about 6 carbon atoms in the chain. Certain alkenyl groups have 2 to about 4 carbon atoms in the chain. Branched may mean that one or more lower alkyl groups such as methyl, ethyl, or propyl are attached to a linear alkenyl chain. Exemplary alkenyl groups include ethenyl, propenyl, n-butenyl, and i-butenyl. A $C_2$-$C_6$ alkenyl group is an alkenyl group containing between 2 and 6 carbon atoms.

The term "alkenylene," by itself or as part of another substituent, means, unless otherwise stated, a divalent radical derived from an alkene.

The term "alkynyl" means an aliphatic hydrocarbon group containing a carbon-carbon triple bond and which may be straight or branched having about 2 to about 6 carbon atoms in the chain. Certain alkynyl groups have 2 to about 4 carbon atoms in the chain. Branched may mean that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl. A $C_2$-$C_6$ alkynyl group is an alkynyl group containing between 2 and 6 carbon atoms.

The term "alkynylene," by itself or as part of another substituent, means, unless otherwise stated, a divalent radical derived from an alkyne.

The term "cycloalkyl" means a monocyclic or polycyclic saturated or partially unsaturated carbon ring containing 3-18 carbon atoms. Examples of cycloalkyl groups include, without limitation, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl. A $C_3$-$C_8$ cycloalkyl is a cycloalkyl group containing between 3 and 8 carbon atoms. A cycloalkyl group can be fused (e.g., decalin) or bridged (e.g., norbornane).

A "cycloalkylene," alone or as part of another substituent, means a divalent radical derived from a cycloalkyl.

The terms "heterocyclyl" or "heterocycloalkyl" or "heterocycle" refers to a monocyclic or polycyclic 3 to 24-membered ring containing carbon and at least one heteroatom selected from oxygen, phosphorous, nitrogen, and sulfur and wherein there is not delocalized $\pi$ electrons (aromaticity) shared among the ring carbon or heteroatom(s). Heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl. A heterocyclyl or heterocycloalkyl ring can also be fused or bridged, e.g., can be a bicyclic ring.

A "heterocyclylene" or "heterocycloalkylene," alone or as part of another substituent, means a divalent radical derived from a "heterocyclyl" or "heterocycloalkyl" or "heterocycle."

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl may refer to multiple rings fused together wherein at least one of the fused rings is an aryl ring.

An "arylene," alone or as part of another substituent, means a divalent radical derived from an aryl.

The term "heteroaryl" refers to an aryl group (or rings) that contains at least one heteroatom such as N, O, or S, wherein the nitrogen and sulfur atom(s) are optionally oxidized, and the nitrogen atom(s) is optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described herein.

The term "heteroaryl" may also include multiple condensed ring systems that have at least one such aromatic ring, which multiple condensed ring systems are further described below. The term may also include multiple condensed ring systems (e.g., ring systems comprising 2, 3 or 4 rings) wherein a heteroaryl group, as defined above, can be condensed with one or more rings selected from heteroaryls (to form for example a naphthyridinyl such as 1,8-naphthyridinyl), heterocycles, (to form for example a 1,2,3,4-tetrahydronaphthyridinyl such as 1,2,3,4-tetrahydro-1,8-naphthyridinyl), carbocycles (to form for example 5,6,7,8-tetrahydroquinolyl) and aryls (to form for example indazolyl) to form the multiple condensed ring system. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system and at any suitable atom of the multiple condensed ring system including a carbon atom and heteroatom (e.g., a nitrogen).

A "heteroarylene," alone or as part of another substituent, means a divalent radical derived from a heteroaryl.

Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzo thiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., 0, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

The terms "halo" or "halogen," by themselves or as part of another substituent, mean, unless otherwise stated, a fluorine, chlorine, bromine, or iodine atom. Additionally, terms such as "haloalkyl" may include monohaloalkyl and polyhaloalkyl. For example, the term "halo($C_1$-$C_4$)alkyl" may include, but is not limited to, fluoromethyl, difluoromethyl, trifluoromethyl, 2,2,2-trifluoroethyl, 4-chlorobutyl, 3-bromopropyl, 1-fluoro-2-bromoethyl, and the like.

The term "hydroxyl," as used herein, means —OH.

The term "hydroxyalkyl" as used herein, means an alkyl moiety as defined herein, substituted with one or more, such as one, two or three, hydroxy groups. In certain instances, the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl.

The term "oxo," as used herein, means an oxygen that is double bonded to a carbon atom.

A substituent group, as used herein, may be a group selected from the following moieties:

(A) oxo, halogen, —$CF_3$, —CN, —OH, —$OCH_3$, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, —$OCH_2F$, unsubstituted alkyl, unsubstituted cycloalkyl, unsubstituted heterocycloalkyl, unsubstituted aryl, unsubstituted heteroaryl, and (B) alkyl, cycloalkyl, heterocyclyl, aryl, heteroaryl, substituted with at least one substituent selected from:

(i) oxo, halogen, —$CF_3$, —CN, —OH, —$OCH_3$, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, —$OCH_2F$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —$CF_3$, —CN, —OH, —$OCH_3$, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, —$OCH_2F$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —$CF_3$, —CN, —OH, —$OCH_3$, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, —$OCH_2F$, unsubstituted alkyl, unsubstituted heteroalkyl, unsubstituted cycloalkyl, unsubstituted heterocycloalkyl, unsubstituted aryl, unsubstituted heteroaryl.

An "effective amount" when used in connection with a compound is an amount effective for treating or preventing a disease in a subject as described herein.

The term "carrier", as used in this disclosure, encompasses carriers, excipients, and diluents and may mean a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating may include curing, improving, or at least partially ameliorating the disorder.

The term "prevent" or "preventing" with regard to a subject refers to keeping a disease or disorder from afflicting the subject. Preventing may include prophylactic treatment. For instance, preventing can include administering to the subject a compound disclosed herein before a subject is afflicted with a disease and the administration will keep the subject from being afflicted with the disease.

The term "disorder" is used in this disclosure and means, and is used interchangeably with, the terms disease, condition, or illness, unless otherwise indicated.

The term "administer", "administering", or "administration" as used in this disclosure refers to either directly administering a disclosed compound or pharmaceutically acceptable salt or tautomer of the disclosed compound or a composition to a subject, or administering a prodrug derivative or analog of the compound or pharmaceutically acceptable salt or tautomer of the compound or composition to the subject, which can form an equivalent amount of active compound within the subject's body.

A "patient" or "subject" is a mammal, e.g., a human, mouse, rat, guinea pig, dog, cat, horse, cow, pig, or non-human primate, such as a monkey, chimpanzee, baboon or rhesus.

Compounds

The present disclosure provides a compound having the structure of Formula Ic, (Ic)

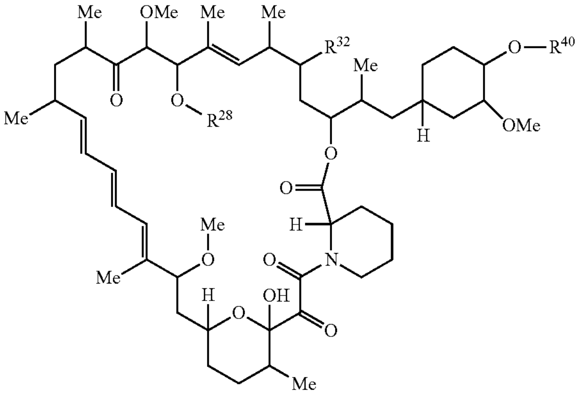

or a pharmaceutically acceptable salt or tautomer thereof, wherein $R^{32}$, $R^{28}$, and $R^{40}$ are described as above.

The present disclosure provides a compound having the structure of Formula Ia, (Ia)

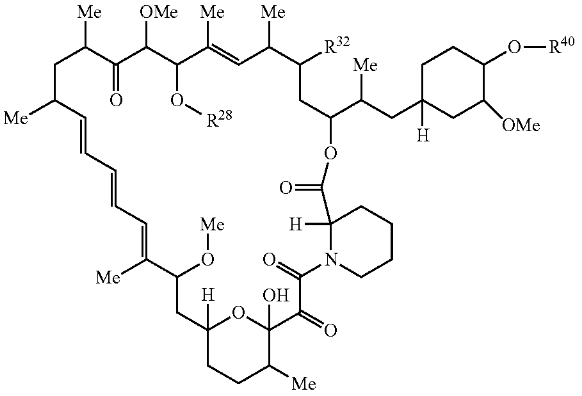

or a pharmaceutically acceptable salt or tautomer thereof, wherein $R^{32}$, $R^{28}$, and $R^{40}$ are described as above.

The present disclosure provides a compound having the structure of Formula I, (I)

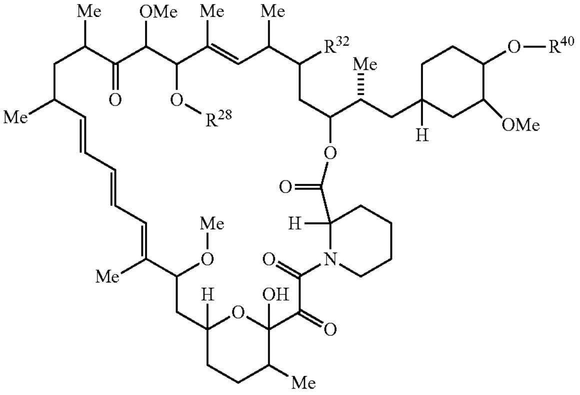

or a pharmaceutically acceptable salt or tautomer thereof, wherein $R^{32}$, $R^{28}$, and $R^{40}$ are described as above.

The present disclosure provides a compound having the structure of Formula Ib.

(Ib)

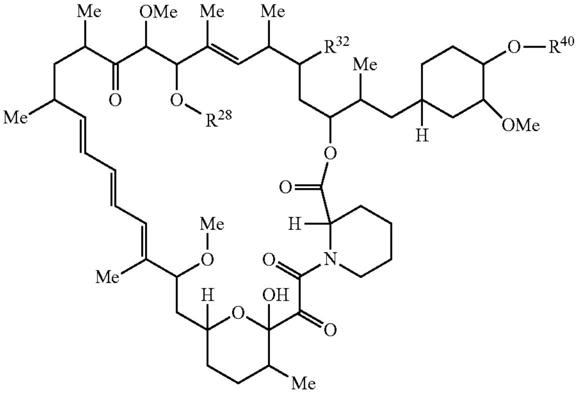

or a pharmaceutically acceptable salt and or tautomer thereof, wherein $R^{32}$, $R^{28}$, and $R^{40}$ are described as above for Formula.

The present disclosure provides a compound having the structure of Formula II, (II)

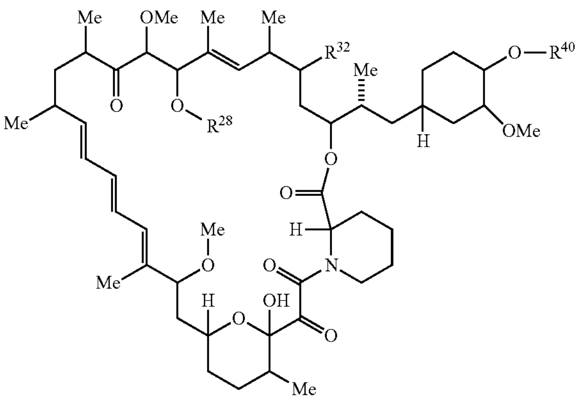

or a pharmaceutically acceptable salt or tautomer thereof, wherein $R^{32}$, $R^{28}$, and $R^{40}$ are described as above.

The present disclosure provides a compound having the structure of Formula IIb.

(IIb)

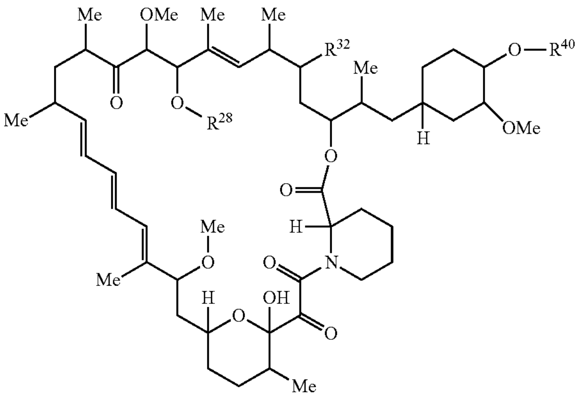

or a pharmaceutically acceptable salt or tautomer thereof, wherein $R^{32}$, $R^{28}$, and $R^{40}$ are described as above for Formula II.

In certain embodiments, a compound has the following formula:

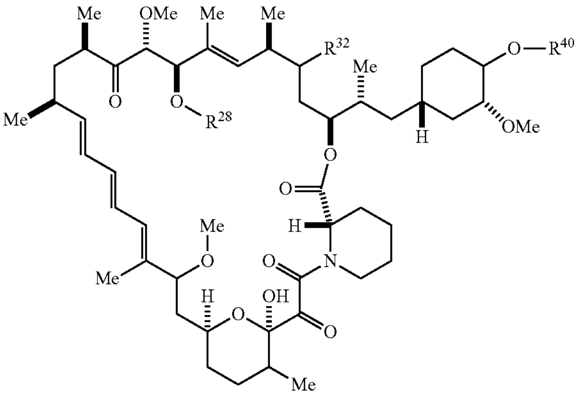

or a pharmaceutically acceptable salt or tautomer thereof.

In certain embodiments, $R^{32}$ is =O. In certain embodiments, $R^{32}$ is —$OR^3$. In certain embodiments, $R^{32}$ is H. In certain embodiments, $R^{32}$ is —$N_3$.

As described above, each $R^3$ is independently H or $(C_1\text{-}C_6)$alkyl. In certain embodiments, $R^3$ is H. In certain embodiments, $R^3$ is $(C_1\text{-}C_6)$alkyl. In certain embodiments, $R^3$ is methyl.

In certain embodiments, $R^{28}$ is H. In certain embodiments, $R^{28}$ is $(C_1\text{-}C_6)$alkyl. In certain embodiments, $R^{40}$ is H.

In certain embodiments, a compound is represented by the structure of Formula I-40b:

(I-40b)

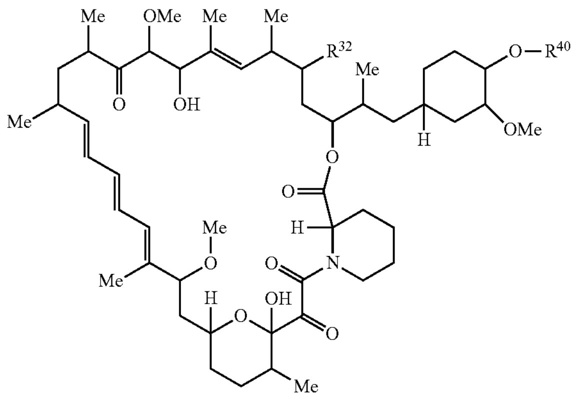

or a pharmaceutically acceptable salt or tautomer thereof, wherein $R^{32}$ and $R^{40}$ are described as above for Formula a, Ic, I, or II.

In certain embodiments, a compound is represented by the structure of Formula I-40.

(I-40)

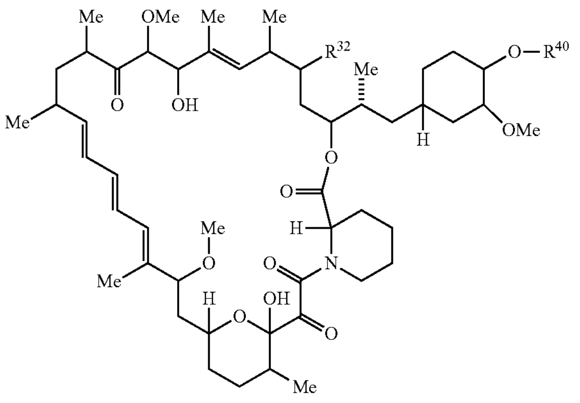

or a pharmaceutically acceptable salt or tautomer thereof, wherein $R^{32}$ and $R^{40}$ are described as above.

In certain embodiments, $R^{40}$ is —C(═$Z^1$)—$R^{40a}$. In certain embodiments, $Z^1$ is O. In certain embodiments, $Z^1$ is S.

In certain embodiments, $R^{40a}$ is —O—($C_1$-$C_6$)alkyl or —O—($C_6$-$C_{10}$)aryl; wherein the aryl is unsubstituted or substituted with 1-5 substituents selected from $NO_2$ and halogen.

In certain embodiments, $R^{40a}$ is -$A^1$-$L^1$-$A^2$-B. In certain embodiments, $R^{40a}$ is -$A^1$-$A^2$-B. In certain embodiments, $R^{40a}$ is -$L^2$-$A^1$-$L^1$-$A^2$-$L^3$-B.

In certain embodiments, $R^{40a}$ is -$A^1$-$L^1$-$A^2$-B, wherein $A^1$ and $A^2$ are absent. In certain embodiments, $R^{40a}$ is -$A^1$-$L^1$-$A^2$-B, wherein $A^2$ is absent. In certain embodiments, $R^{40a}$ is -$A^1$-$L^1$-$A^2$-B, wherein $A^1$ is absent. In certain embodiments, $R^{40a}$ is -$A^1$-$L^1$-$A^2$-B. In certain embodiments, $R^{40a}$ is -$A^1$-$A^2$-B. In certain embodiments, $R^{40a}$ is -$L^2$-$A^1$-$L^1$-$A^2$-$L^3$-B, wherein $L^2$ and $A^1$ are absent. In certain embodiments, $R^{40a}$ is -$L^2$-$A^1$-$L^1$-$A^2$-$L^3$-B, wherein $L^2$ is absent. In certain embodiments, $R^{40a}$ is -$L^2$-$A^1$-$L^1$-$A^2$-$L^3$-B, wherein $L^3$ is absent.

In certain embodiments, a compounds is represented by the structure of Formula I-28b:

(I-28b)

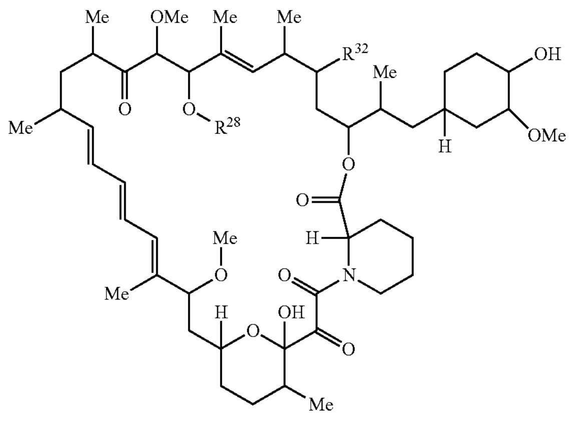

or a pharmaceutically acceptable salt or tautomer thereof, wherein $R^{32}$ and $R^{28}$ are described as above for Formula Ia, Ic, I, or II.

In certain embodiments, a compound is represented by the structure of Formula I-28:

(I-28)

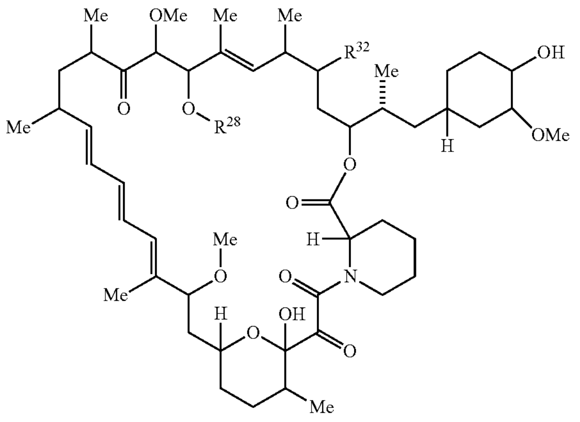

or a pharmaceutically acceptable salt or tautomer thereof, wherein $R^{32}$ and $R^{28}$ are described as above.

In certain embodiments, $R^{28}$ is —C(═$Z^1$)—$R^{28a}$. In certain embodiments, $Z^1$ is O. In certain embodiments, $Z^1$ is S.

In certain embodiments, $R^{28a}$ is —O—($C_1$-$C_6$)alkyl or —O—($C_6$-$C_{10}$)aryl; wherein the aryl is unsubstituted or substituted with 1-5 substituents selected from $NO_2$ and halogen.

In certain embodiments, $R^{28a}$ is -$A^1$-$L^1$-$A^2$-B. In certain embodiments, $R^{28a}$ is -$A^1$-$A^2$-B. In certain embodiments, $R^{28a}$ is -$L^2$-$A^1$-$L^1$-$A^2$-$L^3$-B.

In certain embodiments, $R^{28a}$ is -$A^1$-$L^1$-$A^2$-B, wherein $A^1$ and $A^2$ are absent. In certain embodiments, $R^{28a}$ is -$A^1$-$L^1$-$A^2$-B, wherein $A^2$ is absent. In certain embodiments, $R^{28a}$ is -$A^1$-$L^1$-$A^2$-B, wherein $A^1$ is absent. In certain embodiments, $R^{28a}$ is -$A^1$-$L^1$-$A^2$-B. In certain embodiments, $R^{28a}$ is -$A^1$-$A^2$-B. In certain embodiments, $R^{28a}$ is -$L^2$-$A^1$-$L^1$-$A^2$-$L^3$-B, wherein $L^2$ and $A^1$ are absent. In certain embodiments, $R^{28a}$ is -$L^2$-$A^1$-$L^1$-$A^2$-$L^3$-B, wherein $L^2$ is absent. In certain embodiments, $R^{28a}$ is -$L^2$-$A^1$-$L^1$-$A^2$-$L^3$-B, wherein $L^3$ is absent.

In certain embodiments, the compounds are represented by the structure of Formula I-32b:

(I-32b)

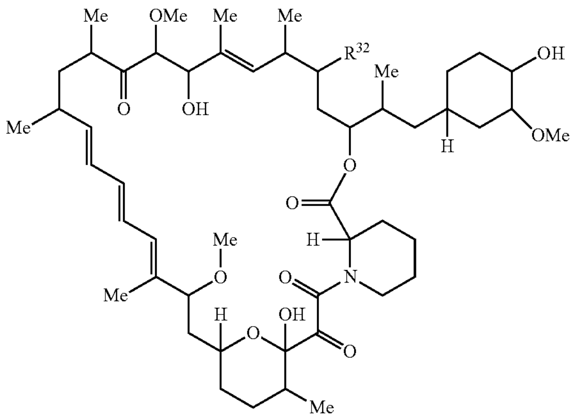

or a pharmaceutically acceptable salt or tautomer thereof, wherein $R^{32}$ is described as above for Formula Ia, Ic, I, or II.

In certain embodiments, $R^{32}$ is —O—C(═$Z^1$)—$R^{32a}$. In certain embodiments, $Z^1$ is O. In certain embodiments, $Z^1$ is S.

In certain embodiments, $R^{32a}$ is —O—($C_1$-$C_6$)alkyl or —O—($C_6$-$C_{10}$)aryl; wherein the aryl is unsubstituted or substituted with 1-5 substituents selected from $N_{02}$ and halogen.

In certain embodiments, $R^{32a}$ is -$A^1$-$L^1$-$A^2$-B. In certain embodiments, $R^{32a}$ is -$A^1$-$A^2$-B. In certain embodiments, $R^{32a}$ is -$L^2$-$A^1$-$L^1$-$A^2$-$L^3$-B.

In certain embodiments, $R^{32a}$ is -$A^1$-$L^1$-$A^2$-B, wherein $A^1$ and $A^2$ are absent. In certain embodiments, $R^{32a}$ is -$A^1$-$L^1$-$A^2$-B, wherein $A^2$ is absent. In certain embodiments, $R^{32a}$ is -$A^1$-$L^1$-$A^2$-B, wherein $A^1$ is absent. In certain embodiments, $R^{32a}$ is -$A^1$-$L^1$-$A^2$-B. In certain embodiments, $R^{32a}$ is -$A^1$-$A^2$-B. In certain embodiments, $R^{32a}$ is -$L^2$-$A^1$-$L^1$-$A^2$-$L^3$-B, wherein $L^2$ and $A^1$ are absent. In certain embodiments, $R^{32a}$ is -$L^2$-$A^1$-$L^1$-$A^2$-$L^3$-B, wherein $L^2$ is absent. In certain embodiments, $R^{32a}$ is -$L^2$-$A^1$-$L^1$-$A^2$-$L^3$-B, wherein $L^3$ is absent.

As described above, each $L^1$ is independently selected from

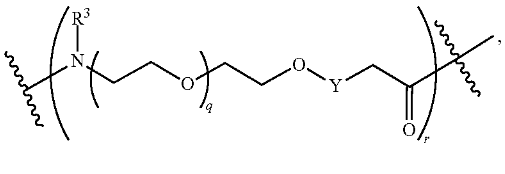,

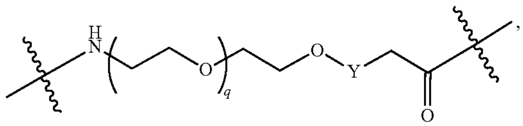,

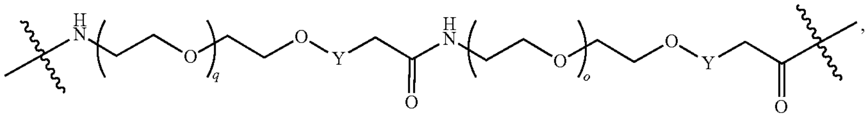,

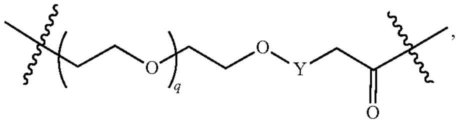,

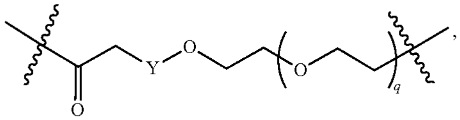,

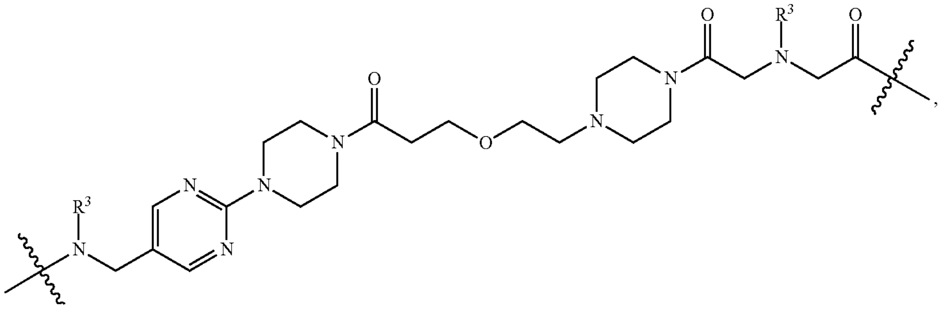,

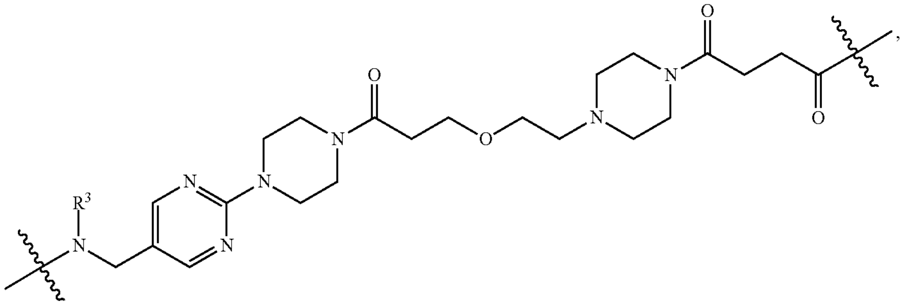,

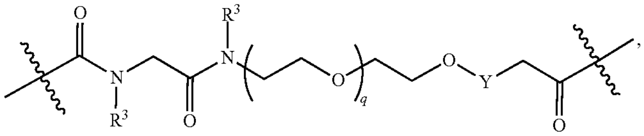,

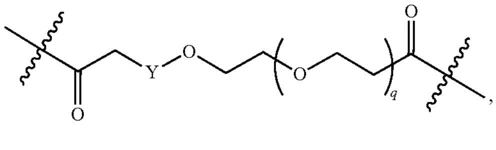, and

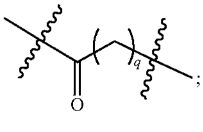;

As described above for Formula Ia, each $L^1$ is independently selected from
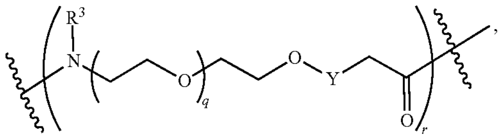,
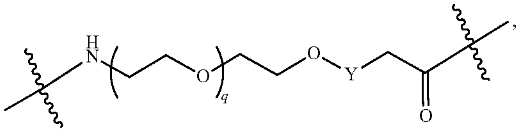,
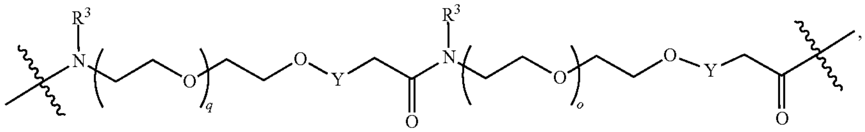,
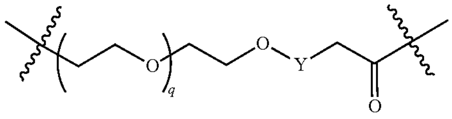,
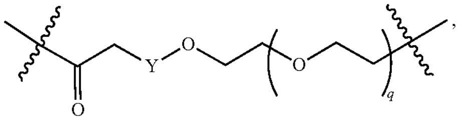,
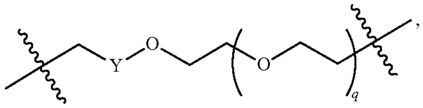,
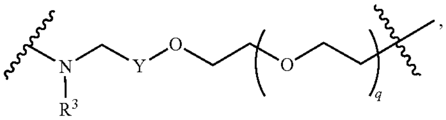,
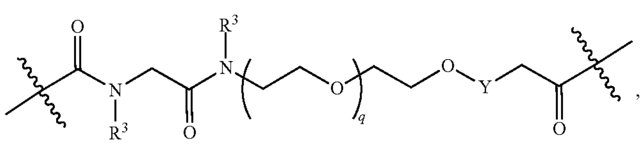,
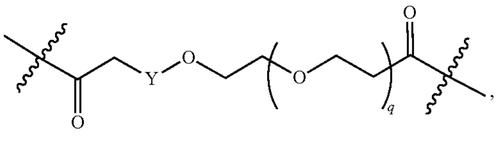,
and 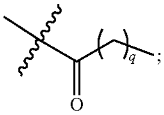;
As described above for Formula Ic, each $L^1$ is independently selected from
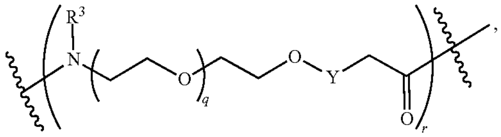,
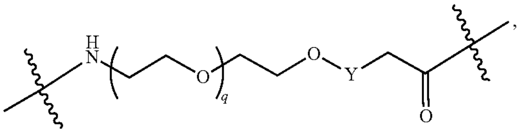,
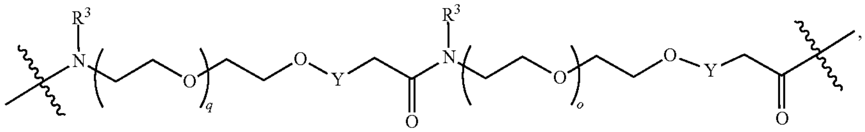,
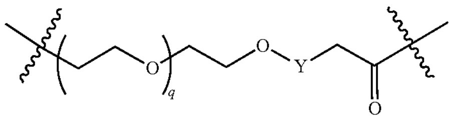,
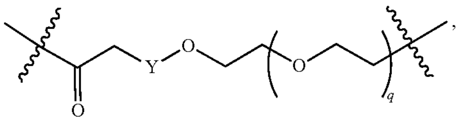,
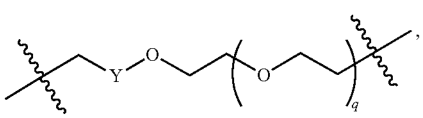,
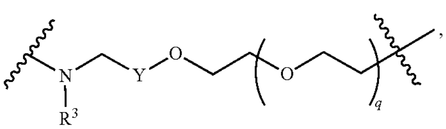,
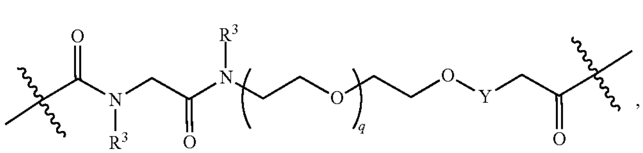,
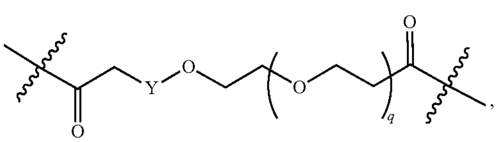, -continued
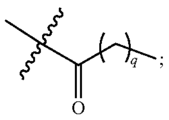
and
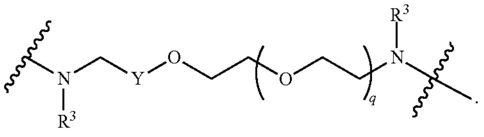
In certain embodiments, $L^1$ is
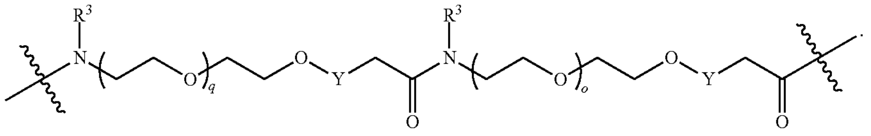
In certain embodiments, $L^1$ is
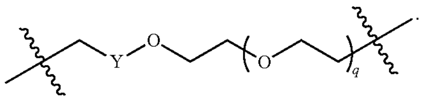
In certain embodiments, $L^1$ is
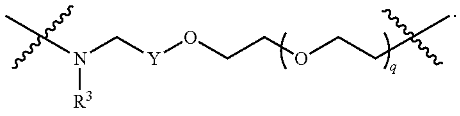
In certain embodiments, $L^1$ is
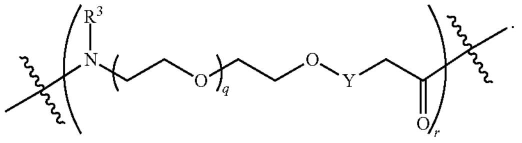
In certain embodiments, $L^1$ is
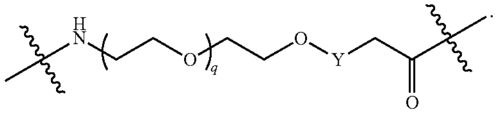
In certain embodiments, $L^1$ is
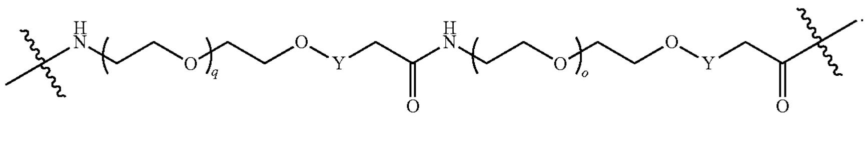

In certain embodiments, $L^1$ is
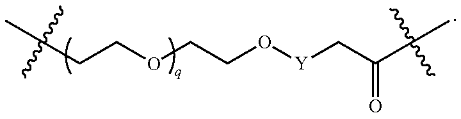
In certain embodiments, $L^1$ is
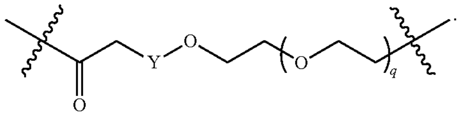
In certain embodiments, $L^1$ is
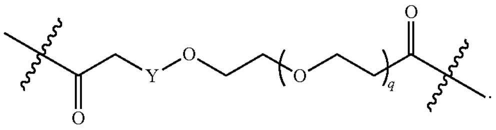
In certain embodiments, $L^1$ is
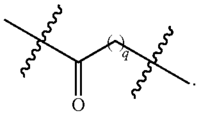
In certain embodiments, $L^1$ is
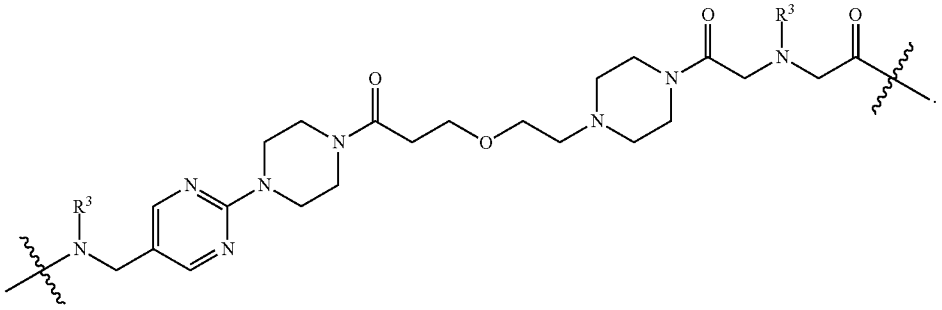
In certain embodiments, $L^1$ is
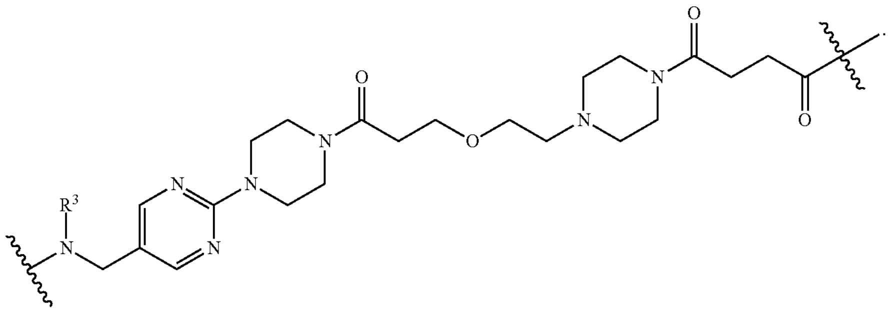
In certain embodiments, $L^1$ is
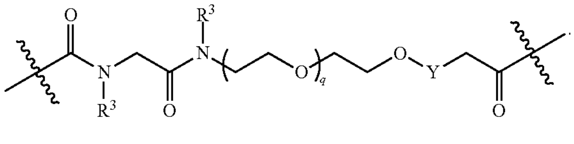
In certain embodiments, $L^1$ is
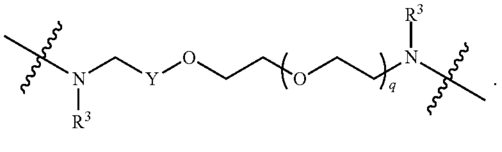

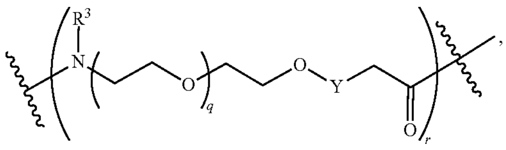,
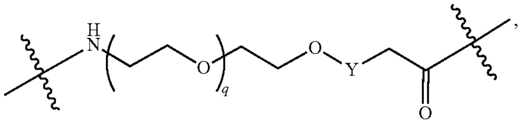,
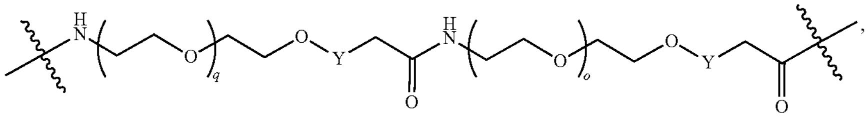,
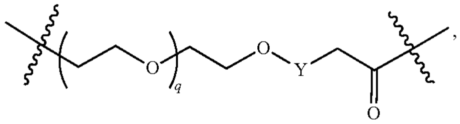,
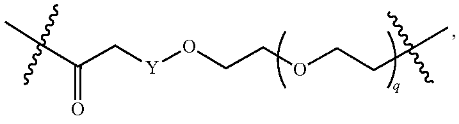,
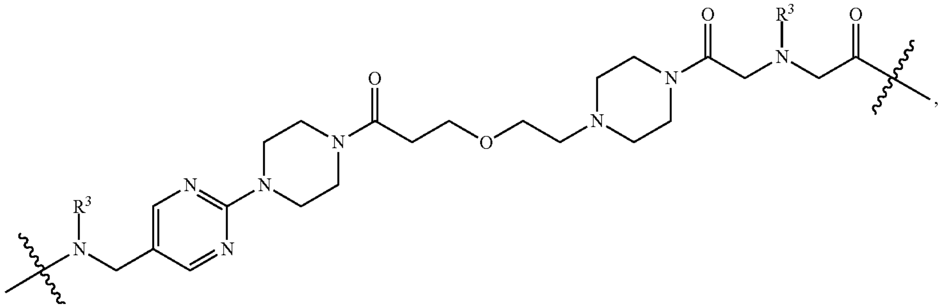,
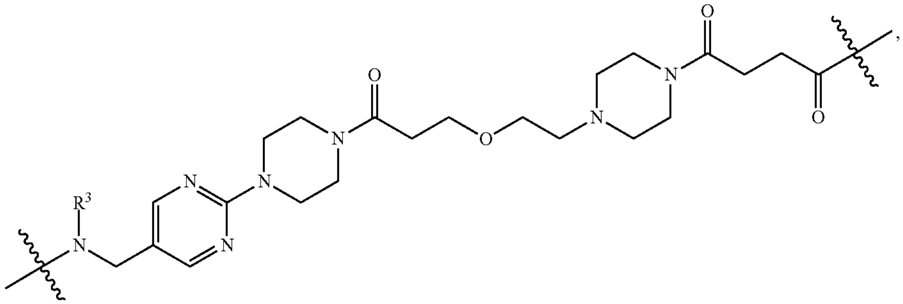,
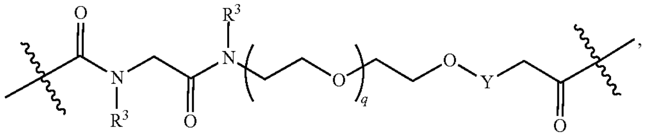,
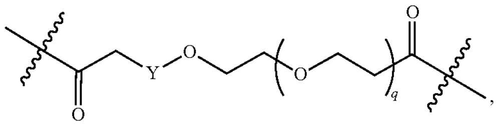, and 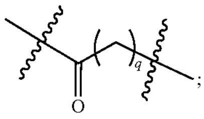;
As described above for Formula Ia and Ic, $L^2$ and $L^3$ are independently absent or are independently selected from
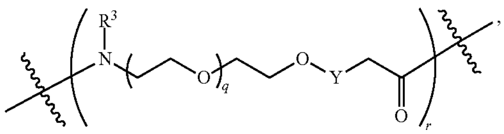,
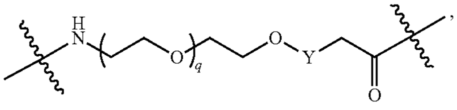,
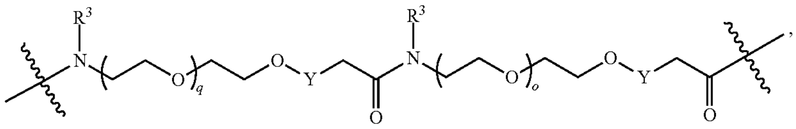, -continued
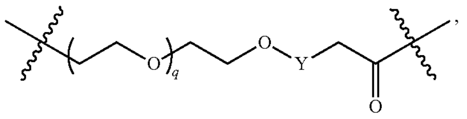
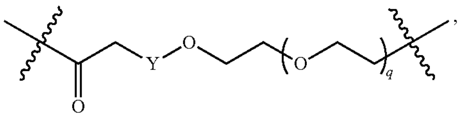
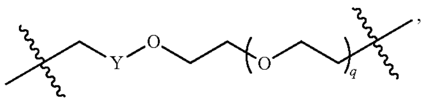
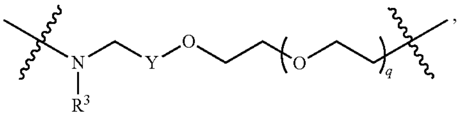
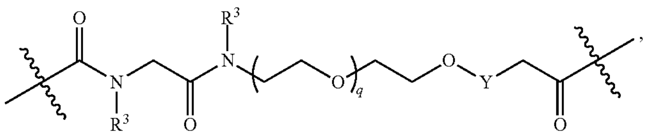
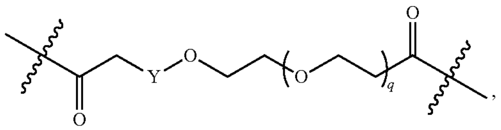
and
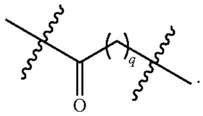
In certain embodiments, $L^2$ is absent. In certain embodiments, $L^2$ is
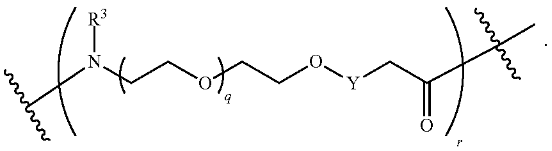
In certain embodiments, $L^2$ is
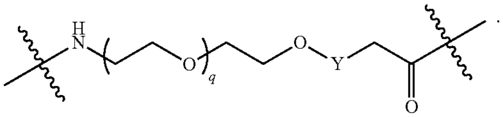
In certain embodiments, $L^2$ is
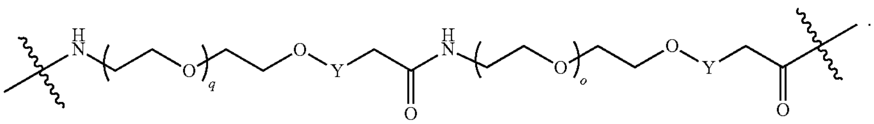

In certain embodiments, $L^2$ is
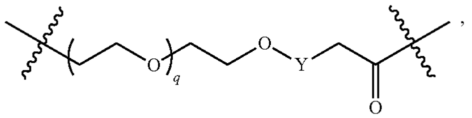
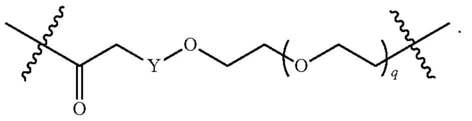
In certain embodiments, $L^2$ is
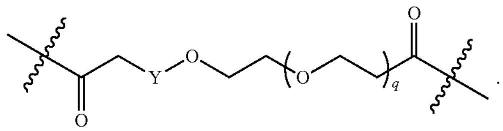
In certain embodiments, $L^2$
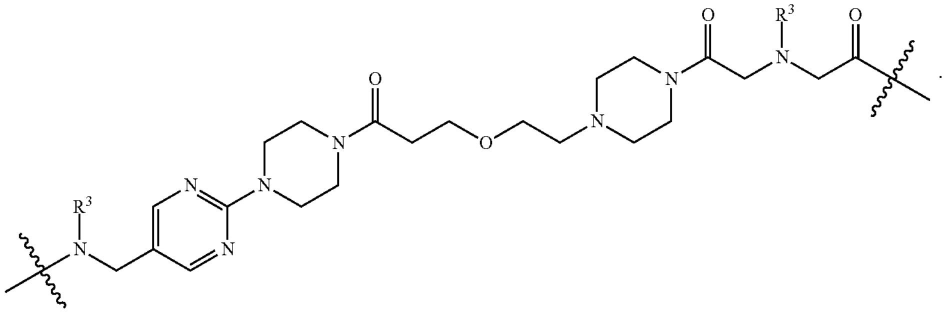
In certain embodiments, $L^2$ is
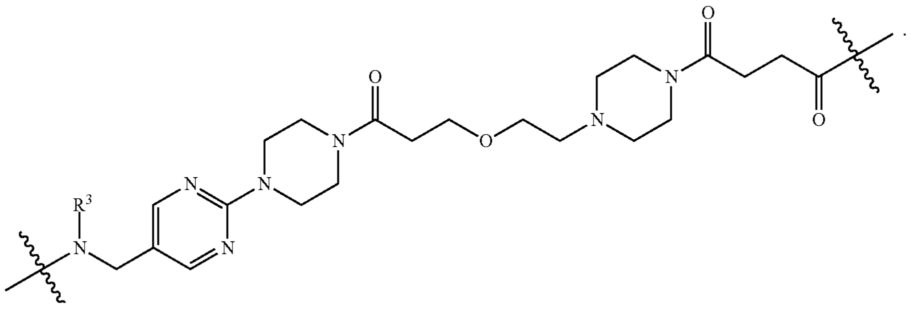
In certain embodiments, $L^2$
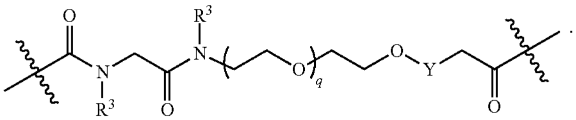
In certain embodiments, $L^2$ is
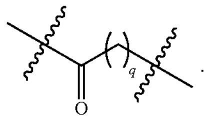

In certain embodiments, $L^2$ is
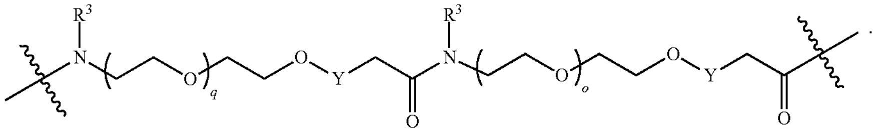
In certain embodiments, $L^2$ is
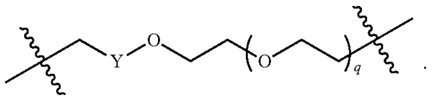
In certain embodiments, $L^2$ is
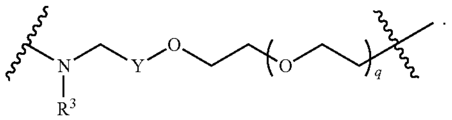
In certain embodiments, $L^3$ is absent. In certain embodiments, $L^3$ is
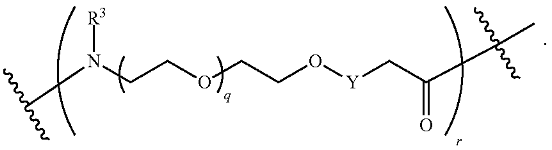
In certain embodiments, $L^3$ is
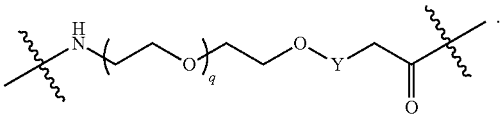
In certain embodiments, $L^3$ is
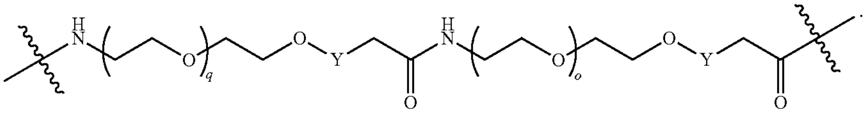
In certain embodiments, $L^3$ is
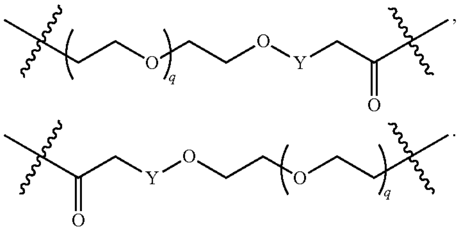
In certain embodiments, $L^3$ is
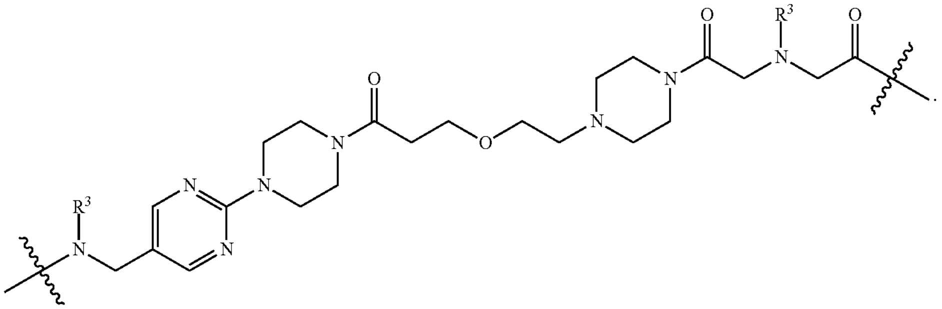

In certain embodiments, $L^3$ is
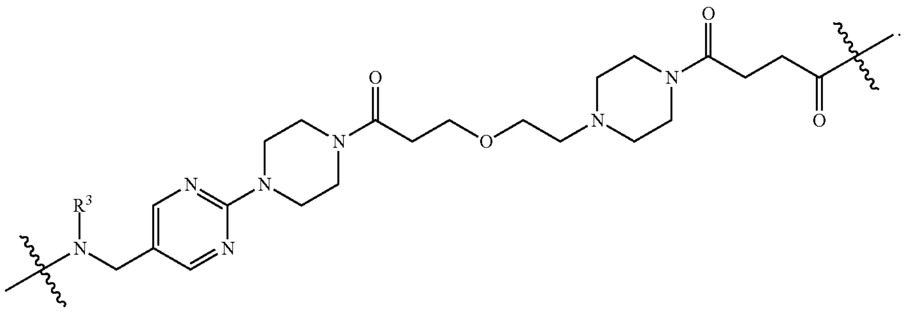
In certain embodiments $L^3$ is
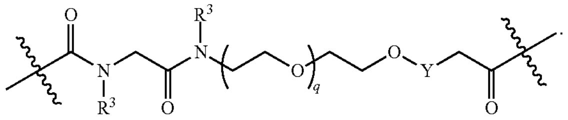
In certain embodiments, $L^3$ is
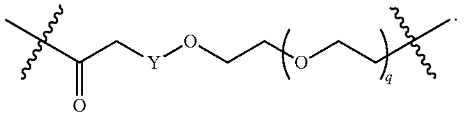
In certain embodiments, $L^3$ is In certain embodiments, $L^2$ is
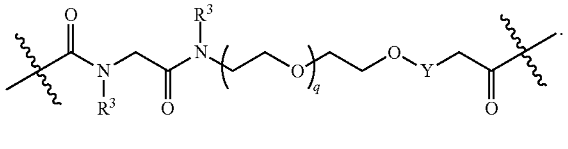
In certain embodiments, $L^2$ is
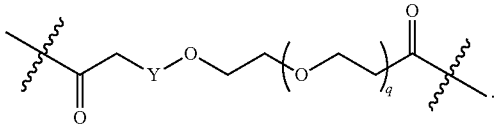
In certain embodiments, $L^2$ is
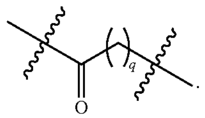
In certain embodiments, $L^3$ is
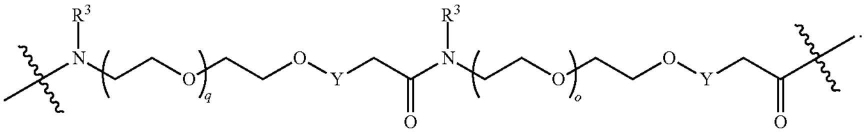

In certain embodiments, $L^3$ is
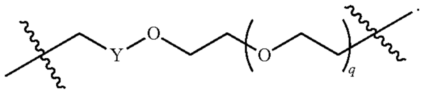
In certain embodiments, $L^3$ is
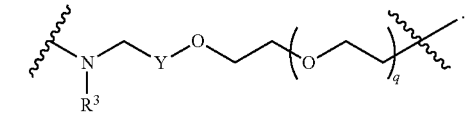
As described above, $A^1$ and $A^2$ are independently absent or are independently selected from
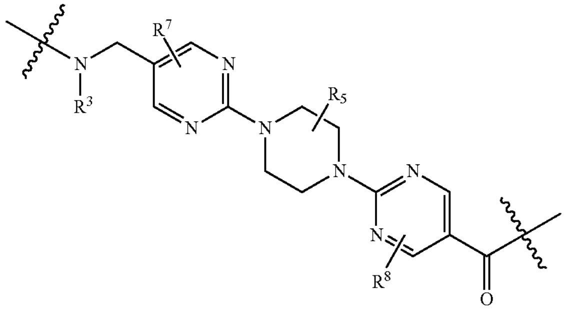
,
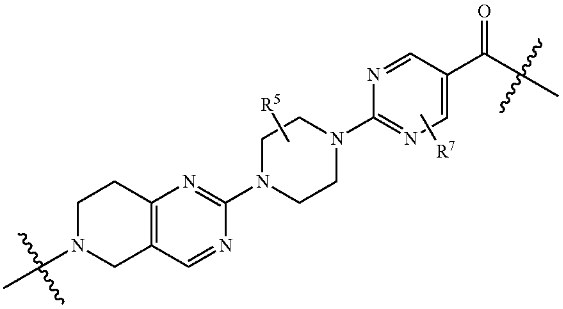
,
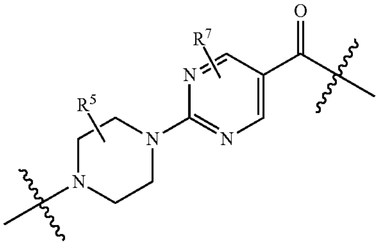
,
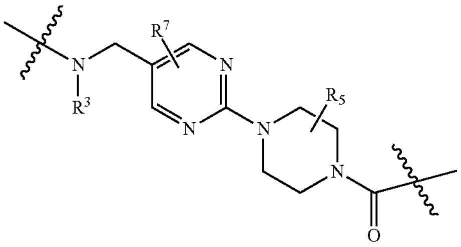
,
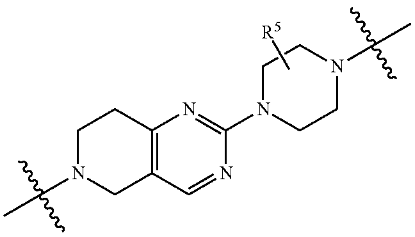
,
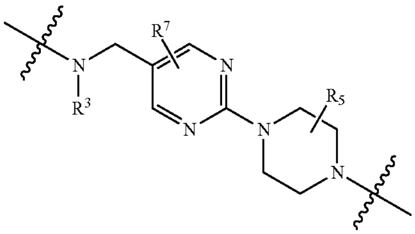
,
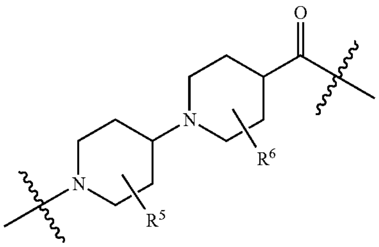
,
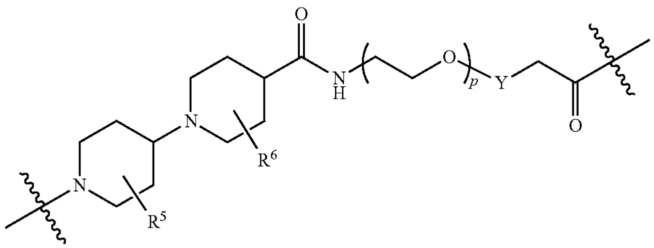
,
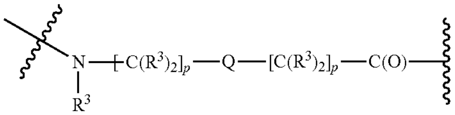
,
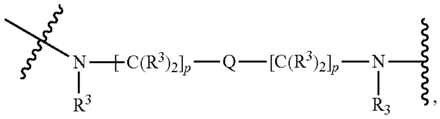
,
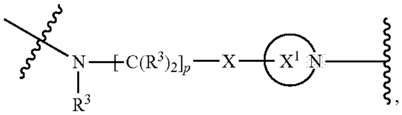
,
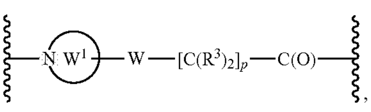
,
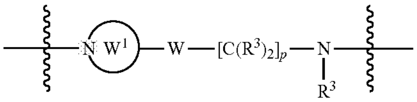
,
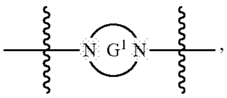
,
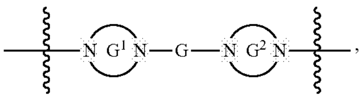
, -continued
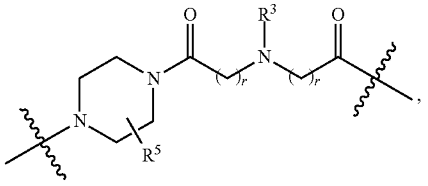
,
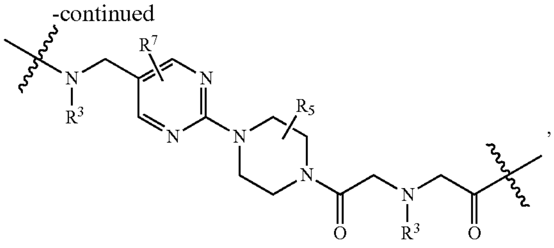
,
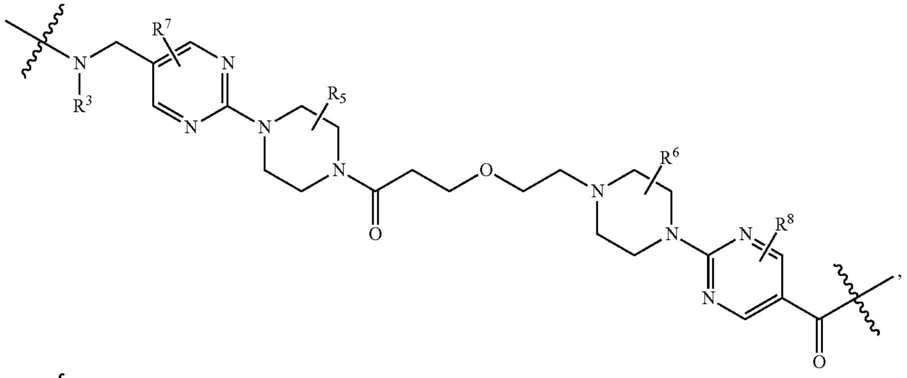
,
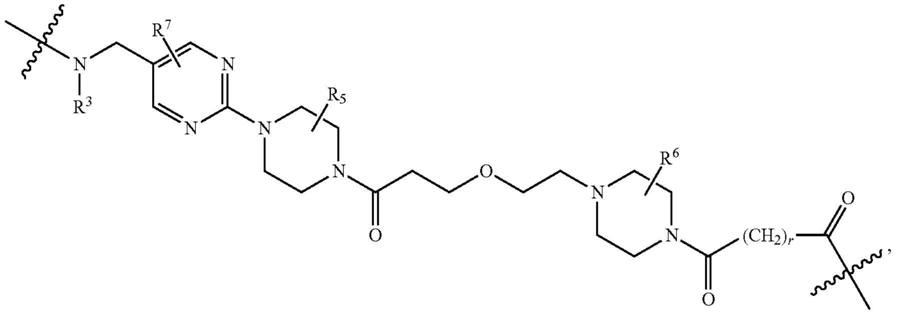
,
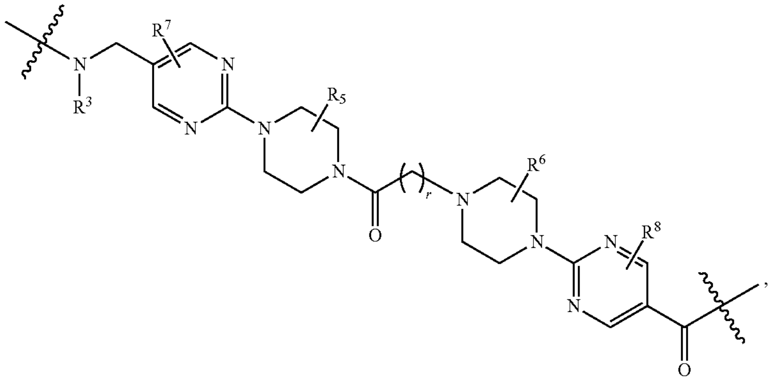
, and
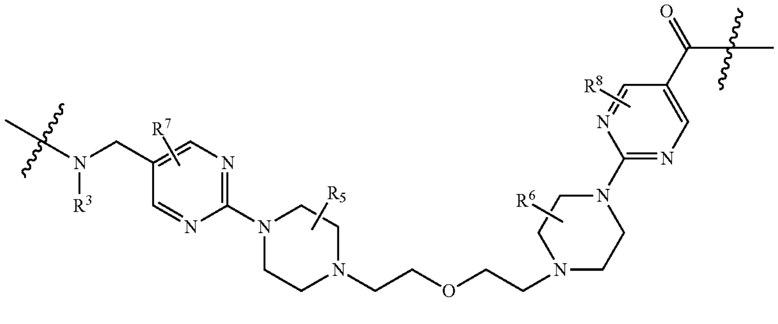
;
each Q is independently 1 to 3 rings selected from arylene, cycloalkylene, heteroarylene, and heterocyclylene;
each X is independently absent or 1 to 2 rings selected from arylene, cycloalkylene, heteroarylene, and heterocyclylene;

each $X^1$ is independently a heteroarylene or heterocyclylene ring;

each W is independently absent or 1 to 2 rings selected from arylene, cycloalkylene, heteroarylene, and heterocyclylene;

each $W^1$ is independently a heteroarylene or heterocyclylene ring;

each G is independently absent or a ring selected from arylene, cycloalkylene, heteroarylene, and heterocyclylene;

each $G^1$ and $G^2$ are independently heteroarylene or heterocyclylene ring.

As described above for Formula Ia, $A^1$ and $A^2$ are independently absent or are independently selected from

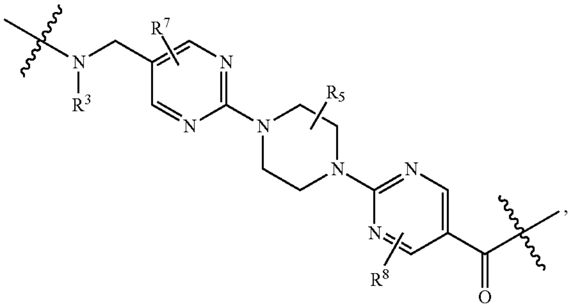

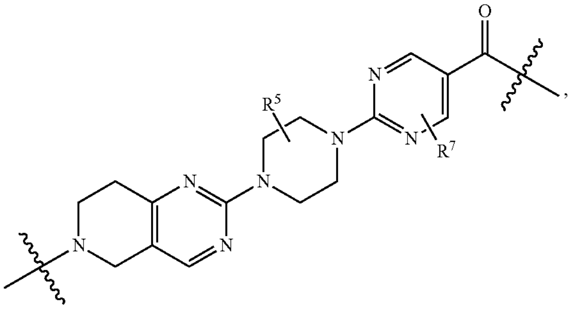

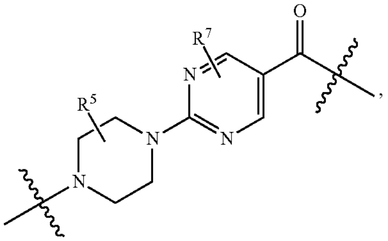

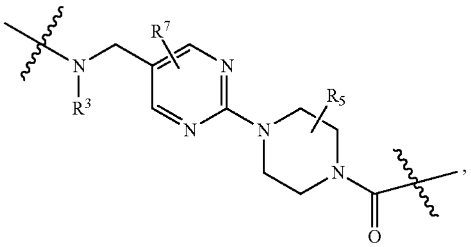

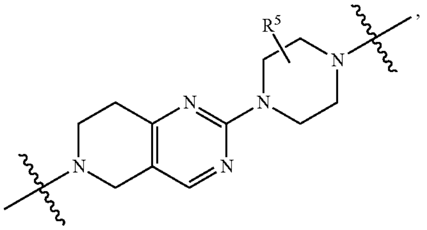

-continued

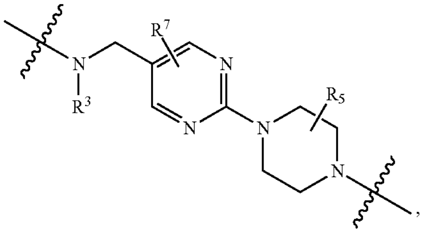

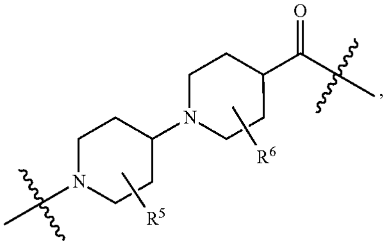

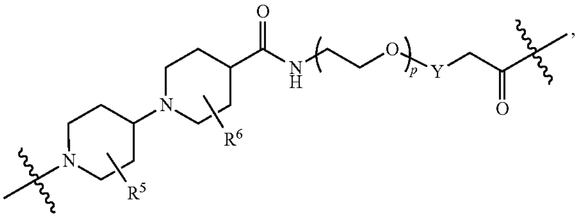

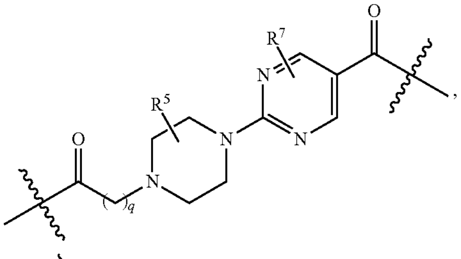

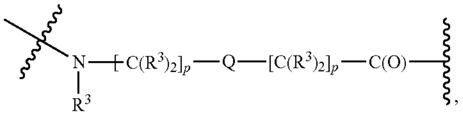

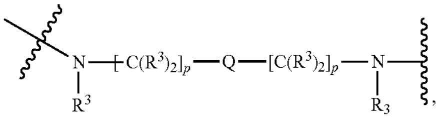

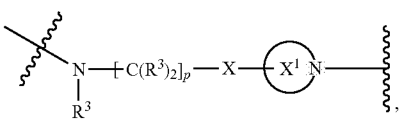

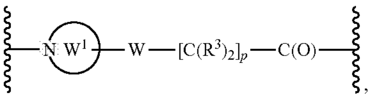

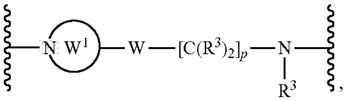

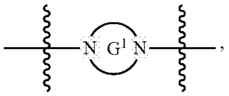

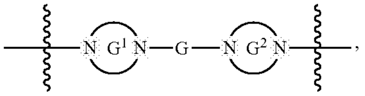

-continued

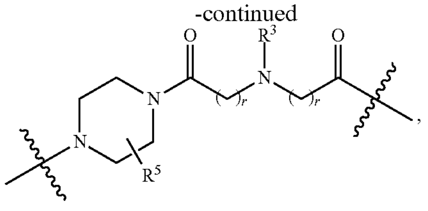

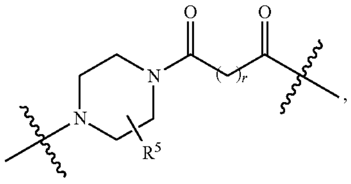

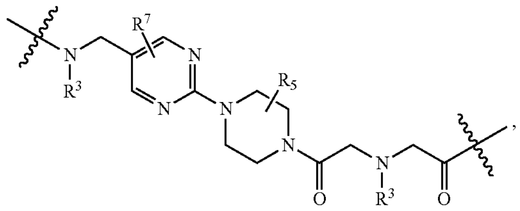

and

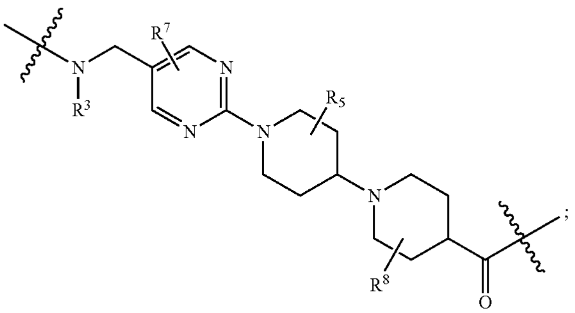

each is independently 1 to 3 rings selected rom arylene, eye oa ene, heteroarylene, and heterocyclylene;

each X is independently absent or 1 to 2 rings selected from arylene, cycloalkylene, heteroarylene, and heterocyclylene;

each $X^1$ is independently a heteroarylene or heterocyclylene ring;

each W is independently absent or 1 to 2 rings selected from arylene, cycloalkylene, heteroarylene, and heterocyclylene;

each $W^1$ is independently a heteroarylene or heterocyclylene ring;

each G is independently absent or a ring selected from arylene, cycloalkylene, heteroarylene, and heterocyclylene;

each $G^1$ and $G^2$ are independently heteroarylene or heterocyclylene ring.

As described above for Formula Ic, $A^1$ and $A^2$ are independently absent or are independently selected from

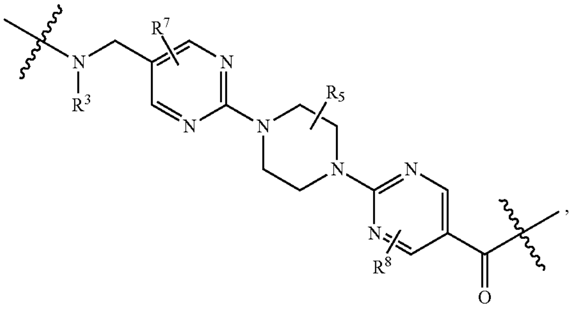

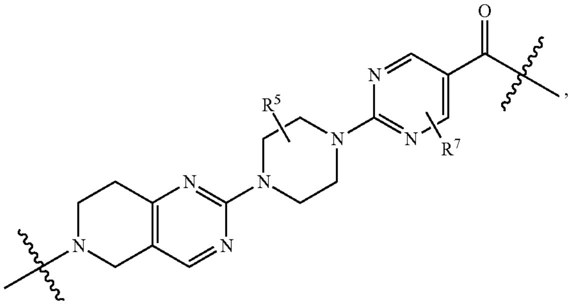

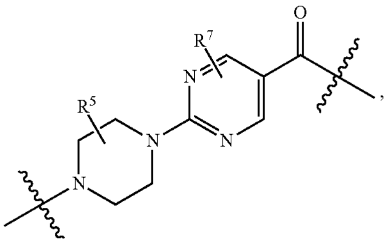

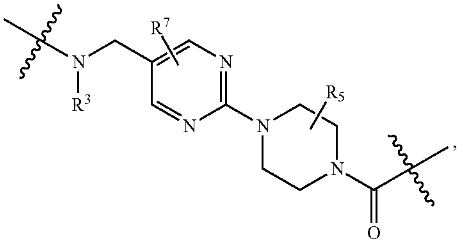

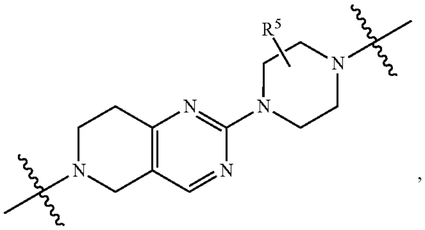

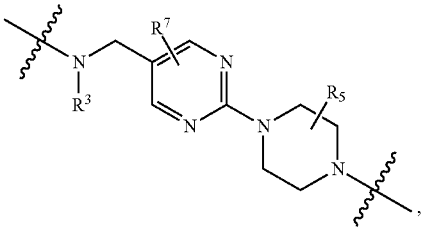

-continued

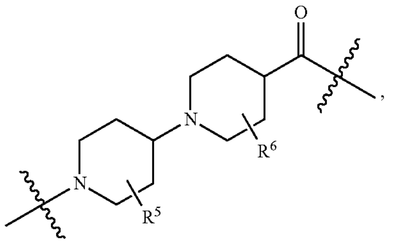

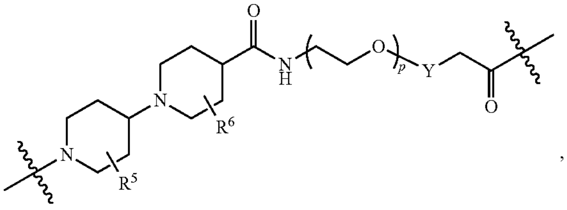

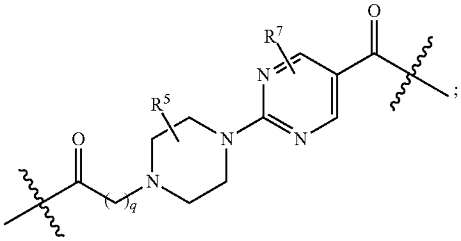

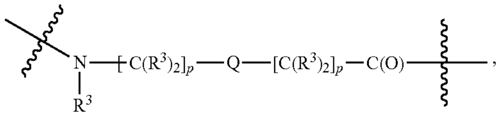

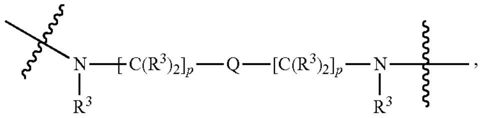

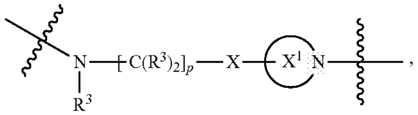

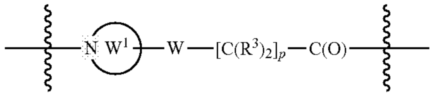

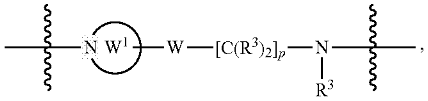

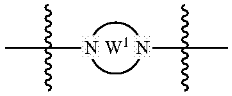

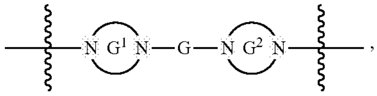

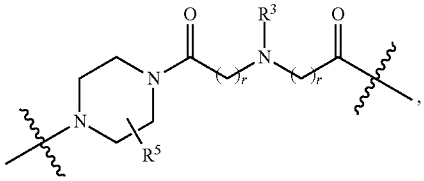

-continued

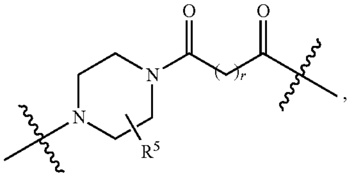

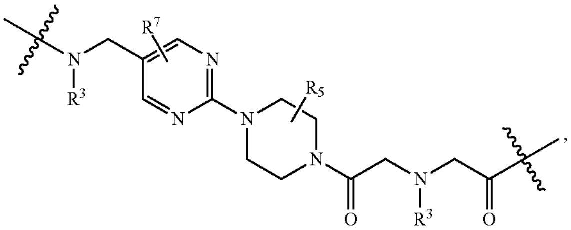

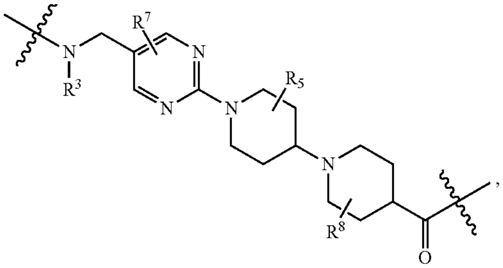

and

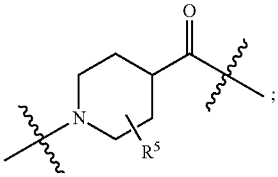

each Q is independently 1 to 3 rings selected from arylene, cycloalkylene, heteroarylene, and heterocyclylene;

each X is independently absent or 1 to 2 rings selected from arylene, cycloalkylene, heteroarylene, and heterocyclylene;

each $X^1$ is independently a heteroarylene or heterocyclylene ring;

each W is independently absent or 1 to 2 rings selected from arylene, cycloalkylene, heteroarylene, and heterocyclylene;

each $W^1$ is independently a heteroarylene or heterocyclylene ring;

each G is independently absent or a ring selected from arylene, cycloalkylene, heteroarylene, and heterocyclylene;

each $G^1$ and $G^2$ are independently heteroarylene or heterocyclylene ring;

For Formula I, the bond on the left side of $A^1$, as drawn, is bound to —C(=$Z^1$)— or $L^2$; and the bond on the right side of the $A^2$ moiety, as drawn, is bound to B or $L^3$. For Formula II, the bond on the left side of $A^1$, as drawn, is bound to —C(=$Z^1$)—; and the bond on the right side of the $A^2$ moiety, as drawn, is bound to B. For Formula Ia and Ic, the bond on the left side of $A^1$, as drawn, is bound to —C(=$Z^1$)— or $L^2$; and wherein the bond on the right side of the $A^2$ moiety, as drawn, is bound to B or $L^3$.-

In certain embodiments, $A^1$ is absent. In certain embodiments, $A^1$ is

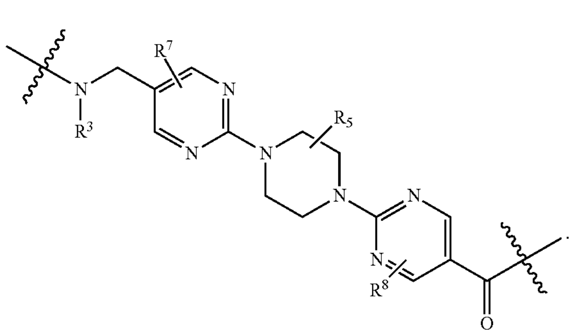

In certain embodiments, $A^1$ is

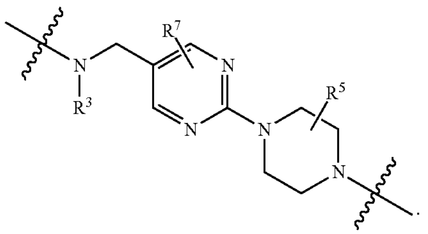

In certain embodiments, $A^1$ is

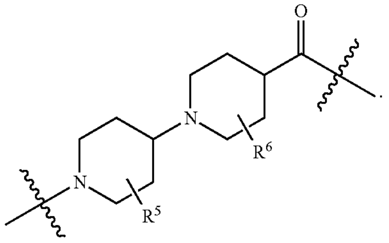

In certain embodiments, $A^1$ is

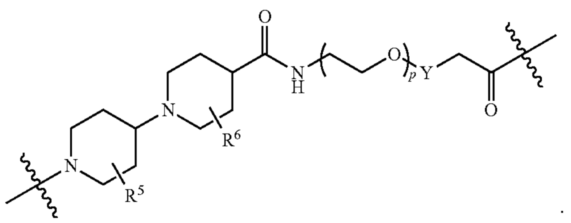

In certain embodiments, $A^1$ is

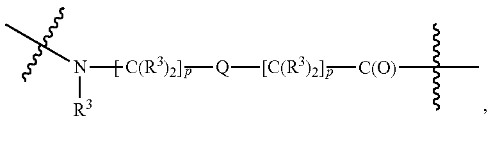

wherein each Q is independently 1 to 3 rings selected from arylene, cycloalkylene, heteroarylene, and heterocyclylene.

In certain embodiments, $A^1$ is

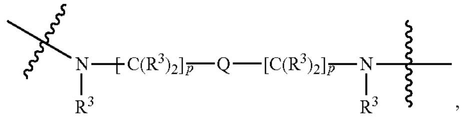

wherein each Q is independently 1 to 3 rings selected from arylene, cycloalkylene, heteroarylene, and heterocyclylene.

In certain embodiments, $A^1$ is

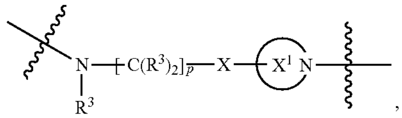

wherein each X is independently absent or 1 to 2 rings selected from arylene, cycloalkylene, heteroarylene, and heterocyclylene; and each $X^1$ is a heteroarylene or heterocyclylene ring.

In certain embodiments, $A^1$ is

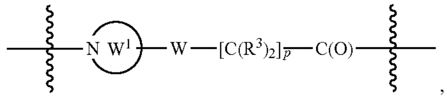

wherein each W is independently absent or 1 to 2 rings selected from arylene, cycloalkylene, heteroarylene, and heterocyclylene; and each $W^1$ is a heteroarylene or heterocyclylene ring.

In certain embodiments, $A^1$ is

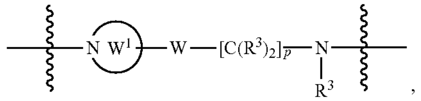

wherein each W is independently absent or 1 to 2 rings selected from arylene, cycloalkylene, heteroarylene, and heterocyclylene; and each $W^1$ is a heteroarylene or heterocyclylene ring.

In certain embodiments, $A^1$ is

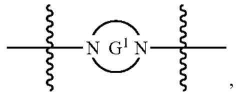

wherein each G is independently absent or a ring selected from arylene, cycloalkylene, heteroarylene, and heterocyclylene.

In certain embodiments, $A^1$ is

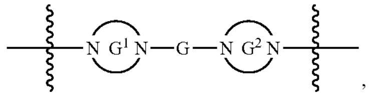

wherein each G is independently absent or a ring selected from arylene, cycloalkylene, heteroarylene, and heterocyclylene; and each $G^1$ and $G^2$ are independently heteroarylene or heterocyclylene ring.
In certain embodiments, $A^1$ is
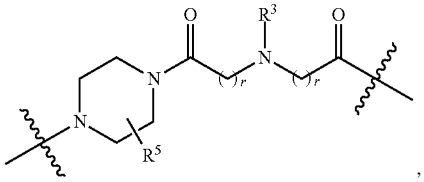
,
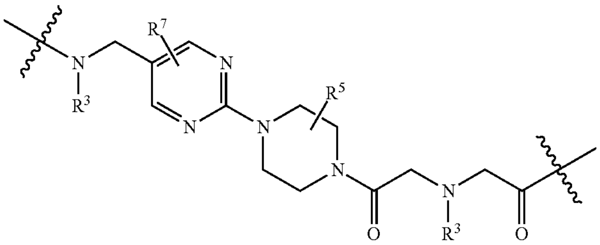
,
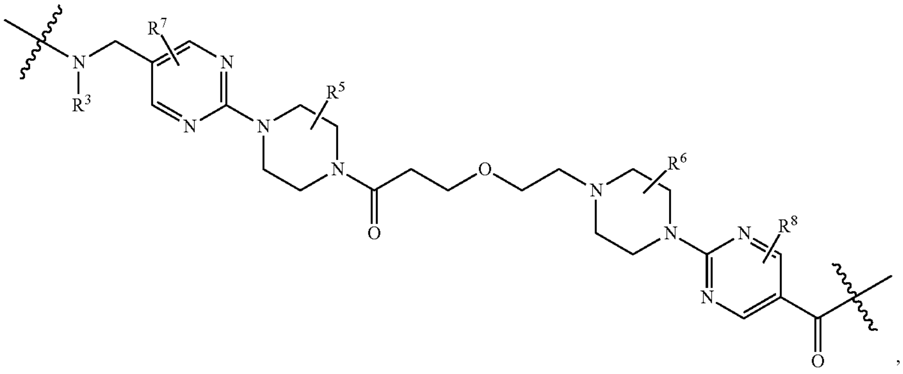
,
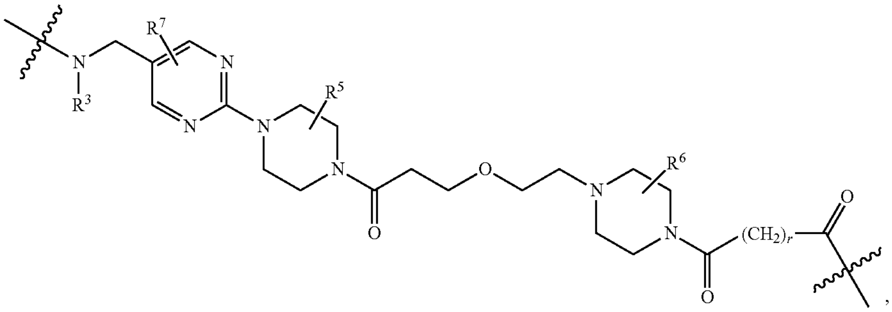
,
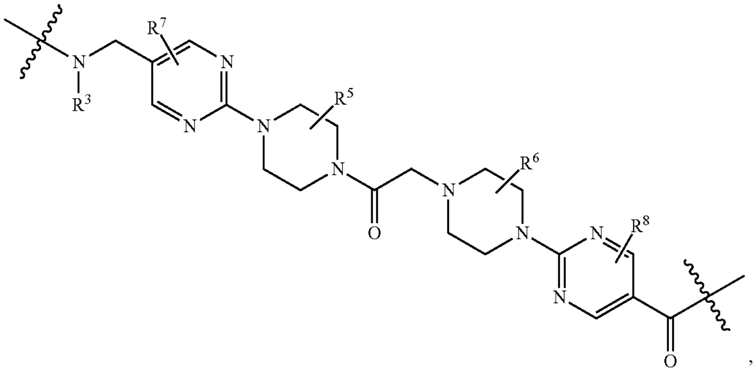
, or -continued
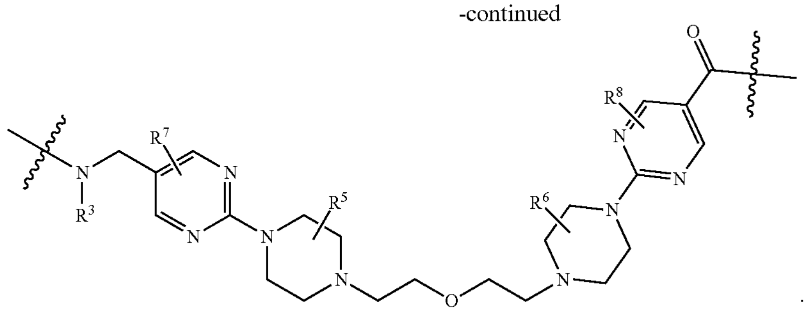
In certain embodiments, $A^1$ is
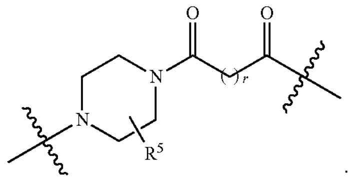
In certain embodiments, $A^1$ is
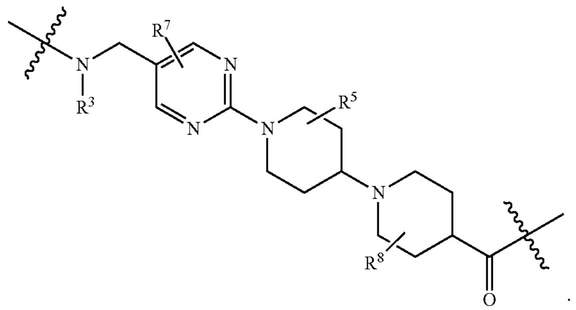
In certain embodiments, $A^1$ is
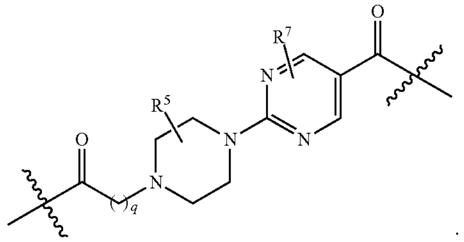
In certain embodiments, $A^1$ is
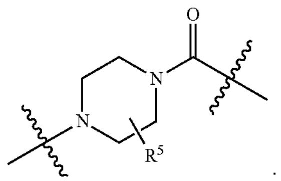
In certain embodiments, $A^2$ is absent. In certain embodiments, $A^2$ is
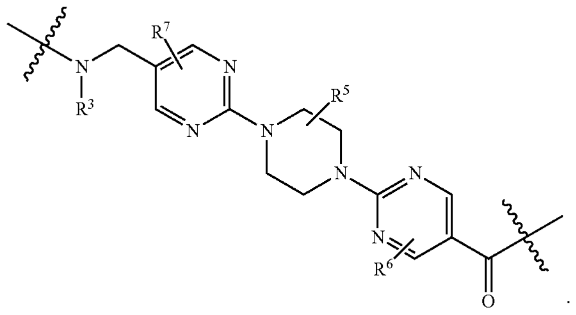
In certain embodiments, $A^2$ is
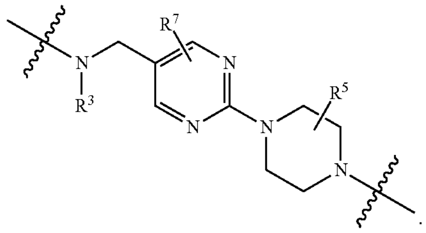
In certain embodiments, $A^2$ is
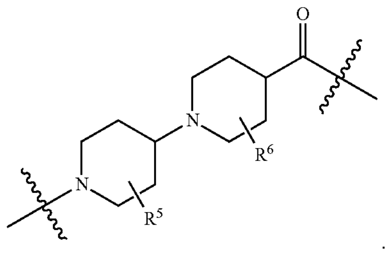

In certain embodiments, $A^2$ is

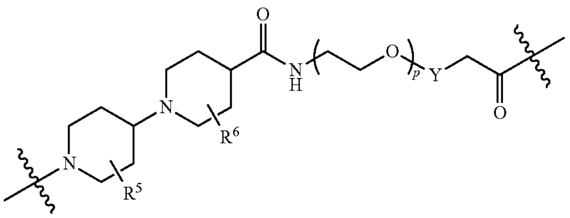

.

In certain embodiments, $A^2$ is

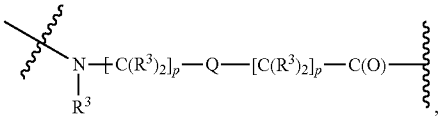

wherein each Q is independently 1 to 3 rings selected from arylene, cycloalkylene, heteroarylene, and heterocyclylene.

In certain embodiments, $A^2$ is

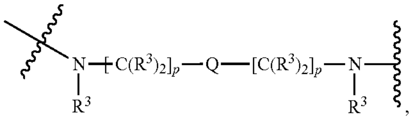

wherein each Q is independently 1 to 3 rings selected from arylene, cycloalkylene, heteroarylene, and heterocyclylene.

In certain embodiments, $A^2$ is

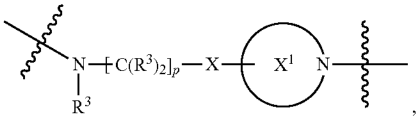

wherein each X is independently absent or 1 to 2 rings selected from arylene, cycloalkylene, heteroarylene, and heterocyclylene; and each $X^1$ is independently a heteroarylene or heterocyclylene ring.

In certain embodiments, $A^2$ is

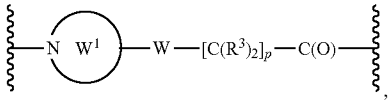

wherein each W is independently absent or 1 to 2 rings selected from arylene, cycloalkylene, heteroarylene, and heterocyclylene; and each $W^1$ is independently a heteroarylene or heterocyclylene ring.

In certain embodiments, $A^2$ is

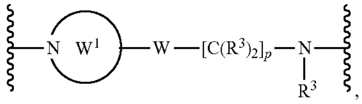

wherein each W is independently absent or 1 to 2 rings selected from arylene, cycloalkylene, heteroarylene, and heterocyclylene; and each $W^1$ is independently a heteroarylene or heterocyclylene ring.

In certain embodiments, $A^2$ is

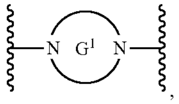

wherein each G is independently absent or a ring selected from arylene, cycloalkylene, heteroarylene, and heterocyclylene.

In certain embodiments, $A^2$ is

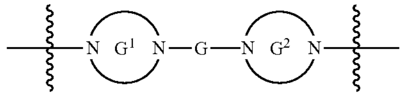

, wherein each G is independently absent or a ring selected from arylene, cycloalkylene, heteroarylene, and heterocyclylene; and each $G^1$ and $G^2$ are independently a heteroarylene or heterocyclylene ring.

In certain embodiments, $A^2$ is

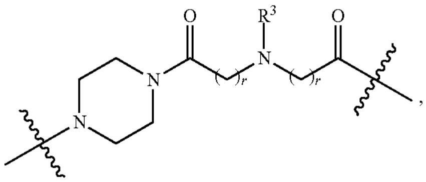

,

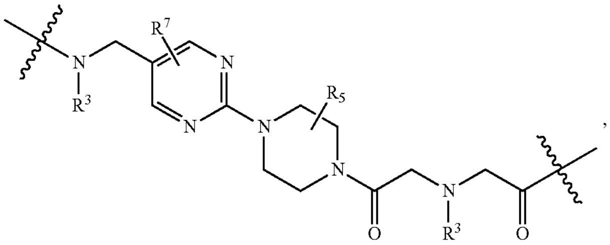

,

-continued
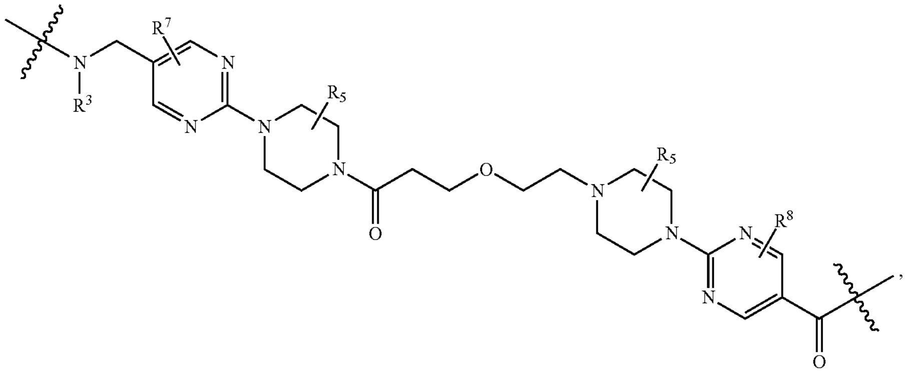
,
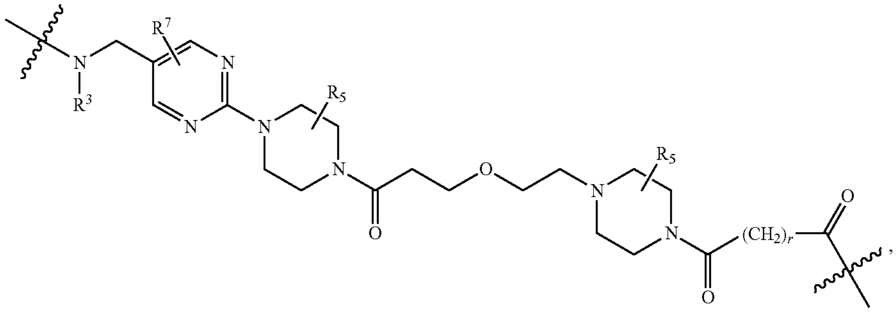
,
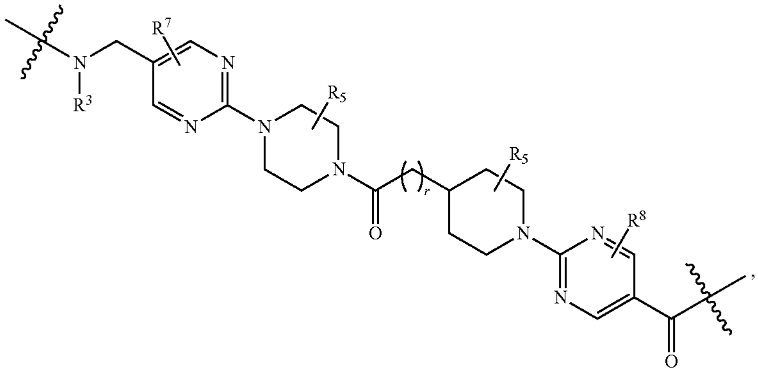
, or
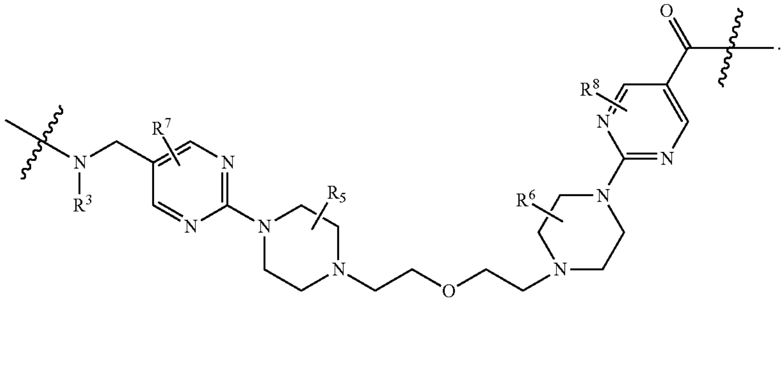
.

In certain embodiments, $A^2$ is
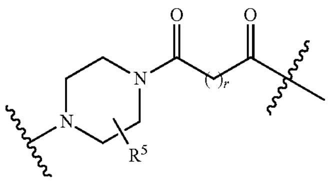
.
In certain embodiments, $A^2$ is
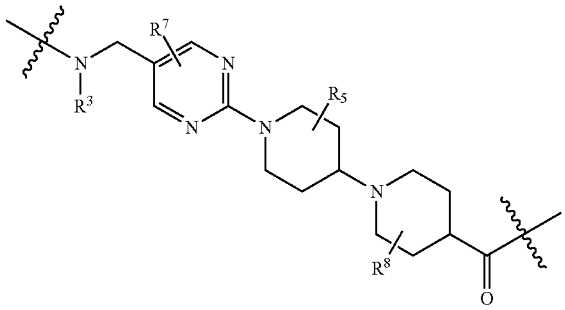
.
In certain embodiments, $A^2$ is
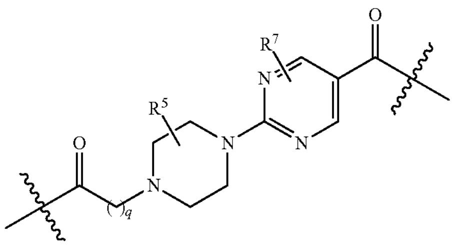
.
In certain embodiments, $A^2$ is
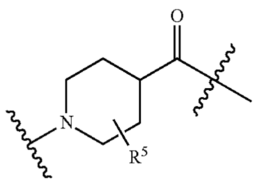
.
As described above, each B is independently selected from
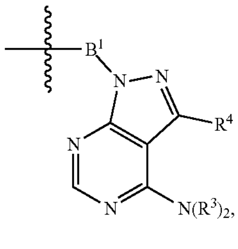
-continued
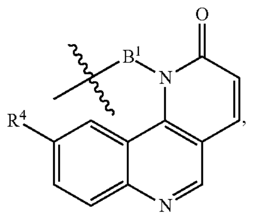
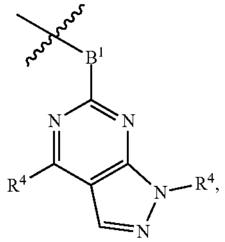
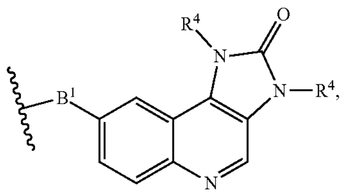
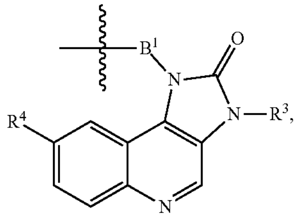
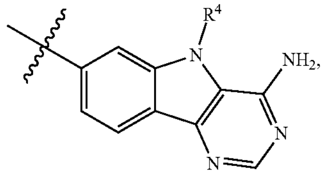
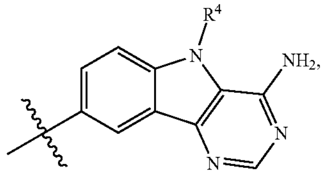
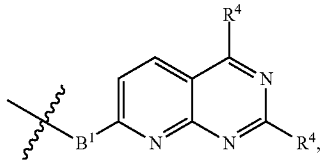
and
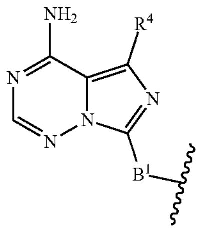

-continued

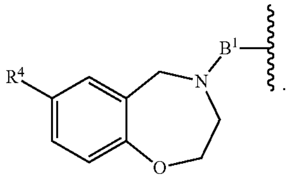

In certain embodiments, B is

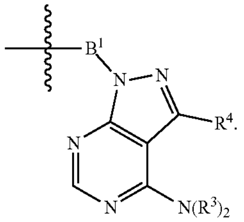

In certain embodiments, B is

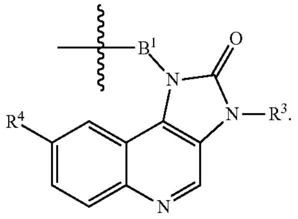

In certain embodiments, B is

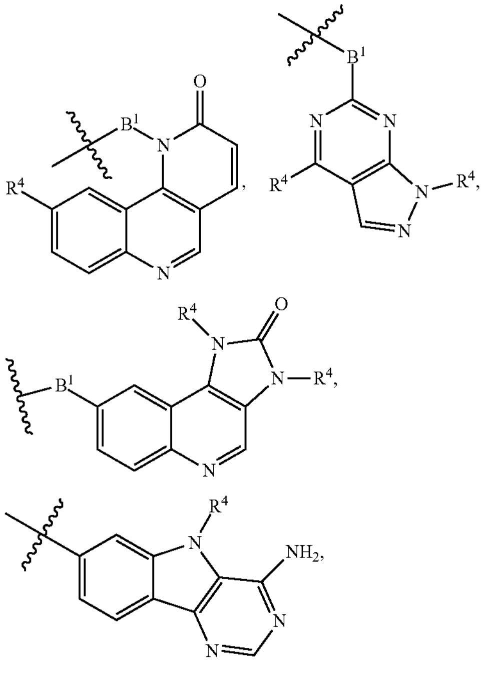

-continued

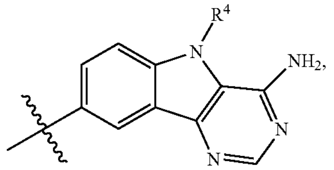

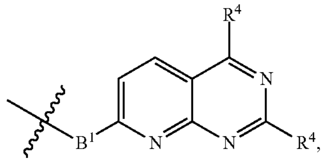

or

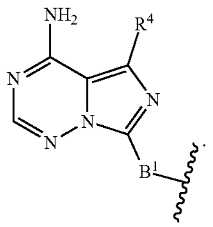

In certain embodiments, B is

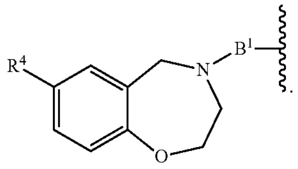

As described above, each $B^1$ is independently selected from

 $NR^3$-$(C(R^3)_2)_n$-,

 $NR^3$-$(C(R^3)_2)_n$-$(C_6$-$C_{10})$arylene-$(C(R^3)_2)$n-,

 $NR^3$-$(C(R^3)_2)_n$-heteroarylene-,

 $(C_6$-$C_{10})$arylene-,

 $NR^3$-$(C(R^3)_2)_n$-$NR^3C(O)$-,

 $NR^3$-$(C(R^3)_2)_n$-heteroarylene-heteroclylene-$(C_6C_{10})$arylene,

 heteroarylene-heteroclylene-$(C_6C_{10})$arylene,

-continued
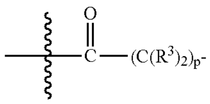
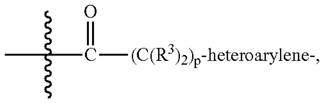
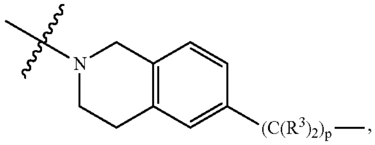
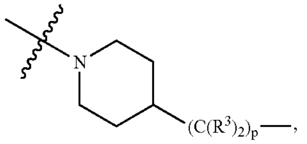
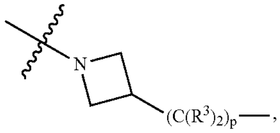
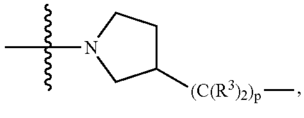
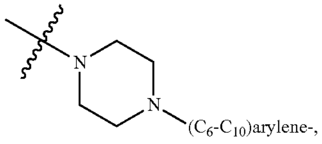
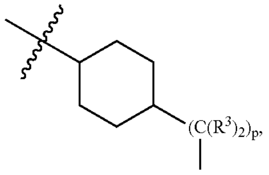
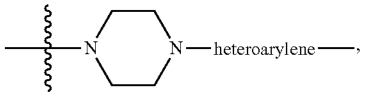
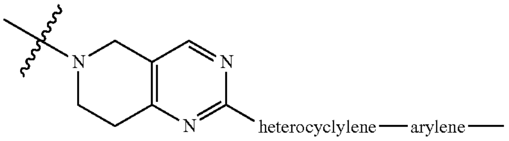
and
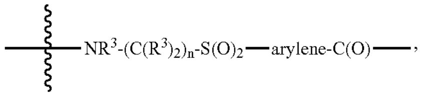
wherein the
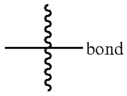
bond on the left side of $B^1$,
as drawn, is bound to $A^2$ or $L^1$; and wherein the heteroarylene, heterocyclylene, and arylene are each independently optionally substituted with alkyl, hydroxyalkyl, haloalkyl, alkoxy, halogen, or hydroxyl.
As described above for Formula Ic, each $B^1$ is independently selected from
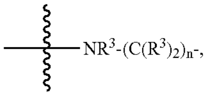
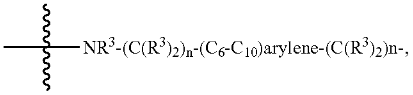
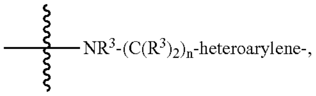
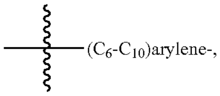
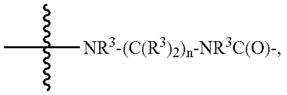
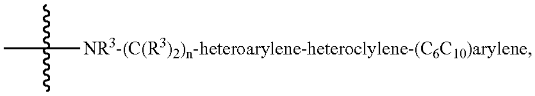
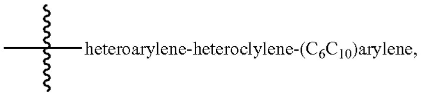
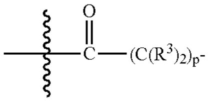
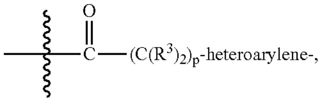
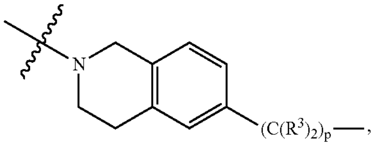
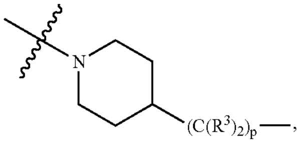
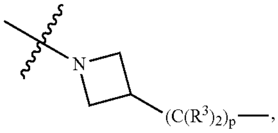
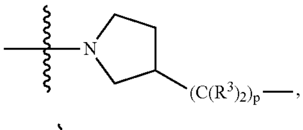
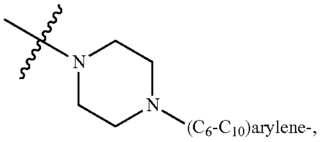

-continued

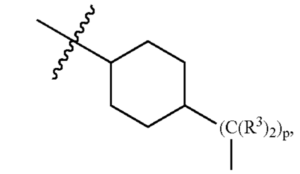

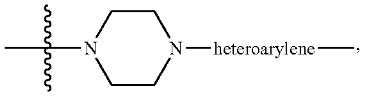

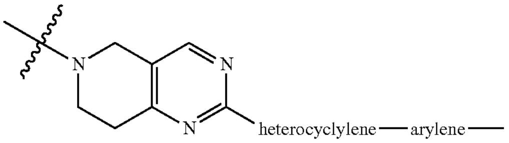

and

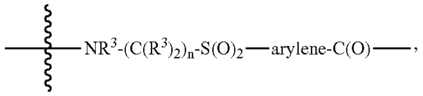

wherein the

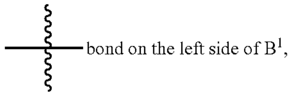

as drawn, is bound to $A^2$, $L^3$, or $L^1$; and wherein the heteroarylene, heterocyclylene, and arylene are each independently optionally substituted with alkyl, hydroxyalkyl, haloalkyl, alkoxy, halogen, or hydroxyl.

In certain embodiments, $B^1$ is

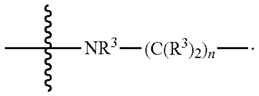

In certain embodiments, $B^1$ is

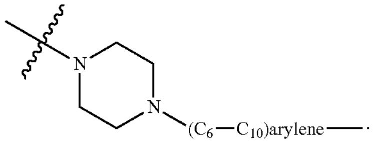

In certain embodiments, $B^1$ is

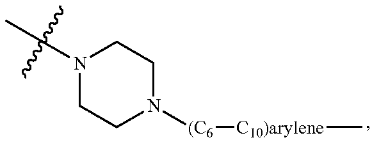

wherein arylene is optionally substituted with haloalkyl.

In certain embodiments, $B^1$ is

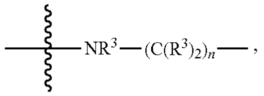

-continued

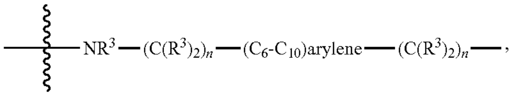

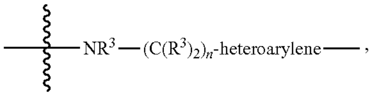

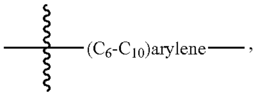

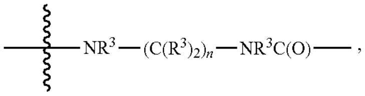

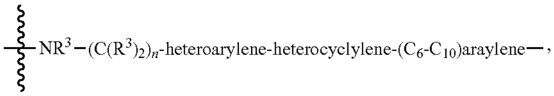

or

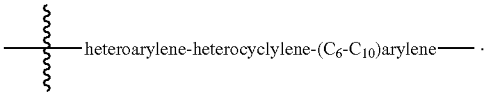

In certain embodiments, $B^1$ is

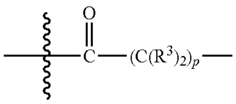

or

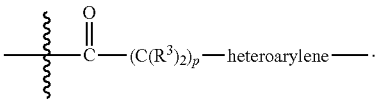

In certain embodiments, $B^1$ is

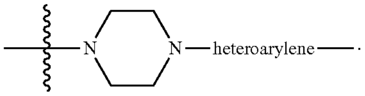

In certain embodiments, $B^1$ is

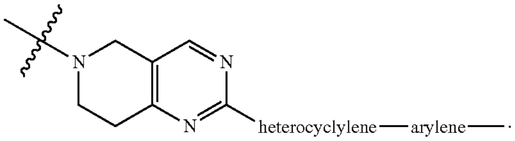

In certain embodiments, $B^1$ is

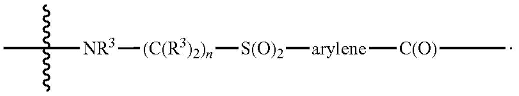

In certain embodiments, $B^1$ is

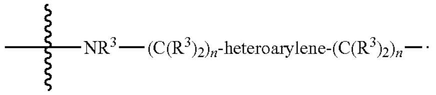

In certain embodiments, $B^1$ is

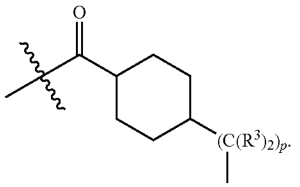

In certain embodiments, $B^1$ is

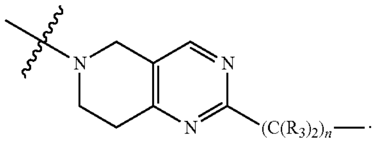

In certain embodiments, $B^1$ is

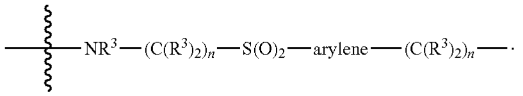

In certain embodiments, in $B^1$, the heteroaryl, heterocyclyl, and arylene are optionally substituted with alkyl, hydroxyalkyl, haloalkyl, alkoxy, halogen, or hydroxyl.

In certain embodiments, $R^3$ is H. In certain embodiments, $R^3$ is $(C_1\text{-}C_6)$alkyl.

In certain embodiments, $R^4$ is H. In certain embodiments, $R^4$ is $(C_1\text{-}C_6)$alkyl. In certain embodiments, $R^4$ is halogen. In certain embodiments, $R^4$ is 5-12 membered heteroaryl, 5-12 membered heterocyclyl, or $(C_6\text{-}C_{10})$aryl, wherein the heteroaryl, heterocyclyl, and aryl are optionally substituted with —$N(R^3)_2$, —$OR^3$, halogen, $(C_1\text{-}C_6)$alkyl, —$(C_1\text{-}C_6)$alkylene-heteroaryl, —$(C_1\text{-}C_6)$alkylene-CN, or —C(O)$NR^3$-heteroaryl. In certain embodiments, $R^4$ is —C(O)$NR^3$-heterocyclyl. In certain embodiments, $R^4$ is 5-12 membered heteroaryl, optionally substituted with —$N(R^3)_2$ or —$OR^3$.

As described above, each $R^5$ is independently H, $(C_1\text{-}C_6)$alkyl, —C(O)$OR^3$, or —$N(R^3)_2$, wherein the alkyl of $(C_1\text{-}C_6)$alkyl is optionally substituted with —$N(R^3)_2$ or —$OR^3$. In certain embodiments, $R^5$ is H. In certain embodiments, $R^5$ is $(C_1\text{-}C_6)$alkyl, wherein the alkyl is optionally substituted with —$N(R^3)_2$ or —$OR^3$. In certain embodiments, $R^5$ is —C(O)$OR^3$. In certain embodiments, $R^5$ is —$N(R^3)_2$.

As described above, each $R^6$ is independently H, $(C_1\text{-}C_6)$alkyl, —C(O)$OR^3$, or —$N(R^3)_2$, wherein the alkyl of $(C_1\text{-}C_6)$alkyl is optionally substituted with —$N(R^3)_2$ or —$OR^3$. In certain embodiments, $R^6$ is H. In certain embodiments, $R^6$ is $(C_1\text{-}C_6)$alkyl, wherein the alkyl is optionally substituted with —$N(R^3)_2$ or —$OR^3$. In certain embodiments, $R^6$ is —C(O)$OR^3$. In certain embodiments, $R^6$ is —$N(R^3)_2$.

le;1.5qAs described above, each $R^7$ is independently H, $(C_1\text{-}C_6)$alkyl, —C(O)$OR^3$, or —$N(R^3)_2$, wherein the alkyl of $(C_1\text{-}C_6)$alkyl is optionally substituted with —$N(R^3)_2$ or —$OR^3$. In certain embodiments, $R^7$ is H. In certain embodiments, $R^7$ is $(C_1\text{-}C_6)$alkyl, wherein the alkyl is optionally substituted with —$N(R^3)_2$ or —$OR^3$. In certain embodiments, $R^7$ is —C(O)$OR^3$. In certain embodiments, $R^7$ is —$N(R^3)_2$.

As described above, each $R^8$ is independently H, $(C_1\text{-}C_6)$alkyl, —C(O)$OR^3$, or —$N(R^3)_2$, wherein the alkyl of $(C_1\text{-}C_6)$alkyl is optionally substituted with —$N(R^3)_2$ or —$OR^3$. In certain embodiments, $R^8$ is H. In certain embodiments, $R^8$ is $(C_1\text{-}C_6)$alkyl, wherein the alkyl is optionally substituted with —$N(R^3)_2$ or —$OR^3$. In certain embodiments, $R^8$ is —C(O)$OR^3$. In certain embodiments, $R^8$ is —$N(R^3)_2$.

As described above, each Y is independently $C(R^3)_2$ or a bond. In certain embodiments, Y is $C(R^3)_2$. In certain embodiments, Y is $CH_2$. In certain embodiments, Y is a bond.

In certain embodiments, n is 1, 2, 3, 4, 5, 6, 7, or 8, or any range derivable therein. In certain embodiments, n is 1, 2, 3, or 4. In certain embodiments, n is 5, 6, 7, or 8. In certain embodiments, n is 9, 10, 11, or 12.

In certain embodiments, o is an integer from zero to 10, or any range derivable therein. In certain embodiments, o is 0, 1, 2, 3, 4, or 5. In certain embodiments, o is 6, 7, 8, 9, or 10. In certain embodiments, o is one to 7. In certain embodiments, o is one to 8. In certain embodiments, o is one to 9. In certain embodiments, o is 3 to 8.

In certain embodiments, o is an integer from zero to 30, or any range derivable therein. In certain embodiments, o is an integer from zero to 30, 29, 28, 27, or 26. In certain embodiments, o is an integer from zero to 25, 24, 23, 22, or 21. In certain embodiments, o is an integer from zero to 20, 19, 18, 17, or 16. In certain embodiments, o is an integer from zero to 15, 14, 13, 12, or 11.

In certain embodiments, p is 0, 1, 2, 3, 4, 5, or 6, or any range derivable therein. In certain embodiments, p is 7, 8, 9, 10, 11, or 12. In certain embodiments, p is 0, 1, 2, or 3. In certain embodiments, p is 4, 5, or 6.

In certain embodiments, q is an integer from zero to 10, or any range derivable therein. In certain embodiments, q is 0, 1, 2, 3, 4, or 5. In certain embodiments, q is 6, 7, 8, 9, or 10. In certain embodiments, q is one to 7. In certain embodiments, q is one to 8. In certain embodiments, q is one to 9. In certain embodiments, q is 3 to 8.

In certain embodiments, q is an integer from zero to 30, or any range derivable therein. In certain embodiments, q is an integer from zero to 30, 29, 28, 27, or 26. In certain embodiments, q is an integer from zero to 25, 24, 23, 22, or 21. In certain embodiments, q is an integer from zero to 20, 19, 18, 17, or 16. In certain embodiments, q is an integer from zero to 15, 14, 13, 12, or 11.

As described above, r is an integer from one to 6. In certain embodiments, r is one. In certain embodiments, r is 2. In certain embodiments, r is 3. In certain embodiments, r is 4. In certain embodiments, r is 5. In certain embodiments, r is 6.

As described above, when $R^{28}$ and $R^{40}$ are H, then $R^{32}$ is not =O. In certain embodiments, the compound is not rapamycin, as shown below:

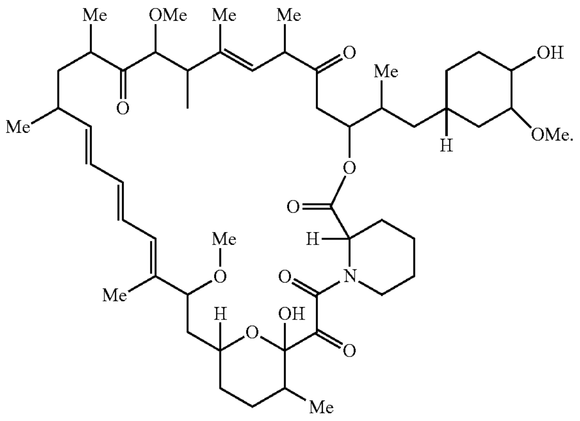 [SMILES: COC1CC2CCC(C)C(O)(O2)C(=O)C(=O)N2CCCCC2C(=O)OC(C(C)CC2CCC(O)C(OC)C2)CC(=O)C(C)/C=C(\C)C(C)C(OC)C(=O)C(C)CC(C)/C=C/C=C/C=C/1C]

In certain embodiments, in Formula Ia or Ic, $R^{32}$ is —O—C(═$Z^1$)—$R^{32a}$. In certain embodiments, $R^{32}$ is —O—C(═Z)—$R^{32a}$; wherein $R^{32a}$ is -$A^1$-$L^1$-$A^2$-B; -$A^1$-$A^2$-B; or -$L^2$-$A^1$-$L^1$-$A^2$-$L^3$-B. In certain embodiments, in Formula Ia or Ic, $R^{28}$ is —C(═$Z^1$)—$R^{28a}$. In certain embodiments, $R^{28}$ is —C(═$Z^1$)—$R^{28a}$; wherein $R^{28a}$ is -$A^1$-$L^1$-$A^2$-B; -$A^1$-$A^2$-B; or -$L^2$-$A^1$-$L^1$-$A^2$-$L^3$-B. In certain embodiments, in Formula Ia or Ic, $R^{40}$ is —C(═$Z^1$)—$R^{40a}$. In certain embodiments, $R^{40}$ is —C(═$Z^1$)—$R^{40a}$. wherein $R^{40a}$ is -$A^1$-$L^1$-$A^2$-B; -$A^1$-$A^2$-B; or -$L^2$-$A^1$-$L^1$-$A^2$-$L^3$-B.

The present disclosure provides a compound of Formula Ia or Ic, or a pharmaceutically acceptable salt or tautomer thereof, having one, two, or three of the following features:

a) $R^{32}$ is —O—C(═$Z^1$)—$R^{32a}$;

b) $R^{28}$ is —C(═$Z^1$)—$R^{28a}$;

c) $R^{40}$ is —C(═$Z^1$)—$R^{40a}$.

The present disclosure provides a compound of Formula Ia or Ic, or a pharmaceutically acceptable salt or tautomer thereof, having one, two, or three of the following features:

a) $R^{32}$ is —O—C(═$Z^1$)—$R^{32a}$; wherein $R^{32a}$ is -$A^1$-$L^1$-$A^2$-B; -$A^1$-$A^2$-B; or -$L^2$-$A^1$-$L^1$-$A^2$-$L^3$-B;

b) $R^{28}$ is —C(═$Z^1$)—$R^{28a}$; wherein $R^{28a}$ is -$A^1$-$L^1$-$A^2$-B; -$A^1$-$A^2$-B; or -$L^2$-$A^1$-$L^1$-$A^2$-$L^3$-B;

c) $R^{40}$ is —C(═$Z^1$)—$R^{40a}$. wherein $R^{40a}$ is -$A^1$-$L^1$-$A^2$-B; -$A^1$-$A^2$-B; or -$L^2$-$A^1$-$L^1$-$A^2$-$L^3$-B.

The present disclosure provides a compound of Formula Ia or Ic, or a pharmaceutically acceptable salt or tautomer thereof, having one, two, or three of the following features:

a) $R^{40}$ is —C(═$Z^1$)—$R^{40a}$;

b) $R^{40a}$ is -$A^1$-$L^1$-$A^2$-B; -$A^1$-$A^2$-B; -$L^2$-$A^1$-$L^1$-$A^2$-$L^3$-B;

c) $R^{32}$ is —$OR^3$, such as —OH.

The present disclosure provides a compound of Formula Ia or Ic, or a pharmaceutically acceptable salt or tautomer thereof, having one, two, three, or four of the following features:

a) one of $R^{28a}$, $R^{32a}$, and $R^{40a}$ is -$A^1$-$L^1$-$A^2$-B;

b) $A^1$ is absent;

c) $A^2$ is absent;

d) $L^1$ is

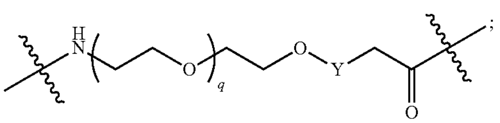

e) B is

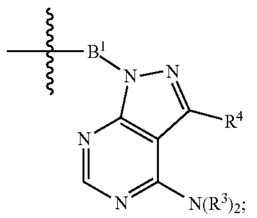

f) $B^1$ is

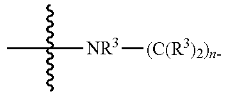

or

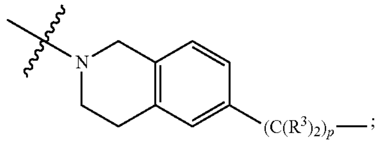

g) $R^4$ is 5-12 membered heteroaryl, optionally substituted with —$N(R^3)_2$ or —$OR^3$.

The present disclosure provides a compound of formula:

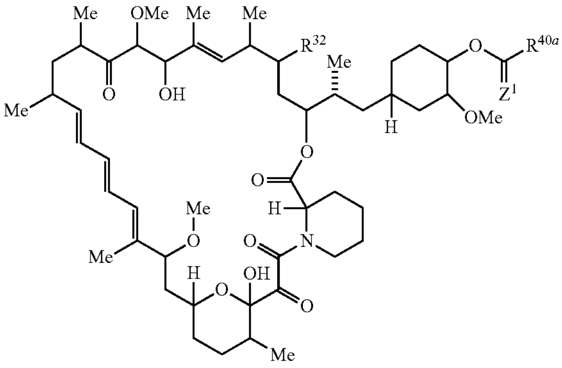

or

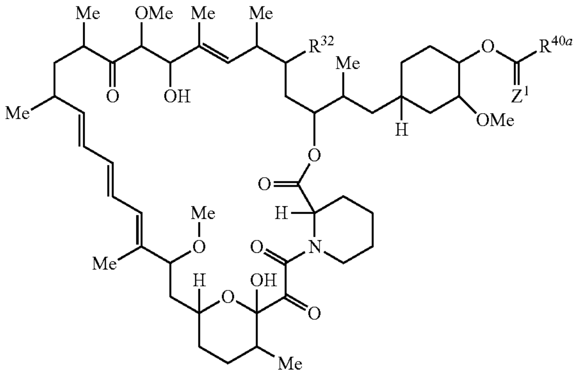

or a pharmaceutically acceptable salt or tautomer thereof, having one, two, three, or four of the following features:

a) $Z^1$ is O;

b) $A^1$ is absent;

c) $L^1$ is

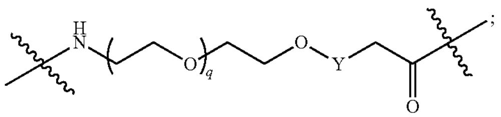

d) B is

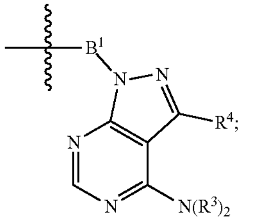

e) $B^1$ is

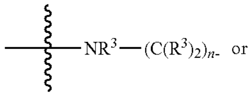

or

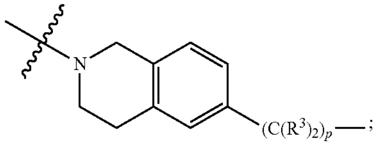

f) $R^4$ is 5-12 membered heteroaryl, optionally substituted with —$N(R^3)_2$ or —$OR^3$; and g) $R^{32}$ is =O.

In the above, $R^{40a}$ can be -$A^1$-$L^1$-$A^2$-B; -$A^1$-$A^2$-B; or -$L^2$-$A^1$-$L^1$-$A^2$-$L^3$-B.

The present disclosure provides a compound of formula:

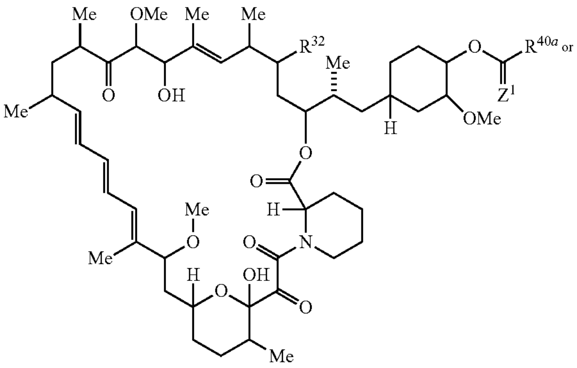

or

-continued

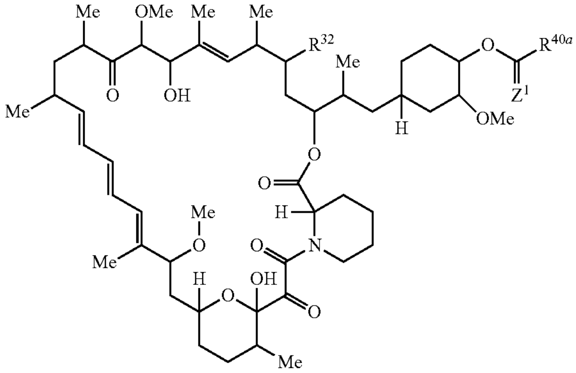

or a pharmaceutically acceptable salt or tautomer thereof, having one, two, three, or four of the following features:

a) $Z^1$ is O;

b) $A^1$ is absent c) $L^1$ is

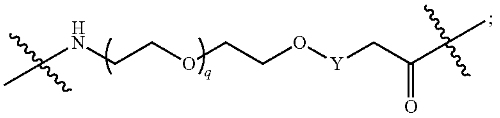

d) B is

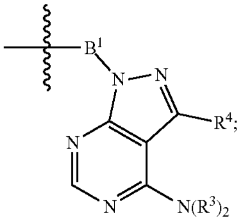

e) $B^1$ is

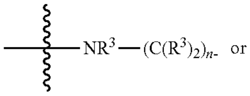

or

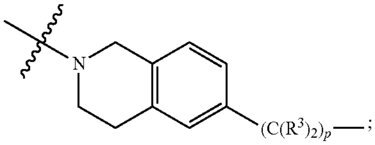

f) $R^4$ is 5-12 membered heteroaryl, optionally substituted with —$N(R^3)_2$ or —$OR^3$; and g) $R^{32}$ is —OH.

In the above, $R^{40a}$ can be -$A^1$-$L^1$-$A^2$-B; -$A^1$-$A^2$-B; or -$L^2$-$A^1$-$L^1$-$A^2$-$L^3$-B.

The present disclosure provides a compound of formula:

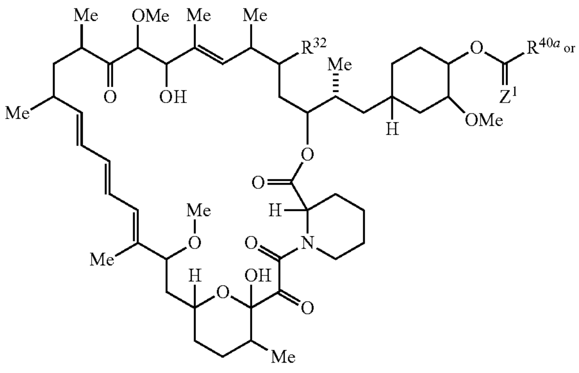

or

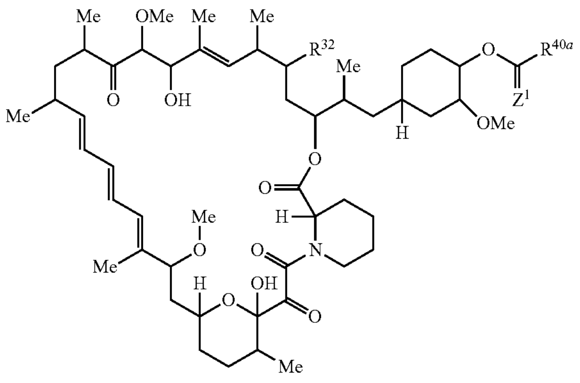

or a pharmaceutically acceptable salt or tautomer thereof, having one, two, three, or four of the following features:

a) $Z^1$ is O;

b) $A^1$ is

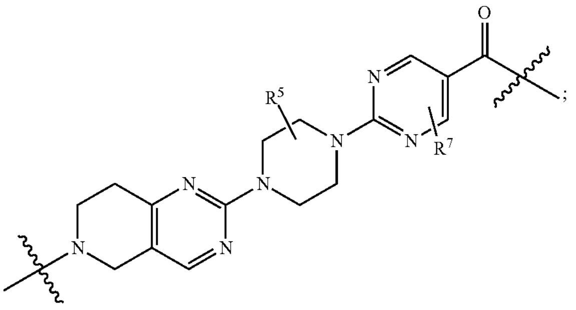

c) $L^1$ is

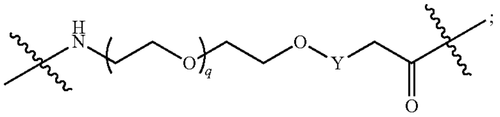

d) B is

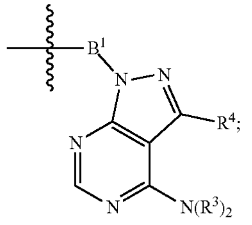

e) $B^1$ is

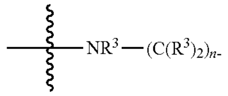

or

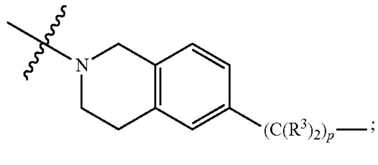

f) $R^4$ is 5-12 membered heteroaryl, optionally substituted with —$N(R^3)_2$ or —$OR^3$; and g) $R^{32}$ is =O.

In the above, $R^{40a}$ can be -$A^1$-$L^1$-$A^2$-B; -$A^1$-$A^2$-B; or -$L^2$-$A^1$-$L^1$-$A^2$-$L^3$-B.

The present disclosure provides a compound of formula:

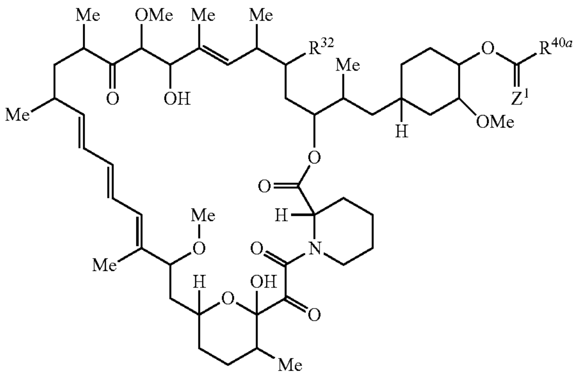

or a pharmaceutically acceptable salt or tautomer thereof, having one, two, three, or four of the following features:

a) $Z^1$ is O;

b) $A^1$ is absent;

c) $L^1$ is

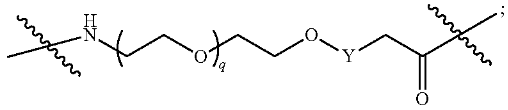

d) B is

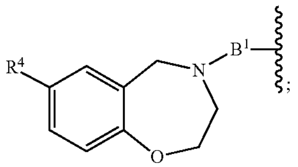

e) $B^1$ is

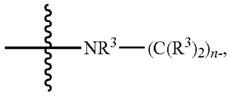

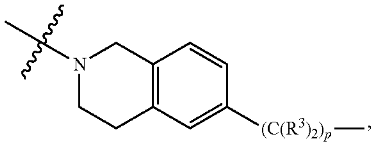

or

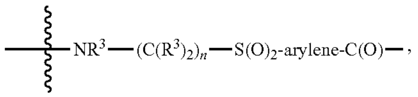

wherein the arylene is optionally substituted with alkyl, hydroxyalkyl, haloalkyl, alkoxy, halogen, or hydroxyl;

f) $R^4$ is 5-12 membered heteroaryl, optionally substituted with —$N(R^3)_2$ or —$OR^3$; and g) $R^{32}$ is —OH.

In the above, $R^{40a}$ can be -$A^1$-$L^1$-$A^2$-B; -$A^1$-$A^2$-B; or -$L^2$-$A^1$-$L^1$-$A^2$-$L^3$-B.

The present disclosure provides a compound of formula:

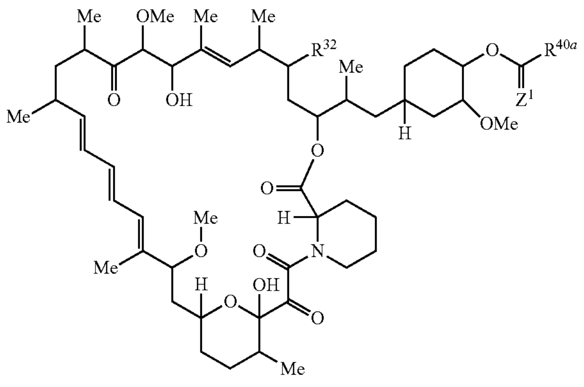

or a pharmaceutically acceptable salt or tautomer thereof, having one, two, three, or four of the following features:

a) $Z^1$ is O;

b) $A^1$ is

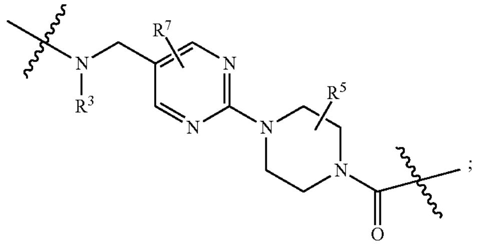

c) $A^2$ is

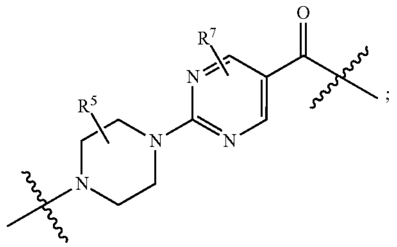

d) $L^1$ is

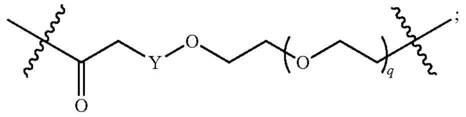

e) B is

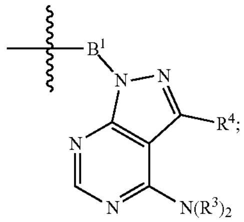

f) $B^1$ is

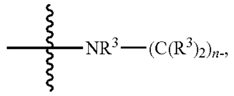

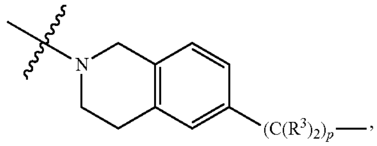

or

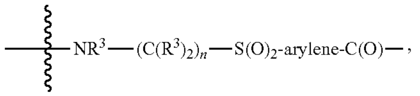

wherein the arylene is optionally substituted with alkyl, hydroxyalkyl, haloalkyl, alkoxy, halogen, or hydroxyl;

g) $R^4$ is 5-12 membered heteroaryl, optionally substituted with —$N(R^3)_2$ or —$OR^3$; and h) $R^{32}$ is —OH.

In the above, $R^{40a}$ can be $-A^1-L^1-A^2-B$; $-A^1-A^2-B$; or $-L^2-A^1-L^1-A^2-L^3-B$.

In certain embodiments, in Formula Ia or Ic, $R^{41a}$ is any organic moiety, which may have a molecular weight (e.g. the sum of the atomic masses of the atoms of the substituent) of less than 15 g/mol, 50 g/mol, 100 g/mol, 150 g/mol, 200 g/mol, 250 g/mol, 300 g/mol, 350 g/mol, 400 g/mol, 450 g/mol, or 500 g/mol.

In certain embodiments, the present disclosure provides for a compound selected from below or a pharmaceutically acceptable salt or tautomer thereof, Example 1
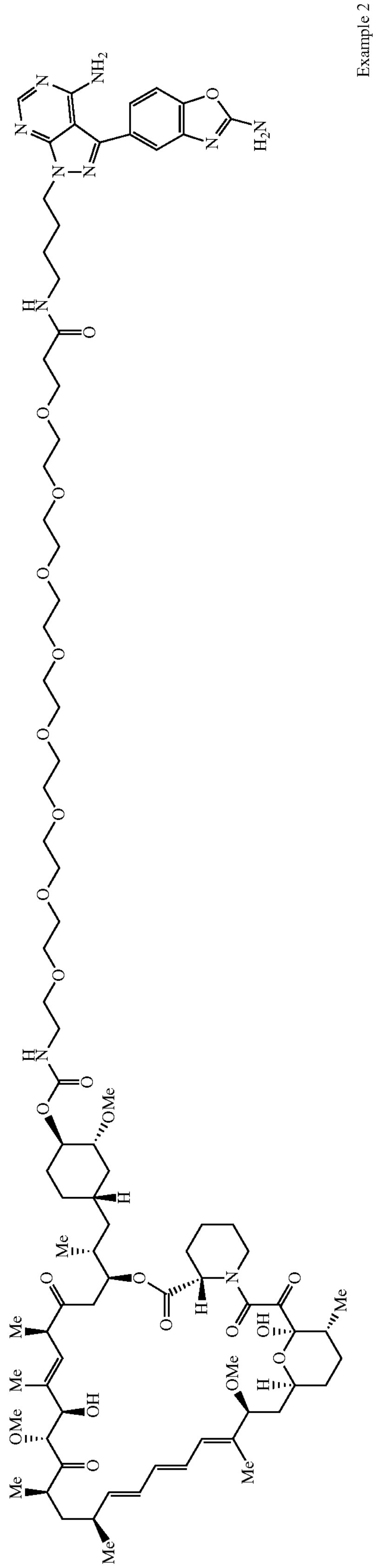
Example 2
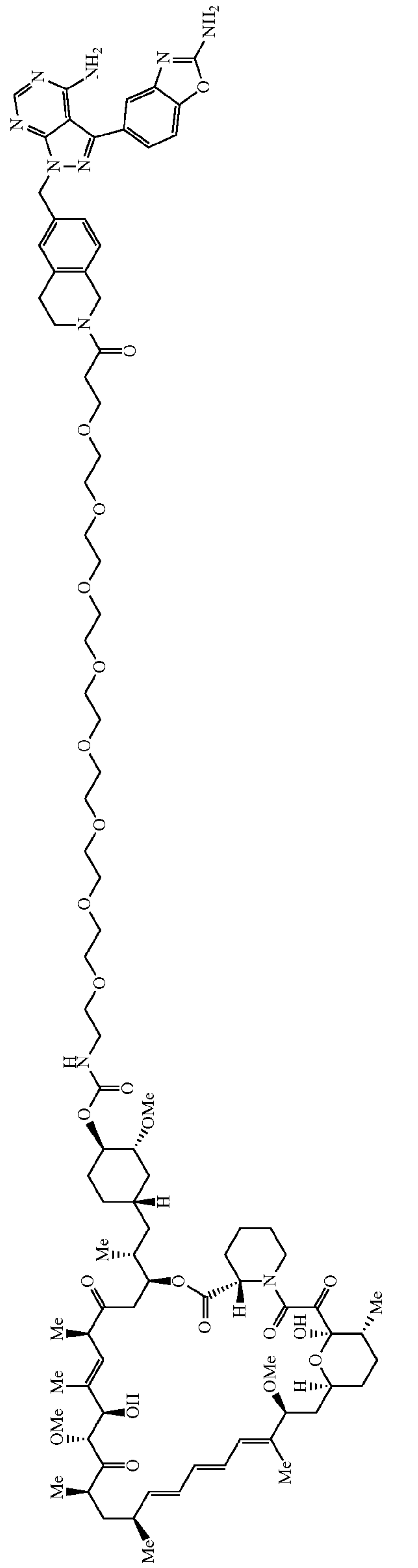

-continued
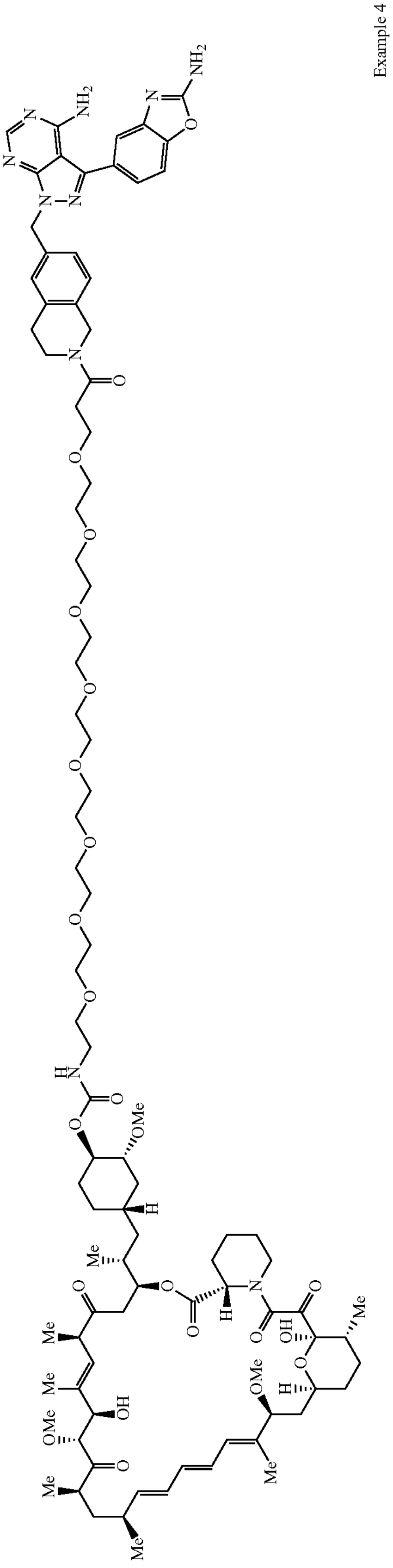
Example 3
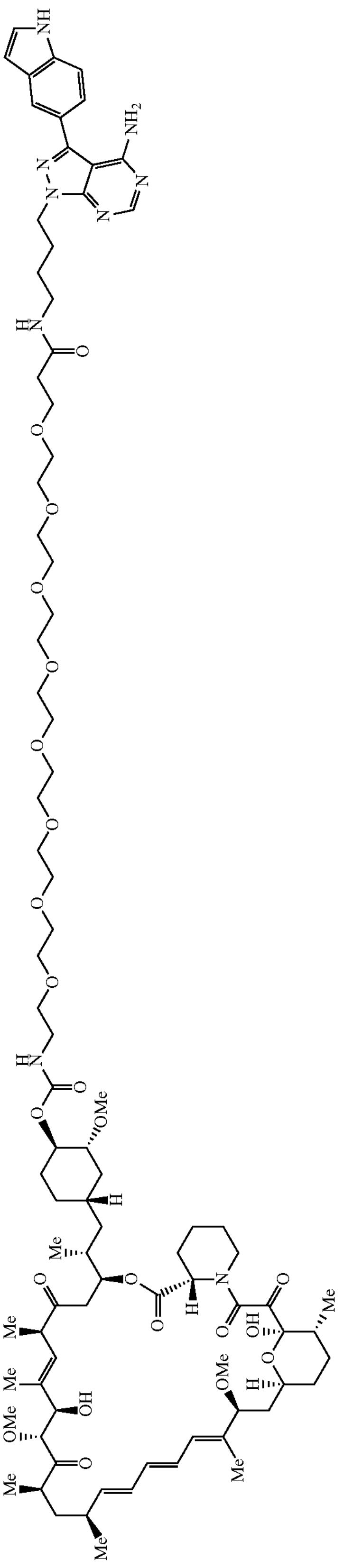
Example 4

-continued
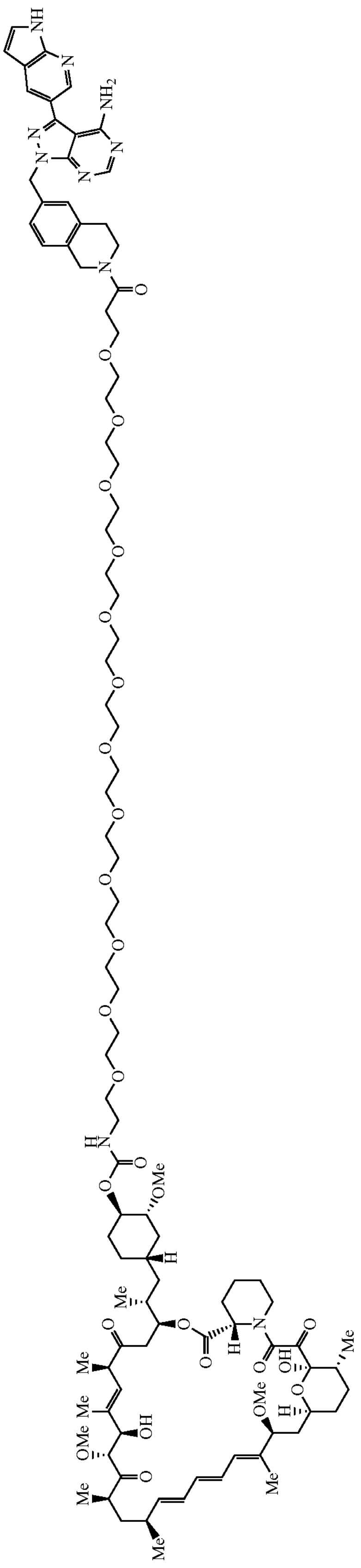
Example 5
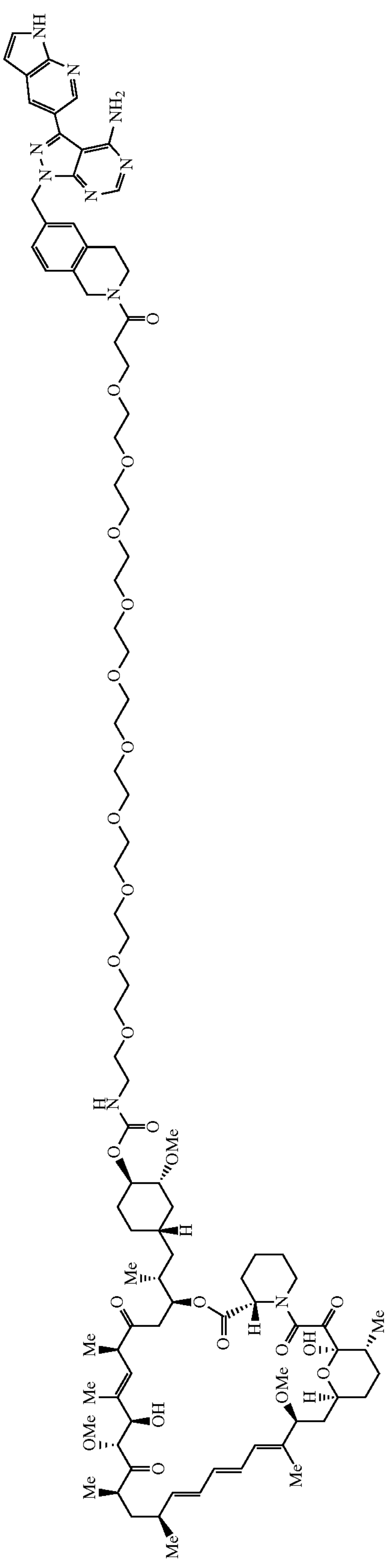
Example 6

-continued
Example 7
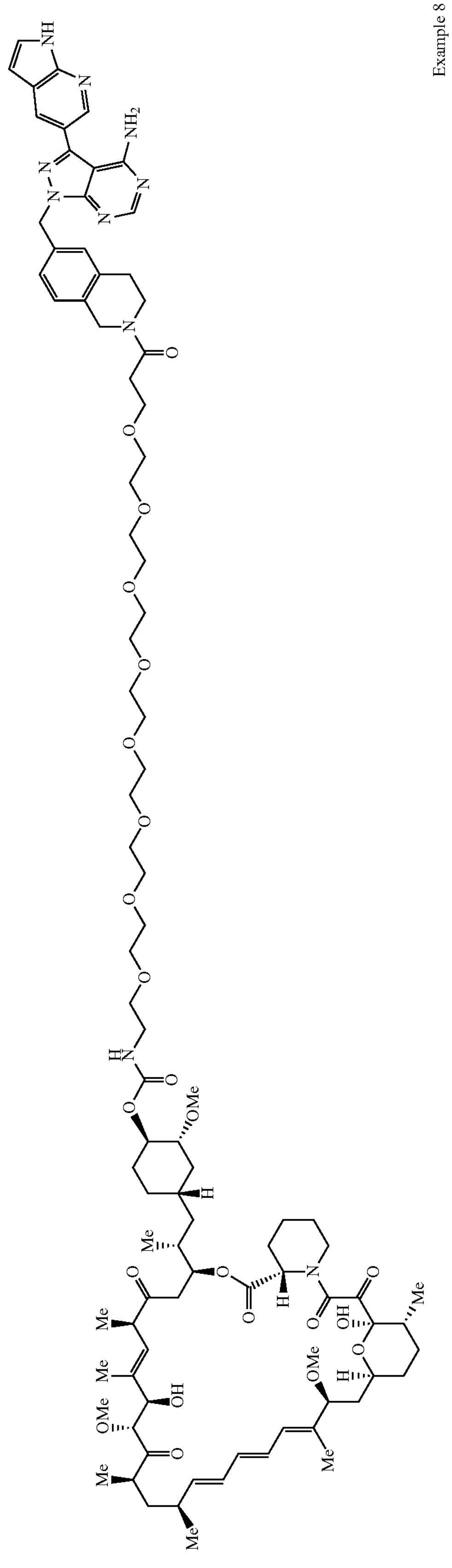
Example 8
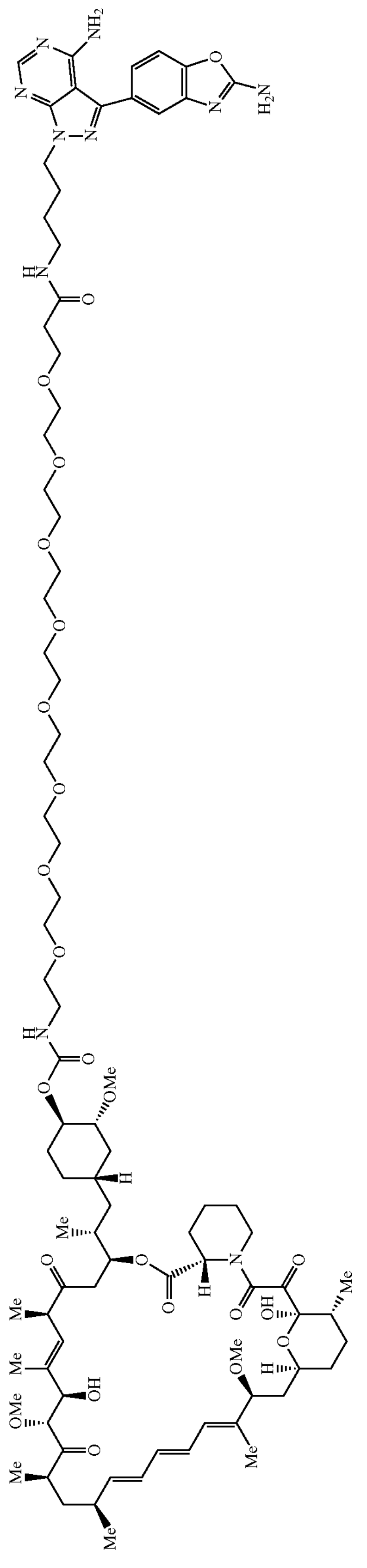

-continued
Example 9
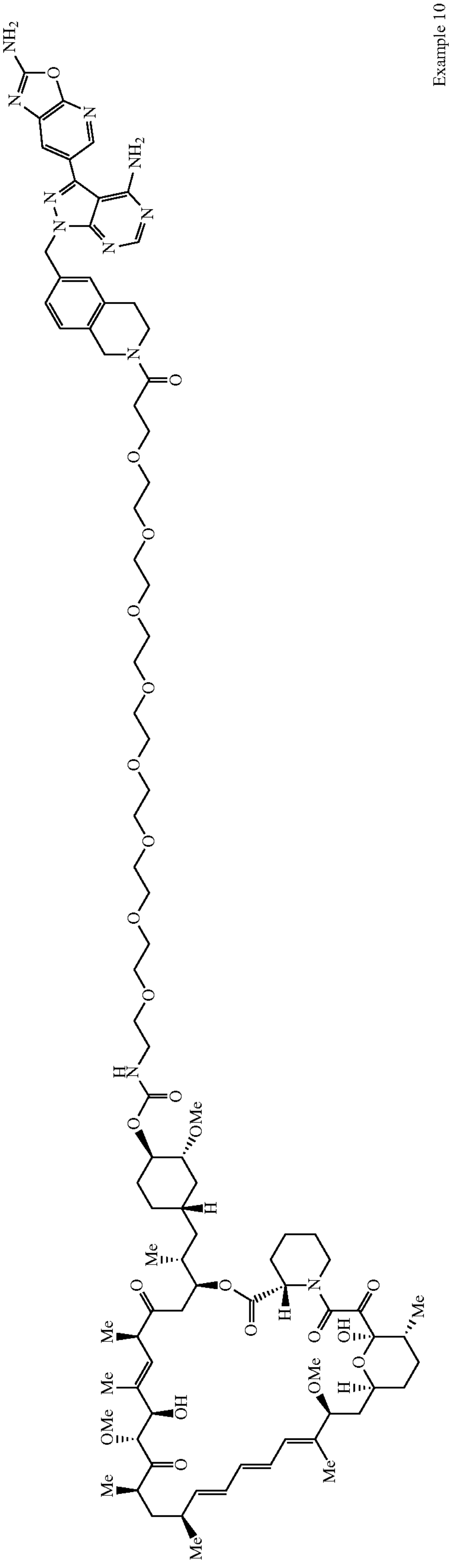
Example 10
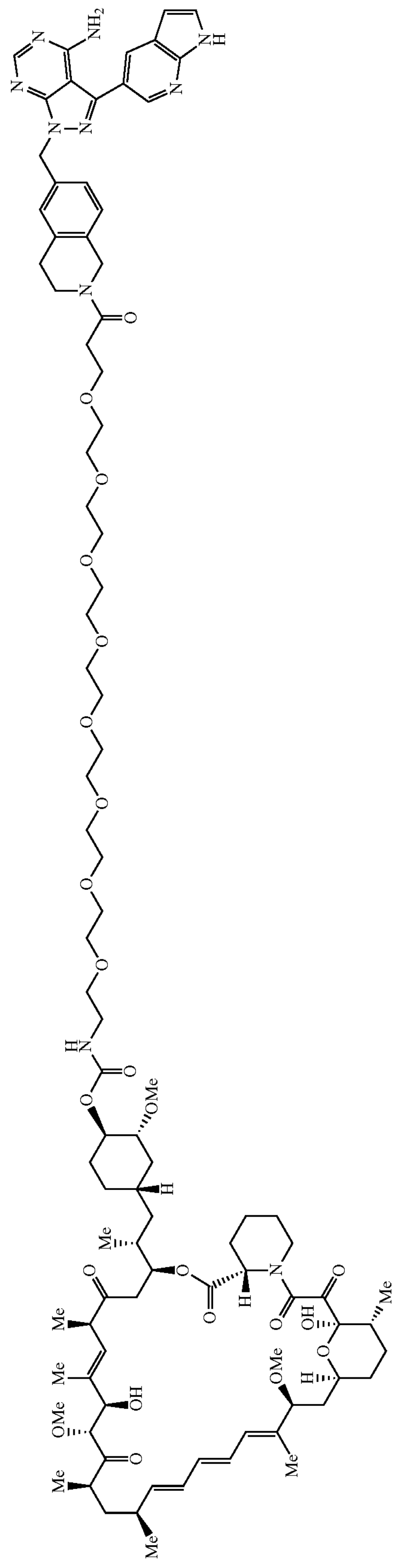

-continued
Example 11
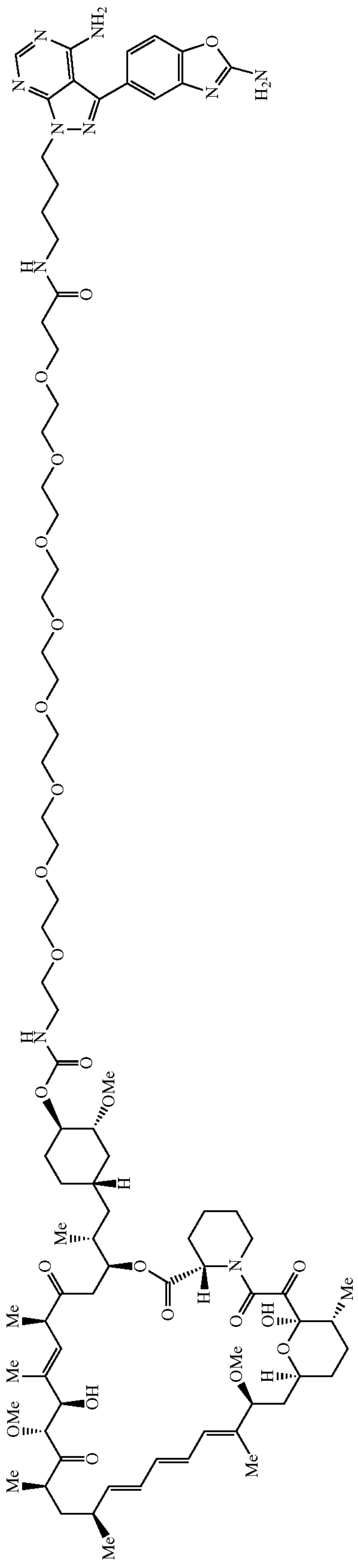
Example 12
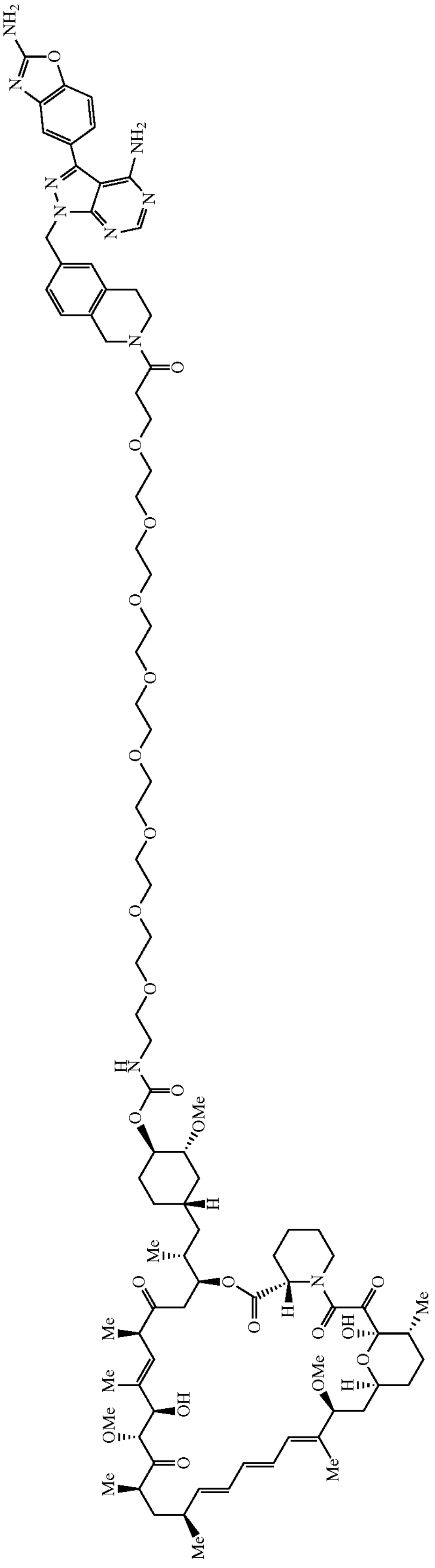

-continued
Example 13
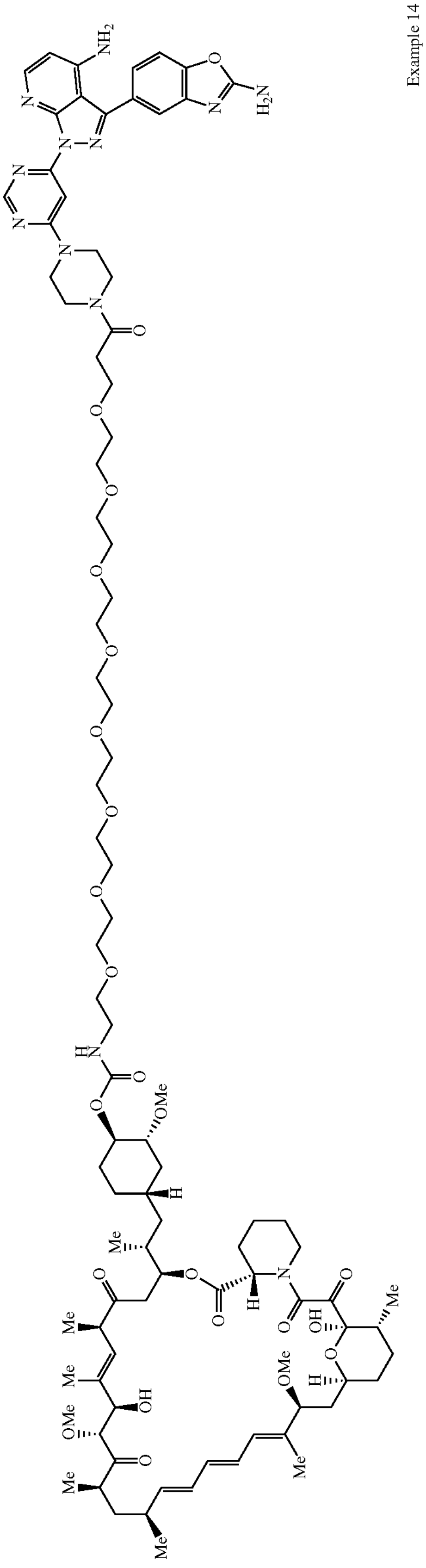
Example 14
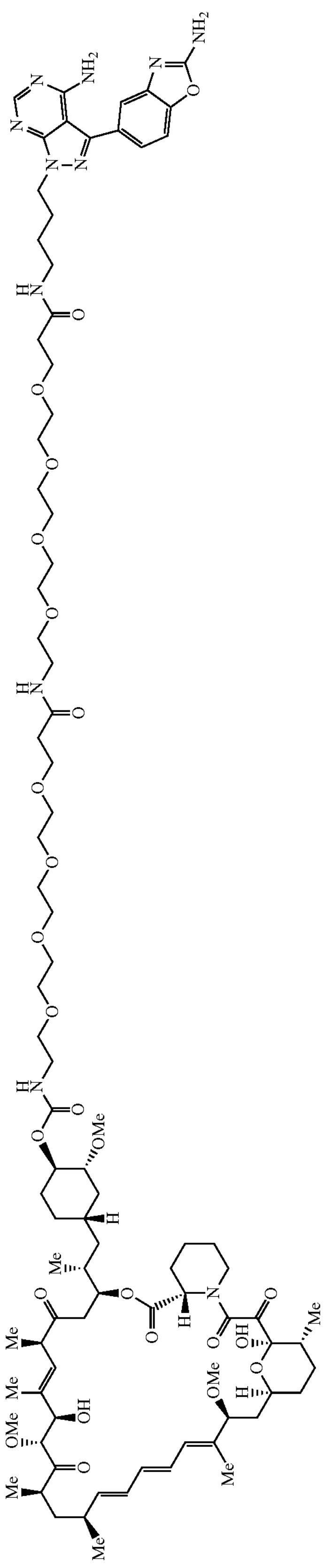

-continued
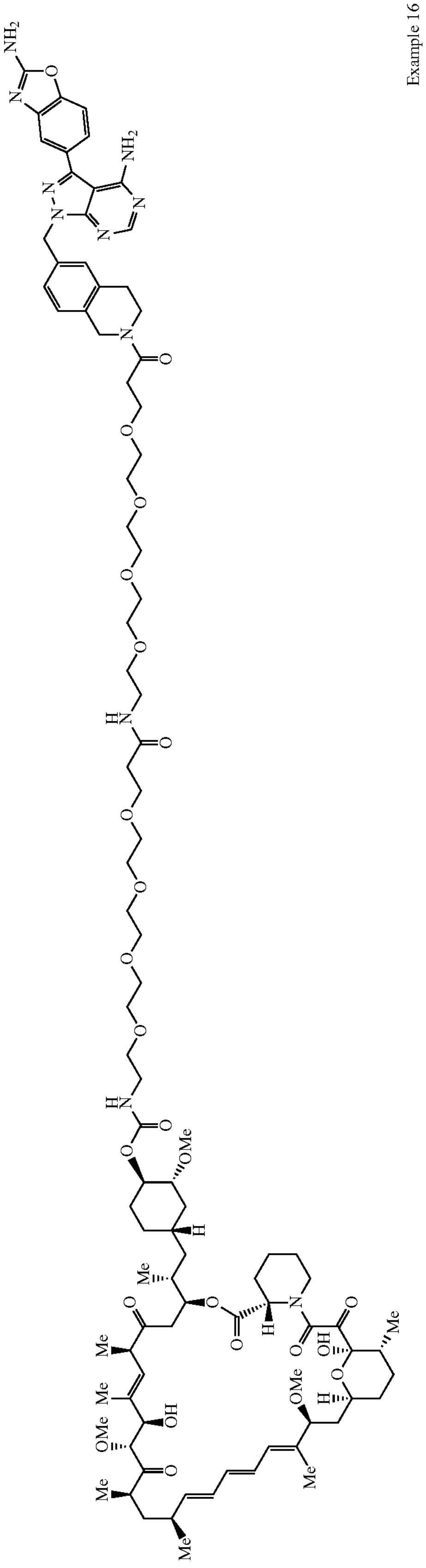
Example 15
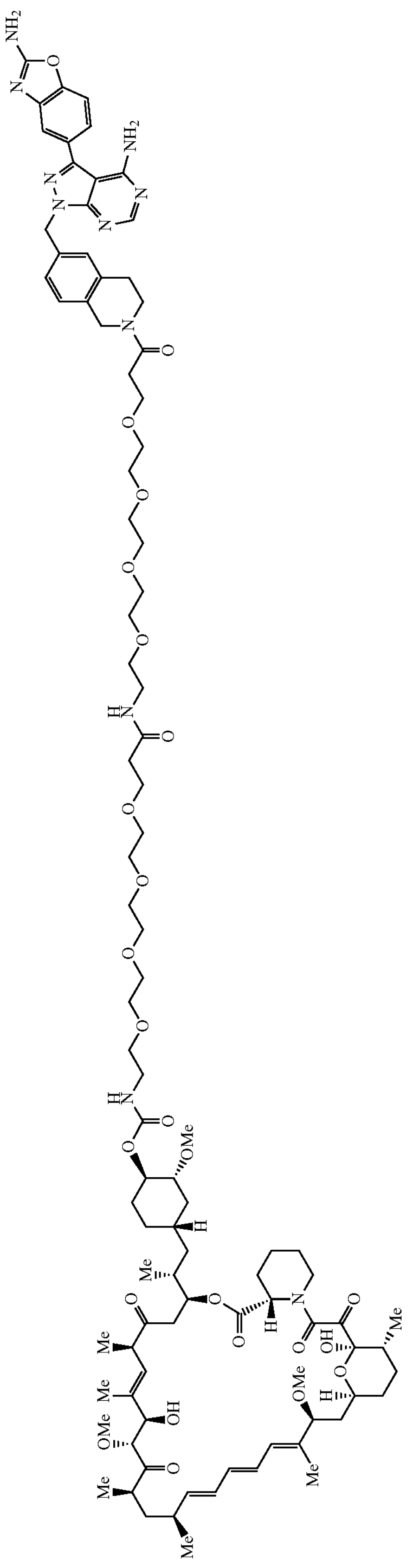
Example 16

-continued
Example 17
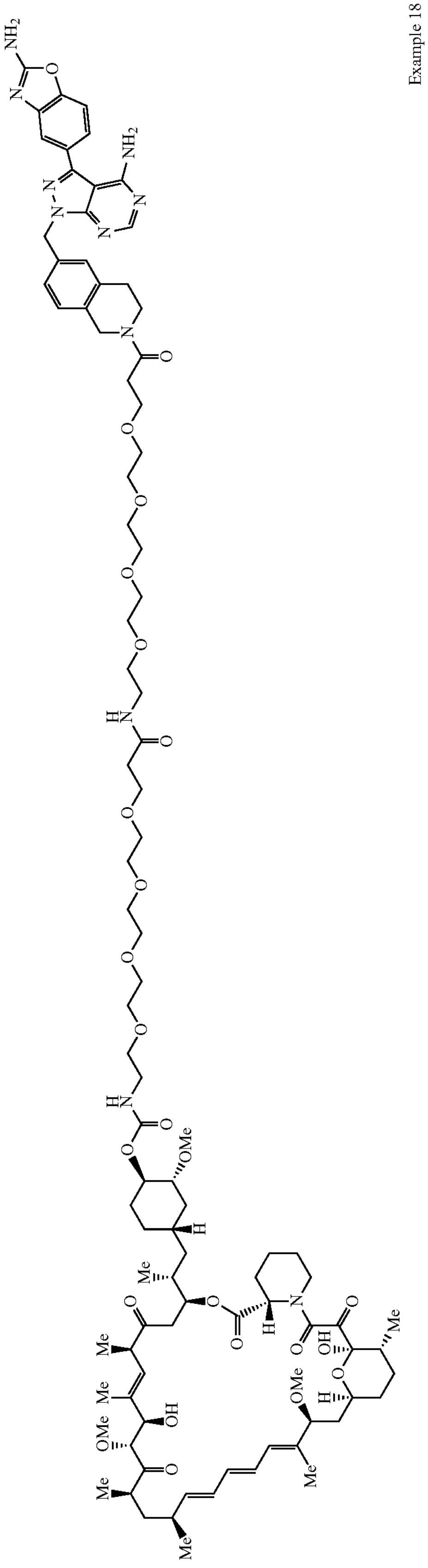
Example 18
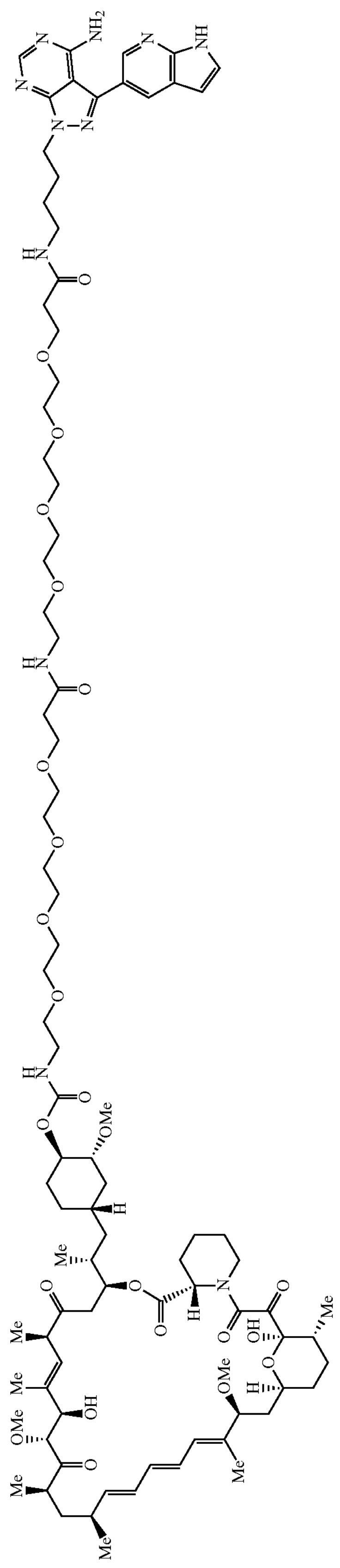

-continued
Example 19
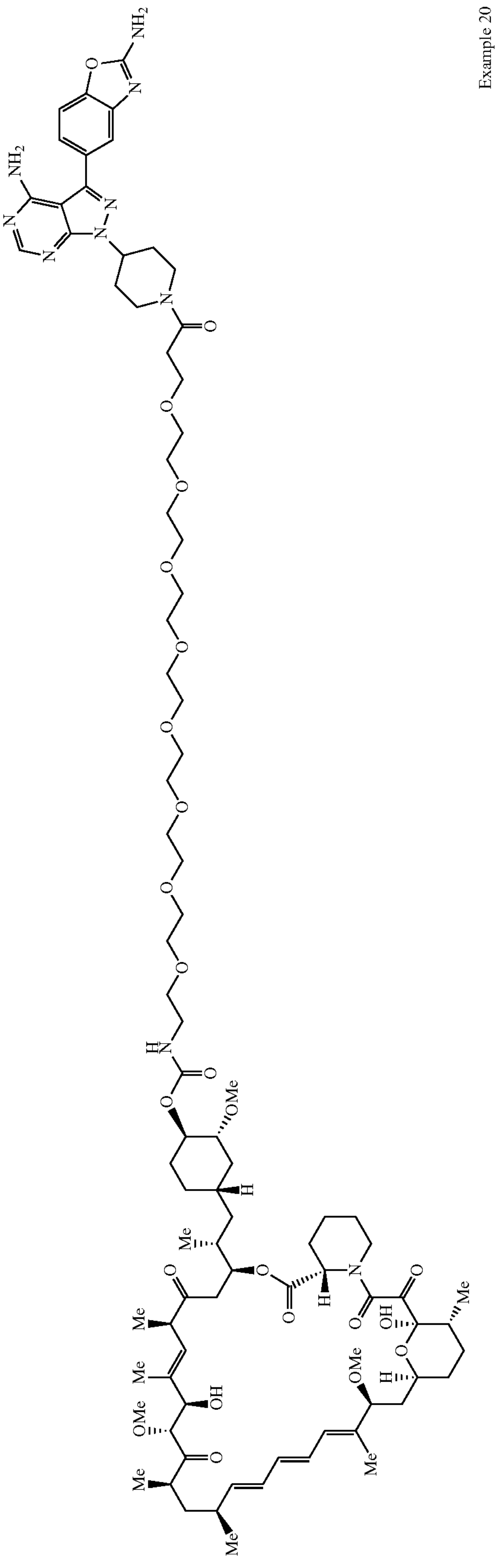
Example 20
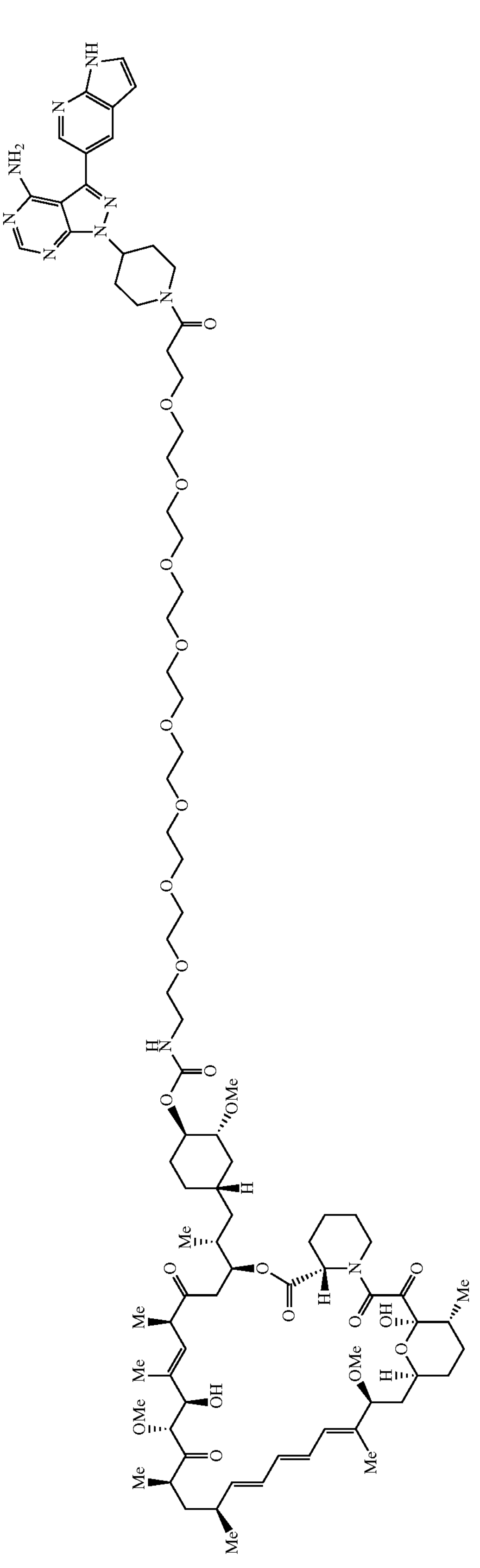

-continued
Example 21
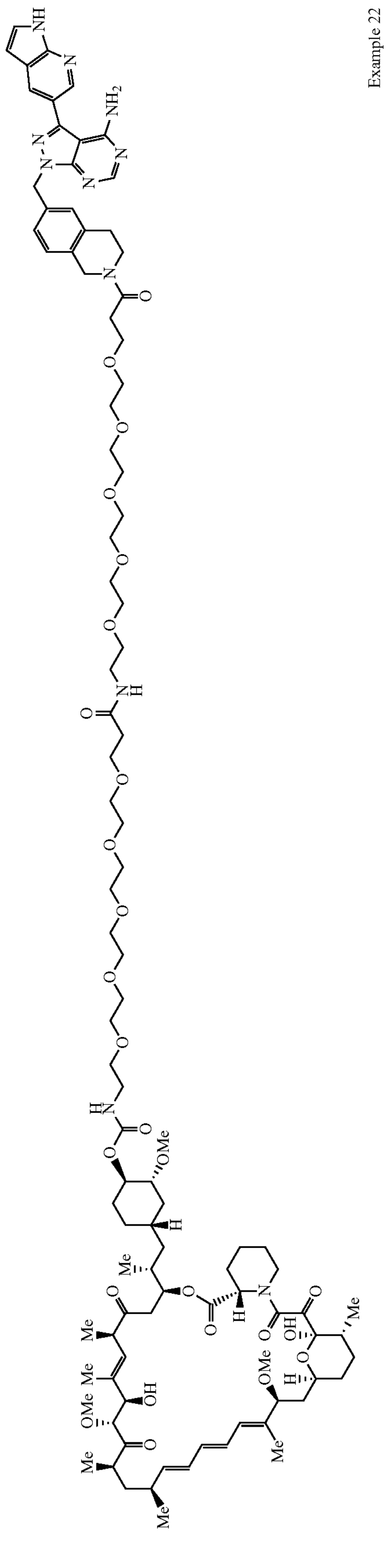
Example 22
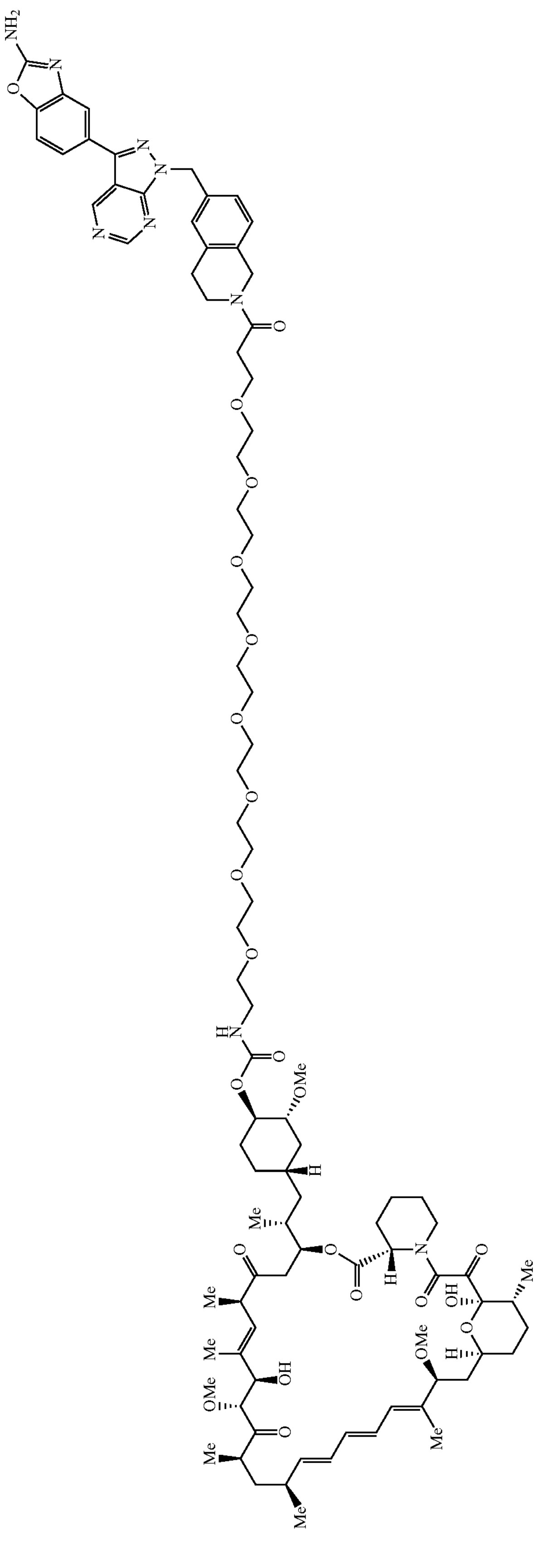

-continued
Example 23
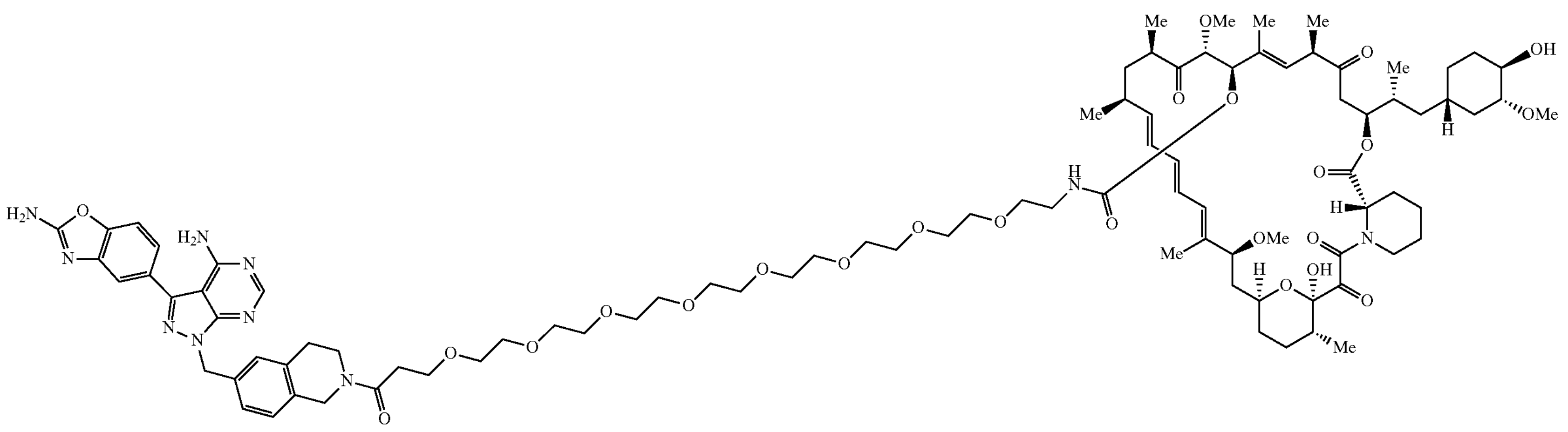
Example 24
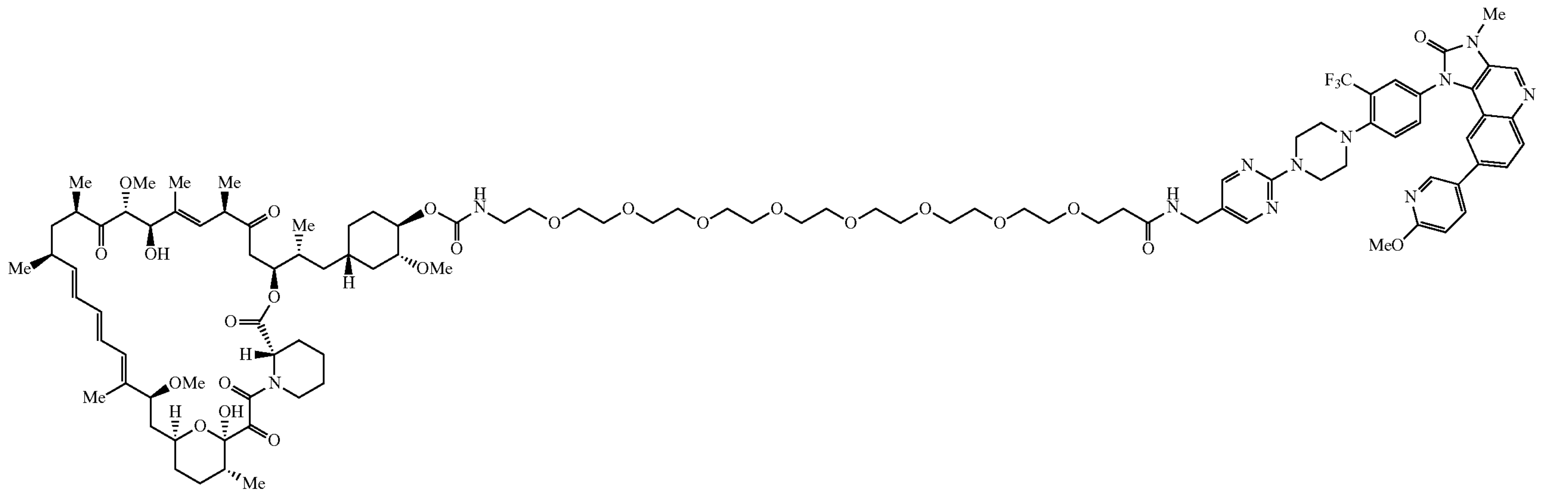

-continued
Example 25
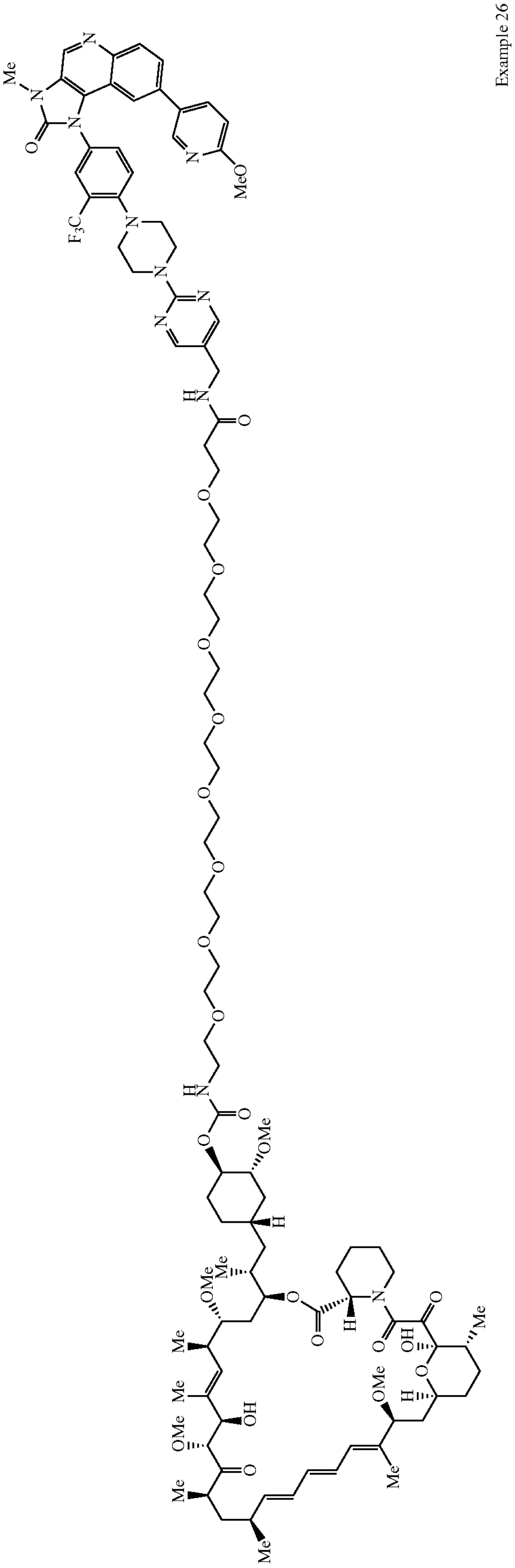
Example 26
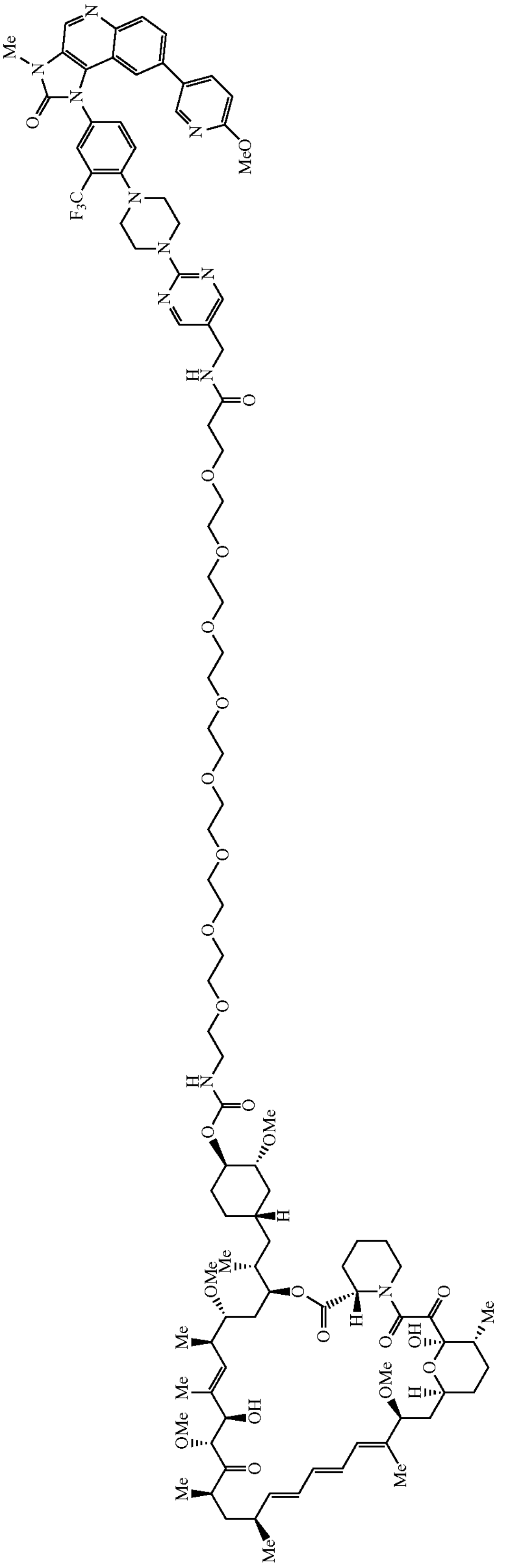

-continued
Example 27
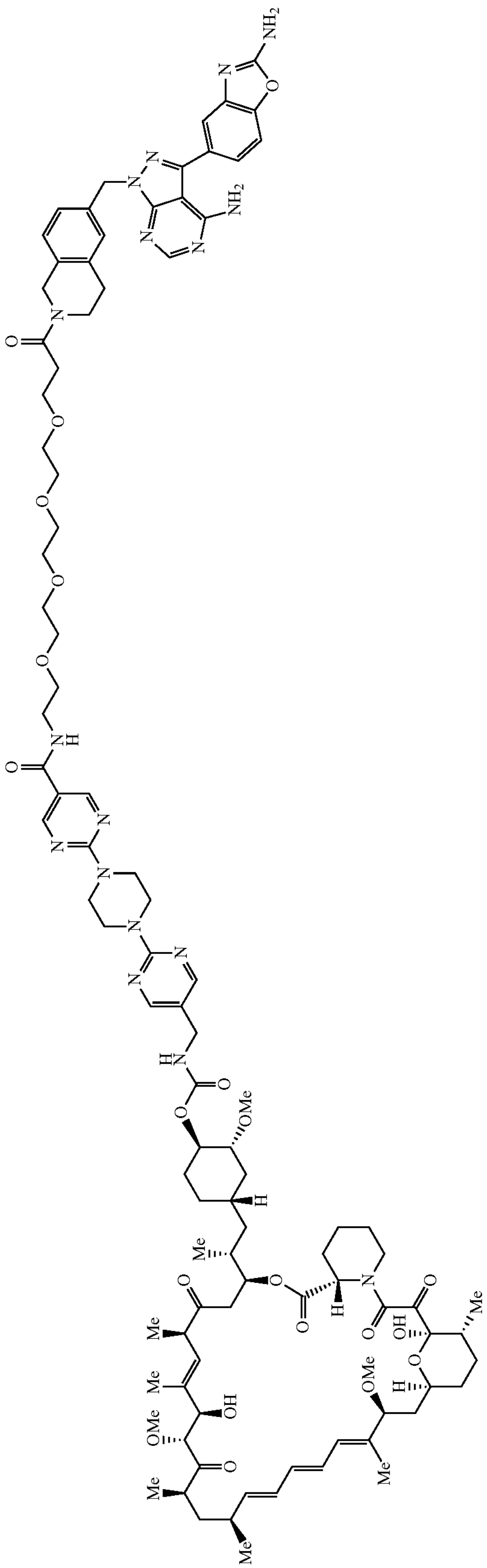
Example 28
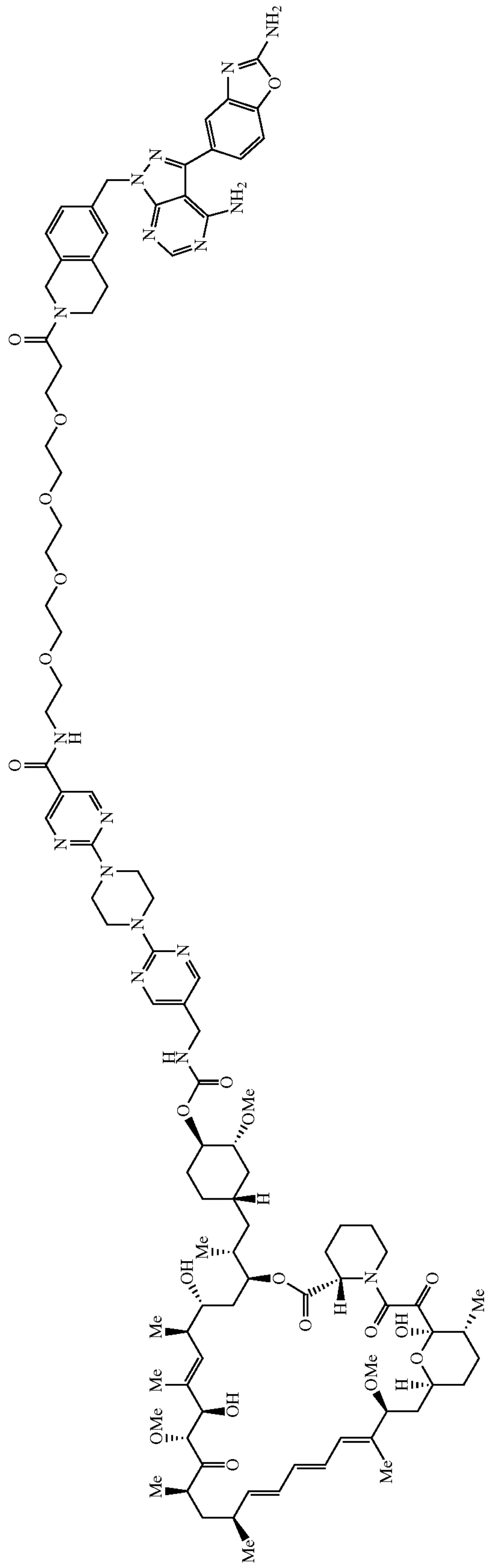

-continued
Example 29
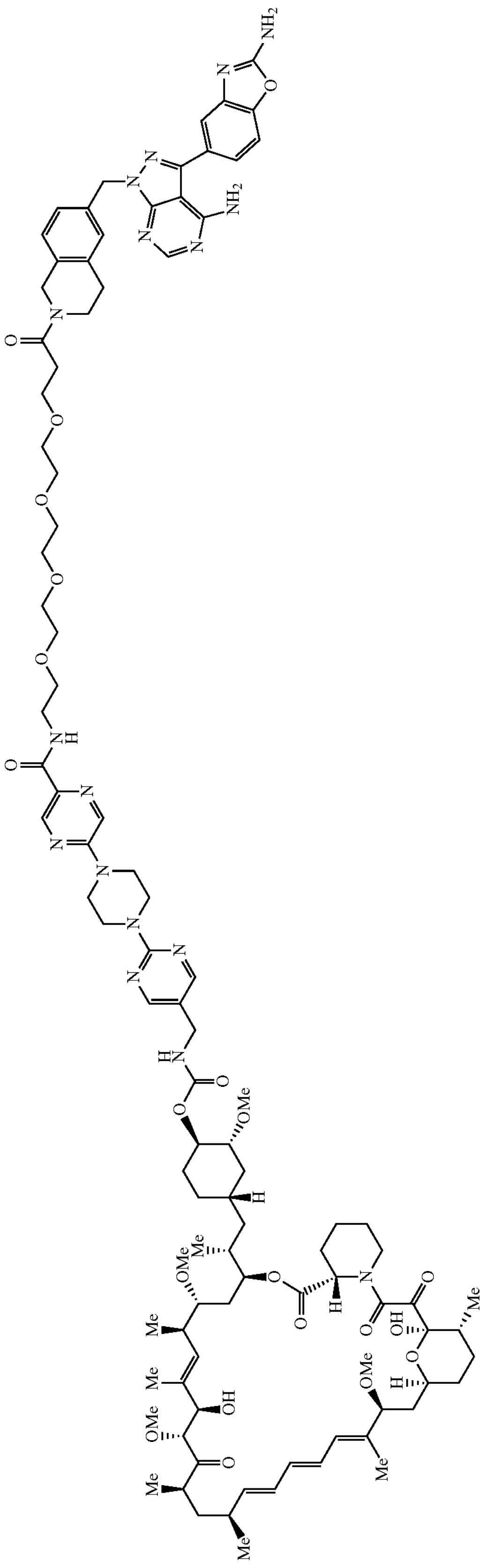
Example 30
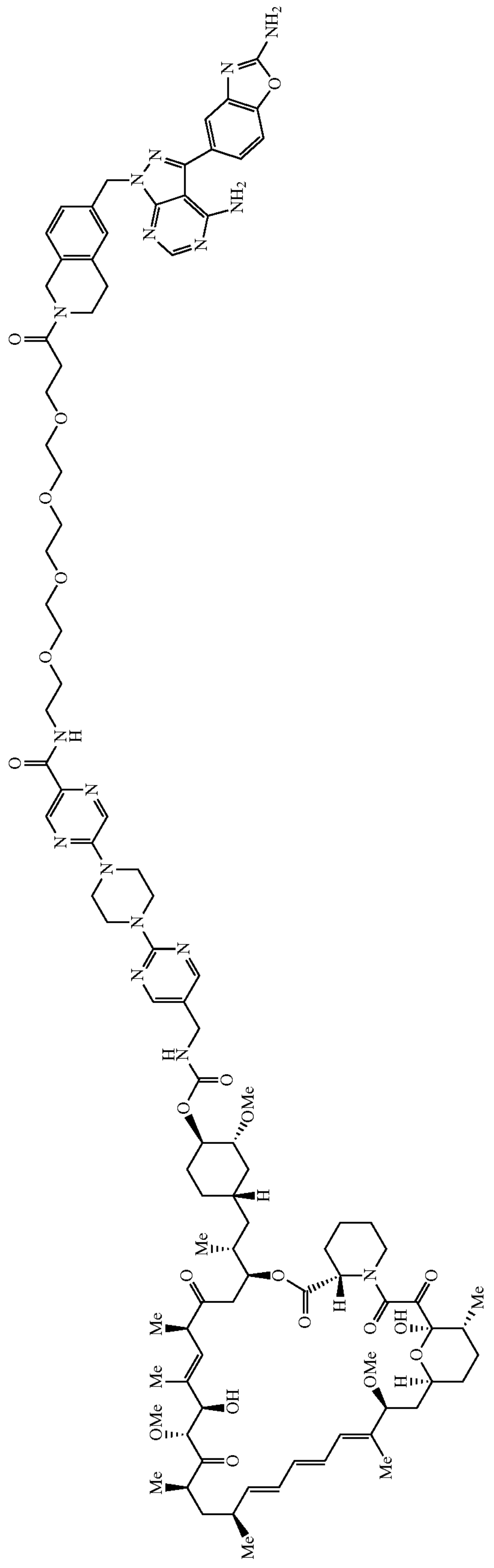

-continued
Example 31
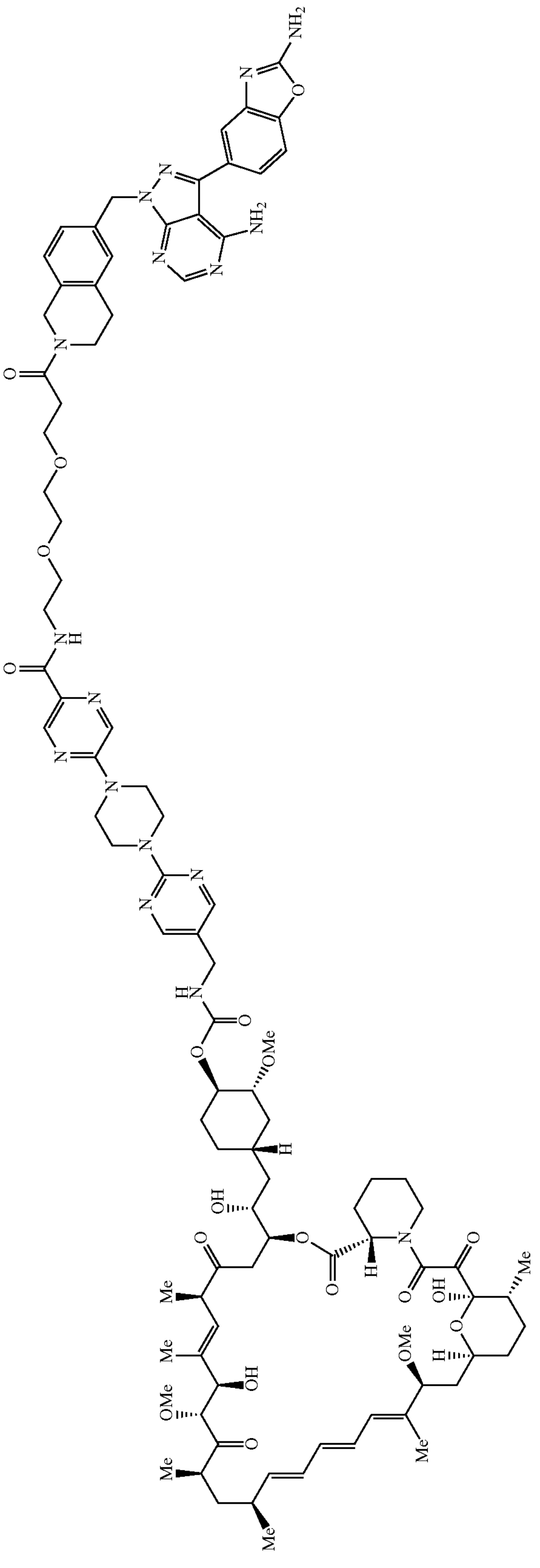

-continued
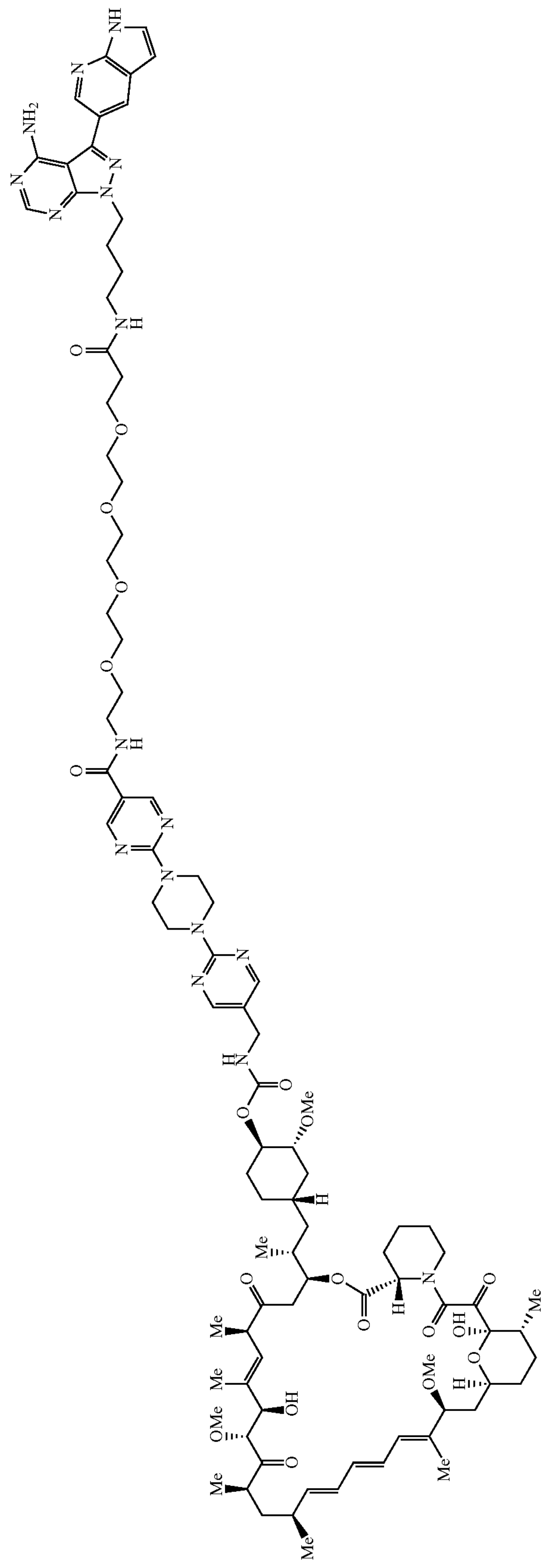
Example 32

-continued
Example 33
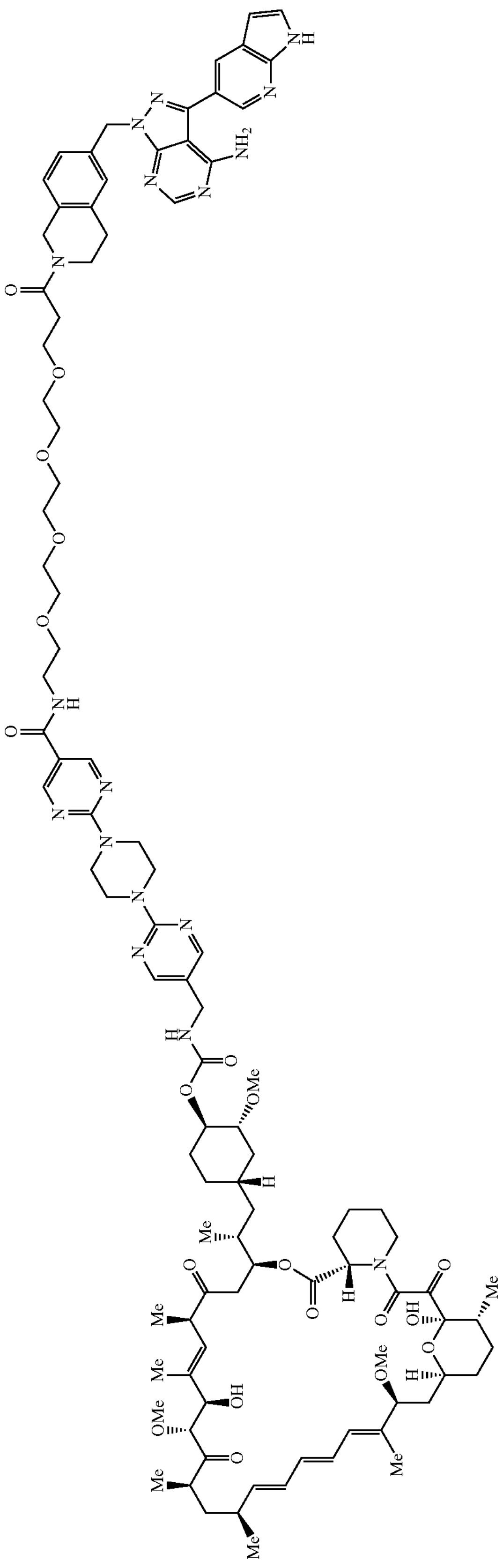

-continued
Example 34
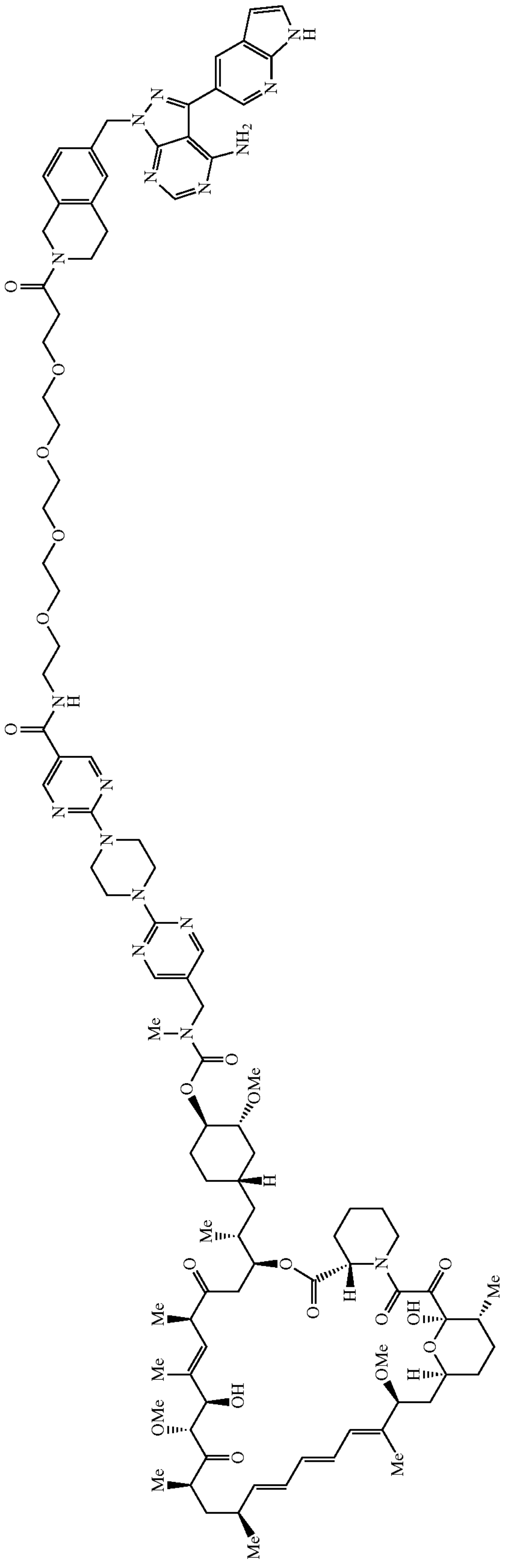

-continued
Example 35
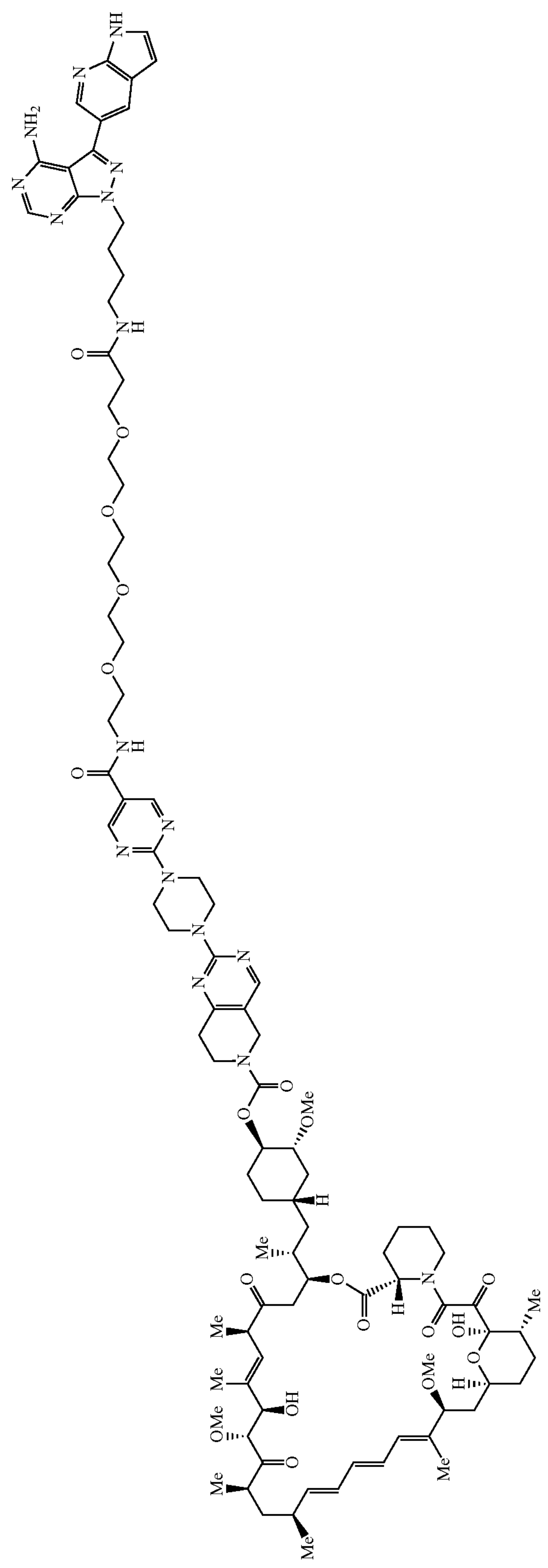

-continued
Example 36
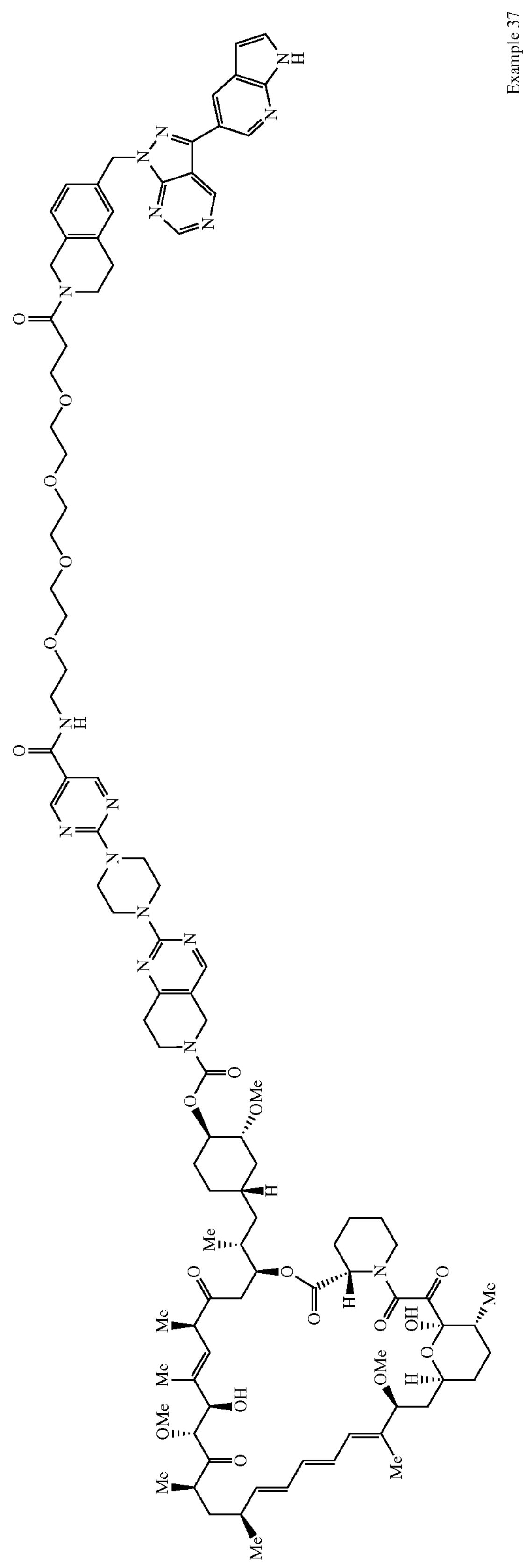
Example 37
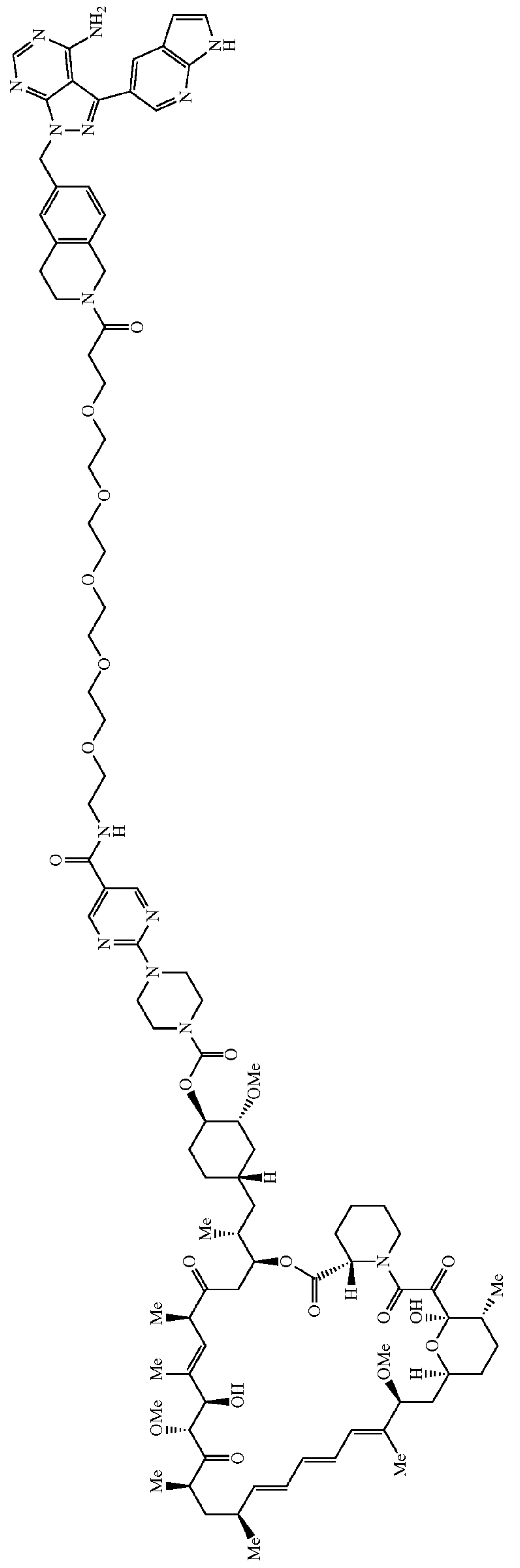

-continued
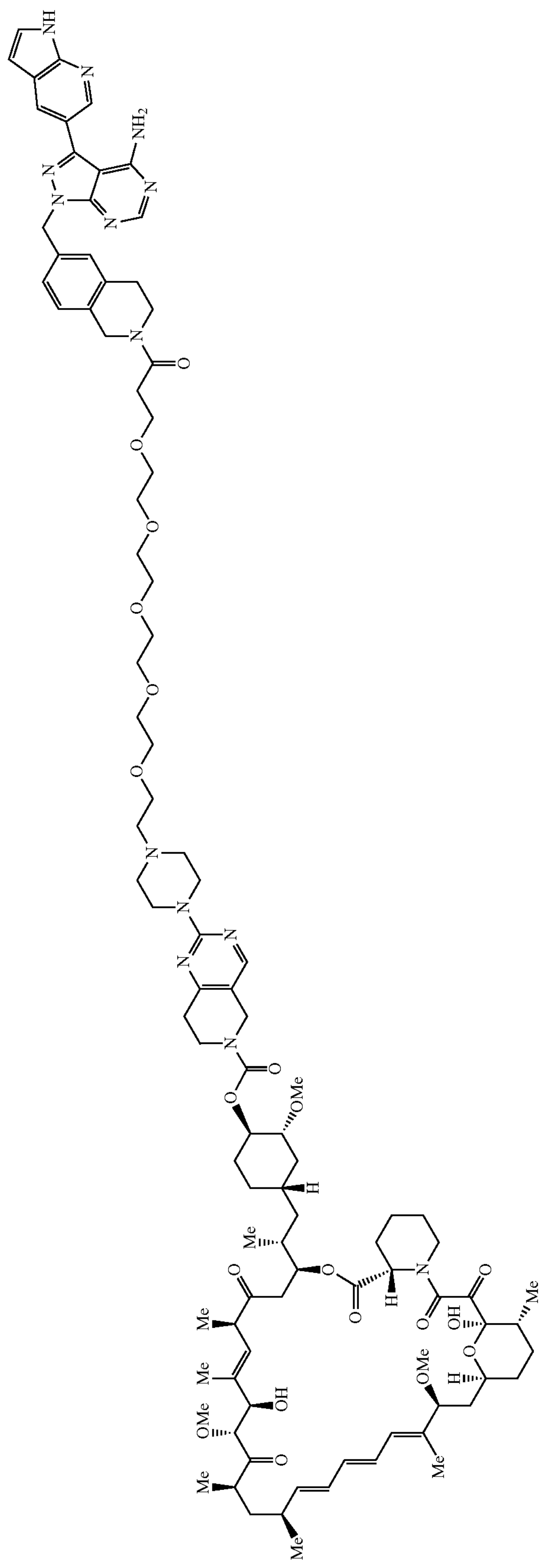
Example 38

-continued
Example 39
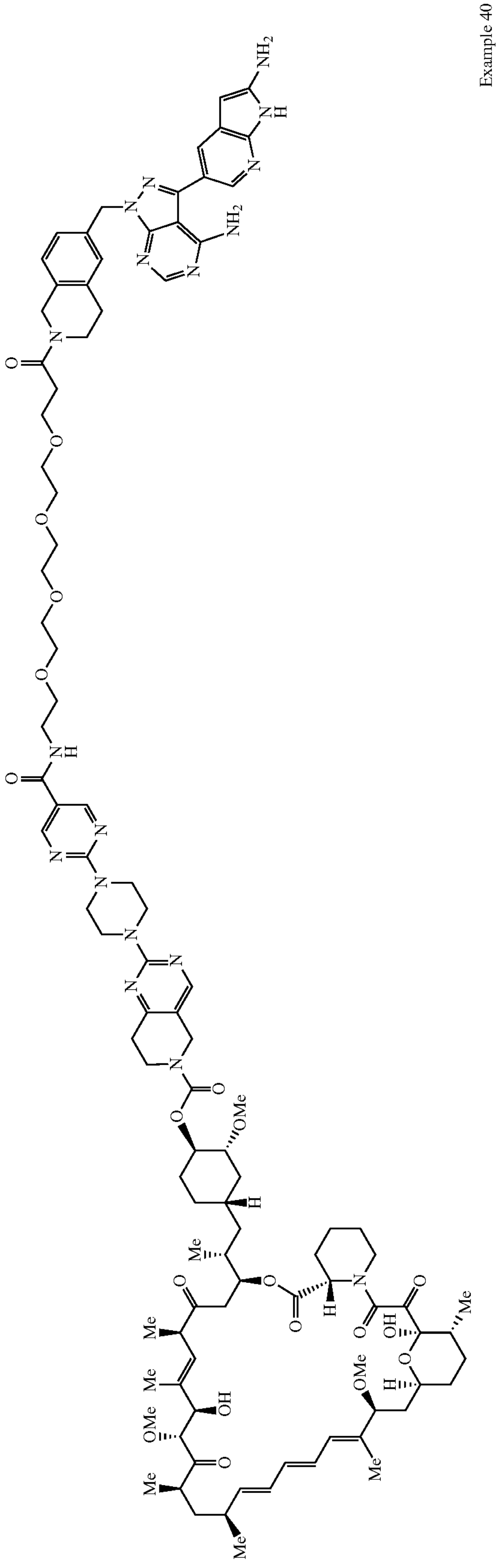
Example 40
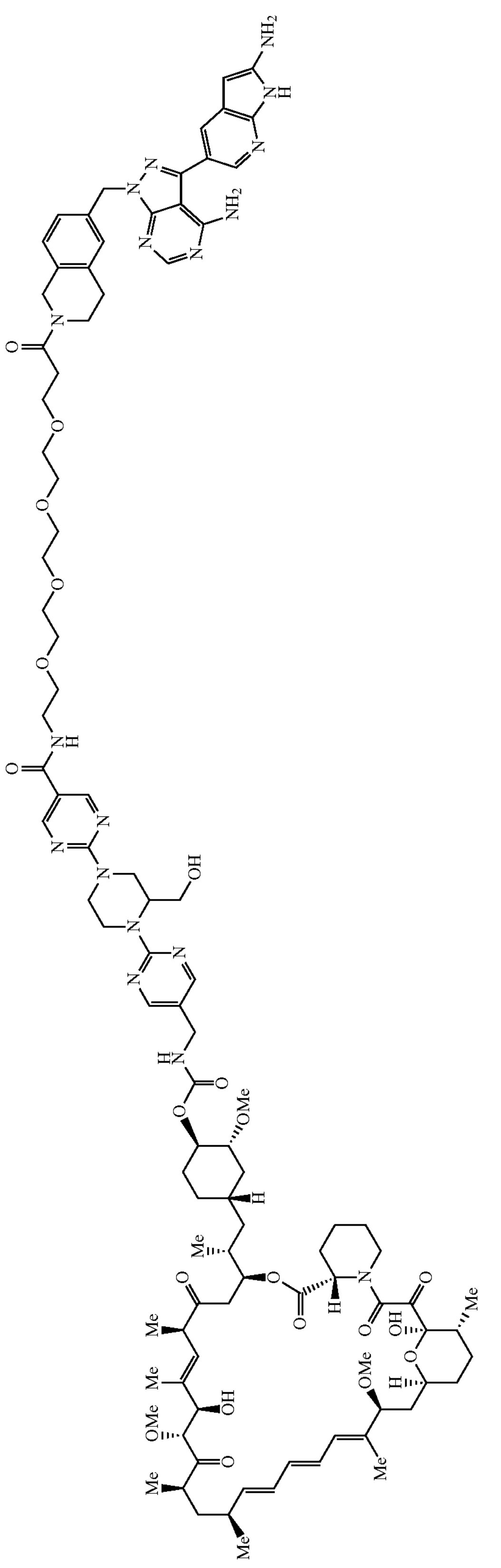

-continued
Example 41
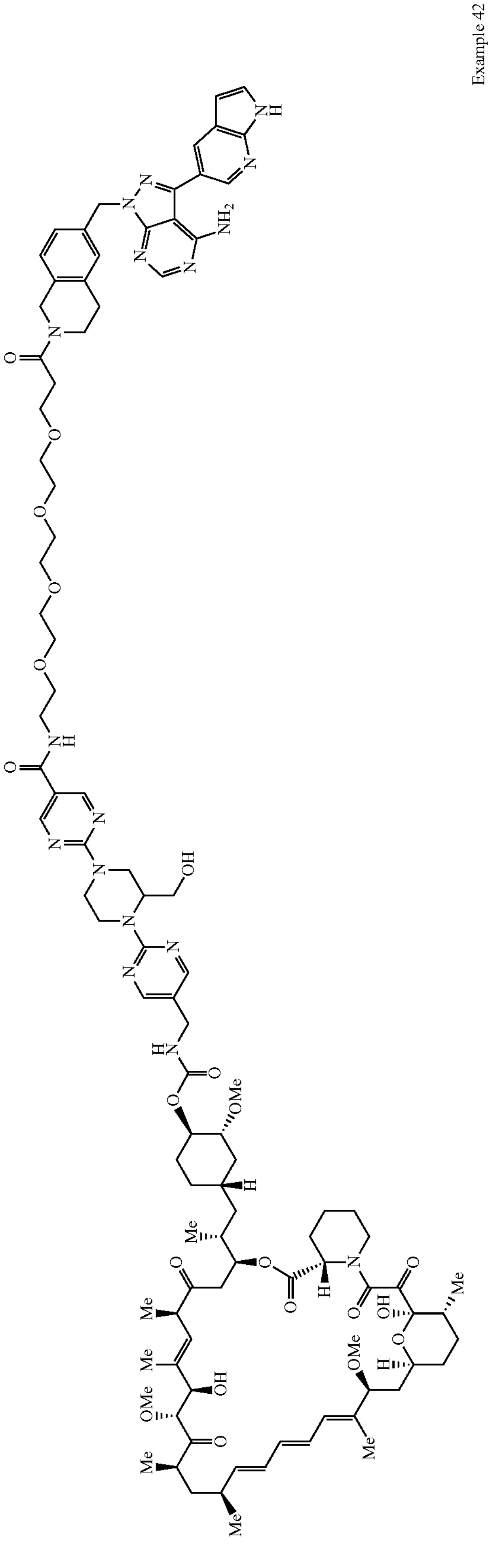
Example 42
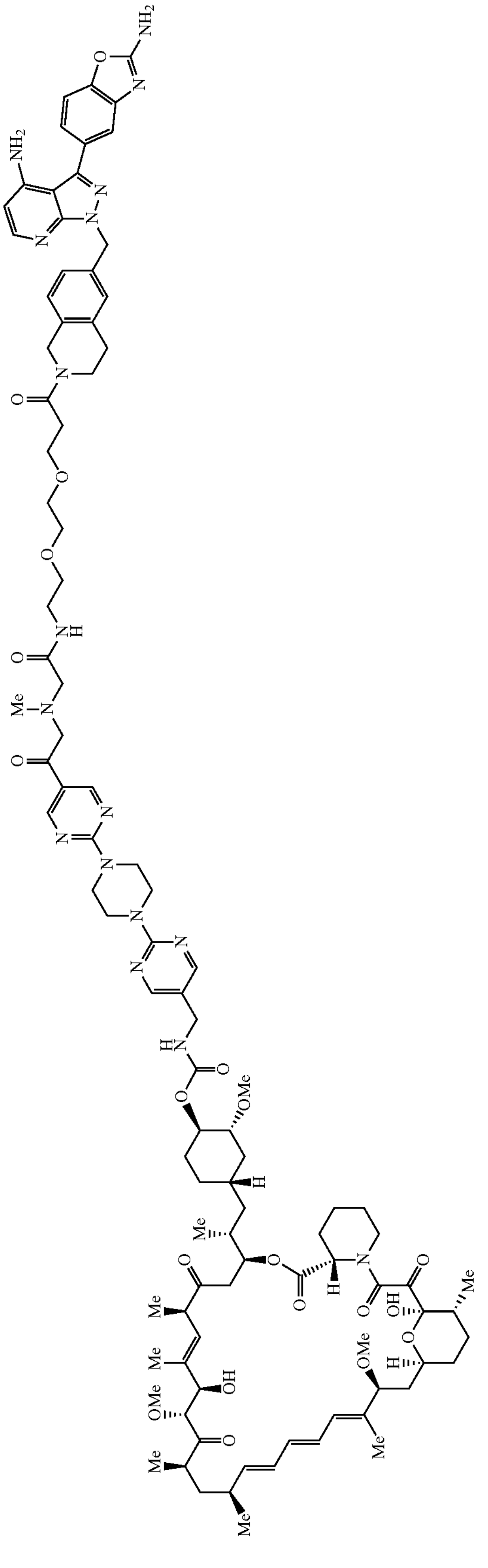

-continued
Example 43
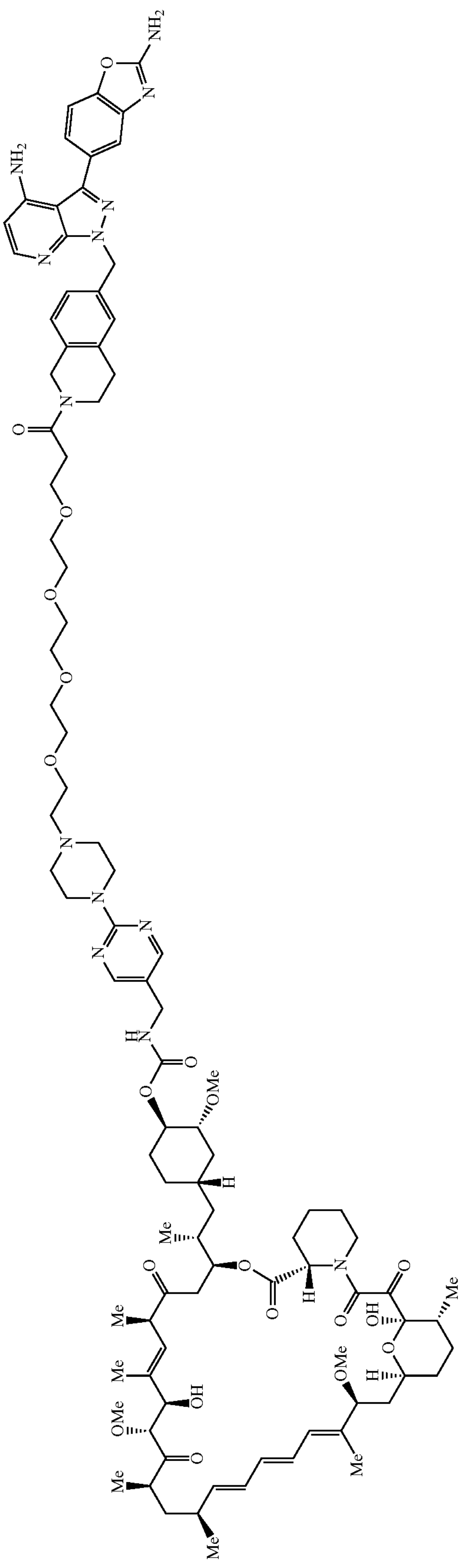
Example 44
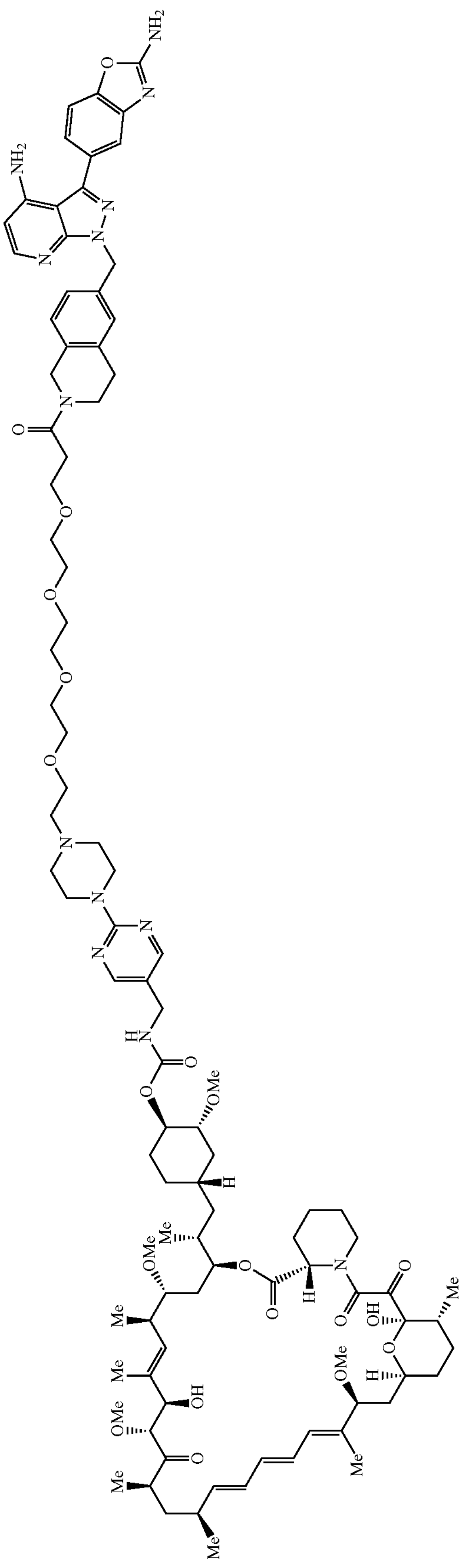

-continued
Example 45
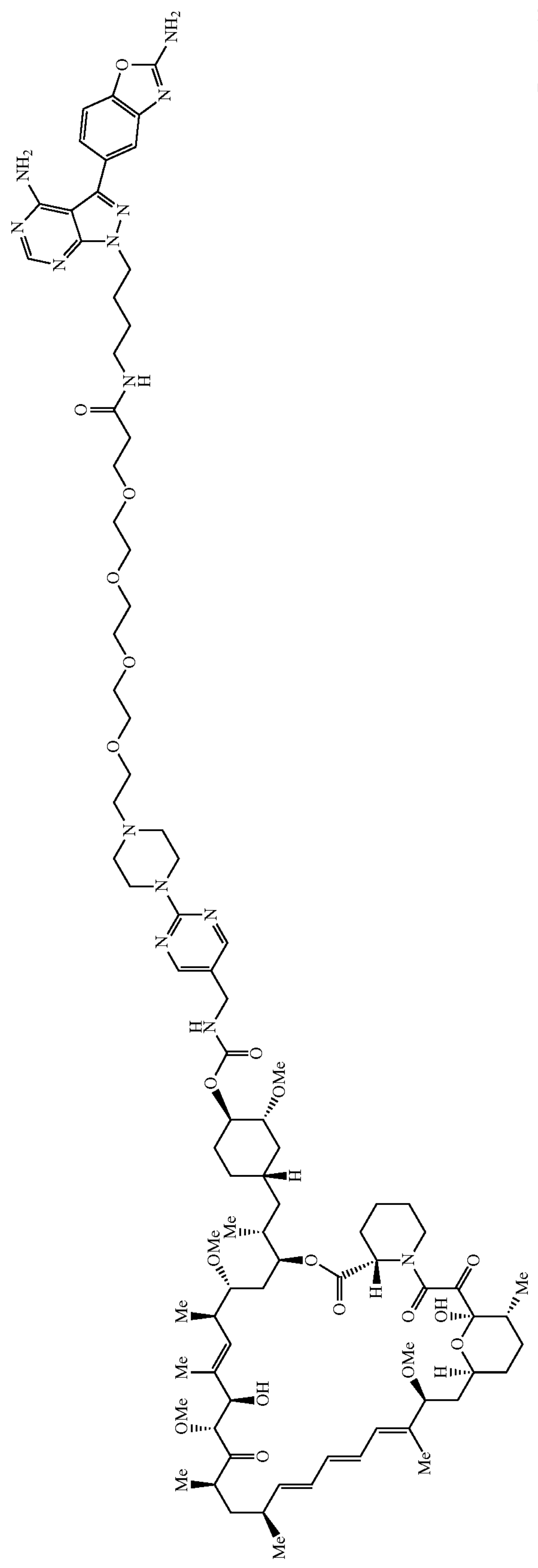
Example 46
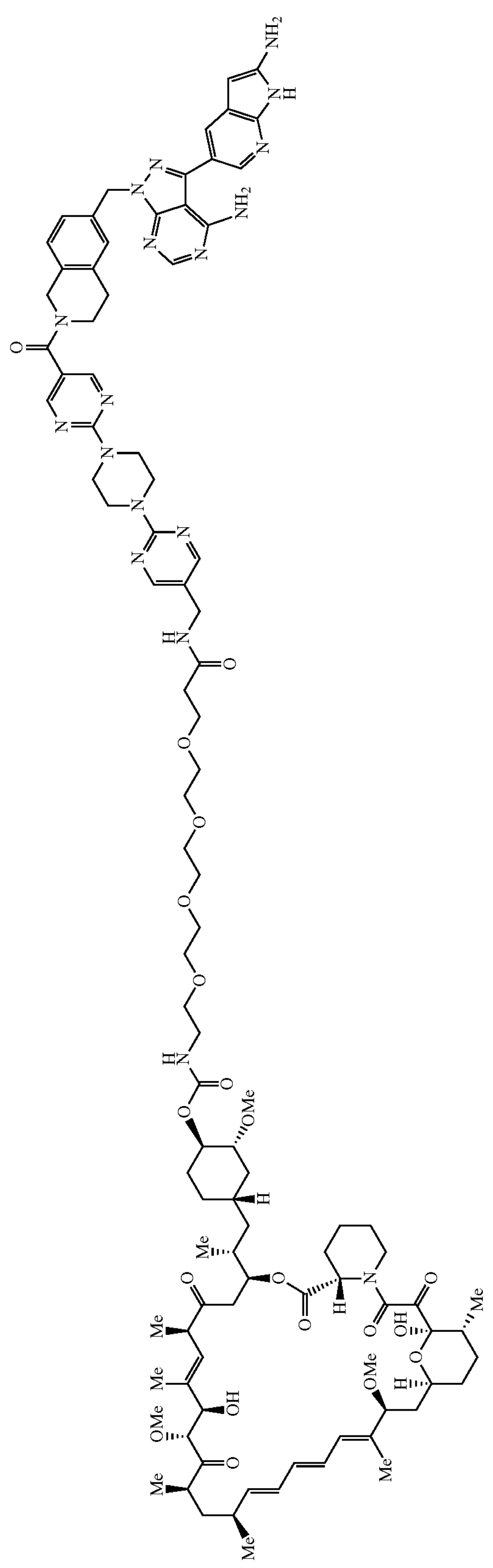

-continued
Example 47
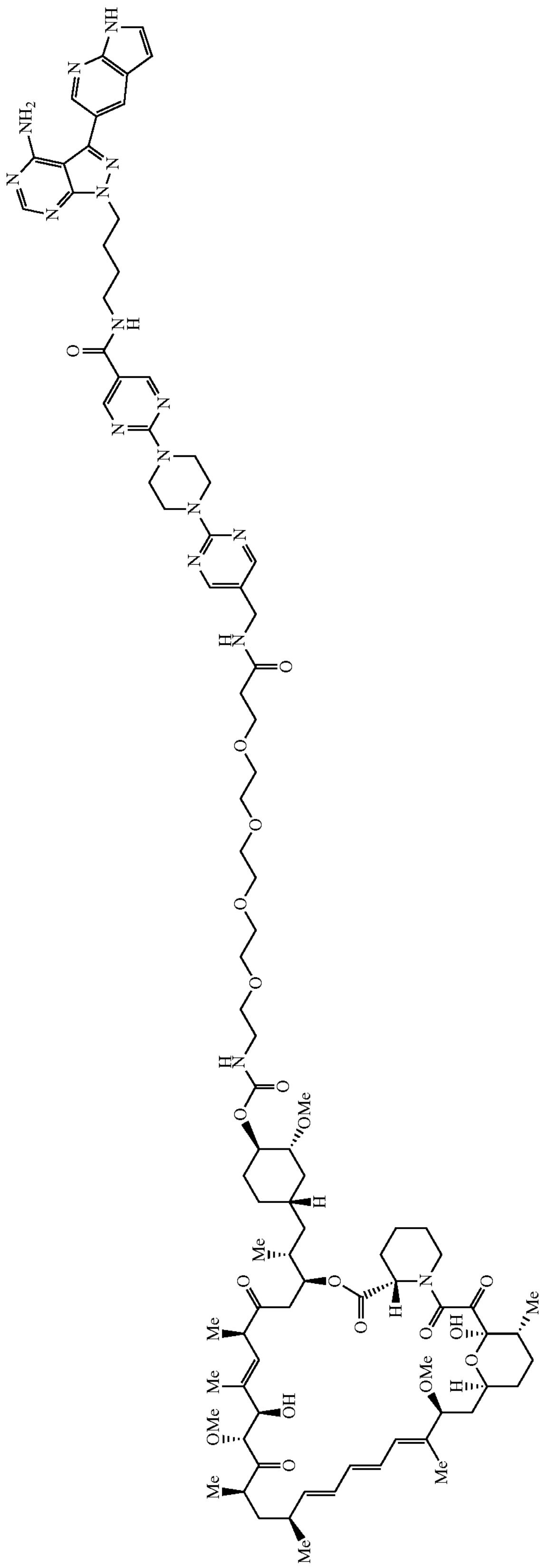

-continued
Example 48
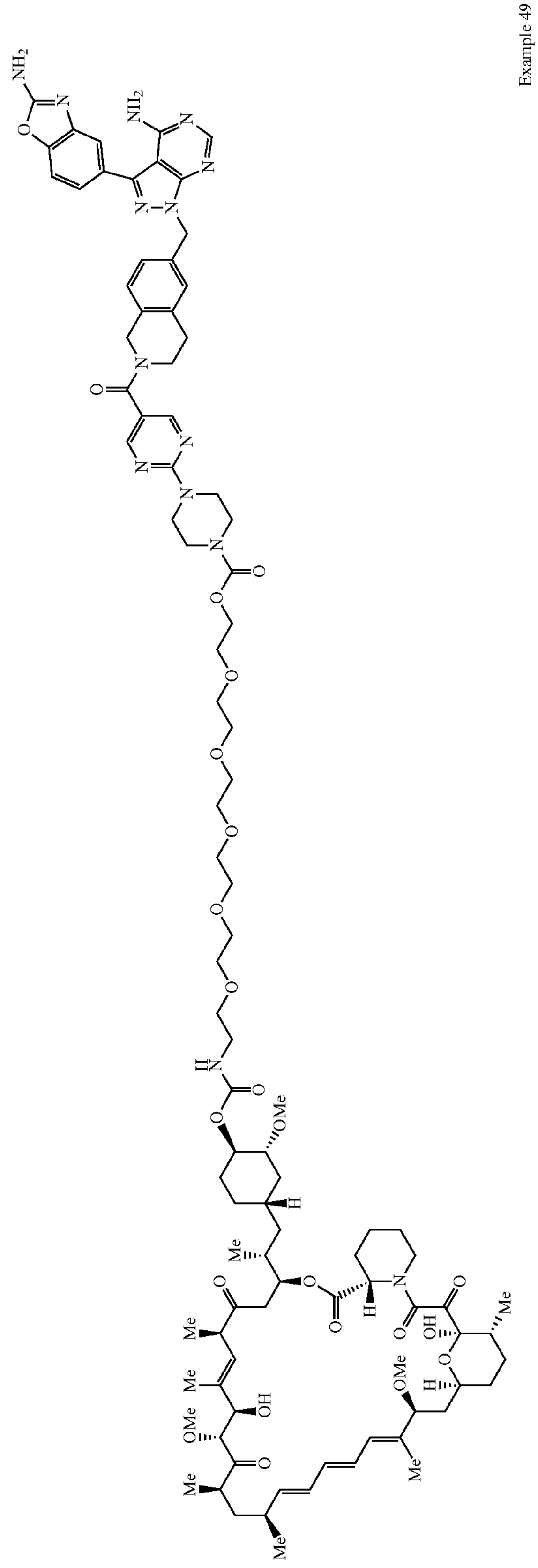
Example 49
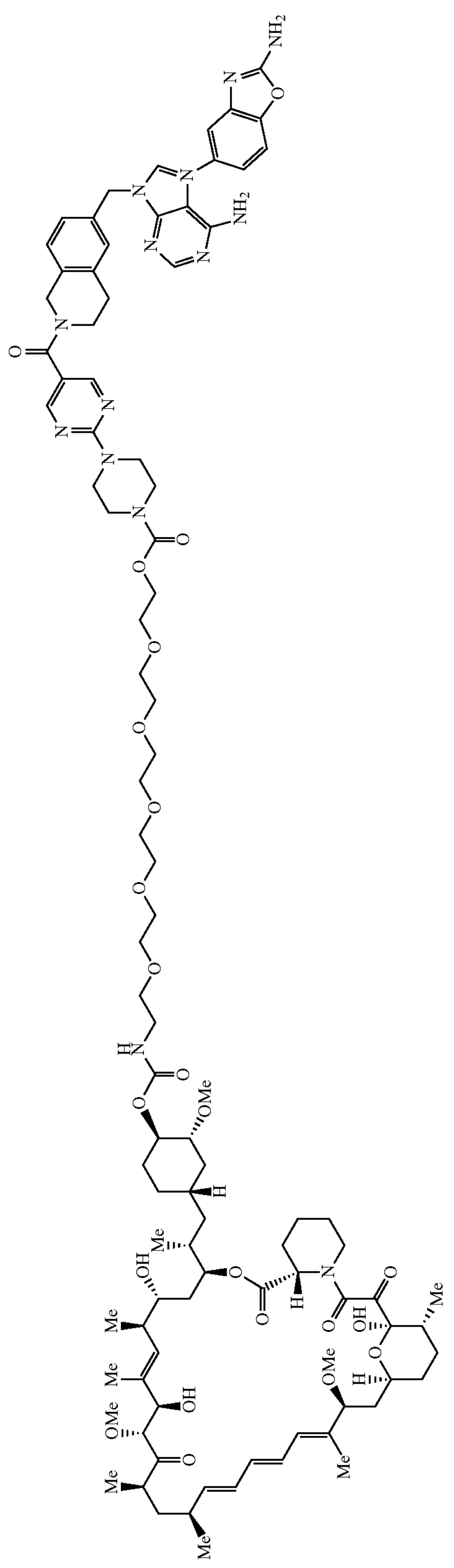

-continued
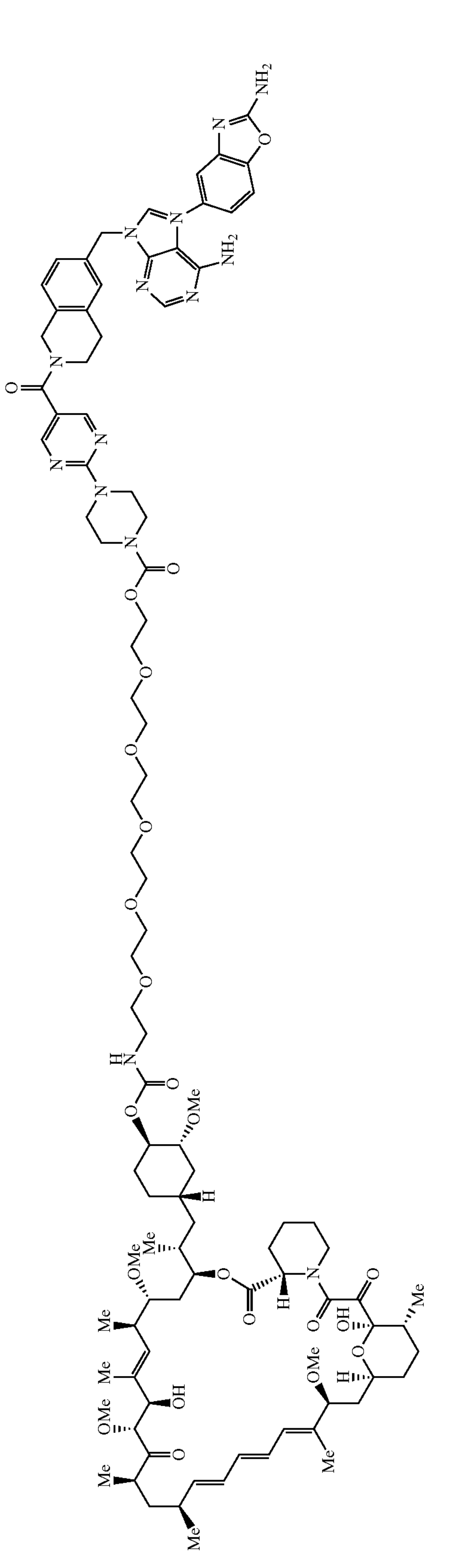
Example 50

-continued
Example 51
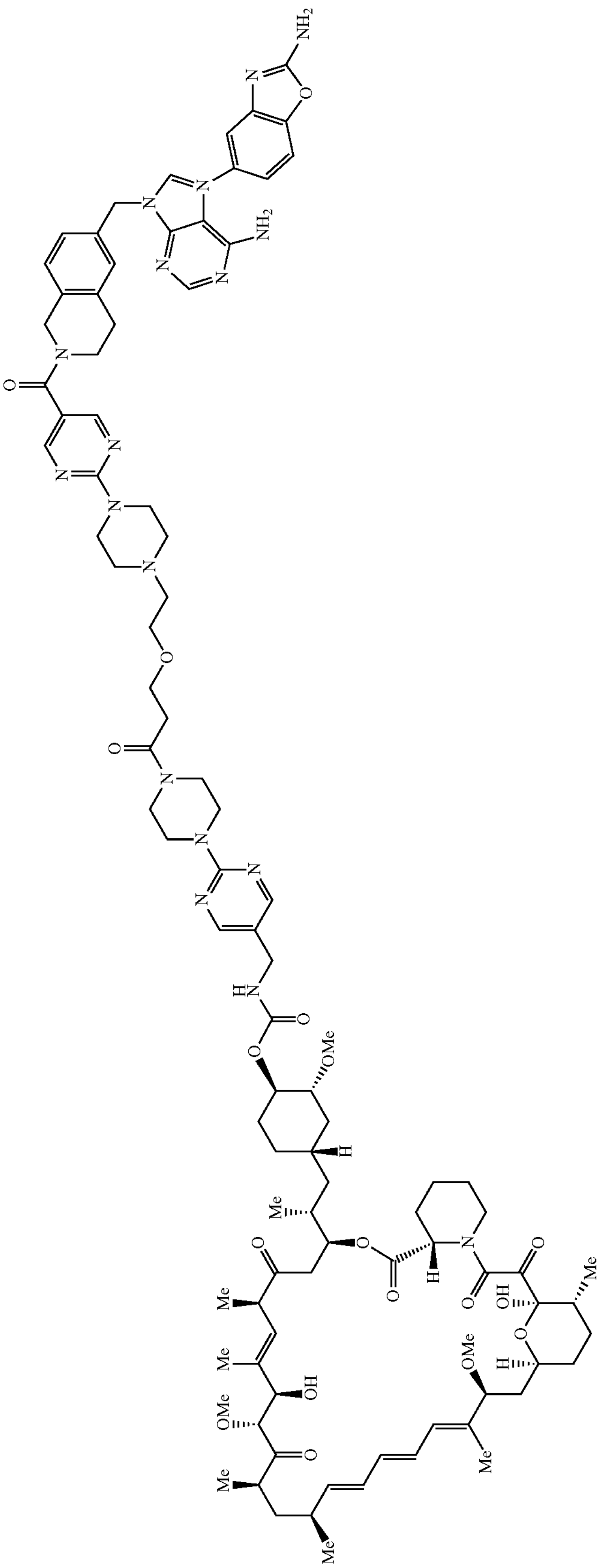

-continued
Example 52
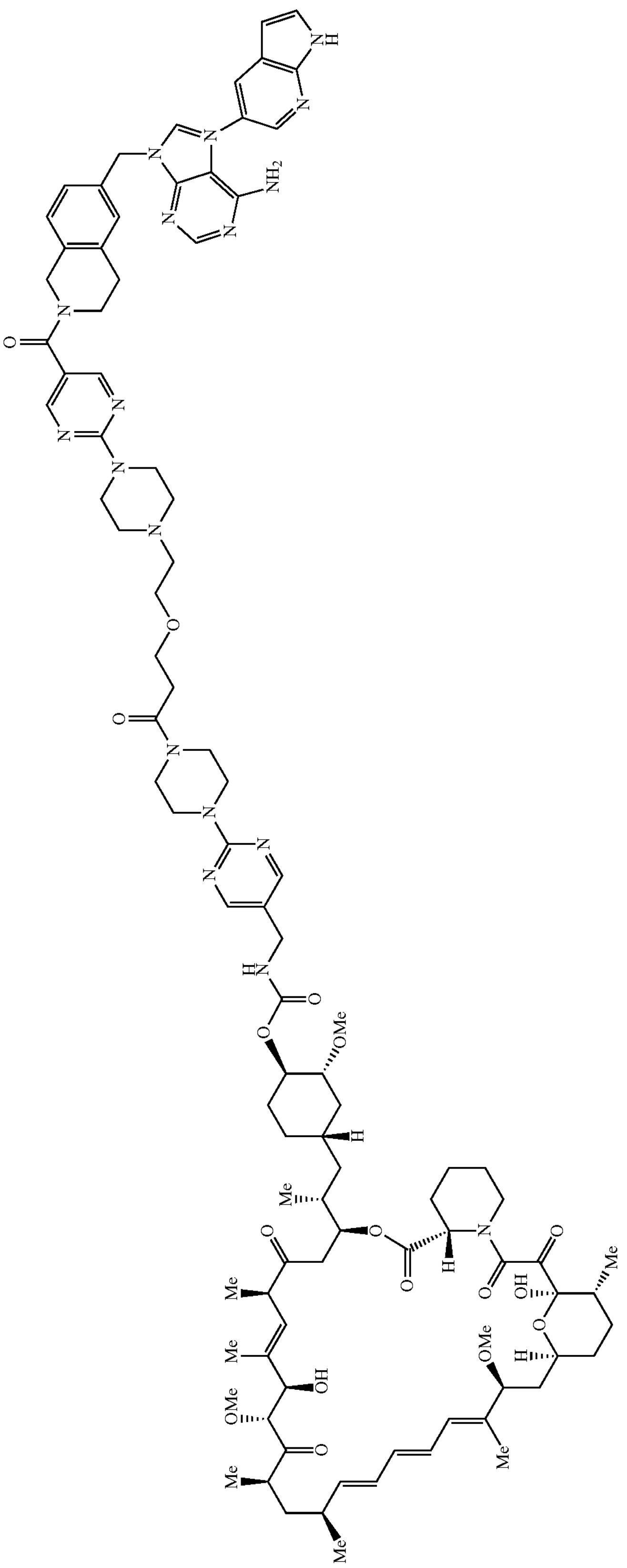

-continued
Example 53
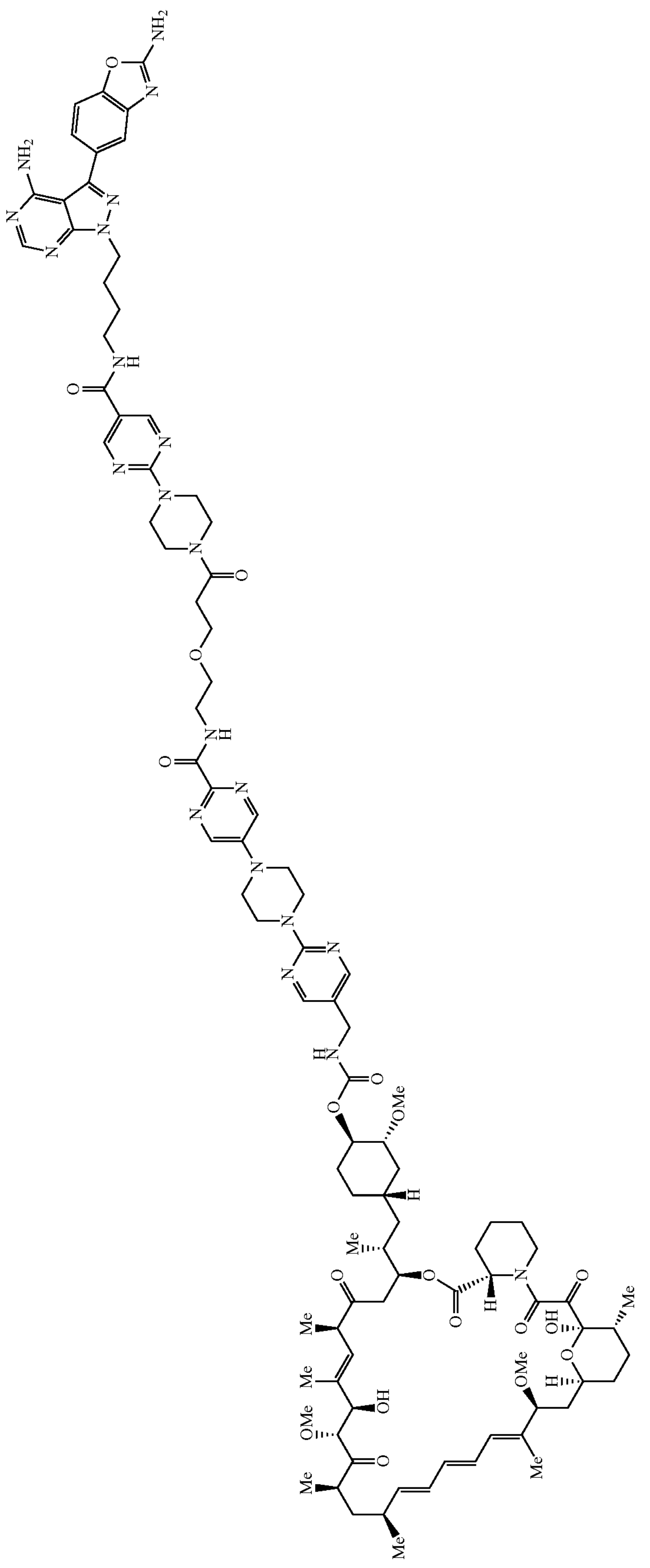

-continued
Example 54
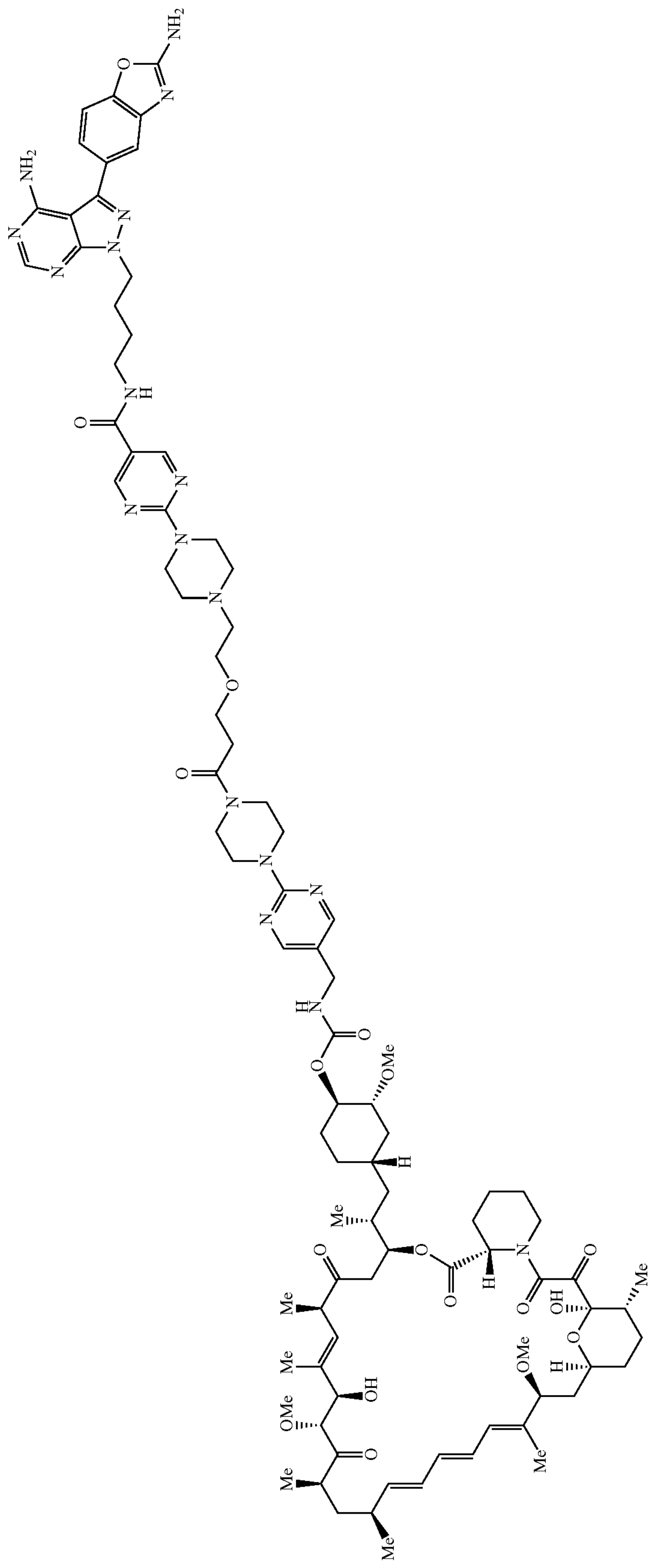

-continued
Example 55
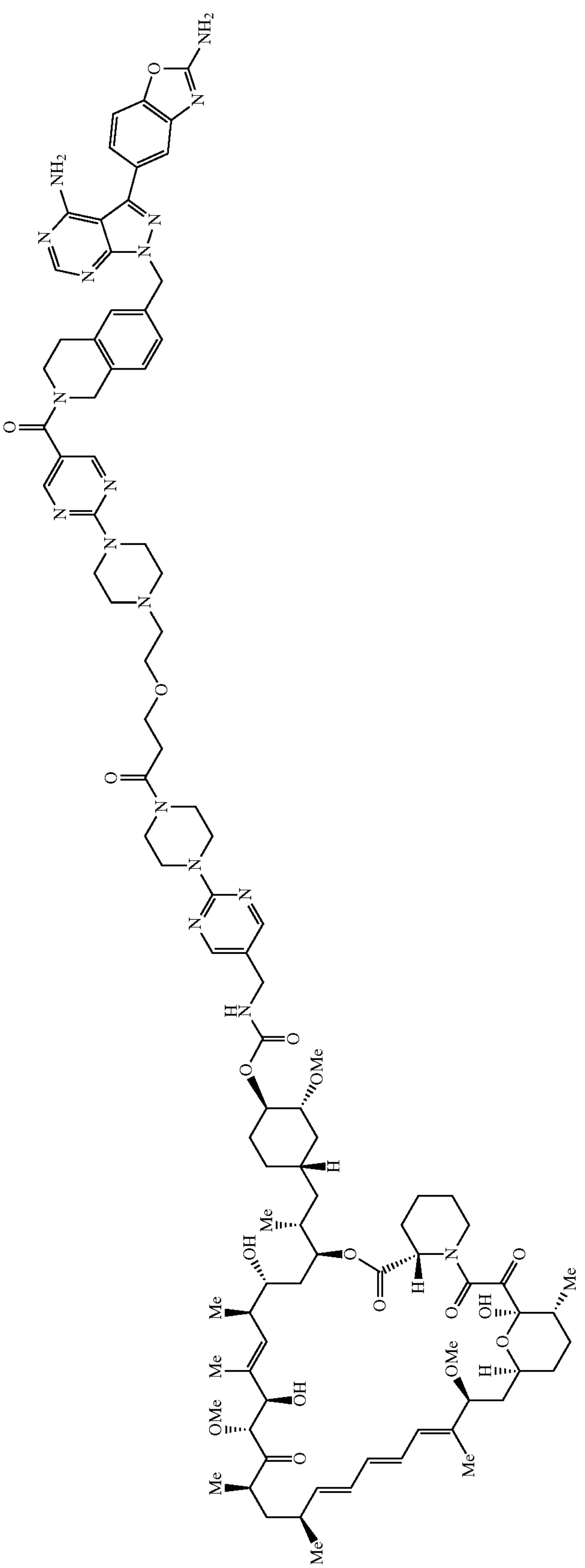

-continued
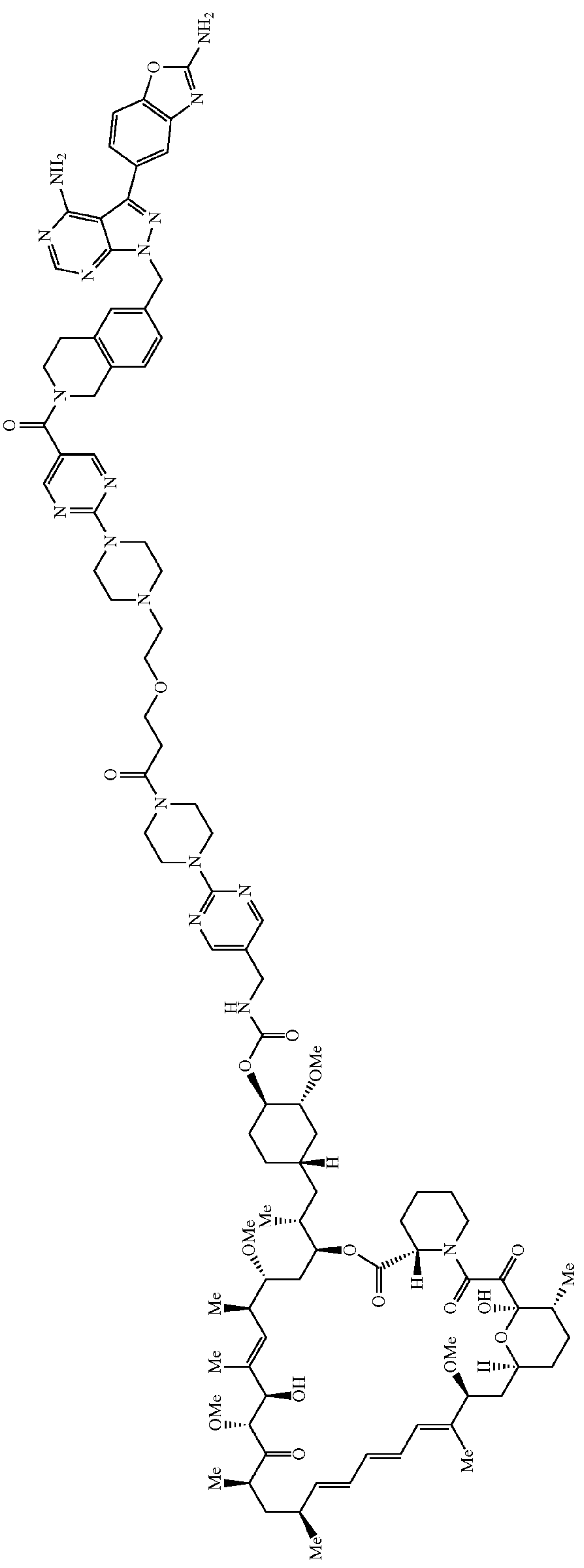
Example 56

-continued
Example 57
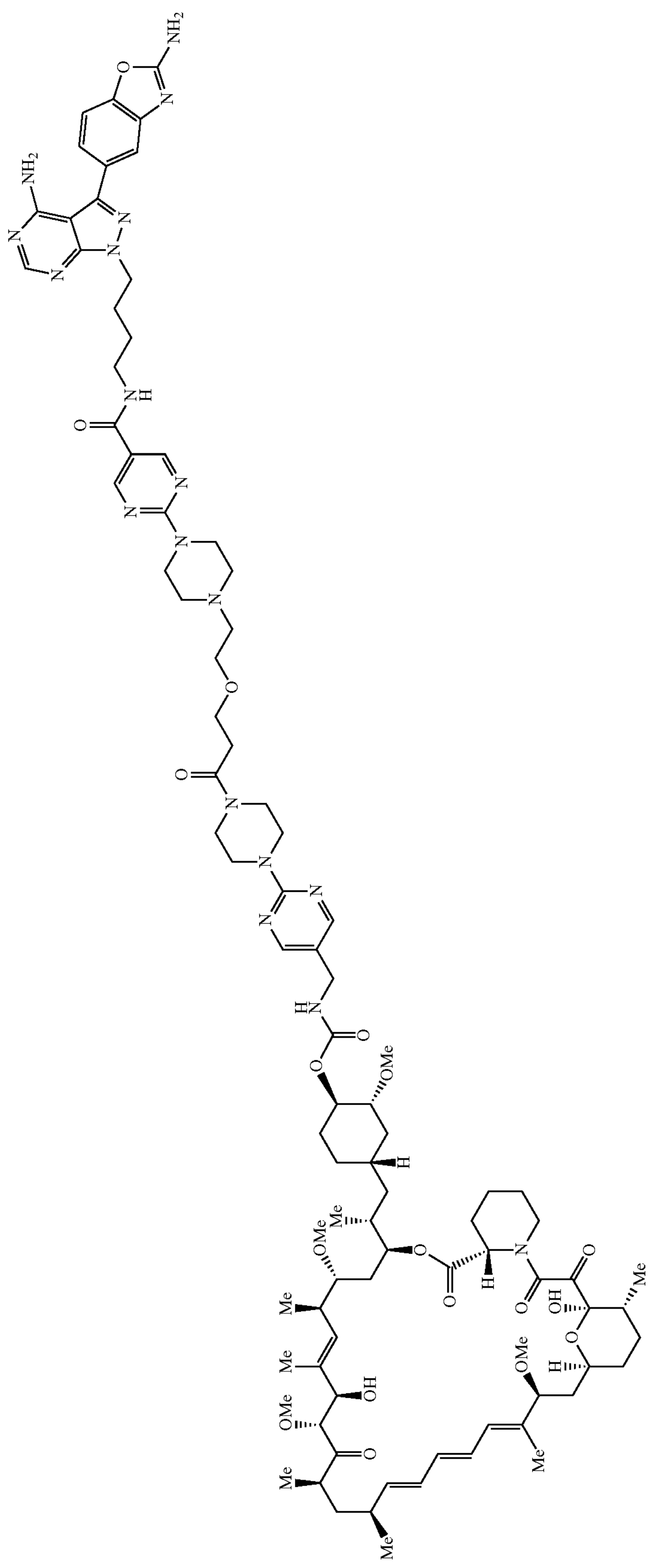

-continued
Example 58
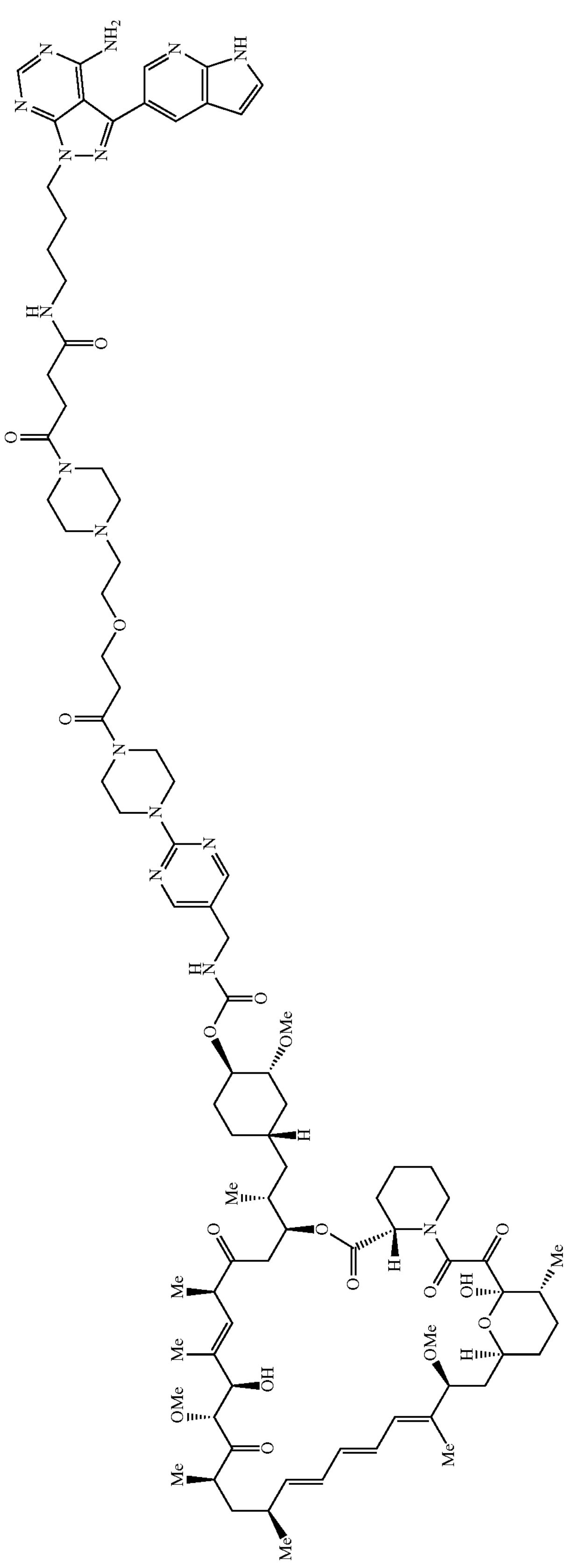

-continued
Example 59
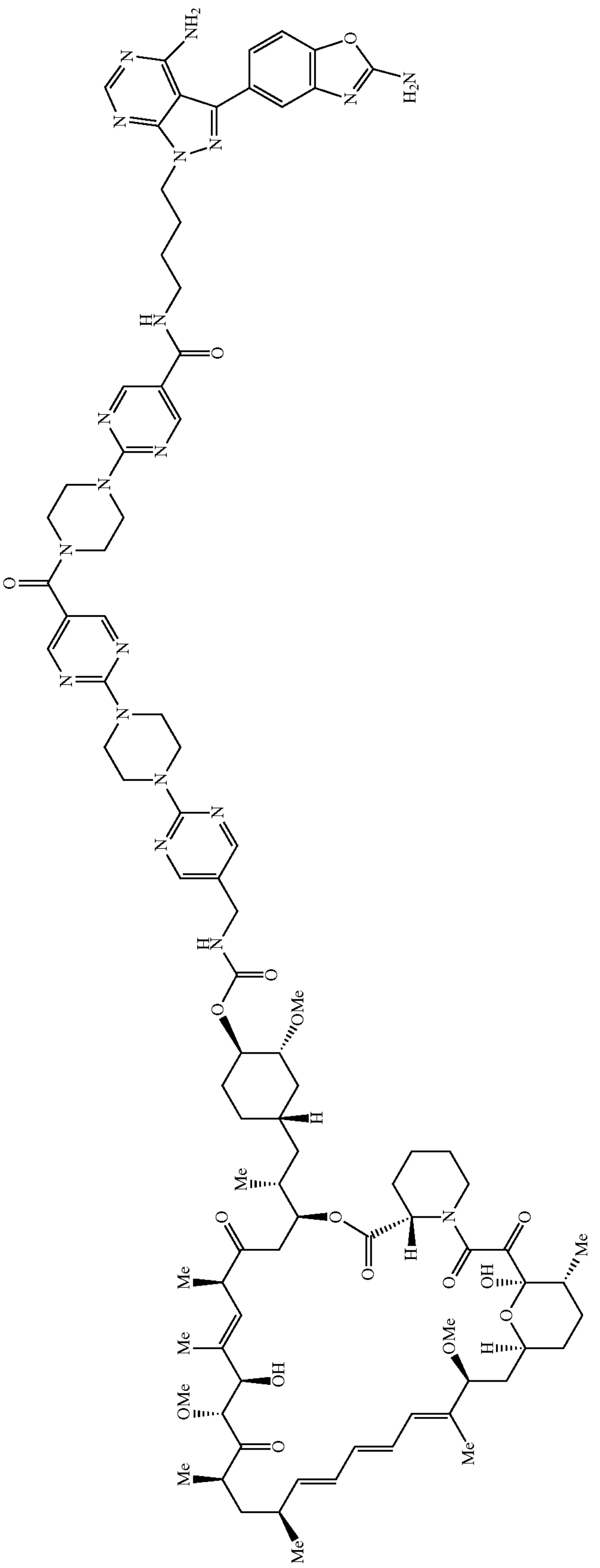

-continued
Example 60
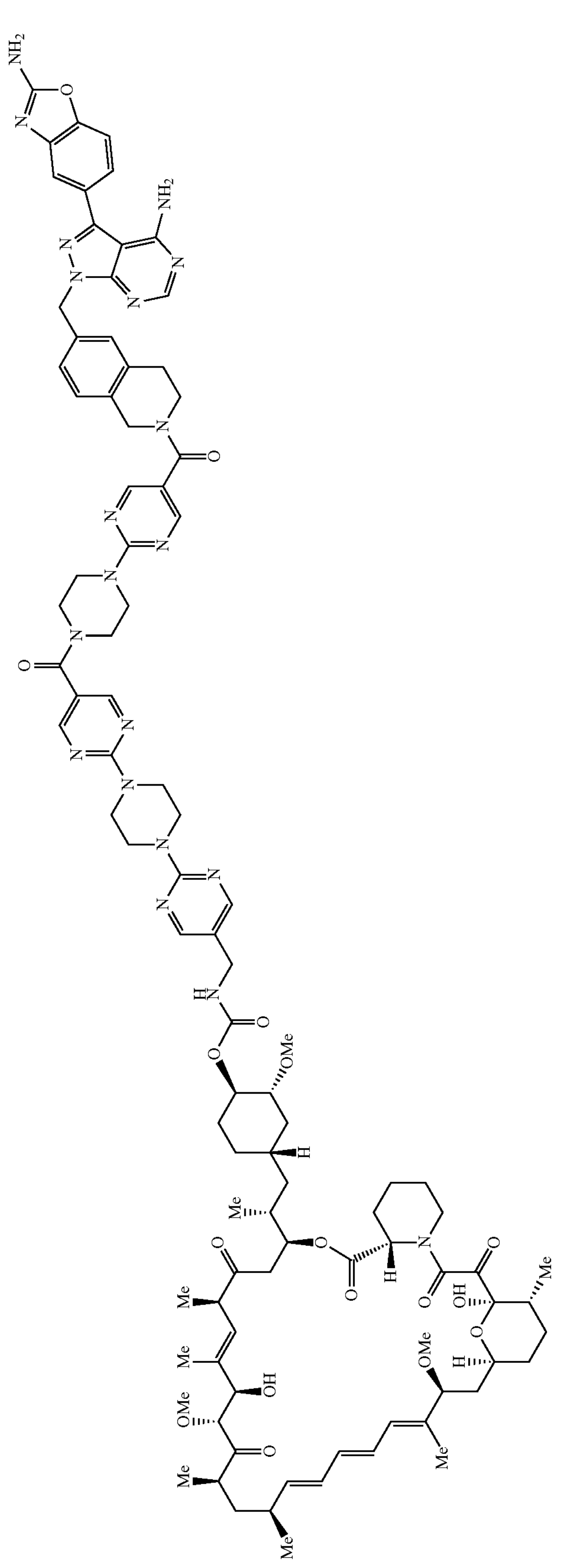

-continued
Example 61
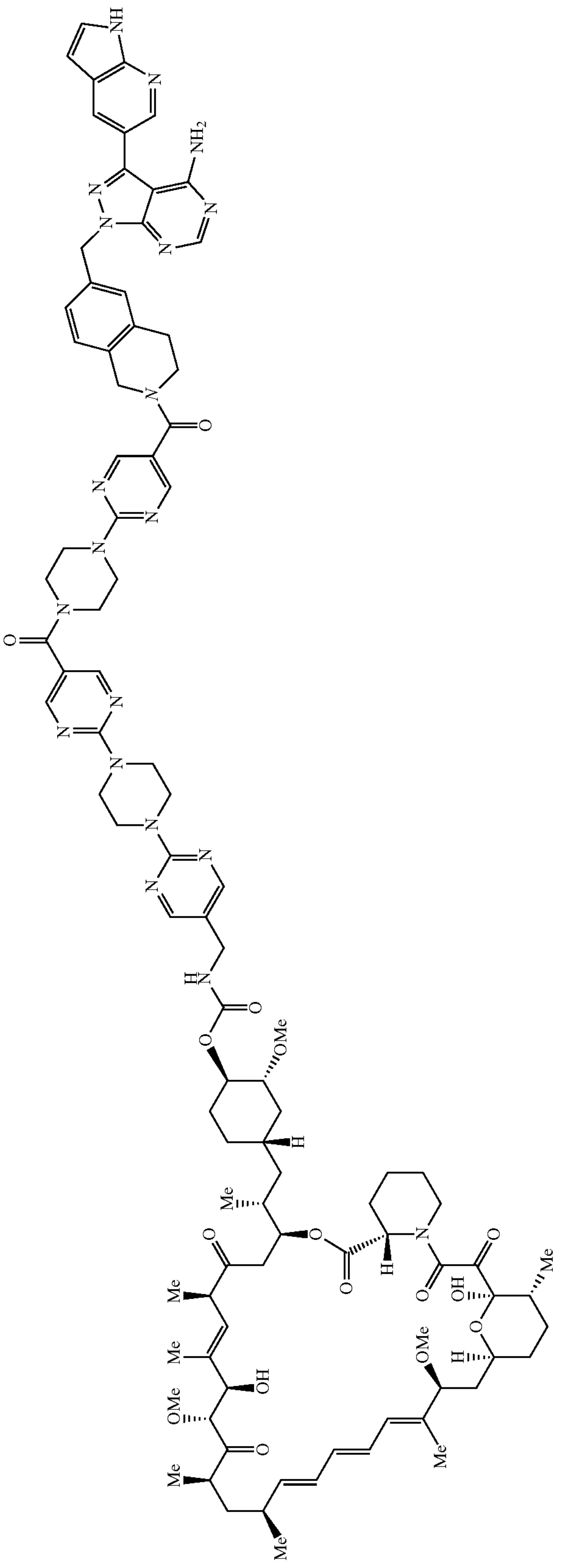

-continued
Example 62
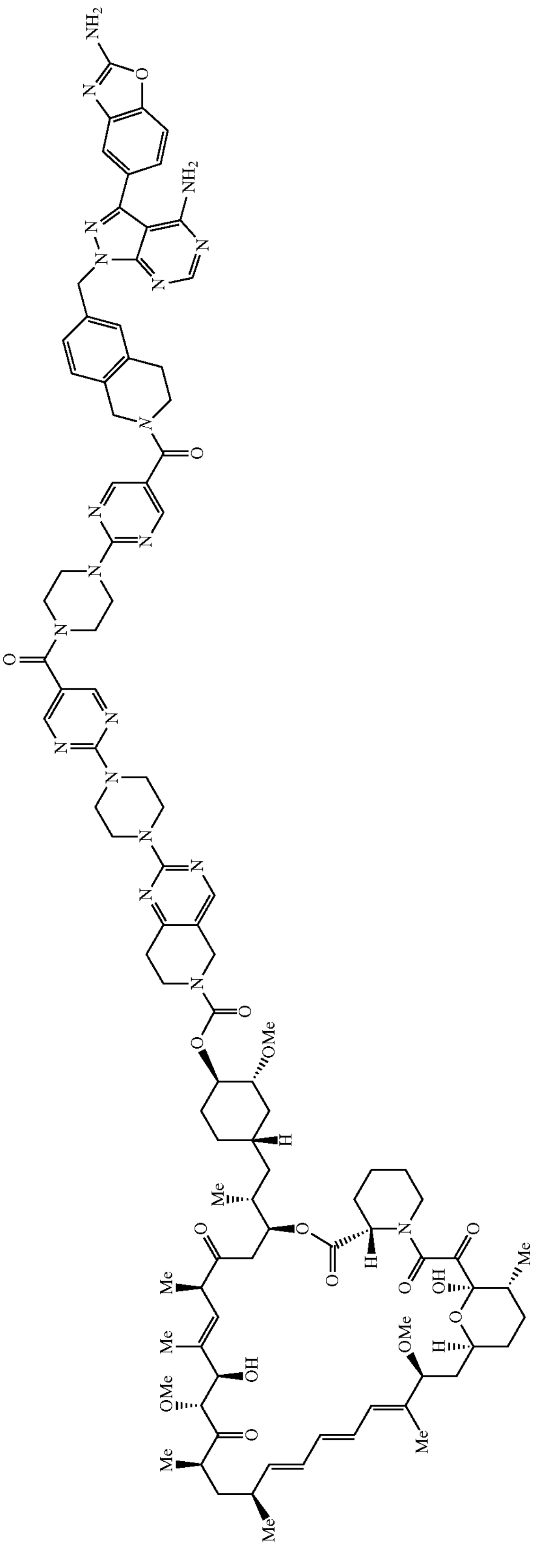

-continued
Example 63
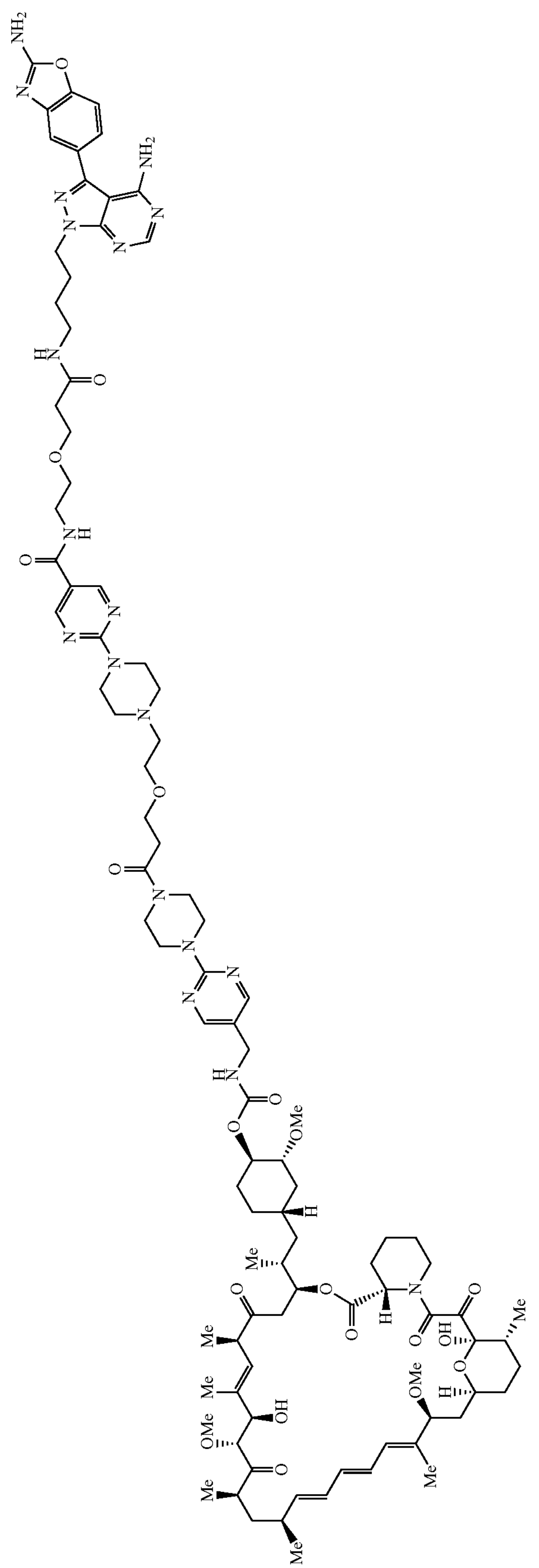

-continued
Example 64
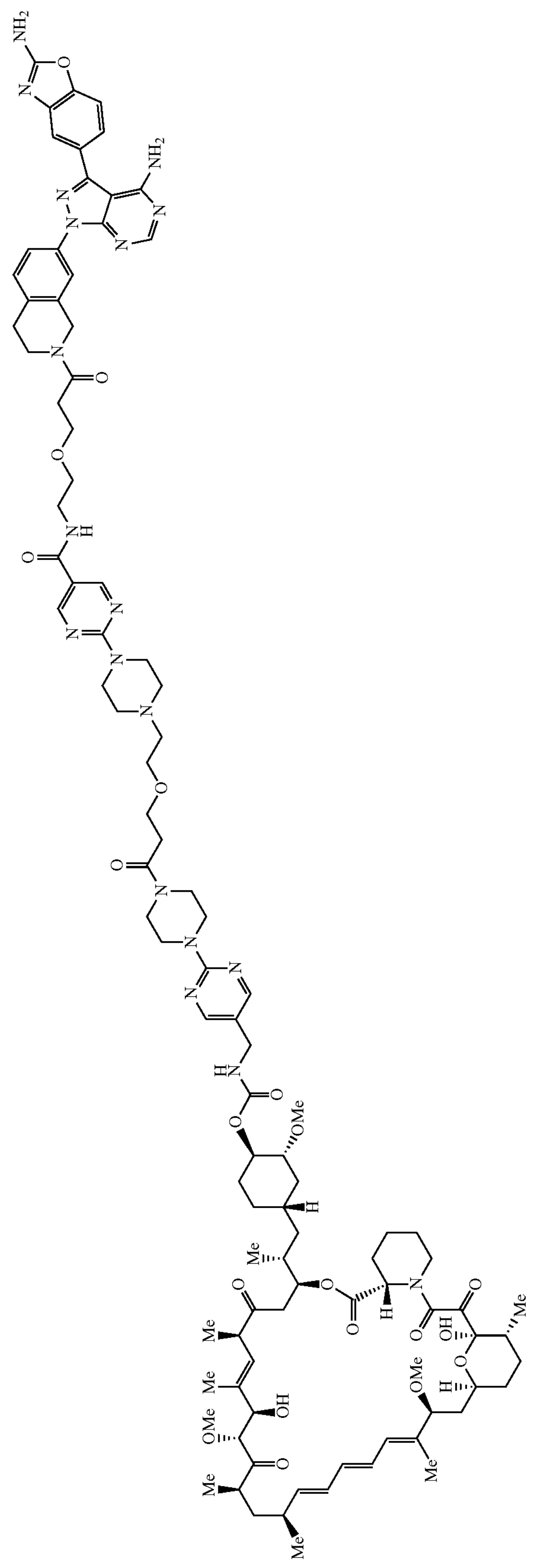

-continued
Example 65
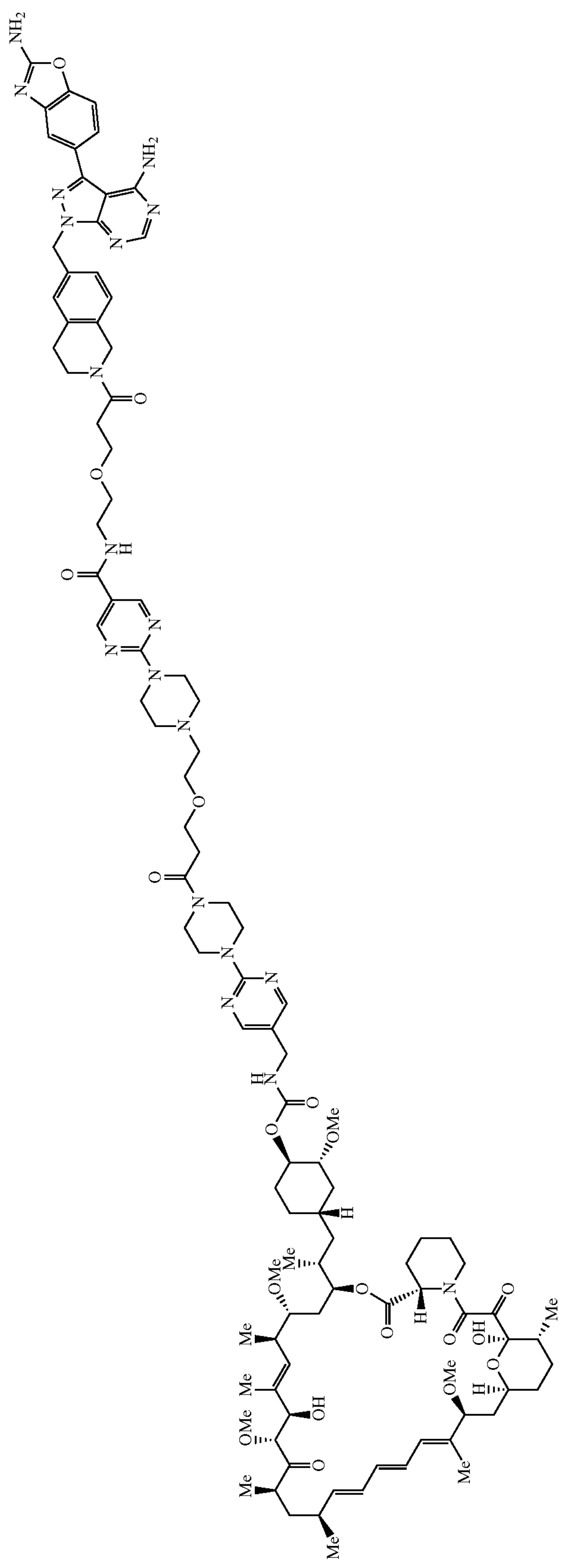

-continued
Example 66
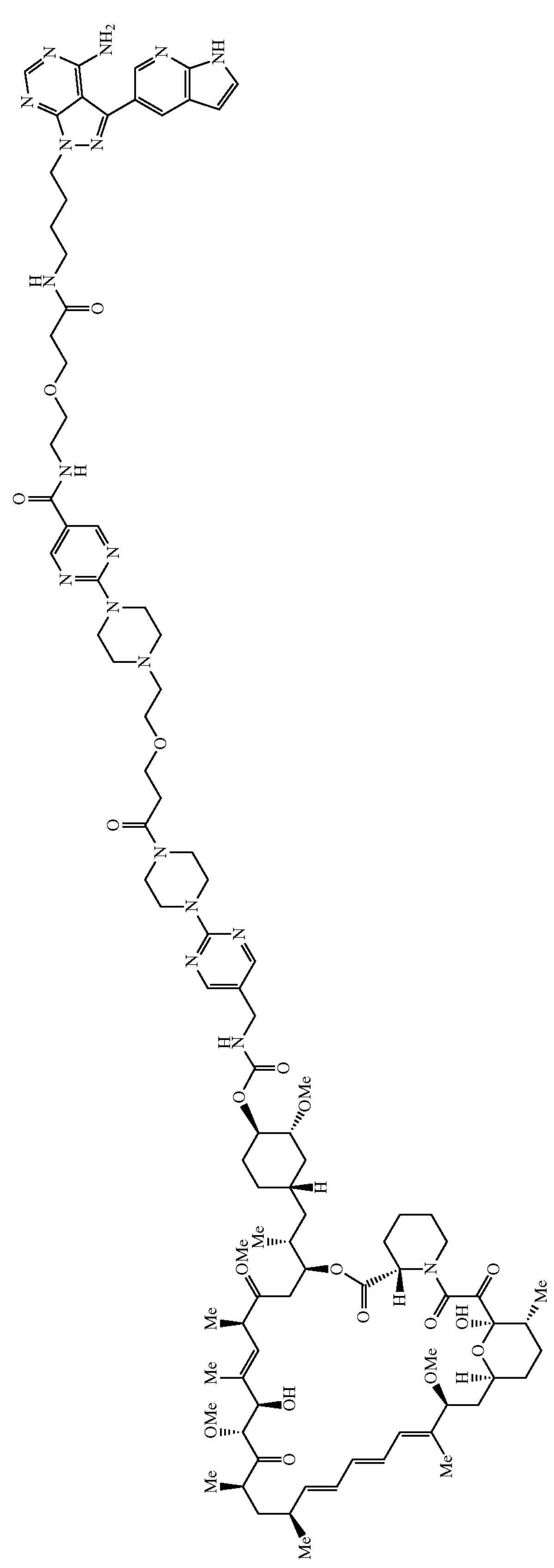
Example 67
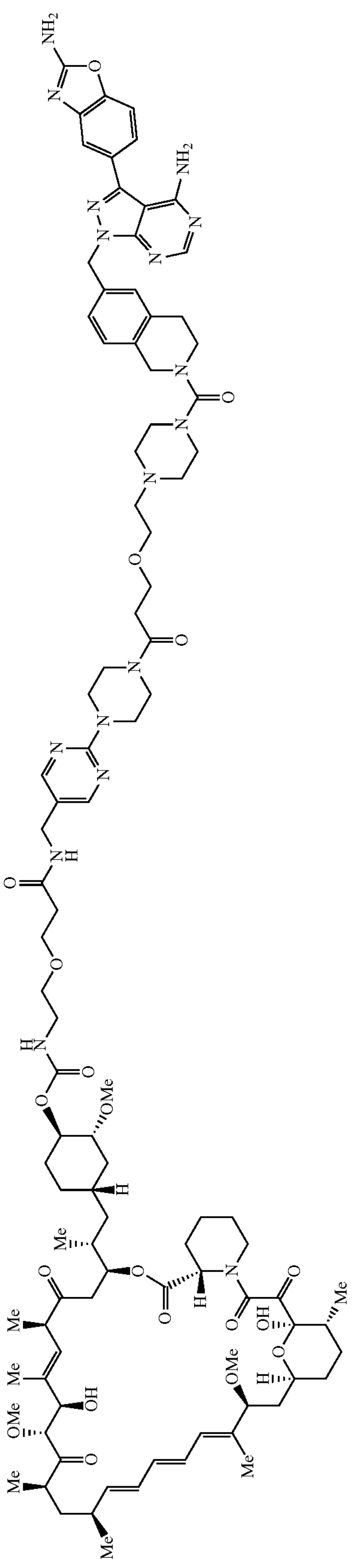

-continued
Example 68
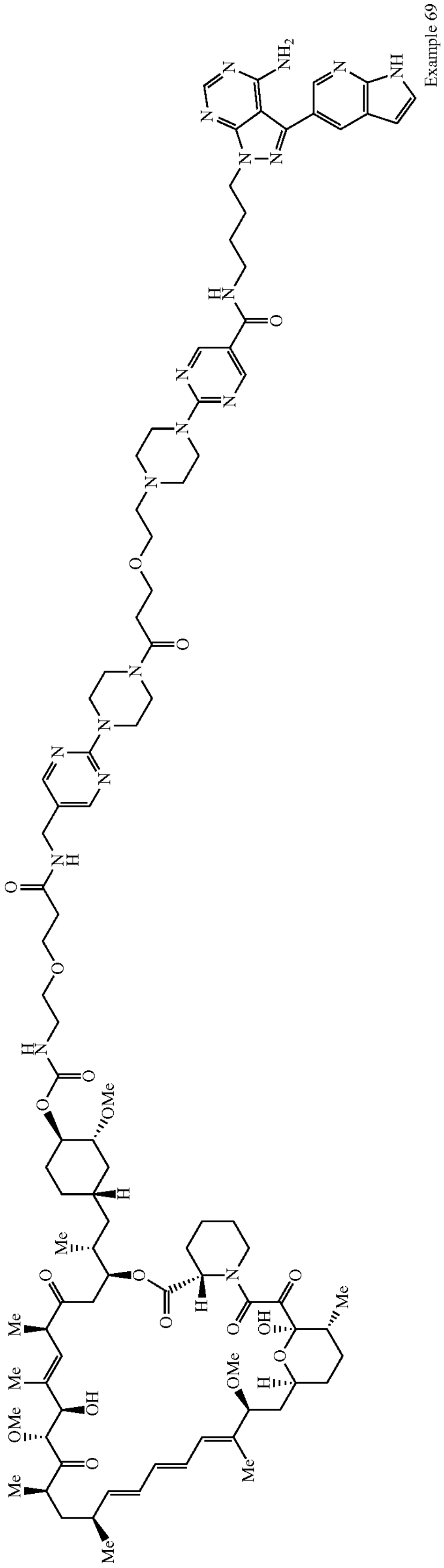
Example 69
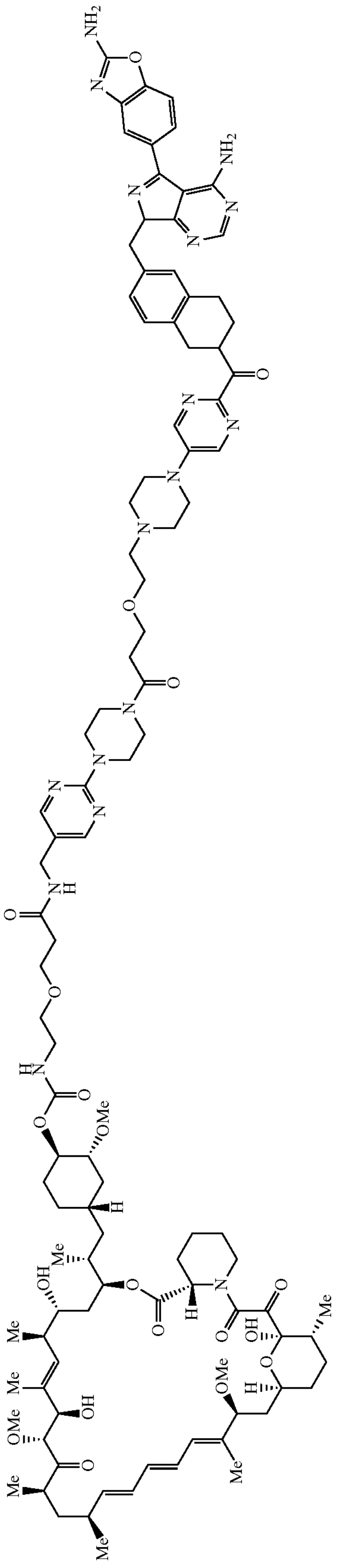

-continued
Example 70
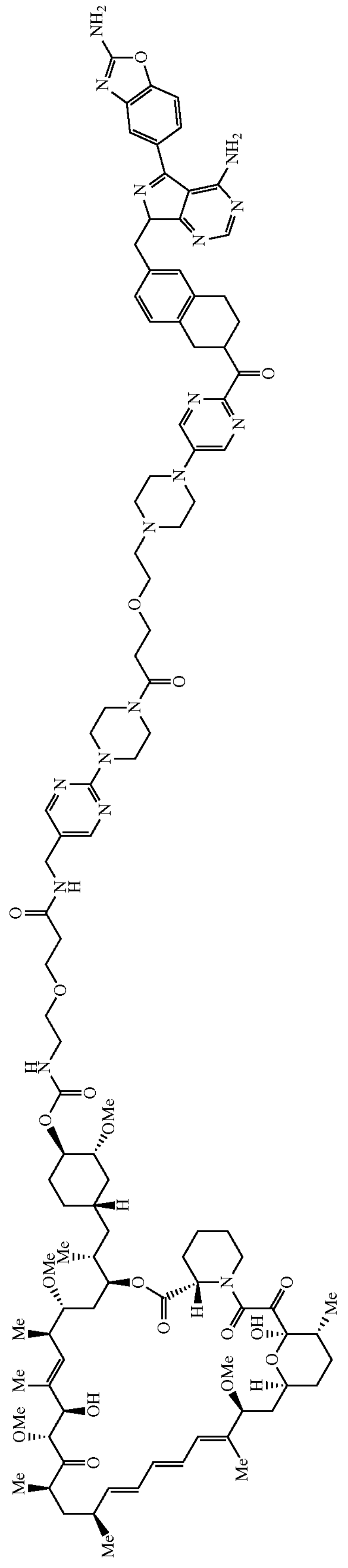

In certain embodiments, the present disclosure provides for a compound selected from below or a pharmaceutically acceptable salt or tautomer thereof, Example 71
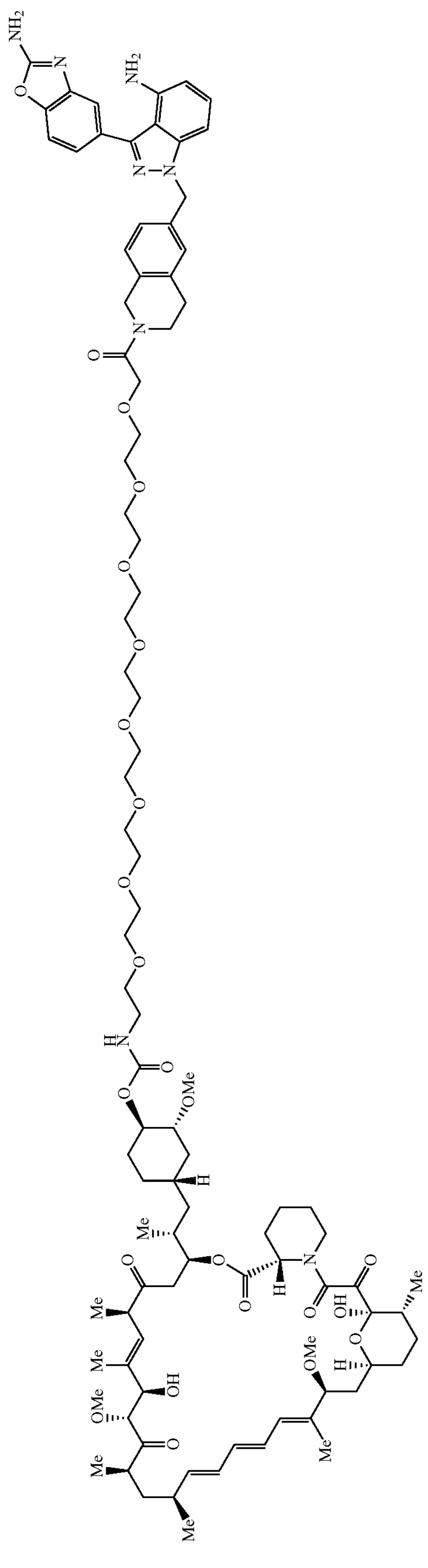
Example 72
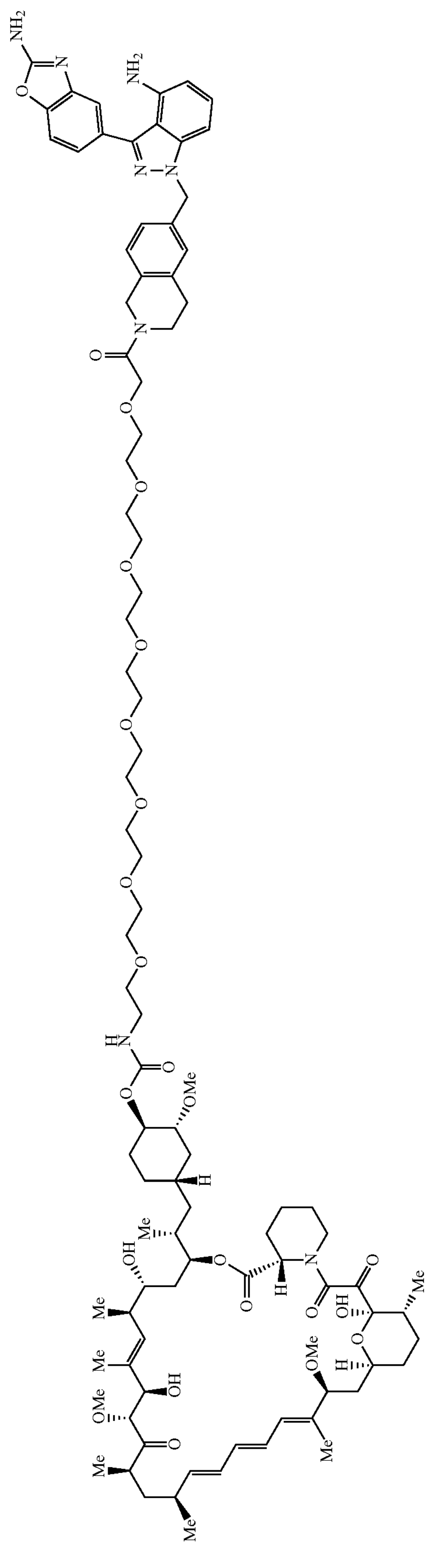

-continued
Example 73
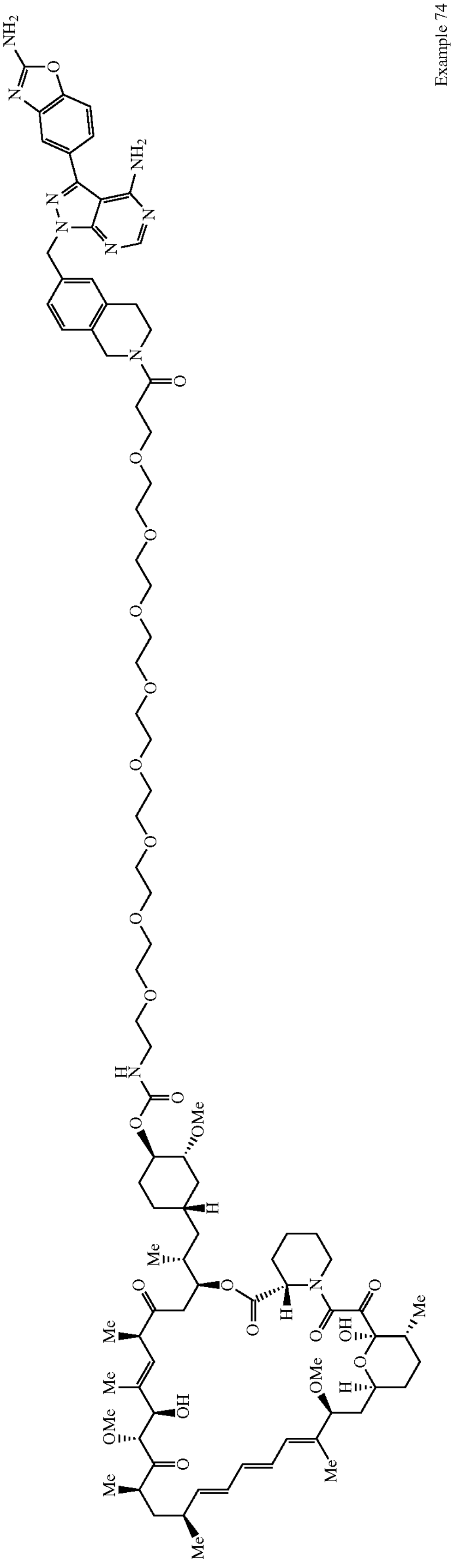
Example 74
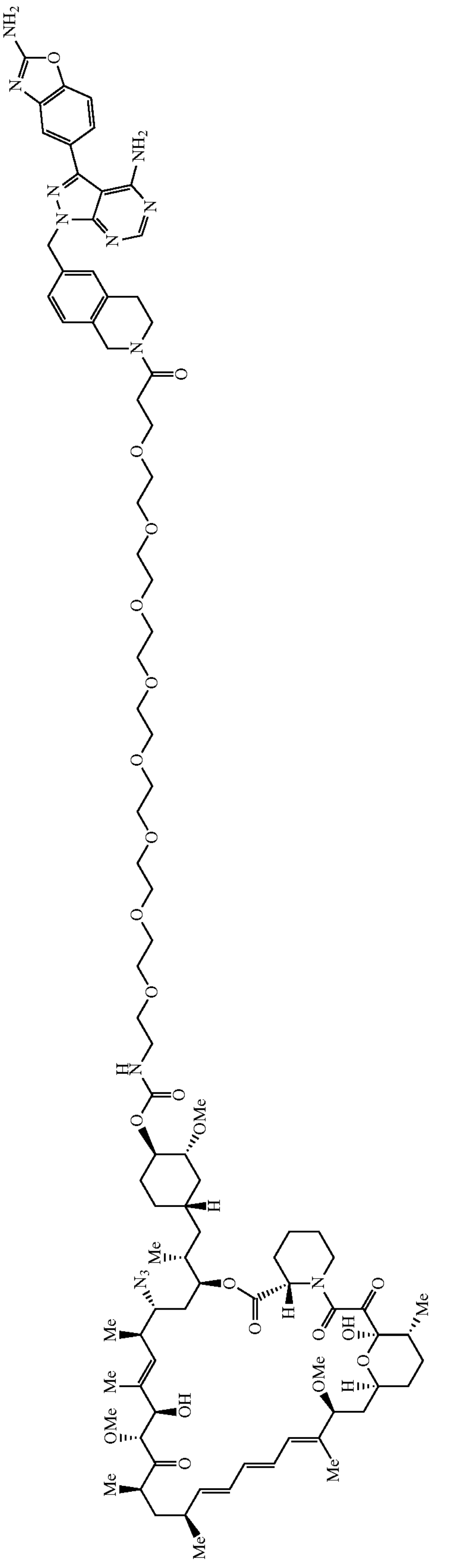

-continued
Example 75
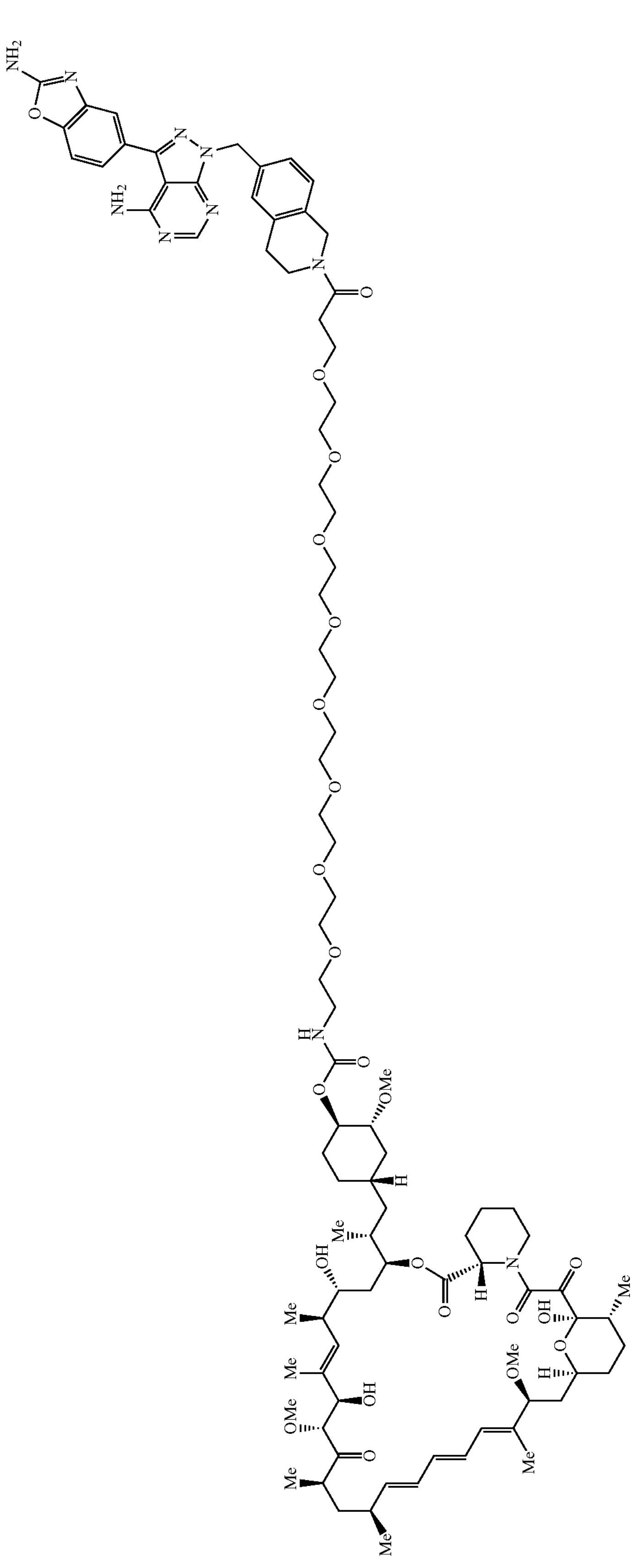

-continued
Example 76
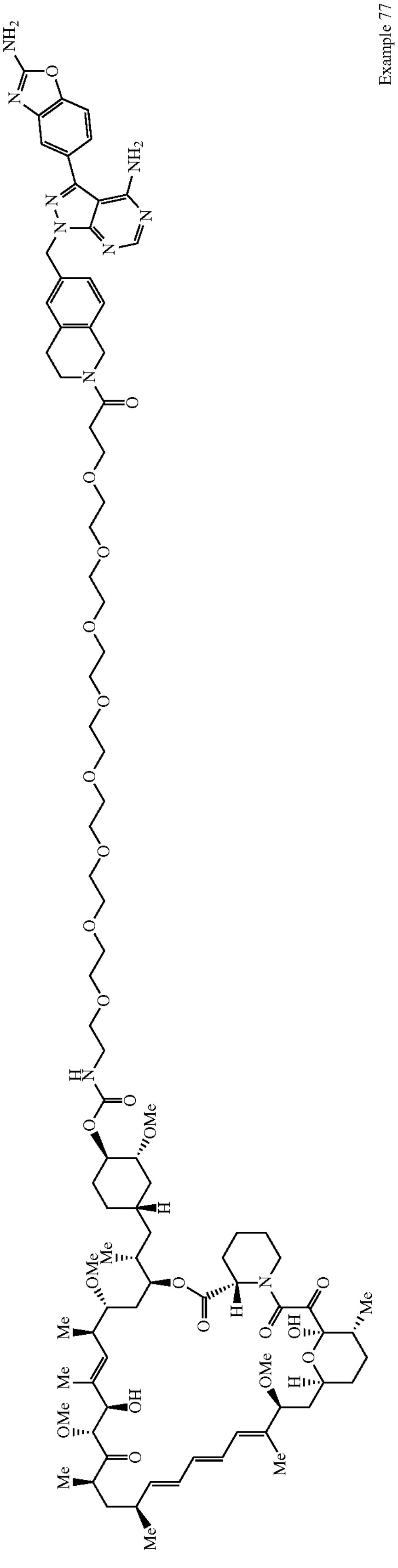
Example 77
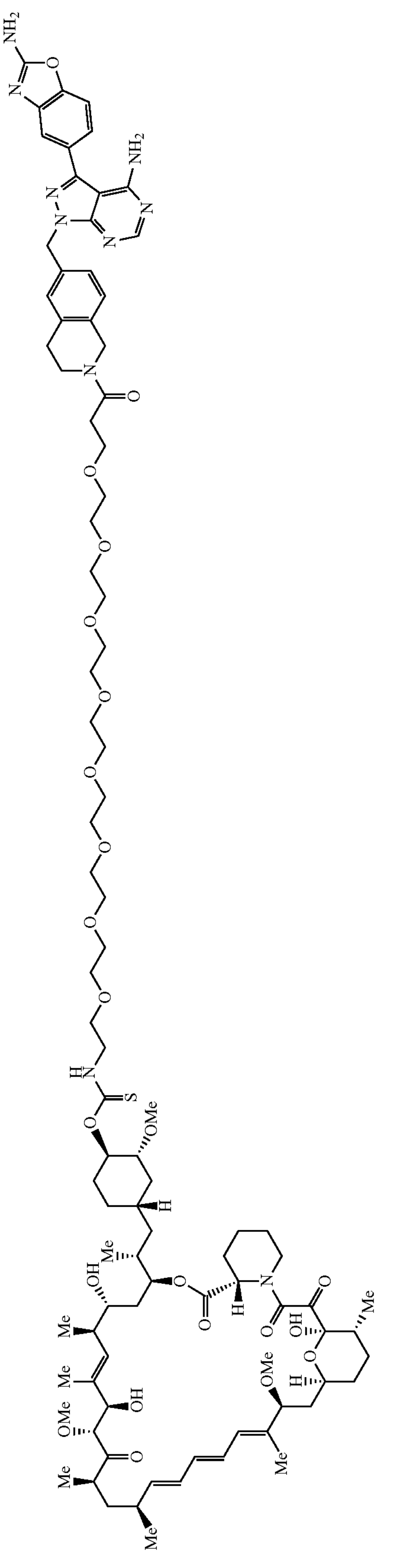

-continued
Example 78
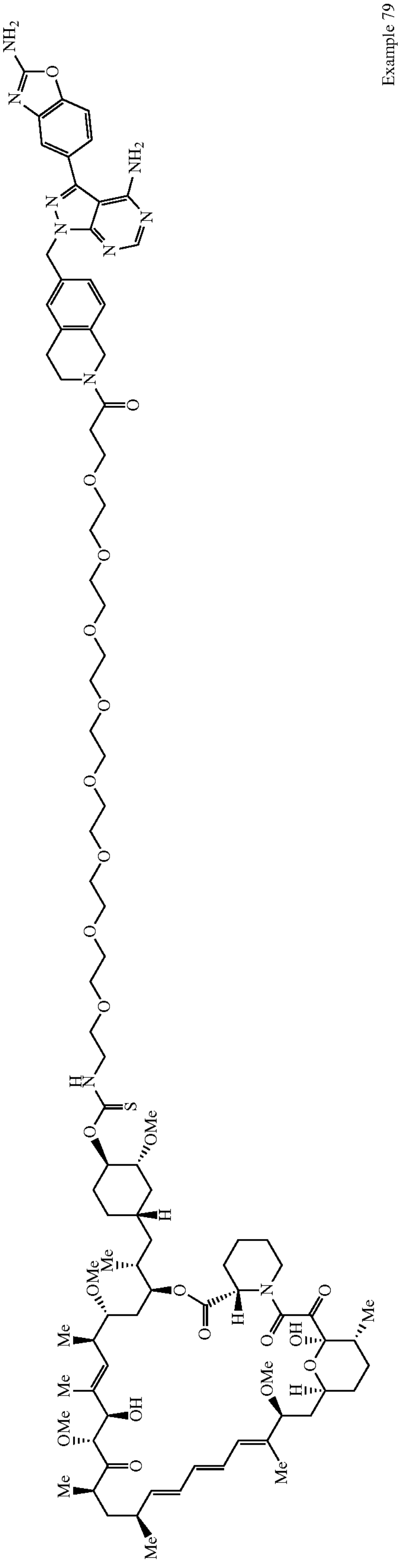
Example 79
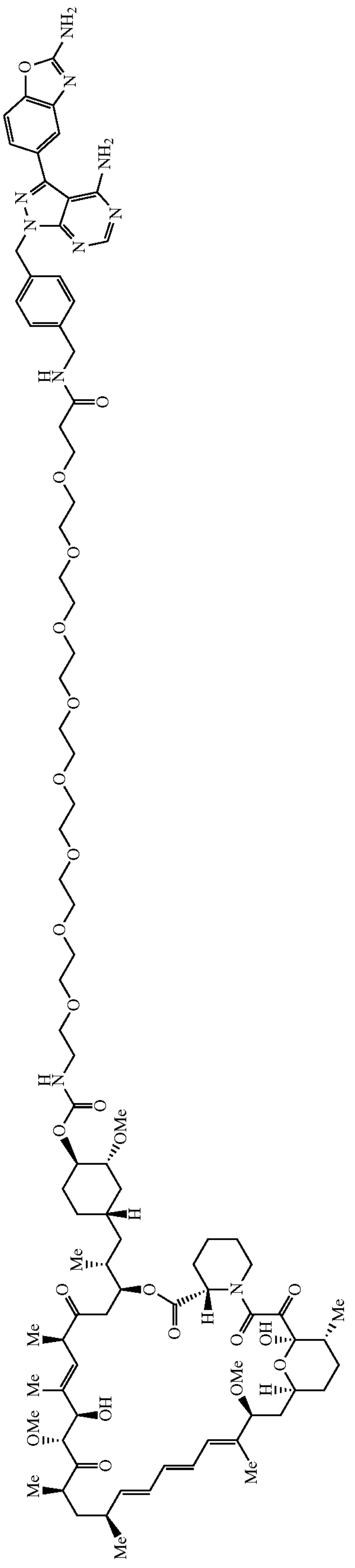

-continued
Example 80
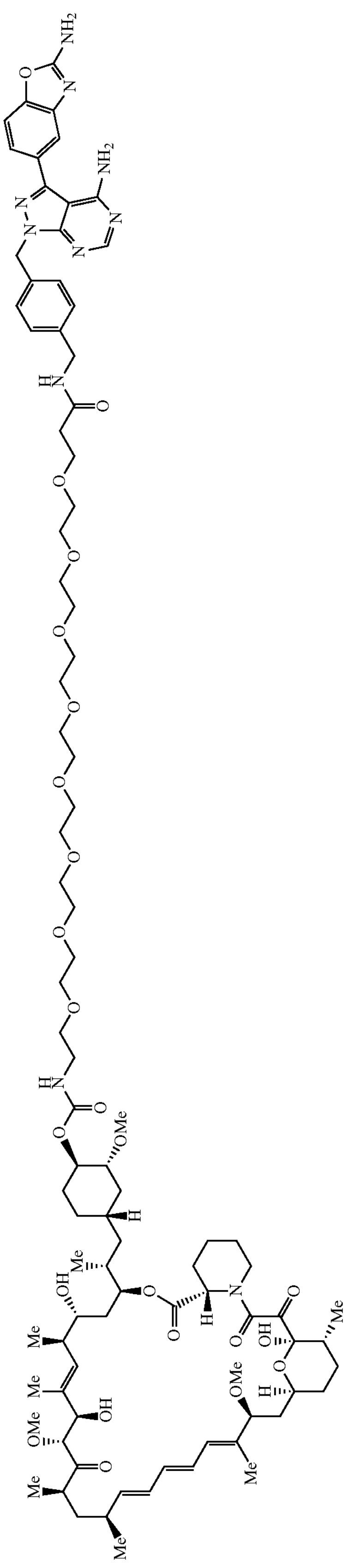
Example 81
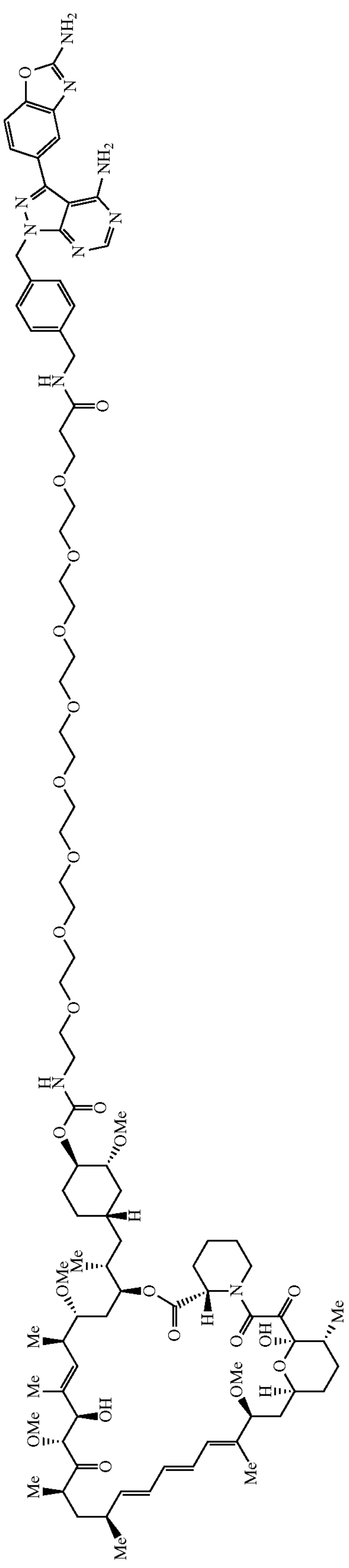

-continued
Example 82
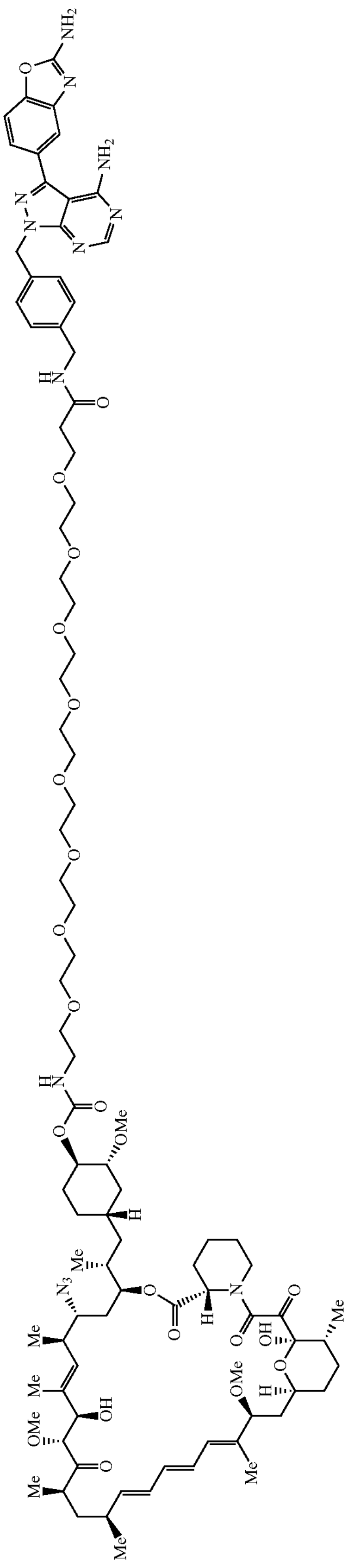
Example 83
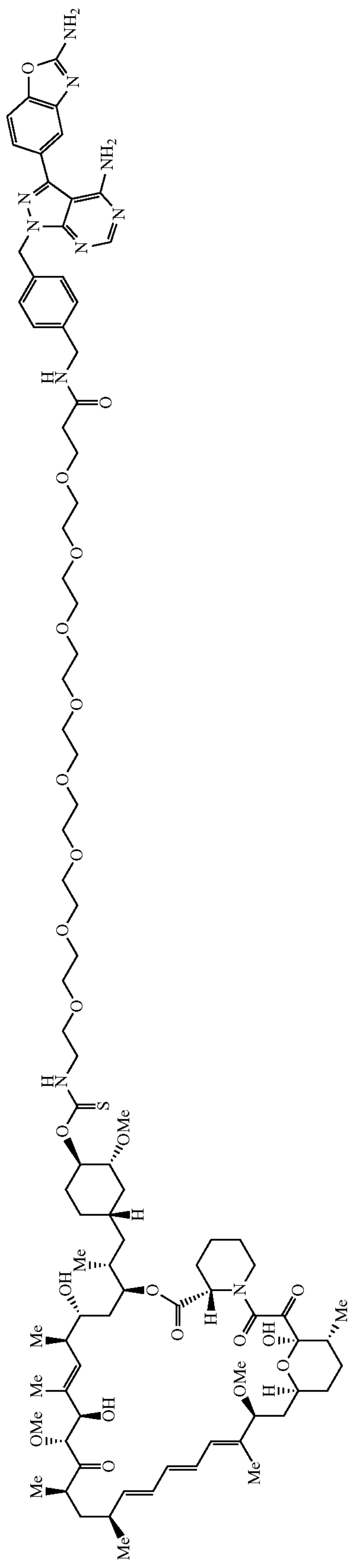

-continued
Example 84
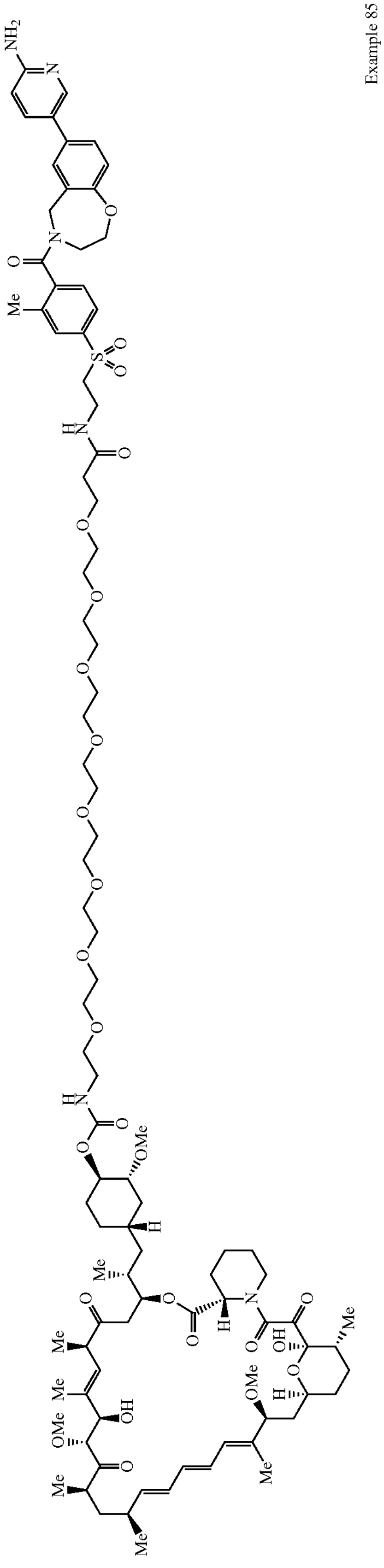
Example 85
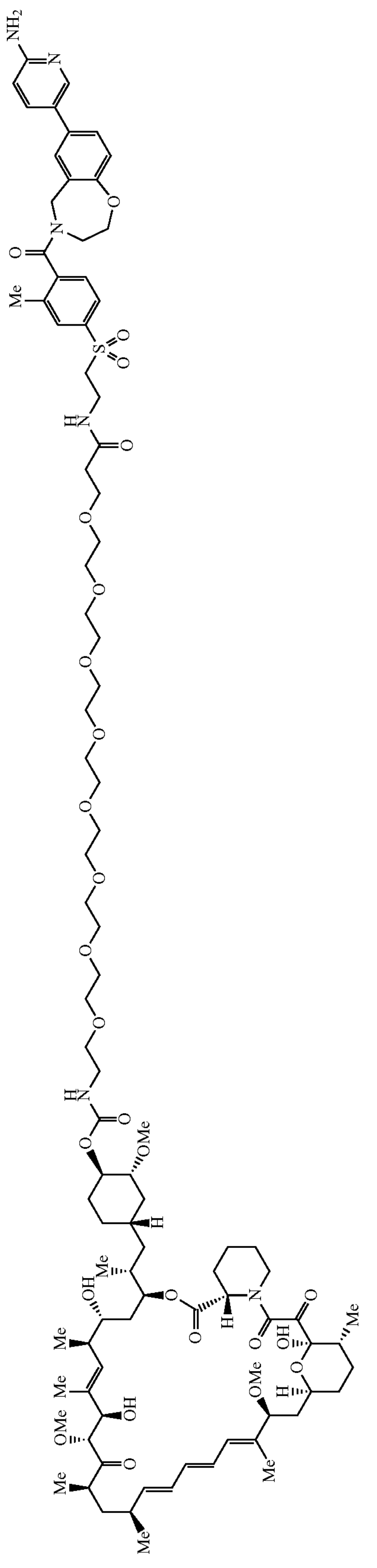

-continued
Example 86
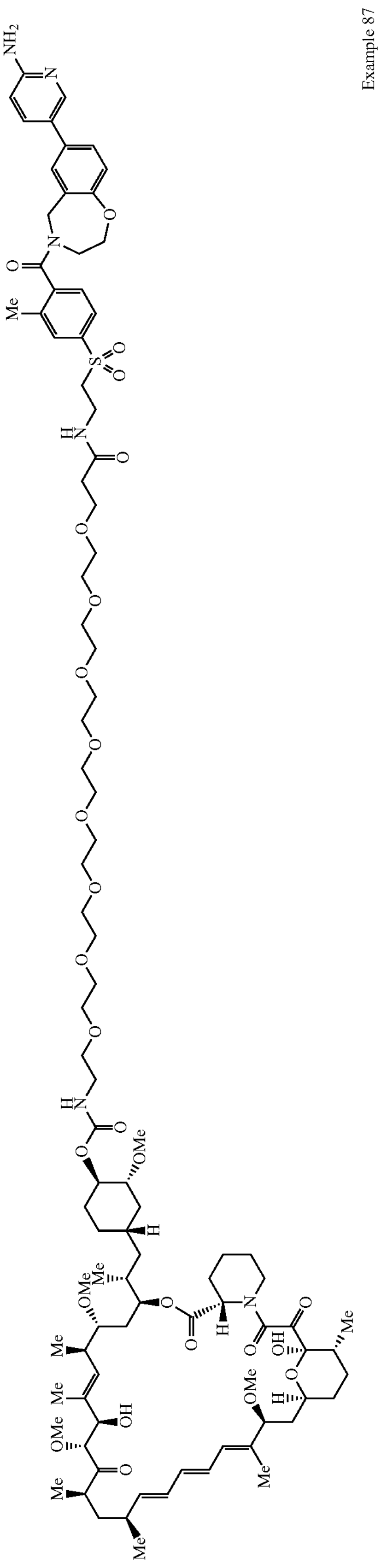
Example 87
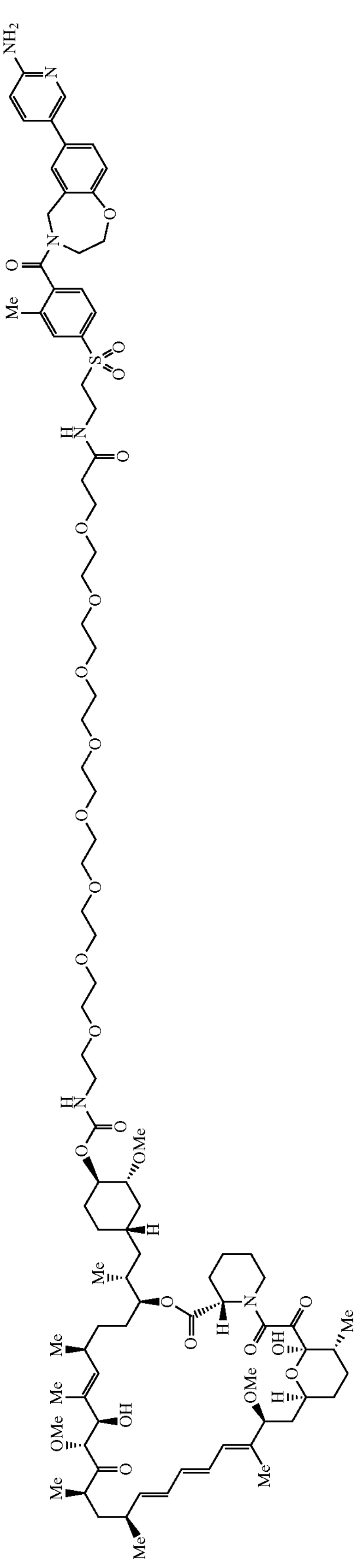

-continued
Example 88
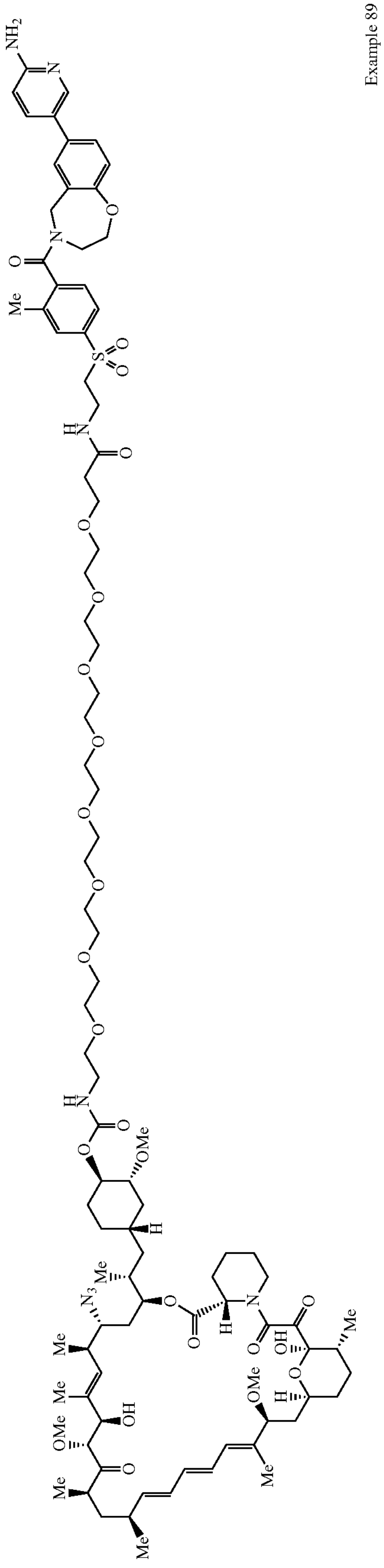
Example 89
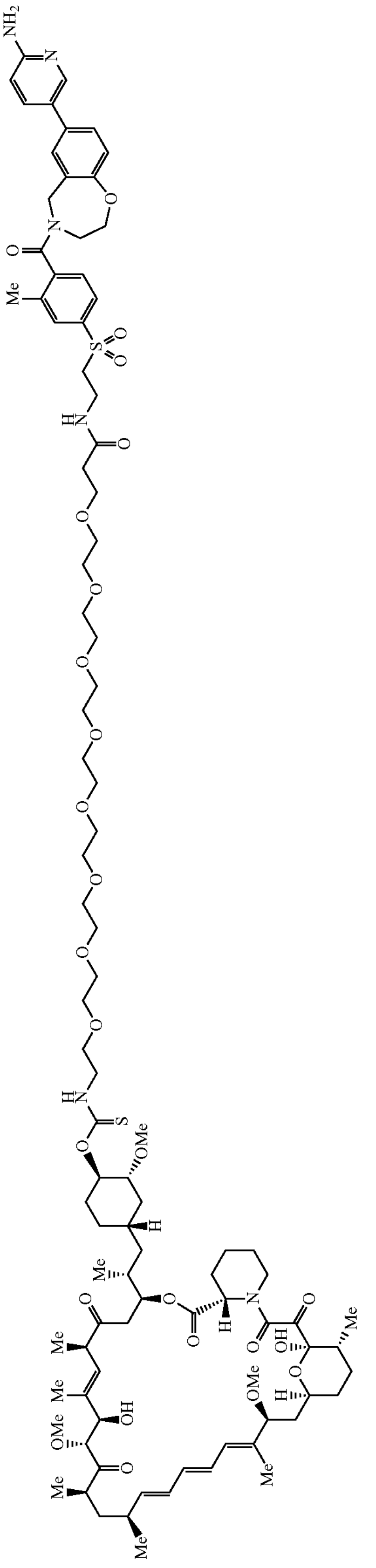

-continued
Example 90
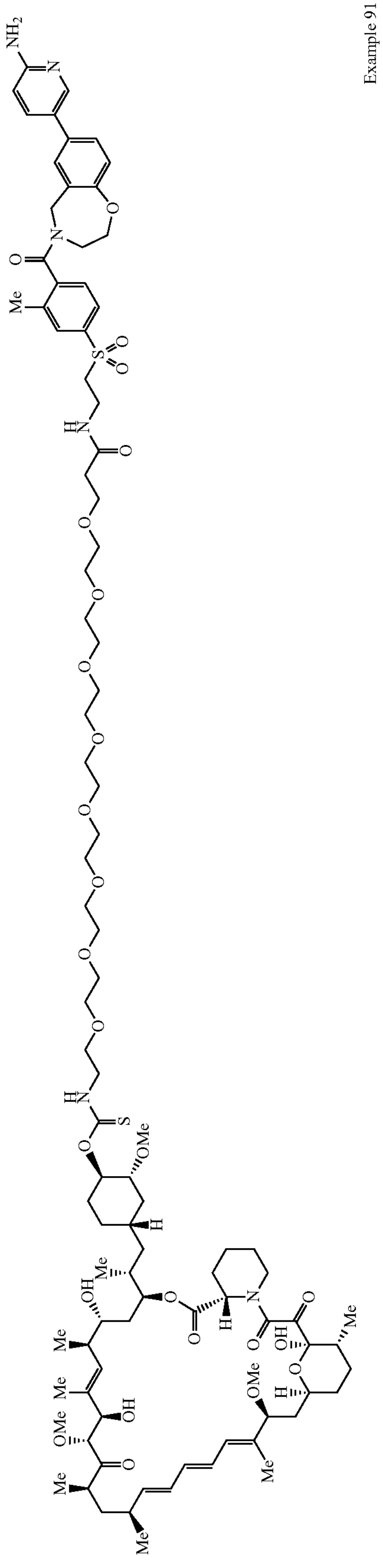
Example 91
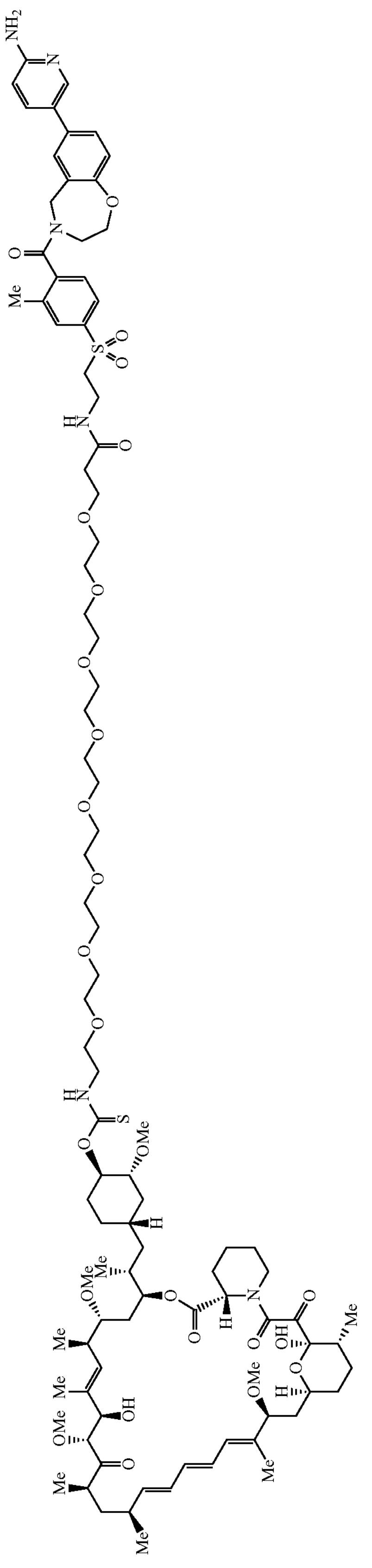

-continued
Example 92
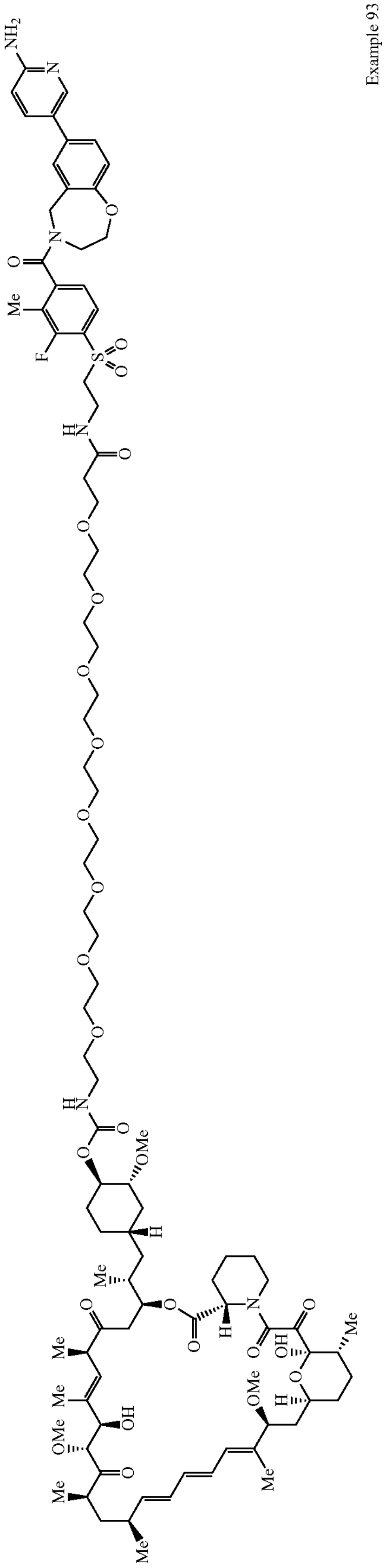
Example 93
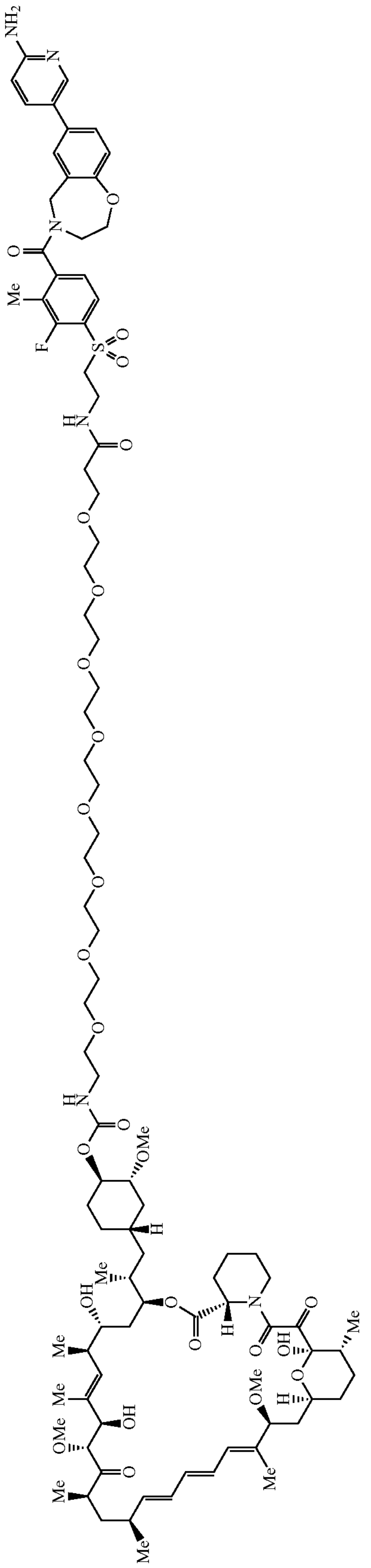

-continued
Example 94
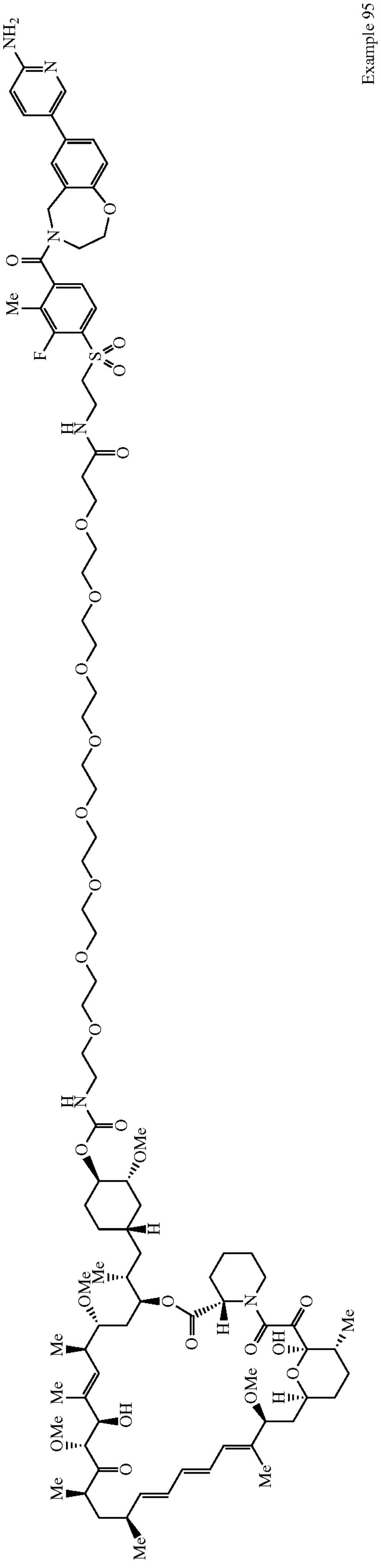
Example 95
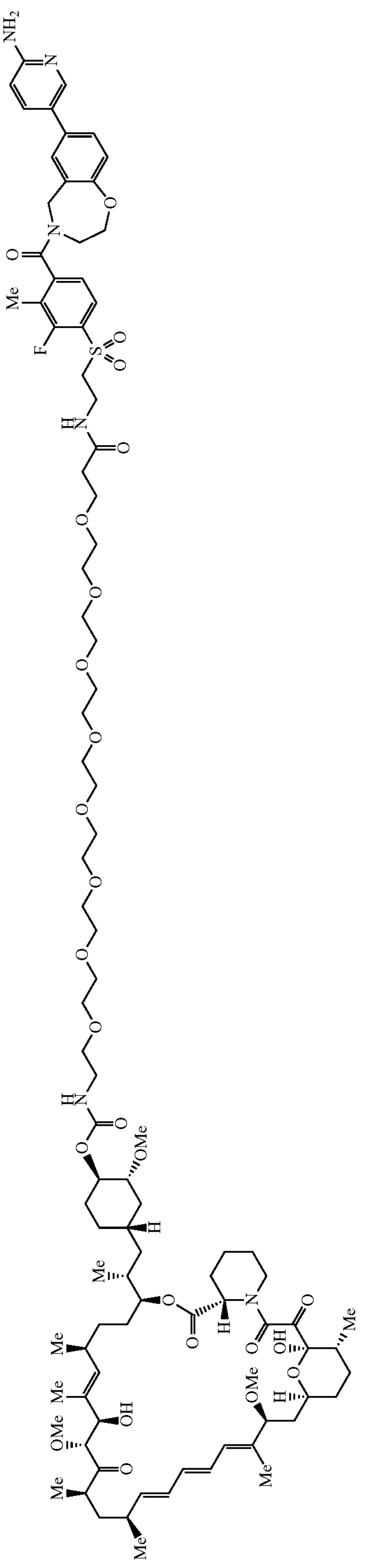

-continued
Example 96
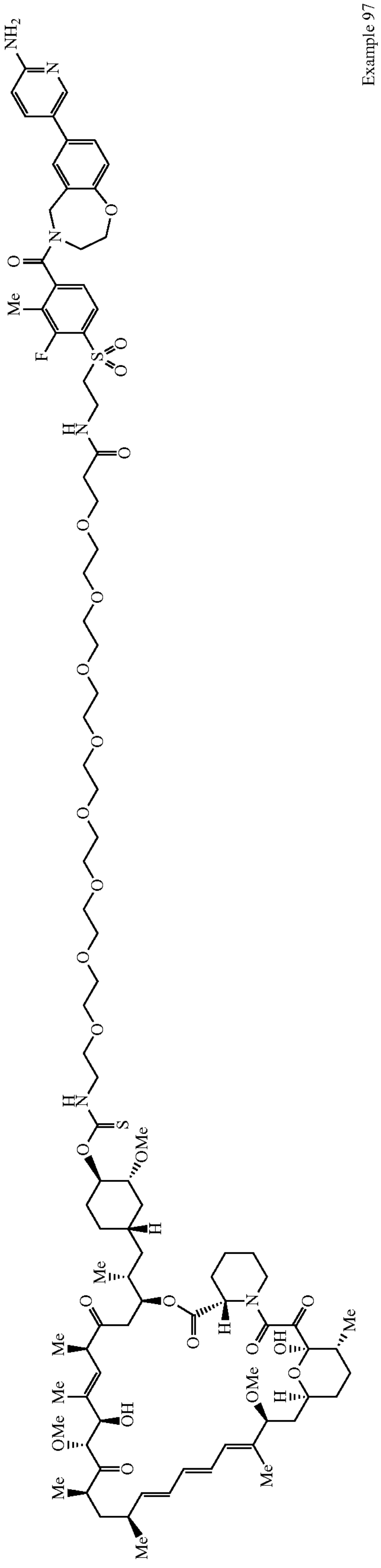
Example 97
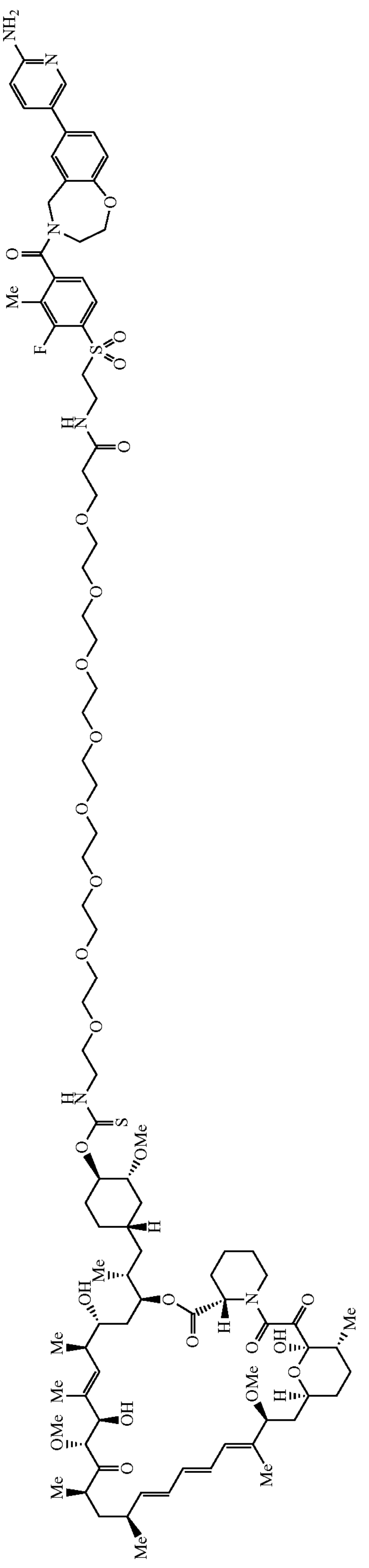

-continued
Example 98
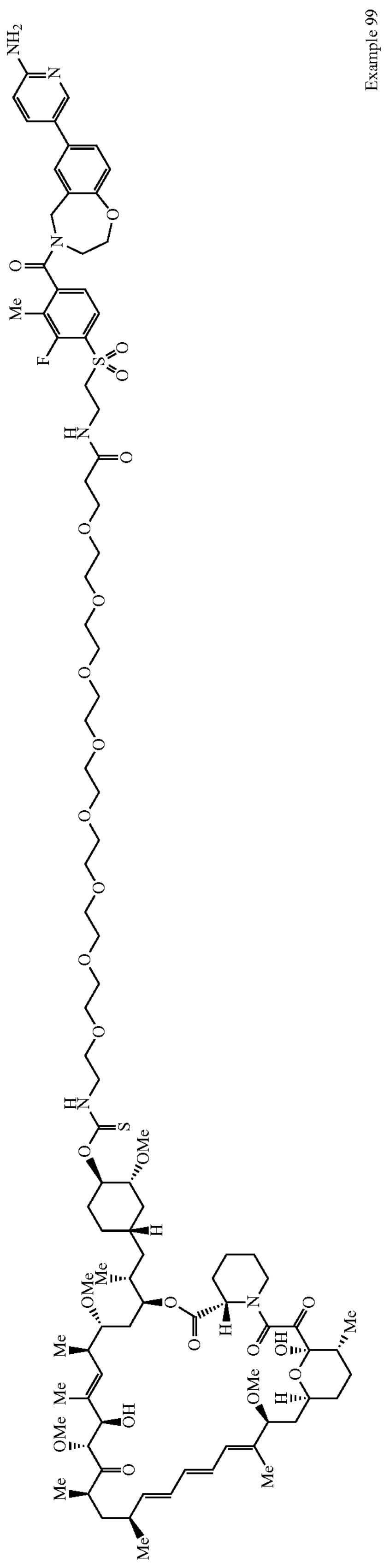
Example 99
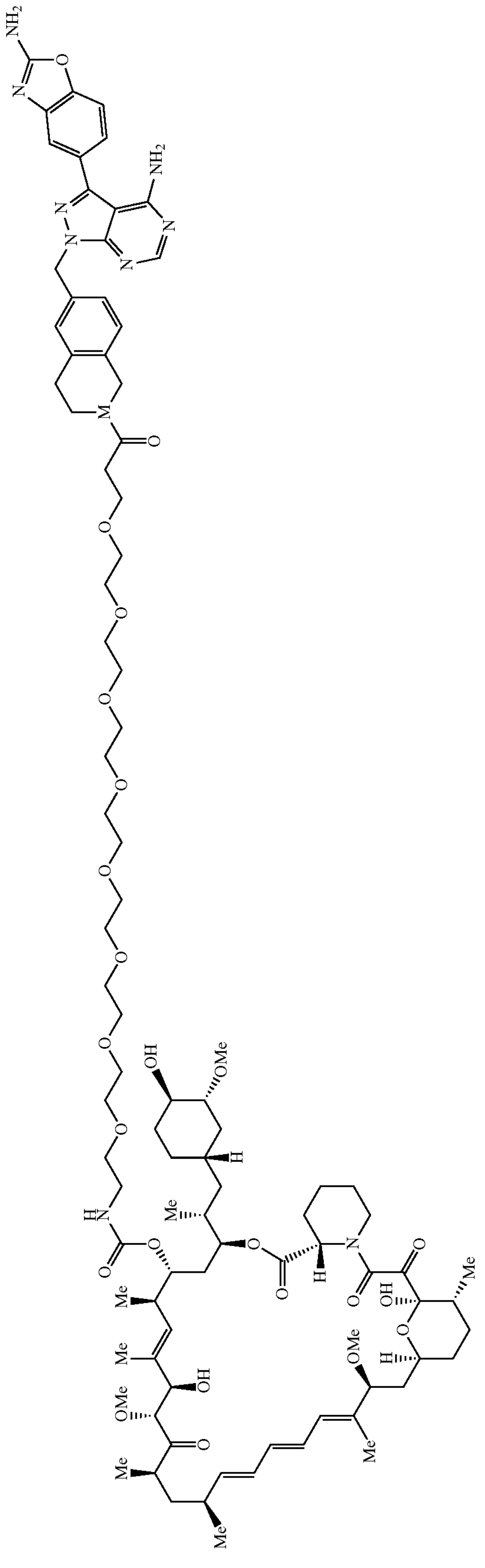

-continued
Example 100
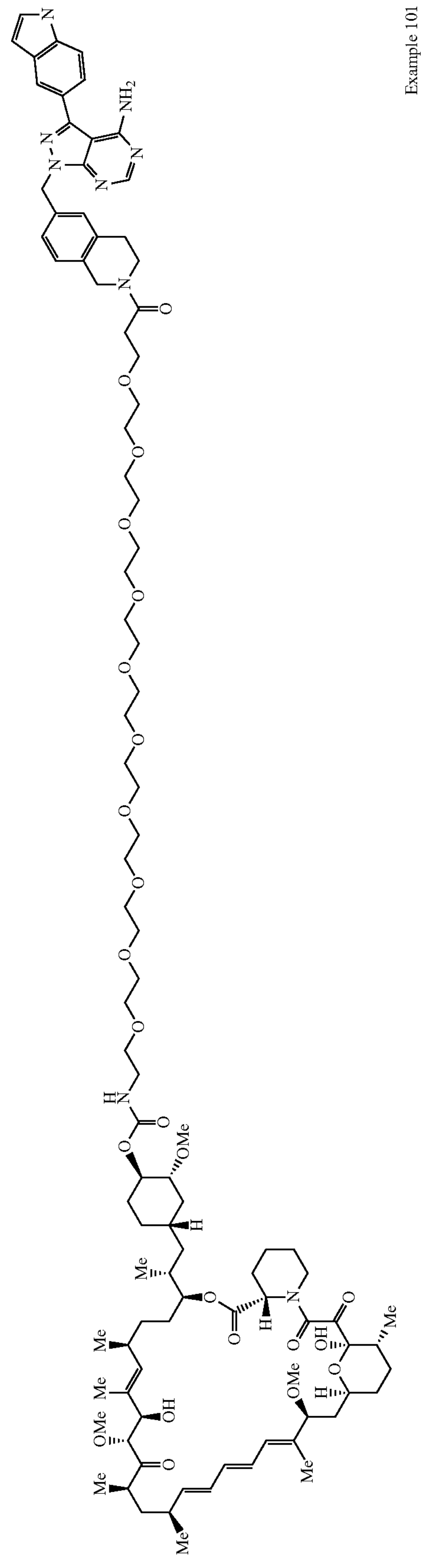
Example 101
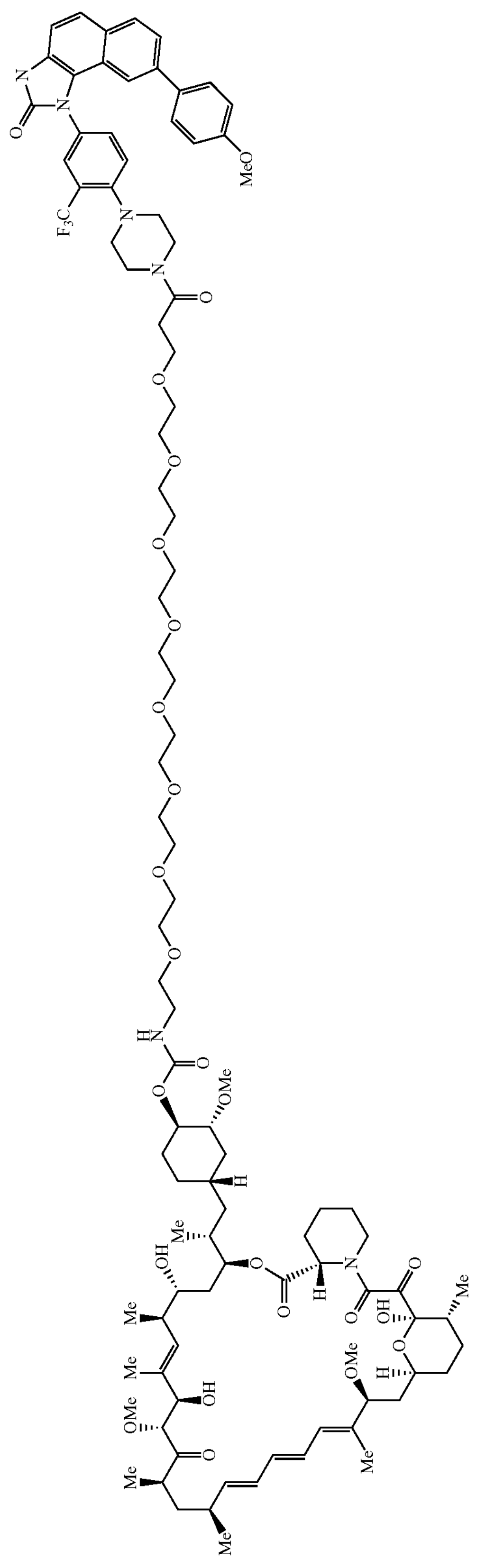

-continued
Example 102
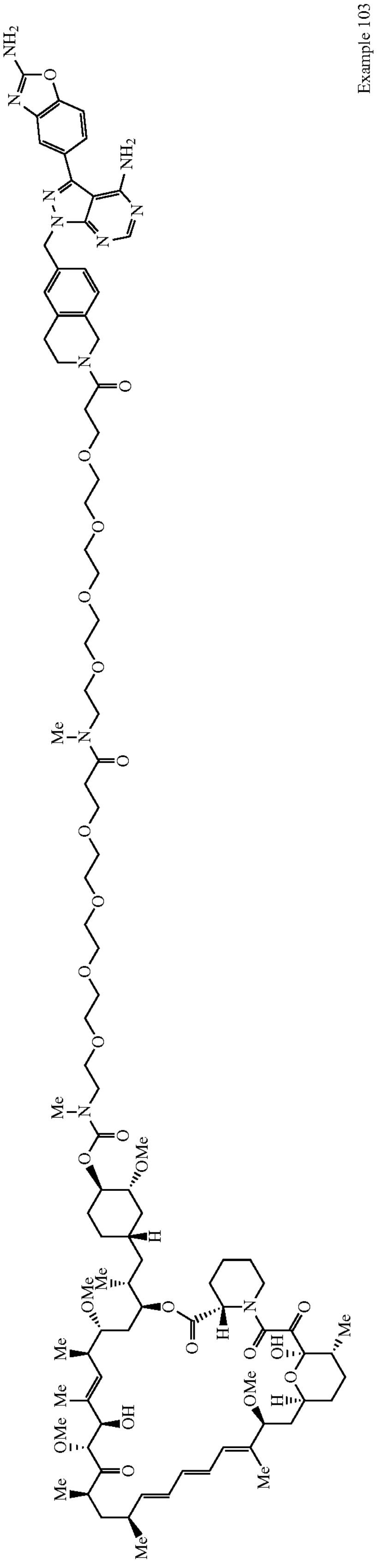
Example 103
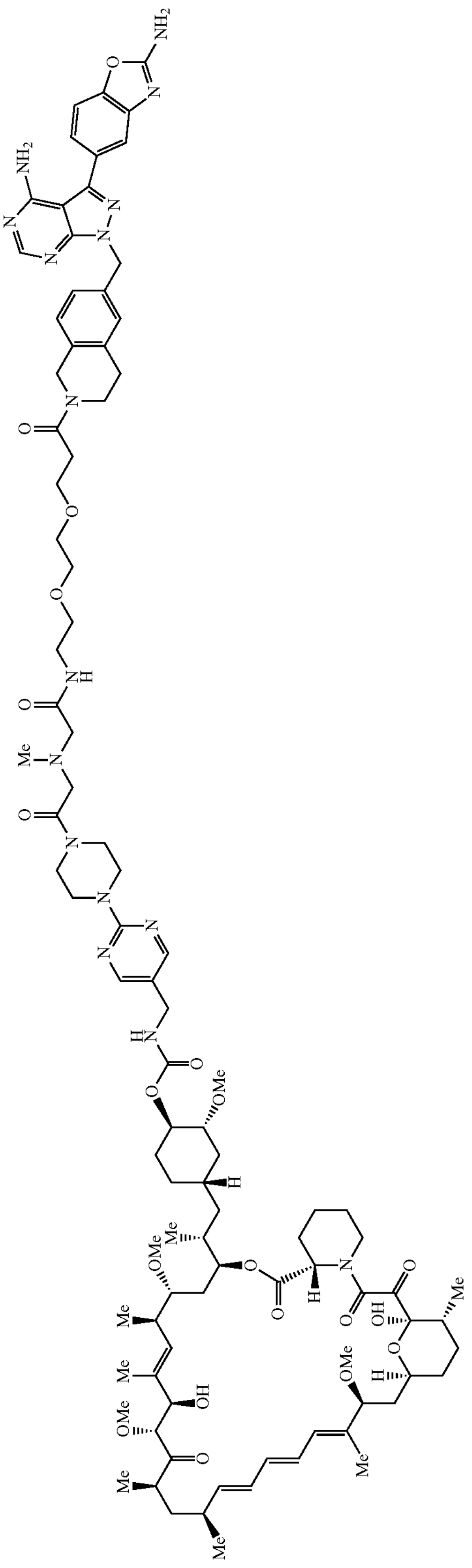

-continued
Example 104
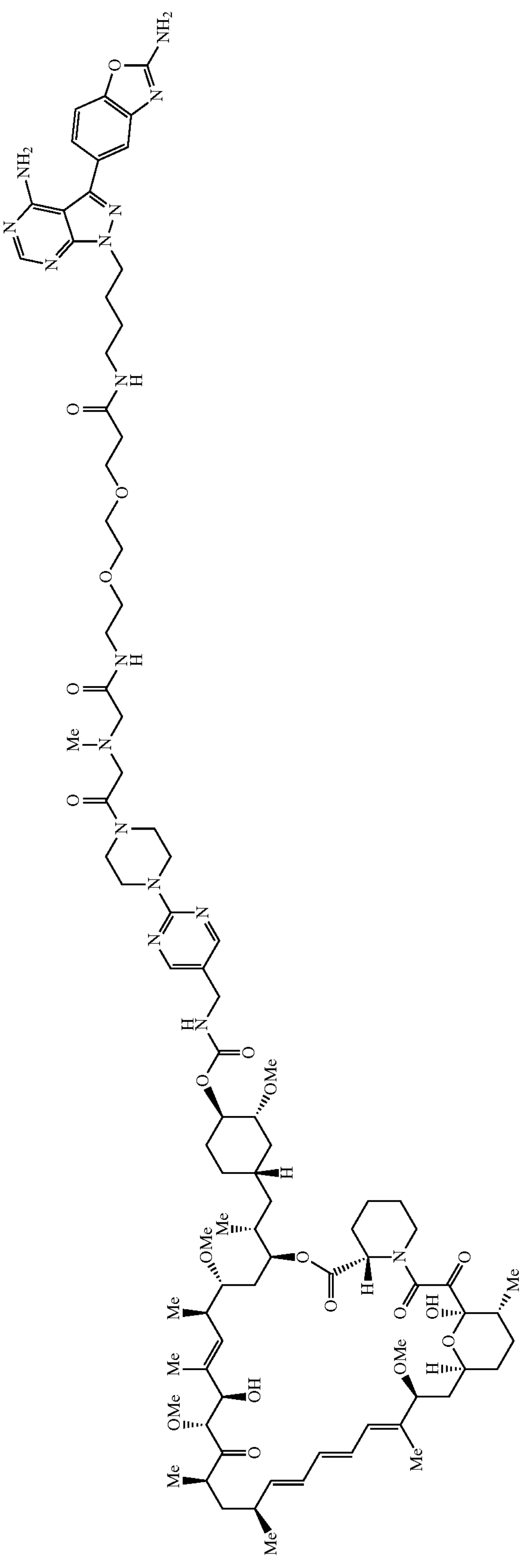

-continued
Example 105
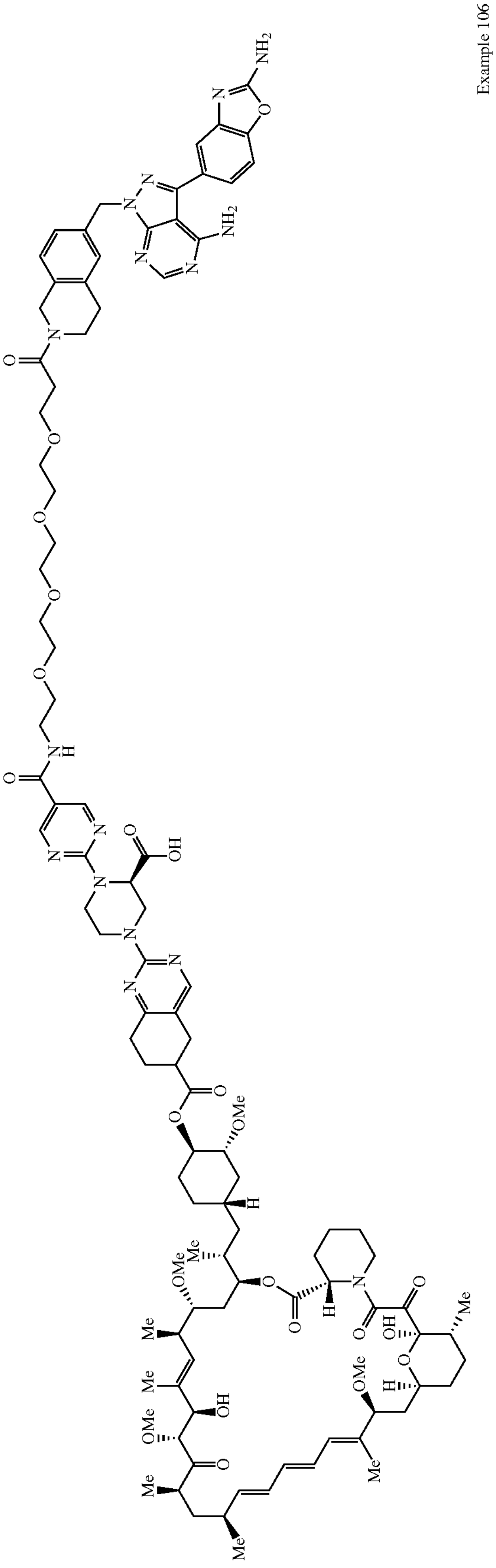
Example 106
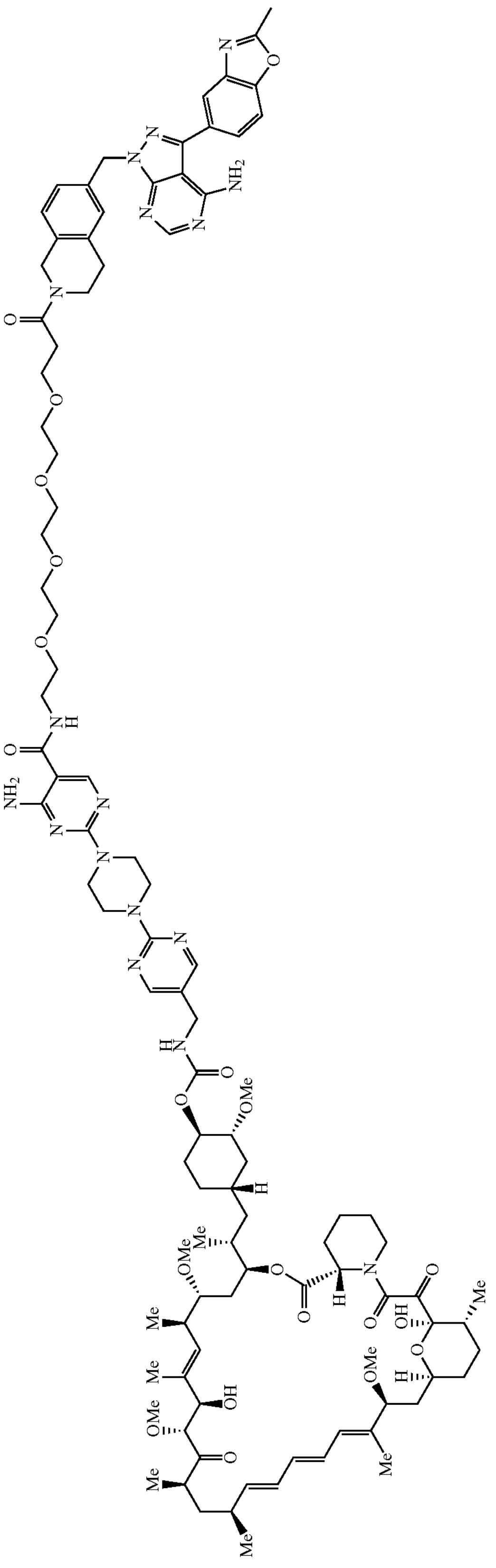

-continued
Example 107
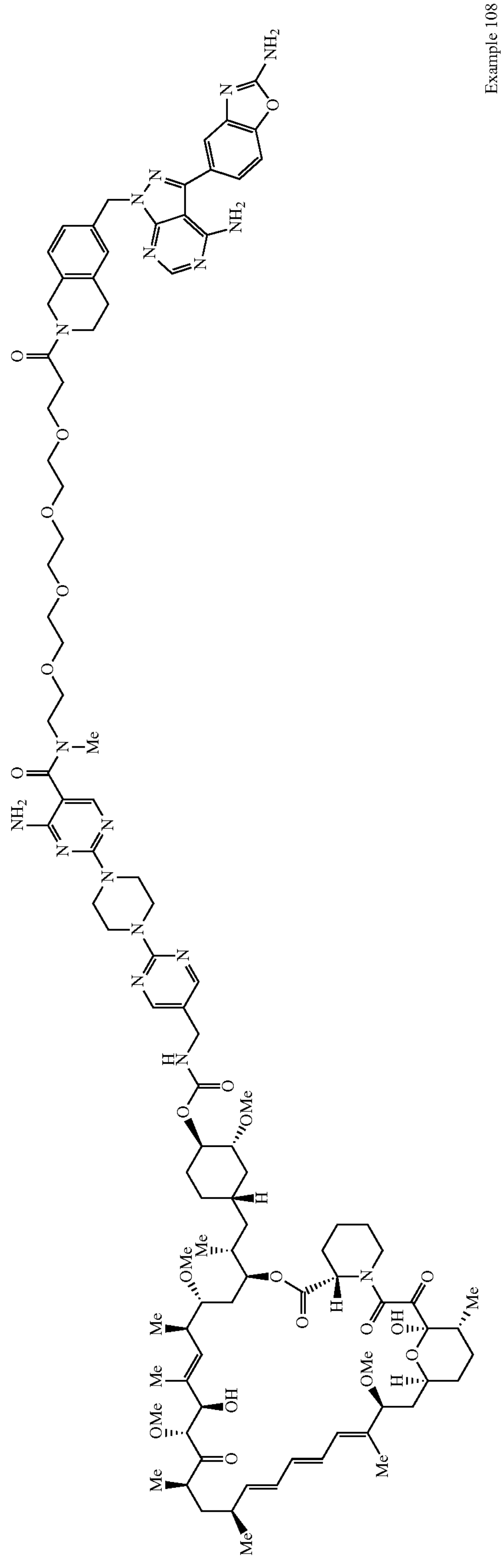
Example 108
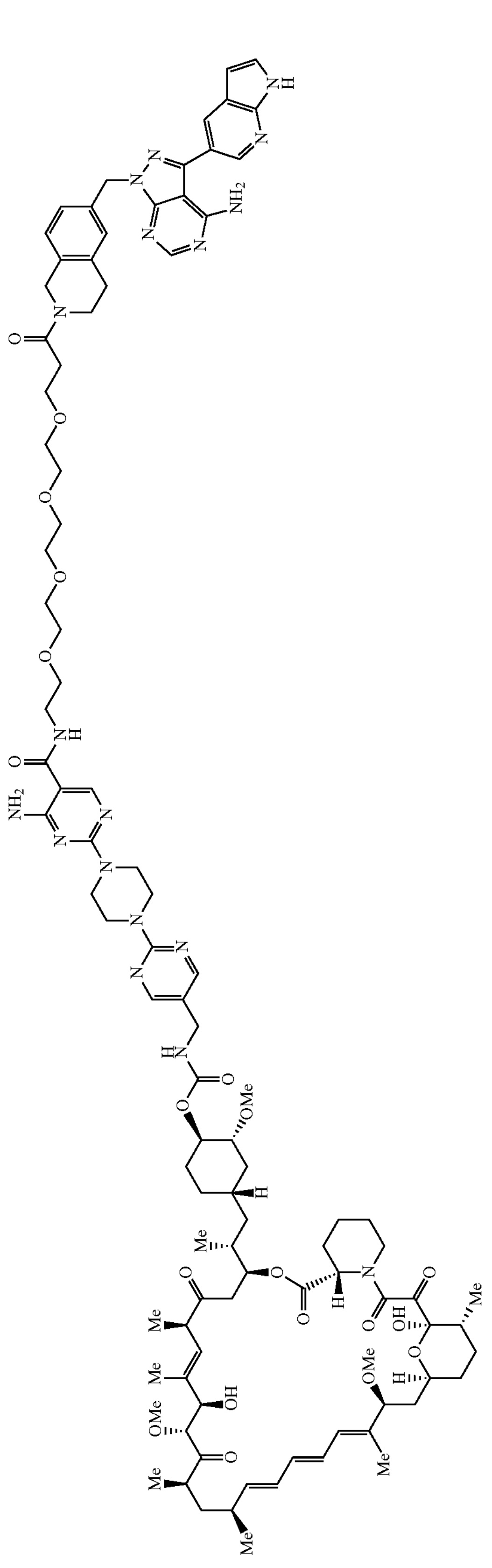

-continued
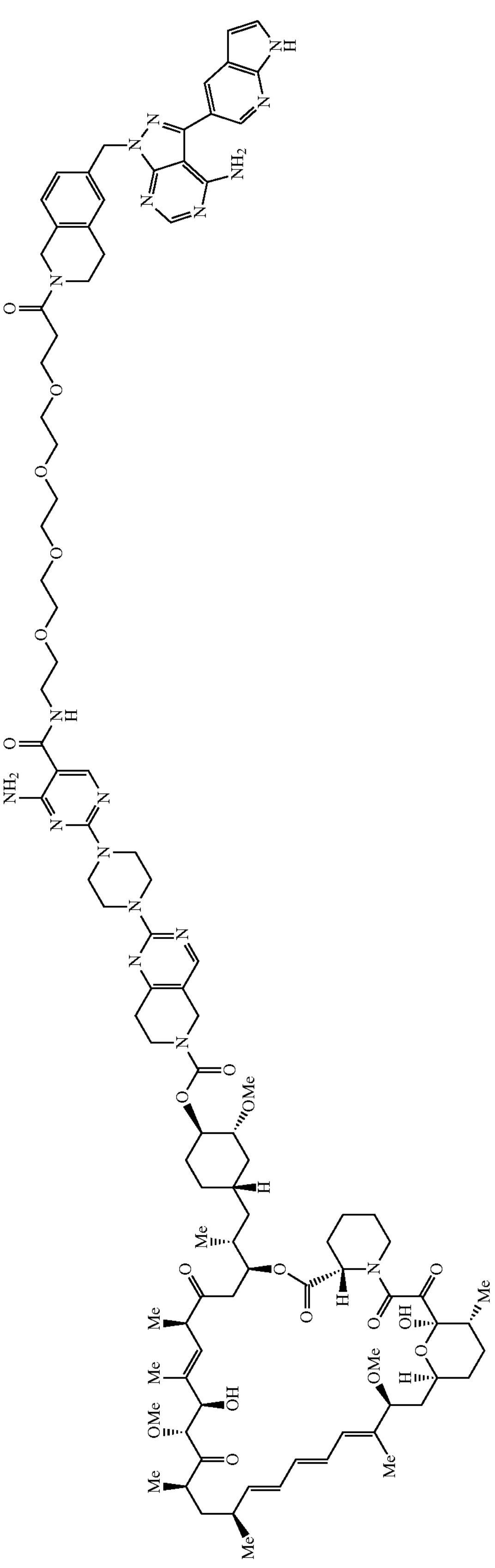
Example 109
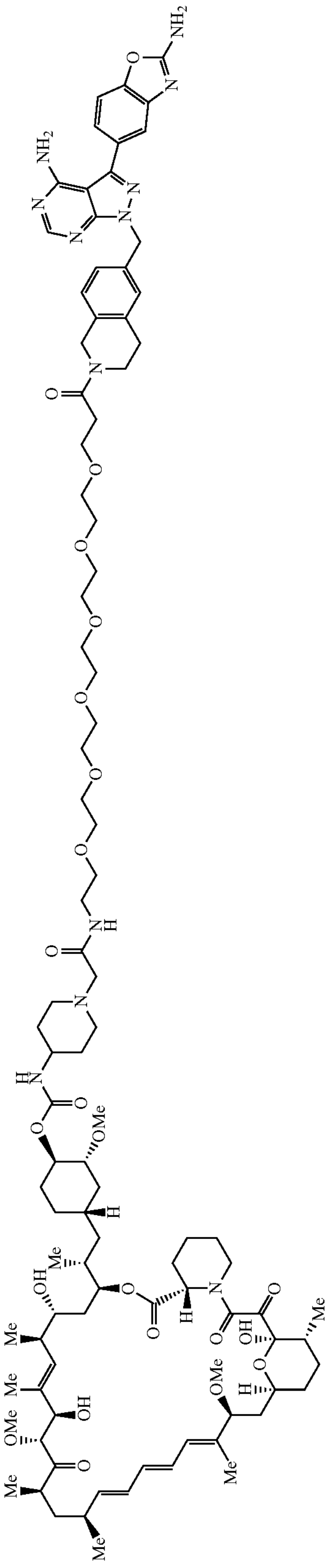
Example 110

-continued
Example 111
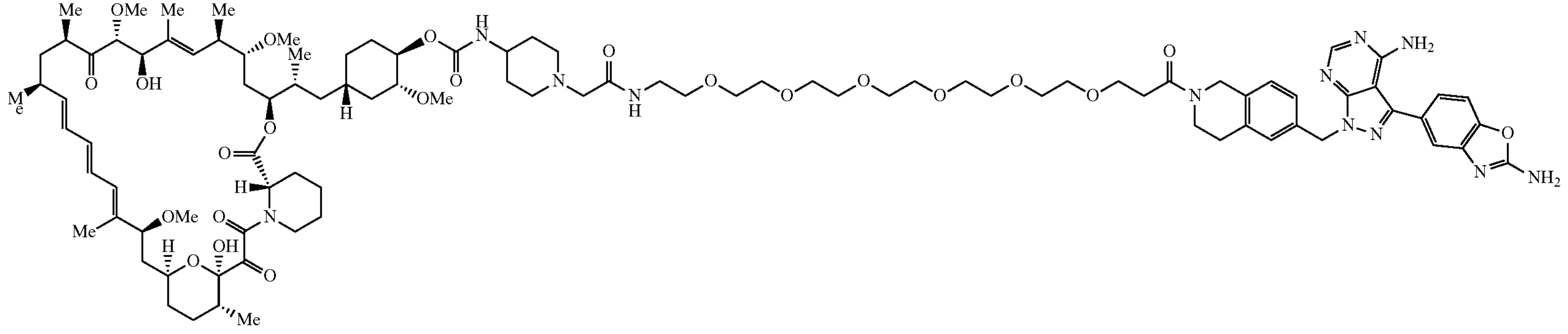
Example 112
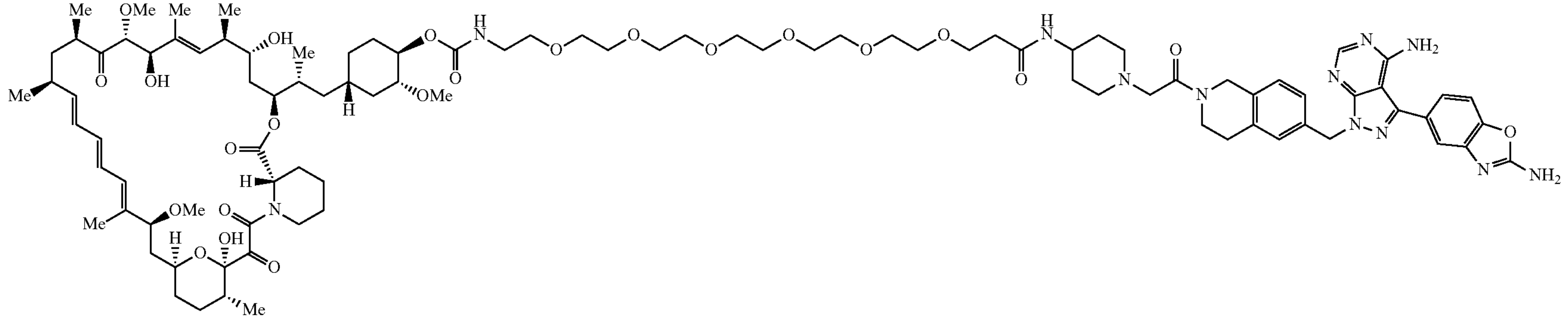

-continued
Example 113
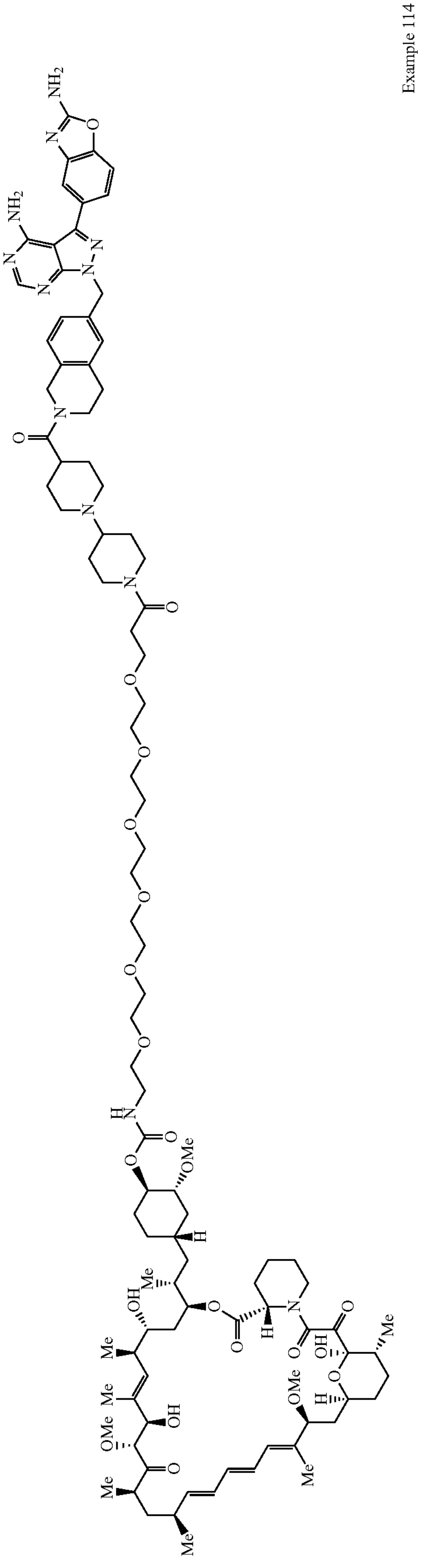
Example 114
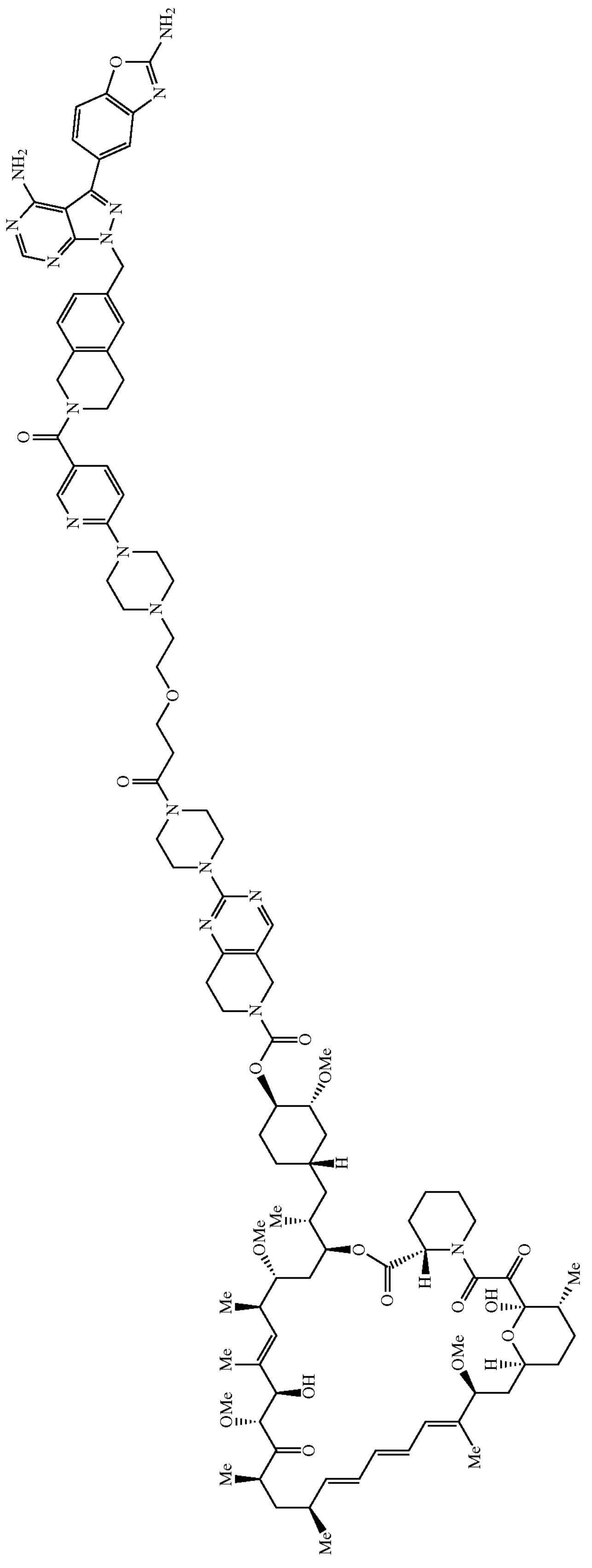

-continued
Example 115
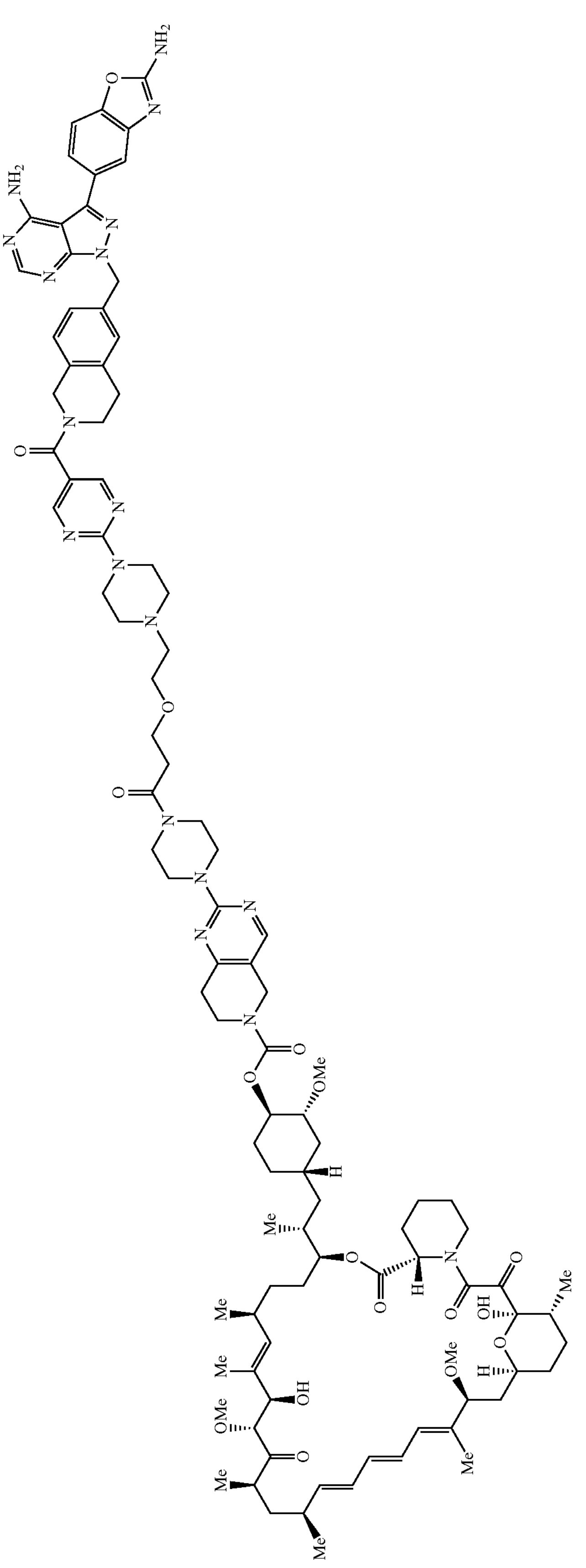

-continued
Example 116
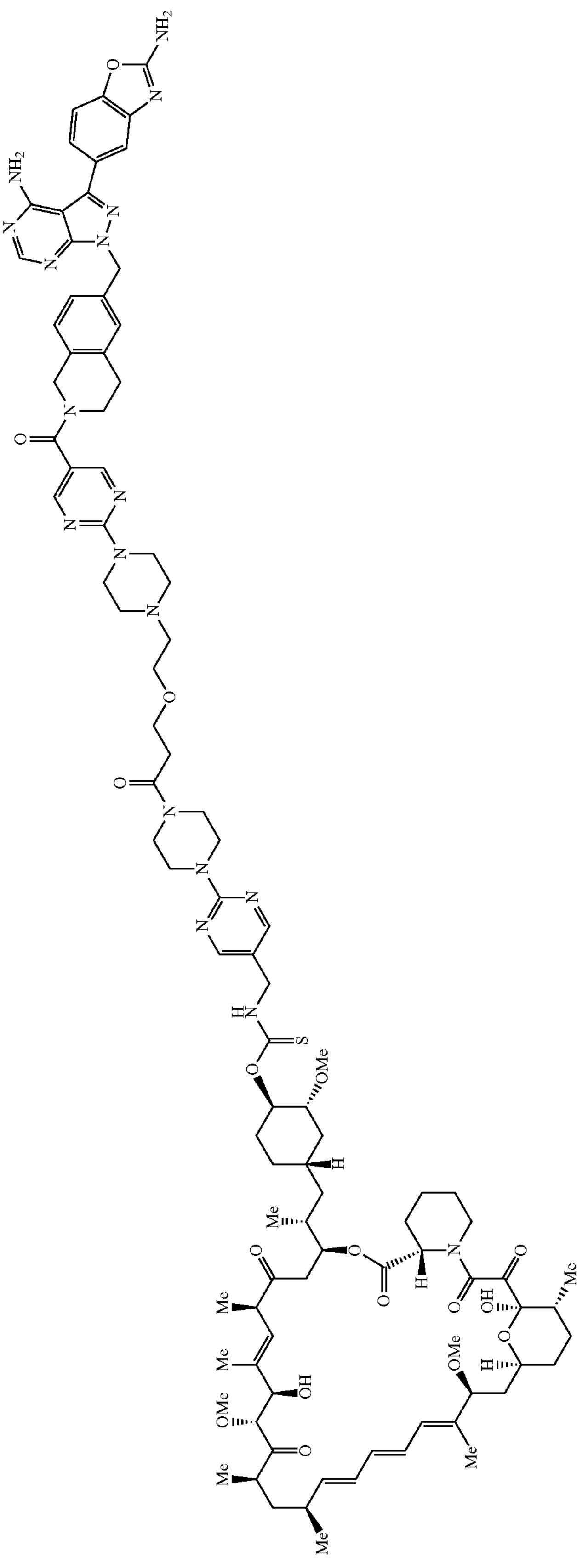

-continued
Example 117
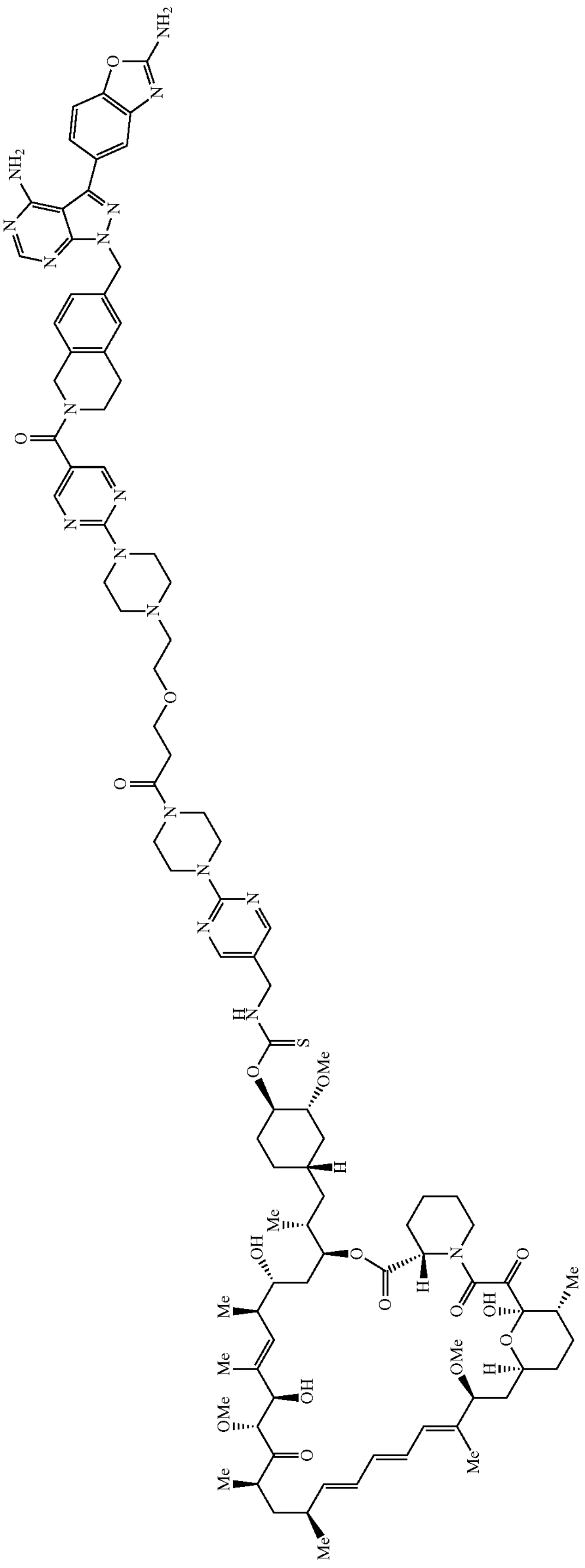

-continued
Example 118
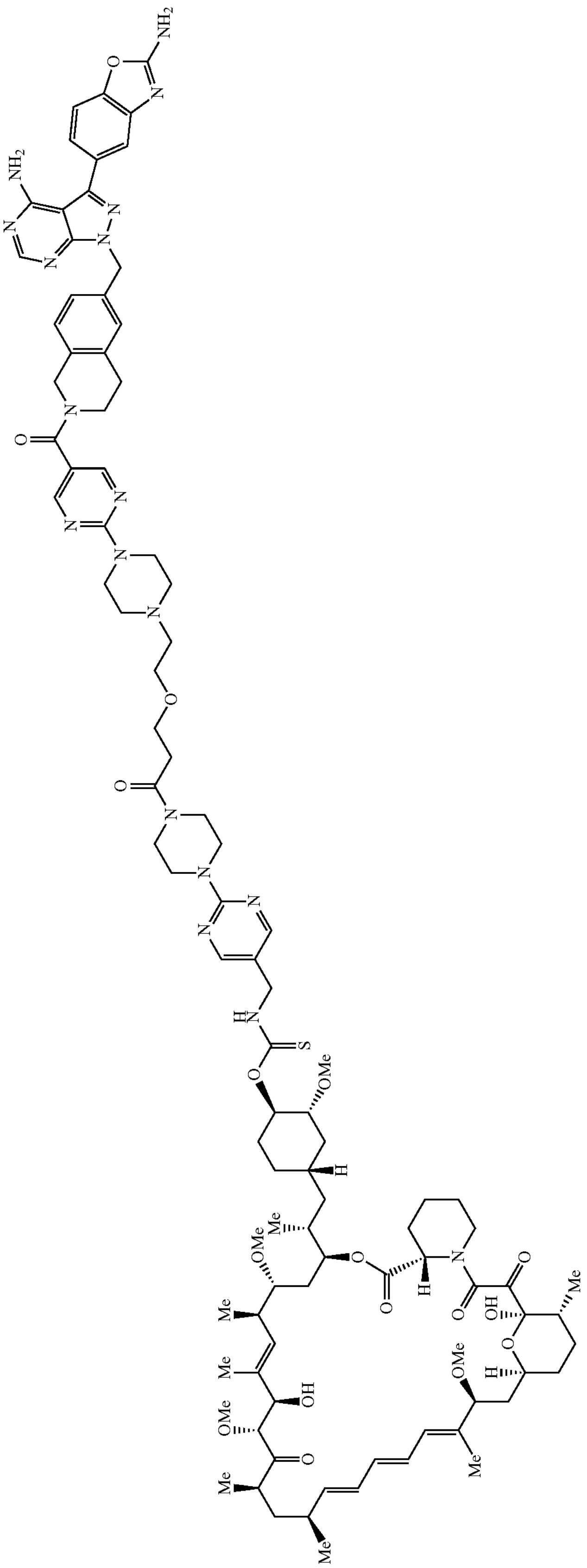

-continued
Example 118
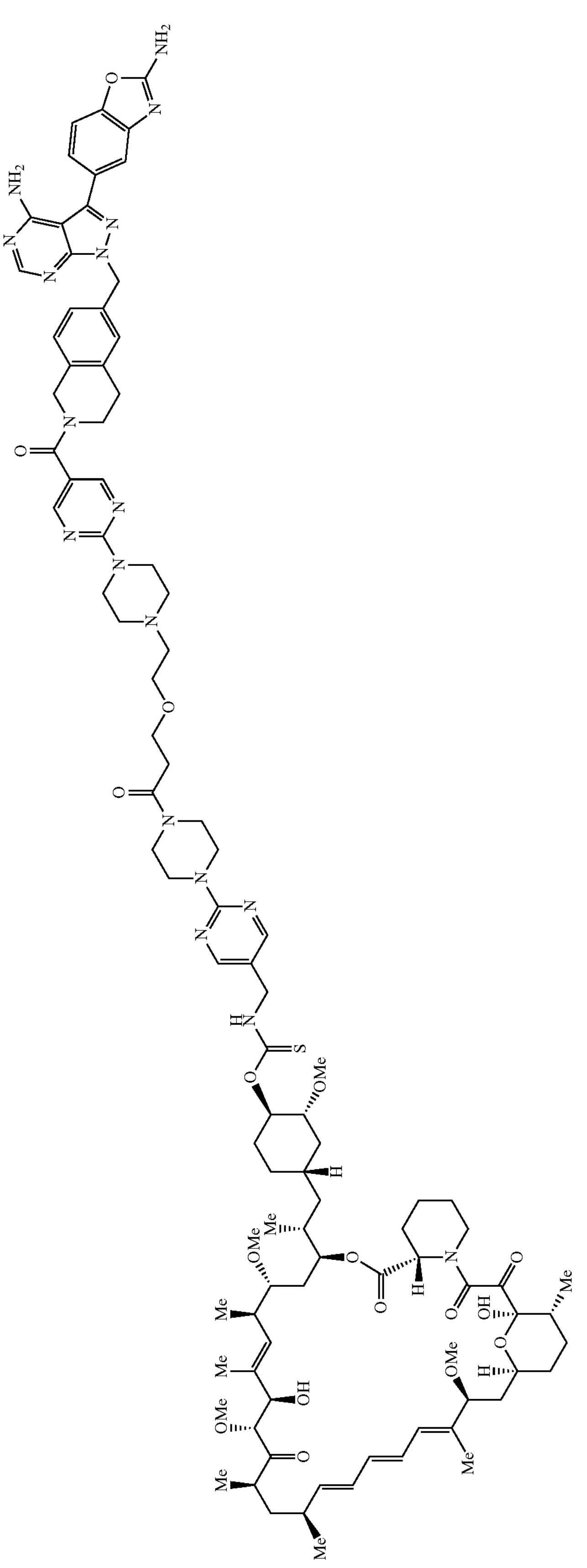

-continued
Example 120
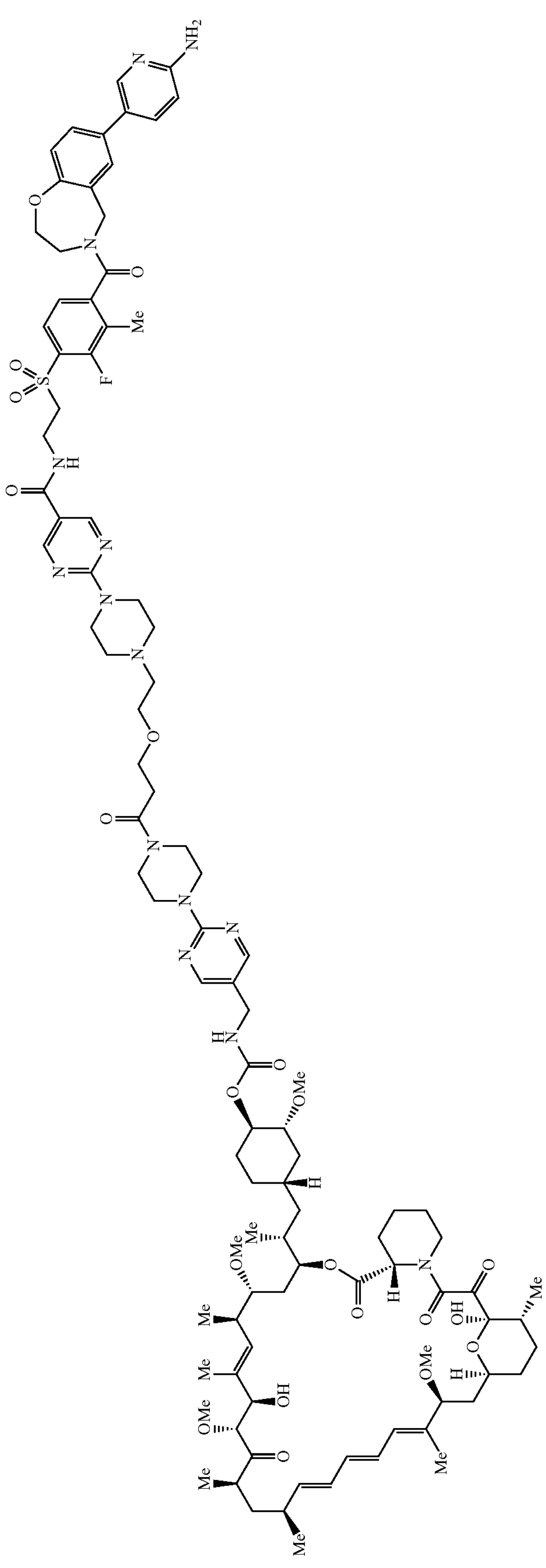

-continued
Example 121
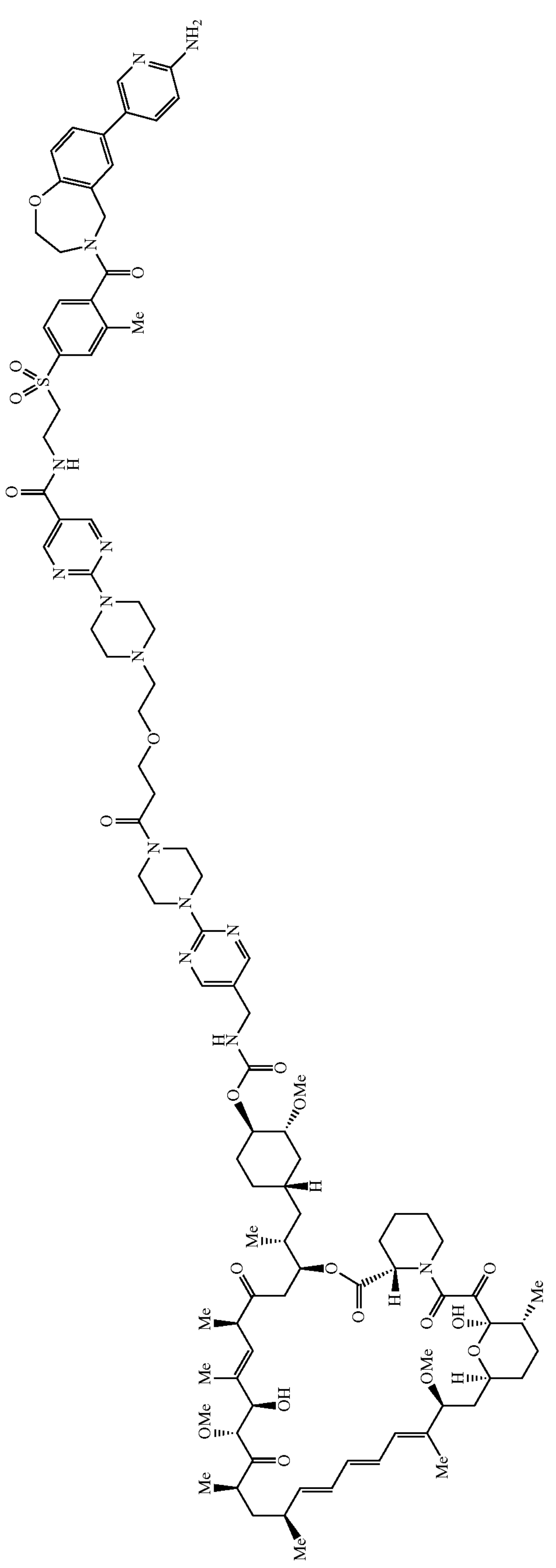

-continued
Example 122
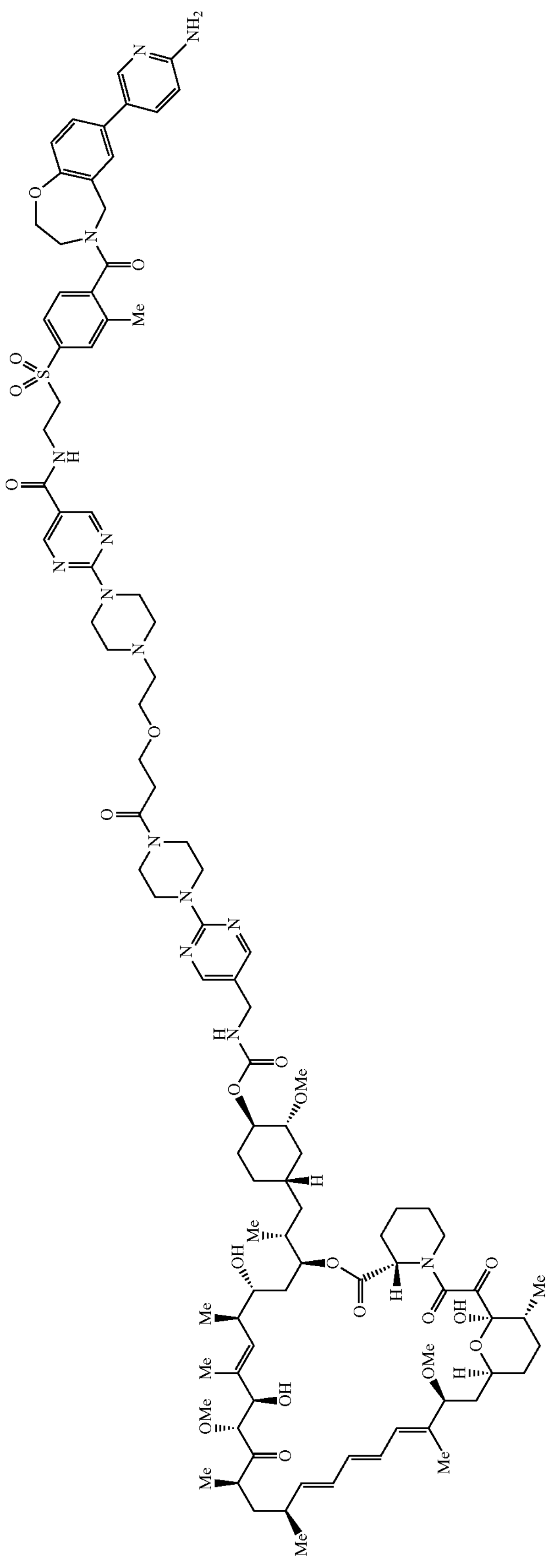

-continued
Example 123
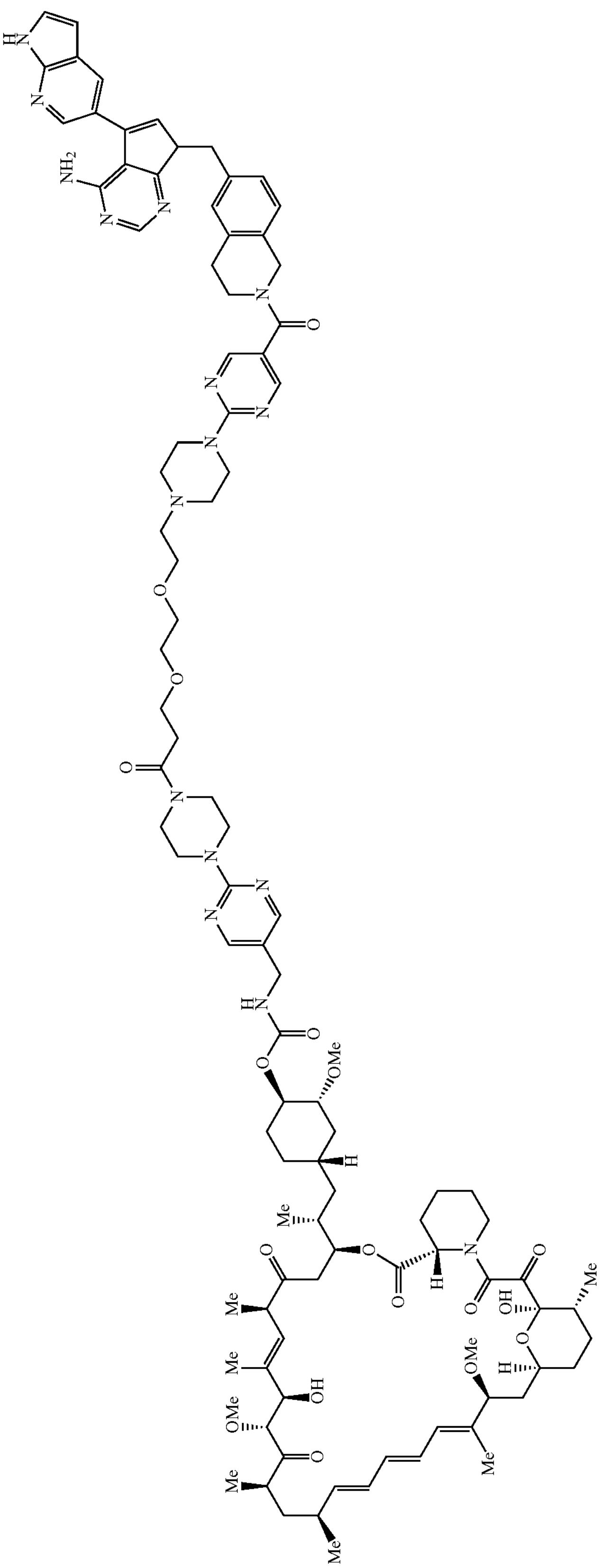

-continued
Example 124
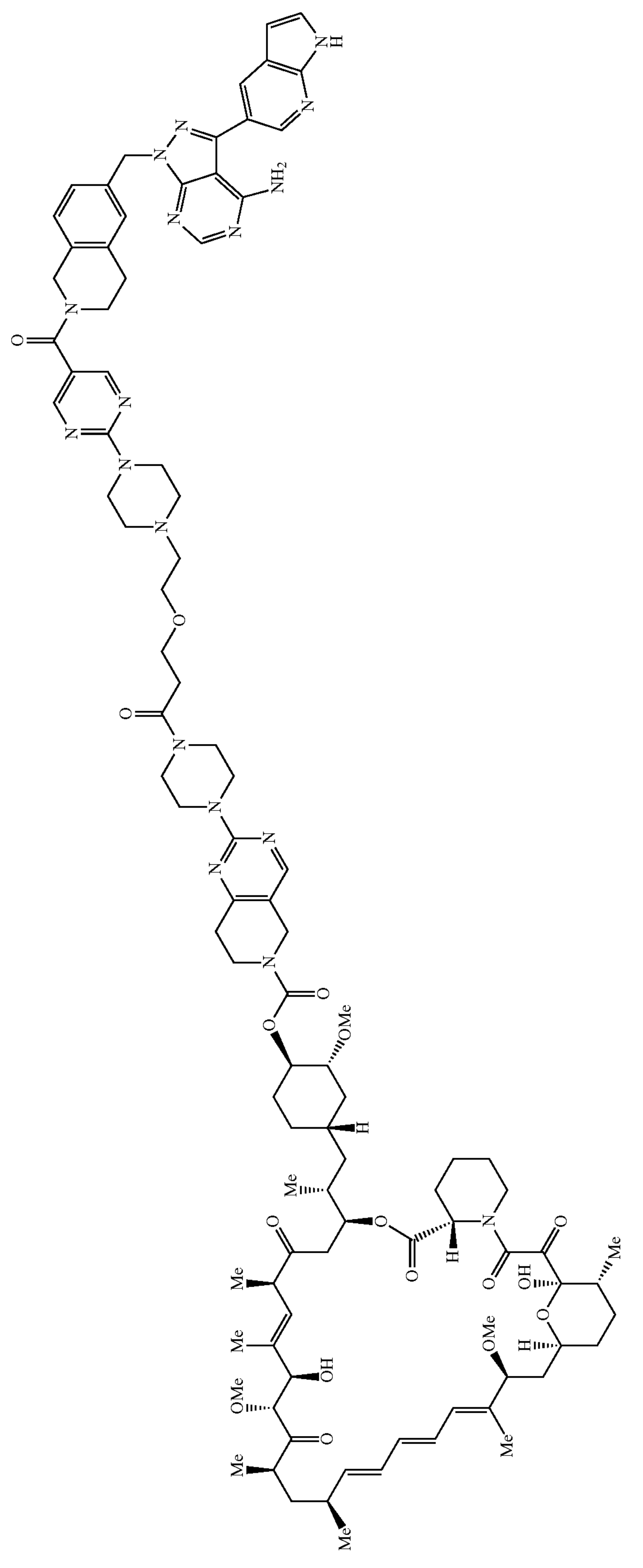

-continued
Example 125
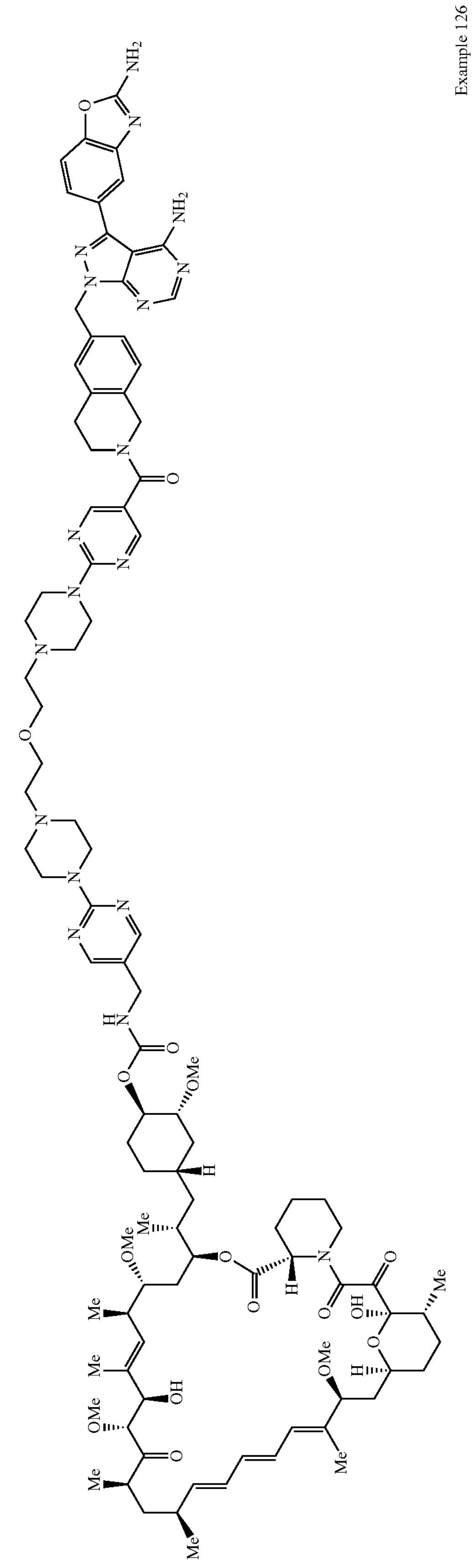
Example 126
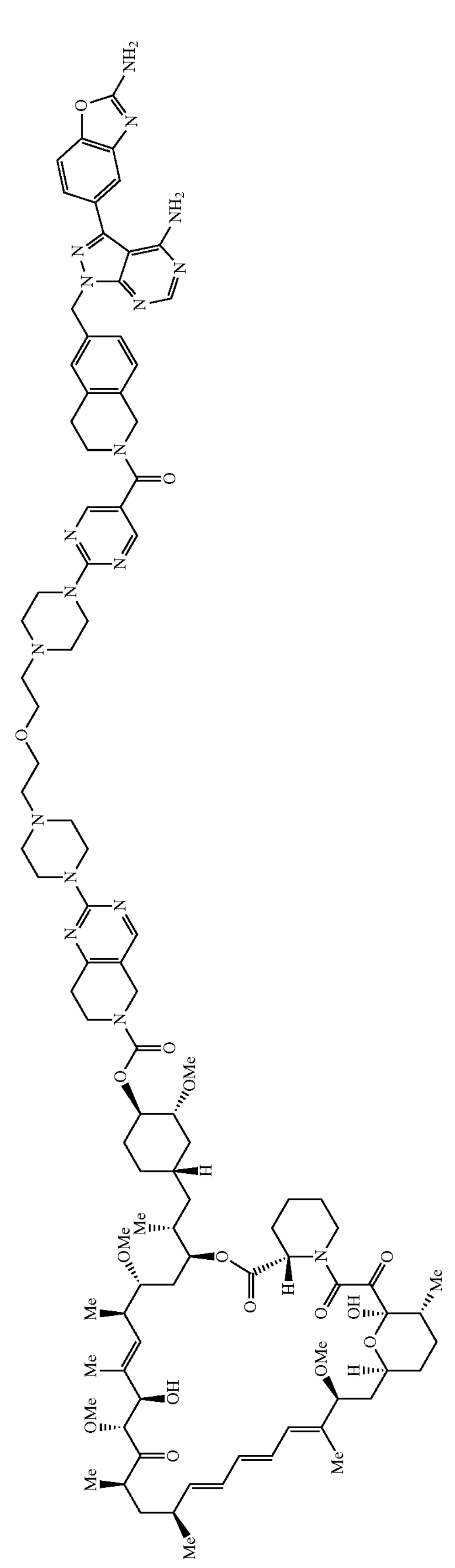

-continued
Example 127
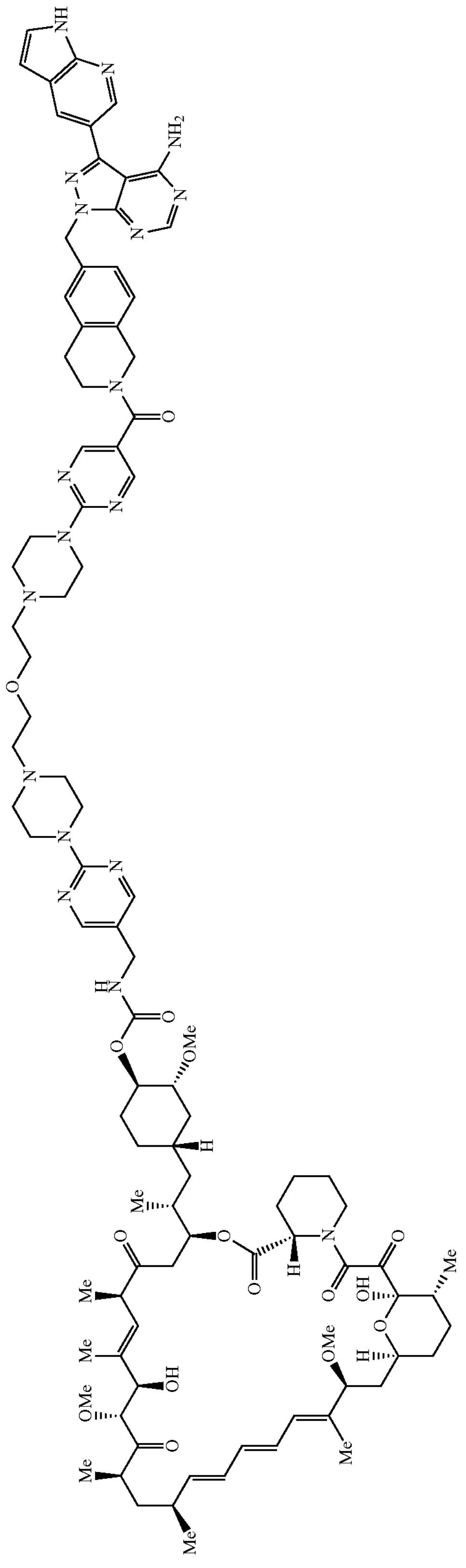
Example 128
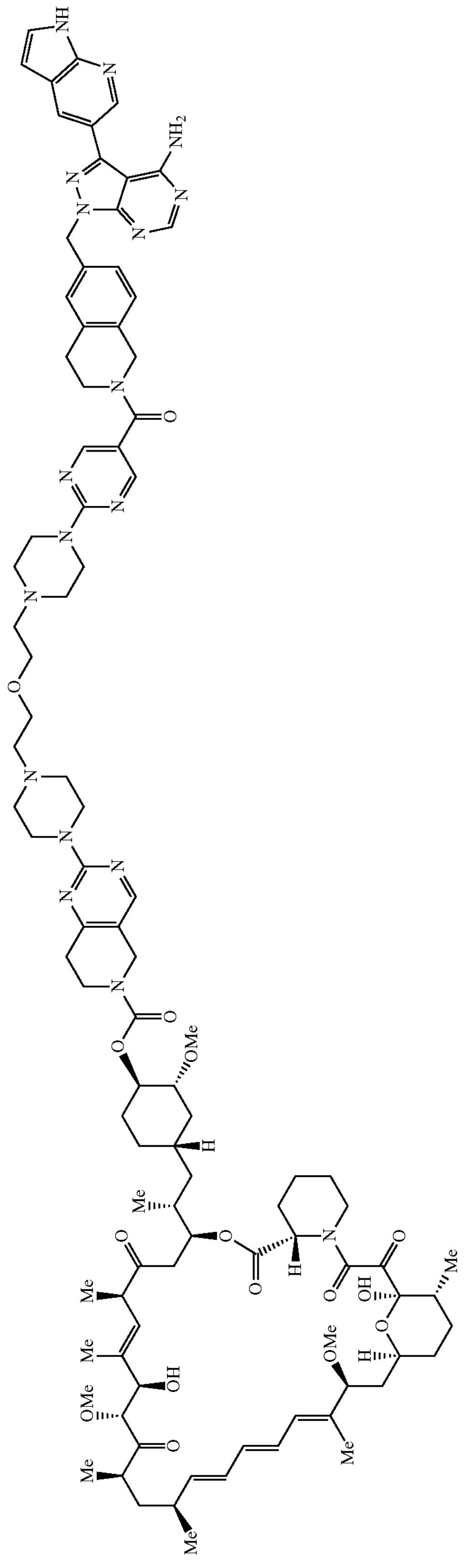

-continued
Example 129
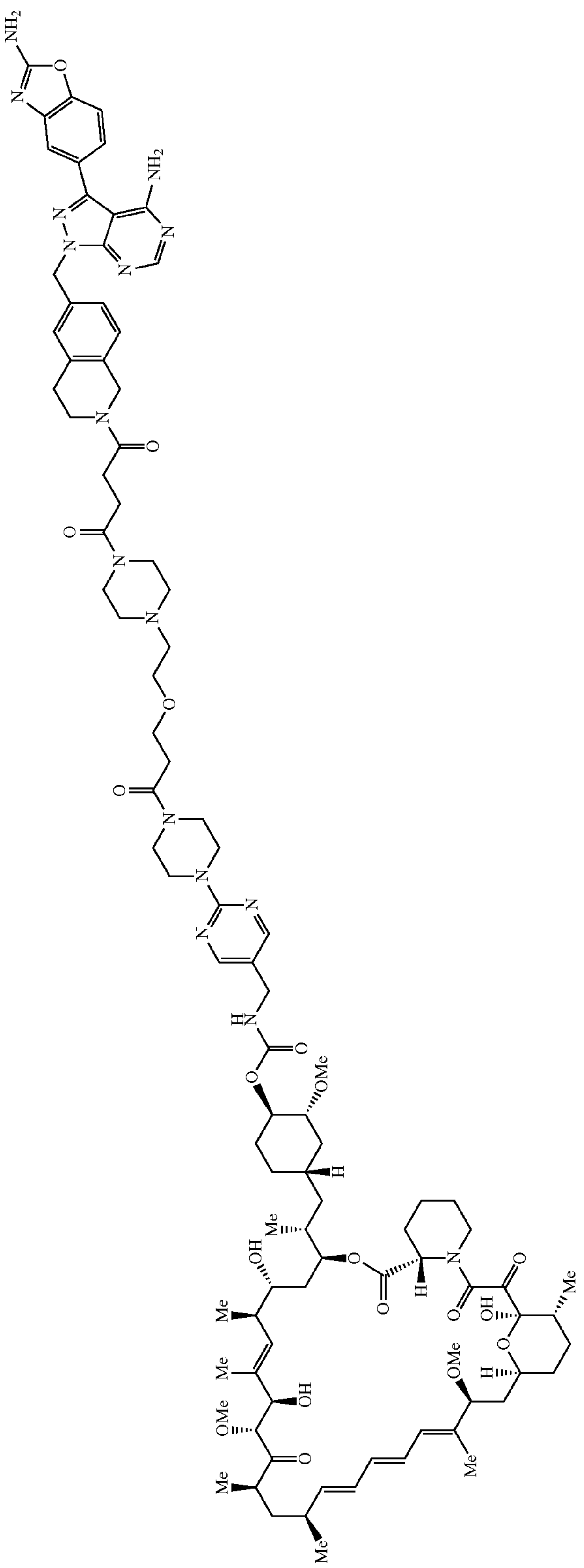

-continued
Example 130
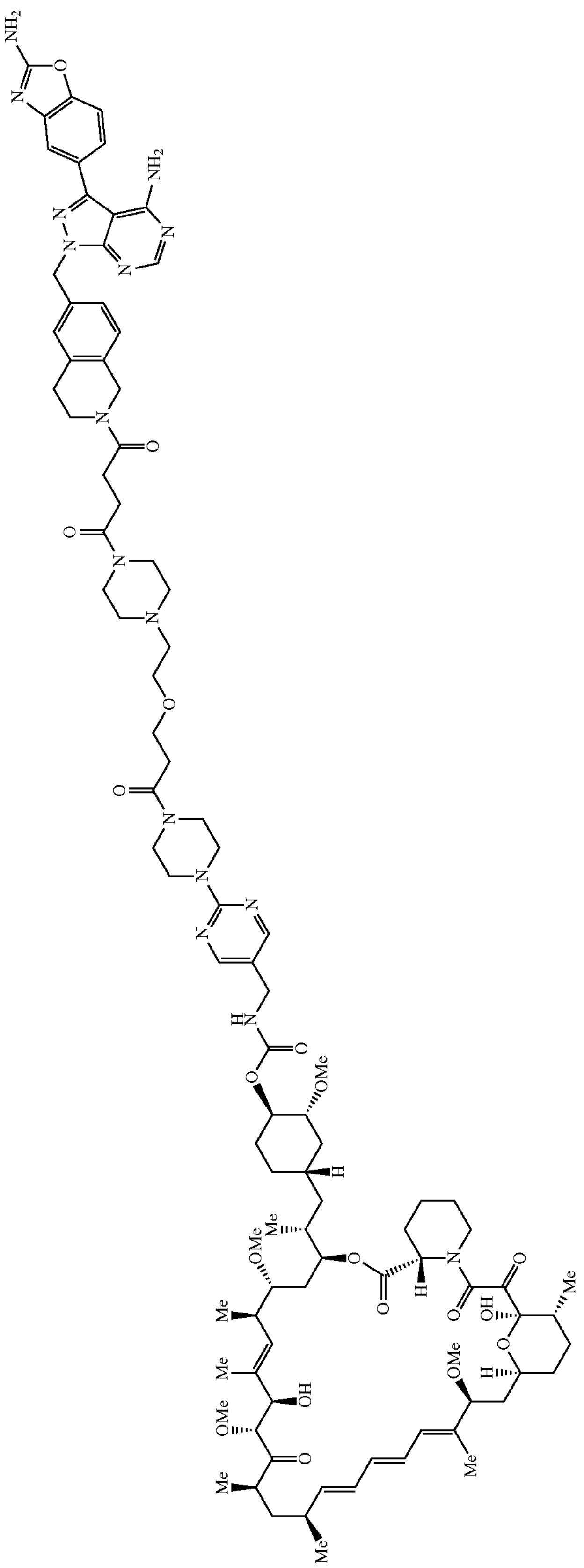

-continued
Example 131
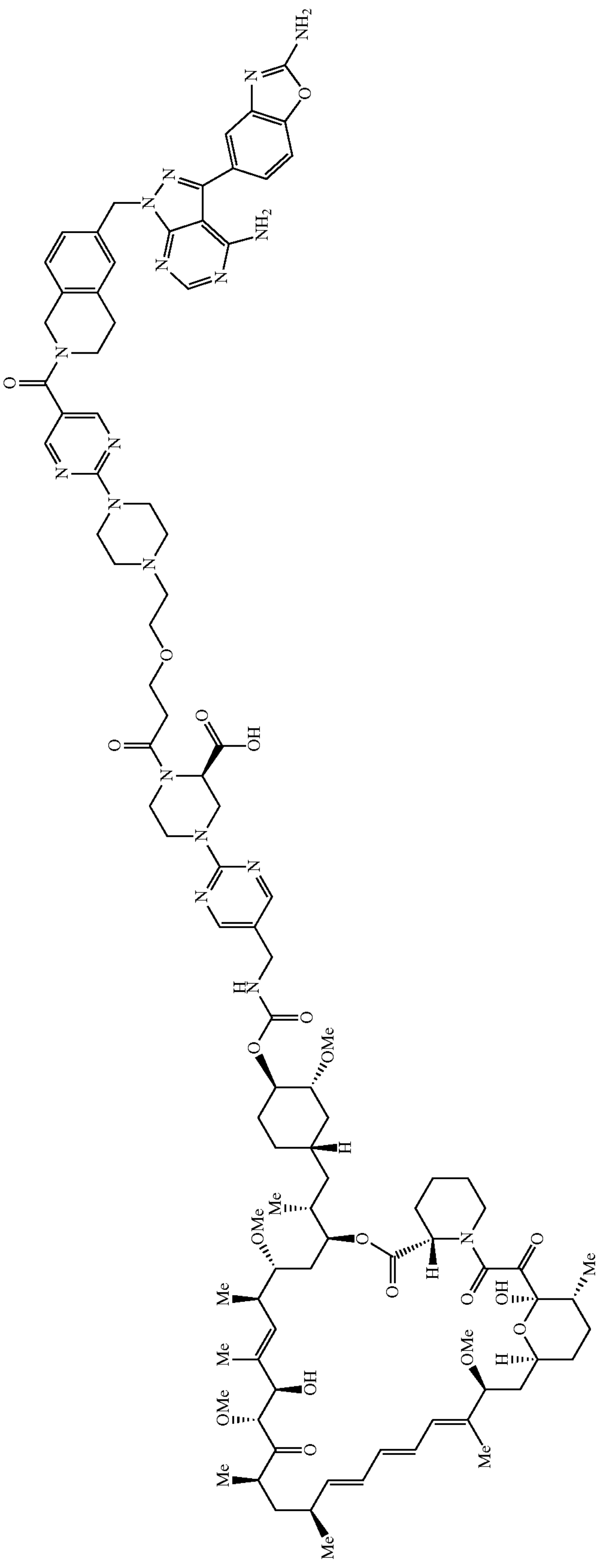

-continued
Example 132
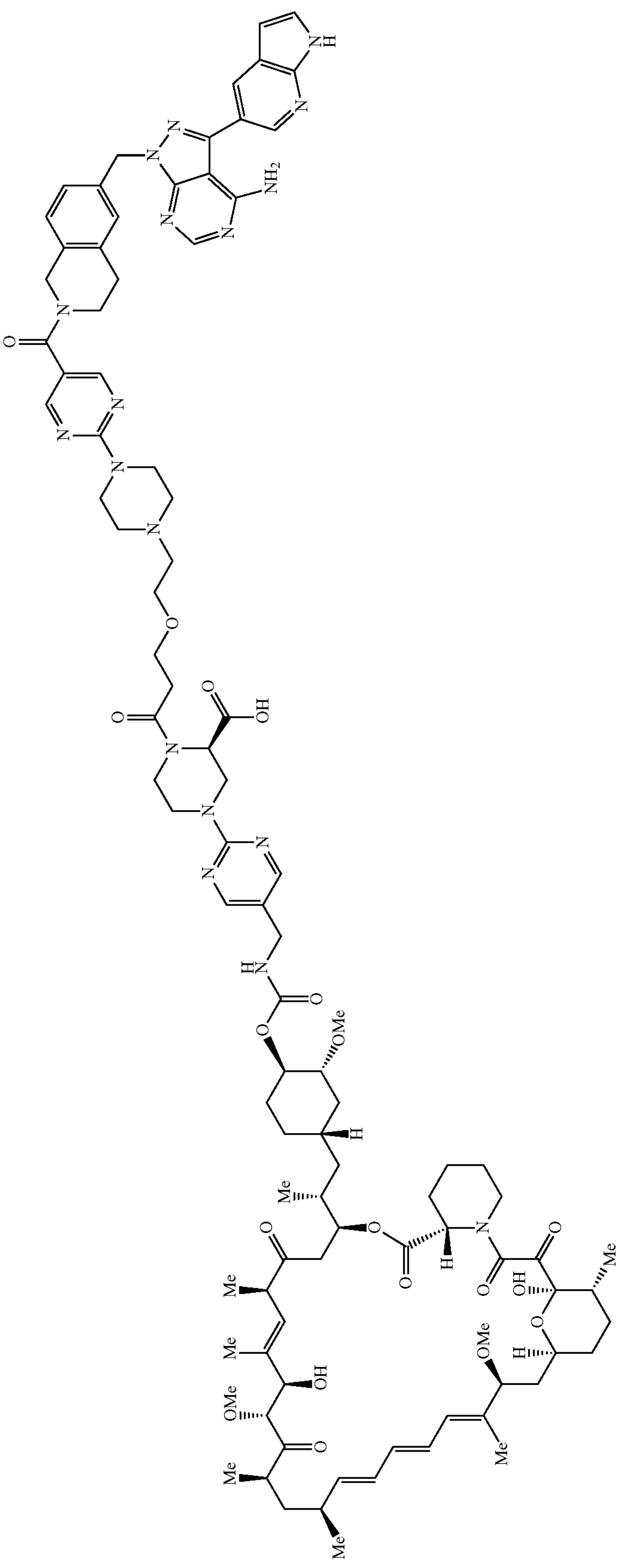

-continued
Example 133
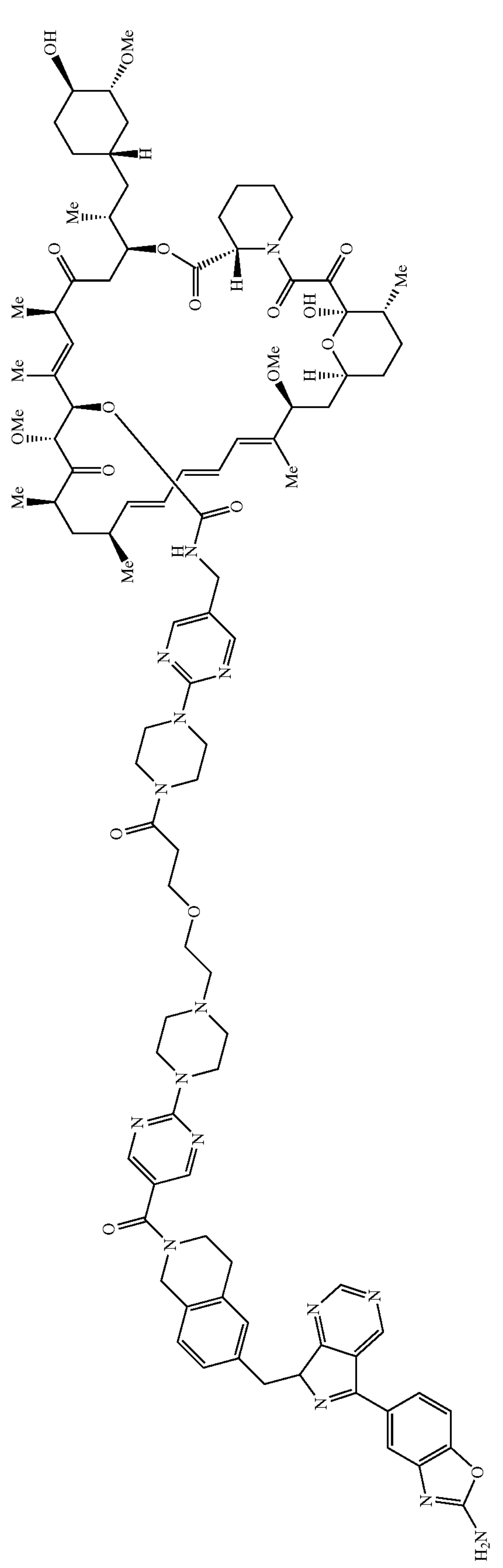

-continued
Example 134
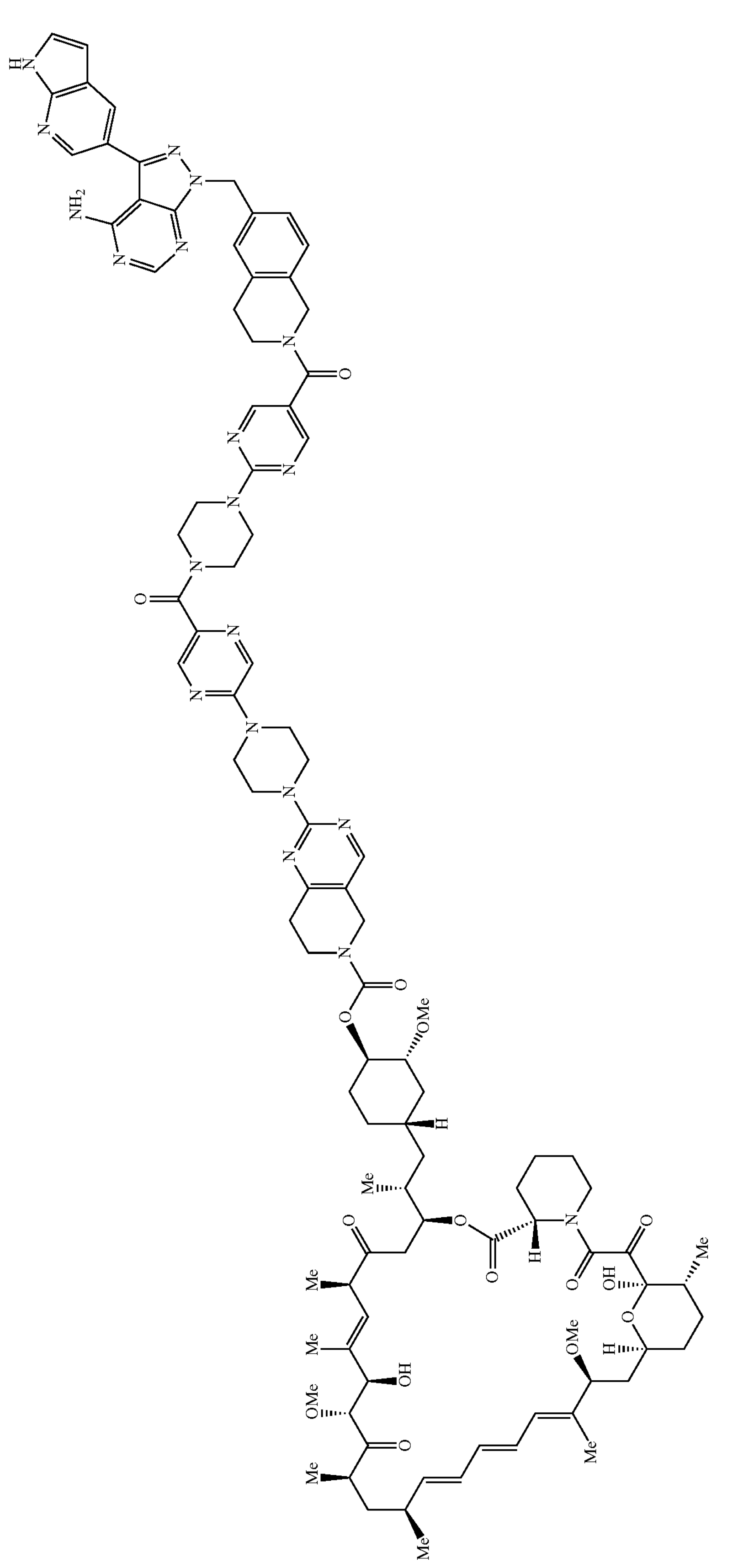

-continued
Example 135
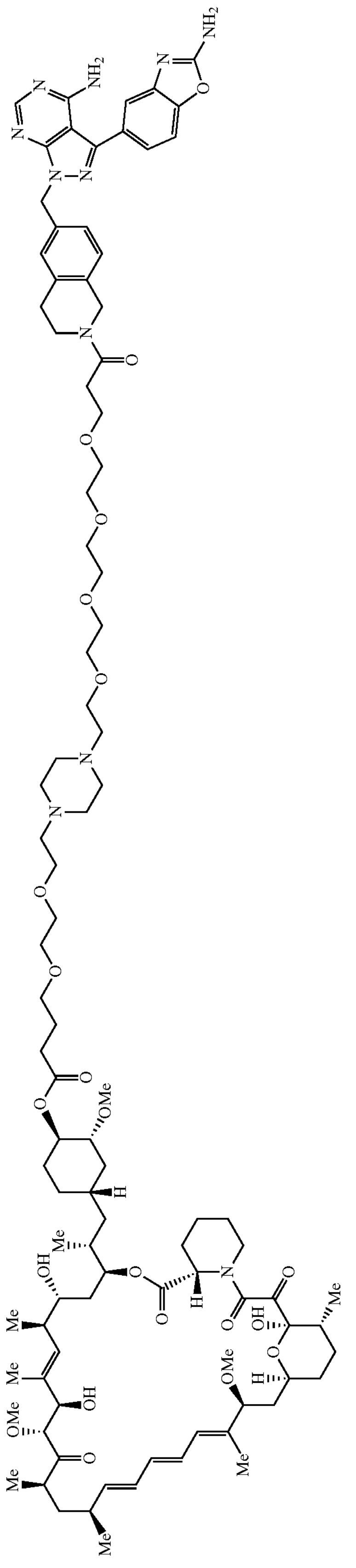

In certain embodiments, the present disclosure provides for a compound selected from below or a pharmaceutically acceptable salt or tautomer thereof, Example 136
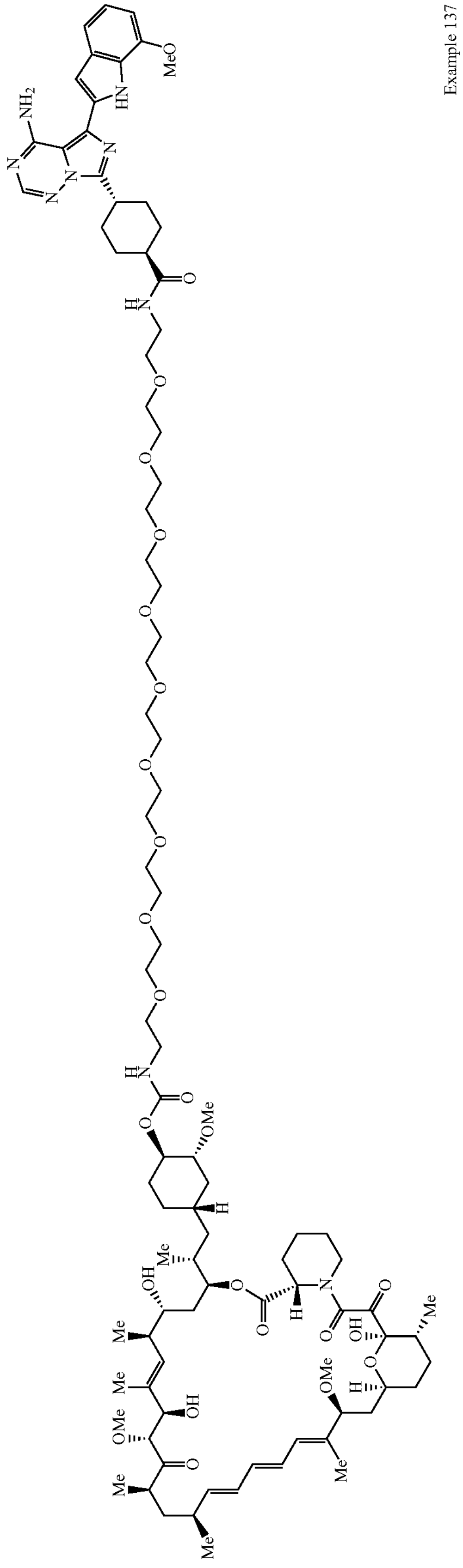
Example 137
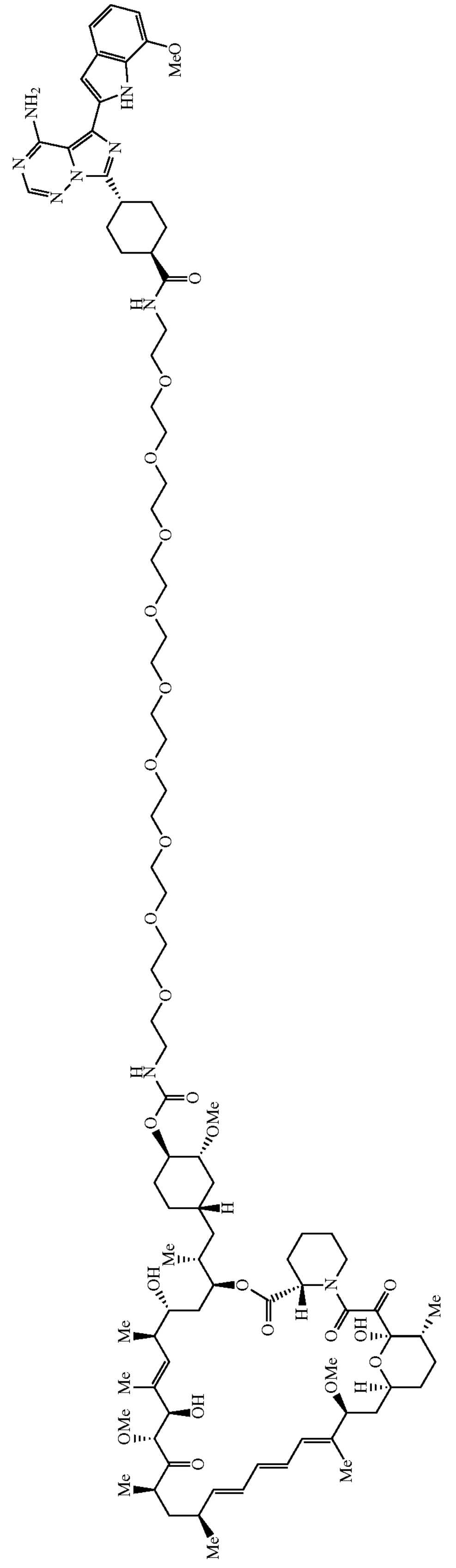

-continued
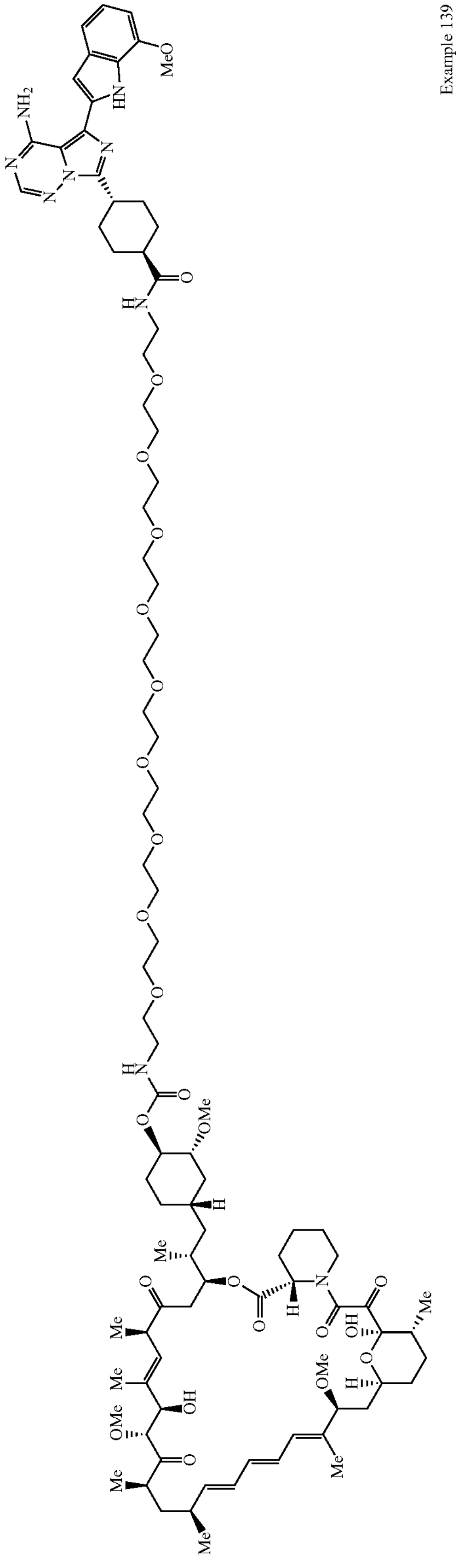
Example 138
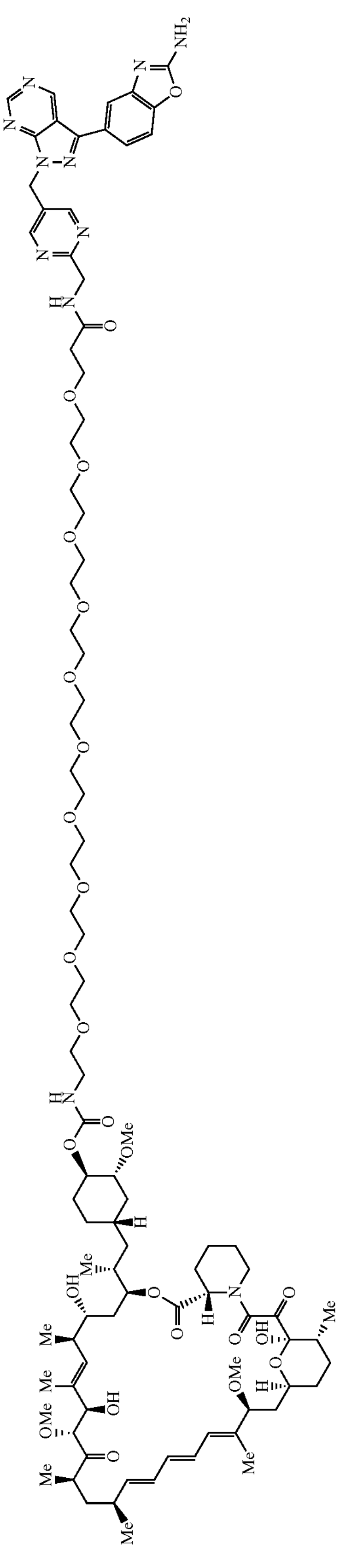
Example 139

-continued
Example 140
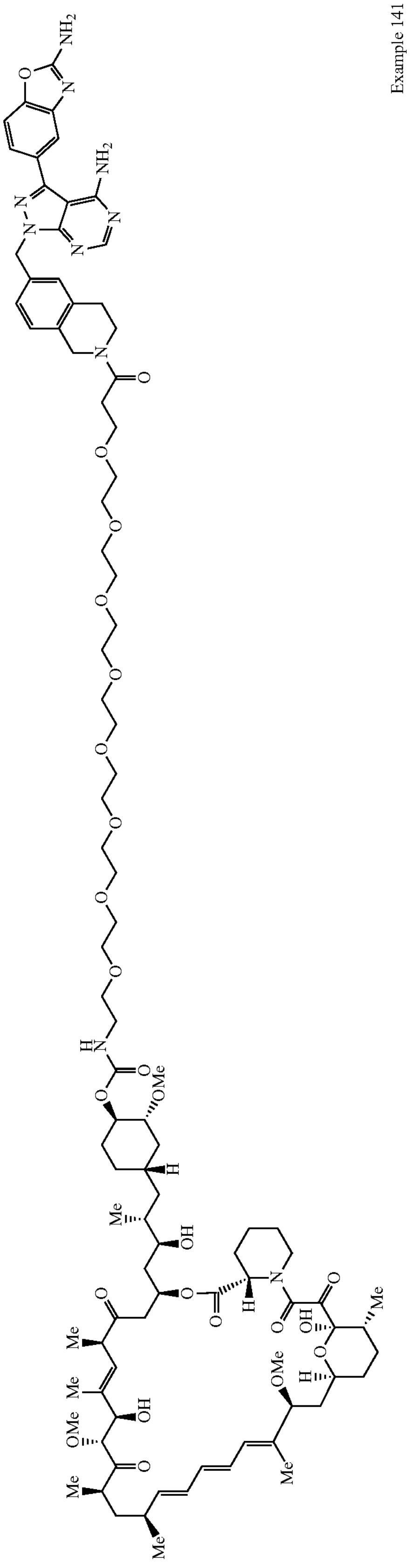
Example 141
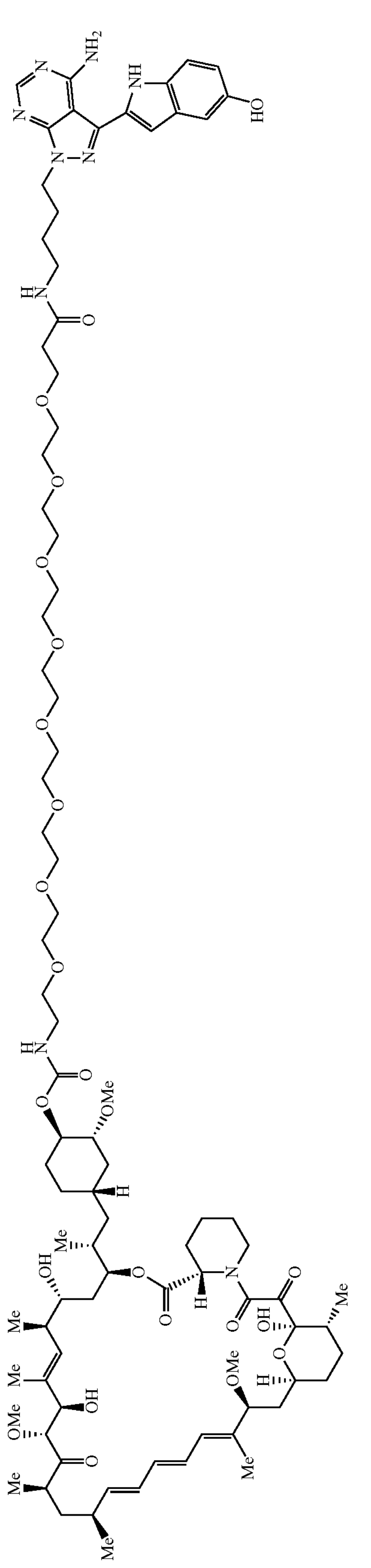

-continued
Example 142
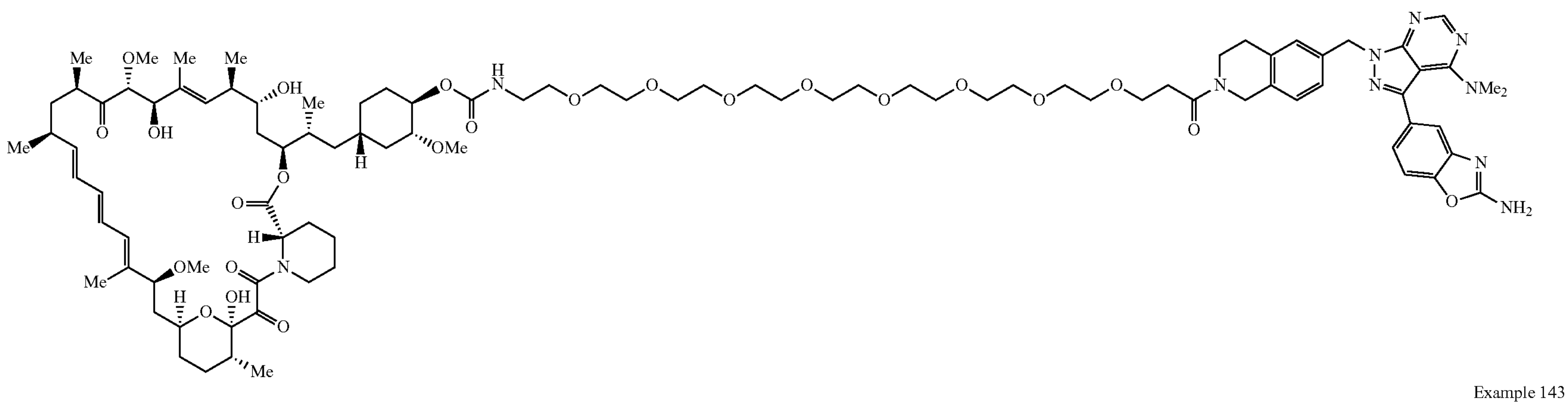
Example 143
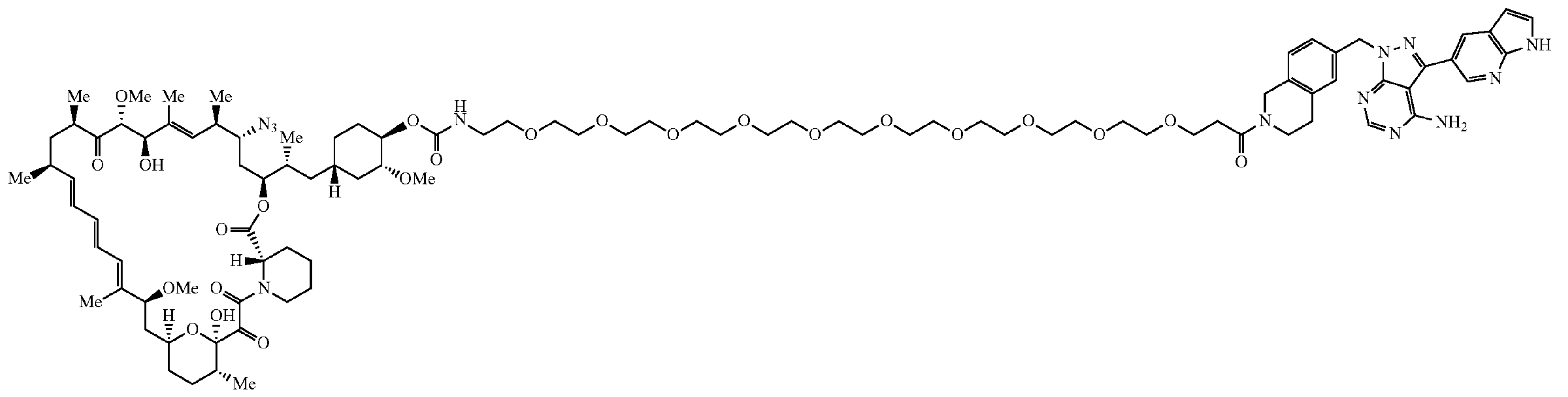

-continued
Example 144
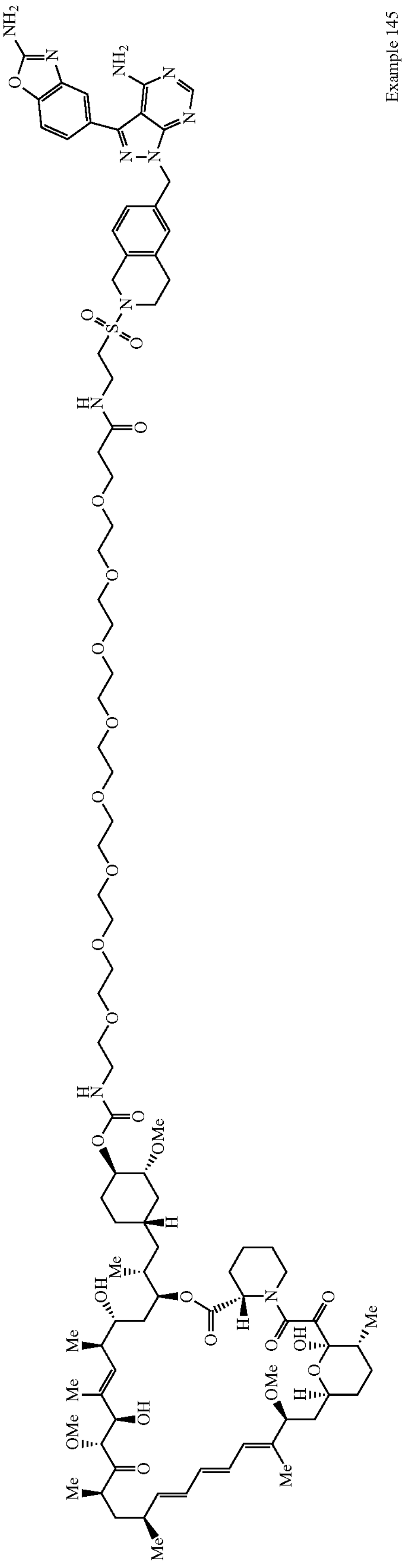
Example 145
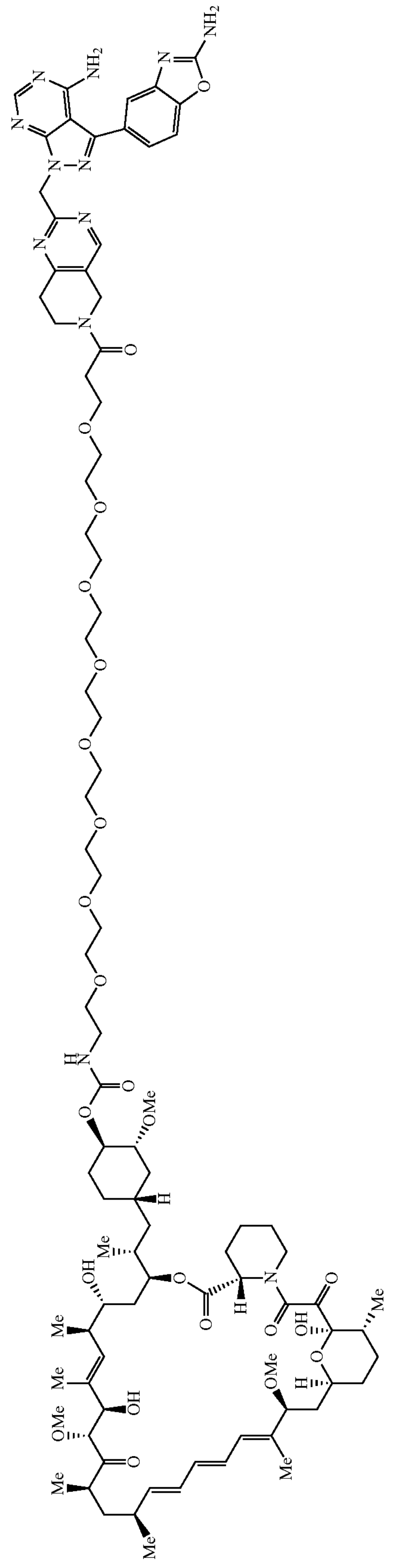

-continued
Example 146
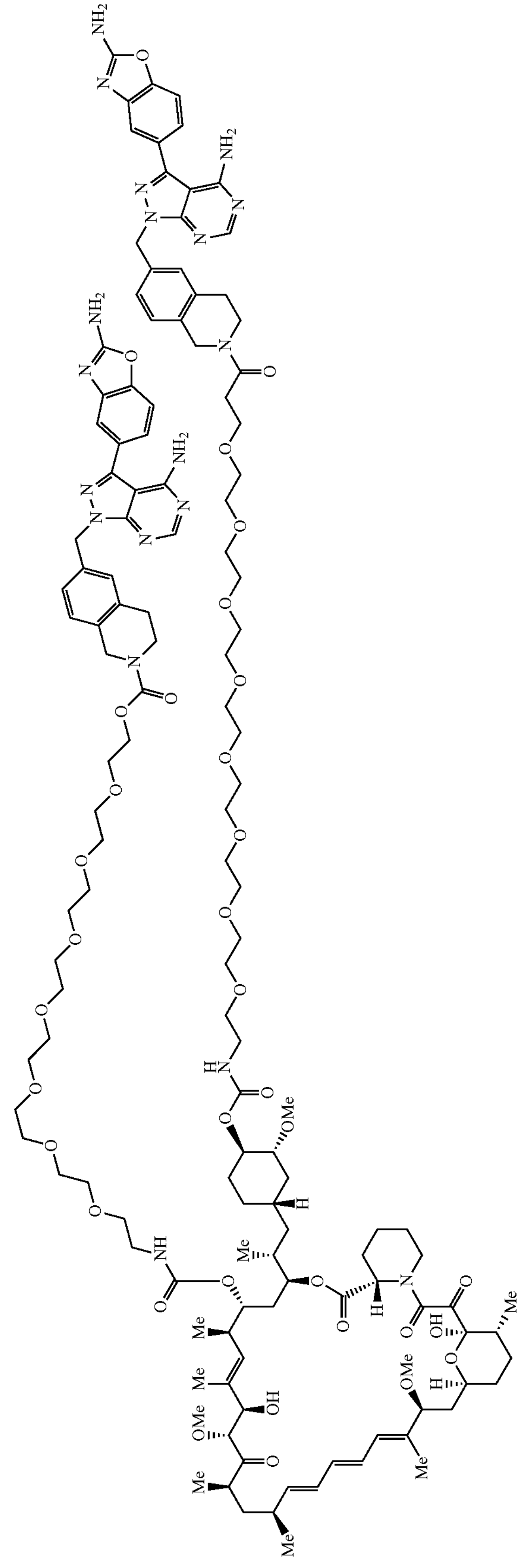
Example 147
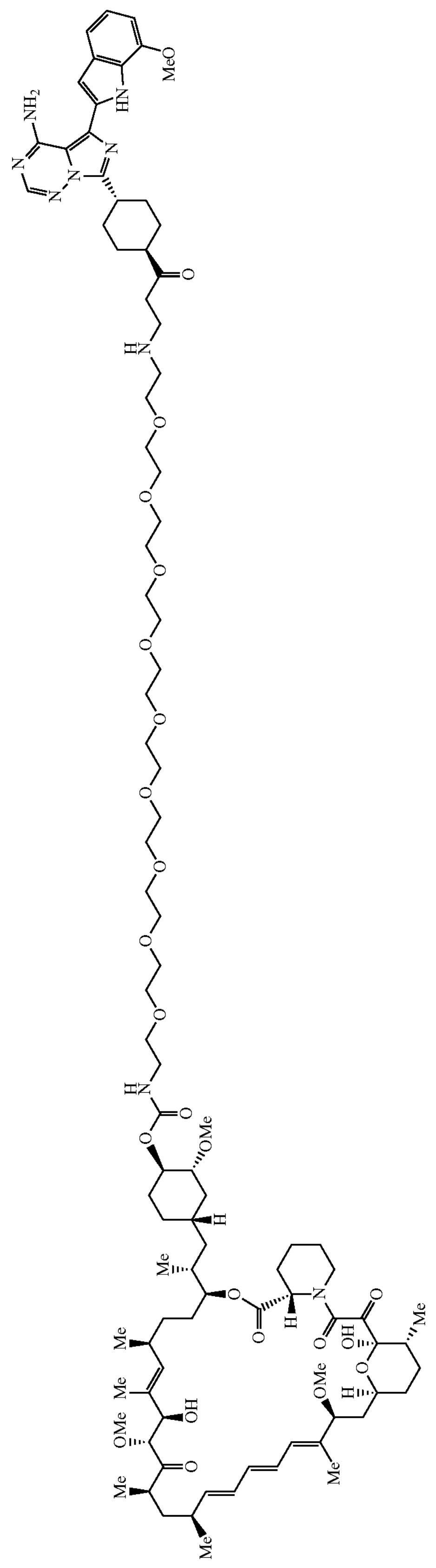

-continued
Example 148
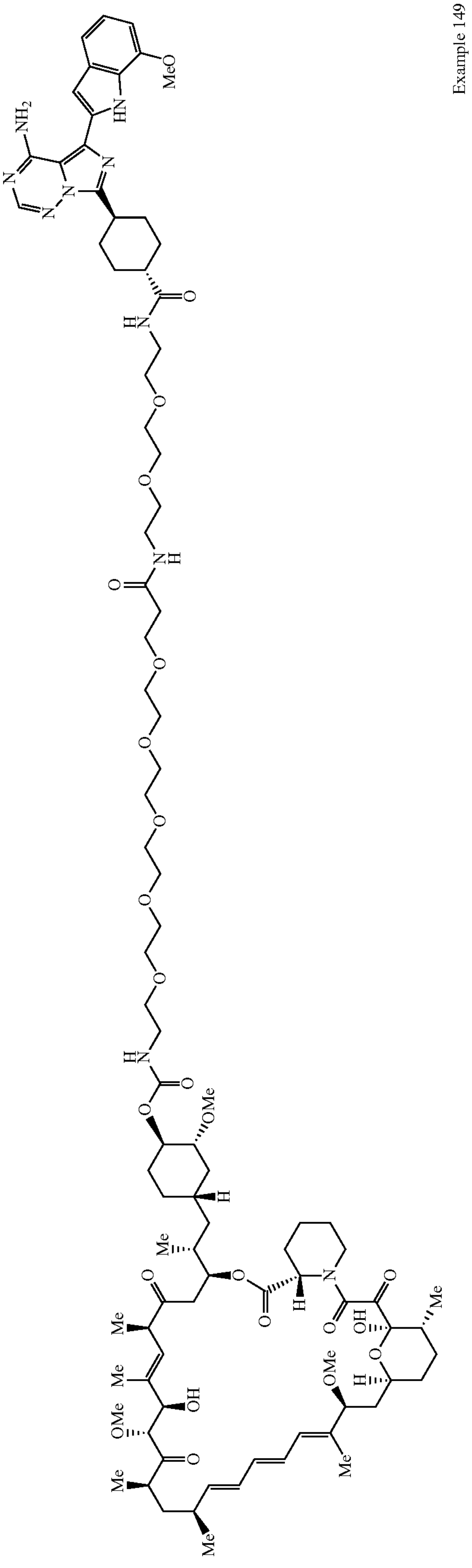
Example 149
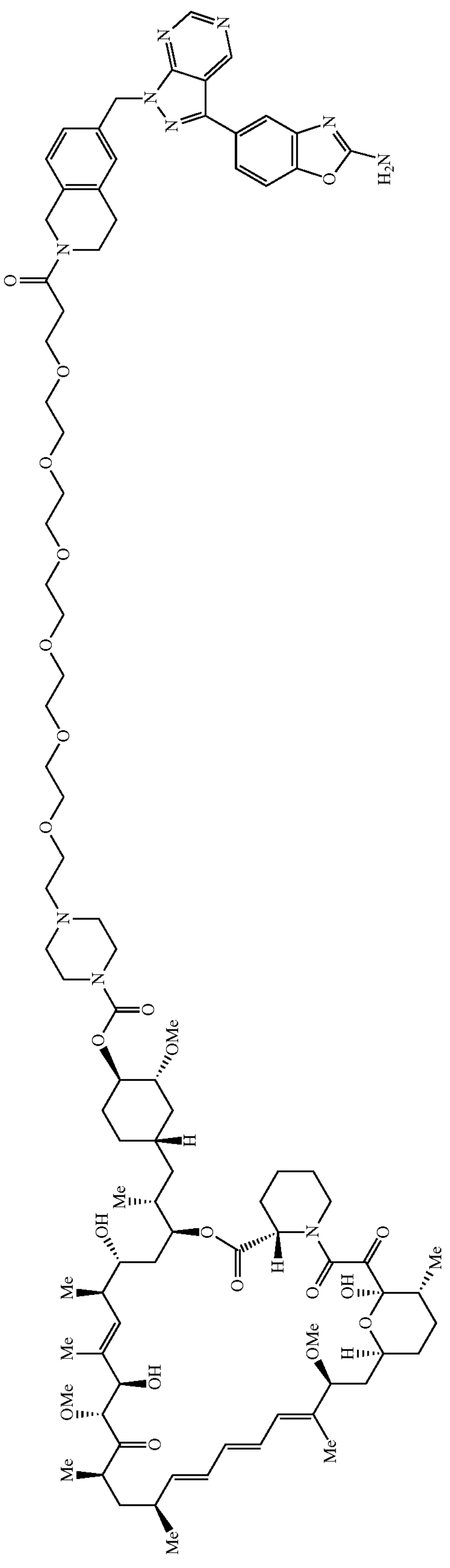

-continued
Example 150
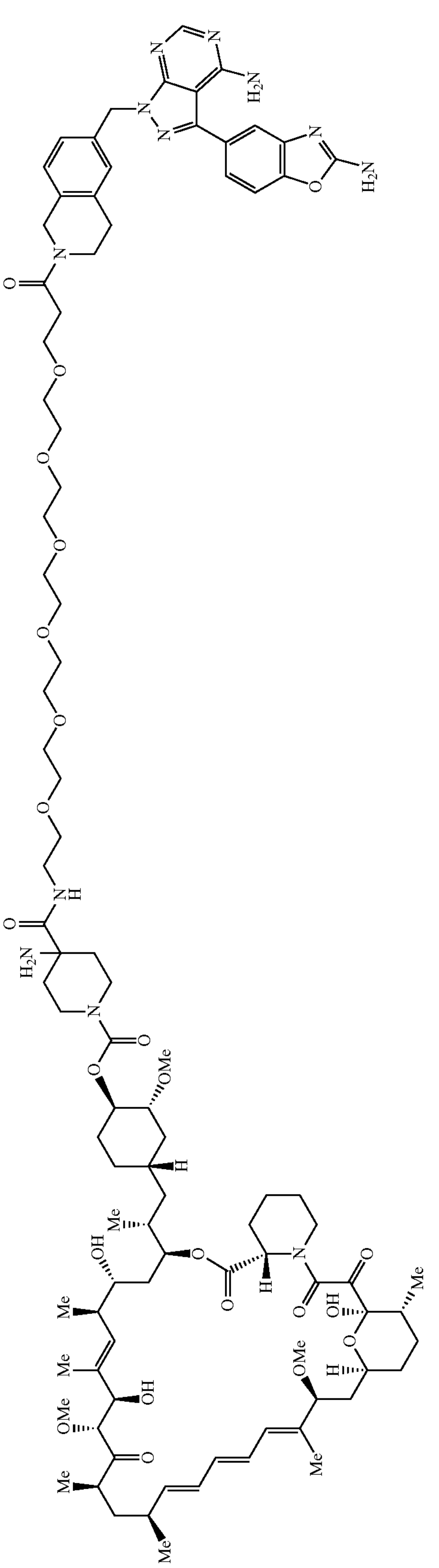

-continued
Example 151
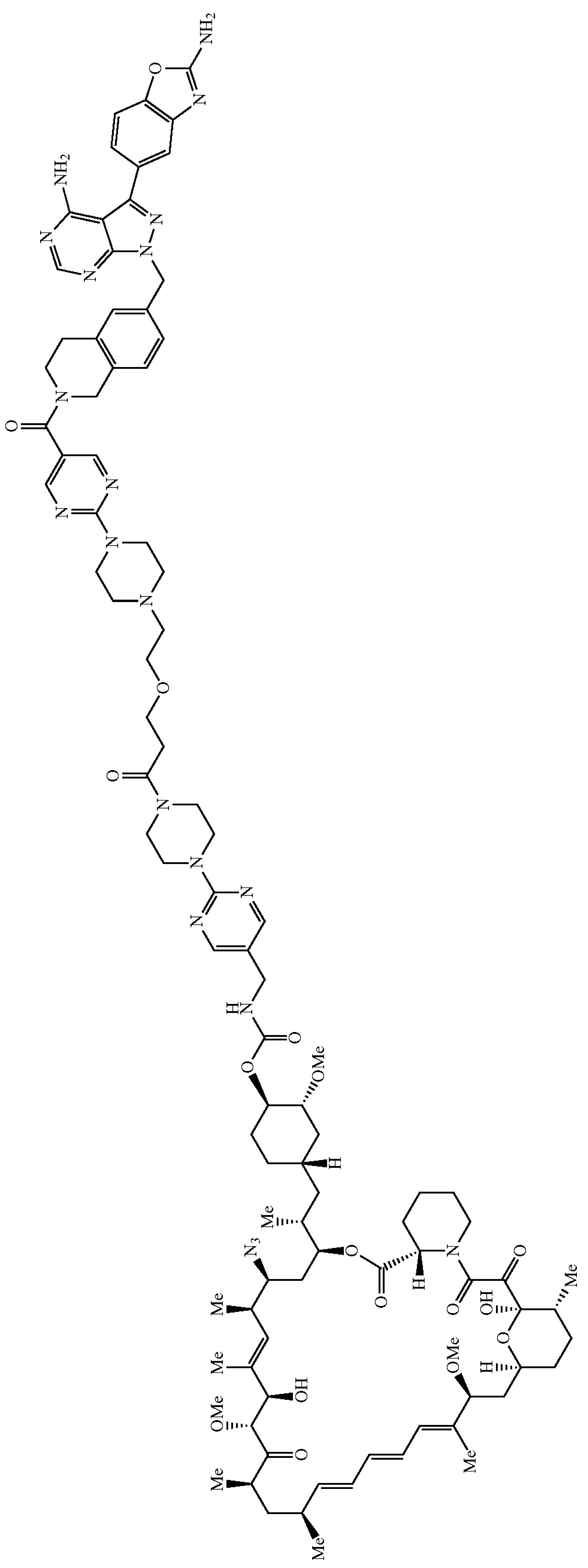
Example 152
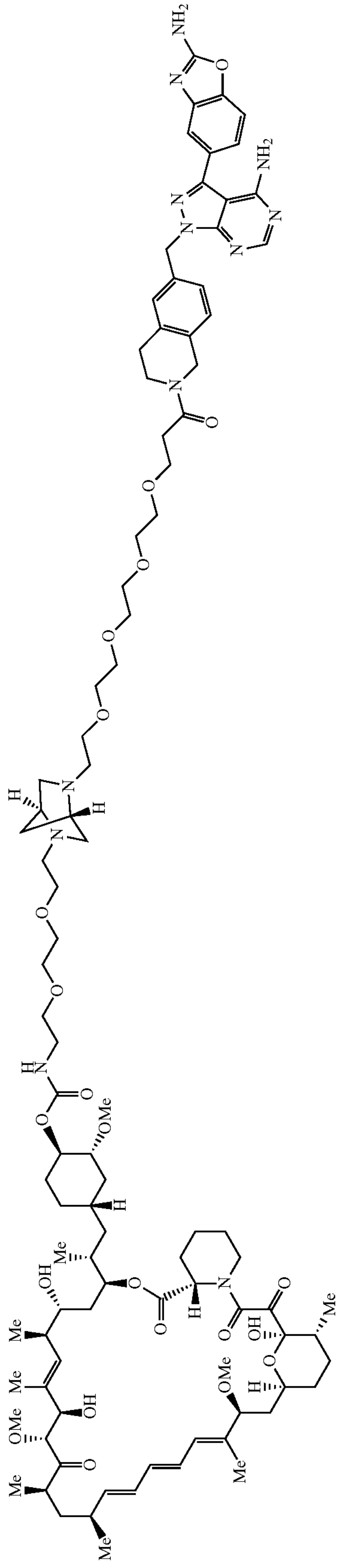

The compounds of the disclosure may include pharmaceutically acceptable salts of the compounds disclosed herein. Representative "pharmaceutically acceptable salts" may include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate, 1,1-methene-bis-2-hydroxy-3-naphthoate, einbonate, pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

"Pharmaceutically acceptable salt" may also include both acid and base addition salts. "Pharmaceutically acceptable acid addition salt" may refer to those salts which retain the biological effectiveness and properties of the free bases, which are not biologically or otherwise undesirable, and which may be formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, l-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" may refer to those salts that retain the biological effectiveness and properties of the free acids, which are not biologically or otherwise undesirable. These salts may be prepared from addition of an inorganic base or an organic base to the free acid. Salts derived from inorganic bases may include, but are not limited to, the sodium, potassium, lithium, ammonium, calcium, magnesium, iron, zinc, copper, manganese, aluminum salts and the like. For example, inorganic salts may include, but are not limited to, ammonium, sodium, potassium, calcium, and magnesium salts. Salts derived from organic bases may include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like.

Unless otherwise stated, structures depicted herein may also include compounds which differ only in the presence of one or more isotopically enriched atoms. For example, compounds having the present structure except for the replacement of a hydrogen atom by deuterium or tritium, or the replacement of a carbon atom by $^{13}C$ or $^{14}C$, or the replacement of a nitrogen atom by $^{15}N$, or the replacement of an oxygen atom with $^{17}O$ or $^{18}O$ are within the scope of the disclosure. Such isotopically labeled compounds are useful as research or diagnostic tools.

In some embodiments, one or more deuterium atoms may be introduced into the PEG moiety of any compound of the present invention. Mechanisms for such modifications are known in the art starting from commercially available starting materials, such as isotopically enriched hydroxylamine building blocks. In some embodiments, a tritium or a deuterium may be introduced at the C32 position of compounds of the present invention using, for example, a commercially available isotopically pure reducing agent and methods known to those in the art. In some embodiments, $^{14}C$ may be introduced into the C40 carbamate moiety of compounds of the present invention using commercially available materials and methods known to those of skill in the art. In some embodiments, an isotope such as deuterium or tritium may be introduced into the $R^{40a}$ substituent of a compound of Formula Ia, Ic, I or II, using commercially available starting materials and methods known to those of skill in the art.

Methods of Synthesizing Disclosed Compounds

The compounds of the present disclosure may be made by a variety of methods, including standard chemistry. Suitable synthetic routes are depicted in the schemes given below.

The compounds of any of the formulae described herein may be prepared by methods known in the art of organic synthesis as set forth in part by the following synthetic schemes and examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula I, Ia, Ib, II, or IIb, or a pharmaceutically acceptable salt or tautomer of any of the foregoing.

The compounds of any of the formulae described herein may be prepared by methods which avoid the use of metal-mediated cycloaddition reactions which require the use of azide-containing compounds. Azide containing compounds present potential safety hazards associated with their preparation and storage (e.g., explosion due to high energy decomposition). Also, the reaction schemes herein can avoid the use of copper or ruthenium metals in the penultimate or ultimate synthetic steps, which can be advantageous. Avoiding the use of copper or ruthenium metals in the penultimate or ultimate synthetic steps reduces the potential for contamination of the final compounds with undesirable metal impurities.

As rapamycin can be an expensive starting material, good yields on reactions are advantageous. The reaction schemes herein provide better yields than other reaction schemes. In the reaction schemes herein, there is no need to alkylate at the C40-hydroxyl of rapamycin, which is advantageous for providing as much as a 5-fold improved overall yield in preparing bivalent compounds from rapamycin compared to other reaction schemes.

There is an additional synthetic improvement associated with better yields. Avoiding the need to alkylate at the C40-hydroxyl gives as much as a 5-fold improved overall yield in preparing bivalent compounds from rapamycin.

Those skilled in the art will recognize if a stereocenter exists in any of the compounds of the present disclosure. Accordingly, the present disclosure may include both possible stereoisomers (unless specified in the synthesis) and may include not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be effected by any suitable method known in the art. See, for example, "Stereochemistry of Organic Compounds" by E. L. Eliel, S. H. Wilen, and L. N. Mander (Wiley-Interscience, 1994).

of organic synthesis. By way of example, compounds of the disclosure can be synthesized using the methods described below, together with synthetic methods known in the art of synthetic organic chemistry, or variations thereon as appreciated by those skilled in the art. These methods may include but are not limited to those methods described below.

The term "tautomers" may refer to a set of compounds that have the same number and type of atoms, but differ in bond connectivity and are in equilibrium with one another. A "tautomer" is a single member of this set of compounds. Typically a single tautomer is drawn but it may be understood that this single structure may represent all possible tautomers that might exist. Examples may include enol-ketone tautomerism. When a ketone is drawn it may be understood that both the enol and ketone forms are part of the disclosure.

In addition to tautomers that may exist at all amide, carbonyl, and oxime groups within compounds of Formula I, Ia, Ib, Ic, II, or IIb, compounds in this family readily interconvert via a ring-opened species between two major isomeric forms, known as the pyran and oxepane isomers (shown below). This interconversion can be promoted by magnesium ions, mildly acidic conditions, or alkylamine salts, as described in the following references: i) Hughes, P. F.; Musser, J.; Conklin, M.; Russo, R. 1992. *Tetrahedron Lett.* 33(33): 4739-32. ii) Zhu, T. 2007. U.S. Pat. No. 7,241,771; Wyeth. iii) Hughes, P. F. 1994. U.S. Pat. No. 5,344,833; American Home Products Corp. The scheme below shows an interconversion between the pyran and oxepane isomers in compounds of Formula I, Ia, Ib, Ic, II, or IIb.

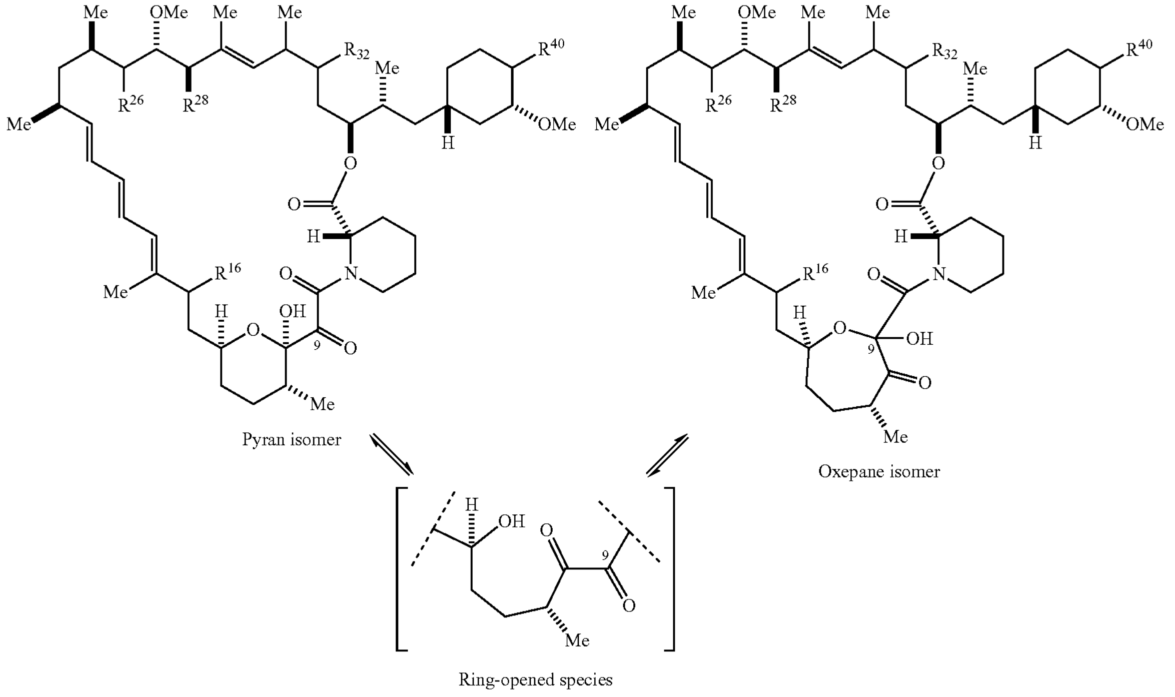

Preparation of Compounds

The compounds described herein may be made from commercially available starting materials or synthesized using known organic, inorganic, and/or enzymatic processes.

The compounds of the present disclosure can be prepared in a number of ways well known to those skilled in the art As this interconversion occurs under mild condition, and the thermodynamic equilibrium position may vary between different members of compounds of Formula I, Ia, Ib, Ic, II, or IIb, both isomers are contemplated for the compounds of Formula I, Ia, Ib, Ic, II, or IIb. For the sake of brevity, the pyran isomer form of all intermediates and compounds of Formula I, Ia, Ib, Ic, II, or IIb is shown.

General Assembly Approaches for Bifunctional Rapalogs

With reference to the schemes below, rapamycin is Formula RAP,

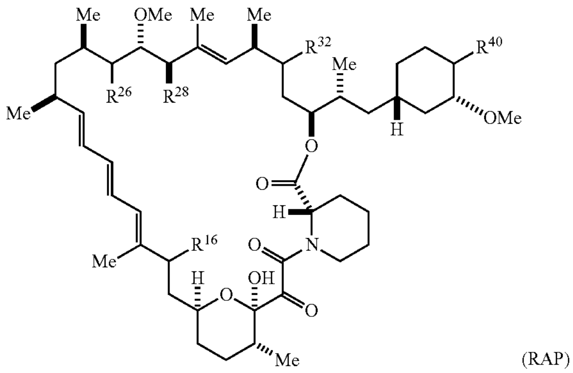

(RAP)

where $R^{16}$ is —$OCH_3$; $R^{26}$ is =O; $R^{28}$ is —OH; $R^{32}$ is =O; and $R^{40}$ is —OH. A "rapalog" refers to an analog or derivative of rapamycin. For example, with reference to the schemes below, a rapalog can be rapamycin that is substituted at any position, such as $R^{16}$, $R^{26}$, $R^{28}$, $R^{32}$, or $R^{40}$. An active site inhibitor (AS inhibitor) is an active site mTOR inhibitor. In certain embodiments, AS inhibitor is depicted by B, in Formula I, Ia, Ib, Ic, II, or IIb.

Series 1 Bifunctional Rapalogs

A general structure of Series 1 bifunctional rapalogs is shown in Scheme 1 below. For these types of bifunctional rapalogs, the linker may include variations where q=0 to 30, such as q=1 to 7, and r=1 to 6. The linker amine can include substitutions, such as R=H and C1-C6 alkyl groups. The carbamate moiety, where $Z^1$=O or S, can be attached to the rapalog at $R^{40}$ or $R^{28}$ (Formula I, Ia, Ib, Ic, II, or IIb), including variations found in Table 1 in the Examples Section. An mTOR active site inhibitor can attach to the linker via a primary or secondary amine, and may include variations found in Table 2 in the Examples Section.

Scheme 1. Series 1 bifunctional rapalogs.

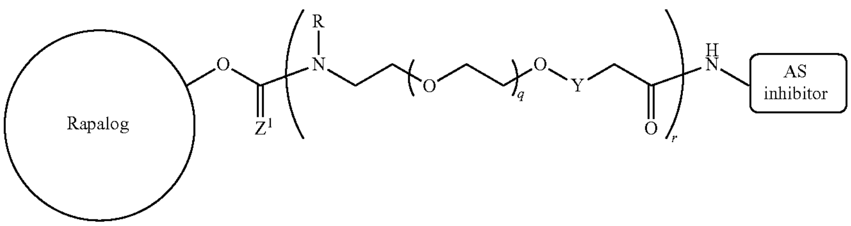

Series 1 Bifunctional rapalog

Series 2 Bifunctional Rapalogs

A general structure of Series 2 bifunctional rapalogs is shown in Scheme 2 below. For these types of bifunctional rapalogs, the linker may include variations where q=0 to 30, such as q=1 to 7. The linker amine can include substitutions, such as R=H and C1-C6 alkyl groups. The pre-linker amine can include substitutions, such as $R^2$=H, C1-C6 alkyl groups, and cycloalkyl including 4 to 8-membered rings. The carbamate moiety, where $Z^1$=O or S, can be attached to the rapalog at $R^{40}$ or $R^{28}$ (Formula I, Ia, Ib, Ic, II, or IIb), including variations found in Table 1 in the Examples Section. An mTOR active site inhibitor can attach to the linker via a primary or secondary amine, and may include variations found in Table 2 in the Examples Section.

Scheme 2. Series 2 bifunctional rapalogs.

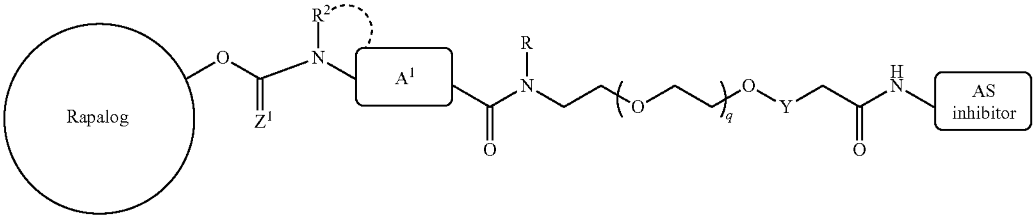

Series 2 Bifunctional rapalog

Series 3 Bifunctional Rapalogs

A general structure of Series 3 bifunctional rapalogs is shown in Scheme 3 below. For these types of bifunctional rapalogs, the linker may include variations where q=0 to 30, such as q=1 to 7. The linker amine can include substitutions, such as R=H and C1-C6 alkyl groups. The post-linker amine can include substitutions, such as $R^2$=H, C1-C6 alkyl groups, and cycloalkyl including 4 to 8-membered rings. The carbamate moiety, where $Z^1$=o or S, can be attached to the rapalog at $R^{40}$ or $R^{28}$ (Formula I, Ia, Ib, Ic, II, or IIb), including variations found in Table 1 in the Examples Section. An mTOR active site inhibitor can attach to the linker via a primary or secondary amine, and may include variations found in Table 2 in the Examples Section.

Scheme 3. Series 3 bifunctional rapalogs

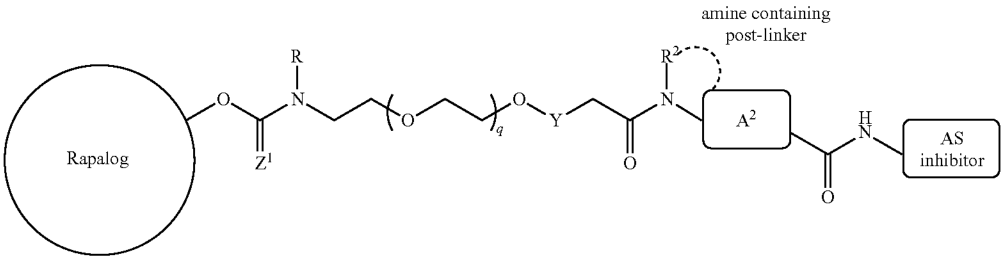

Series 3 Bifunctional rapalog

Series 4 Bifunctional Rapalogs

A general structure of Series 4 bifunctional rapalogs is shown in Scheme 4 below. For these types of bifunctional rapalogs, the linker may include variations where q=0 to 30, such as q=1 to 7. The linker amine can include substitutions, such as R=H and C1-C6 alkyl groups. The pre- and post-linker amines can each include substitutions, such as $R^2$=H, C1-C6 alkyl groups, and cycloalkyl including 4 to 8-membered rings. The carbamate moiety, where $Z^1$=O or S, can be attached to the rapalog at $R^{40}$ or $R^{28}$ (Formula I, Ia, Ib, Ic, II, or IIb), including variations found in Table 1 in the Examples Section. An mTOR active site inhibitor can attach to the linker via a primary or secondary amine, and may include variations found in Table 2 in the Examples Section.

Scheme 4. Series 4 bifunctional rapalogs

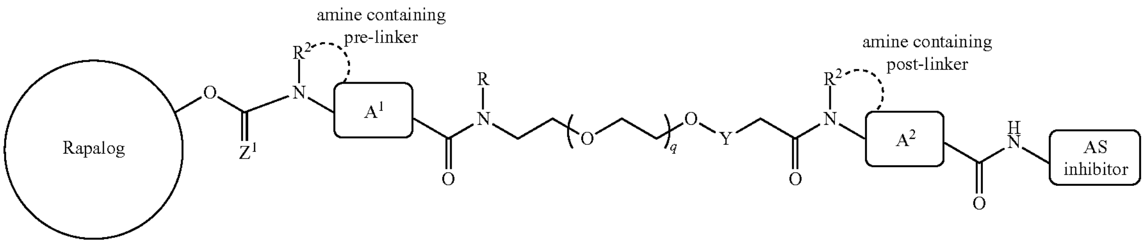

Series 4 Bifunctional rapalog

Series 5 Bifunctional Rapalogs

A general structure of Series 5 bifunctional rapalogs is shown in Scheme 5 below. For these types of bifunctional rapalogs, the pre-linker amine can include substitutions, such as $R^2$=H, C1-C6 alkyl groups, and cycloalkyl including 4 to 8-membered rings. The carbamate moiety, where $Z^1$=O or S, can be attached to the rapalog at $R^{40}$ or $R^{28}$ (Formula I, Ia, Ib, Ic, II, or IIb), including variations found in Table 1 in the Examples Section. An mTOR active site inhibitor can attach to the linker via a primary or secondary amine, and may include variations found in Table 2 in the Examples Section.

Scheme 5. Series 5 bifunctional rapalogs

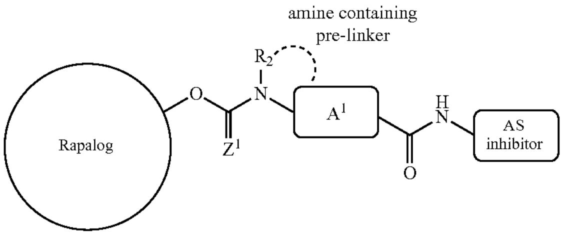

Series 5 Bifunctional rapalog

Series 6 Bifunctional Rapalogs

A general structure of Series 6 bifunctional rapalogs is shown in Scheme 6 below. For these types of bifunctional rapalogs, the linker may include variations where q=0 to 30, such as q=1 to 7. The linker amines can include substitutions, such as R=H and C1-C6 alkyl groups. The post-linker amine can include substitutions, such as $R^2$=H, C1-C6 alkyl groups, and cycloalkyl including 4 to 8-membered rings. The carbamate moiety, where $Z^1$=O or S, can be attached to the rapalog at $R^{40}$ or $R^{28}$ (Formula I, Ia, Ib, Ic, II, or IIb), including variations found in Table 1 in the Examples Section. An mTOR active site inhibitor can attach to the linker via a primary or secondary amine, and may include variations found in Table 2 in the Examples Section.

Scheme 6. Series 6 bifunctional rapalogs.

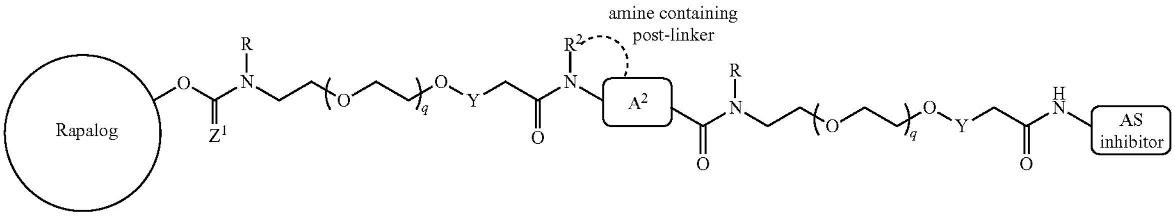

Series 6 Bifunctional rapalog

Series 7 Bifunctional Rapalogs

A general structure of Series 7 bifunctional rapalogs is shown in Scheme 7 below. For these types of bifunctional rapalogs, the linker may include variations where q=0 to 30, such as q=1 to 7. The linker amine can include substitutions, such as R=H and C1-C6 alkyl groups. The pre- and post-linker amines can each include substitutions, such as $R^2$=H, C1-C6 alkyl groups, and cycloalkyl including 4 to 8-membered rings. The carbamate moiety, where $Z^1$=O or S, can be attached to the rapalog at $R^{40}$ or $R^{28}$ (Formula I, Ia, Ib, Ic, II, or IIb), including variations found in Table 1 in the Examples Section. An mTOR active site inhibitor can attach to the linker via a primary or secondary amine, and may include variations found in Table 2 in the Examples Section.

Scheme 7. Series 7 bifunctional rapalogs

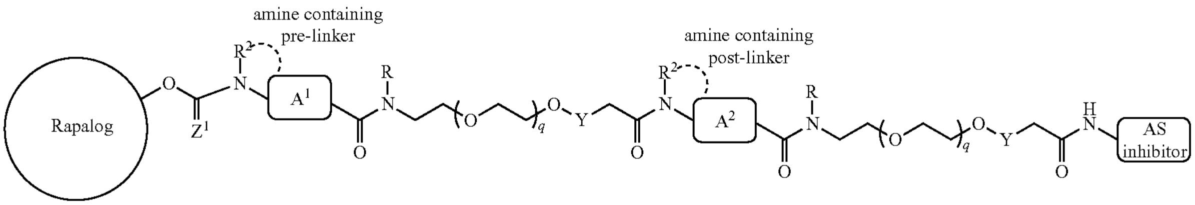

Series 7 Bifunctional rapalog

Series 8 Bifunctional Rapalogs

A general structure of Series 8 bifunctional rapalogs is shown in Scheme 8 below. For these types of bifunctional rapalogs, the linker may include variations where q=0 to 30, such as q=1 to 7. The linker amine can include substitutions, such as R═H and C1-C6 alkyl groups. The post-linker amine can include substitutions, such as $R^2$═H, C1-C6 alkyl groups, and cycloalkyl including 4 to 8-membered rings. The carbamate moiety, where $Z^1$═O or S, can be attached to the rapalog at $R^{40}$ or $R^{28}$ (Formula I, Ia, Ib, Ic, II, or IIb), including variations found in Table 1 in the Examples Section. An mTOR active site inhibitor can attach to the linker via a primary or secondary amine, and may include variations found in In certain embodiments, administering can include oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration can be by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. The compositions of Scheme 8. Series 8 bifunctional rapalogs

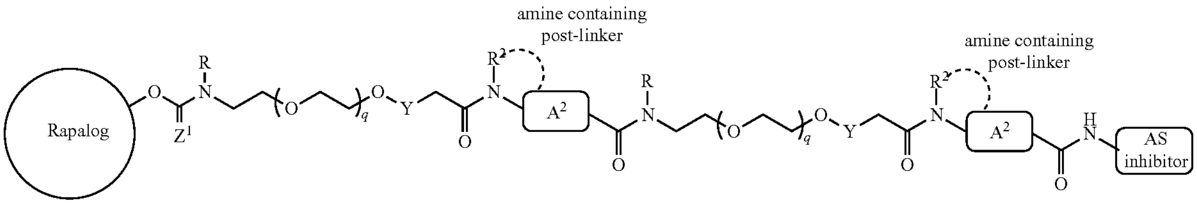

Series 8 Bifunctional rapalog

Pharmaceutical Compositions

Another aspect provides a pharmaceutical composition including a pharmaceutically acceptable excipient and a compound of the present invention, or pharmaceutically acceptable salt or tautomer thereof.

In embodiments of the pharmaceutical compositions, a compound of the present invention, or a pharmaceutically acceptable salt or tautomer thereof, may be included in a therapeutically effective amount.

Administration of the disclosed compounds or compositions can be accomplished via any mode of administration for therapeutic agents. These modes may include systemic or local administration such as oral, nasal, parenteral, transdermal, subcutaneous, vaginal, buccal, rectal, topical, intrathecal, or intracranial administration modes.

the present disclosure can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present disclosure may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present disclosure can also be delivered as microspheres for slow release in the body. For example, microspheres can be administered via intradermal injection of drug-containing microspheres, which slowly release subcutaneously (see Rao, J. Biomater Set Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). In another embodiment, the formulations of the compositions of the present disclosure can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46: 1576-1587, 1989). The compositions of the present disclosure can also be delivered as nanoparticles.

Depending on the intended mode of administration, the disclosed compounds or pharmaceutical compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, intrathecal, subcutaneous or intramuscular form, and all using forms well known to those skilled in the pharmaceutical arts.

Illustrative pharmaceutical compositions are tablets and gelatin capsules comprising a compound of the disclosure and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, alginic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described for instance in U.S. Pat. No. 5,262,564, the contents of which are hereby incorporated by reference.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the disclosure relates to a pharmaceutical composition comprising a compound, or a pharmaceutically acceptable salt or tautomer thereof, of the present disclosure and a pharmaceutically acceptable carrier. The pharmaceutically acceptable carrier can further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The compounds described herein can be used in combination with one another, with other active agents known to be useful in treating cancer, autoimmune disease, inflammatory disease, metabolic disease, neurodegenerative disease, fungal infection, or transplant rejection, or with adjunctive agents that may not be effective alone, but may contribute to the efficacy of the active agent. The compounds described herein can be used in combination with other active agents known to be longevity agents or anti-aging agents.

In embodiments of the pharmaceutical compositions, the pharmaceutical composition may include a second agent (e.g., therapeutic agent). In embodiments of the pharmaceutical compositions, the pharmaceutical composition may include a second agent (e.g., therapeutic agent) in a therapeutically effective amount. In certain embodiments, the second agent is an anti-cancer agent. In certain embodiments, the second agent is an immunotherapeutic agent. In certain embodiments, the second agent is an immune-oncological agent. In certain embodiments, the second agent is an anti-autoimmune disease agent. In embodiments, the second agent is an anti-inflammatory disease agent. In certain embodiments, the second agent is an anti-neurodegenerative disease agent. In certain embodiments, the second agent is an anti-metabolic disease agent. In certain embodiments, the second agent is an anti-cardiovascular disease agent. In certain embodiments, the second agent is an anti-aging agent. In certain embodiments, the second agent is a longevity agent. In certain embodiments, the second agent is an agent for treating or preventing transplant rejection. In certain embodiments, the second agent is an agent for treating or preventing fungal infection. In certain embodiments, the second agent is immune system repressor. In certain embodiments, the second agent is an mTOR modulator. In certain embodiments, the second agent is an mTOR inhibitor. In certain embodiments, the second agent is an active site mTOR inhibitor. In certain embodiments, the second agent is a rapamycin. In certain embodiments, the second agent is a rapamycin analog. In certain embodiments, the second agent is an mTOR pathway inhibitor. In certain embodiments, the second agent is CDK4/6 inhibitor; anti-PD1/PD-L1, PI3K inhibitor; or Ras inhibitor.

"Anti-cancer agent" or "anti-cancer drug" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anticancer agent is an agent approved by the FDA or similar regulatory agency of a country other than the USA, for treating cancer. Examples of anti-cancer agents include, but are not limited to, rapamycin, rapamycin analog, bevacizumab, PP242, ΓN 128, MLN0128, anti-androgens (e.g., Casodex, Flutamide, MDV3100, or ARN-509), MEK (e.g. MEK1, MEK2, or MEK and MEK2) inhibitors (e.g. XL518, CI-1040, PD035901, selumetinib/AZD6244, GSK1 120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP 16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®), geldanamycin, 17-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine dacliximab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-1 receptor inhibitor; interferon agonists; interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{U}$ $^{1}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™) panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, pyrrolo benzodiazepines (e.g. tomaymycin), carboplatin, CC-1065 and CC-1065 analogs including amino-CBIs, nitrogen mustards (such as chlorambucil and melphalan), dolastatin and dolastatin analogs (including auristatins: eg. monomethyl auristatin E), anthracycline antibiotics (such as doxorubicin, daunorubicin, etc.), duocarmycins and duocarmycin analogs, enediynes (such as neocarzinostatin and calicheamicins), leptomycin derivaties, maytansinoids and maytansinoid analogs (e.g. mertansine), methotrexate, mitomycin C, taxoids, vinca alkaloids (such as vinblastine and vincristine), epothilones (e.g. epothilone B), camptothecin and its clinical analogs topotecan and irinotecan, ΓNK128, PP242, PP121, MLN0128, AZD8055, AZD2014, VP-BEZ235, BGT226, SFl 126, Torin 1, Torin 2, WYE 687, WYE 687 salt (e.g., hydrochloride), PF04691502, PI-103, CC-223, OSI-027, XL388, KU-0063794, GDC-0349, PKI-587, rapamycin, deforolimus (AP23573, MK-8669, ridaforolimus), temsirolimus (CCI-779), ABT478, everolimus (RAD001) or the like.

mTOR and Methods of Treatment

The term "mTOR" refers to the protein "mechanistic target of rapamycin (serine/threonine kinase)" or "mammalian target of rapamycin." The term "mTOR" may refer to the nucleotide sequence or protein sequence of human mTOR (e.g., Entrez 2475, Uniprot P42345, RefSeq NM_004958, or RefSeq NP 004949) (SEQ ID NO: 1). The term "mTOR" may include both the wild-type form of the nucleotide sequences or proteins as well as any mutants thereof. In some embodiments, "mTOR" is wild-type mTOR. In some embodiments, "mTOR" is one or more mutant forms. The term "mTOR" XYZ may refer to a nucleotide sequence or protein of a mutant mTOR wherein the Y numbered amino acid of mTOR that normally has an X amino acid in the wildtype, instead has a Z amino acid in the mutant. In embodiments, an mTOR is the human mTOR. In embodiments, the mTOR has the nucleotide sequence corresponding to reference number GL206725550 (SEQ ID NO:2). In embodiments, the mTOR has the nucleotide sequence corresponding to RefSeq NM_004958.3 (SEQ ID NO:2). In embodiments, the mTOR has the protein sequence corresponding to reference number GL4826730 (SEQ ID NO: 1). In embodiments, the mTOR has the protein sequence corresponding to RefSeq NP_004949.1 (SEQ ID NO: 1). In embodiments, the mTOR has the following amino acid sequence:

(SEQ ID NO: 1)

```
MLGTGPAAATTAATTSSNVSVLQQFASGLKSRNEETRAKAAKELQHYVTM

ELREMSQEESTRFYDQLNHHIFELVSSSDANERKGGILAIASLIGVEGGN
```

-continued

```
ATRIGRFANYLRNLLPSNDPWMEMASKAIGRLAMAGDTFTAEYVEFEVKR

ALEWLGADRNEGRRHAAVLVLRELAISVPTFFFQQVQPFFDNIFVAVWDP

KQAIREGAVAALRACLILTTQREPKEMQKPQWYRHTFEEAEKGFDETLAK

EKGMNRDDRIHGALLILNELVRISSMEGERLREEMEEITQQQLVHDKYCK

DLMGFGTKPRHITPFTSFQAVQPQQSNALVGLLGYSSHQGLMGFGTSPSP

AKSTLVESRCCRDLMEEKFDQVCQWVLKCRNSKNSLIQMTILNLLPRLAA

FRPSAFTDTQYLQDTMNHVLSCVKKEKERTAAFQALGLLSVAVRSEFKVY

LPRVLDIIRAALPPKDFAHKRQKAMQVDATVFTCISMLARAMGPGIQQDI

KELLEPMLAVGLSPALTAVLYDLSRQIPQLKKDIQDGLLKMLSLVLMHKP

LRHPGMPKGLAHQLASPGLTTLPEASDVGSITLALRTLGSFEFEGHSLTQ

FVRHCADHFLNSEHKEIRMEAARTCSRLLTPSIHLISGHAHVVSQTAVQV

VADVLSKLLWGITDPDPDIRYCVLASLDERFDAHLAQAENLQALFVALND

QVFEIRELAICTVGRLSSMNPAFVMPFLRKMLIQILTELEHSGIGRIKEQ

SARMLGHLVSNAPRLIRPYMEPILKALILKLKDPDPDPNPGVINNVLATI

GELAQVSGLEMRKWVDELFIIIMDMLQDSSLLAKRQVALWTLGQLVASTG

YWEPYRKYPTLLEVLLNFLKTEQNQGTRREAIRVLGLLGALDPYKFIKVN

IGMIDQSRDASAVSLSESKSSQDSSDYSTSEMLVNMGNLPLDEFYPAVSM

VALMRIFRDQSLSHHHTMVVQAITFIFKSLGLKCVQFLPQVMPTFLNVIR

VCDGAIREFLFQQLGMLVSFVKSHIRPYMDEIVTLMREFWVMNTSIQSTI

ILLIEQIVVALGGEFKLYLPQLIPHMLRVFMHDNSPGRIVSIKLLAAIQL

FGANLDDYLHLLLPPIVKLFDAPEAPLPSRKAALETVDRLTESLDFTDYA

SRIIHPIVRTLDQSPELRSTAMDTLSSLVFQLGKKYQIFIPMVNKVLVRH

RINHQRYDVLICRIVKGYTLADEEEDPLIYQHRMLRSGQGDALASGPVET

GPMKKLHVSTINLQKAWGAARRVSKDDWLEWLRRLSLELLKDSSSPSLRS

CWALAQAYNPMARDLFNAAFVSCWSELNEDQQDELIRSIELALTSQDIAE

VTQTLLNLAEFMEHSDKGPLPLRDDNGIVLLGERAAKCRAYAKALHYKEL

EFQKGPTPAILESLISINNKLQQPEAAAGVLEYAMKHFGELEIQATWYEK

LHEWEDALVAYDKKMDTNKDDPELMLGRMRCLEALGEWGQLHQQCCEKWT

LVNDETQAKMARMAAAAAWGLGQWDSMEEYTCMIPRDTHDGAFYRAVLAL

HQDLFSLAQQCIDKARDLLDAELTAMAGESYSRAYGAMVSCHMLSELEEV

IQYKLVPERREIIRQIWWERLQGCQRIVEDWQKILMVRSLVVSPHEDMRT

WLKYASLCGKSGRLALAHKTLVLLLGVDPSRQLDHPLPTVHPQVTYAYMK

NMWKSARKIDAFQHMQHFVQTMQQQAQHAIATEDQQHKQELHKLMARCFL

KLGEWQLNLQGINESTIPKVLQYYSAATEHDRSWYKAWHAWAVMNFEAVL

HYKHQNQARDEKKKLRHASGANITNATTAATTAATATTTASTEGSNSESE

AESTENSPTPSPLQKKVTEDLSKTLLMYTVPAVQGFFRSISLSRGNNLQD

TLRVLTLWFDYGHWPDVNEALVEGVKAIQIDTWLQVIPQLIARIDTPRPL

VGRLIHQLLTDIGRYHPQALIYPLTVASKSTTTARHNAANKILKNMCEHS

NTLVQQAMMVSEELIRVAILWHEMWHEGLEEASRLYFGERNVKGMFEVLE

PLHAMMERGPQTLKETSFNQAYGRDLMEAQEWCRKYMKSGNVKDLTQAWD

LYYHVFRRISKQLPQLTSLELQYVSPKLLMCRDLELAVPGTYDPNQPIIR
```

-continued

```
IQSIAPSLQVITSKQRPRKLTLMGSNGHEFVFLLKGHEDLRQDERVMQLF
GLVNTLLANDPTSLRKNLSIQRYAVIPLSTNSGLIGWVPHCDTLHALIRD
YREKKKILLNIEHRIMLRMAPDYDHLTLMQKVEVFEHAVNNTAGDDLAKL
LWLKSPSSEVWFDRRTNYTRSLAVMSMVGYILGLGDRHPSNLMLDRLSGK
ILHIDFGDCFEVAMTREKFPEKIPFRLTRMLTNAMEVTGLDGNYRITCHT
VMEVLREHKDSVMAVLEAFVYDPLLNWRLMDTNTKGNKRSRTRTDSYSAG
QSVEILDGVELGEPAHKKTGTTVPESIHSFIGDGLVKPEALNKKAIQIIN
RVRDKLTGRDFSHDDTLDVPTQVELLIKQATSHENLCQCYIGWCPFW
```

(SEQ ID NO: 1)

In embodiments, the mTOR is a mutant mTOR. In embodiments, the mutant mTOR is associated with a disease that is not associated with wildtype mTOR. In embodiments, the mTOR may include at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations, or any range derivable therein) compared to the sequence above.

The term "mTORC1" refers to the protein complex including mTOR and Raptor (regulatory-associated protein of mTOR). mTORC1 may also include MLST8 (mammalian lethal with SEC 13 protein 8), PRAS40, and/or DEPTOR. mTORC1 may function as a nutrient/energy/redox sensor and regulator of protein synthesis. The term "mTORC1 pathway" or "mTORC1 signal transduction pathway" may refer to a cellular pathway including mTORC1. An mTORC1 pathway includes the pathway components upstream and downstream from mTORC1. An mTORC1 pathway is a signaling pathway that is modulated by modulation of mTORC1 activity. In embodiments, an mTORC1 pathway is a signaling pathway that is modulated by modulation of mTORC1 activity but not by modulation of mTORC2 activity. In embodiments, an mTORC1 pathway is a signaling pathway that is modulated to a greater extent by modulation of mTORC1 activity than by modulation of mTORC2 activity.

The term "mTORC2" refers to the protein complex including mTOR and RICTOR (rapamycin-insensitive companion of mTOR). mTORC2 may also include GβL, mSIN1 (mammalian stress-activated protein kinase interacting protein 1), Protor 1/2, DEPTOR, TTI1, and/or TEL2. mTORC2 may regulate cellular metabolism and the cytoskeleton. The term "mTORC2 pathway" or "mTORC2 signal transduction pathway" may refer to a cellular pathway including mTORC2. An mTORC2 pathway includes the pathway components upstream and downstream from mTORC2. An mTORC2 pathway is a signaling pathway that is modulated by modulation of mTORC2 activity. In embodiments, an mTORC2 pathway is a signaling pathway that is modulated by modulation of mTORC2 activity but not by modulation of mTORC1 activity. In embodiments, an mTORC2 pathway is a signaling pathway that is modulated to a greater extent by modulation of mTORC2 activity than by modulation of mTORC1 activity.

The term "rapamycin" or "sirolimus" refers to a macrolide produced by the bacteria *Streptomyces hygroscopicus*. Rapamycin may prevent the activation of T cells and B cells. Rapamycin has the IUPAC name (3S,6R,7E,9R, 10R, 12R, 14S, 15E, 17E, 19E,21S,23S,26R,27R,34aS)-9,10,12,13,14, 21,22,23,24,25,26,27,32,33,34,34α-hexadecahydro-9,27-dihydroxy-3-[(1R)-2-[(1S,3R,4R)-4-hydroxy-3-methoxycyclohexyl]-1-methylethyl]-10,21-dimethoxy-6,8,12,14,20, 26-hexamethyl-23,27-epoxy-3H-pyrido[2,1-c][1,4]-oxaazacyclohentriacontine-1,5,11,28,29(4H,6H, 31H)-pentone. Rapamycin has the CAS number 53123-88-9. Rapamycin may be produced synthetically (e.g., by chemical synthesis) or through use of a production method that does not include use of *Streptomyces hygroscopicus*.

"Analog" is used in accordance with its plain ordinary meaning within chemistry and biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof.

The term "rapamycin analog" or "rapalog" refers to an analog or derivative (e.g., a prodrug) of rapamycin.

The terms "active site mTOR inhibitor" and "ATP mimetic" refers to a compound that inhibits the activity of mTOR (e.g., kinase activity) and binds to the active site of mTOR (e.g., the ATP binding site, overlapping with the ATP binding site, blocking access by ATP to the ATP binding site of mTOR). Examples of active site mTOR inhibitors include, but are not limited to, INK128, PP242, PP121, MLN0128, AZD8055, AZD2014, NVP-BEZ235, BGT226, SF1126, Torin 1, Torin 2, WYE 687, WYE 687 salt (e.g., hydrochloride), PF04691502, PI-103, CC-223, OSI-027, XL388, KU-0063794, GDC-0349, and PKI-587. In embodiments, an active site mTOR inhibitor is an asTORi. In some embodiments, "active site inhibitor" may refer to "active site mTOR inhibitor."

The term "FKBP" refers to the protein Peptidyl-prolyl cis-trans isomerase. For non-limiting examples of FKBP, see Cell Mol Life Sci. 2013 September; 70(18):3243-75. In embodiments, "FKBP" may refer to "FKBP-12" or "FKBP 12" or "FKBP 1 A." In embodiments, "FKBP" may refer to the human protein. Included in the term "FKBP" is the wildtype and mutant forms of the protein. In embodiments, "FKBP" may refer to the wildtype human protein. In embodiments, "FKBP" may refer to the wildtype human nucleic acid. In embodiments, the FKBP is a mutant FKBP. In embodiments, the mutant FKBP is associated with a disease that is not associated with wildtype FKBP. In embodiments, the FKBP includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations, or any range derivable therein) compared to wildtype FKBP.

The term "FKBP-12" or "FKBP 12" or "FKBP1A" may refer to the protein "Peptidyl-prolyl cis-trans isomerase FKBP 1 A." In embodiments, "FKBP-12" or "FKBP 12" or "FKBP 1 A" may refer to the human protein. Included in the term "FKBP-12" or "FKBP 12" or "FKBP 1 A" are the wildtype and mutant forms of the protein. In embodiments, "FKBP-12" or "FKBP 12" or "FKBP 1 A" may refer to the protein associated with Entrez Gene 2280, OMIM 186945, UniProt P62942, and/or RefSeq (protein) NP 000792 (SEQ ID NO:3). In embodiments, the reference numbers immediately above may refer to the protein, and associated nucleic acids, known as of the date of filing of this application. In embodiments, "FKBP-12" or "FKBP 12" or "FKBP 1 A" may refer to the wildtype human protein. In embodiments, "FKBP-12" or "FKBP 12" or "FKBP1A" may refer to the wildtype human nucleic acid. In embodiments, the FKBP-12 is a mutant FKBP-12. In embodiments, the mutant FKBP-12 is associated with a disease that is not associated with wildtype FKBP-12. In embodiments, the FKBP-12 may include at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations, or any range derivable therein) compared to wildtype FKBP-12. In embodiments, the FKBP-12 has the protein sequence corresponding to reference number GI:206725550. In embodiments, the FKBP-12 has the protein sequence corresponding to RefSeq NP_000792.1 (SEQ ID NO:3).

The term "4E-BP1" or "4EBP1" or "EIF4EBP1" refers to the protein "Eukaryotic translation initiation factor 4E-binding protein 1." In embodiments, "4E-BP1" or "4EBP1" or "EIF4EBP1" may refer to the human protein. Included in the term "4E-BP1" or "4EBP1" or "EIF4EBP1" are the wildtype and mutant forms of the protein. In embodiments, "4E-BP1" or "4EBP1" or "EIF4EBP1" may refer to the protein associated with Entrez Gene 1978, OMIM 602223, UniProt Q13541, and/or RefSeq (protein) NP_004086 (SEQ ID NO:4). In embodiments, the reference numbers immediately above may refer to the protein, and associated nucleic acids, known as of the date of filing of this application. In embodiments, "4E-BP1" or "4EBP1" or "EIF4EBP1" may refer to the wildtype human protein. In embodiments, "4E-BP T" or "4EBP1" or "EIF4EBP1" may refer to the wildtype human nucleic acid. In embodiments, the 4EBP1 is a mutant 4EBP1. In embodiments, the mutant 4EBP1 is associated with a disease that is not associated with wildtype 4EBP1. In embodiments, the 4EBP1 may include at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations, or any range derivable therein) compared to wildtype 4EBP1. In embodiments, the 4EBP1 has the protein sequence corresponding to reference number GL4758258. In embodiments, the 4EBP1 has the protein sequence corresponding to RefSeq NP_004086.1 (SEQ ID NO:4).

The term "Akt" refers to the serine/threonine specific protein kinase involved in cellular processes such as glucose metabolism, apoptosis, proliferation, and other functions, also known as "protein kinase B" (PKB) or "Akt1." In embodiments, "Akt" or "AM" or "PKB" may refer to the human protein. Included in the term "Akt" or "Akt1" or "PKB" are the wildtype and mutant forms of the protein. In embodiments, "Akt" or "Akt1" or "PKB" may refer to the protein associated with Entrez Gene 207, OMIM 164730, UniProt P31749, and/or RefSeq (protein) NP_005154 (SEQ ID NO:5). In embodiments, the reference numbers immediately above may refer to the protein, and associated nucleic acids, known as of the date of filing of this application. In embodiments, "Akt" or "Akt1" or "PKB" may refer to the wildtype human protein. In embodiments, "Akt" or "Akt1" or "PKB" may refer to the wildtype human nucleic acid. In embodiments, the Akt is a mutant Akt. In embodiments, the mutant Akt is associated with a disease that is not associated with wildtype Akt. In embodiments, the Akt may include at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations, or any range derivable therein) compared to wildtype Akt. In embodiments, the Akt has the protein sequence corresponding to reference number GI: 62241011. In embodiments, the Akt has the protein sequence corresponding to RefSeq NP_005154.2 (SEQ ID NO:5).

The present disclosure provides a method of treating a disease or disorder mediated by mTOR comprising administering to the subject suffering from or susceptible to developing a disease or disorder mediated by mTOR a therapeutically effective amount of one or more disclosed compositions or compounds. The present disclosure provides a method of preventing a disease or disorder mediated by mTOR comprising administering to the subject suffering from or susceptible to developing a disease or disorder mediated by mTOR a therapeutically effective amount of one or more disclosed compositions or compounds. The present disclosure provides a method of reducing the risk of a disease or disorder mediated by mTOR comprising administering to the subject suffering from or susceptible to developing a disease or disorder mediated by mTOR a therapeutically effective amount of one or more disclosed compositions or compounds.

In some embodiments, the disease is cancer or an immune-mediated disease. In some embodiments, the cancer is selected from brain and neurovascular tumors, head and neck cancers, breast cancer, lung cancer, mesothelioma, lymphoid cancer, stomach cancer, kidney cancer, renal carcinoma, liver cancer, ovarian cancer, ovary endometriosis, testicular cancer, gastrointestinal cancer, prostate cancer, glioblastoma, skin cancer, melanoma, neuro cancers, spleen cancers, pancreatic cancers, blood proliferative disorders, lymphoma, leukemia, endometrial cancer, cervical cancer, vulva cancer, prostate cancer, penile cancer, bone cancers, muscle cancers, soft tissue cancers, intestinal or rectal cancer, anal cancer, bladder cancer, bile duct cancer, ocular cancer, gastrointestinal stromal tumors, and neuro-endocrine tumors. In some embodiments, the disorder is liver cirrhosis. In some embodiments, the immune-mediated disease is selected from resistance by transplantation of heart, kidney, liver, medulla ossium, skin, cornea, lung, pancreas, intestinum tenue, limb, muscle, nerves, duodenum, small-bowel, or pancreatic-islet-cell; graft-versus-host diseases brought about by medulla ossium transplantation; rheumatoid arthritis, systemic lupus erythematosus, Hashimoto's thyroiditis, multiple sclerosis, myasthenia gravis, type I diabetes, uveitis, allergic encephalomyelitis, and glomerulonephritis. In certain embodiments, the disease is tuberous sclerosis complex (TSC). In certain embodiments, the disease is pancreatic neuroendocrine tumor (PNET), mantle cell lymphoma (MCL), colorectal cancer or bowel cancer (CRC), uterine cancer, ovarian cancer, bladder cancer, genitourinary tract cancer, or renal cell carcinoma (RCC).

The present disclosure provides a method of treating cancer comprising administering to the subject a therapeutically effective amount of one or more disclosed compositions or compounds. In some embodiments, the cancer is selected from brain and neurovascular tumors, head and neck cancers, breast cancer, lung cancer, mesothelioma, lymphoid cancer, stomach cancer, kidney cancer, renal carcinoma, liver cancer, ovarian cancer, ovary endometriosis, testicular cancer, gastrointestinal cancer, prostate cancer, glioblastoma, skin cancer, melanoma, neuro cancers, spleen cancers, pancreatic cancers, blood proliferative disorders, lymphoma, leukemia, endometrial cancer, cervical cancer, vulva cancer, prostate cancer, penile cancer, bone cancers, muscle cancers, soft tissue cancers, intestinal or rectal cancer, anal cancer, bladder cancer, bile duct cancer, ocular cancer, gastrointestinal stromal tumors, and neuro-endocrine tumors. In some embodiments, the disorder is liver cirrhosis. In certain embodiments, the disease is tuberous sclerosis complex (TSC). In certain embodiments, the disease is pancreatic neuroendocrine tumor (PNET), mantle cell lymphoma (MCL), colorectal cancer or bowel cancer (CRC), uterine cancer, ovarian cancer, bladder cancer, genitourinary tract cancer, or renal cell carcinoma (RCC).

In certain embodiments, cancer includes human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma. In certain embodiments, the disease is multiple myeloma. In certain embodiments, the disease is breast cancer. In certain embodiments, the disease is triple negative breast cancer.

In certain embodiments, cancer includes cancer, neoplasm or malignant tumors found in mammals (e.g. humans), including leukemia, carcinomas and sarcomas. Exemplary cancers that may be treated with a compound or method provided herein include cancer of the prostate, thyroid, endocrine system, brain, breast, cervix, colon, head and neck, liver, kidney, lung, non-small cell lung, melanoma, mesothelioma, ovary, sarcoma, stomach, uterus, Medulloblastoma, colorectal cancer, pancreatic cancer. Additional examples may include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

In certain embodiments, the disease is leukemia. The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number of aberrant cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocyte leukemia, micromyeloblastic leukemia, monocytic leukemia, myeloblasts leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

In certain embodiments, the disease is sarcoma. The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

In certain embodiments, the disease is melanoma. The term "melanoma" is taken to mean a tumor arising from the melanocyte system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

In certain embodiments, the disease is carcinoma. The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatinifori carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

The present disclosure provides a method of treating an immune-mediated disease comprising administering to the subject a therapeutically effective amount of one or more disclosed compositions or compounds. In some embodiments, the immune-mediated disease is selected from resistance by transplantation of heart, kidney, liver, medulla ossium, skin, cornea, lung, pancreas, intestinum tenue, limb, muscle, nerves, duodenum, small-bowel, or pancreatic-islet-cell; graft-versus-host diseases brought about by medulla ossium transplantation; rheumatoid arthritis, systemic lupus erythematosus, Hashimoto's thyroiditis, multiple sclerosis, myasthenia gravis, type I diabetes, uveitis, allergic encephalomyelitis, and glomerulonephritis.

In certain embodiments, the disease is autoimmune disease. As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressier's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

The present disclosure provide a method of treating an age related condition comprising administering to the subject a therapeutically effective amount of one or more disclosed compositions or compounds. In certain embodiments, the age related condition is selected from sarcopenia, skin atrophy, muscle wasting, brain atrophy, atherosclerosis, arteriosclerosis, pulmonary emphysema, osteoporosis, osteoarthritis, high blood pressure, erectile dysfunction, dementia, Huntington's disease, Alzheimer's disease, cataracts, age-related macular degeneration, prostate cancer, stroke, diminished life expectancy, impaired kidney function, and age-related hearing loss, aging-related mobility disability (e.g., frailty), cognitive decline, age-related dementia, memory impairment, tendon stiffness, heart dysfunction such as cardiac hypertrophy and systolic and diastolic dysfunction, immunosenescence, cancer, obesity, and diabetes.

In certain embodiments, the disclosed compositions or compounds can be used with regard to immunosenescence. Immunosenescence may refer to a decrease in immune function resulting in impaired immune response, e.g., to cancer, vaccination, infectious pathogens, among others. It involves both the host's capacity to respond to infections and the development of long-term immune memory, especially by vaccination. This immune deficiency is ubiquitous and found in both long- and short-lived species as a function of their age relative to life expectancy rather than chronological time. It is considered a major contributory factor to the increased frequency of morbidity and mortality among the elderly. Immunosenescence is not a random deteriorative phenomenon, rather it appears to inversely repeat an evolutionary pattern and most of the parameters affected by immunosenescence appear to be under genetic control. Immunosenescence can also be sometimes envisaged as the result of the continuous challenge of the unavoidable exposure to a variety of antigens such as viruses and bacteria. Immunosenescence is a multifactorial condition leading to many pathologically significant health problems, e.g., in the aged population. Age-dependent biological changes such as depletion of hematopoietic stem cells, an increase in PD1+ lymphocytes, a decline in the total number of phagocytes and NK cells and a decline in humoral immunity contribute to the onset of immunosenescence. In one aspect, immunosenescence can be measured in an individual by measuring telomere length in immune cells (See, e.g., U.S. Pat. No. 5,741,677). Immunosenescence can also be determined by documenting in an individual a lower than normal number of naive CD4 and/or CD8 T cells, T cell repertoire, the number of PD1-expressing T cells, e.g., a lower than normal number of PD-1 negative T cells, or response to vaccination in a subject greater than or equal to 65 years of age. In certain embodiments, mTOR selective modulation of certain T-cell populations may improve vaccine efficacy in the aging population and enhance effectiveness of cancer immunotherapy. The present disclosure provides a method of treating immunosenescence comprising administering to the subject a therapeutically effective amount of one or more disclosed compositions or compounds.

In certain embodiments, a disease that may be treated with a compound, pharmaceutical composition, or method described herein is organ or tissue transplant rejection (e.g. heart, lung, combined heart-lung, liver, kidney, pancreatic, skin or corneal transplants; graft-versus-host disease), restenosis, Hamartoma syndromes (e.g., tuberous sclerosis or Cowden Disease), Lymphangioleiomyomatosis, Retinitis pigmentosis, encephalomyelitis, insulin-dependent diabetes mellitus, lupus, dermatomyositis, arthritis, rheumatic diseases, Steroid-resistant acute Lymphoblastic Leukemia, fibrosis, scleroderma, pulmonary fibrosis, renal fibrosis, cystic fibrosis, Pulmonary hypertension, Multiple sclerosis, VHL syndrome, Carney complex, Familial adenonamtous polyposis, Juvenile polyposis syndrome, Birt-Hogg-Duke syndrome, Familial hypertrophic cardiomyopathy, Wolf-Parkinson-White syndrome, Parkinson's disease, Huntingtin's disease, Alzheimer's disease, dementias caused by tau mutations, spinocerebellar ataxia type 3, motor neuron disease caused by SOD1 mutations, neuronal ceroid lipofucinoses/Batten disease (pediatric neurodegeneration), wet macular degeneration, dry macular degeneration, muscle wasting (atrophy, cachexia), myopathies (e.g., Danon's disease), bacterial infection, viral infection, *M. tuberculosis*, group A *streptococcus*, HSV type I, HIV infection, Neurofibromatosis (e.g., Neurofibromatosis type 1), or Peutz-Jeghers syndrome.

In certain embodiments, the disease is neurodegenerative disease. As used herein, the term "neurodegenerative disease" refers to a disease or condition in which the function of a subject's nervous system becomes impaired. Examples of neurodegenerative diseases that may be treated with a compound, pharmaceutical composition, or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoff s disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, or *Tabes dorsalis*.

In certain embodiments, the disease is metabolic disease. As used herein, the term "metabolic disease" refers to a disease or condition in which a subject's metabolism or metabolic system (e.g., function of storing or utilizing energy) becomes impaired. Examples of metabolic diseases that may be treated with a compound, pharmaceutical composition, or method described herein include diabetes (e.g., type I or type II), obesity, metabolic syndrome, or a mitochondrial disease (e.g., dysfunction of mitochondria or aberrant mitochondrial function).

In certain embodiments, the disease is fungal disease. As used herein, the term "fungal disease" refers to a disease or condition associated with a fungus infection of the subject. Examples of fungal diseases that may be treated with a compound, pharmaceutical composition, or method described herein include infection with *Mucor circinelloides, zygomycetes, Cryptococcus neoformans, Candida albicans*, yeast, and *Saccharomyces cerevisiae* among others.

In certain embodiments, the disease is inflammatory disease. As used herein, the term "inflammatory disease" refers to a disease or condition characterized by aberrant inflammation (e.g. an increased level of inflammation compared to a control such as a healthy person not suffering from a disease). Examples of inflammatory diseases include traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis.

In certain embodiments, the disease is cardiovascular disease. As used herein, the term "cardiovascular disease" refers to a disease or condition in which the function of a subject's cardiovascular system becomes impaired. Examples of cardiovascular diseases that may be treated with a compound, pharmaceutical composition, or method described herein include congestive heart failure; arrhythmogenic syndromes (e.g., paroxysomal tachycardia, delayed after depolarizations, ventricular tachycardia, sudden tachycardia, exercise-induced arrhythmias, long QT syndromes, or bidirectional tachycardia); thromboembolic disorders (e.g., arterial cardiovascular thromboembolic disorders, venous cardiovascular thromboembolic disorders, or thromboembolic disorders in the chambers of the heart); atherosclerosis; restenosis; peripheral arterial disease; coronary bypass grafting surgery; carotid artery disease; arteritis; myocarditis; cardiovascular inflammation; vascular inflammation; coronary heart disease (CHD); unstable angina (UA); unstable refractory angina; stable angina (SA); chronic stable angina; acute coronary syndrome (ACS); myocardial infarction (first or recurrent); acute myocardial infarction (AMI); myocardial infarction; non-Q wave myocardial infarction; non-STE myocardial infarction; coronary artery disease; ischemic heart disease; cardiac ischemia; ischemia; ischemic sudden death; transient ischemic attack; stroke; peripheral occlusive arterial disease; venous thrombosis; deep vein thrombosis; thrombophlebitis; arterial embolism; coronary arterial thrombosis; cerebral arterial thrombosis, cerebral embolism; kidney embolism; pulmonary embolism; thrombosis (e.g., associated with prosthetic valves or other implants, indwelling catheters, stents, cardiopulmonary bypass, hemodialysis); thrombosis (e.g., associated with atherosclerosis, surgery, prolonged immobilization, arterial fibrillation, congenital thrombophilia, cancer, diabetes, hormones, or pregnancy); or cardiac arrhythmias (e.g., supraventricular arrhythmias, atrial arrhythmias, atrial flutter, or atrial fibrillation).

In an aspect is provided a method of treating a disease associated with an aberrant level of mTOR activity in a subject in need of such treatment. The disease may be caused by an upregulation of mTOR. The method may include administering to the subject one or more compositions or compounds described herein. The method may include administering to the subject a therapeutically effective amount of one or more compositions or compounds described herein (e.g., an mTOR modulator (e.g., inhibitor) as described above).

In an aspect is provided one or more compositions or compounds as described herein for use as a medicament. In embodiments, the medicament is useful for treating a disease caused by an upregulation of mTOR. The use may include administering to the subject one or more compositions or compounds described herein. The use may include administering to the subject a therapeutically effective amount of one or more compositions or compounds described herein (e.g., an mTOR modulator (e.g., inhibitor) as described above).

In an aspect is provided one or more compositions or compounds as described herein for use in the treatment of a disease caused by aberrant levels of mTORC1 activity in a subject in need of such treatment. The disease may be caused by an upregulation of mTORC1. The use may include administering to the subject one or more compositions or compounds described herein. The use may include administering to the subject a therapeutically effective amount of one or more compositions or compounds described herein (e.g., an mTORC1 modulator (e.g., inhibitor) as described above).

Upregulation of mTOR can result in an increased amount of mTOR activity compared to normal levels of mTOR activity in a particular subject or a population of healthy subjects. The increased amount of mTOR activity may result in, for example, excessive amounts of cell proliferation thereby causing the disease state.

The subject of treatment for the disease is typically a mammal. The mammal treated with the compound (e.g., compound described herein, mTOR modulator (e.g., inhibitor)) may be a human, nonhuman primate, and/or nonhuman mammal (e.g., rodent, canine).

In another aspect is provided a method of treating an mTOR activity-associated disease in a subject in need of such treatment, the method including administering one or more compositions or compounds as described herein, including embodiments (e.g., a claim, embodiment, example, table, figure, or claim) to the subject.

In another aspect is provided one or more compositions or compounds as described herein for use as a medicament. In embodiments, the medicament may be useful for treating an mTORC1 activity-associated disease in a subject in need of such treatment. In embodiments, the use may include administering one or more compositions or compounds as described herein, including embodiments (e.g., an aspect, embodiment, example, table, figure, or claim) to the subject.

In another aspect is provided one or more compositions or compounds for use in the treatment of an mTOR activity-associated disease in a subject in need of such treatment. In embodiments, the use may include administering one or more compositions or compounds as described herein, including embodiments (e.g., an aspect, embodiment, example, table, figure, or claim) to the subject.

In embodiments, the mTOR activity-associated disease or disease associated with aberrant levels of mTOR activity is cancer. In embodiments, the mTOR activity-associated disease or disease associated with aberrant levels of mTOR activity is an autoimmune disease. In embodiments, the mTOR activity-associated disease or disease associated with aberrant levels of mTOR activity is an inflammatory disease. In embodiments, the mTOR activity-associated disease or disease associated with aberrant levels of mTOR activity is a neurodegenerative disease. In embodiments, the mTOR activity-associated disease or disease associated with aberrant levels of mTOR activity is a metabolic disease. In embodiments, the mTOR activity-associated disease or disease associated with aberrant levels of mTOR activity is transplant rejection. In embodiments, the mTOR activity-associated disease or disease associated with aberrant levels of mTOR activity is fungal infection. In embodiments, the mTOR activity-associated disease or disease associated with aberrant levels of mTOR activity is a cardiovascular disease.

In embodiments, the mTOR activity-associated disease or disease associated with aberrant levels of mTOR activity is aging. In embodiments, the mTOR activity-associated disease or disease associated with aberrant levels of mTOR activity is dying of an age-related disease. In embodiments, the mTOR activity-associated disease or disease associated with aberrant levels of mTOR activity is an age-related condition. In certain embodiments, the age related condition is selected from the group consisting of sarcopenia, skin atrophy, muscle wasting, brain atrophy, atherosclerosis, arteriosclerosis, pulmonary emphysema, osteoporosis, osteoarthritis, high blood pressure, erectile dysfunction, dementia, Huntington's disease, Alzheimer's disease, cataracts, age-related macular degeneration, prostate cancer, stroke, diminished life expectancy, impaired kidney function, and age-related hearing loss, aging-related mobility disability (e.g., frailty), cognitive decline, age-related dementia, memory impairment, tendon stiffness, heart dysfunction such as cardiac hypertrophy and systolic and diastolic dysfunction, immunosenescence, cancer, obesity, and diabetes. In certain embodiments, mTOR selective modulation of certain T-cell populations may improve vaccine efficacy in the aging population and enhance effectiveness of cancer immunotherapy. The present disclosure provides a method of treating immunosenescence comprising administering to the subject a therapeutically effective amount of one or more disclosed compounds.

In embodiments, the mTOR activity-associated disease or disease associated with aberrant levels of mTOR activity is cancer (e.g., carcinomas, sarcomas, adenocarcinomas, lymphomas, leukemias, solid cancers, lymphoid cancers; cancer of the kidney, breast, lung, bladder, colon, gastrointestinal, ovarian, prostate, pancreas, stomach, brain, head and neck, skin, uterine, esophagus, liver; testicular cancer, glioma, hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), multiple myeloma, and breast cancer (e.g., triple negative breast cancer)).

In embodiments, the mTOR activity-associated disease or disease associated with aberrant levels of mTOR activity is Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressier's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatry Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, Wegener's granulomatosis (i.e., Granulomatosis with Polyangiitis (GPA), traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, atopic dermatitis, Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HTV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoff s disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, *Tabes dorsalis*, diabetes (e.g., type I or type II), obesity, metabolic syndrome, a mitochondrial disease (e.g., dysfunction of mitochondria or aberrant mitochondrial function), fungal infection, transplant rejection, or a cardiovascular disease (e.g., congestive heart failure; arrhythmogenic syndromes (e.g., paroxysomal tachycardia, delayed after depolarizations, ventricular tachycardia, sudden tachycardia, exercise-induced arrhythmias, long QT syndromes, or bidirectional tachycardia); thromboembolic disorders (e.g., arterial cardiovascular thromboembolic disorders, venous cardiovascular thromboembolic disorders, or thromboembolic disorders in the chambers of the heart); atherosclerosis; restenosis; peripheral arterial disease; coronary bypass grafting surgery; carotid artery disease; arteritis; myocarditis; cardiovascular inflammation; vascular inflammation; coronary heart disease (CHD); unstable angina (UA); unstable refractory angina; stable angina (SA); chronic stable angina; acute coronary syndrome (ACS); myocardial infarction (first or recurrent); acute myocardial infarction (AMI); myocardial infarction; non-Q wave myocardial infarction; non-STE myocardial infarction; coronary artery disease; ischemic heart disease; cardiac ischemia; ischemia; ischemic sudden death; transient ischemic attack; stroke; peripheral occlusive arterial disease; venous thrombosis; deep vein thrombosis; thrombophlebitis; arterial embolism; coronary arterial thrombosis; cerebral arterial thrombosis, cerebral embolism; kidney embolism; pulmonary embolism; thrombosis (e.g., associated with prosthetic valves or other implants, indwelling catheters, stents, cardiopulmonary bypass, hemodialysis); thrombosis (e.g., associated with atherosclerosis, surgery, prolonged immobilization, arterial fibrillation, congenital thrombophilia, cancer, diabetes, hormones, or pregnancy); or cardiac arrhythmias (e.g., supraventricular arrhythmias, atrial arrhythmias, atrial flutter, or atrial fibrillation).

In an aspect is provided a method of treating a disease including administering an effective amount of one or more compositions or compounds as described herein. In an aspect is provided one or more compositions or compounds as described herein for use as a medicament (e.g., for treatment of a disease). In an aspect is provided one or more compositions or compounds as described herein for use in the treatment of a disease (e.g., including administering an effective amount of one or more compositions or compounds as described herein). In embodiments, the disease is cancer. In embodiments, the disease is an autoimmune disease. In embodiments, the disease is an inflammatory disease. In embodiments, the disease is a neurodegenerative disease. In embodiments, the disease is a metabolic disease. In embodiments, the disease is fungal infection. In embodiments, the disease is transplant rejection. In embodiments, the disease is a cardiovascular disease.

In embodiments, the disease is cancer (e.g., carcinomas, sarcomas, adenocarcinomas, lymphomas, leukemias, solid cancers, lymphoid cancers; cancer of the kidney, breast, lung, bladder, colon, ovarian, prostate, pancreas, stomach, brain, head and neck, skin, uterine, esophagus, liver; testicular cancer, glioma, hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), multiple myeloma, and breast cancer (e.g., triple negative breast cancer)).

In embodiments, the disease is Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, Wegener's granulomatosis (i.e., Granulomatosis with Polyangiitis (GPA), traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, atopic dermatitis, Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HTV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoff's disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, *Tabes dorsalis*, diabetes (e.g., type I or type II), obesity, metabolic syndrome, a mitochondrial disease (e.g., dysfunction of mitochondria or aberrant mitochondrial function), fungal infection, transplant rejection, or a cardiovascular disease (e.g., congestive heart failure; arrhythmogenic syndromes (e.g., paroxysomal tachycardia, delayed after depolarizations, ventricular tachycardia, sudden tachycardia, exercise-induced arrhythmias, long QT syndromes, or bidirectional tachycardia); thromboembolic disorders (e.g., arterial cardiovascular thromboembolic disorders, venous cardiovascular thromboembolic disorders, or thromboembolic disorders in the chambers of the heart); atherosclerosis; restenosis; peripheral arterial disease; coronary bypass grafting surgery; carotid artery disease; arteritis; myocarditis; cardiovascular inflammation; vascular inflammation; coronary heart disease (CHD); unstable angina (UA); unstable refractory angina; stable angina (SA); chronic stable angina; acute coronary syndrome (ACS); myocardial infarction (first or recurrent); acute myocardial infarction (AMI); myocardial infarction; non-Q wave myocardial infarction; non-STE myocardial infarction; coronary artery disease; ischemic heart disease; cardiac ischemia; ischemia; ischemic sudden death; transient ischemic attack; stroke; peripheral occlusive arterial disease; venous thrombosis; deep vein thrombosis; thrombophlebitis; arterial embolism; coronary arterial thrombosis; cerebral arterial thrombosis, cerebral embolism; kidney embolism; pulmonary embolism; thrombosis (e.g., associated with prosthetic valves or other implants, indwelling catheters, stents, cardiopulmonary bypass, hemodialysis); thrombosis (e.g., associated with atherosclerosis, surgery, prolonged immobilization, arterial fibrillation, congenital thrombophilia, cancer, diabetes, hormones, or pregnancy); or cardiac arrhythmias (e.g., supraventricular arrhythmias, atrial arrhythmias, atrial flutter, or atrial fibrillation). In embodiments, the disease is a polycystic disease. In embodiments, the disease is polycystic kidney disease. In embodiments, the disease is stenosis. In embodiments, the disease is restenosis. In embodiments, the disease is neointimal proliferation. In embodiments, the disease is neointimal hyperplasia.

In another aspect is provided a method of treating aging in a subject in need of such treatment, the method including administering one or more compositions or compounds as described herein, including embodiments (e.g., a claim, embodiment, example, table, figure, or claim) to the subject. The present disclosure provides a method of treating immunosenescence comprising administering to the subject a therapeutically effective amount of one or more disclosed compounds or compositions.

In another aspect is provided one or more compositions or compounds as described herein for use as a medicament. In embodiments, the medicament may be useful for treating aging in a subject in need of such treatment. In embodiments, the use may include administering one or more compositions or compounds as described herein, including embodiments (e.g., an aspect, embodiment, example, table, figure, or claim) to the subject.

In another aspect is provided one or more compositions or compounds disclosed herein for use in the treatment of aging in a subject in need of such treatment. In embodiments, the use may include administering one or more compositions or compounds as described herein, including embodiments (e.g., an aspect, embodiment, example, table, figure, or claim) to the subject.

In another aspect is provided a method of extending life span or inducing longevity in a subject in need of such treatment, the method including administering one or more compositions or compounds as described herein, including embodiments (e.g., a claim, embodiment, example, table, figure, or claim) to the subject.

In another aspect is provided one or more compositions or compounds as described herein for use as a medicament. In embodiments, the medicament may be useful for extending life span or inducing longevity in a subject in need of such treatment. In embodiments, the use may include administering one or more compositions or compounds as described herein, including embodiments (e.g., an aspect, embodiment, example, table, figure, or claim) to the subject.

In another aspect is provided one or more compositions or compounds for use in extending life span or inducing longevity in a subject in need of such treatment. In embodiments, the use may include administering one or more compositions or compounds as described herein, including embodiments (e.g., an aspect, embodiment, example, table, figure, or claim) to the subject.

In an aspect is provided a method of treating a polycystic disease in a subject in need of such treatment. The polycystic disease may be polycystic kidney disease. The method may include administering to the subject one or more compositions or compounds described herein. The method may include administering to the subject a therapeutically effective amount of one or more compositions or compounds described herein (e.g., an mTOR modulator (e.g., inhibitor) as described above).

In an aspect is provided one or more compositions or compounds as described herein for use as a medicament. In embodiments, the medicament is useful for treating a polycystic disease. The polycystic disease may be polycystic kidney disease. The use may include administering to the subject one or more compositions or compounds described herein. The use may include administering to the subject a therapeutically effective amount of one or more compositions or compounds described herein (e.g., an mTOR modulator (e.g., inhibitor) as described above).

In an aspect is provided one or more compositions or compounds as described herein for use in the treatment of a polycystic disease in a subject in need of such treatment. The polycystic disease may be polycystic kidney disease. The use may include administering to the subject one or more compositions or compounds described herein. The use may include administering to the subject a therapeutically effective amount of one or more compositions or compounds described herein (e.g., an mTOR modulator (e.g., inhibitor) as described above).

In an aspect is provided a method of treating stenosis in a subject in need of such treatment. The stenosis may be restenosis. The method may include administering to the subject one or more compositions or compounds described herein. In embodiments the one or more compositions or compounds are administered in a drug eluting stent. The method may include administering to the subject a therapeutically effective amount of one or more compositions or compounds described herein (e.g., an mTOR modulator (e.g., inhibitor) as described above).

In an aspect is provided one or more compositions or compounds as described herein for use as a medicament. In embodiments, the medicament is useful for treating stenosis. The stenosis may be restenosis. The use may include administering to the subject one or more compositions or compounds described herein. In embodiments the compound is administered in a drug eluting stent. The use may include administering to the subject a therapeutically effective amount of one or more compositions or compounds described herein (e.g., an mTOR modulator (e.g., inhibitor) as described above).

In an aspect is provided one or more compositions or compounds as described herein for use in the treatment of stenosis in a subject in need of such treatment. The stenosis may be restenosis. The use may include administering to the subject one or more compositions or compounds described herein. In embodiments the one or more compositions or compounds are administered in a drug eluting stent. The use may include administering to the subject a therapeutically effective amount of one or more compositions or compounds described herein (e.g., an mTOR modulator (e.g., inhibitor) as described above).

In embodiments, the disease is a disease described herein and the compound is a compound described herein and the composition is a composition described herein.

Methods of Modulating mTOR

In some embodiments, compounds disclosed herein are more selective inhibitors of mTORC1 versus mTORC2. In some embodiments, compounds disclosed herein are more selective inhibitors of mTORC2 versus mTORC1. In some embodiments, compounds disclosed herein exhibit no selectivity difference between mTORC1 and mTORC2.

In another aspect is provided a method of modulating mTORC1 activity in a subject in need thereof, including administering to the subject an effective amount of a compound as described herein, or a pharmaceutically acceptable salt thereof. In embodiments, the method includes inhibiting mTORC1 activity. In embodiments, the method includes inhibiting mTORC1 activity and not inhibiting mTORC2 activity.

In embodiments, the method includes inhibiting mTORC1 activity more than inhibiting mTORC2 activity. In embodiments, the method includes inhibiting mTORC1 activity at least 1.1 fold as much as inhibiting mTORC2 activity (e.g., at least 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold).

In another aspect is provided a method of modulating mTORC2 activity in a subject in need thereof, including administering to the subject an effective amount of a compound as described herein, or a pharmaceutically acceptable salt thereof. In embodiments, the method includes inhibiting mTORC2 activity. In embodiments, the method includes inhibiting mTORC2 activity and not inhibiting mTORC1 activity.

In embodiments, the method includes inhibiting mTORC2 activity more than inhibiting mTORC1 activity. In embodiments, the method includes inhibiting mTORC2 activity at least 1.1 fold as much as inhibiting mTORC1 activity (e.g., at least 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold).

In some embodiments, the mTOR is in a cell. In some embodiments, the cell is a mammalian cell, such as a human cell. The cell may be isolated in vitro, form part of a tissue in vitro, or may form part of an organism.

EXEMPLARY EMBODIMENTS

Some embodiments of this disclosure are Embodiment I, as follows:

Embodiment I-1. A compound of Formula I:

(I)

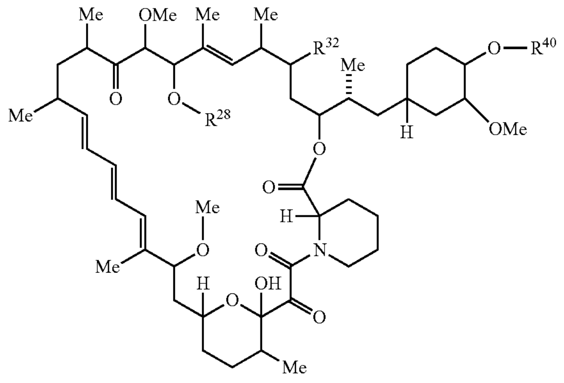

or a pharmaceutically acceptable salt or tautomer thereof, wherein:

$R^{32}$ is —H, =O or —$OR^3$.

$R^{28}$ is —H or —C(=$Z^1$)—$R^{28a}$.

$R^{40}$ is —H or —C(=$Z^1$)—$R^{41a}$;

wherein at least one of $R^{28}$ and $R^{40}$ is not H;

$Z^1$ is O or S;

$R^{28a}$ and $R^{40a}$ are independently -$A^1$-$L^1$-$A^2$-B; -$A^1$-$A^2$-B; -$L^2$-$A^1$-$L^1$-$A^2$-$L^3$-B; —O—($C_1$-$C_6$)alkyl; or —O—($C_6$-$C_{10}$)aryl; wherein the aryl is unsubstituted or substituted with 1-5 substituents selected from —$NO_2$ and halogen;

$A^1$ and $A^2$ are independently absent or are independently selected from
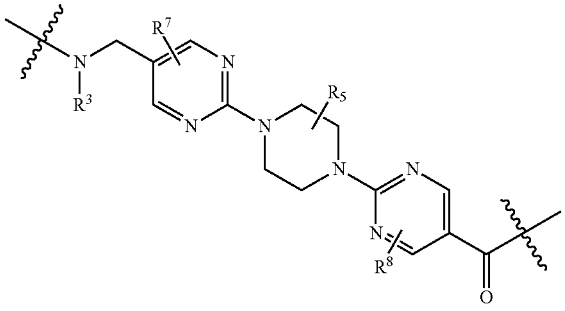,
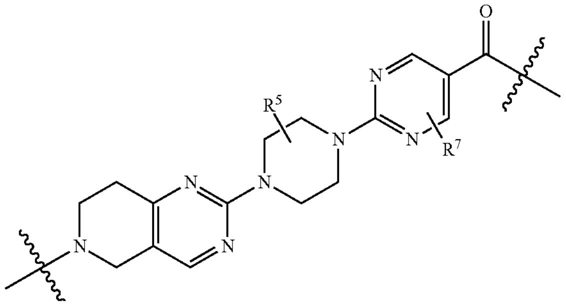,
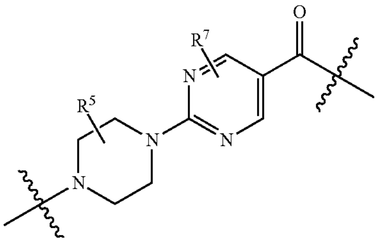,
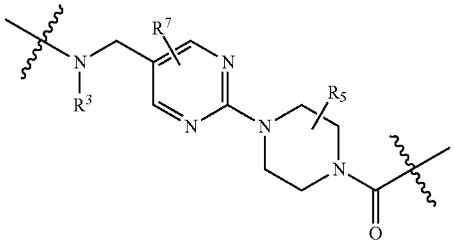,
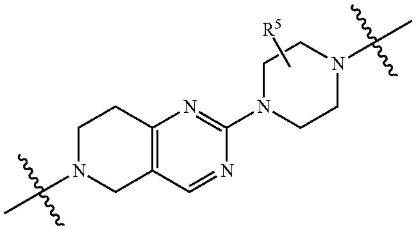,
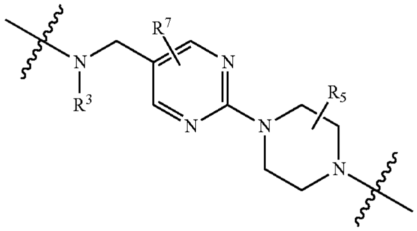,
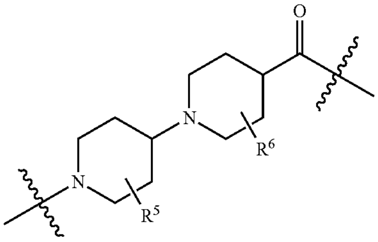,
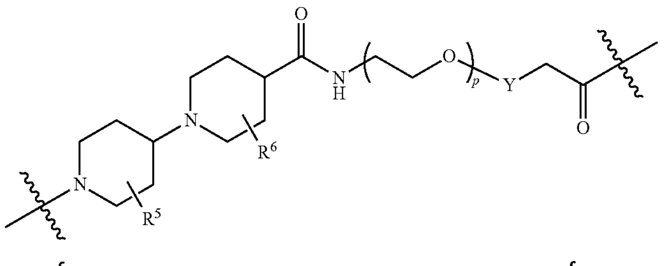,
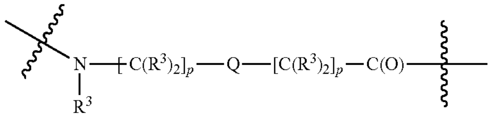,
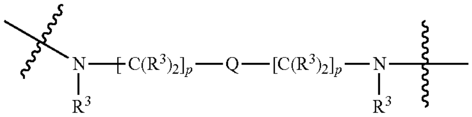,
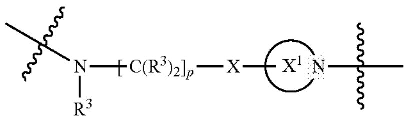,
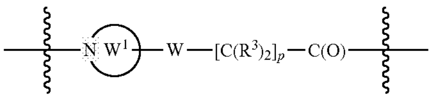

-continued
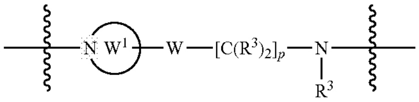
,
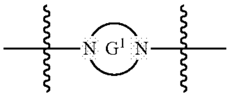
,
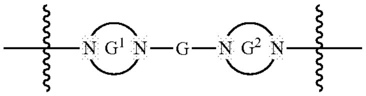
,
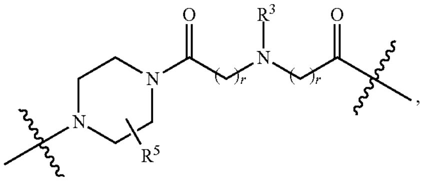
,
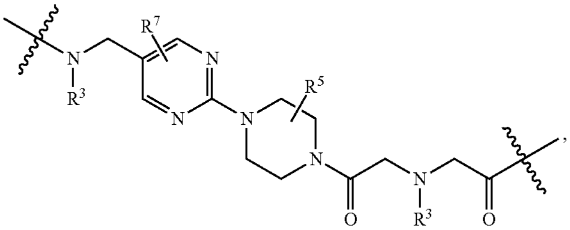
,
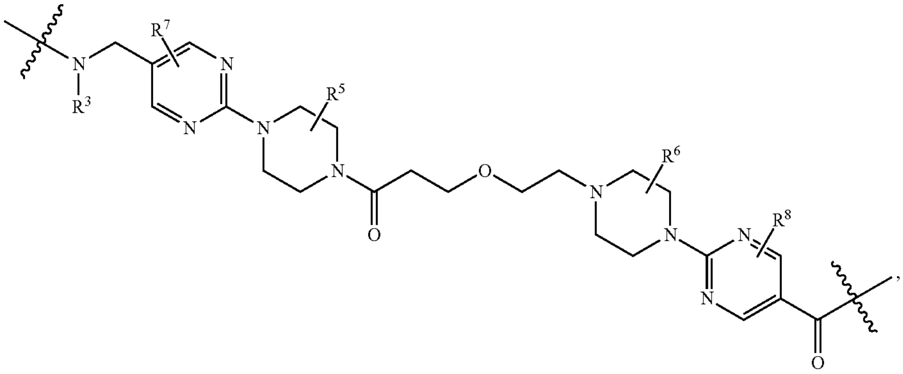
,
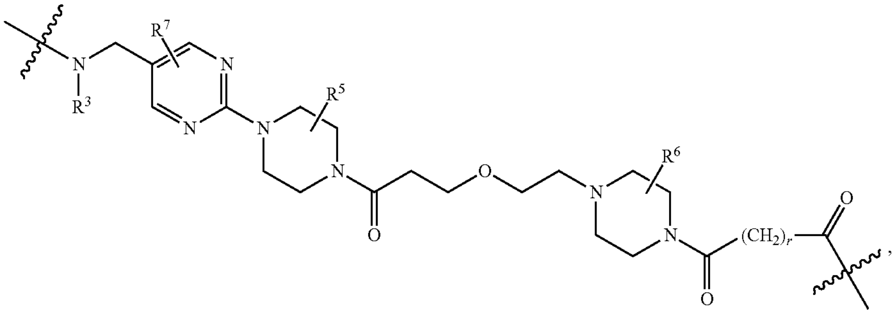
,
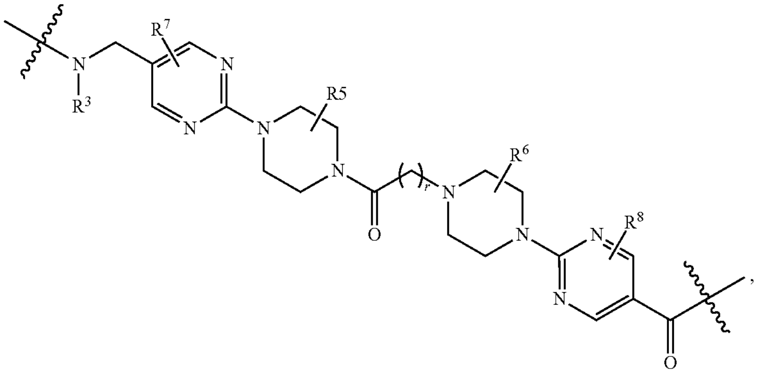
, and
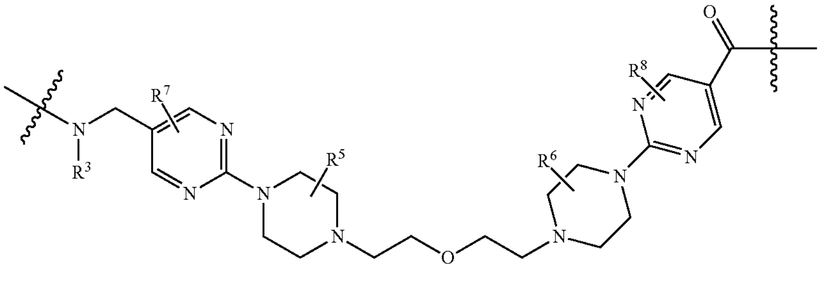
;

wherein the bond on the left side of $A^1$, as drawn, is bound to —C(=$Z^1$)— or $L^2$; and wherein the bond on the right side of the $A^2$ moiety, as drawn, is bound to B or $L^3$;

each Q is independently 1 to 3 rings selected from arylene, cycloalkylene, heteroarylene, and heterocyclylene;

each X is independently absent or 1 to 2 rings selected from arylene, cycloalkylene, heteroarylene, and heterocyclylene;

each $X^1$ is independently a heteroarylene or heterocyclylene ring;

each W is independently absent or 1 to 2 rings selected from arylene, cycloalkylene, heteroarylene, and heterocyclylene;

each $W^1$ is a heteroarylene or heterocyclylene ring;

each G is independently absent or a ring selected from arylene, cycloalkylene, heteroarylene, and heterocyclylene;

each $G^1$ and $G^2$ are independently heteroarylene or heterocyclylene ring;

L is selected from

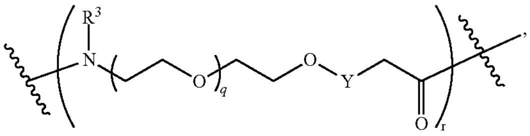
,
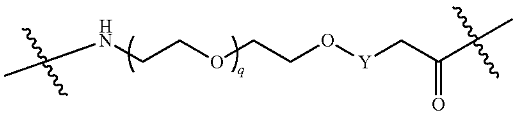
,
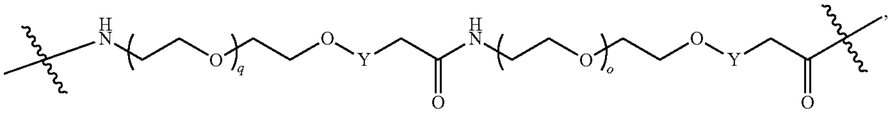
,
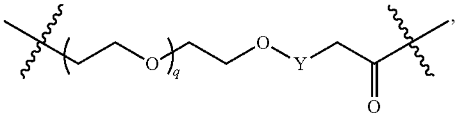
,
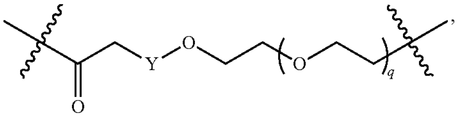
,
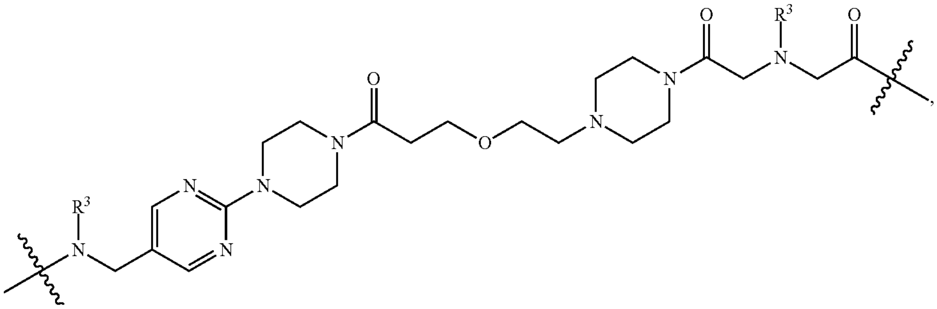
,
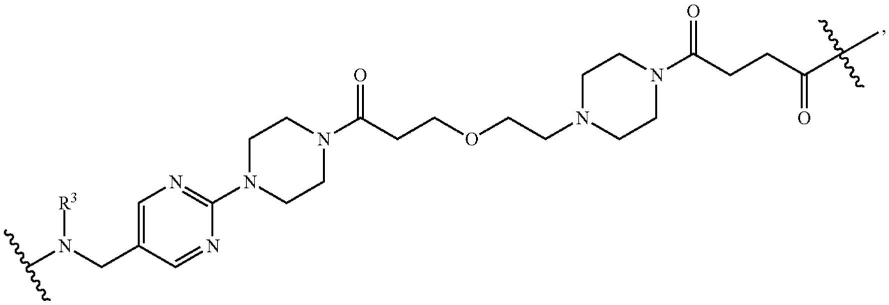
,
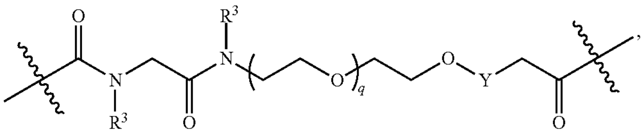
,
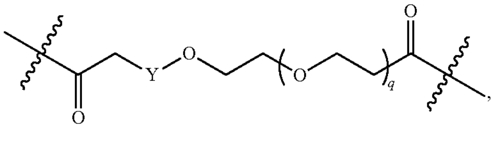
, and
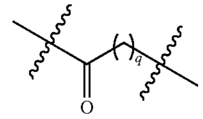
;

$L^2$ and $L^3$ are independently absent or are independently selected from
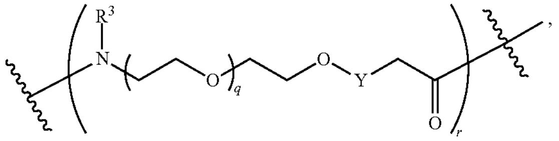
,
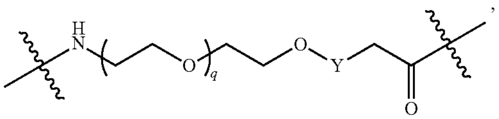
,
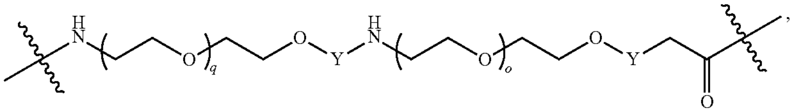
,
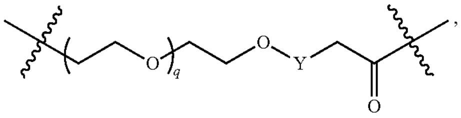
,
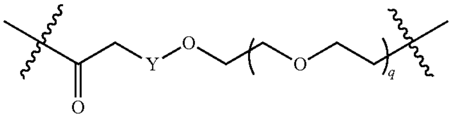
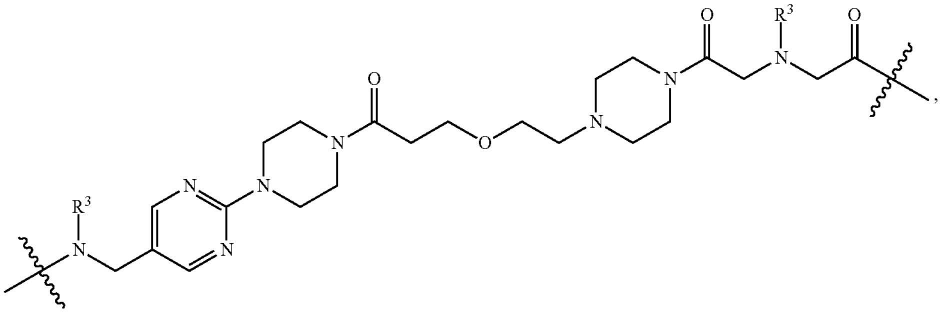
,
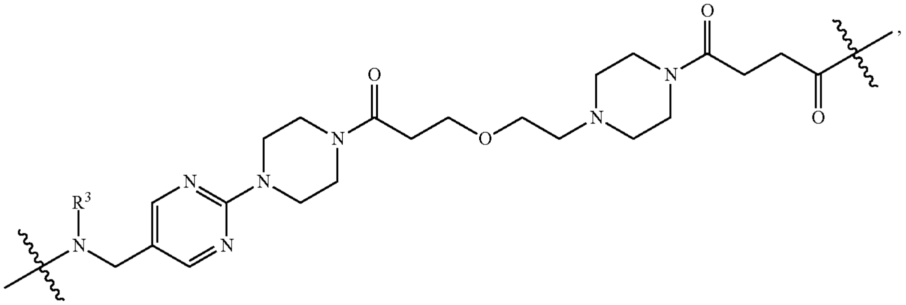
,
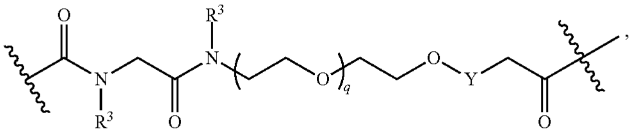
,
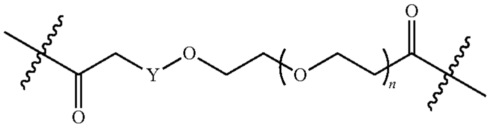
, and
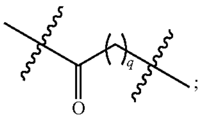
;
B is selected from
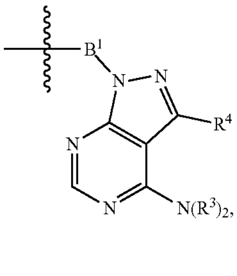
-continued
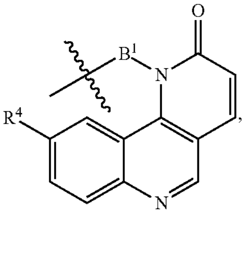

-continued
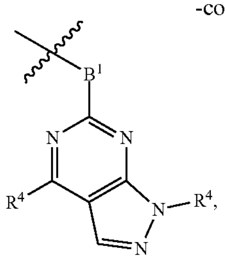
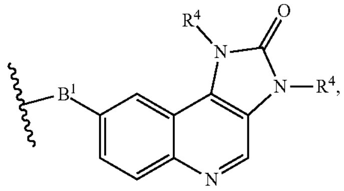
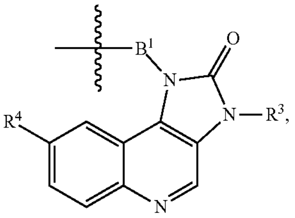
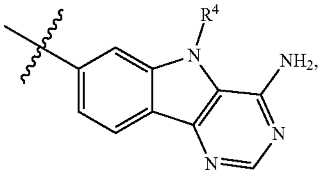
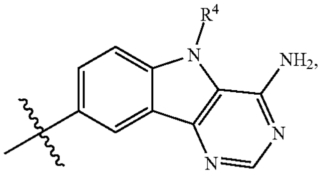
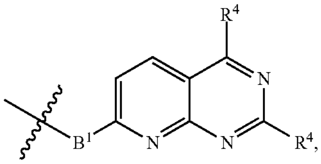
and
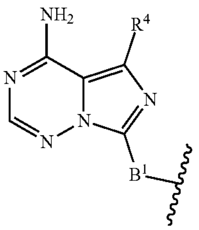
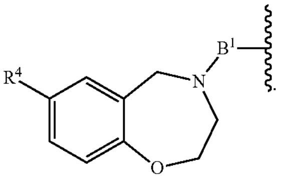
$B^1$ is selected from
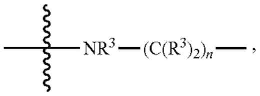
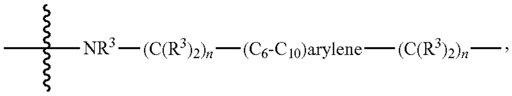
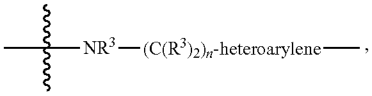
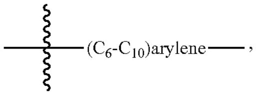
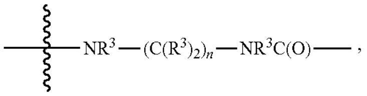
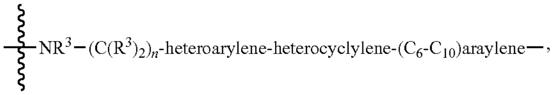
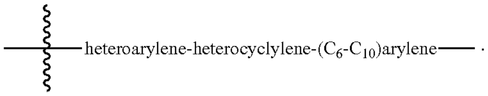
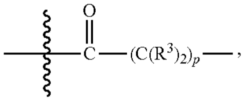
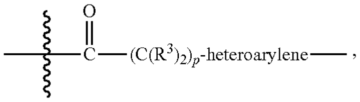
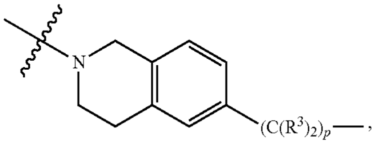
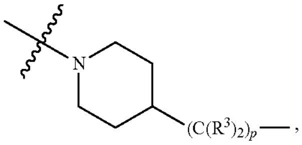
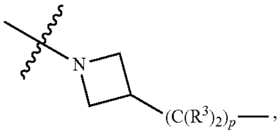
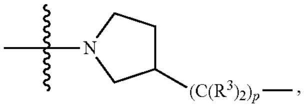
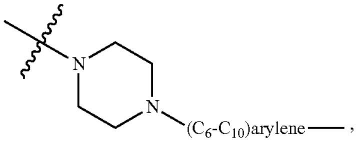

-continued

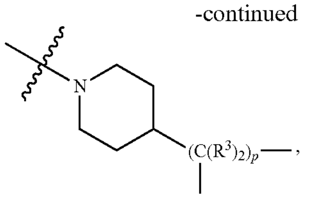

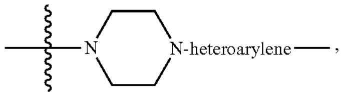

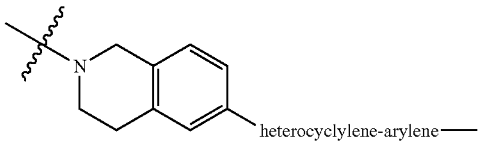

and

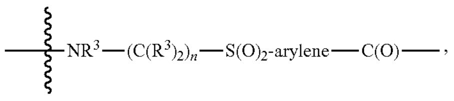

wherein the 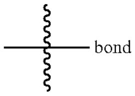 bond on the left side of $B^1$, as drawn, is bound to $A^2$, $L^3$, or $L^1$; and wherein the heteroarylene, heterocyclylene, and arylene are optionally substituted with alkyl, hydroxyalkyl, haloalkyl, alkoxy, halogen, or hydroxyl;

each $R^3$ is independently H or $(C_1\text{-}C_6)$alkyl;

each $R^4$ is independently H, $(C_1\text{-}C_6)$alkyl, halogen, 5-12 membered heteroaryl, 5-12 membered heterocyclyl, $(C_6\text{-}C_{10})$aryl, wherein the heteroaryl, heterocyclyl, and aryl are optionally substituted with —$N(R^3)_2$, —$OR^3$, halogen, $(C_1\text{-}C_6)$alkyl, —$(C_1\text{-}C_6)$alkylene-heteroaryl, —$(C_1\text{-}C_6)$alkylene-CN, —C(O)$NR^3$-heteroaryl; or —C(O)$NR^3$-heterocyclyl;

each $R^5$ is independently H, $(C_1\text{-}C_6)$alkyl, —C(O)$OR^3$, or —$N(R^3)_2$, wherein the alkyl is optionally substituted with —$N(R^3)_2$ or —$OR^3$;

each $R^6$ is independently H, $(C_1\text{-}C_6)$alkyl, —C(O)$OR^3$, or —$N(R^3)_2$, wherein the alkyl is optionally substituted with —$N(R^3)_2$ or —$OR^3$;

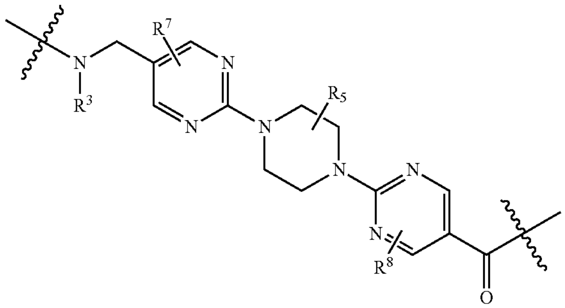

, each $R^7$ is independently H, $(C_1\text{-}C_6)$alkyl, —C(O)$OR^3$, or —$N(R^3)_2$, wherein the alkyl is optionally substituted with —$N(R^3)_2$ or —$OR^3$;

each $R^8$ is independently H, $(C_1\text{-}C_6)$alkyl, —C(O)$OR^3$, or —$N(R^3)_2$, wherein the alkyl is optionally substituted with —$N(R^3)_2$ or —$OR^3$;

each Y is independently $C(R^3)_2$ or a bond;

each n is independently a number from one to 12;

each o is independently a number from zero to 30;

each p is independently a number from zero to 12;

each q is independently a number from zero to 30; and each r is independently a number from one to 6.

Embodiment I-2. A compound of Formula II.

(II)

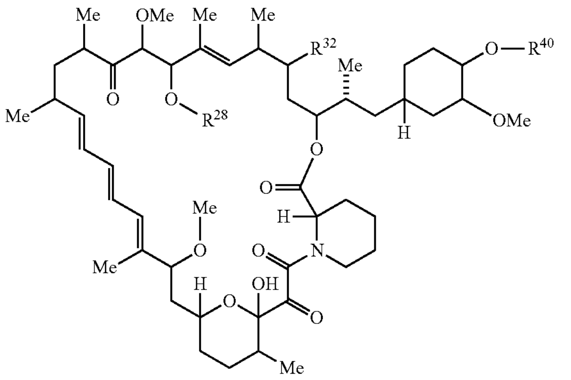

or a pharmaceutically acceptable salt or tautomer thereof, wherein:

$R^{32}$ is —H, =O or —$OR^3$;

$R^{28}$ is —H or —C(=$Z^1$)—$R^{28a}$;

$R^{40}$ is —H or —C(=$Z^1$)—$R^{41a}$;

wherein at least one of $R^{28}$ and $R^{40}$ is not H;

$Z^1$ is O or S;

$R^{28a}$ and $R^{40a}$ are independently -$A^1$-$L^1$-$A^2$-B; -$A^1$-$A^2$-B; —O—$(C_1\text{-}C_6)$alkyl; or —O—$(C_6\text{-}C_{10})$aryl; wherein the aryl is unsubstituted or substituted with 1-5 substituents selected from —$NO_2$ and halogen;

$A^1$ and $A^2$ are independently absent or are independently selected from

-continued
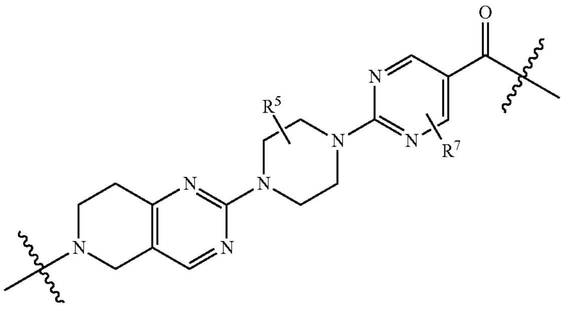,
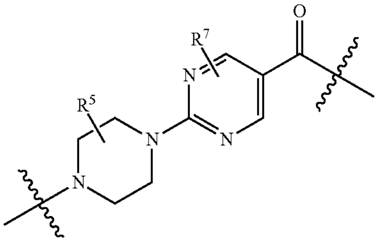,
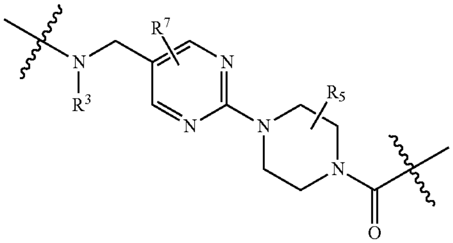,
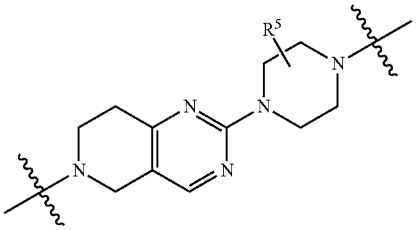,
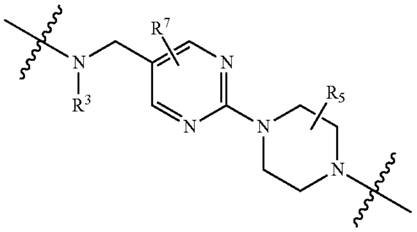,
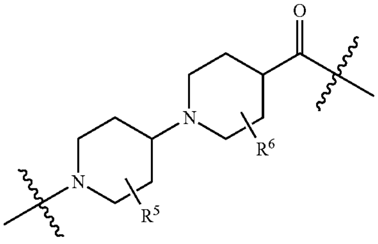,
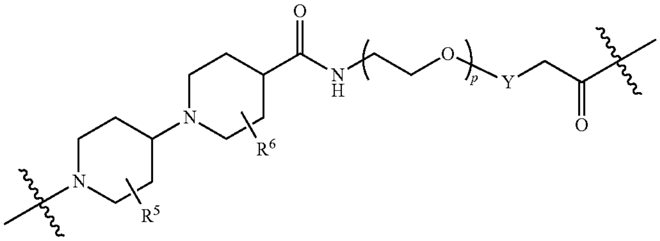,
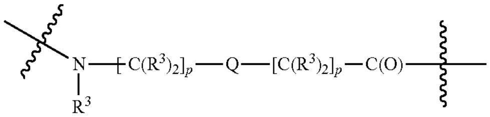,
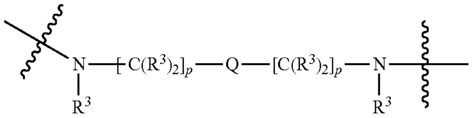,
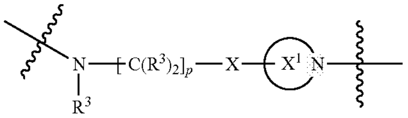,
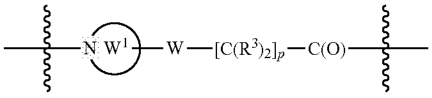
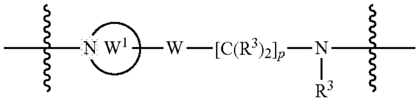,
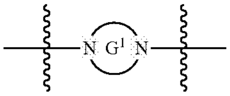,
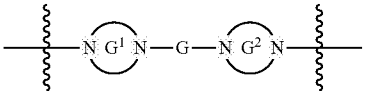,
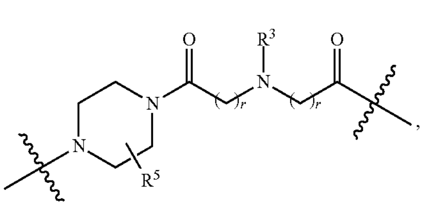,
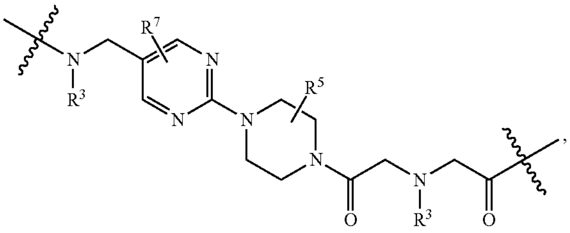, -continued

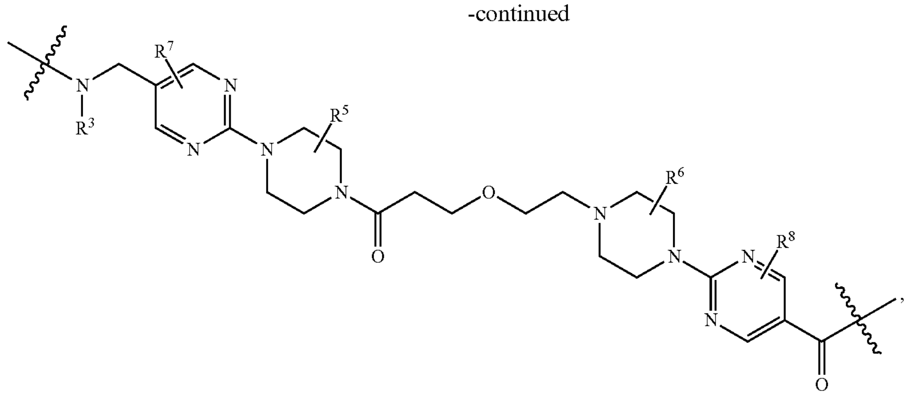

,

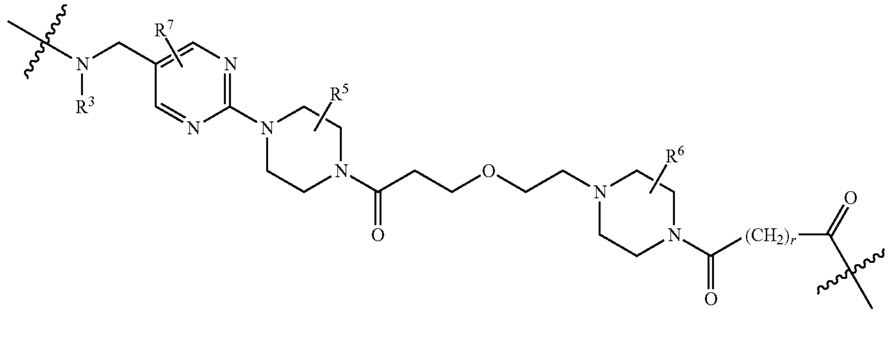

,

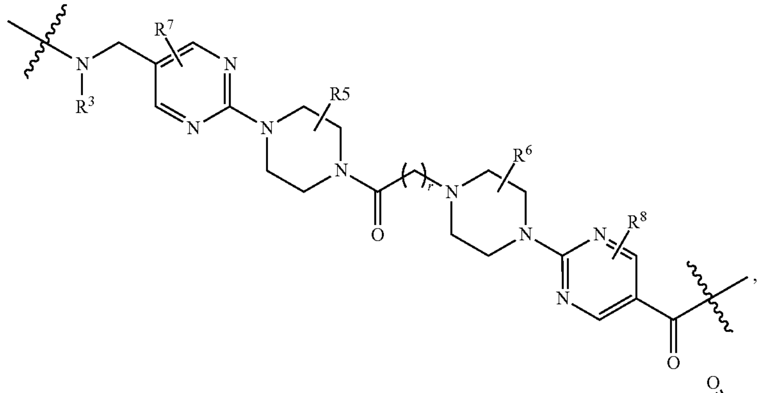

, and

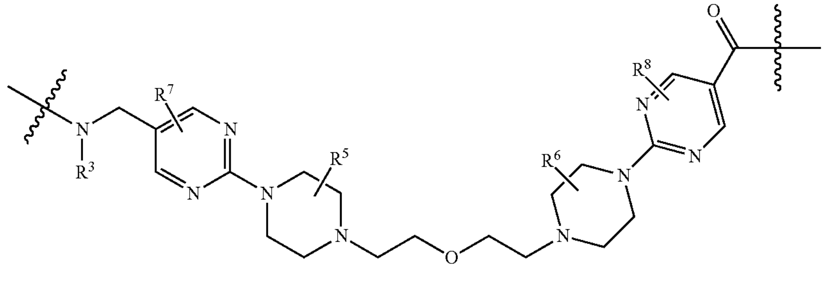

;

wherein the bond on the left side of $A^1$, as drawn, is bound to —C(=$Z^1$)— or $L^2$; and wherein the bond on the right side of the $A^2$ moiety, as drawn, is bound to B or $L^3$;

each Q is independently 1 to 3 rings selected from arylene, cycloalkylene, heteroarylene, and heterocyclylene;

each X is independently absent or 1 to 2 rings selected from arylene, cycloalkylene, heteroarylene, and heterocyclylene;

each $X^1$ is a heteroarylene or heterocyclylene ring;

each W is independently absent or 1 to 2 rings selected from arylene, cycloalkylene, heteroarylene, and heterocyclylene;

each $W^1$ is a heteroarylene or heterocyclylene ring;

each G is independently absent or a ring selected from arylene, cycloalkylene, heteroarylene, and heterocyclylene;

each $G^1$ and $G^2$ are independently heteroarylene or heterocyclylene ring;

$L^1$ is selected from
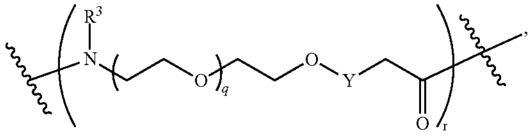
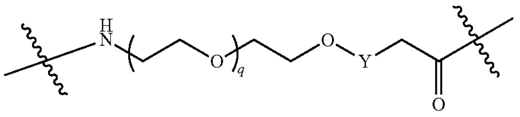
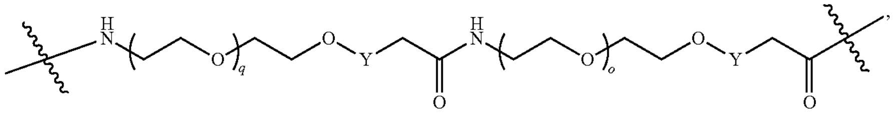
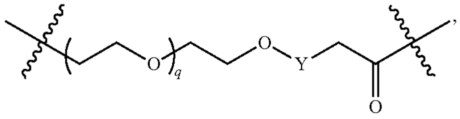
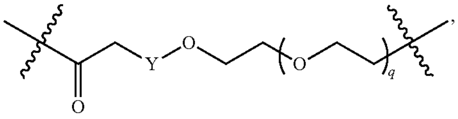
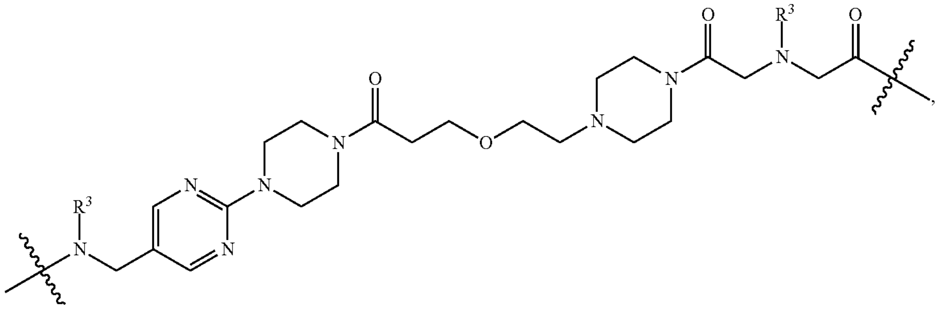
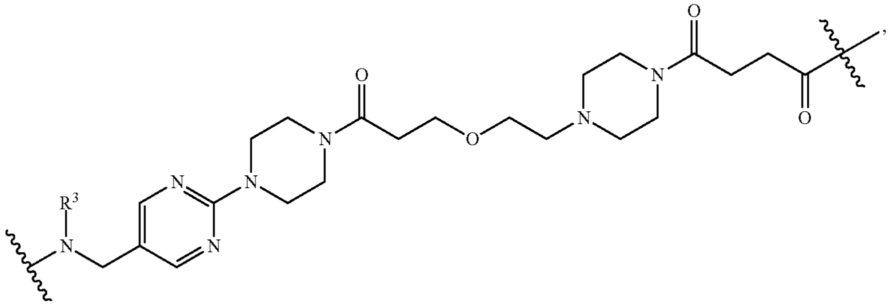
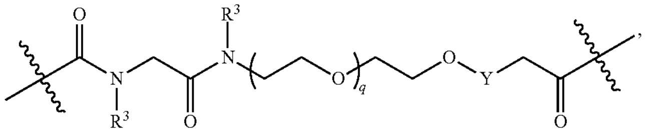
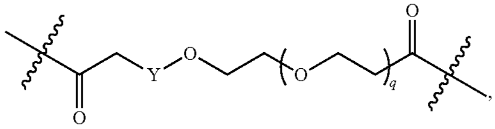
and
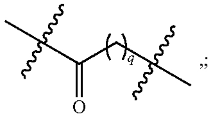
B is selected from
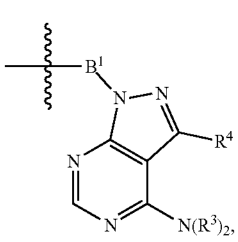
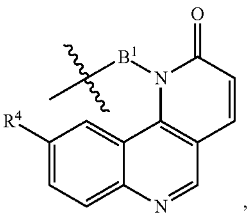
-continued
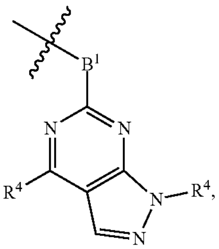

-continued
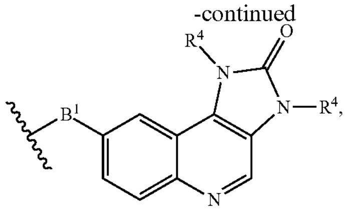
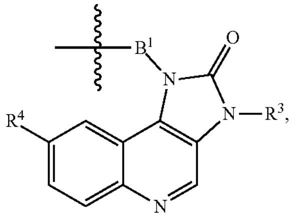
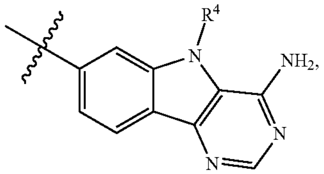
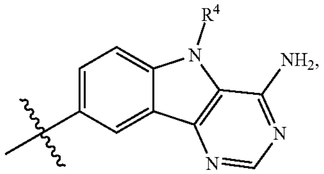
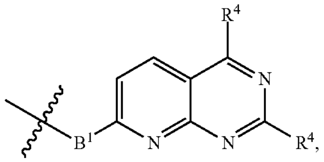
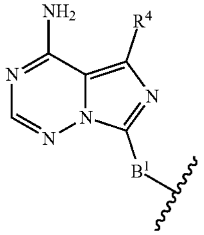
and
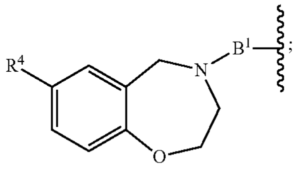
$B^1$ is selected from
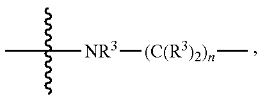
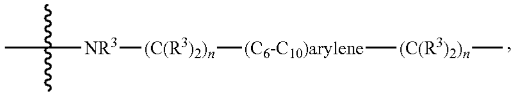
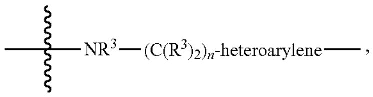
-continued
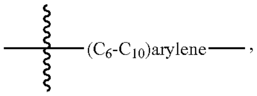
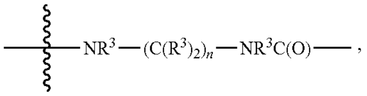
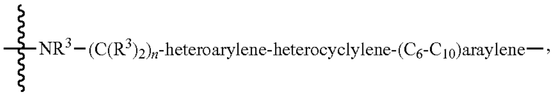
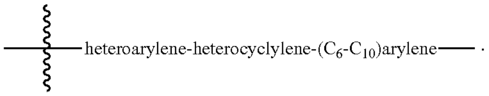
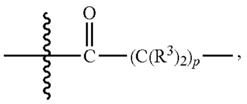
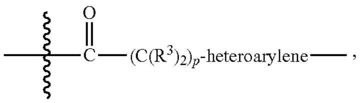
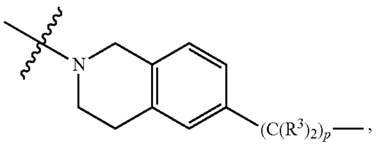
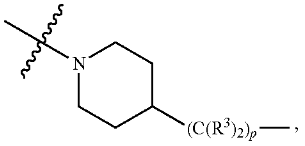
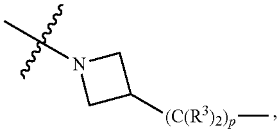
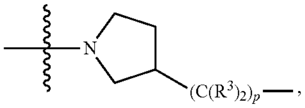
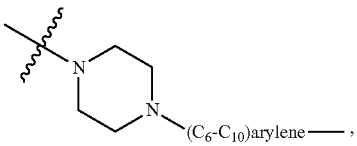
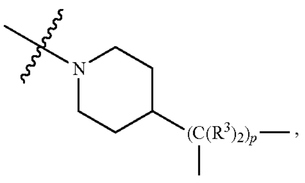
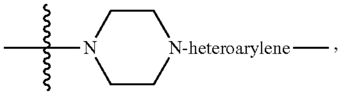
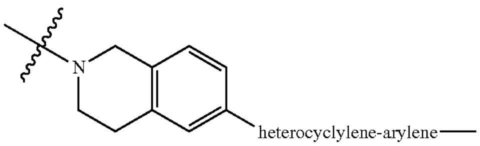
and -continued

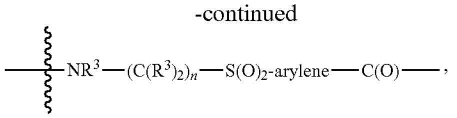

wherein the 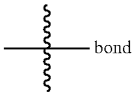 bond on the left side of $B^1$, as drawn, is bound to $A^2$ or $L^1$; and wherein the heteroarylene, heterocyclylene, and arylene are optionally substituted with alkyl, hydroxyalkyl, haloalkyl, alkoxy, halogen, or hydroxyl;

each $R^3$ is independently H or $(C_1\text{-}C_6)$alkyl;

each $R^4$ is independently H, $(C_1\text{-}C_6)$alkyl, halogen, 5-12 membered heteroaryl, 5-12 membered heterocyclyl, $(C_6\text{-}C_{10})$aryl, wherein the heteroaryl, heterocyclyl, and aryl are optionally substituted with $—N(R^3)_2$, $—OR^3$, halogen, $(C_1\text{-}C_6)$alkyl, $—(C_1\text{-}C_6)$alkylene-heteroaryl, $—(C_1\text{-}C_6)$alkylene-CN, $—C(O)NR^3$-heteroaryl; or $—C(O)NR^3$-heterocyclyl;

each $R^5$ is independently H, $(C_1\text{-}C_6)$alkyl, $—C(O)OR^3$, or $—N(R^3)_2$, wherein the alkyl is optionally substituted with $—N(R^3)_2$ or $—OR^3$;

each $R^6$ is independently H, $(C_1\text{-}C_6)$alkyl, $—C(O)OR^3$, or $—N(R^3)_2$, wherein the alkyl is optionally substituted with $—N(R^3)_2$ or $—OR^3$;

each $R^7$ is independently H, $(C_1\text{-}C_6)$alkyl, $—C(O)OR^3$, or $—N(R^3)_2$, wherein the alkyl is optionally substituted with $—N(R^3)_2$ or —OR;

each $R^8$ is independently H, $(C_1\text{-}C_6)$alkyl, $—C(O)OR^3$, or $—N(R^3)_2$, wherein the alkyl is optionally substituted with $—N(R^3)_2$ or $—OR^3$;

each Y is independently $C(R^3)_2$ or a bond;

each n is independently a number from one to 12;

each o is independently a number from zero to 30;

each p is independently a number from zero to 12;

each q is independently a number from zero to 30; and each r is independently a number from one to 6.

Embodiment I-3. The compound of Embodiment I-1 or I-2, wherein $R^{32}$ is $=O$.

Embodiment I-4. The compound of Embodiment I-1 or I-2, wherein $R^{32}$ is $—OR^3$.

Embodiment I-5. The compound of any one of Embodiments I-1 to I-4, wherein the compounds are represented by the structure of Formula I-40:

(I-40)

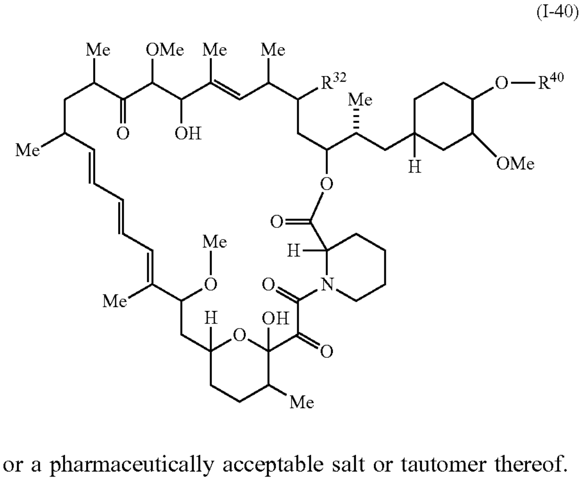

or a pharmaceutically acceptable salt or tautomer thereof.

Embodiment I-6. The compound of Embodiment I-5, wherein $Z^1$ is O.

Embodiment I-7. The compound of Embodiment I-5, wherein $Z^1$ is S.

Embodiment I-8. The compound of any one of Embodiments I-5 to I-7, wherein $R^{40a}$ is $-A^1\text{-}L^1\text{-}A^2\text{-}B$, wherein $A^1$ and $A^2$ are absent.

Embodiment I-9. The compound of any one of Embodiments I-5 to I-7, wherein $R^{40a}$ is $-A^1\text{-}L^1\text{-}A^2\text{-}B$, wherein $A^2$ is absent.

Embodiment I-10. The compound of any one of Embodiments I-5 to I-7, wherein $R^{40a}$ is $-A^1\text{-}L^1\text{-}A^2\text{-}B$, wherein $A^1$ is absent.

Embodiment I-11. The compound of any one of Embodiments I-5 to I-7, wherein $R^{40a}$ is $-A^1\text{-}L^1\text{-}A^2\text{-}B$.

Embodiment I-12. The compound of any one of Embodiments I-5 to I-7, wherein $R^{40a}$ is $-A^1\text{-}A^2\text{-}B$.

Embodiment I-13. The compound of any one of Embodiments I-5 to I-7, wherein $R^{40a}$ is $-L^2\text{-}A^1\text{-}L^1\text{-}A^2\text{-}L^3\text{-}B$, wherein $L^2$ and $A^1$ are absent.

Embodiment I-14. The compound of any one of Embodiments I-5 to I-7, wherein $R^{40a}$ is $-L^2\text{-}A^1\text{-}L^1\text{-}A^2\text{-}L^3\text{-}B$, wherein $L^2$ is absent.

Embodiment I-15. The compound of any one of Embodiments I-5 to I-7, wherein $R^{40a}$ is $-L^2\text{-}A^1\text{-}L^1\text{-}A^2\text{-}L^3\text{-}B$, wherein $L^3$ is absent.

Embodiment I-16. The compound of any one of Embodiments I-5 to I-7, wherein $R^{40a}$ is $—O—(C_1\text{-}C_6)$alkyl or $—O—(C_6\text{-}C_{10})$aryl; wherein the aryl is unsubstituted or substituted with 1-5 substituents selected from $—NO_2$ and halogen.

Embodiment I-17. The compound of any one of Embodiments I-1 to I-4, wherein the compounds are represented by the structure of Formula I-28:

(I-28)

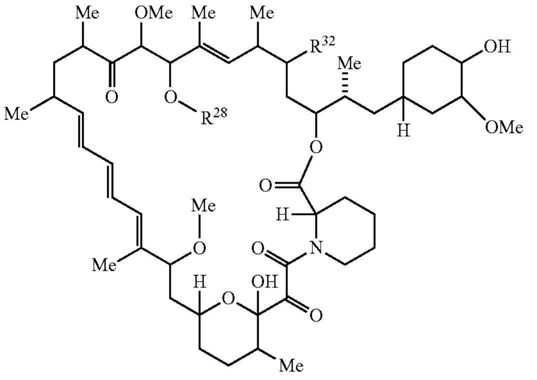

or a pharmaceutically acceptable salt or tautomer thereof.

Embodiment I-18. The compound of Embodiment I-17, wherein $Z^1$ is O.

Embodiment I-19. The compound of Embodiment I-17, wherein $Z^1$ is S.

Embodiment I-20. The compound of any one of Embodiments I-17 to I-19, wherein $R^{28a}$ is $-A^1\text{-}L^1\text{-}A^2\text{-}B$, wherein $A^1$ and $A^2$ are absent.

Embodiment I-21. The compound of any one of Embodiments I-17 to I-19, wherein $R^{28a}$ is $-A^1\text{-}L^1\text{-}A^2\text{-}B$, wherein $A^2$ is absent.

Embodiment I-22. The compound of any one of Embodiments I-17 to I-19, wherein $R^{28a}$ is $-A^1\text{-}L^1\text{-}A^2\text{-}B$, wherein $A^1$ is absent.

Embodiment I-23. The compound of any one of Embodiments I-17 to I-19, wherein $R^{28a}$ is $-A^1-L^1-A^2-B$.

Embodiment I-24. The compound of any one of Embodiments I-17 to I-19, wherein $R^{28a}$ is $-A^1-A^2-B$.

Embodiment I-25. The compound of any one of Embodiments I-17 to I-19, wherein $R^{28a}$ is $-L^2-A^1-L^1-A^2-L^3-B$, wherein $L^2$ and $A^1$ are absent.

Embodiment I-26. The compound of any one of Embodiments I-17 to I-19, wherein $R^{28a}$ is $-L^2-A^1-L^1-A^2-L^3-B$, wherein $L^2$ is absent.

Embodiment I-27. The compound of any one of Embodiments I-17 to I-19, wherein $R^{28a}$ is $-L^2-A^1-L^1-A^2-L^3-B$, wherein $L^3$ is absent.

Embodiment I-28. The compound of any one of Embodiments I-17 to I-19, wherein $R^{28a}$ is —O—($C_1$-$C_6$)alkyl or —O—($C_6$-$C_{10}$)aryl; wherein the aryl is unsubstituted or substituted with 1-5 substituents selected from —$NO_2$ and halogen.

Embodiment I-29. The compound of any one of Embodiments I-1 to I-11, I-13 to I-15, I-17 to I-23, and I-25 to I-27, wherein $L^1$ is

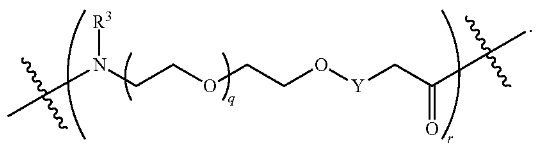

Embodiment I-30. The compound of any one of Embodiments I-1 to I-11, I-13 to I-15, I-17 to I-23, and I-25 to I-27, wherein $L^1$ is

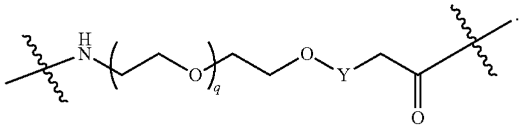

Embodiment I-31. The compound of any one of Embodiments I-1 to I-11, I-13 to I-15, I-17 to I-23, and I-25 to I-27, wherein $L^1$ is

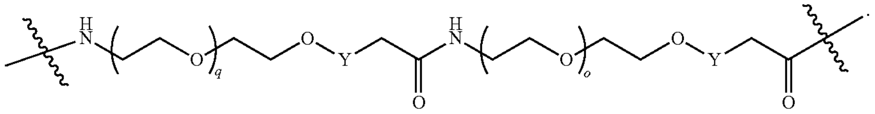

Embodiment I-32. The compound of any one of Embodiments I-1 to I-11, I-13 to I-15, I-17 to I-23, and I-25 to I-27, wherein $L^1$ is

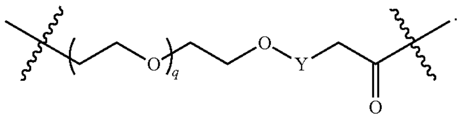

Embodiment I-33. The compound of any one of Embodiments I-1 to I-11, I-13 to I-15, I-17 to I-23, and I-25 to I-27, wherein $L^1$ is

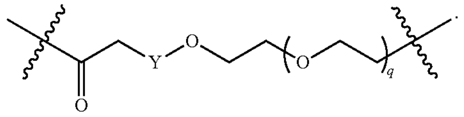

Embodiment I-34. The compound of any one of Embodiments I-1 to I-7, I-15, I-17 to I-19, and I-27, wherein $L^2$ is

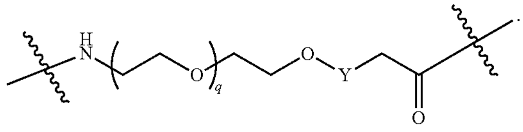

Embodiment I-35. The compound of any one of Embodiments I-1 to I-7, I-13 to I-14, I-17 to I-19, and I-25 to I-26, wherein $L^3$ is lp;1p

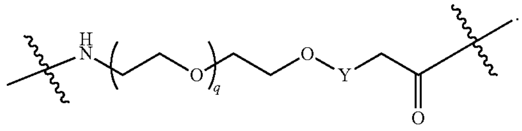

Embodiment I-36. The compound of any one of Embodiments I-1 to I-8, I-10, I-13, I-17 to I-19, I-20, I-22, I-25 and I-29 to I-35, wherein $A^1$ is absent.

Embodiment I-37. The compound of any one of Embodiments I-1 to I-7, I-9, I-11 to I-12, I-14 to I-15, I-17 to I-19, I-21, I-23 to I-24, I-26 to I-27, and I-29 to I-35, wherein $A^1$ is

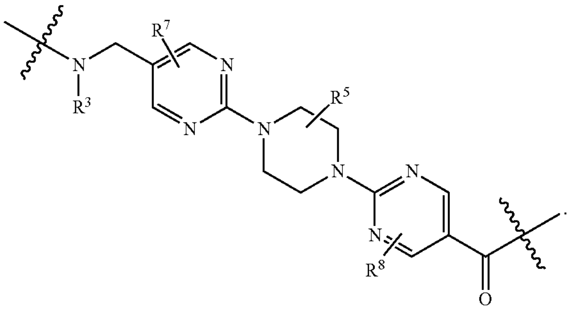

Embodiment I-38. The compound of any one of Embodiments I-1 to I-7, I-9, I-11 to I-12, I-14 to I-15, I-17 to I-19, I-21, I-23 to I-24, I-26 to I-27, and I-29 to I-35, wherein $A^1$ is

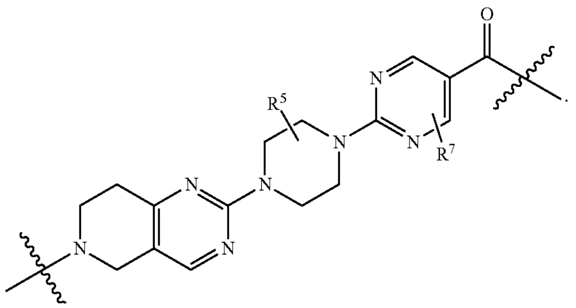

Embodiment I-39. The compound of any one of Embodiments I-1 to I-7, I-9, I-11 to I-12, I-14 to I-15, I-17 to I-19, I-21, I-23 to I-24, I-26 to I-27, and I-29 to I-35, wherein $A^1$ is

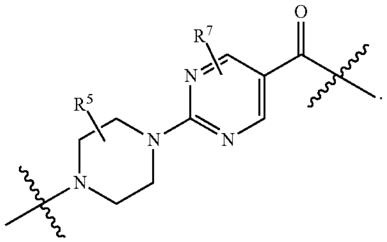

Embodiment I-40. The compound of any one of Embodiments I-1 to I-7, I-9, I-11 to I-12, I-14 to I-15, I-17 to I-19, I-21, I-23 to I-24, I-26 to I-27, and I-29 to I-35, wherein $A^1$ is

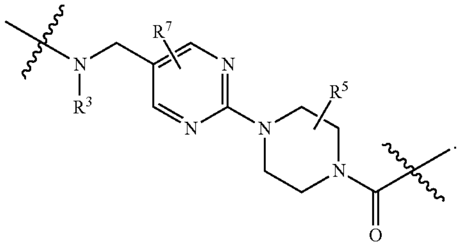

Embodiment I-41. The compound of any one of Embodiments I-1 to I-7, I-9, I-11 to I-12, I-14 to I-15, I-17 to I-19, I-21, I-23 to I-24, I-26 to I-27, and I-29 to I-35, wherein $A^1$

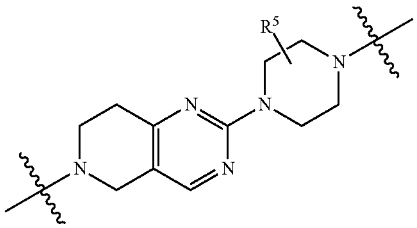

Embodiment I-42. The compound of any one of Embodiments I-1 to I-7, I-9, I-11 to I-12, I-14 to I-15, I-17 to I-19, I-21, I-23 to I-24, I-26 to I-27, and I-29 to I-35, wherein $A^1$ is

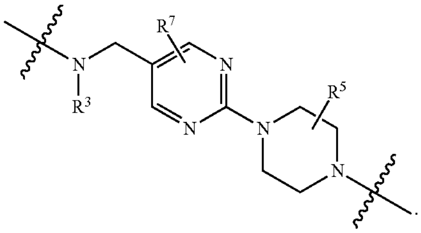

Embodiment I-43. The compound of any one of Embodiments I-1 to I-7, I-9, I-11 to I-12, I-14 to I-15, I-17 to I-19, I-21, I-23 to I-24, I-26 to I-27, and I-29 to I-35, wherein $A^1$ is

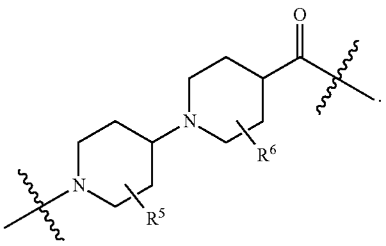

Embodiment I-44. The compound of any one of Embodiments I-1 to I-7, I-9, I-11 to I-12, I-14 to I-15, I-17 to I-19, I-21, I-23 to I-24, I-26 to I-27, and I-29 to I-35, wherein $A^1$ is

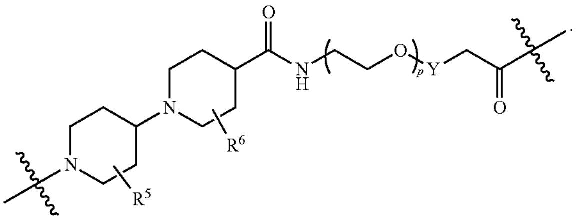

Embodiment I-45. The compound of any one of Embodiments I-1 to I-9, I-17 to I-21, and I-29 to I-44, wherein $A^2$ is absent.

Embodiment I-46. The compound of any one of Embodiments I-1 to I-7, I-10 to I-15, I-17 to I-19, I-22 to I-27 and I-29 to I-44, wherein $A^2$ is

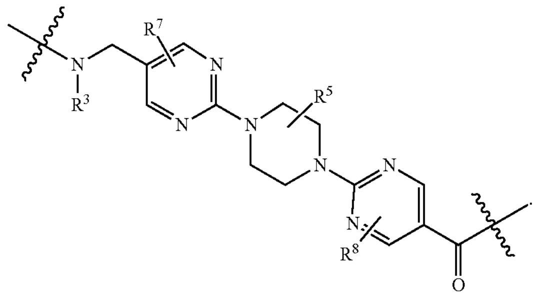

Embodiment I-47. The compound of any one of Embodiments I-1 to I-7, I-10 to I-15, I-17 to I-19, I-22 to I-27 and I-29 to I-44, wherein $A^2$ is

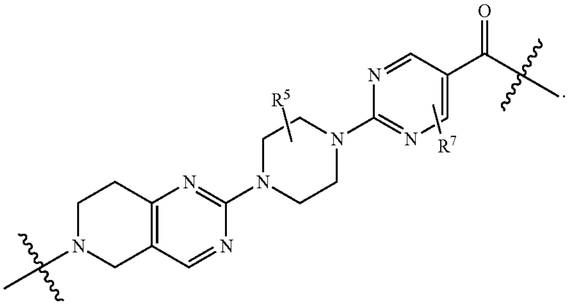

Embodiment I-48. The compound of any one of Embodiments I-1 to I-7, I-10 to I-15, I-17 to I-19, I-22 to I-27 and I-29 to I-44, wherein $A^2$ is

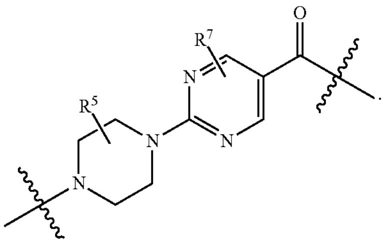

Embodiment I-49. The compound of any one of Embodiments I-1 to I-7, I-10 to I-15, I-17 to I-19, I-22 to I-27 and I-29 to I-44, wherein $A^2$ is

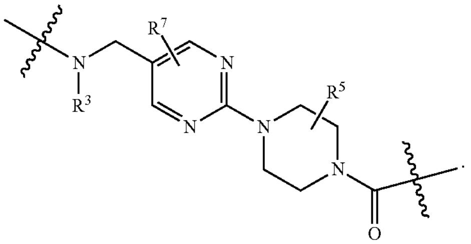

Embodiment I-50. The compound of any one of Embodiments I-1 to I-7, I-10 to I-15, I-17 to I-19, I-22 to I-27 and I-29 to I-44, wherein $A^2$ is

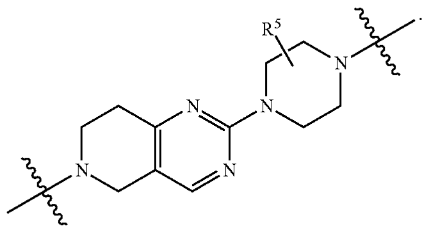

Embodiment I-51. The compound of any one of Embodiments I-1 to I-7, I-10 to I-15, I-17 to I-19, I-22 to I-27 and I-29 to I-44, wherein $A^2$ is

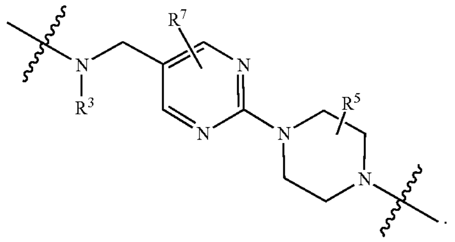

Embodiment I-52. The compound of any one of Embodiments I-1 to I-7, I-10 to I-15, I-17 to I-19, I-22 to I-27 and I-29 to I-44, wherein $A^2$ is

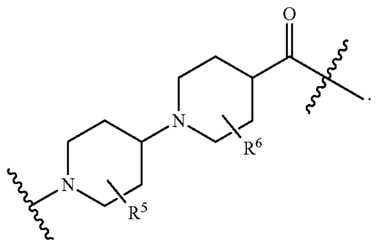

Embodiment I-53. The compound of any one of Embodiments I-1 to I-7, I-10 to I-15, I-17 to I-19, I-22 to I-27 and I-29 to I-44, wherein $A^2$ is

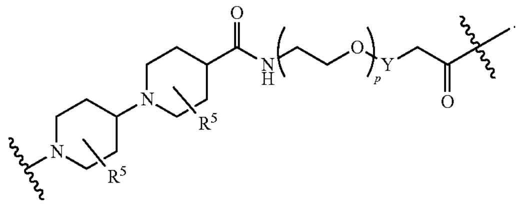

Embodiment I-54. The compound of any one of Embodiments I-1 to I-53, wherein B is

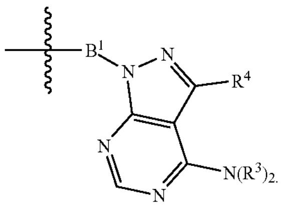

Embodiment I-55. The compound of any one of Embodiments I-1 to I-53, wherein B is

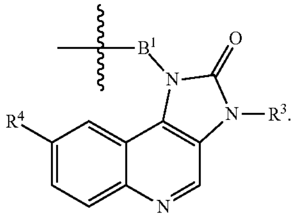

Embodiment I-56. The compound of any one of Embodiments I-1 to I-53, wherein $B^1$ is

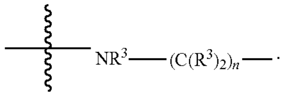

Embodiment I-57. The compound of any one of Embodiments I-1 to I-53, wherein $B^1$ is

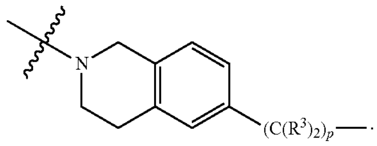

Embodiment I-58. The compound of any one of Embodiments I-1 to I-57, wherein $R^4$ is 5-12 membered heteroaryl, optionally substituted with —$N(R^3)_2$, —$OR^3$, halogen, ($C_1$-$C_6$)alkyl, —($C_1$-$C_6$)alkylene-heteroaryl, —($C_1$-$C_6$)alkylene-CN, or —C(O)$NR^3$-heteroaryl.

Embodiment I-59. The compound of any one of Embodiments I-1 to I-58, or a pharmaceutically acceptable salt or tautomer thereof, wherein compound has the following formula:

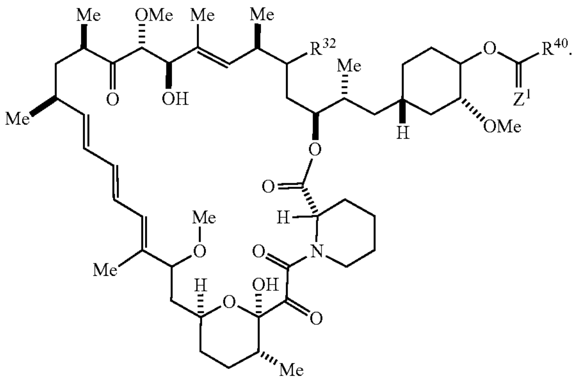

Embodiment I-60. A compound selected from the group consisting of

Example 1
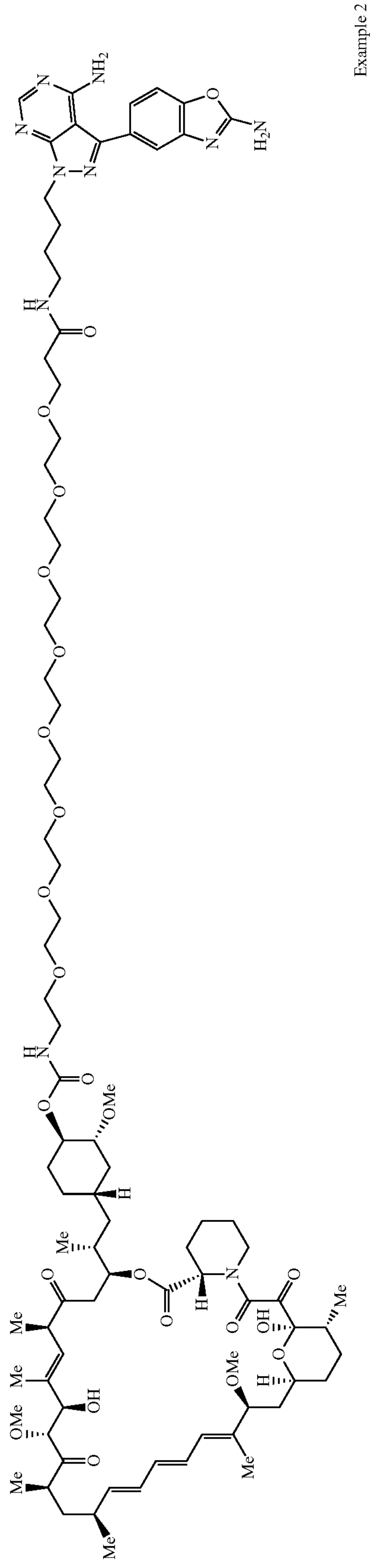
Example 2
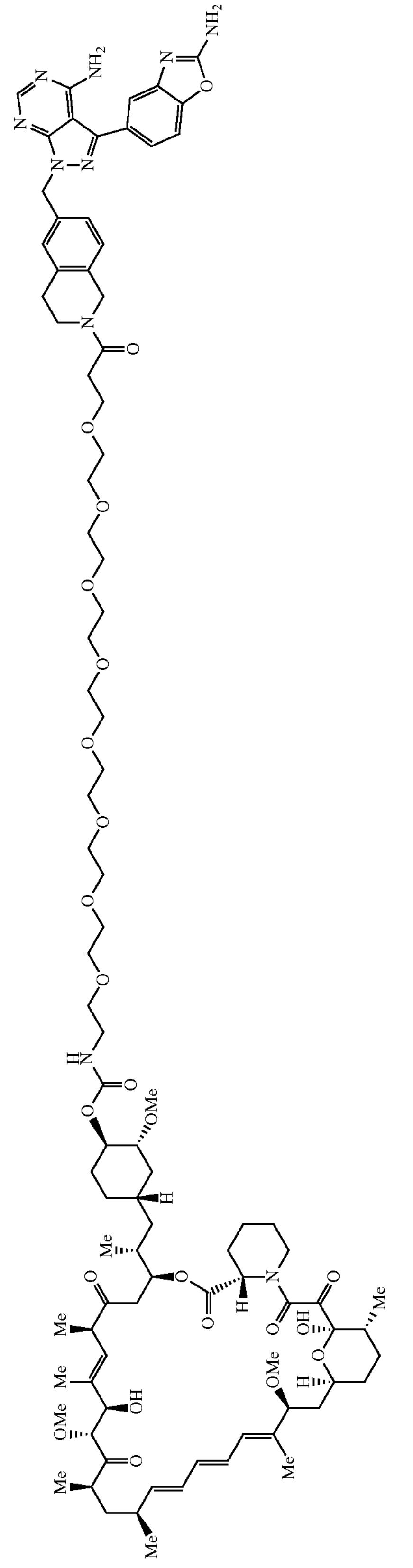

-continued
Example 3
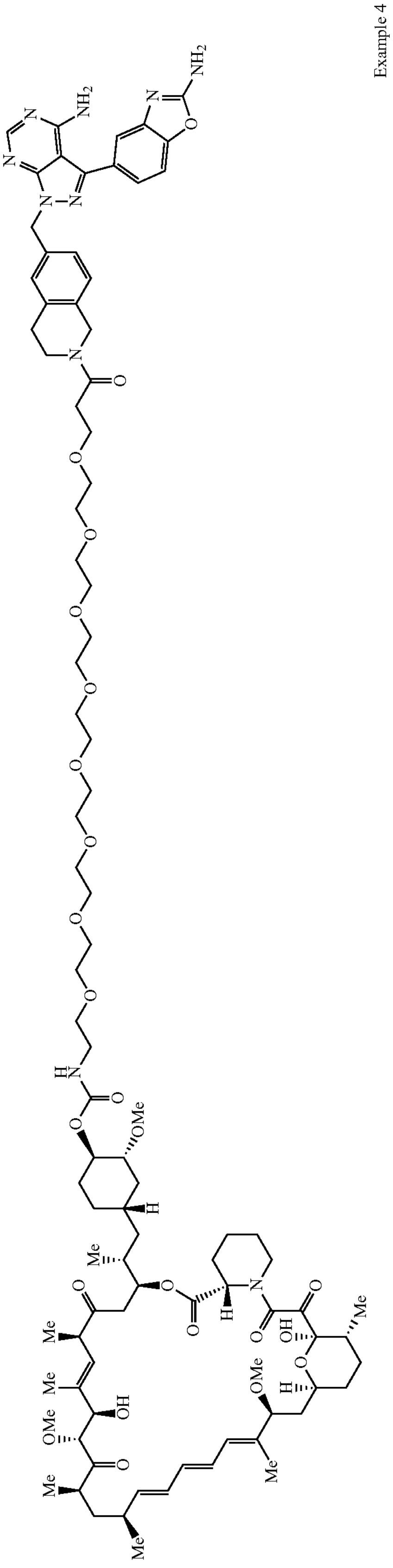
Example 4
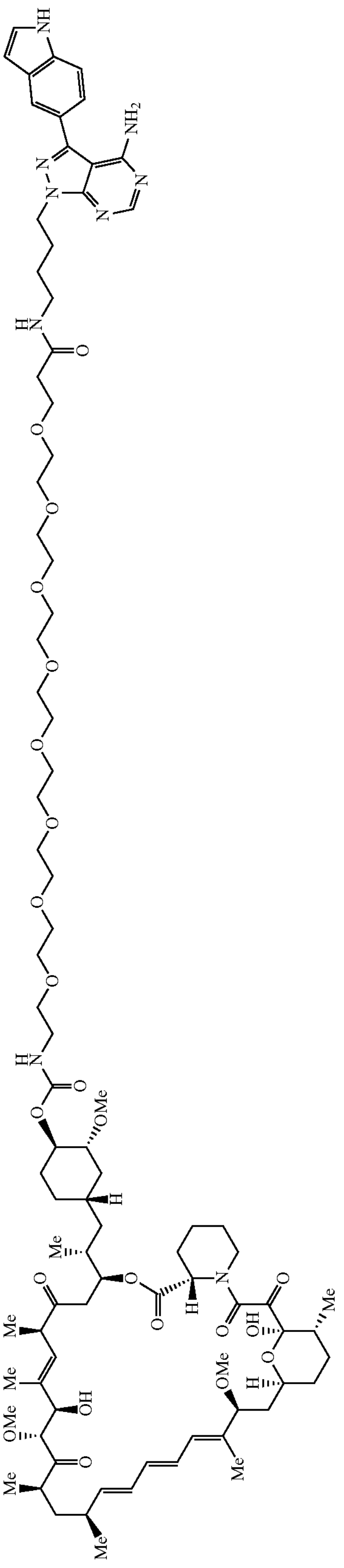

-continued
Example 5
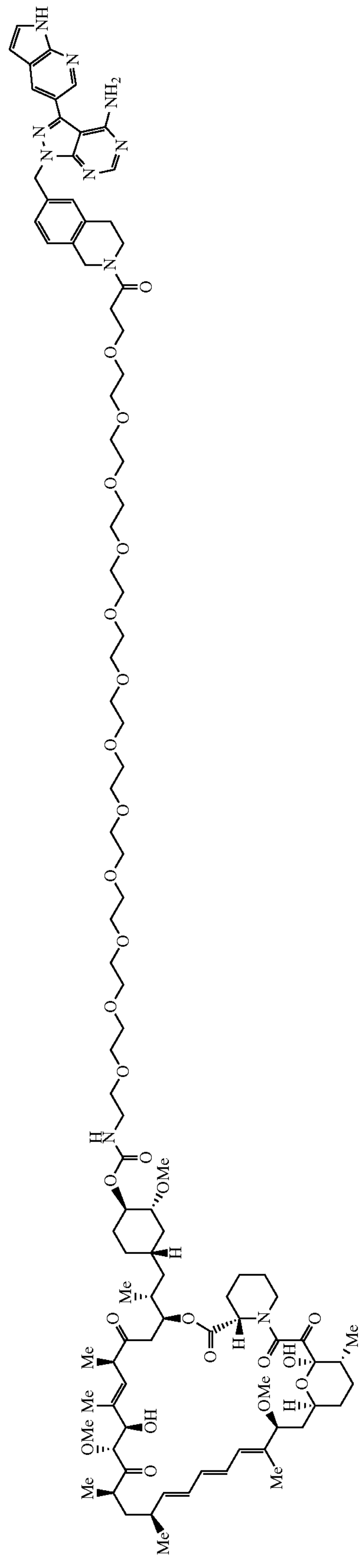
Example 6
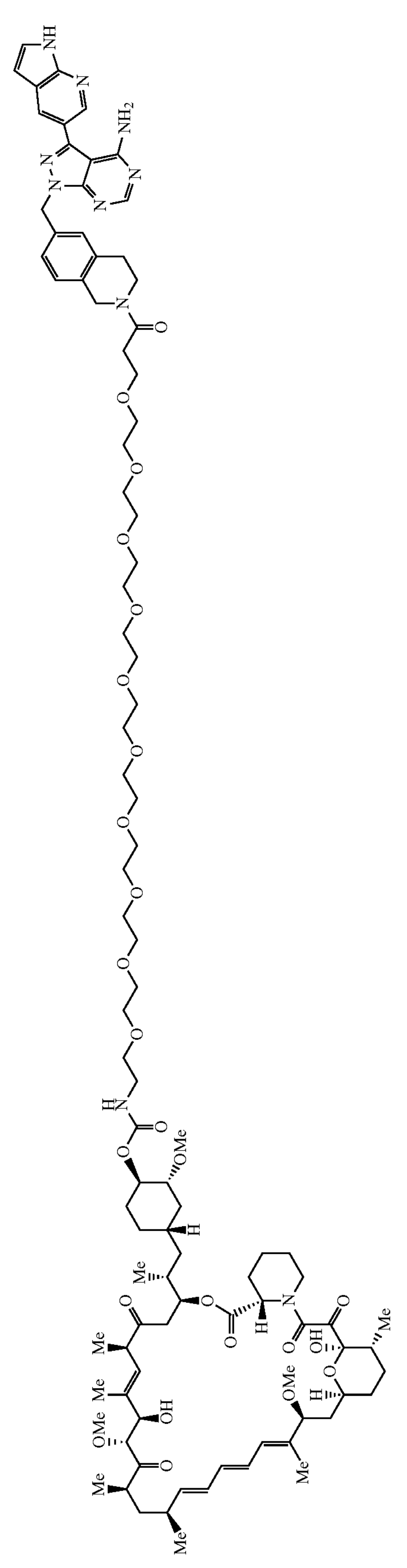

-continued
Example 7
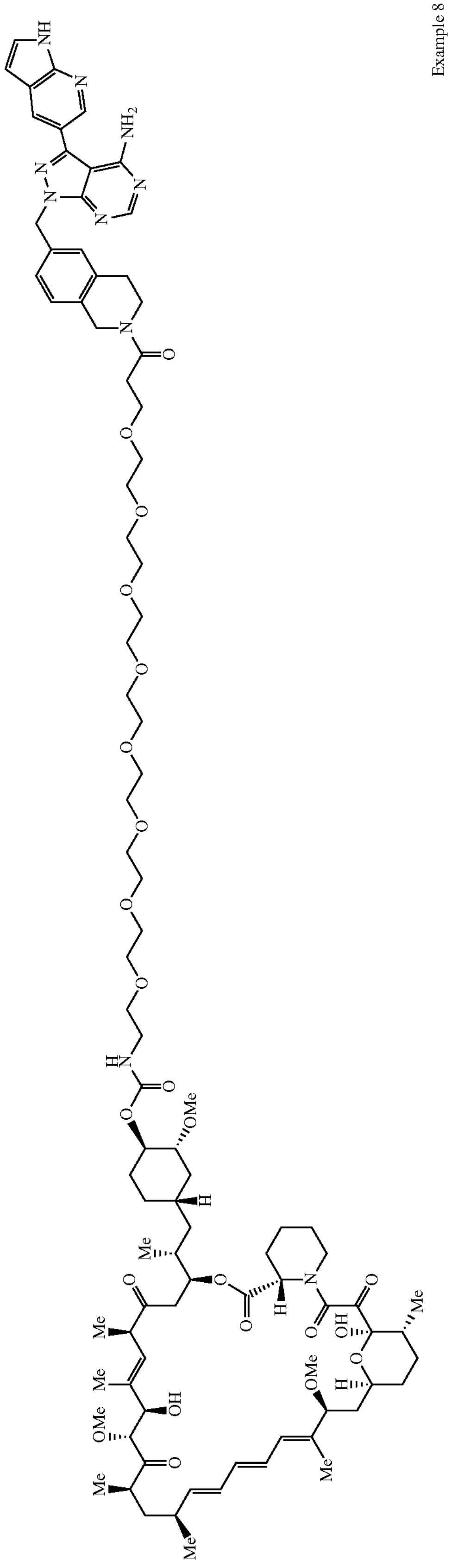
Example 8
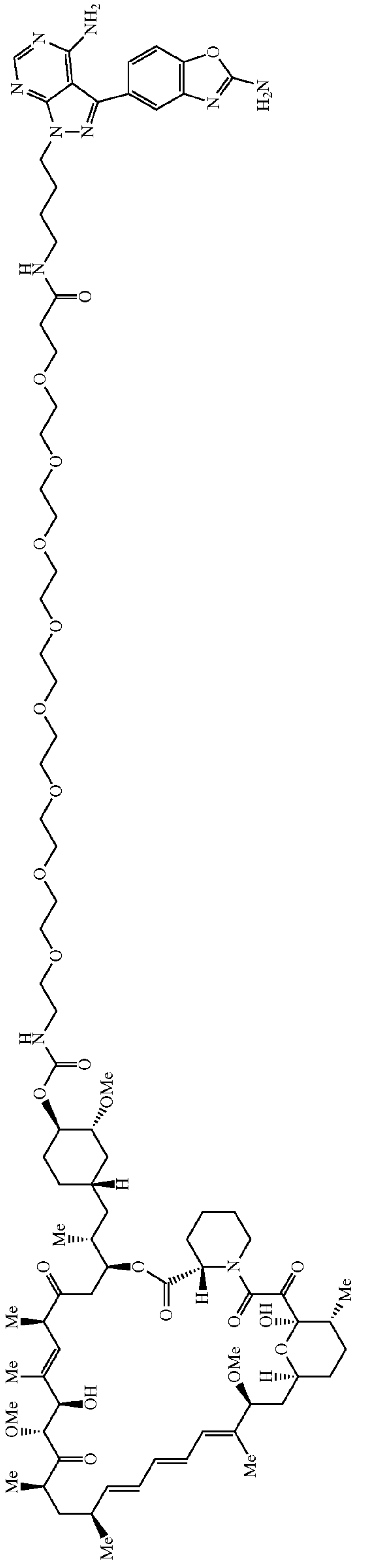

-continued
Example 9
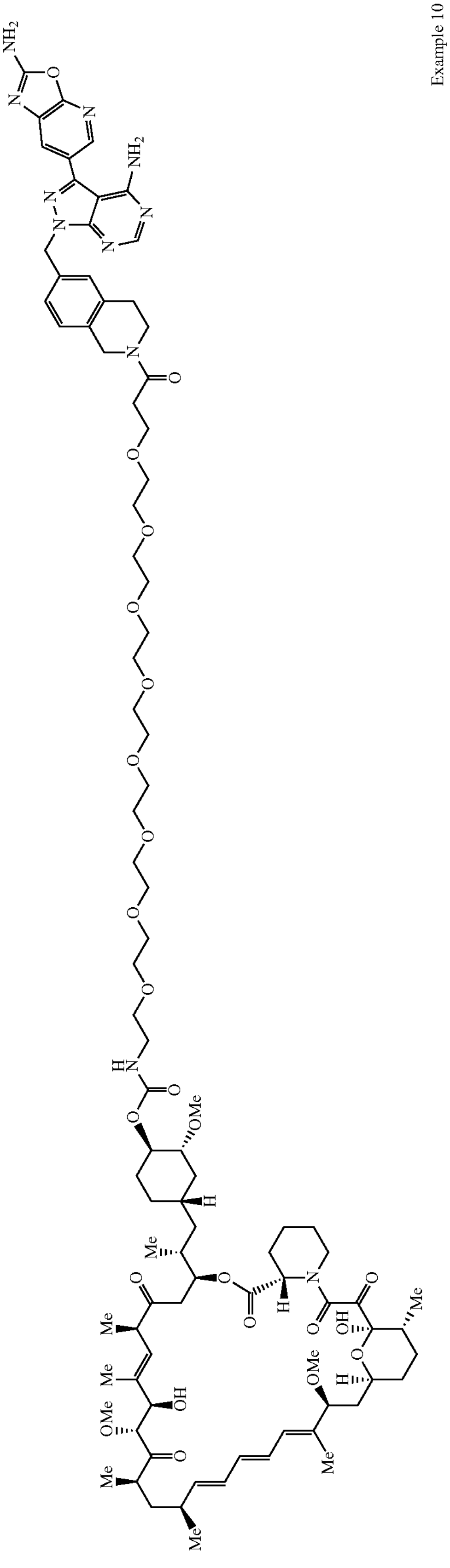
Example 10
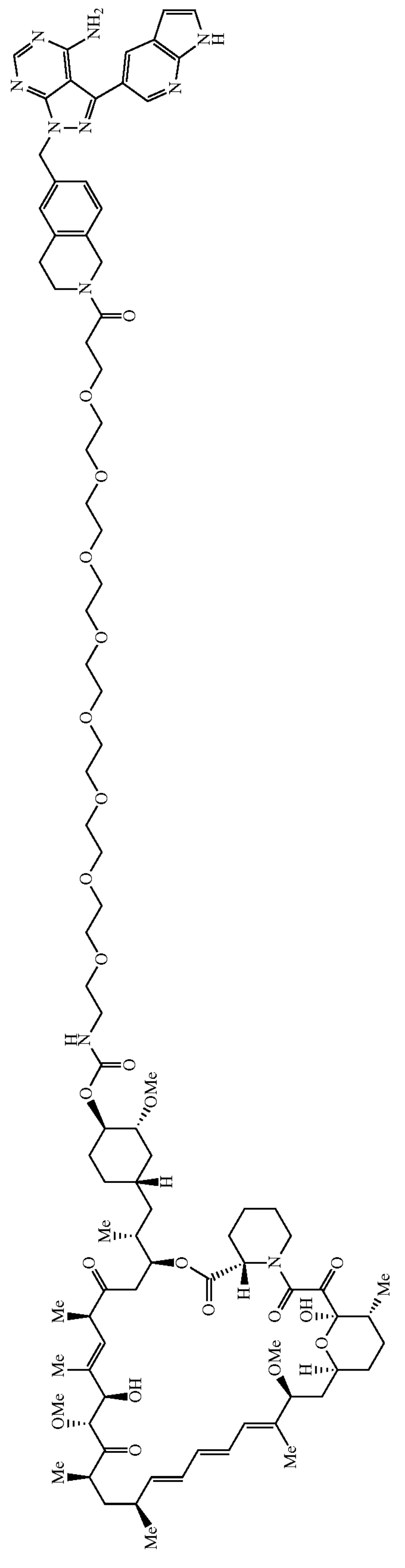

-continued
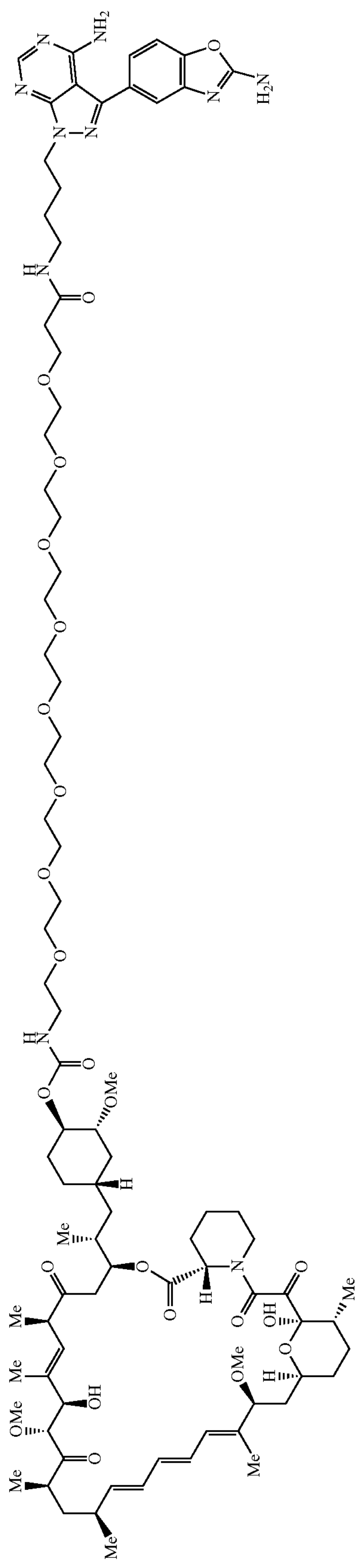
Example 11
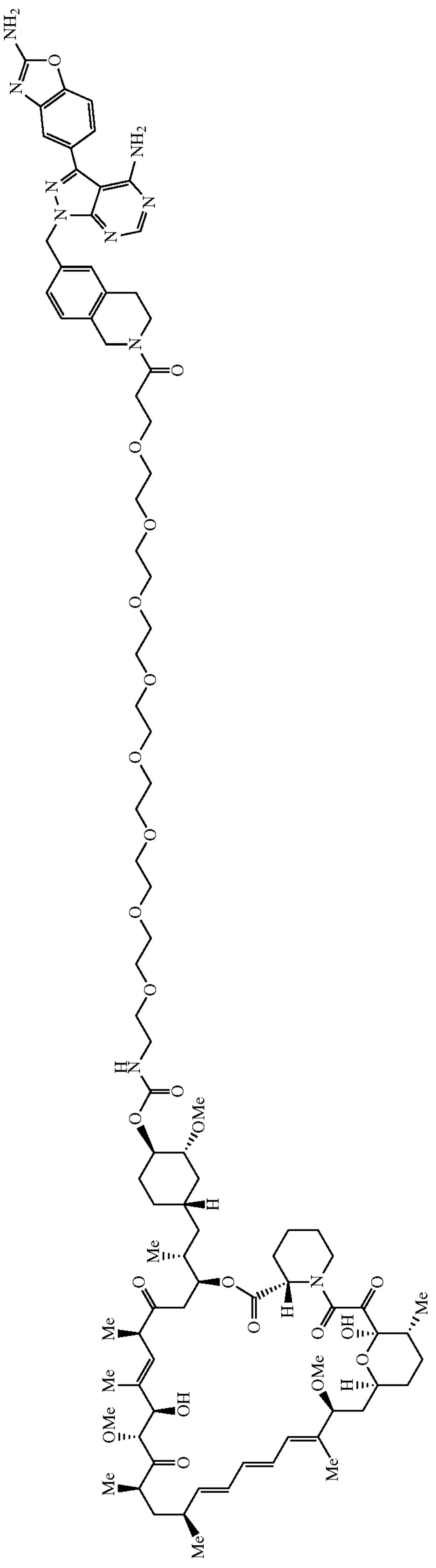
Example 12

-continued
Example 13
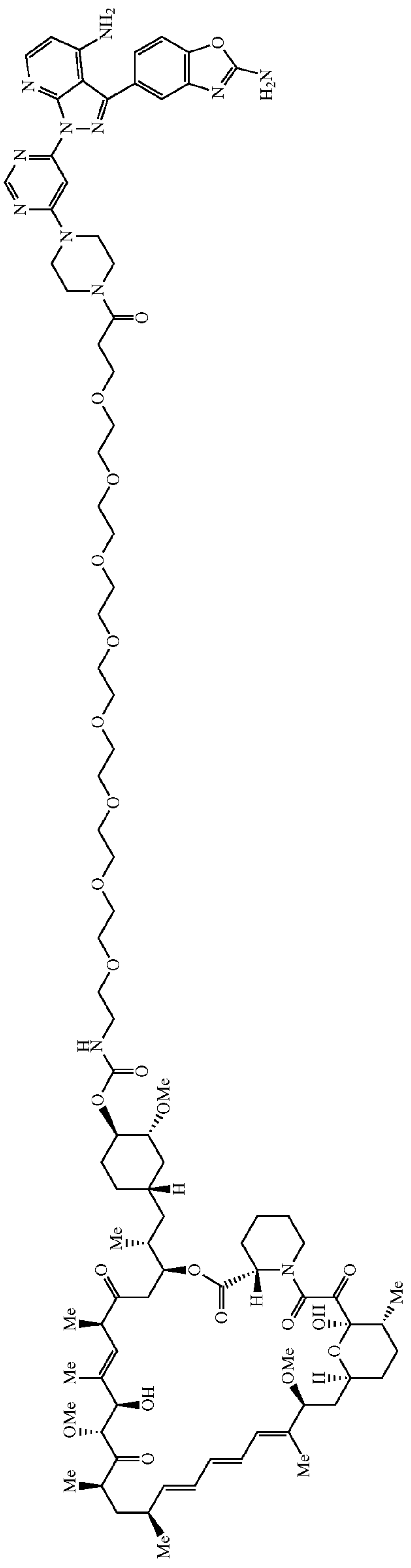
Example 14
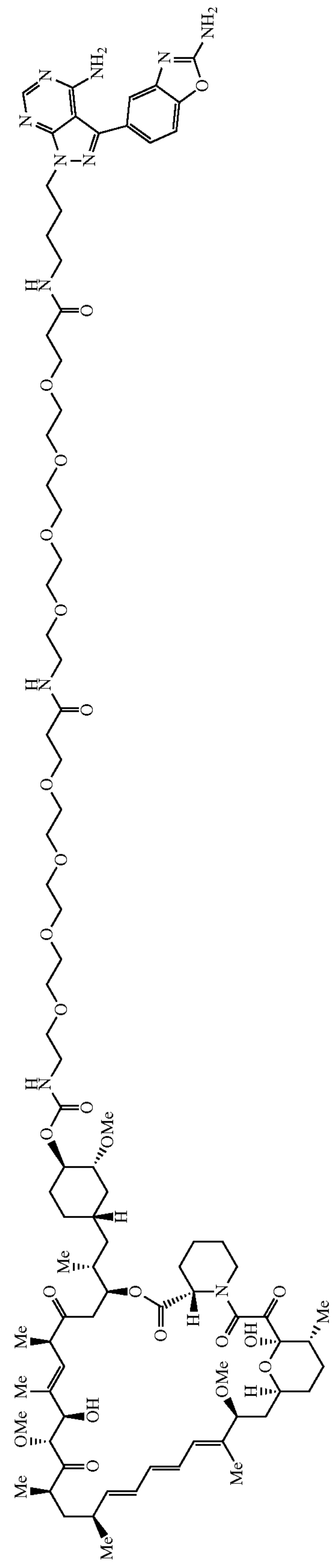

-continued
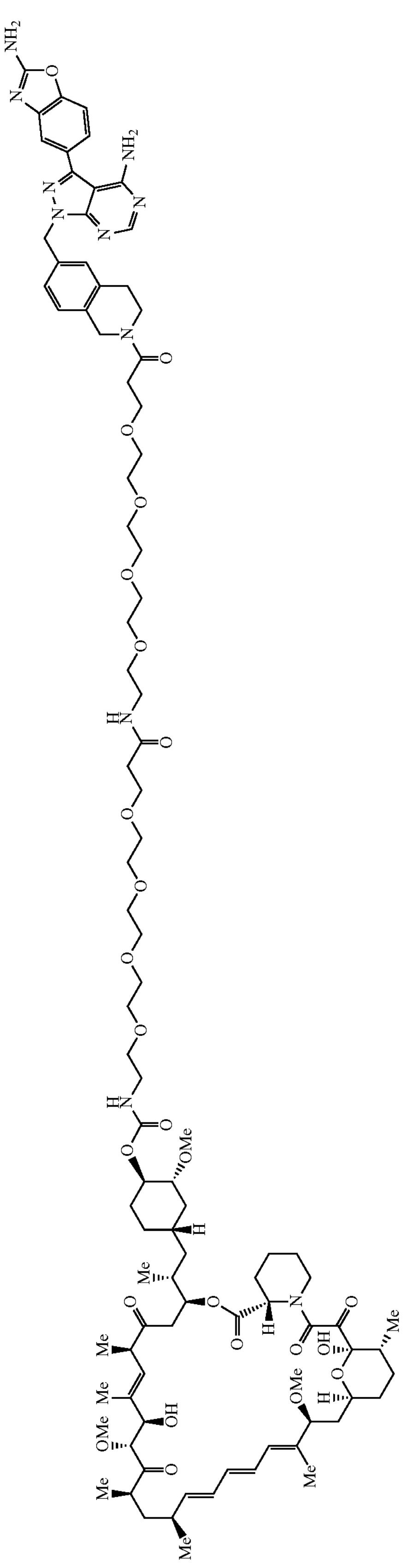
Example 15
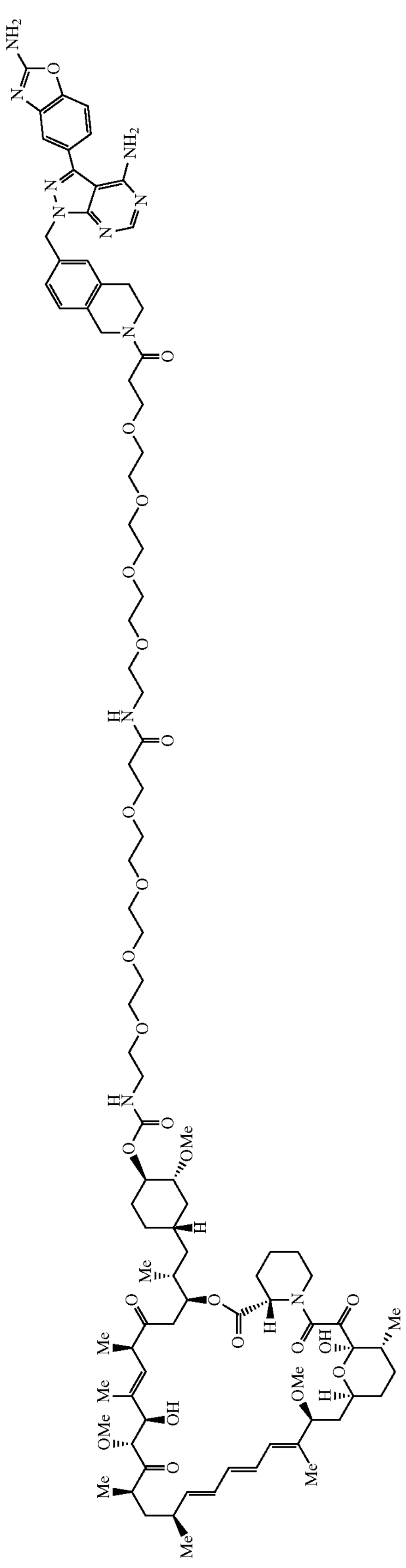
Example 16

-continued
Example 17
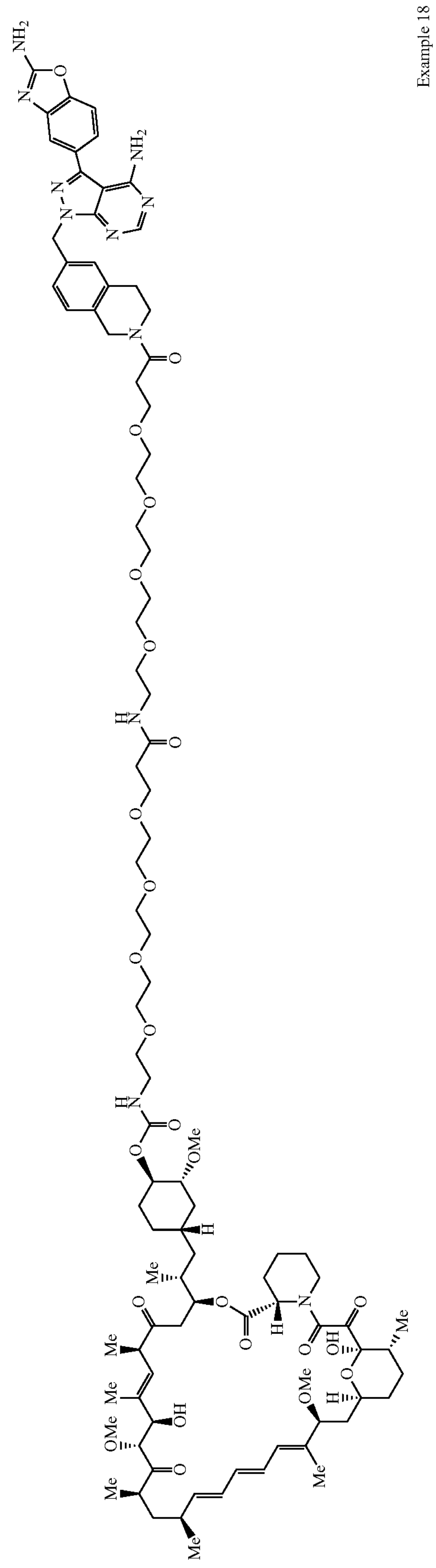
Example 18
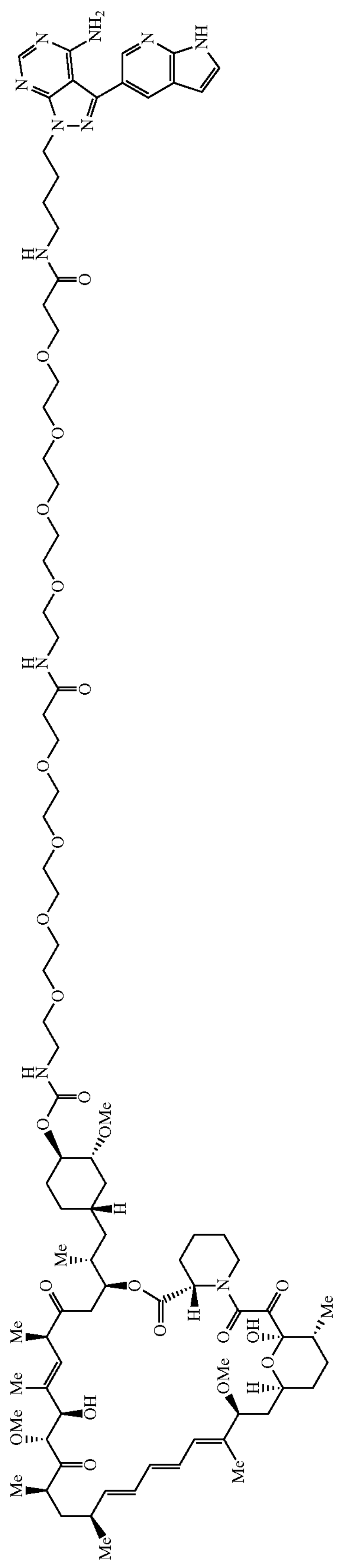

-continued
Example 19
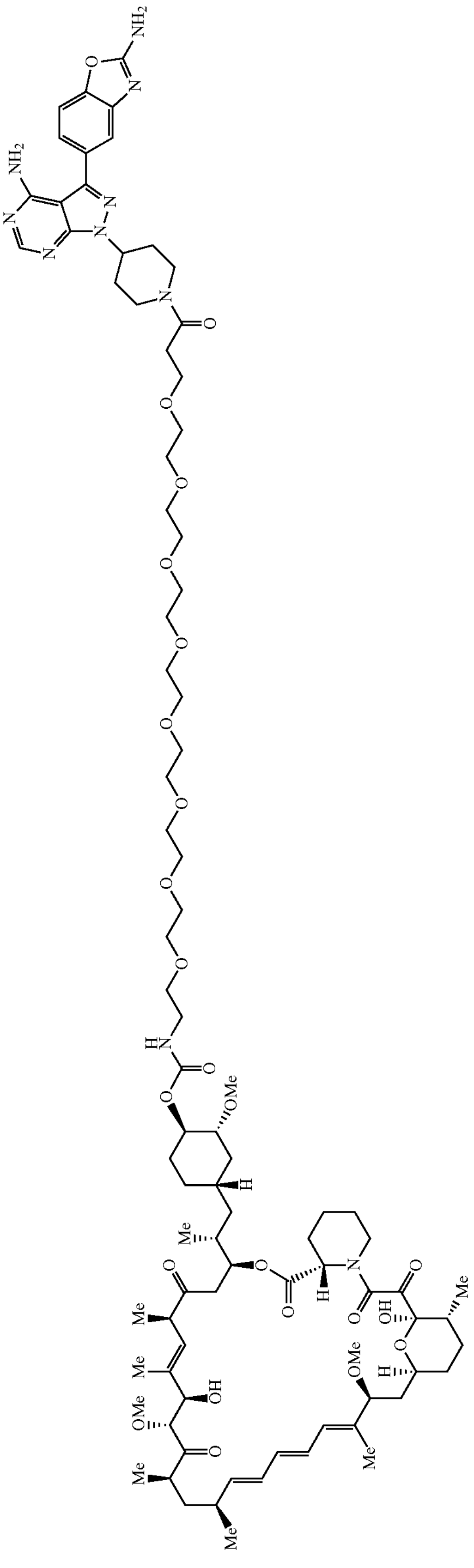
Example 20
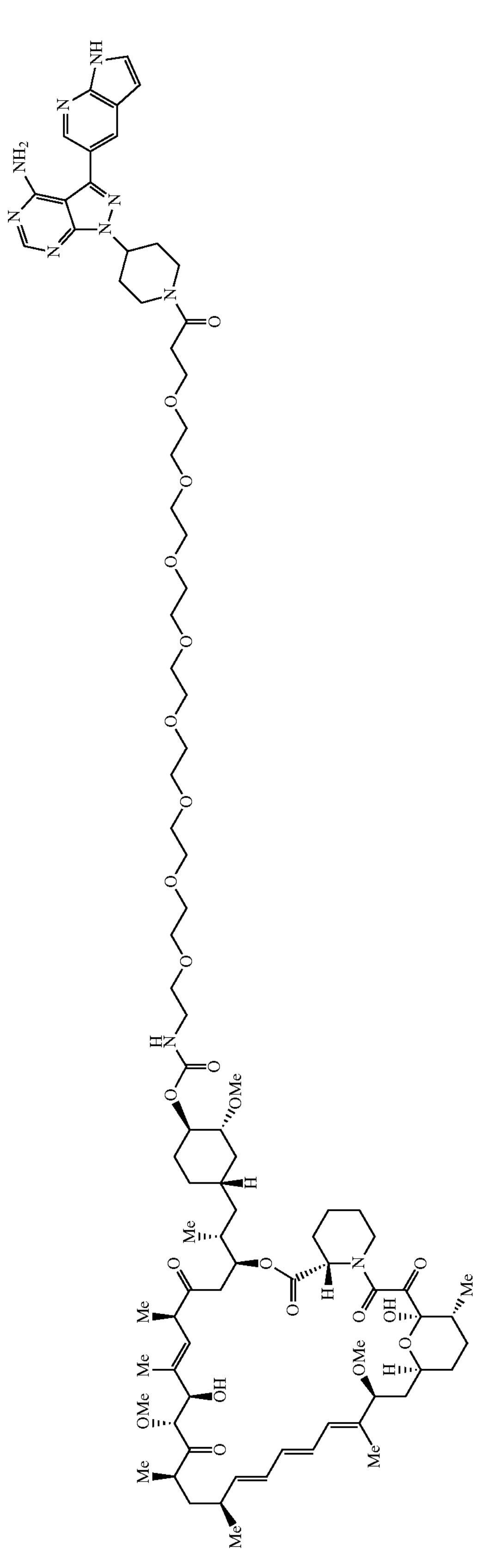

-continued
Example 21
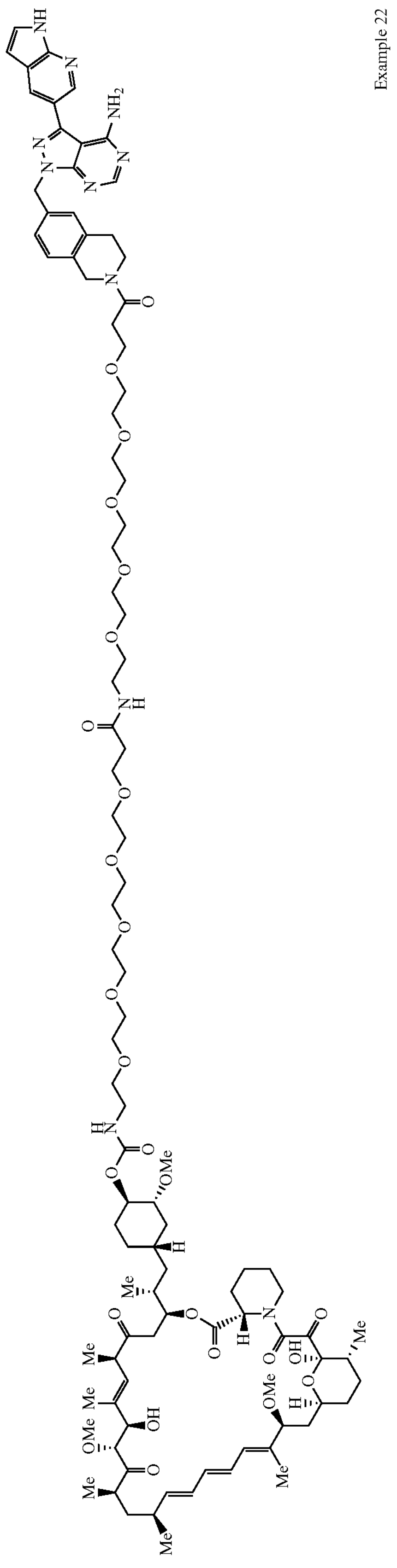
Example 22
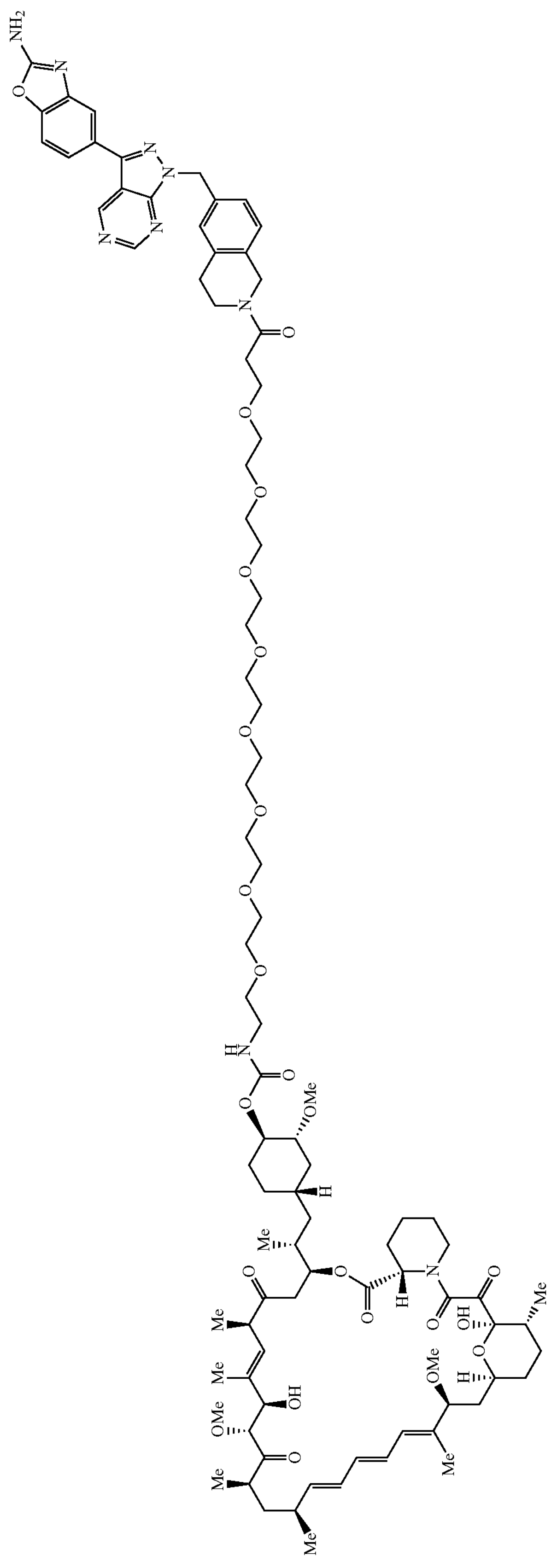

-continued
Example 23
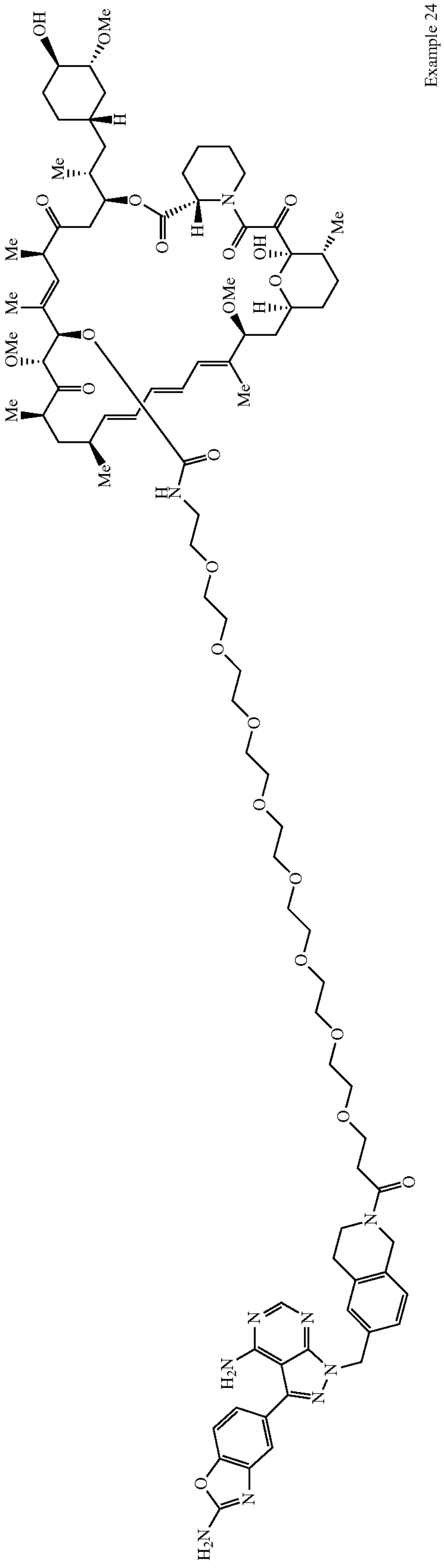
Example 24
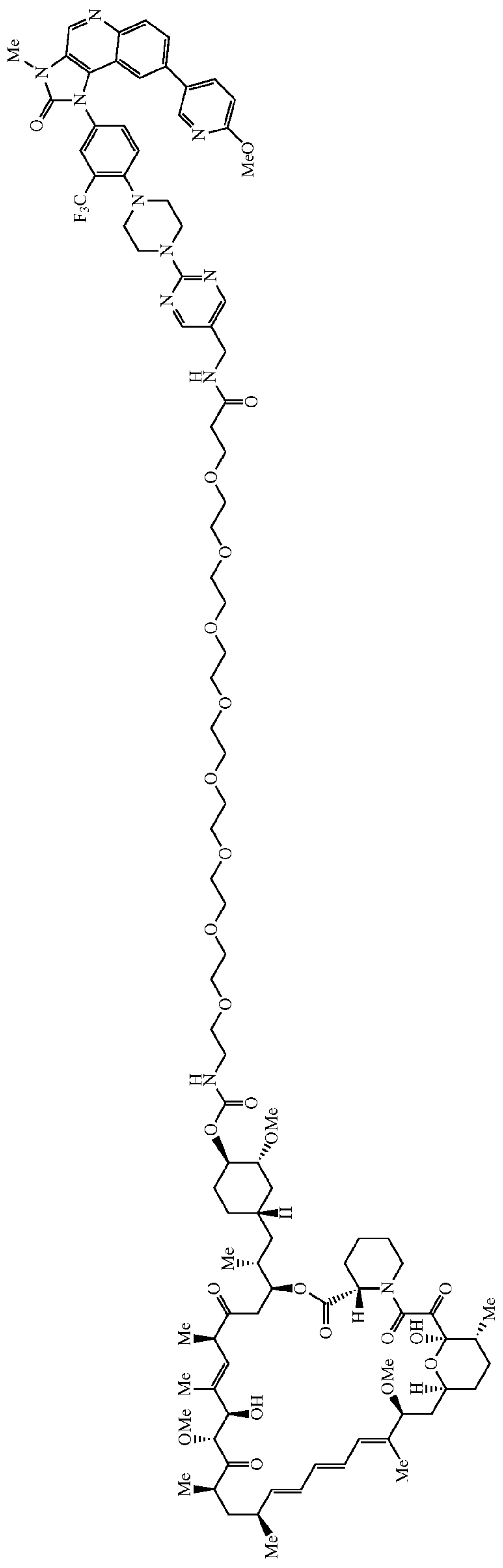

-continued
Example 25
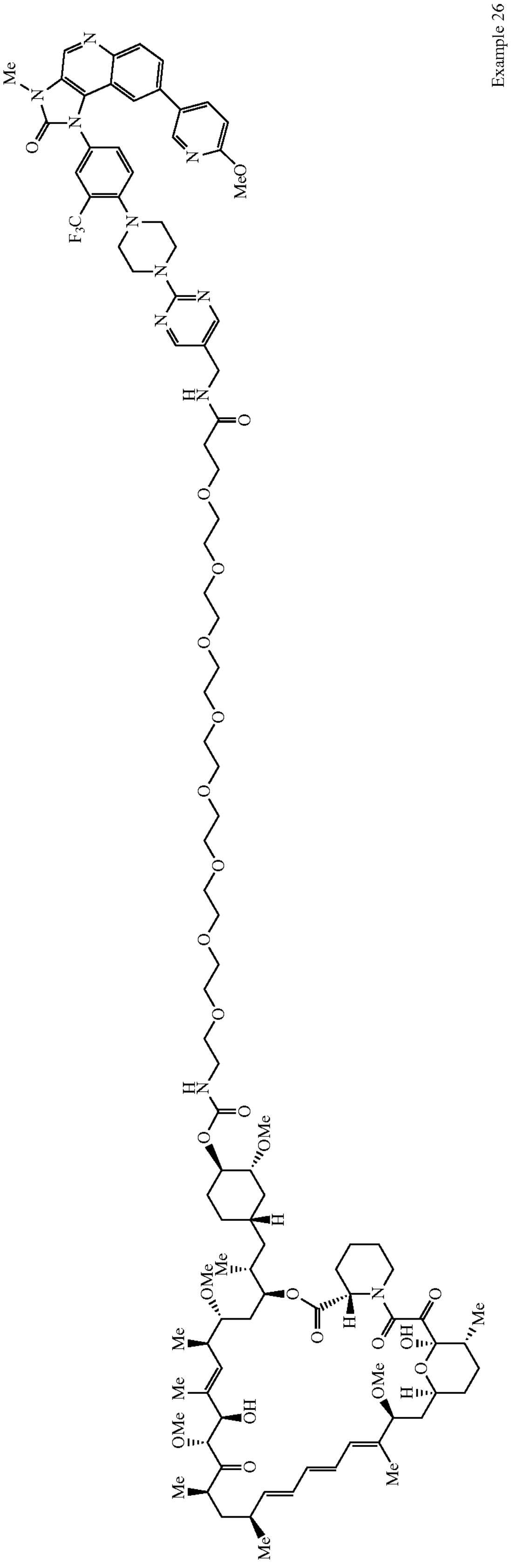
Example 26
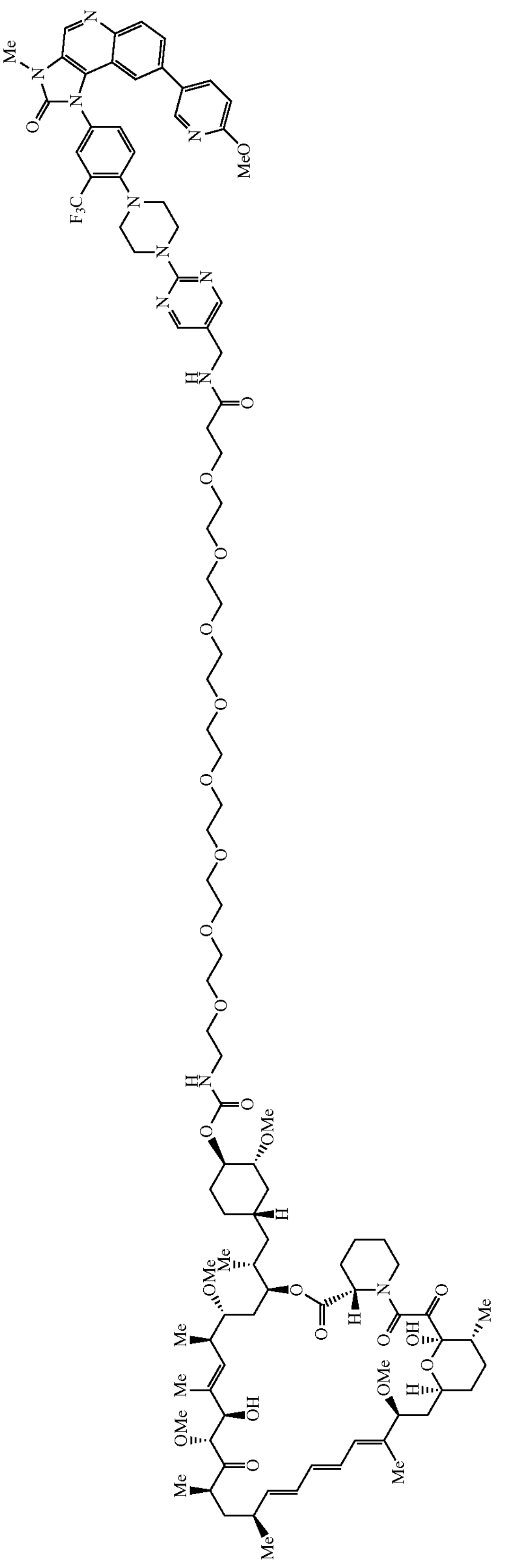

-continued
Example 27
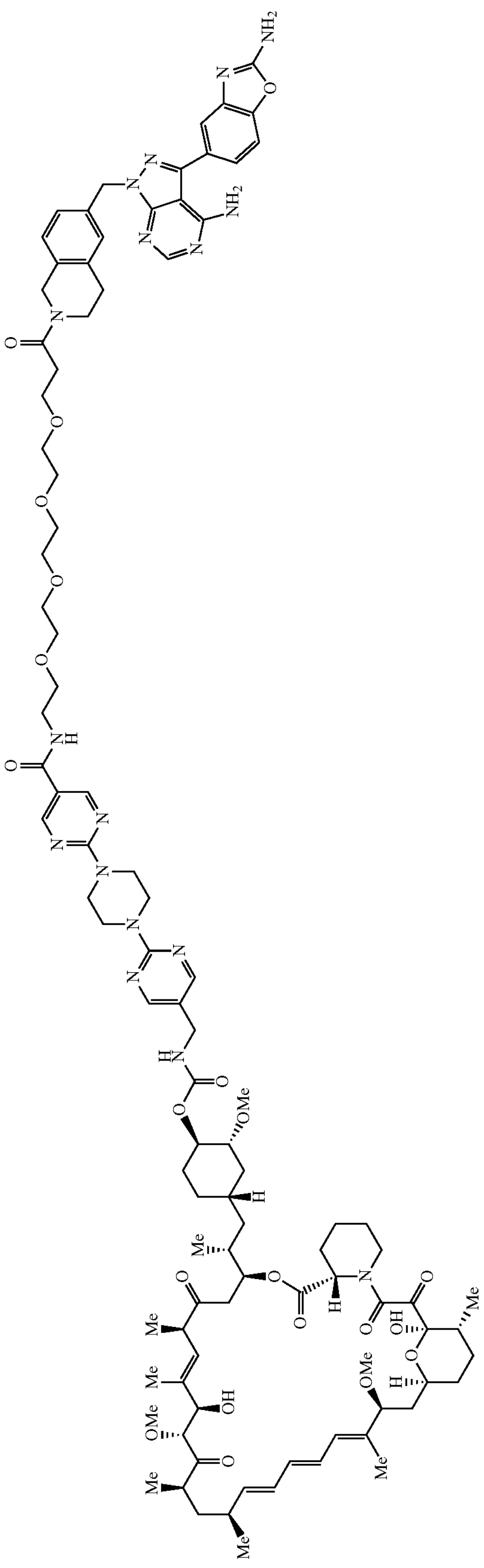
Example 28
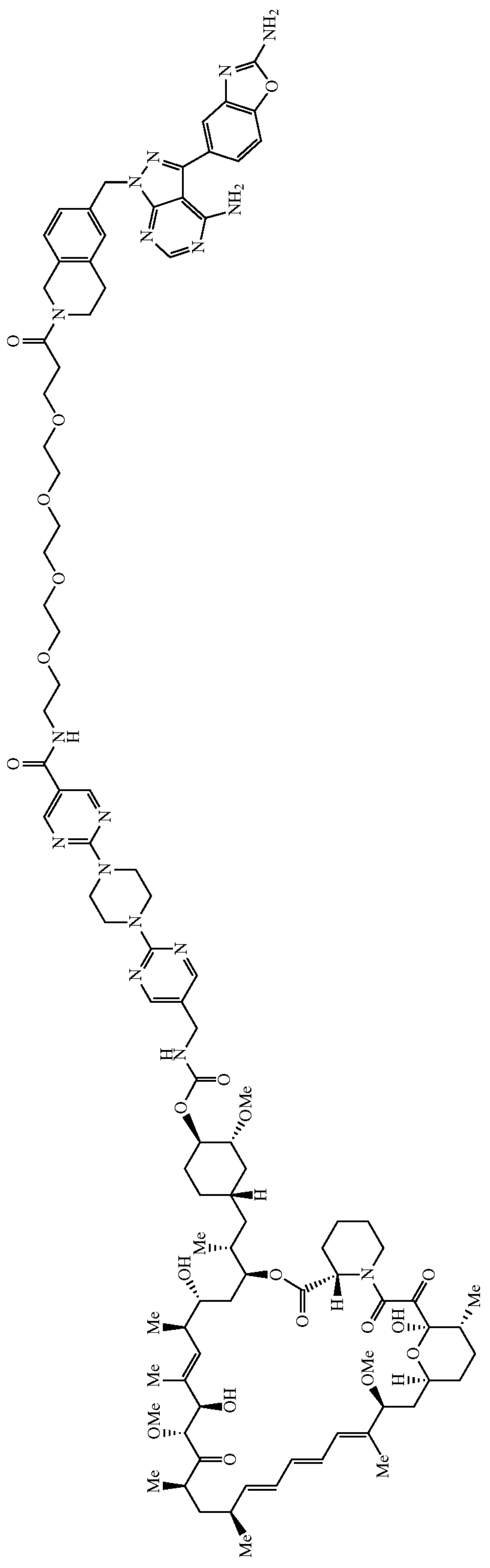

-continued
Example 29
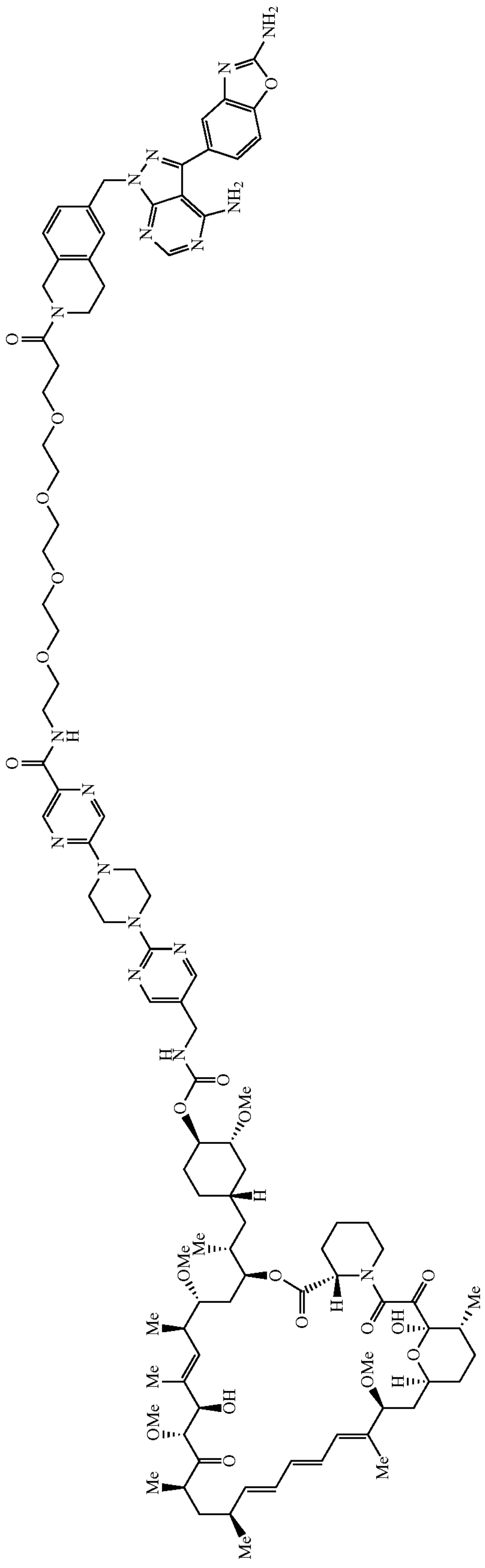
Example 30
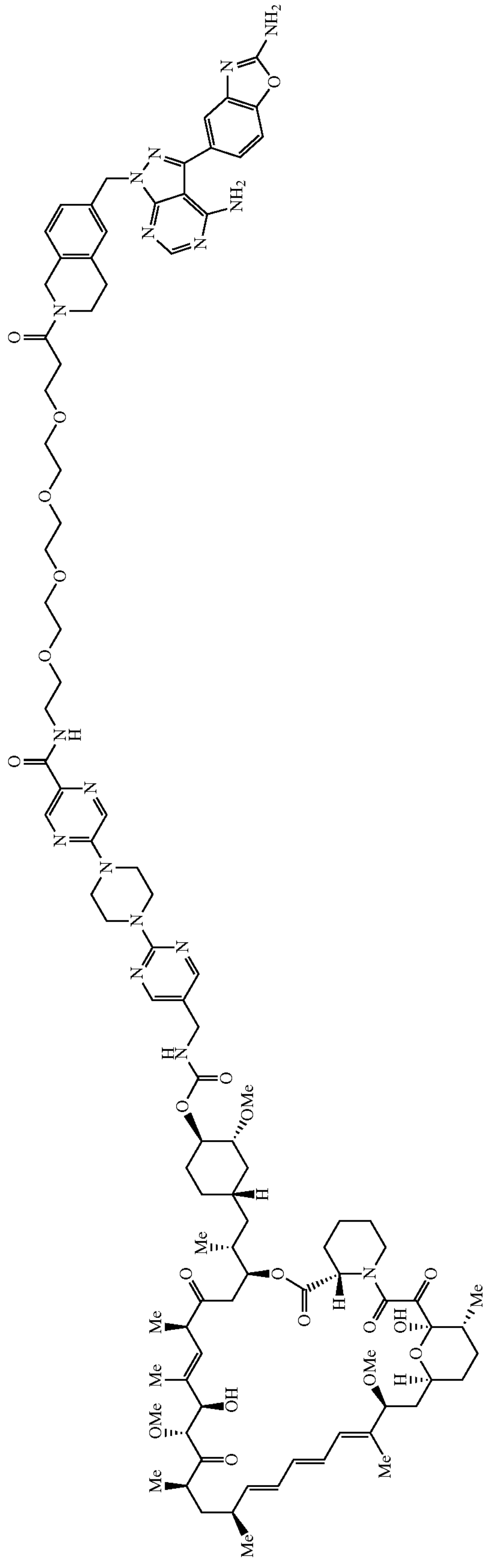

-continued
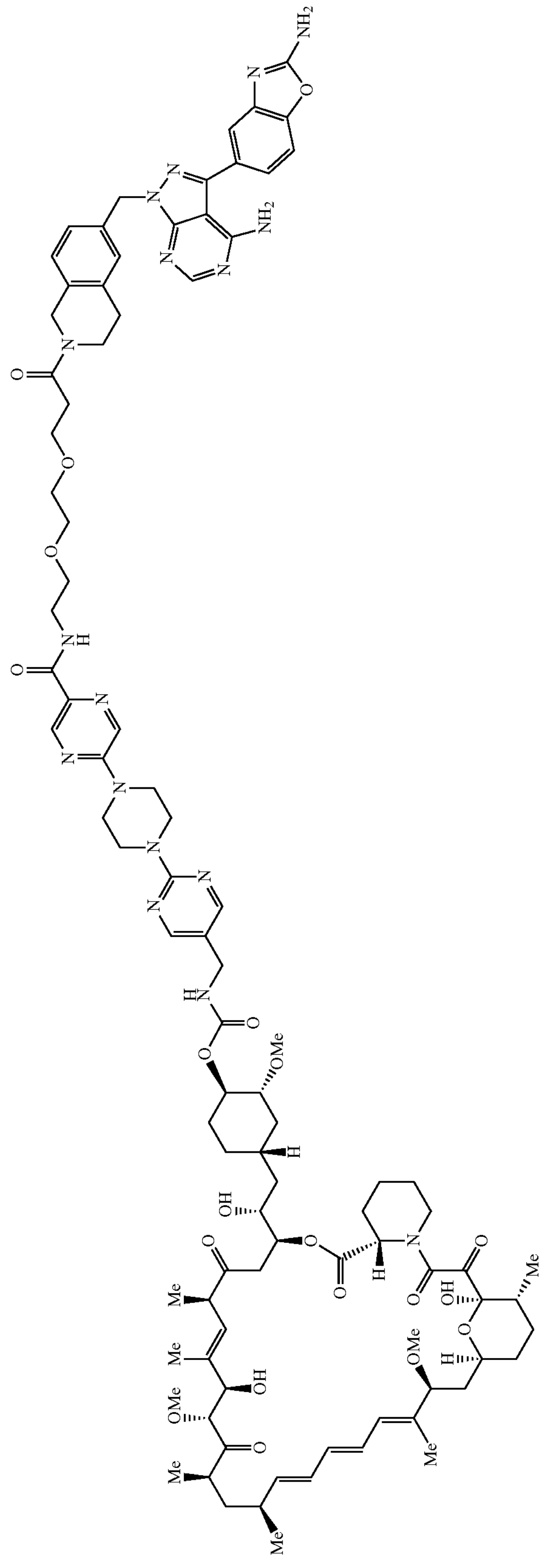
Example 31

-continued
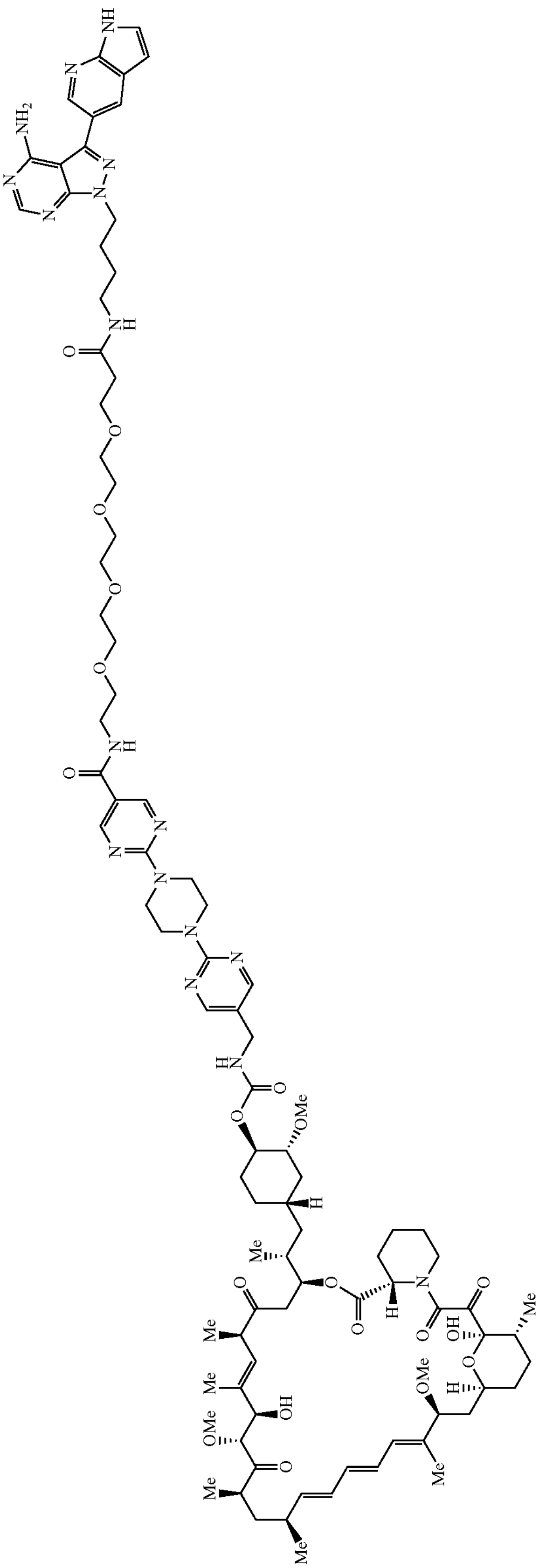
Example 32

-continued
Example 33
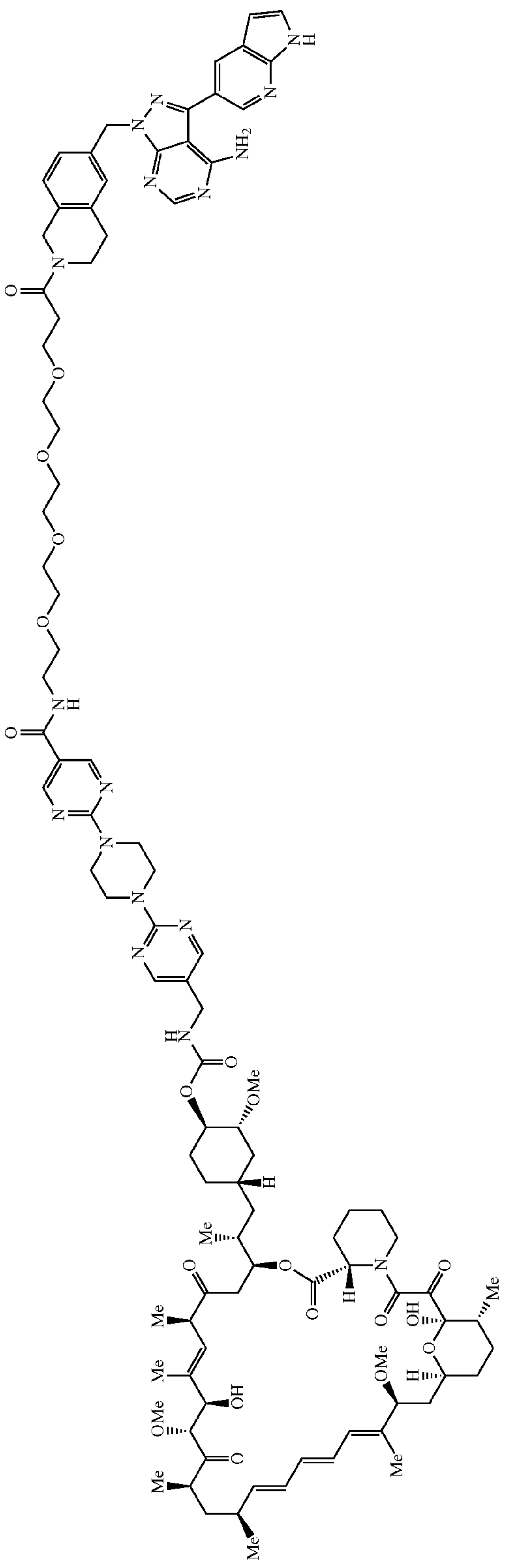

-continued
Example 34
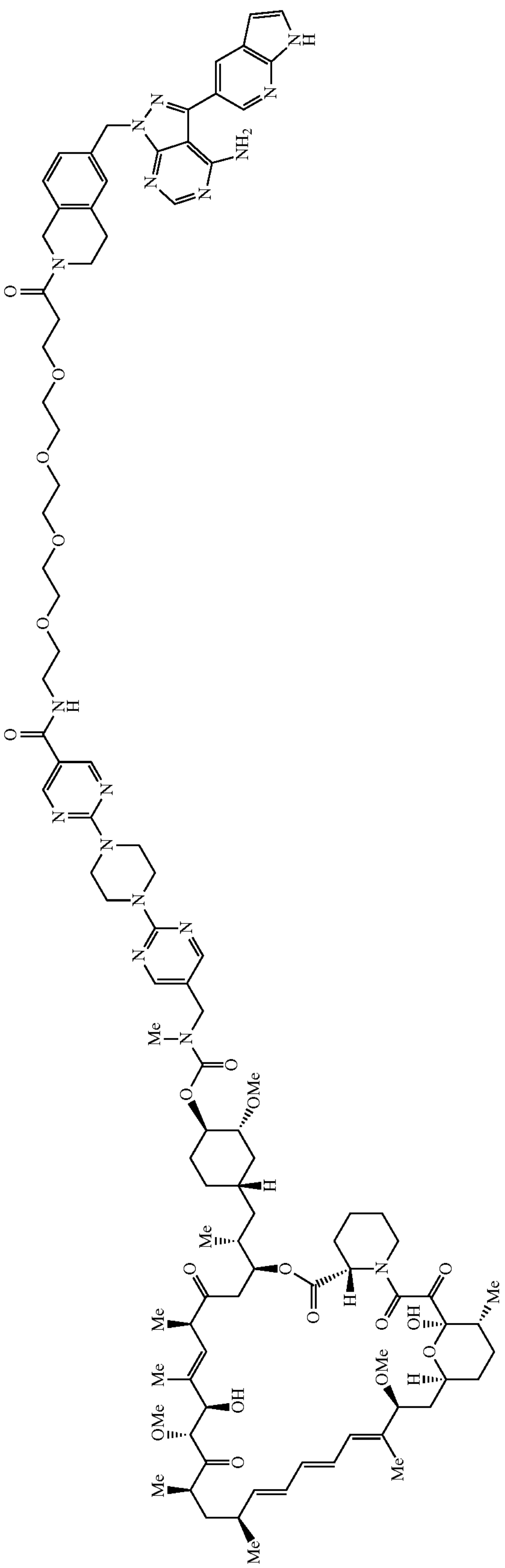

-continued
Example 35
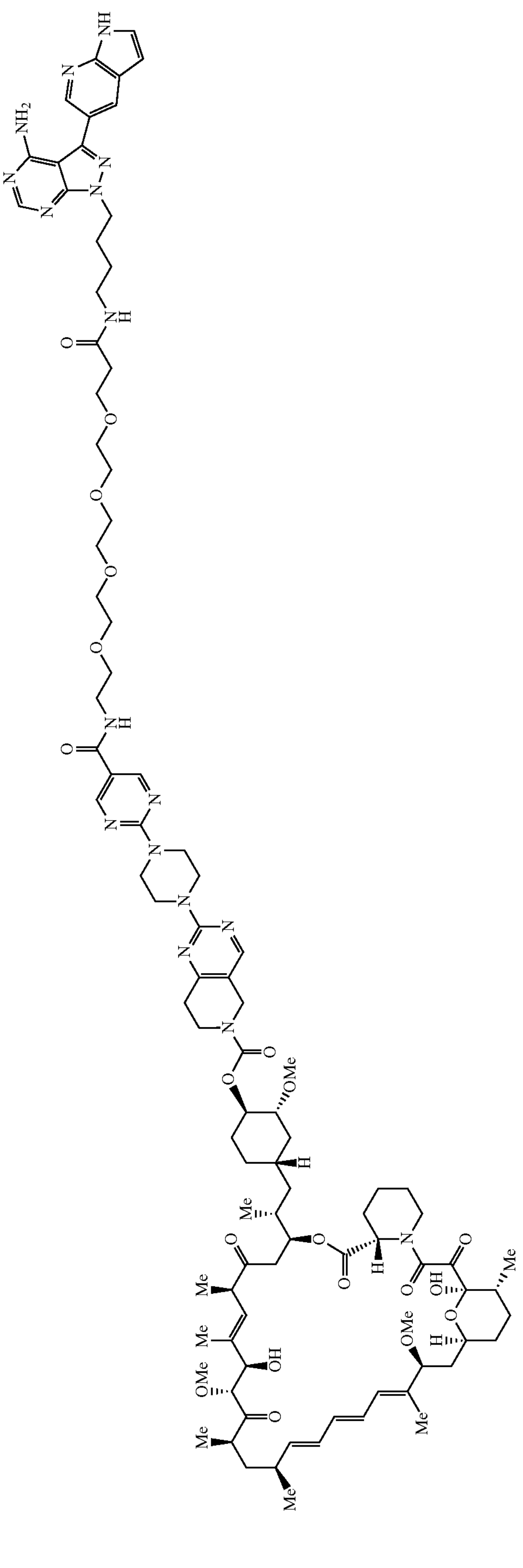

-continued
Example 36
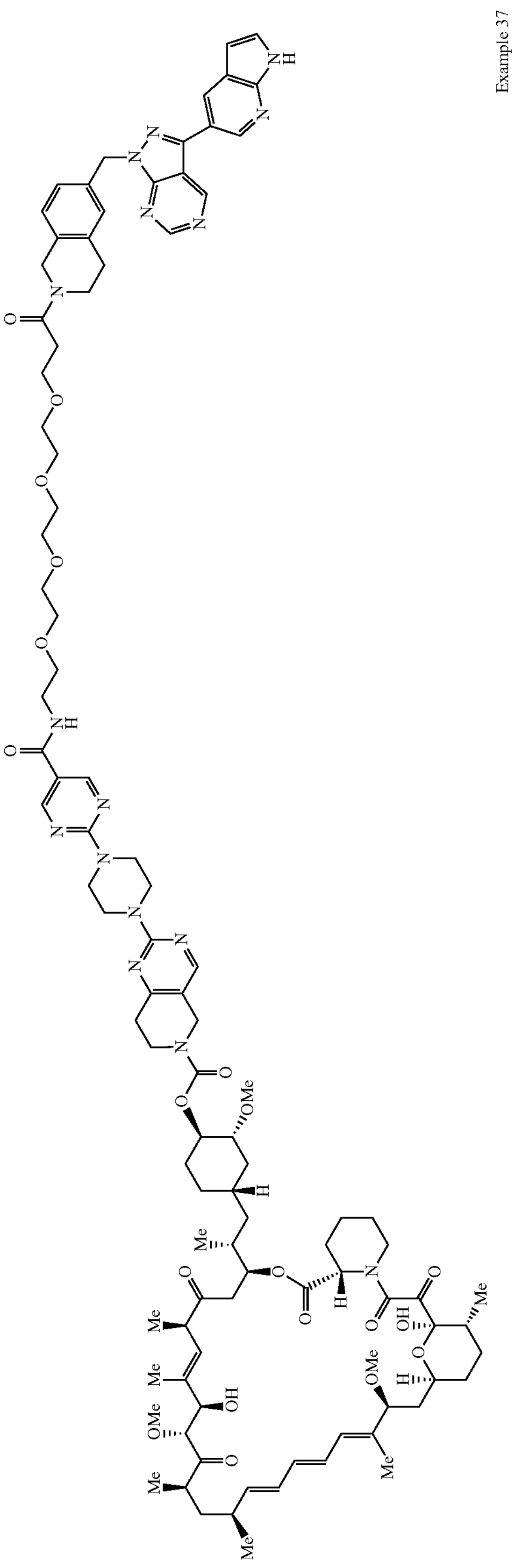
Example 37
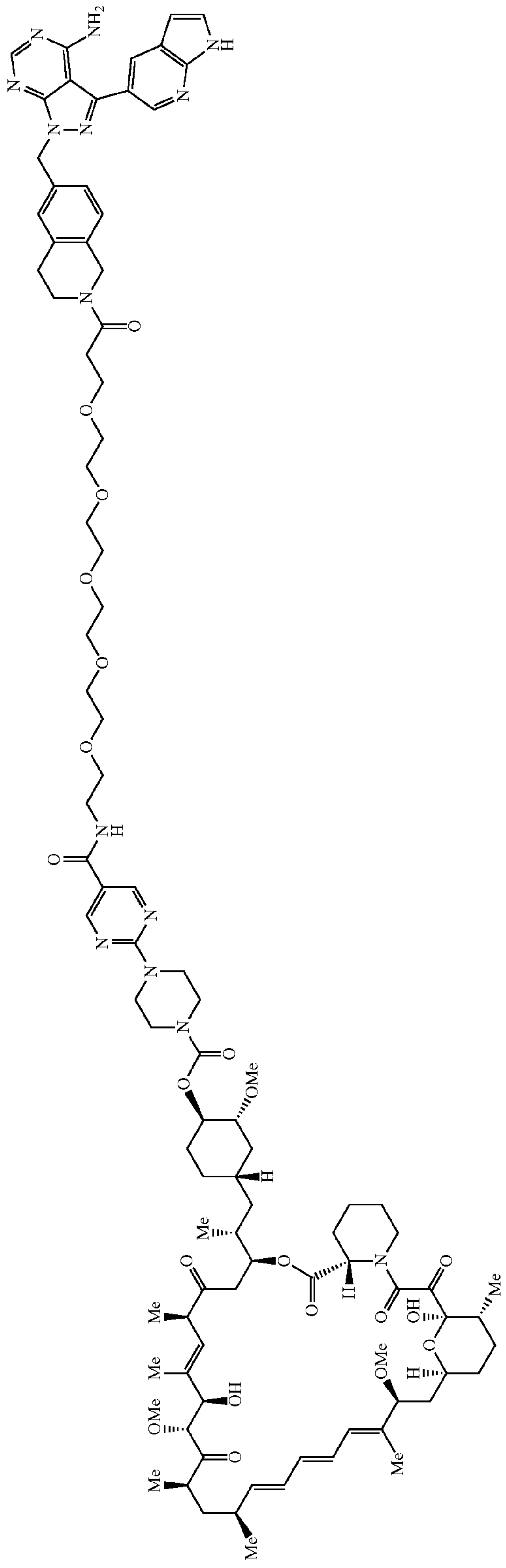

-continued
Example 38
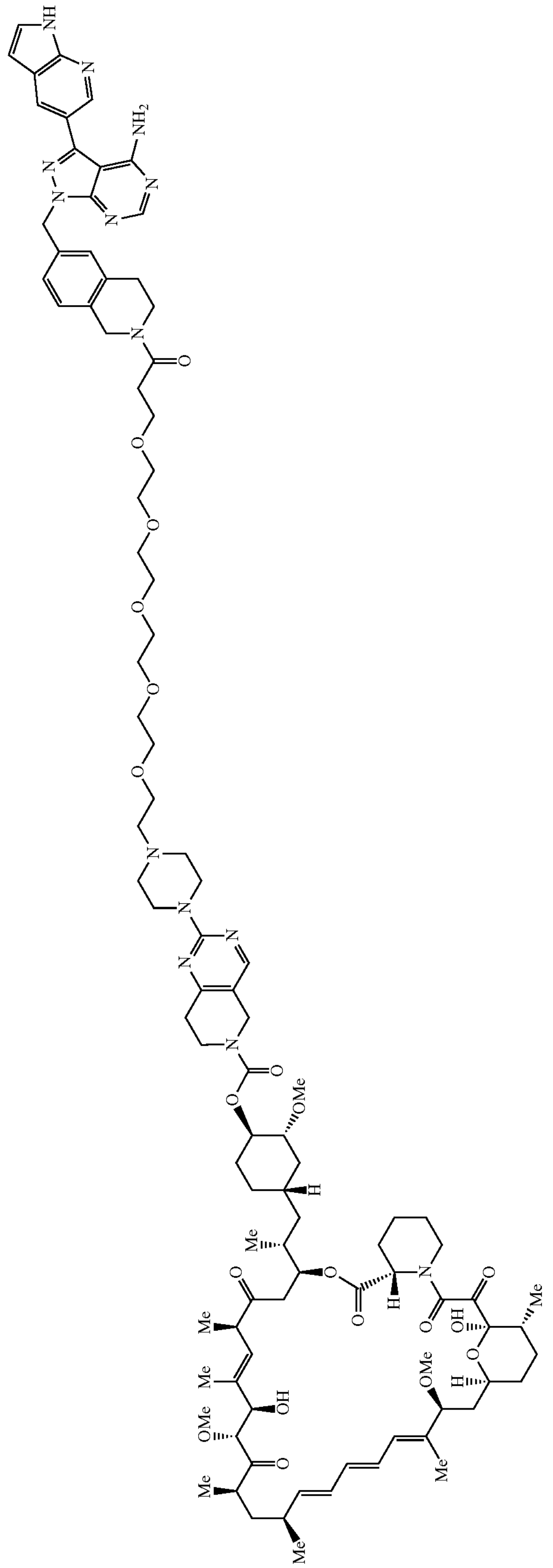

-continued
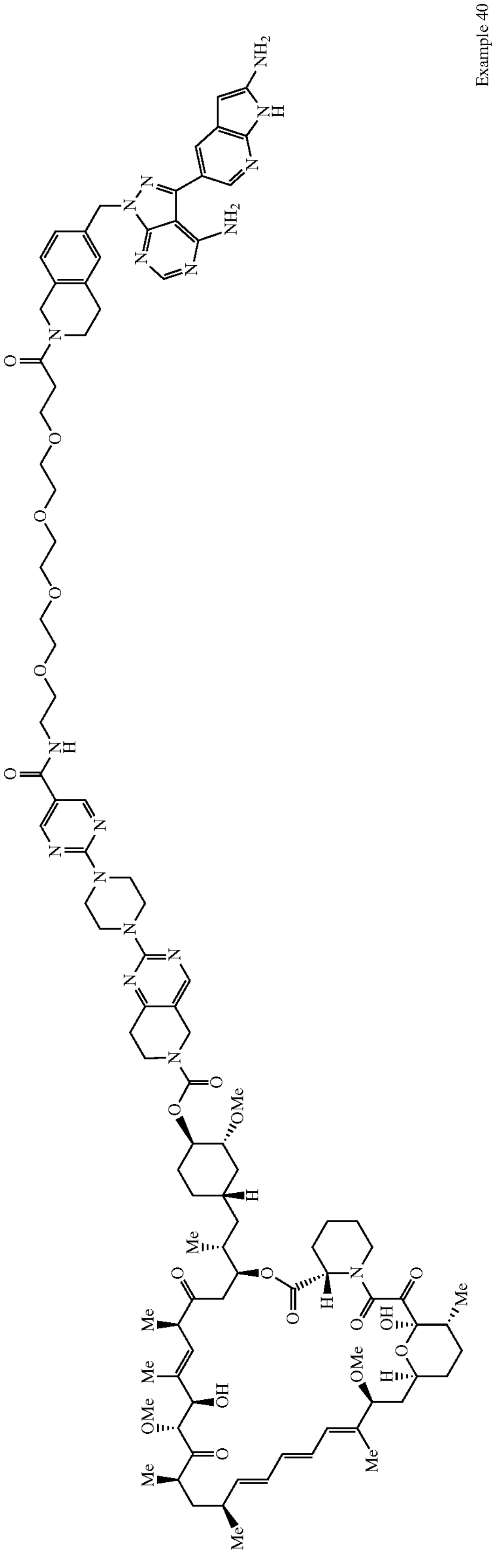
Example 39
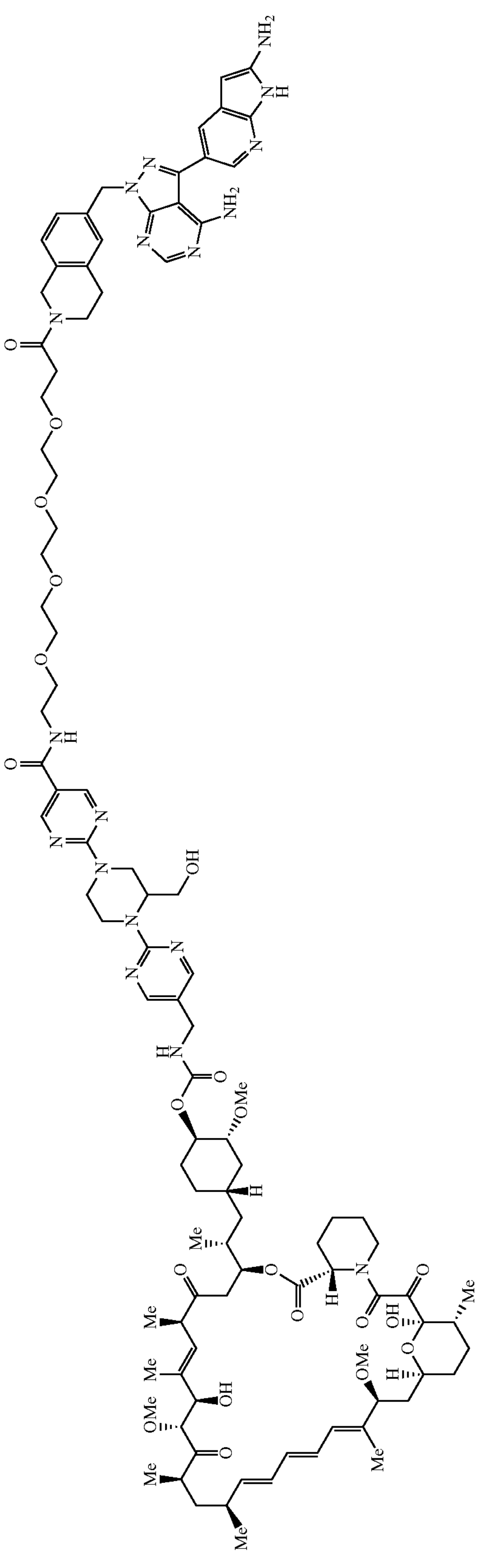
Example 40

-continued
Example 41
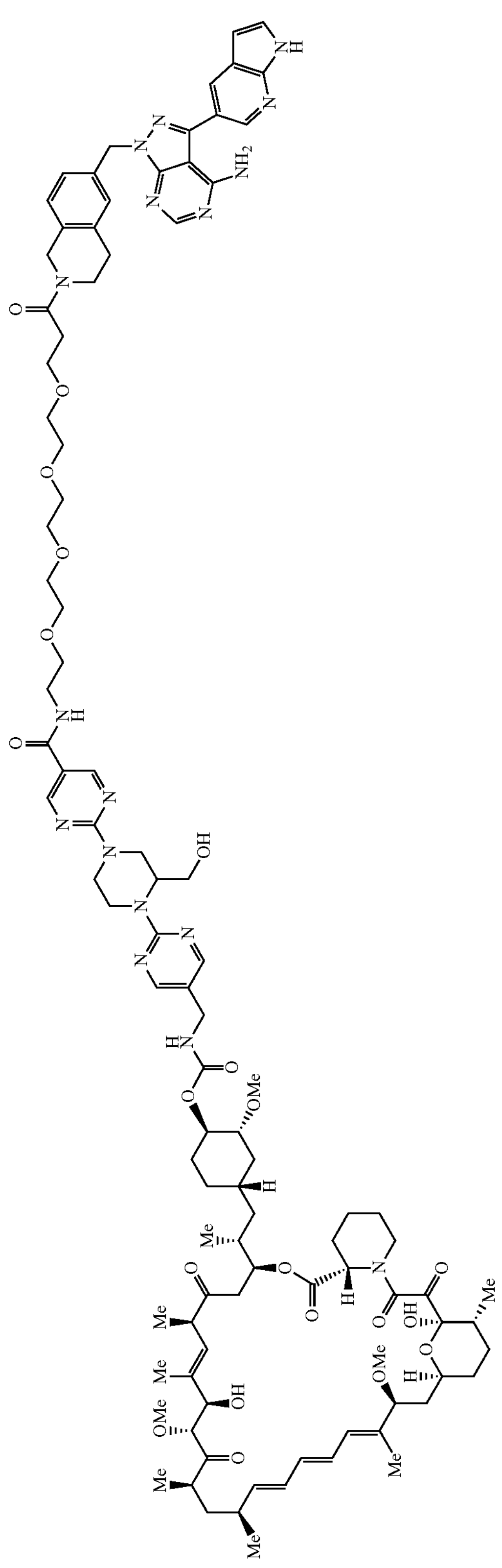
Example 42
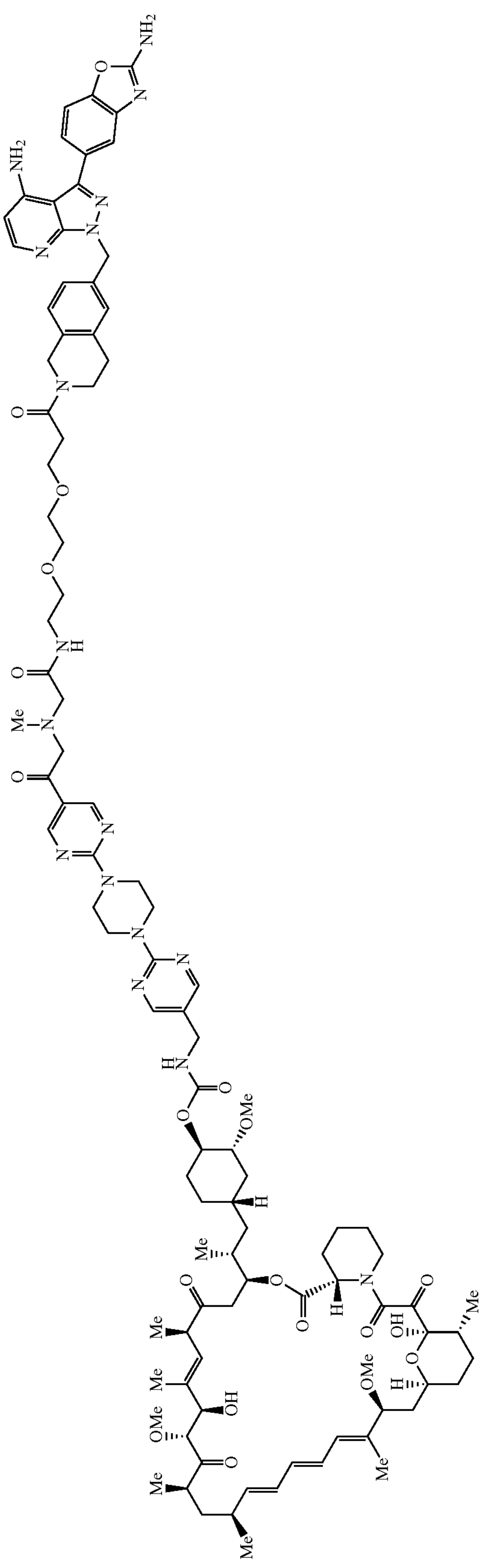

-continued
Example 43
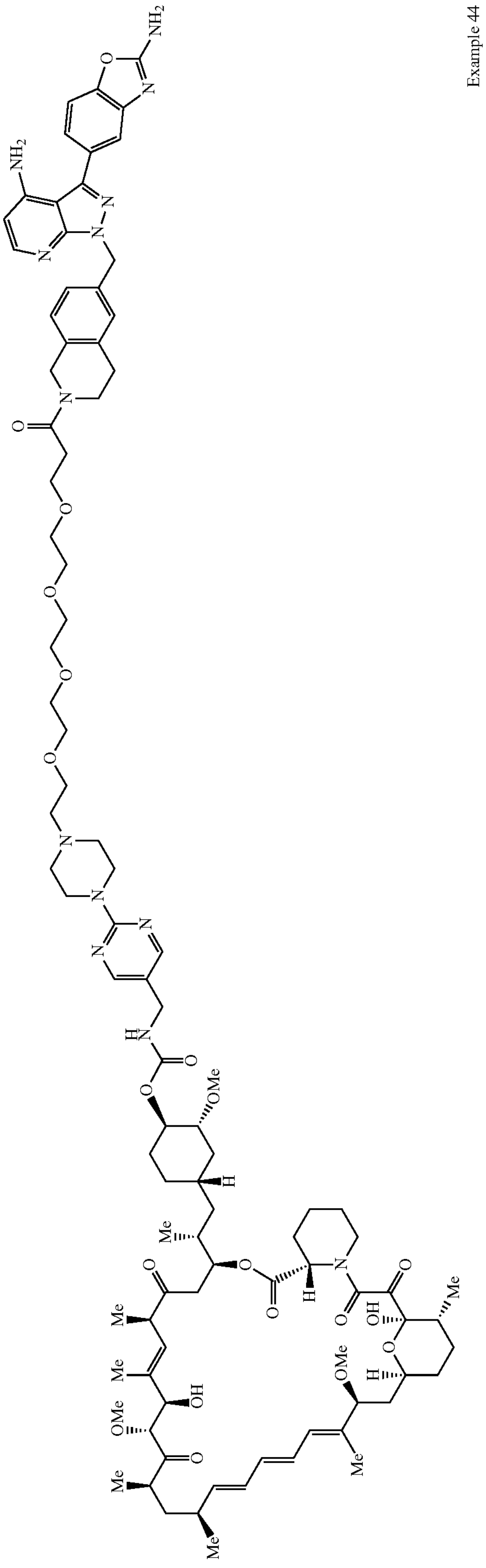
Example 44
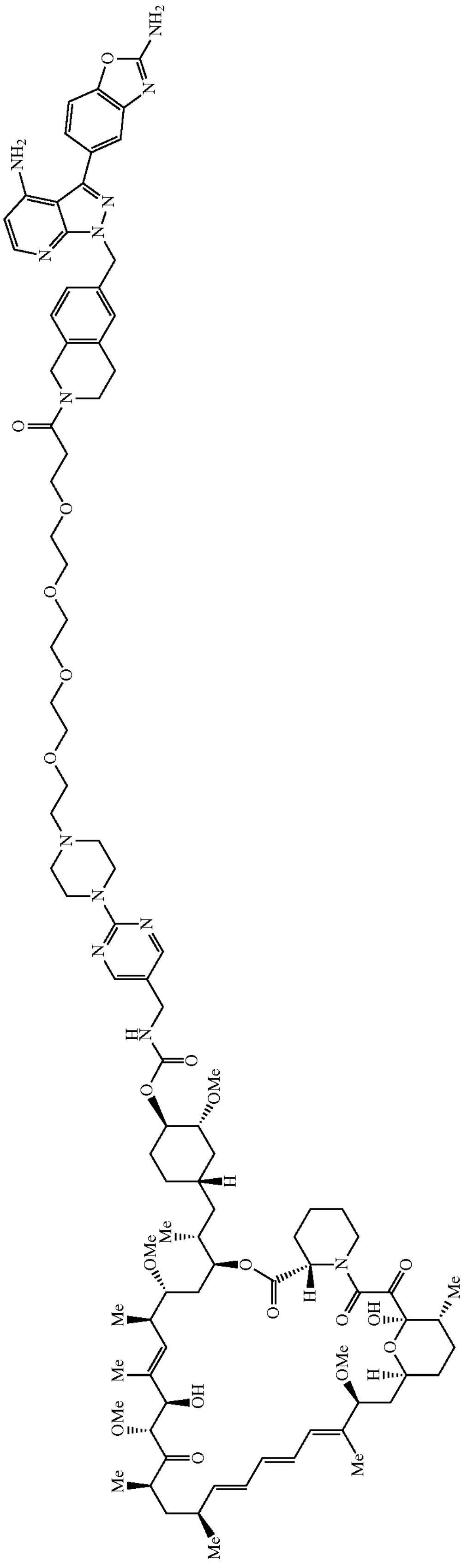

-continued
Example 45
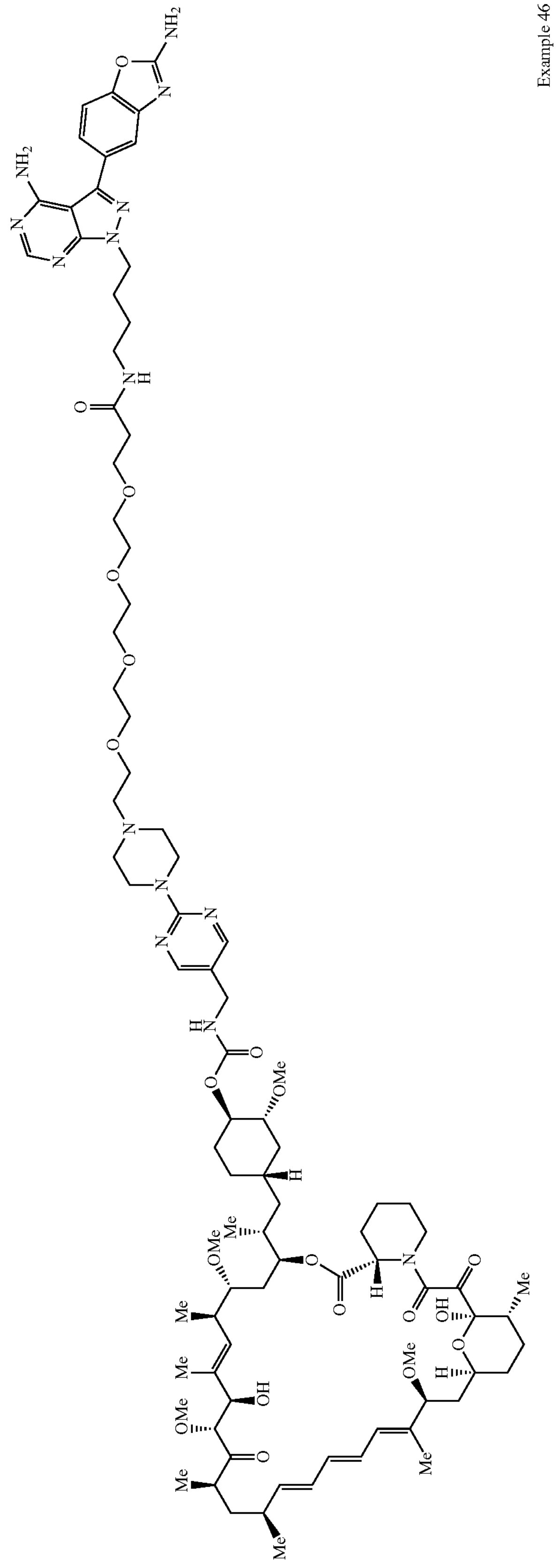
Example 46
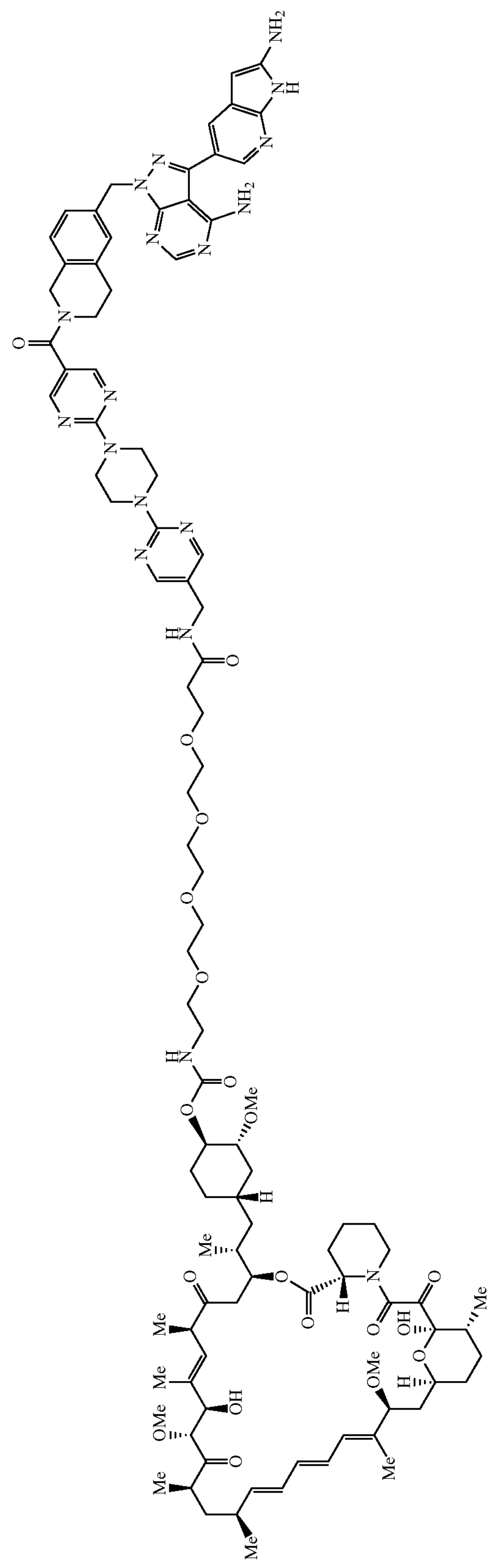

-continued
Example 47
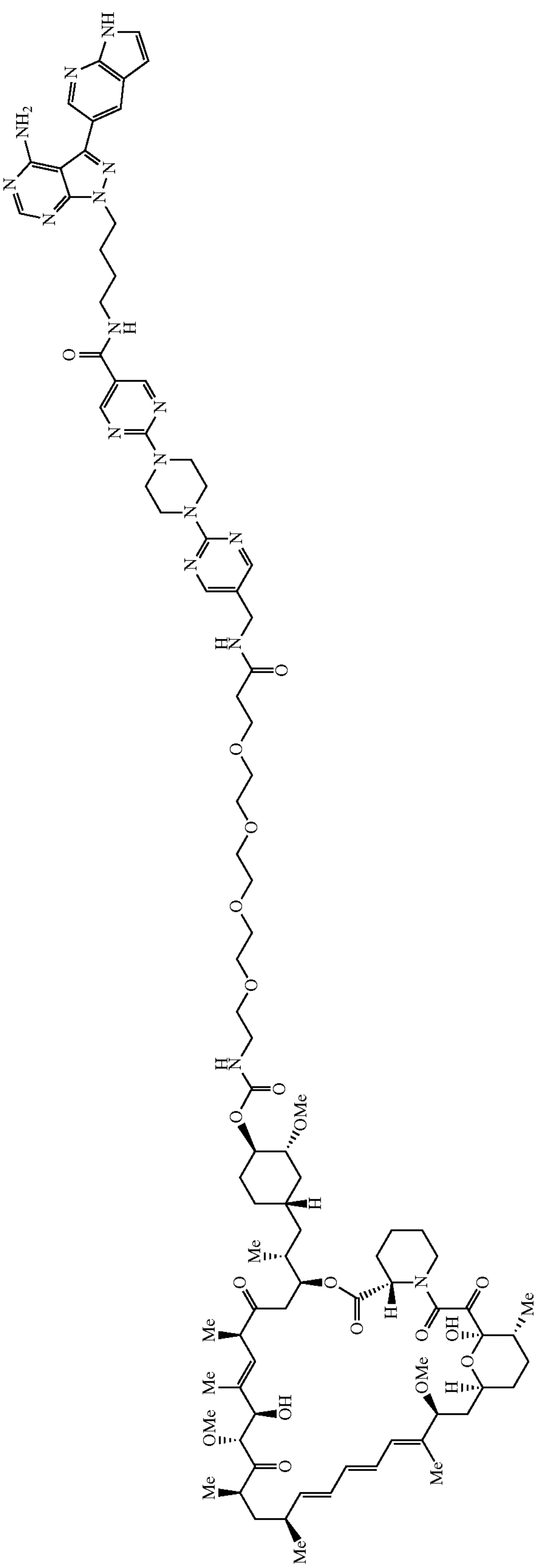

-continued
Example 48
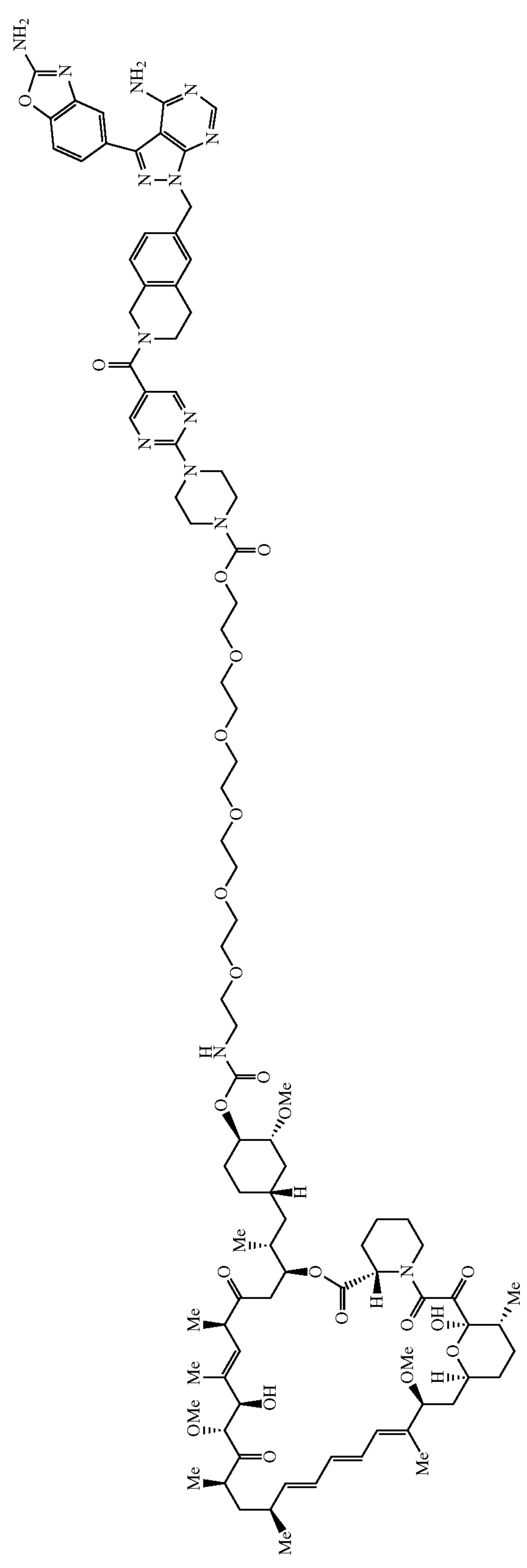
Example 49
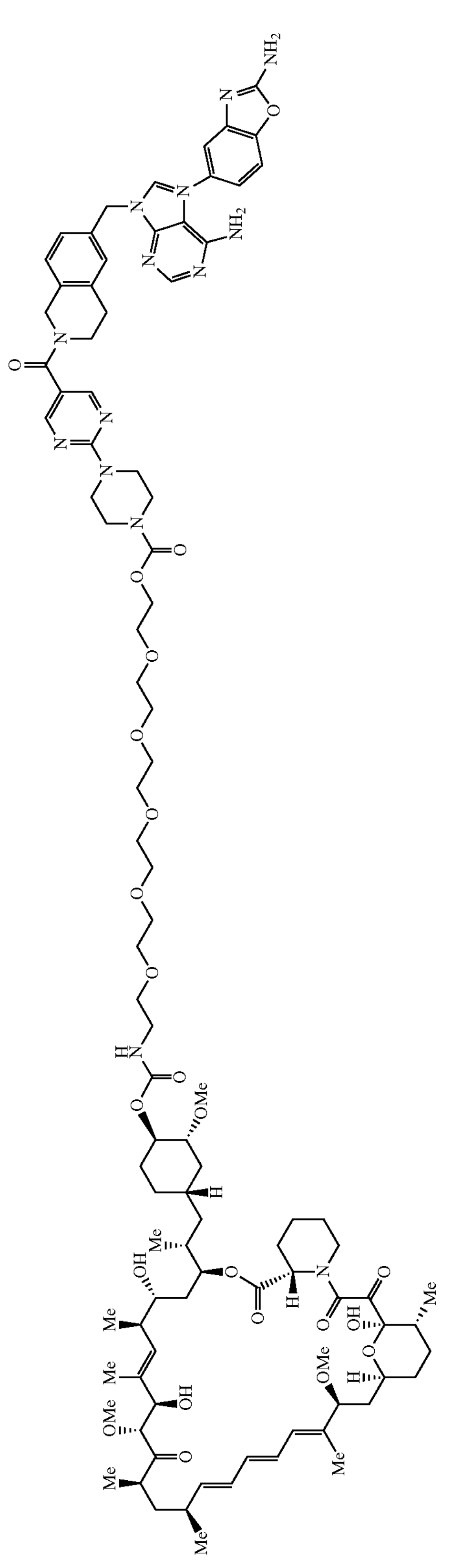

-continued
Example 50
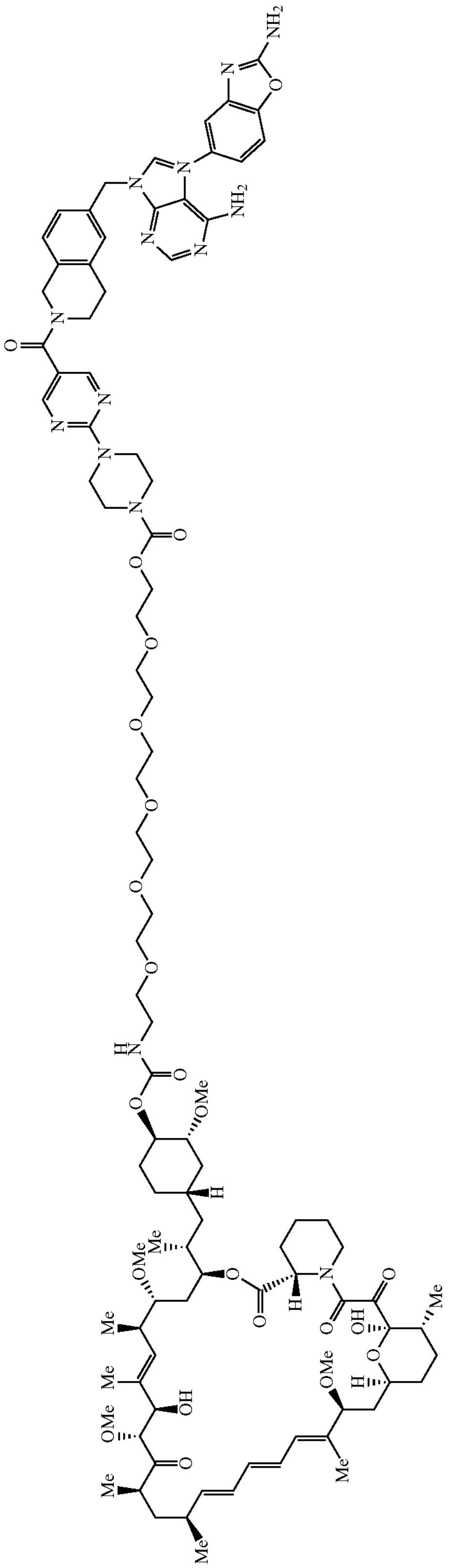

-continued
Example 51
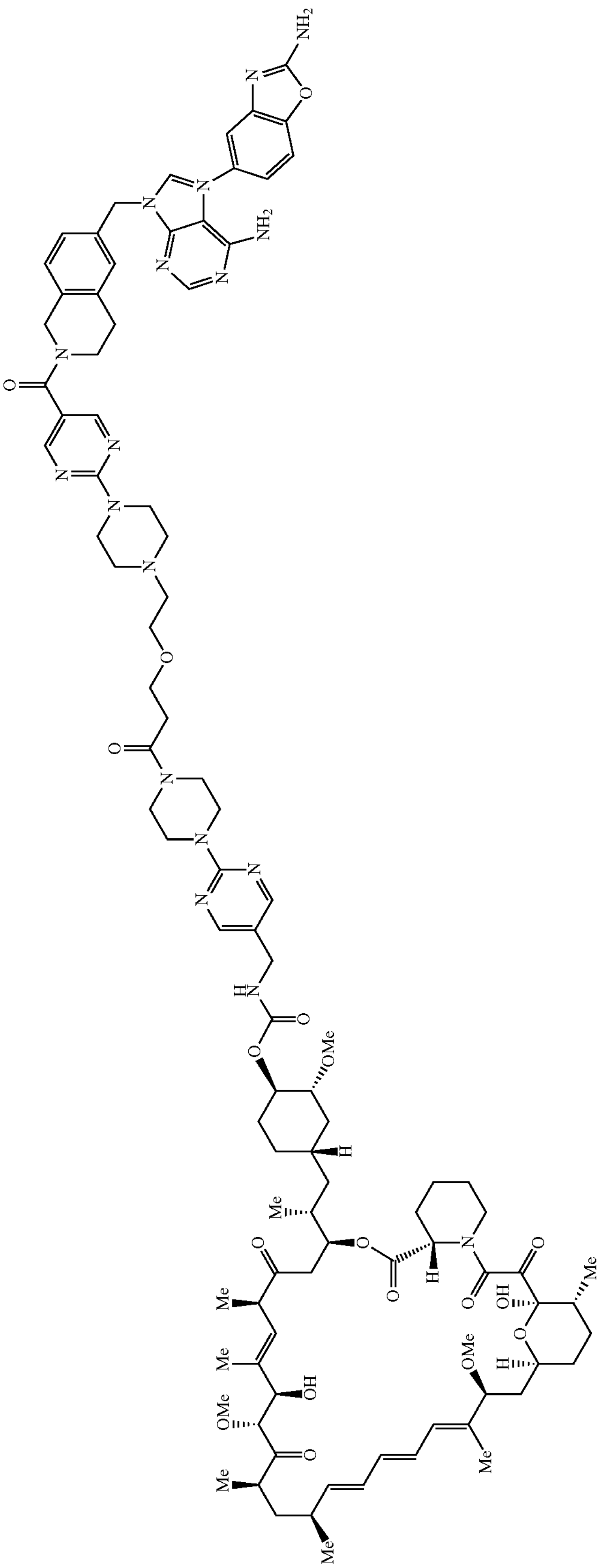

-continued
Example 52
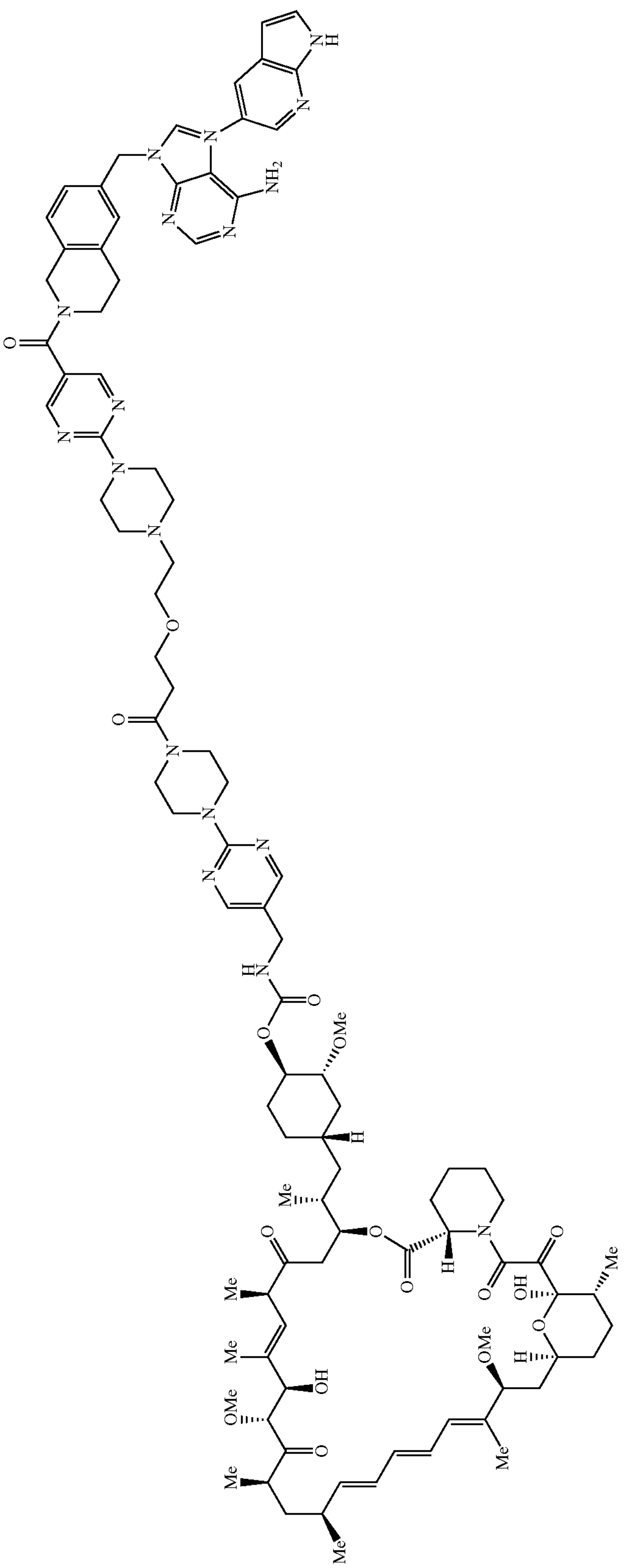

-continued
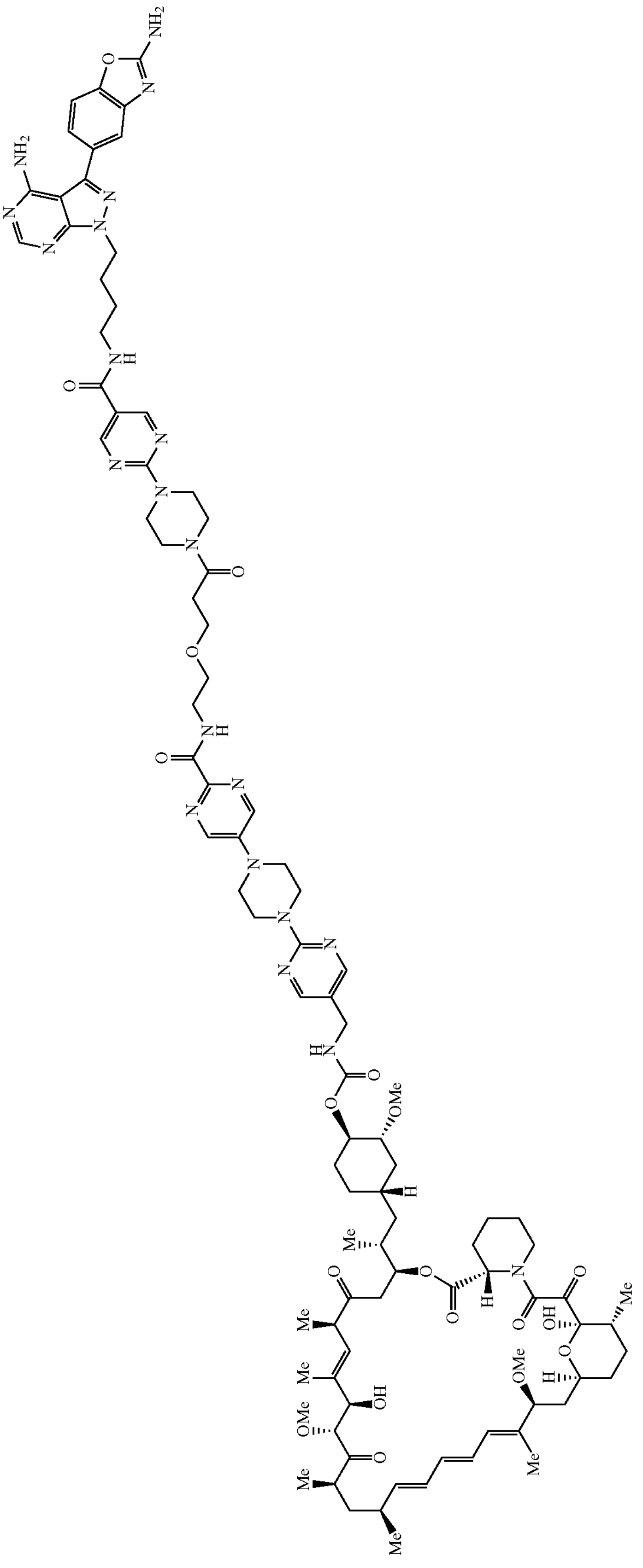
Example 53

-continued
Example 54
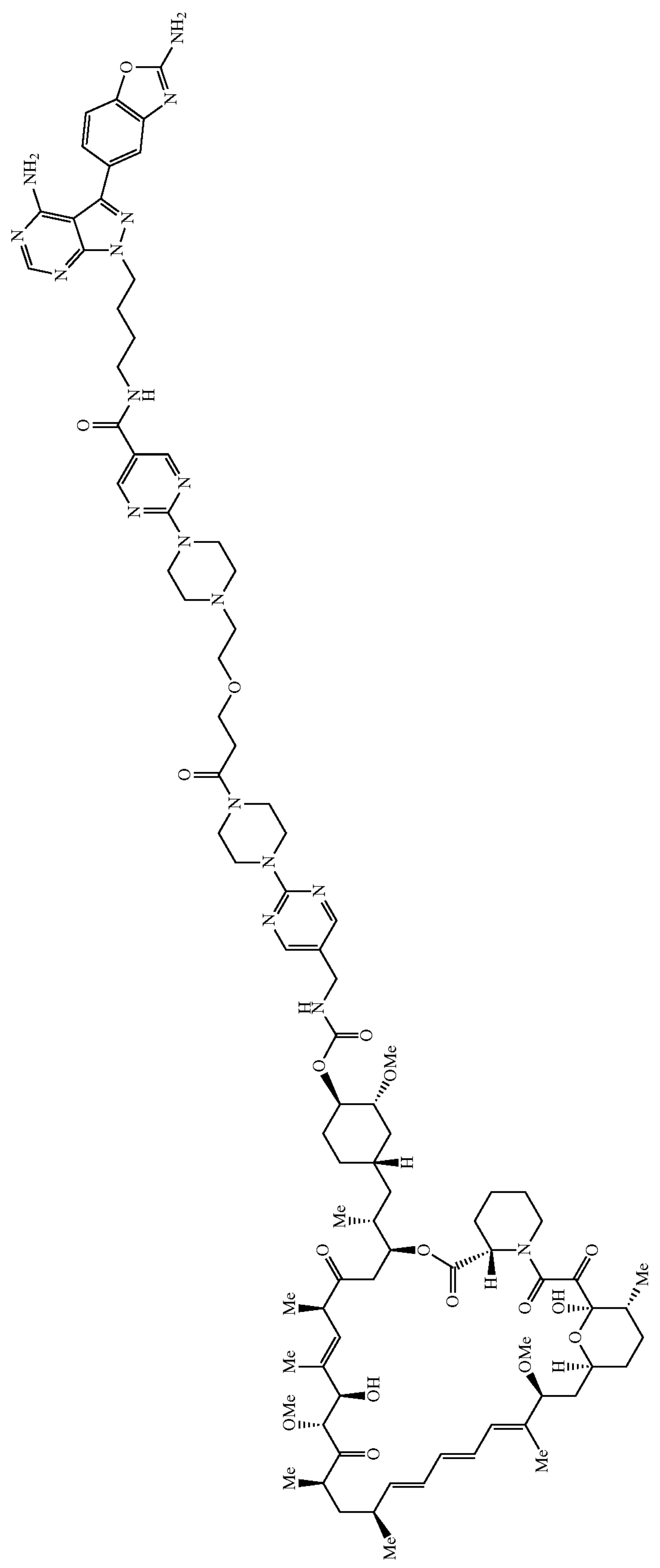

-continued
Example 55
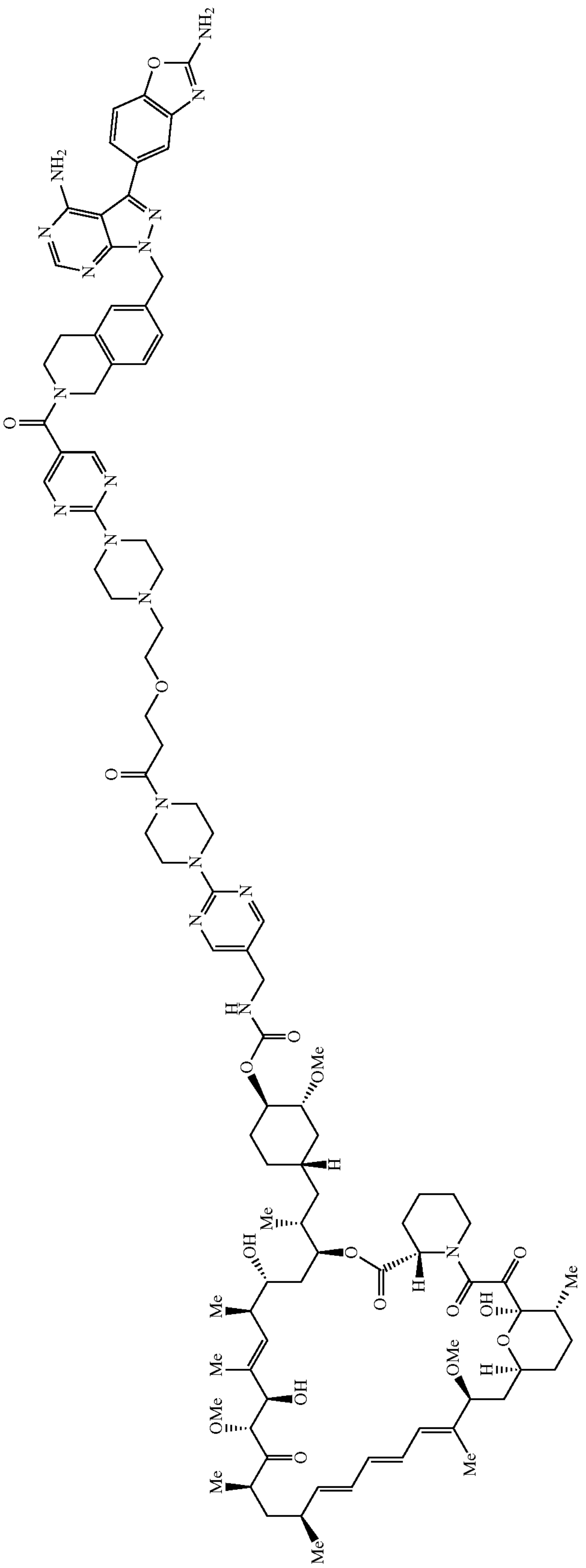

-continued
Example 56
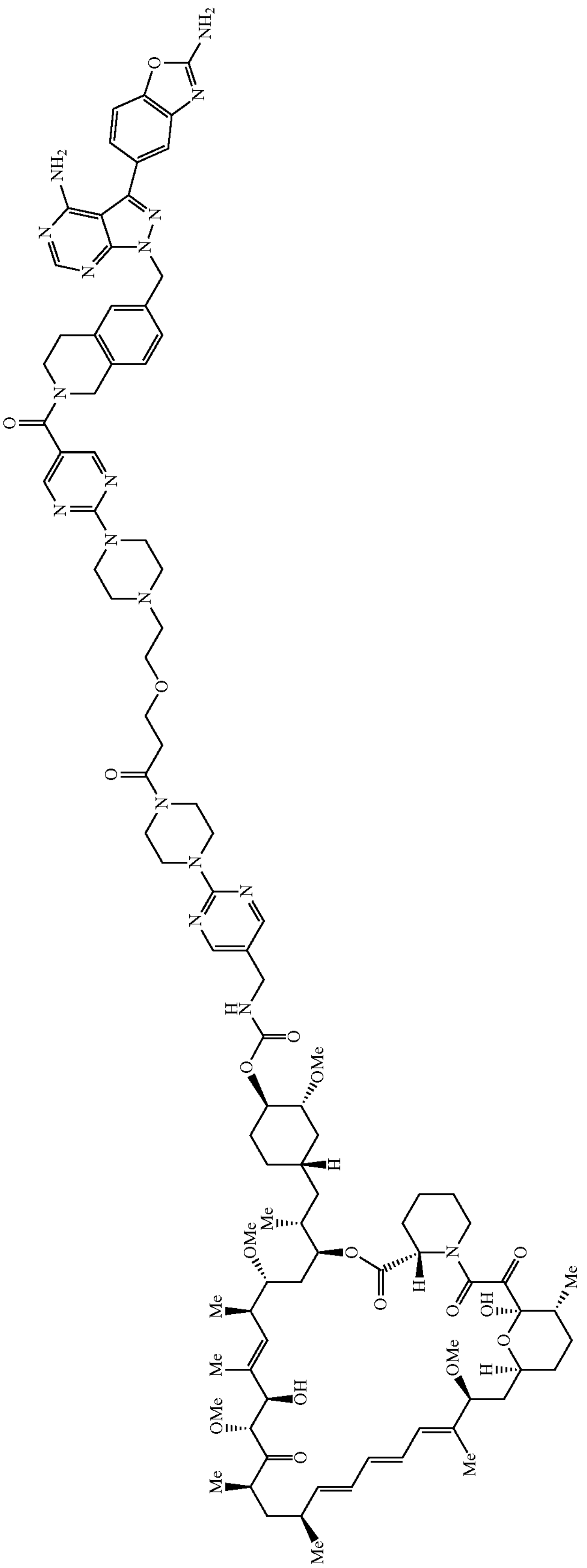

-continued
Example 57
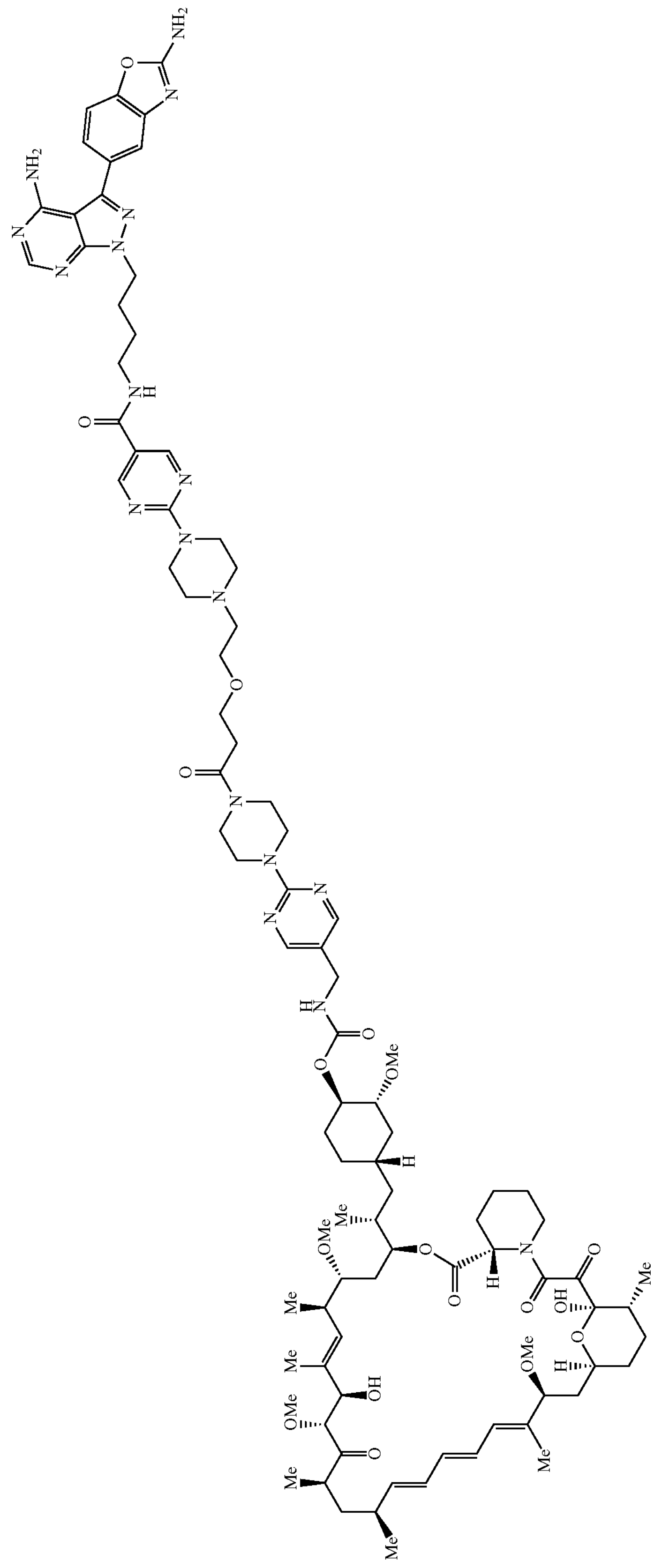

-continued
Example 58
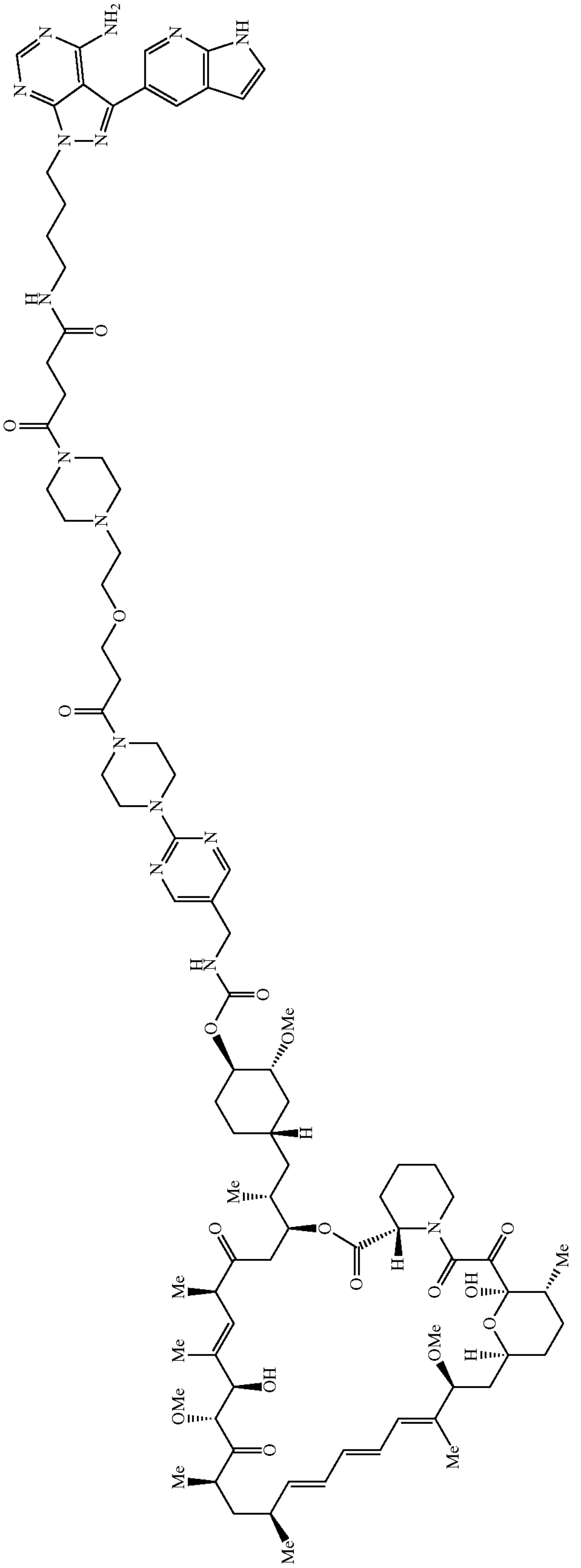

-continued
Example 59
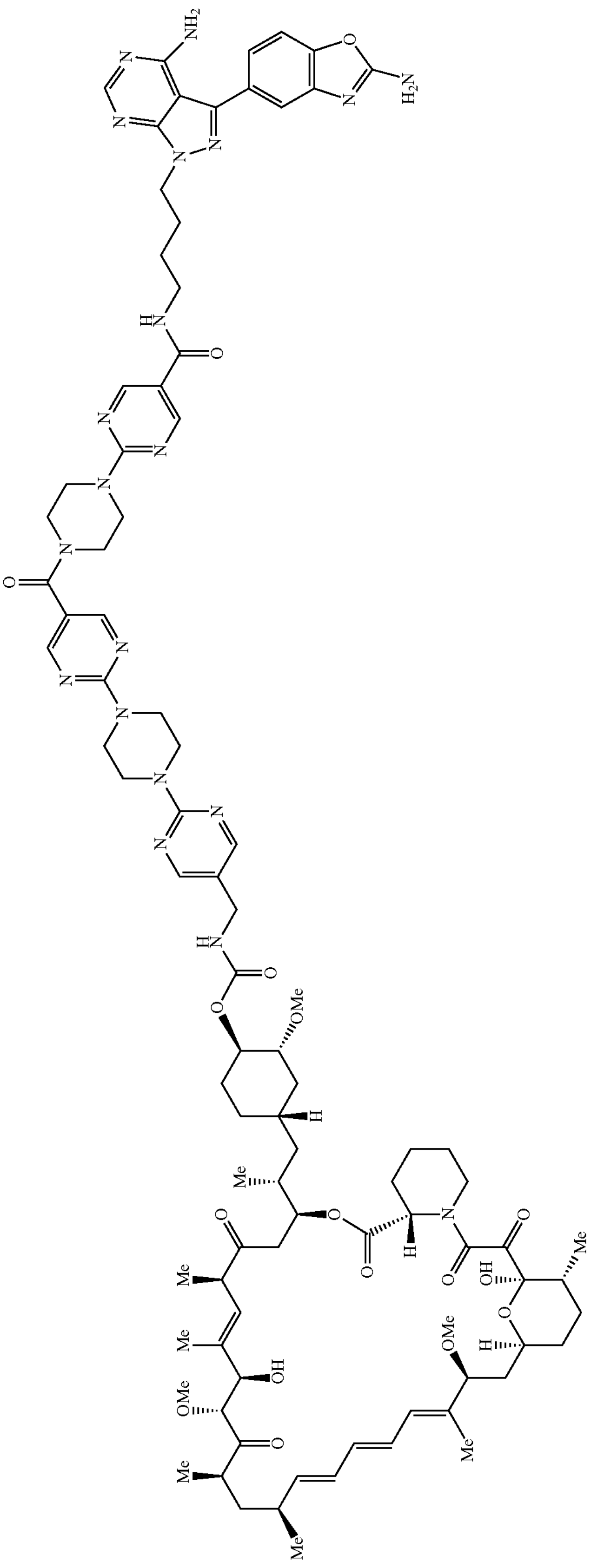

-continued
Example 60
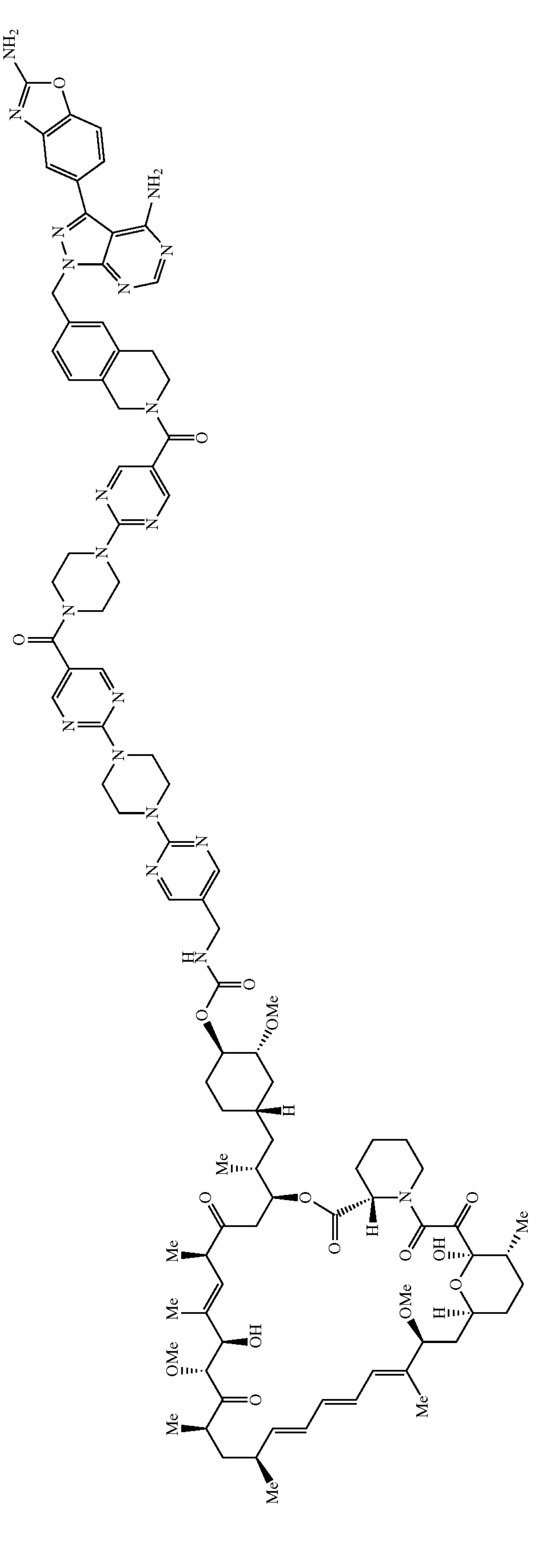

-continued
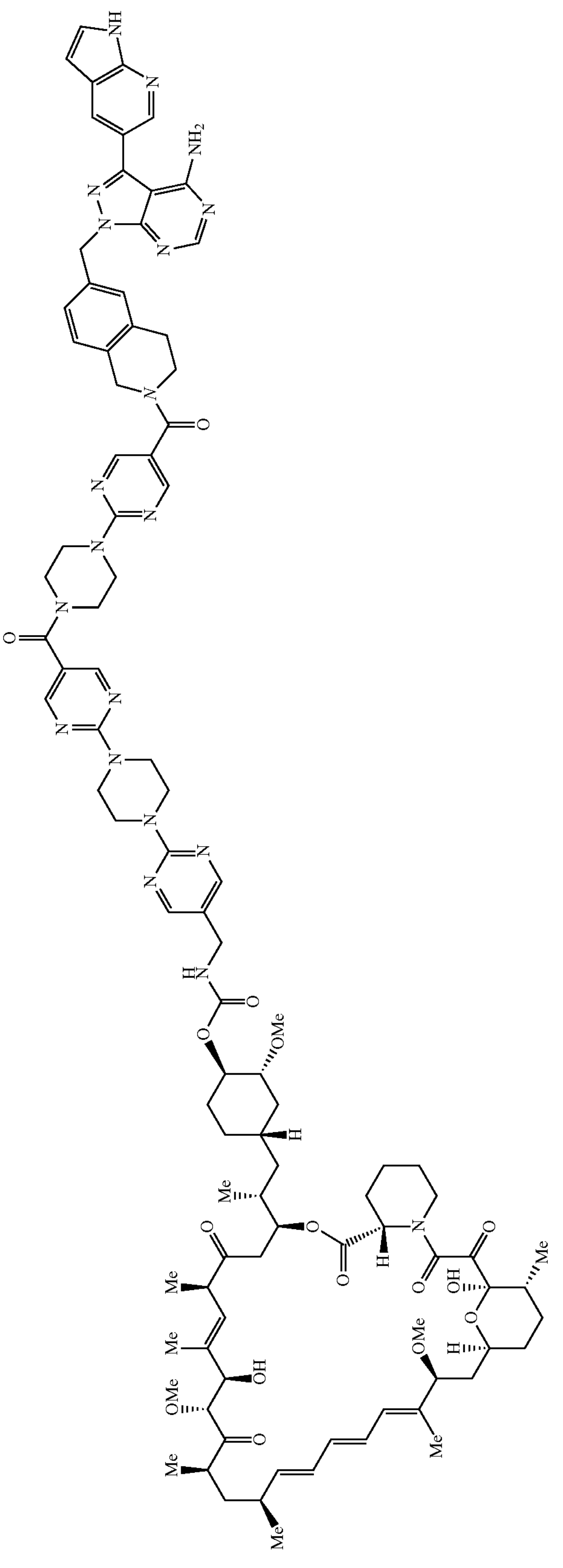
Example 61

-continued
Example 62
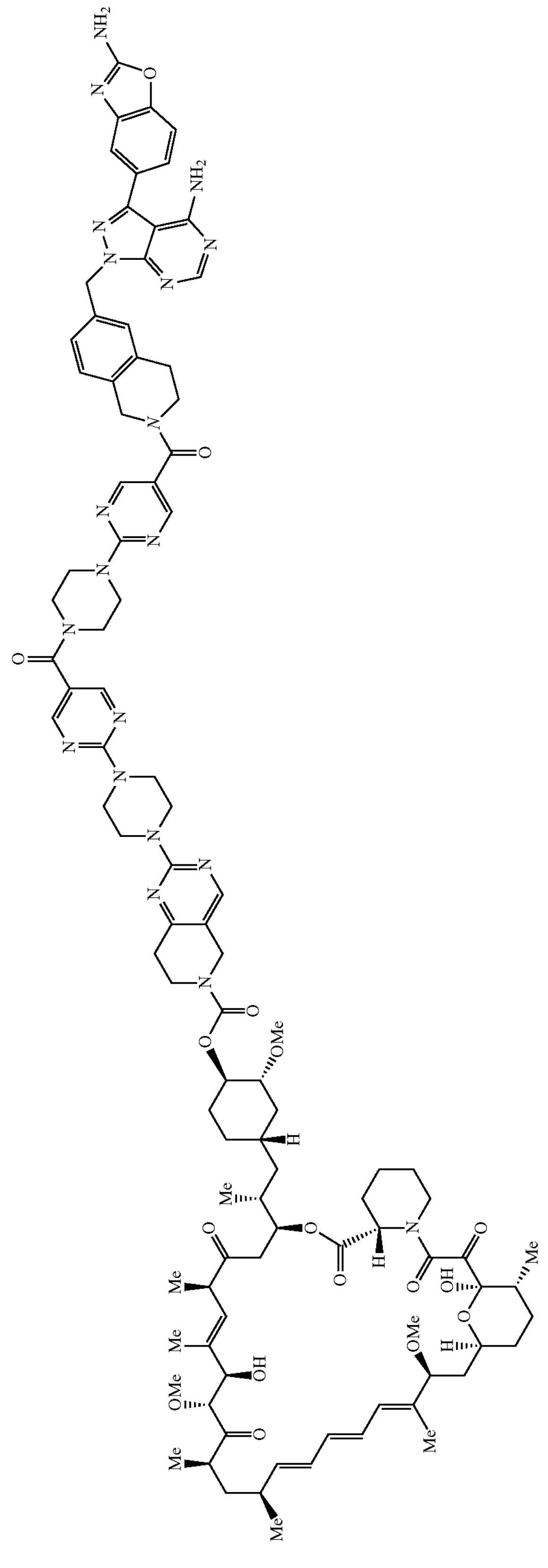

-continued
Example 63
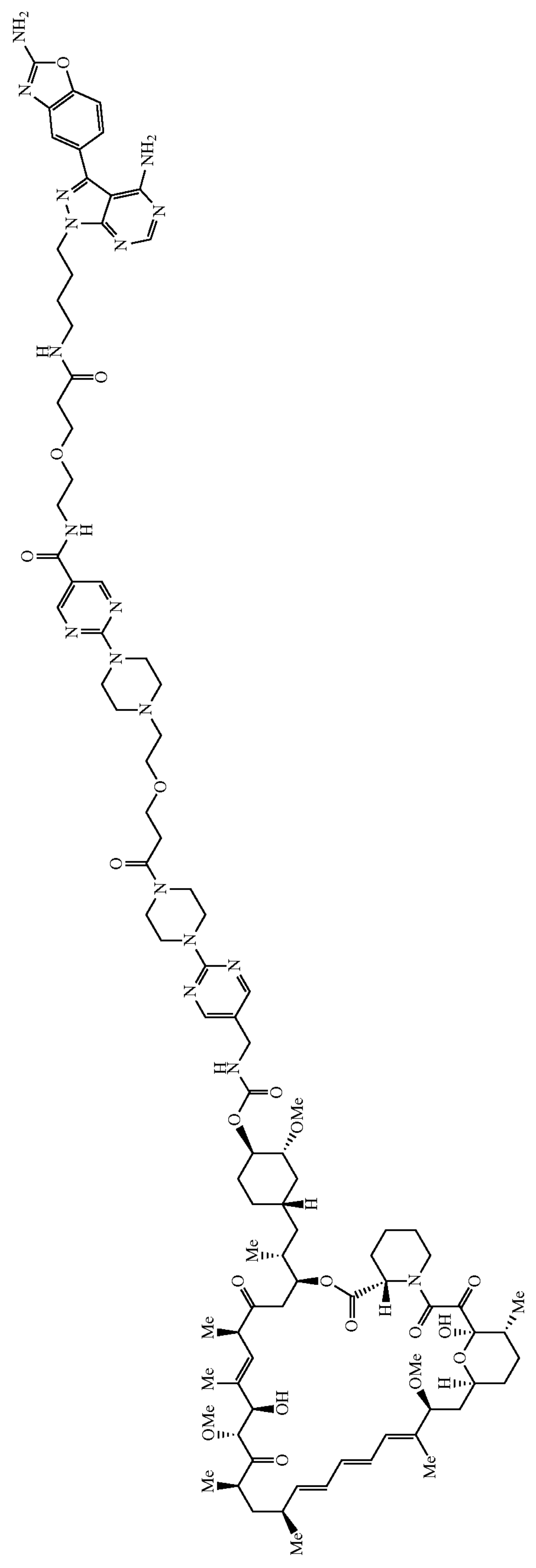

-continued
Example 64
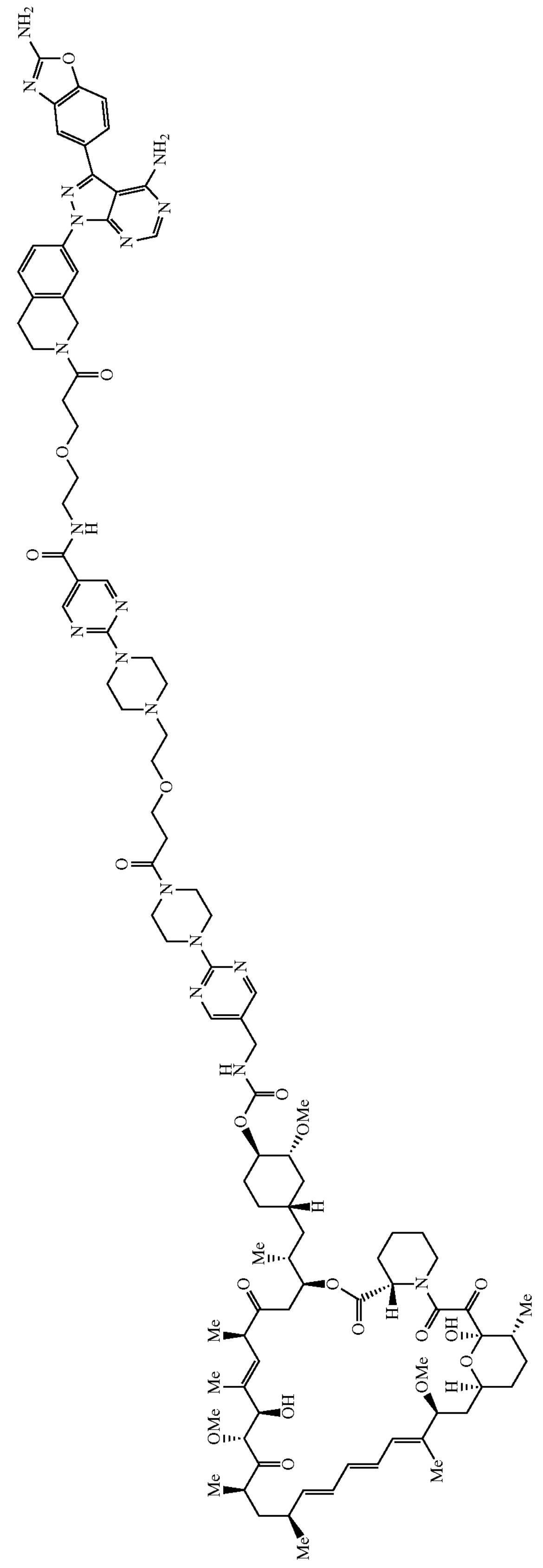

-continued
Example 65
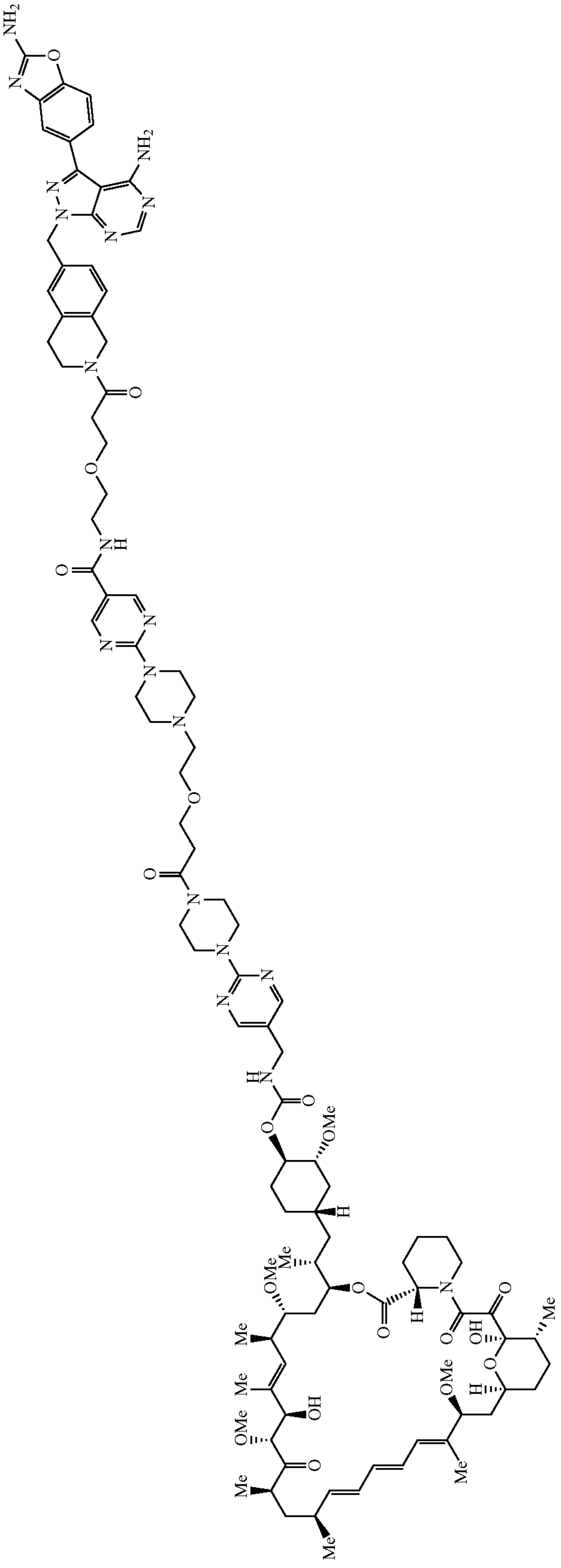

-continued
Example 66
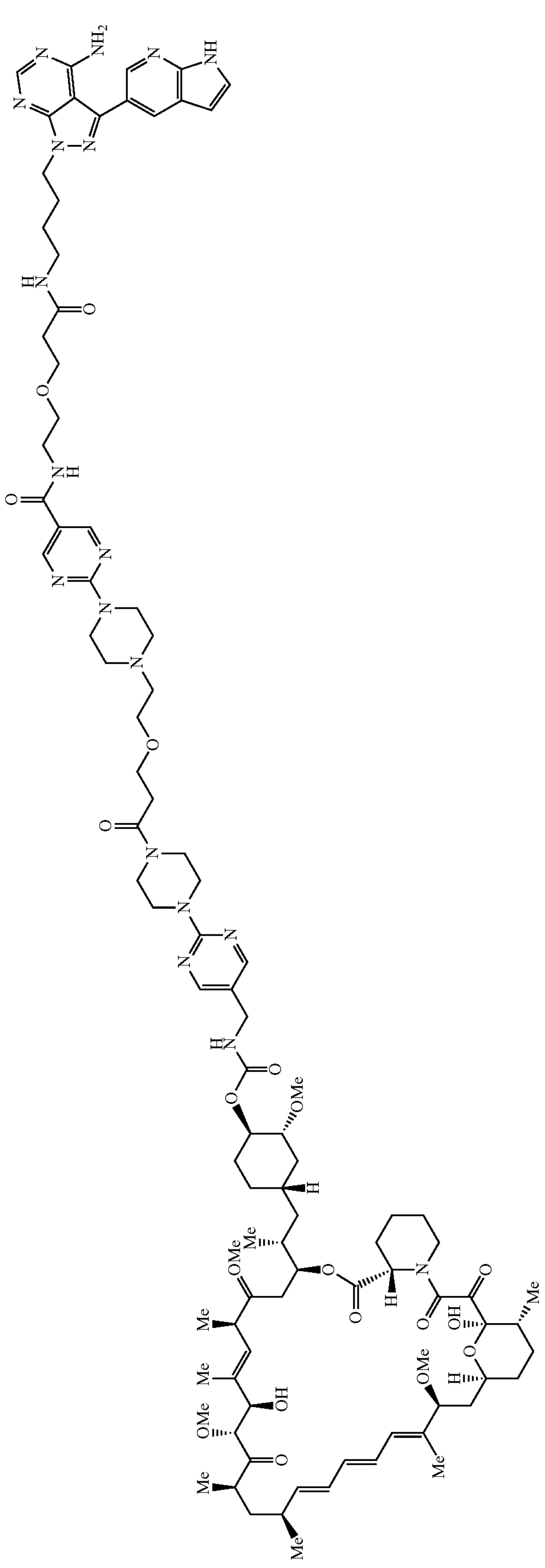
Example 67
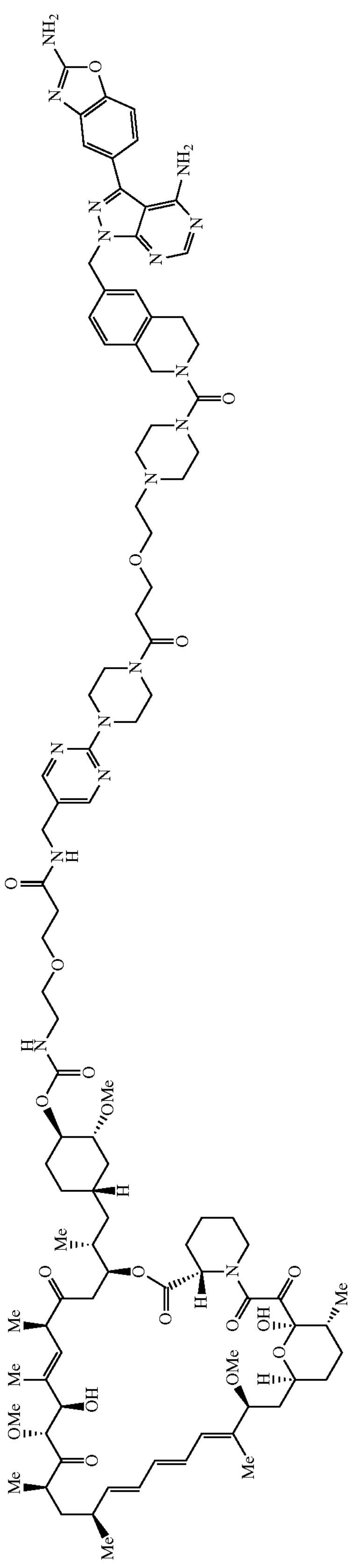

-continued
Example 68
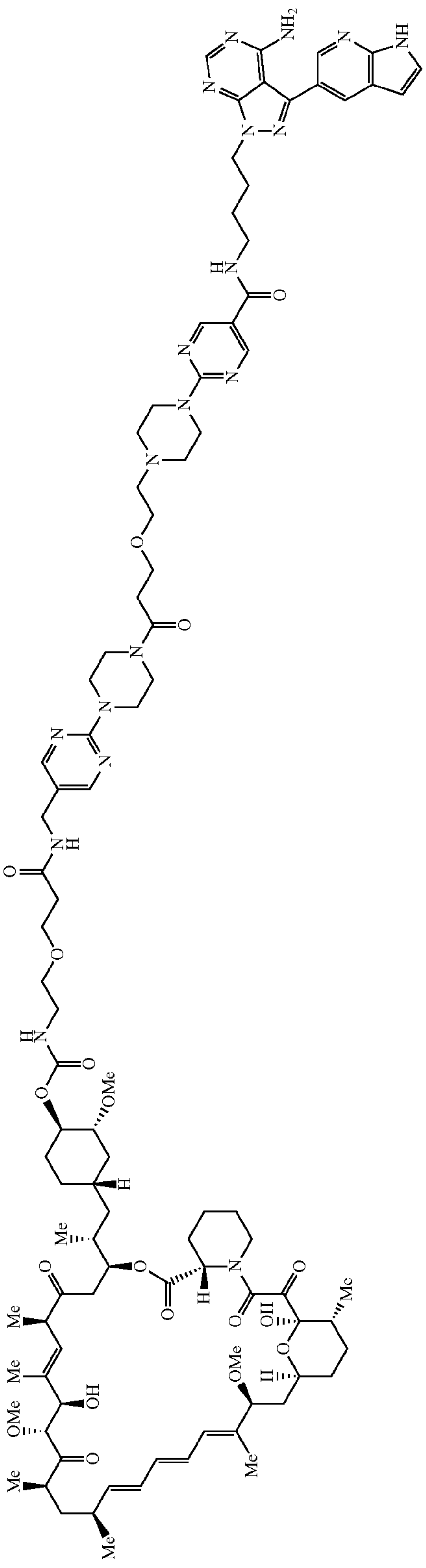
Example 69
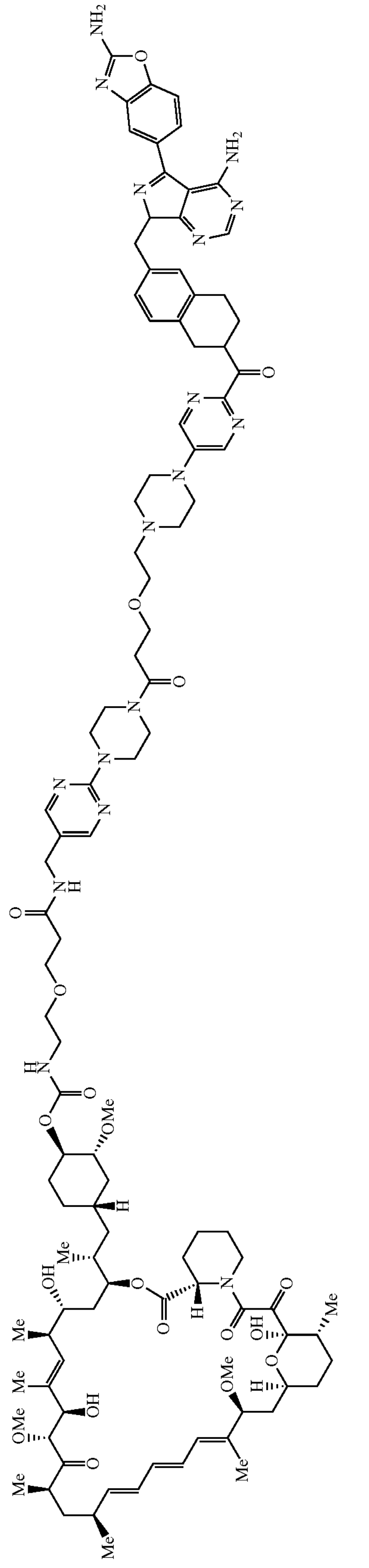

-continued
Example 70
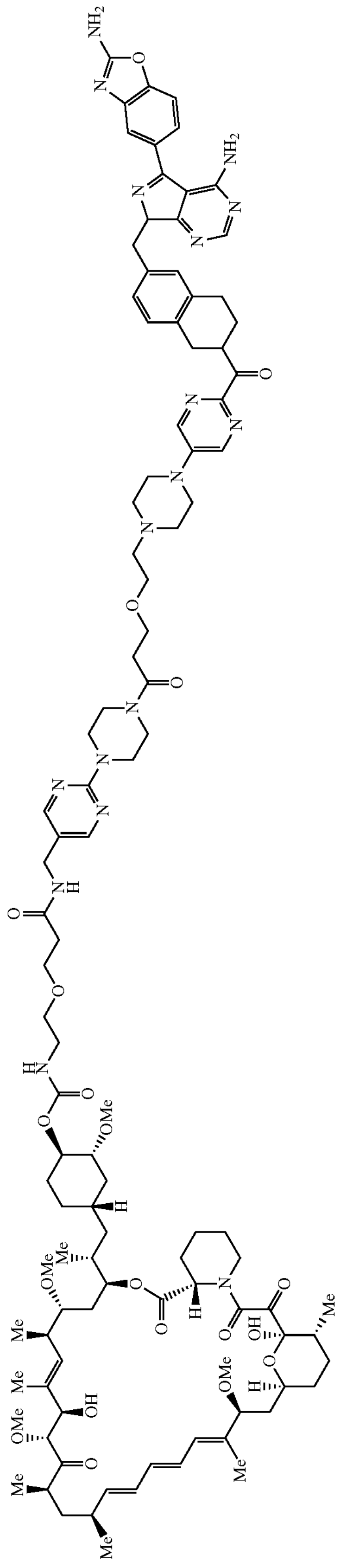

or a pharmaceutically acceptable salt or isomer thereof.

Embodiment I-61. A pharmaceutical composition comprising a compound of any one of Embodiments I-1 to I-60, or a pharmaceutically acceptable salt thereof, and at least one of a pharmaceutically acceptable carrier, diluent, or excipient.

Embodiment I-62. A method of treating a disease or disorder mediated by mTOR comprising administering to the subject suffering from or susceptible to developing a disease or disorder mediated by mTOR a therapeutically effective amount of one or more compounds of any one of Embodiments I-1 to I-60, or a pharmaceutically acceptable salt thereof.

Embodiment I-63. A method of preventing a disease or disorder mediated by mTOR comprising administering to the subject suffering from or susceptible to developing a disease or disorder mediated by mTOR a therapeutically effective amount of one or more compounds of any one of Embodiments I-1 to I-60, or a pharmaceutically acceptable salt thereof.

Embodiment I-64. A method of reducing the risk of a disease or disorder mediated by mTOR comprising administering to the subject suffering from or susceptible to developing a disease or disorder mediated by mTOR a therapeutically effective amount of one or more compounds of any one of Embodiments I-1 to I-60, or a pharmaceutically acceptable salt thereof.

Embodiment I-65. The method of any one of Embodiments I-62 to I-64, wherein the disease is cancer or an immune-mediated disease.

Embodiment I-66. The method of Embodiment I-65, wherein the cancer is selected from brain and neurovascular tumors, head and neck cancers, breast cancer, lung cancer, mesothelioma, lymphoid cancer, stomach cancer, kidney cancer, renal carcinoma, liver cancer, ovarian cancer, ovary endometriosis, testicular cancer, gastrointestinal cancer, prostate cancer, glioblastoma, skin cancer, melanoma, neuro cancers, spleen cancers, pancreatic cancers, blood proliferative disorders, lymphoma, leukemia, endometrial cancer, cervical cancer, vulva cancer, prostate cancer, penile cancer, bone cancers, muscle cancers, soft tissue cancers, intestinal or rectal cancer, anal cancer, bladder cancer, bile duct cancer, ocular cancer, gastrointestinal stromal tumors, and neuro-endocrine tumors.

Embodiment I-67. The method of Embodiment I-65, wherein the immune-mediated disease is selected from resistance by transplantation of heart, kidney, liver, medulla ossium, skin, cornea, lung, pancreas, intestinum tenue, limb, muscle, nerves, duodenum, small-bowel, or pancreatic-islet-cell; graft-versus-host diseases brought about by medulla ossium transplantation; rheumatoid arthritis, systemic lupus erythematosus, Hashimoto's thyroiditis, multiple sclerosis, myasthenia gravis, type I diabetes, uveitis, allergic encephalomyelitis, and glomerulonephritis.

Embodiment I-68. A method of treating cancer comprising administering to the subject a therapeutically effective amount of one or more compounds of any one of Embodiments I-1 to I-60, or a pharmaceutically acceptable salt thereof.

Embodiment I-69. The method of Embodiment I-68, wherein the cancer is selected from brain and neurovascular tumors, head and neck cancers, breast cancer, lung cancer, mesothelioma, lymphoid cancer, stomach cancer, kidney cancer, renal carcinoma, liver cancer, ovarian cancer, ovary endometriosis, testicular cancer, gastrointestinal cancer, prostate cancer, glioblastoma, skin cancer, melanoma, neuro cancers, spleen cancers, pancreatic cancers, blood proliferative disorders, lymphoma, leukemia, endometrial cancer, cervical cancer, vulva cancer, prostate cancer, penile cancer, bone cancers, muscle cancers, soft tissue cancers, intestinal or rectal cancer, anal cancer, bladder cancer, bile duct cancer, ocular cancer, gastrointestinal stromal tumors, and neuro-endocrine tumors.

Embodiment I-70. A method of treating an immune-mediated disease comprising administering to the subject a therapeutically effective amount of one or more compounds of any one of Embodiments I-1 to I-60, or a pharmaceutically acceptable salt thereof.

Embodiment I-71. The method of Embodiment I-70, wherein the immune-mediated disease is selected from resistance by transplantation of heart, kidney, liver, medulla ossium, skin, cornea, lung, pancreas, intestinum tenue, limb, muscle, nerves, duodenum, small-bowel, or pancreatic-islet-cell; graft-versus-host diseases brought about by medulla ossium transplantation; rheumatoid arthritis, systemic lupus erythematosus, Hashimoto's thyroiditis, multiple sclerosis, myasthenia gravis, type I diabetes, uveitis, allergic encephalomyelitis, and glomerulonephritis.

Embodiment I-72. A method of treating an age related condition comprising administering to the subject a therapeutically effective amount of one or more compounds of any one of Embodiments I-1 to I-60, or a pharmaceutically acceptable salt thereof.

Embodiment I-73. The method of Embodiment I-72, wherein the age related condition is selected from sarcopenia, skin atrophy, muscle wasting, brain atrophy, atherosclerosis, arteriosclerosis, pulmonary emphysema, osteoporosis, osteoarthritis, high blood pressure, erectile dysfunction, dementia, Huntington's disease, Alzheimer's disease, cataracts, age-related macular degeneration, prostate cancer, stroke, diminished life expectancy, impaired kidney function, and age-related hearing loss, aging-related mobility disability (e.g., frailty), cognitive decline, age-related dementia, memory impairment, tendon stiffness, heart dysfunction such as cardiac hypertrophy and systolic and diastolic dysfunction, immunosenescence, cancer, obesity, and diabetes.

Embodiment I-74. A compound of any one of Embodiments I-1 to I-60, or a pharmaceutically acceptable salt thereof, for use in treating, preventing, or reducing the risk of a disease or condition mediated by mTOR.

Embodiment I-75. Use of a compound of any of Embodiments I-1 to I-60, or a pharmaceutically acceptable salt thereof, in the manufacture of a medicament for treating, preventing, or reducing the risk of a disease or disorder mediated by mTOR.

Embodiment I-76. A compound of any one of Embodiments I-1 to I-60, or a pharmaceutically acceptable salt thereof, for use in treating cancer.

Embodiment I-77. Use of a compound of any one of Embodiments I-1 to I-60, or a pharmaceutically acceptable salt thereof, in the manufacture of a medicament for treating cancer.

Embodiment I-78. A compound of any one of Embodiments I-1 to I-60, or a pharmaceutically acceptable salt thereof, for use in treating an immune-mediated disease.

Embodiment I-79. Use of a compound of any one of Embodiments I-1 to I-60, or a pharmaceutically acceptable salt thereof, in the manufacture of a medicament for treating an immune-mediated disease.

Embodiment I-80. A compound of any one of Embodiments I-1 to I-60, or a pharmaceutically acceptable salt thereof, for use in treating an age related condition.

Embodiment I-81. Use of a compound of any one of Embodiments I-1 to I-60, or a pharmaceutically acceptable salt thereof, in the manufacture of a medicament for treating an age related condition.

Some embodiments of this disclosure are Embodiment II, as follows:

Embodiment II-1. A compound of Formula Ic:

(Ic)

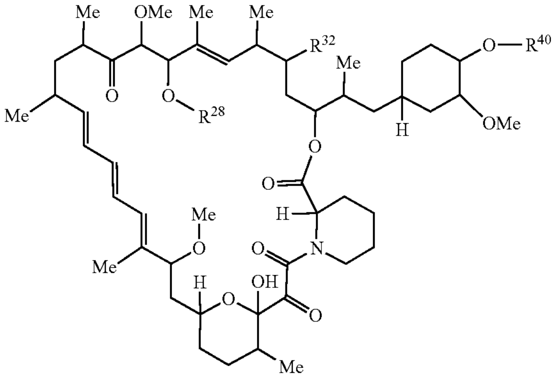

or a pharmaceutically acceptable salt or tautomer thereof, wherein:

$R^{32}$ is —H, =O, —$OR^3$, —$N_3$, or —O—C(=$Z^1$)—$R^{32a}$;

$R^{28}$ is —H, ($C_1$-$C_6$)alkyl, or —C(=$Z^1$)—$R^{28a}$;

$R^{40}$ is —H or —C(=$Z^1$)—$R^{40a}$;

wherein when $R^{28}$ and $R^{40}$ are H, then $R^{32}$ is not =O;

each $Z^1$ is independently O or S;

$R^{28a}$, $R^{32a}$, an d $R^{40a}$ are independently -$A^1$-$L^1$-$A^2$-B; -$A^1$-$A^2$-B; -$L^2$-$A^1$-$L^1$-$A^2$-$L^3$-B; —O—($C_1$-$C_6$)alkyl; or —O—($C_6$-$C_{10}$)aryl; wherein the aryl of —O—($C_6$-$C_{10}$)aryl is unsubstituted or substituted with 1-5 substituents selected from —$NO_2$ and halogen;

$A^1$ and $A^2$ are independently absent or are independently selected from

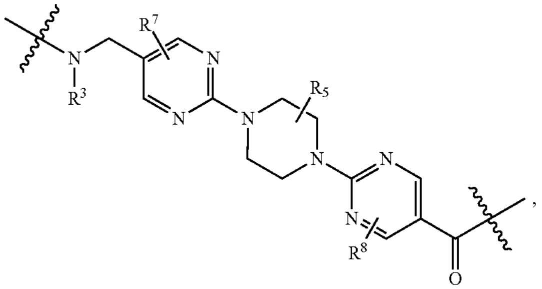

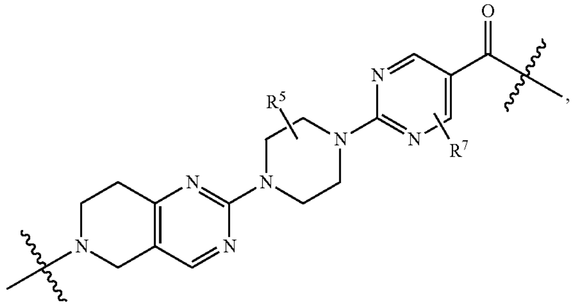

-continued

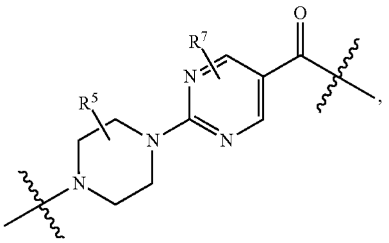

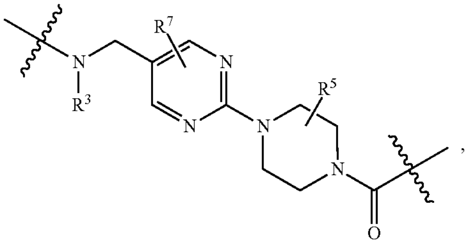

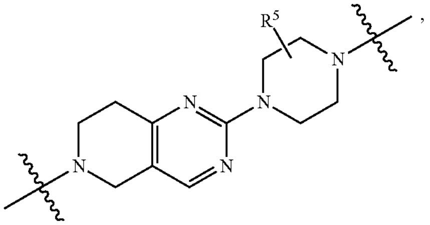

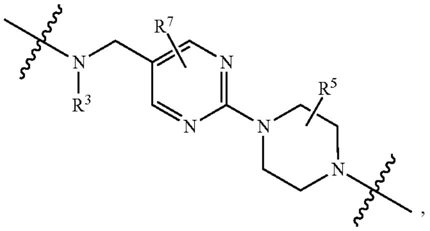

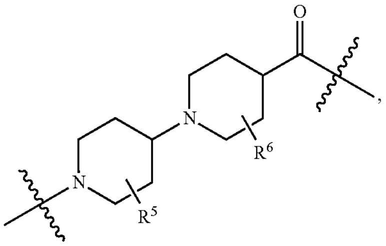

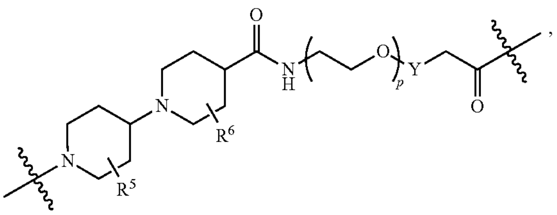

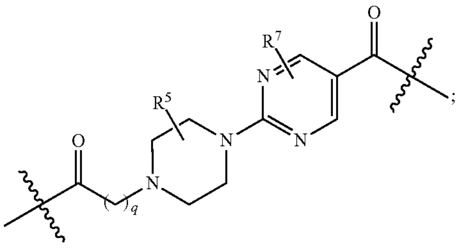

-continued

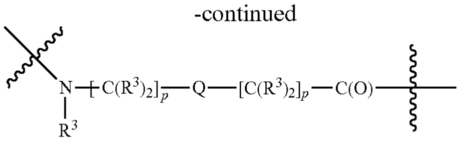,

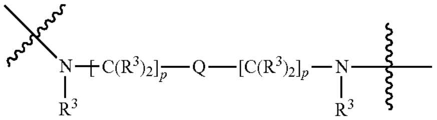,

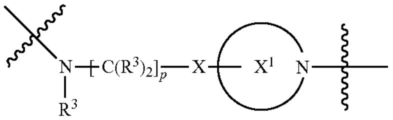,

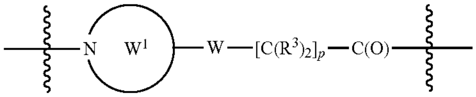,

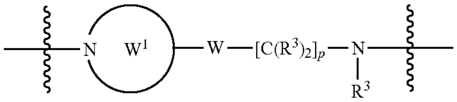,

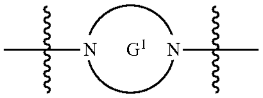,

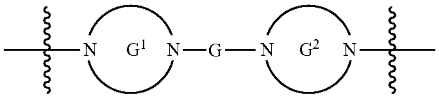,

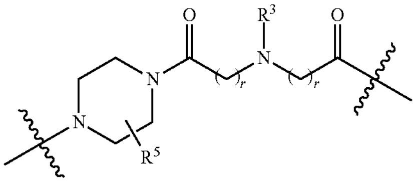,

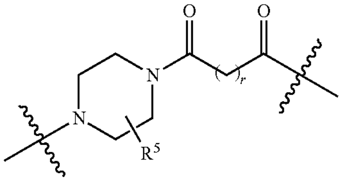,

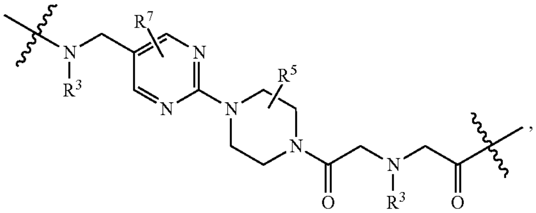,

-continued

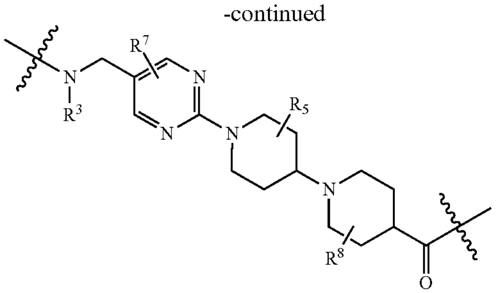, and

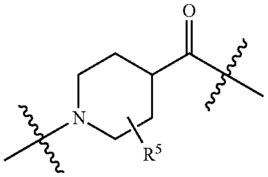;

wherein the bond on the left side of $A^1$, as drawn, is bound to —C(=$Z^1$)— or $L^2$; and wherein the bond on the right side of the $A^2$ moiety, as drawn, is bound to B or $L^3$;

each Q is independently 1 to 3 rings selected from arylene, cycloalkylene, heteroarylene, and heterocyclylene;

each X is independently absent or 1 to 2 rings selected from arylene, cycloalkylene, heteroarylene, and heterocyclylene;

each $X^1$ is independently a heteroarylene or heterocyclylene ring;

each W is independently absent or 1 to 2 rings selected from arylene, cycloalkylene, heteroarylene, and heterocyclylene;

each $W^1$ is independently a heteroarylene or heterocyclylene ring;

each G is independently absent or a ring selected from arylene, cycloalkylene, heteroarylene, and heterocyclylene;

each $G^1$ and $G^2$ are independently heteroarylene or heterocyclylene ring;

each $L^1$ is independently selected from

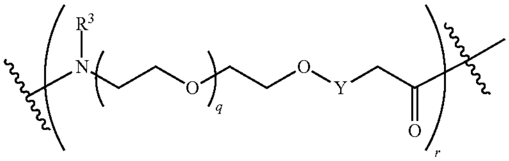,

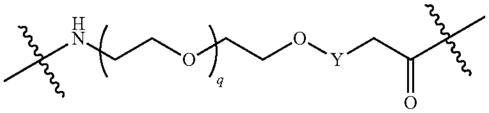,

-continued
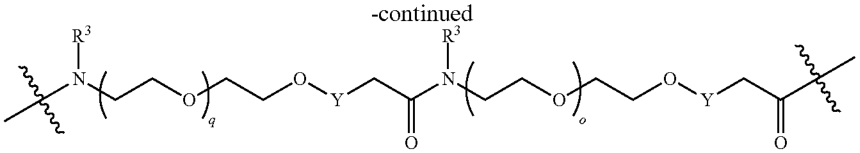
,
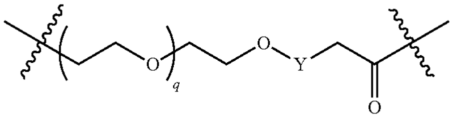
,
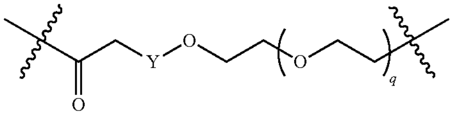
,
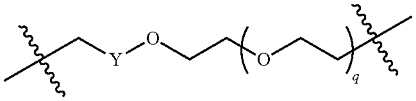
,
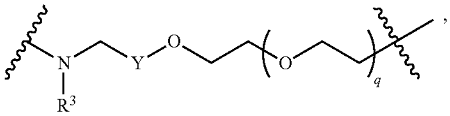
,
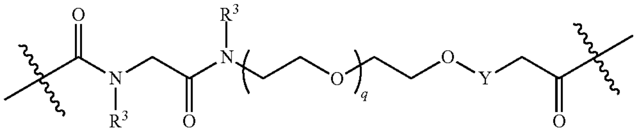
,
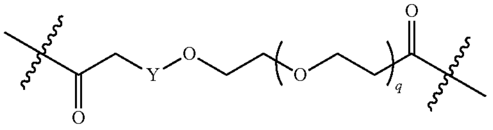
,
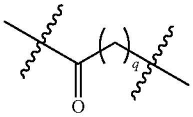
, and
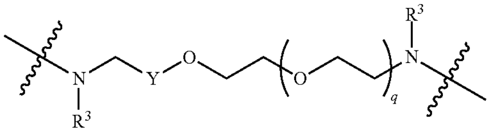
;
$L^2$ and $L^3$ are independently absent or are independently selected from
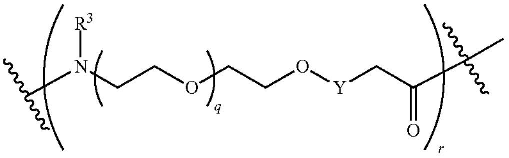
,
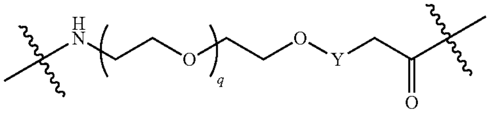
,
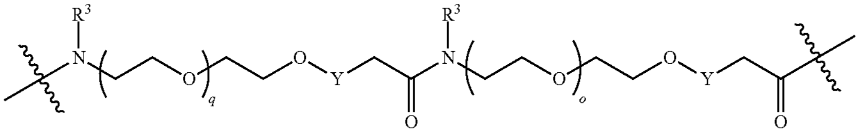
,
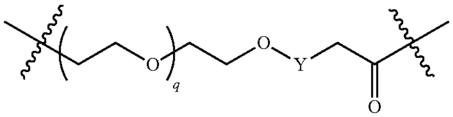
, -continued
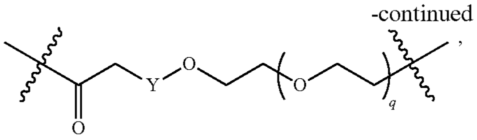
,
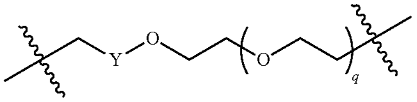
,
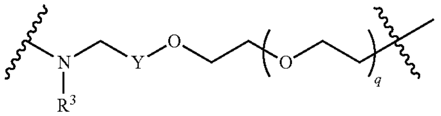
,
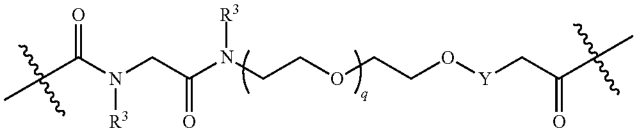
,
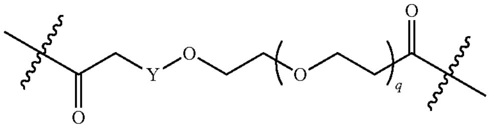
, and
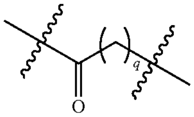
;
each B is independently selected from
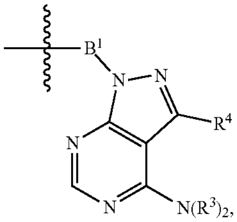
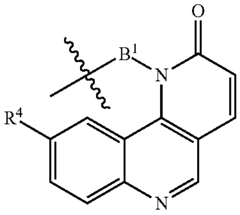
,
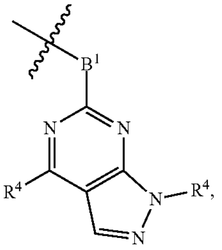
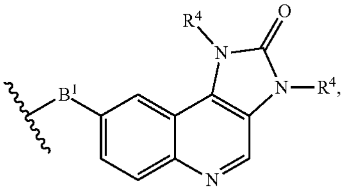
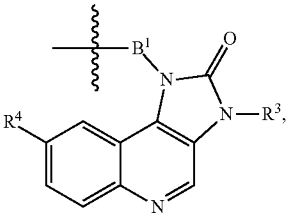
-continued
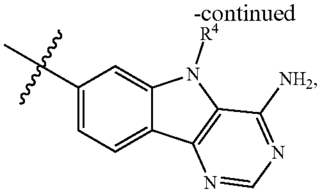
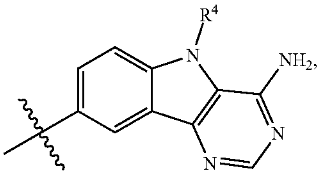
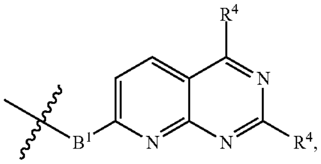
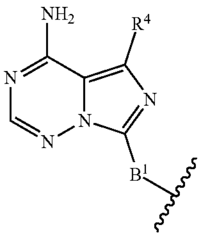
and
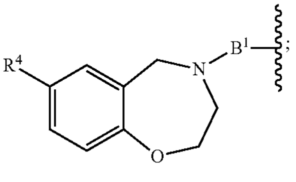

each $B^1$ is independently selected from

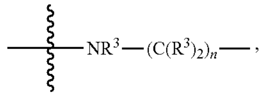

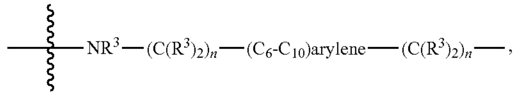

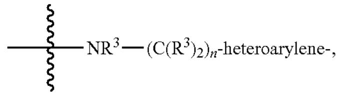

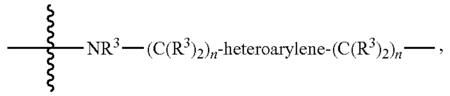

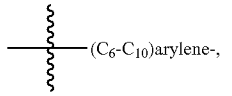

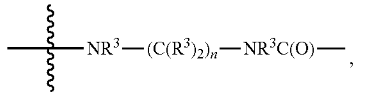

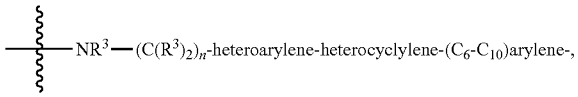

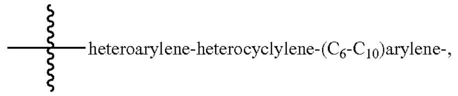

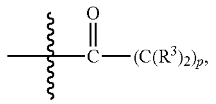

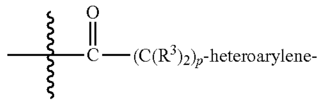

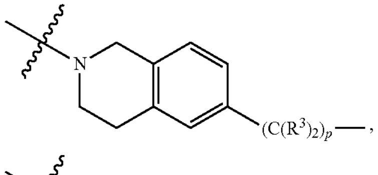

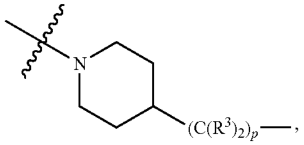

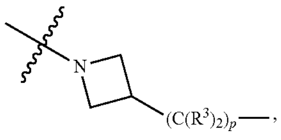

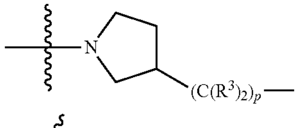

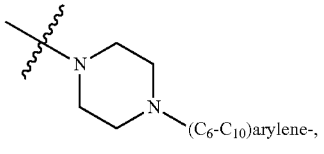

-continued

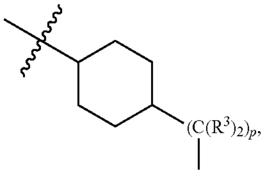

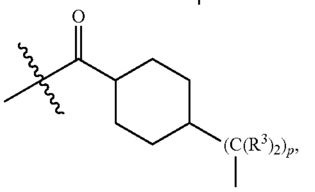

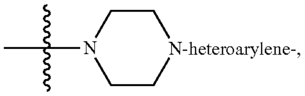

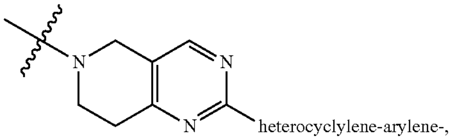

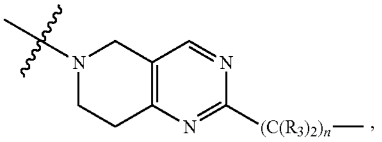

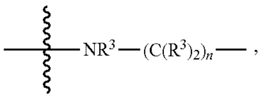

$S(O)_2$-arylene-C(O)—, and

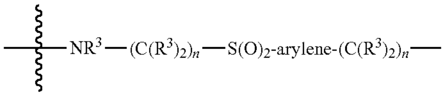

wherein the  bond on the left side of $B^1$, as drawn, is bound to $A^2$, $L^1$, or $L^1$; and wherein the heteroarylene, heterocyclylene, and arylene are each independently optionally substituted with alkyl, hydroxyalkyl, haloalkyl, alkoxy, halogen, or hydroxyl;

each $R^3$ is independently H or $(C_1-C_6)$alkyl;

each $R^4$ is independently H, $(C_1-C_6)$alkyl, halogen, 5-12 membered heteroaryl, 5-12 membered heterocyclyl, $(C_6-C_{10})$aryl, wherein the heteroaryl, heterocyclyl, and aryl are optionally substituted with —$N(R^3)_2$, —$OR^3$, halogen, $(C_1-C_6)$alkyl, —$(C_1-C_6)$alkylene-heteroaryl, —$(C_1-C_6)$alkylene-CN, —C(O)$NR^3$-heteroaryl, or —C(O)$NR^3$-heterocyclyl;

each $R^5$ is independently H, $(C_1-C_6)$alkyl, —C(O)$OR^3$, or —$N(R^3)_2$, wherein the alkyl of $(C_1-C_6)$alkyl is optionally substituted with —$N(R^3)_2$ or —$OR^3$;

each $R^6$ is independently H, $(C_1-C_6)$alkyl, —C(O)$OR^3$, or —$N(R^3)_2$, wherein the alkyl of $(C_1-C_6)$alkyl is optionally substituted with —$N(R^3)_2$ or —$OR^3$;

each $R^7$ is independently H, $(C_1-C_6)$alkyl, —C(O)$OR^3$, or —$N(R^3)_2$, wherein the alkyl of $(C_1-C_6)$alkyl is optionally substituted with —$N(R^3)_2$ or —$OR^3$;

each $R^8$ is independently H, $(C_1-C_6)$alkyl, —C(O)$OR^3$, or —$N(R^3)_2$, wherein the alkyl of $(C_1-C_6)$alkyl is optionally substituted with —$N(R^3)_2$ or —$OR^3$;

each Y is independently $C(R^3)_2$ or a bond;
each n is independently an integer from one to 12;
each o is independently an integer from zero to 30;
each p is independently an integer from zero to 12;
each q is independently an integer from zero to 30; and
each r is independently an integer from one to 6.
Embodiment II-1A. A compound of Formula Ia:

(Ia)

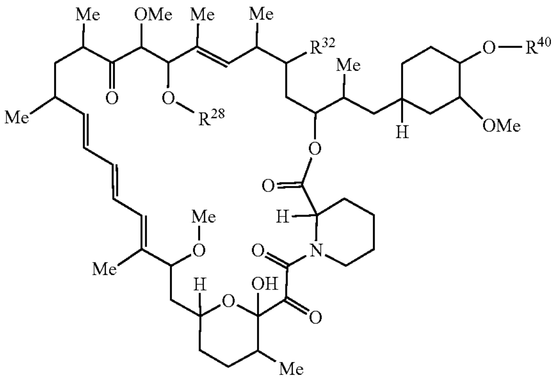

or a pharmaceutically acceptable salt or tautomer thereof, wherein:

$R^{32}$ is —H, =O, —$OR^3$, —$N_3$, or —O—C(=$Z^1$)—$R^{32a}$.
$R^{28}$ is —H, ($C_1$-$C_6$)alkyl, or —C(=$Z^1$)—$R^{28a}$;
$R^{40}$ is —H or —C(=$Z^1$)—$R^{40a}$;
wherein when $R^{28}$ and $R^{40}$ are H, then $R^{32}$ is not =O;
each $Z^1$ is independently O or S;
$R^{28a}$, $R^{32a}$, and $R^{40a}$ are independently -$A^1$-$L^1$-$A^2$-B; -$A^1$-$A^2$-B; -$L^2$-$A^1$-$L^1$-$A^2$-$L^3$-B; —O—($C_1$-$C_6$)alkyl; or —O—($C_6$-$C_{10}$)aryl; wherein the aryl of —O—($C_6$-$C_{10}$)aryl is unsubstituted or substituted with 1-5 substituents selected from —$NO_2$ and halogen;
$A^1$ and $A^2$ are independently absent or are independently selected from

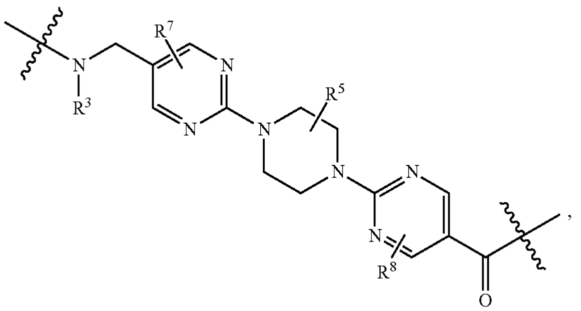

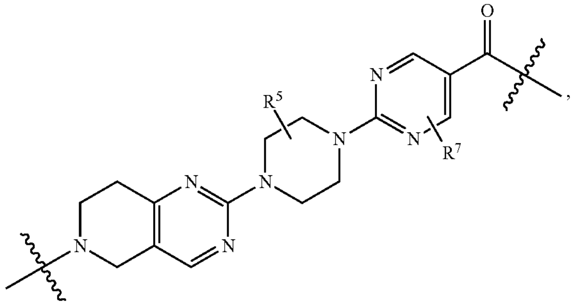

-continued

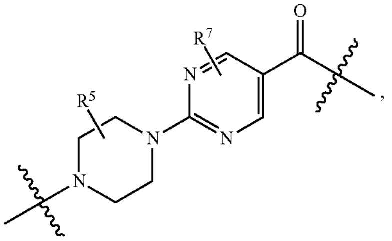

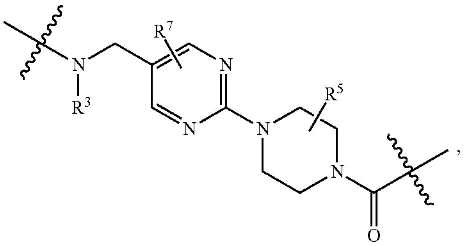

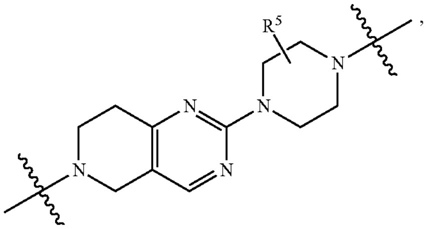

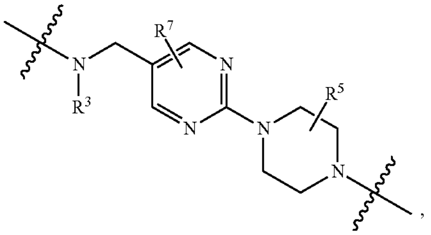

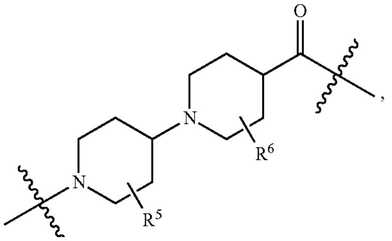

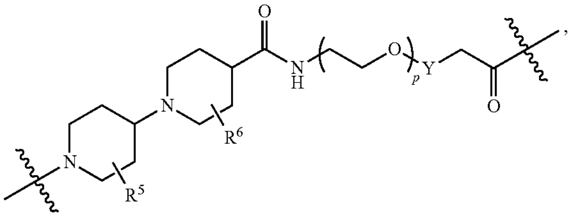

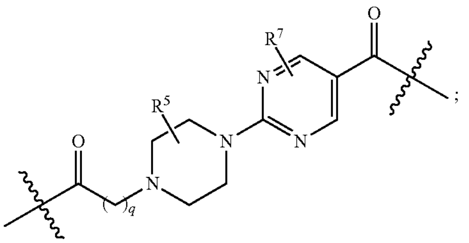

-continued

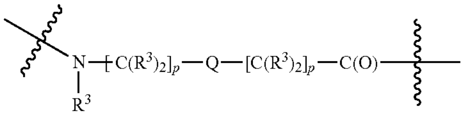,

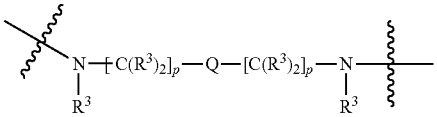,

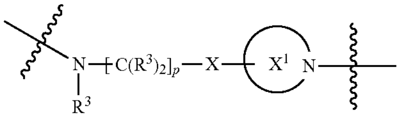,

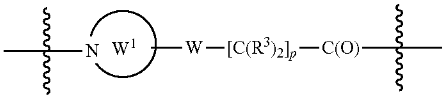

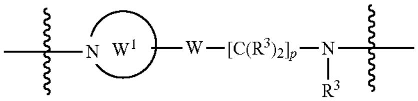,

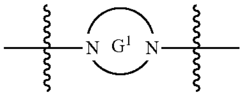,

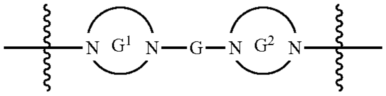,

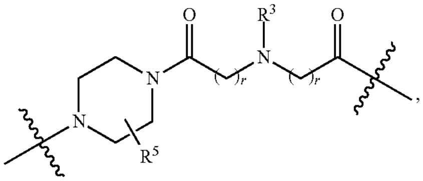,

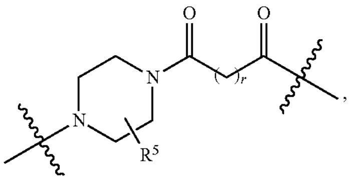,

-continued

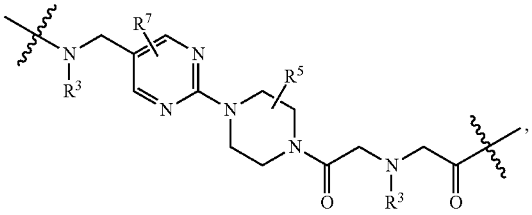, and

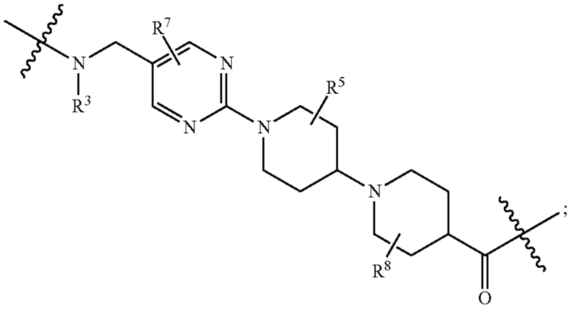;

wherein the bond on the left side of $A^1$, as drawn, is bound to —C(=$Z^1$)— or $L^2$; and wherein the bond on the right side of the $A^2$ moiety, as drawn, is bound to B or $L^3$;

each Q is independently 1 to 3 rings selected from arylene, cycloalkylene, heteroarylene, and heterocyclylene;

each X is independently absent or 1 to 2 rings selected from arylene, cycloalkylene, heteroarylene, and heterocyclylene;

each $X^1$ is independently a heteroarylene or heterocyclylene ring;

each W is independently absent or 1 to 2 rings selected from arylene, cycloalkylene, heteroarylene, and heterocyclylene;

each $W^1$ is independently a heteroarylene or heterocyclylene ring;

each G is independently absent or a ring selected from arylene, cycloalkylene, heteroarylene, and heterocyclylene;

each $G^1$ and $G^2$ are independently heteroarylene or heterocyclylene ring;

each $L^1$ is independently selected from

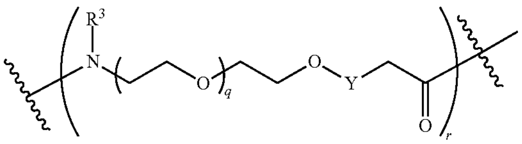,

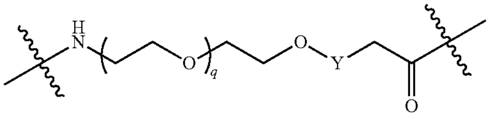,

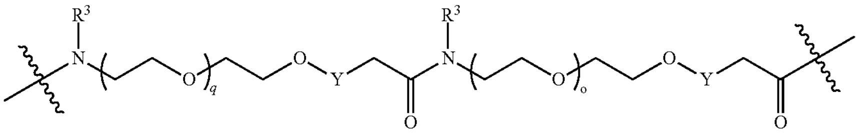,

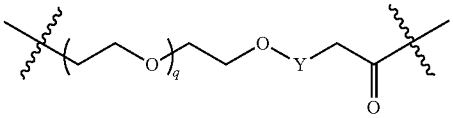,

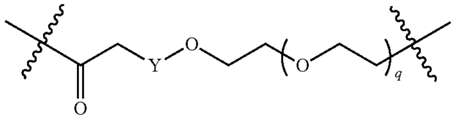,

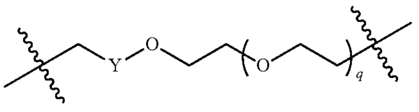,

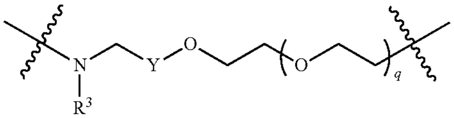,

-continued
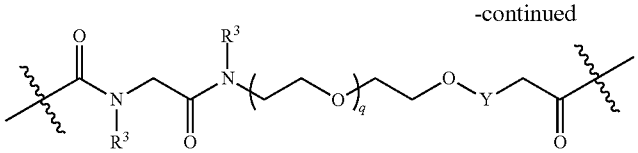,
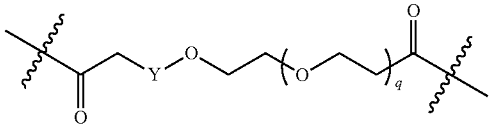, and 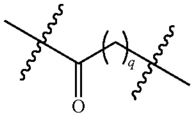;
$L^2$ and $L^3$ are independently absent or are independently selected from
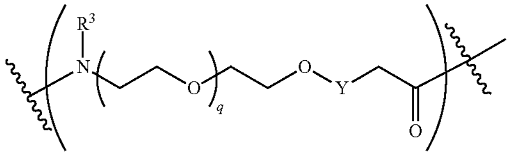,
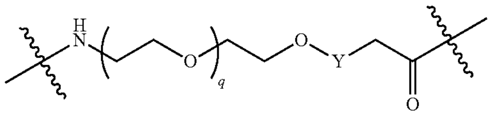,
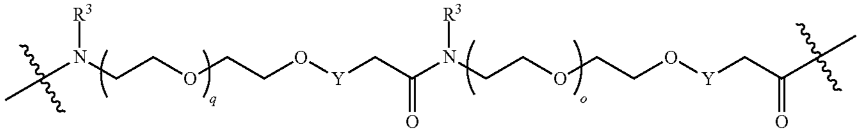,
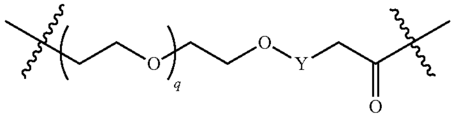,
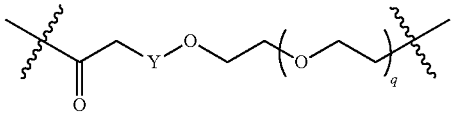,
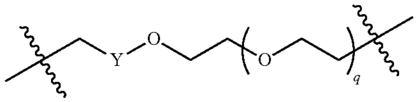,
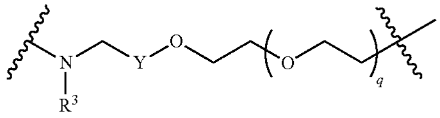,
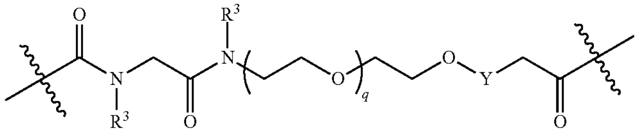,
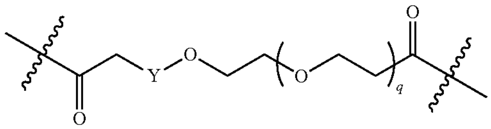, and 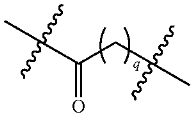;

each B is independently selected from
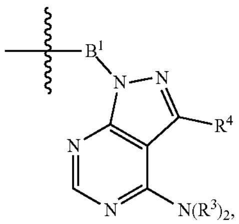
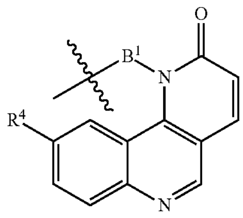
,
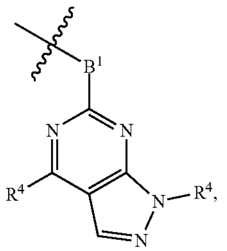
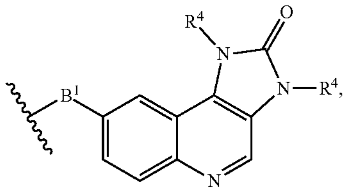
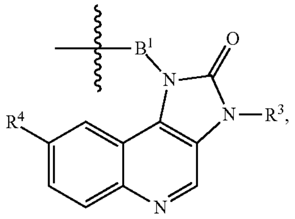
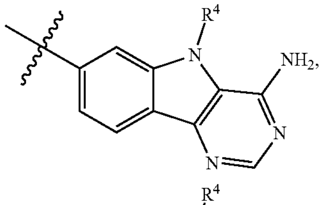
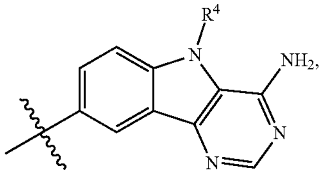
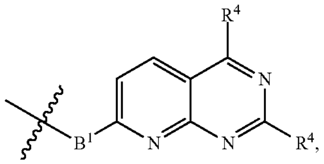
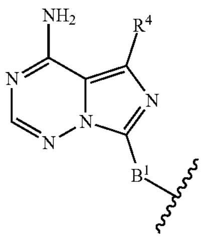
and
-continued
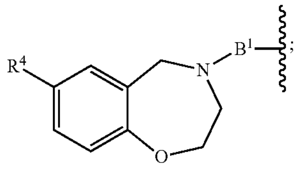
$B^1$ is selected from
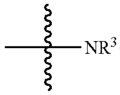 $NR^3—(C(R^3)_2)_n—$,
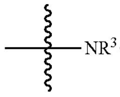 $NR^3—(C(R^3)_2)_n—(C_6\text{-}C_{10})$arylene$—(C(R^3)_2)_n—$,
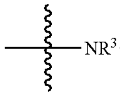 $NR^3—(C(R^3)_2)_n$-heteroarylene-,
 $(C_6\text{-}C_{10})$arylene-,
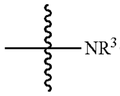 $NR^3—(C(R^3)_2)_n—NR^3C(O)—$,
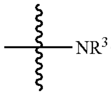 $NR^3—(C(R^3)_2)_n$-heteroarylene-heterocyclylene-$(C_6\text{-}C_{10})$arylene-,
 heteroarylene-heterocyclylene-$(C_6\text{-}C_{10})$arylene-,
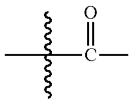 $—(C(R^3)_2)_p$,
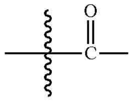 $—(C(R^3)_2)_p$-heteroarylene-
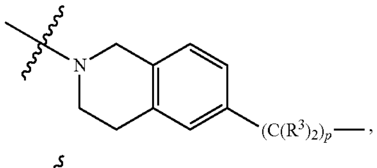
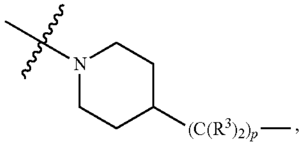
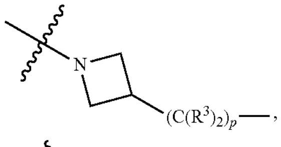
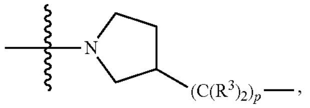

-continued

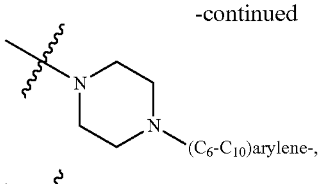

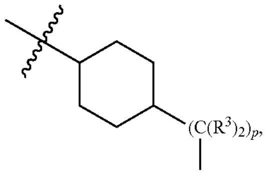

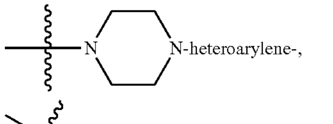

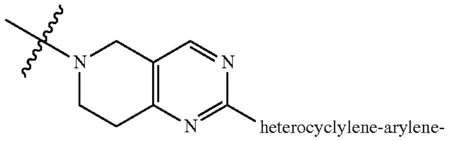

and

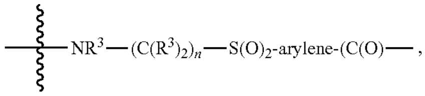

, wherein the 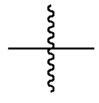 bond on the left side of $B^1$, as drawn, is bound to $A^2$, $L^3$, or $L^1$; and wherein the heteroarylene, heterocyclylene, and arylene are optionally substituted with alkyl, hydroxyalkyl, haloalkyl, alkoxy, halogen, or hydroxyl;

each $R^3$ is independently H or $(C_1\text{-}C_6)$alkyl;

each $R^4$ is independently H, $(C_1\text{-}C_6)$alkyl, halogen, 5-12 membered heteroaryl, 5-12 membered heterocyclyl, $(C_6\text{-}C_{10})$aryl, wherein the heteroaryl, heterocyclyl, and aryl are optionally substituted with —$N(R^3)_2$, —$OR^3$, halogen, $(C_1\text{-}C_6)$alkyl, —$(C_1\text{-}C_6)$alkylene-heteroaryl, —$(C_1\text{-}C_6)$alkylene-CN, —$C(O)NR^3$-heteroaryl, or —$C(O)NR^3$-heterocyclyl;

each $R^5$ is independently H, $(C_1\text{-}C_6)$alkyl, —$C(O)OR^3$, or —$N(R^3)_2$, wherein the alkyl of $(C_1\text{-}C_6)$alkyl is optionally substituted with —$N(R^3)_2$ or —$OR^3$;

each $R^6$ is independently H, $(C_1\text{-}C_6)$alkyl, —$C(O)OR^3$, or —$N(R^3)_2$, wherein the alkyl of $(C_1\text{-}C_6)$alkyl is optionally substituted with —$N(R^3)_2$ or —$OR^3$;

each $R^7$ is independently H, $(C_1\text{-}C_6)$alkyl, —$C(O)OR^3$, or —$N(R^3)_2$, wherein the alkyl of $(C_1\text{-}C_6)$alkyl is optionally substituted with —$N(R^3)_2$ or —$OR^3$;

each $R^8$ is independently H, $(C_1\text{-}C_6)$alkyl, —$C(O)OR^3$, or —$N(R^3)_2$, wherein the alkyl of $(C_1\text{-}C_6)$alkyl is optionally substituted with —$N(R^3)_2$ or —$OR^3$;

each Y is independently $C(R^3)_2$ or a bond;

each n is independently an integer from one to 12;

each o is independently an integer from zero to 30;

each p is independently an integer from zero to 12;

each q is independently an integer from zero to 30; and each r is independently an integer from one to 6.

Embodiment II-2. The compound of Embodiment II-1, wherein $R^{32}$ is =O.

Embodiment II-3. The compound of Embodiment II-1, wherein $R^{32}$ is —$OR^3$.

Embodiment II-4. The compound of any one of Embodiments II-1 to II-3, or a pharmaceutically acceptable salt or tautomer thereof, wherein the compound is represented by the structure of Formula (I-40b):

(I-40b)

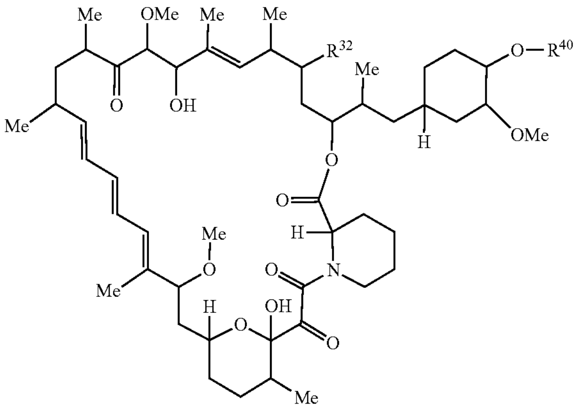

wherein $R^{40}$ is —$C(=Z^1)$—$R^{40a}$.

Embodiment II-5. The compound of Embodiment II-4, wherein $Z^1$ is O.

Embodiment II-6. The compound of Embodiment II-4, wherein $Z^1$ is S.

Embodiment II-7. The compound of any one of Embodiments II-4 to II-6, wherein $R^{40a}$ is $-A^1-L^1-A^2-B$, wherein $A^1$ and $A^2$ are absent.

Embodiment II-8. The compound of any one of Embodiments II-4 to II-6, wherein $R^{40a}$ is $-A^1-L^1-A^2-B$, wherein $A^2$ is absent.

Embodiment II-9. The compound of any one of Embodiments II-4 to II-6, wherein $R^{40a}$ is $-A^1-L^1-A^2-B$, wherein $A^1$ is absent.

Embodiment II-10. The compound of any one of Embodiments II-4 to II-6, wherein $R^{40a}$ is $-A^1-L^1-A^2-B$.

Embodiment II-11. The compound of any one of Embodiments II-4 to II-6, wherein $R^{40a}$ is $-A^1-A^2-B$.

Embodiment II-12. The compound of any one of Embodiments II-4 to II-6, wherein $R^{40a}$ is $-L^2-A^1-L^1-A^2-L^3-B$, wherein $L^2$ and $A^1$ are absent.

Embodiment II-13. The compound of any one of Embodiments II-4 to II-6, wherein $R^{40a}$ is $-L^2-A^1-L^1-A^2-L^3-B$, wherein $L^2$ is absent.

Embodiment II-14. The compound of any one of Embodiments II-4 to II-6, wherein $R^{40a}$ is $-L^2-A^1-L^1-A^2-L^3-B$, wherein $L^3$ is absent.

Embodiment II-15. The compound of any one of Embodiments II-4 to II-6, wherein $R^{40a}$ is —O—$(C_1\text{-}C_6)$alkyl or —O—$(C_6\text{-}C_{10})$aryl; wherein the aryl of —O—$(C_6\text{-}C_{10})$aryl is unsubstituted or substituted with 1-5 substituents selected from —$NO_2$ and halogen.

Embodiment II-16. The compound of any one of Embodiments II-1 to II-3, or a pharmaceutically acceptable salt or tautomer thereof, wherein the compounds are represented by the structure of Formula (I-28b):

(I-28b)

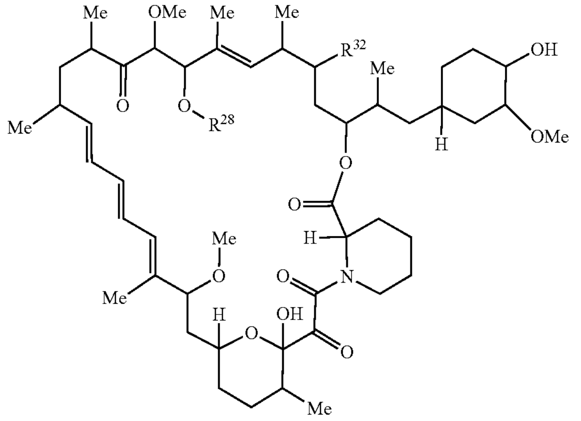

wherein $R^{28}$ is —C(=$Z^1$)—$R^{28a}$.

Embodiment II-17. The compound of Embodiment II-16, wherein $Z^1$ is O.

Embodiment II-18. The compound of Embodiment II-16, wherein $Z^1$ is S.

Embodiment II-19. The compound of any one of Embodiments II-16 to II-18, wherein $R^{28a}$ is -$A^1$-$L^1$-$A^2$-B, wherein $A^1$ and $A^2$ are absent.

Embodiment II-20. The compound of any one of Embodiments II-16 to II-18, wherein $R^{28a}$ is -$A^1$-$L^1$-$A^2$-B, wherein $A^2$ is absent.

Embodiment II-21. The compound of any one of Embodiments II-16 to II-18, wherein $R^{28a}$ is -$A^1$-$L^1$-$A^2$-B, wherein $A^1$ is absent.

Embodiment II-22. The compound of any one of Embodiments II-16 to II-18, wherein $R^{28a}$ is -$A^1$-$L^1$-$A^2$-B.

Embodiment II-23. The compound of any one of Embodiments II-16 to II-18, wherein $R^{28a}$ is -$A^1$-$A^2$-B.

Embodiment II-24. The compound of any one of Embodiments II-16 to II-18, wherein $R^{28a}$ is -$L^2$-$A^1$-$L^1$-$A^2$-$L^3$-B, wherein $L^2$ and $A^1$ are absent.

Embodiment II-25. The compound of any one of Embodiments II-16 to II-18, wherein $R^{28a}$ is -$L^2$-$A^1$-$L^1$-$A^2$-$L^3$-B, wherein $L^2$ is absent.

Embodiment II-26. The compound of any one of Embodiments II-16 to II-18, wherein $R^{28a}$ is -$L^2$-$A^1$-$L^1$-$A^2$-$L^3$-B, wherein $L^3$ is absent.

Embodiment II-27. The compound of any one of Embodiments II-16 to II-18, wherein $R^{28a}$ is —O—($C_1$-$C_6$)alkyl or —O—($C_6$-$C_{10}$)aryl; wherein the aryl of —O—($C_6$-$C_{10}$)aryl is unsubstituted or substituted with 1-5 substituents selected from —$NO_2$ and halogen.

Embodiment II-28. The compound of Embodiment II-1, or a pharmaceutically acceptable salt or tautomer thereof, wherein the compound is represented by the structure of Formula (I-32b):

(I-32b)

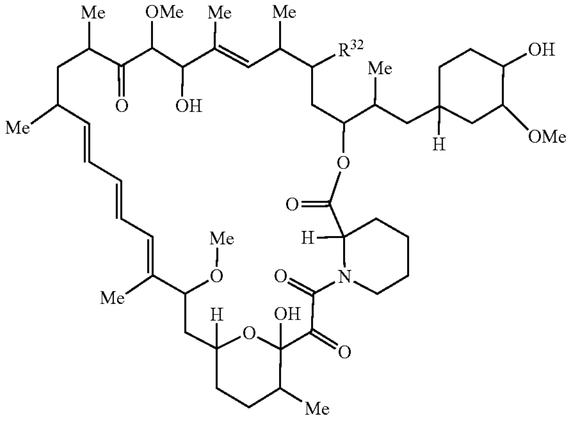

wherein $R^{32}$ is —O—C(=$Z^1$)—$R^{32a}$.

Embodiment II-29. The compound of Embodiment II-28, wherein $Z^1$ is O.

Embodiment II-30. The compound of Embodiment II-28, wherein $Z^1$ is S.

Embodiment II-31. The compound of any one of Embodiments II-28 to II-30, wherein $R^{32a}$ is -$A^1$-$L^1$-$A^2$-B, wherein $A^1$ and $A^2$ are absent.

Embodiment II-32. The compound of any one of Embodiments II-28 to II-30, wherein $R^{32a}$ is -$A^1$-$L^1$-$A^2$-B, wherein $A^2$ is absent.

Embodiment II-33. The compound of any one of Embodiments II-28 to II-30, wherein $R^{32a}$ is -$A^1$-$L^1$-$A^2$-B, wherein $A^1$ is absent.

Embodiment II-34. The compound of any one of Embodiments II-28 to II-30, wherein $R^{32a}$ is -$A^1$-$L^1$-$A^2$-B.

Embodiment II-35. The compound of any one of Embodiments II-28 to II-30, wherein $R^{32a}$ is -$A^1$-$A^2$-B.

Embodiment II-36. The compound of any one of Embodiments II-28 to II-30, wherein $R^{32a}$ is -$L^2$-$A^1$-$L^1$-$A^2$-$L^3$-B, wherein $L^2$ and $A^1$ are absent.

Embodiment II-37. The compound of any one of Embodiments II-28 to II-30, wherein $R^{32a}$ is -$L^2$-$A^1$-$L^1$-$A^2$-$L^3$-B, wherein $L^2$ is absent.

Embodiment II-38. The compound of any one of Embodiments II-28 to II-30, wherein $R^{32a}$ is -$L^2$-$A^1$-$L^1$-$A^2$-$L^3$-B, wherein $L^3$ is absent.

Embodiment II-39. The compound of any one of Embodiments II-28 to II-30, wherein $R^{32a}$ is —O—($C_1$-$C_6$)alkyl or —O—($C_6$-$C_{10}$)aryl; wherein the aryl of —O—($C_6$-$C_{10}$)aryl is unsubstituted or substituted with 1-5 substituents selected from —$NO_2$ and halogen.

Embodiment II-40. The compound of any one of Embodiments II-1 to II-10, II-12 to II-22, II-24 to II-35, and II-36 to II-39, wherein $L^1$ is

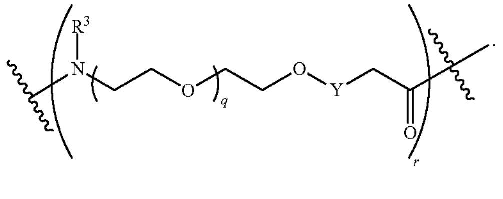

Embodiment II-41. The compound of any one Embodiments II-1 to II-10, II-12 to II-22, II-24 to II-35, and II-36 to II-39, wherein $L^1$ is

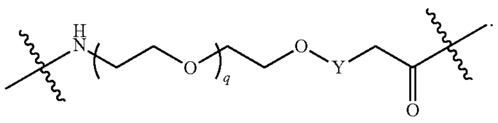

Embodiment II-42. The compound of any one of Embodiments II-1 to II-10, II-12 to II-22, 24-35, and 36-39, wherein $L^1$ is

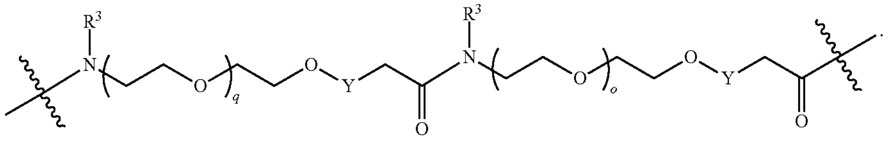

Embodiment II-43. The compound of any one of Embodiments II-1 to II-10, II-12 to II-22, II-24 to II-35, and II-36 to II-39, wherein $L^1$ is

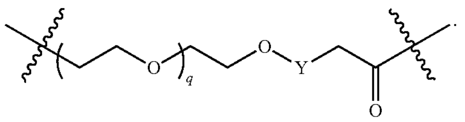

Embodiment II-44. The compound of any one of Embodiments II-1 to II-10, II-12 to II-22, II-24 to II-35, and II-36 to II-39, wherein $L^1$ is

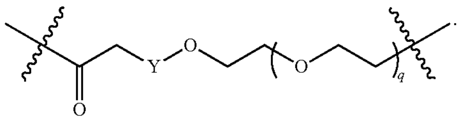

Embodiment II-45. The compound of any one of Embodiments II-1 to II-10, II-12 II-22, II-24 to II-35, and II-36 to II-39, wherein $L^1$ is

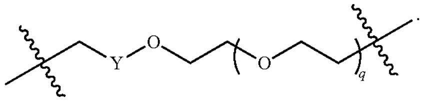

Embodiment II-46. The compound of any one of Embodiments II-1 to II-6, II-12 to II-18, II-24 to II-30, and II-36 to II-45, wherein $L^2$ is

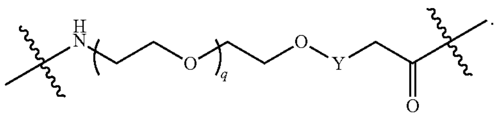

Embodiment II-47. The compound of any one of Embodiments II-1 to II-6, II-12 to II-18, II-24 to II-30, and II-36 to II-45, wherein $L^3$ is

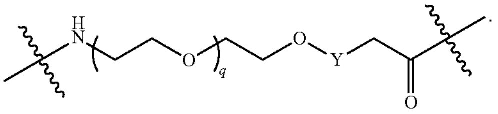

Embodiment II-48. The compound of any one of Embodiments II-1 to II-7, II-9, II-12, II-16 to II-19, II-21, II-24, II-28 to II-31, II-33, II-36, and II-39 to II-45, wherein $A^1$ is absent.

Embodiment II-49. The compound of any one of Embodiments II-1 to II-6, II-8, II-10 to II-11, II-13 to II-18, II-20, II-22 to II-23, II-25 to II-30, II-32, II-34 to II-35, and II-37 to II-45, wherein $A^1$ is

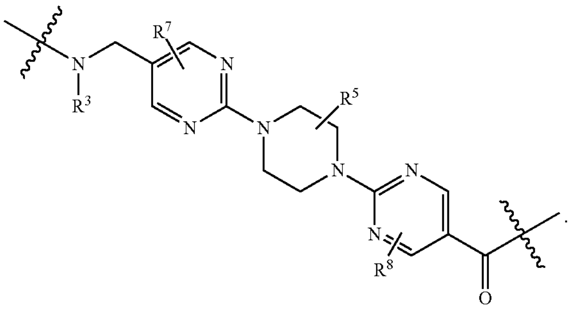

Embodiment II-50. The compound of any one of Embodiments II-1 to II-6, II-8, II-10 to II-11, II-13 to II-18, II-20, II-22 to II-23, II-25 to II-30, II-32, II-34 to II-35, and II-37 to II-45, wherein $A^1$ is

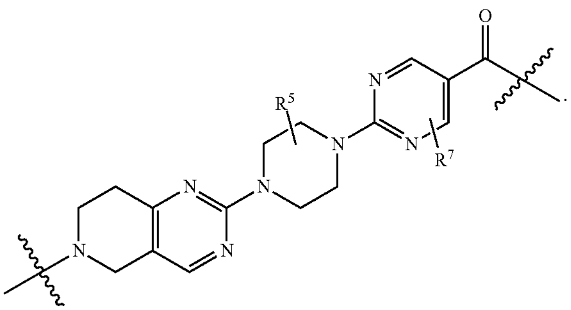

Embodiment II-51. The compound of any one of Embodiments II-1 to II-6, II-8, II-10 to II-11, II-13 to II-18, II-20, II-22 to II-23, II-25 to II-30, II-32, II-34 to II-35, and II-37 to II-45, wherein $A^1$ is

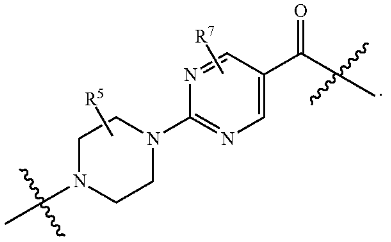

Embodiment II-52. The compound of any one of Embodiments II-1 to II-6, II-8, II-10 to II-11, II-13 to II-18, II-20, II-22 to II-23, II-25 to II-30, II-32, II-34 to II-35, and II-37 to II-45, wherein $A^1$ is

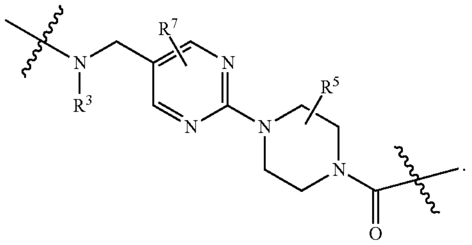

Embodiment II-53. The compound of any one of Embodiments II-1 to II-6, II-8, II-10 to II-11, II-13 to II-18, II-20, II-22 to II-23, II-25 to II-30, II-32, II-34 to II-35, and II-37 to II-45, wherein $A^1$ is

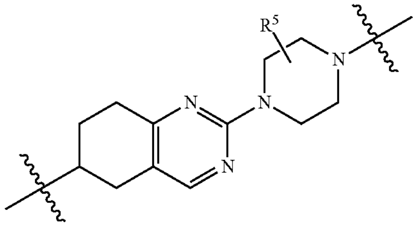

Embodiment II-54. The compound of any one of Embodiments II-1 to II-6, II-8, II-10 to II-11, II-13 to II-18, II-20, II-22 to II-23, II-25 to II-30, II-32, II-34 to II-35, and II-37 to II-45, wherein $A^1$ is

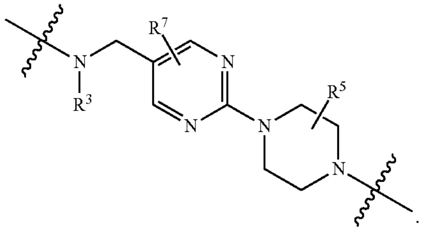

Embodiment II-55. The compound of any one of Embodiments II-1 to II-6, II-8, II-10 to II-11, II-13 to II-18, II-20, II-22 to II-23, II-25 to II-30, II-32, II-34 to II-35, and II-37 to II-45, wherein $A^1$ is

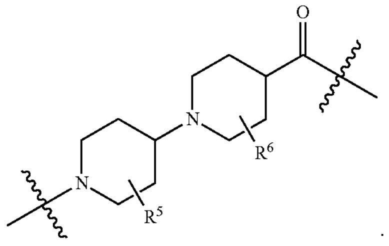

Embodiment II-56. The compound of any one of Embodiments II-1 to II-6, II-8, II-10 to II-11, II-13 to II-18, II-20, II-22 to II-23, II-25 to II-30, II-32, II-34 to II-35, and II-37 to II-45, wherein $A^1$ is

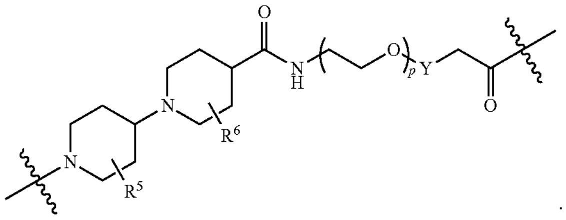

Embodiment II-57. The compound of any one of Embodiments II-1 to II-8, II-15 to II-20, II-27 to II-32, and II-39 to II-45, wherein $A^2$ is absent.

Embodiment II-58. The compound of any one of Embodiments II-1 to II-6, II-9 to II-18, II-21 to II-30, and II-33 to II-45, wherein $A^2$ is

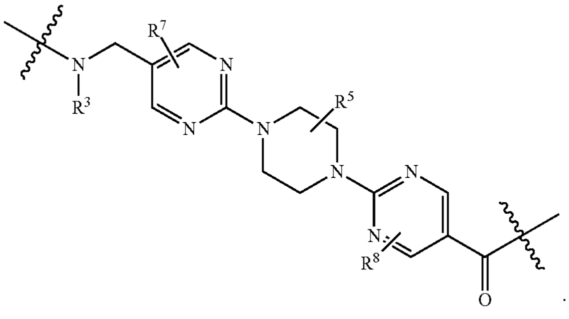

Embodiment II-59. The compound of any one of Embodiments II-1 to II-6, II-9 to II-18, II-21 to II-30, and II-33 to II-45, wherein $A^2$ is

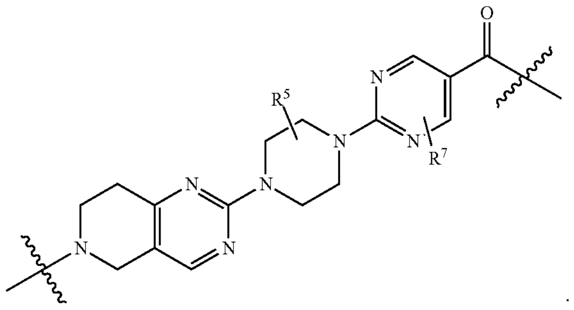

Embodiment II-60. The compound of any one of Embodiments II-1 to II-6, II-9 to II-18, II-21 to II-30, and II-33 to II-45, wherein $A^2$ is

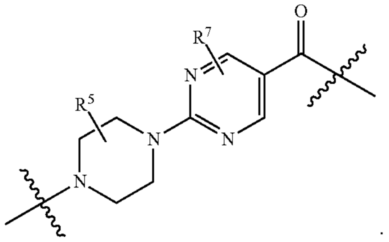

Embodiment II-61. The compound of any one of Embodiments II-1 to II-6, II-9 to II-18, II-21 to II-30, and II-33 to II-45, wherein $A^2$ is

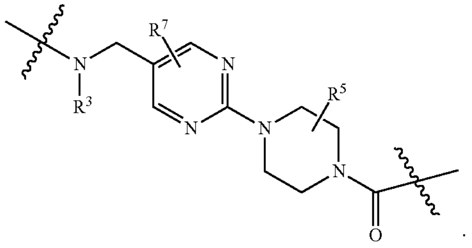

Embodiment II-62. The compound of any one of Embodiments II-1 to II-6, II-9 to II-18, II-21 to II-30, and II-33 to Ii-45, wherein $A^2$ is

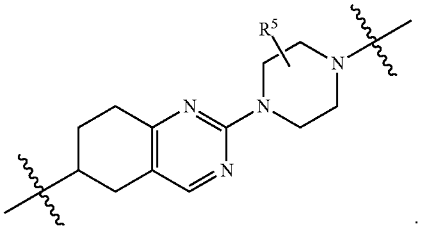

Embodiment II-63. The compound of any one of Embodiments II-1 to II-6, II-9 to II-18, II-21 to II-30, and II-33 to II-45, wherein $A^2$ is

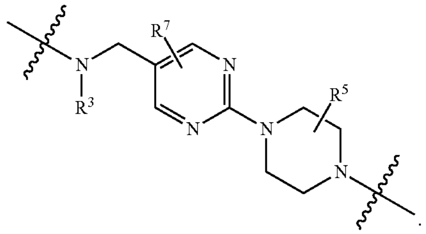

Embodiment II-64. The compound of any one of Embodiments II-1 to II-6, II-9 to II-18, II-21 to II-30, and II-33 to II-45, wherein $A^2$ is

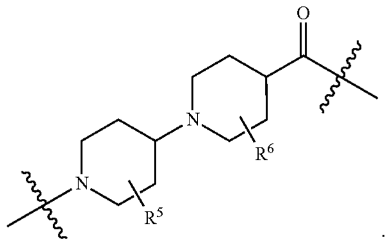

Embodiment II-65. The compound of any one of Embodiments II-1 to II-6, II-9 to II-18, II-21 to II-30, and II-33 to II-45, wherein $A^2$ is

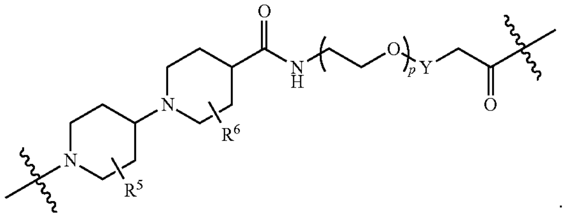

Embodiment II-66. The compound of any one of Embodiments II-1 to II-65, wherein B is

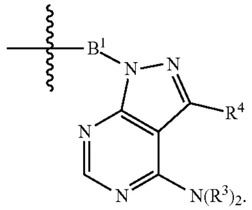

Embodiment II-67. The compound of any one of Embodiments II-1 to II-65, wherein B is

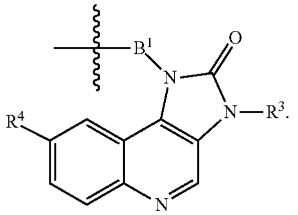

Embodiment II-68. The compound of any one of Embodiments II-1 to II-65, wherein $B^1$ is

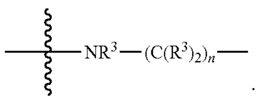

Embodiment II-69. The compound of any one of Embodiments II-1 to II-65, wherein $B^1$ is

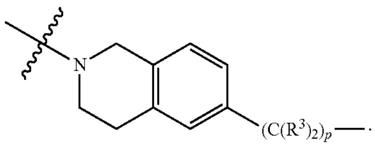

Embodiment II-70. The compound of any one of Embodiments II-1 to II-69, wherein $R^4$ is 5-12 membered heteroaryl, optionally substituted with —$N(R^3)_2$, —$OR^3$, halogen, $(C_1$-$C_6)$alkyl, —$(C_1$-$C_6)$alkylene-heteroaryl, —$(C_1$-$C_6)$alkylene-CN, or —$C(O)NR^3$-heteroaryl.

Embodiment II-71. The compound of any one of Embodiments II-1 to II-70, or a pharmaceutically acceptable salt or tautomer thereof, wherein compound has the following formula:

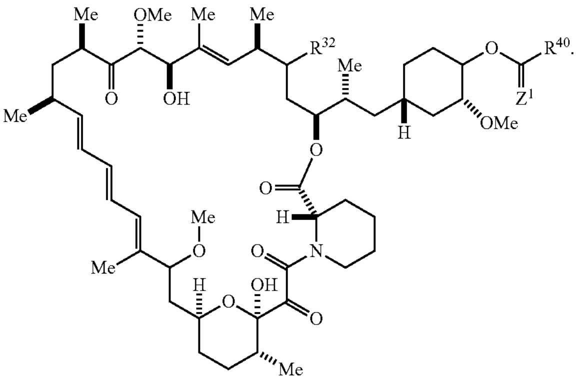

Embodiment II-72. A compound selected from the group consisting of:

Example 1
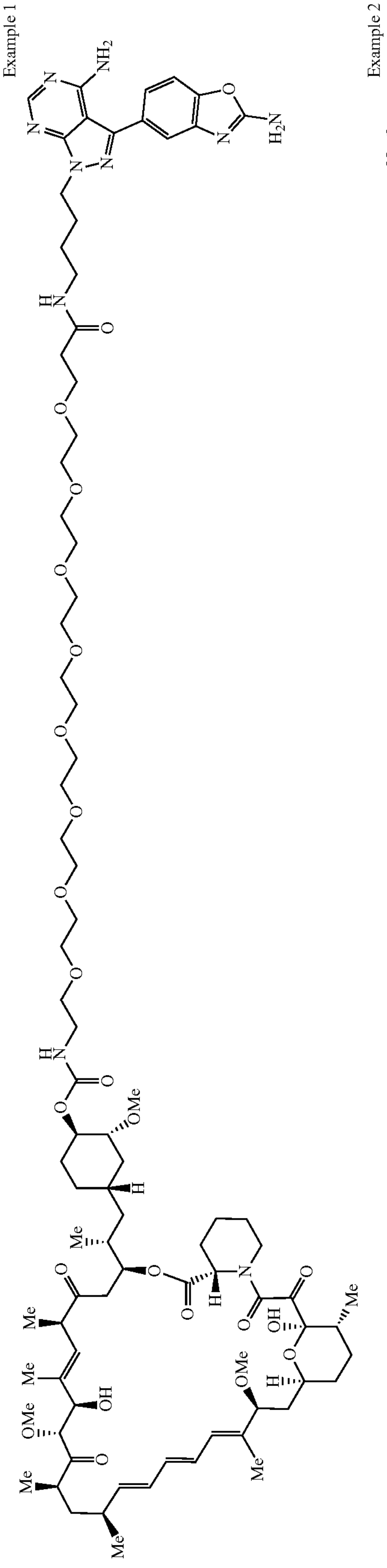
Example 2
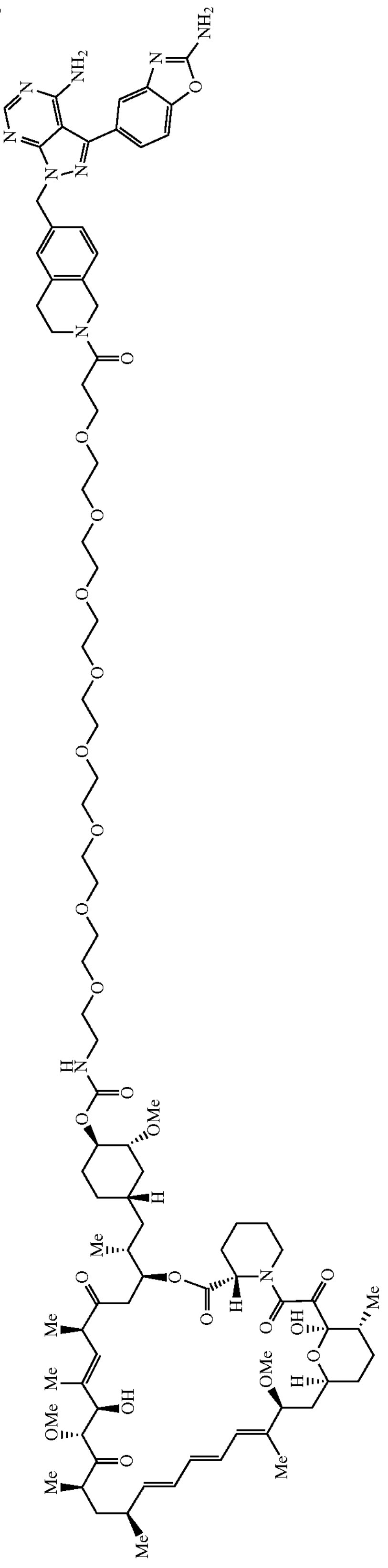

-continued
Example 3
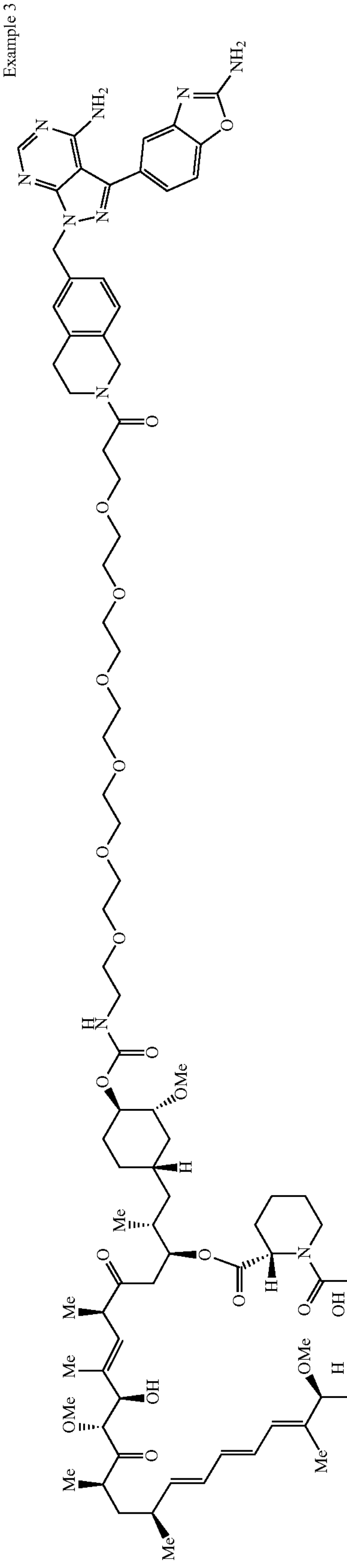
Example 4
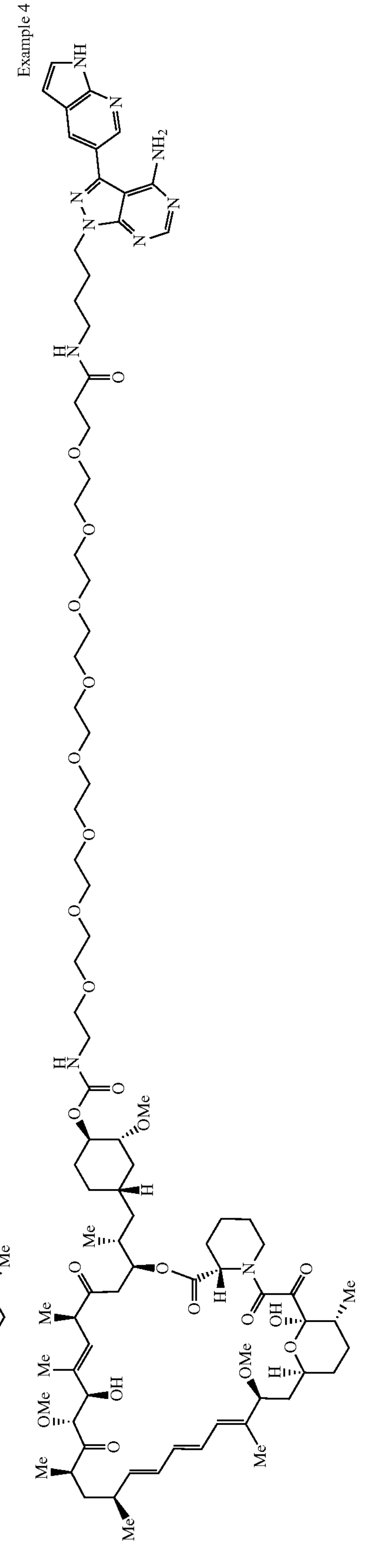

-continued
Example 5
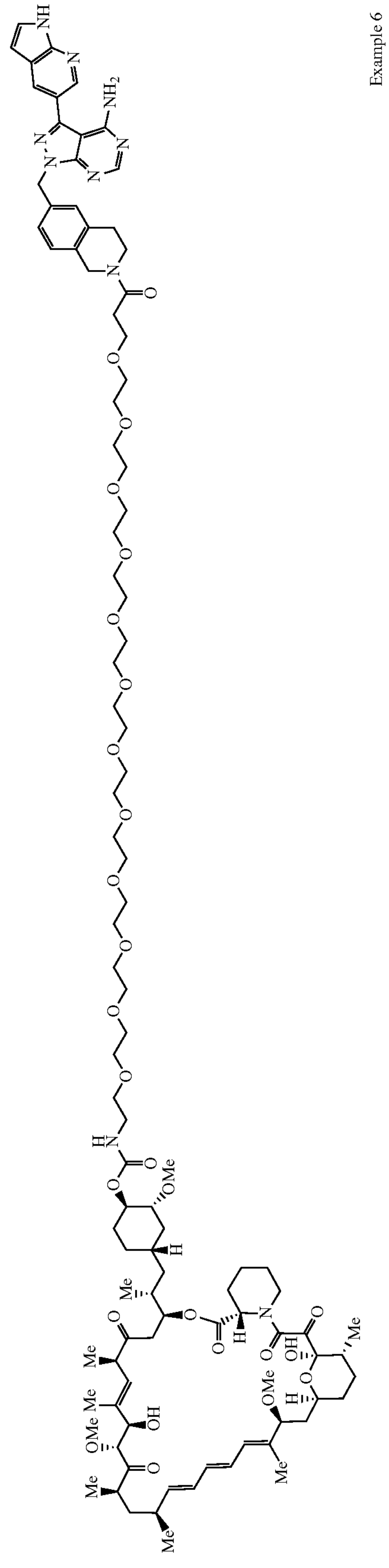
Example 6
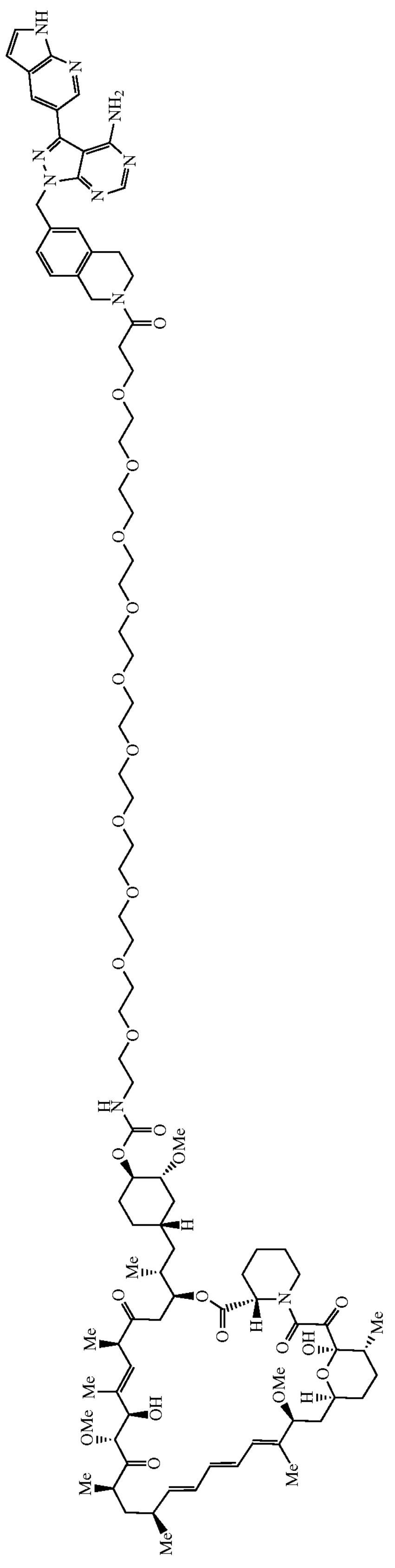

-continued
Example 7
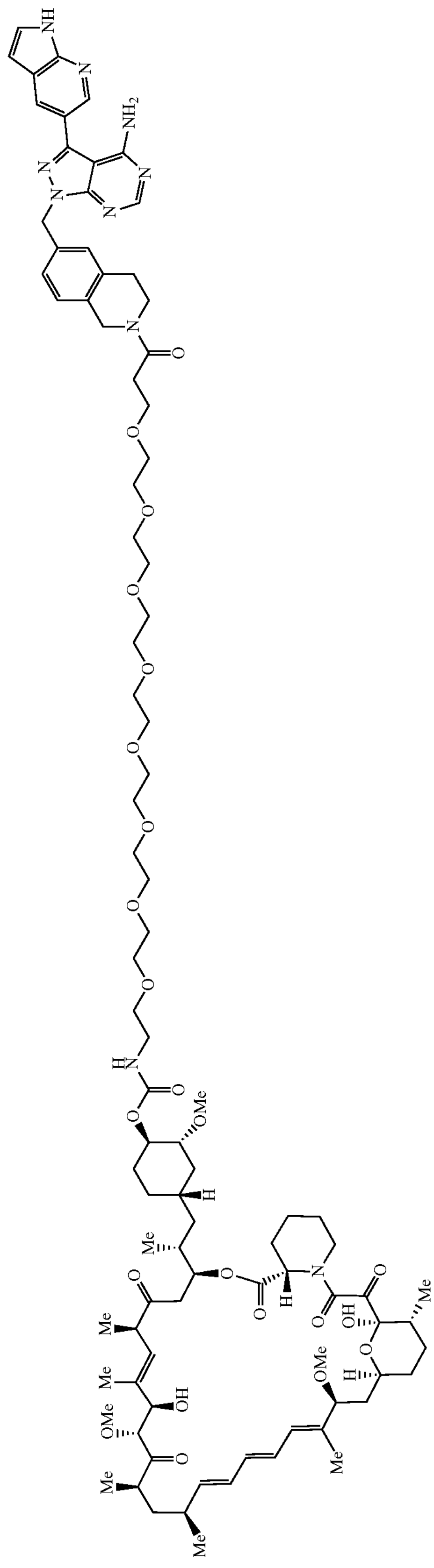
Example 8
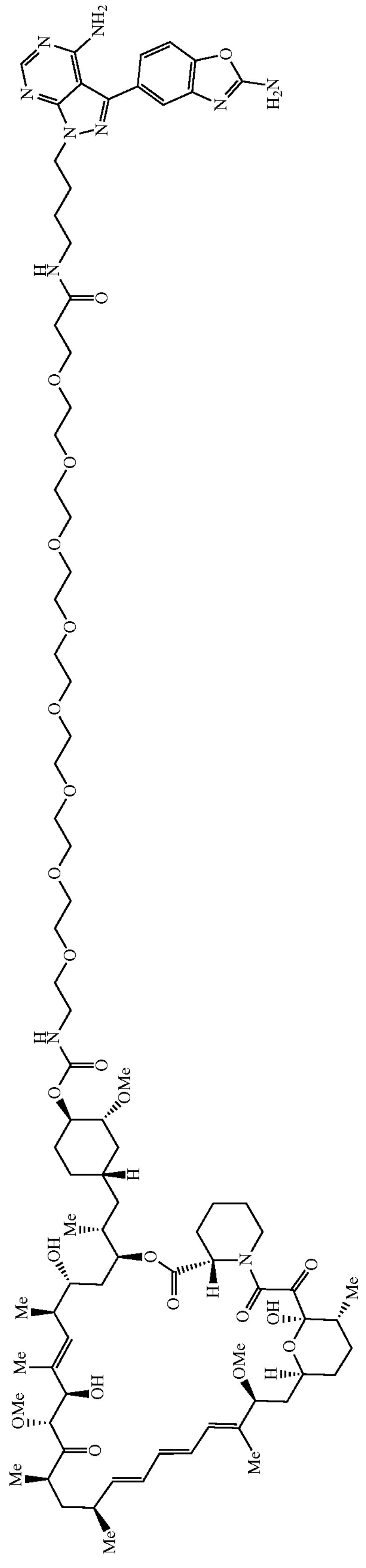

-continued
Example 9
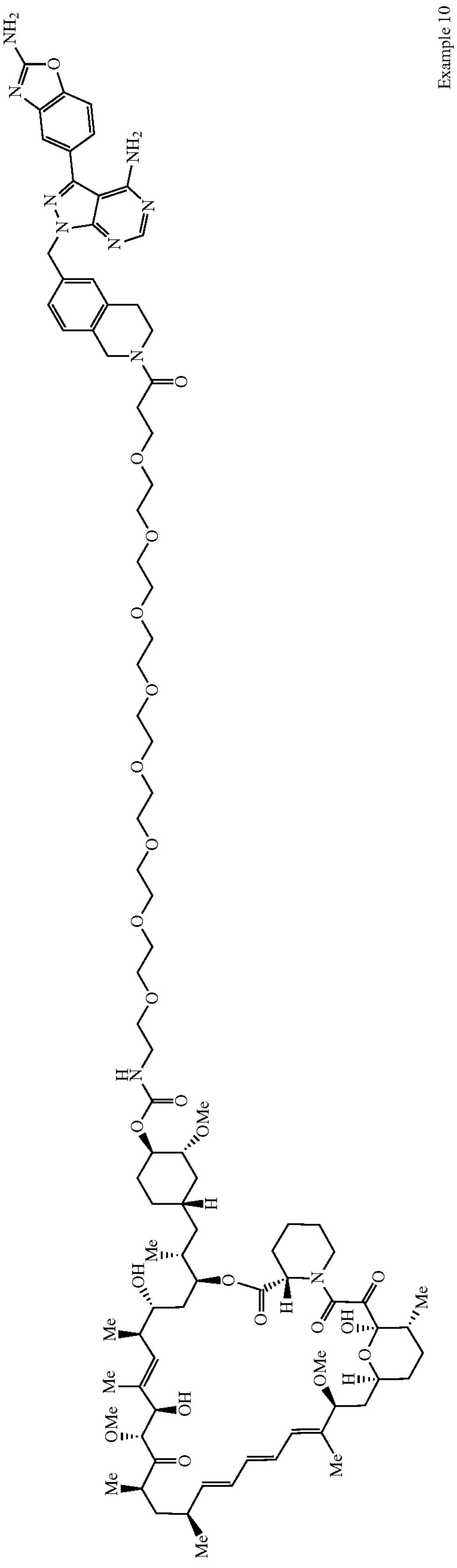
Example 10
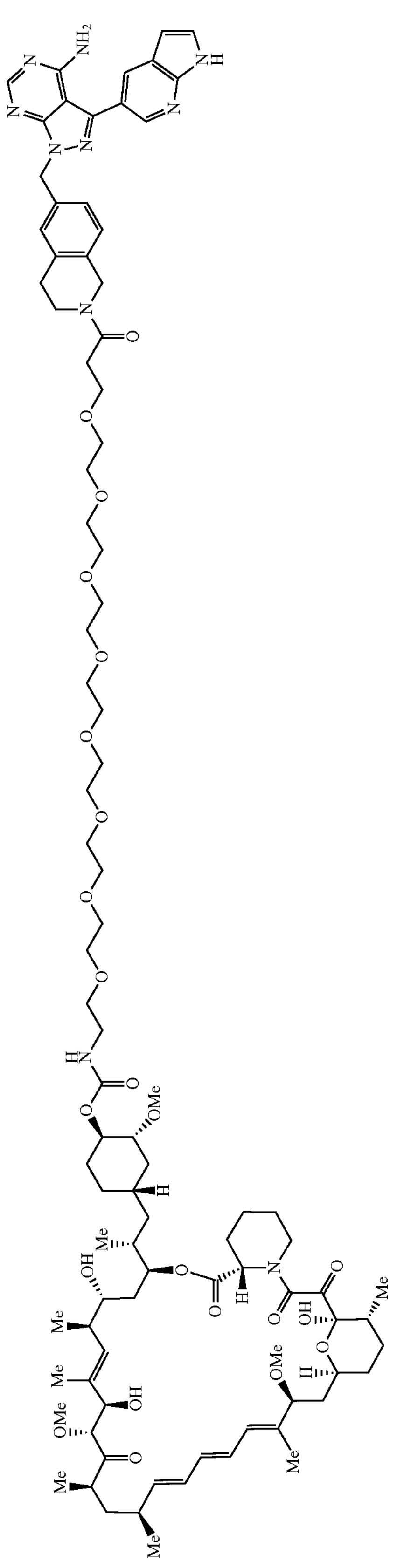

-continued
Example 11
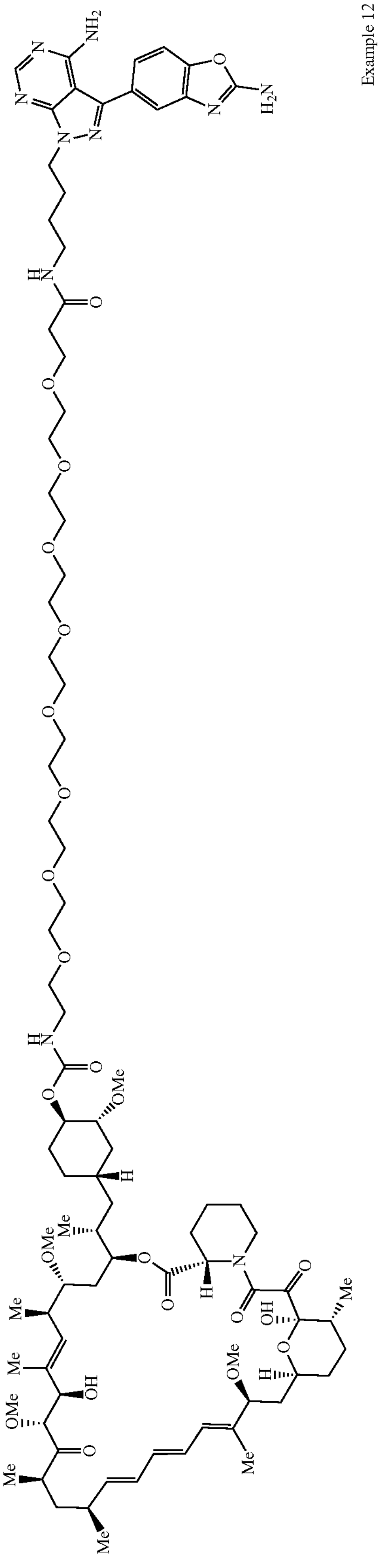
Example 12
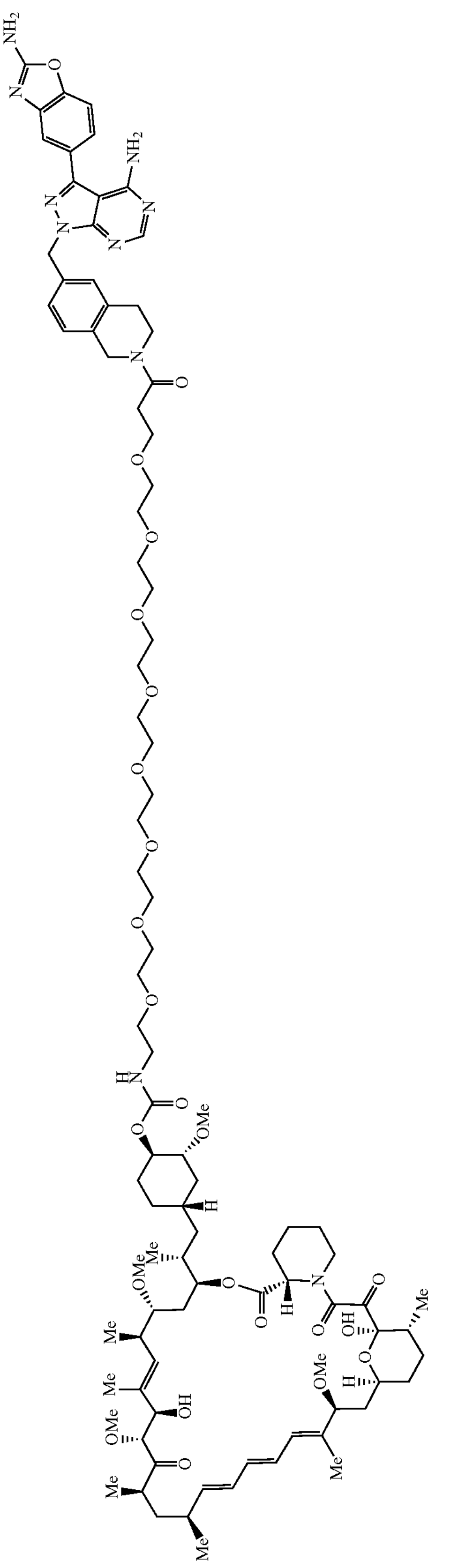

-continued
Example 13
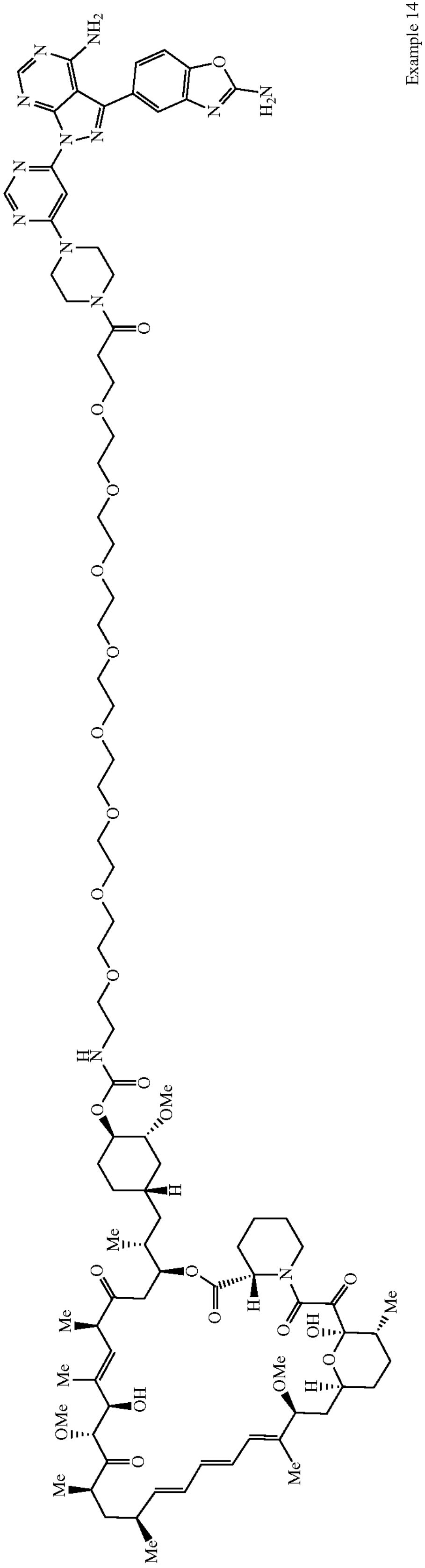
Example 14
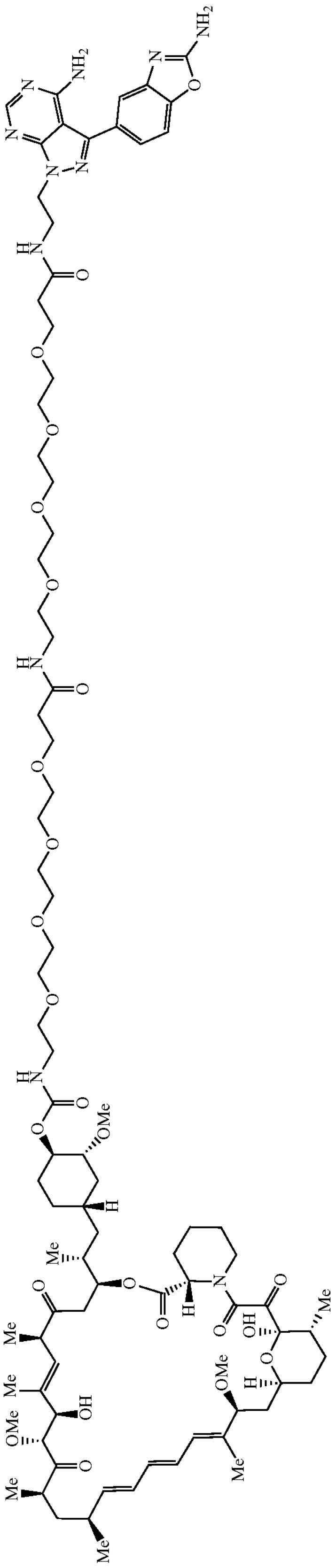

-continued
Example 15
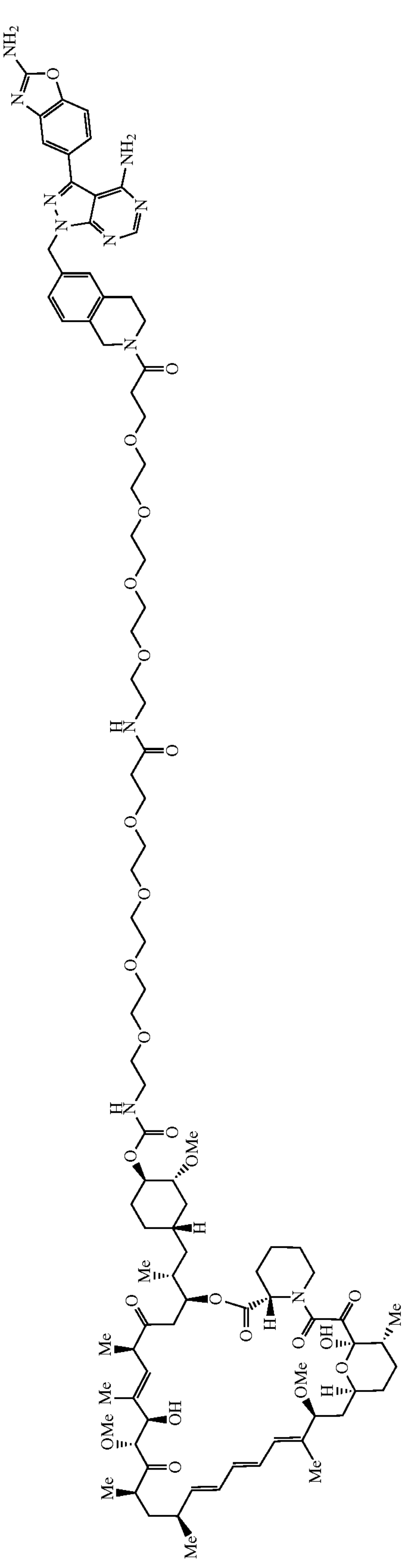
Example 16
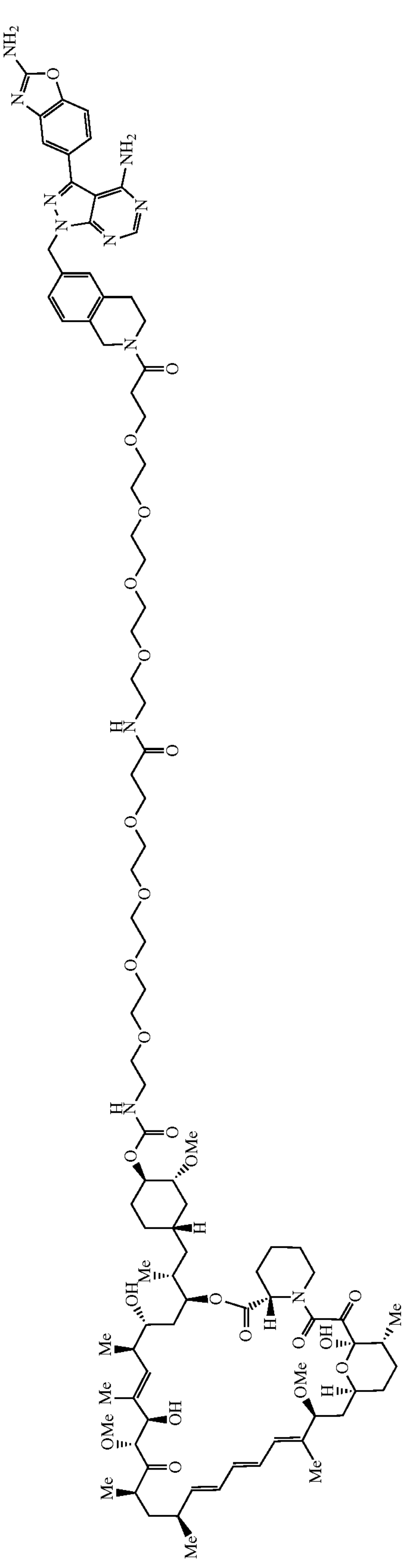

-continued
Example 17
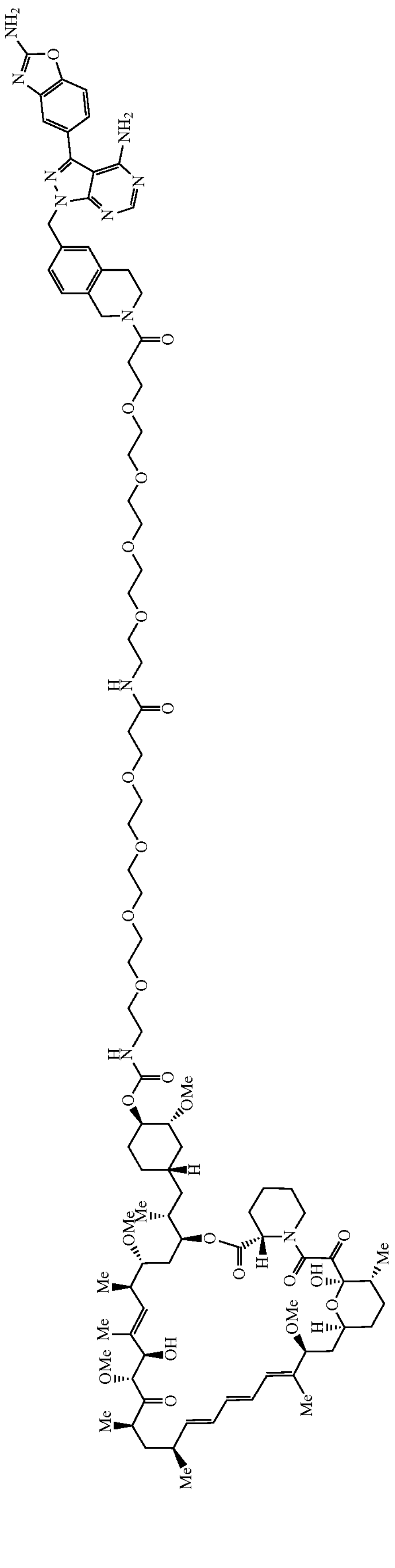
Example 18
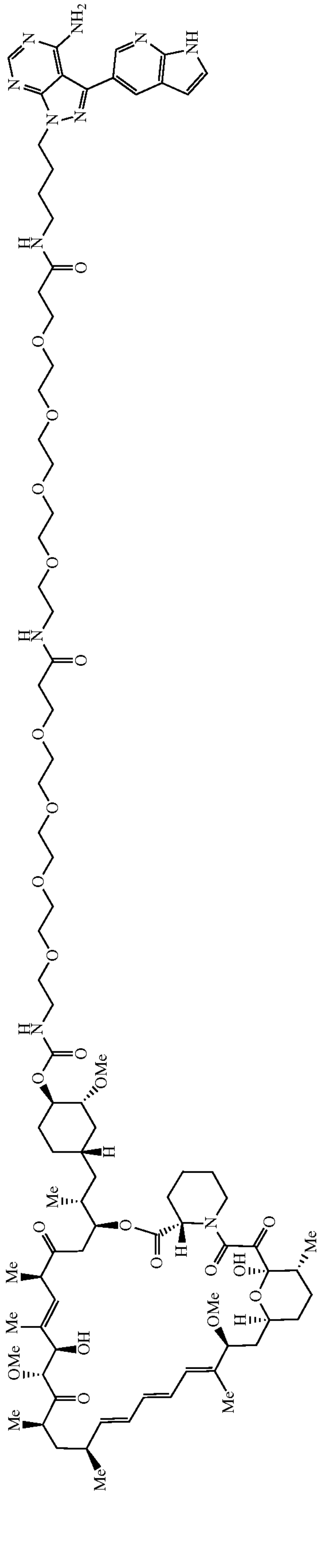

-continued
Example 19
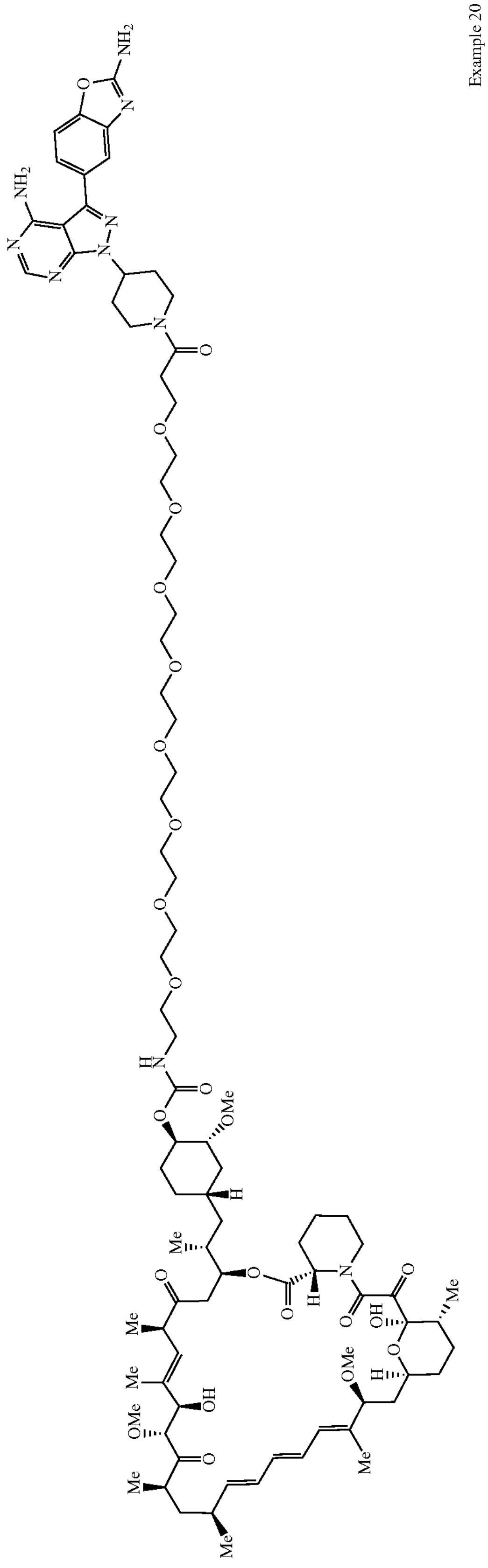
Example 20
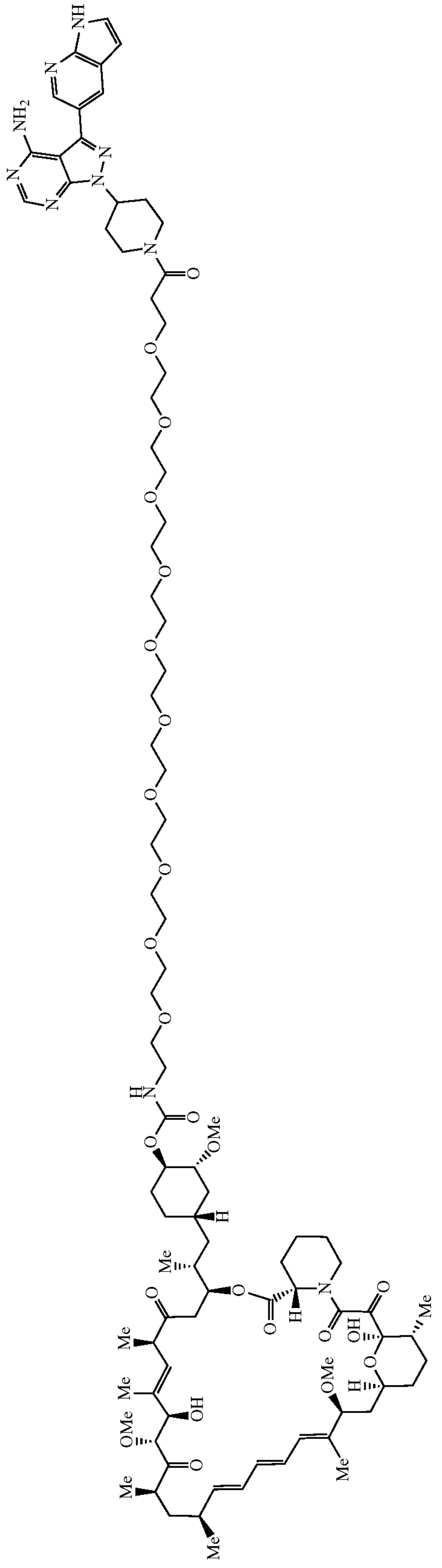

-continued
Example 21
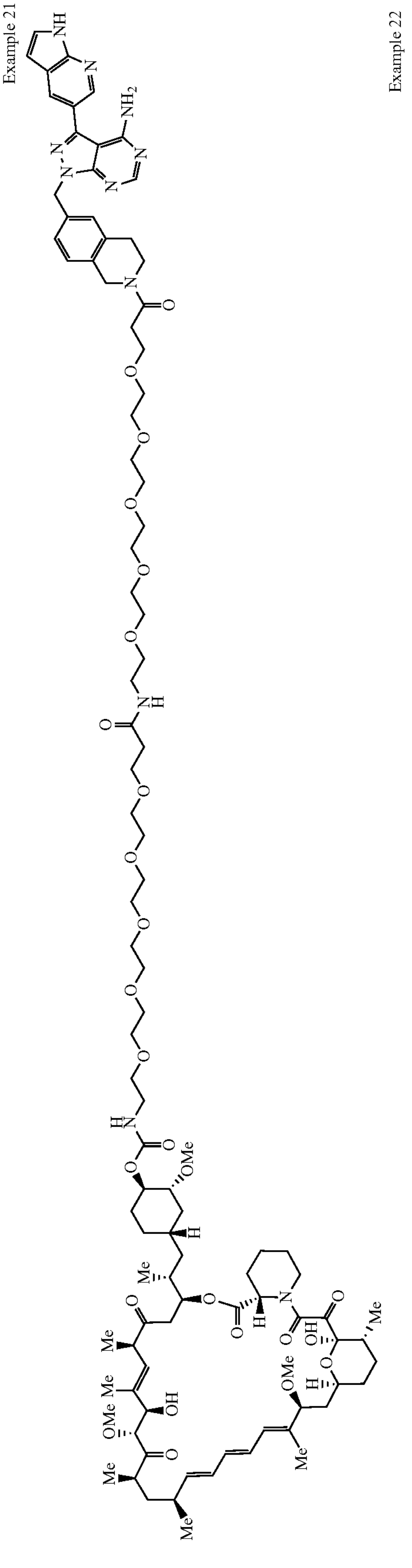
Example 22
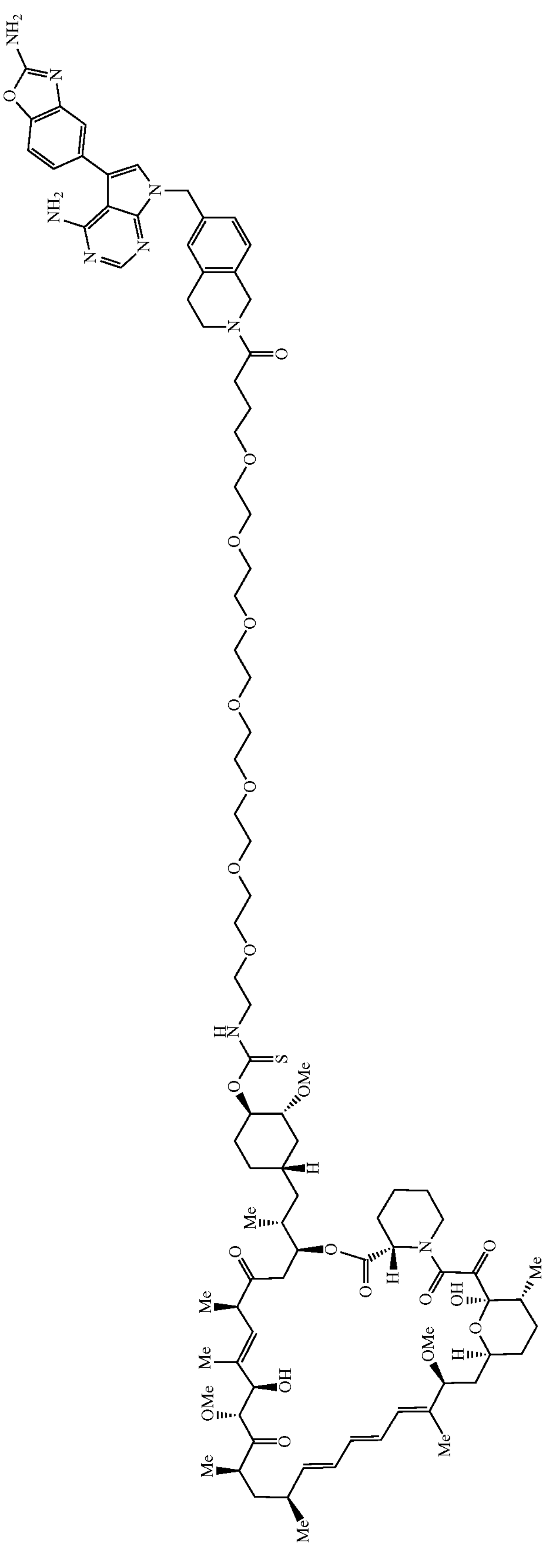

-continued
Example 23
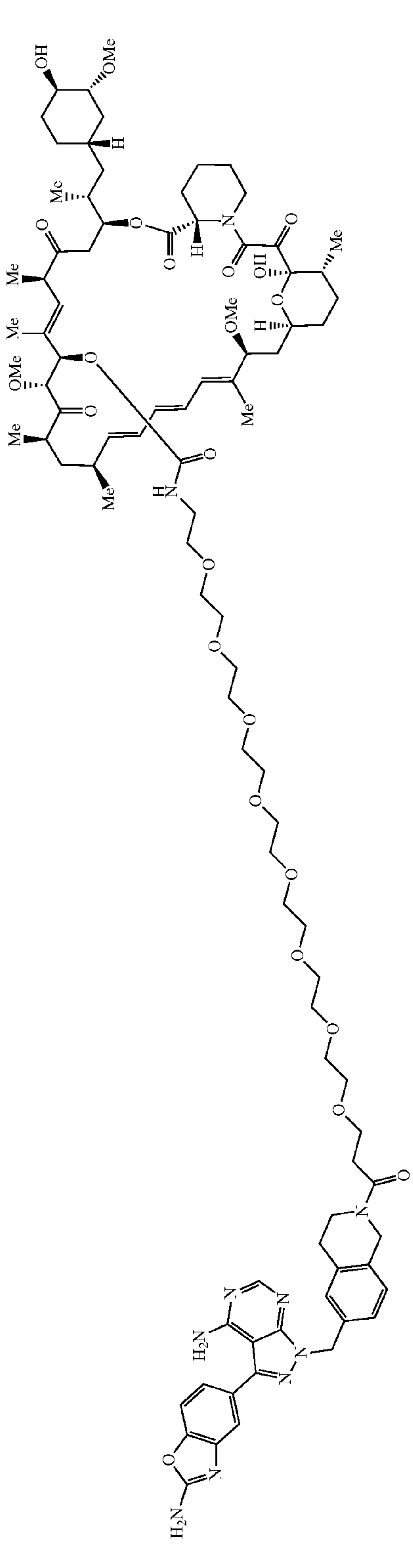
Example 24
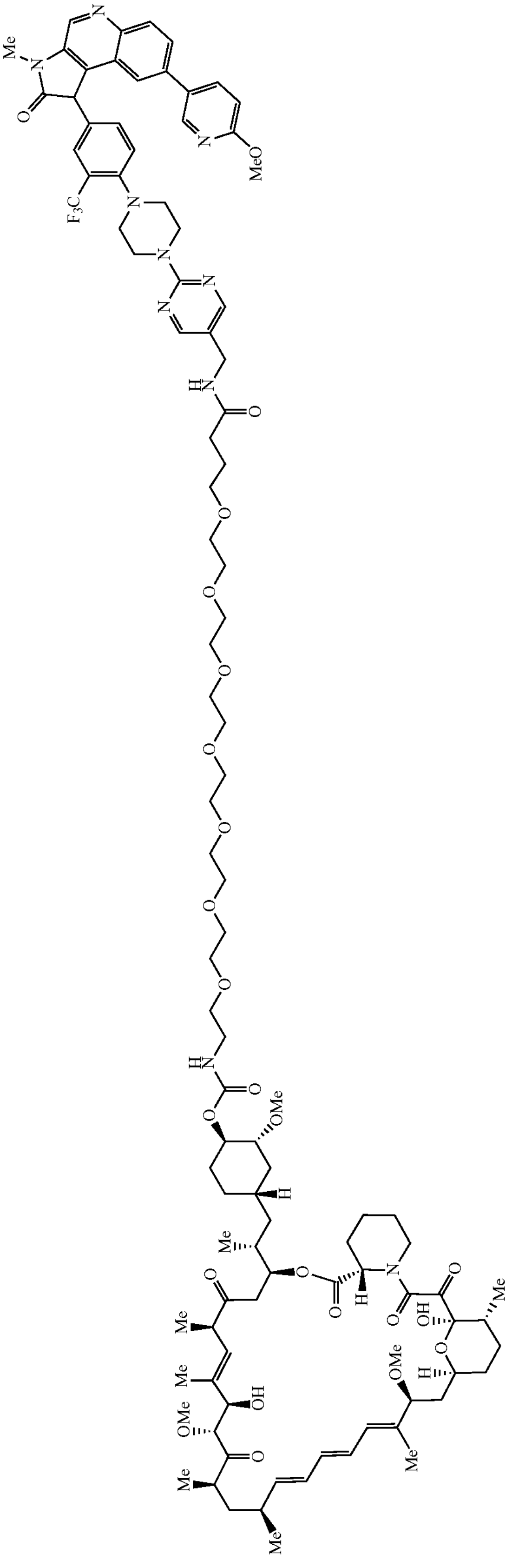

-continued
Example 25
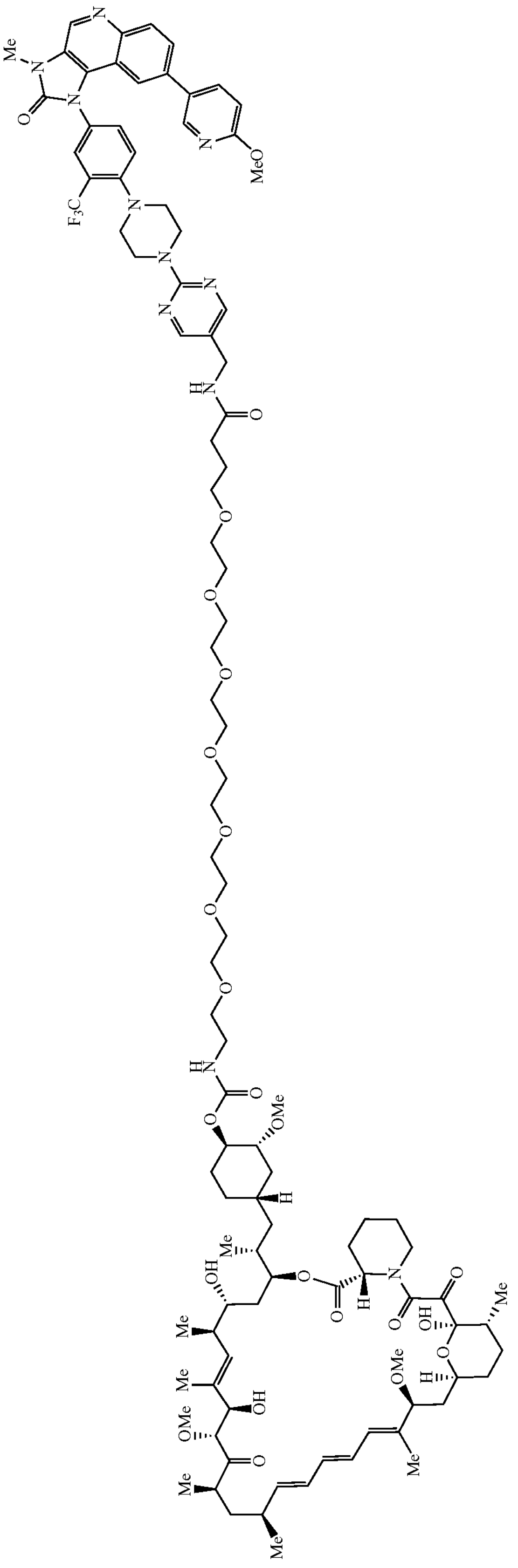

-continued
Example 26
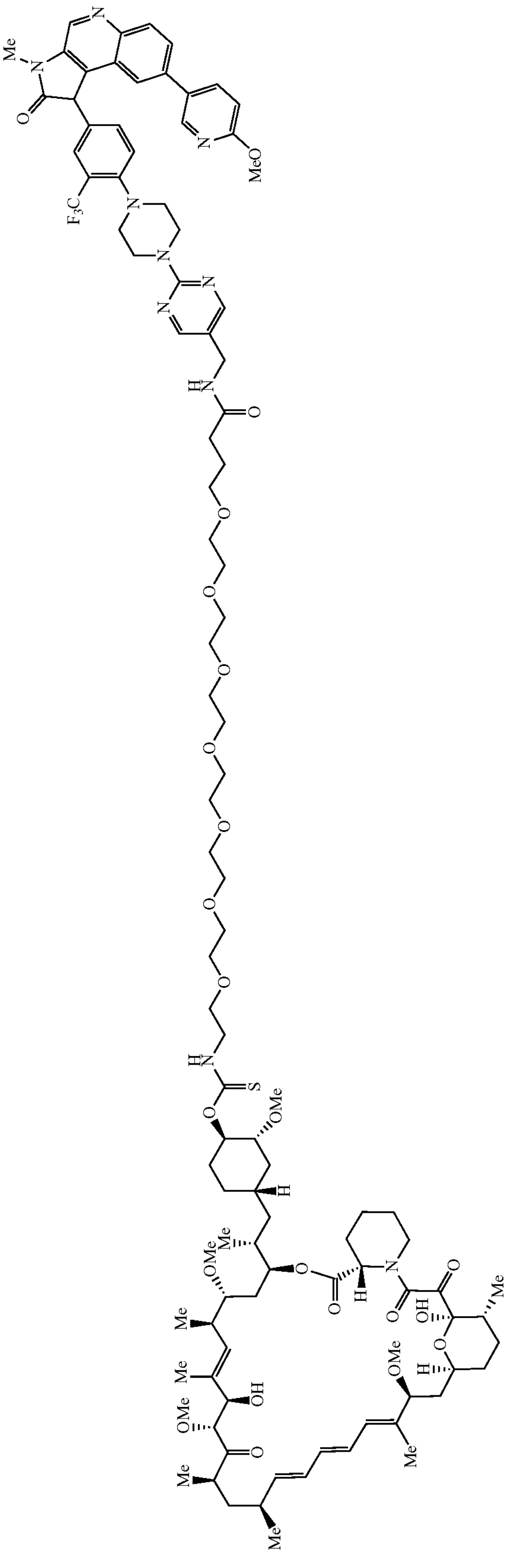
Example 27
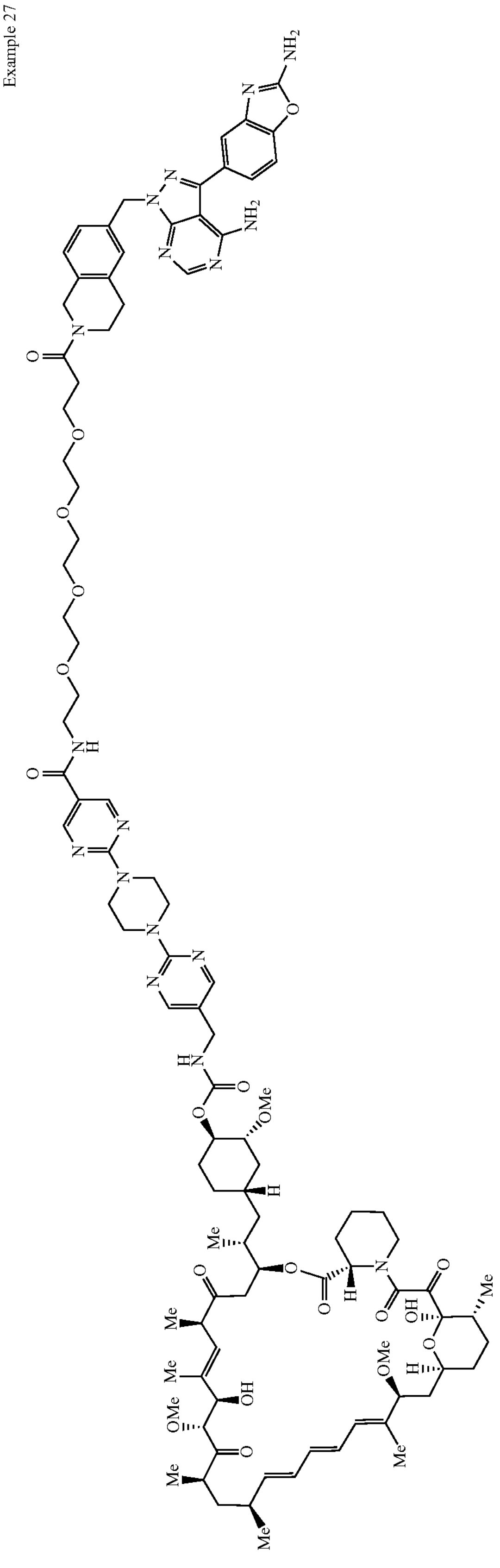

-continued
Example 28
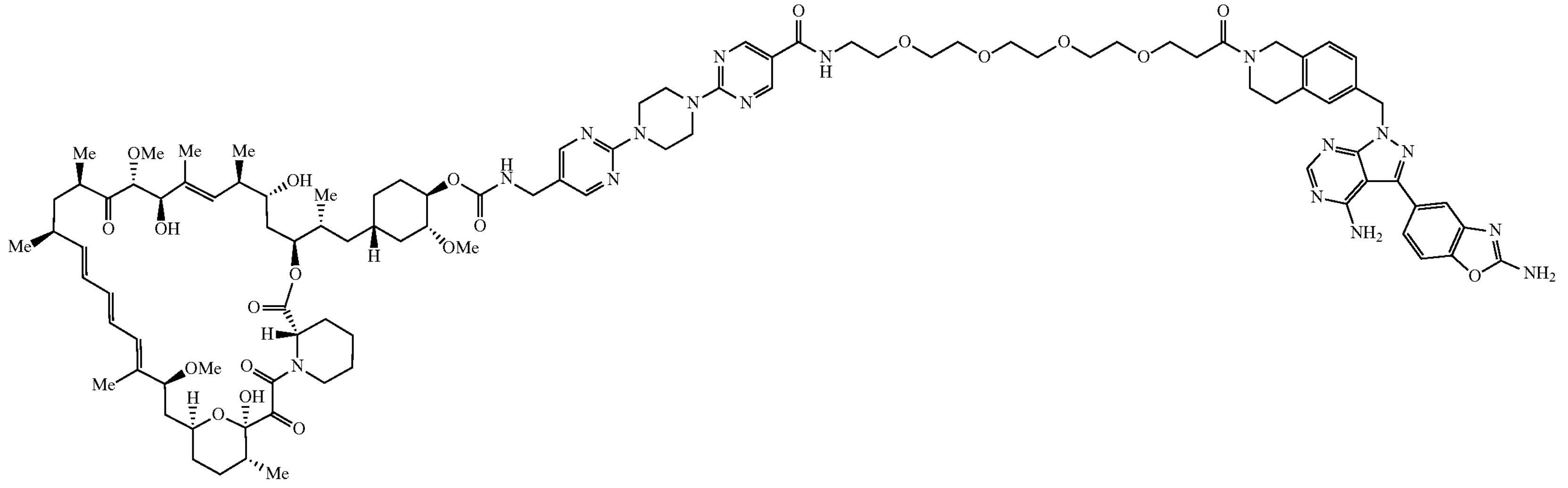
Example 29
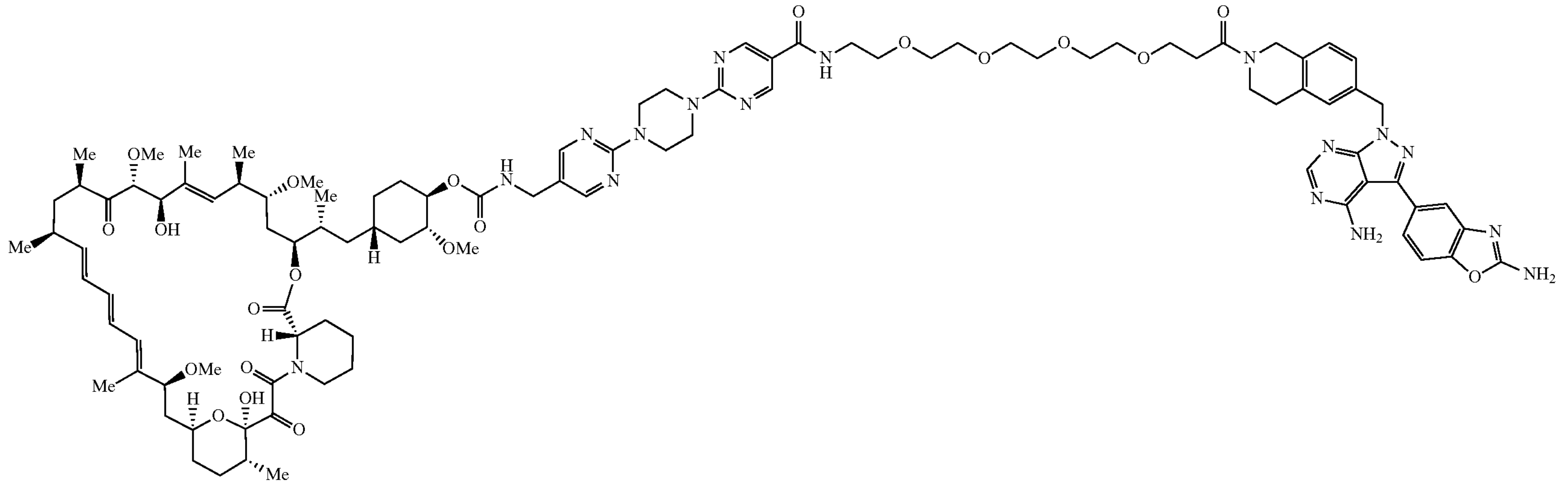

-continued
Example 30
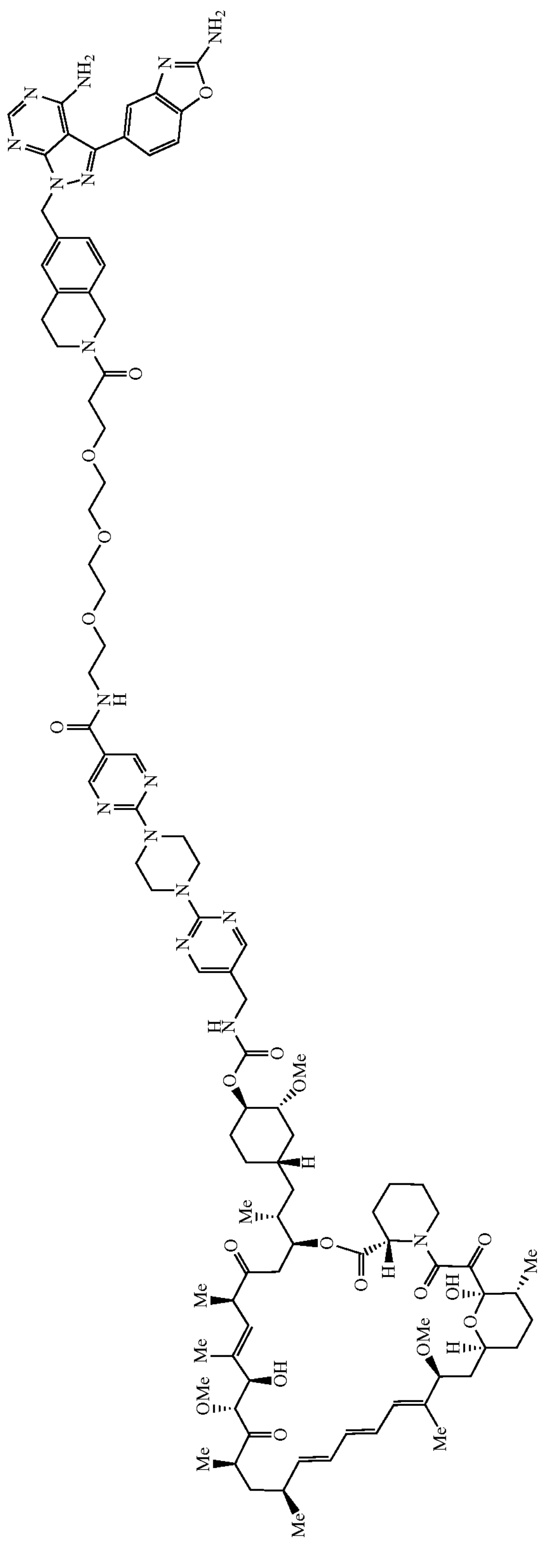

-continued
Example 31
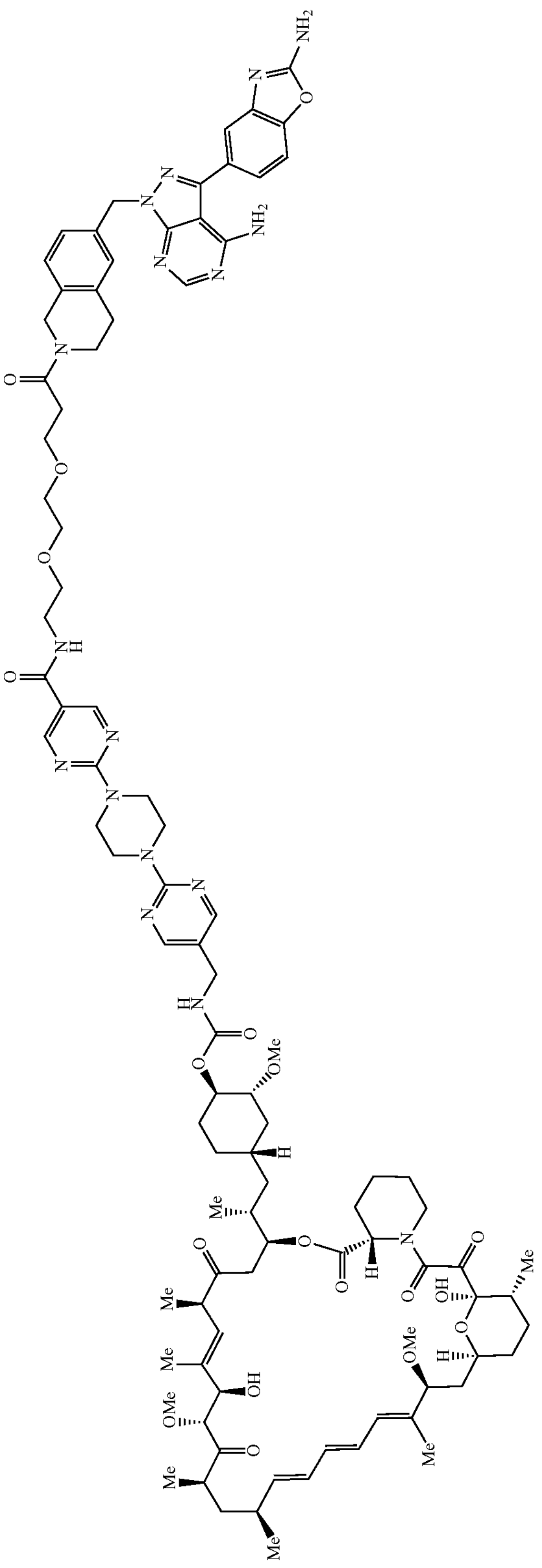

-continued
Example 32
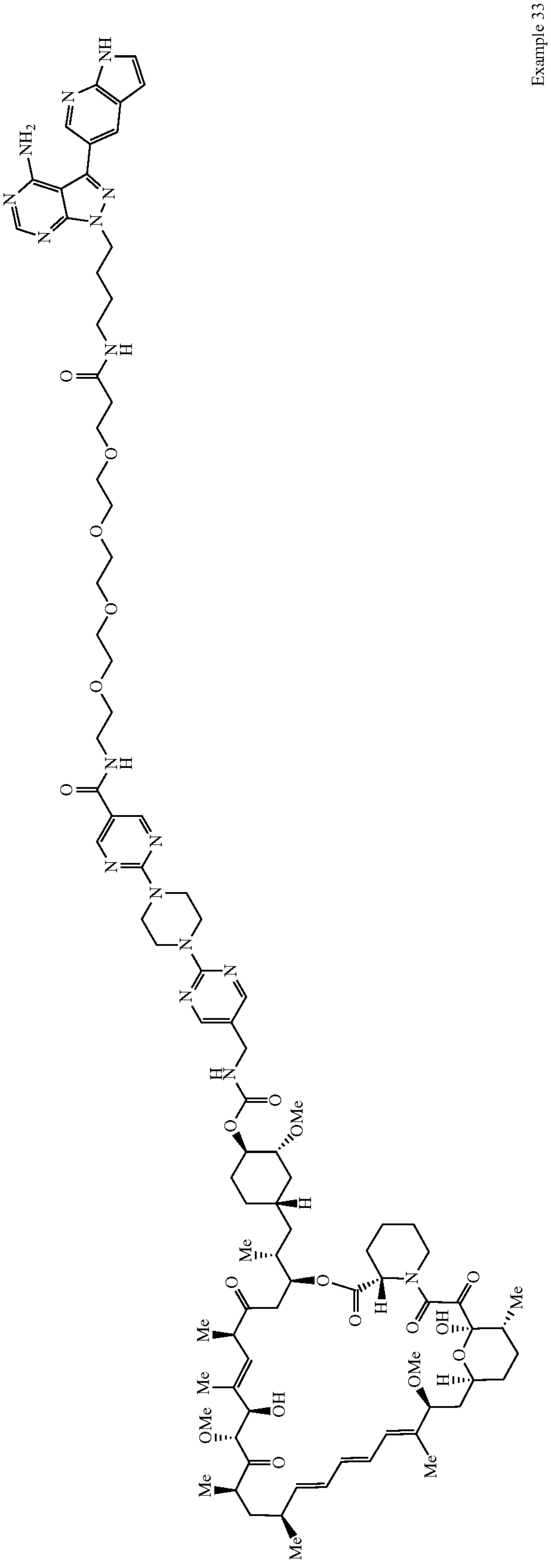
Example 33
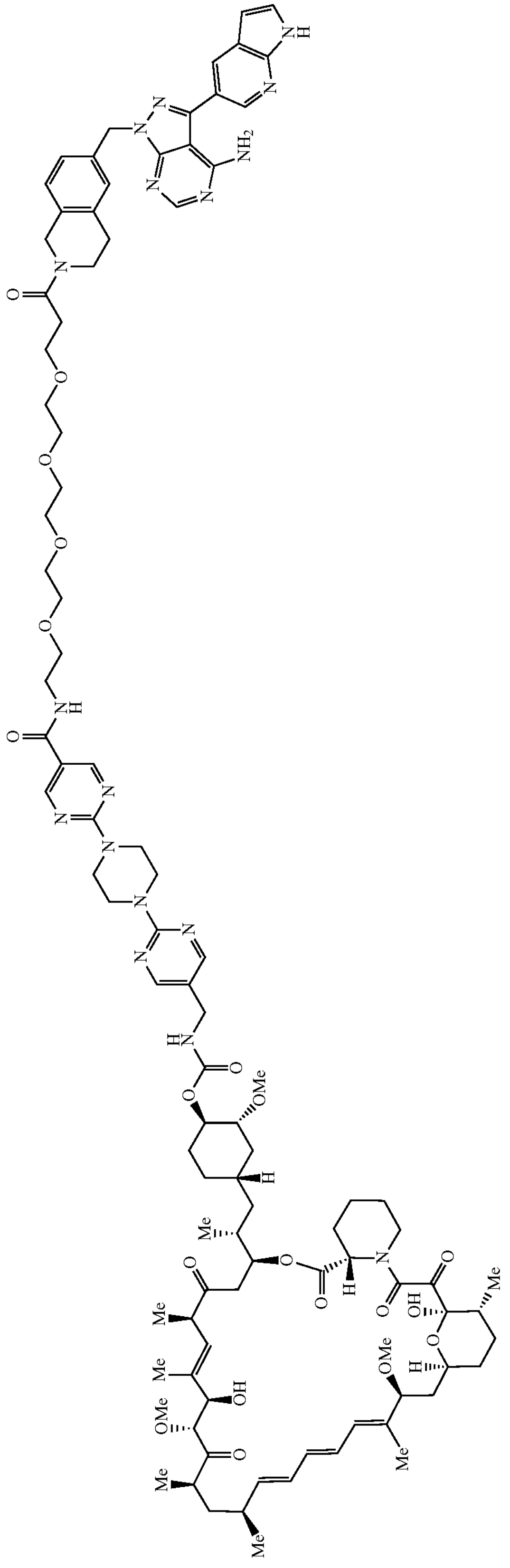

-continued
Example 34
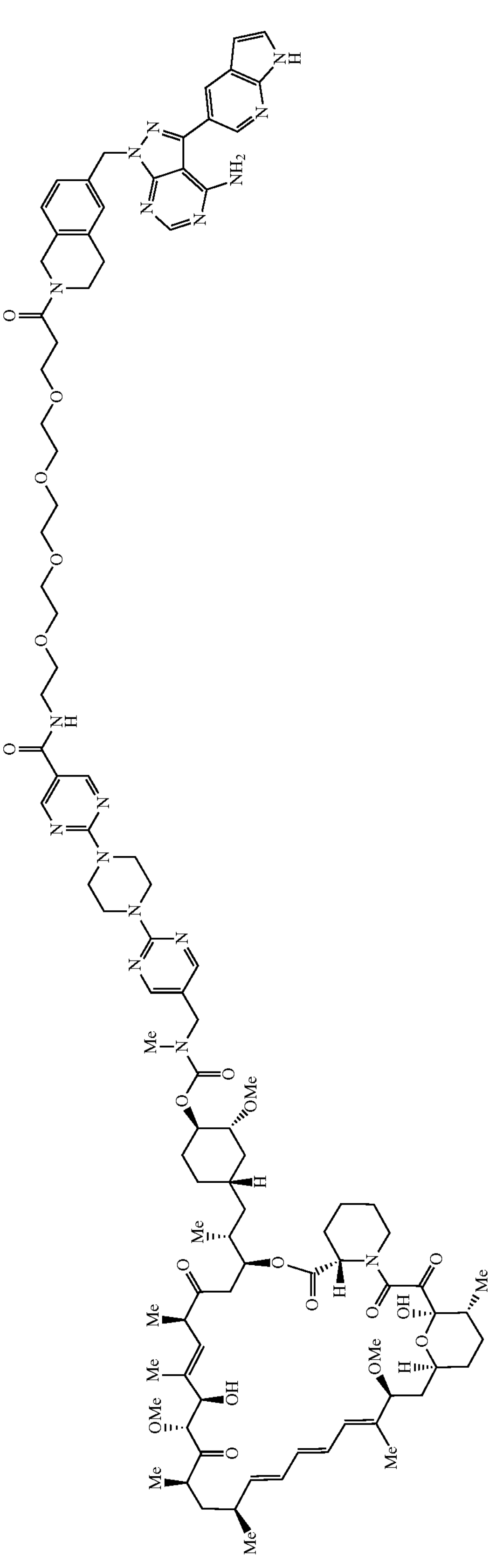
Example 35
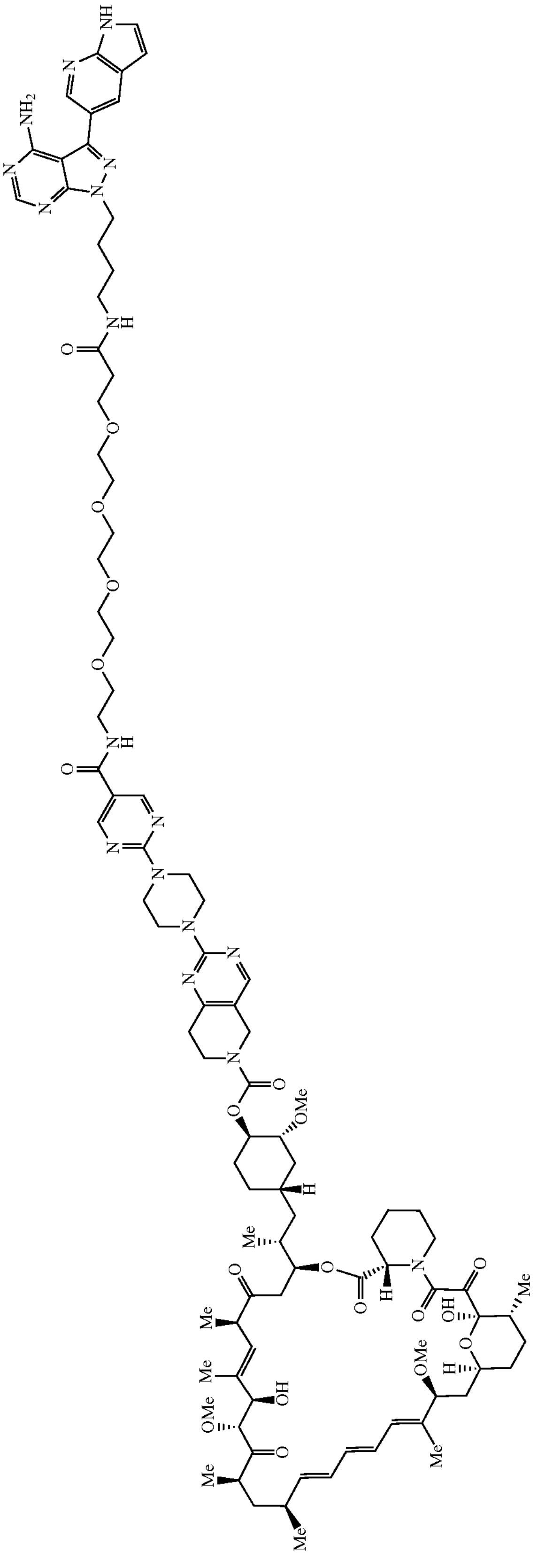

-continued
Example 36
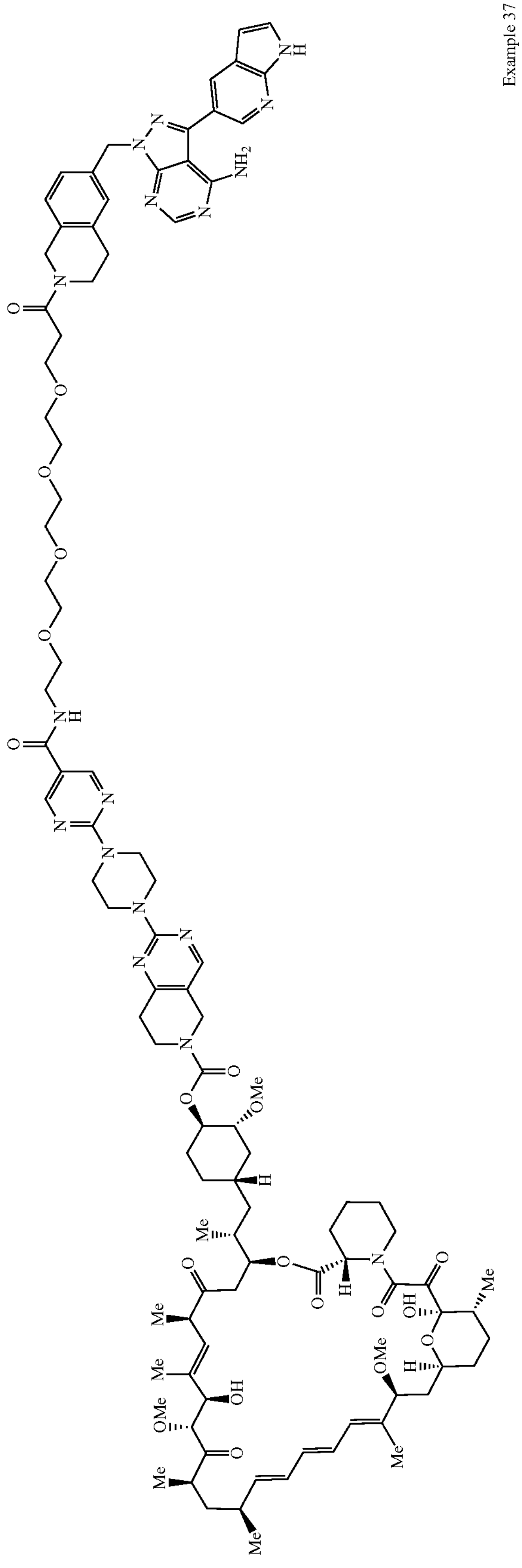
Example 37
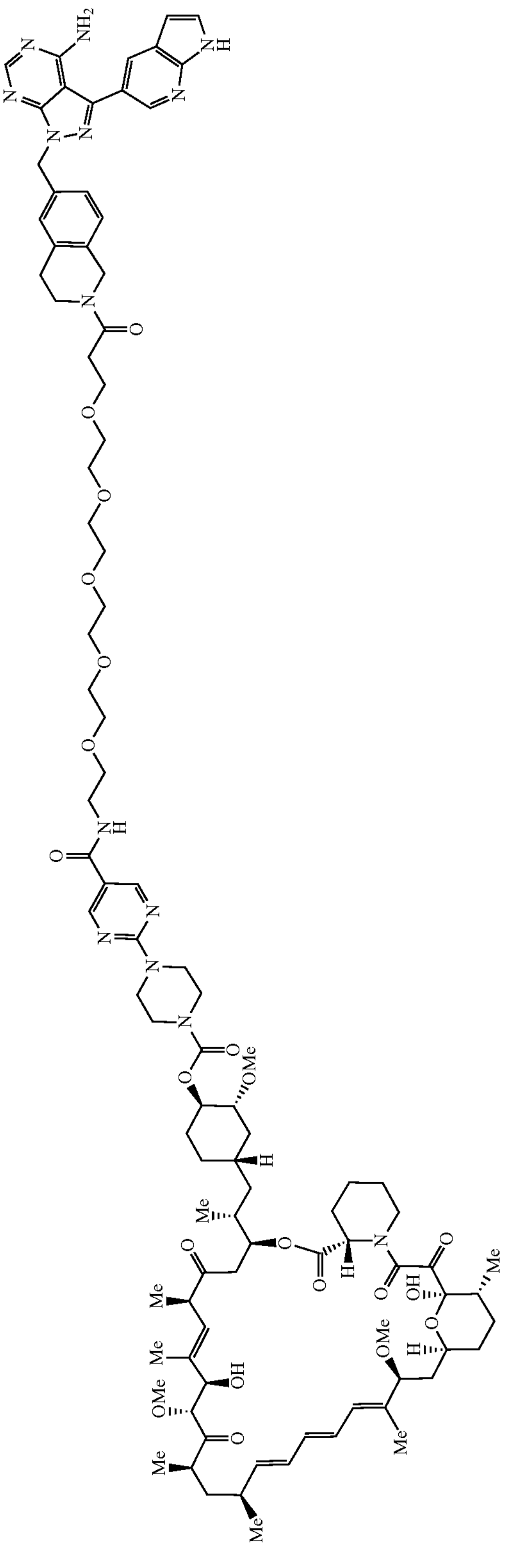

-continued
Example 38
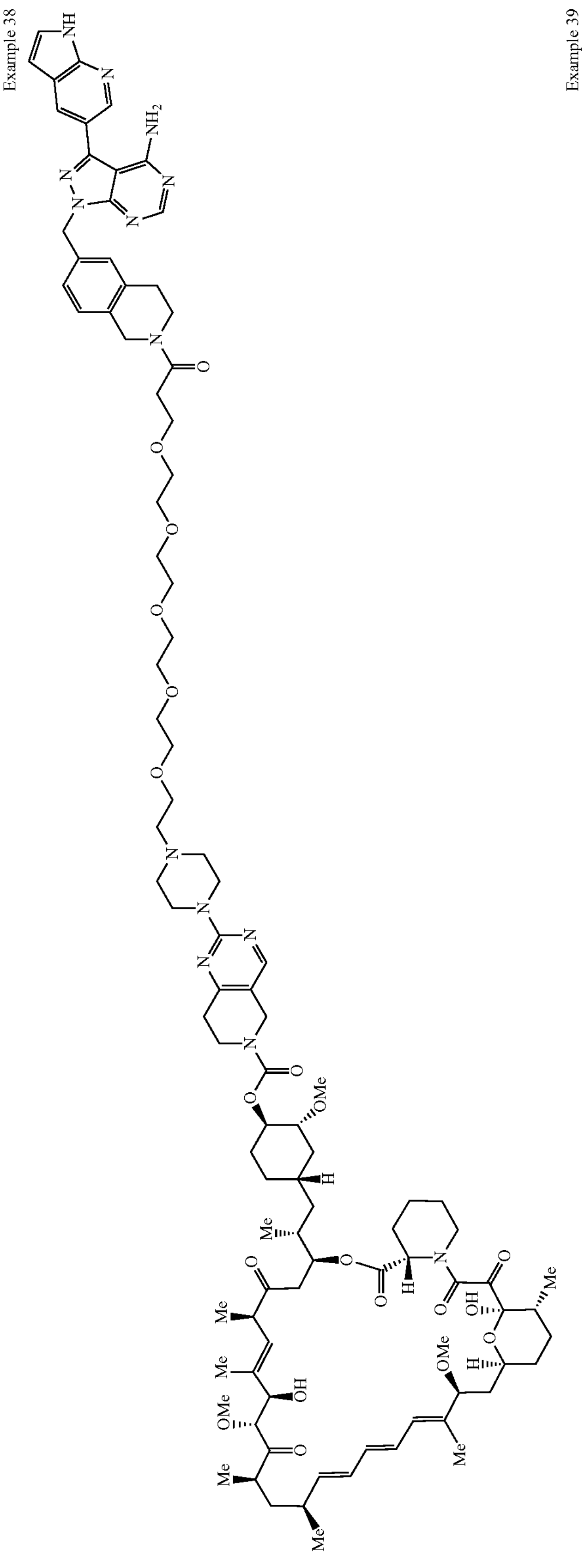
Example 39
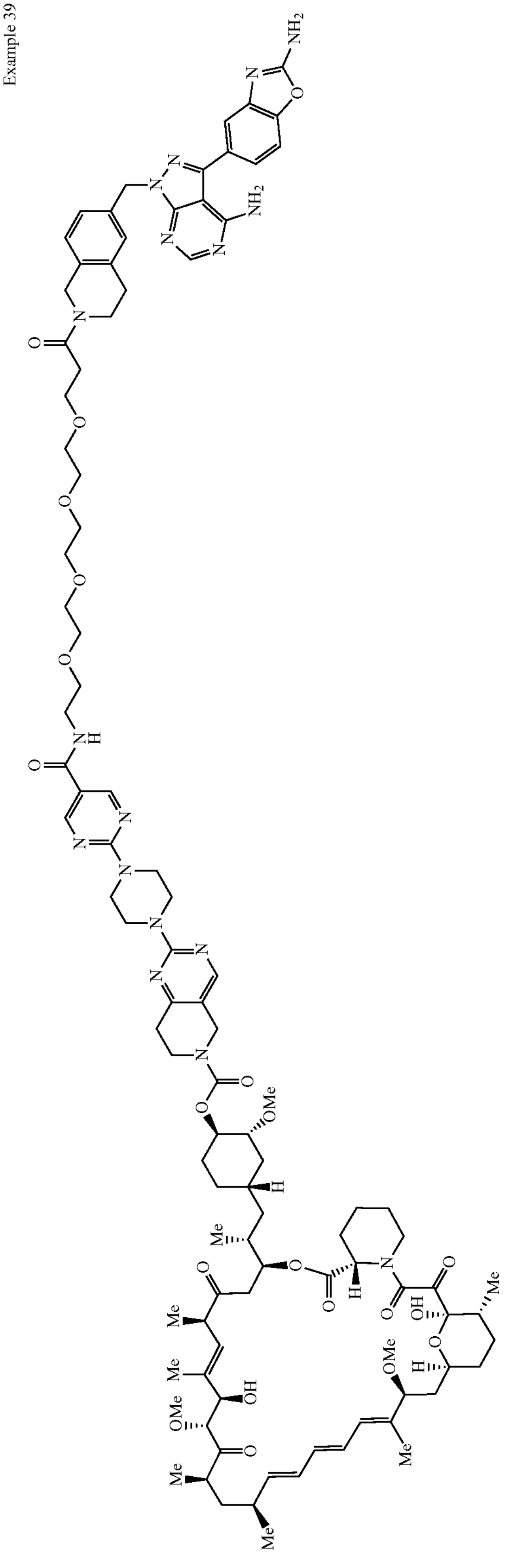

-continued
Example 40
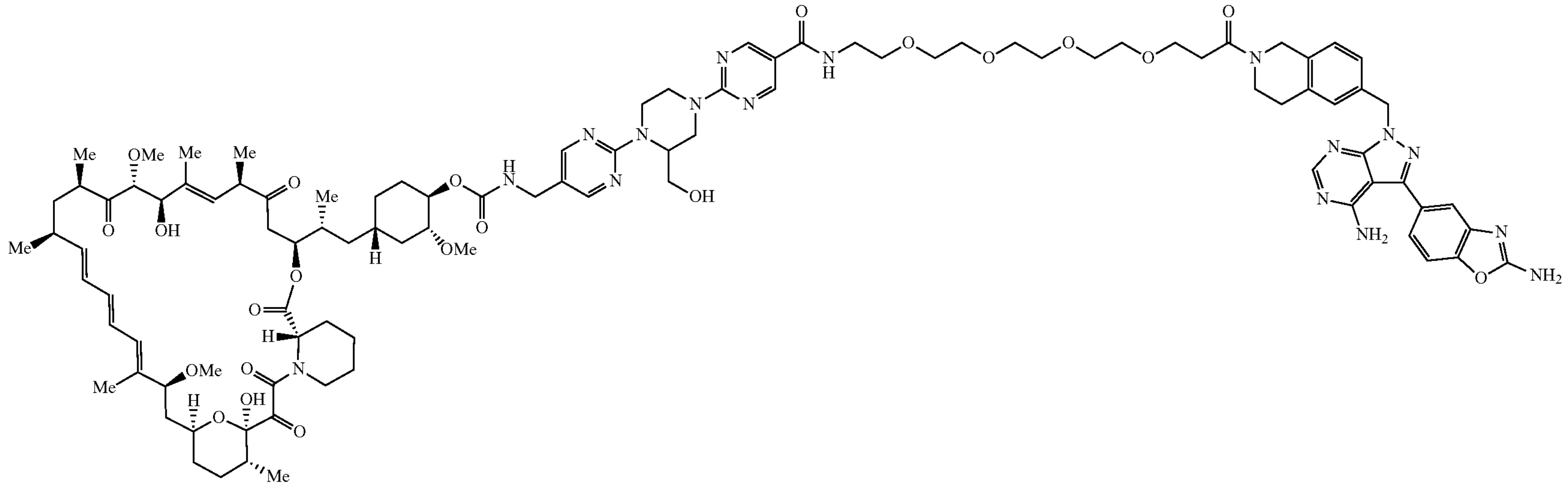
Example 41
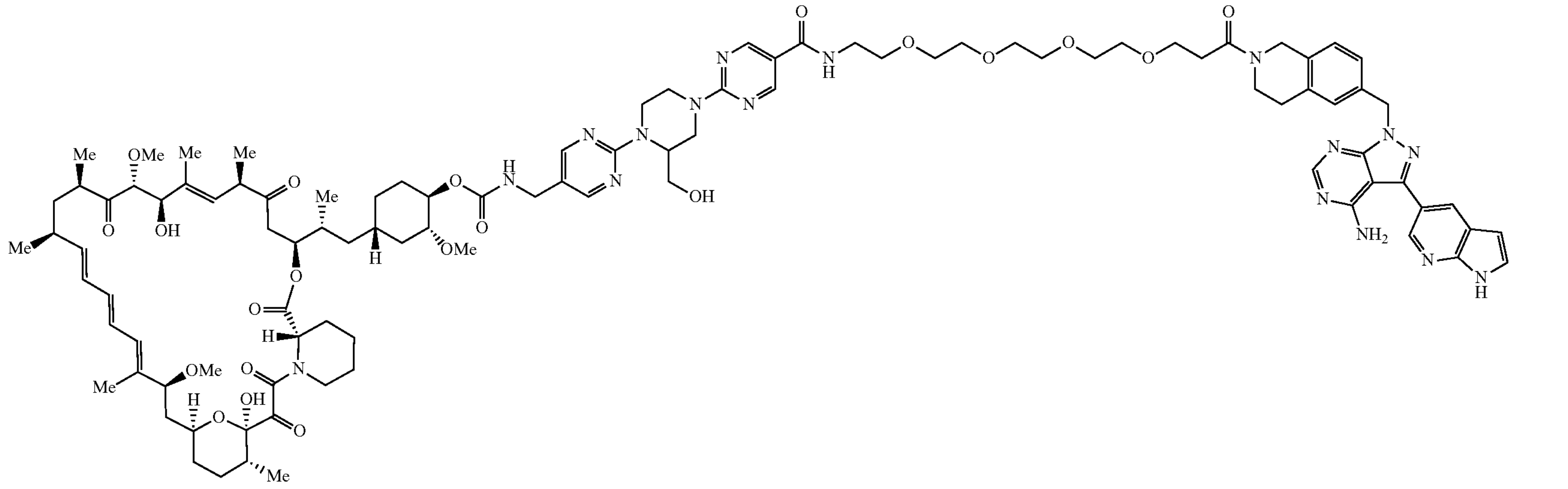

-continued
Example 42
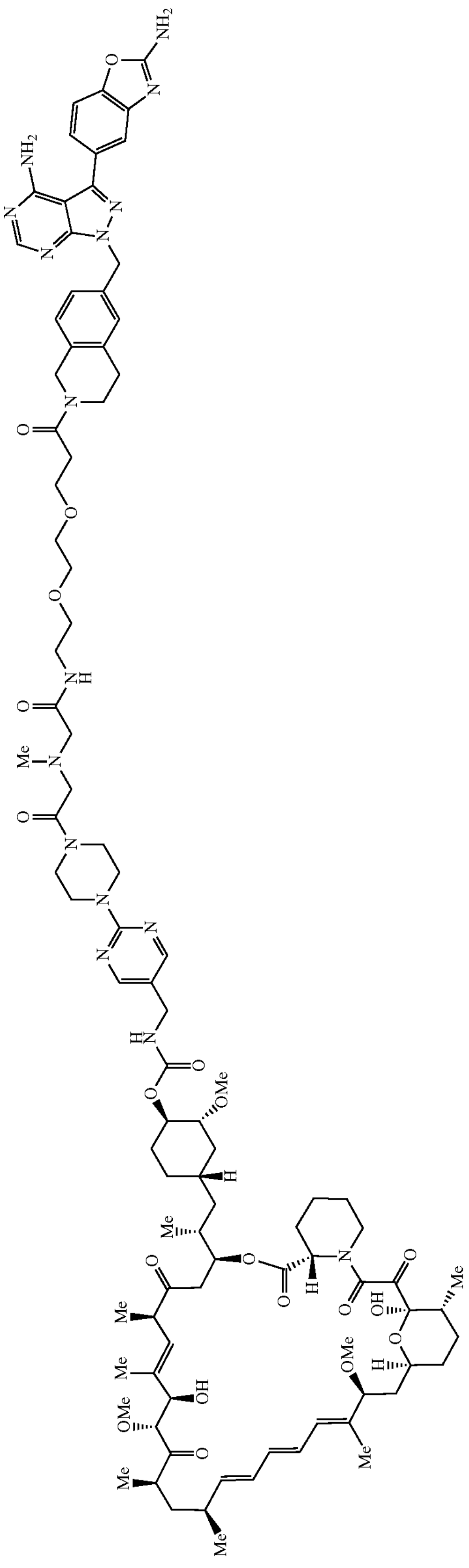
Example 43
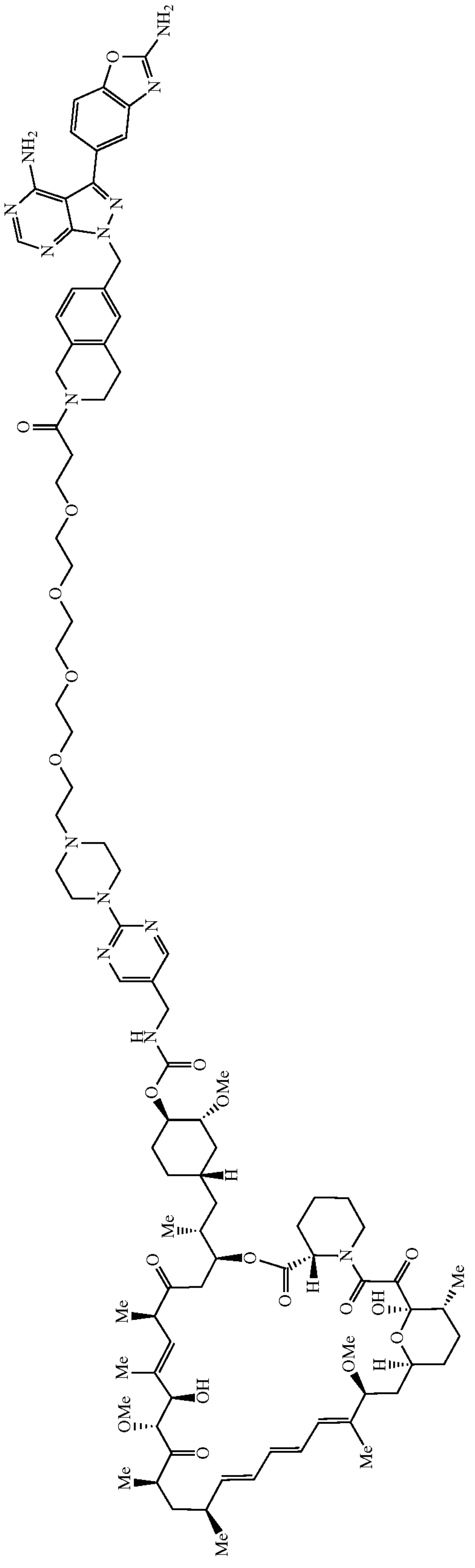

-continued
Example 44
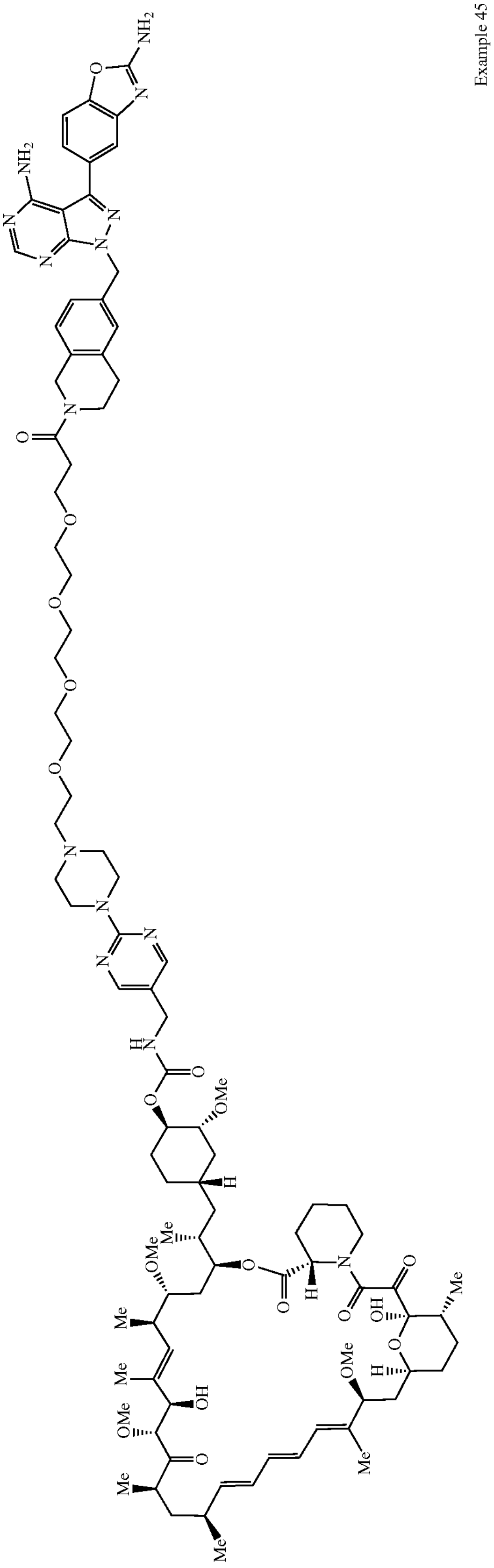
Example 45
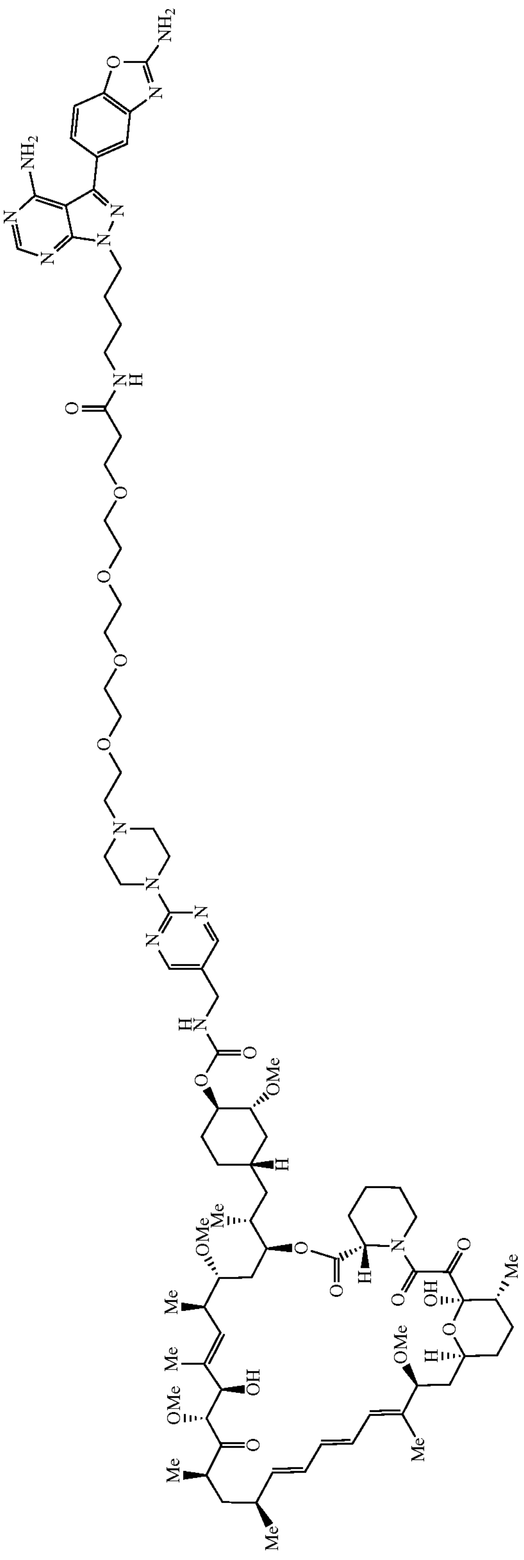

-continued
Example 46
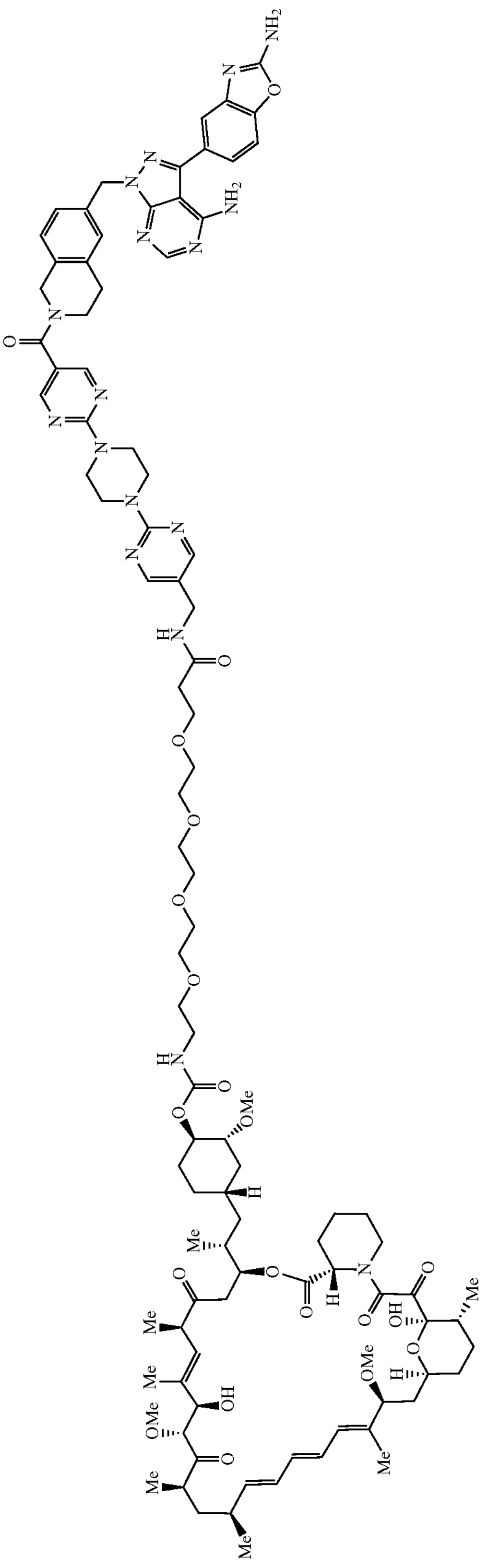
Example 47
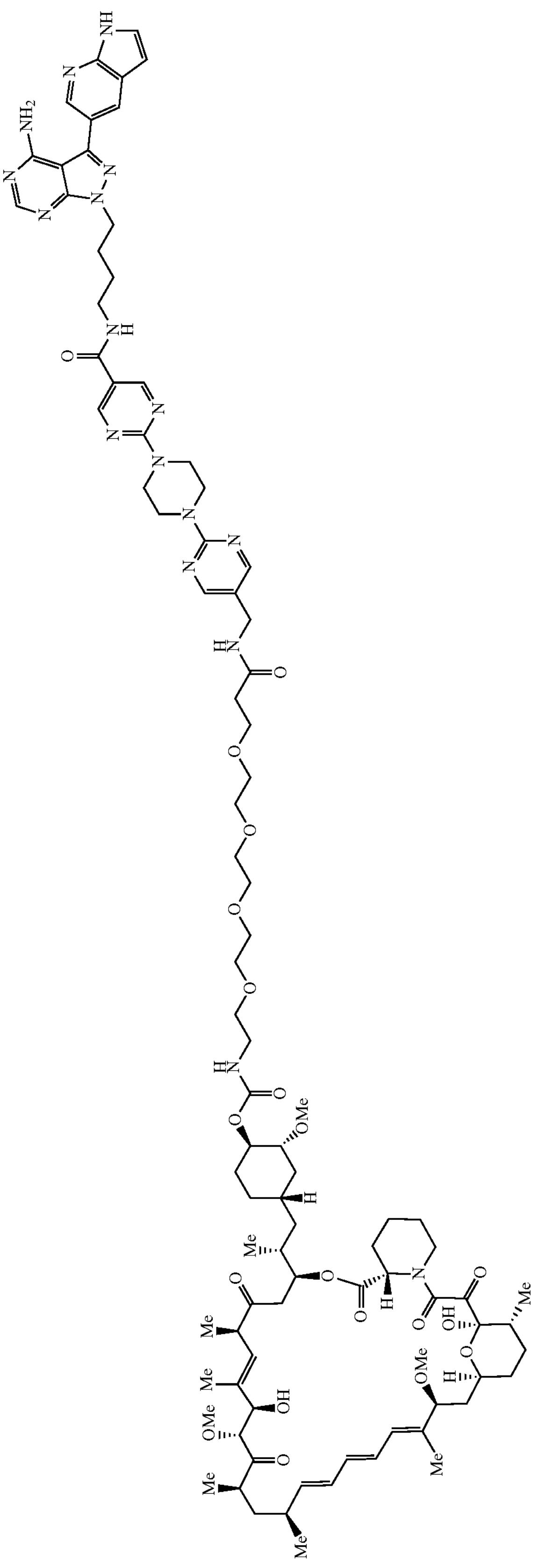

-continued
Example 48
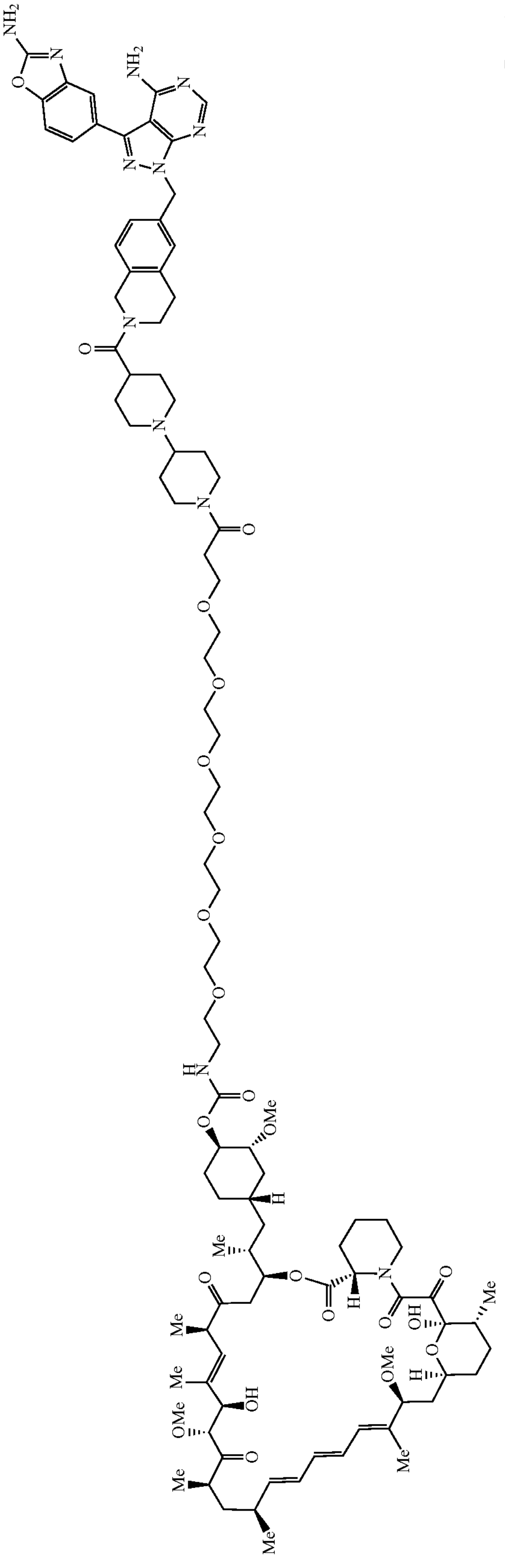
Example 49
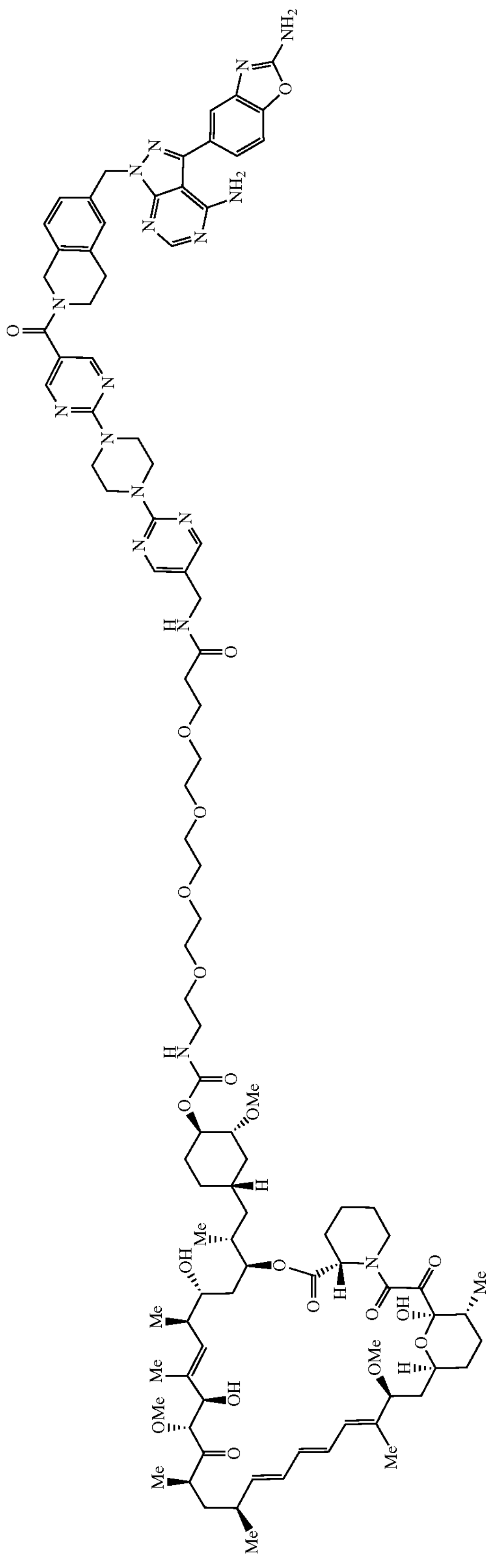

-continued
Example 50
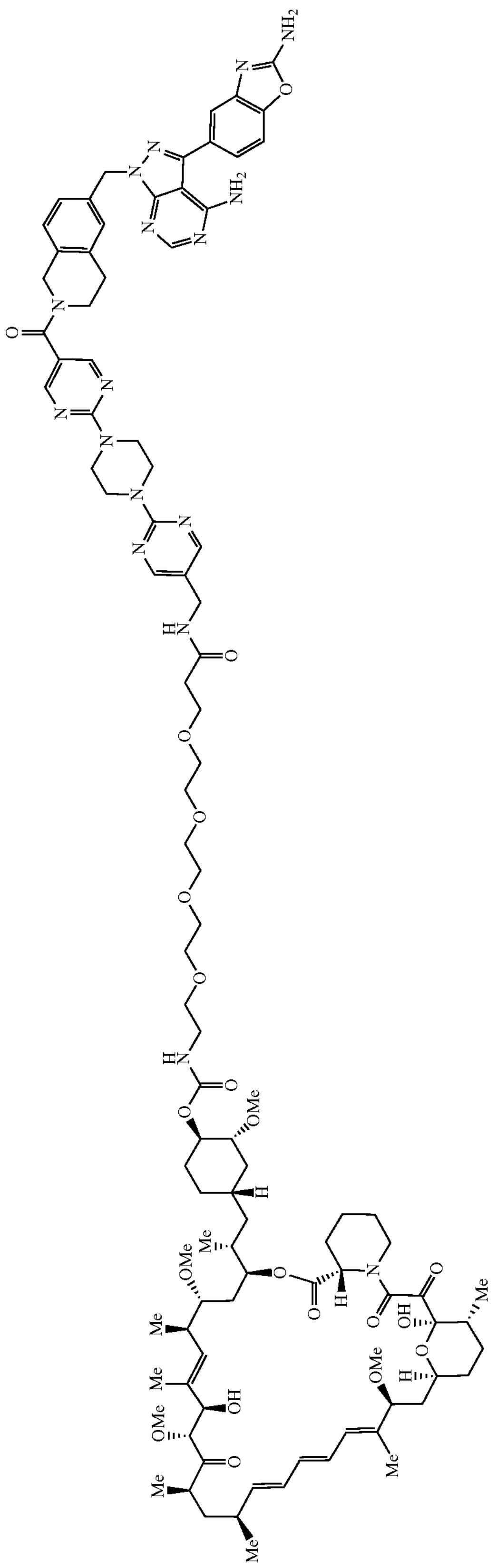

-continued
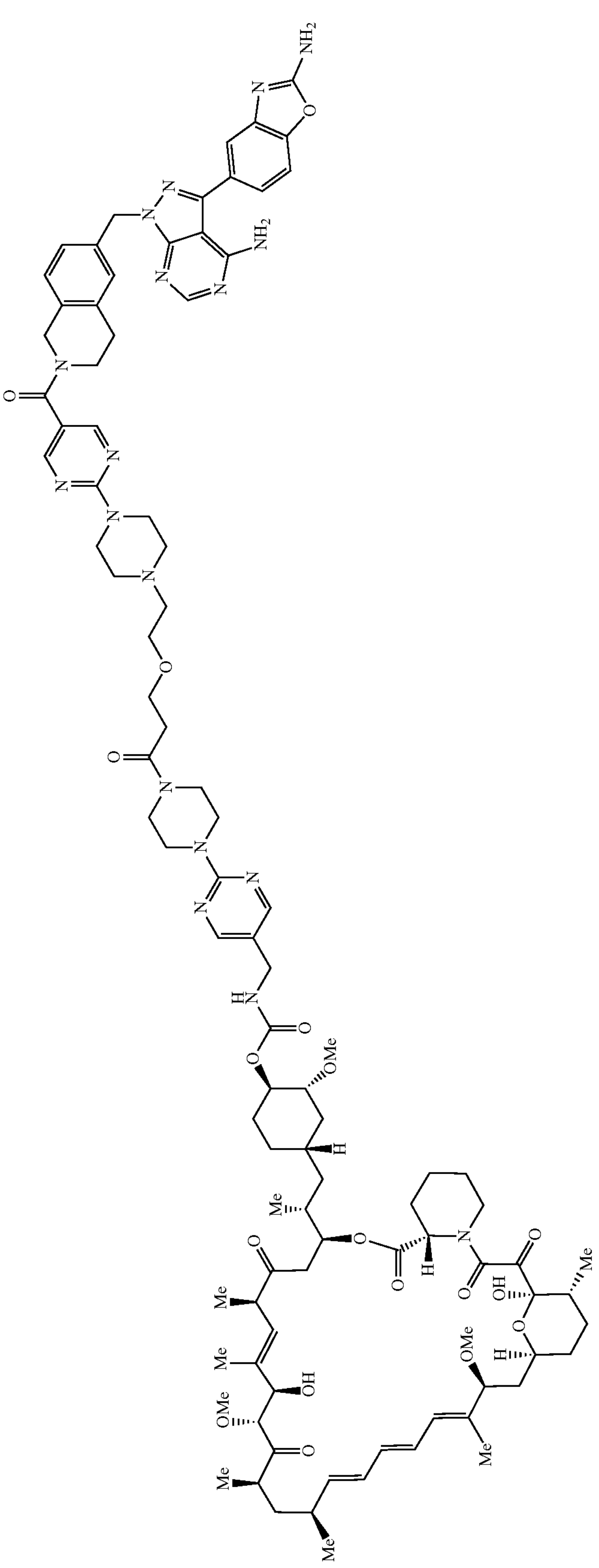
Example 51

-continued
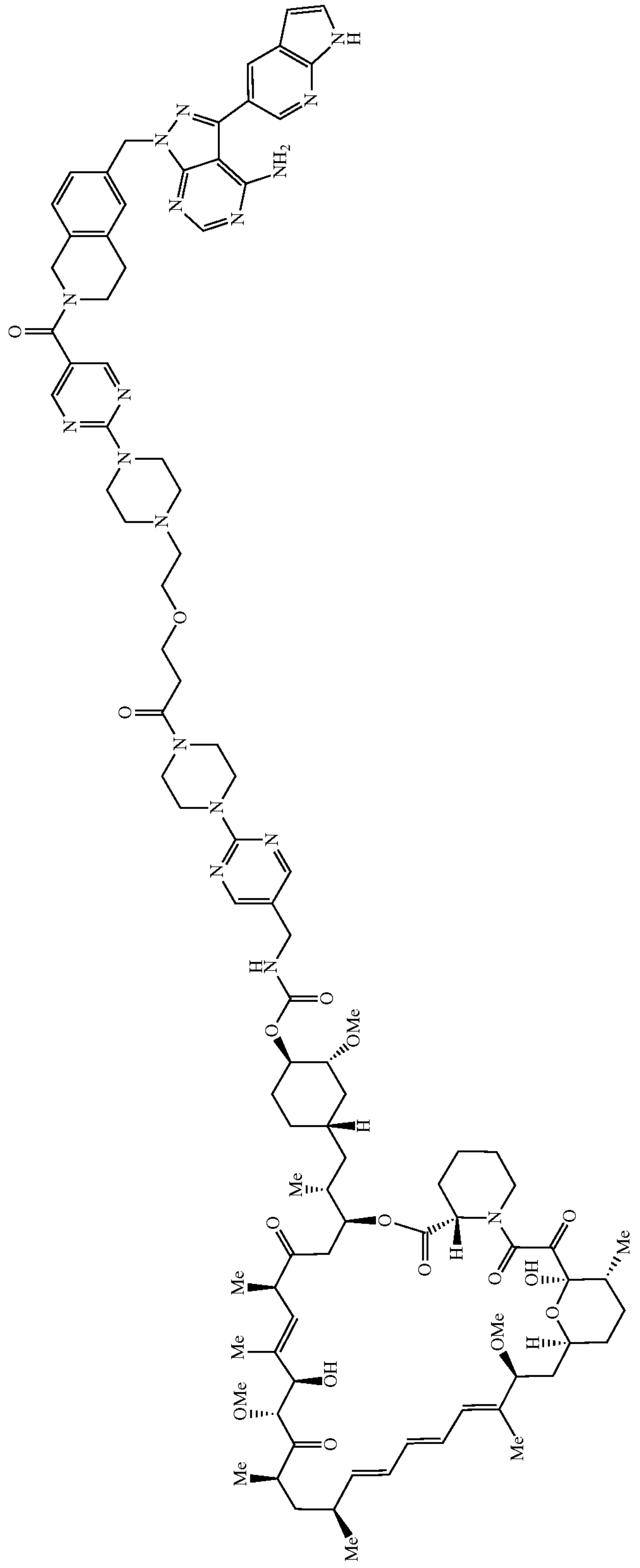
Example 52

-continued
Example 53
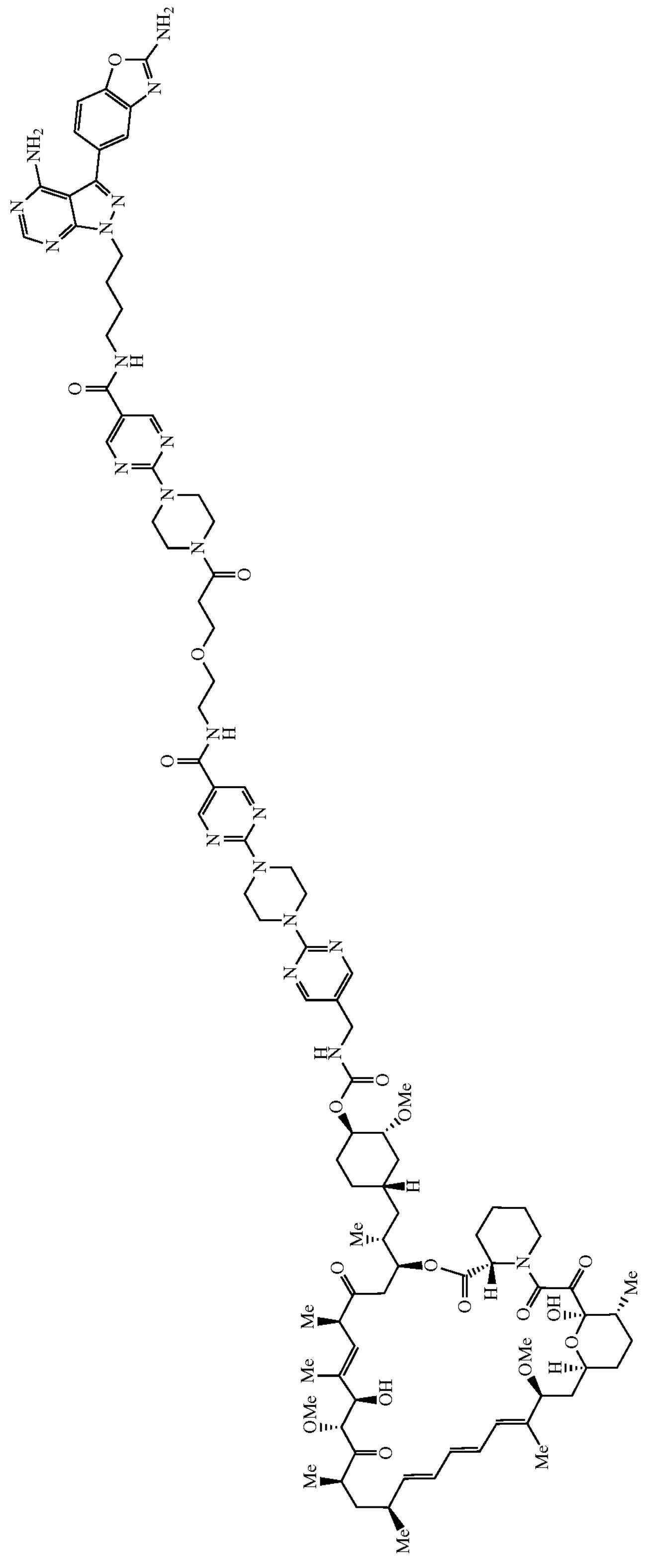

-continued
Example 54
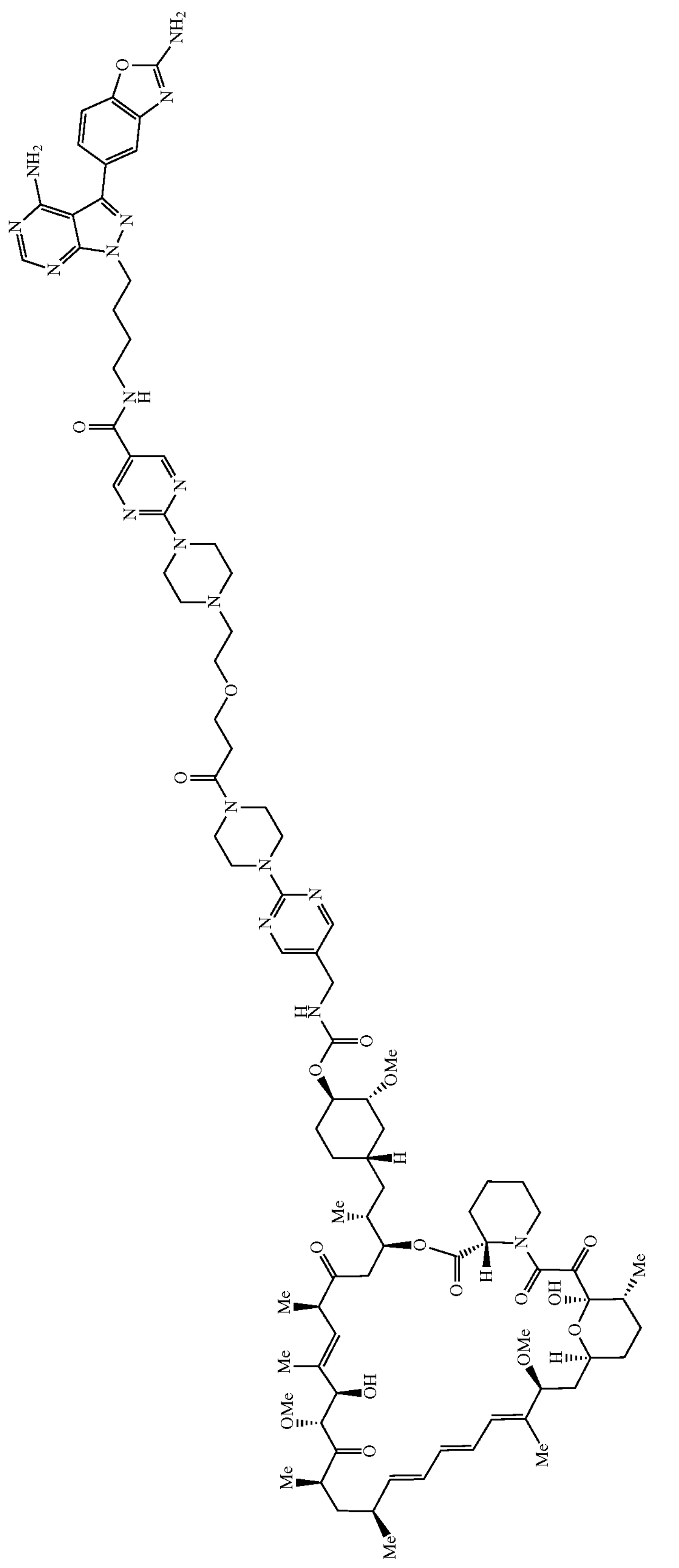

-continued
Example 55
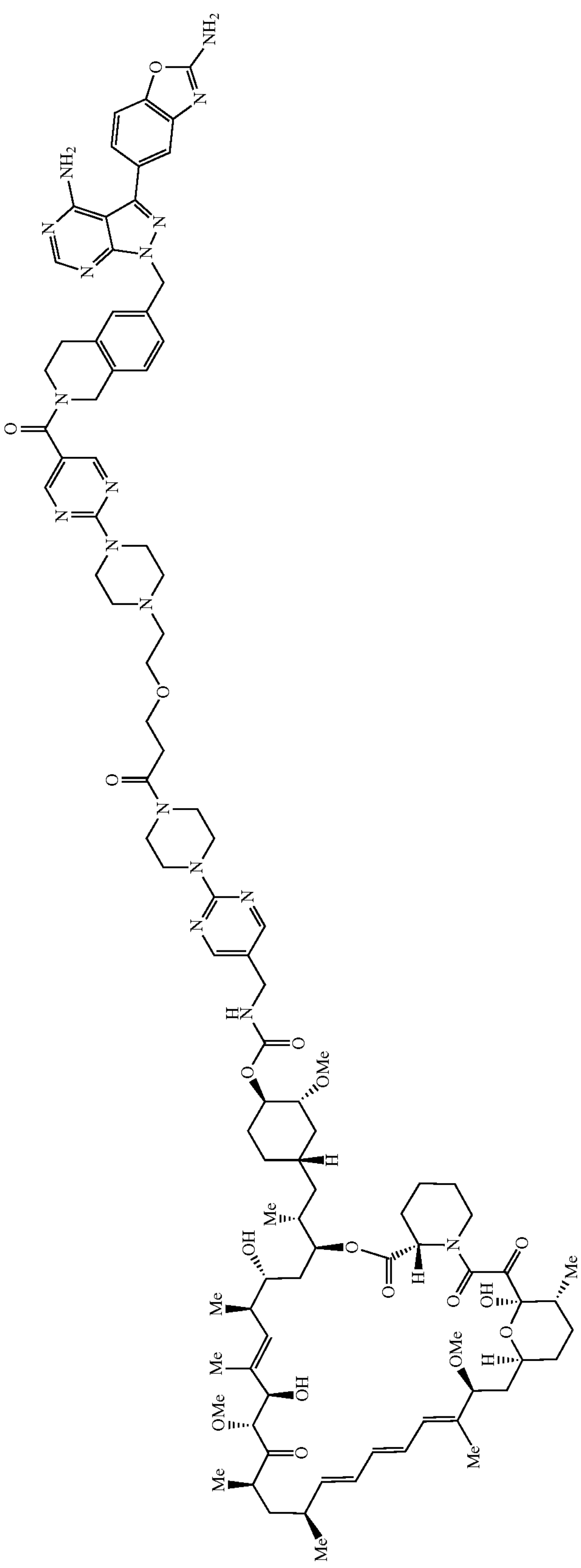

-continued
Example 56
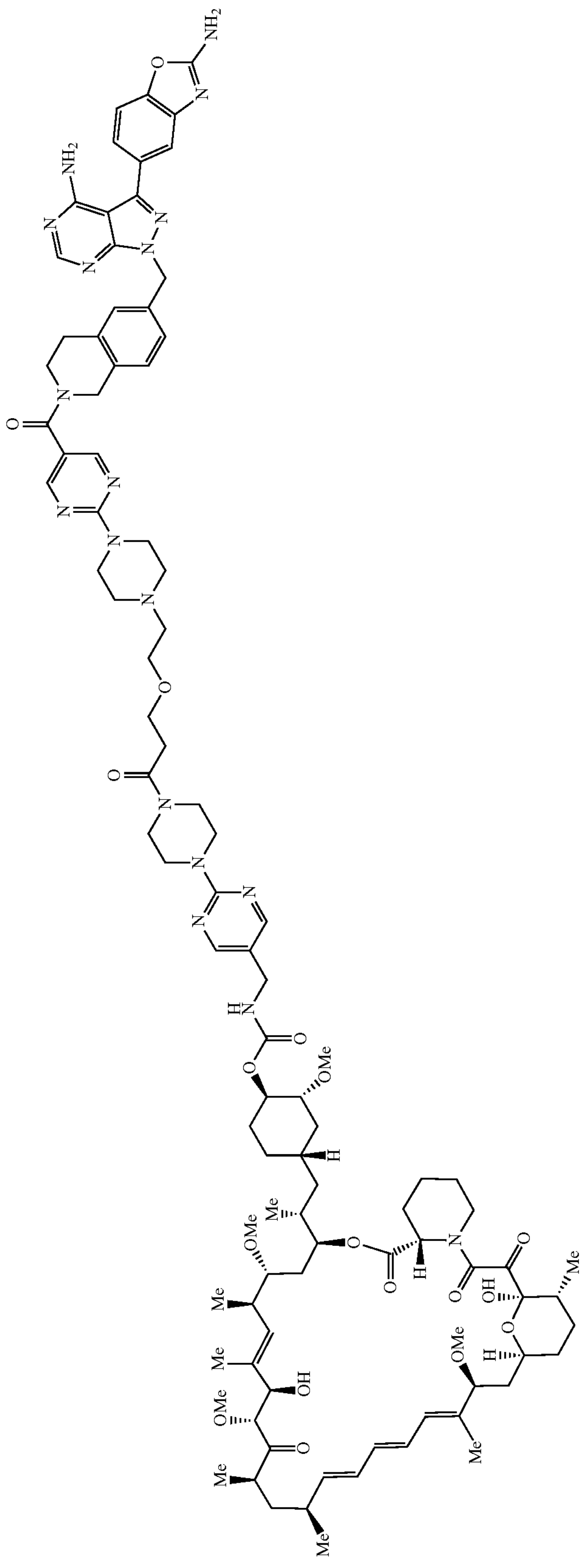

-continued
Example 57
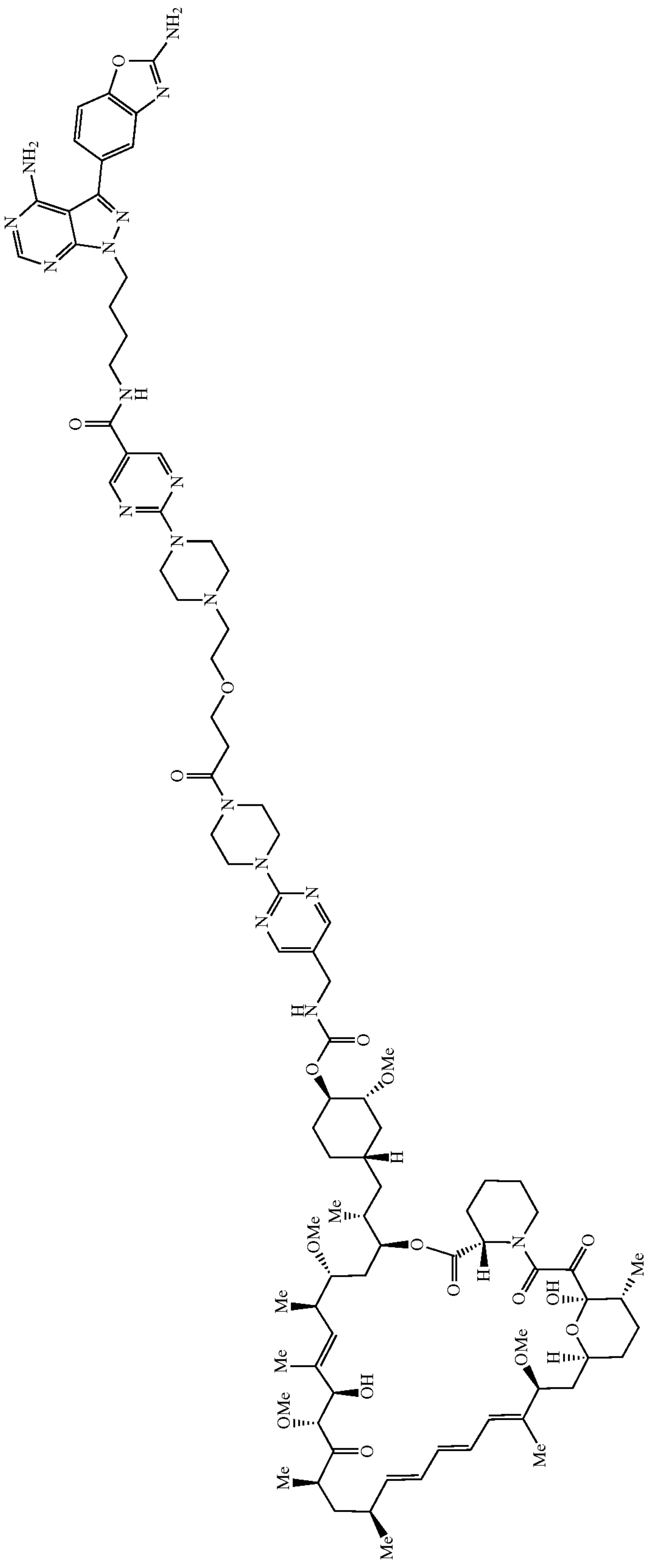

-continued
Example 58
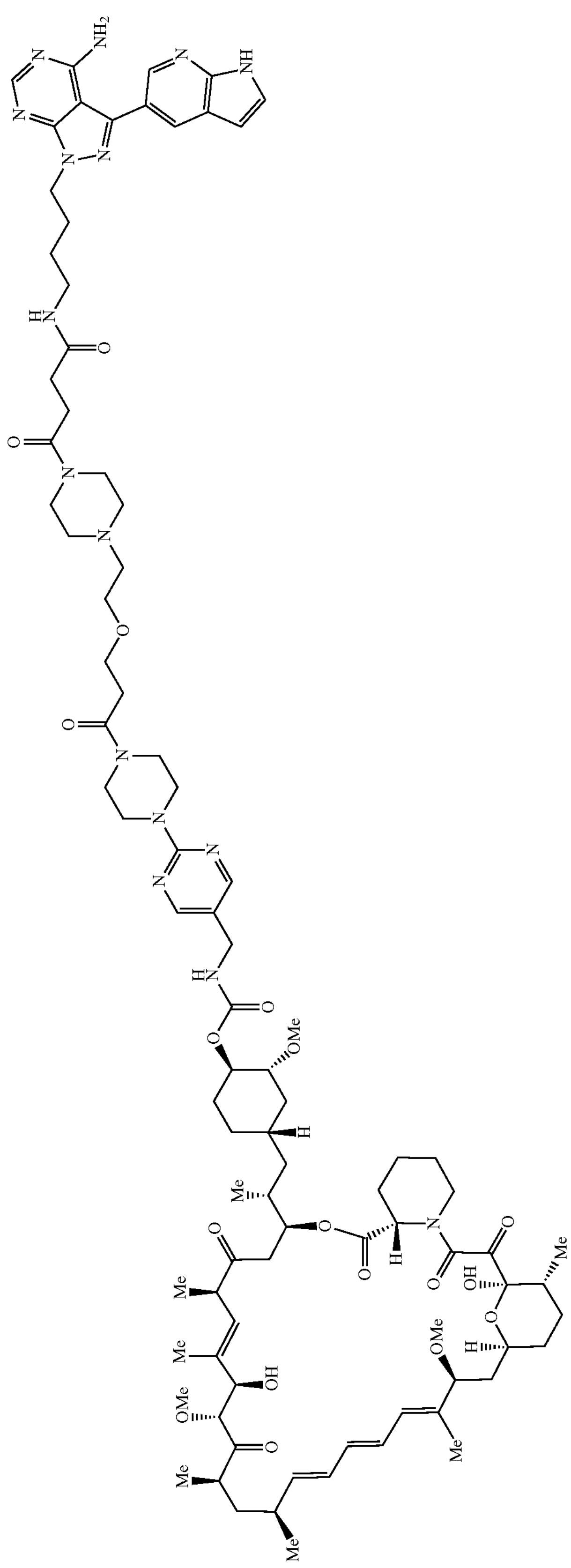

-continued
Example 59
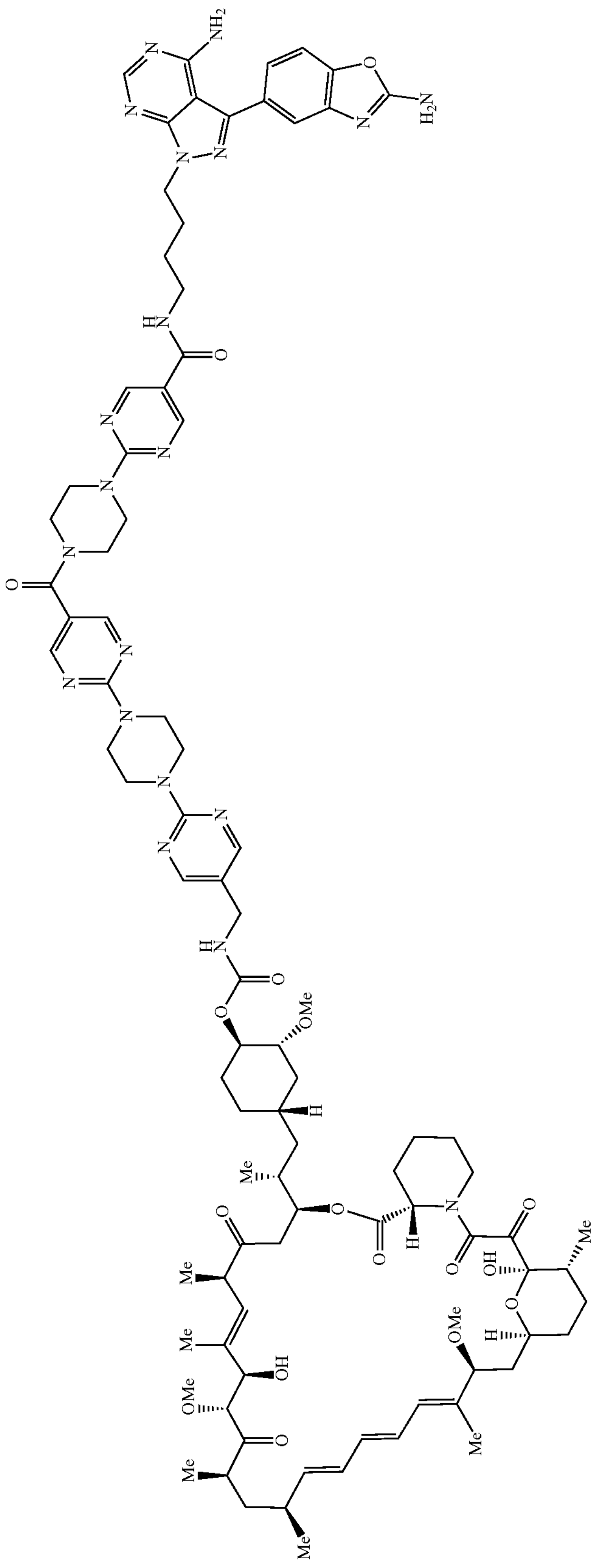

-continued
Example 60
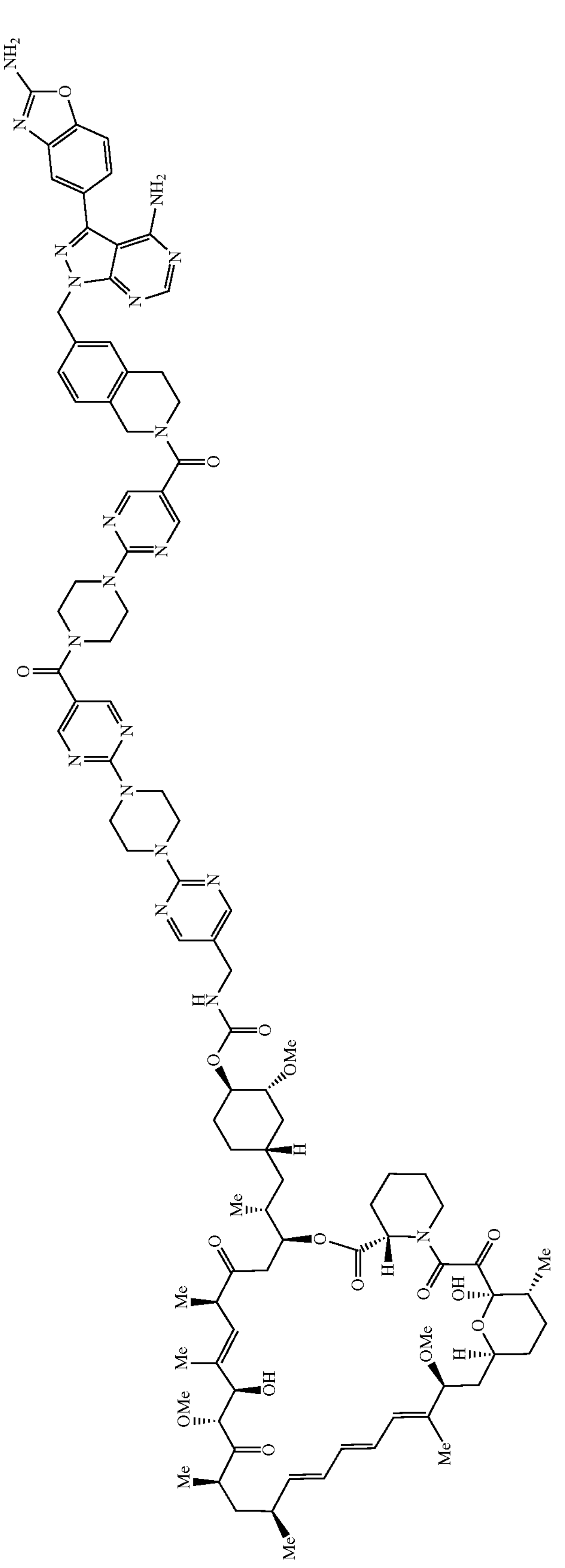

-continued
Example 61
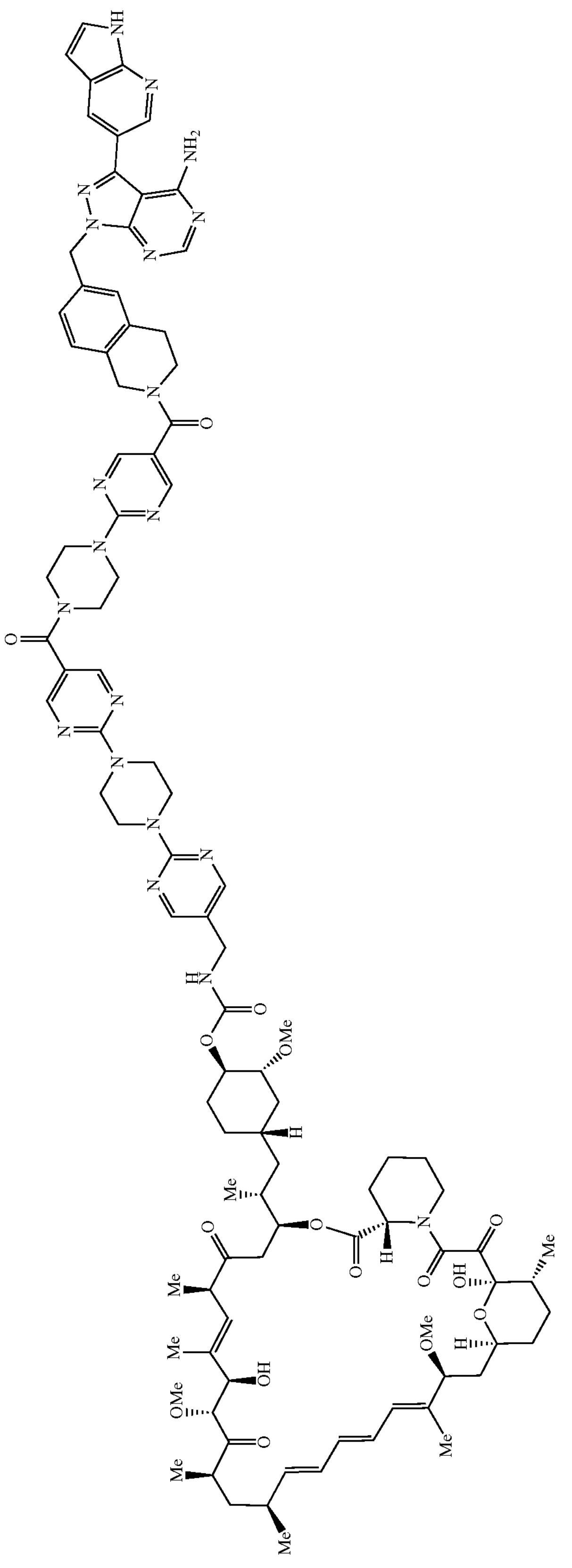

-continued
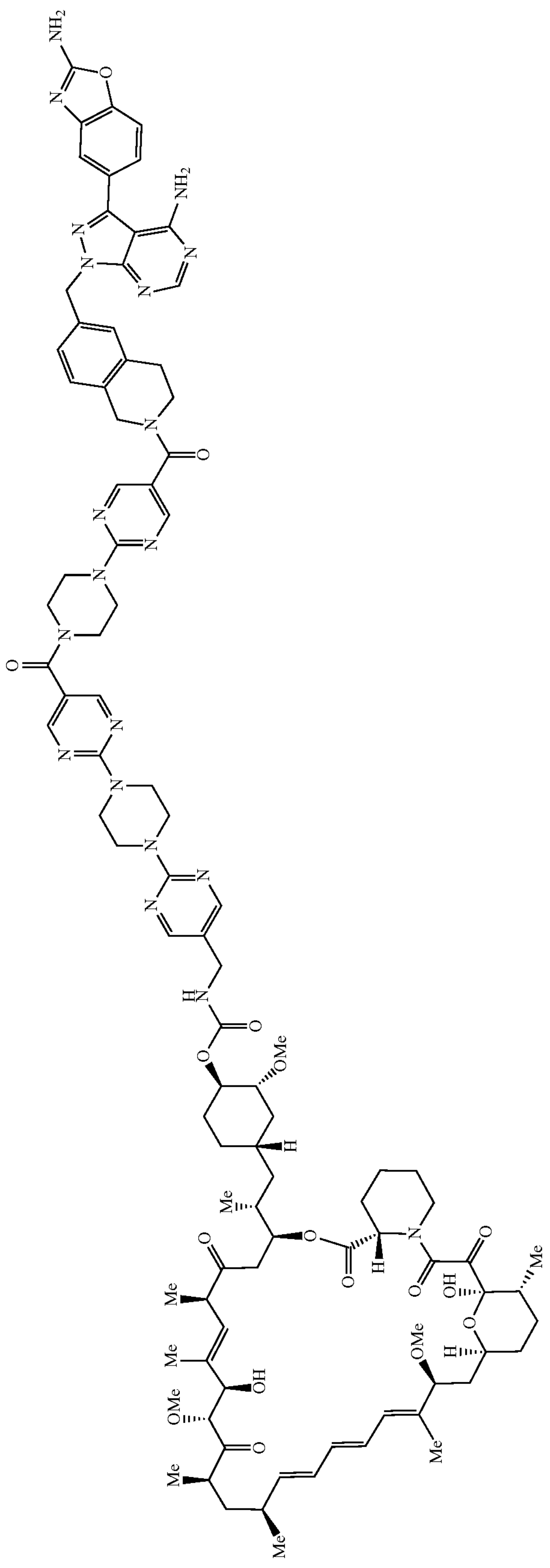
Example 62

-continued
Example 63
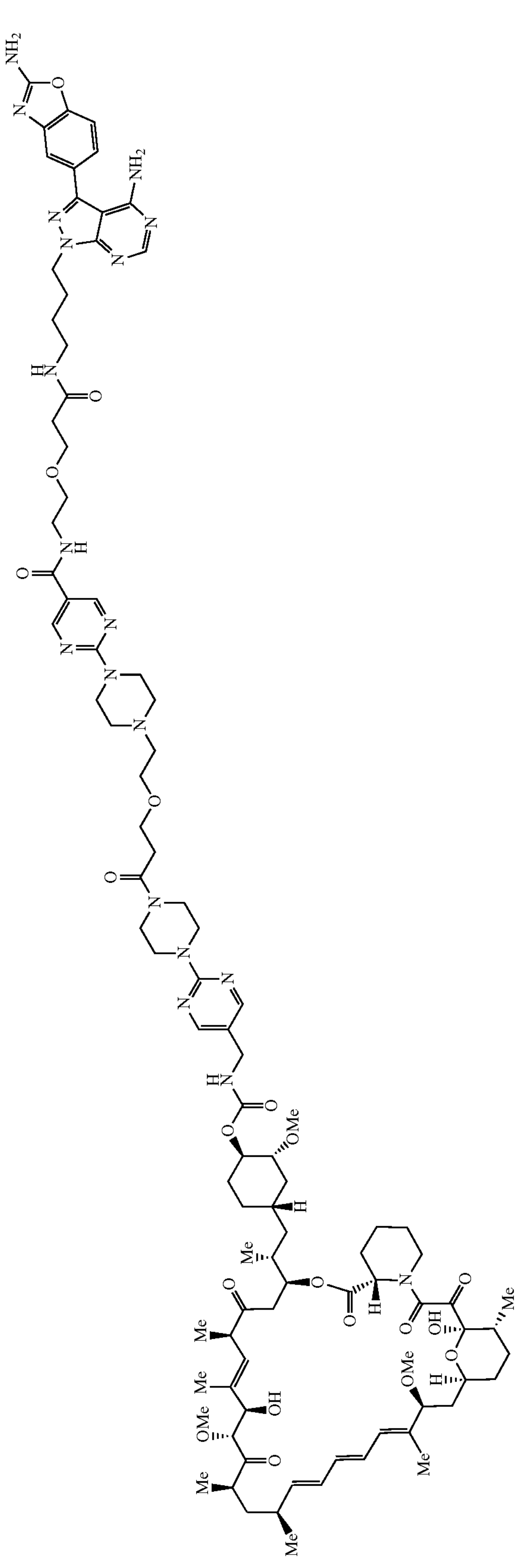

-continued
Example 64
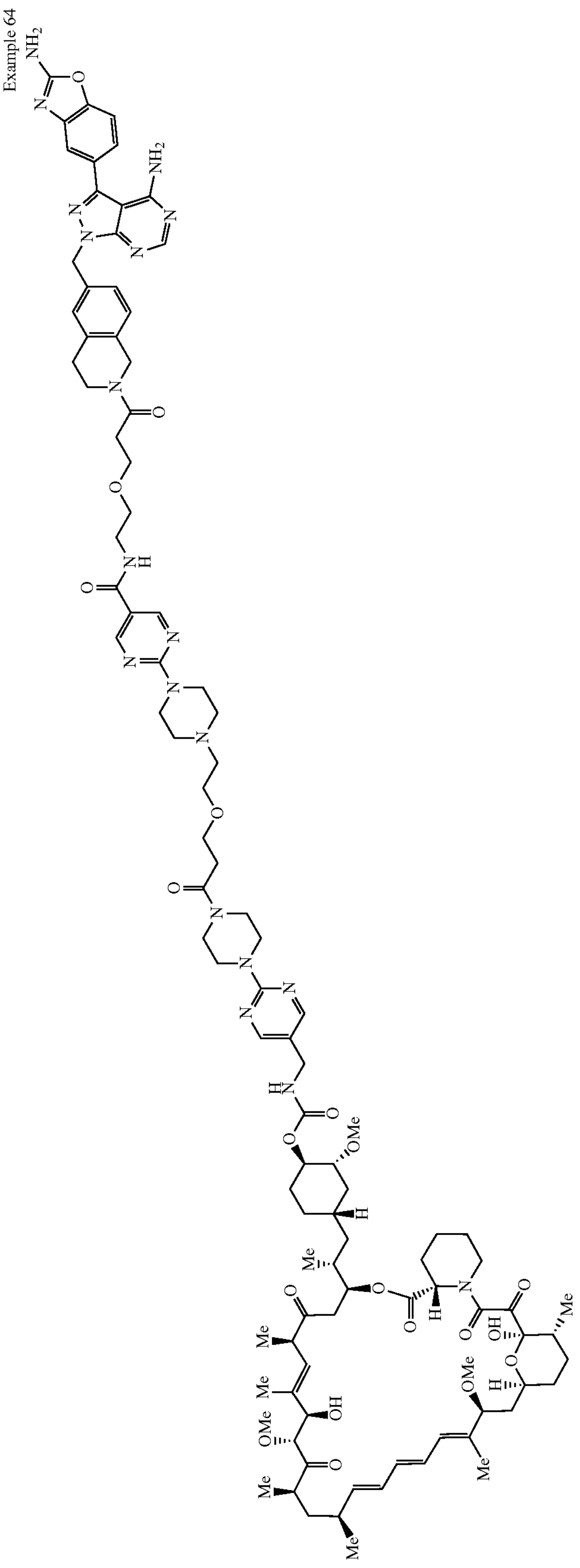

-continued
Example 65
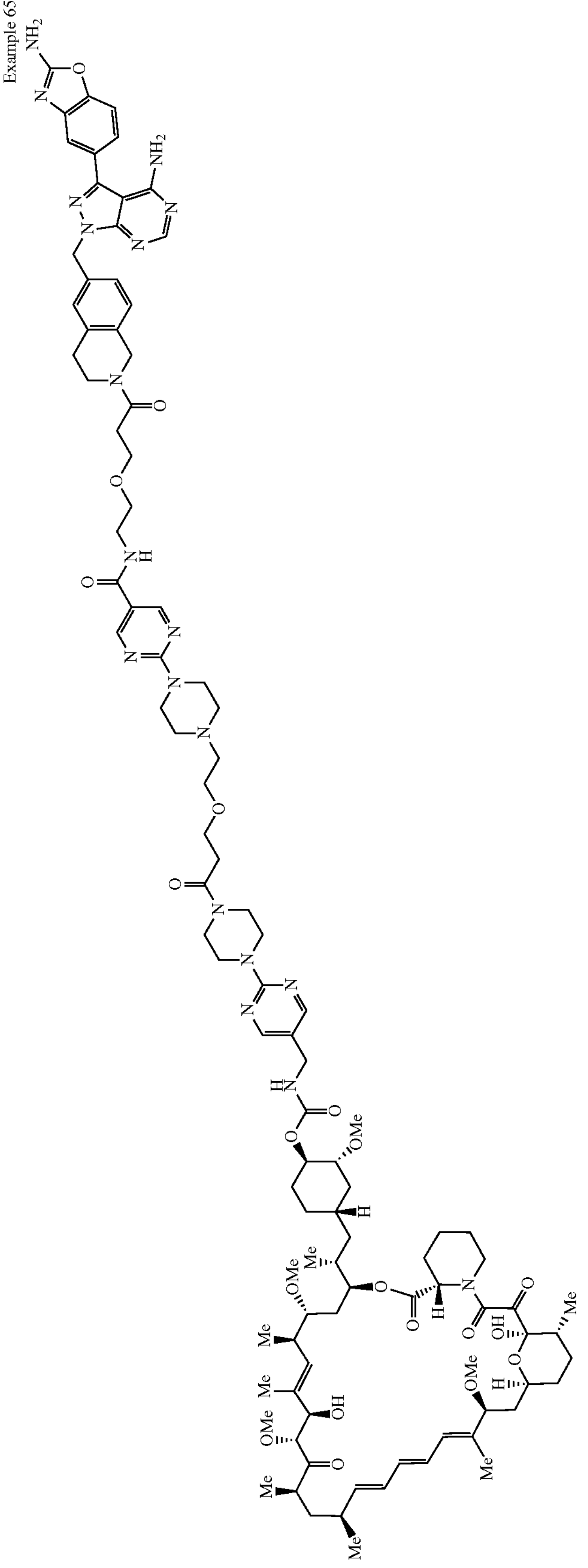

-continued
Example 66
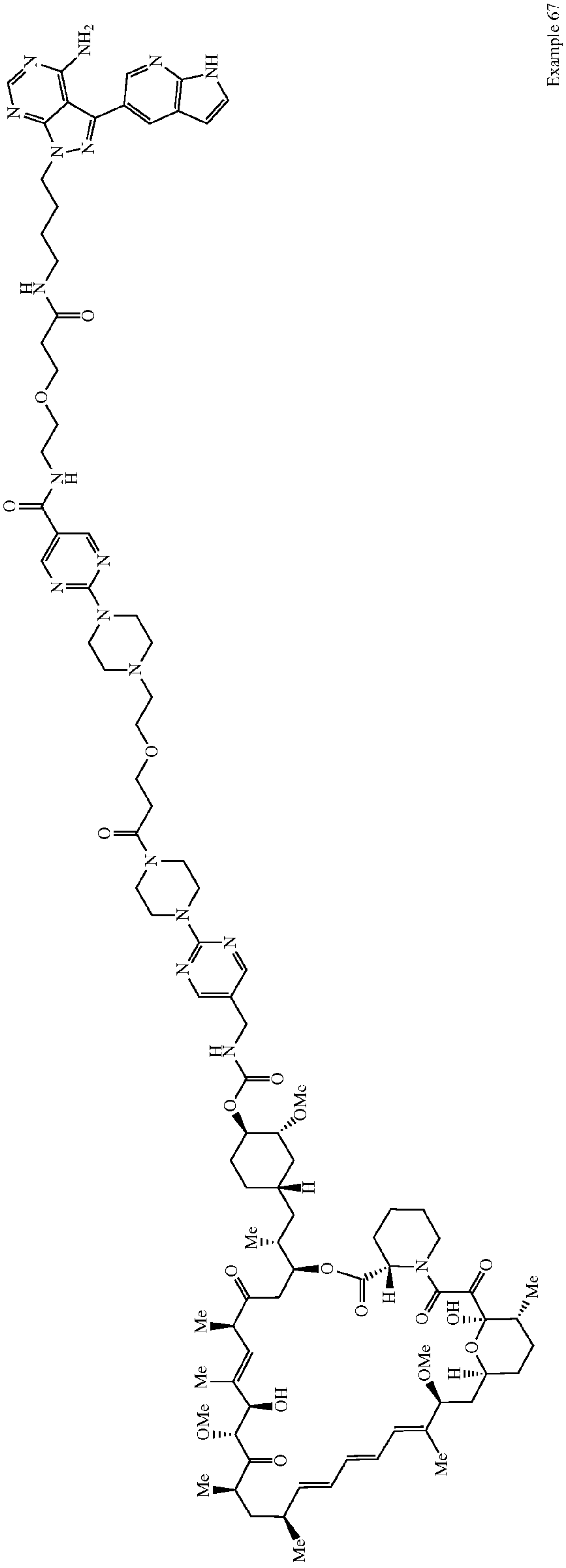
Example 67
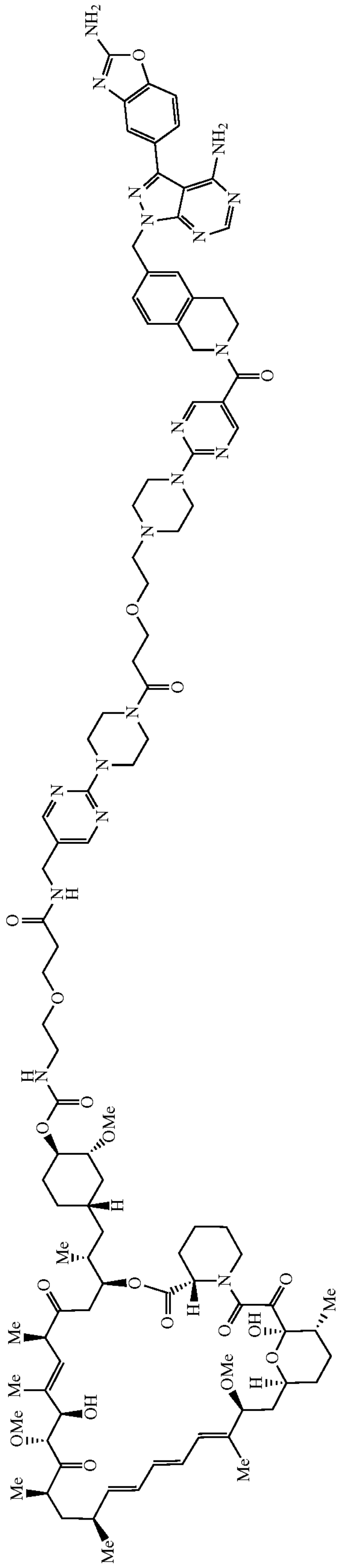

-continued
Example 68
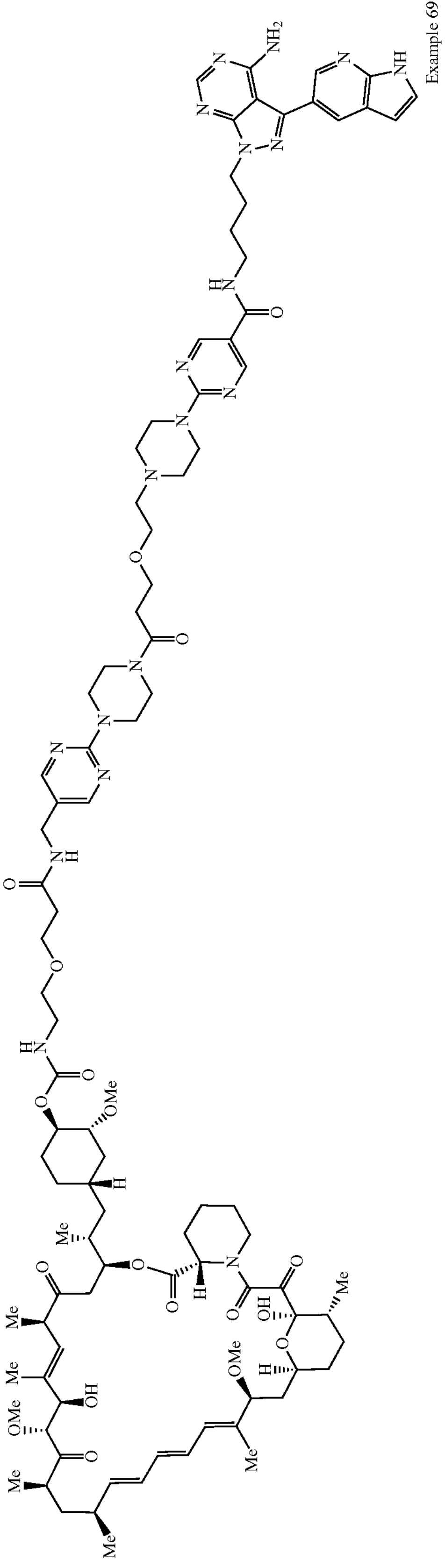
Example 69
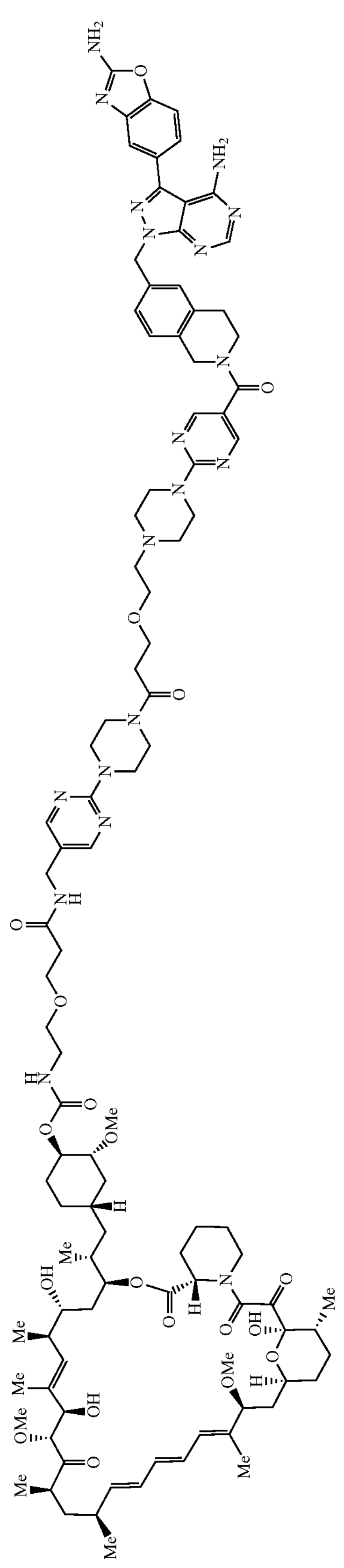

-continued
Example 70
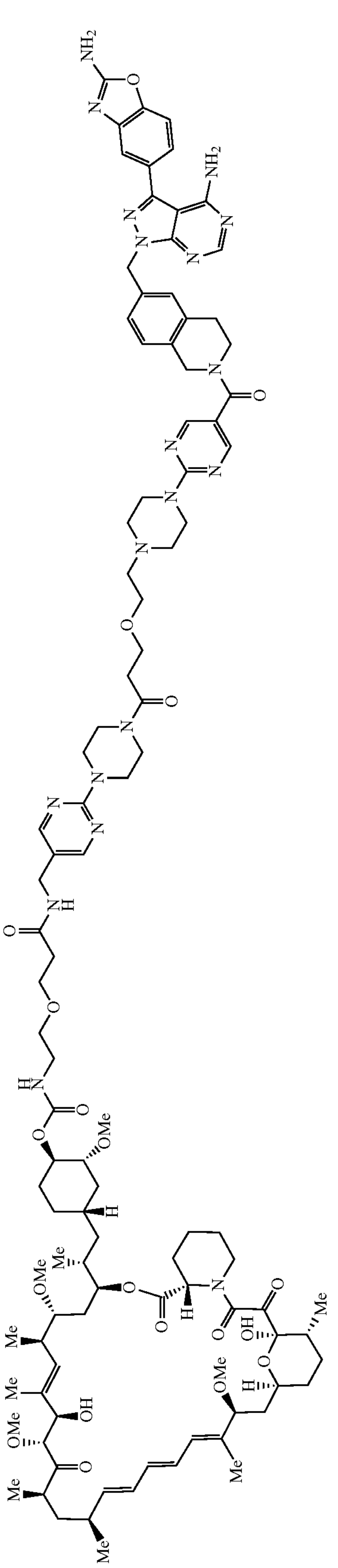

or a pharmaceutically acceptable salt or tautomer thereof.

Embodiment II-73. A compound selected from the group consisting of:

Example 71
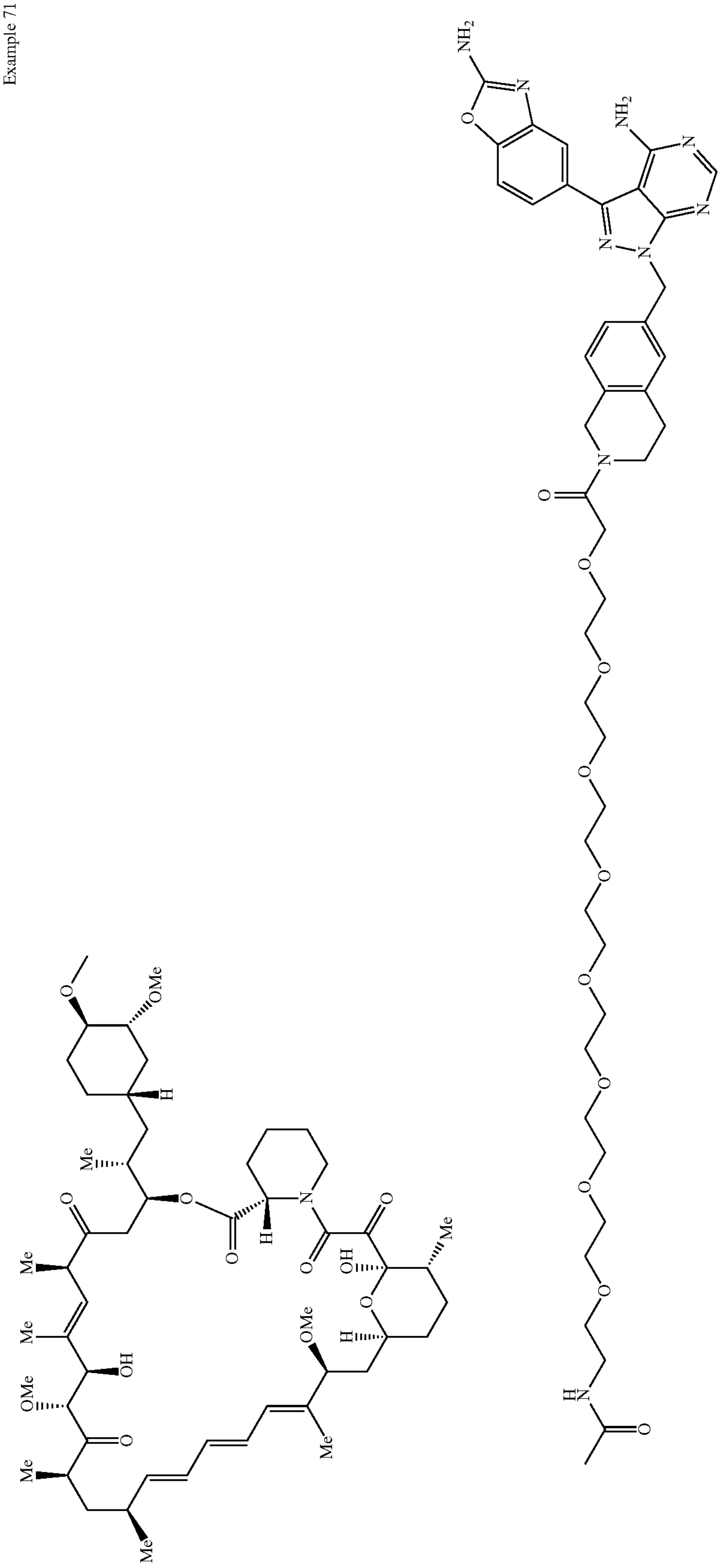

-continued
Example 72
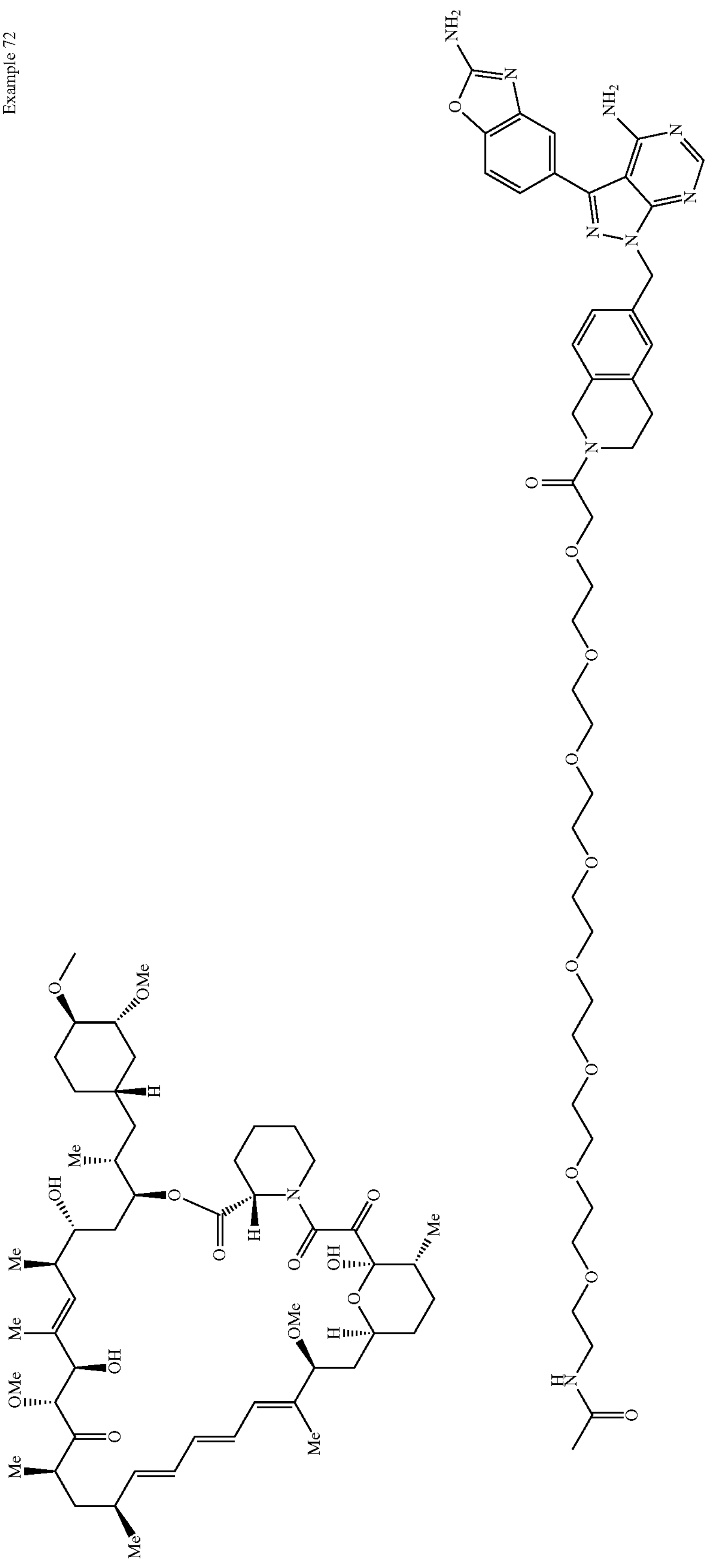

-continued
Example 73
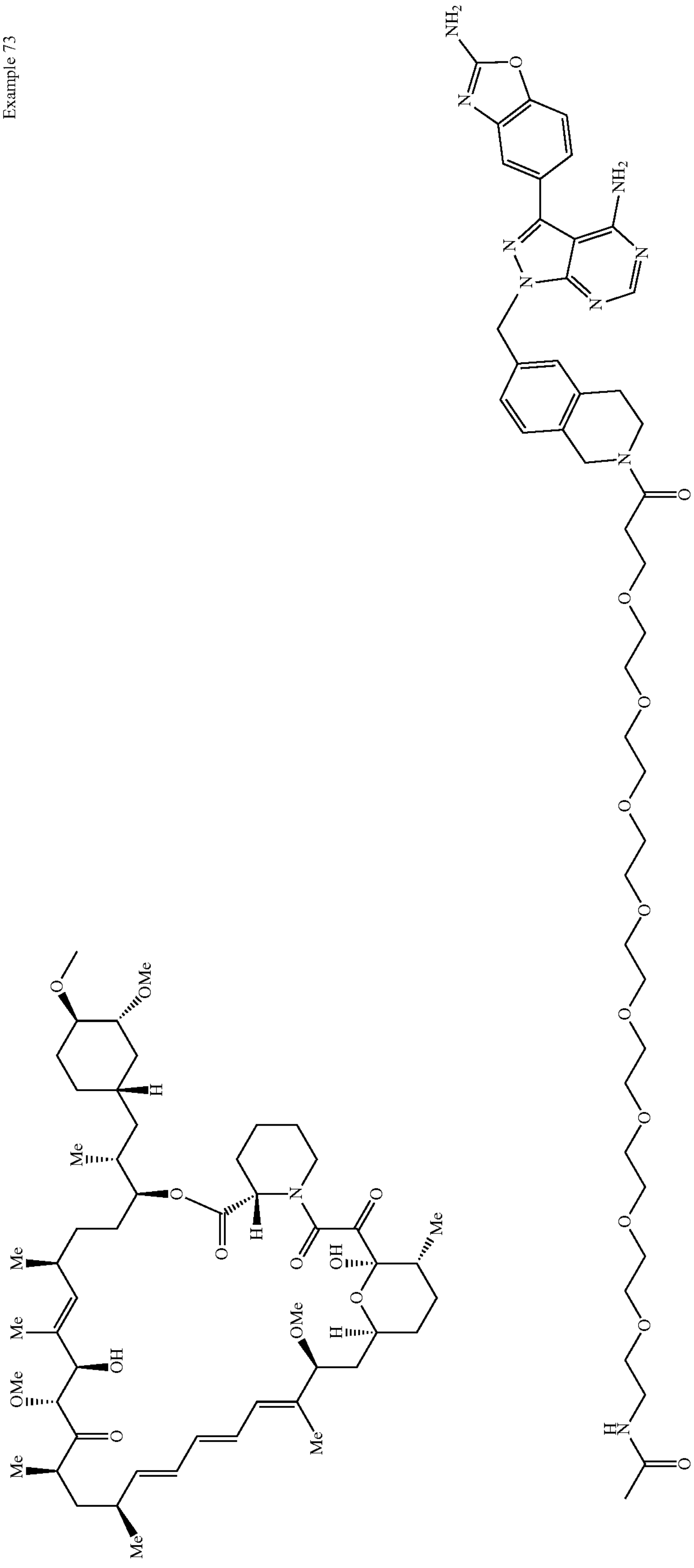

-continued
Example 74
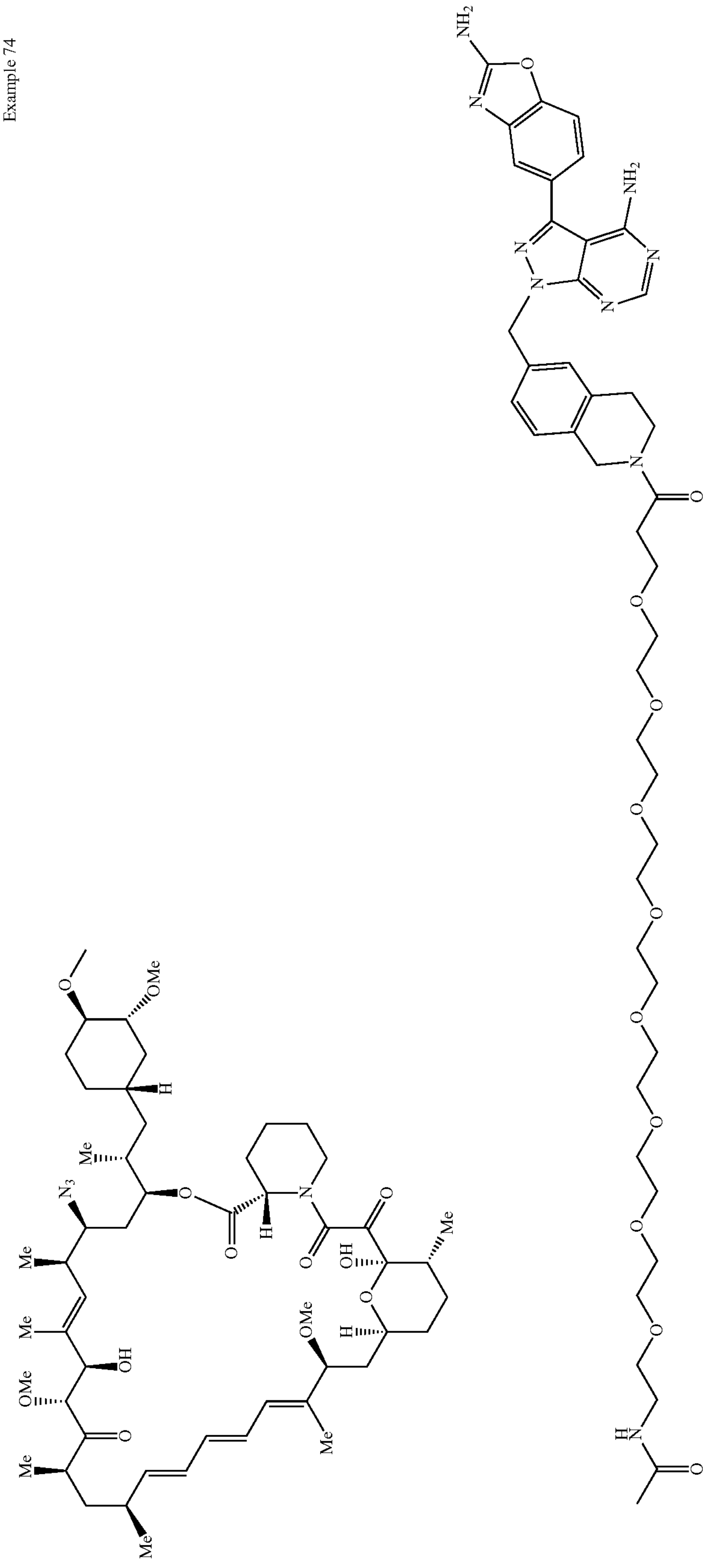

-continued
Example 75
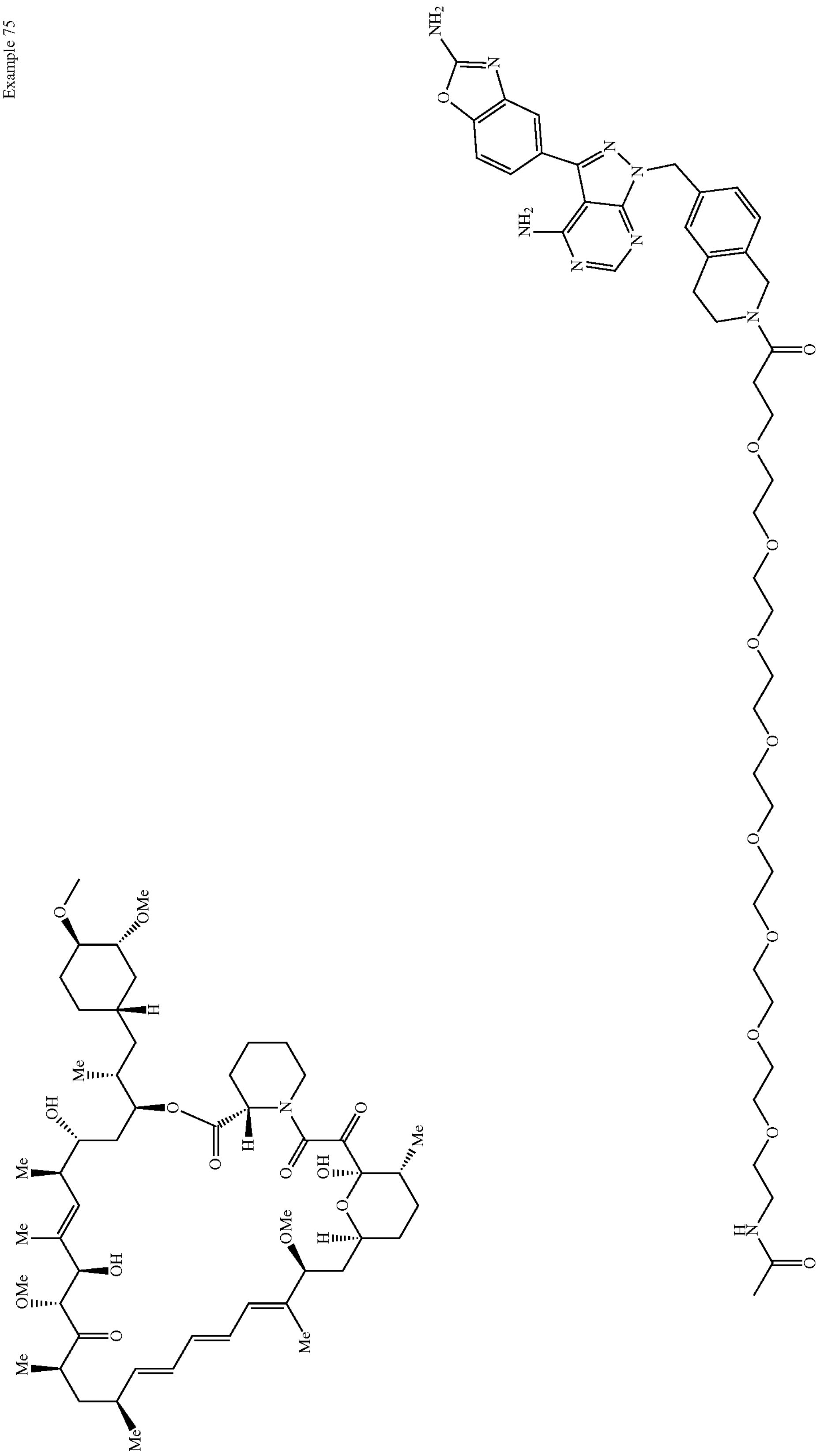

-continued
Example 76
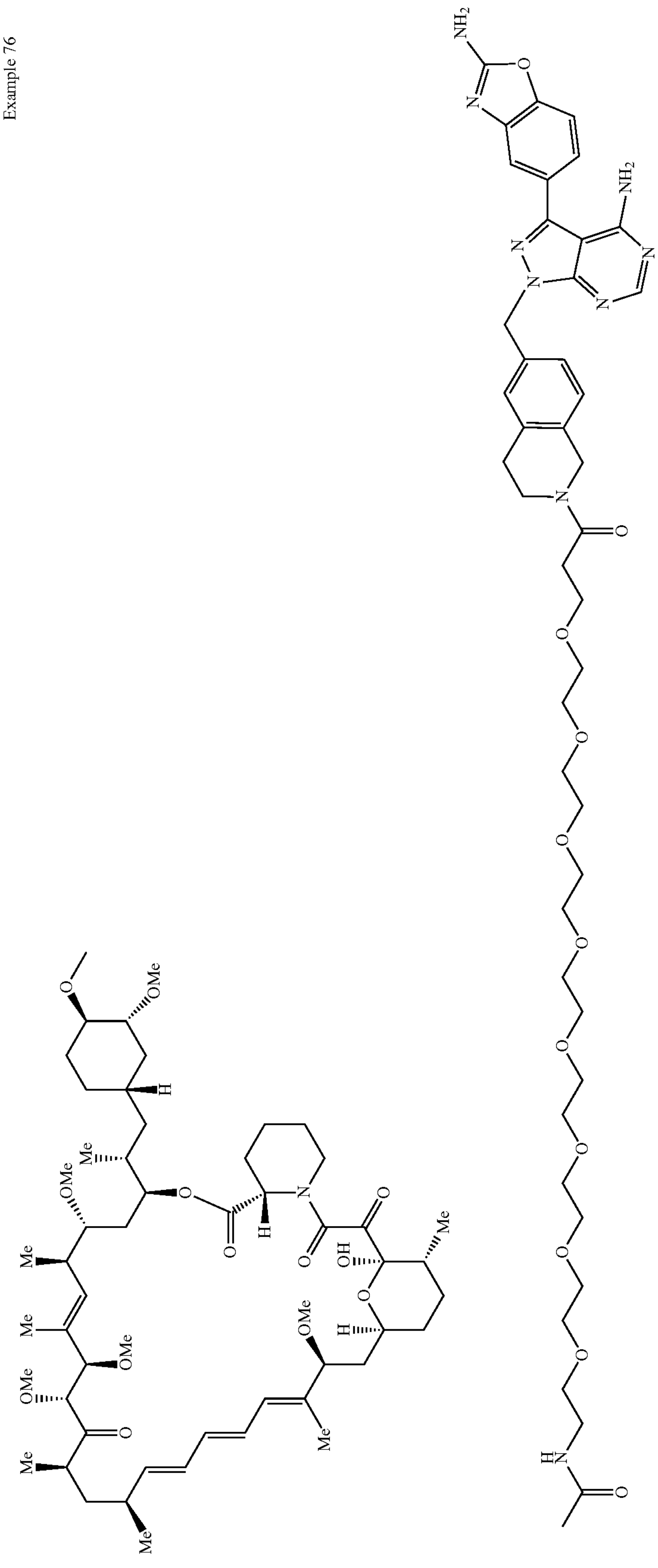

-continued
Example 77
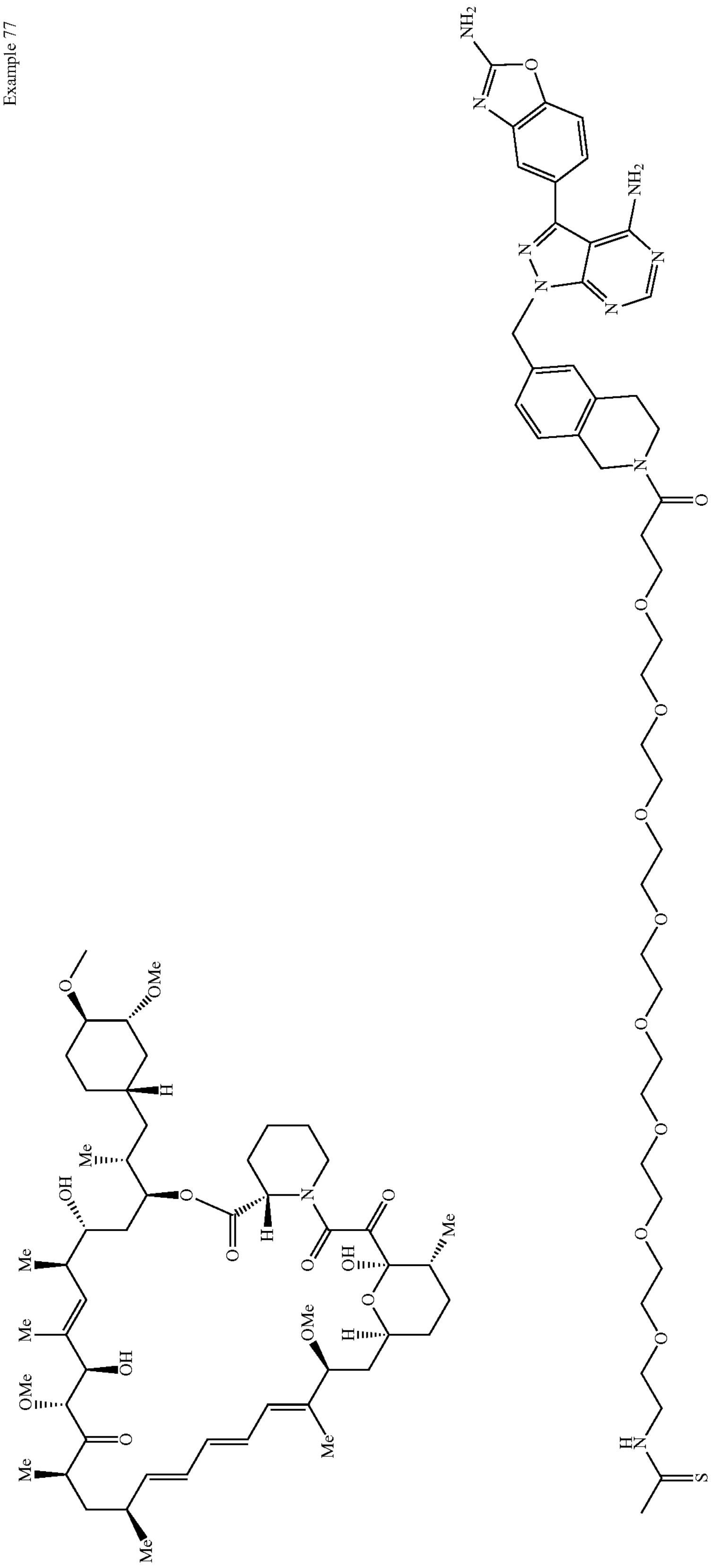

-continued
Example 78
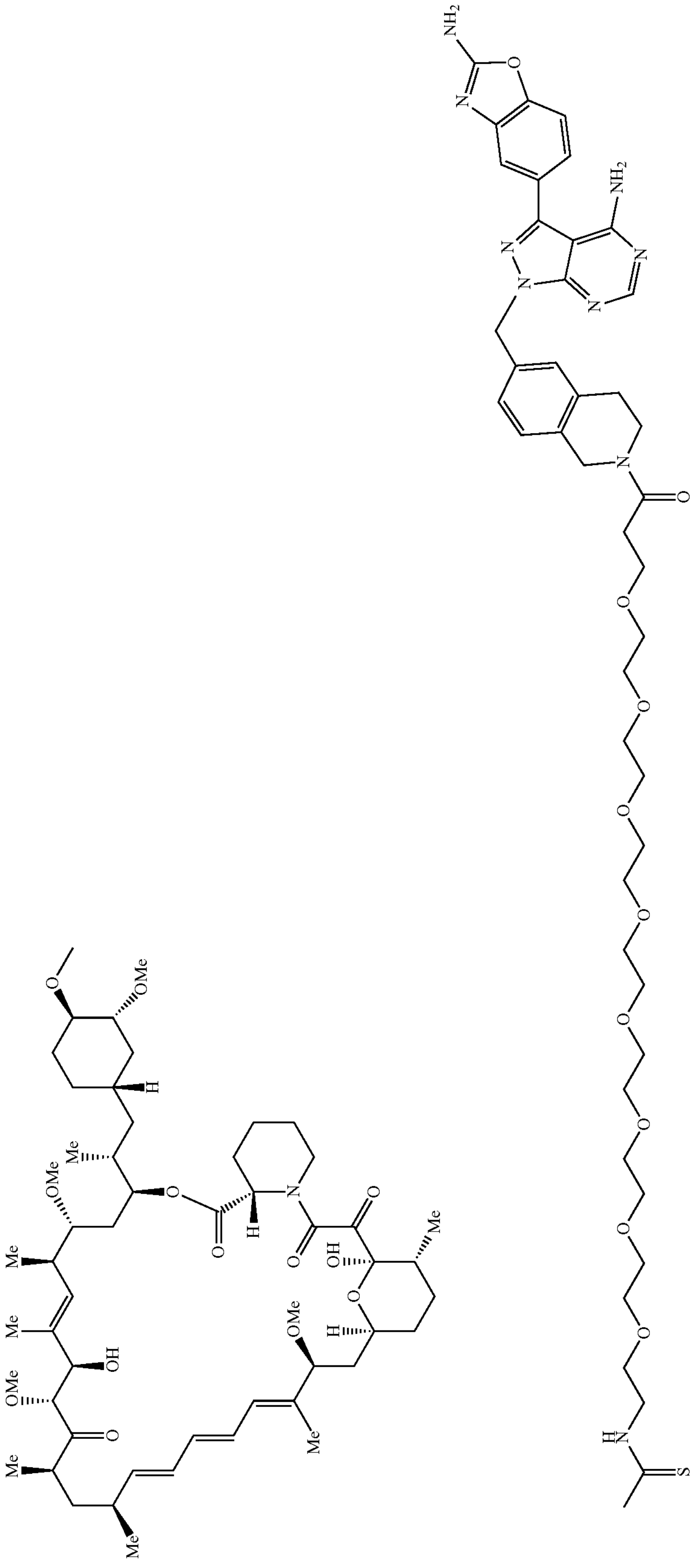

-continued
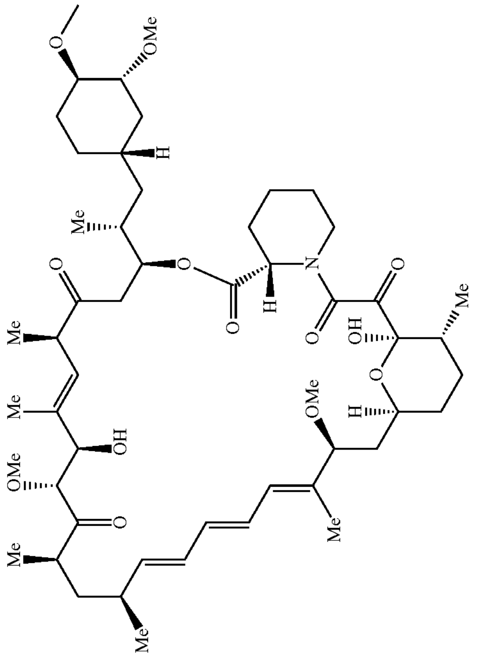
Example 79
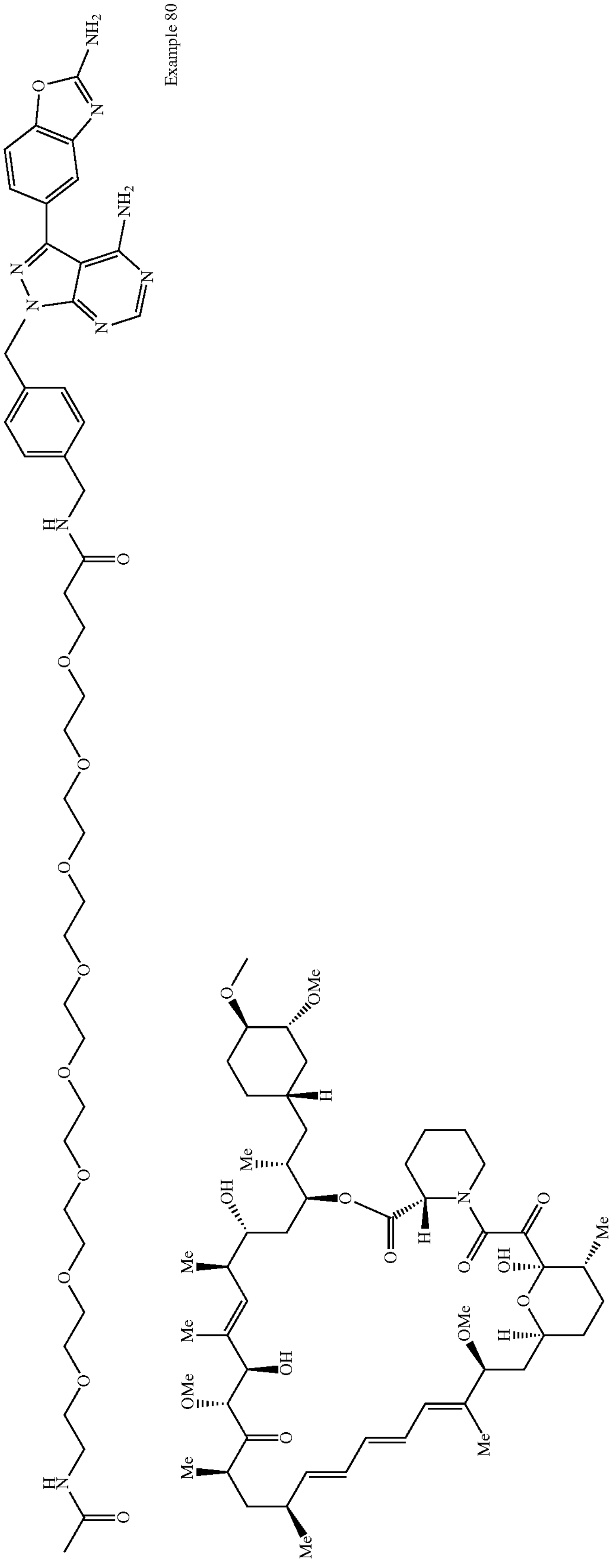
Example 80

-continued
Example 81
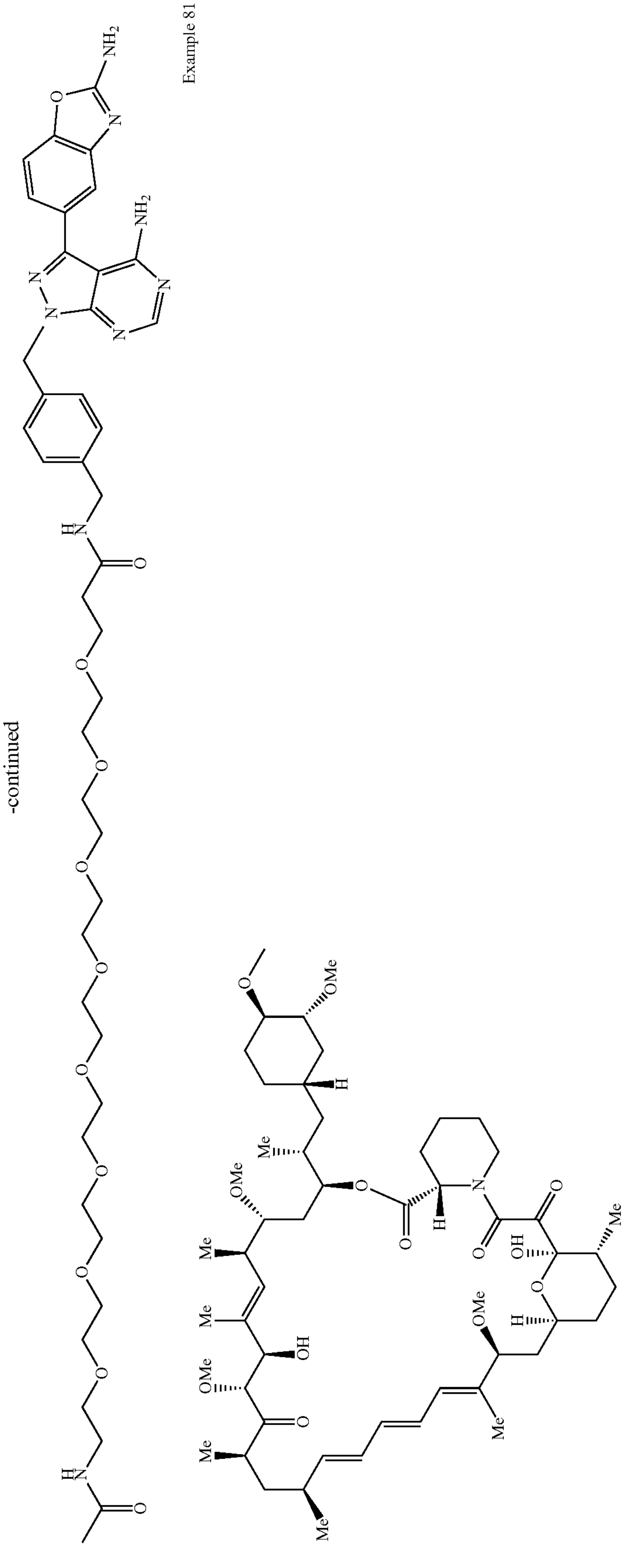
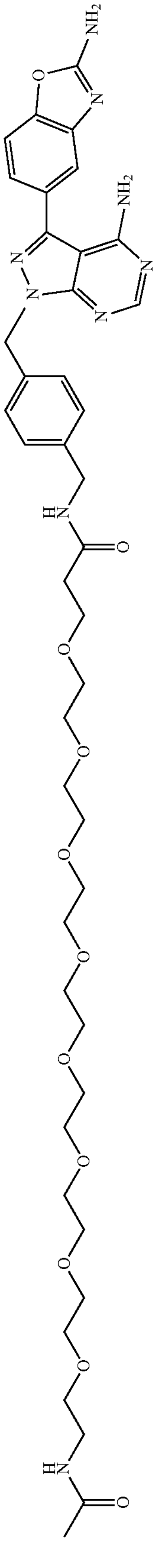

-continued
Example 82
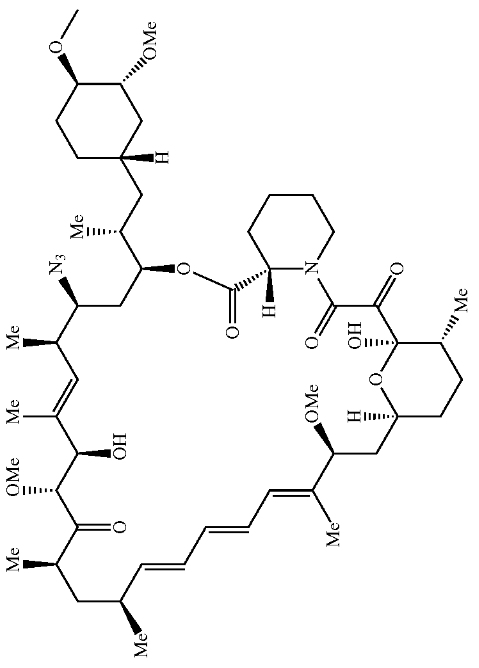
Example 83
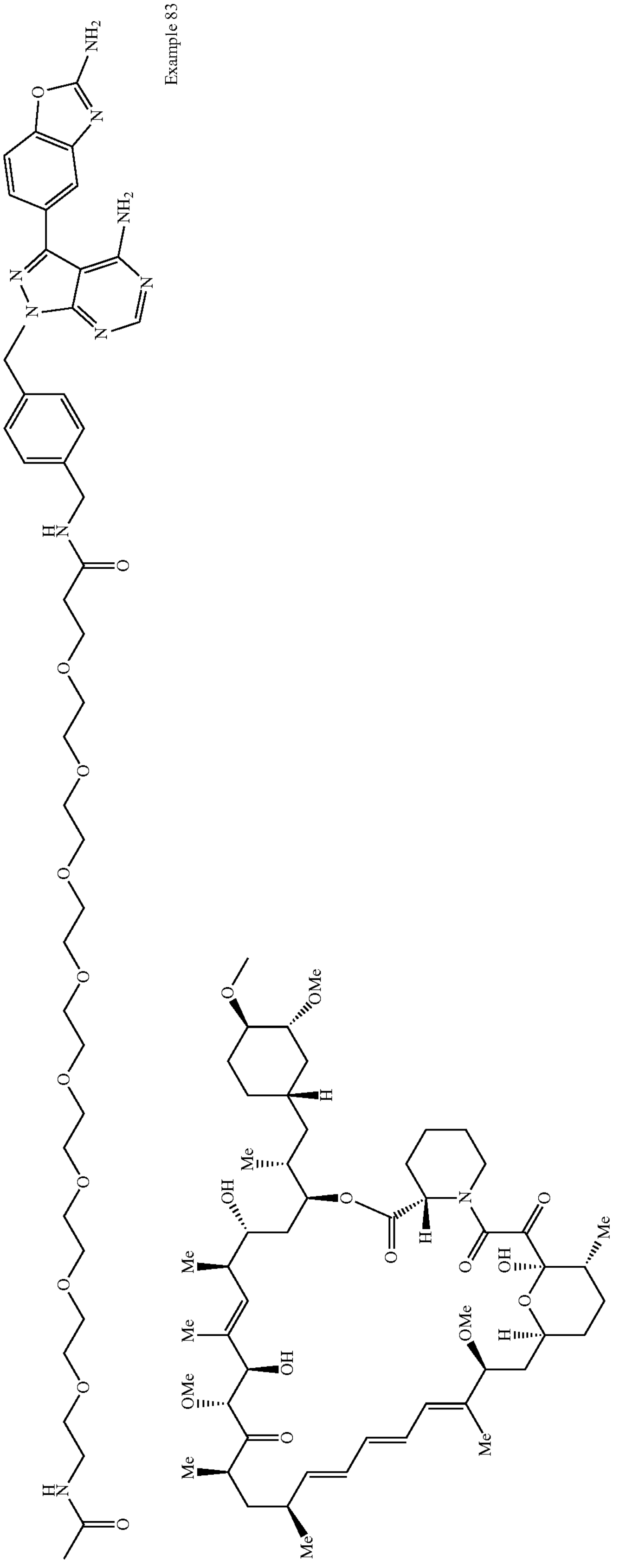

-continued
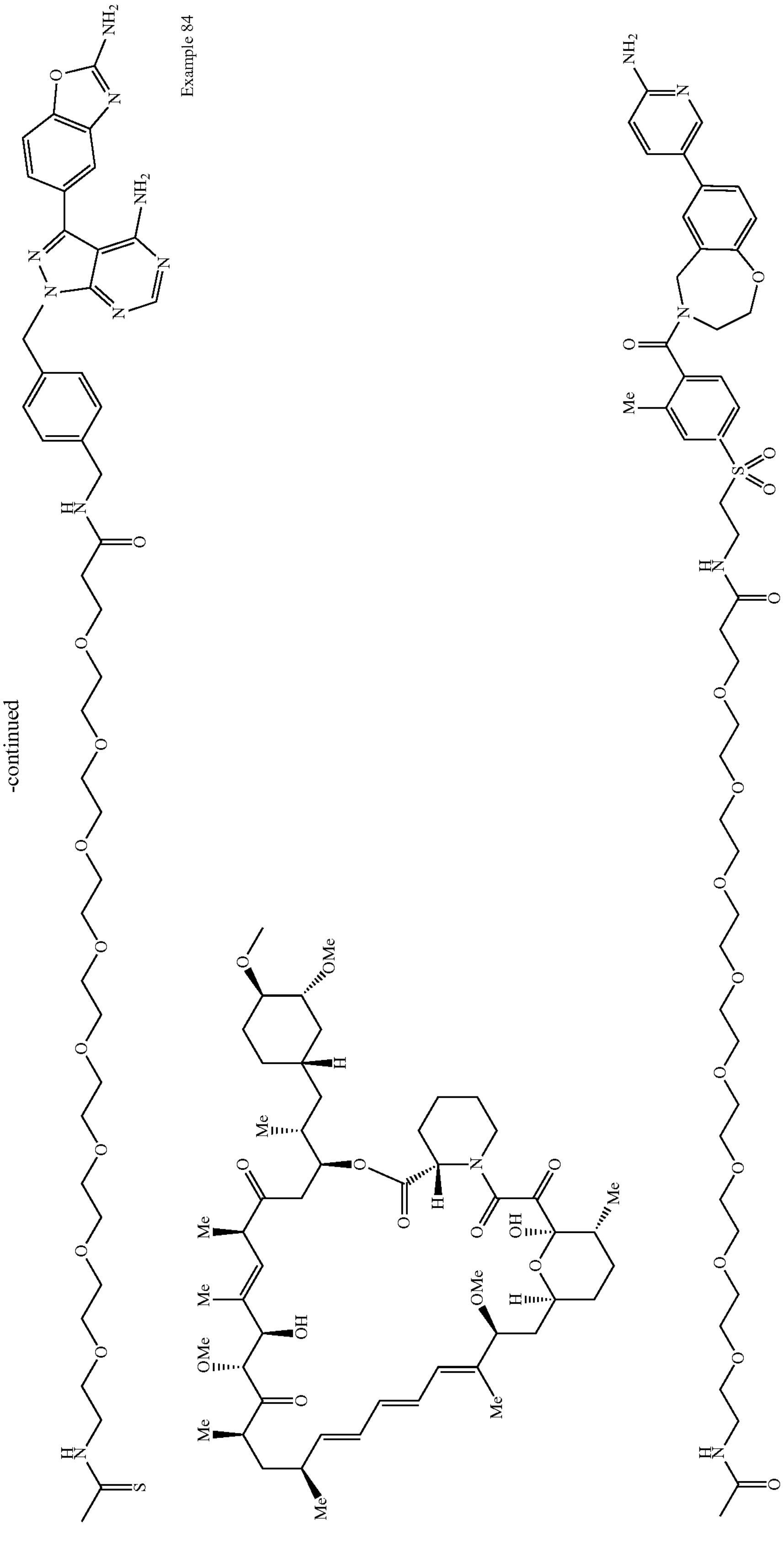
Example 84

-continued
Example 85
Example 86
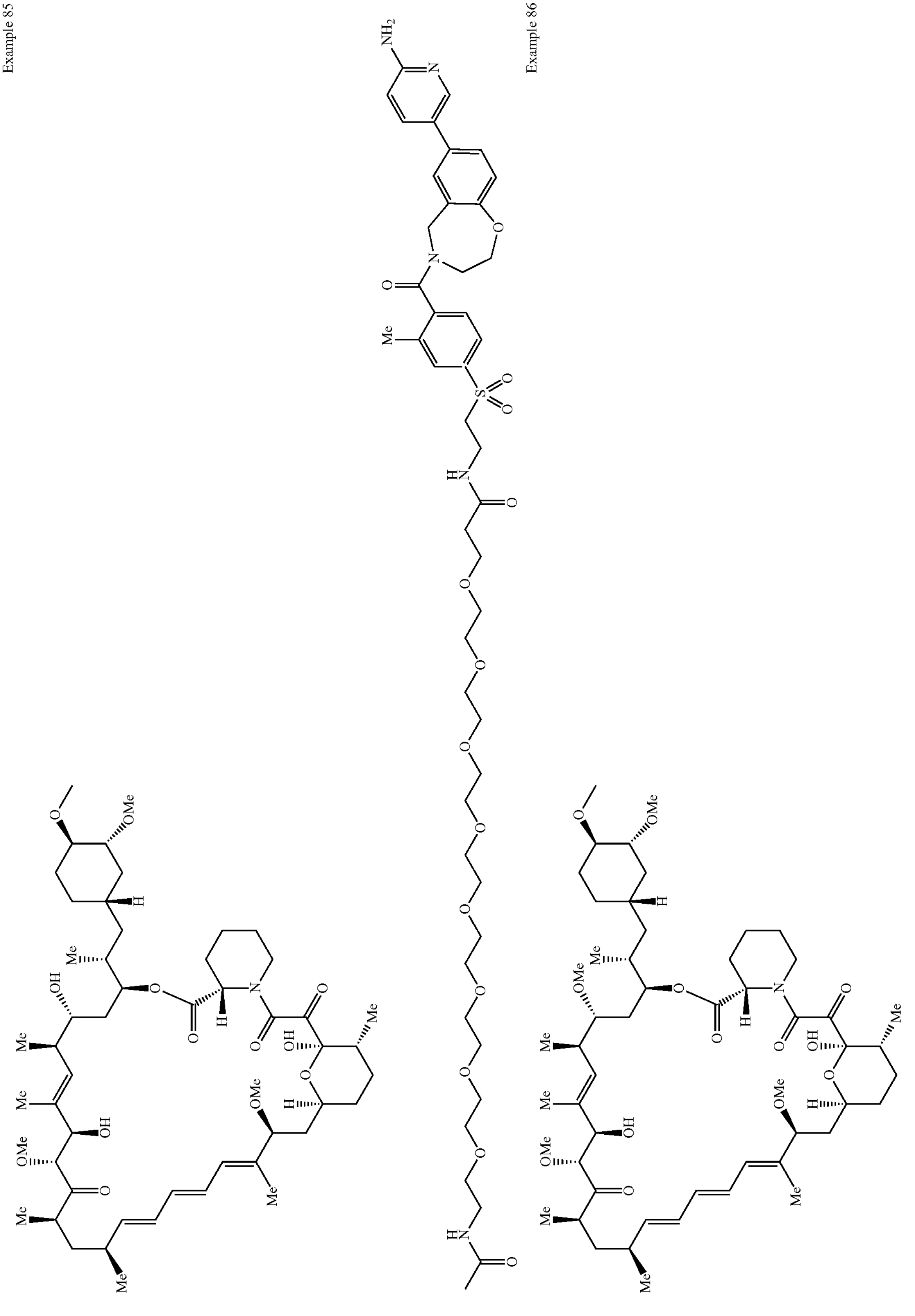

-continued
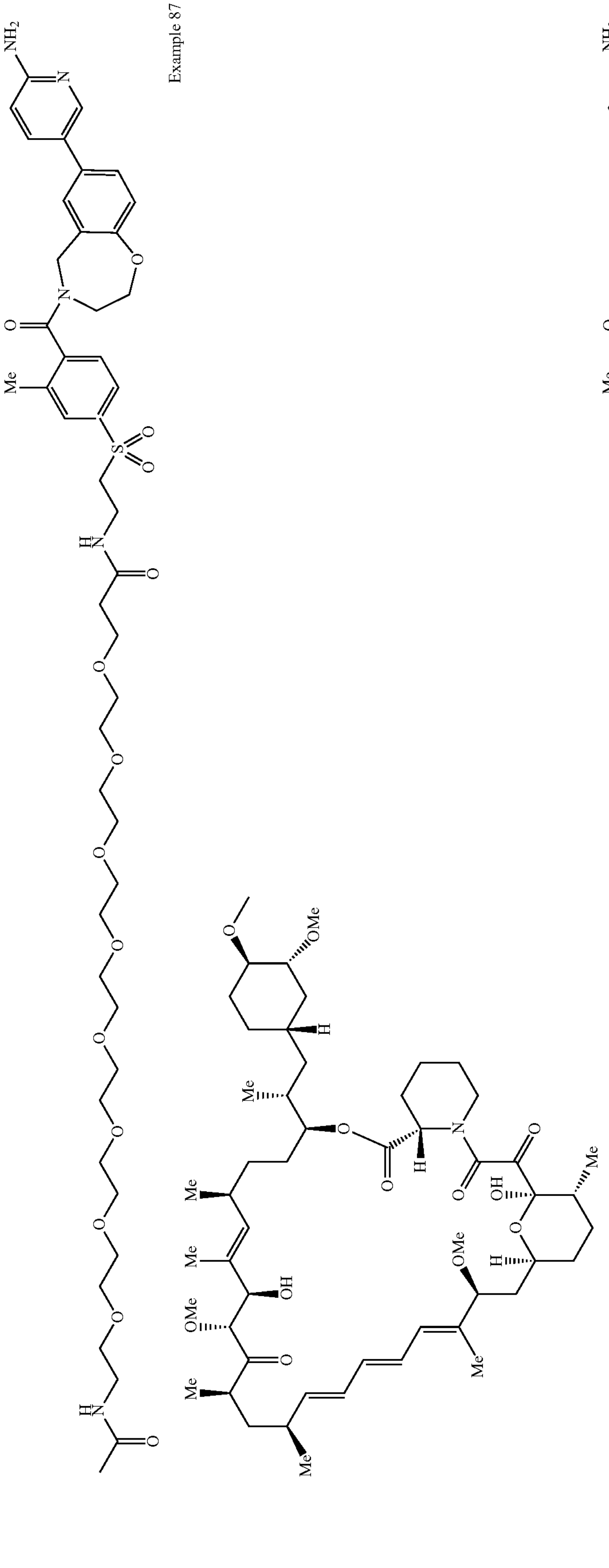
Example 87
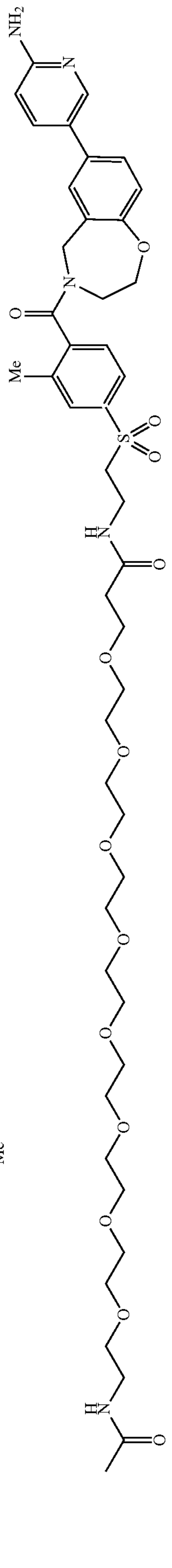

-continued
Example 88
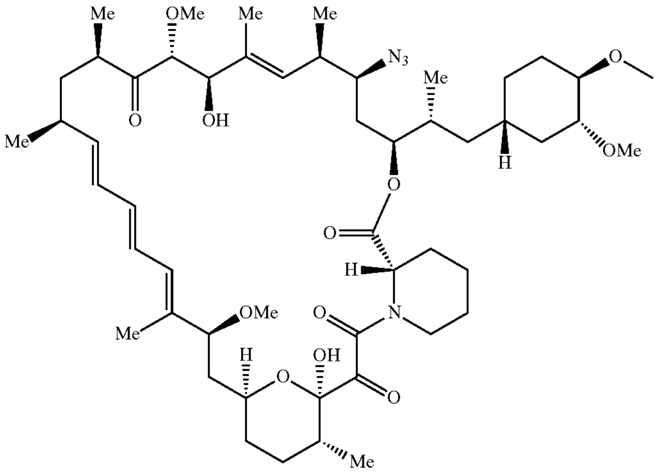
Example 89
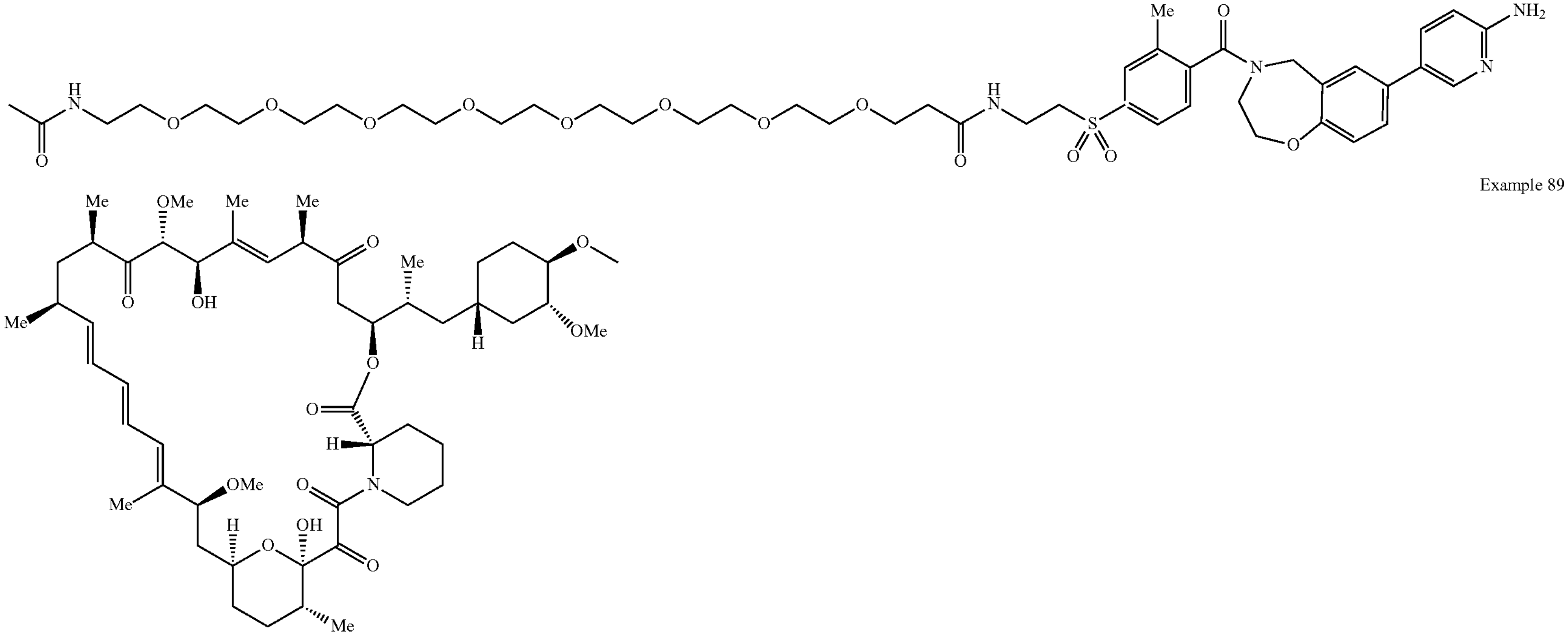

-continued
Example 90
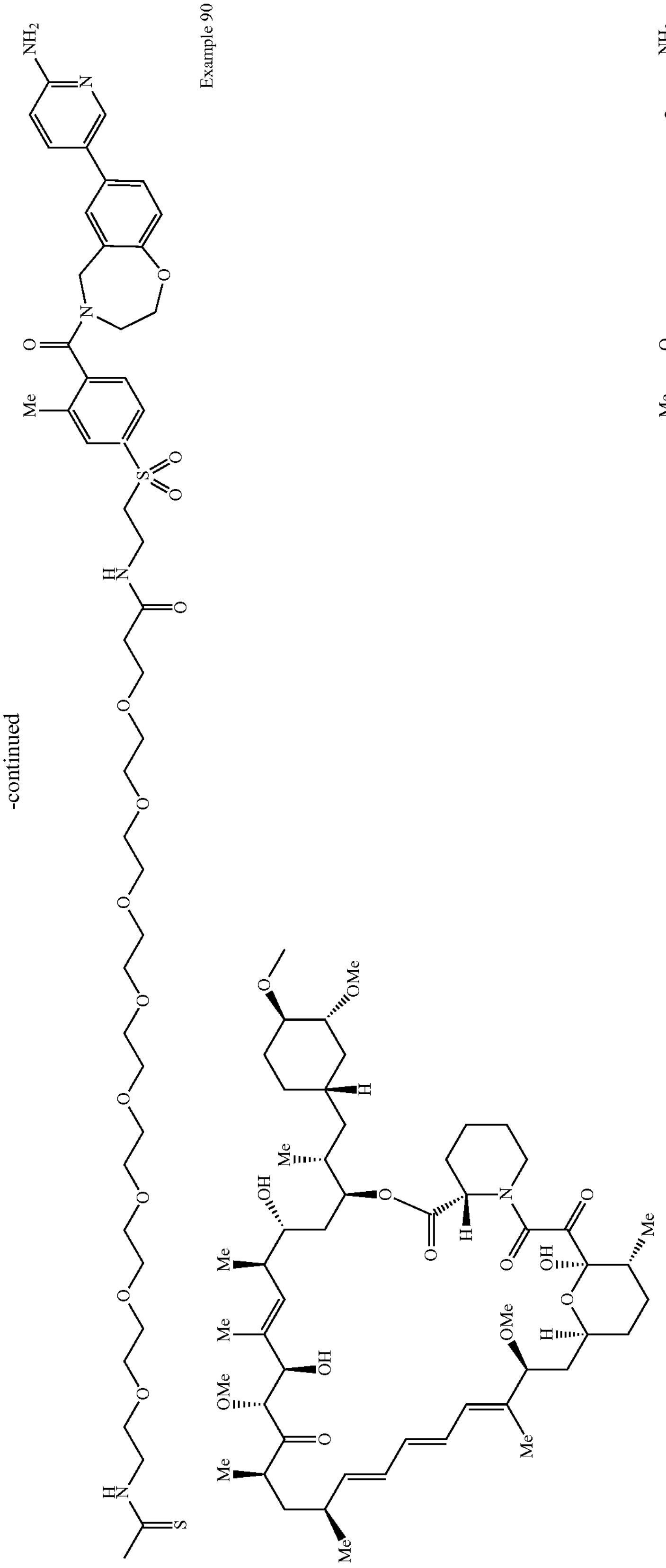
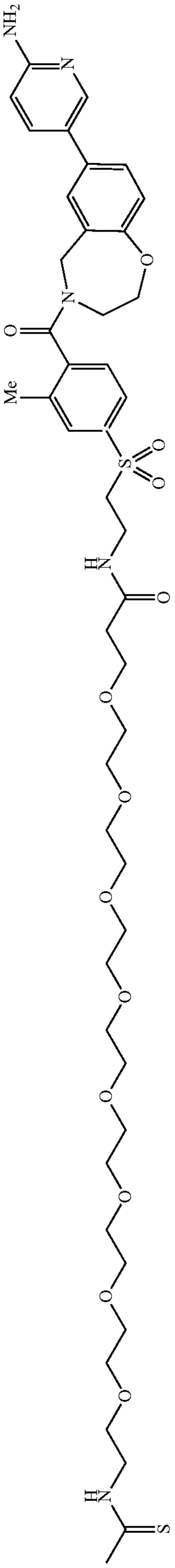

-continued
Example 91
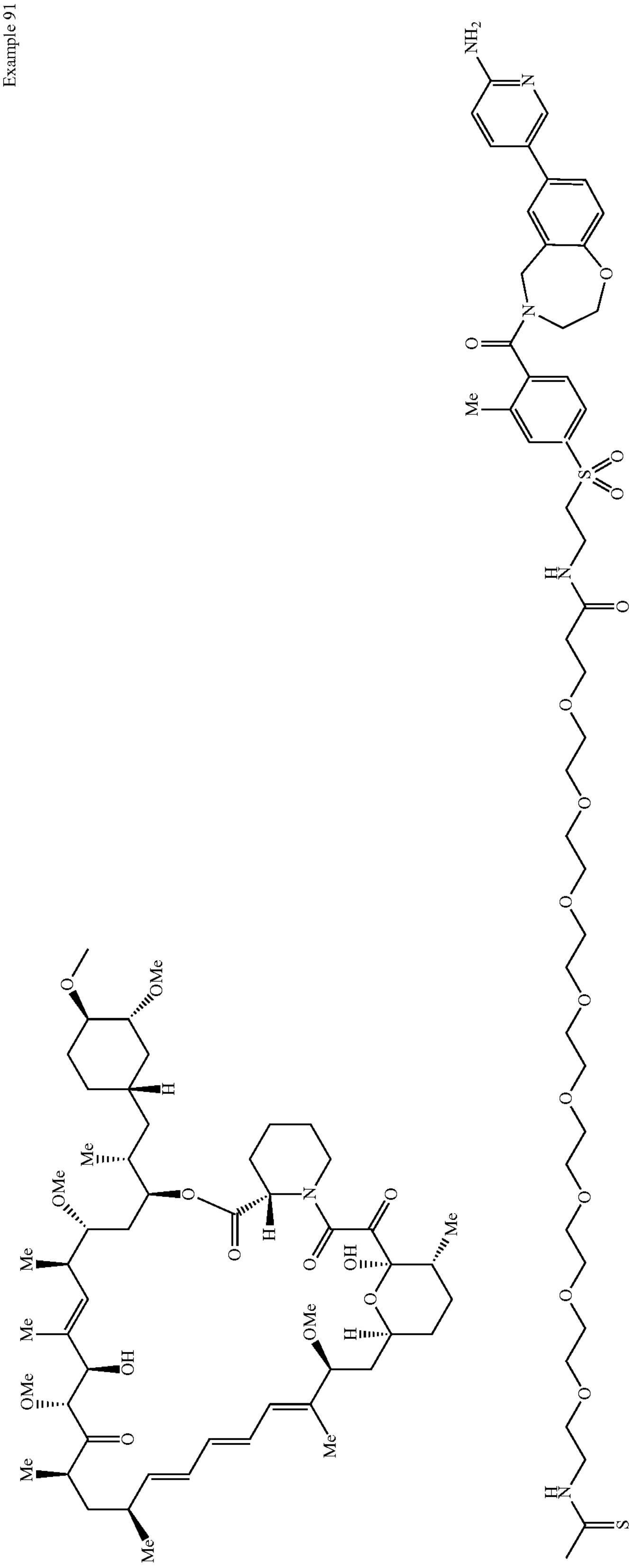
Example 92
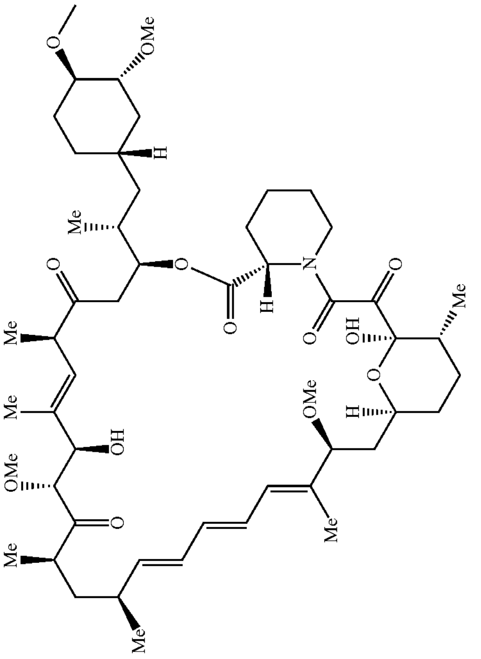

-continued
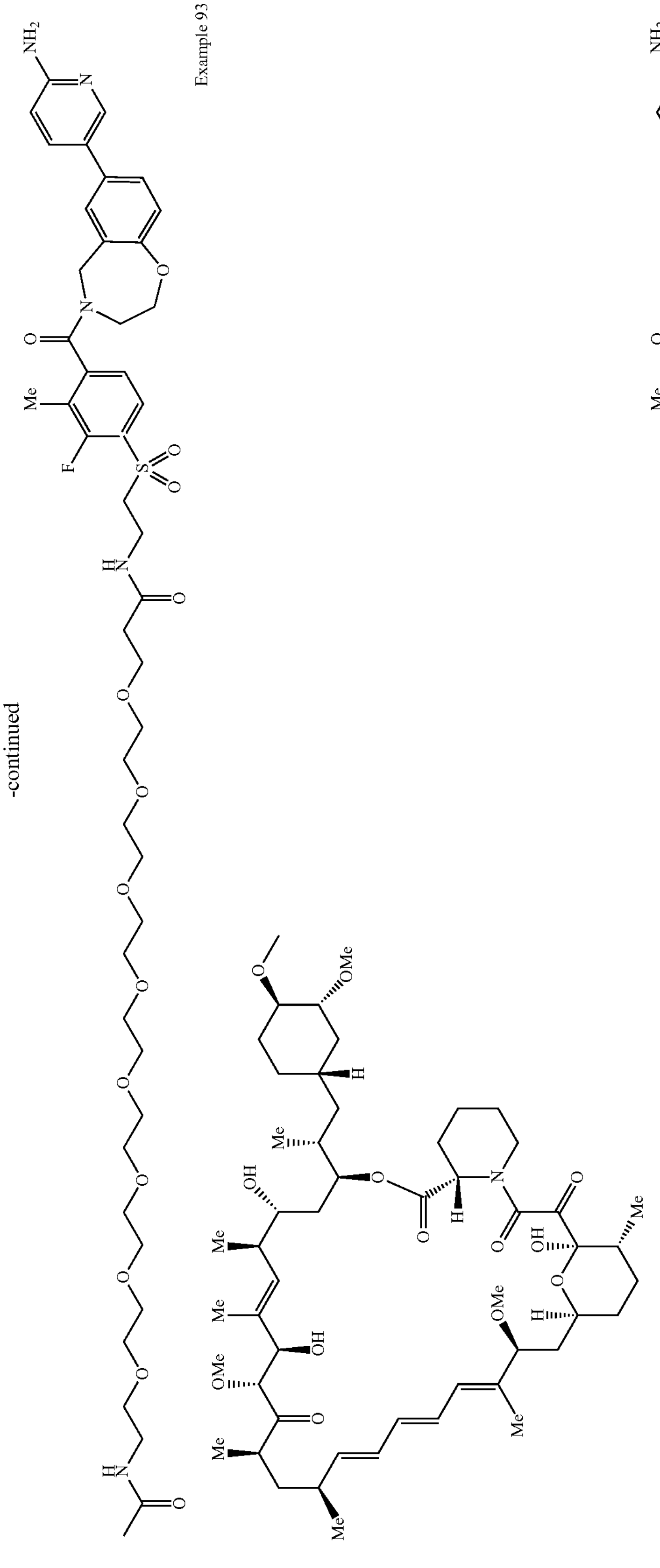
Example 93
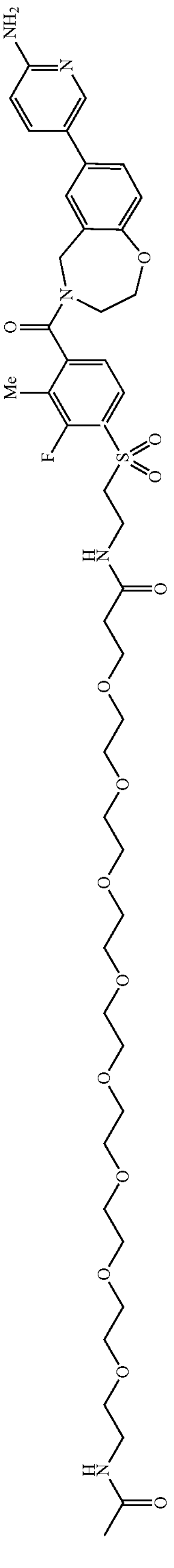

-continued
Example 94
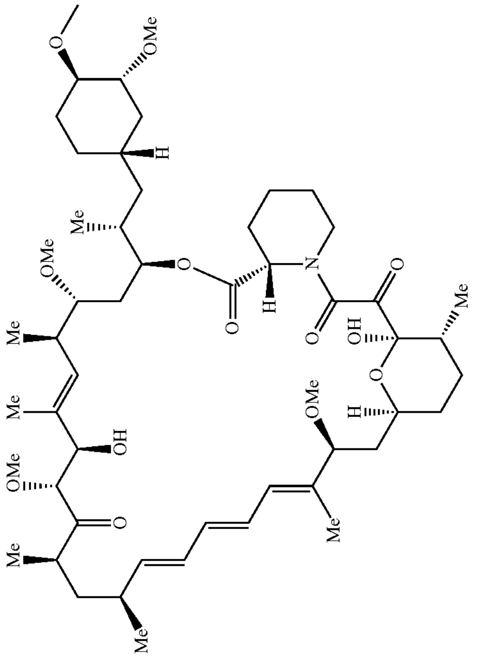
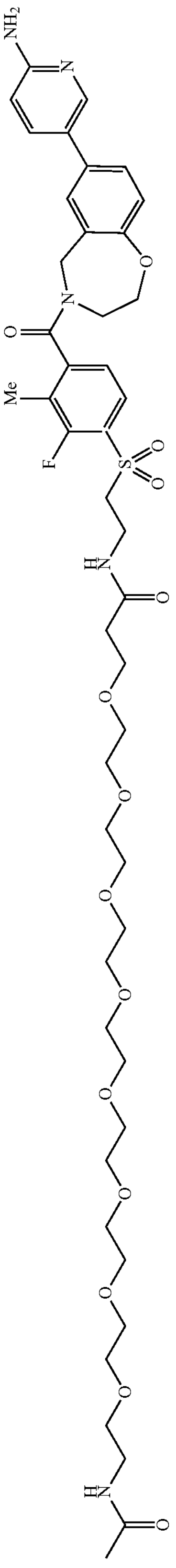
Example 95
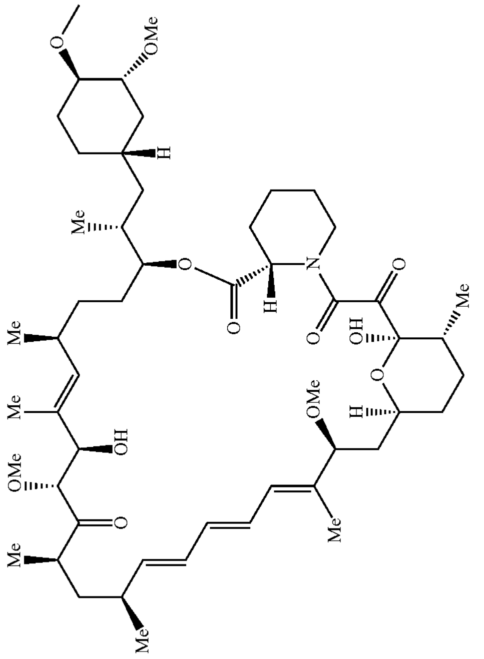

-continued
Example 96
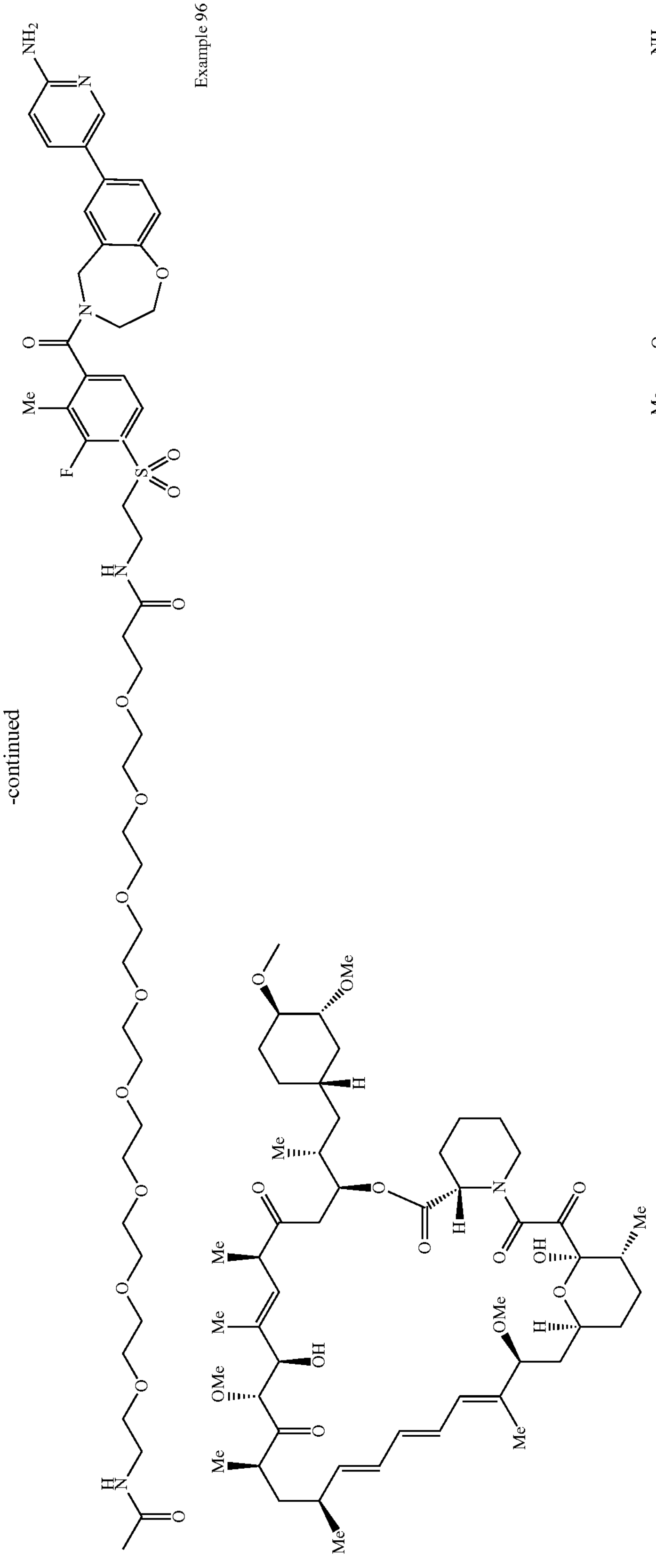
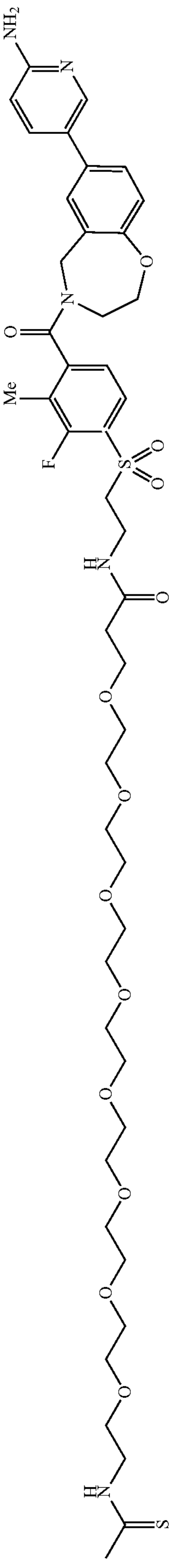

-continued
Example 97
Example 98
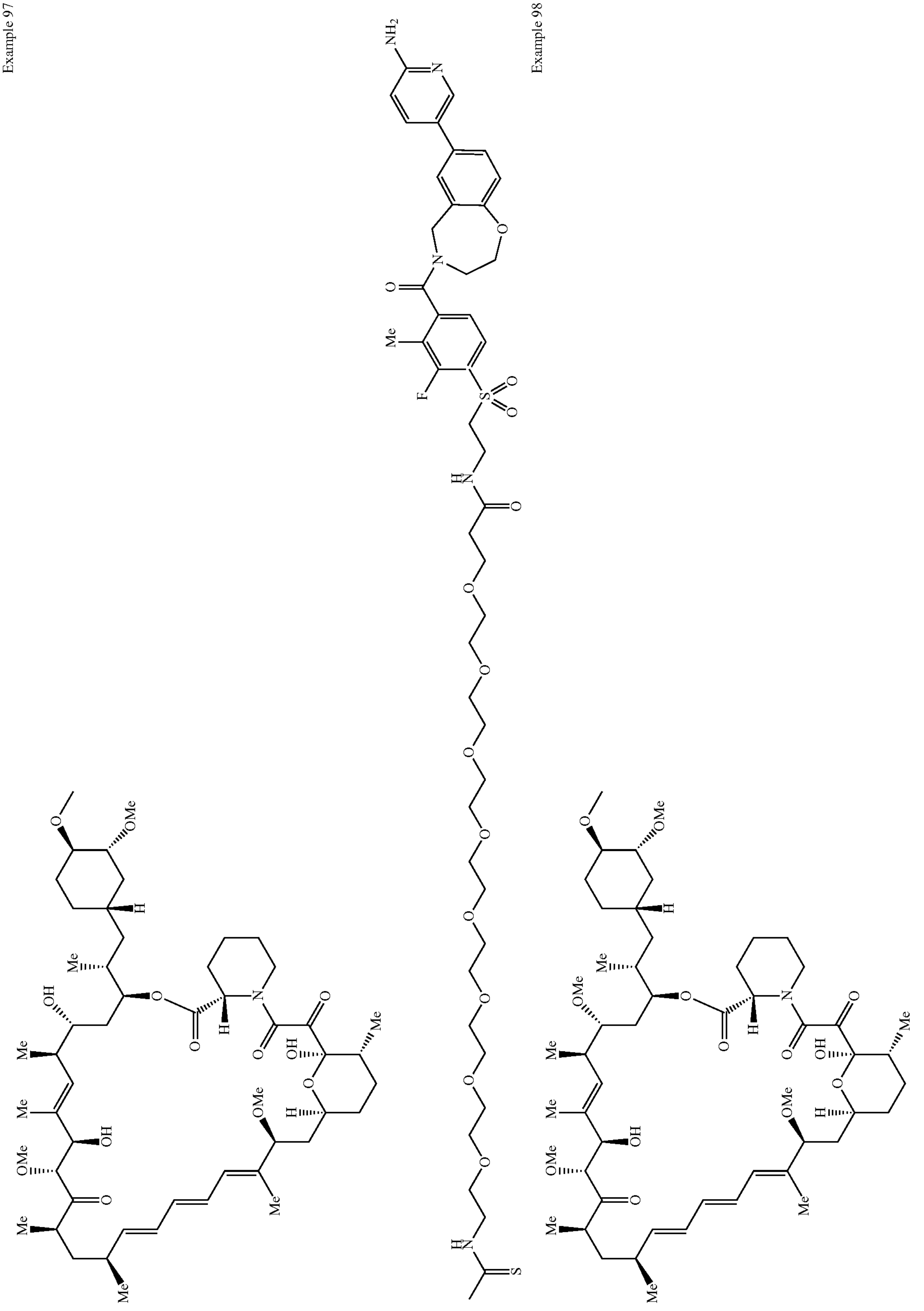

-continued
Example 99
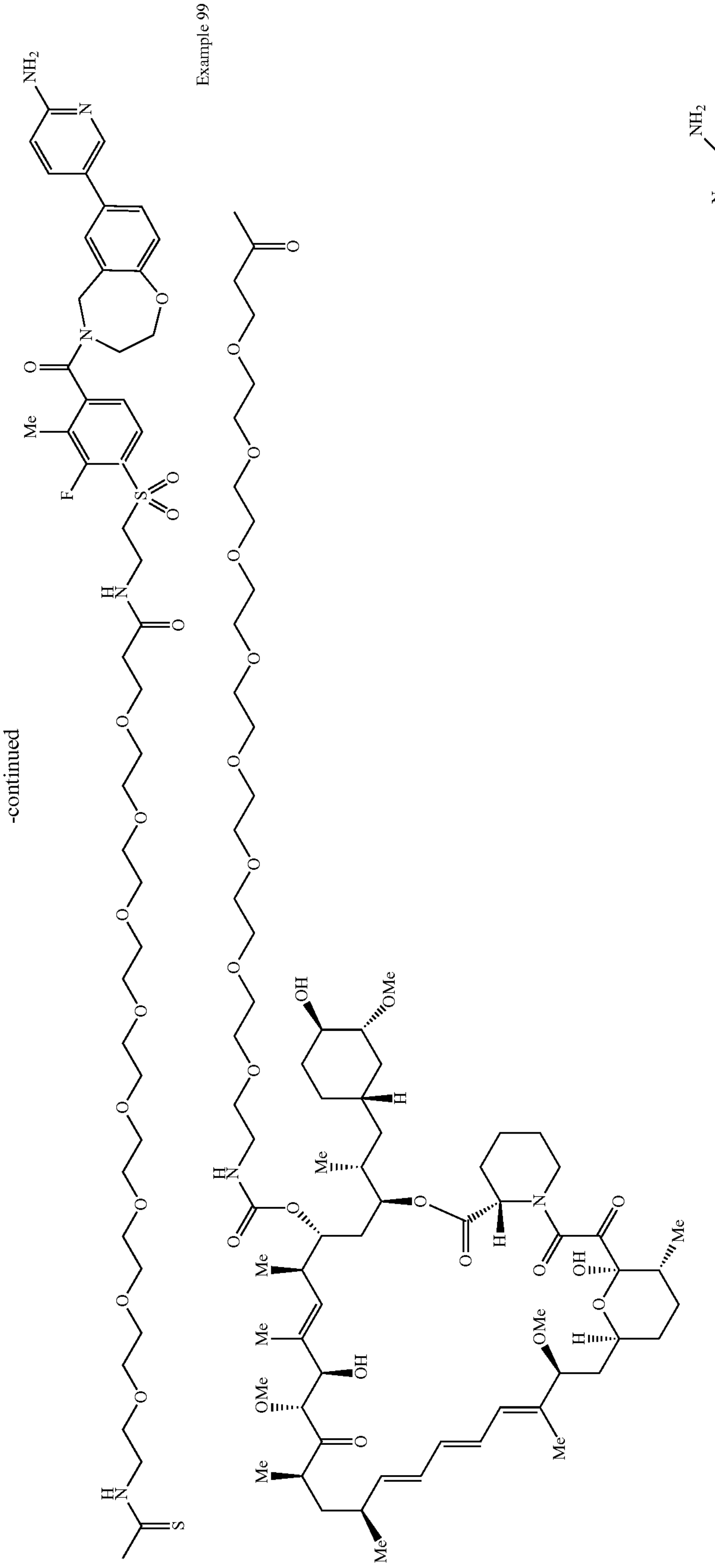
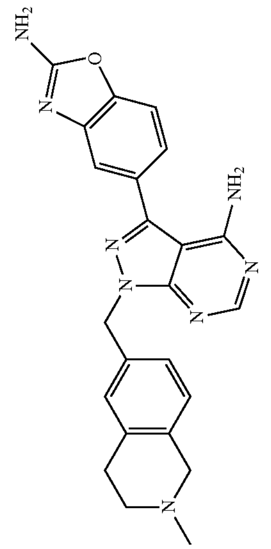

-continued
Example 100
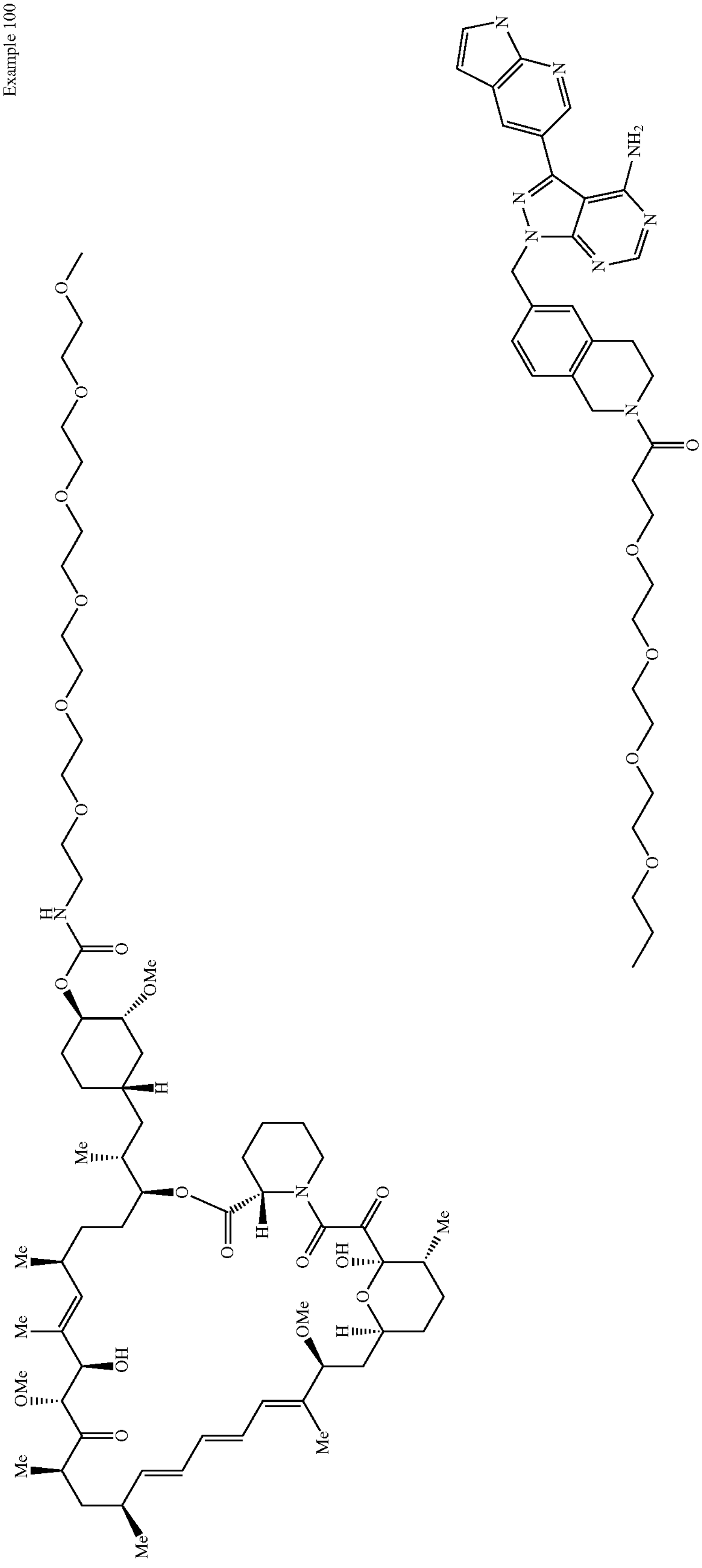

-continued
Example 101
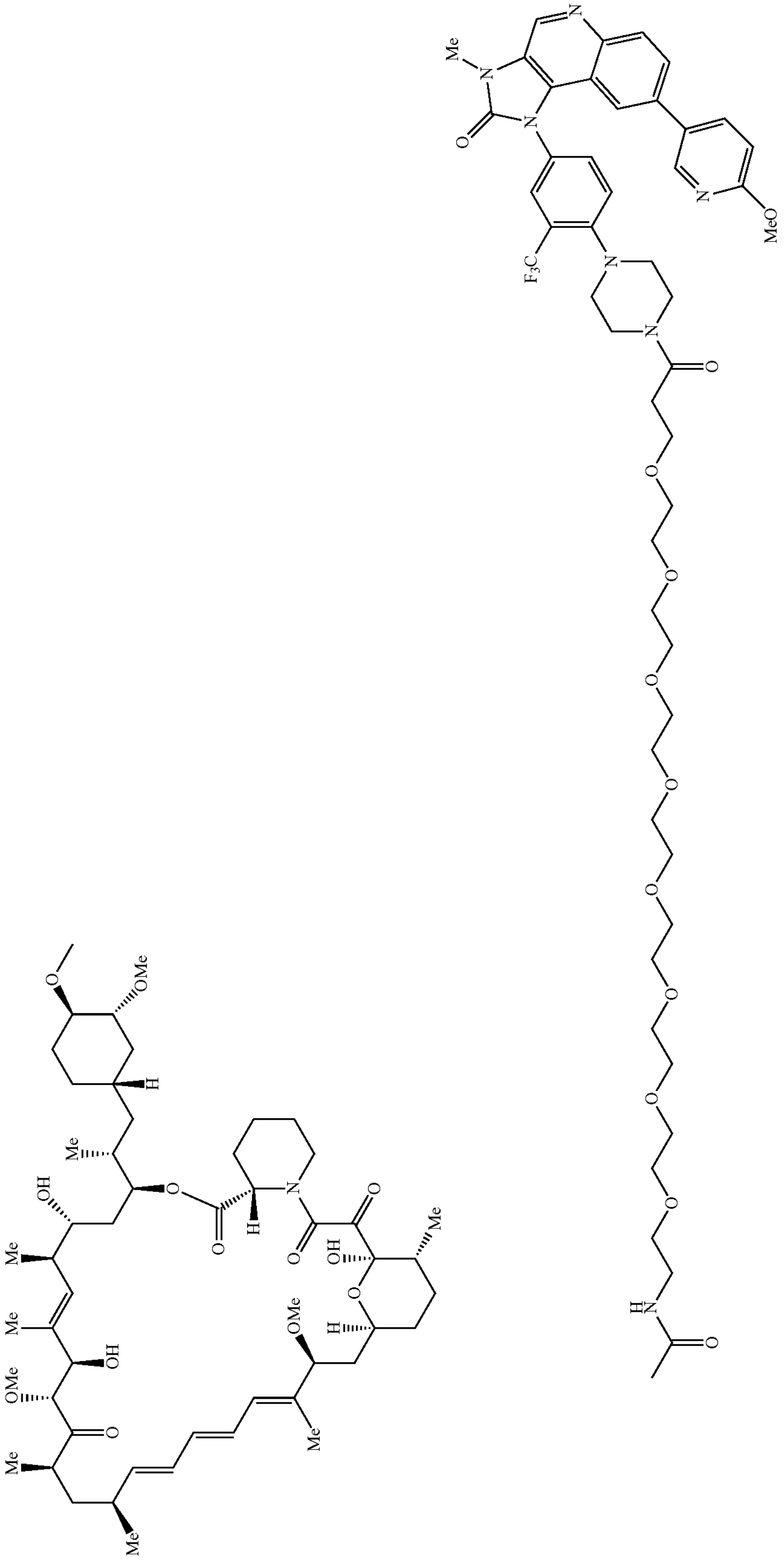

-continued
Example 102
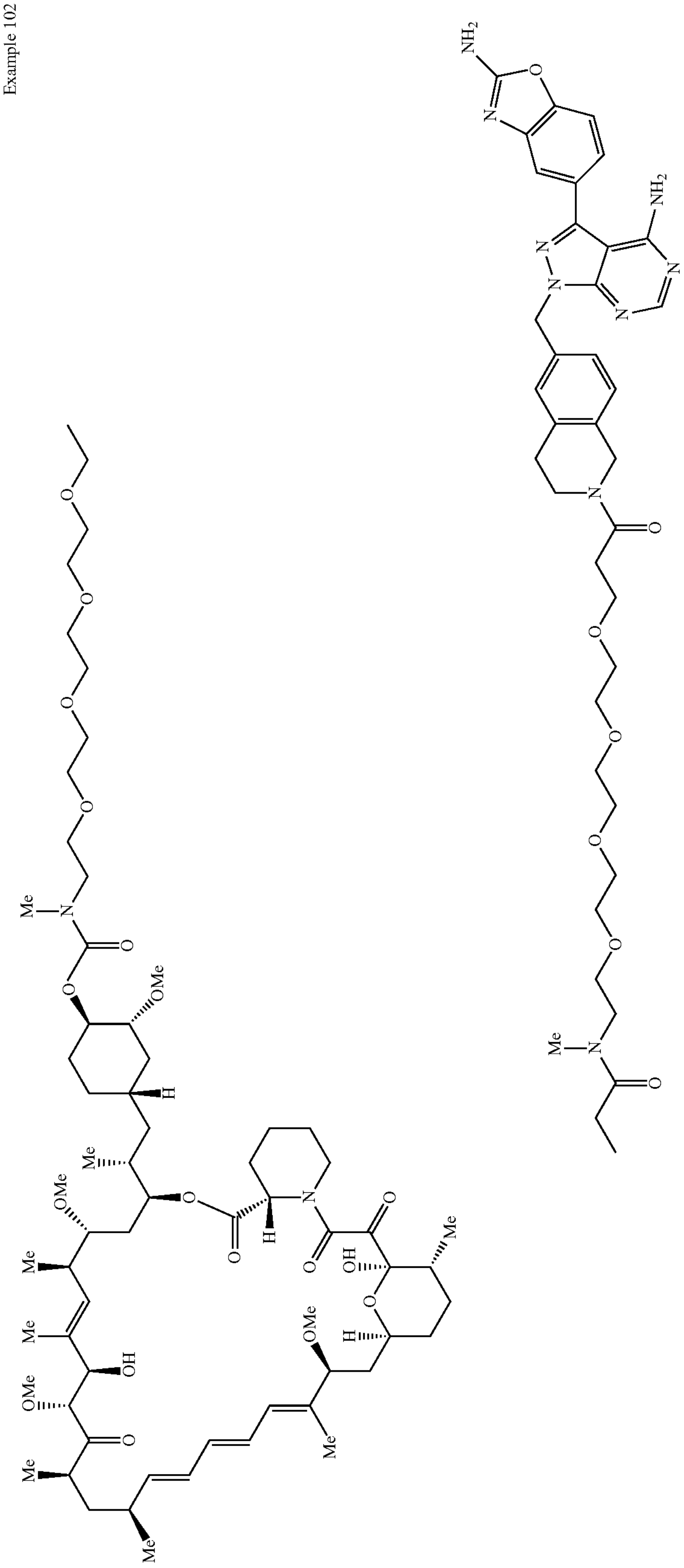

-continued
Example 103
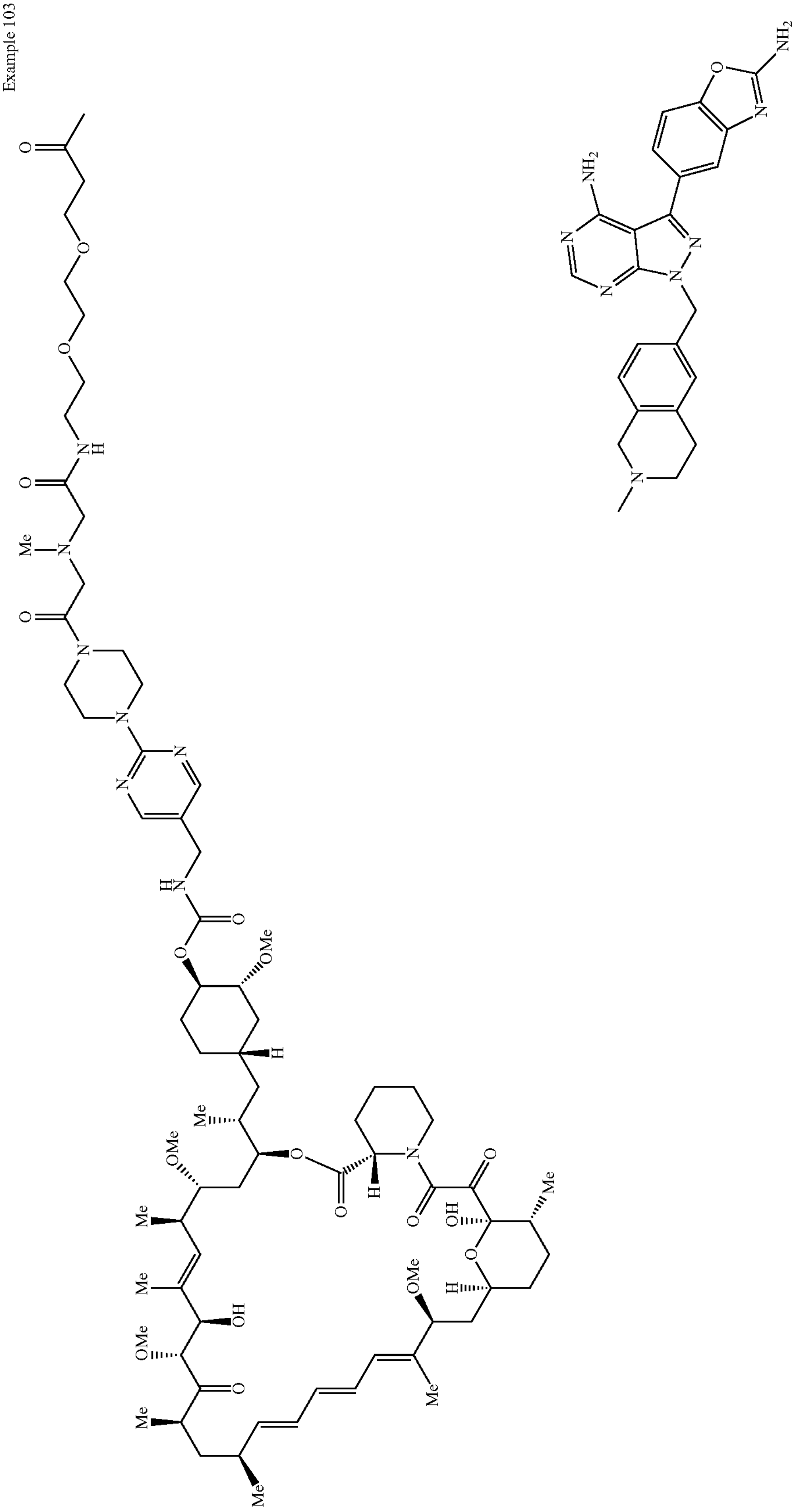

-continued
Example 104
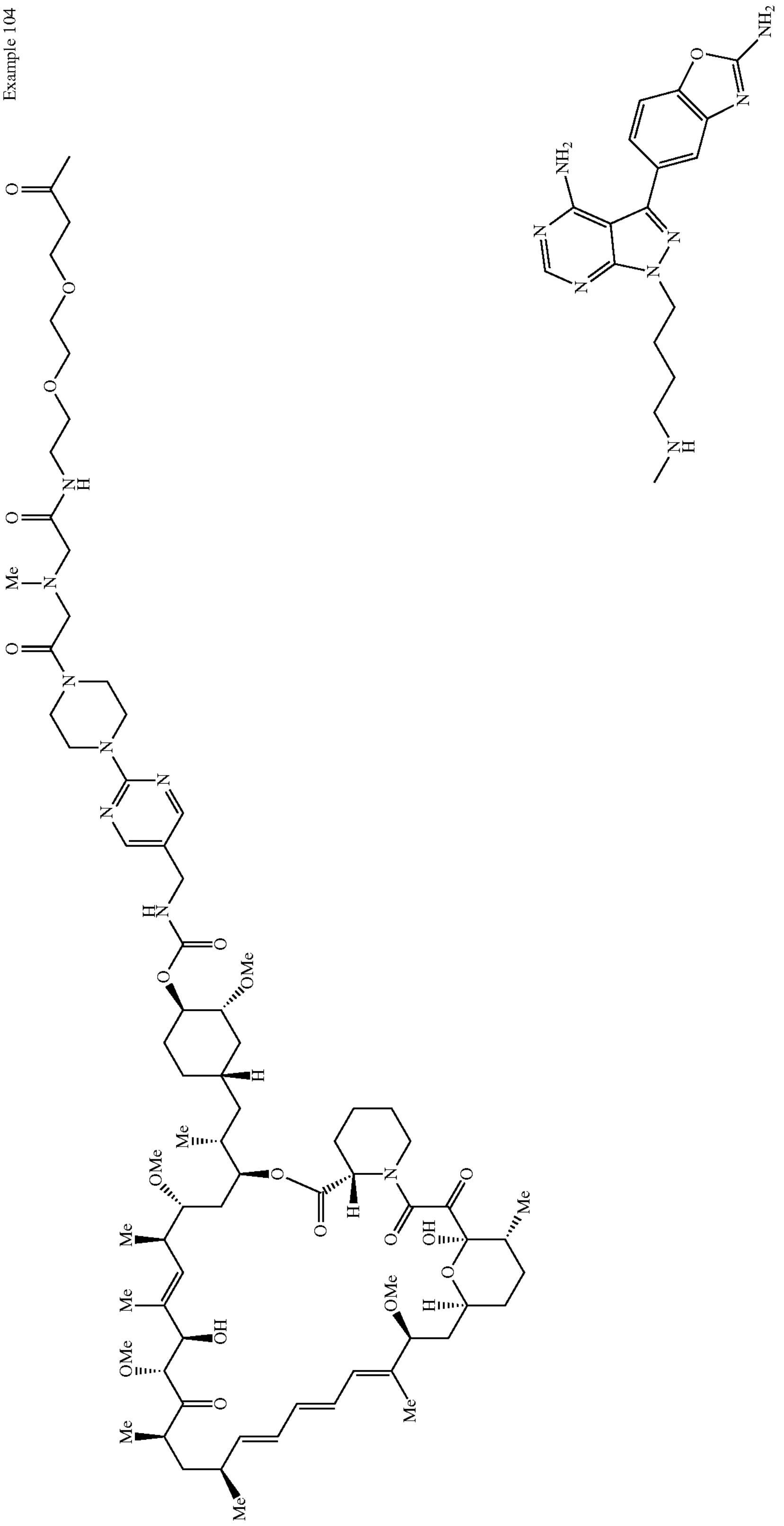

-continued
Example 105
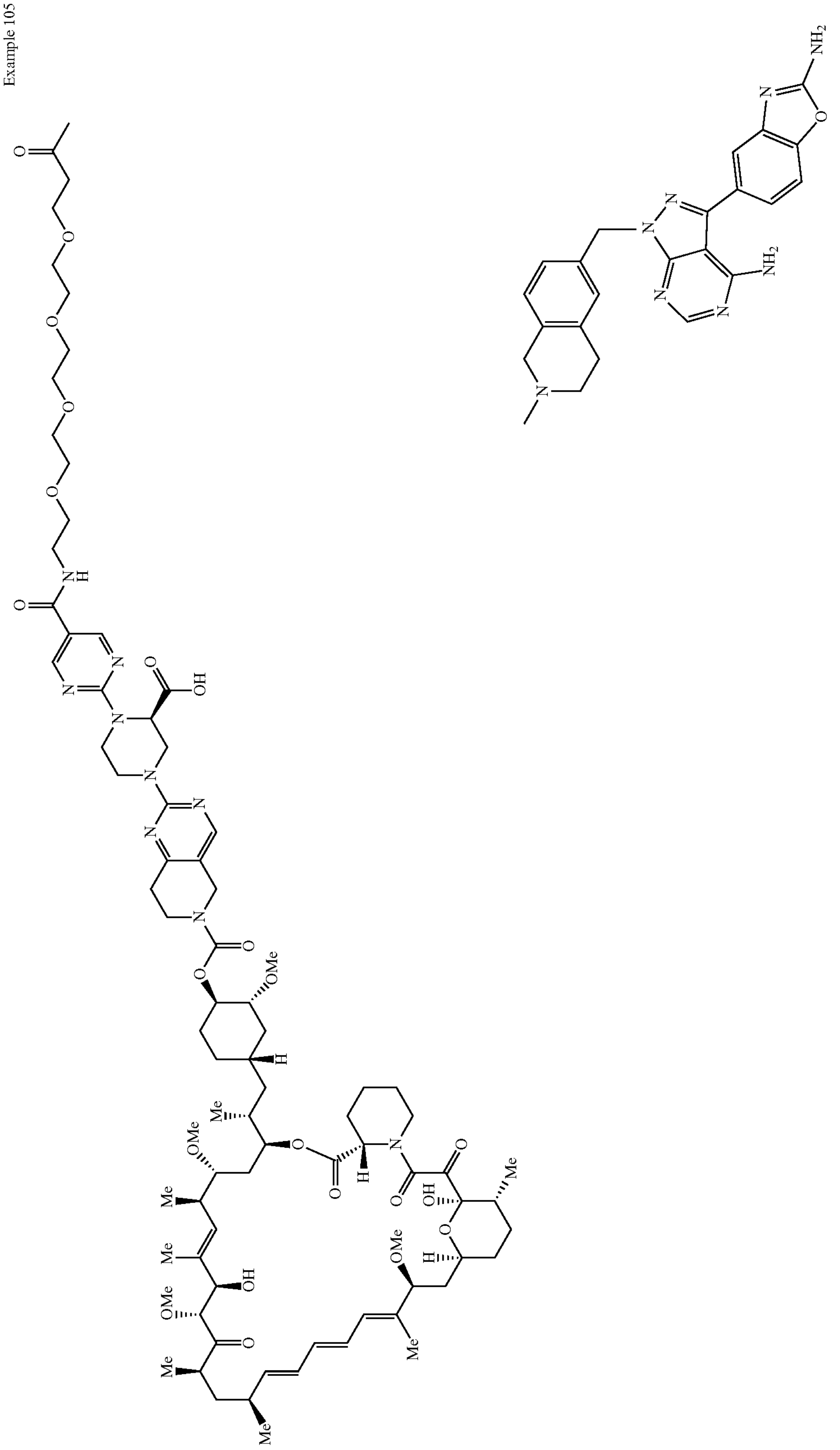

-continued
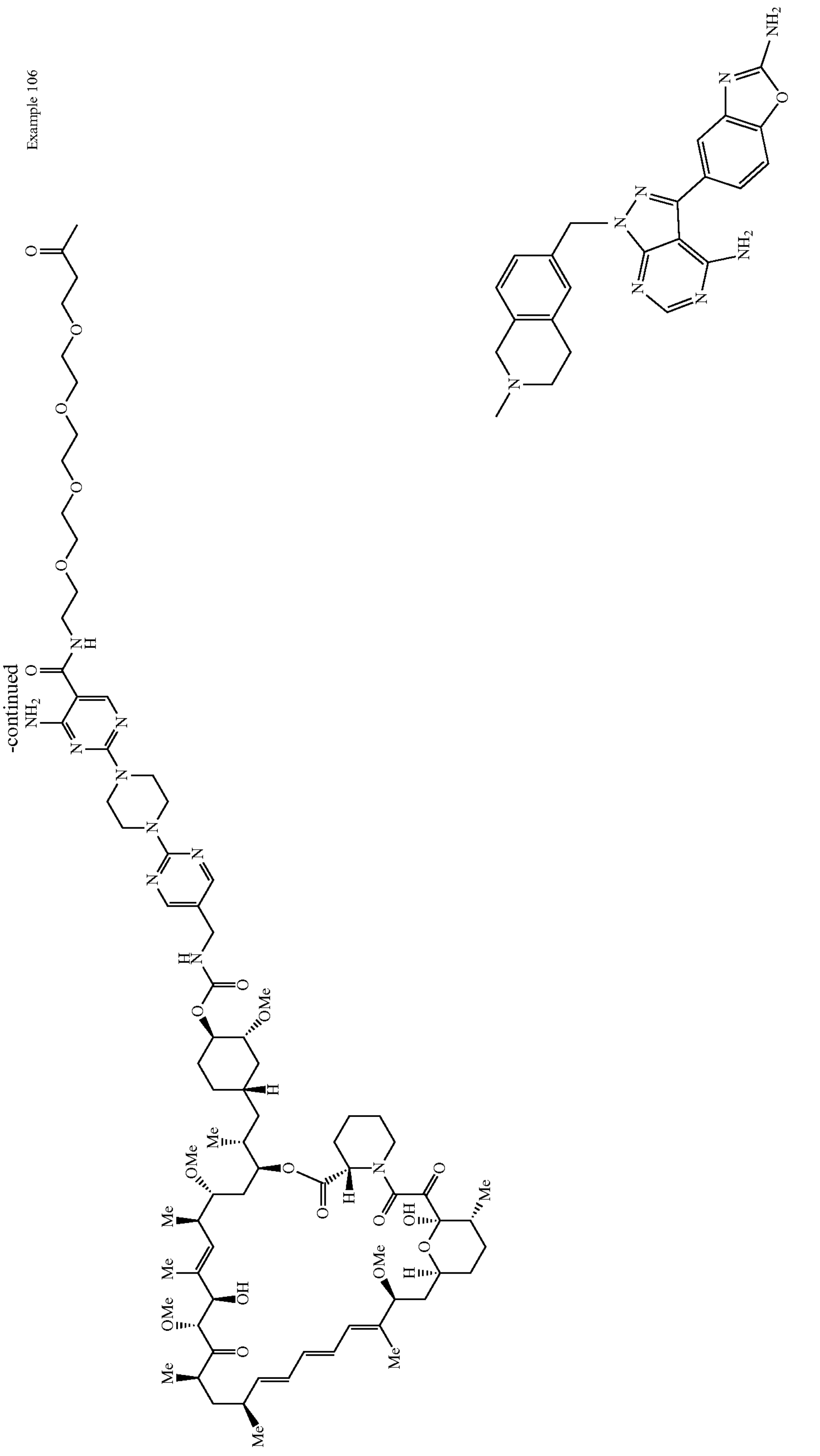
Example 106

-continued
Example 107
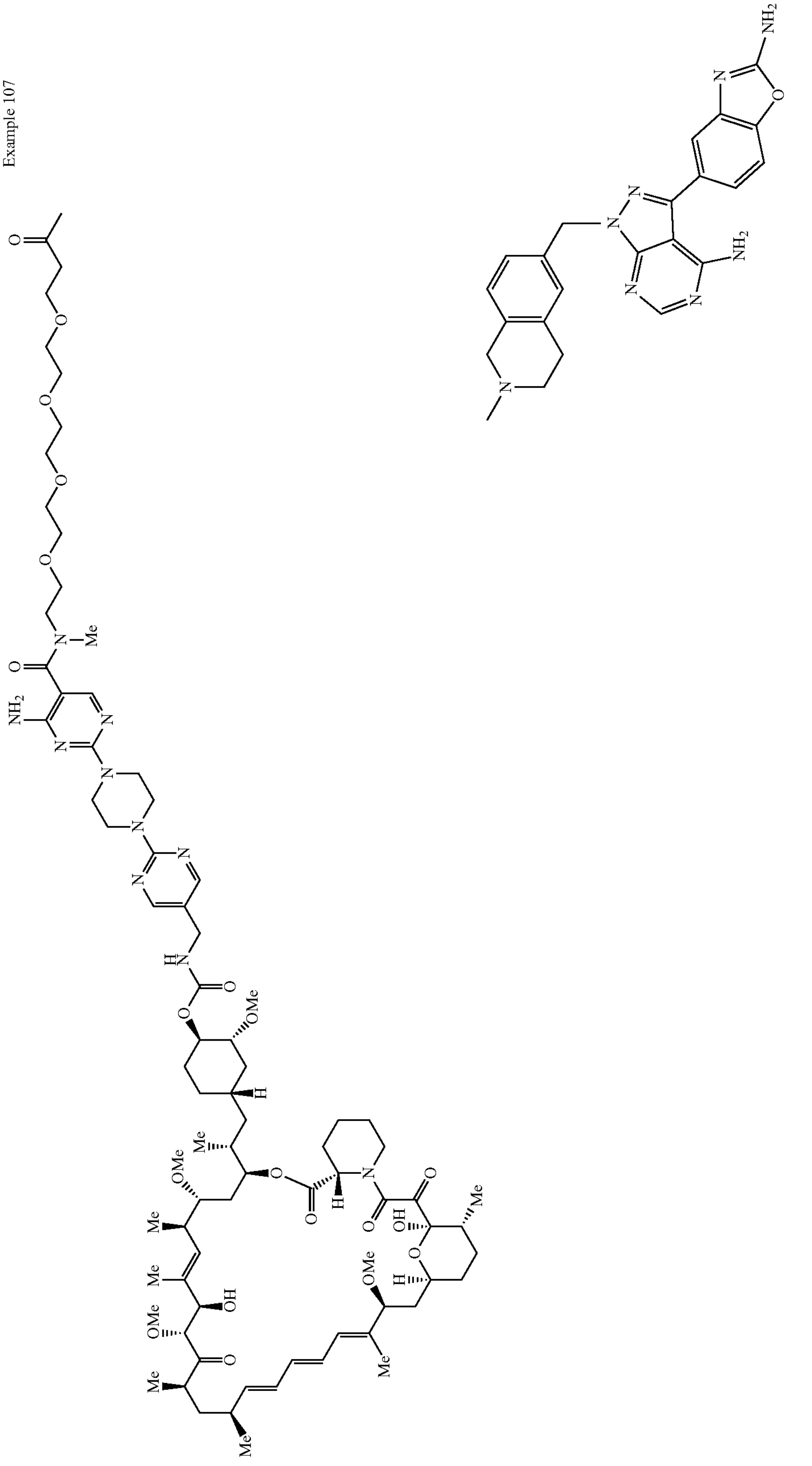

-continued
Example 108
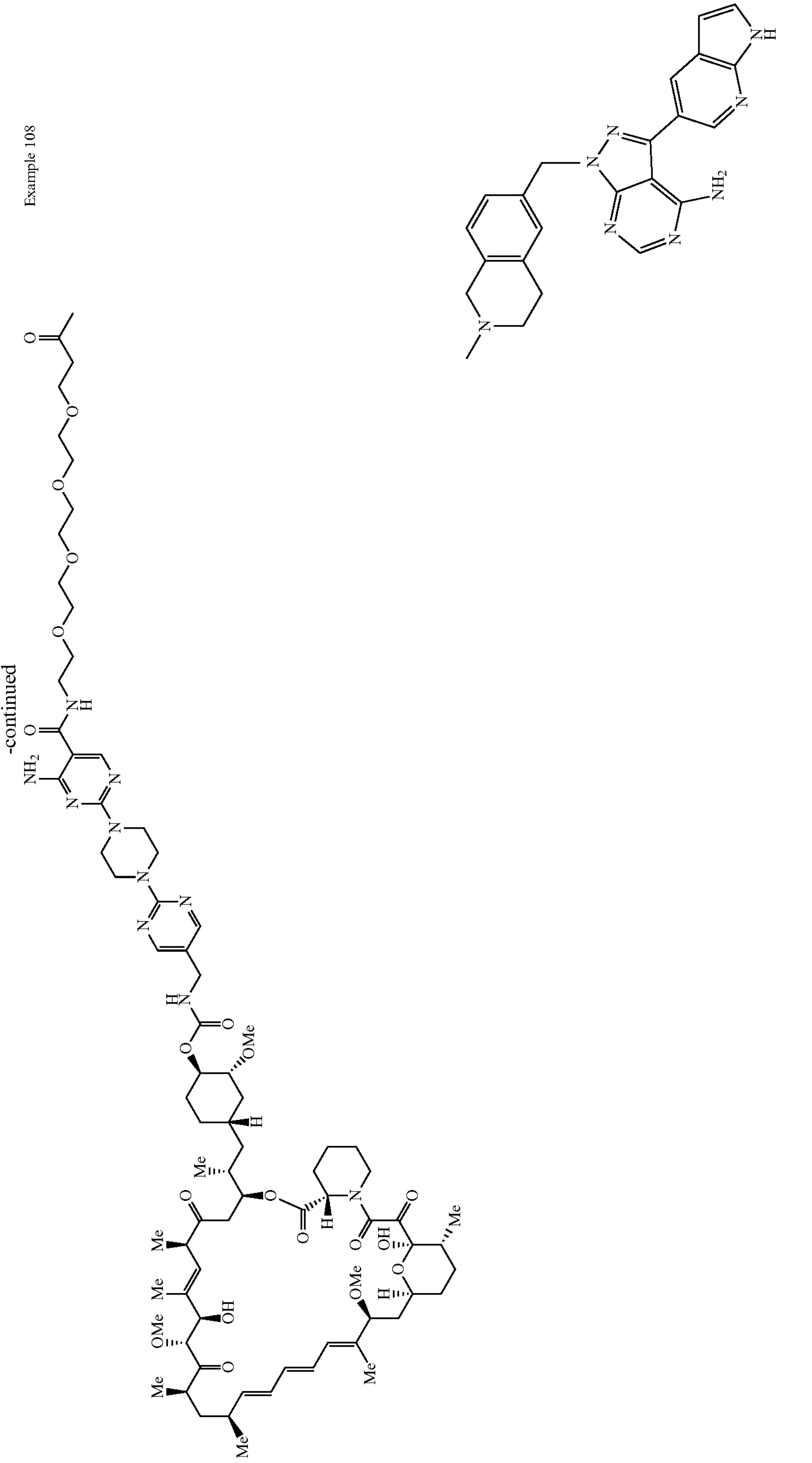

-continued
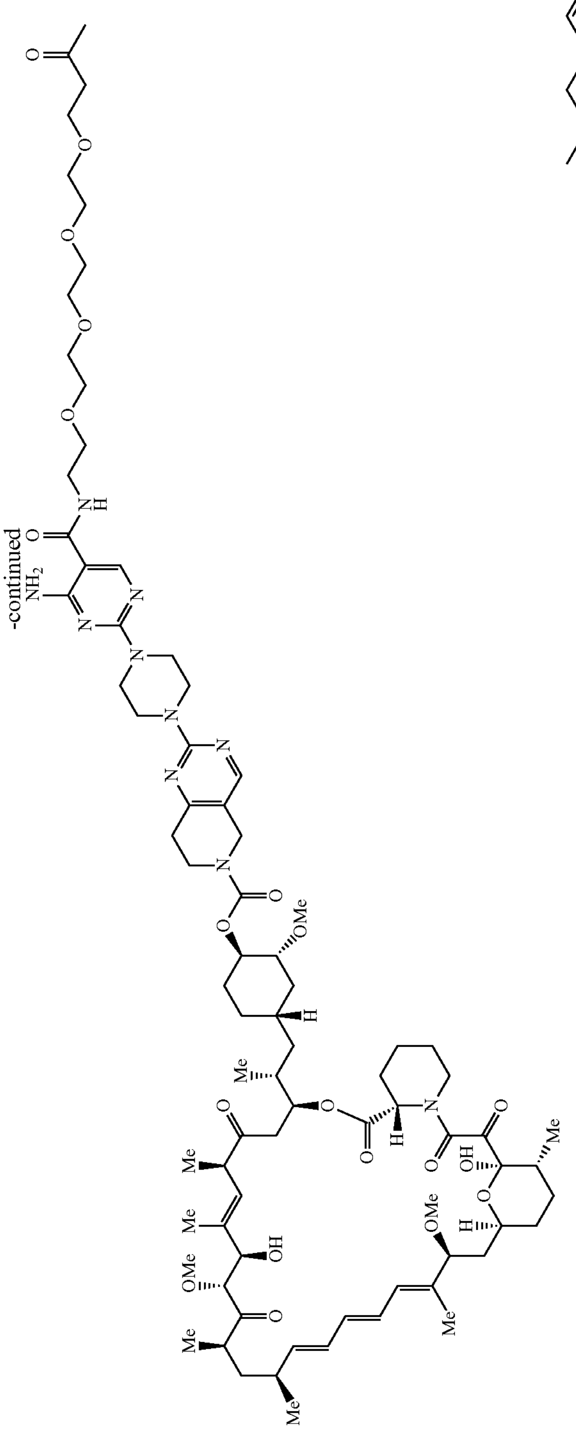
Example 109
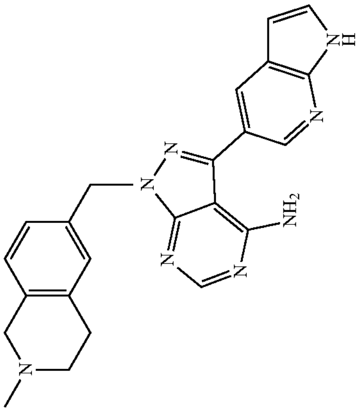

-continued
Example 110
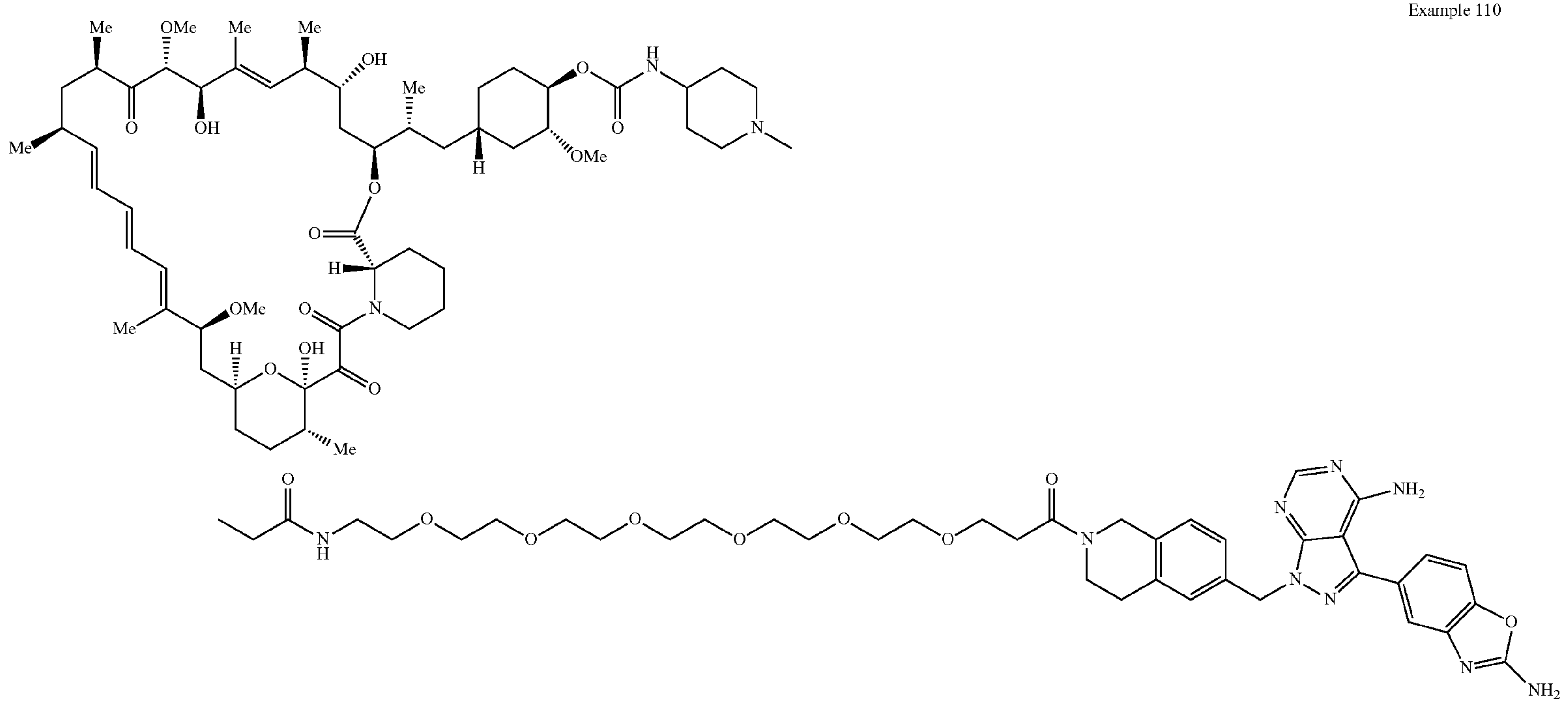

-continued
Example 111
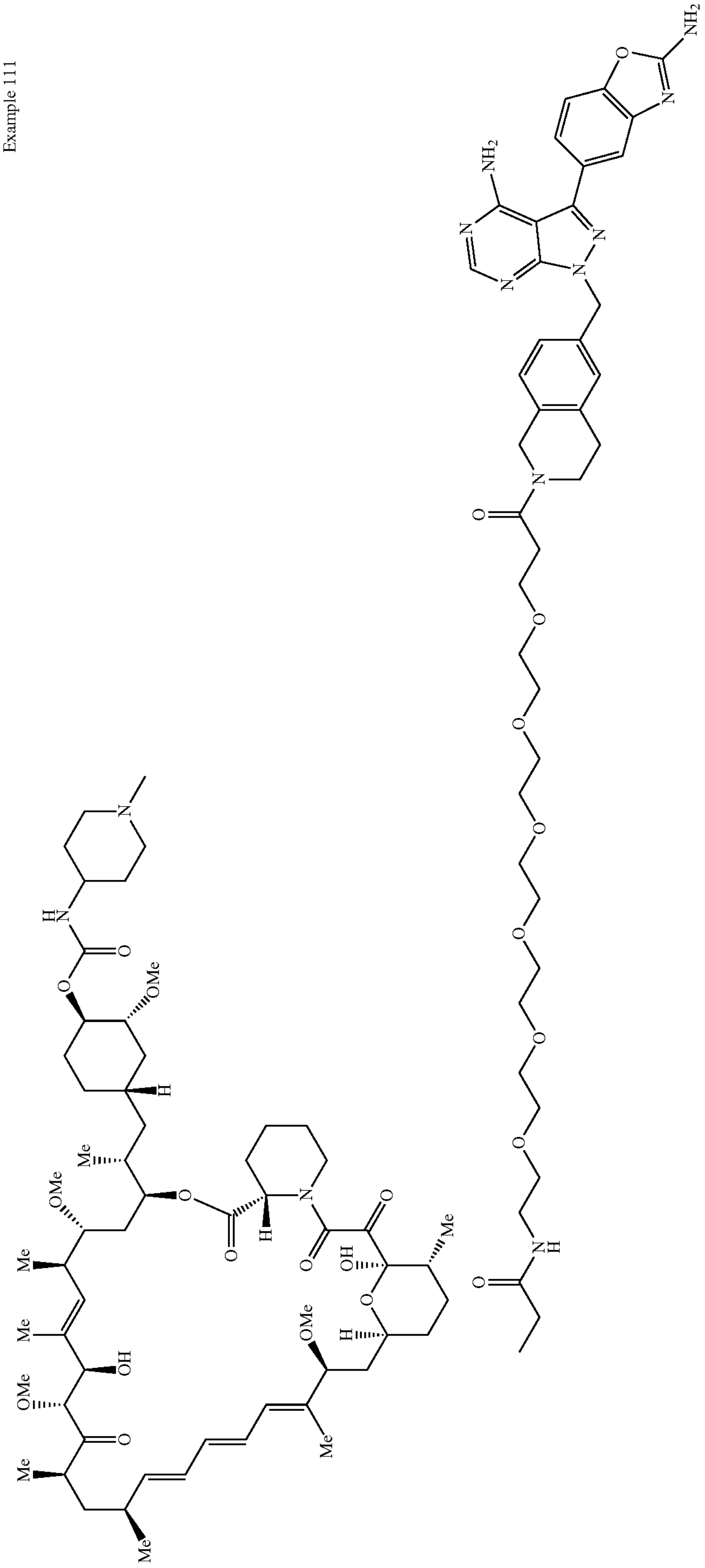

-continued
Example 112
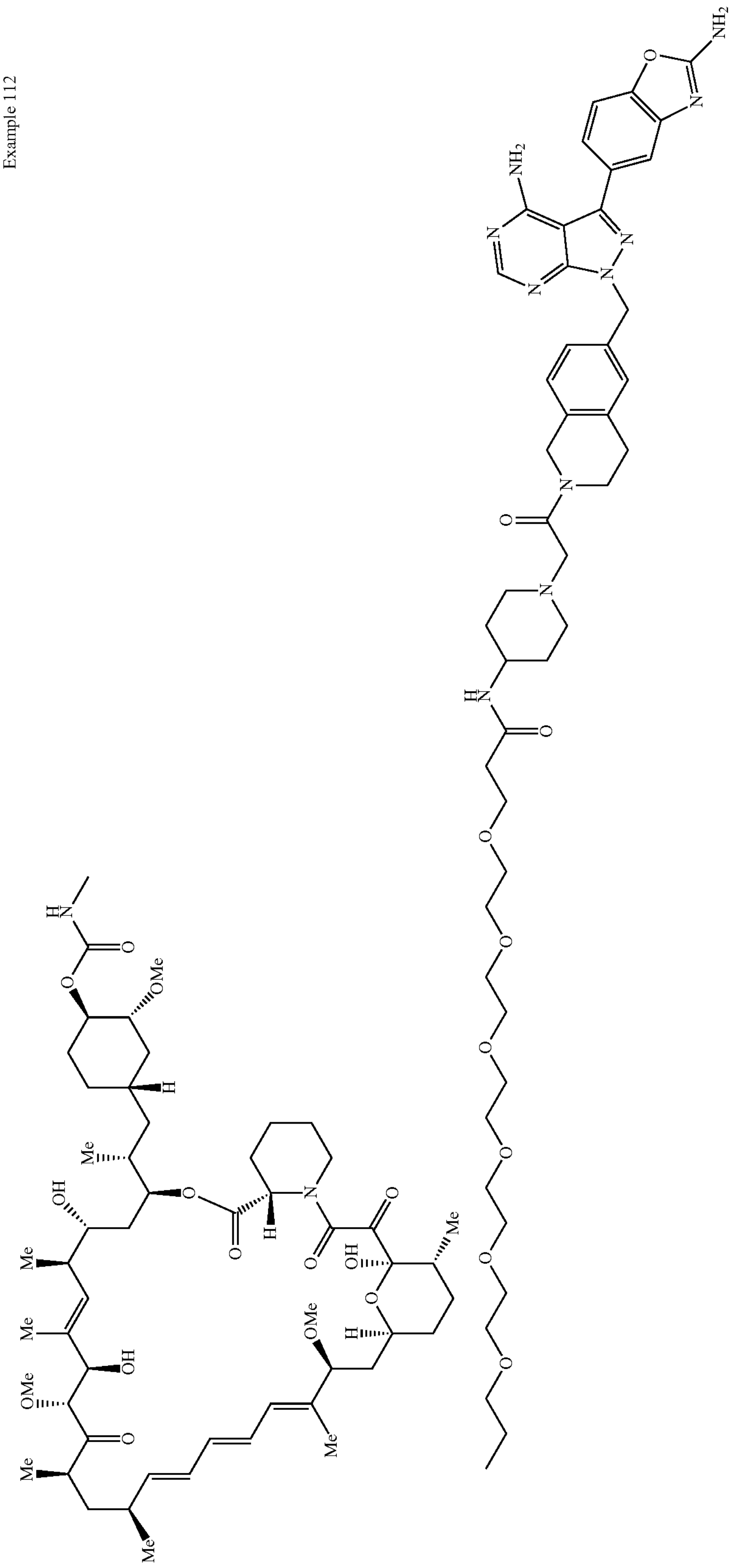

-continued
Example 113
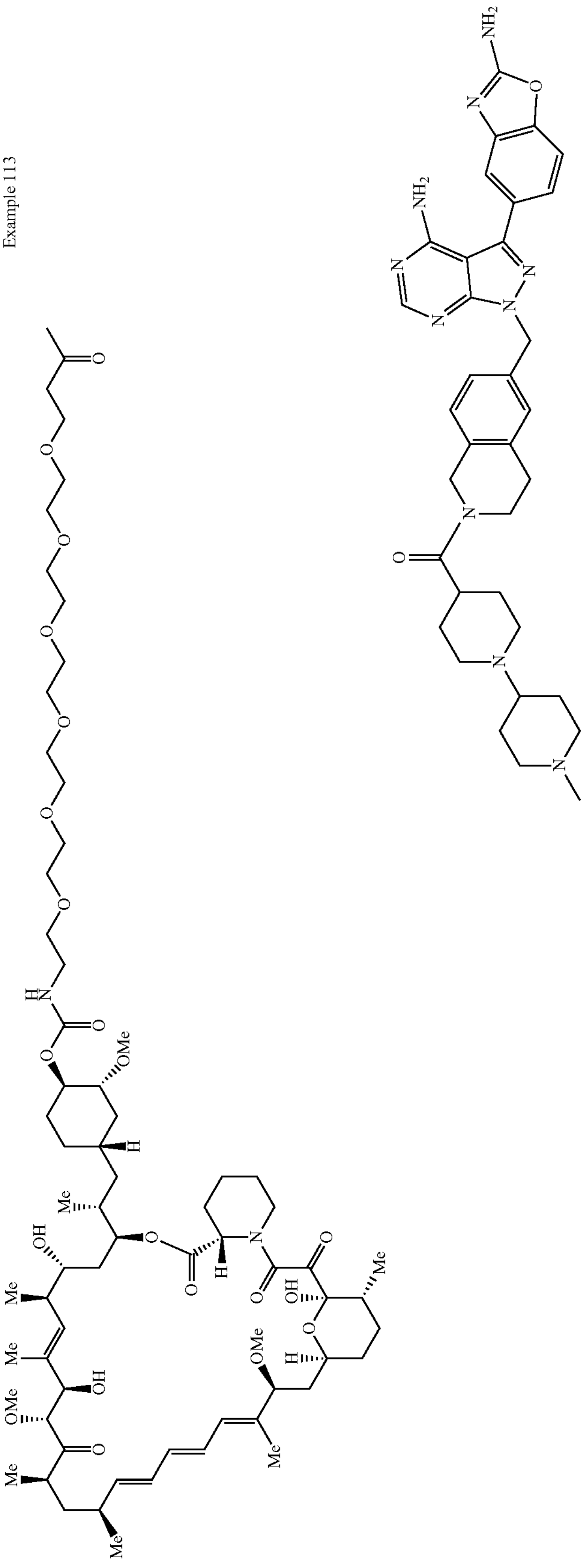

-continued
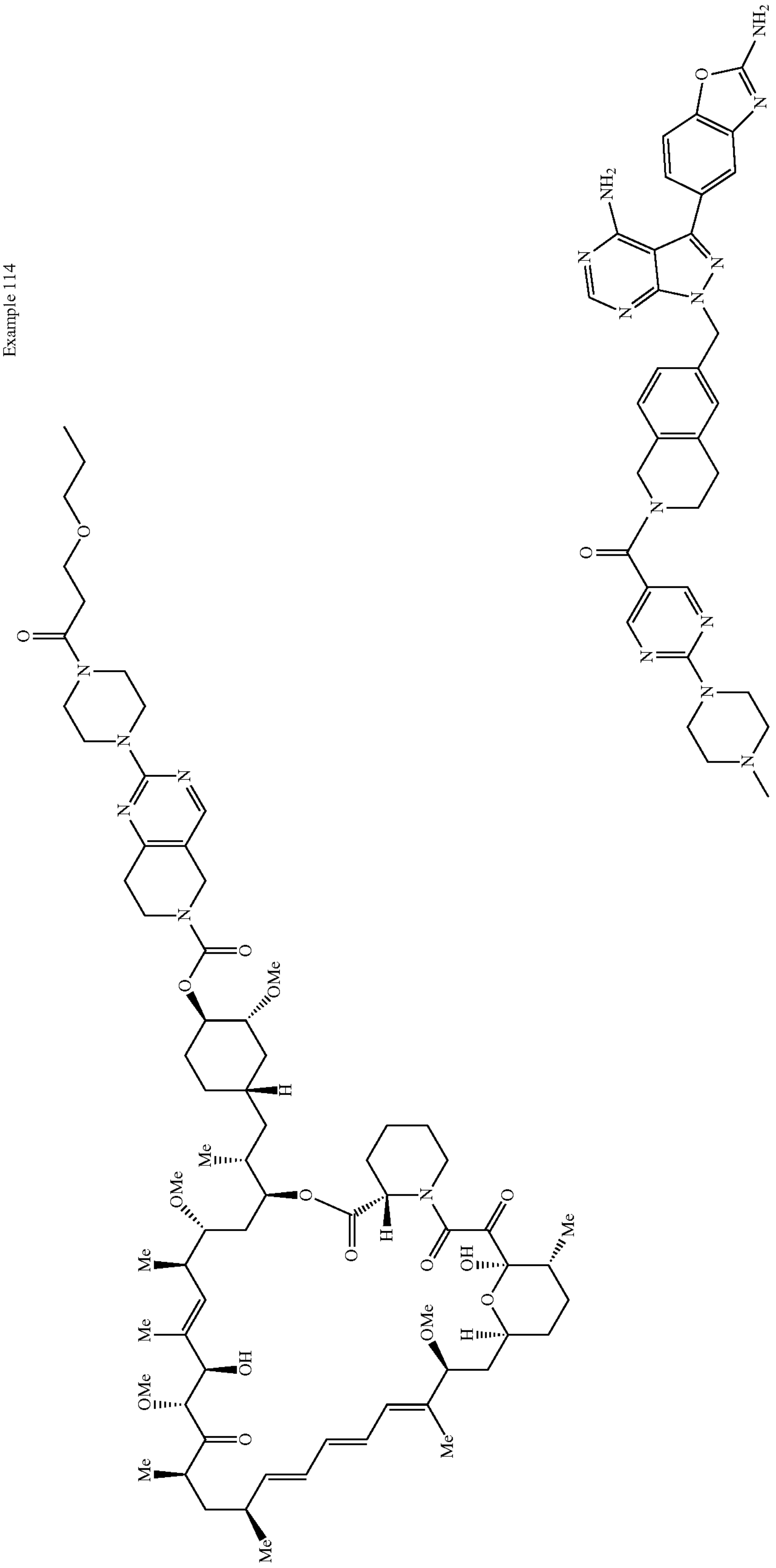
Example 114

-continued
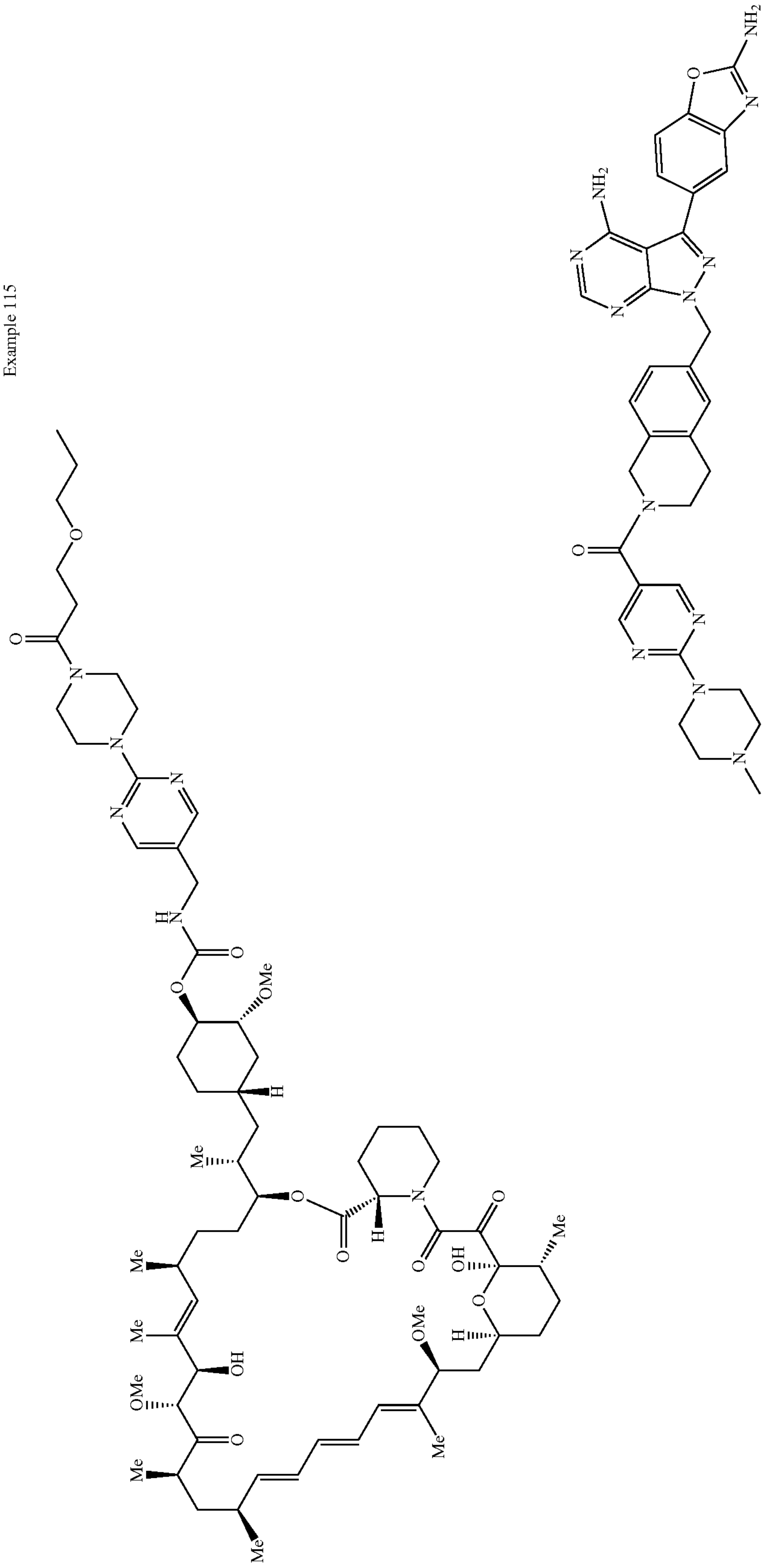
Example 115

-continued
Example 116
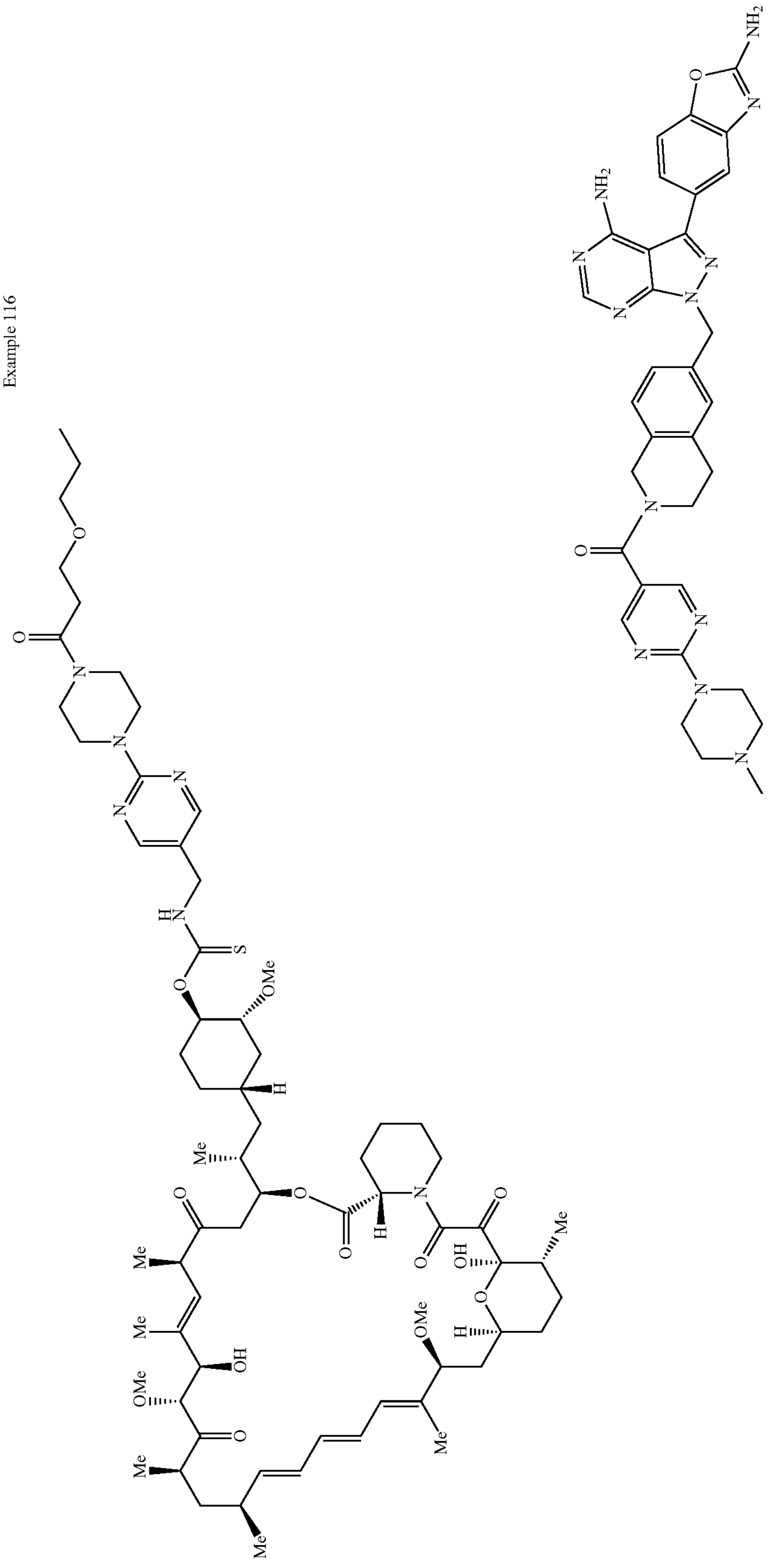

-continued
Example 117
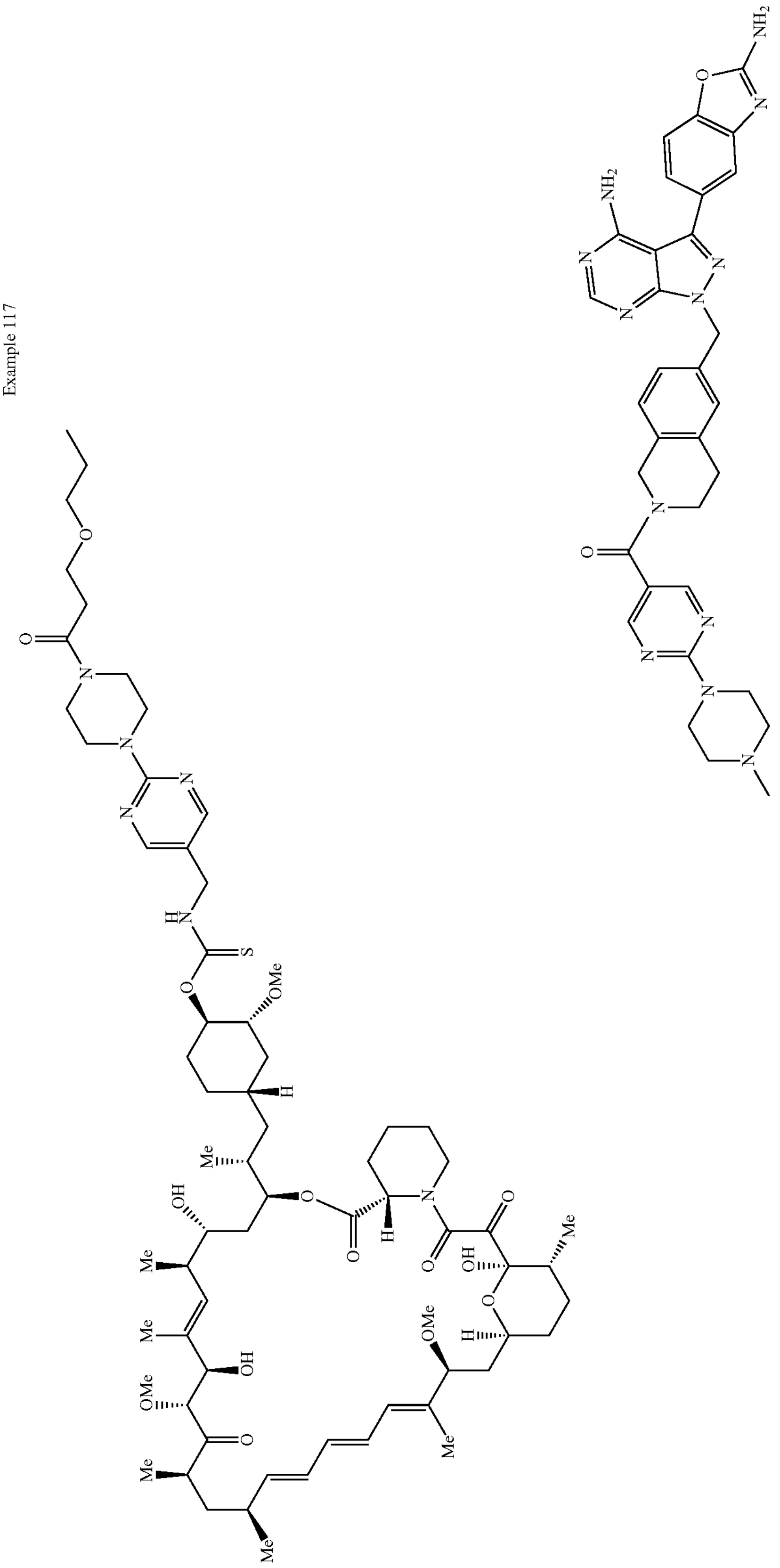

-continued
Example 118
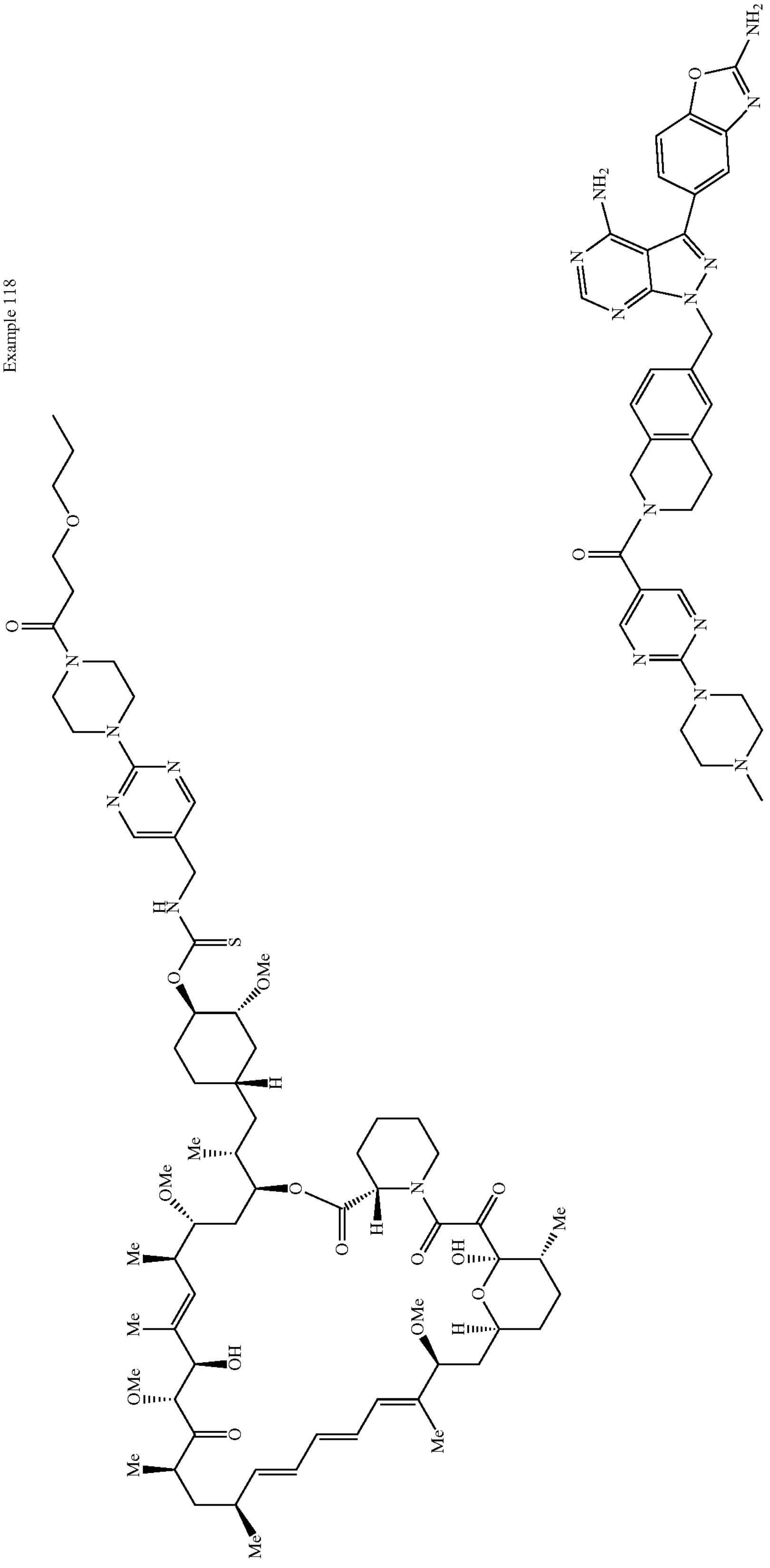

-continued
Example 119
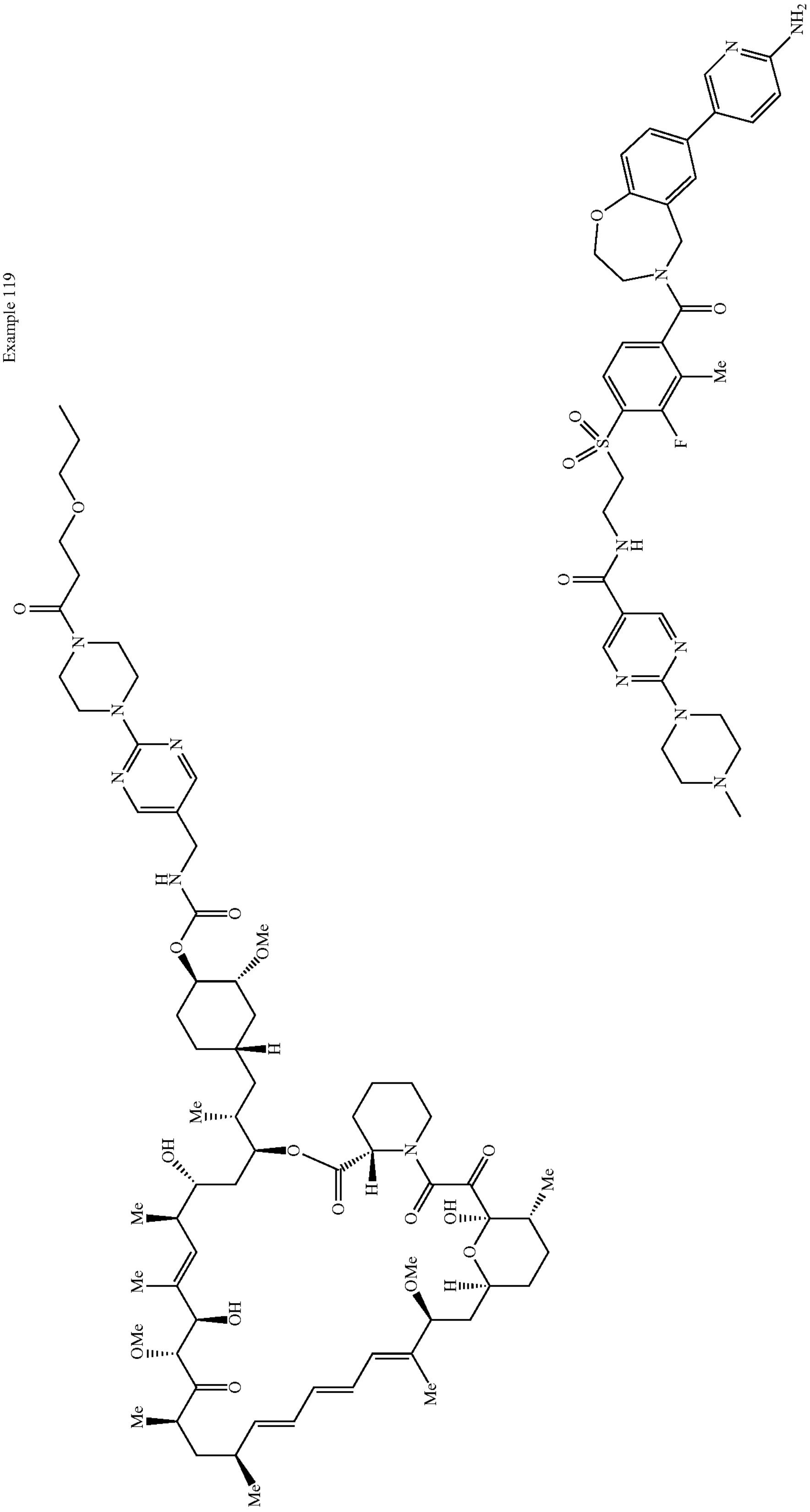

-continued
Example 120
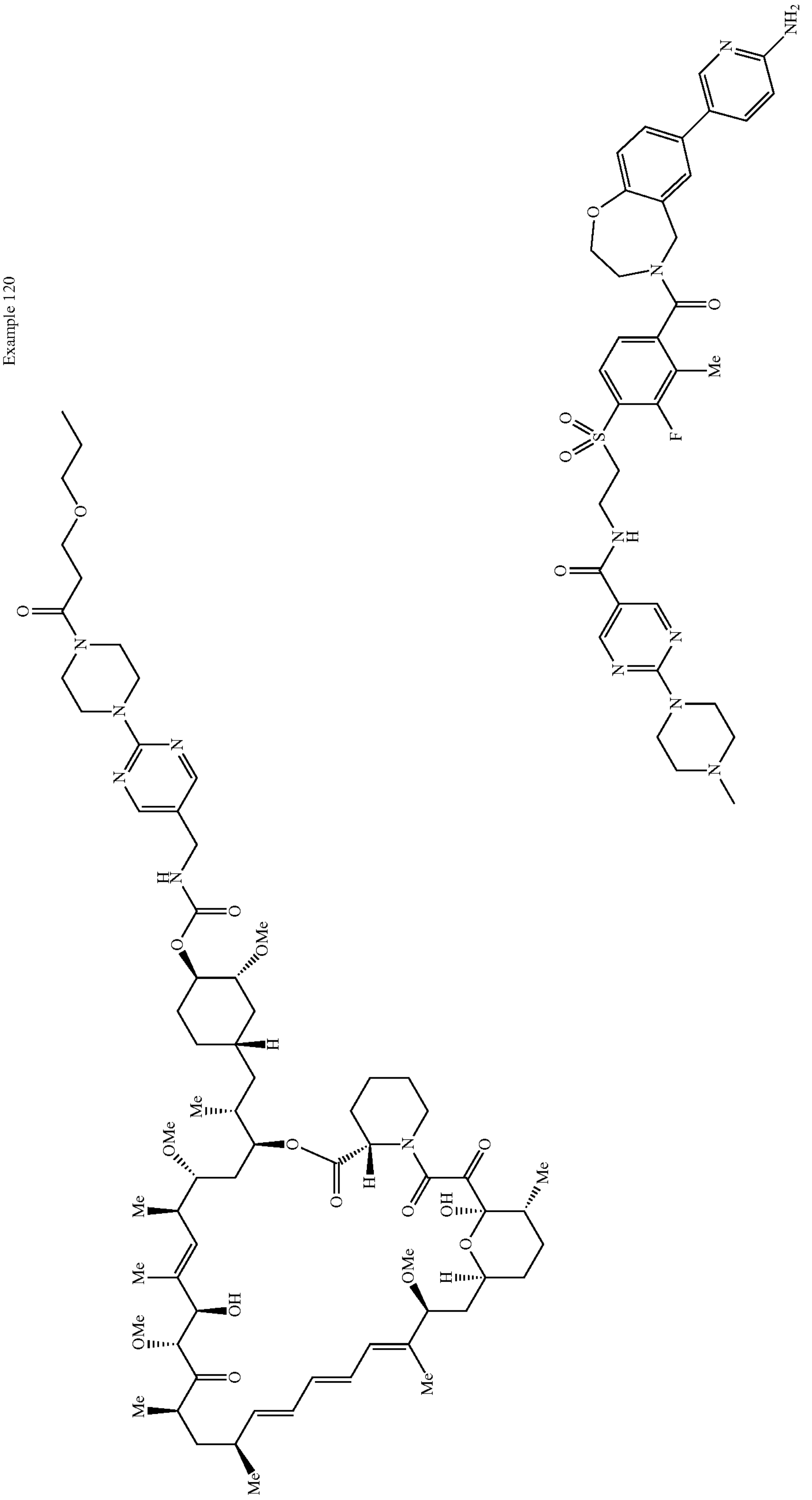

-continued
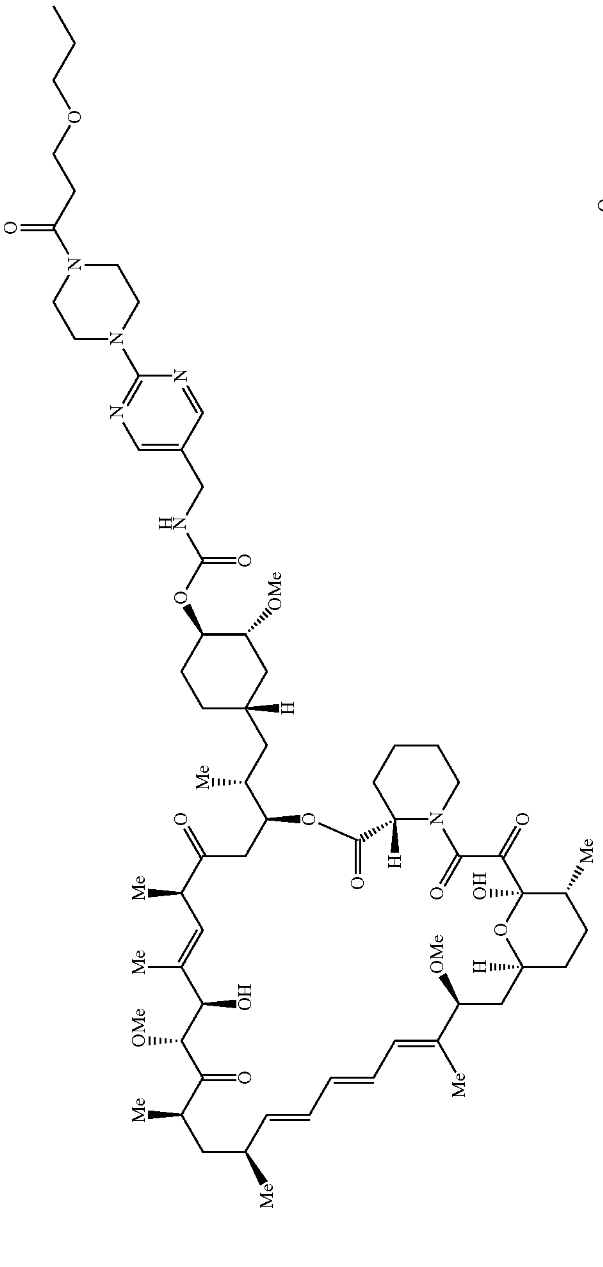
Example 121
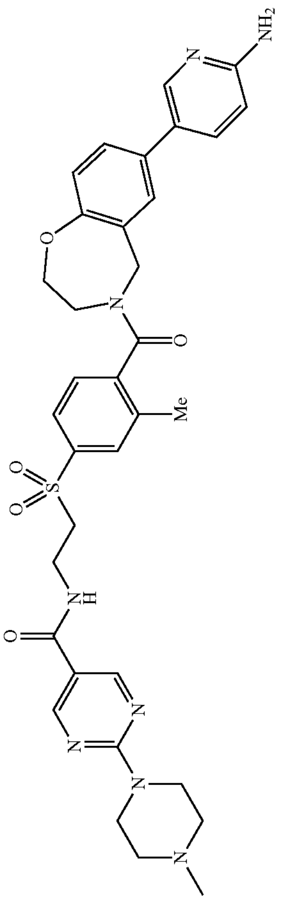

-continued
Example 122
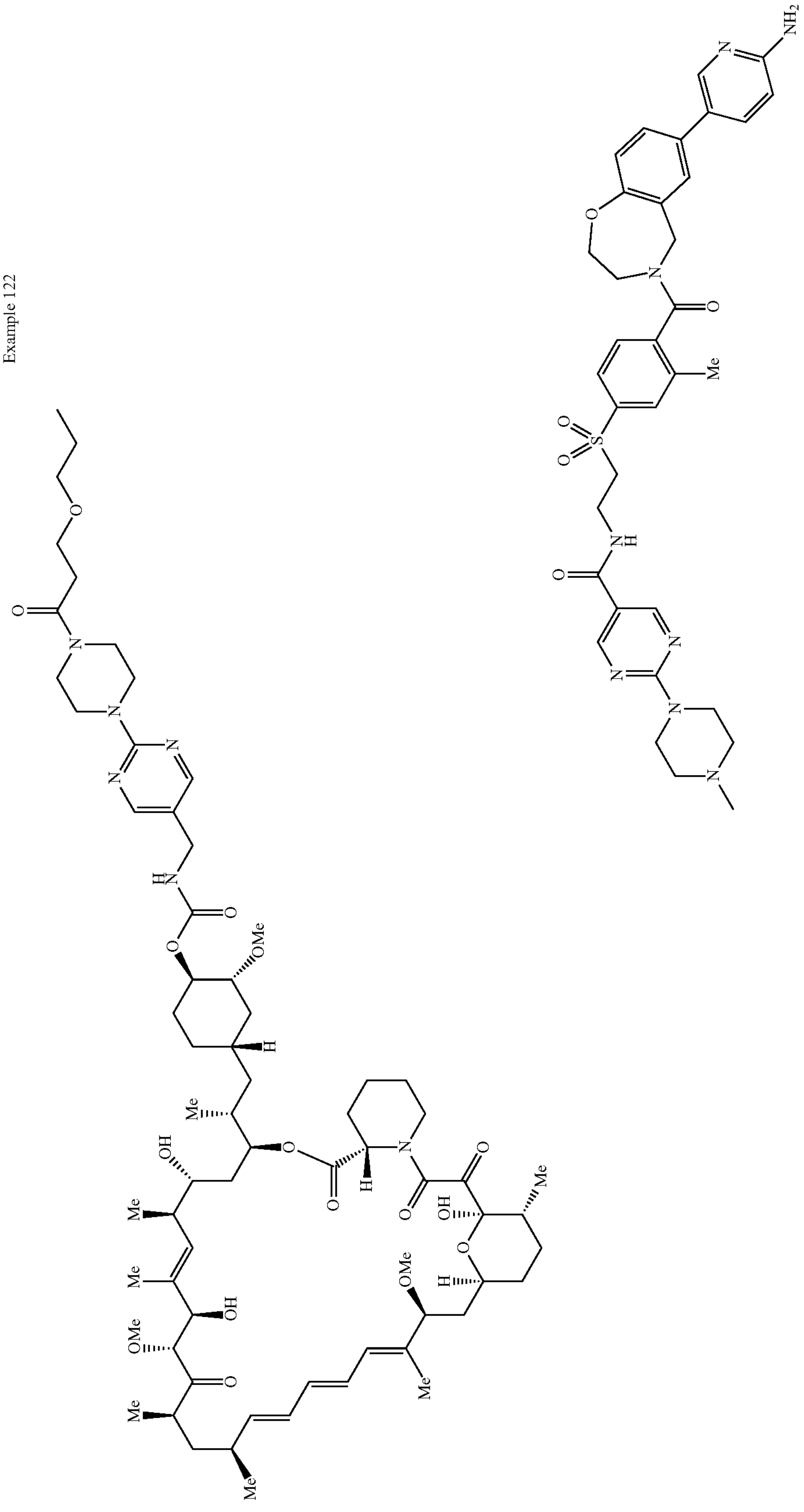

-continued
Example 123
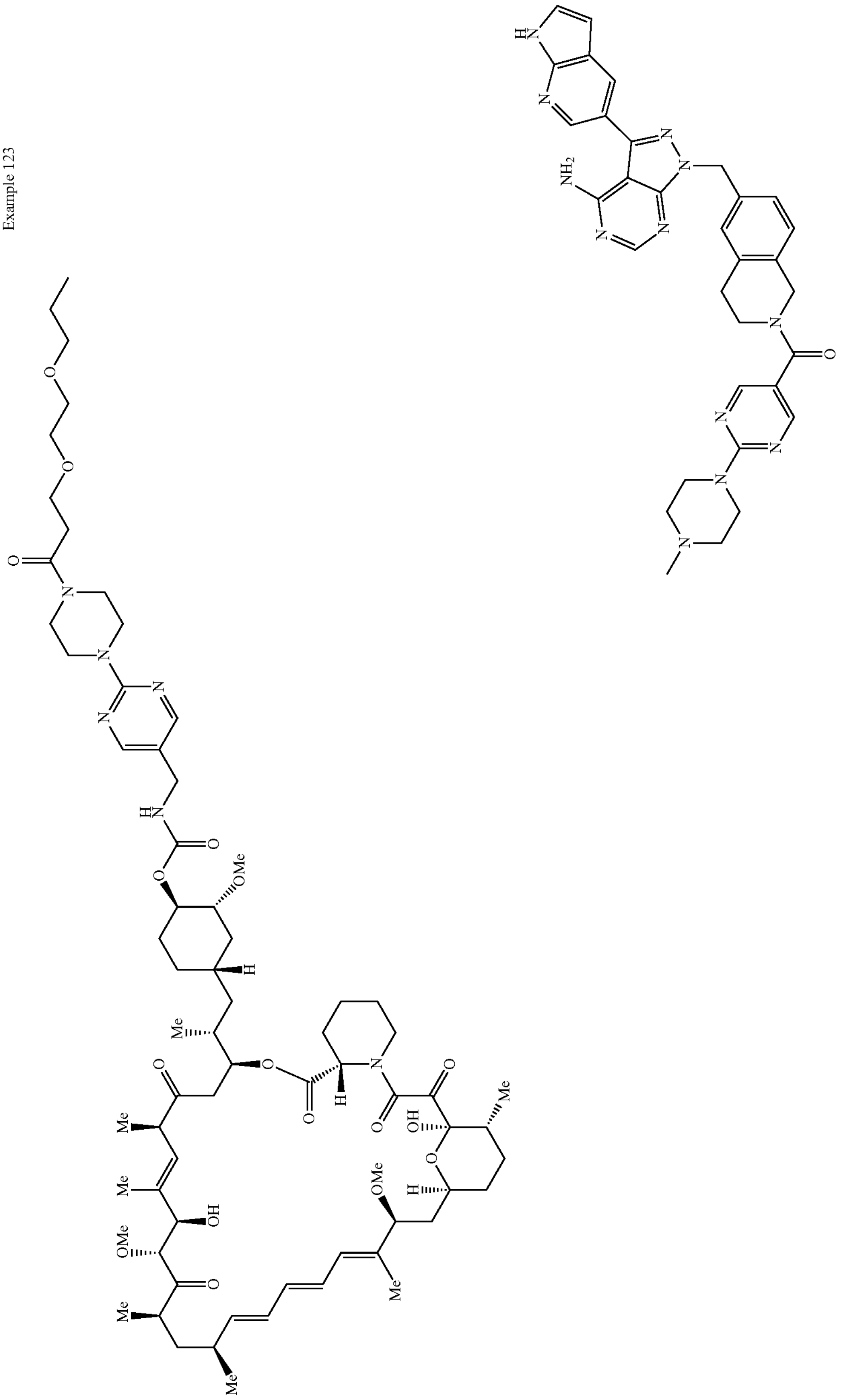

-continued
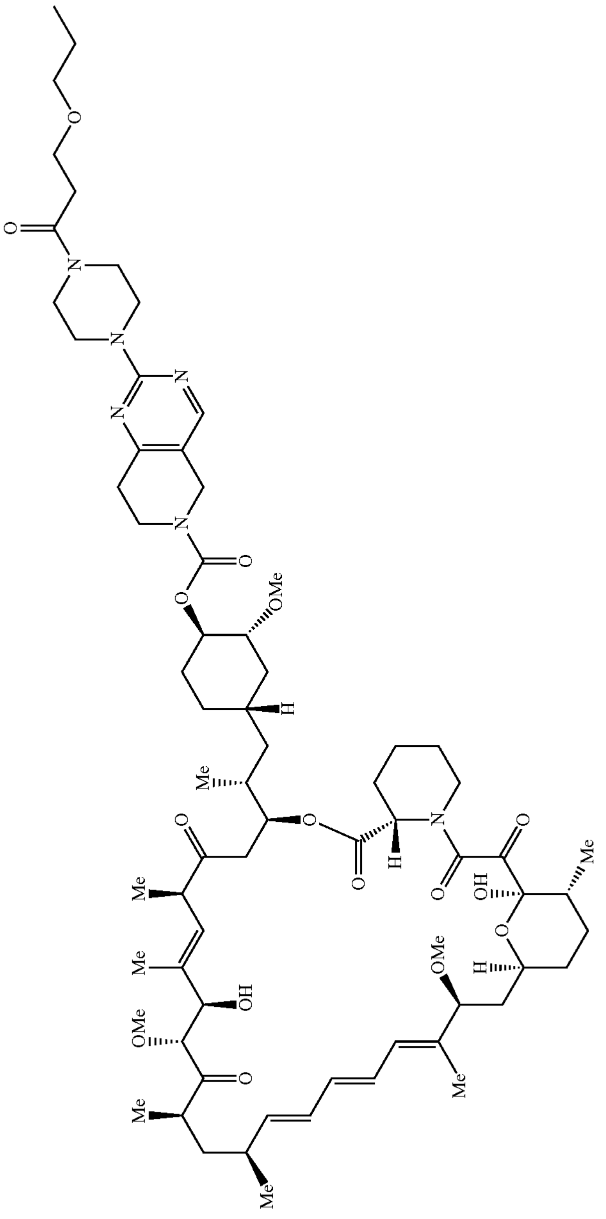
Example 124
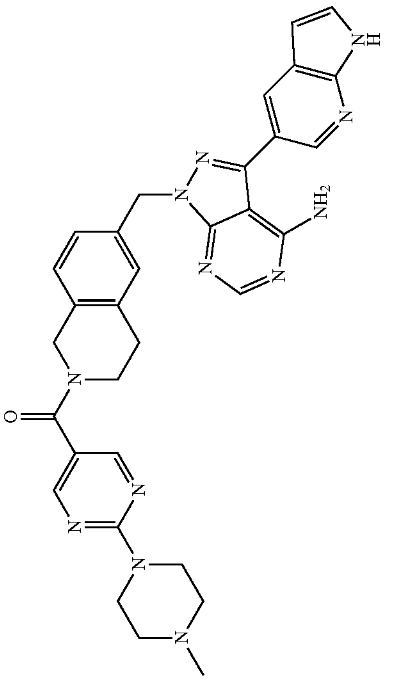

-continued
Example 125
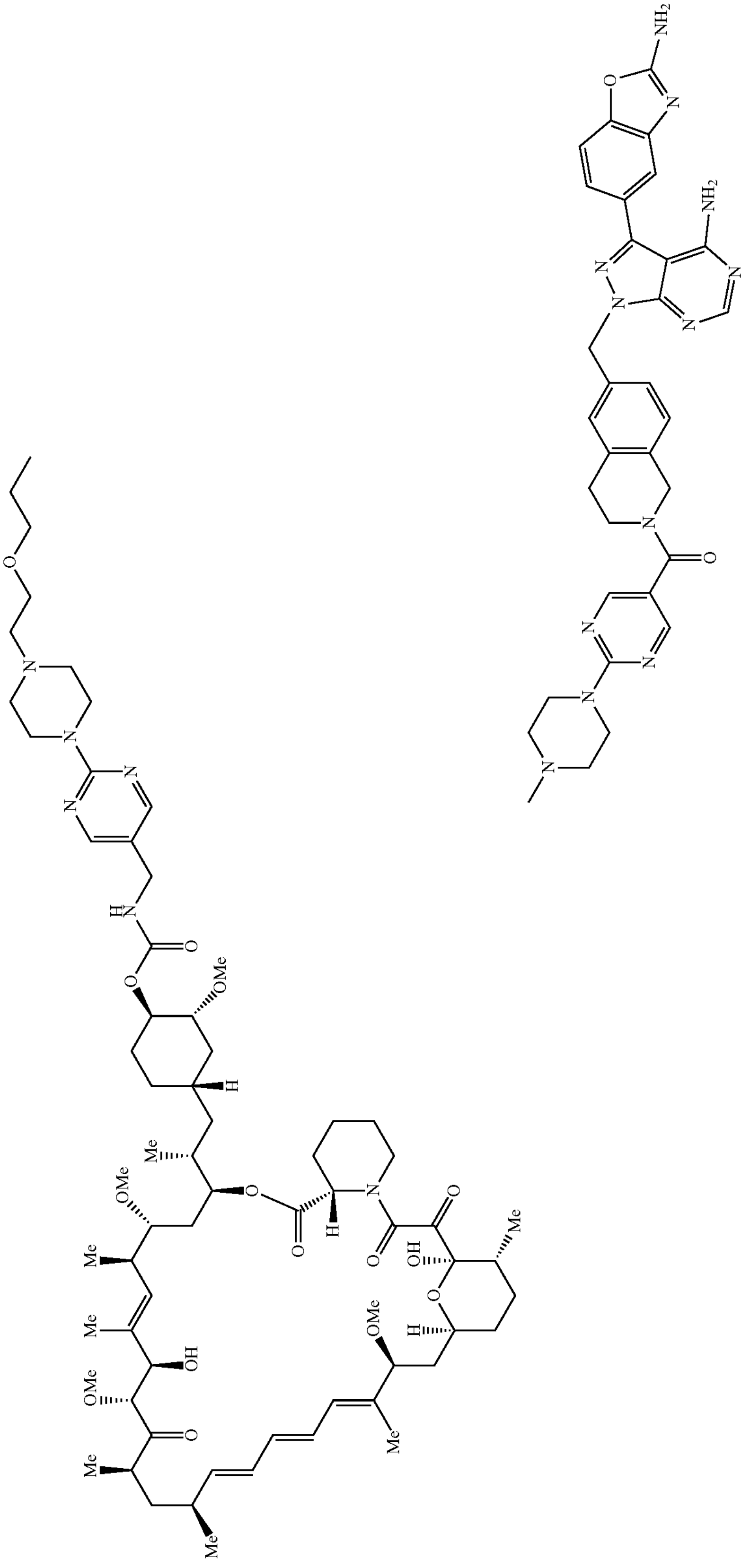

-continued
Example 126
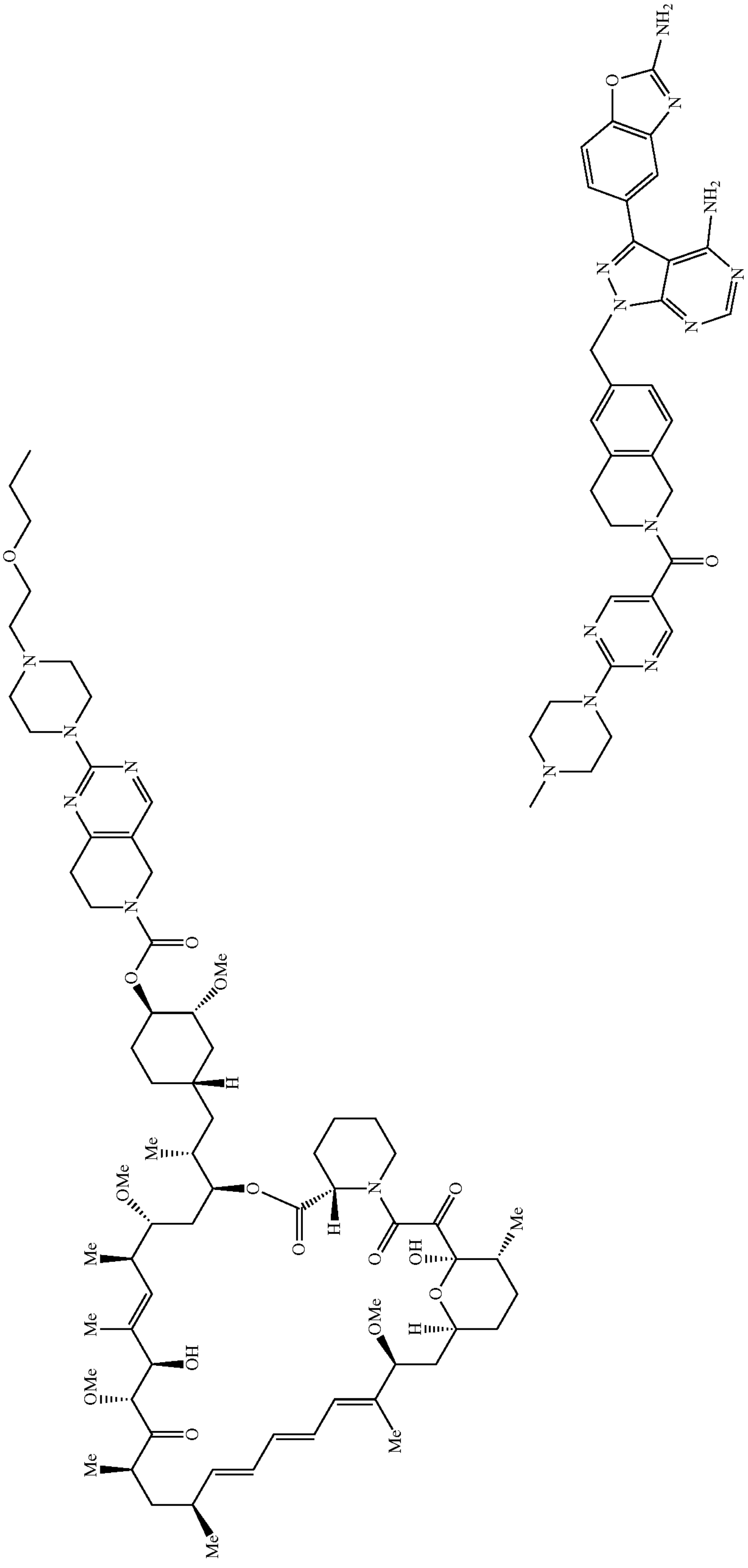

-continued
Example 127
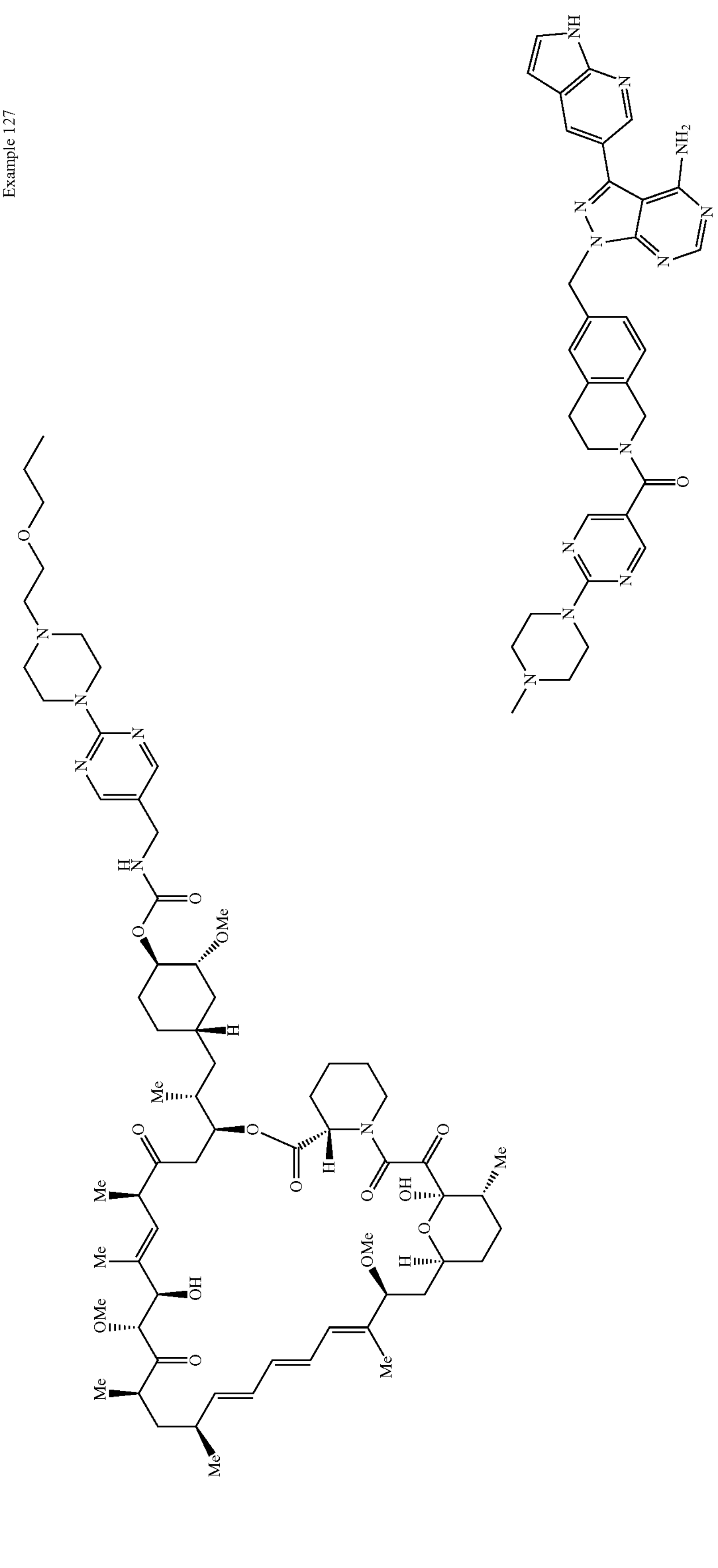

-continued
Example 128
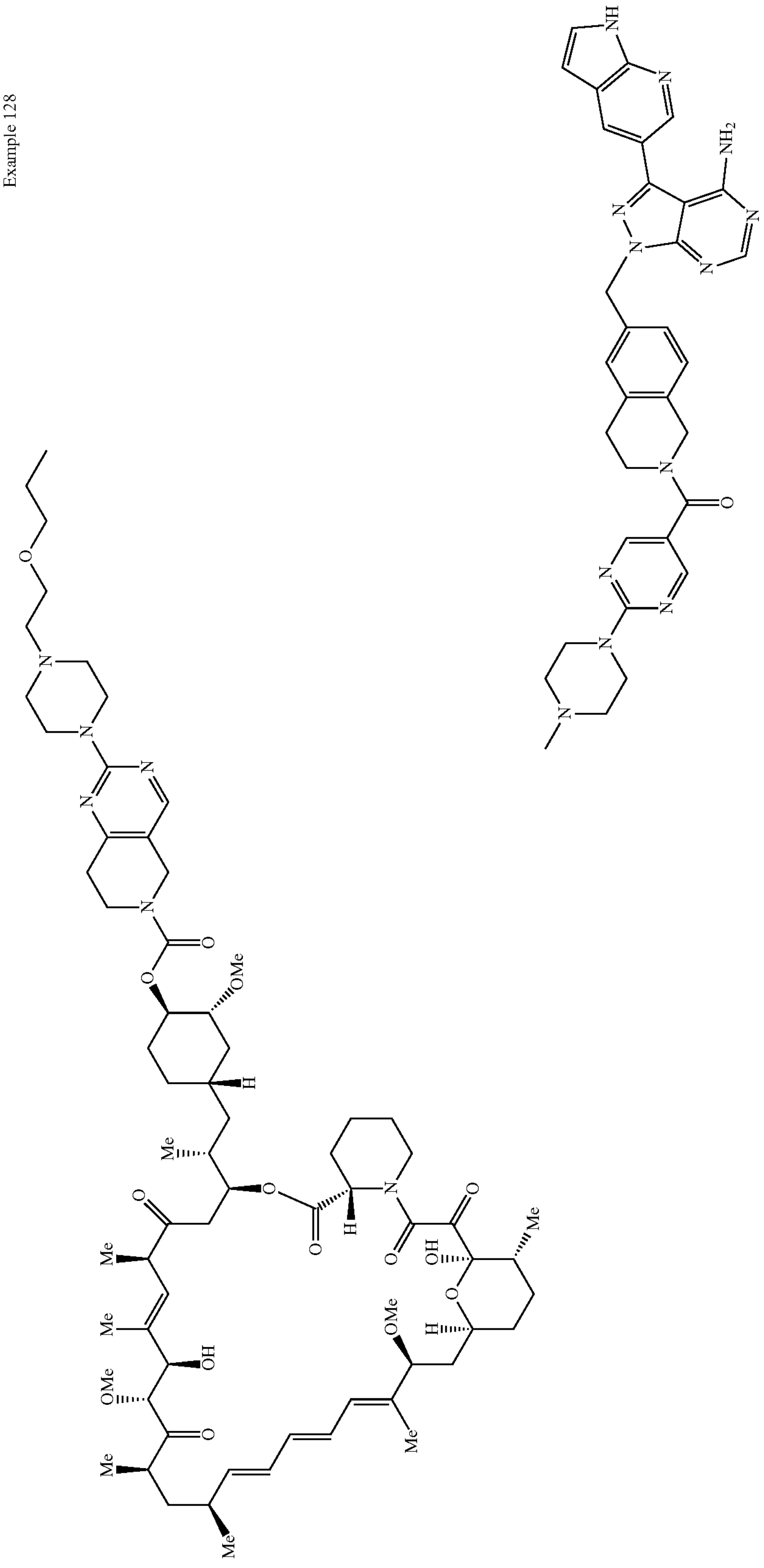

-continued
Example 129
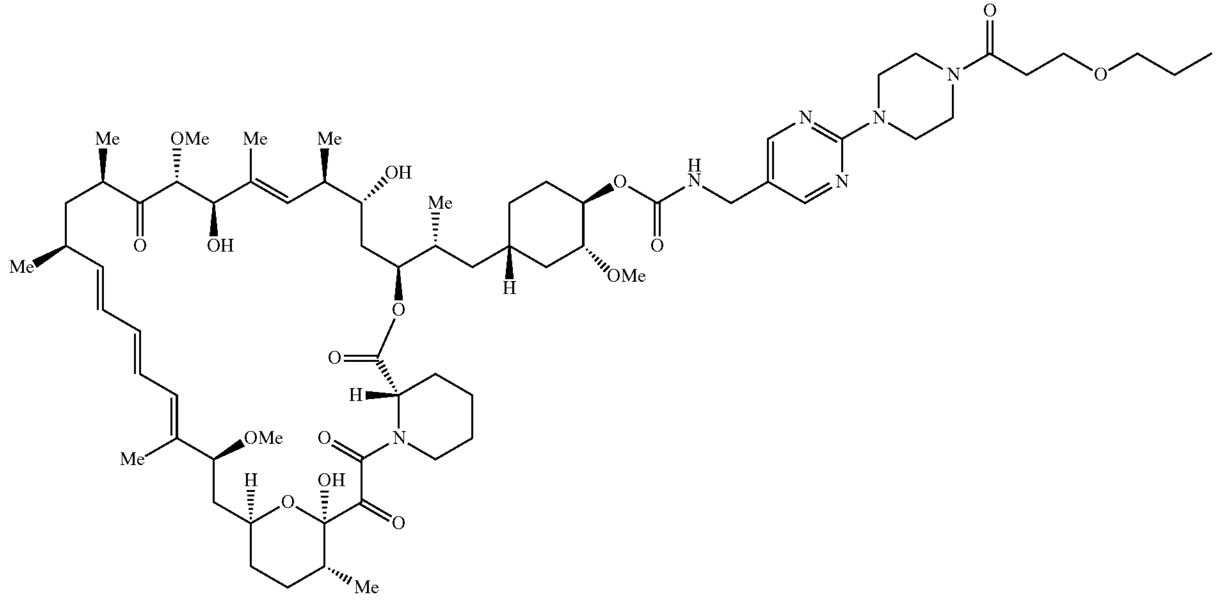
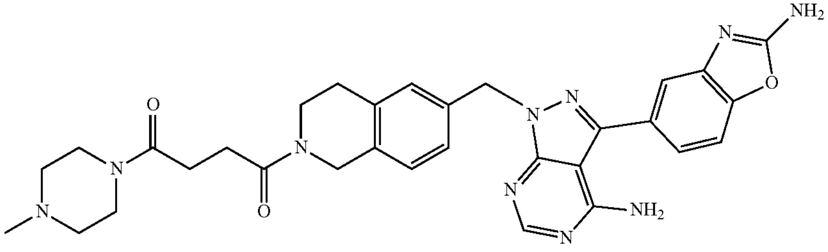

-continued
Example 130
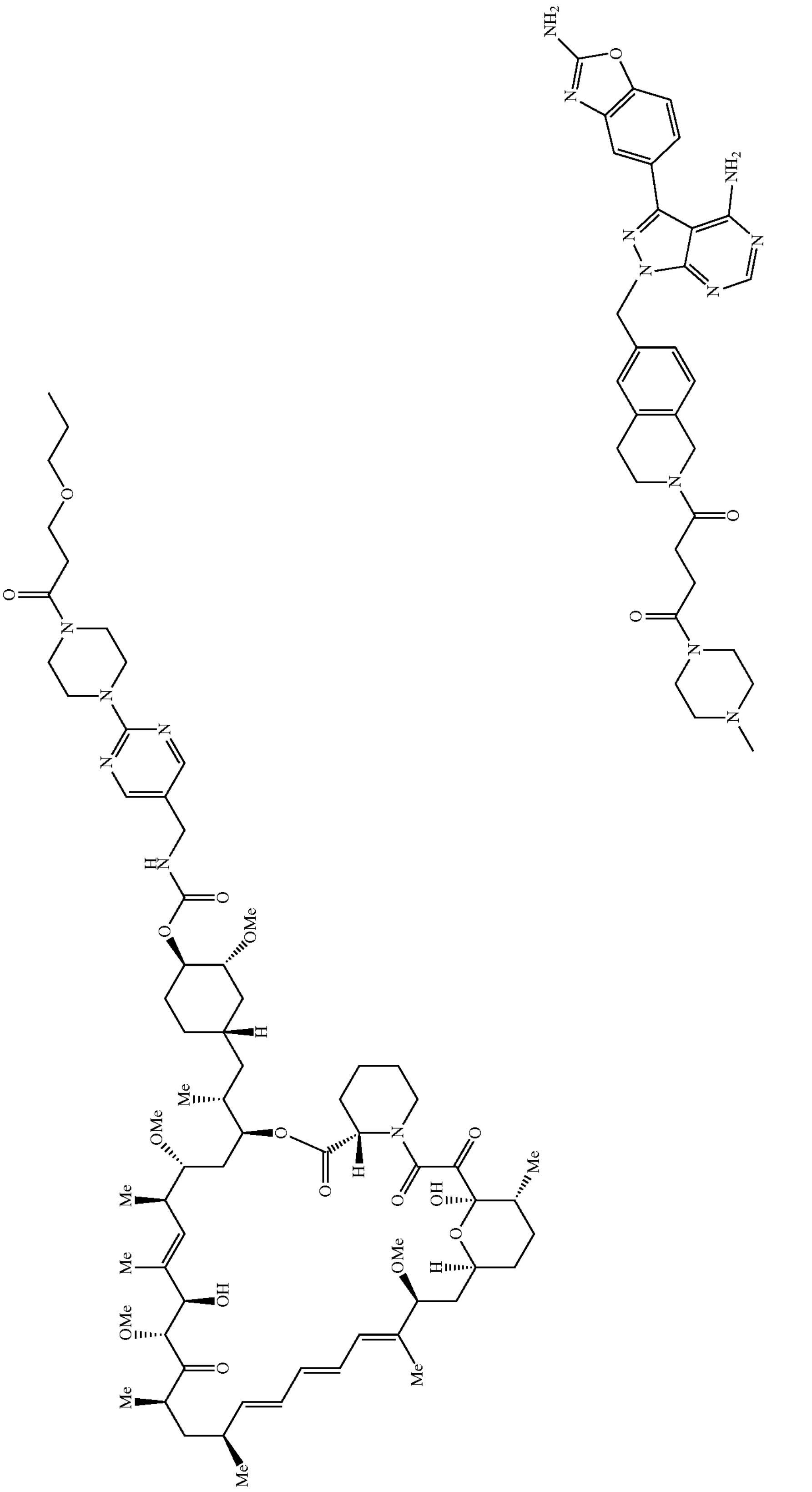

-continued
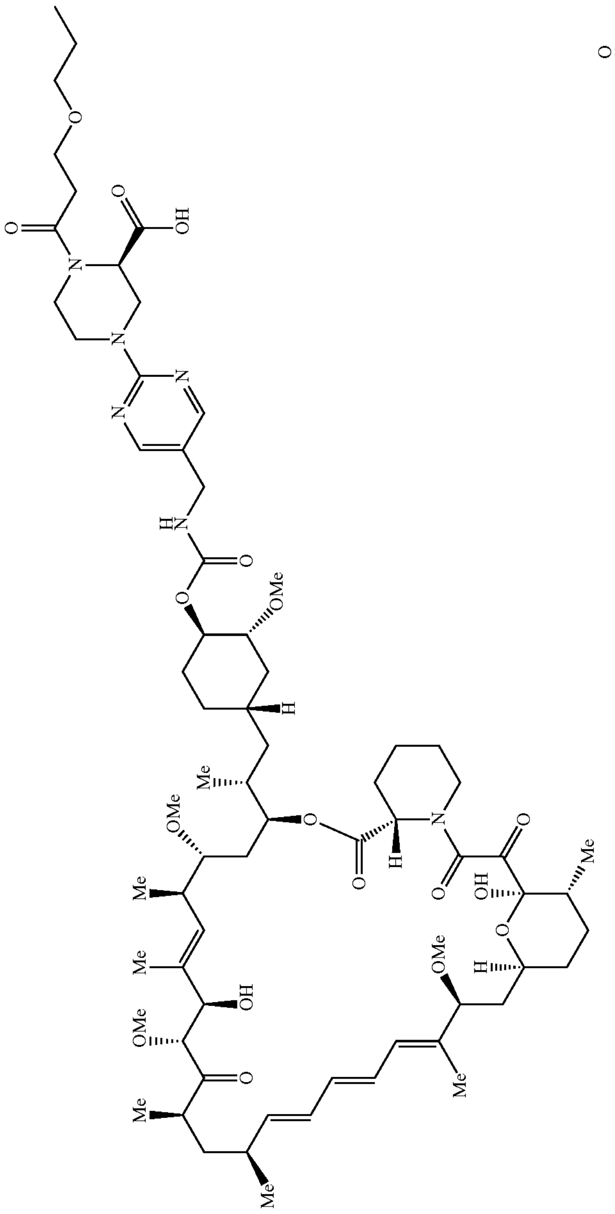
Example 131
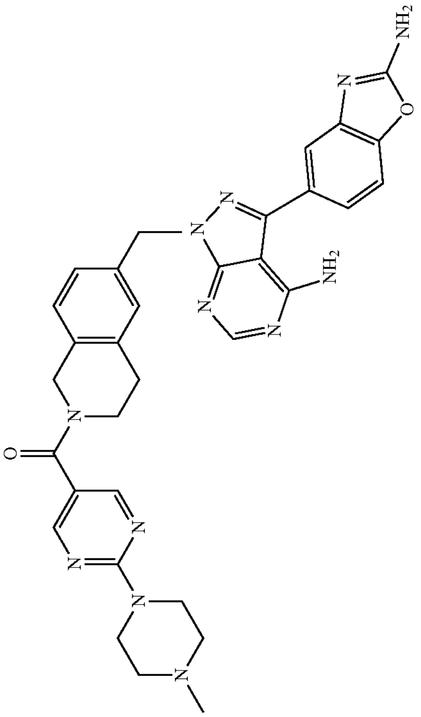

Example 132
-continued
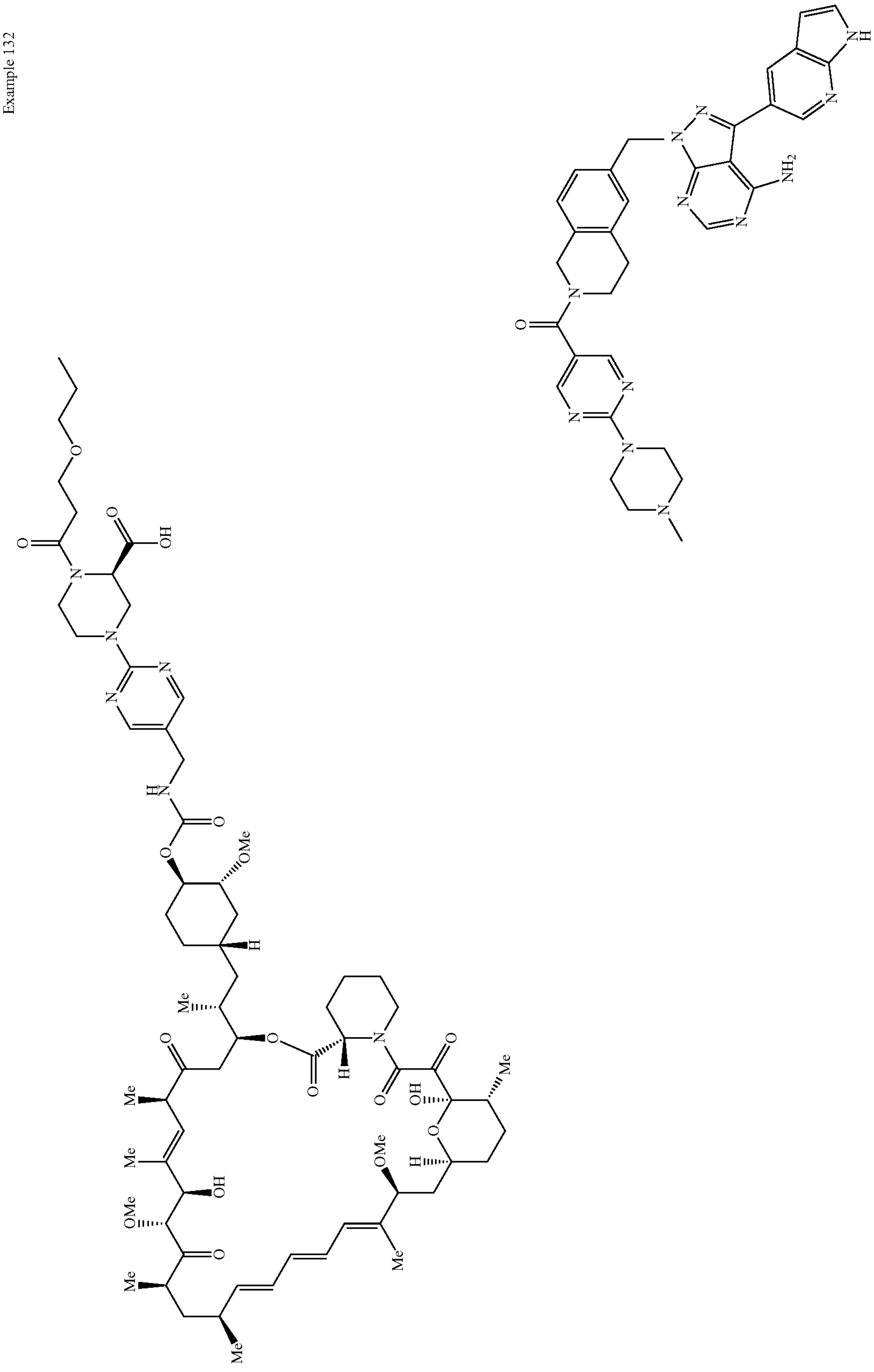

-continued
Example 133
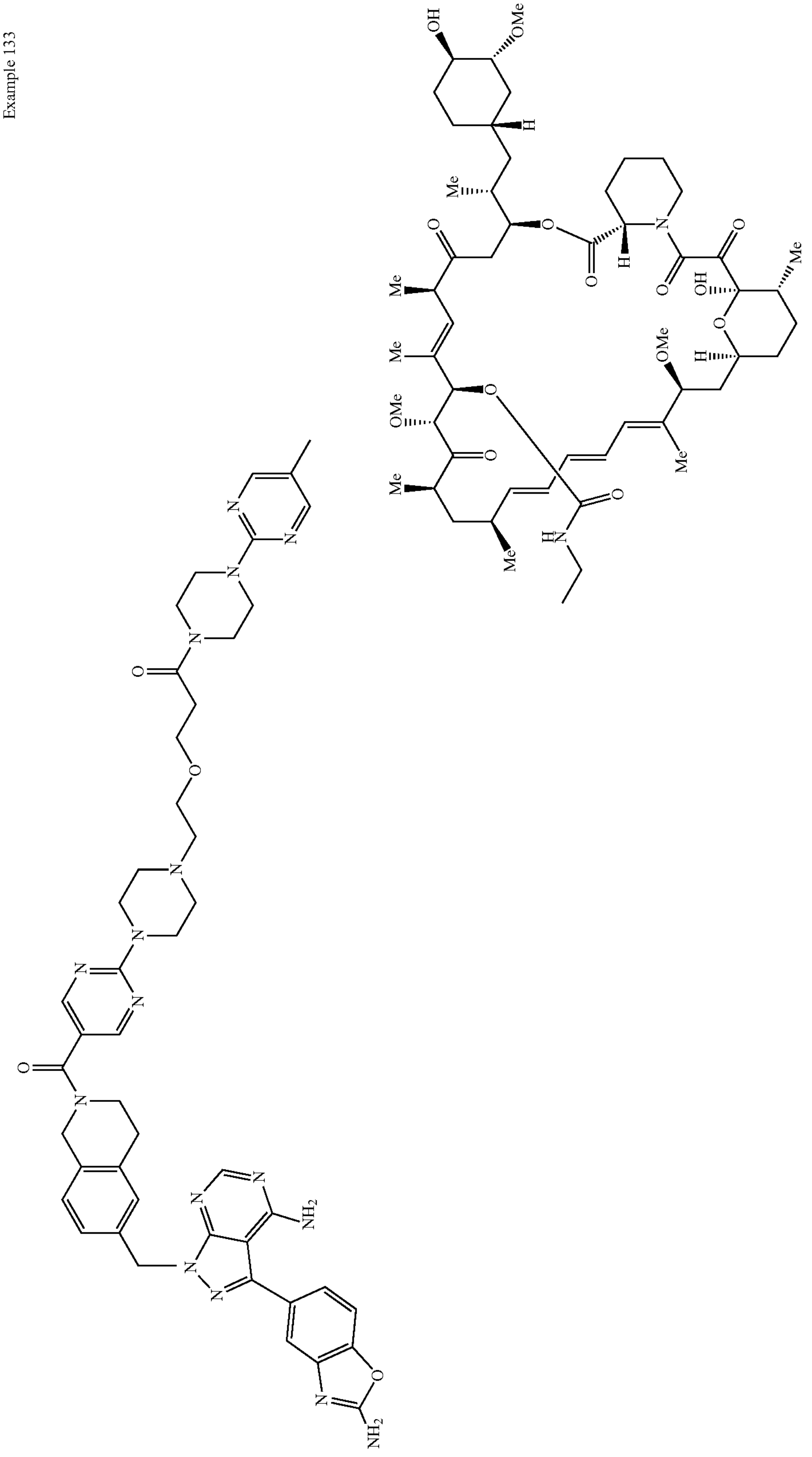

Example 134
-continued
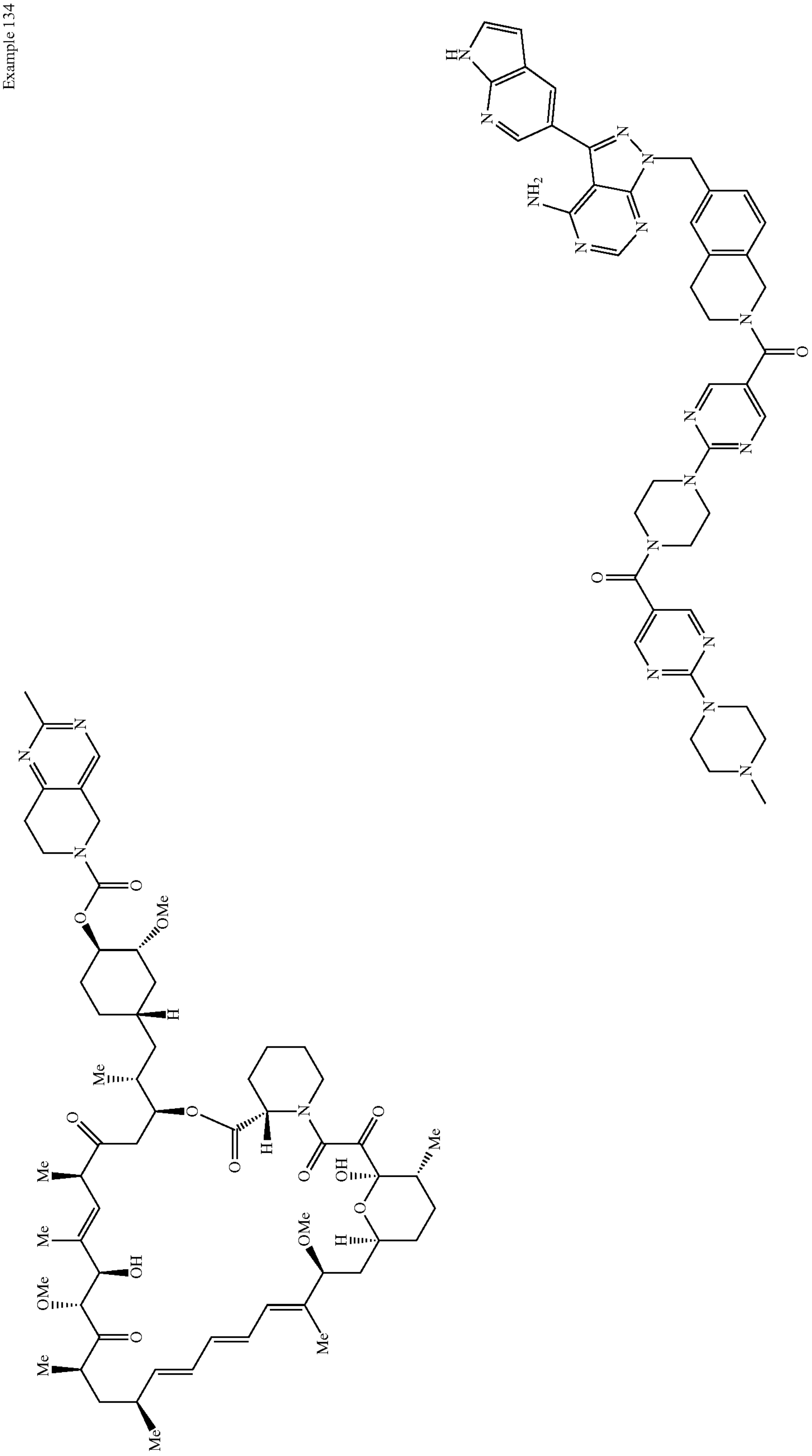

-continued
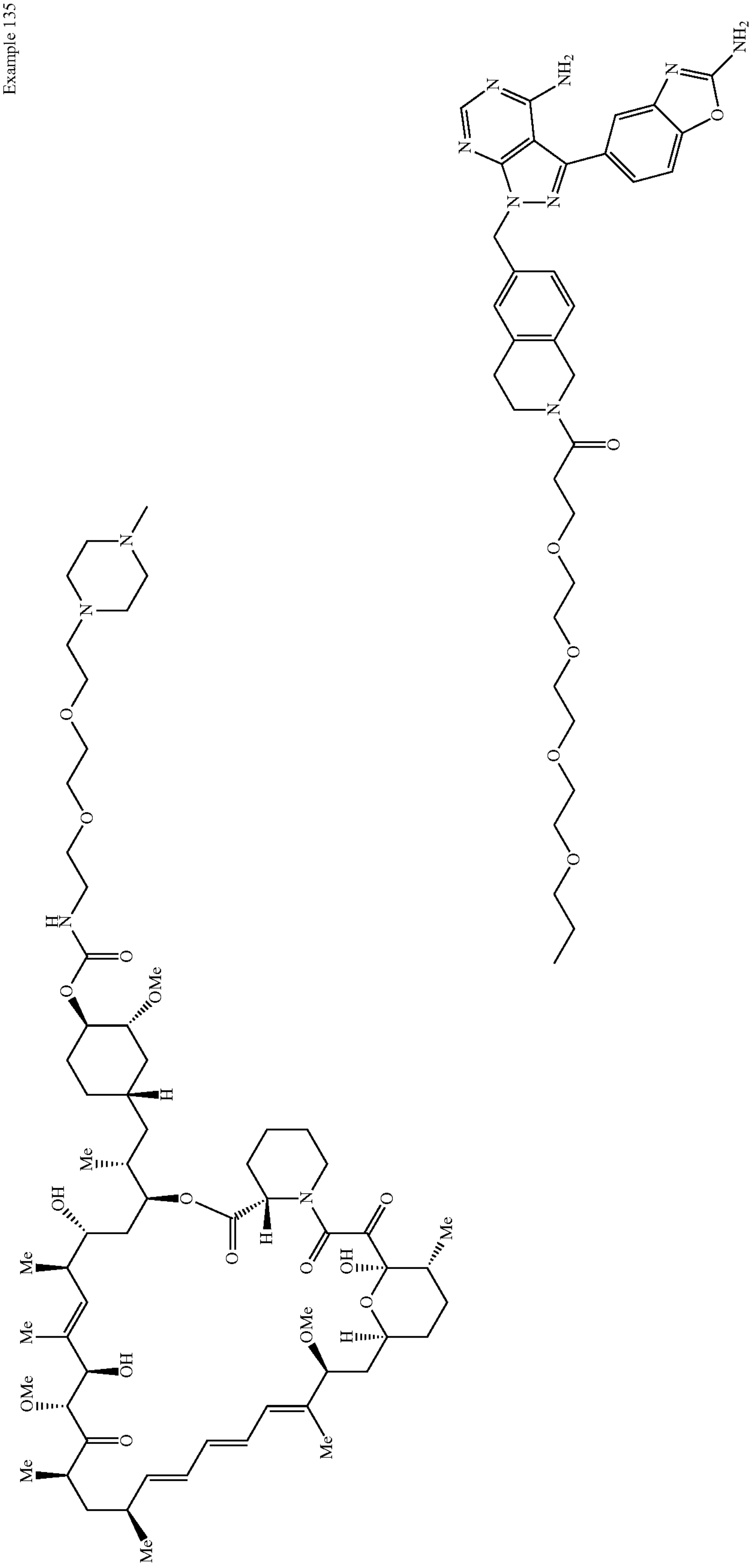
Example 135 or a pharmaceutically acceptable salt or tautomer thereof.

Embodiment II-74. A compound selected from the group consisting of:

Example 136
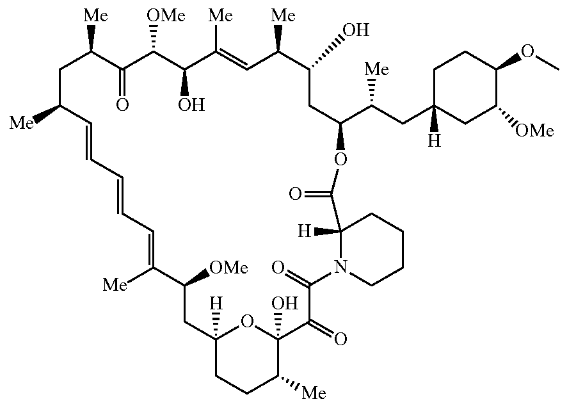
Example 137
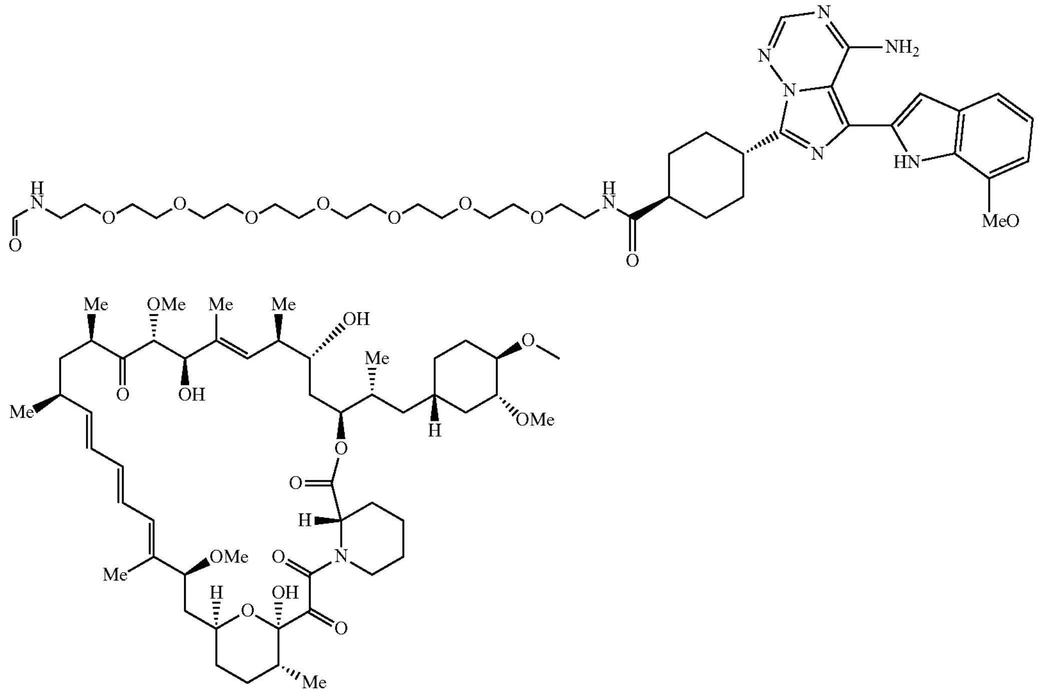

-continued
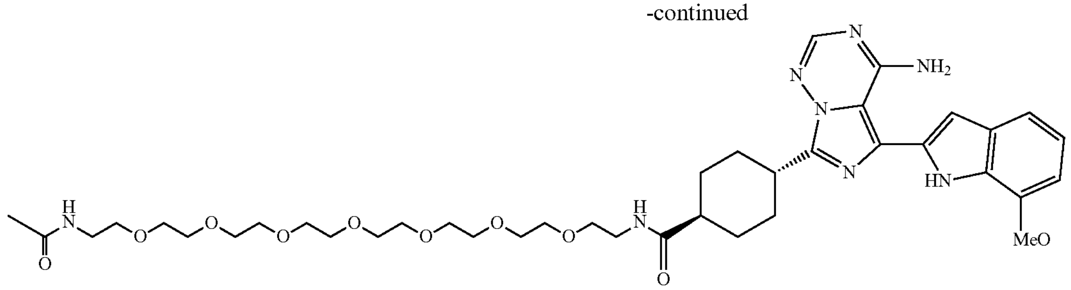
Example 138
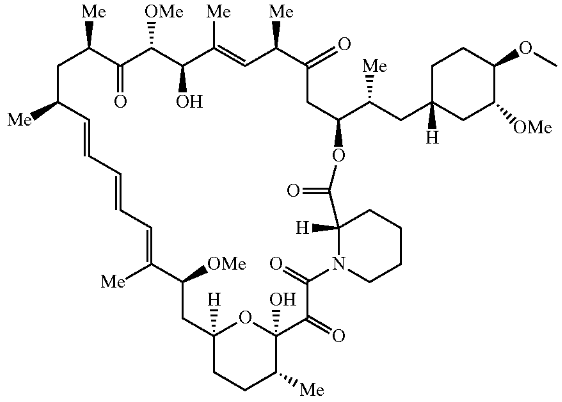
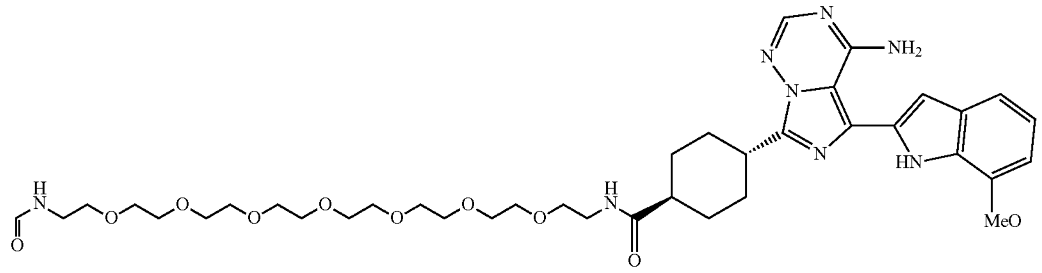

-continued
Example 139
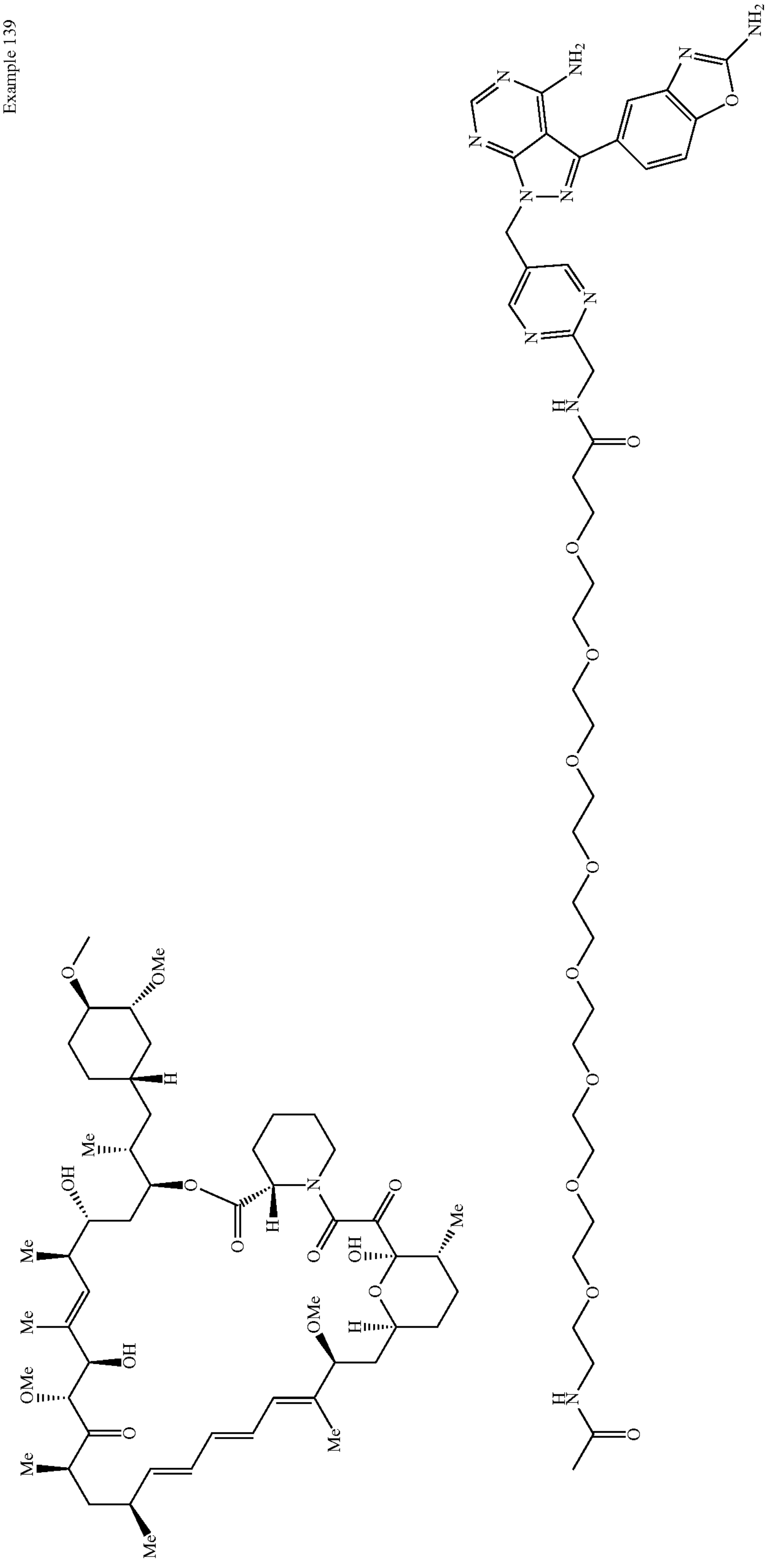

-continued
Example 140
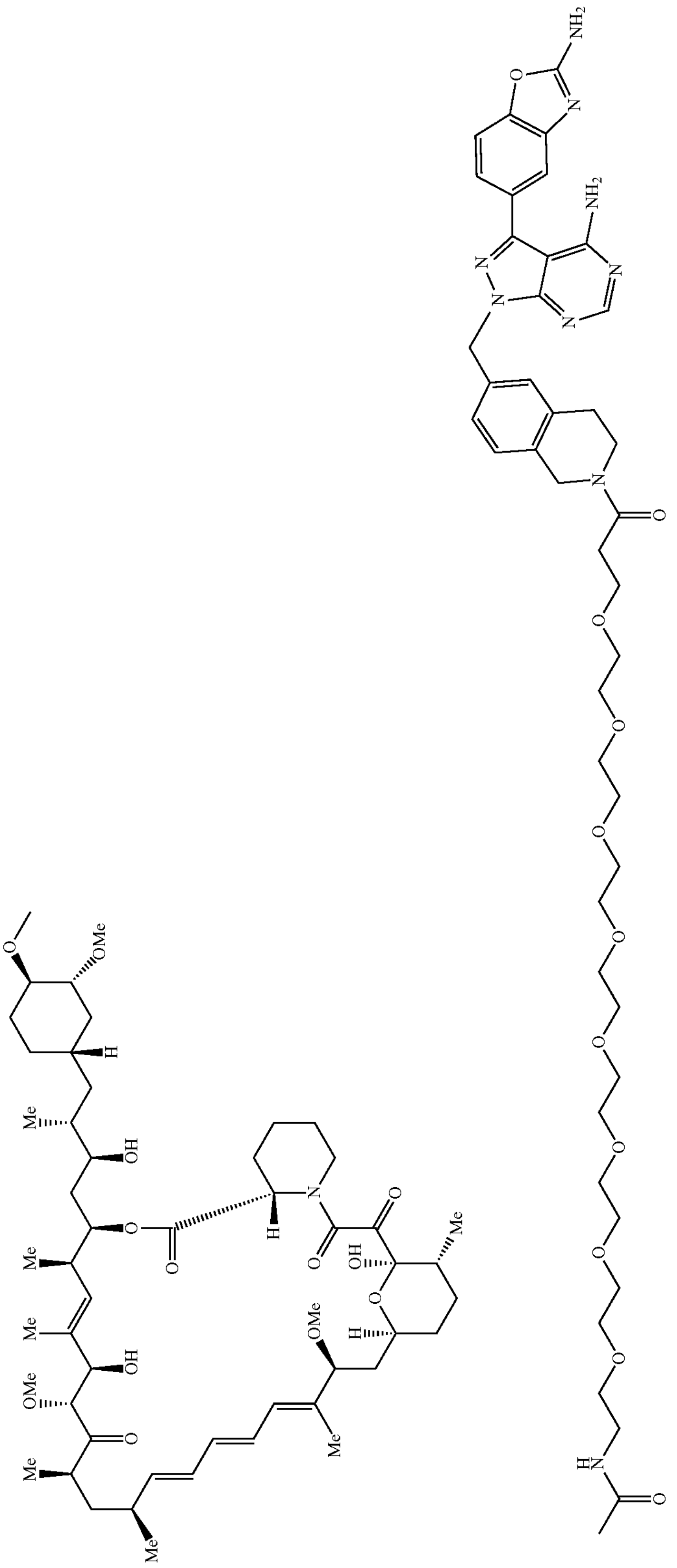

-continued
Example 141
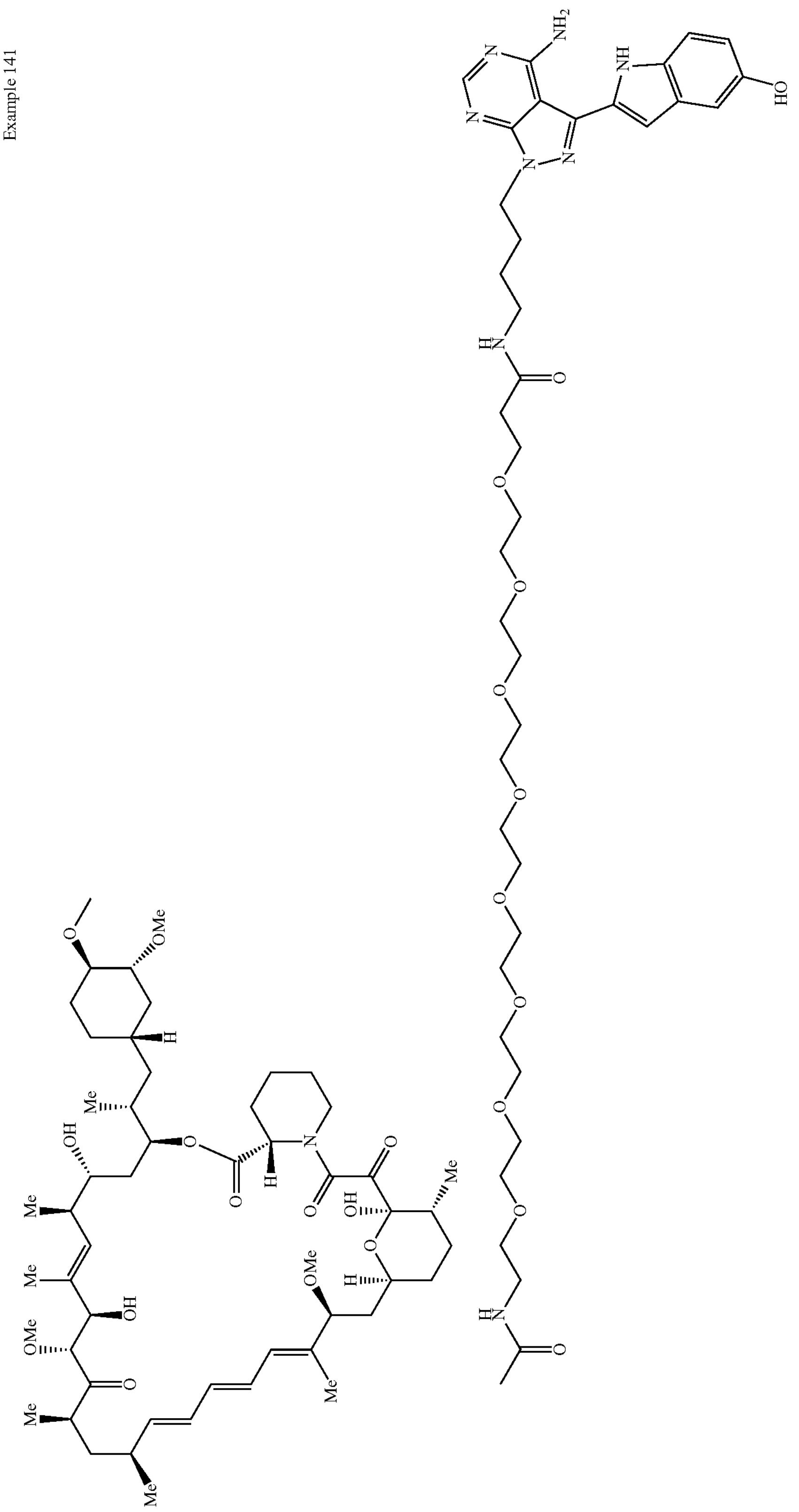

-continued
Example 142
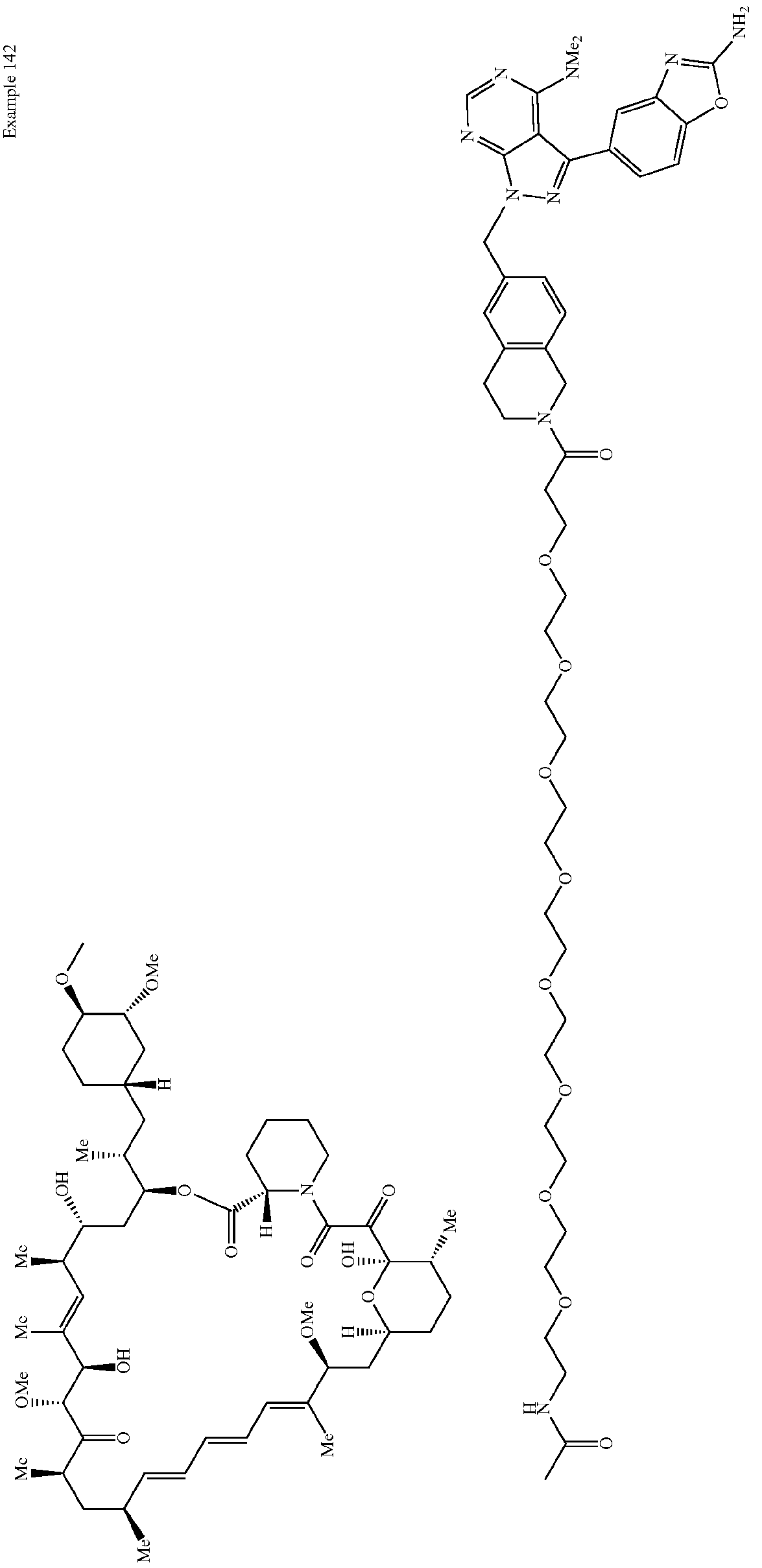

-continued
Example 143
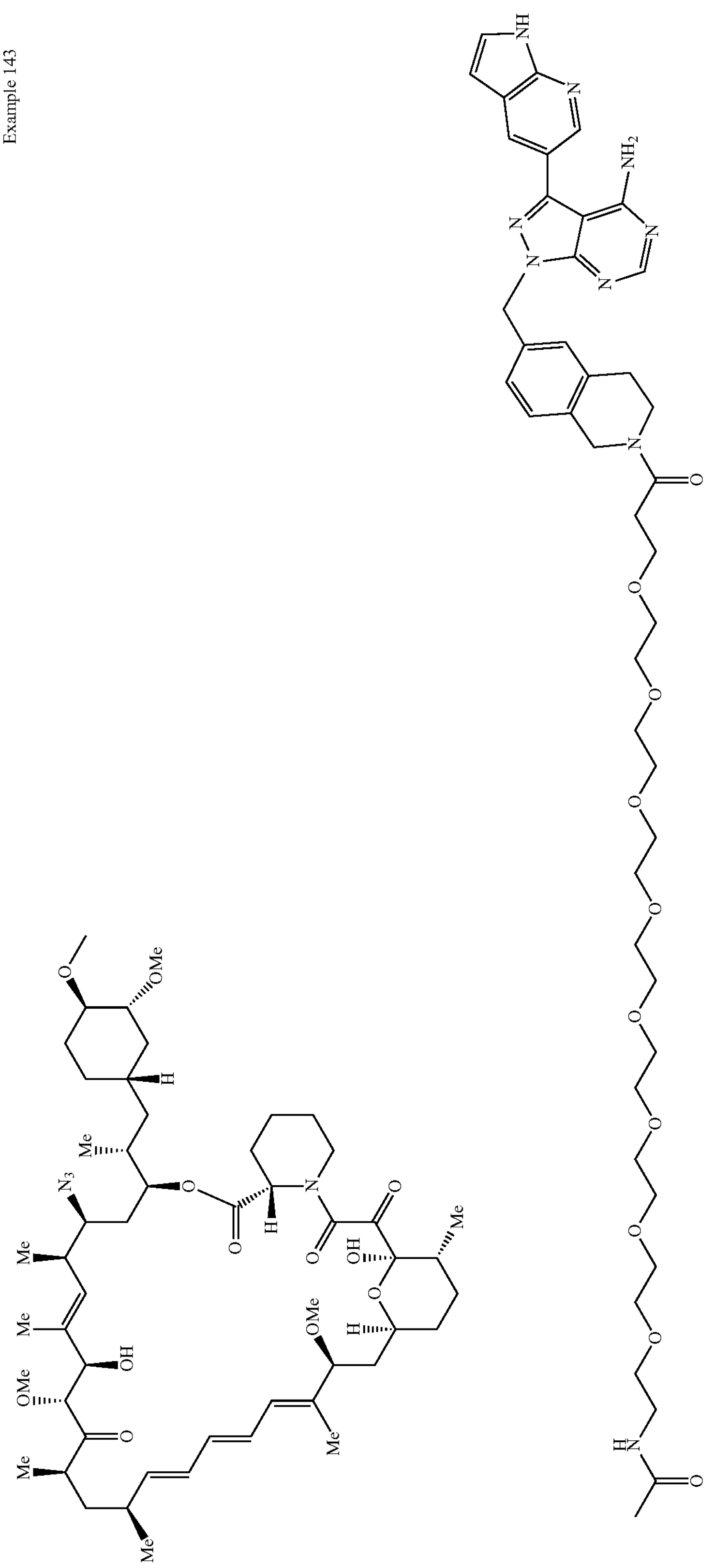

-continued
Example 144
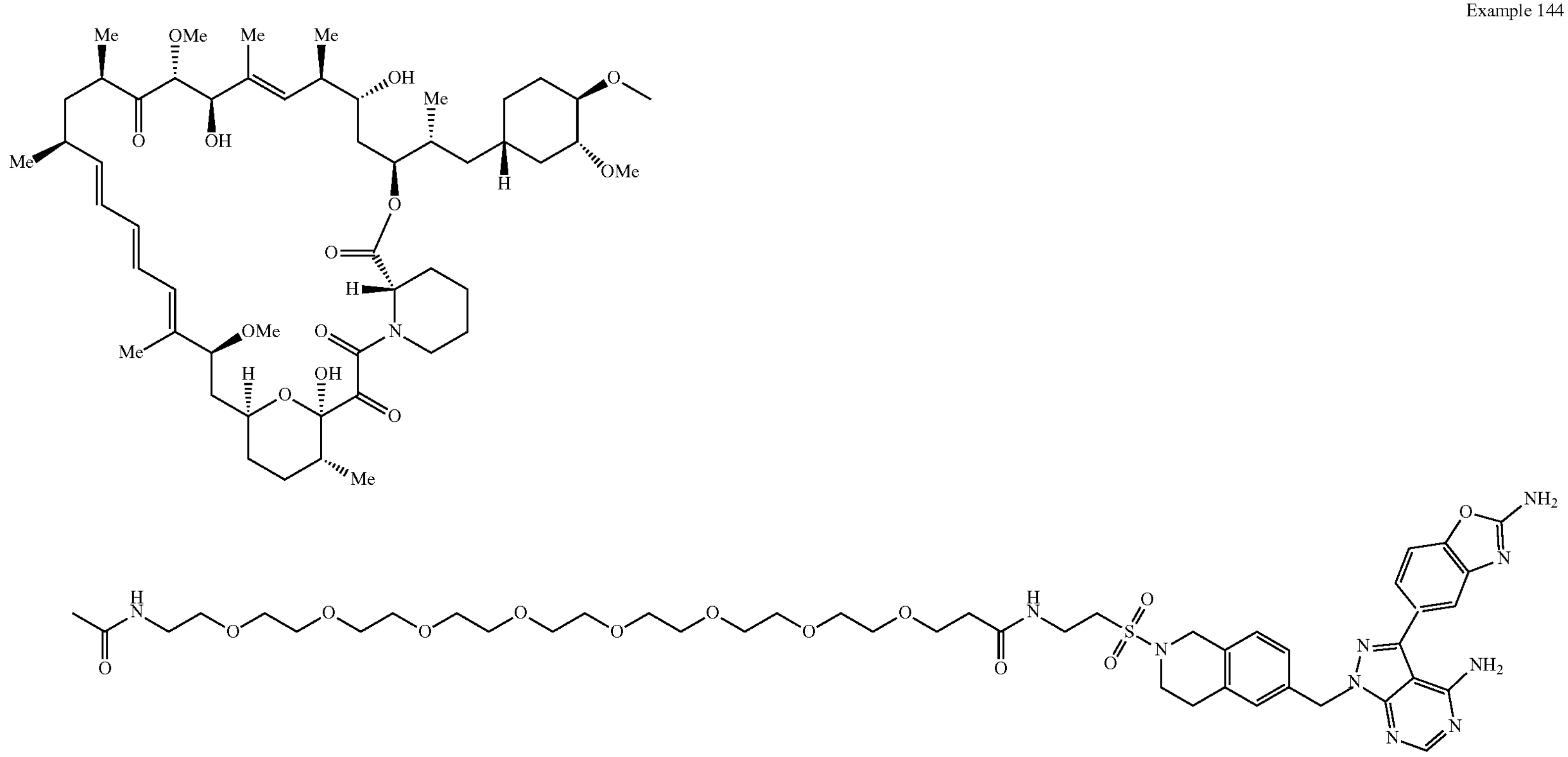

-continued
Example 145
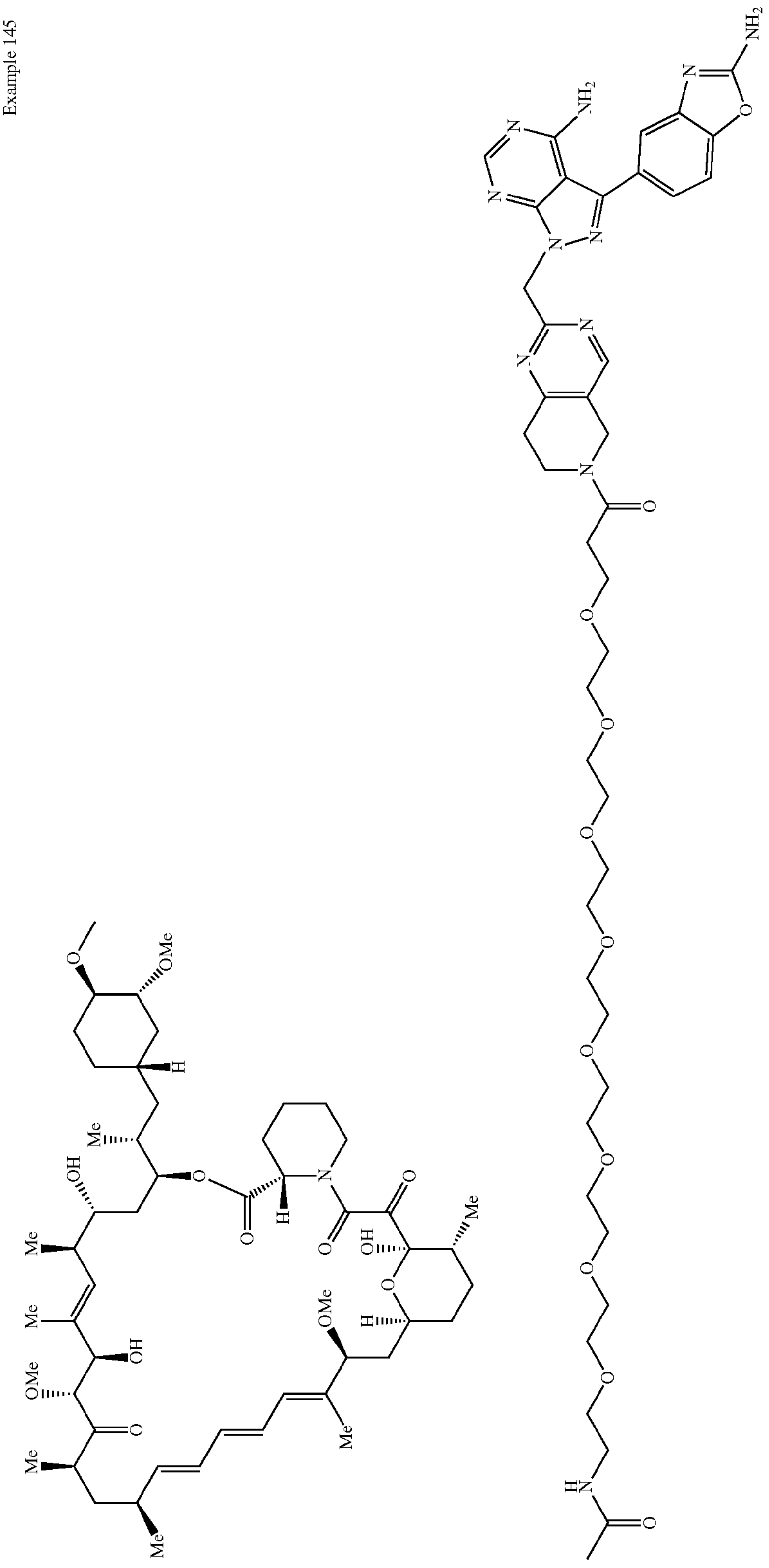

-continued
Example 146
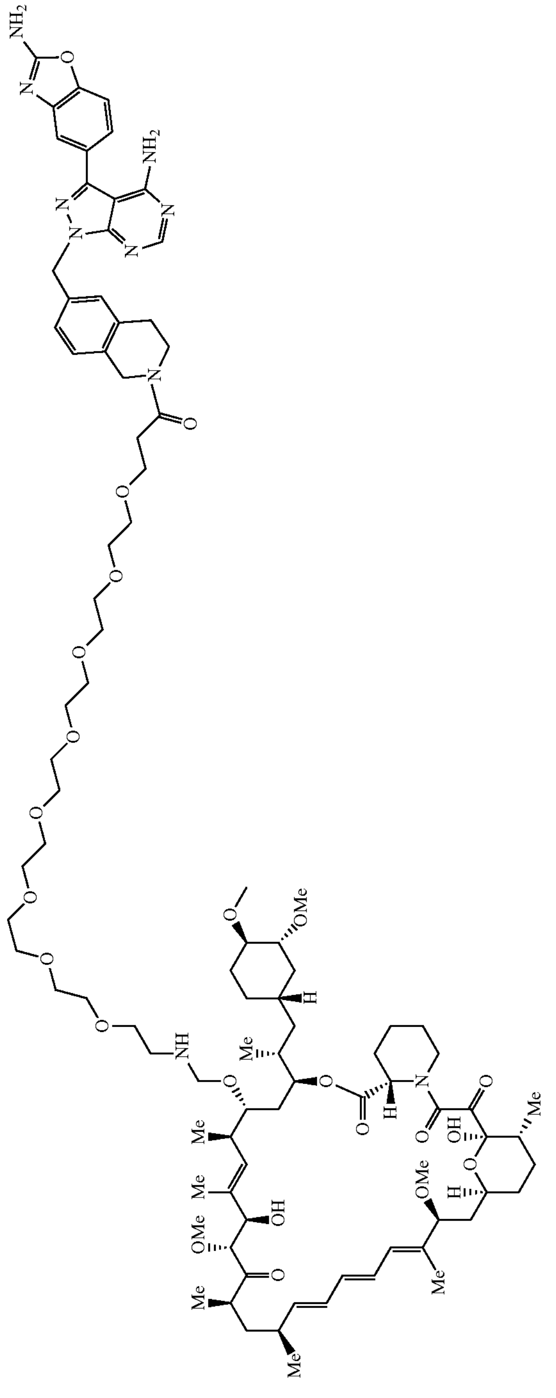
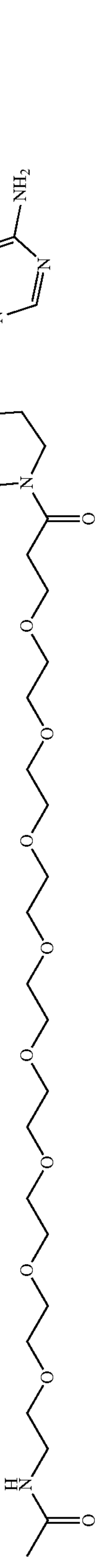

-continued
Example 147
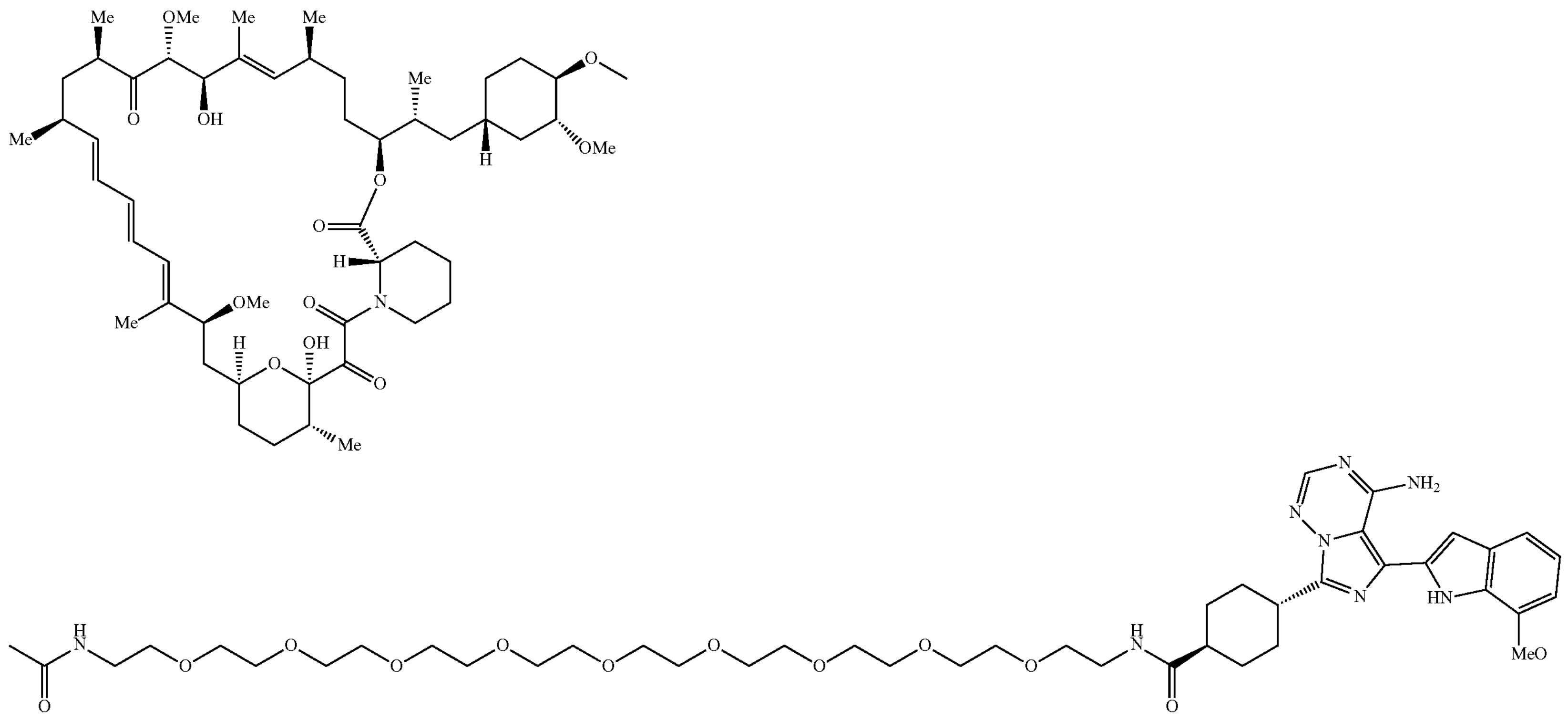

-continued
Example 148
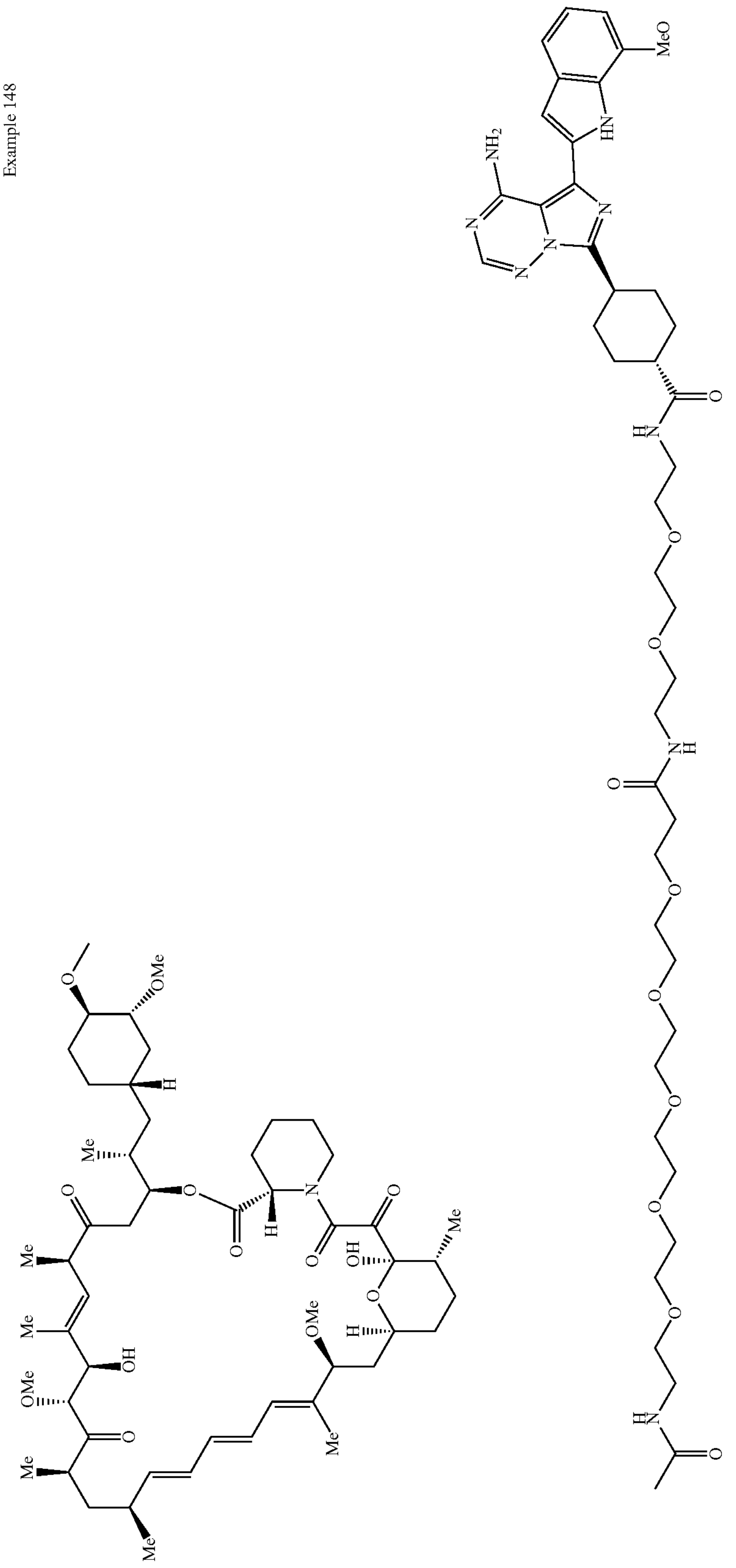

-continued
Example 149
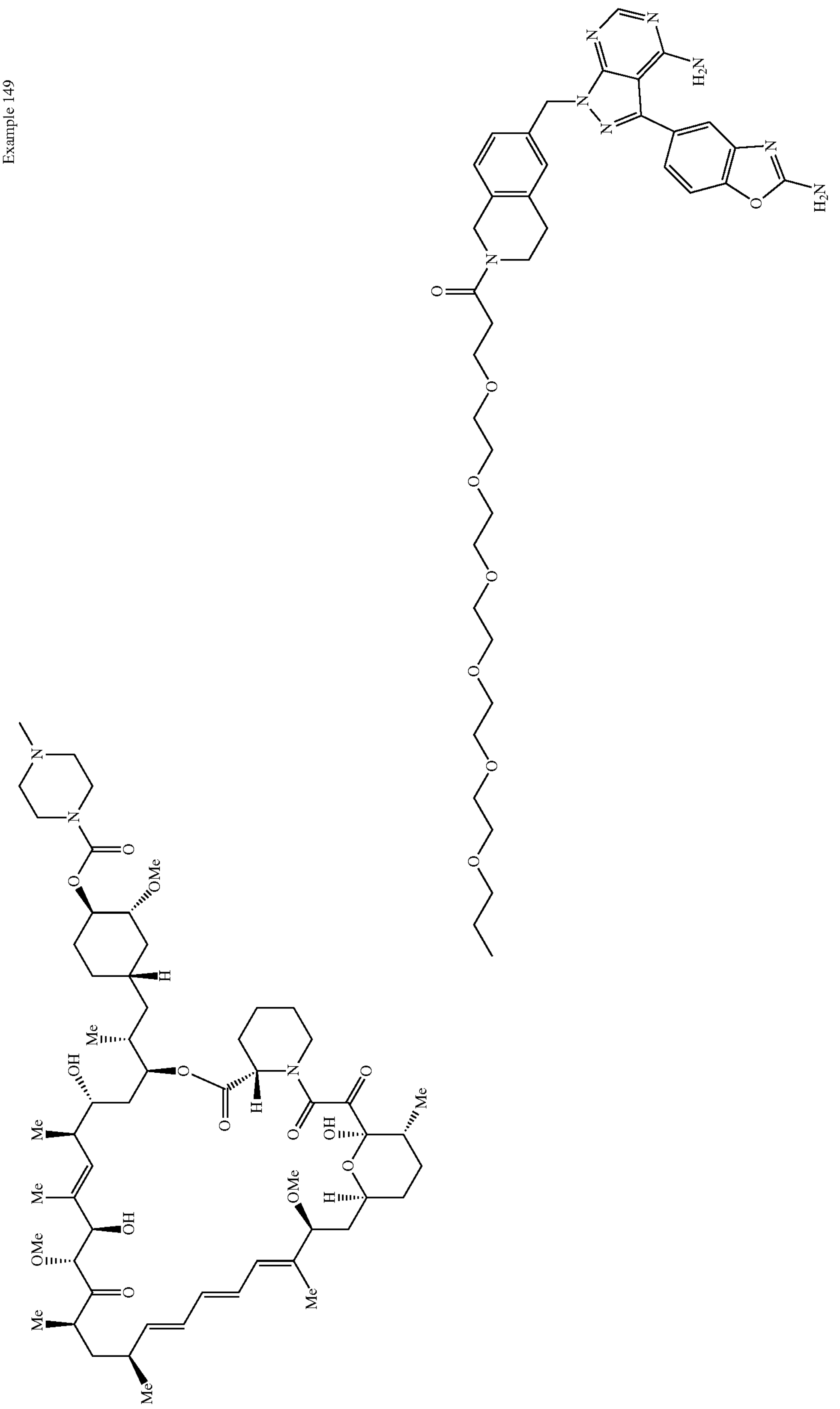

-continued
Example 150
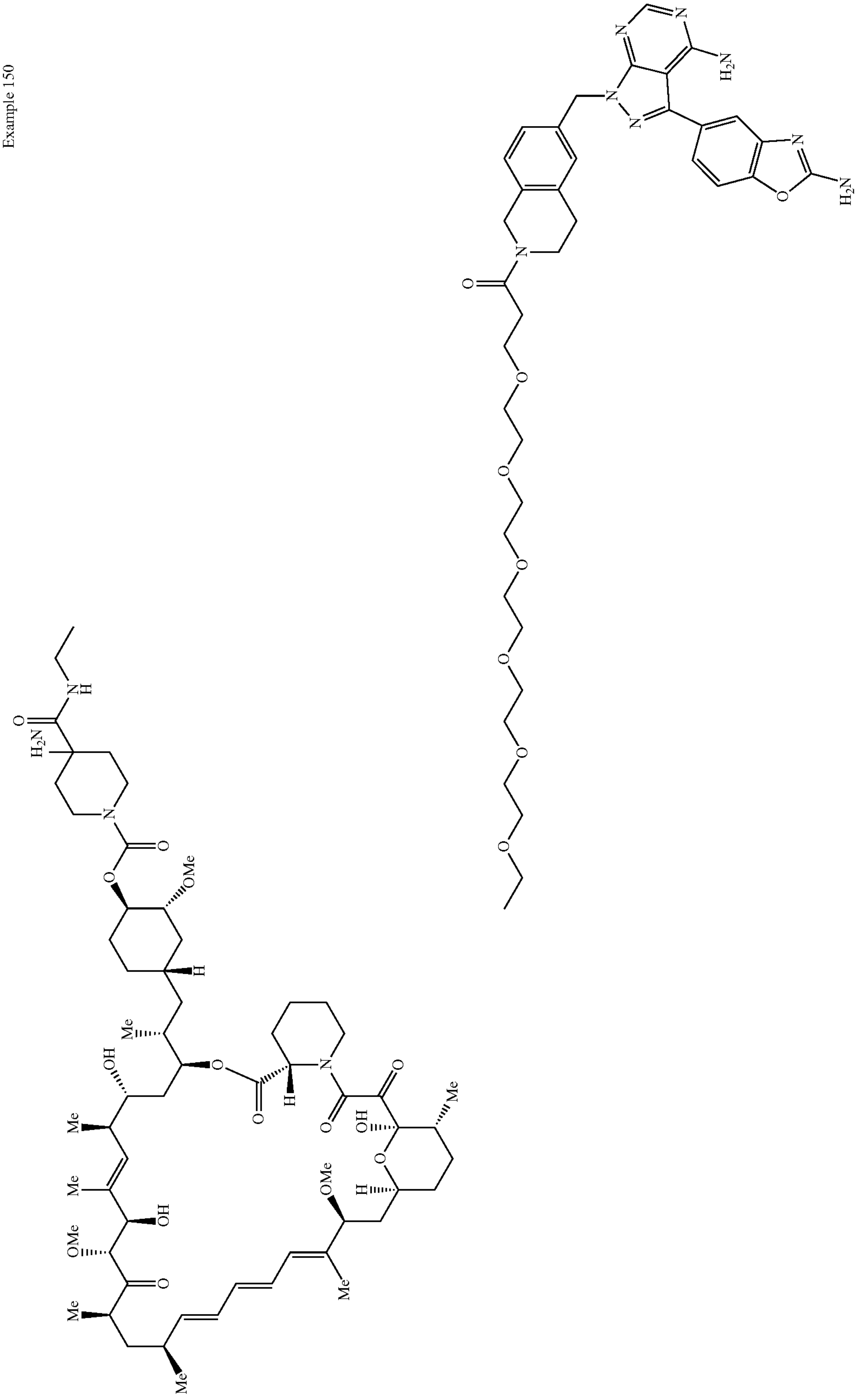

Example 151
-continued
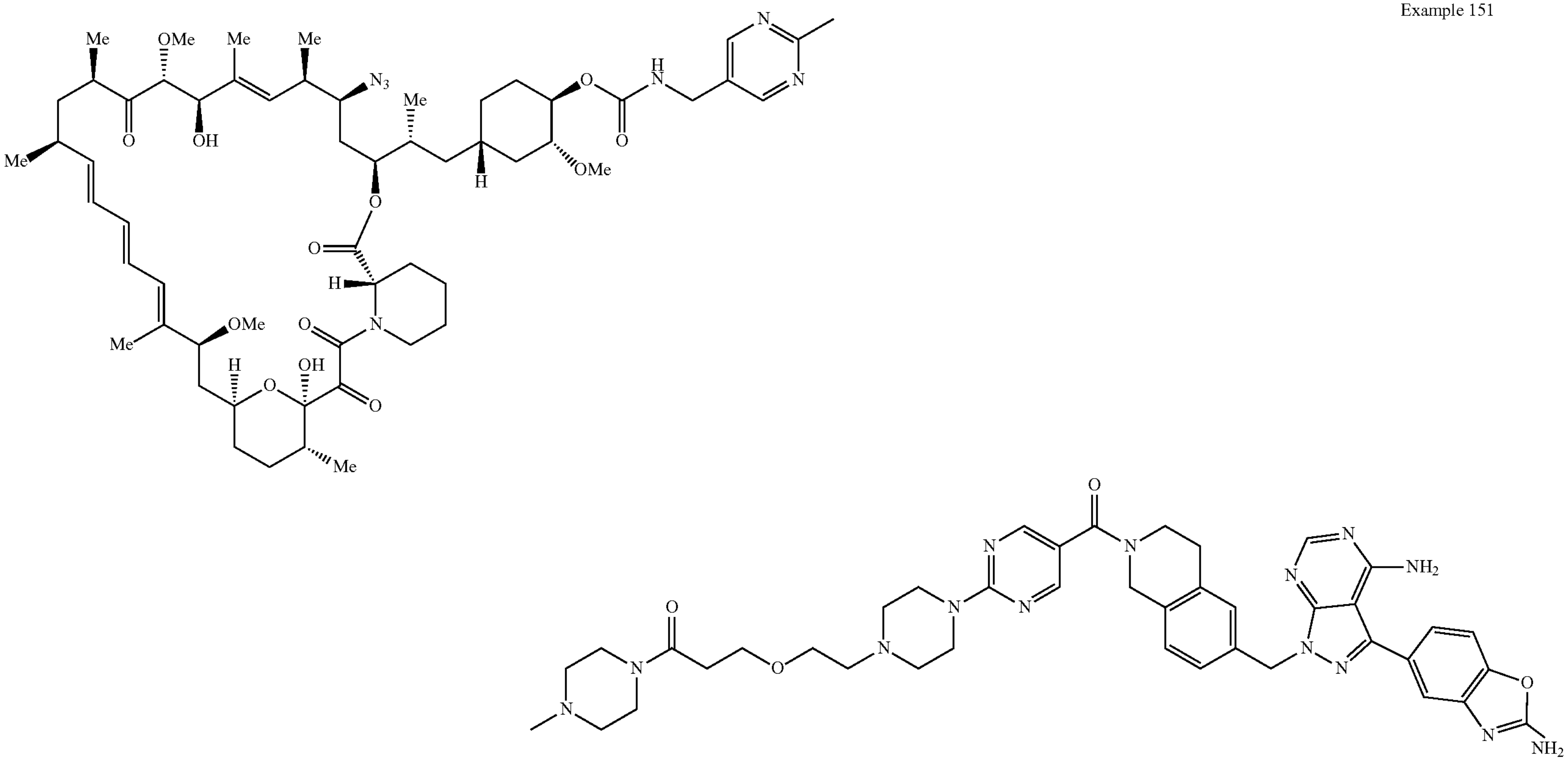

-continued
Example 152
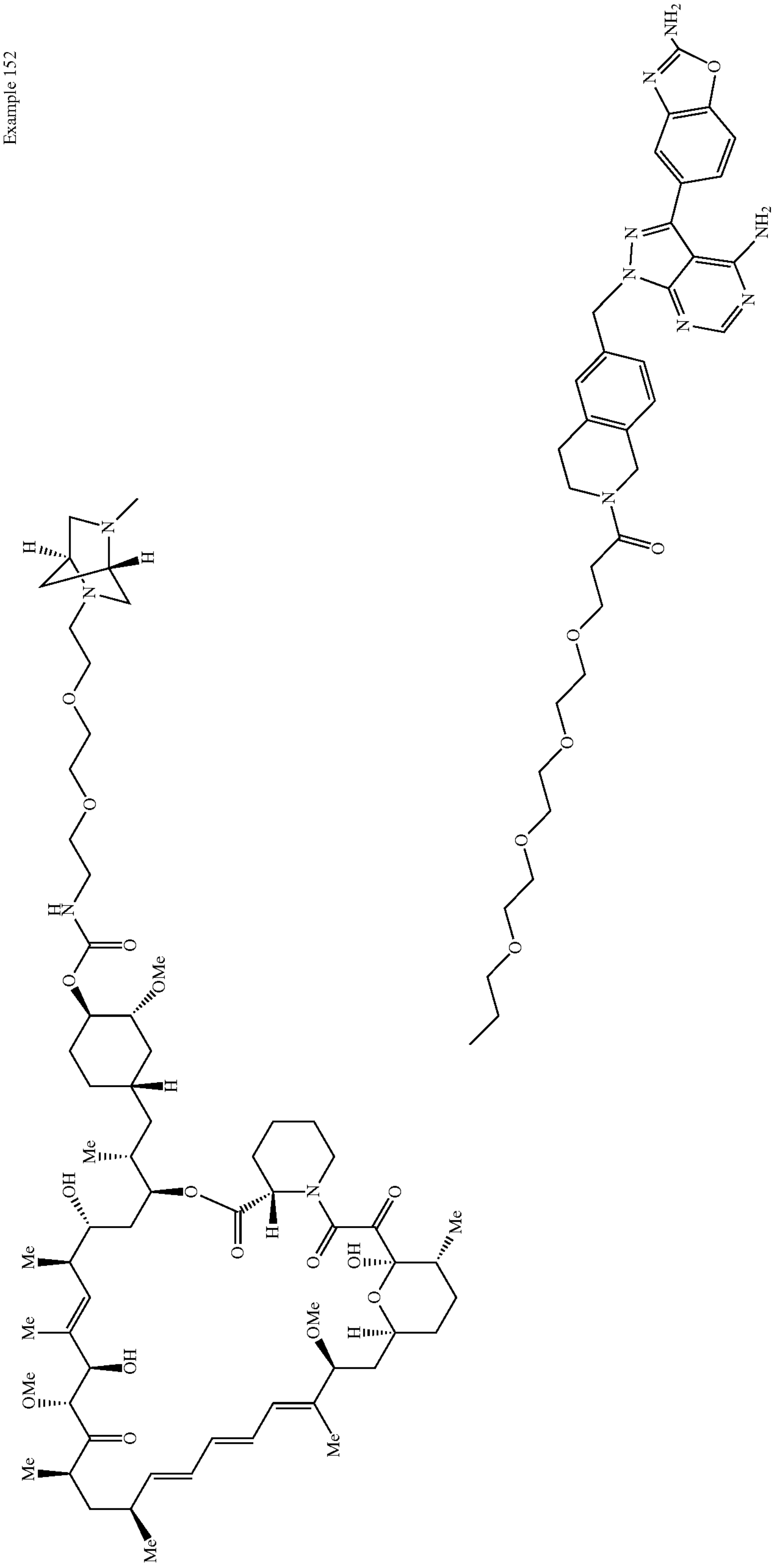

or a pharmaceutically acceptable salt or tautomer thereof.

Embodiment II-75. A pharmaceutical composition comprising a compound of any one of Embodiments II-1 to II-74, or a pharmaceutically acceptable salt thereof, and at least one of a pharmaceutically acceptable carrier, diluent, or excipient.

Embodiment II-76. A method of treating a disease or disorder mediated by mTOR comprising administering to the subject suffering from or susceptible to developing a disease or disorder mediated by mTOR a therapeutically effective amount of one or more compounds of any one of Embodiments II-1 to II-74, or a pharmaceutically acceptable salt thereof.

Embodiment II-77. A method of preventing a disease or disorder mediated by mTOR comprising administering to the subject suffering from or susceptible to developing a disease or disorder mediated by mTOR a therapeutically effective amount of one or more compounds of any one of Embodiments II-1 to II-74, or a pharmaceutically acceptable salt thereof.

Embodiment II-78. A method of reducing the risk of a disease or disorder mediated by mTOR comprising administering to the subject suffering from or susceptible to developing a disease or disorder mediated by mTOR a therapeutically effective amount of one or more compounds of any one of Embodiments II-1 to II-74, or a pharmaceutically acceptable salt thereof.

Embodiment II-79. The method of any one of Embodiments II-76 to II-78, wherein the disease is cancer or an immune-mediated disease.

Embodiment II-80. The method of Embodiment II-79, wherein the cancer is selected from brain and neurovascular tumors, head and neck cancers, breast cancer, lung cancer, mesothelioma, lymphoid cancer, stomach cancer, kidney cancer, renal carcinoma, liver cancer, ovarian cancer, ovary endometriosis, testicular cancer, gastrointestinal cancer, prostate cancer, glioblastoma, skin cancer, melanoma, neuro cancers, spleen cancers, pancreatic cancers, blood proliferative disorders, lymphoma, leukemia, endometrial cancer, cervical cancer, vulva cancer, prostate cancer, penile cancer, bone cancers, muscle cancers, soft tissue cancers, intestinal or rectal cancer, anal cancer, bladder cancer, bile duct cancer, ocular cancer, gastrointestinal stromal tumors, and neuro-endocrine tumors.

Embodiment II-81. The method of Embodiment II-79, wherein the immune-mediated disease is selected from resistance by transplantation of heart, kidney, liver, medulla ossium, skin, cornea, lung, pancreas, intestinum tenue, limb, muscle, nerves, duodenum, small-bowel, or pancreatic-islet-cell; graft-versus-host diseases brought about by medulla ossium transplantation; rheumatoid arthritis, systemic lupus erythematosus, Hashimoto's thyroiditis, multiple sclerosis, myasthenia gravis, type I diabetes, uveitis, allergic encephalomyelitis, and glomerulonephritis.

Embodiment II-82. A method of treating cancer comprising administering to the subject a therapeutically effective amount of one or more compounds of any one of Embodiments II-1 to II-74, or a pharmaceutically acceptable salt thereof.

Embodiment II-83. The method of Embodiment II-82, wherein the cancer is selected from brain and neurovascular tumors, head and neck cancers, breast cancer, lung cancer, mesothelioma, lymphoid cancer, stomach cancer, kidney cancer, renal carcinoma, liver cancer, ovarian cancer, ovary endometriosis, testicular cancer, gastrointestinal cancer, prostate cancer, glioblastoma, skin cancer, melanoma, neuro cancers, spleen cancers, pancreatic cancers, blood proliferative disorders, lymphoma, leukemia, endometrial cancer, cervical cancer, vulva cancer, prostate cancer, penile cancer, bone cancers, muscle cancers, soft tissue cancers, intestinal or rectal cancer, anal cancer, bladder cancer, bile duct cancer, ocular cancer, gastrointestinal stromal tumors, and neuro-endocrine tumors.

Embodiment II-84. A method of treating an immune-mediated disease comprising administering to the subject a therapeutically effective amount of one or more compounds of any one of Embodiments II-1 to II-74, or a pharmaceutically acceptable salt thereof.

Embodiment II-85. The method of Embodiment II-84, wherein the immune-mediated disease is selected from resistance by transplantation of heart, kidney, liver, medulla ossium, skin, cornea, lung, pancreas, intestinum tenue, limb, muscle, nerves, duodenum, small-bowel, or pancreatic-islet-cell; graft-versus-host diseases brought about by medulla ossium transplantation; rheumatoid arthritis, systemic lupus erythematosus, Hashimoto's thyroiditis, multiple sclerosis, myasthenia gravis, type I diabetes, uveitis, allergic encephalomyelitis, and glomerulonephritis.

Embodiment II-86. A method of treating an age related condition comprising administering to the subject a therapeutically effective amount of one or more compounds of any one of Embodiments II-1 to II-74, or a pharmaceutically acceptable salt thereof.

Embodiment II-87. The method of Embodiment II-86, wherein the age related condition is selected from sarcopenia, skin atrophy, muscle wasting, brain atrophy, atherosclerosis, arteriosclerosis, pulmonary emphysema, osteoporosis, osteoarthritis, high blood pressure, erectile dysfunction, dementia, Huntington's disease, Alzheimer's disease, cataracts, age-related macular degeneration, prostate cancer, stroke, diminished life expectancy, impaired kidney function, and age-related hearing loss, aging-related mobility disability (e.g., frailty), cognitive decline, age-related dementia, memory impairment, tendon stiffness, heart dysfunction such as cardiac hypertrophy and systolic and diastolic dysfunction, immunosenescence, cancer, obesity, and diabetes.

Embodiment II-88. A compound of any one of Embodiments II-1 to II-74, or a pharmaceutically acceptable salt thereof, for use in treating, preventing, or reducing the risk of a disease or condition mediated by mTOR.

Embodiment II-89. Use of a compound of any of Embodiments II-1 to II-74, or a pharmaceutically acceptable salt thereof, in the manufacture of a medicament for treating, preventing, or reducing the risk of a disease or disorder mediated by mTOR.

Embodiment II-90. A compound of any one of claims 1-74, or a pharmaceutically acceptable salt thereof, for use in treating cancer.

Embodiment II-91. Use of a compound of any one of Embodiments II-1 to II-74, or a pharmaceutically acceptable salt thereof, in the manufacture of a medicament for treating cancer.

Embodiment II-92. A compound of any one of Embodiments II-1 to II-74, or a pharmaceutically acceptable salt thereof, for use in treating an immune-mediated disease.

Embodiment II-93. Use of a compound of any one of Embodiments II-1 to II-74, or a pharmaceutically acceptable salt thereof, in the manufacture of a medicament for treating an immune-mediated disease.

Embodiment II-94. A compound of any one of Embodiments II-1 to II-74, or a pharmaceutically acceptable salt thereof, for use in treating an age related condition.

Embodiment II-95. Use of a compound of any one of Embodiments II-1 to II-74, or a pharmaceutically acceptable salt thereof, in the manufacture of a medicament for treating an age related condition.

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Definitions used in the following examples and elsewhere herein are:

$CH_2Cl_2$, DCM Methylene chloride, Dichloromethane
$CH_3CN$, MeCN Acetonitrile
DIPEA Diisopropylethyl amine or Hunig's base
DMA Dimethylacetamide
DME Dimethoxyethane
DMF N,N-Dimethylformamide
EDCI 1-Ethyl-3-(3-dimethylaminopropyl)carbodiimide
EtOAc Ethyl acetate
h hour
$H_2O$ Water
HCl Hydrochloric acid
HOBt Hydroxybenzotriazole
HPLC High-performance liquid chromatography
LCMS Liquid chromatography-mass spectrometry
MeOH Methanol
MTBE Methyl tert-butyl ether
$Na_2SO_4$ Sodium sulfate
PEG Polyethylene glycol
TBDMS tert-butyldimethylsilyl
TFA Trifluoroacetic acid
THF Tetrahydrofuran
TMS Tetramethylsilane Series 1 Bifunctional Rapalogs A general structure of Series 1 bifunctional rapalogs is shown in Scheme 1 below. For these types of bifunctional rapalogs, the linker may include variations where q=0 to 30, such as q=1 to 7, and r=1 to 6. The linker amine can include substitutions, such as R═H and C1-C6 alkyl groups. The carbamate moiety, where $Z^1$═O or S, can be attached to the rapalog at $R^{40}$ or $R^{28}$ (Formula I and II), including variations found in Table 1 in the Examples Section. An mTOR active site inhibitor can attach to the linker via a primary or secondary amine, and may include variations found in Table 2 in the Examples Section.

Scheme 1. Series 1 bifunctional rapalogs.

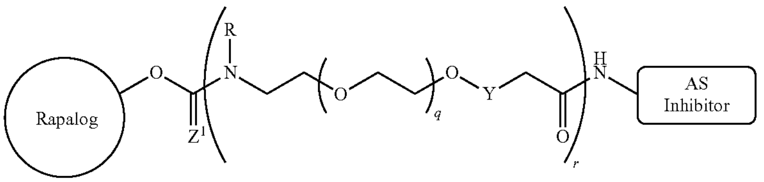

Series 1 Bifunctional rapalog

Series 2 Bifunctional Rapalogs

A general structure of Series 2 bifunctional rapalogs is shown in Scheme 2 below. For these types of bifunctional rapalogs, the linker may include variations where q=0 to 30, such as q=1 to 7. The linker amine can include substitutions, such as R═H and C1-C6 alkyl groups. The pre-linker amine can include substitutions, such as $R^2$═H, C1-C6 alkyl groups, and cycloalkyl including 4 to 8-membered rings. The carbamate moiety, where $Z^1$═O or S, can be attached to the rapalog at $R^{40}$ or $R^{28}$ (Formula I and II), including variations found in Table 1 in the Examples Section. An mTOR active site inhibitor can attach to the linker via a primary or secondary amine, and may include variations found in Table 2 in the Examples Section.

Scheme 2. Series 2 bifunctional rapalogs.

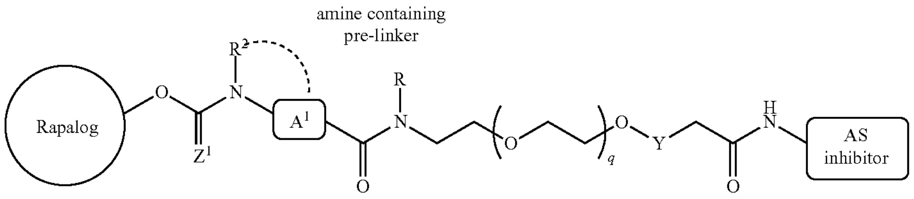

Series 2 Bifunctional rapalog

Series 3 Bifunctional Rapalogs

A general structure of Series 3 bifunctional rapalogs is shown in Scheme 3 below. For these types of bifunctional rapalogs, the linker may include variations where q=0 to 30, such as q=1 to 7. The linker amine can include substitutions, such as R═H and C1-C6 alkyl groups. The post-linker amine can include substitutions, such as $R^2$═H, C1-C6 alkyl groups, and cycloalkyl including 4 to 8-membered rings. The carbamate moiety, where $Z^1$═O or S, can be attached to the rapalog at $R^{40}$ or $R^{28}$ (Formula I and II), including variations found in Table 1 in the Examples Section. An mTOR active site inhibitor can attach to the linker via a primary or secondary amine, and may include variations found in Table 2 in the Examples Section.

Series 5 Bifunctional Rapalogs

A general structure of Series 5 bifunctional rapalogs is shown in Scheme 5 below. For these types of bifunctional rapalogs, the pre-linker amine can include substitutions, such as $R^2$═H, C1-C6 alkyl groups, and cycloalkyl including 4 to 8-membered rings. The carbamate moiety, where $Z^1$═O or S, can be attached to the rapalog at $R^{40}$ or $R^{28}$ (Formula I and II), including variations found in Table 1 in the Examples Section. An mTOR active site inhibitor can attach to the linker via a primary or secondary amine, and may include variations found in Table 2 in the Examples Section.

Scheme 3. Series 3 bifunctional rapalogs

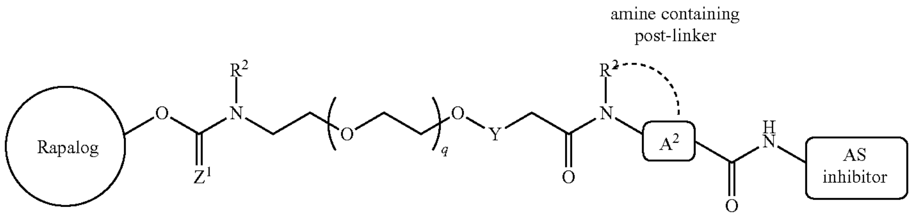

Series 3 Bifunctional rapalog

Series 4 Bifunctional Rapalogs

A general structure of Series 4 bifunctional rapalogs is shown in Scheme 4 below. For these types of bifunctional rapalogs, the linker may include variations where q=0 to 30, such as q=1 to 7. The linker amine can include substitutions, such as R═H and C1-C6 alkyl groups. The pre- and post-linker amines can each include substitutions, such as $R^2$═H, C1-C6 alkyl groups, and cycloalkyl including 4 to 8-membered rings. The carbamate moiety, where $Z^1$═O or S, can be attached to the rapalog at $R^{40}$ or $R^{28}$ (Formula I and II), including variations found in Table 1 in the Examples Section. An mTOR active site inhibitor can attach to the linker via a primary or secondary amine, and may include variations found in Table 2 in the Examples Section.

Scheme 5. Series 5 bifunctional rapalogs

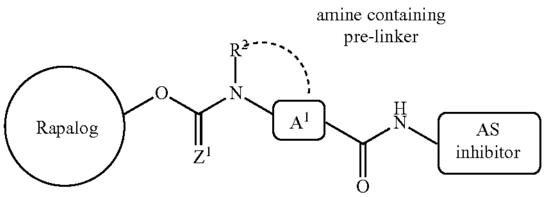

Series 5 Bifunctional rapalog

Scheme 4. Series 4 bifunctional rapalogs

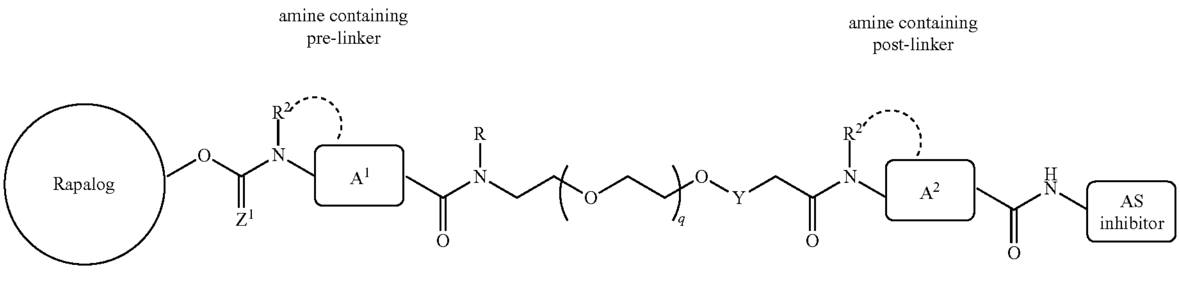

Series 4 Bifunctional rapalog

Series 6 Bifunctional Rapalogs

A general structure of Series 6 bifunctional rapalogs is shown in Scheme 6 below. For these types of bifunctional rapalogs, the linker may include variations where q=0 to 30, such as q=1 to 7. The linker amines can include substitutions, such as R═H and C1-C6 alkyl groups. The post-linker amine can include substitutions, such as $R^2$═H, C1-C6 alkyl groups, and cycloalkyl including 4 to 8-membered rings. The carbamate moiety, where $Z^1$═O or S, can be attached to the rapalog at $R^{40}$ or $R^{28}$ (Formula I and II), including variations found in Table 1 in the Examples Section. An mTOR active site inhibitor can attach to the linker via a primary or secondary amine, and may include variations found in Table 2 in the Examples Section.

Scheme 6. Series 6 bifunctional rapalogs.

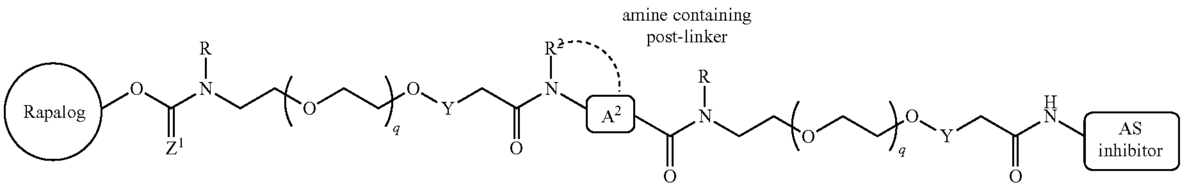

Series 6 Bifunctional rapalog

Series 7 Bifunctional Rapalogs

A general structure of Series 7 bifunctional rapalogs is shown in Scheme 7 below. For these types of bifunctional rapalogs, the linker may include variations where q=0 to 30, such as q=1 to 7. The linker amine can include substitutions, such as R═H and C1-C6 alkyl groups. The pre- and post-linker amines can each include substitutions, such as $R^2$═H, C1-C6 alkyl groups, and cycloalkyl including 4 to 8-membered rings. The carbamate moiety, where $Z^1$═O or S, can be attached to the rapalog at $R^{40}$ or $R^{28}$ (Formula I or II), including variations found in Table 1 in the Examples Section. An mTOR active site inhibitor can attach to the linker via a primary or secondary amine, and may include variations found in Table 2 in the Examples Section.

Scheme 7. Series 7 bifunctional rapalogs

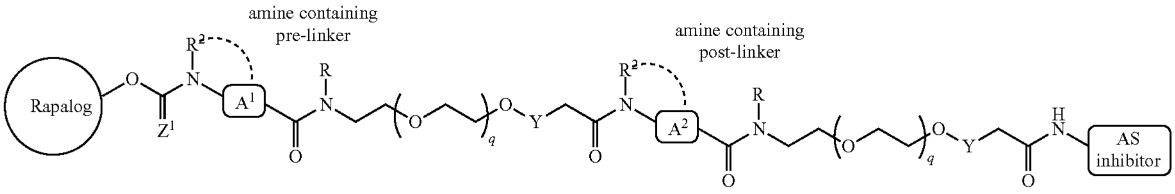

Series 7 Bifunctional rapalog

Series 8 Bifunctional Rapalogs

A general structure of Series 8 bifunctional rapalogs is shown in Scheme 8 below. For these types of bifunctional rapalogs, the linker may include variations where q=0 to 30, such as q=1 to 7. The linker amine can include substitutions, such as R=H and C1-C6 alkyl groups. The post-linker amine can include substitutions, such as $R^2$=H, C1-C6 alkyl groups, and cycloalkyl including 4 to 8-membered rings. The carbamate moiety, where $Z^1$=O or S, can be attached to the rapalog at $R^{40}$ or $R^{28}$ (Formula I or II), including variations found in Table 1 in the Examples Section. An mTOR active site inhibitor can attach to the linker via a primary or secondary amine, and may include variations found in Table 2 in the Examples Section.

Scheme 8. Series 8 bifunctional rapalogs

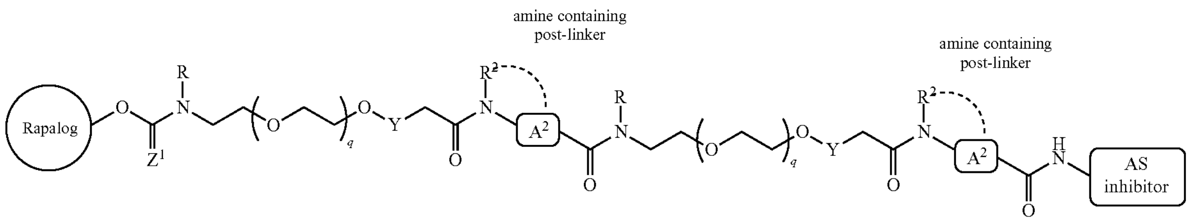

Series 8 Bifunctional rapalog

TABLE 1

| Carbonate and thiocarbonate containing rapalog monomers. | |
|---|---|
| Carbonate containing rapalog | |
| 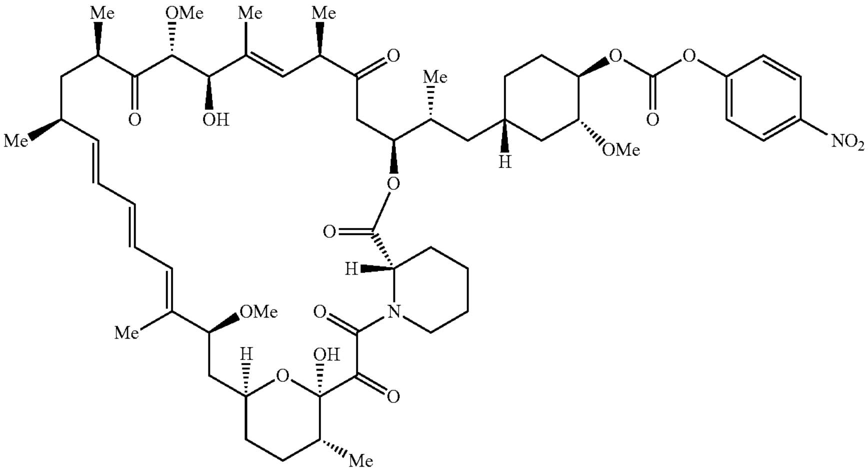 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)Oc3ccc([N+](=O)[O-])cc3)[C@H](OC)C2)CC(=O)[C@H](C)/C=C(\C)[C@@H](O)[C@@H](OC)C(=O)[C@H](C)C[C@H](C)/C=C/C=C/C=C/1C] | Monomer 1 |
| 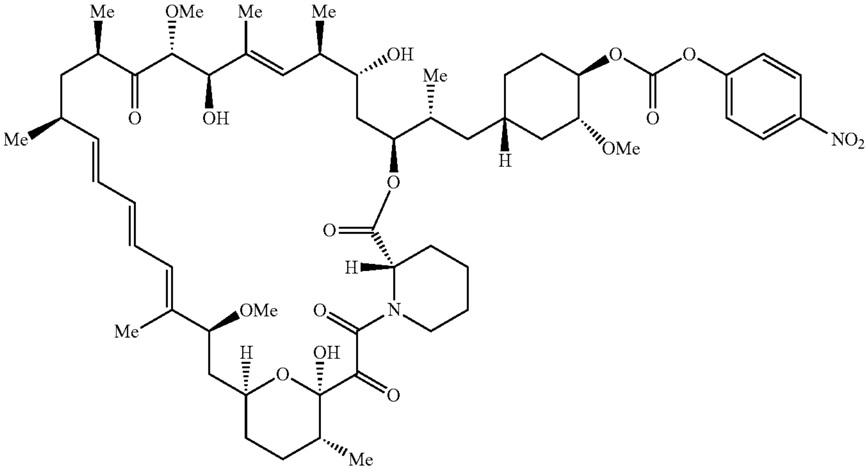 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)Oc3ccc([N+](=O)[O-])cc3)[C@H](OC)C2)C[C@@H](O)[C@H](C)/C=C(\C)[C@@H](O)[C@@H](OC)C(=O)[C@H](C)C[C@H](C)/C=C/C=C/C=C/1C] | Monomer 2 |

TABLE 1-continued
| Carbonate and thiocarbonate containing rapalog monomers. |
|---|
| Carbonate containing rapalog |
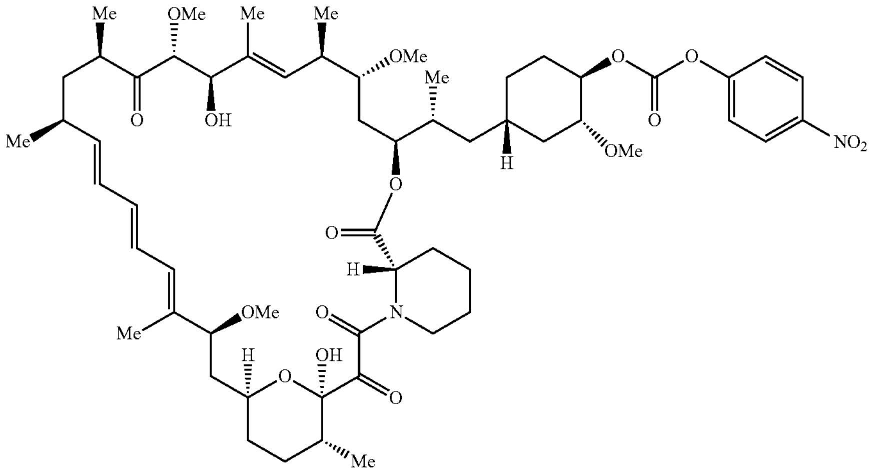 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)Oc3ccc([N+](=O)[O-])cc3)[C@H](OC)C2)C[C@@H](OC)[C@H](C)/C=C(\C)[C@@H](O)[C@@H](OC)C(=O)[C@H](C)C[C@H](C)/C=C/C=C/C=C/1C]
Monomer 3
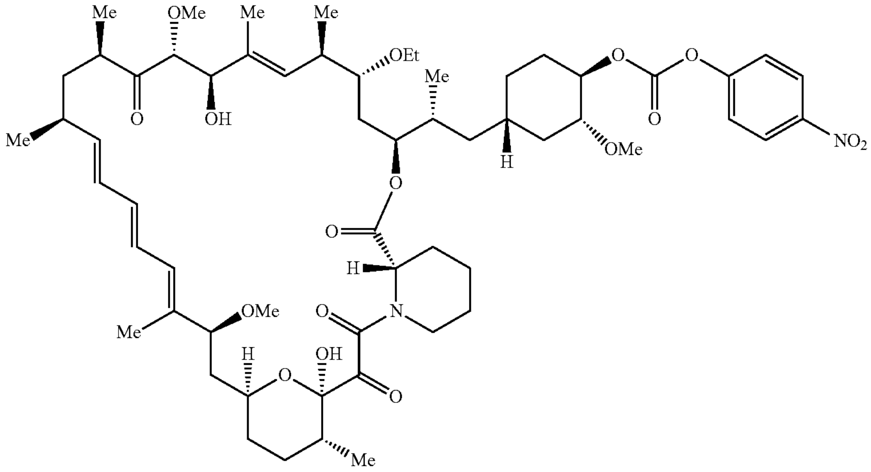
Monomer 4
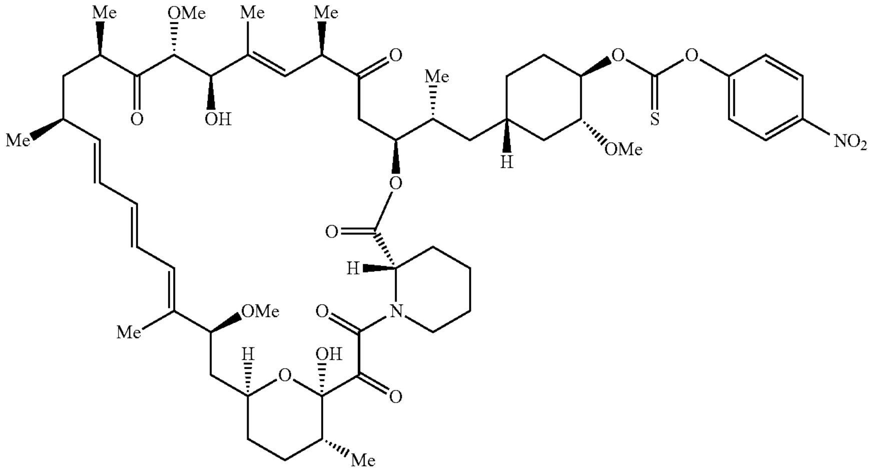
Monomer 5

TABLE 1-continued
| Carbonate and thiocarbonate containing rapalog monomers. | |
|---|---|
| Carbonate containing rapalog | |
| 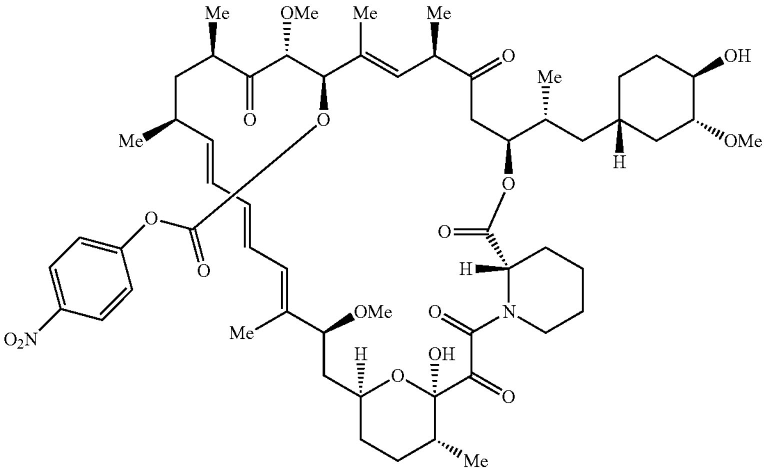 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](OC(=O)Oc2ccc([N+](=O)[O-])cc2)[C@@H](OC)C(=O)[C@H](C)C[C@H](C)/C=C/C=C/C=C/1C] | Monomer 6 |
| 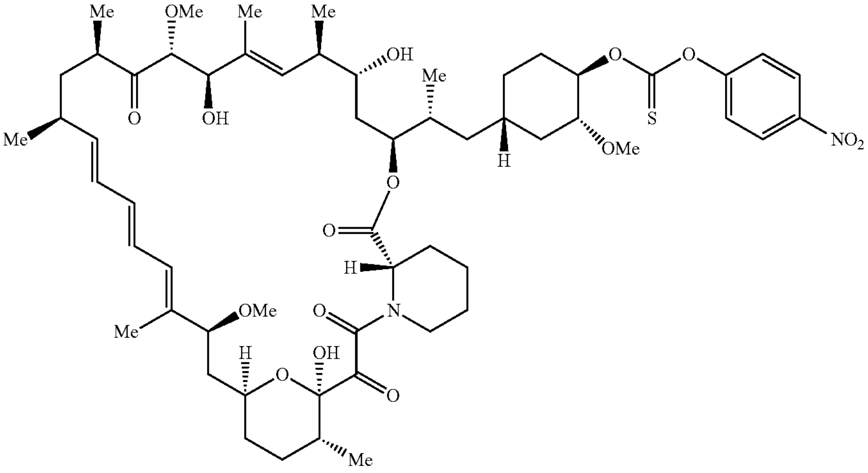 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=S)Oc3ccc([N+](=O)[O-])cc3)[C@H](OC)C2)C[C@@H](O)[C@H](C)/C=C(\C)[C@@H](O)[C@@H](OC)C(=O)[C@H](C)C[C@H](C)/C=C/C=C/C=C/1C] | Monomer 7 |
| 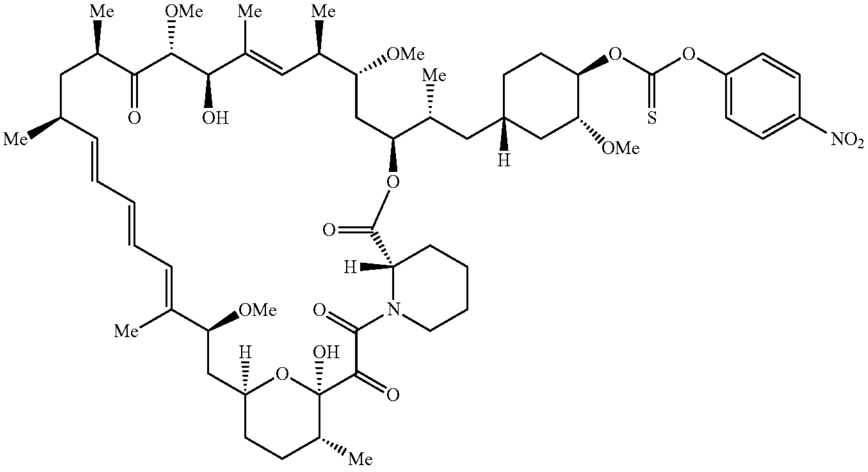 | Monomer 8 |

TABLE 1-continued
| Carbonate and thiocarbonate containing rapalog monomers. |
| --- |
| Carbonate containing rapalog |
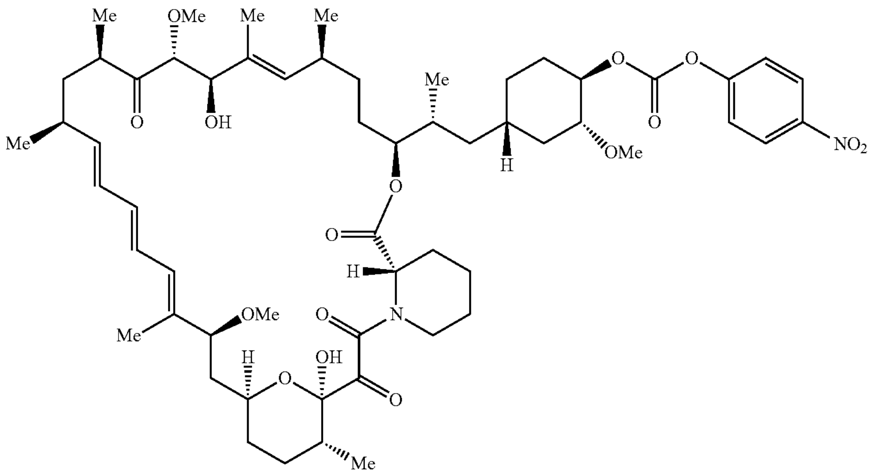 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)Oc3ccc([N+](=O)[O-])cc3)[C@H](OC)C2)CC[C@H](C)/C=C(\C)[C@@H](O)[C@@H](OC)C(=O)[C@H](C)C[C@H](C)/C=C/C=C/C=C/1C]
Monomer 9
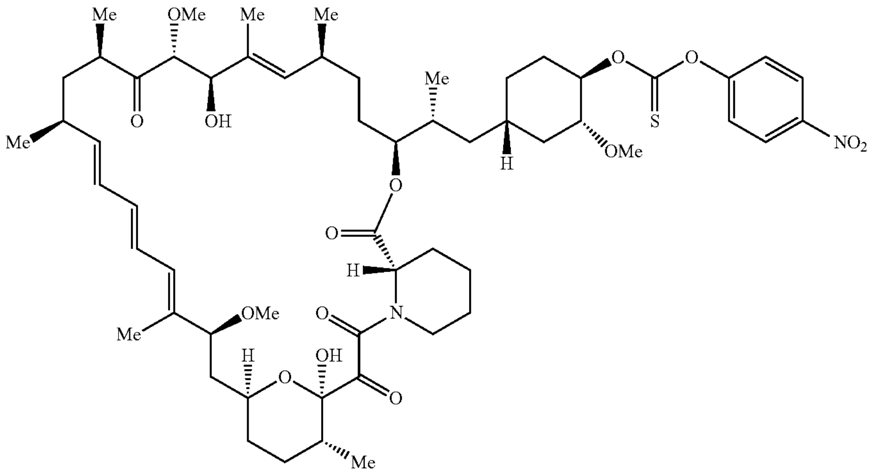 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=S)Oc3ccc([N+](=O)[O-])cc3)[C@H](OC)C2)CC[C@H](C)/C=C(\C)[C@@H](O)[C@@H](OC)C(=O)[C@H](C)C[C@H](C)/C=C/C=C/C=C/1C]
Monomer 10
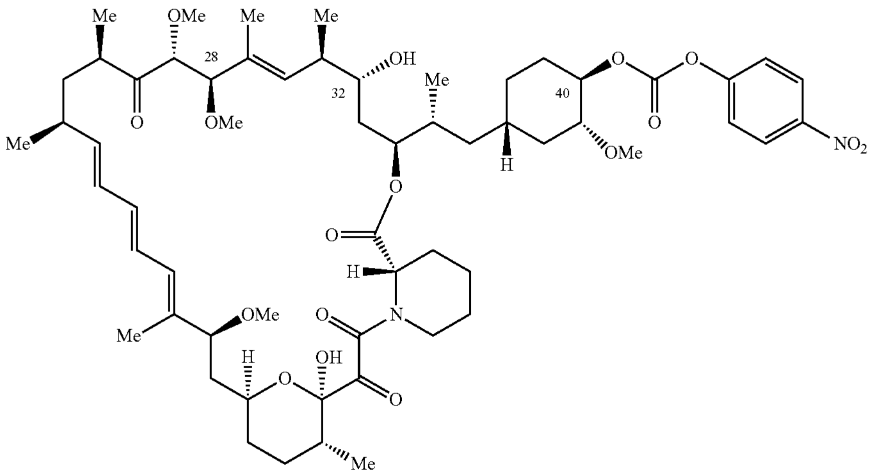 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)Oc3ccc([N+](=O)[O-])cc3)[C@H](OC)C2)C[C@@H](O)[C@H](C)/C=C(\C)[C@@H](OC)[C@@H](OC)C(=O)[C@H](C)C[C@H](C)/C=C/C=C/C=C/1C]
Monomer 11

TABLE 1-continued
| Carbonate and thiocarbonate containing rapalog monomers. | |
|---|---|
| Carbonate containing rapalog | |
| 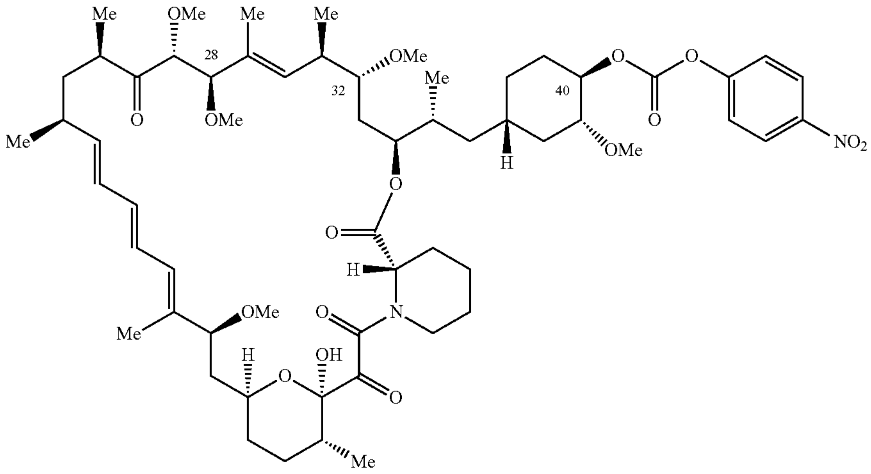 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)Oc3ccc([N+](=O)[O-])cc3)[C@H](OC)C2)C[C@@H](OC)[C@H](C)/C=C(\C)[C@@H](OC)[C@@H](OC)C(=O)[C@H](C)C[C@H](C)/C=C/C=C/C=C/1C] | Monomer 12 |
| 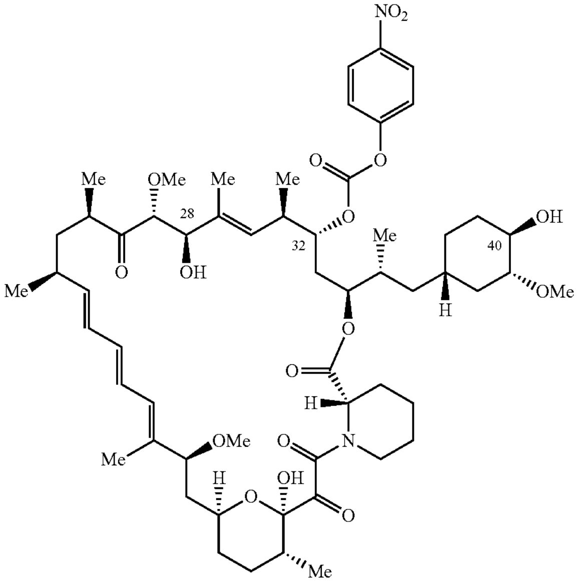 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)C[C@@H](OC(=O)Oc2ccc([N+](=O)[O-])cc2)[C@H](C)/C=C(\C)[C@@H](O)[C@@H](OC)C(=O)[C@H](C)C[C@H](C)/C=C/C=C/C=C/1C] | Monomer 13 |
| 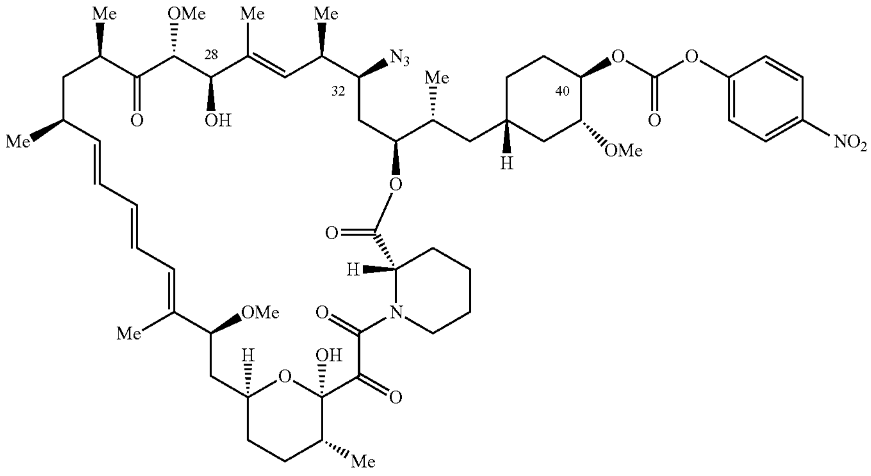 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)Oc3ccc([N+](=O)[O-])cc3)[C@H](OC)C2)C[C@H](N=[N+]=[N-])[C@H](C)/C=C(\C)[C@@H](O)[C@@H](OC)C(=O)[C@H](C)C[C@H](C)/C=C/C=C/C=C/1C] | Monomer 14 |

TABLE 1-continued
| Carbonate and thiocarbonate containing rapalog monomers. |
| --- |
| Carbonate containing rapalog |
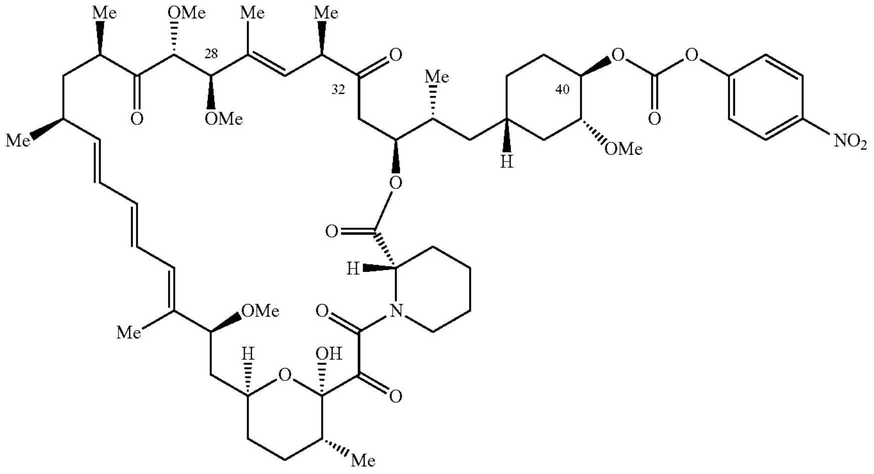 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)Oc3ccc([N+](=O)[O-])cc3)[C@H](OC)C2)CC(=O)[C@H](C)/C=C(\C)[C@@H](OC)[C@@H](OC)C(=O)[C@H](C)C[C@H](C)/C=C/C=C/C=C/1C]
Monomer 15
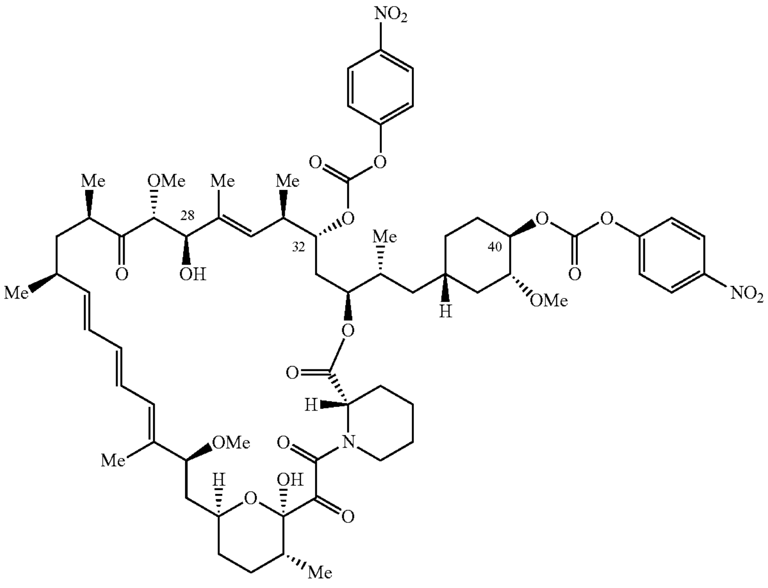 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)Oc3ccc([N+](=O)[O-])cc3)[C@H](OC)C2)C[C@@H](OC(=O)Oc2ccc([N+](=O)[O-])cc2)[C@H](C)/C=C(\C)[C@@H](O)[C@@H](OC)C(=O)[C@H](C)C[C@H](C)/C=C/C=C/C=C/1C]
Monomer 16

TABLE 1-continued
| Carbonate and thiocarbonate containing rapalog monomers. |
| --- |
| Carbonate containing rapalog |
| Monomer 17 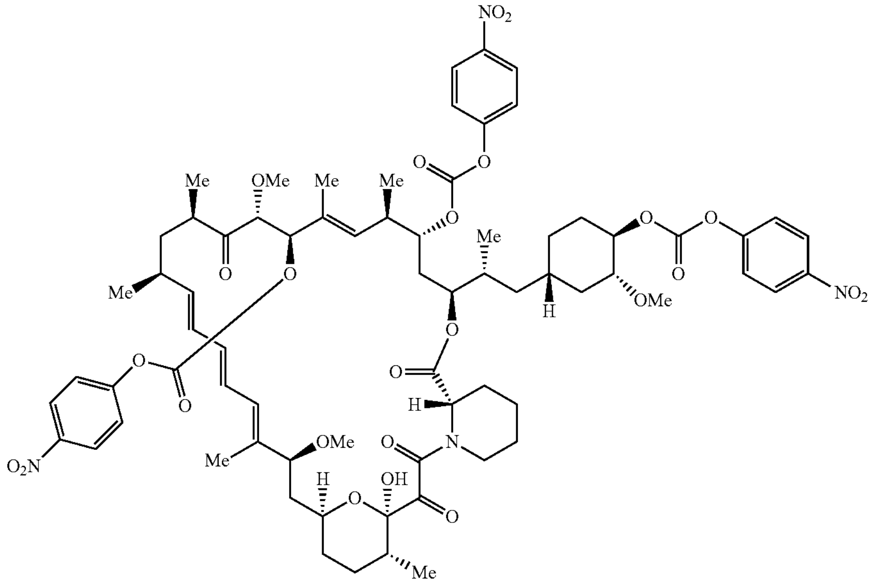 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)Oc3ccc([N+](=O)[O-])cc3)[C@H](OC)C2)C[C@@H](OC(=O)Oc2ccc([N+](=O)[O-])cc2)[C@H](C)/C=C(\C)[C@@H](OC(=O)Oc2ccc([N+](=O)[O-])cc2)[C@@H](OC)C(=O)[C@H](C)C[C@H](C)/C=C/C=C/C=C/1C] |
TABLE 2
| Active Site inhibitor monomers. Active Site inhibitor monomers |
| --- |
| 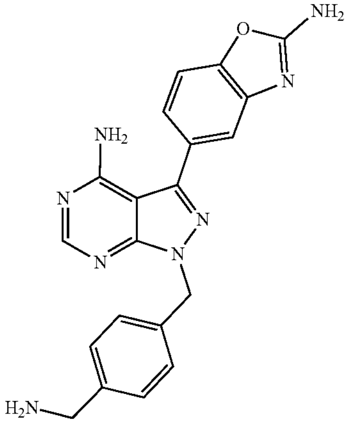 [SMILES: NCc1ccc(Cn2nc(-c3ccc4oc(N)nc4c3)c3c(N)ncnc32)cc1] |
| Monomer A |
| 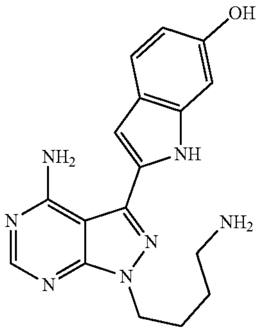 [SMILES: NCCCCn1nc(-c2cc3ccc(O)cc3[nH]2)c2c(N)ncnc21] |
| Monomer B |
TABLE 2-continued
| Active Site inhibitor monomers. Active Site inhibitor monomers |
| --- |
| 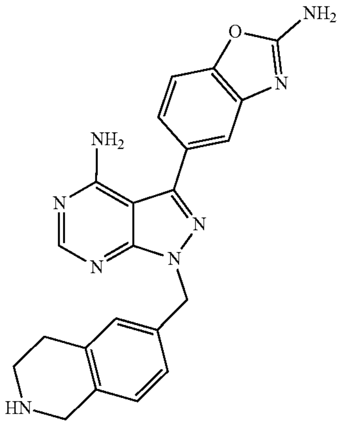 [SMILES: Nc1nc2cc(-c3nn(Cc4ccc5c(c4)CCNC5)c4ncnc(N)c34)ccc2o1] |
| Monomer C |
| 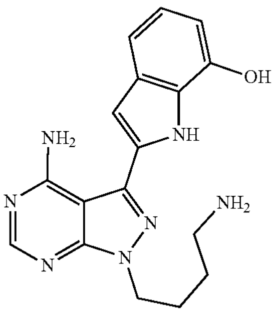 [SMILES: NCCCCn1nc(-c2cc3cccc(O)c3[nH]2)c2c(N)ncnc21] |
| Monomer D |

TABLE 2-continued
Active Site inhibitor monomers.
Active Site inhibitor monomers
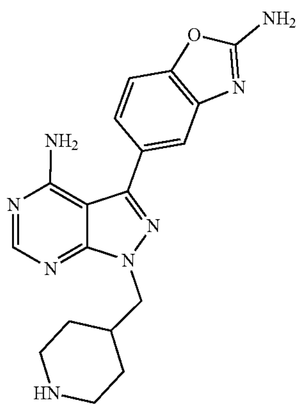 [SMILES: Nc1nc2cc(-c3nn(CC4CCNCC4)c4ncnc(N)c34)ccc2o1]
Monomer E
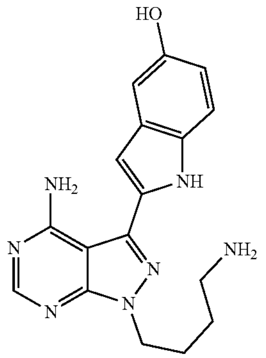 [SMILES: NCCCCn1nc(-c2cc3cc(O)ccc3[nH]2)c2c(N)ncnc21]
Monomer F
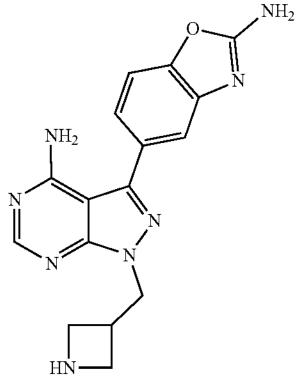 [SMILES: Nc1nc2cc(-c3nn(CC4CNC4)c4ncnc(N)c34)ccc2o1]
Monomer G
TABLE 2-continued
Active Site inhibitor monomers.
Active Site inhibitor monomers
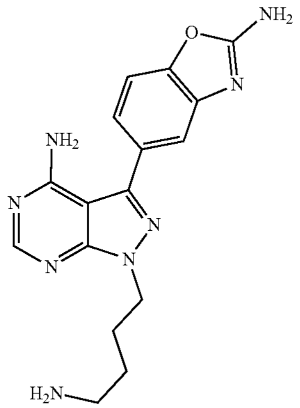 [SMILES: NCCCCn1nc(-c2ccc3oc(N)nc3c2)c2c(N)ncnc21]
Monomer H
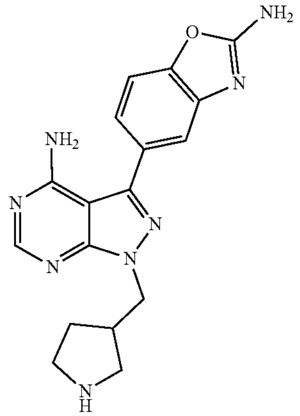 [SMILES: Nc1nc2cc(-c3nn(CC4CCNC4)c4ncnc(N)c34)ccc2o1]
Monomer I
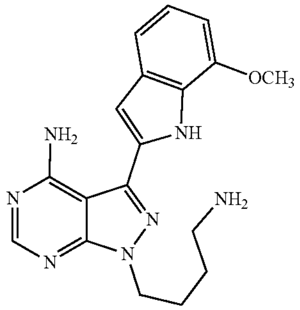 [SMILES: COc1cccc2cc(-c3nn(CCCCN)c4ncnc(N)c34)[nH]c12]
Monomer J
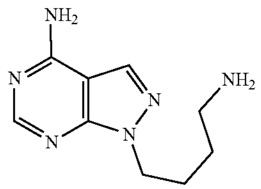 [SMILES: NCCCCn1ncc2c(N)ncnc21]
Monomer K TABLE 2-continued
Active Site inhibitor monomers.
Active Site inhibitor monomers
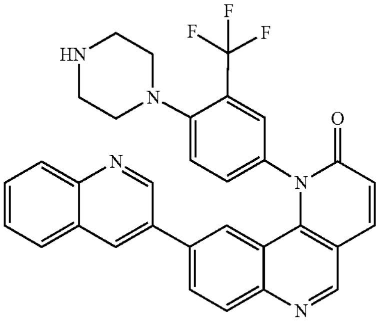 [SMILES: O=c1ccc2cnc3ccc(-c4cnc5ccccc5c4)cc3c2n1-c1ccc(N2CCNCC2)c(C(F)(F)F)c1]
Monomer L
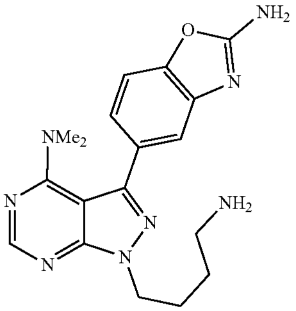 [SMILES: CN(C)c1ncnc2c1c(-c1ccc3oc(N)nc3c1)nn2CCCCN]
Monomer M
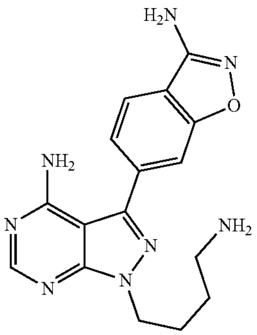 [SMILES: NCCCCn1nc(-c2ccc3c(N)noc3c2)c2c(N)ncnc21]
Monomer N
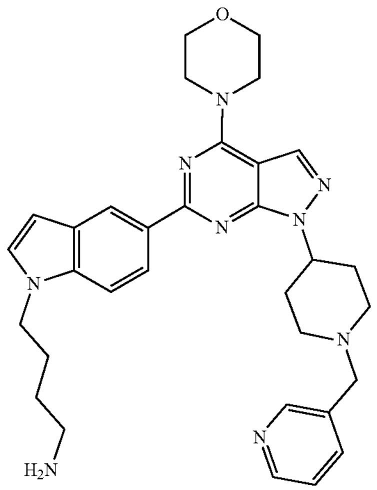 [SMILES: NCCCCn1ccc2cc(-c3nc(N4CCOCC4)c4cnn(C5CCN(Cc6cccnc6)CC5)c4n3)ccc21]
Monomer O
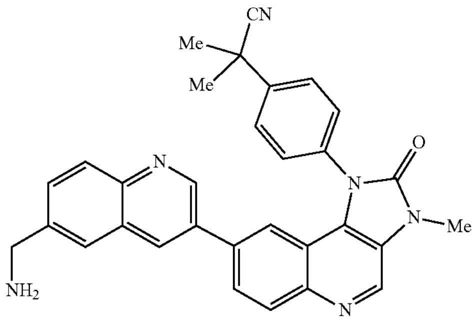 [SMILES: Cn1c(=O)n(-c2ccc(C(C)(C)C#N)cc2)c2c3cc(-c4cnc5ccc(CN)cc5c4)ccc3ncc21]
Monomer P
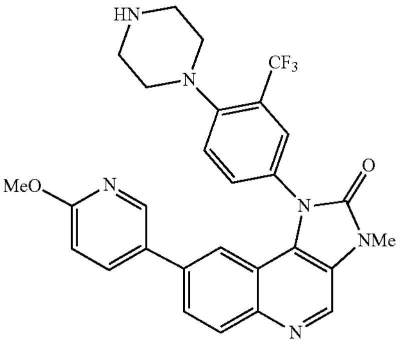 [SMILES: COc1ccc(-c2ccc3ncc4c(c3c2)n(-c2ccc(N3CCNCC3)c(C(F)(F)F)c2)c(=O)n4C)cn1]
Monomer Q TABLE 2-continued
| Active Site inhibitor monomers. Active Site inhibitor monomers |
| --- |
| 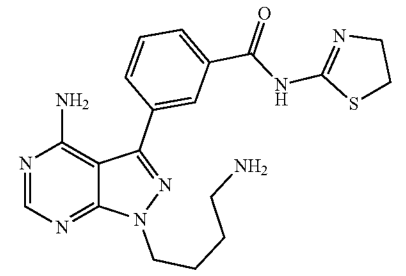 [SMILES: NCCCCn1nc(-c2cccc(C(=O)NC3=NCCS3)c2)c2c(N)ncnc21] |
| Monomer R |
| 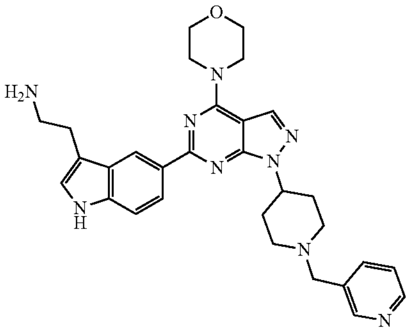 [SMILES: NCCc1c[nH]c2ccc(-c3nc(N4CCOCC4)c4cnn(C5CCN(Cc6cccnc6)CC5)c4n3)cc12] |
| Monomer S |
| 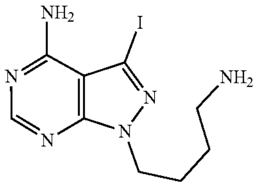 |
| Monomer T |
| 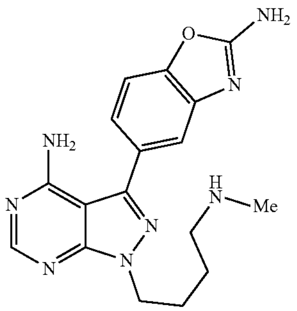 [SMILES: CNCCCCn1nc(-c2ccc3oc(N)nc3c2)c2c(N)ncnc21] |
| Monomer U |
TABLE 2-continued
| Active Site inhibitor monomers. Active Site inhibitor monomers |
| --- |
| 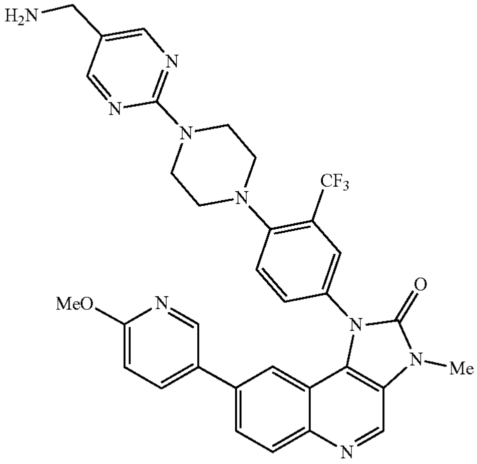 [SMILES: COc1ccc(-c2ccc3ncc4c(c3c2)n(-c2ccc(N3CCN(c5ncc(CN)cn5)CC3)c(C(F)(F)F)c2)c(=O)n4C)cn1] |
| Monomer V |
| 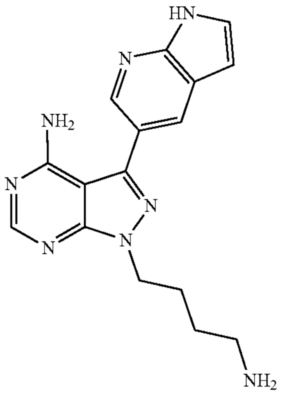 [SMILES: NCCCCn1nc(-c2cnc3[nH]ccc3c2)c2c(N)ncnc21] |
| Monomer W |
| 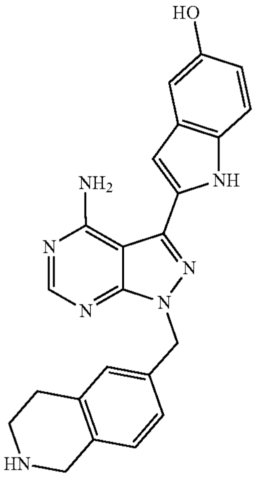 [SMILES: Nc1ncnc2c1c(-c1cc3cc(O)ccc3[nH]1)nn2Cc1ccc2c(c1)CCNC2] |
| Monomer X |

TABLE 2-continued
| Active Site inhibitor monomers. Active Site inhibitor monomers |
| --- |
| 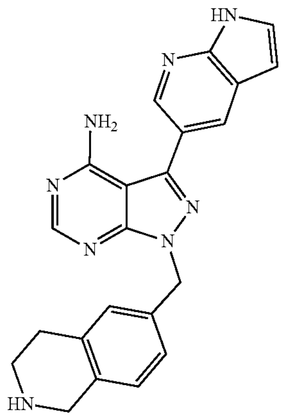 [SMILES: Nc1ncnc2c1c(-c1cnc3[nH]ccc3c1)nn2Cc1ccc2c(c1)CCNC2] Monomer Y |
| 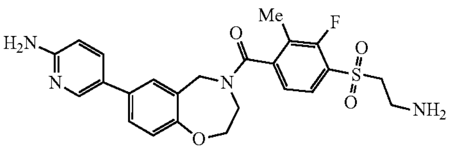 [SMILES: Cc1c(C(=O)N2CCOc3ccc(-c4ccc(N)nc4)cc3C2)ccc(S(=O)(=O)CCN)c1F] Monomer Z |
| 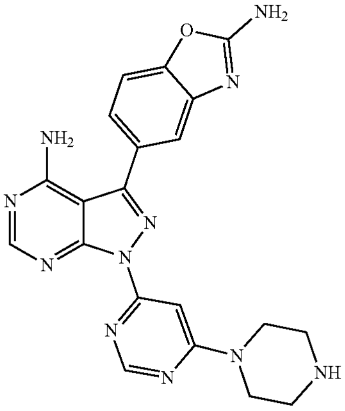 [SMILES: Nc1nc2cc(-c3nn(-c4cc(N5CCNCC5)ncn4)c4ncnc(N)c34)ccc2o1] Monomer AA |
TABLE 2-continued
| Active Site inhibitor monomers. Active Site inhibitor monomers |
| --- |
| 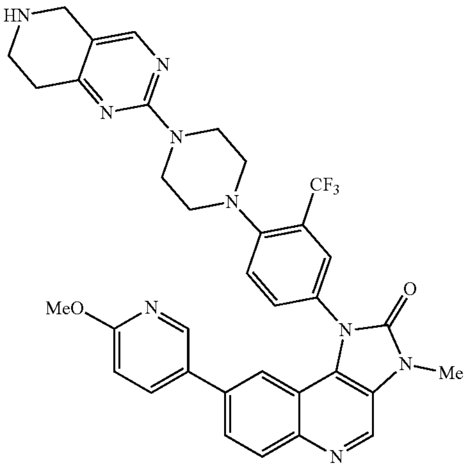 [SMILES: COc1ccc(-c2ccc3ncc4c(c3c2)n(-c2ccc(N3CCN(c5ncc6c(n5)CCNC6)CC3)c(C(F)(F)F)c2)c(=O)n4C)cn1] Monomer AB |
| 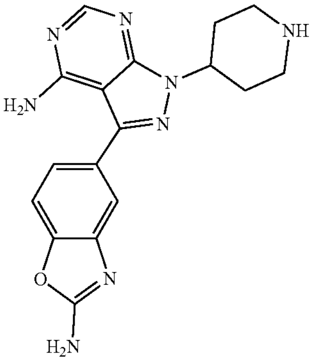 [SMILES: Nc1nc2cc(-c3nn(C4CCNCC4)c4ncnc(N)c34)ccc2o1] Monomer AC |
| 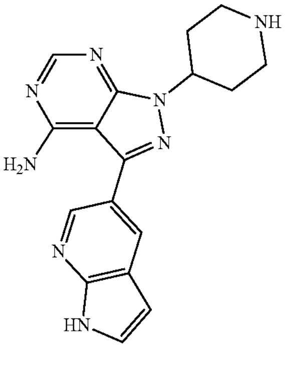 [SMILES: Nc1ncnc2c1c(-c1cnc3[nH]ccc3c1)nn2C1CCNCC1] Monomer AD |
| 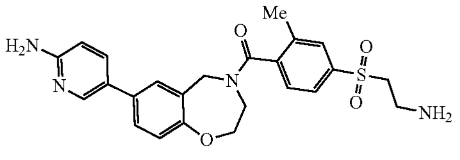 [SMILES: Cc1cc(S(=O)(=O)CCN)ccc1C(=O)N1CCOc2ccc(-c3ccc(N)nc3)cc2C1] Monomer AE |

TABLE 2-continued
Active Site inhibitor monomers.
Active Site inhibitor monomers
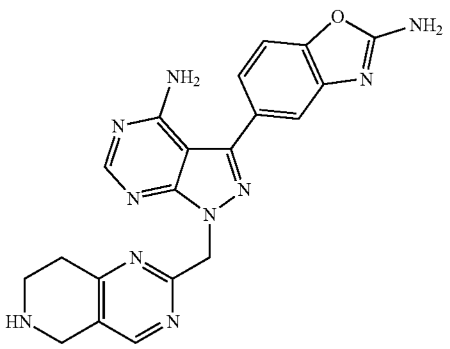 [SMILES: Nc1nc2cc(-c3nn(Cc4ncc5c(n4)CCNC5)c4ncnc(N)c34)ccc2o1]
Monomer AF
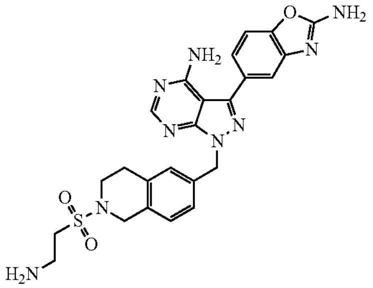 [SMILES: NCCS(=O)(=O)N1CCc2cc(Cn3nc(-c4ccc5oc(N)nc5c4)c4c(N)ncnc43)ccc2C1]
Monomer AG
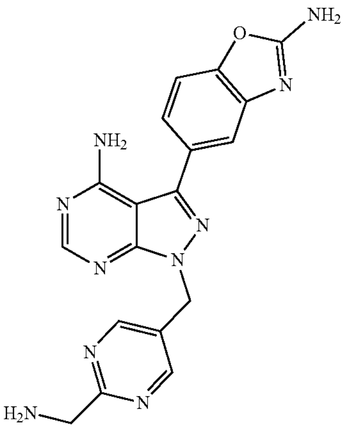 [SMILES: NCc1ncc(Cn2nc(-c3ccc4oc(N)nc4c3)c3c(N)ncnc32)cn1]
Monomer AH
TABLE 2-continued
Active Site inhibitor monomers.
Active Site inhibitor monomers
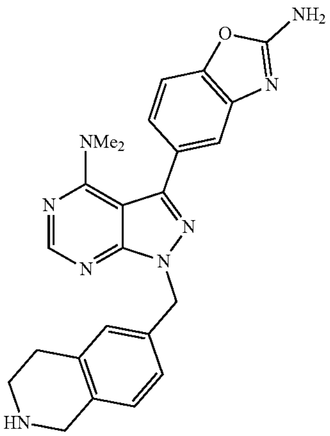 [SMILES: CN(C)c1ncnc2c1c(-c1ccc3oc(N)nc3c1)nn2Cc1ccc2c(c1)CCNC2]
Monomer AI
TABLE 3
Active Site inhibitor monomers
Active Site Inhibitor
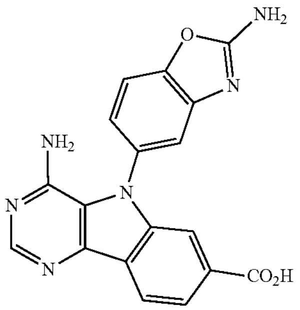 [SMILES: Nc1nc2cc(-n3c4cc(C(=O)O)ccc4c4ncnc(N)c43)ccc2o1]
Monomer AJ
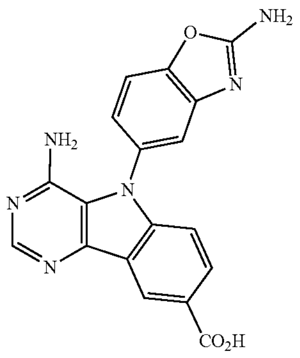 [SMILES: Nc1nc2cc(-n3c4ccc(C(=O)O)cc4c4ncnc(N)c43)ccc2o1]
Monomer AK TABLE 3-continued
Active Site inhibitor monomers
Active Site Inhibitor
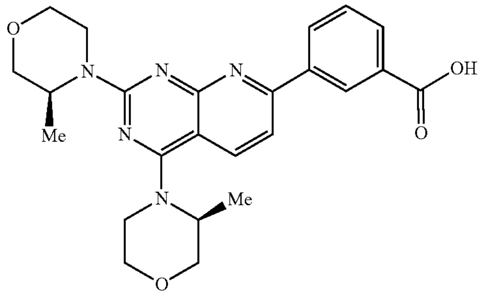 [SMILES: C[C@H]1COCCN1c1nc(N2CCOC[C@@H]2C)c2ccc(-c3cccc(C(=O)O)c3)nc2n1]
Monomer AL
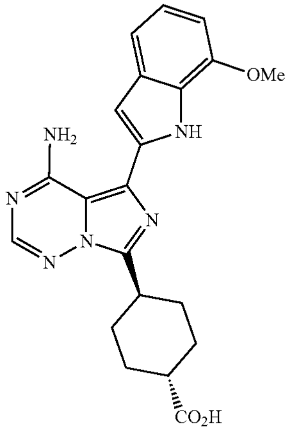 [SMILES: COc1cccc2cc(-c3nc([C@H]4CC[C@H](C(=O)O)CC4)n4ncnc(N)c34)[nH]c12]
Monomer AM
TABLE 3-continued
Active Site inhibitor monomers
Active Site Inhibitor
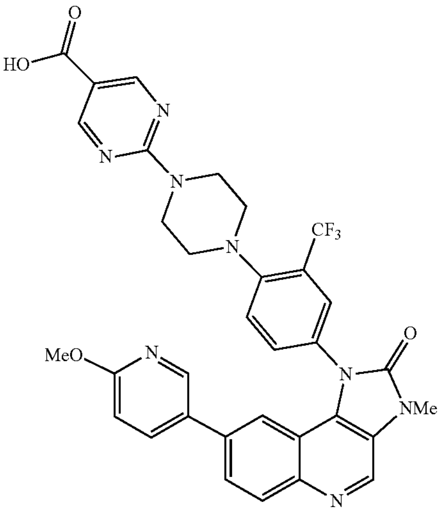 [SMILES: COc1ccc(-c2ccc3ncc4c(c3c2)n(-c2ccc(N3CCN(c5ncc(C(=O)O)cn5)CC3)c(C(F)(F)F)c2)c(=O)n4C)cn1]
Monomer AN
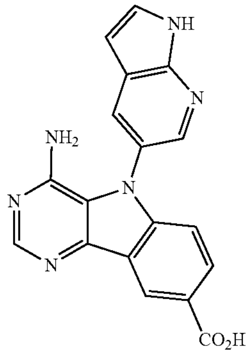 [SMILES: Nc1ncnc2c3cc(C(=O)O)ccc3n(-c3cnc4[nH]ccc4c3)c12]
Monomer AO
TABLE 4
Amine containing pre- and post-linkers.
Amide containing block
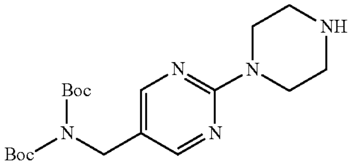 [SMILES: CC(C)(C)OC(=O)N(Cc1cnc(N2CCNCC2)nc1)C(=O)OC(C)(C)C]
Building block A TABLE 4-continued
| Amine containing pre- and post-linkers. Amide containing block |
|---|
| 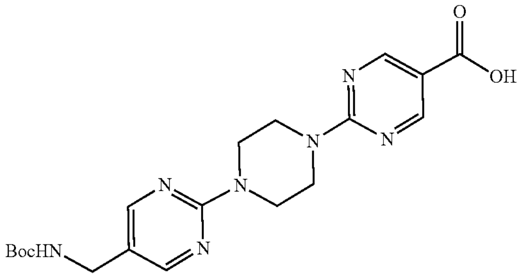 [SMILES: CC(C)(C)OC(=O)NCc1cnc(N2CCN(c3ncc(C(=O)O)cn3)CC2)nc1] Building block B |
| 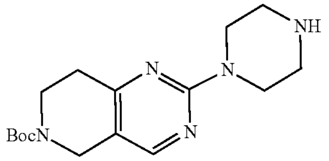 [SMILES: CC(C)(C)OC(=O)N1CCc2nc(N3CCNCC3)ncc2C1] Building block C |
| 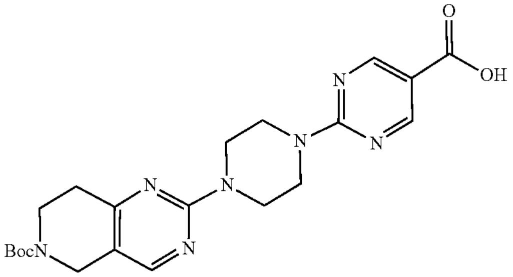 [SMILES: CC(C)(C)OC(=O)N1CCc2nc(N3CCN(c4ncc(C(=O)O)cn4)CC3)ncc2C1] Building block D |
| 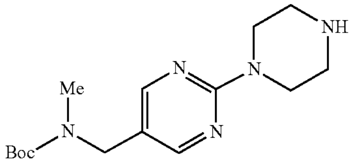 [SMILES: CN(Cc1cnc(N2CCNCC2)nc1)C(=O)OC(C)(C)C] Building block E |
| 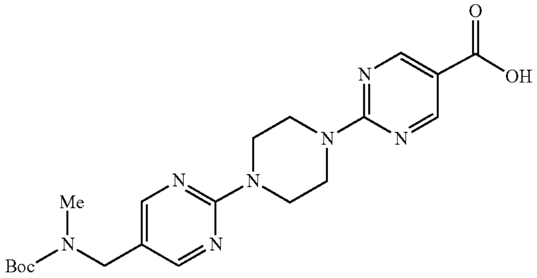 [SMILES: CN(Cc1cnc(N2CCN(c3ncc(C(=O)O)cn3)CC2)nc1)C(=O)OC(C)(C)C] Building block F |

TABLE 4-continued
| Amine containing pre- and post-linkers. Amide containing block |
|---|
| 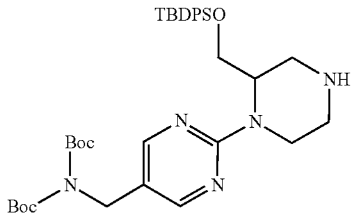 |
| Building block G |
| 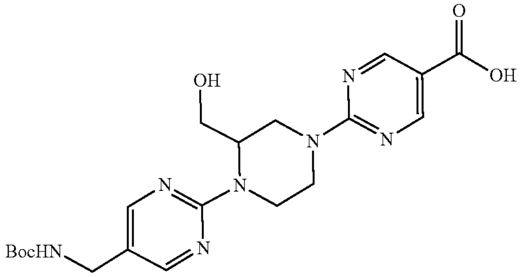 [SMILES: CC(C)(C)OC(=O)NCc1cnc(N2CCN(c3ncc(C(=O)O)cn3)CC2CO)nc1] |
| Building block H |
| 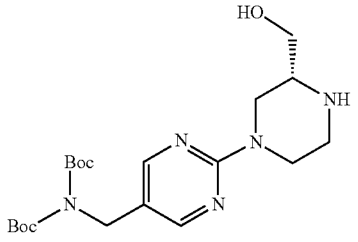 [SMILES: CC(C)(C)OC(=O)N(Cc1cnc(N2CCN[C@@H](CO)C2)nc1)C(=O)OC(C)(C)C] |
| Building block I |
| 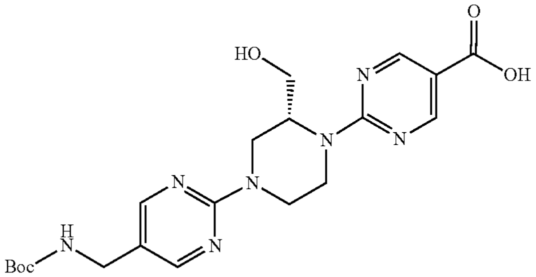 [SMILES: CC(C)(C)OC(=O)NCc1cnc(N2CCN(c3ncc(C(=O)O)cn3)[C@@H](CO)C2)nc1] |
| Building block J |
| 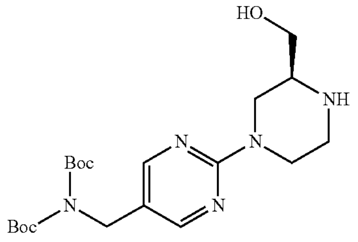 [SMILES: CC(C)(C)OC(=O)N(Cc1cnc(N2CCN[C@H](CO)C2)nc1)C(=O)OC(C)(C)C] |
| Building block K |

TABLE 4-continued
| Amine containing pre- and post-linkers. Amide containing block |
| --- |
| 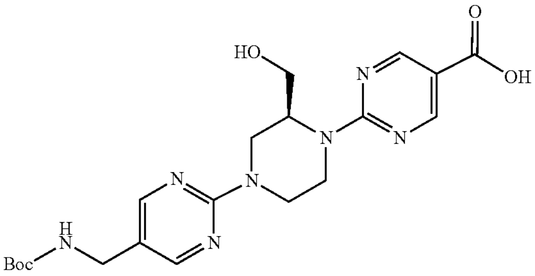 [SMILES: CC(C)(C)OC(=O)NCc1cnc(N2CCN(c3ncc(C(=O)O)cn3)[C@H](CO)C2)nc1] |
| Building block L |
| 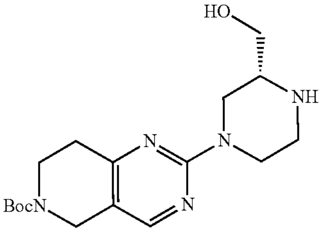 [SMILES: CC(C)(C)OC(=O)N1CCc2nc(N3CCN[C@@H](CO)C3)ncc2C1] |
| Building block M |
| 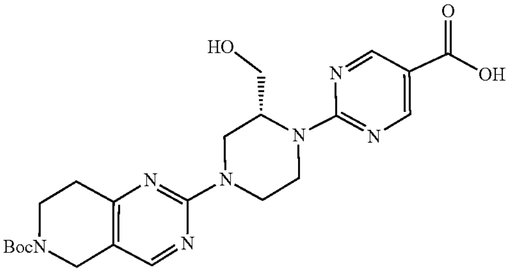 [SMILES: CC(C)(C)OC(=O)N1CCc2nc(N3CCN(c4ncc(C(=O)O)cn4)[C@@H](CO)C3)ncc2C1] |
| Building block N |
| 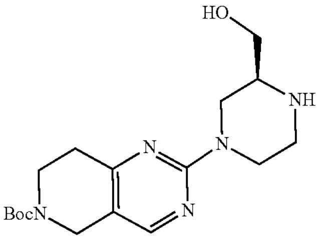 [SMILES: CC(C)(C)OC(=O)N1CCc2nc(N3CCN[C@H](CO)C3)ncc2C1] |
| Building block O |
| 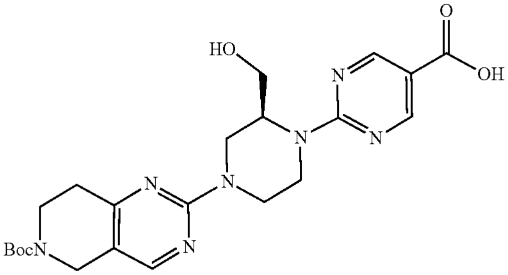 [SMILES: CC(C)(C)OC(=O)N1CCc2nc(N3CCN(c4ncc(C(=O)O)cn4)[C@H](CO)C3)ncc2C1] |
| Building block P |

TABLE 4-continued
| Amine containing pre- and post-linkers. Amide containing block |
| --- |
| 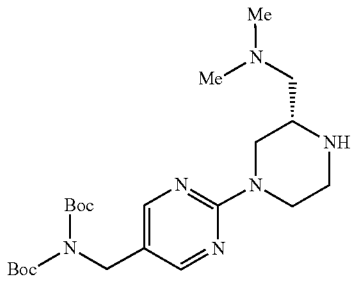 [SMILES: CN(C)C[C@H]1CN(c2ncc(CN(C(=O)OC(C)(C)C)C(=O)OC(C)(C)C)cn2)CCN1] Building block Q |
| 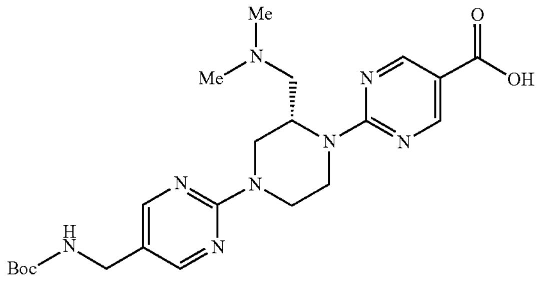 [SMILES: CN(C)C[C@H]1CN(c2ncc(CNC(=O)OC(C)(C)C)cn2)CCN1c1ncc(C(=O)O)cn1] Building block R |
| 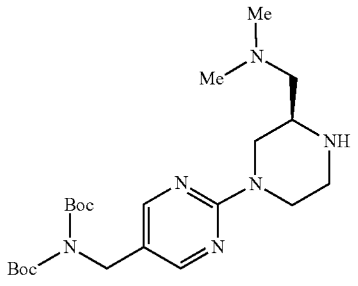 [SMILES: CN(C)C[C@@H]1CN(c2ncc(CN(C(=O)OC(C)(C)C)C(=O)OC(C)(C)C)cn2)CCN1] Building block S |
| 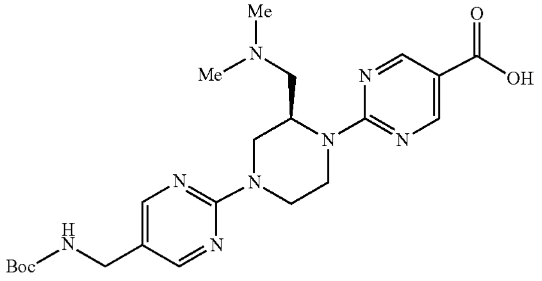 [SMILES: CN(C)C[C@@H]1CN(c2ncc(CNC(=O)OC(C)(C)C)cn2)CCN1c1ncc(C(=O)O)cn1] Building block T |

TABLE 4-continued
| Amine containing pre- and post-linkers. Amide containing block |
| --- |
| 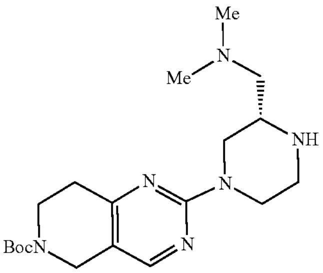 [SMILES: CN(C)C[C@H]1CN(c2ncc3c(n2)CCN(C(=O)OC(C)(C)C)C3)CCN1] |
| Building block U |
| 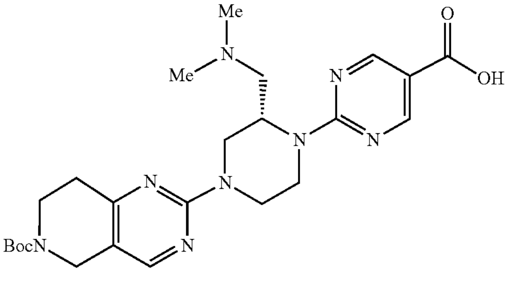 [SMILES: CN(C)C[C@H]1CN(c2ncc3c(n2)CCN(C(=O)OC(C)(C)C)C3)CCN1c1ncc(C(=O)O)cn1] |
| Building block V |
| 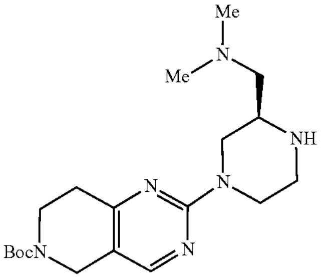 [SMILES: CN(C)C[C@@H]1CN(c2ncc3c(n2)CCN(C(=O)OC(C)(C)C)C3)CCN1] |
| Building block W |
| 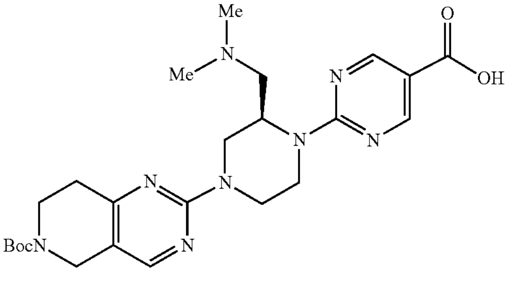 [SMILES: CN(C)C[C@@H]1CN(c2ncc3c(n2)CCN(C(=O)OC(C)(C)C)C3)CCN1c1ncc(C(=O)O)cn1] |
| Building block X |
| 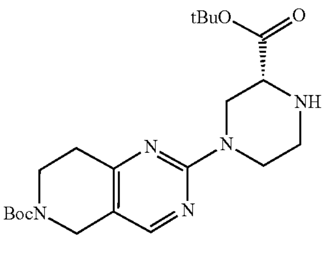 [SMILES: CC(C)(C)OC(=O)[C@H]1CN(c2ncc3c(n2)CCN(C(=O)OC(C)(C)C)C3)CCN1] |
| Building block Y |

TABLE 4-continued
| Amine containing pre- and post-linkers. Amide containing block |
|---|
| 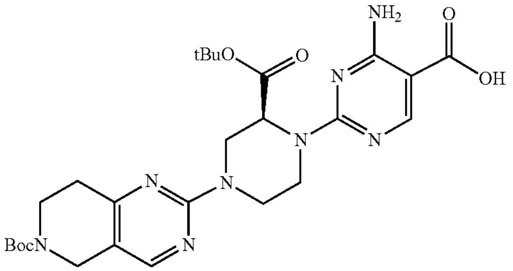 [SMILES: CC(C)(C)OC(=O)[C@@H]1CN(c2ncc3c(n2)CCN(C(=O)OC(C)(C)C)C3)CCN1c1ncc(C(=O)O)c(N)n1] Building block Z |
| 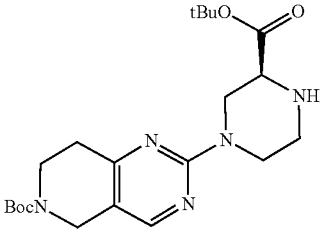 [SMILES: CC(C)(C)OC(=O)[C@@H]1CN(c2ncc3c(n2)CCN(C(=O)OC(C)(C)C)C3)CCN1] Building block AA |
| 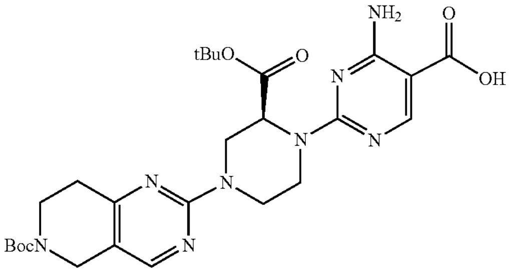 [SMILES: CC(C)(C)OC(=O)[C@@H]1CN(c2ncc3c(n2)CCN(C(=O)OC(C)(C)C)C3)CCN1c1ncc(C(=O)O)c(N)n1] Building block AB |
| 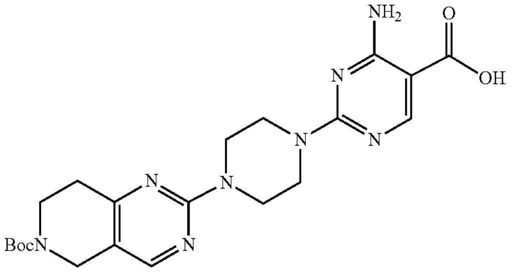 [SMILES: CC(C)(C)OC(=O)N1CCc2nc(N3CCN(c4ncc(C(=O)O)c(N)n4)CC3)ncc2C1] Building block AC |
| 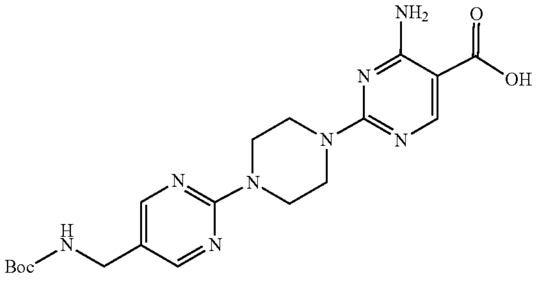 [SMILES: CC(C)(C)OC(=O)NCc1cnc(N2CCN(c3ncc(C(=O)O)c(N)n3)CC2)nc1] Building block AD |

TABLE 4-continued
| Amine containing pre- and post-linkers. Amide containing block |
|---|
| 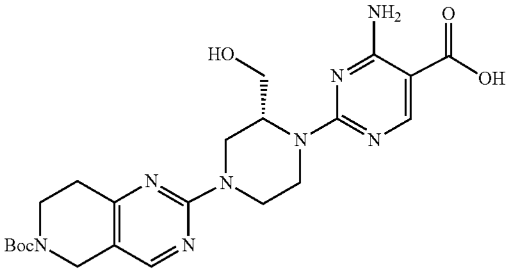 [SMILES: CC(C)(C)OC(=O)N1CCc2nc(N3CCN(c4ncc(C(=O)O)c(N)n4)[C@@H](CO)C3)ncc2C1] |
| Building block AE |
| 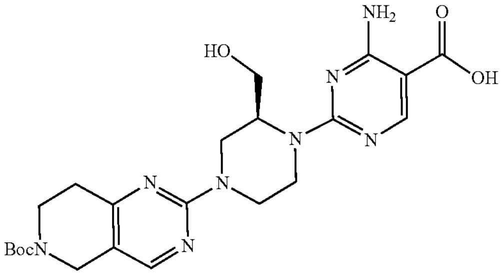 [SMILES: CC(C)(C)OC(=O)N1CCc2nc(N3CCN(c4ncc(C(=O)O)c(N)n4)[C@H](CO)C3)ncc2C1] |
| Building block AF |
| 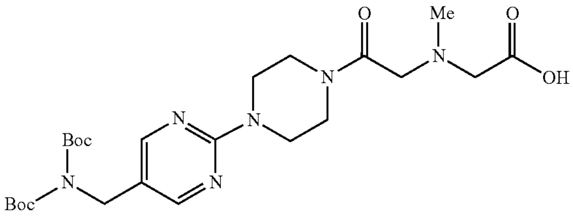 [SMILES: CN(CC(=O)O)CC(=O)N1CCN(c2ncc(CN(C(=O)OC(C)(C)C)C(=O)OC(C)(C)C)cn2)CC1] |
| Building block AG |
| 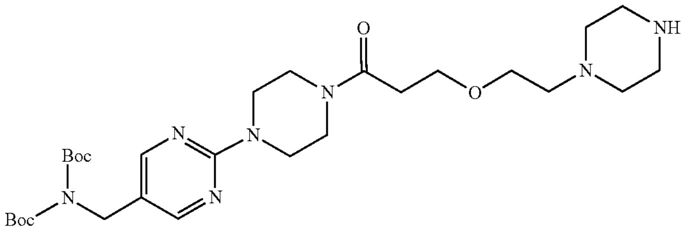 [SMILES: CC(C)(C)OC(=O)N(Cc1cnc(N2CCN(C(=O)CCOCCN3CCNCC3)CC2)nc1)C(=O)OC(C)(C)C] |
| Building block AH |
| 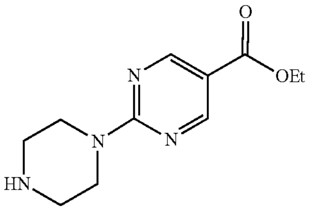 [SMILES: CCOC(=O)c1cnc(N2CCNCC2)nc1] |
| Building block AI |

TABLE 4-continued
| Amine containing pre- and post-linkers. Amide containing block |
|---|
| 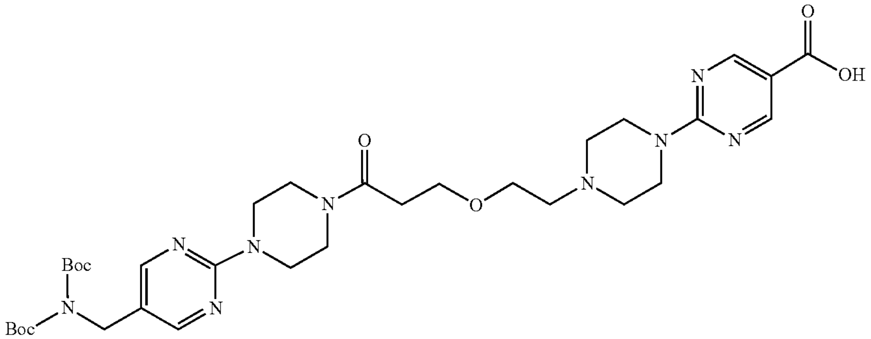 [SMILES: CC(C)(C)OC(=O)N(Cc1cnc(N2CCN(C(=O)CCOCCN3CCN(c4ncc(C(=O)O)cn4)CC3)CC2)nc1)C(=O)OC(C)(C)C] Building block AJ |
| 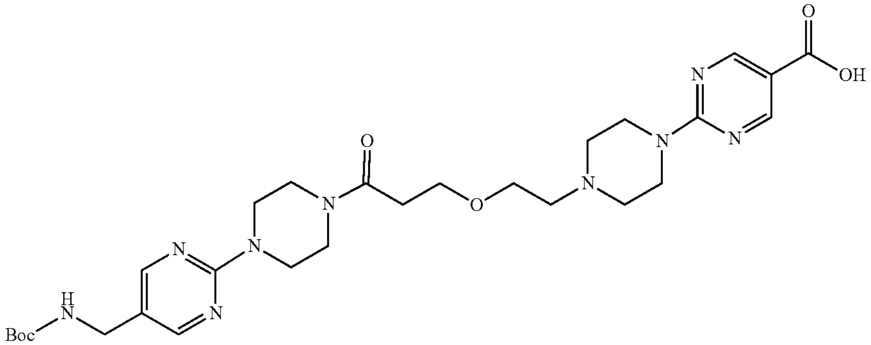 [SMILES: CC(C)(C)OC(=O)NCc1cnc(N2CCN(C(=O)CCOCCN3CCN(c4ncc(C(=O)O)cn4)CC3)CC2)nc1] Building block AK |
| 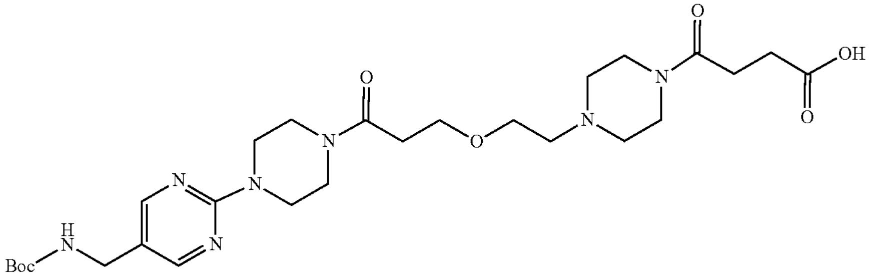 [SMILES: CC(C)(C)OC(=O)NCc1cnc(N2CCN(C(=O)CCOCCN3CCN(C(=O)CCC(=O)O)CC3)CC2)nc1] Building block AL |
| 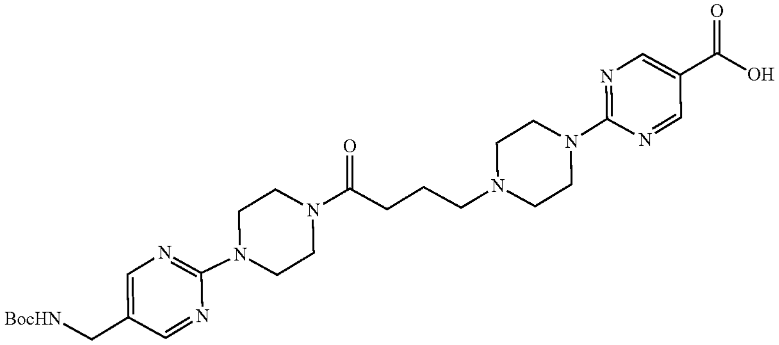 [SMILES: CC(C)(C)OC(=O)NCc1cnc(N2CCN(C(=O)CCCN3CCN(c4ncc(C(=O)O)cn4)CC3)CC2)nc1] Building block AM |

TABLE 4-continued
| Amine containing pre- and post-linkers. Amide containing block |
| --- |
| 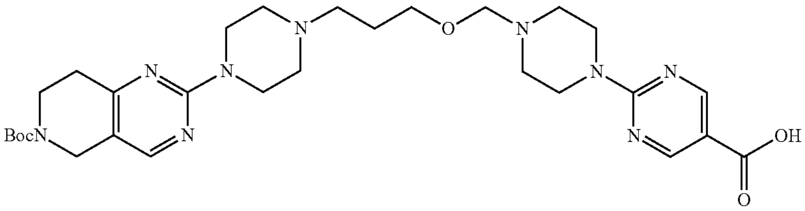 [SMILES: CC(C)(C)OC(=O)N1CCc2nc(N3CCN(CCCOCN4CCN(c5ncc(C(=O)O)cn5)CC4)CC3)ncc2C1] Building block AN |
| 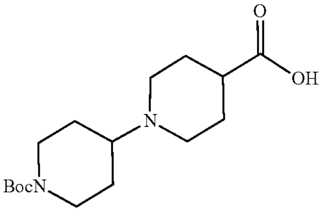 [SMILES: CC(C)(C)OC(=O)N1CCC(N2CCC(C(=O)O)CC2)CC1] Building block AO |
| 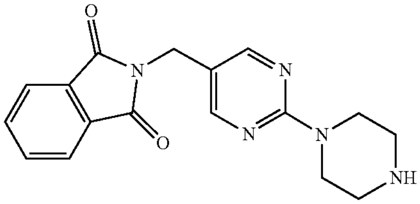 [SMILES: O=C1c2ccccc2C(=O)N1Cc1cnc(N2CCNCC2)nc1] Building block AP |
| 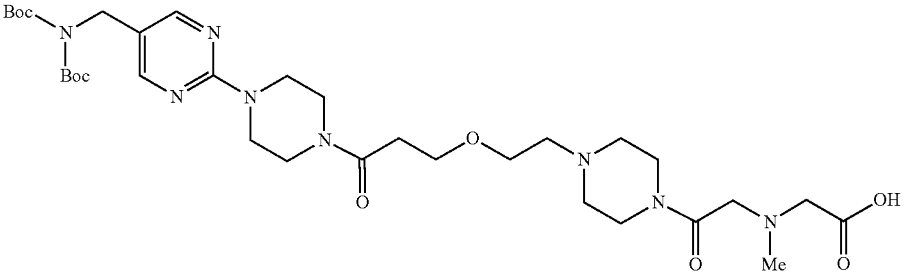 [SMILES: CN(CC(=O)O)CC(=O)N1CCN(CCOCCC(=O)N2CCN(c3ncc(CN(C(=O)OC(C)(C)C)C(=O)OC(C)(C)C)cn3)CC2)CC1] Building block AQ |
| 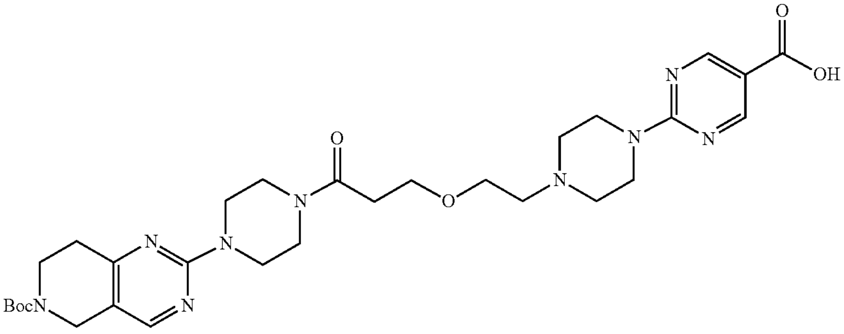 [SMILES: CC(C)(C)OC(=O)N1CCc2nc(N3CCN(C(=O)CCOCCN4CCN(c5ncc(C(=O)O)cn5)CC4)CC3)ncc2C1] Building block AR |

TABLE 4-continued
| Amine containing pre- and post-linkers. Amide containing block |
| --- |
| 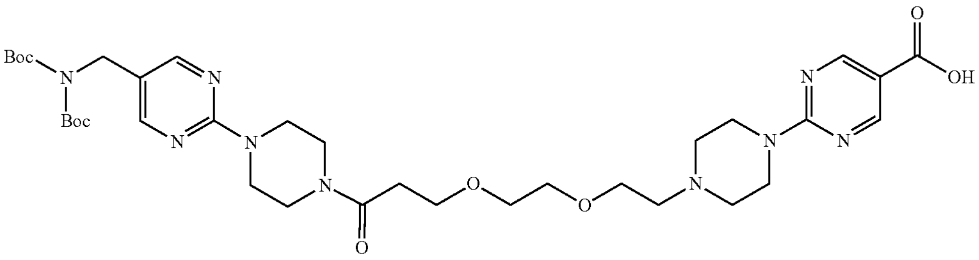 [SMILES: CC(C)(C)OC(=O)N(Cc1cnc(N2CCN(C(=O)CCOCCOCCN3CCN(c4ncc(C(=O)O)cn4)CC3)CC2)nc1)C(=O)OC(C)(C)C] |
| Building block AS |
| 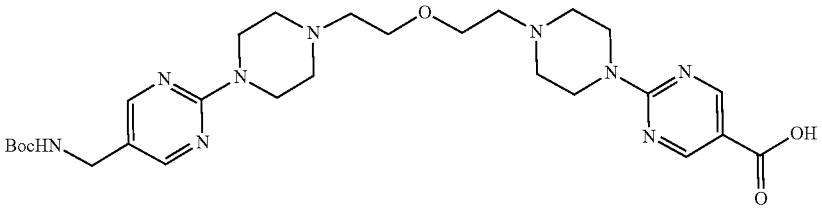 [SMILES: CC(C)(C)OC(=O)NCc1cnc(N2CCN(CCOCCN3CCN(c4ncc(C(=O)O)cn4)CC3)CC2)nc1] |
| Building block AT |
| 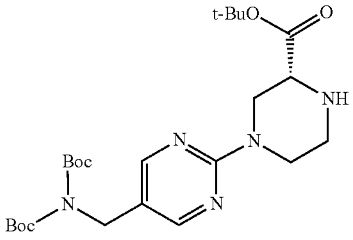 [SMILES: CC(C)(C)OC(=O)[C@H]1CN(c2ncc(CN(C(=O)OC(C)(C)C)C(=O)OC(C)(C)C)cn2)CCN1] |
| Building block AU |
| 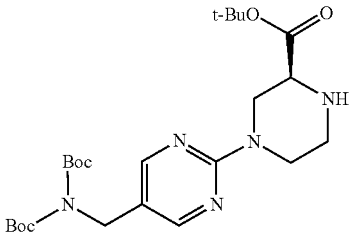 [SMILES: CC(C)(C)OC(=O)[C@@H]1CN(c2ncc(CN(C(=O)OC(C)(C)C)C(=O)OC(C)(C)C)cn2)CCN1] |
| Building block AV |
| 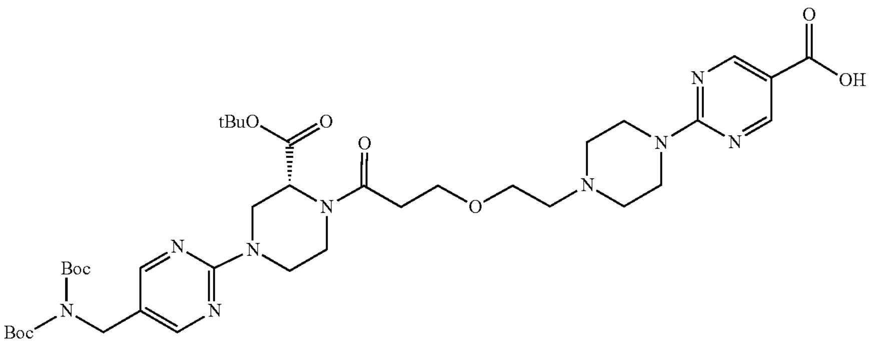 [SMILES: CC(C)(C)OC(=O)[C@H]1CN(c2ncc(CN(C(=O)OC(C)(C)C)C(=O)OC(C)(C)C)cn2)CCN1C(=O)CCOCCN1CCN(c2ncc(C(=O)O)cn2)CC1] |
| Building block AW |

TABLE 4-continued
| Amine containing pre- and post-linkers. Amide containing block |
| --- |
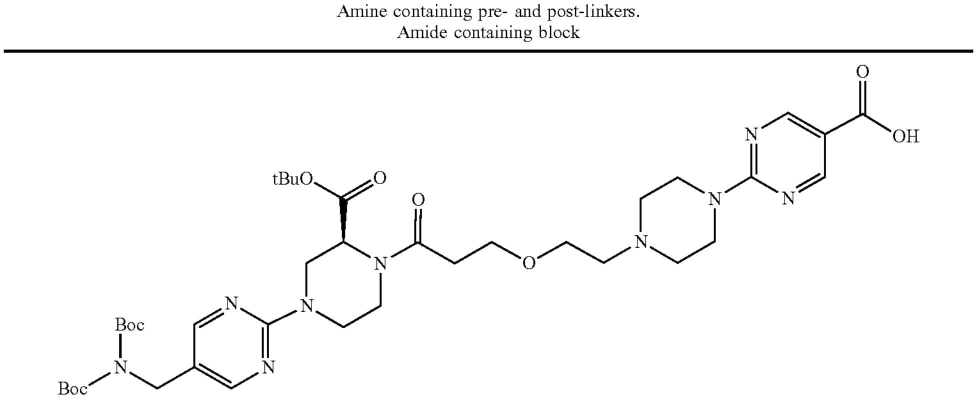
Building block AX
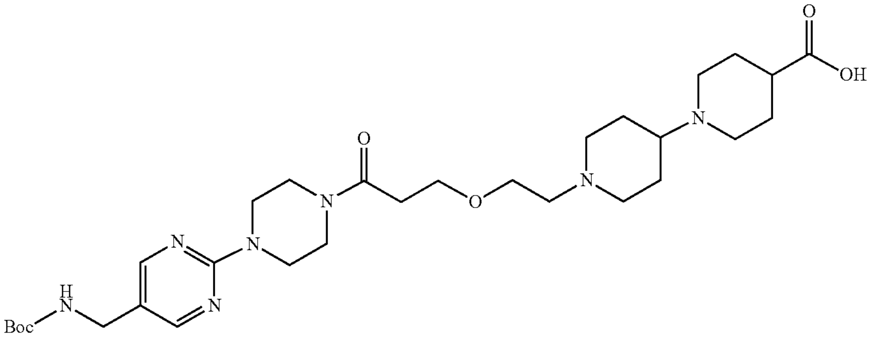 [SMILES: CC(C)(C)OC(=O)NCc1cnc(N2CCN(C(=O)CCOCCN3CCC(N4CCC(C(=O)O)CC4)CC3)CC2)nc1]
Building block AY
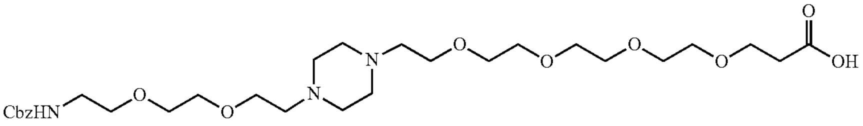 [SMILES: O=C(O)CCOCCOCCOCCOCCN1CCN(CCOCCOCCNC(=O)OCc2ccccc2)CC1]
Building block AZ
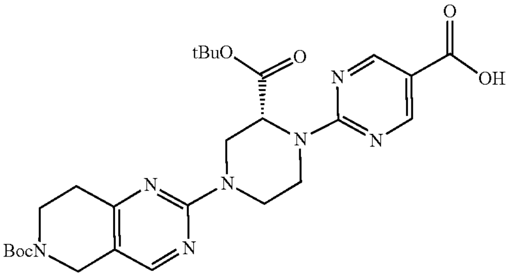 [SMILES: CC(C)(C)OC(=O)[C@H]1CN(c2ncc3c(n2)CCN(C(=O)OC(C)(C)C)C3)CCN1c1ncc(C(=O)O)cn1]
Building block BA
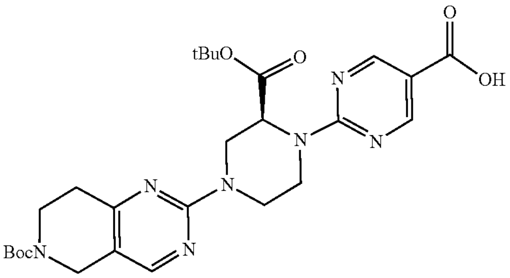 [SMILES: CC(C)(C)OC(=O)[C@@H]1CN(c2ncc3c(n2)CCN(C(=O)OC(C)(C)C)C3)CCN1c1ncc(C(=O)O)cn1]
Building block BB TABLE 4-continued
Amine containing pre- and post-linkers.
Amide containing block
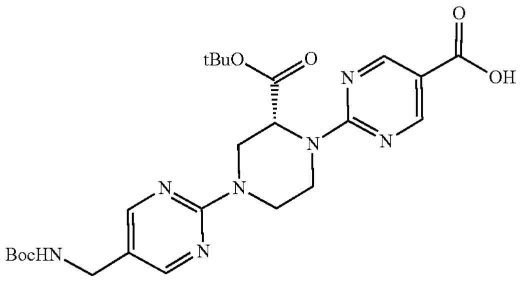 [SMILES: CC(C)(C)OC(=O)NCc1cnc(N2CCN(c3ncc(C(=O)O)cn3)[C@@H](C(=O)OC(C)(C)C)C2)nc1]
Building block BC
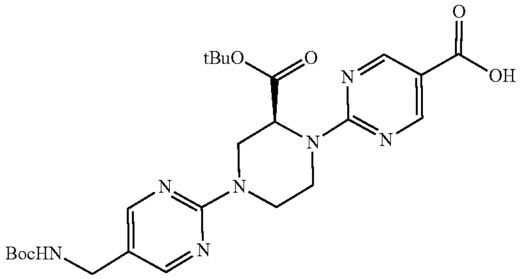 [SMILES: CC(C)(C)OC(=O)NCc1cnc(N2CCN(c3ncc(C(=O)O)cn3)[C@H](C(=O)OC(C)(C)C)C2)nc1]
Building block BD
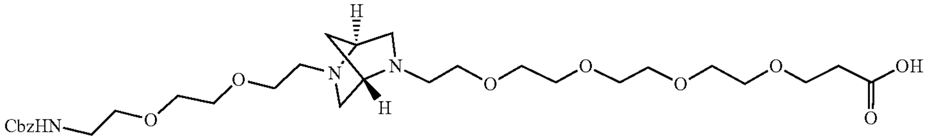
Building block BE
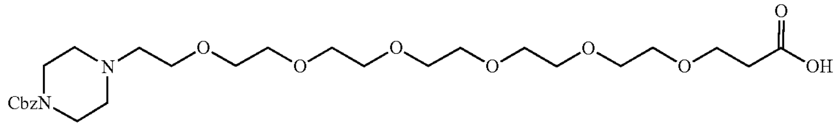 [SMILES: O=C(O)CCOCCOCCOCCOCCOCCOCCN1CCN(C(=O)OCc2ccccc2)CC1]
Building block BF
Preparation of Active Site Inhibitor Monomers
Monomer A. 5-(4-amino-1-(4-(aminomethyl)benzyl)-1H-pyrazolo[3,4-d]pyrimidin-3-yl)benzo[d]oxazol-2-amine trifluoroacetic acid salt
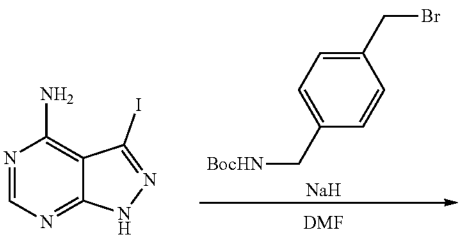
-continued
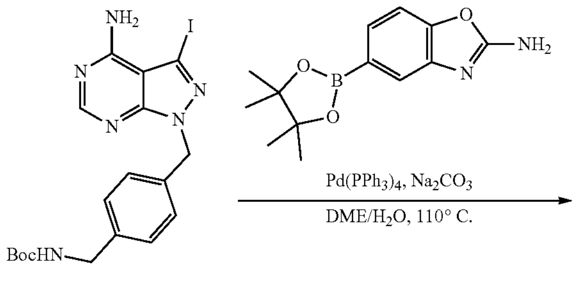

-continued

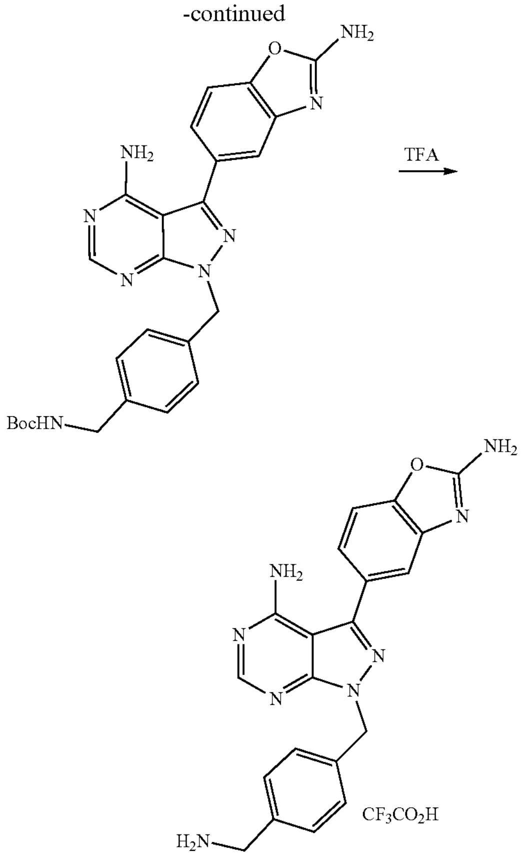

Step 1: Synthesis of tert-butyl 4-((4-amino-3-iodo-1H-pyrazolo[3,4-d]pyrimidin-1-yl)methyl)benzylcarbamate To a solution of 3-iodo-1H-pyrazolo[3,4-d]pyrimidin-4-amine (3.8 g, 14.56 mmol, 1.0 equiv) in DMF (20 mL) was added NaH (582.27 mg, 14.56 mmol, 60 wt. %, 1.0 equiv) at 0° C. and the reaction solution was stirred at this temperature for 30 min, then tert-butyl 4-(bromomethyl)benzylcarbamate (4.59 g, 15.29 mmol, 1.05 equiv) was added to the reaction at 0° C. and the reaction solution was stirred at room temperature for 2 h. The solution was poured into $H_2O$ (80 mL) and the solid that precipitated out was filtered. The solid cake was washed with $H_2O$ (2×10 mL) and then dried under reduced pressure to give tert-butyl 4-((4-amino-3-iodo-1H-pyrazolo[3,4-d]pyrimidin-1-yl)methyl)benzylcarbamate (5 g, 53% yield) as a yellow solid. LCMS (ESI) m/z: [M+Na] calcd for $C_{18}H_{21}N_6O_2$: 503.07; found 503.2.

Step 2: Synthesis of tert-butyl 4-((4-amino-3-(2-aminobenzo[d]oxazol-5-yl)-1H-pyrazolo[3,4-d]pyrimidin-1-yl)methyl)benzylcarbamate To a bi-phasic suspension of tert-butyl 4-((4-amino-3-iodo-1H-pyrazolo[3,4-d]pyrimidin-1-yl)methyl)benzylcarbamate (5 g, 7.68 mmol, 1.0 equiv), 5-(4,4,5,5-tetramethyl-1,3,2-dioxaborolan-2-yl)benzo[d]oxazol-2-amine (2.40 g, 9.22 mmol, 1.2 equiv) and $Pd(PPh_3)_4$ (887.66 mg, 768.16 μmol, 0.1 equiv) in DME (100 mL) and $H_2O$ (50 mL) was added $Na_2CO_3$ (1.91 g, 23.04 mmol, 3.0 equiv) at room temperature under $N_2$. The mixture was stirred at 110° C. for 3 h. The reaction mixture was cooled to room temperature and filtered, the filtrate was extracted by EtOAc (3×50 mL). The organic phases were combined and washed with brine (10 mL), dried over $Na_2SO_4$, filtered, and the filtrate was concentrated under reduced pressure to give a residue. The residue was purified by silica gel chromatography (0→20% MeOH/EtOAc) to give tert-butyl 4-((4-amino-3-(2-aminobenzo[d]oxazol-5-yl)-1H-pyrazolo[3,4-d]pyrimidin-1-yl)methyl)benzylcarbamate (4.5 g, 82% yield) as a yellow solid. LCMS (ESI) m/z: [M+H] calcd for $C_{25}H_{26}N_8O_3$: 487.22; found 487.2.

Step 3: Synthesis of 5-(4-amino-1-(4-(aminomethyl)benzyl)-1H-pyrazolo[3,4-d] pyrimidin-3-yl)benzol[d]oxazol-2-amine To a solution of tert-butyl 4-((4-amino-3-(2-aminobenzo[d]oxazol-5-yl)-1H-pyrazolo[3,4-d]pyrimidin-1-yl)methyl)benzylcarbamate (4.5 g, 6.29 mmol, 1.0 equiv) in DCM (50 mL) was added TFA (30.80 g, 270.12 mmol, 20 mL, 42.95 equiv) at 0° C. The reaction solution was stirred at room temperature for 2 h. The reaction solution was concentrated under reduced pressure to give a residue, which was dissolved in 10 mL of MeCN, then poured into MTBE (100 mL). The solid that precipitated was then filtered and the solid cake was dried under reduced pressure to give 5-[4-amino-1-[[4-(aminomethyl)phenyl]methyl]pyrazolo[3,4-d]pyrimidin-3-yl]-1,3-benzoxazol-2-amine (2.22 g, 71% yield, TFA) as a yellow solid. LCMS (ESI) m/z: [M+H] calcd for $C_{20}H_{18}N_8O$: 387.16; found 387.1.

Monomer B. 2-(4-amino-1-(4-aminobutyl)-1H-pyrazolo[3,4-d]pyrimidin-3-yl)-1H-indol-6-ol trifluoroacetic acid salt

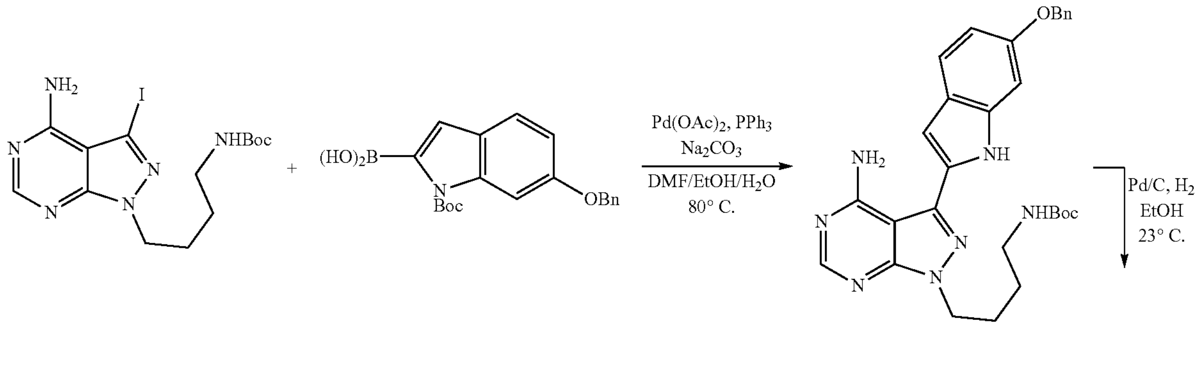

-continued

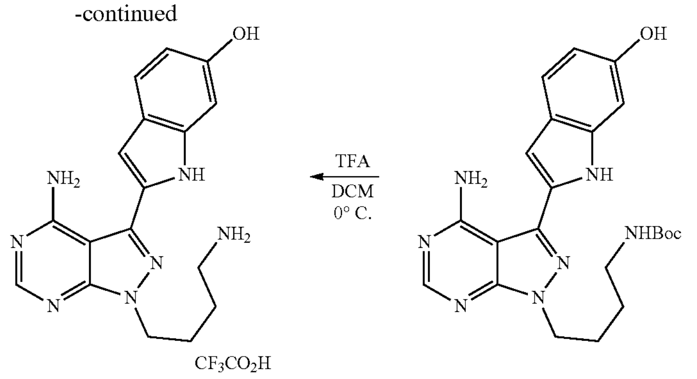

Step 1: Synthesis of tert-butyl N-(4-{4-amino-3-[6-(benzyloxy)-1H-indol-2-yl]-1H-pyrazolo[3,4-d]pyrimidin-1-yl}butyl)carbamate To a mixture of tert-butyl (4-(4-amino-3-iodo-1H-pyrazolo[3,4-d]pyrimidin-1-yl)butyl)carbamate (300 mg, 694 μmol, 1.0 equiv) and (6-(benzyloxy)-1-(tert-butoxycarbonyl)-1H-indol-2-yl)boronic acid (763 mg, 2.08 mmol, 3.0 equiv) in DMF (2.6 mL), EtOH (525 μL), and $H_2O$ (350 μL) were added $Pd(OAc)_2$ (15.5 mg, 69 μmol, 0.1 equiv), triphenylphosphine (36.1 mg, 138 μmol, 0.2 equiv), and sodium carbonate (440 mg, 4.16 mmol, 6.0 equiv). The reaction was heated at 80° C. for 20 h, cooled to room temperature, and quenched with $H_2O$ (10 mL) and EtOAc (10 mL). The mixture was transferred to a separatory funnel and the aqueous phase was extracted with EtOAc (3×20 mL). The combined organic phase was washed with sat. aq. NaCl (1×20 mL), dried over $Na_2SO_4$, filtered, and concentrated under reduced pressure. The crude material was purified by silica gel chromatography (20→85% EtOAc/heptane) to provide the product (201 mg, 46% yield) as an orange solid. LCMS (ESI) m/z: [M+H] calcd for $C_{29}H_{33}N_7O_3$: 528.27; found 528.2.

Step 2: Synthesis of tert-butyl (4-(4-amino-3-(6-hydroxy-1H-indol-2-yl)-1H-pyrazolo[3,4-d]pyrimidin-1-yl)butyl)carbamate To a solution of tert-butyl N-(4-{4-amino-3-[6-(benzyloxy)-1H-indol-2-yl]-1H-pyrazolo[3,4-d]pyrimidin-1-yl}butyl)carbamate (1.0 equiv) in EtOH is added Pd/C (10 mol %). The reaction is purged with $H_2$ and the reaction allowed to stir under an atmosphere of H2 until consumption of starting material, as determined by LCMS. The reaction is then diluted with EtOAc, filtered over Celite, and concentrated under reduced pressure. The resultant residue is purified by silica gel chromatography to afford the desired product.

Step 3: Synthesis of 2-(4-amino-1-(4-aminobutyl)-1H-pyrazolo[3,4-d]pyrimidin-3-yl)-1H-indol-6-ol To a solution of tert-butyl (4-(4-amino-3-(6-hydroxy-1H-indol-2-yl)-1H-pyrazolo[3,4-d]pyrimidin-1-yl)butyl)carbamate (1.0 equiv) in anhydrous DCM is added TFA (50 equiv.) dropwise at 0° C. The reaction is stirred at 0° C. and warmed to room temperature. Once the reaction is complete, as determined by LCMS, the reaction is concentrated under reduced pressure. The residue is triturated with MeCN, then dripped into MTBE over 10 min. The supernatant is removed and the precipitate is collected by filtration under $N_2$ to give 2-(4-amino-1-(4-aminobutyl)-1H-pyrazolo[3,4-d]pyrimidin-3-yl)-1H-indol-6-ol.

Monomer C. 5-(4-amino-1-((1,2,3,4-tetrahydroisoquinolin-6-yl)methyl)-1H-pyrazolo[3,4-d]pyrimidin-3-yl)benzo[d]oxazol-2-amine trifluoroacetic acid salt

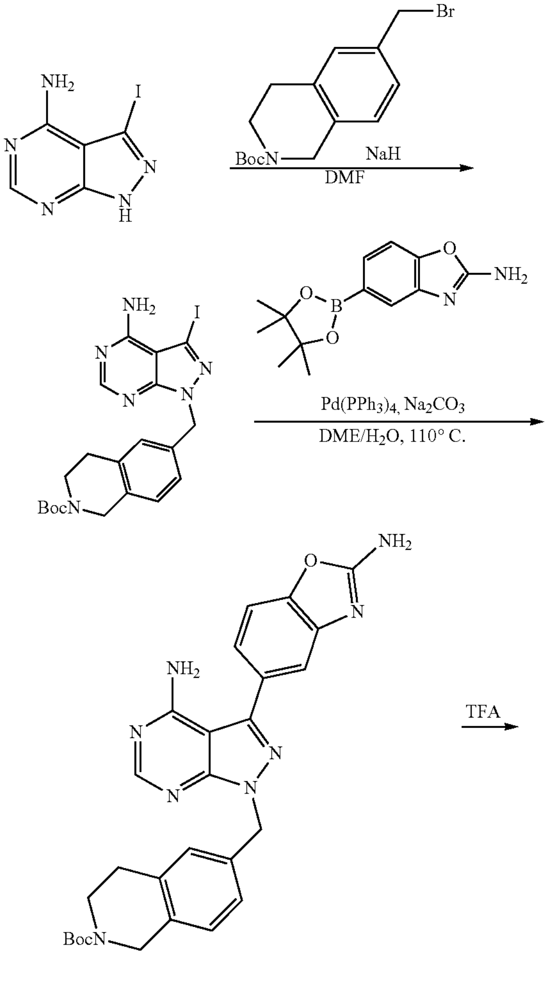

-continued

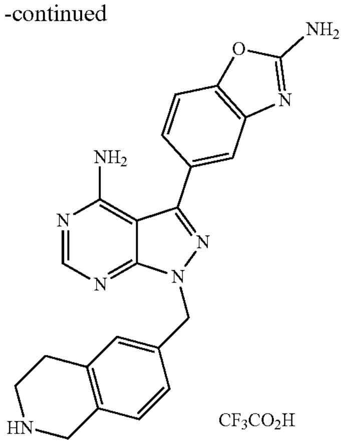

Step 1: Synthesis of tert-butyl 6-((4-amino-3-iodo-1H-pyrazolo[3,4-d]pyrimidin-1-yl)methyl)-3,4-dihydroisoquinoline-2(1H)-carboxylate To a suspension of 3-iodo-1H-pyrazolo[3,4-d]pyrimidin-4-amine (5 g, 19.16 mmol, 1.0 equiv) in DMF (50.0 mL) was added NaH (766.22 mg, 19.16 mmol, 60 wt. %, 1.0 equiv) at 4° C. The mixture was stirred at 4° C. for 30 min. To the reaction mixture was added tert-butyl 6-(bromomethyl)-3,4-dihydroisoquinoline-2(1H)-carboxylate (6.87 g, 21.07 mmol, 1.1 equiv) in DMF (30 mL) at 4° C. The mixture was stirred at room temperature for 2 h. The mixture was then cooled to 4° C. and $H_2O$ (400 mL) was added and the mixture was stirred for 30 min. The resulting precipitate was collected by filtration to give crude tert-butyl 6-((4-amino-3-iodo-1H-pyrazolo[3,4-d]pyrimidin-1-yl)methyl)-3,4-dihydroisoquinoline-2(1H)-carboxylate (9.7 g, 76% yield) as a light yellow solid. The crude product was used for the next step directly.

Step 2: Synthesis of tert-butyl 6-((4-amino-3-(2-aminobenzo[d]oxazol-5-yl)-1H-pyrazolo[3,4-d]pyrimidin-1-yl)methyl)-3,4-dihydroisoquinoline-2(1H)-carboxylate To a bi-phasic suspension of tert-butyl 6-((4-amino-3-iodo-1H-pyrazolo[3,4-d]pyrimidin-1-yl)methyl)-3,4-dihydroisoquinoline-2(1H)-carboxylate (9.7 g, 14.63 mmol, 1.0 equiv), 5-(4,4,5,5-tetramethyl-1,3,2-dioxaborolan-2-yl)benzo[d]oxazol-2-amine (4.57 g, 17.55 mmol, 1.2 equiv), and $Na_2CO_3$ (7.75 g, 73.14 mmol, 5.0 equiv) in DME (120.0 mL) and $H_2O$ (60 mL) was added $Pd(PPh_3)_4$ (1.69 g, 1.46 mmol, 0.1 equiv) at room temperature under $N_2$. The mixture was stirred at 110° C. for 3 h. The reaction mixture was then cooled to room temperature and partitioned between EtOAc (100 mL) and $H_2O$ (100 mL). The aqueous layer was separated and extracted with EtOAc (2×60 mL). The organic layers were combined, washed with brine (80 mL) and dried over anhydrous $Na_2SO_4$, filtered and the filtrate was concentrated under reduced pressure. The residue was purified by silica gel chromatography (1→100% EtOAc/petroleum ether, then 20→50% MeOH/EtOAc) to afford tert-butyl 6-((4-amino-3-(2-aminobenzo[d]oxazol-5-yl)-1H-pyrazolo[3,4-d]pyrimidin-1-yl)methyl)-3,4-dihydroisoquinoline-2(1H)-carboxylate (4.5 g, 58% yield) as a light yellow solid.

Step 3: Synthesis of 5-(4-amino-1-((1,2,3,4-tetrahydroisoquinolin-6-yl)methyl)-1H-pyrazolo[3,4-d]pyramidin-3-yl)benzo[d]oxazol-2-amine To neat TFA (32.5 mL, 438.97 mmol, 50.0 equiv) was added tert-butyl 6-((4-amino-3-(2-aminobenzo[d]oxazol-5-yl)-1H-pyrazolo[3,4-d]pyrimidin-1-yl)methyl)-3,4-dihydroisoquinoline-2(1H)-carboxylate (4.5 g, 8.78 mmol, 1.0 equiv) at room temperature. The mixture was stirred for 30 min and then concentrated under reduced pressure. The oily residue was triturated with MeCN (8 mL), then dripped into MTBE (350 mL) over 10 min. The supernatant was removed and then the precipitate was collected by filtration under $N_2$ to give 5-(4-amino-1-((1,2,3,4-tetrahydroisoquinolin-6-yl)methyl)-1H-pyrazolo[3,4-d]pyrimidin-3-yl)benzo[d]oxazol-2-amine (5.72 g, over 100% yield, TFA) as a light pink solid. LCMS (ESI) m/z: [M+H] calcd for $C_{22}H_{20}N_8O$: 413.18; found 413.2.

Monomer D. 2-(4-amino-1-(4-aminobutyl)-1H-pyrazolo[3,4-d]pyrimidin-3-yl)-1H-indol-7-ol trifluoroacetic acid salt

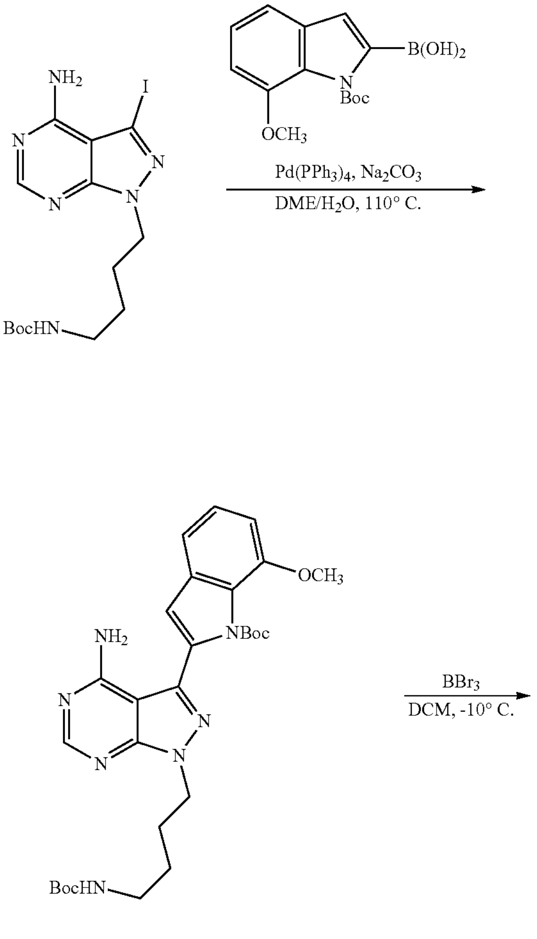

-continued

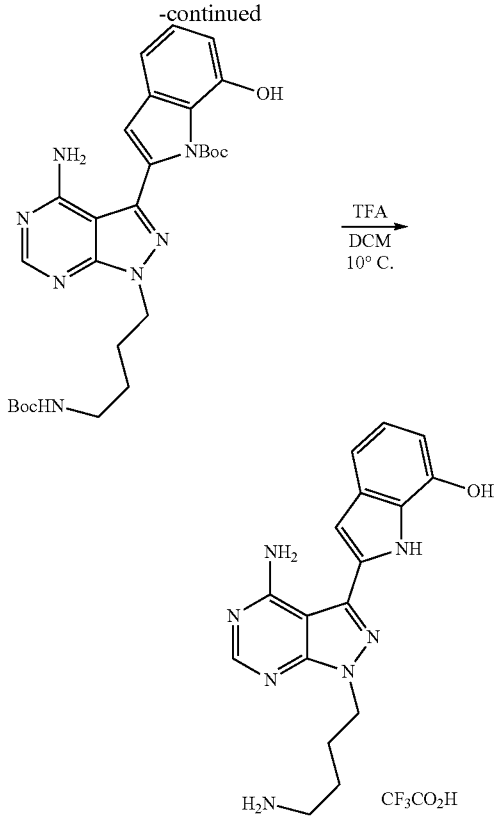

Step 2: Synthesis of tert-butyl 2-(4-amino-1-(4-((tert-butoxycarbonyl)amino)butyl)-1H-pyrazolo[3,4-d]pyrimidin-3-yl)-7-hydroxy-1H-indole-1-carboxylate To a solution of tert-butyl 2-(4-amino-1-(4-((tert-butoxycarbonyl)amino)butyl)-1H-pyrazolo[3,4-d]pyrimidin-3-yl)-7-methoxy-1H-indole-1-carboxylate (1.0 equiv) in DCM at −10° C. is added $BBr_3$ (2.0 equiv). The reaction is allowed to stir until consumption of starting material, as determined by LCMS. The reaction is quenched by slow addition of sat. aq. $NaHCO_3$, transferred to a separatory funnel and the mixture is extracted with DCM. The organic phase is washed with sat. aq. NaCl, dried over $Na_2SO_4$, filtered, and concentrated under reduced pressure. The desired product is isolated after chromatography on silica gel.

Step 3: Synthesis of 2-(4-amino-1-(4-aminobutyl)-1H-pyrazolo[3,4-d]pyrimidin-3-yl)-1H-indol-7-ol To a solution of tert-butyl 2-(4-amino-1-(4-((tert-butoxycarbonyl)amino)butyl)-1H-pyrazolo[3,4-d]pyrimidin-3-yl)-7-hydroxy-1H-indole-1-carboxylate (1.0 equiv) in DCM at 0° C. is added TFA dropwise. The reaction is stirred at 0° C. and warmed to room temperature. Once the reaction is complete, as determined by LCMS, the reaction is concentrated under reduced pressure. The residue is triturated with MeCN, then dripped into MTBE over 10 min. The supernatant is removed and the precipitate is collected by filtration under $N_2$ to give 2-(4-amino-1-(4-aminobutyl)-1H-pyrazolo[3,4-d]pyrimidin-3-yl)-1H-indol-7-ol.

Monomer E. 5-(4-amino-1-(piperidin-4-ylmethyl)-1H-pyrazolo[3,4-d]pyrimidin-3-yl)benzo[d]oxazol-2-amine trifluoroacetic acid salt

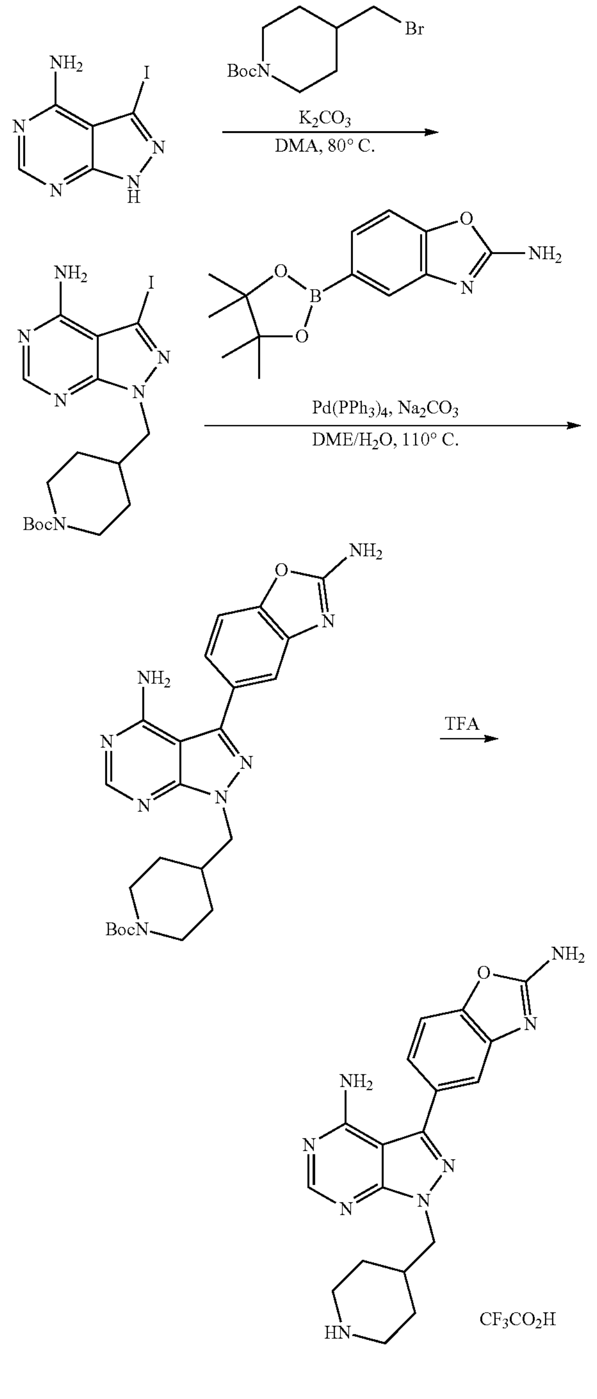

Step 1: Synthesis of tert-butyl 4-((4-amino-3-iodo-1H-pyrazolo[3,4-d]pyrimidin-1-yl)methyl)piperidine-1-carboxylate To a solution of 3-iodo-1H-pyrazolo[3,4-d]pyrimidin-4-amine (3 g, 11.49 mmol, 1.0 equiv) in DMA (30 mL) was added tert-butyl 4-(bromomethyl)piperidine-1-carboxylate (3.36 g, 12.07 mmol, 1.05 equiv) and $K_2CO_3$ (4.77 g, 34.48 mmol, 3.0 equiv), then the reaction was stirred at 80° C. for 3 h. The reaction mixture was filtered to remove $K_2CO_3$ and the filtrate was poured into $H_2O$ (200 mL). A solid precipitated was then filtered to give tert-butyl 4-((4-amino-3-iodo-1H-pyrazolo[3,4-d]pyrimidin-1-yl)methyl)piperidine-1-carboxylate (3 g, 57% yield) as a light yellow solid. LCMS (ESI) m/z: [M+H] calcd for $C_{16}H_{23}IN_6O_2$: 459.10; found 459.1.

Step 2: Synthesis of tert-butyl 4-((4-amino-3-(2-aminobenzo[d]oxazol-5-yl)-1H-pyrazolo[3,4-d]pyrimidin-1-yl)methyl)piperidine-1-carboxylate To a bi-phasic suspension of tert-butyl 4-((4-amino-3-iodo-1H-pyrazolo[3,4-d]pyrimidin-1-yl)methyl)piperidine-1-carboxylate (3 g, 6.55 mmol, 1.0 equiv) and 5-(4,4,5,5-tetramethyl-1,3,2-dioxaborolan-2-yl)benzo[d]oxazol-2-amine (2.04 g, 7.86 mmol, 1.2 equiv) and $Na_2CO_3$ (3.47 g, 32.73 mmol, 5.0 equiv) in DME (60 mL) and $H_2O$ (30 mL) was added $Pd(PPh_3)_4$ (756.43 mg, 654.60 μmol, 0.1 equiv) at room temperature under $N_2$. The mixture was stirred at 110° C. for 3 h and the two batches were combined together. The reaction mixture was cooled and partitioned between EtOAc (500 mL) and $H_2O$ (500 mL). The aqueous layer was separated and extracted with EtOAc (3×300 mL). All the organic layers were combined, washed with brine (20 mL), dried over anhydrous $Na_2SO_4$, filtered, and the filtrate was concentrated under reduced pressure to give tert-butyl 4-((4-amino-3-(2-aminobenzo[d]oxazol-5-yl)-1H-pyrazolo[3,4-d]pyrimidin-1-yl)methyl)piperidine-1-carboxylate (4.5 g, 74% yield) as a yellow solid. LCMS (ESI) m/z: [M+H] calcd for $C23H_{28}N_8O_3$: 465.24; found 465.2.

Step 3: Synthesis of 5-(4-amino-1-(piperidin-4-ylmethyl)-1H-pyrazolo[3,4-d]pyrimidin-3-yl)benzol[d]oxazol-2-amine A solution of tert-butyl 4-((4-amino-3-(2-aminobenzo[d]oxazol-5-yl)-1H-pyrazolo[3,4-d]pyrimidin-1-yl)methyl)piperidine-1-carboxylate (2.5 g, 5.38 mmol, 1.0 equiv) in TFA (25 mL) was stirred at room temperature for 30 min. The reaction solution was concentrated under reduced pressure to remove TFA. The residue was added to MTBE (400 mL) and a solid precipitated, which was then filtered to give 5-(4-amino-1-(piperidin-4-ylmethyl)-1H-pyrazolo[3,4-d]pyrimidin-3-yl)benzo[d]oxazol-2-amine (2.7 g, over 100% yield, TFA) as a yellow solid. LCMS (ESI) m/z: [M+H] calcd for $C_{18}H_{20}N_8O$: 365.18; found 365.1.

Monomer F. 2-(4-amino-1-(4-aminobutyl)-1H-pyrazolo[3,4-d]pyrimidin-3-yl)-1H-indol-5-ol trifluoroacetic acid salt

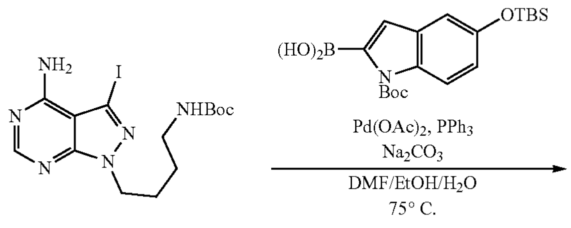

-continued

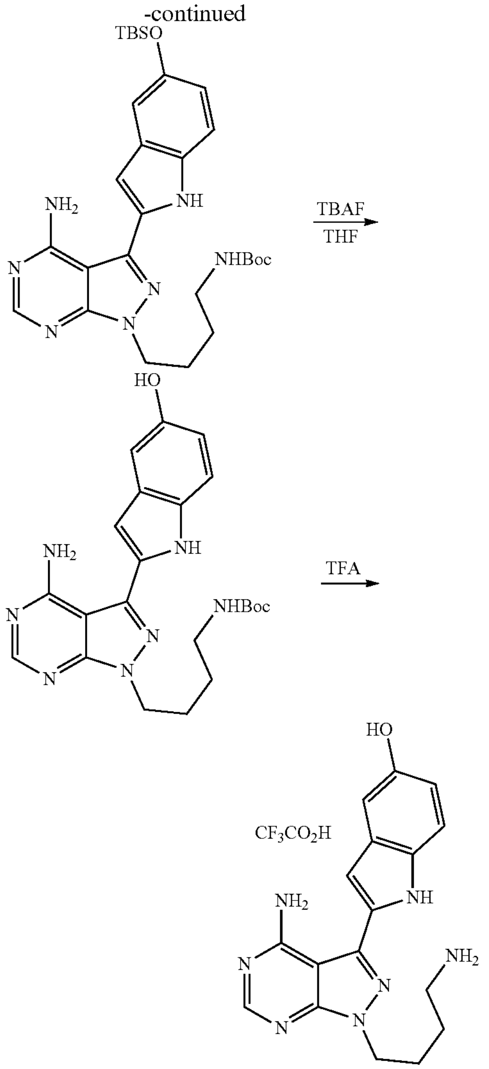

Step 1: Synthesis of tert-butyl (4-(4-amino-3-(5-((tert-butyldimethylsilyl)oxy)-1H-indol-2-yl)-1H-pyrazolo[3,4-d]pyrimidin-1-yl)butyl)carbamate To a solution of tert-butyl (4-(4-amino-3-iodo-1H-pyrazolo[3,4-d]pyrimidin-1-yl)butyl)carbamate (1.0 g, 2.31 mmol, 1.0 equiv) in dioxane (10.5 mL) and $H_2O$ (3.5 mL) was added (1-(tert-butoxycarbonyl)-5-((tert-butyldimethylsilyl)oxy)-1H-indol-2-yl)boronic acid (1.54 g, 2.78 mmol, 1.2 equiv), $K_3PO_4$ (1.47 g, 6.94 mmol, 3.0 equiv), $Pd_2(dba)_3$ (211.84 mg, 231.34 μmol, 0.1 equiv), and SPhos (189.95 mg, 462.69 μmol, 0.2 equiv) at room temperature under $N_2$. The sealed tube was heated at 150° C. for 20 min in a microwave. This was repeated for 9 additional batches. The 10 batches were combined and the reaction mixture was cooled and partitioned between EtOAc (60 mL) and $H_2O$ (80 mL). The aqueous layer was separated and extracted with EtOAc (2×50 mL). The organic layers were combined, washed with brine (60 mL) and dried over anhydrous $Na_2SO_4$. The suspension was filtered and the filtrate was concentrated under reduced pressure. The crude material was purified by silica gel chromatography (1→75% EtOAc/petroleum ether). The desired fractions were combined and evaporated under reduced pressure to give tert-butyl (4-(4- amino-3-(5-((tert-butyldimethylsilyl)oxy)-1H-indol-2-yl)-1H-pyrazolo[3,4-d]pyrimidin-1-yl)butyl)carbamate (10 g, 60% yield) as a light yellow solid.

Step 2: Synthesis of tert-butyl (4-(4-amino-3-(5-hydroxy-1H-indol-2-yl)-1H-pyrazolo[3,4-d]pyrimidin-1-yl)butyl)carbamate To a mixture of tert-butyl (4-(4-amino-3-(5-((tert-butyldimethylsilyl)oxy)-1H-indol-2-yl)-1H-pyrazolo[3,4-d]pyrimidin-1-yl)butyl)carbamate (10 g, 18.12 mmol, 1.0 equiv) in THF (100 mL) was added TBAF.3$H_2O$ (1 M, 54.37 mL, 3.0 equiv) in one portion at room temperature under $N_2$. The mixture was stirred for 1 h and then $H_2O$ (100 mL) was added to the reaction mixture. The layers were separated and the aqueous phase was extracted with EtOAc (2×80 mL). The combined organic phase was washed with brine (100 mL), dried with anhydrous $Na_2SO_4$, filtered and concentrated under reduced pressure. The residue was purified by silica gel chromatography (1→67% EtOAc/petroleum ether) to afford tert-butyl (4-(4-amino-3-(5-hydroxy-1H-indol-2-yl)-1H-pyrazolo[3,4-d]pyrimidin-1-yl)butyl)carbamate (7 g, 87% yield) as a light pink solid.

Step 3: Synthesis of 2-[4-amino-1-(4-aminobutyl) pyrazolo[3,4-d]pyrimidin-3-yl]-1H-indol-5-ol To TFA (50.0 mL, 675.26 mmol, 38.9 equiv) was added tert-butyl (4-(4-amino-3-(5-hydroxy-TH-indol-2-yl)-1H-pyrazolo[3,4-d]pyrimidin-1-yl)butyl)carbamate (7.6 g, 17.37 mmol, 1.0 equiv) at room temperature. The mixture was stirred for 40 min and was then concentrated under reduced pressure. The oily residue was triturated with MeCN (20 mL), then added dropwise into MTBE (300 mL) for 10 min. The supernatant was removed and then the precipitate was collected by filtration under $N_2$ to give 2-[4-amino-1-(4-aminobutyl)pyrazolo[3,4-d]pyrimidin-3-yl]-1H-indol-5-ol (7.79 g, 91% yield, TFA) as light yellow solid. LCMS (ESI) m/z: [M+H] calcd for $C_{17}H_{19}N_7O$: 338.17; found 338.2.

Monomer G. 5-(4-amino-1-(azetidin-3-ylmethyl)-1H-pyrazolo[3,4-d]pyrimidin-3-yl)benzo[d]oxazol-2-amine trifluoroacetic acid salt

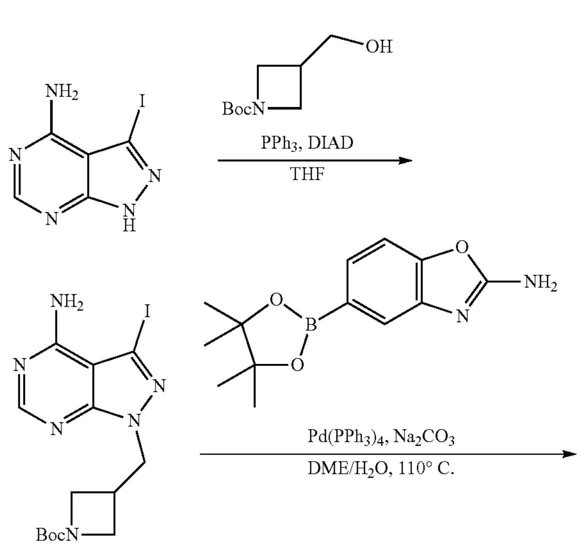

-continued

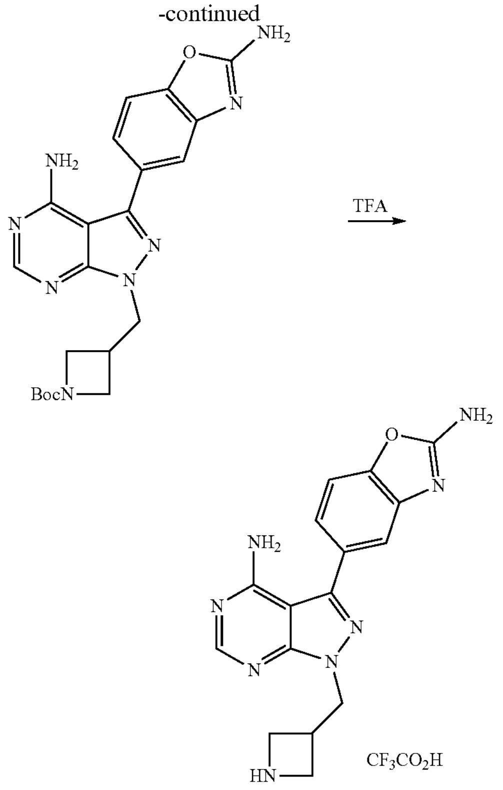

Step 1: Synthesis of tert-butyl 3-((4-amino-3-iodo-1H-pyrazolo[3,4-d]pyrimidin-1-yl) methyl)azetidine-1-carboxylate To a solution of 3-iodo-1H-pyrazolo[3,4-d]pyrimidin-4-amine (4 g, 15.32 mmol, 1.0 equiv), tert-butyl 3-(hydroxymethyl)azetidine-1-carboxylate (3.01 g, 16.09 mmol, 1.05 equiv) and $PPh_3$ (6.03 g, 22.99 mmol, 1.5 equiv) in THF (80 mL) cooled to 0° C. was added DIAD (4.47 mL, 22.99 mmol, 1.5 equiv), dropwise. After the addition was complete, the reaction was stirred at room temperature for 14 h. The reaction was poured into $H_2O$ (200 mL) and then extracted with EtOAc (3×50 mL). The organic layers were combined and washed with brine (2×50 mL). The organic phase was dried over $Na_2SO_4$, filtered, the filtrate was concentrated under reduced pressure to give a residue. The residue was purified by silica gel chromatography (0→100% EtOAc/petroleum ether) to give tert-butyl 3-((4-amino-3-iodo-1H-pyrazolo[3,4-d]pyrimidin-1-yl)methyl) azetidine-1-carboxylate (4.2 g, 64% yield) as a white solid. LCMS (ESI) m/z: [M+H] calcd for $C_{14}H_{19}IN_6O_2$: 431.07; found 431.0.

Step 2: Synthesis of tert-butyl 3-((4-amino-3-(2-aminobenzo[d]oxazol-5-yl)-1H-pyrazolo [3,4-d] pyrimidin-1-yl)methyl)azetidine-1-carboxylate To a bi-phasic suspension of tert-butyl 3-((4-amino-3-iodo-1H-pyrazolo[3,4-d]pyrimidin-1-yl) methyl)azetidine-1-carboxylate (4 g, 9.30 mmol, 1.0 equiv), 5-(4,4,5,5-tetramethyl-1,3,2-dioxaborolan-2-yl)benzo[d]oxazol-2-amine (2.90 g, 11.16 mmol, 1.2 equiv) and $Na_2CO_3$ (4.93 g, 46.49 mmol, 5.0 equiv) in DME (100 mL) and $H_2O$ (50 mL) was added $Pd(PPh_3)_4$ (1.07 g, 929.71 μmol, 0.1 equiv) at room temperature under $N_2$. The mixture was stirred at 110° C. for 3 h. The reaction mixture was then cooled to room temperature and filtered, and the filtrate was extracted by EtOAc (3×50 mL). The organic layers were combined and washed with brine (10 mL), dried over $Na_2SO_4$, filtered and the filtrate was concentrated under reduced pressure to give a residue. The residue was purified by silica gel chromatography (0→20% MeOH/EtOAc) to give tert-butyl 3-((4-amino-3-(2-aminobenzo[d]oxazol-5-yl)-1H-pyrazolo [3,4-d]pyrimidin-1-yl)methyl)azetidine-1-carboxylate (3.5 g, 80% yield) as a yellow solid. LCMS (ESI) m/z: [M+H] calcd for $C21H_{24}N_8O_3$: 437.20; found 437.2.

Step 3: Synthesis of 5-(4-amino-1-(azetidin-3-ylmethyl)-1H-pyrazolo[3,4-d]pyrimidin-3-yl)benzol[d]oxazol-2-amine To a solution of tert-butyl 3-((4-amino-3-(2-aminobenzo[d]oxazol-5-yl)-1H-pyrazolo[3,4-d] pyrimidin-1-yl)methyl) azetidine-1-carboxylate (3.29 g, 6.87 mmol, 1.0 equiv) in DCM (20 mL) was added TFA (7.50 mL, 101.30 mmol, 14.7 equiv) at 0° C. The reaction was warmed to room temperature and stirred for 2 h. The reaction solution was concentrated under reduced pressure to give a residue. The residue was dissolved in MeCN (6 mL) and then poured into MTBE (80 mL). A solid precipitated, which was filtered and the solid cake was dried under reduced pressure to give 5-[4-amino-1-(azetidin-3-ylmethyl)pyrazolo[3,4-d]pyrimidin-3-yl]-1,3-benzoxazol-2-amine (4.34 g, over 100% yield, TFA) as a yellow solid. LCMS (ESI) m/z: [M+H] calcd for $C_{16}H_{16}N_8O$: 337.15; found 337.1.

Monomer H. 5-(4-amino-1-(4-aminobutyl)-1H-pyrazolo[3,4-d]pyrimidin-3-yl)benzo[d]-oxazol-2-amine trifluoroacetic acid salt

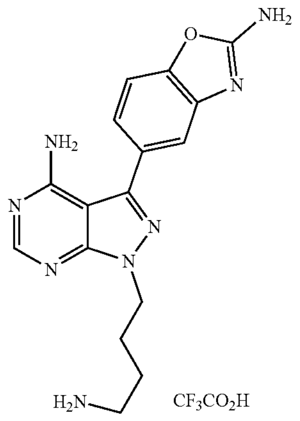 [SMILES: NCCCCn1nc(-c2ccc3oc(N)nc3c2)c2c(N)ncnc21 ; "CF3CO2H"]

This monomer was synthesized following the procedures outlined in *Nature* 2015, 534, 272-276, which is incorporated by reference in its entirety.

Monomer I. 5-(4-amino-1-(pyrrolidin-3-ylmethyl)-1H-pyrazolo[3,4-d]pyrimidin-3-yl)benzo[d]oxazol-2-amine trifluoroacetic acid salt

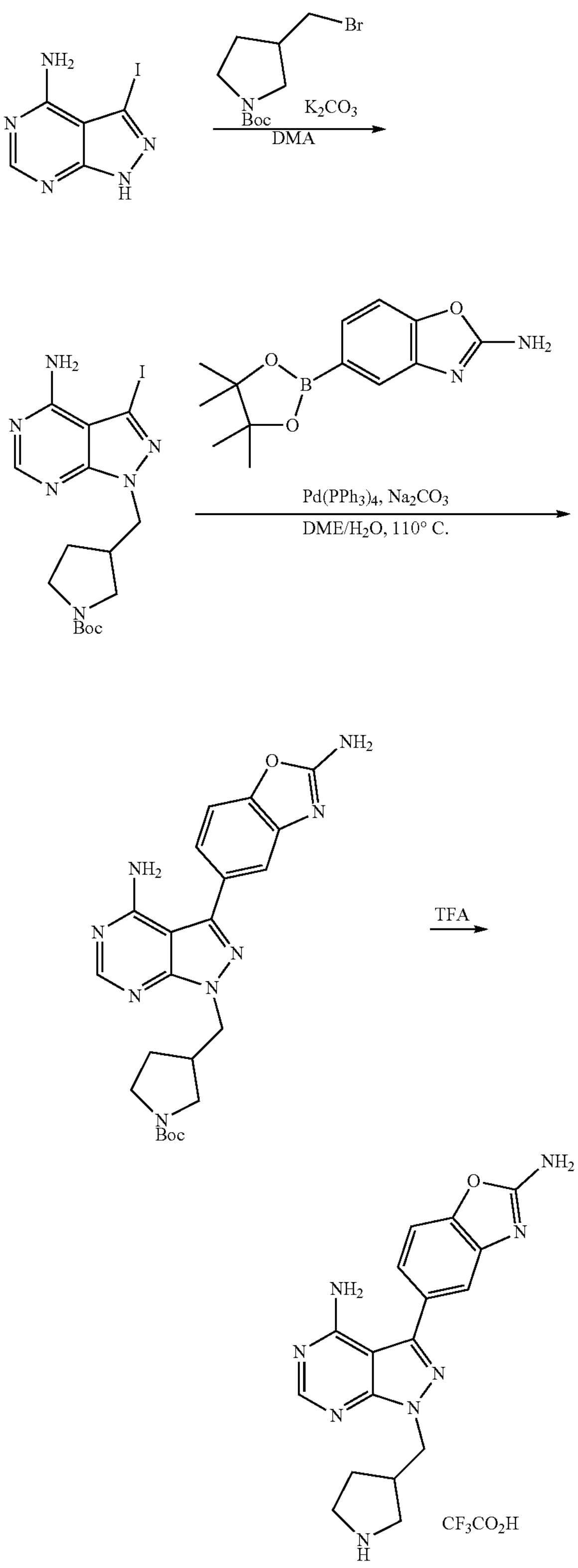

Step 1: Synthesis of tert-butyl 3-((4-amino-3-iodo-1H-pyrazolo[3,4-d]pyrimidin-1-yl) methyl)pyrrolidine-1-carboxylate A suspension of 3-iodo-1H-pyrazolo[3,4-d]pyrimidin-4-amine (4.5 g, 17.24 mmol, 1.0 equiv), tert-butyl 3-(bromomethyl)pyrrolidine-1-carboxylate (4.78 g, 18.10 mmol, 1.05 equiv) and $K_2CO_3$ (7.15 g, 51.72 mmol, 3.0 equiv) in DMA (40 mL) was heated to 85° C. The reaction was stirred at 85° C. for 3 h, at which point the solution was cooled to room temperature. Then, $H_2O$ (80 mL) was added to the reaction, and a solid precipitated out. The mixture was filtered, and the solid cake was washed with $H_2O$ (2×40 mL), and then dried under reduced pressure to give tert-butyl 3-((4-amino-3-iodo-1H-pyrazolo[3,4-d]pyrimidin-1-yl) methyl)pyrrolidine-1-carboxylate (6 g, 78% yield) as a yellow solid. LCMS (ESI) m/z: [M+H] calcd for $C_{15}H_{21}IN_6O_2$: 445.08; found 445.1.

Step 2: Synthesis of tert-butyl 3-[[4-amino-3-(2-amino-1,3-benzoxazol-5-yl)pyrazolo[3,4-d]pyrimidin-1-yl]methyl]pyrrolidine-1-carboxylate To a bi-phasic suspension of tert-butyl 3-((4-amino-3-iodo-1H-pyrazolo[3,4-d]pyrimidin-1-yl) methyl)pyrrolidine-1-carboxylate (4 g, 9.00 mmol, 1.0 equiv), 5-(4,4,5,5-tetramethyl-1,3,2-dioxaborolan-2-yl)benzo[d]oxazol-2-amine (2.81 g, 10.80 mmol, 1.2 equiv) and $Na_2CO_3$ (4.77 g, 45.02 mmol, 5.0 equiv) in DME (120 mL) and $H_2O$ (60 mL) was added $Pd(PPh_3)_4$ (1.04 g, 900.35 μmol, 0.1 equiv) at room temperature under $N_2$. The mixture was stirred at 110° C. for 3 h. The reaction mixture was cooled to room temperature and filtered and the filtrate was extracted with EtOAc (3×50 mL). The organic phases were combined and washed with brine (50 mL), dried over $Na_2SO_4$, filtered and concentrated under reduced pressure to give a residue. The residue was purified by silica gel chromatography (0→20% MeOH/EtOAc) to give tert-butyl 3-((4-amino-3-(2-aminobenzo[d]oxazol-5-yl)-1H-pyrazolo[3,4-d]pyrimidin-1-yl) methyl)pyrrolidine-1-carboxylate (3 g, 64% yield) as a yellow solid. LCMS (ESI) m/z: [M+H] calcd for $C_{22}H_{26}N_8O_3$: 451.21, found 451.2.

Step 3: Synthesis of 5-(4-amino-1-(pyrrolidin-3-ylmethyl)-1H-pyrazolo[3,4-d]pyrimidin-3-yl)benzo[d]oxazol-2-amine To a solution of tert-butyl 3-((4-amino-3-(2-aminobenzo[d]oxazol-5-yl)-1H-pyrazolo[3,4-d]pyrimidin-1-yl)methyl) pyrrolidine-1-carboxylate (3 g, 6.66 mmol, 1.0 equiv) in DCM (40 mL) was added TFA (20 mL) at 0° C., dropwise. The reaction mixture was warmed to room temperature and stirred for 2 h. The reaction solution was then concentrated under reduced pressure to give a residue. The residue was dissolved in MeCN (4 mL), then poured into MTBE (100 mL), and a solid precipitated out. The solid was filtered and the cake was dried under reduced pressure to give 5-(4-amino-1-(pyrrolidin-3-ylmethyl)-1H-pyrazolo[3,4-d]pyrimidin-3-yl)benzo[d]oxazol-2-amine (4.00 g, over 100% yield, TFA) as a yellow solid. LCMS (ESI) m/z: [M+H] calcd for $C_{17}H_{18}N_8O$: 351.17; found 351.2.

Monomer J. 1-(4-aminobutyl)-3-(7-methoxy-1H-indol-2-yl)-1H-pyrazolo[3,4-d]pyrimidin-4-aminetrifluoroacetic acid salt

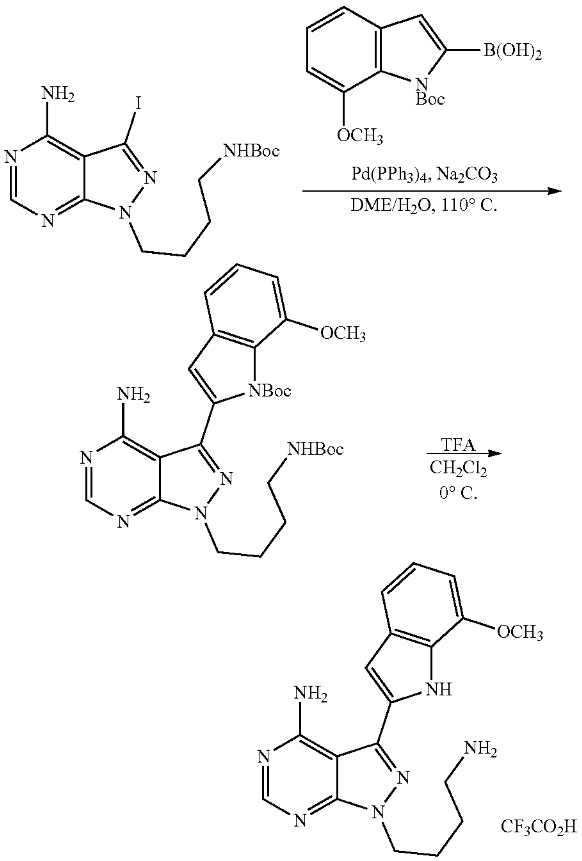

Step 1: Synthesis of tert-butyl 2-(4-amino-1-(4-((tert-butoxycarbonyl)amino)butyl)-1H-pyrazolo[3,4-d]pyrimidin-3-yl)-7-methoxy-1H-indole-1-carboxylate To a mixture of tert-butyl (4-(4-amino-3-iodo-1H-pyrazolo[3,4-d]pyrimidin-1-yl)butyl)carbamate (1.0 equiv) and (1-(tert-butoxycarbonyl)-7-methoxy-1H-indol-2-yl)boronic acid (3.0 equiv) in DME and $H_2O$ is added $Pd(PPh_3)_4$ (0.1 equiv) and sodium carbonate (6.0 equiv). The reaction is heated at 80° C. until completion, as determined by LCMS and TLC analysis. The reaction is then quenched with $H_2O$ and EtOAc. The mixture is transferred to a separatory funnel and the aqueous phase is extracted with EtOAc. The organic phase is washed with sat. aq. NaCl, dried over $Na_2SO_4$, filtered, and concentrated under reduced pressure. The desired product is isolated after chromatography on silica gel.

Step 2: Synthesis of 1-(4-aminobutyl)-3-(7-methoxy-1H-indol-2-yl)-1H-pyrazolo[3,4-d]pyrimidin-4-amine To a solution of tert-butyl 2-(4-amino-1-(4-((tert-butoxycarbonyl)amino)butyl)-1H-pyrazolo[3,4-d]pyrimidin-3-yl)-7-hydroxy-1H-indole-1-carboxylate (1.0 equiv) in DCM at 0° C. is added TFA dropwise. The reaction is stirred at 0° C. and warmed to room temperature. Once the reaction is complete, as determined by LCMS, the reaction is concentrated under reduced pressure. The residue is triturated with MeCN, then dripped into MTBE over 10 min. The supernatant is removed and the precipitate is collected by filtration under $N_2$ to give 1-(4-aminobutyl)-3-(7-methoxy-1H-indol-2-yl)-1H-pyrazolo[3,4-d]pyrimidin-4-amine.

Monomer K. Synthesis of 1-(4-aminobutyl)-1H-pyrazolo[3,4-d]pyrimidin-4-amine trifluoroacetic acid salt

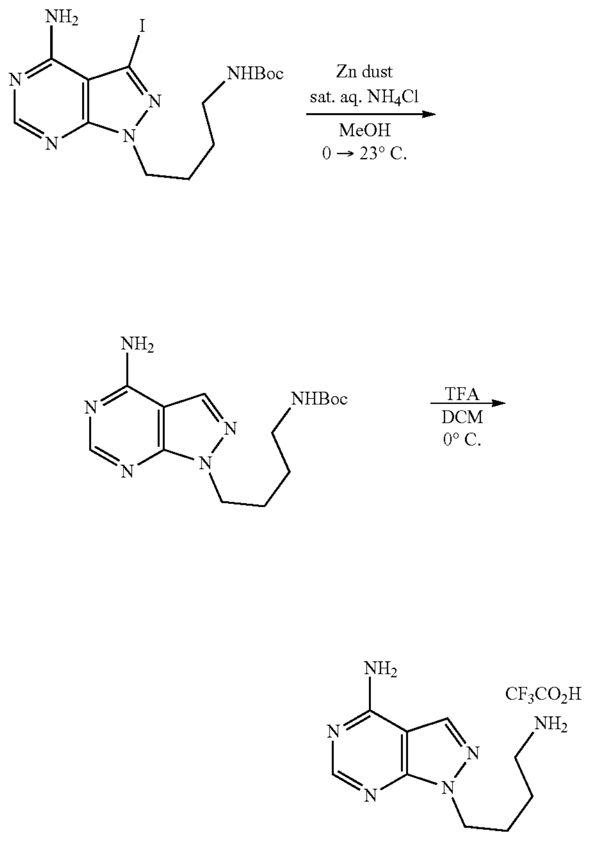

Step 1: Synthesis of tert-butyl (4-(4-amino-1H-pyrazolo[3,4-d]pyrimidin-1-yl)butyl)carbamate To a mixture of tert-butyl (4-(4-amino-3-iodo-1H-pyrazolo[3,4-d]pyrimidin-1-yl)butyl)carbamate (300 mg, 694 μmol, 1.0 equiv) in MeOH (14 mL) at 0° C. was added zinc dust (226 mg, 3.46 mmol, 5.0 equiv). Sat. aq. $NH_4Cl$ (14 mL) was added to the reaction mixture and the reaction was warmed to room temperature and stirred for 18 h. The reaction was quenched by EtOAc (40 mL) and $H_2O$ (10 mL) and the mixture was transferred to a separatory funnel. The aqueous phase was extracted with EtOAc (3×20 mL) and the combined organic phases were washed with sat. aq. $NaHCO_3$ (15 mL), dried over $Na_2SO_4$, filtered, and concentrated under reduced pressure to provide the product (210 mg, 99% yield) as a light yellow solid that was used without further purification. LCMS (ESI) m/z: [M+H] calcd for $C_{14}H_{22}N_6O_2$: 307.19; found 307.1.

Step 2: Synthesis of 1-(4-aminobutyl)-1H-pyrazolo[3,4-d]pyrimidin-4-amine

To a solution of tert-butyl (4-(4-amino-1H-pyrazolo[3,4-d]pyrimidin-1-yl)butyl)carbamate (210 mg, 691 μmol) in DCM (3.5 mL) at 0° C. was added TFA (3.5 mL), dropwise. After 3 h, the reaction was warmed to room temperature and concentrated under reduced pressure to provide the trifluoroacetate salt of the product (220 mg, 99% yield) as a brown oil, which was used without further purification. LCMS (ESI) m/z: [M+H] calcd for $C_9H_{14}N_6$: 207.13; found 207.1.

Monomer L. 1-[4-(piperazin-1-yl)-3-(trifluoromethyl)phenyl]-9-(quinolin-3-yl)-1H,2H-benzo[h]1,6-naphthyridin-2-one

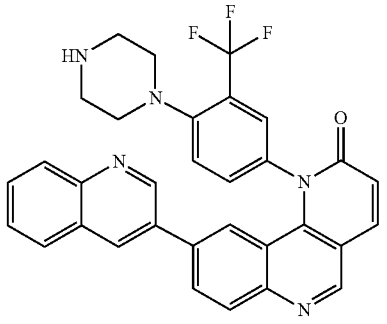 [SMILES: O=c1ccc2cnc3ccc(-c4cnc5ccccc5c4)cc3c2n1-c1ccc(N2CCNCC2)c(C(F)(F)F)c1]

The preparation of this monomer has been previously reported in the literature. See the following references: i) Liu, Qingsong; Chang, Jae Won; Wang, Jinhua; Kang, Seong A.; Thoreen, Carson C.; Markhard, Andrew; Hur, Wooyoung; Zhang, Jianming; Sim, Taebo; Sabatini, David M.; et al From Journal of Medicinal Chemistry (2010), 53(19), 7146-7155. ii) Gray, Nathanael; Chang, Jae Won; Zhang, Jianming; Thoreen, Carson C.; Kang, Seong Woo Anthony; Sabatini, David M.; Liu, Qingsong From PCT Int. Appl. (2010), WO 2010044885A2, which are incorporated by reference in their entirety.

Monomer M. 5-(1-(4-aminobutyl)-4-(dimethyl-amino)-1H-pyrazolo[3,4-d]pyrimidin-3-yl)benzo[d]oxazol-2-amine trifluoroacetic acid salt

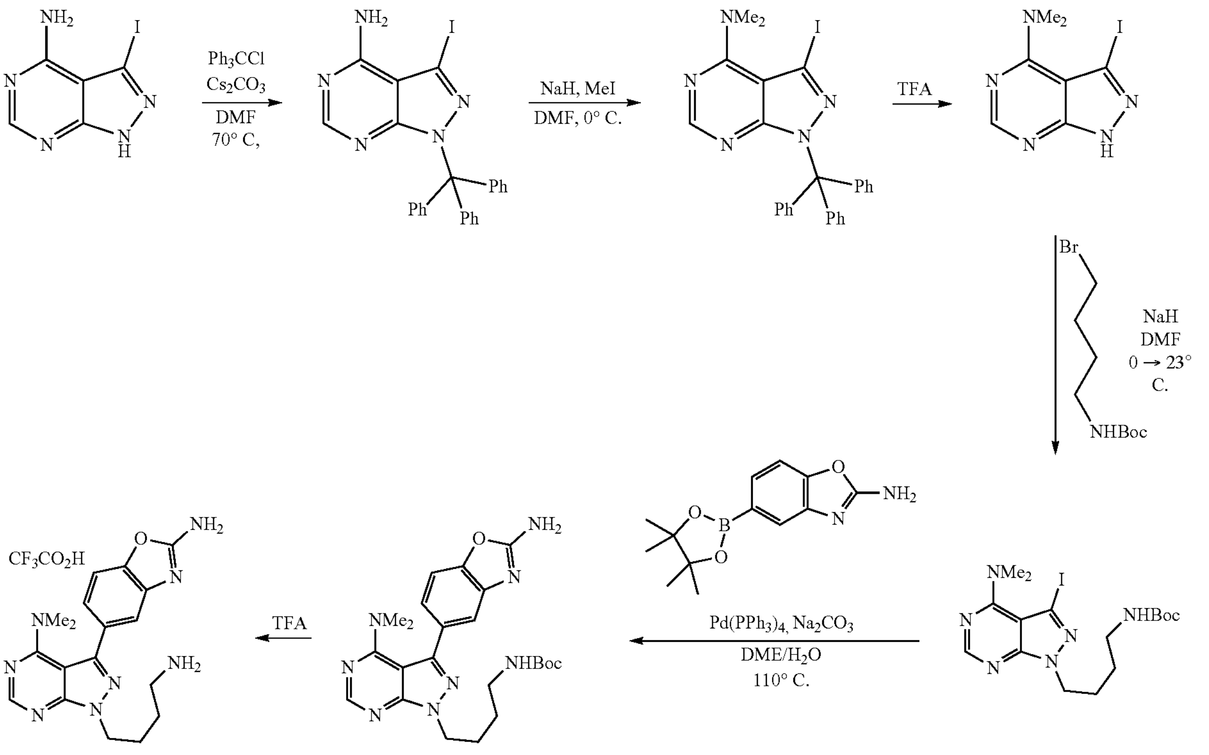

Step 1: Synthesis of 3-iodo-1-trityl-1H-pyrazolo[3,4-d]pyrimidin-4-amine

A suspension of 3-iodo-1H-pyrazolo[3,4-d]pyrimidin-4-amine (10.5 g, 40.23 mmol, 1.0 equiv) in DMF (170.0 mL) was treated with $Cs_2CO_3$ (19.7 g, 60.34 mmol, 1.5 equiv) and [chloro(diphenyl)methyl]benzene (13.5 g, 48.27 mmol, 1.2 equiv) at room temperature. The reaction mixture was stirred at 70° C. for 4 h under a nitrogen atmosphere. The reaction mixture was added to $H_2O$ (1200 mL). The precipitate was filtered and washed with $H_2O$. The residue was purified by silica gel chromatography (0→60% EtOAc/petroleum ether) to afford 3-iodo-1-trityl-1H-pyrazolo[3,4-d]pyrimidin-4-amine (15.40 g, 73.5% yield) as a white solid.

Step 2: Synthesis of 3-iodo-N,N-dimethyl-1-trityl-1H-pyrazolo[3,4-d]pyrimidin-4-amine To a suspension of NaH (2.98 g, 74.50 mmol, 60 wt. %, 2.5 equiv) in DMF (150 mL) was added the solution of 3-iodo-1-trityl-1H-pyrazolo[3,4-d]pyrimidin-4-amine (15.0 g, 29.80 mmol, 1.0 equiv) in DMF (50 mL) at 0° C. The mixture was stirred at 0° C. for 10 min. To the reaction mixture was then added iodomethane (16.92 g, 119.20 mmol, 7.42 mL, 4.0 equiv) at 0° C. The mixture was stirred at room temperature for 2 h, at which point $H_2O$ (1400 mL) was added at 0° C. The mixture was stirred for an additional 10 min at 0° C. The resulting precipitate was collected by filtration to give crude product, which was purified by silica gel chromatography (1%→25% EtOAc/petroleum ether) twice to afford 3-iodo-N,N-dimethyl-1-trityl-1H-pyrazolo[3,4-d]pyrimidin-4-amine (9.0 g, 89% yield) as a white solid.

Step 3: Synthesis of 3-iodo-N,N-dimethyl-1H-pyrazolo[3,4-d]pyrimidin-4-amine

To a cooled solution of TFA (19.1 mL, 258.1 mmol, 15.0 equiv) in DCM (100.0 mL) was added 3-iodo-N,N-dimethyl-1-trityl-1H-pyrazolo[3,4-d]pyrimidin-4-amine (9.10 g, 17.12 mmol, 1.0 equiv) at 4° C. The mixture was stirred at room temperature for 1 h. The residue was poured into $H_2O$ (100 mL) and the aqueous phase was extracted with DCM (2×50 mL). To the aqueous phase was then added a saturated aqueous solution of $NaHCO_3$ until the solution was pH 8. The resulting precipitate was collected by filtration to give 3-iodo-N,N-dimethyl-1H-pyrazolo[3,4-d]pyrimidin-4-amine (3.40 g, 68.7% yield) as a white solid.

Step 4: Synthesis of tert-butyl (4-(4-(dimethyl-amino)-3-iodo-1H-pyrazolo[3,4-d]pyrimidin-1-yl)butyl)carbamate To a suspension of 3-iodo-N,N-dimethyl-1H-pyrazolo[3,4-d]pyrimidin-4-amine (1.7 g, 5.88 mmol, 1.0 equiv) in DMF (20 mL) was added NaH (247 mg, 6.17 mmol, 60 wt. %, 1.05 equiv) at 4° C. The mixture was stirred at 4° C. for 30 min. To the reaction mixture was then added tert-butyl N-(4-bromobutyl)carbamate (2.22 g, 8.82 mmol, 1.81 mL, 1.5 equiv) in DMF (10 mL) at 4° C. The mixture was stirred at room temperature for 2 h. To the mixture was then added $H_2O$ (100 mL) at 4° C. The mixture was stirred for an additional 30 min at 4° C. and the resulting precipitate was collected by filtration to give crude product. The residue was purified by silica gel chromatography (0→75% EtOAc/petroleum ether) to afford tert-butyl(4-(4-(dimethylamino)-3-iodo-1H-pyrazolo[3,4-d]pyrimidin-1-yl)butyl)carbamate (2.0 g, 56% yield) as a white solid.

Step 5: Synthesis of tert-butyl (4-(3-(2-aminobenzo[d]oxazol-5-yl)-4-(dimethylamino)-1H-pyrazolo[3,4-d]pyrimidin-1-yl)butyl)carbamate To a bi-phasic suspension of tert-butyl (4-(4-(dimethylamino)-3-iodo-1H-pyrazolo[3,4-d]pyrimidin-1-yl)butyl) carbamate (4.0 g, 8.69 mmol, 1.0 equiv), 5-(4,4,5,5-tetramethyl-1,3,2-dioxaborolan-2-yl)benzo[d]oxazol-2-amine (3.4 g, 13.03 mmol, 1.5 equiv), and $Na_2CO_3$ (4.6 g, 43.45 mmol, 5.0 equiv) in DME (80.0 mL) and $H_2O$ (40.0 mL) was added $Pd(PPh_3)_4$ (1.0 g, 868.98 µmol, 0.1 equiv) at room temperature under $N_2$. The mixture was stirred at 110° C. for 3 h. The reaction mixture was then cooled and partitioned between EtOAc (300 mL) and $H_2O$ (600 mL). The aqueous layer was separated and extracted with EtOAc (2×100 mL). The organic layers were combined, washed with brine (2×60 mL) and dried over anhydrous $Na_2SO_4$, filtered, and concentrated under reduced pressure. The crude material was purified by silica gel column chromatography (50% EtOAc/hexanes followed by 20% MeOH/EtOAc). The desired fractions were combined and concentrated under reduced pressure to give tert-butyl (4-(3-(2-aminobenzo[d]oxazol-5-yl)-4-(dimethylamino)-1H-pyrazolo[3,4-d]pyramidin-1-yl) butyl)carbamate (3.2 g, 78.9% yield) as a light brown solid.

Step 6: Synthesis of 5-(1-(4-aminobutyl)-4-(dimethylamino)-1H-pyrazolo[3,4-d]pyrimidin-3-yl)benzo[d]oxazol-2-amine To TFA (20.82 mL, 281.27 mmol, 36.5 equiv) was added tert-butyl (4-(3-(2-aminobenzo[d]oxazol-5-yl)-4-(dimethylamino)-1H-pyrazolo[3,4-d]pyrimidin-1-yl)butyl)carbamate (3.6 g, 7.72 mmol, 1.0 equiv) at room temperature. The mixture was stirred for 30 min, at which point the mixture was concentrated under reduced pressure. The oily residue was triturated with MeCN (8 mL) and MTBE (60 mL) for 10 min. The supernatant was removed and then the precipitate was collected by filtration under $N_2$ to give 5-(1-(4-aminobutyl)-4-(dimethylamino)-1H-pyrazolo[3,4-d]pyrimidin-3-yl)benzo[d]oxazol-2-amine (4.0 g, crude, TFA) as a light brown solid.

To 1 M NaOH (107.2 mL, 14.7 equiv) was added 5-(1-(4-aminobutyl)-4-(dimethylamino)-1H-pyrazolo[3,4-d]pyrimidin-3-yl)benzo[d]oxazol-2-amine (3.5 g, crude, TFA) at room temperature. The mixture was stirred for 10 min and then the aqueous phase was extracted with DCM (3×50 mL). The combined organic phase was washed with brine (50 mL), dried with anhydrous $Na_2SO_4$, filtered and concentrated under reduced pressure. TFA (539.37 µL, 7.28 mmol, 1.0 equiv) was added and concentrated under reduced pressure. MeCN (10 mL) was then added, followed by MTBE (150 mL). The resulting precipitate was collected by filtration to give 5-(1-(4-aminobutyl)-4-(dimethylamino)-1H-pyrazolo[3,4-d]pyrimidin-3-yl)benzo[d]oxazol-2-amine (1.3 g, 36.6% yield, TFA) as a light brown product. LCMS (ESI) m/z: [M+H] calcd for $C_{18}H_{22}N_8O$: 367.19; found 367.1.

Monomer N. 6-(4-amino-1-(4-aminobutyl)-1H-pyrazolo[3,4-d]pyrimidin-3-yl)benzo-[d]isoxazol-3-amine trifluoroacetic acid salt

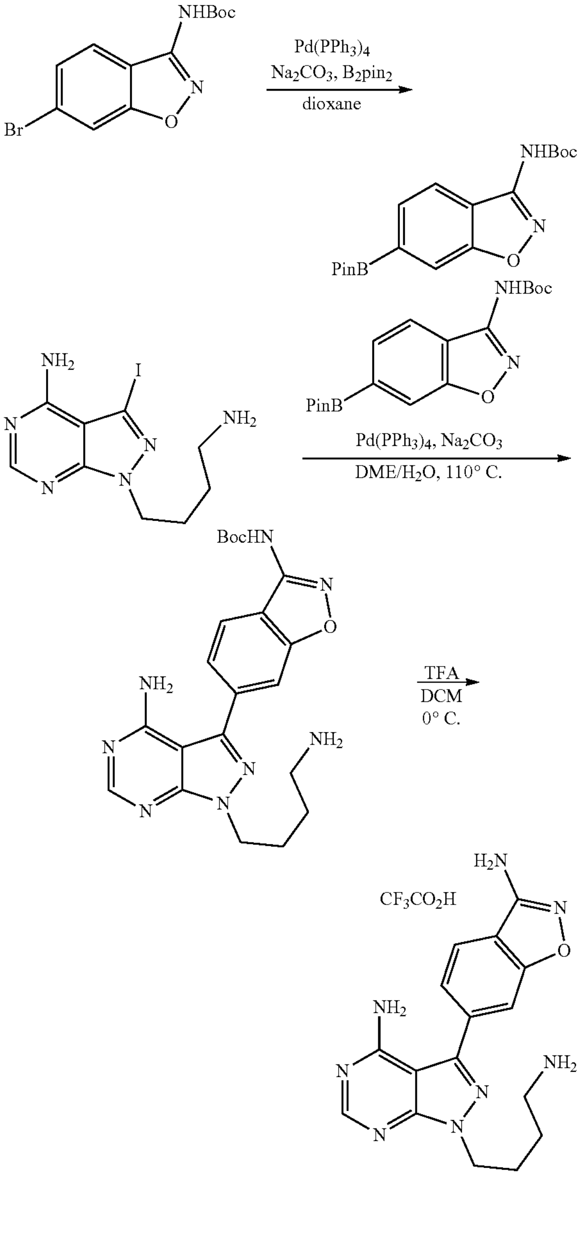

Step 1: Synthesis of tert-butyl (6-(4,4,5,5-tetramethyl-1,3,2-dioxaborolan-2-yl)benzo[d]isoxazol-3-yl)carbamate To a solution of tert-butyl (6-bromobenzo[d]isoxazol-3-yl)carbamate (1.0 equiv) in dioxane is added $Pd(PPh_3)_4$ (0.1 equiv), sodium carbonate (6.0 equiv), and bis(pinacolato) diboron (3.0 equiv). The reaction mixture is stirred and heated until completion, as determined by LCMS and TLC analysis. The reaction is cooled to room temperature, quenched with sat. aq. $NaHCO_3$, and the mixture transferred to a separatory funnel. The aqueous phase is extracted with EtOAc and the organic phase is washed with sat. aq. NaCl, dried over $Na_2SO_4$, filtered, and concentrated under reduced pressure. The desired product is isolated after purification by silica gel chromatography.

Step 2: Synthesis of tert-butyl (4-(4-amino-3-(3-((tert-butoxycarbonyl)amino)benzo[d]isoxazol-6-yl)-1H-pyrazolo[3,4-d]pyrimidin-1-yl)butyl)carbamate To a mixture of tert-butyl (4-(4-amino-3-iodo-TH-pyrazolo[3,4-d]pyrimidin-1-yl)butyl)carbamate (1.0 equiv) and tert-butyl (6-(4,4,5,5-tetramethyl-1,3,2-dioxaborolan-2-yl)benzo[d]isoxazol-3-yl)carbamate (3.0 equiv) in DME and $H_2O$ is added $Pd(PPh_3)_4$ (0.1 equiv) and sodium carbonate (6.0 equiv). The reaction is heated at 80° C. until completion, as determined by LCMS and TLC analysis. The reaction is then quenched with $H_2O$ and EtOAc. The mixture is transferred to a separatory funnel and the aqueous phase is extracted with EtOAc. The organic phase is washed with sat. aq. NaCl, dried over $Na_2SO_4$, filtered, and concentrated under reduced pressure. The desired product is isolated after chromatography on silica gel.

Step 3: Synthesis of 6-(4-amino-1-(4-aminobutyl)-1H-pyrazolo[3,4-d]pyrimidin-3-yl)benzo-[d]isoxazol-3-amine To a solution of tert-butyl (4-(4-amino-3-(3-((tert-butoxycarbonyl)amino)benzo[d]isoxazol-6-yl)-1H-pyrazolo[3,4-d]pyrimidin-1-yl)butyl)carbamate (1.0 equiv) in DCM at 0° C. is added TFA, dropwise. The reaction is stirred at 0° C. and warmed to room temperature. Once the reaction is complete, as determined by LCMS, the reaction is concentrated under reduced pressure. The residue is triturated with MeCN, then added dropwise into MTBE over 10 min. The supernatant is removed and the precipitate is collected by filtration under $N_2$ to give 6-(4-amino-1-(4-aminobutyl)-1H-pyrazolo[3,4-d]pyrimidin-3-yl)benzo-[d]isoxazol-3-amine.

Monomer O. 4-(5-(4-morpholino-1-(1-(pyridin-3-ylmethyl)piperidin-4-yl)-1H-pyrazolo[3,4-d]pyrimidin-6-yl)-1H-indol-1-yl)butan-1-amine trifluoroacetic acid salt

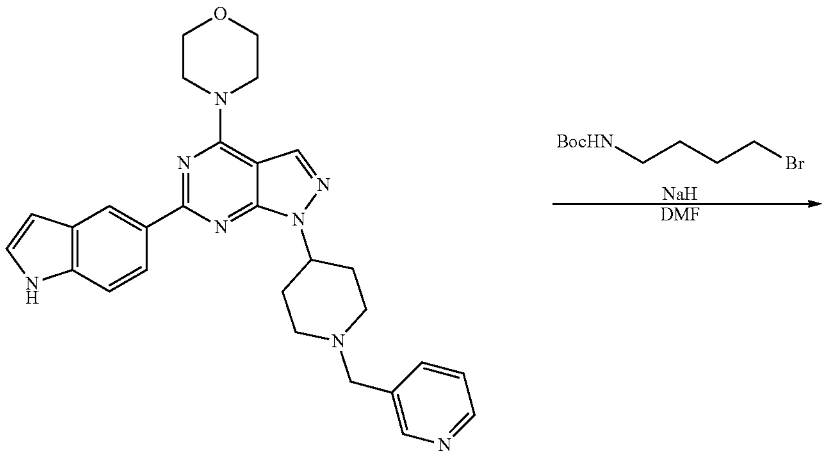

WAY-600

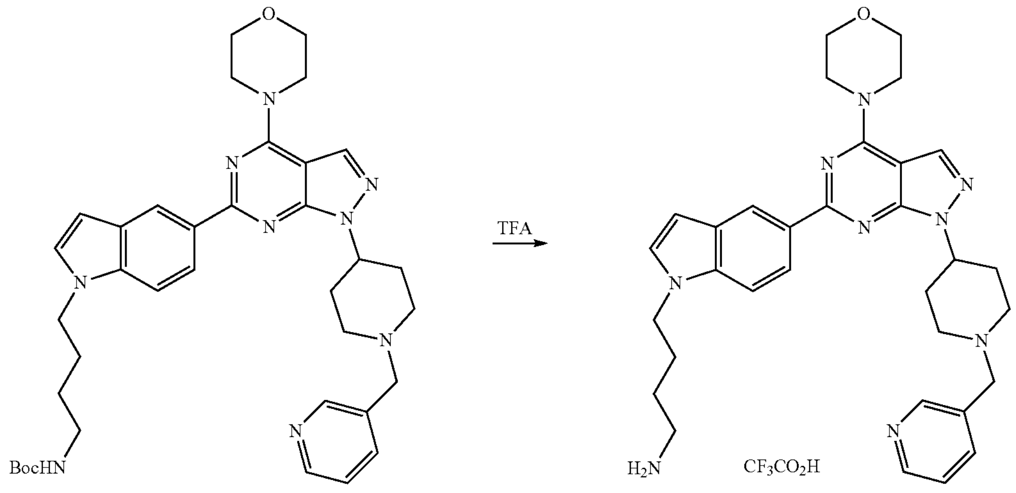

The synthesis of this monomer proceeds by alkylation of WAY-600 (CAS #1062159-35-6) with tert-butyl (4-bromobutyl)carbamate under basic conditions, followed by Boc-deprotection using TFA to produce the TFA salt.

Reference for preparation of WAY-600: Discovery of Potent and Selective Inhibitors of the Mammalian Target of Rapamycin (mTOR) Kinase: Nowak, P.; Cole, D. C.; Brooijmans, N.; Bursavich, M. G.; Curran, K. J.; Ellingboe, J. W.; Gibbons, J. J.; Hollander, I.; Hu, Y.; Kaplan, J.; Malwitz, D. J.; Toral-Barza, L.; Verheijen, J. C.; Zask, A.; Zhang, W.-G.; Yu, K. 2009; Journal of Medicinal Chemistry Volume 52, Issue 22, 7081-89, which is incorporated by reference in its entirety.

Monomer P. 2-(4-(8-(6-(aminomethyl)quinolin-3-yl)-3-methyl-2-oxo-2,3-dihydro-1H-imidazo[4,5-c]quinolin-1-yl)phenyl)-2-methylpropanenitrile trifluoroacetic acid salt

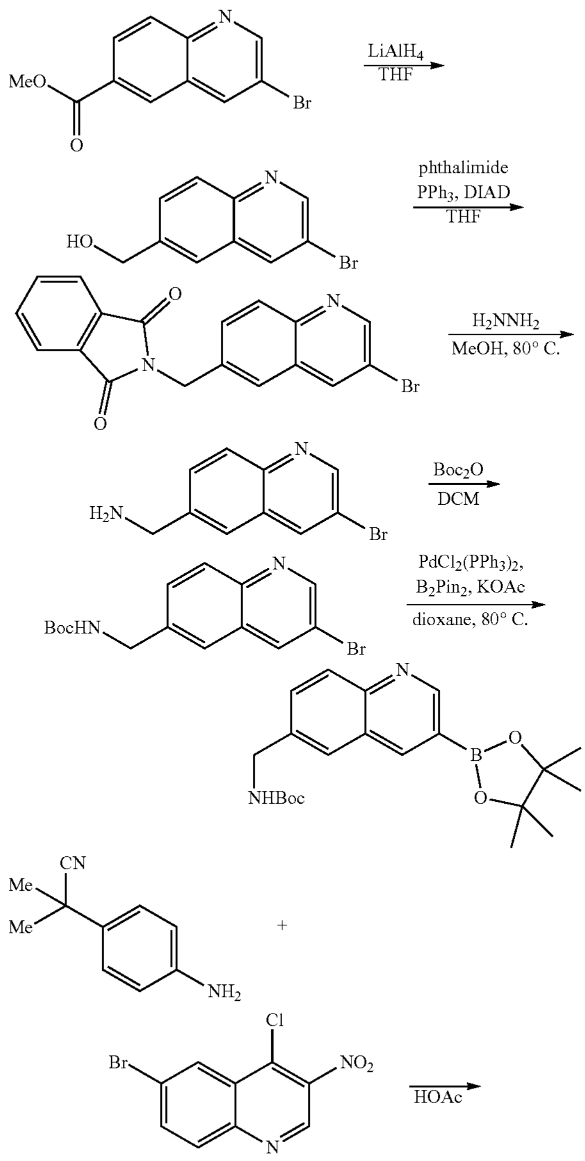

-continued

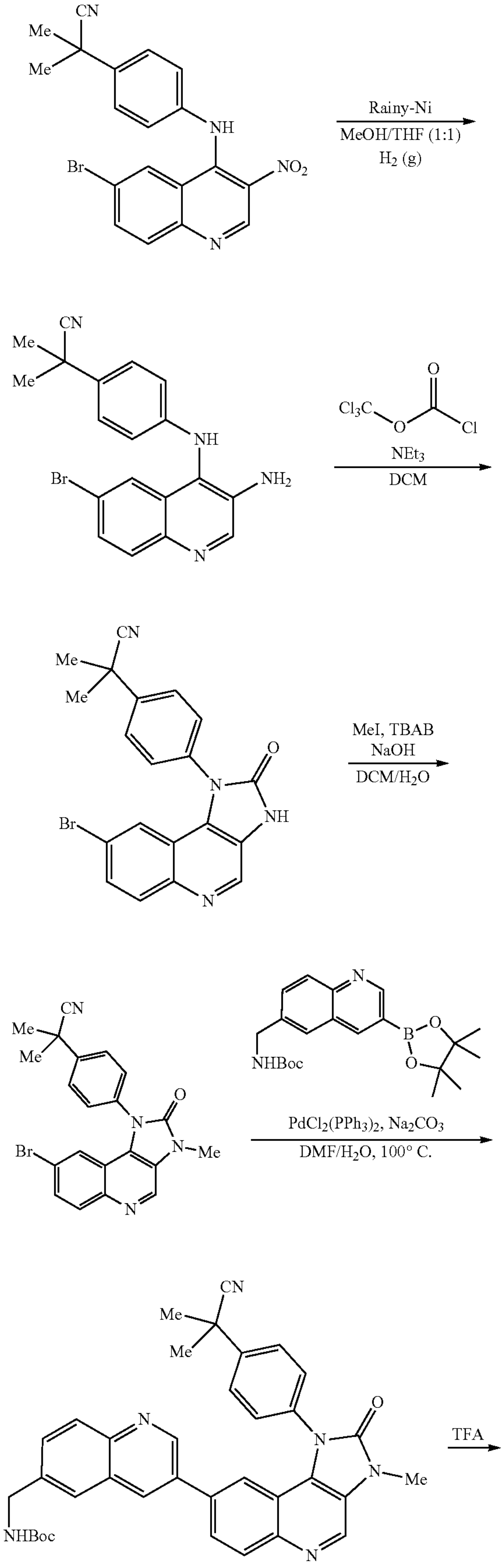

-continued

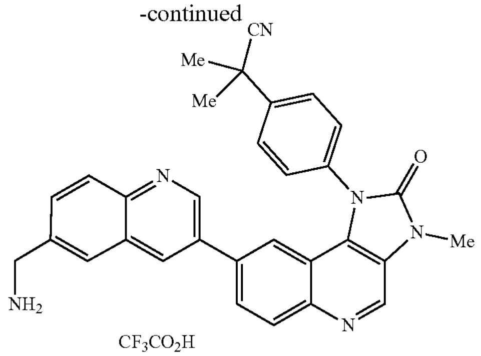

The synthesis of this monomer proceeds first by synthesis of the Suzuki reaction coupling partner (3-(4,4,5,5-tetramethyl-1,3,2-dioxaborolane)quinolin-6-yl)-N-boc-methanamine starting from methyl 3-bromoquinoline-6-carboxylate. Reduction of the methyl ester with lithium aluminum hydride followed by Mitsunobu reaction with phthalimide and hydrazine cleavage provides the benzylic amine. Protection of the benzylic amine with di-tert-butyl dicarbonate followed by a Miyaura borylation reaction provides (3-(4,4,5,5-tetramethyl-1,3,2-dioxaborolane)quinolin-6-yl)-N-boc-methanamine.

An SNAr reaction of 2-(4-aminophenyl)-2-methylpropanenitrile with 6-bromo-4-chloro-3-nitroquinoline provides the substituted amino-nitro-pyridine. Reduction of the nitro group with Raney-Ni under a hydrogen atmosphere followed by cyclization with trichloromethyl chloroformate provides the aryl-substituted urea. Substitution of the free N—H of the urea with methyl iodide mediated by tetrabutylammonium bromide and sodium hydroxide followed by Suzuki coupling of (3-(4,4,5,5-tetramethyl-1,3,2-dioxaborolane)quinolin-6-yl)-N-boc-methanamine and then Boc-deprotection using TFA produces the TFA salt.

Reference for preparation of 2-[4-(8-bromo-3-methyl-2-oxo-2,3-dihydro-imidazo [4,5-c]quinolin-1-yl)-phenyl]-2-methyl-propionitrile: Vannucchi, A. M.; Bogani, C.; Bartalucci, N. 2016. JAK PI3K/mTOR combination therapy. U.S. Pat. No. 9,358,229. Novartis Pharma AG, Incyte Corporation, which is incorporated by reference in its entirety.

Monomer Q. 8-(6-methoxypyridin-3-yl)-3-methyl-1-[4-(piperazin-1-yl)-3-(trifluoromethyl)phenyl]-1H,2H,3H-imidazo[4,5-c]quinolin-2-one

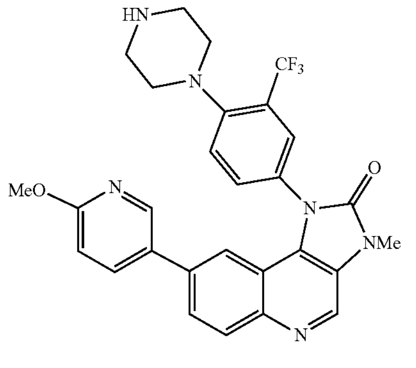 [SMILES: COc1ccc(-c2ccc3ncc4c(c3c2)n(-c2ccc(N3CCNCC3)c(C(F)(F)F)c2)c(=O)n4C)cn1]

This monomer is a commercially available chemical known as BGT226(CAS #1245537-68-1). At the time this application was prepared, it was available for purchase from several vendors as the free amine.

Monomer R. 3-(4-amino-1-(4-aminobutyl)-1H-pyrazolo[3,4-d]pyrimidin-3-yl)-N-(4,5-dihydrothiazol-2-yl)benzamide trifluoroacetic acid salt

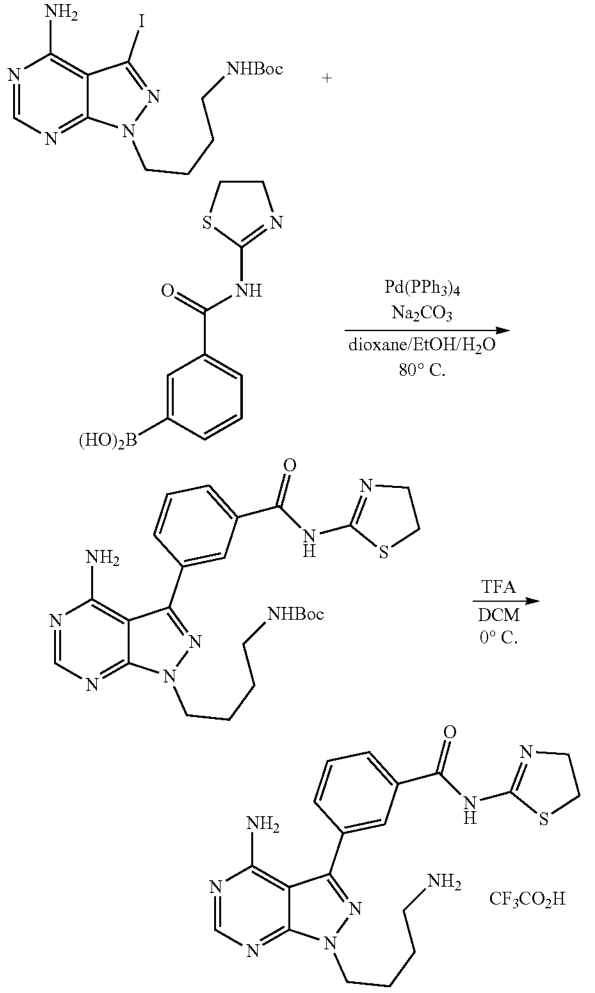

Step 1: Synthesis of tert-butyl (4-(4-amino-3-(3-((4,5-dihydrothiazol-2-yl)carbamoyl)phenyl)-1H-pyrazolo[3,4-d]pyrimidin-1-yl)butyl)carbamate To a solution of (3-((4,5-dihydrothiazol-2-yl)carbamoyl)phenyl)boronic acid (500 mg, 1.15 mmol, 1.0 equiv) and tert-butyl (4-(4-amino-3-iodo-1H-pyrazolo[3,4-d]pyrimidin-1-yl)butyl)carbamate (575 mg, 2.30 mmol, 2.0 equiv) in dioxane (19.1 mL), EtOH (3.8 mL), and $H_2O$ (2.3 mL) was added $Pd(PPh_3)_4$ (265 mg, 230 μmol, 0.2 equiv) and sodium carbonate (730 mg, 6.89 mmol, 6.0 equiv). The reaction mixture was sonicated until formation of a clear, yellow solution, which was subsequently heated at 80° C. for 14 h. The reaction was then diluted with sat. aq. NaCl (30 mL) and the mixture transferred to a separatory funnel. The aqueous phase was extracted with DCM (3×25 mL). The combined organic phases were dried over $Na_2SO_4$, filtered, and concentrated under reduced pressure. The desired product was isolated as a yellow solid (324 mg, 53% yield) after silica gel chromatography (0→15% MeOH/DCM). LCMS (ESI) m/z: [M+H] calcd for $C_{24}H_{30}N_8O_3S$: 511.22; found 511.2.

Step 2: Synthesis of 3-(4-amino-1-(4-aminobutyl)-1H-pyrazolo[3,4-d]pyrimidin-3-yl)-N-(4,5-dihydrothiazol-2-yl)benzamide To a solution of tert-butyl (4-(4-amino-3-(3-((4,5-dihydrothiazol-2-yl)carbamoyl)phenyl)-1H-pyrazolo[3,4-d]pyrimidin-1-yl)butyl)carbamate (324 mg, 614 μmol) in DCM (4.1 mL) at 0° C. was added TFA (1.5 mL), dropwise. After 1 h, the reaction was warmed to room temperature and concentrated under reduced pressure to provide the trifluoroacetate salt of the product as a yellow solid (320 mg, 99% yield). Used without further purification. LCMS (ESI) m/z: [M+H] calcd for $C_{19}H_{22}N_8OS$: 411.16; found 411.1.

Monomer S. 2-(5-(4-morpholino-1-(1-(pyridin-3-ylmethyl)piperidin-4-yl)-1H-pyrazolo[3,4-d]pyrimidin-6-yl)-1H-indol-3-yl)ethan-1-amine

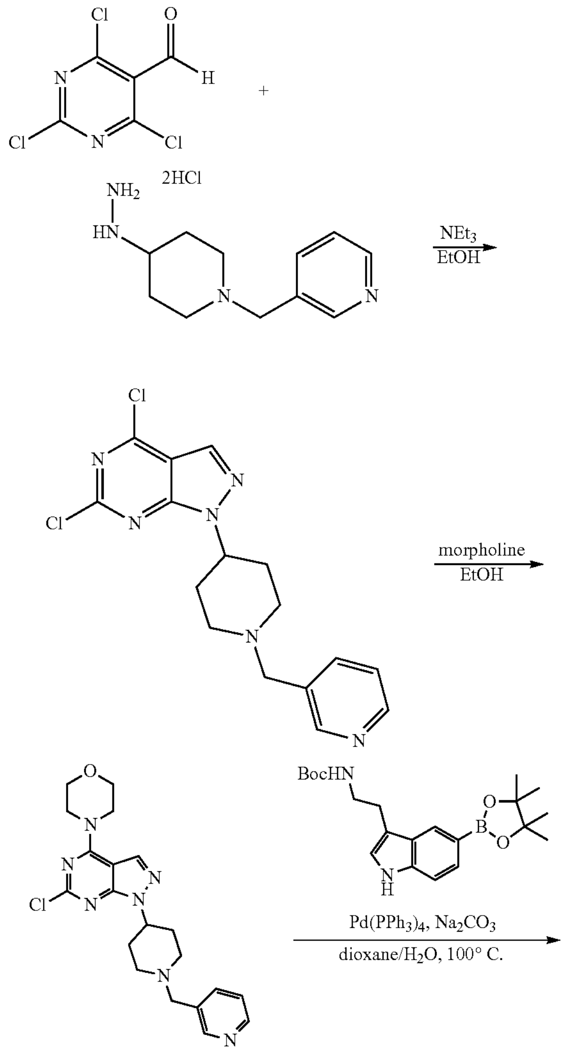

-continued

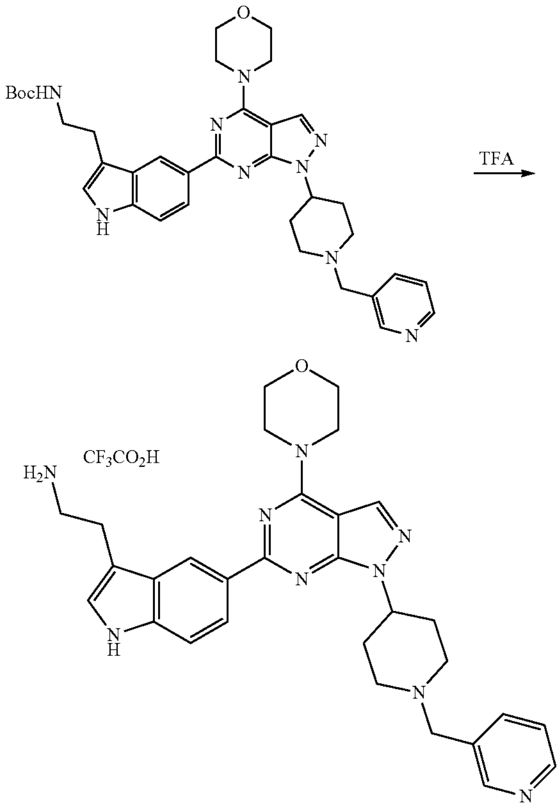

The synthesis of this monomer proceeds by condensation of 2,4,6-trichloropyrimidine-5-carbaldehyde with 3-((4-hydrazineylpiperidin-1-yl)methyl)pyridine hydrochloride. Reaction of the product with morpholine followed by a Suzuki reaction with boronic ester gives the Boc-protected amine. Final deprotection with TFA gives the monomer. This synthesis route follows closely to the reported preparation of highly related structures in the following references: i) Nowak, Pawel; Cole, Derek C.; Brooijmans, Natasja; Curran, Kevin J.; Ellingboe, John W.; Gibbons, James J.; Hollander, Irwin; Hu, Yong Bo; Kaplan, Joshua; Malwitz, David J.; et al From Journal of Medicinal Chemistry (2009), 52(22), 7081-7089. ii) Zask, Arie; Nowak, Pawel Wojciech; Verheijen, Jeroen; Curran, Kevin J.; Kaplan, Joshua; Malwitz, David; Bursavich, Matthew Gregory; Cole, Derek Cecil; Ayral-Kaloustian, Semiramis; Yu, Ker; et al From PCT Int. Appl. (2008), WO 2008115974 A2 20080925, which are incorporated by reference in their entirety.

Monomer T. 1-(4-aminobutyl)-3-iodo-1H-pyrazolo[3,4-d]pyrimidin-4-amine trifluoroacetic acid salt

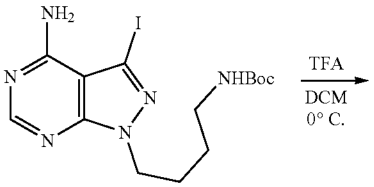

-continued

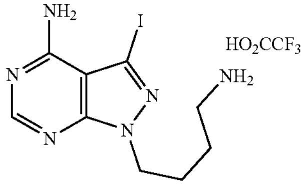

To a mixture of tert-butyl (4-(4-amino-3-iodo-1H-pyrazolo[3,4-d]pyrimidin-1-yl)butyl)carbamate (496 mg, 1.14 mmol, 1.0 equiv) in DCM (5.7 mL) at 0° C. was added TFA (1.5 mL) dropwise. The reaction was allowed to stir at 0° C. for 1 h, at which time the reaction was concentrated under reduced pressure to provide a yellow solid (505 mg, 99% yield) which was taken on without further purification. LCMS (ESI) m/z: [M+H] calcd for $C_9H_{13}IN_6$: 333.02; found 332.9.

Monomer U. 5-(4-amino-1-(4-(methylamino)butyl)-1H-pyrazolo[3,4-d]pyrimidin-3-yl)benzo[d]oxazol-2-amine trifluoroacetic acid salt

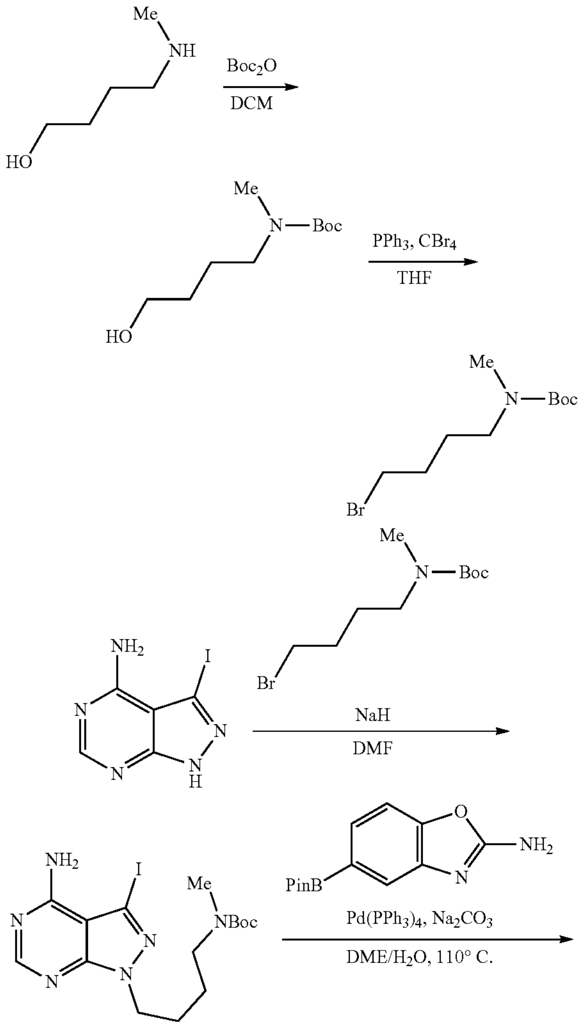

-continued

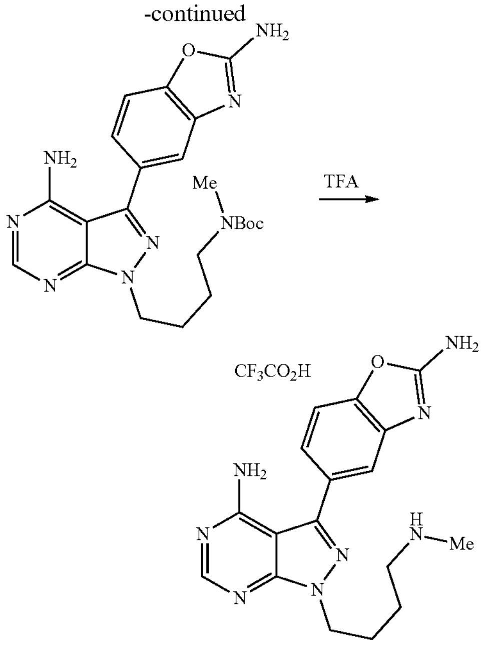

Step 1: Synthesis of tert-butyl (4-hydroxybutyl)(methyl)carbamate

To a solution of 4-(methylamino)butan-1-ol (0.5 g, 4.85 mmol, 104.2 mL, 1.0 equiv) in DCM (10 mL) at room temperature was added $Boc_2O$ (1.06 g, 4.85 mmol, 1.11 mL, 1.0 equiv). The mixture was stirred for 3 h at room temperature and then the mixture was concentrated under reduced pressure at 30° C. The residue was purified by silica gel chromatography (100/1 to 3/1 petroleum ether/EtOAc) to afford tert-butyl (4-hydroxybutyl)(methyl)carbamate (0.9 g, 91.4% yield) as a colorless oil.

Step 2: Synthesis of tert-butyl (4-bromobutyl)(methyl)carbamate

To a solution of tert-butyl (4-hydroxybutyl)(methyl)carbamate (0.9 g, 4.43 mmol, 1.0 equiv) in THF (20 mL) at room temperature was added $PPh_3$ (2.21 g, 8.41 mmol, 1.9 equiv) and $CBr_4$ (2.79 g, 8.41 mmol, 1.9 equiv). The mixture was stirred for 1 h and then the reaction mixture was filtered and concentrated. The residue was purified by silica gel chromatography (1/0 to 4/1 petroleum ether/EtOAc) to afford tert-butyl (4-bromobutyl)(methyl) carbamate (1.1 g, 93.3% yield) as a colorless oil.

Step 3: Synthesis of tert-butyl (4-(4-amino-3-iodo-1H-pyrazolo[3,4-d]pyrimidin-1-yl) butyl) (methyl) carbamate To a suspension of 3-iodo-1H-pyrazolo[3,4-d]pyrimidin-4-amine (0.9 g, 3.45 mmol, 1.0 equiv) in DMF (10 mL) at 4° C. was added NaH (137.92 mg, 3.45 mmol, 60 wt. %, 1.0 equiv). The mixture was stirred at 4° C. for 30 min and then a solution of tert-butyl (4-bromobutyl)(methyl)carbamate (1.01 g, 3.79 mmol, 25.92 mL, 1.1 equiv) in DMF (3 mL) was added. The mixture was stirred at room temperature for 3 h, at which point $H_2O$ (100 mL) was added. The aqueous phase was extracted with EtOAc (3×30 mL) and the combined organic phases were washed with brine (20 mL), dried with anhydrous $Na_2SO_4$, filtered and concentrated under reduced pressure. The residue was purified by silica gel chromatography (1/0 to 0/1 petroleum ether/EtOAc) to afford tert-butyl (4-(4-amino-3-iodo-1H-pyrazolo[3,4-d]pyrimidin-1-yl)butyl) (methyl) carbamate (1.2 g, 78% yield) as a white solid. LCMS (ESI) m/z: [M+H] calcd for $C_{15}H_{23}IN_6O_2$: 447.10; found 447.1.

Step 4: Synthesis of tert-butyl (4-(4-amino-3-(2-aminobenzo[d]oxazol-5-yl)-1H-pyrazolo[3,4-d] pyrimidin-1-yl)butyl)(methyl)carbamate To a bi-phasic suspension of tert-butyl (4-(4-amino-3-iodo-1H-pyrazolo[3,4-d]pyrimidin-1-yl)butyl)(methyl)carbamate (1.2 g, 2.69 mmol, 1.0 equiv), 5-(4,4,5,5-tetramethyl-1,3,2-dioxaborolan-2-yl)benzo[d]oxazol-2-amine (1.19 g, 3.23 mmol, 1.2 equiv), and $Na_2CO_3$ (1.42 g, 13.44 mmol, 5.0 equiv) in DME (20 mL) and $H_2O$ (10 mL) at room temperature was added $Pd(PPh_3)_4$ (310.71 mg, 268.89 μmol, 0.1 equiv) under $N_2$. The mixture was stirred at 110° C. for 3 h and then the reaction mixture was cooled and partitioned between EtOAc (20 mL) and $H_2O$ (15 mL). The aqueous layer was separated and extracted with EtOAc (3×20 mL). The combined organic layers were washed with brine (2×20 mL), dried over anhydrous $Na_2SO_4$, filtered and concentrated under reduced pressure. The crude product was purified by silica gel chromatography (1/0 to 4/1 EtOAc/MeOH) to give tert-butyl (4-(4-amino-3-(2-aminobenzo[d]oxazol-5-yl)-1H-pyrazolo [3,4-d]pyrimidin-1-yl)butyl)(methyl) carbamate (0.78 g, 62.5% yield) as an orange solid.

Step 5: Synthesis of 5-(4-amino-1-(4-(methylamino) butyl)-1H-pyrazolo[3,4-d] pyrimidin-3-yl) benzo[d] oxazol-2-amine A solution of tert-butyl(4-(4-amino-3-(2-aminobenzo[d] oxazol-5-yl)-1H-pyrazolo[3,4-d]pyrimidin-1-yl)butyl) (methyl)carbamate (0.78 g, 1.72 mmol, 1.0 equiv) in TFA (5 mL) at room temperature was stirred for 30 min. The solution was concentrated under reduced pressure and the oily residue was triturated with MeCN (1 mL) and then added to MTBE (100 mL). The supernatant was removed and then the precipitate was collected by filtration under $N_2$ to give 5-(4-amino-1-(4-(methylamino) butyl)-1H-pyrazolo [3,4-d]pyrimidin-3-yl)benzo[d]oxazol-2-amine bis-trifluorosulfonate (0.959 g, 93% yield) as an orange solid. LCMS (ESI) m/z: [M+H] calcd for $C_{17}H_{20}N_8O$: 353.18; found 353.1.

Monomer V. 1-(4-(4-(5-(aminomethyl)pyrimidin-2-yl)piperazin-1-yl)-3-(trifluoromethyl)phenyl)-8-(6-methoxypyridin-3-yl)-3-methyl-1,3-dihydro-2H-imidazo[4,5-c]quinolin-2-one

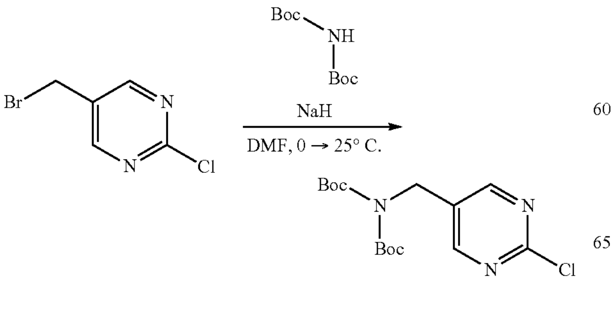

-continued

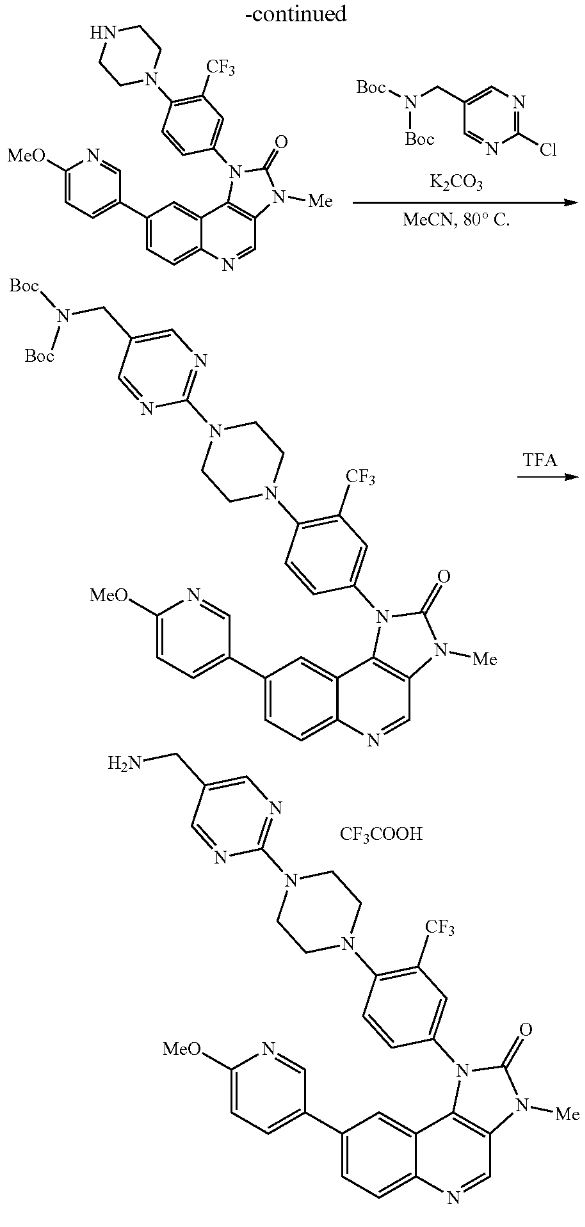

Step 1: Synthesis of tert-butyl N-tert-butoxycarbonyl-N-[(2-chloropyrimidin-5-yl)methyl] carbamate To a solution of tert-butyl N-tert-butoxycarbonylcarbamate (7.33 g, 33.74 mmol, 1.0 equiv) in DMF (80 mL) was added NaH (1.62 g, 40.49 mmol, 60 wt. %, 1.2 equiv) at 0° C. The mixture was stirred at 0° C. for 30 min and then 5-(bromomethyl)-2-chloropyrimidine (7 g, 33.74 mmol, 1 equiv) was added. The reaction mixture was stirred at room temperature for 1.5 h and then the mixture was poured into sat. $NH_4Cl$ (300 mL) and stirred for 5 min. The aqueous phase was extracted with EtOAc (3×80 mL) and the combined organic phases were washed with brine (50 mL), dried over anhydrous $Na_2SO_4$, filtered and concentrated under reduced pressure. The residue was purified by silica gel chromatography (20:1 to 1:1 petroleum ether/EtOAc) to afford tert-butyl N-tert-butoxycarbonyl-N-[(2-chloro pyrimidin-5-yl)methyl]carbamate (7.0 g, 60.3% yield) as a white solid. LCMS (ESI) m/z: [M+H] calcd for $C_{15}H_{22}ClN_3O_4$: 344.14; found 344.2.

Step 2: Synthesis of tert-butyl N-tert-butoxycarbonyl-N-[[2-[4-[4-[8-(6-methoxy-3-pyridyl)-3-methyl-2-oxo-imidazo[4,5-c]quinolin-1-yl]-2-(trifluoromethyl)phenyl]piperazin-1-yl]pyrimidin-5-yl]methyl] carbamate To a solution of 8-(6-methoxy-3-pyridyl)-3-methyl-1-[4-piperazin-1-yl-3-(trifluoromethyl)phenyl]imidazo[4,5-c] quinolin-2-one (0.4 g, 748.32 μmol, 1.0 equiv) in MeCN (7 mL) was added tert-butyl N-tert-butoxycarbonyl-N-[(2-chloropyrimidin-5-yl)methyl]carbamate (514.55 mg, 1.50 mmol, 2.0 equiv) and $K_2CO_3$ (413.69 mg, 2.99 mmol, 4 equiv) at room temperature. The reaction mixture was stirred at 80° C. for 14 h and then the mixture was cooled to room temperature, filtered and concentrated under reduced pressure. The residue was purified by washing with MTBE (5 mL) to give tert-butyl N-tert-butoxycarbonyl-N-[[2-[4-[4-[8-(6-methoxy-3-pyridyl)-3-methyl-2-oxo-imidazo[4,5-c] quinolin-1-yl]-2-(trifluoromethyl)phenyl]piperazin-1-yl]pyrimidin-5-yl]methyl]carbamate (0.57 g, 90.5% yield) as a light yellow solid. LCMS (ESI) m/z: [M+H] calcd for $C_{43}H_{46}F_3N_9O_6$: 842.36; found 842.7.

Step 3: Synthesis of 1-[4-[4-[5-(aminomethyl)pyrimidin-2-yl]piperazin-1-yl]-3-(trifluoromethyl) phenyl]-8-(6-methoxy-3-pyridyl)-3-methyl-imidazo[4,5-c]quinolin-2-one A solution of tert-butyl N-tert-butoxycarbonyl-N-[[2-[4-[4-[8-(6-methoxy-3-pyridyl)-3-methyl-2-oxo-imidazo[4,5-c]quinolin-1-yl]-2-(trifluoromethyl)phenyl]piperazin-1-yl] pyrimidin-5-yl]methyl]carbamate (0.95 g, 1.13 mmol, 1 equiv) in TFA (10 mL) was stirred at room temperature for 1 h, at which point the solvent was concentrated. The residue was dissolved in MeCN (10 mL) and then the solution was added to MTBE (150 mL), dropwise. The precipitate was collected to give 1-[4-[4-[5-(aminomethyl)pyrimidin-2-yl] piperazin-1-yl]-3-(trifluoromethyl)phenyl]-8-(6-methoxy-3-pyridyl)-3-methyl-imidazo[4,5-c]quinolin-2-one trifluoromethanesulfonate (0.778 g, 84.8% yield) as a yellow solid. LCMS (ESI) m/z: [M+H] calcd for $C_{33}H_{30}F_3N_9O_2$: 642.26; found 642.4.

Monomer W. 1-(4-aminobutyl)-3-(1H-pyrrolo[2,3-b] pyridin-5-yl)pyrazolo[3,4-d]pyrimidin-4-amine

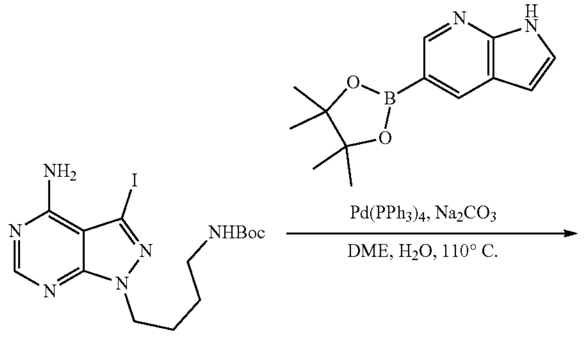

-continued

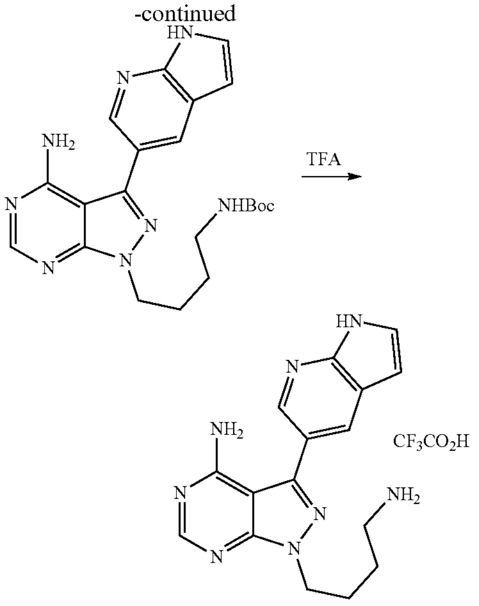

Step 1: Synthesis of tert-butyl N-[4-[4-amino-3-(1H-indol-5-yl)pyrazolo[3,4-d]pyrimidin-1-yl]butyl] carbamate To a bi-phasic suspension of tert-butyl N-[4-(4-amino-3-iodo-pyrazolo[3,4-d]pyrimidin-1-yl)butyl]carbamate (8 g, 18.51 mmol, 1 equiv), 5-(4,4,5,5-tetramethyl-1,3,2-dioxaborolan-2-yl)-1H-pyrrolo[2,3-b]pyridine (5.42 g, 22.21 mmol, 1.2 equiv) and $Na_2CO_3$ (9.81 g, 92.54 mmol, 5 equiv) in diglyme (160 mL) and $H_2O$ (80 mL) was added $Pd(PPh_3)_4$ (2.14 g, 1.85 mmol, 0.1 equiv) at room temperature under $N_2$. The mixture was stirred at 110° C. for 3 h. The reaction mixture was cooled to room temperature, filtered and the filtrate was partitioned between EtOAc (500 mL) and $H_2O$ (500 mL). The aqueous layer was separated and extracted with EtOAc (3×300 mL). The organic layers were combined, washed with brine (20 mL) and dried over anhydrous $Na_2SO_4$, then filtered and the filtrate was concentrated under reduced pressure. The residue was purified by silica gel chromatography (1/0 to 0/1 petroleum ether/EtOAc then 4/1 EtOAc/MeOH) to give tert-butyl N-[4-[4-amino-3-(1H-indol-5-yl)pyrazolo[3,4-d]pyrimidin-1-yl]butyl]carbamate (6.6 g, 84.6% yield) as a yellow solid. LCMS (ESI) m/z: [M+H] calcd for $C_{22}H_{27}N_7O_2$: 422.22; found 423.3.

Step 2: Synthesis of 1-(4-aminobutyl)-3-(1H-pyrrolo[2,3-b]pyridin-5-yl)pyrazolo[3,4-d]pyrimidin-4-amine To tert-butyl N-[4-[4-amino-3-(1H-indol-5-yl)pyrazolo [3,4-d]pyrimidin-1-yl]butyl]carbamate (6.6 g, 15.66 mmol, 1 equiv) was added TFA (66 mL), which was then stirred at room temperature for 30 min. The reaction solution was concentrated under reduced pressure to remove TFA and then MTBE (400 mL) was added to the residue. The suspension was stirred for 15 min, at which point the yellow solid was filtered, and the solid cake dried under reduced pressure to give 1-(4-aminobutyl)-3-(1H-pyrrolo[2,3-b] pyridin-5-yl)pyrazolo[3,4-d]pyrimidin-4-amine (10.2 g, 97.1% yield) as a yellow solid. LCMS (ESI) m/z: [M+H] calcd for $C_{16}H_{18}N_8$: 323.17; found 323.1.

Monomer X. 2-(4-amino-1-((1,2,3,4-tetrahydroisoquinolin-6-yl)methyl)-1H-pyrazolo[3,4-d]pyrimidin-3-yl)-1H-indol-5-ol 2,2,2-trifluoroacetate

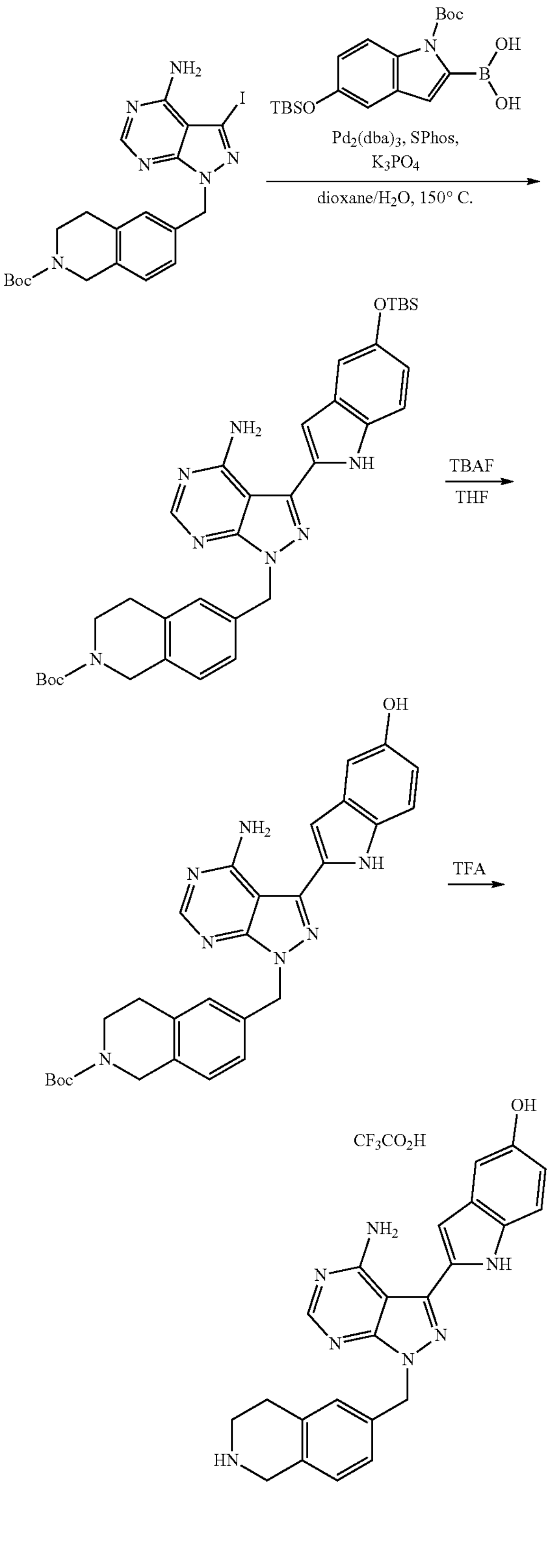

Step 1: Synthesis of tert-butyl 6-((4-amino-3-(5-((tert-butyldimethylsilyl)oxy)-1H-indol-2-yl)-1H-pyrazolo[3,4-d]pyrimidin-1-yl)methyl)-3,4-dihydroisoquinoline-2(1H)-carboxylate To a solution of tert-butyl 6-((4-amino-3-iodo-1H-pyrazolo[3,4-d]pyrimidin-1-yl)methyl)-3,4-dihydroisoquinoline-2(1H)-carboxylate (1 g, 1.97 mmol, 1.0 equiv) in dioxane (10.5 mL) and $H_2O$ (3.5 mL) was added (1-(tert-butoxycarbonyl)-5-((tert-butyldimethylsilyl)oxy)-1H-indol-2-yl)boronic acid (1.16 g, 2.96 mmol, 1.5 equiv), $K_3PO_4$ (1.26 g, 5.92 mmol, 3.0 equiv), $Pd_2(dba)_3$ (180.85 mg, 197.50 μmol, 0.1 equiv), and SPhos (162.16 mg, 394.99 μmol, 0.2 equiv) at room temperature under $N_2$. The sealed tube was heated at 150° C. for 20 min under microwave. The reaction mixture was then cooled and 6 separate batches were combined together. The reaction mixture was partitioned between EtOAc (100 mL) and $H_2O$ (100 mL). The aqueous layer was separated and extracted with EtOAc (3×80 mL). The organic layers were combined, washed with brine (100 mL) and dried over anhydrous $Na_2SO_4$. The solution was filtered and the filtrate was concentrated under reduced pressure. The crude material was purified by silica gel column chromatography (100/1 to ¼ petroleum ether/EtOAc) to give tert-butyl 6-((4-amino-3-(5-((tert-butyldimethylsilyl)oxy)-1H-indol-2-yl)-1H-pyrazolo [3,4-d]pyrimidin-1-yl)methyl)-3,4-dihydroisoquinoline-2(1H)-carboxylate (6.17 g, 82.9% yield) as a light yellow solid.

Step 2: Synthesis of tert-butyl 6-((4-amino-3-(5-hydroxy-1H-indol-2-yl)-1H-pyrazolo[3,4-d]pyrimidin-1-yl)methyl)-3,4-dihydroisoquinoline-2(1H)-carboxylate To a mixture of tert-butyl 6-((4-amino-3-(5-((tert-butyldimethylsilyl)oxy)-1H-indol-2-yl)-1H-pyrazolo[3,4-d]pyrimidin-1-yl)methyl)-3,4-dihydroisoquinoline-2(1H)-carboxylate (6.17 g, 9.86 mmol, 1.0 equiv) in THF (100 mL) was added tetrabutylammonium fluoride trihydrate (1 M, 10.84 mL, 1.1 equiv) in one portion at 0° C. under $N_2$. The mixture was stirred at 0° C. for 1 h and was then added to $H_2O$ (100 mL). The aqueous phase was extracted with EtOAc (3×80 mL) and the combined organic phase was washed with brine (2×80 mL), dried with anhydrous $Na_2SO_4$, filtered and concentrated under reduced pressure. The residue was purified by silica gel chromatography (1/1 to 0/1 petroleum ether/EtOAc) to afford tert-butyl 6-((4-amino-3-(5-hydroxy-1H-indol-2-yl)-1H-pyrazolo[3,4-d]pyrimidin-1-yl)methyl)-3,4-dihydroisoquinoline-2(1H)-carboxylate (4 g, 79.3% yield) as a light pink solid. LCMS (ESI) m/z: [M+H] calcd for $C_{28}H_{29}N_7O_3$: 512.24; found 512.3.

Step 3: Synthesis of 2-(4-amino-1-((1,2,3,4-tetrahydroisoquinolin-6-yl)methyl)-1H-pyrazolo[3,4-d]pyrimidin-3-yl)-1H-indol-5-ol 2,2,2-trifluoroacetate To a solution of tert-butyl 6-((4-amino-3-(5-hydroxy-1H-indol-2-yl)-1H-pyrazolo [3,4-d]pyrimidin-1-yl)methyl)-3,4-dihydroisoquinoline-2(1H)-carboxylate (4.5 g, 8.80 mmol, 1.0 equiv) in MeOH (50 mL) was added HCl in MeOH (4 M, 50 mL, 22.7 equiv) at room temperature. The mixture was stirred at room temperature overnight and was then concentrated under reduced pressure. To the crude product was added EtOAc (100 mL) and the resulting precipitate was collected by filtration under $N_2$ to give 2-(4-amino-1-((1,2,3,4-tetrahydroisoquinolin-6-yl)methyl)-1H-pyrazolo

[3,4-d]pyrimidin-3-yl)-1H-indol-5-ol 2,2,2-trifluoroacetate (4.1 g, 85.0% yield, 3HCl) as a light yellow solid. LCMS (ESI) m/z: [M+H] calcd for $C_{23}H_{21}N_7O$: 412.19; found 412.1.

Monomer Y. 3-(1H-pyrrolo[2,3-b]pyridin-5-yl)-1-((1,2,3,4-tetrahydroisoquinolin-6-yl)methyl)-1H-pyrazolo[3,4-d]pyrimidin-4-amine 2,2,2-trifluoroacetate

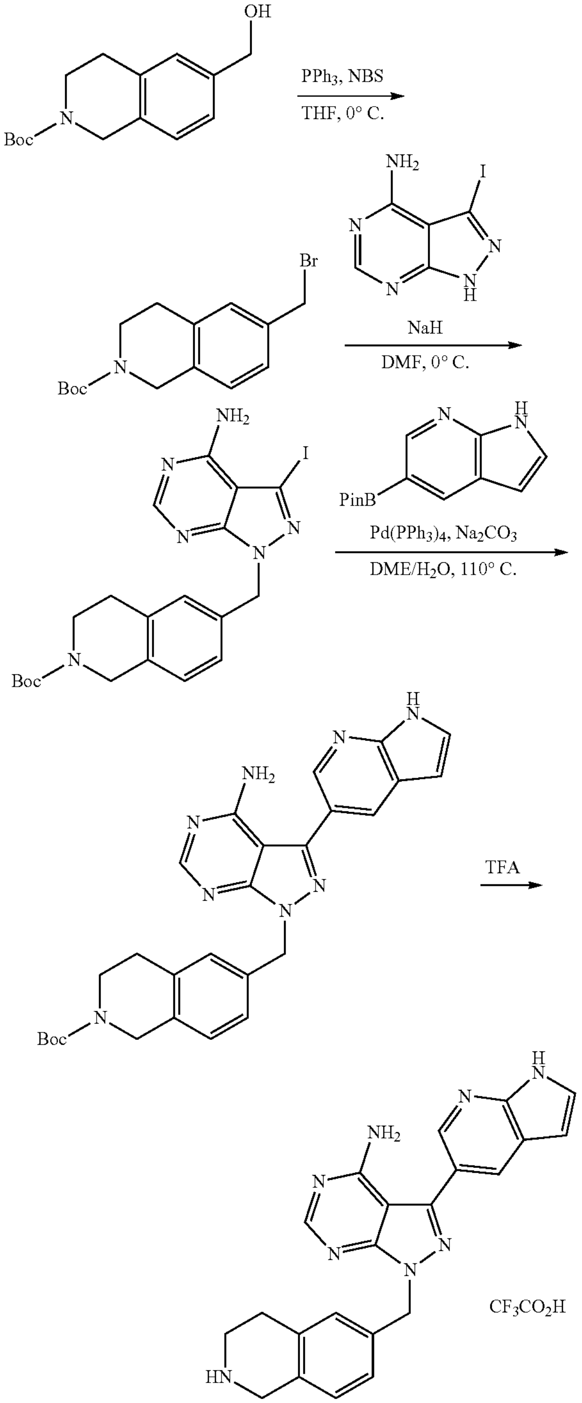

Step 1: Synthesis of tert-butyl 6-(bromomethyl)-3,4-dihydroisoquinoline-2(1H)-carboxylate A solution of NBS (34.07 g, 191.39 mmol, 4 equiv) in THF (200 mL) was added in portions to a solution of tert-butyl 6-(hydroxymethyl)-3,4-dihydroisoquinoline-2(1H)-carboxylate (12.6 g, 47.85 mmol, 1.0 equiv) and triphenylphosphine (37.65 g, 143.55 mmol, 3.0 equiv) in THF (200 mL) at 0° C. After the addition was complete, the mixture was stirred for 1 h at room temperature. EtOAc (150 mL) was added and the mixture was washed with $H_2O$ (200 mL) and brine (150 mL), dried over anhydrous $Na_2SO_4$ and concentrated under reduced pressure. The residue was purified by silica gel chromatography (100/1 to 10/1 petroleum ether/EtOAc) to afford tert-butyl 6-(bromomethyl)-3,4-dihydroisoquinoline-2(1H)-carboxylate (8.56 g, 54.8% yield) as a light yellow solid.

Step 2: Synthesis of tert-butyl 6-((4-amino-3-iodo-TH-pyrazolo[3,4-d]pyrimidin-1-yl) methyl)-3,4-dihydroisoquinoline-2(1H)-carboxylate To a suspension of 3-iodo-1H-pyrazolo[3,4-d]pyrimidin-4-amine (9.5 g, 36.40 mmol, 1.0 equiv) in DMF (110 mL) was added NaH (1.46 g, 36.40 mmol, 60 wt. %, 1.0 equiv) at 0° C. The mixture was stirred at 0° C. for 30 min at which point a solution of tert-butyl 6-(bromomethyl)-3,4-dihydroisoquinoline-2(1H)-carboxylate (12.47 g, 38.22 mmol, 1.05 equiv) in DMF (40 mL) was added at 0° C. The mixture was stirred at room temperature for 1 h and then $H_2O$ (1000 mL) was added at 0° C. The mixture stirred at 0° C. for 30 min and then the resulting precipitate was collected by filtration to give tert-butyl 6-((4-amino-3-iodo-TH-pyrazolo [3,4-d] pyrimidin-1-yl)methyl)-3,4-dihydroisoquinoline-2(1H)-carboxylate (17.8 g, 76.3% yield) as a light yellow solid, which was used the next step directly. LCMS (ESI) m/z: [M+H] calcd for $C_{20}H_{23}IN_6O_2$: 507.10; found 507.1.

Step 3: Synthesis of tert-butyl 6-((4-amino-3-(1H-pyrrolo[2,3-b]pyridin-5-yl)-1H-pyrazolo[3,4-d]pyrimidin-1-yl)methyl)-3,4-dihydroisoquinoline-2(1H)-carboxylate To a bi-phasic suspension of tert-butyl 6-((4-amino-3-iodo-1H-pyrazolo [3,4-d]pyrimidin-1-yl)methyl)-3,4-dihydroisoquinoline-2(1H)-carboxylate (6.5 g, 10.14 mmol, 1.0 equiv), 5-(4,4,5,5-tetramethyl-1,3,2-dioxaborolan-2-yl)-1H-pyrrolo [2,3-b] pyridine (2.97 g, 12.16 mmol, 1.2 equiv), and $Na_2CO_3$ (5.37 g, 50.68 mmol, 5.0 equiv) in diglyme (100 mL) and $H_2O$ (50 mL) was added $Pd(PPh_3)_4$ (1.17 g, 1.01 mmol, 0.1 equiv) at room temperature under $N_2$. The mixture was stirred at 110° C. for 3 h. The reaction mixture was then cooled and partitioned between EtOAc (100 mL) and $H_2O$ (100 mL). The aqueous layer was separated and extracted with EtOAc (2×100 mL). The combined organic phase was washed with brine (100 mL), dried with anhydrous $Na_2SO_4$, filtered and concentrated under reduced pressure. The residue was purified by silica gel chromatography (0/1 to ¼ MeOH/EtOAc) to afford tert-butyl 6-((4-amino-3-(1H-pyrrolo[2,3-b]pyridin-5-yl)-1H-pyrazolo[3,4-d]pyramid in-1-yl) methyl)-3,4-dihydroisoquinoline-2(1H)-carboxylate (3.77 g, 72.1% yield) as alight yellow solid. LCMS (ESI) m/z: [M+H] calcd for $C_{27}H_{28}N_8O_2$: 497.24; found 497.3.

Step 4: Synthesis of 3-(1H-pyrrolo[2,3-b]pyridin-5-yl)-1-((1,2,3,4-tetrahydroiso quinolin-6-yl)methyl)-1H-pyrazolo[3,4-d]pyrimidin-4-amine 2,2,2-trifluoroacetate tert-Butyl 6-((4-amino-3-(1H-pyrrolo[2,3-b]pyridin-5-yl)-1H-pyrazolo[3,4-d]pyrimidin-1-yl)methyl)-3,4-dihydroisoquinoline-2(1H)-carboxylate (3.77 g, 7.59 mmol, 1.0 equiv) was added to TFA (85.36 mL, 1.15 mol, 151.8 equiv) at room temperature. The reaction mixture was stirred for 1 h. It was then concentrated under reduced pressure and the oily residue was triturated with MeCN (3 mL), then dripped into MTBE (200 mL) for 5 min. The supernatant was removed and then the precipitate was collected by filtration under $N_2$ to give the product, which was dissolved in MeCN (20 mL), and finally concentrated under reduced pressure to give 3-(1H-pyrrolo[2,3-b]pyridin-5-yl)-1-((1,2,3,4-tetrahydroisoquinolin-6-yl)methyl)-1H-pyrazolo[3,4-d]pyrimidin-4-amine 2,2,2-trifluoroacetate (4.84 g, 85.0% yield, 3TFA) as a light yellow solid. LCMS (ESI) m/z: [M+H] calcd for $C_{22}H_{20}N_8$: 397.19; found 397.2.

Monomer Z. (4-((2-aminoethyl)sulfonyl)-3-fluoro-2-methylphenyl)(7-(6-aminopyridin-3-yl)-2,3-dihydrobenzo[f][1,4]oxazepin-4(5H)-yl)methanone 2,2,2-trifluoroacetate

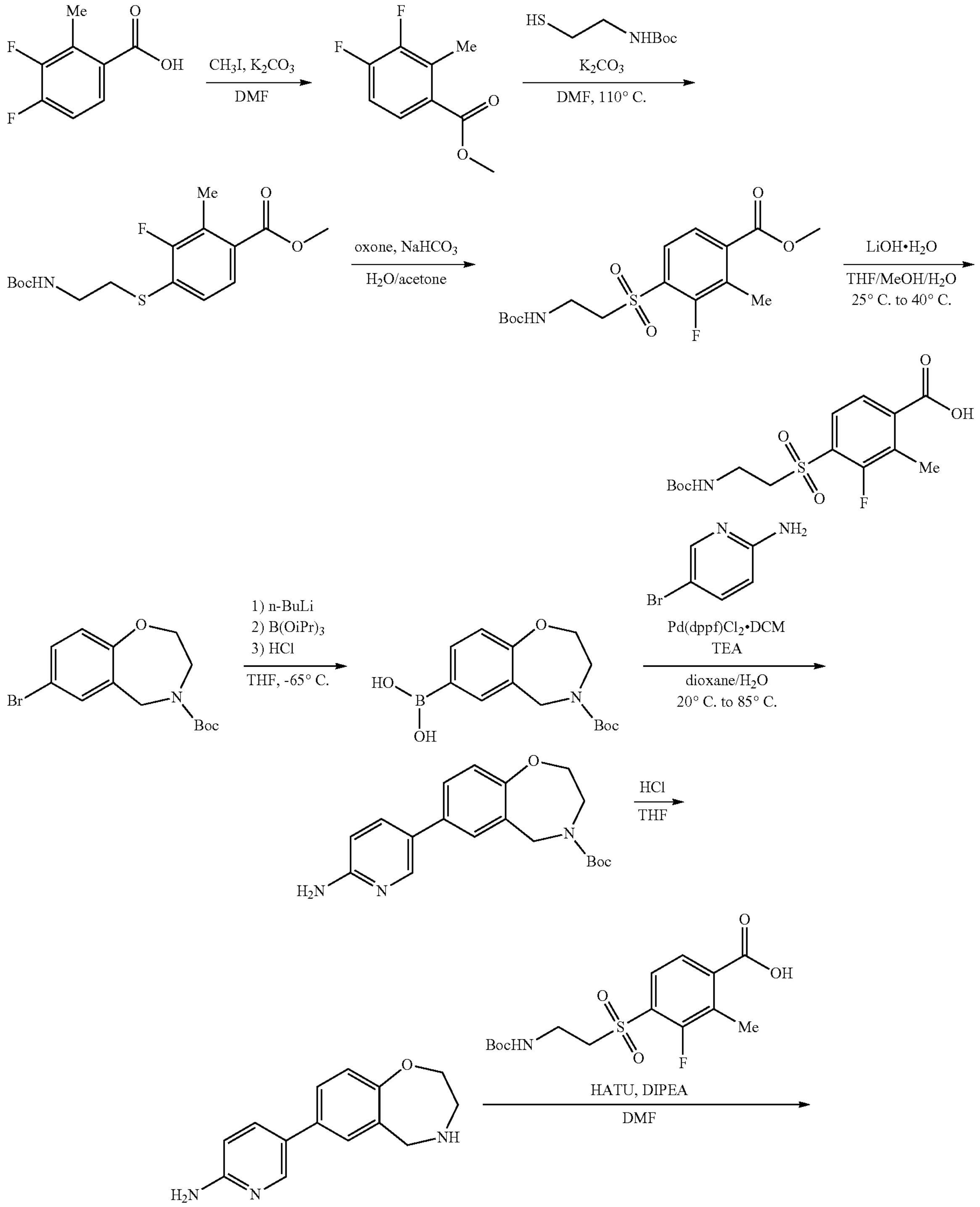

-continued

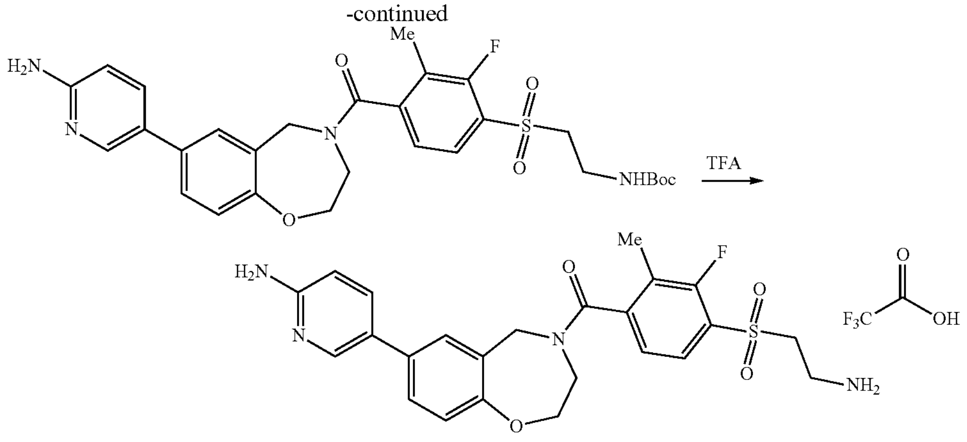

Step 1: Synthesis of methyl 3,4-difluoro-2-methylbenzoate

To a solution of 3,4-difluoro-2-methylbenzoic acid (2 g, 11.62 mmol, 1.0 equiv) in DMF (20 mL) was added $K_2CO_3$ (4.82 g, 34.86 mmol, 3.0 equiv) and iodomethane (3.26 mL, 52.29 mmol, 4.5 equiv) at room temperature. The mixture was stirred at room temperature for 3 h. The solution of methyl 3,4-difluoro-2-methylbenzoate in DMF (20 mL) was used directly in the next step.

Step 2: Synthesis of methyl 4-((2-((tert-butoxycarbonyl)amino)ethyl)thio)-3-fluoro-2-methylbenzoate To a solution of methyl 3,4-difluoro-2-methylbenzoate (2.16 g, 11.28 mmol, 1.0 equiv) in DMF (20 mL) was added tert-butyl (2-mercaptoethyl)carbamate (2.0 g, 11.28 mmol, 1 equiv) and $K_2CO_3$ (3.12 g, 22.56 mmol, 2.0 equiv) at room temperature. The reaction was stirred at 110° C. for 12 h, at which point the mixture was added to $H_2O$ (50 mL). The aqueous solution was then extracted with EtOAc (3x30 mL) and the organic phase was combined and concentrated under reduced pressure. The residue was purified by silica gel chromatography (1/0 to 3/1 petroleum ether/EtOAc) to afford methyl 4-((2-((tert-butoxycarbonyl)amino)ethyl)thio)-3-fluoro-2-methylbenzoate (3.0 g, 76% yield) as light yellow solid.

Step 3: Synthesis of methyl 4-((2-((tert-butoxycarbonyl)amino)ethyl)sulfonyl)-3-fluoro-2-methylbenzoate To a solution of methyl 4-((2-((tert-butoxycarbonyl)amino)ethyl)thio)-3-fluoro-2-methylbenzoate (3.3 g, 9.61 mmol, 1.0 equiv), NaOH (2 M, 4.80 mL, 1.0 equiv), and $NaHCO_3$ (2.42 g, 28.83 mmol, 3.0 equiv) in acetone (30 mL) was added potassium peroxymonosulfate (12.35 g, 20.08 mmol, 2.1 equiv). The mixture was stirred for 12 h at room temperature and then the mixture was acidified to pH 5 by addition of 1N HCl. The aqueous layer was extracted with EtOAc (3x30 mL) and the combined organic phase was washed with brine (20 mL), dried with anhydrous $Na_2SO_4$, filtered and concentrated under reduced pressure. The residue was purified by silica gel chromatography (1/0 to 3/1 petroleum ether/EtOAc) to afford methyl 4-((2-((tert-butoxycarbonyl)amino)ethyl)sulfonyl)-3-fluoro-2-methylbenzoate (2.1 g, 58.2% yield) as a yellow solid. LCMS (ESI) m/z: [M−56+H] calcd for $C_{16}H_{22}FNO_6S$: 320.12; found 320.1.

Step 4: Synthesis of 4-((2-((tert-butoxycarbonyl)amino)ethyl)sulfonyl)-3-fluoro-2-methylbenzoic acid To a solution of methyl 4-((2-((tert-butoxycarbonyl)amino)ethyl)sulfonyl)-3-fluoro-2-methylbenzoate (2.1 g, 5.59 mmol, 1.0 equiv) in THF (20 mL), MeOH (10 mL) and $H_2O$ (10 mL) was added $LiOH \cdot H_2O$ (704.16 mg, 16.78 mmol, 3.0 equiv) at room temperature. The reaction mixture was stirred at 40° C. for 4 h. The mixture was then concentrated under reduced pressure to remove THF and MeOH. The aqueous phase was neutralized with 0.5N HCl and was then extracted with EtOAc (5x20 mL). The combined organic phase was washed with brine (2x20 mL), dried with anhydrous $Na_2SO_4$, filtered and concentrated under reduced pressure to give 4-((2-((tert-butoxycarbonyl)amino)ethyl)sulfonyl)-3-fluoro-2-methylbenzoic acid (2.01 g, 97.1% yield) as a white solid. LCMS (ESI) m/z: [M−100+H] calcd for $C_{15}H_{20}FNO_6S$: 262.11; found 262.1.

Step 5: Synthesis of (4-(tert-butoxycarbonyl)-2,3,4,5-tetrahydrobenzo[f][1,4] oxazepin-7-yl)boronic acid To a solution of tert-butyl 7-bromo-2,3-dihydrobenzo[f][1,4]oxazepine-4(5H)-carboxylate (4 g, 12.19 mmol, 1.0 equiv) in THF (80 mL) at −60° C. was added $B(OiPr)_3$ (4.58 g, 24.38 mmol, 5.60 mL, 2.0 equiv) followed by dropwise addition of n-BuLi (2.5 M, 12.19 mL, 2.5 equiv) in n-hexane. The reaction was stirred at −65° C. for 1 h. The reaction mixture was quenched with 1N HCl (12.25 mL) and allowed to warm to room temperature. The reaction mixture was extracted with EtOAc (3x30 mL), dried over anhydrous $Na_2SO_4$, filtered and concentrated under reduced pressure to give (4-(tert-butoxycarbonyl)-2,3,4,5-tetrahydrobenzo[f][1,4]oxazepin-7-yl)boronic acid (3.5 g, crude) as light yellow oil, which was used to the next step directly. LCMS (ESI) m/z: [M−100+H] calcd for $C_{14}H_{20}BNO_5$: 194.15; found 194.2.

Step 6: Synthesis of tert-butyl 7-(6-aminopyridin-3-yl)-2,3-dihydrobenzo[f][1,4] oxazepine-4(5H)-carboxylate To a solution of (4-(tert-butoxycarbonyl)-2,3,4,5-tetrahydrobenzo[f][1,4]oxazepin-7-yl)boronic acid (4.2 g, 14.33 mmol, 1.0 equiv) in $H_2O$ (20 mL) and dioxane (60 mL) was added 5-bromopyridin-2-amine (2.48 g, 14.33 mmol, 1.0 equiv), Pd(dppf)$Cl_2$.DCM (1.17 g, 1.43 mmol, 0.1 equiv) and $Et_3N$ (4.35 g, 42.99 mmol, 5.98 mL, 3.0 equiv) at room temperature. The mixture was stirred at 85° C. for 12 h. The mixture was then cooled to room temperature and the residue was poured into $H_2O$ (15 mL). The aqueous phase was extracted with EtOAc (3×40 mL) and the combined organic phase was washed with brine (2×40 mL), dried with anhydrous $Na_2SO_4$, filtered and concentrated under reduced pressure. The residue was purified by silica gel chromatography (1/0 to ⅛ petroleum ether/EtOAc) to afford tert-butyl 7-(6-aminopyridin-3-yl)-2,3-dihydrobenzo[f][1,4]oxazepine-4(5H)-carboxylate (3.3 g, 65.0% yield) as light yellow solid. LCMS (ESI) m/z: [M+H] calcd for $C_{19}H_{23}N_3O_3$: 342.18; found 342.2.

Step 7: Synthesis of 5-(2,3,4,5-tetrahydrobenzo[f][1,4]oxazepin-7-yl)pyridin-2-amine To a solution of tert-butyl 7-(6-aminopyridin-3-yl)-2,3-dihydrobenzo[f][1,4]oxazepine-4(5H)-carboxylate (3.3 g, 9.67 mmol, 1.0 equiv) in THF (40 mL) was added HCl in EtOAc (4 M, 100 mL, 41.38 equiv) at room temperature. The mixture was stirred for 3 h. The reaction mixture was filtered and the filter cake was washed with EtOAc (3×15 mL) and then dried under reduced pressure to give 5-(2,3,4,5-tetrahydrobenzo [f][1,4]oxazepin-7-yl)pyridin-2-amine (3 g, 95.1% yield, 2HCl) as a light yellow solid.

Step 8: Synthesis of tert-butyl (2-((4-(7-(6-amino-pyridin-3-yl)-2,3,4,5-tetrahydrobenzo[f][1,4]oxazepine-4-carbonyl)-2-fluoro-3-methylphenyl)sulfonyl)ethyl)carbamate To a solution of 4-((2-((tert-butoxycarbonyl)amino)ethyl)sulfonyl)-3-fluoro-2-methylbenzoic acid (690.08 mg, 1.91 mmol, 1.0 equiv) in DMF (10 mL) was added HATU (1.09 g, 2.86 mmol, 1.5 equiv) and DIPEA (1.66 mL, 9.55 mmol, 5 equiv). The reaction was stirred at room temperature for 30 min and then 5-(2,3,4,5-tetrahydrobenzo[f][1,4]oxazepin-7-yl)pyridin-2-amine (0.6 g, 1.91 mmol, 1.0 equiv, 2HCl) was added. The mixture was stirred for 2 h, at which point $H_2O$ (40 mL) was added. The mixture was stirred for 5 min and the resulting precipitate was collected by filtration to give the crude product. The residue was purified by silica gel chromatography (1/0 to 10/1 EtOAc/MeOH) to afford tert-butyl (2-((4-(7-(6-aminopyridin-3-yl)-2,3,4,5-tetrahydrobenzo[f][1,4] oxazepine-4-carbonyl)-2-fluoro-3-methylphenyl)sulfonyl)ethyl)carbamate (0.538 g, 47.4% yield) as a light yellow solid. LCMS (ESI) m/z: [M+H] calcd for $C_{29}H_{33}FN_4O_6S$: 585.22; found 585.3.

Step 9: Synthesis of (4-((2-aminoethyl)sulfonyl)-3-fluoro-2-methylphenyl)(7-(6-aminopyridin-3-yl)-2,3-dihydrobenzo[f][1,4]oxazepin-4(5H)-yl)methanone 2,2,2-trifluoroacetate A solution tert-butyl (2-((4-(7-(6-aminopyridin-3-yl)-2,3,4,5-tetrahydrobenzo[f][1,4] oxazepine-4-carbonyl)-2-fluoro-3-methylphenyl)sulfonyl)ethyl)carbamate (0.538 g, 920.20 μmol, 1.0 equiv) in TFA (10.35 mL, 139.74 mmol, 151.85 equiv) was stirred at room temperature for 2 h. The solution was then concentrated under reduced pressure. The oily residue was triturated with MeCN (1 mL) and then dripped into MTBE (30 mL) for 10 min. The supernatant was removed and then the precipitate was collected by filtration under $N_2$ to give (4-((2-aminoethyl)sulfonyl)-3-fluoro-2-methylphenyl)(7-(6-aminopyridin-3-yl)-2,3-dihydrobenzo[f][1,4]oxazepin-4(5H)-yl)methanone 2,2,2-trifluoroacetate (0.50 g, 87.4% yield) as light brown solid. LCMS (ESI) m/z: [M+H] calcd for $C_{24}H_{25}FN_4O_4S$: 485.17; found 485.1.

Monomer AA. 5-(4-amino-1-(6-(piperazin-1-yl)pyrimidin-4-yl)-1H-pyrazolo[3,4-d]pyrimidin-3-yl)benzo[d]oxazol-2-amine trifluoroacetic acid salt

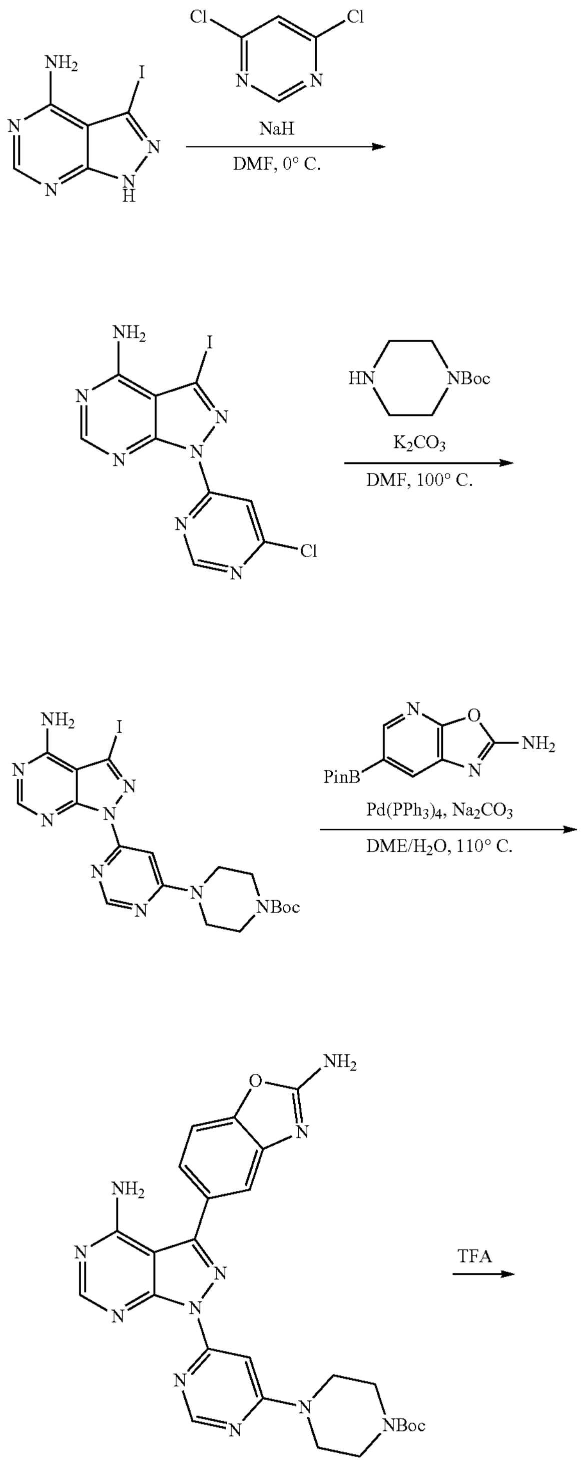

-continued

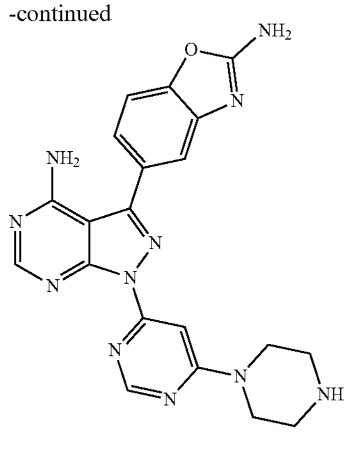

Step 1: Synthesis of 1-(6-chloropyrimidin-4-yl)-3-iodo-1H-pyrazolo[3,4-d]pyrimidin-4-amine To a suspension of 3-iodo-1H-pyrazolo[3,4-d]pyrimidin-4-amine (5 g, 19.16 mmol, 1.0 equiv) in DMF (60 mL) was added NaH (804.53 mg, 20.11 mmol, 60 wt. %, 1.05 equiv) at 0° C. The mixture was stirred at 0° C. for 30 min. To the reaction mixture was then added 4,6-dichloropyrimidine (3.42 g, 22.99 mmol, 1.2 equiv) at 0° C. The mixture was stirred at room temperature for 2.5 h, at which point the reaction mixture was added to $H_2O$ (600 mL). The suspension was then filtered to give the product (7.1 g, 99.2% yield) as yellow solid. LCMS (ESI) m/z: [M+H] calcd for $C_9H_5ClIN_7$: 373.94; found 373.9.

Step 2: Synthesis of tert-butyl 4-(6-(4-amino-3-iodo-1H-pyrazolo[3,4-d]pyrimidin-1-yl)pyrimidin-4-yl)piperazine-1-carboxylate To a solution of 1-(6-chloropyrimidin-4-yl)-3-iodo-1H-pyrazolo[3,4-d]pyrimidin-4-amine (5 g, 13.39 mmol, 1.0 equiv) and tert-butyl piperazine-1-carboxylate (2.99 g, 16.06 mmol, 1.2 equiv) in DMF (50 mL) was added $K_2CO_3$ (3.70 g, 26.77 mmol, 2.0 equiv). The reaction mixture was stirred at 100° C. for 4 h, at which point it was added to $H_2O$ (500 mL). The suspension was then filtered to give the product (6.2 g, 88.5% yield) as yellow solid. LCMS (ESI) m/z: [M+H] calcd for $C_{18}H_{22}IN_9O_2$: 524.09; found 524.2.

Step 3: Synthesis of tert-butyl 4-(6-(4-amino-3-(2-aminobenzo[d]oxazol-5-yl)-1H-pyrazolo[3,4-d]pyrimidin-1-yl)pyrimidin-4-yl)piperazine-1-carboxylate To a bi-phasic suspension of 5-(4,4,5,5-tetramethyl-1,3,2-dioxaborolan-2-yl)benzo[d]oxazol-2-amine (3.08 g, 11.85 mmol, 1.0 equiv), tert-butyl 4-(6-(4-amino-3-iodo-1H-pyrazolo[3,4-d]pyrimidin-1-yl)pyrimidin-4-yl)piperazine-1-carboxylate (6.2 g, 11.85 mmol, 1.0 equiv) and $Na_2CO_3$ (6.28 g, 59.24 mmol, 5.0 equiv) in $H_2O$ (100 mL) and DME (200 mL) was added $Pd(PPh_3)_4$ (1.37 g, 1.18 mmol, 0.1 equiv) at room temperature under $N_2$. The mixture was stirred at 110° C. for 24 h and then the mixture was filtered to give a solid cake. The solid was added to dioxane (20 mL) and stirred at 110° C. for 60 min, then filtered to give the product (3.5 g, 55.8% yield) as brown solid. LCMS (ESI) m/z: [M+H] calcd for $C25H_{27}N_{11}O_3$: 530.24; found 530.3.

Step 4: Synthesis of 5-(4-amino-1-(6-(piperazin-1-yl)pyrimidin-4-yl)-1H-pyrazolo[3,4-d]pyrimidin-3-yl)benzo[d]oxazol-2-amine trifluoroacetic acid salt A solution of tert-butyl 4-(6-(4-amino-3-(2-aminobenzo[d]oxazol-5-yl)-1H-pyrazolo[3,4-d]pyrimidin-1-yl)pyrimidin-4-yl)piperazine-1-carboxylate (3.5 g, 6.61 mmol, 1.0 equiv) in TFA (35 mL) was stirred at room temperature for 1 h. The reaction solution was concentrated under reduced pressure and the resulting crude material was dissolved in MeCN (20 mL) and added dropwise to MTBE (500 mL). The resulting solid was then filtered to give the product (5.5 g, 91.9% yield) as brown solid. LCMS (ESI) m/z: [M+H] calcd for $C_{20}H_{19}N_{11}O$: 430.19; found 430.1.

Monomer AB. 8-(6-methoxypyridin-3-yl)-3-methyl-1-(4-(4-(5,6,7,8-tetrahydropyrido[4,3-d]pyrimidin-2-yl)piperazin-1-yl)-3-(trifluoromethyl)phenyl)-1H-imidazo[4,5-c]quinolin-2(3H)-one trifluoroacetic acid salt

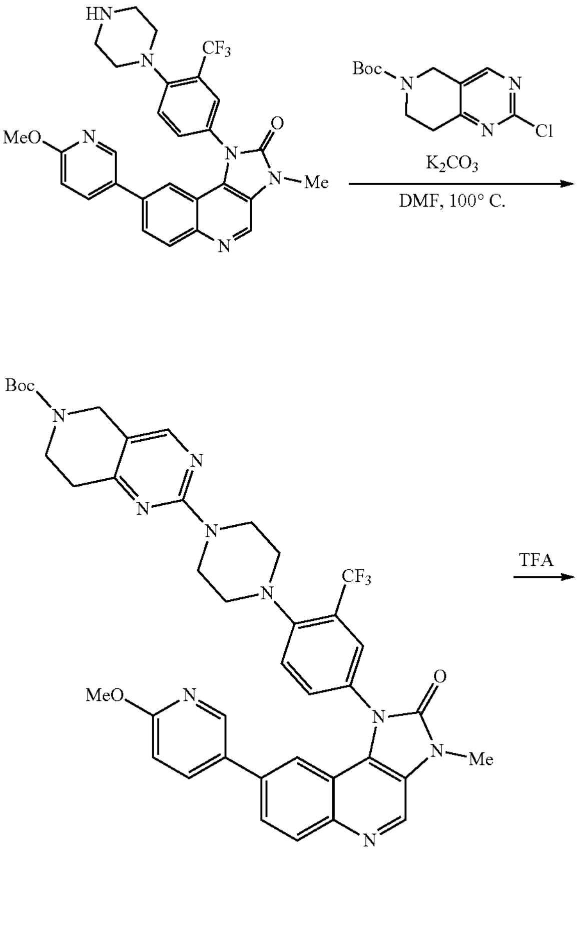

-continued

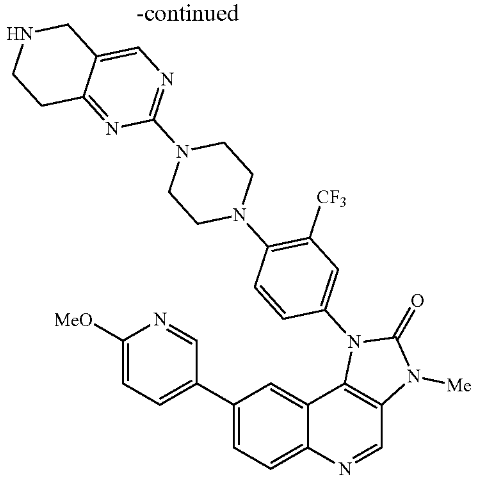

Step 1: Synthesis of tert-butyl 2-(4-(4-(8-(6-methoxypyridin-3-yl)-3-methyl-2-oxo-2,3-dihydro-1H-imidazo[4,5-c]quinolin-1-yl)-2-(trifluoromethyl)phenyl)piperazin-1-yl)-7,8-dihydropyrido[4,3-d]pyrimidine-6(5H)-carboxylate To a mixture of 8-(6-methoxypyridin-3-yl)-3-methyl-1-(4-(piperazin-1-yl)-3-(trifluoromethyl)phenyl)-1H-imidazo[4,5-c]quinolin-2(3H)-one (0.3 g, 561.24 μmol, 1.0 equiv) and tert-butyl 2-chloro-7,8-dihydropyrido[4,3-d]pyrimidine-6(5H)-carboxylate (151.38 mg, 561.24 μmol, 1.0 equiv) in DMF (5 mL) was added $K_2CO_3$ (193.92 mg, 1.40 mmol, 2.5 equiv). The mixture was stirred at 100° C. for 14 h, at which point $H_2O$ (20 mL) was added. The aqueous layer was extracted with EtOAc (3x40 mL) and the combined organic layers were concentrated under reduced pressure. The crude material was purified by column chromatography (30/1 to 15/1 DCM/MeOH) to give the product (0.30 g, 69.6% yield) as a light-yellow solid. LCMS (ESI) m/z: [M+H] calcd for $C_{40}H_{40}F_3N_9O_4$: 768.33; found 768.5.

Step 2: Synthesis of 8-(6-methoxypyridin-3-yl)-3-methyl-1-(4-(4-(5,6,7,8-tetrahydropyrido[4,3-d]pyrimidin-2-yl)piperazin-1-yl)-3-(trifluoromethyl)phenyl)-1H-imidazo[4,5-c]quinolin-2(3H)-one A solution of tert-butyl 2-(4-(4-(8-(6-methoxypyridin-3-yl)-3-methyl-2-oxo-2,3-dihydro-1H-imidazo[4,5-c]quinolin-1-yl)-2-(trifluoromethyl)phenyl)piperazin-1-yl)-7,8-dihydropyrido[4,3-d]pyrimidine-6(5H)-carboxylate (0.8 g, 1.04 mmol, 1.0 equiv) in TFA (8 mL) was stirred at room temperature for 2 h. The solvent was concentrated and the residue was dissolved in MeCN (5 mL), then the solution was added dropwise to MTBE (150 mL). The precipitate was filtered and the solid was dried under reduced pressure to give the product (600 mg, 70.6% yield) as a yellow solid. LCMS (ESI) m/z: [M+H] calcd for $C35H_{32}F_3N_9O_2$: 668.27; found 668.3.

Monomer AC. 5-(4-amino-1-(piperidin-4-ylmethyl)-1H-pyrazolo[3,4-d]pyrimidin-3-yl)benzo[d]oxazol-2-amine trifluoroacetic acid salt

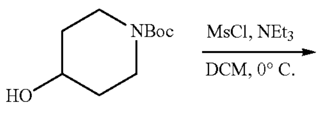

-continued

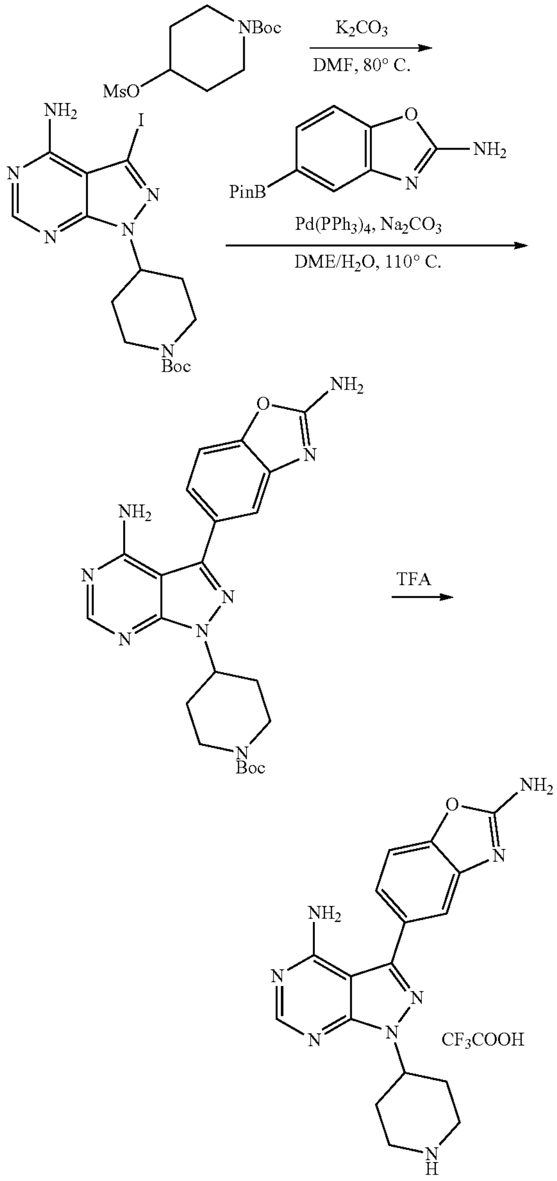

Step 1: Synthesis of tert-butyl 4-((methylsulfonyl)oxy)piperidine-1-carboxylate

To a solution of tert-butyl 4-hydroxypiperidine-1-carboxylate (4 g, 19.87 mmol, 1.0 equiv) and $Et_3N$ (3.87 mL, 27.82 mmol, 1.4 equiv) in DCM (40 mL) was added MsCl (2.15 mL, 27.82 mmol, 1.4 equiv) at 0° C. Then the reaction mixture was stirred at room temperature for 1 h. $H_2O$ (50 mL) was added and the aqueous phase was extracted with DCM (3x50 mL). The combined organic phase was washed with brine, dried with anhydrous $Na_2SO_4$, filtered and concentrated under reduced pressure to give the product (5.62 g, 101% crude yield) as yellow solid which was used directly in the next step.

Step 2: Synthesis of tert-butyl 4-(4-amino-3-iodo-1H-pyrazolo[3,4-d]pyrimidin-1-yl)piperidine-1-carboxylate To a suspension of 3-iodo-1H-pyrazolo[3,4-d]pyrimidin-4-amine (5 g, 19.16 mmol, 1.0 equiv) and tert-butyl 4-((methylsulfonyl)oxy)piperidine-1-carboxylate (5.62 g, 20.11 mmol, 1.05 equiv) in DMF (100 mL) was added $K_2CO_3$ (5.29 g, 38.31 mmol, 2.0 equiv). The mixture was stirred at 80° C. for 12 h. The reaction mixture was then added to $H_2O$ (400 mL) at 0° C. The resulting precipitate was filtered to give the product (5.0 g, 58.8% yield) as yellow solid. LCMS (ESI) m/z: [M+H] calcd for $C_{15}H_{21}IN_6O_2$: 445.09; found 445.1.

Step 3: Synthesis of tert-butyl 4-(4-amino-3-(2-aminobenzo[d]oxazol-5-yl)-1H-pyrazolo[3,4-d]pyrimidin-1-yl)piperidine-1-carboxylate To a suspension of tert-butyl 4-(4-amino-3-iodo-1H-pyrazolo[3,4-d]pyrimidin-1-yl)piperidine-1-carboxylate (5 g, 11.25 mmol, 1.0 equiv), 5-(4,4,5,5-tetramethyl-1,3,2-dioxaborolan-2-yl)benzo[d]oxazol-2-amine (3.51 g, 13.51 mmol, 1.2 equiv) and $Na_2CO_3$ (5.96 g, 56.27 mmol, 5.0 equiv) in $H_2O$ (50 mL) and DME (100 mL) was added $Pd(PPh_3)_4$ (1.30 g, 1.13 mmol, 0.1 equiv) at room temperature under $N_2$. The mixture was stirred at 110° C. for 3 h. The reaction mixture was then cooled to room temperature and filtered. The filtrate was partitioned between EtOAc (100 mL) and $H_2O$ (100 mL) and then the aqueous layer was separated and extracted with EtOAc (3×100 mL). The combined organic layer was washed with brine (20 mL) and dried over anhydrous $Na_2SO_4$, filtered, and concentrated under reduced pressure. The residue was triturated with EtOAc (30 mL) and filtered to give the product (3.6 g, 71% yield) as yellow solid. LCMS (ESI) m/z: [M+H] calcd for $C_{22}H_{26}N_8O_3$: 451.22; found 451.3.

Step 4: Synthesis of 5-(4-amino-1-(piperidin-4-yl)-1H-pyrazolo[3,4-d]pyrimidin-3-yl)benzo[d]oxazol-2-amine trifluoroacetic acid salt A solution of tert-butyl 4-(4-amino-3-(2-aminobenzo[d]oxazol-5-yl)-1H-pyrazolo[3,4-d]pyrimidin-1-yl)piperidine-1-carboxylate (1.4 g, 3.11 mmol, 1.0 equiv) in TFA (10 mL) was stirred at room temperature for 30 min. The reaction solution was concentrated under reduced pressure and the crude solid was dissolved in MeCN (20 mL). The solution was added dropwise to MTBE (100 mL) and the resulting solid was filtered to give the product (1.6 g, 85.8% yield) as yellow solid. LCMS (ESI) m/z: [M+H] calcd for $C_{17}H_{18}N_8O_3$: 351.17; found 351.1.

Monomer AD. 1-(piperidin-4-yl)-3-(1H-pyrrolo[2,3-b]pyridin-5-yl)-1H-pyrazolo[3,4-d]pyrimidin-4-amine trifluoroacetic acid salt

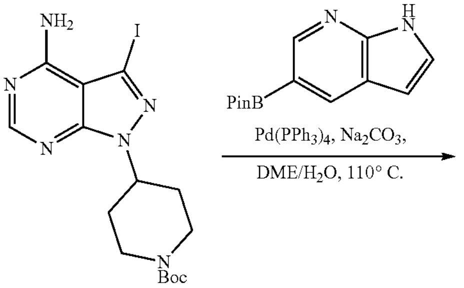

-continued

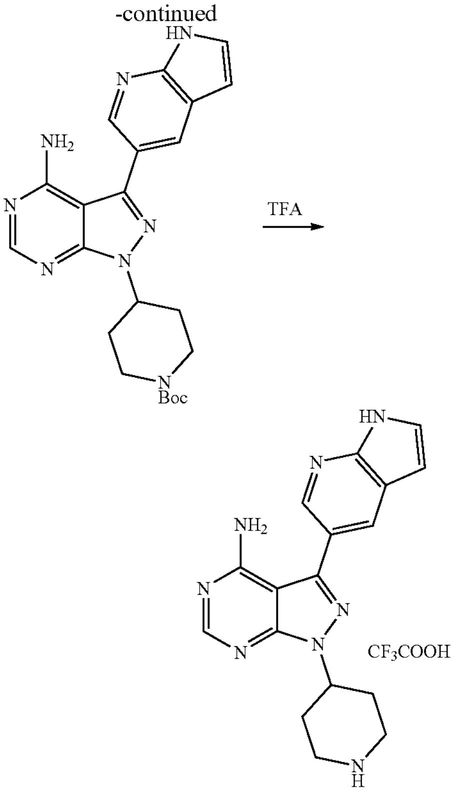

Step 1: Synthesis of tert-butyl 4-(4-amino-3-(1H-pyrrolo[2,3-b]pyridin-5-yl)-1H-pyrazolo[3,4-d]pyrimidin-1-yl)piperidine-1-carboxylate To a suspension of 5-(4,4,5-trimethyl-1,3,2-dioxaborolan-2-yl)-1H-pyrrolo[2,3-b]pyridine (857.12 mg, 3.51 mmol, 1.2 equiv), tert-butyl 4-(4-amino-3-iodo-1H-pyrazolo[3,4-d]pyrimidin-1-yl)piperidine-1-carboxylate (1.3 g, 2.93 mmol, 1.0 equiv) and $Na_2CO_3$ (1.55 g, 14.63 mmol, 5.0 equiv) in DME (20 mL) and $H_2O$ (10 mL) was added $Pd(PPh_3)_4$ (338.13 mg, 292.62 μmol, 0.1 equiv) at room temperature under $N_2$. The mixture was stirred at 110° C. for 3 h. The reaction mixture was then cooled to room temperature and filtered. The filtrate was partitioned between EtOAc (50 mL) and $H_2O$ (50 mL) and the aqueous layer was separated and extracted with EtOAc (3×50 mL). The combined organic layer were washed with brine, dried over anhydrous $Na_2SO_4$, filtered, and concentrated under reduced pressure. The residue was triturated with EtOAc (10 mL), filtered, the solid cake was dried under reduced pressure to give the product (1.0 g, 78.7% yield) as yellow solid.

Step 2: Synthesis of 1-(piperidin-4-yl)-3-(1H-pyrrolo[2,3-b]pyridin-5-yl)-1H-pyrazolo[3,4-d]pyrimidin-4-amine trifluoroacetic acid salt A solution of tert-butyl 4-(4-amino-3-(1H-pyrrolo[2,3-b]pyridin-5-yl)-1H-pyrazolo[3,4-d]pyrimidin-1-yl)piperidine-1-carboxylate (1.5 g, 3.45 mmol, 1.0 equiv) in TFA (10 mL) was stirred at room temperature for 30 min. The reaction solution was concentrated under reduced pressure and the crude residue was dissolved in MeCN (20 mL). The solution was added dropwise to MTBE (100 mL) and the resulting solid was filtered to give the product (1.19 g, 74.2% yield)

as light yellow solid. LCMS (ESI) m/z: [M+H] calcd for $C_{17}H_{18}N_8$: 335.18; found 335.1.

Monomer AE. (4-((2-aminoethyl)sulfonyl)-2-methylphenyl)(7-(6-aminopyridin-3-yl)-2,3-dihydrobenzo[f][1,4]oxazepin-4(5H)-yl)methanone

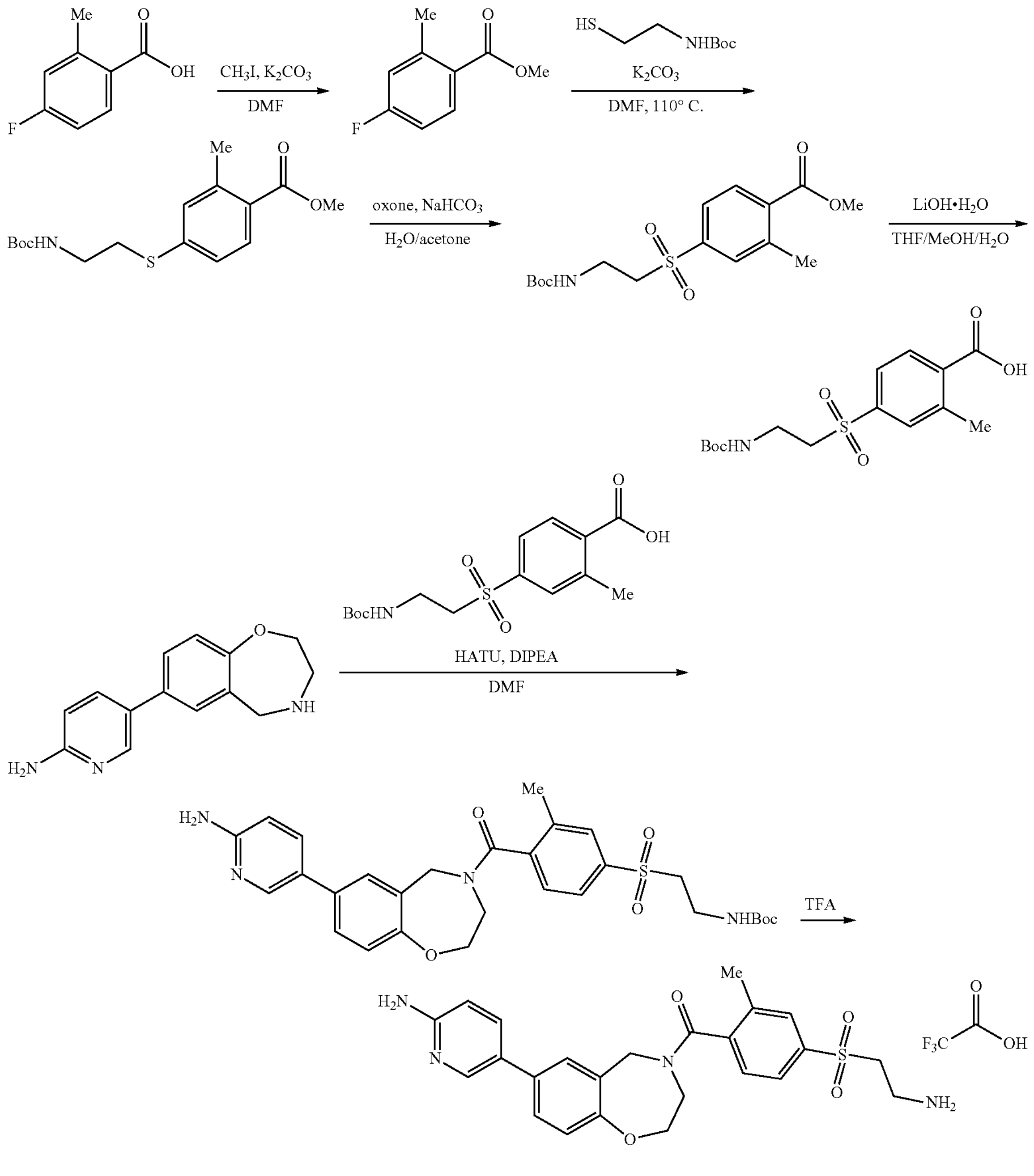

Step 1: Synthesis of methyl 4-fluoro-2-methylbenzoate

To a solution of 4-fluoro-2-methylbenzoic acid (86 g, 557.94 mmol, 1.0 equiv) in DMF (900 mL) was added $K_2CO_3$ (231.33 g, 1.67 mol, 3.0 equiv) and iodomethane (79.19 g, 557.94 mmol, 34.73 mL, 1.0 equiv). The mixture was stirred at room temperature for 1 h. The solution of methyl 4-fluoro-2-methylbenzoate in DMF (900 mL) was used directly in the next step.

Step 2: Synthesis of methyl 4-((2-((tert-butoxycarbonyl)amino)ethyl)thio)-2-methylbenzoate To a solution of methyl 4-fluoro-2-methylbenzoate (93.8 g, 557.94 mmol, 1.0 equiv) in DMF (900 mL) was added tert-butyl (2-mercaptoethyl)carbamate (98.91 g, 557.97 mmol, 1.0 equiv) and $K_2CO_3$ (154.23 g, 1.12 mol, 2.0 equiv). The reaction was stirred at 110° C. for 12 h, at which point the mixture was cooled to room temperature and added to $H_2O$ (1000 mL). The aqueous layer was then extracted with EtOAc (3×600 mL) and the combined organic layers were washed with brine, dried, and concentrated under reduced pressure. Purification by silica gel chromatography (0→25% EtOAc/petroleum ether) afforded the desired product as a colorless oil (144 g, 79% yield).

Step 3: Synthesis of methyl 4-((2-((tert-butoxycarbonyl)amino)ethyl)sulfonyl)-2-methylbenzoate To two separate batches containing a solution of methyl 4-((2-((tert-butoxycarbonyl)amino)ethyl)thio)-2-methylbenzoate (72 g, 221.25 mmol, 1.0 equiv), NaOH (2 M, 110.6 mL, 1.0 equiv), and $NaHCO_3$ (55.76 g, 663.75 mmol, 3.0 equiv) in acetone (750 mL) was added potassium peroxymonosulfate (284.28 g, 462.41 mmol, 2.1 equiv). The mixture was stirred for 12 h at room temperature, at which point the two batches were combined and then the mixture was acidified to pH 5 by addition of 1N HCl. The aqueous layer was extracted with EtOAc (3×1500 mL) and the combined organic phases were washed with brine (2×500 mL), dried, and concentrated under reduced pressure. Purification by silica gel chromatography (0→25% EtOAc/petroleum ether) afforded the desired product as a white solid (120 g, 76% yield).

Step 4: Synthesis of 4-((2-((tert-butoxycarbonyl)amino)ethyl)sulfonyl)-2-methylbenzoic acid To a solution of methyl 4-((2-((tert-butoxycarbonyl)amino)ethyl)sulfonyl)-2-methylbenzoate (35 g, 97.92 mmol, 1.0 equiv) in THF (200 mL), MeOH (100 mL) and $H_2O$ (100 mL) was added $LiOH \cdot H_2O$ (12.33 g, 293.77 mmol, 3.0 equiv) at room temperature. The reaction mixture was stirred at 40° C. for 1 h. The mixture was then concentrated under reduced pressure to remove THF and MeOH. The aqueous phase was neutralized with 0.5N HCl and the resulting precipitate was isolated by filtration. The solid cake was washed with $H_2O$ (3×20 mL) to afford the desired product as a white solid (25 g, 74% yield).

Step 5: Synthesis of tert-butyl (2-((4-(7-(6-aminopyridin-3-yl)-2,3,4,5-tetrahydrobenzo[f][1,4]oxazepine-4-carbonyl)-3-methylphenyl)sulfonyl)ethyl)carbamate To a solution of 4-((2-((tert-butoxycarbonyl)amino)ethyl)sulfonyl)-2-methylbenzoic acid (9.7 g, 28.25 mmol, 1.0 equiv) and 5-(2,3,4,5-tetrahydrobenzo[f][1,4]oxazepin-7-yl)pyridin-2-amine (8.88 g, 28.25 mmol, 1.0 equiv, 2HCl) in DMF (120 mL) was added HATU (16.11 g, 42.37 mmol, 1.5 equiv) and DIPEA (18.25 g, 141.24 mmol, 24.60 mL, 5.0 equiv). The reaction was stirred at room temperature for 1 h, at which point the reaction mixture was poured into $H_2O$ (1000 mL). The mixture was stirred for 5 min and the resulting precipitate was collected by filtration to give the crude product. The crude product was triturated with EtOAc (100 mL), filtered, and the solid cake was dried under reduced pressure to afford the desired product as a white solid (14 g, 87% yield).

Step 6: Synthesis of (4-((2-aminoethyl)sulfonyl)-2-methylphenyl)(7-(6-aminopyridin-3-yl)-2,3-dihydrobenzo[f][1,4]oxazepin-4(5H)-yl)methanone A solution tert-butyl (2-((4-(7-(6-aminopyridin-3-yl)-2,3,4,5-tetrahydrobenzo[f][1,4] oxazepine-4-carbonyl)-3-methylphenyl)sulfonyl)ethyl)carbamate (19 g, 33.53 mmol, 1.0 equiv) in TFA (100 mL) was stirred at room temperature for 30 min. The solution was then concentrated under reduced pressure. The residue was triturated with MeCN (30 mL) and then dripped into MTBE (600 mL) and stirred for 20 min. The suspension was filtered and the resulting solid was dissolved in MeCN (30 mL) and concentrated under reduced pressure to afford the desired product as a light yellow solid (24 g, TFA salt). LCMS (ESI) m/z: [M+H] calcd for $C_{24}H_{26}N_4O_4S$: 467.18; found 467.1.

Monomer AF. 5-(4-amino-1-((5,6,7,8-tetrahydropyrido[4,3-d]pyrimidin-2-yl)methyl)-1H-pyrazolo[3,4-d]pyrimidin-3-yl)benzo[d]oxazol-2-amine

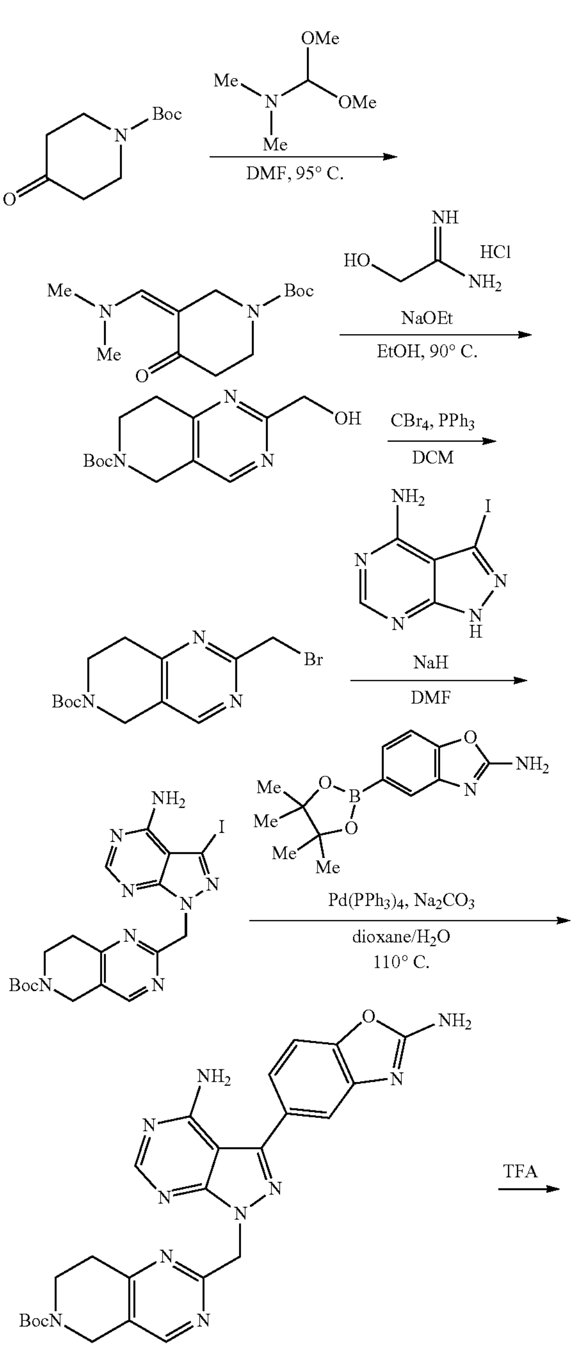

-continued

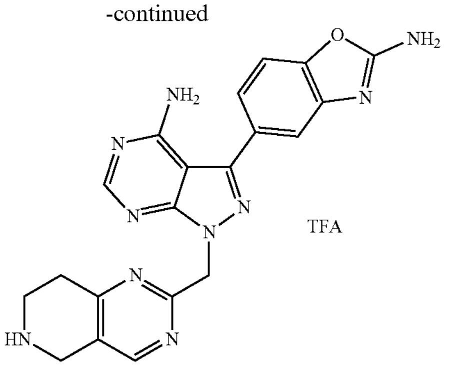

Step 1: Synthesis of (Z)-tert-butyl 3-((dimethylamino)methylene)-4-oxopiperidine-1-carboxylate A solution of tert-butyl 4-oxopiperidine-1-carboxylate (15 g, 75.28 mmol, 1.0 equiv) and 1,1-dimethoxy-N,N-dimethylmethanamine (11.00 mL, 82.81 mmol, 1.1 equiv) in DMF (105 mL) was stirred at 95° C. for 12 h. The reaction mixture was then concentrated under reduced pressure and the resulting residue was dissolved in EtOAc (30 mL) and washed with brine (3×30 mL). The aqueous phase was extracted with EtOAc (50 mL), and the combined organic phases were dried and concentrated under reduced pressure to afford the desired product as a yellow solid (10.1 g, 53% yield).

Step 2: Synthesis of tert-butyl 2-(hydroxymethyl)-7,8-dihydropyrido[4,3-d]pyrimidine-6(5H)-carboxylate To a solution of NaOEt (1.98 g, 29.10 mmol, 1.0 equiv) in EtOH (70 mL) was added (Z)-tert-butyl 3-((dimethylamino)methylene)-4-oxopiperidine-1-carboxylate (7.4 g, 29.10 mmol, 1.0 equiv) and 2-hydroxyacetimidamide hydrochloride (3.54 g, 32.01 mmol, 1.1 equiv). The reaction mixture was heated to 90° C. for 12 h, at which point the mixture was cooled to room temperature and concentrated under reduced pressure. The residue was partitioned with EtOAc (40 mL) and washed with sat. $NaHCO_3$ (40 mL). The aqueous phase was extracted with EtOAc (3×20 mL) and the combined organic phases were washed with brine (2×50 mL), dried, and concentrated under reduced pressure. Purification by silica gel chromatography (25% EtOAc/petroleum ether) afforded the desired product as a yellow solid (7.24 g, 94% yield).

Step 3: Synthesis of tert-butyl 2-(bromomethyl)-7,8-dihydropyrido[4,3-d]pyrimidine-6(5H)-carboxylate To a solution of tert-butyl 2-(hydroxymethyl)-7,8-dihydropyrido[4,3-d]pyrimidine-6(5H)-carboxylate (6.24 g, 23.52 mmol, 1.0 equiv) and $PPh_3$ (12.34 g, 47.04 mmol, 2.0 equiv) in DCM (140 mL) was added $CBr_4$ (14.82 g, 44.69 mmol, 1.9 equiv). The mixture was stirred at room temperature for 3 h, at which point mixture was concentrated under reduced pressure. The residue was partitioned between EtOAc (20 mL) and $H_2O$ (20 mL), the aqueous phase was extracted with EtOAc (3×20 mL). The combined organic phases were washed with brine (2×50 mL), dried, and concentrated under reduced pressure. Purification by silica gel chromatography (14% EtOAc/petroleum ether) afforded the desired product as a yellow solid (3.6 g, 47% yield).

Step 4: Synthesis of tert-butyl 2-((4-amino-3-iodo-1H-pyrazolo[3,4-d]pyrimidin-1-yl)methyl)-7,8-dihydropyrido[4,3-d]pyrimidine-6(5H)-carboxylate To a solution of 3-iodo-1H-pyrazolo[3,4-d]pyrimidin-4-amine (1.59 g, 6.09 mmol, 1.0 equiv) in DMF (15 mL) was added NaH (243.73 mg, 6.09 mmol, 60 wt. %, 1.0 equiv) at 0° C. The suspension was stirred for 30 min and then tert-butyl 2-(bromomethyl)-7,8-dihydropyrido[4,3-d]pyrimidine-6(5H)-carboxylate (2.2 g, 6.70 mmol, 1.1 equiv) was added. The reaction mixture was warmed to room temperature and stirred for 3 h. The mixture was poured into $H_2O$ at 0° C. and the precipitate was collected by filtration to afford the desired product as a brown solid (2.5 g, 66% yield).

Step 5: Synthesis of tert-butyl 2-((4-amino-3-(2-aminobenzo[d]oxazol-5-yl)-1H-pyrazolo[3,4-d]pyrimidin-1-yl)methyl)-7,8-dihydropyrido[4,3-d]pyrimidine-6(5H)-carboxylate To a solution of tert-butyl 2-((4-amino-3-iodo-TH-pyrazolo[3,4-d]pyrimidin-1-yl)methyl)-7,8-dihydropyrido[4,3-d]pyrimidine-6(5H)-carboxylate (4.55 g, 8.95 mmol, 1.0 equiv), 5-(4,4,5,5-tetramethyl-1,3,2-dioxaborolan-2-yl)benzo[d]oxazol-2-amine (2.79 g, 10.74 mmol, 1.2 equiv) and $Na_2CO_3$ (4.74 g, 44.76 mmol, 5.0 equiv) in dioxane (70 mL) and $H_2O$ (35 mL) was added $Pd(PPh_3)_4$ (1.03 g, 895.11 μmol, 0.1 equiv). The reaction mixture was heated to 110° C. for 3 h, at which point the mixture was cooled to room temperature and poured into $H_2O$ at 0° C. The precipitate was filtered, and the solid cake was dried under reduced pressure. The crude product was washed with EtOAc (50 mL) to afford the desired product as light yellow solid (3.14 g, 68% yield).

Step 6: Synthesis of 5-(4-amino-1-((5,6,7,8-tetrahydropyrido[4,3-d]pyrimidin-2-yl)methyl)-1H-pyrazolo[3,4-d]pyrimidin-3-yl)benzo[d]oxazol-2-amine A solution of tert-butyl 2-((4-amino-3-(2-aminobenzo[d]oxazol-5-yl)-1H-pyrazolo[3,4-d]pyrimidin-1-yl)methyl)-7,8-dihydropyrido[4,3-d]pyrimidine-6(5H)-carboxylate (3.14 g, 6.10 mmol, 1.0 equiv) in TFA (20 mL) was stirred at room temperature for 30 min. The mixture was concentrated under reduced pressure and the resulting residue was added dissolved in MeCN (7 mL) and added to MTBE (700 mL). The precipitate was collected by filtration to afford the desired product as a brown solid (4.25 g, 92% yield, 3 TFA). LCMS (ESI) m/z: [M+H] calcd for $C_{20}H_{18}N_{10}O$: 415.18; found 415.1.

Monomer AG. 5-(4-amino-1-((2-((2-aminoethyl)sulfonyl)-1,2,3,4-tetrahydroisoquinolin-6-yl)methyl)-1H-pyrazolo[3,4-d]pyrimidin-3-yl)benzo[d]oxazol-2-amine

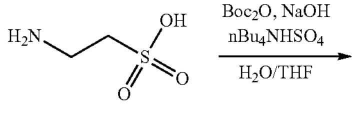

-continued

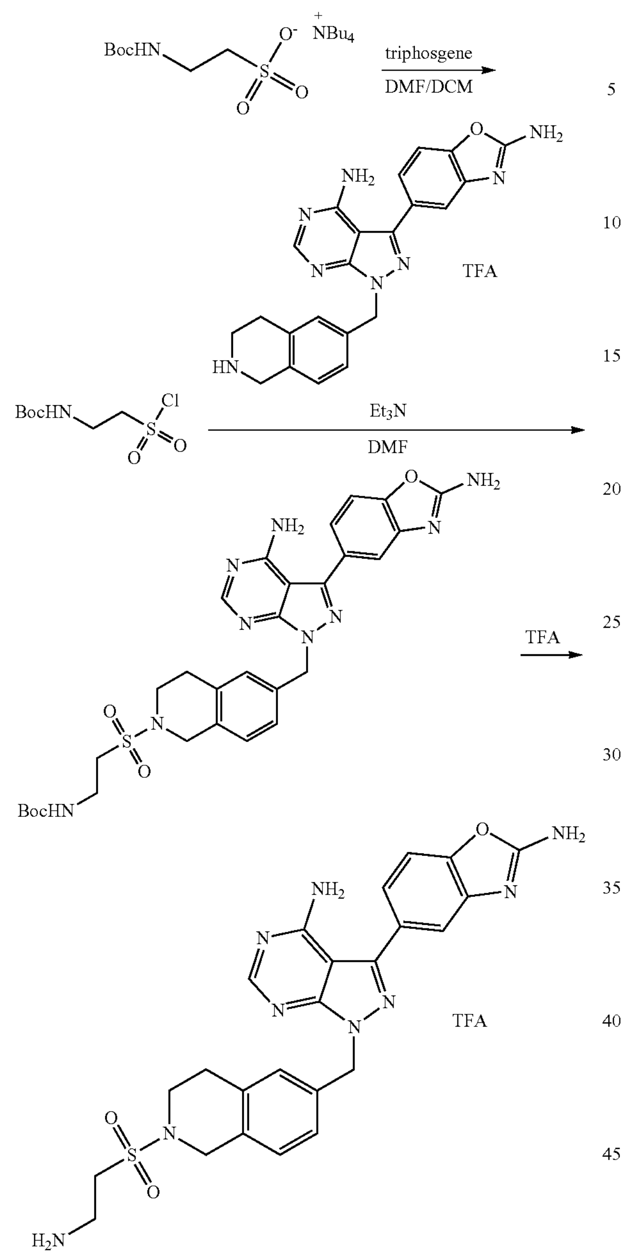

Step 1: Synthesis of N-Boc taurine tetrabutylammonium salt

To a solution of 2-aminoethanesulfonic acid (10.00 mL, 79.91 mmol, 1.0 equiv) in THF (60 mL) and aqueous NaOH (2 M, 40 mL, 1.0 equiv) was added $Boc_2O$ (18.31 g, 83.90 mmol, 1.05 equiv). The mixture was stirred at room temperature for 15 h, at which point the mixture was extracted with EtOAc (10 mL). The aqueous phase was diluted with $H_2O$ (450 mL), treated with $LiOH{\cdot}H_2O$ (3.35 g, 79.83 mmol, 1.0 equiv) and $nBu_4NHSO_4$ (27.13 g 79.90 mmol, 1.0 equiv) and stirred for 30 min. This mixture was extracted with DCM (3×80 mL), and the combined organic phases were dried and concentrated under reduced pressure to afford the desired product as a colorless oil (34.26 g, 91% yield).

Step 2: Synthesis of tert-butyl (2-(chlorosulfonyl)ethyl)carbamate

To a solution of N-Boc taurine tetrabutylammonium salt (4.7 g, 10.05 mmol, 1.0 equiv) in DCM (42 mL) was added DMF (77.32 μL, 1.00 mmol, 0.1 equiv) followed by a solution of triphosgene (0.5 M, 8.04 mL, 0.4 equiv) in DCM at 0° C. The mixture was warmed to room temperature and stirred for 30 min. The solution of tert-butyl (2-(chlorosulfonyl)ethyl)carbamate (2.45 g, crude) in DCM was used directly in the next step.

Step 3: Synthesis of tert-butyl (2-((6-((4-amino-3-(2-aminobenzo[d]oxazol-5-yl)-1H-pyrazolo[3,4-d]pyrimidin-1-yl)methyl)-3,4-dihydroisoquinolin-2(1H)-yl)sulfonyl)ethyl)carbamate To a solution of 5-(4-amino-1-((1,2,3,4-tetrahydroisoquinolin-6-yl)methyl)-1H-pyrazolo[3,4-d]pyrimidin-3-yl)benzo[d]oxazol-2-amine (6.04 g, 9.44 mmol, 1.0 equiv, 2TFA) in DMF (40 mL) was added $Et_3N$ (7.88 mL, 56.63 mmol, 6.0 equiv). A solution of tert-butyl (2-(chlorosulfonyl)ethyl)carbamate in DCM (42 mL) at 0° C. was added. The mixture was warmed to room temperature and stirred 16 h. The reaction mixture was concentrated under reduced pressure to remove DCM and the resulting solution was purified by reverse phase chromatography (15→45% $MeCN/H_2O$) to afford the desired product as a white solid (5.8 g, 83% yield, TFA). LCMS (ESI) m/z: [M+H] calcd for $C_{29}H_{33}N_9O_5S$: 620.24; found 620.3.

Step 4: Synthesis of 5-(4-amino-1-((2-((2-aminoethyl)sulfonyl)-1,2,3,4-tetrahydroisoquinolin-6-yl)methyl)-1H-pyrazolo[3,4-d]pyrimidin-3-yl)benzo[d]oxazol-2-amine A solution of tert-butyl (2-((6-((4-amino-3-(2-aminobenzo[d]oxazol-5-yl)-1H-pyrazolo[3,4-d]pyrimidin-1-yl)methyl)-3,4-dihydroisoquinolin-2(1H)-yl)sulfonyl)ethyl)carbamate (5.8 g, 9.36 mmol, 1.0 equiv) in TFA (48 mL) was stirred at room temperature for 0.5 h, at which point the reaction mixture was concentrated under reduced pressure. The crude product dissolved in MeCN (30 mL) and was added dropwise into MTBE (200 mL). The mixture was stirred for 5 min and filtered, the filter cake was dried under reduced pressure to afford the desired product as a yellow solid (3.6 g, 62% yield, 2.2TFA). LCMS (ESI) m/z: [M+H] calcd for $C_{24}H_{25}N_9O_3S$: 520.19; found 520.1.

Monomer AH. tert-butyl ((5-((4-amino-3-(2-aminobenzo[d]oxazol-5-yl)-1H-pyrazolo[3,4-d]pyrimidin-1-yl)methyl)pyrimidin-2-yl)methyl)carbamate

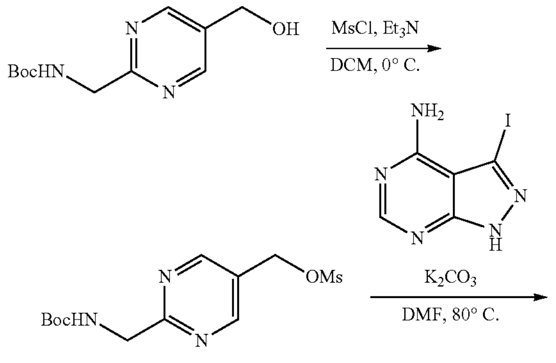

-continued

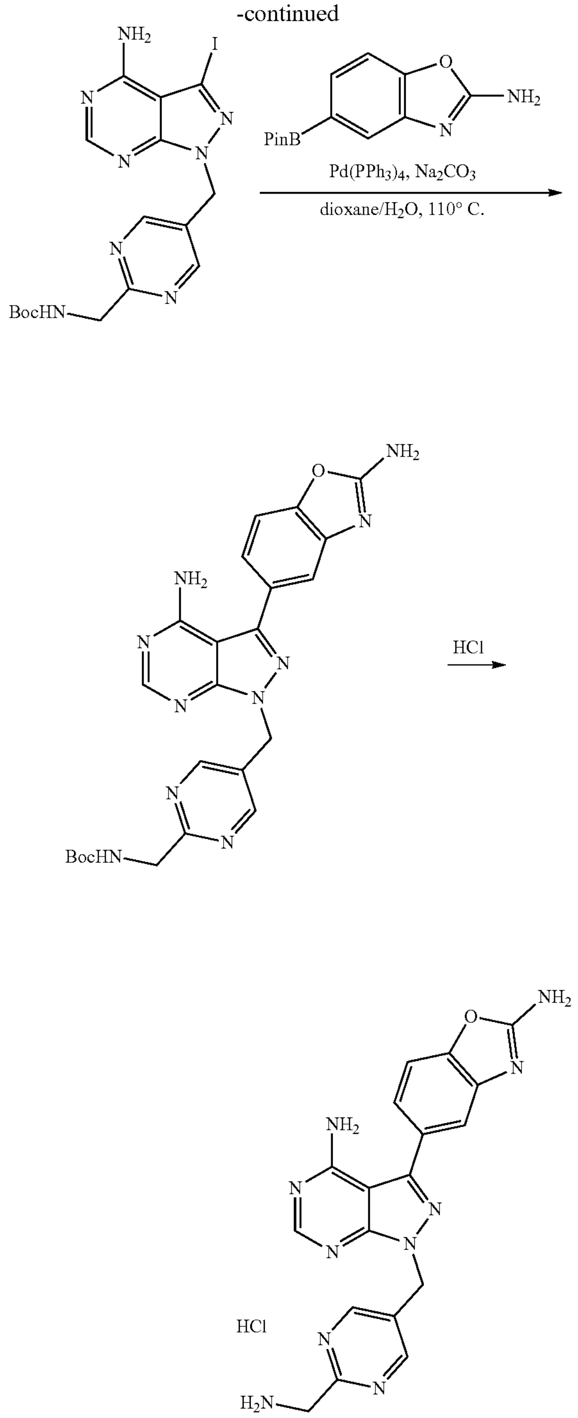

Step 1: Synthesis of (2-(((tert-butoxycarbonyl)amino)methyl)pyrimidin-5-yl)methyl methanesulfonate To a solution of tert-butyl ((5-(hydroxymethyl)pyrimidin-2-yl)methyl)carbamate (4.2 g, 17.55 mmol, 1.0 equiv) in DCM (42 mL) at 0° C. was added $Et_3N$ (7.33 mL, 52.66 mmol, 3.0 equiv) followed by MsCl (2.41 g, 21.06 mmol, 1.63 mL, 1.2 equiv). The mixture was stirred at 0° C. for 10 min, and then $H_2O$ (15 mL) was added. The reaction mixture was extracted with DCM (5×10 mL) and the combined organic phases were washed with brine (5 mL), dried, filtered, and concentrated under reduced pressure to afford the desired product (5.5 g, 98.7% yield) as a colorless solid.

Step 2: Synthesis of tert-butyl ((5-((4-amino-3-iodo-1H-pyrazolo[3,4-d]pyrimidin-1-yl)methyl)pyrimidin-2-yl)methyl)carbamate To a solution of (2-(((tert-butoxycarbonyl)amino)methyl)pyrimidin-5-yl)methyl methanesulfonate (5.47 g, 17.24 mmol, 1.2 equiv) and 3-iodo-1H-pyrazolo[3,4-d] pyrimidin-4-amine (3.75 g, 14.37 mmol, 1.0 equiv) in DMF (55 mL) at room temperature was added $K_2CO_3$ (5.96 g, 43.10 mmol, 3 equiv). The mixture was stirred at 80° C. for 5 h, at which point $H_2O$ (100 mL) and brine (20 mL) were poured into the reaction mixture. The solution was extracted with EtOAc (10×30 mL) and the combined organic phases were dried, filtered, and concentrated under reduced pressure. Purification by silica gel chromatography (0→30% EtOAc/MeOH) afforded the desired product (2 g, 28.9% yield) as a yellow solid.

Step 3: Synthesis of tert-butyl ((5-((4-amino-3-(2-aminobenzo[d]oxazol-5-yl)-1H-pyrazolo[3,4-d]pyrimidin-1-yl)methyl)pyrimidin-2-yl)methyl)carbamate To a solution of tert-butyl ((5-((4-amino-3-iodo-1H-pyrazolo[3,4-d]pyrimidin-1-yl)methyl)pyrimidin-2-yl)methyl) carbamate (2 g, 4.15 mmol, 1.0 equiv), 5-(4,4,5,5-tetramethyl-1,3,2-dioxaborolan-2-yl)-1,3-benzoxazol-2-amine (1.13 g, 4.35 mmol, 1.05 equiv) and $Na_2CO_3$ (688.39 mg, 8.29 mmol, 2.0 equiv) in dioxane (20 mL) and $H_2O$ (10 mL) was added $Pd(PPh_3)_4$ (479.21 mg, 414.70 μmol, 0.1 equiv). The mixture was stirred at 110° C. for 1 h, at which time the mixture was cooled to room temperature, filtered, and the solid cake washed with MeOH (3×10 mL). The filtrate was concentrated under reduced pressure to remove MeOH and then added dropwise into $H_2O$ (50 mL). The resulting suspension was filtered, and the filter cake was washed with $H_2O$ (3×10 mL). The solid cake was stirred in MeOH (20 mL) for 30 min. The resulting suspension was filtered, and the filter cake washed with MeOH (3×8 mL). The filter cake was dried under reduced pressure to afford the desired product (1.03 g, 48.9% yield) as a white solid. LCMS (ESI) m/z: [M+H] calcd for $C_{23}H_{24}N_{10}O_3$: 489.21; found 489.2.

Step 4: Synthesis of 5-(4-amino-1-{[2-(aminomethyl)pyrimidin-5-yl]methyl}-1H-pyrazolo[3,4-d]pyrimidin-3-yl)-1,3-benzoxazol-2-amine To tert-butyl ((5-((4-amino-3-(2-aminobenzo[d]oxazol-5-yl)-1H-pyrazolo[3,4-d]pyrimidin-1-yl)methyl)pyrimidin-2-yl)methyl)carbamate (100 mg, 0.205 mmol, 1.0 equiv) was added con. HCl (850 μL, 10.2 mmol, 50 equiv). The reaction was stirred for 1 h and was then poured into acetone (3 mL). The resulting precipitate was filtered, washed with acetone, and dried under reduced pressure to afford the desired product (80 mg, 92% yield) as a brown solid. LCMS (ESI) m/z: [M+H] calcd for $C_{18}H_{16}N_{10}O$: 389.16; found 389.0.

Monomer AI. 5-(4-(dimethylamino)-1-((1,2,3,4-tetrahydroisoquinolin-6-yl)methyl)-1H-pyrazolo[3,4-d]pyrimidin-3-yl)benzo[d]oxazol-2-amine trifluoroacetic acid salt

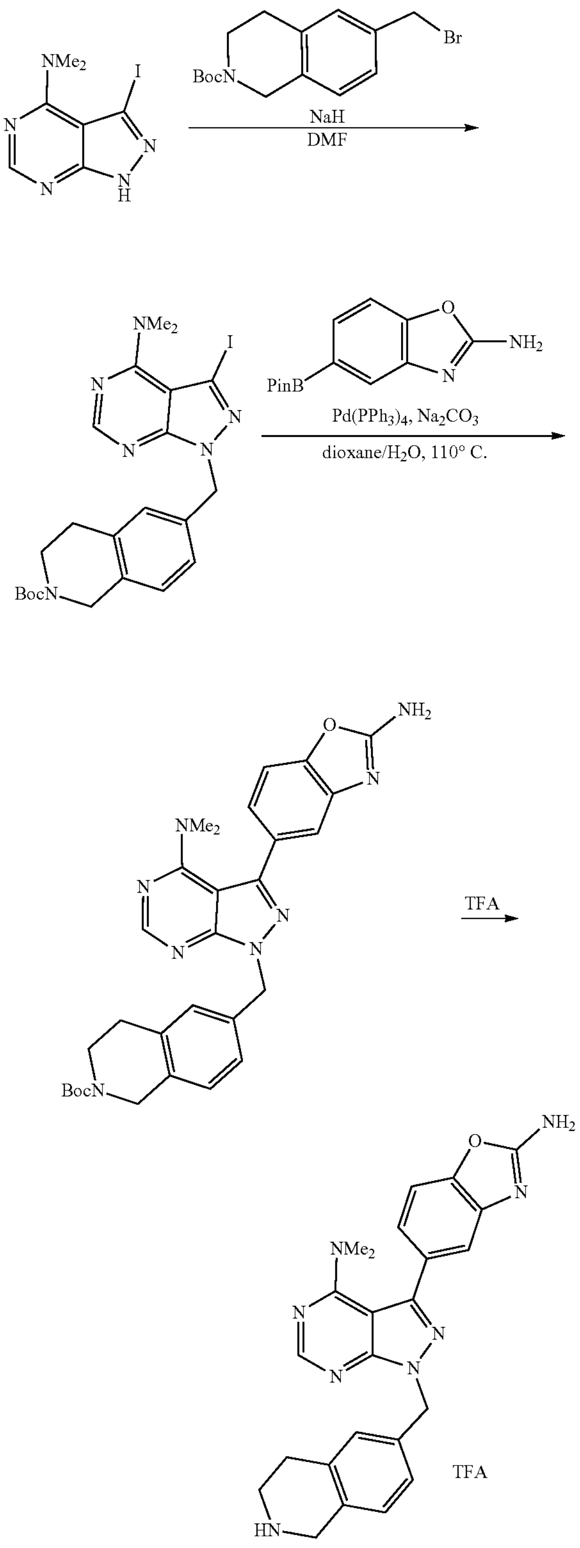

Step 1: Synthesis of tert-butyl 6-((4-(dimethylamino)-3-iodo-1H-pyrazolo[3,4-d]pyrimidin-1-yl)methyl)-3,4-dihydroisoquinoline-2(1H)-carboxylate To a solution of 3-iodo-N,N-dimethyl-1H-pyrazolo[3,4-d]pyrimidin-4-amine (3.6 g, 12.45 mmol, 1.0 equiv) in DMF (36 mL) at 0° C. was added NaH (523.00 mg, 13.08 mmol, 60 wt. %, 1.05 equiv). The mixture was stirred at 0° C. for 30 min. To the reaction mixture was then added a solution of tert-butyl 6-(bromomethyl)-3,4-dihydroisoquinoline-2(1H)-carboxylate (4.47 g, 13.70 mmol, 1.1 equiv) in DMF (18 mL) at 0° C. The mixture was stirred at room temperature for 2 h. The reaction mixture was then added to cold $H_2O$ (200 mL) and stirred for 30 min. The resulting precipitate was collected by filtration to afford the desired product (6 g, 71.9% yield) as a white solid.

Step 2: Synthesis of tert-butyl 6-((3-(2-aminobenzo[d]oxazol-5-yl)-4-(dimethylamino)-1H-pyrazolo[3,4-d]pyrimidin-1-yl)methyl)-3,4-dihydroisoquinoline-2(1H)-carboxylate To a solution of tert-butyl 6-((4-(dimethylamino)-3-iodo-1H-pyrazolo[3,4-d]pyrimidin-1-yl)methyl)-3,4-dihydroisoquinoline-2(1H)-carboxylate (2 g, 2.96 mmol, 1.0 equiv) and 5-(4,4,5,5-tetramethyl-1,3,2-dioxaborolan-2-yl)benzo[d]oxazol-2-amine (922.81 mg, 3.55 mmol, 1.2 equiv) in dioxane (24 mL) and $H_2O$ (12 mL) was added $Na_2CO_3$ (1.57 g, 14.78 mmol, 5.0 equiv) and $Pd(PPh_3)_4$ (341.66 mg, 295.66 μmol, 0.1 equiv). The mixture was stirred at 110° C. for 12 h. The reaction mixture was then poured into cold $H_2O$ (200 mL) and stirred for 30 min. The resulting precipitate was collected by filtration. Purification by silica gel chromatography (5→100% petroleum ether/EtOAc) afforded the desired product (1.2 g, 72.3% yield) as a yellow solid.

Step 3: Synthesis of 5-(4-(dimethylamino)-1-((1,2,3,4-tetrahydroisoquinolin-6-yl)methyl)-1H-pyrazolo[3,4-d]pyrimidin-3-yl)benzo[d]oxazol-2-amine A solution of tert-butyl 6-((3-(2-aminobenzo[d]oxazol-5-yl)-4-(dimethylamino)-1H-pyrazolo[3,4-d]pyrimidin-1-yl)methyl)-3,4-dihydroisoquinoline-2(1H)-carboxylate (1.7 g, 3.14 mmol, 1.0 equiv) in TFA (10 mL) was stirred at room temperature for 30 min. The reaction mixture was then concentrated under reduced pressure. The residue was added to MeCN (10 mL) and the solution was added dropwise into MTBE (200 mL). The resulting solid was dissolved in MeCN (30 mL) and the solution was concentrated under reduced pressure to afford the desired product (1.67 g, 92.9% yield,) as a yellow solid. LCMS (ESI) m/z: [M+H] calcd for $C_{24}H_{24}N_8O$: 441.22; found 441.2.

Monomer AJ. 4-amino-5-(2-aminobenzo[d]oxazol-5-yl)-5H-pyrimido[5,4-b]indole-7-carboxylic acid

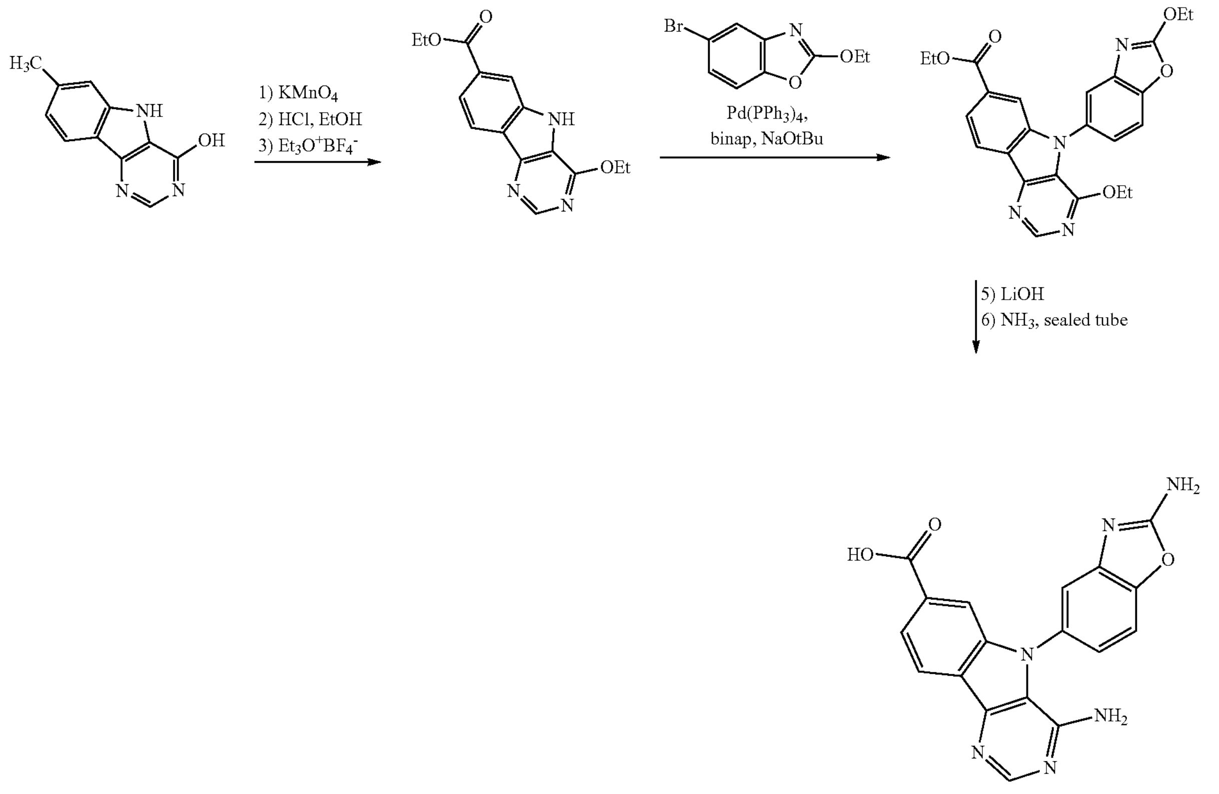

This monomer can be prepared from 7-methyl-5H-pyrimido[5,4-b]indol-4-ol by benzylic oxidation to the carboxylic acid, conversion to the ethyl ester, followed by O-ethylation with triethyloxonium tetrafluoroboroate. Palladium-mediated arylation followed by ester hydrolysis and final ammonia-olysis provides the monomer.

Monomer AK. 4-amino-5-(2-aminobenzo[d]oxazo-5-yl)-5H-pyrimido[5,4-b]indole-8-carboxylic acid

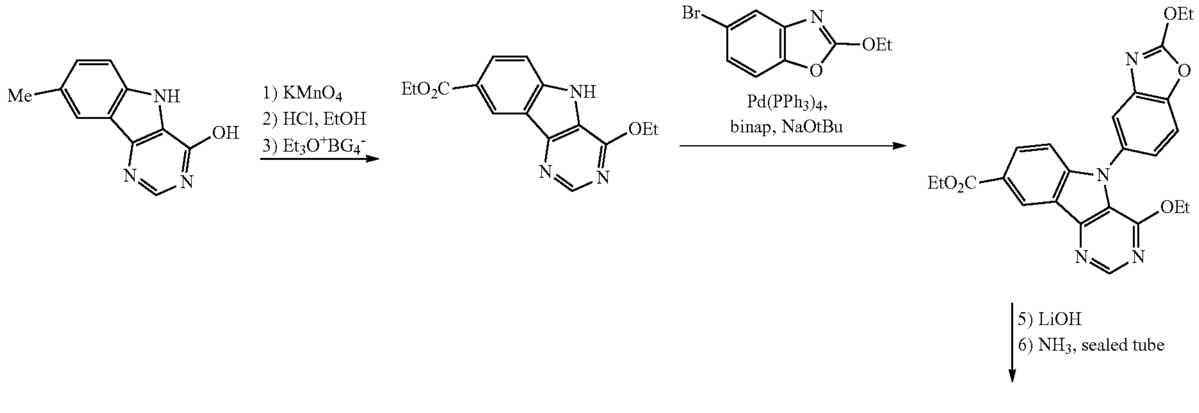

-continued

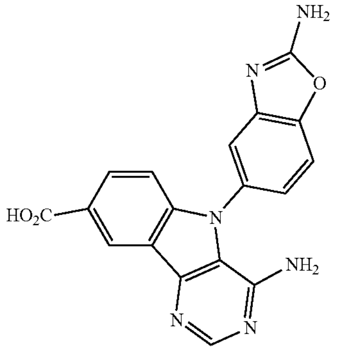

This monomer can be prepared following a similar route as that to prepare the previous monomer, but using the isomeric starting material from 8-methyl-5H-pyrimido[5,4-b]indol-4-ol. Benzylic oxidation to the carboxylic acid, conversion to the ethyl ester, followed by O-ethylation with triethyloxonium tetrafluoroborate and palladium-mediated arylation, followed by ester hydrolysis and final ammonia-olysis provides the monomer.

Monomer AL. 3-(2,4-bis((S)-3-methylmorpholino)-4a,8a-dihydropyrido[2,3-d]pyrimidin-7-yl)benzoic acid

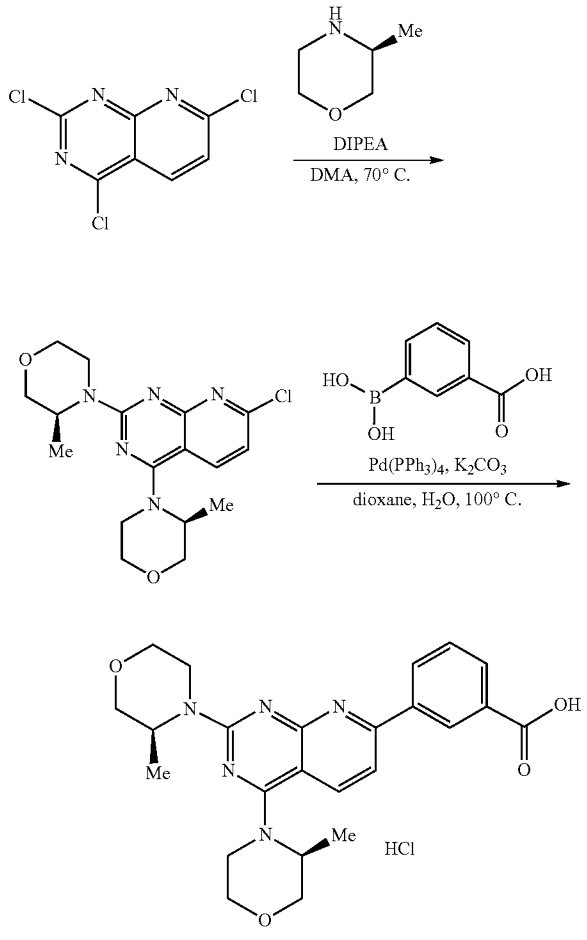

Step 1: Synthesis of (3S)-4-[7-chloro-2-[(3S)-3-methylmorpholin-4-yl]pyrido[2,3-d]pyrimidin-4-yl] 3-methyl-morpholine To a solution of 2,4,7-trichloropyrido[2,3-d]pyrimidine (4.0 g, 17.06 mmol, 1.0 equiv) in DMA (10 mL) was added (3S)-3-methylmorpholine (4.31 g, 42.65 mmol, 2.5 equiv) and DIPEA (5.51 g, 42.65 mmol, 7.43 mL, 2.5 equiv). The reaction solution was heated to 70° C. for 48 h. The reaction suspension was cooled to room temperature, poured into cold $H_2O$ (50 mL) to precipitate out a solid. The solid was filtered and the filter cake was rinsed with $H_2O$, and dried under reduced pressure to give the crude product, which was purified by column chromatography on silica gel (0→100% petroleum ether/EtOAc) to give (3S)-4-[7-chloro-2-[(3S)-3-methylmorpholin-4-yl]pyrido[2,3-d] pyrimidin-4-yl] 3-methyl-morpholine (3.5 g, 56.4% yield) as a yellow solid. LCMS (ESI) m/z: [M+H] calcd for $C_{17}H_{22}ClN_5O_2$: 364.15; found 364.2.

Step 2: Synthesis of 3-[2,4-bis[(3S)-3-methylmorpholin-4-yl]pyrido[2,3-d]pyrimidin-7-yl]benzoic acid To a solution of (3S)-4-[7-chloro-2-[(3S)-3-methylmorpholin-4-yl]pyrido[2,3-d]pyrimidin-4-yl]-3-methyl-morpholine (2 g, 5.50 mmol, 1.0 equiv) and 3-boronobenzoic acid (1.09 g, 6.60 mmol, 1.2 equiv) in 1,4-dioxane (40 mL) was added a solution of $K_2CO_3$ (911.65 mg, 6.60 mmol, 1.2 equiv) in $H_2O$ (4 mL), followed by $Pd(PPh_3)_4$ (317.60 mg, 274.85 μmol, 0.05 equiv). The solution was degassed for 10 min and refilled with $N_2$, then the reaction mixture was heated to 100° C. under $N_2$ for 5 h. The reaction was cooled to room temperature and filtered. The filtrate was acidified by HCl (2N) to pH 3, and the aqueous layer was washed with EtOAc (3x20 mL). The aqueous phase was concentrated under reduced pressure to give a residue, which was purified by column chromatography on silica gel (50%→100% petroleum ether/EtOAc) to give 3-[2,4-bis[(3S)-3-methylmorpholin-4-yl]pyrido[2,3-d]pyrimidin-7-yl]benzoic acid hydrochloride (2.5 g, 89.9% yield) as a yellow solid. LCMS (ESI) m/z: [M+H] calcd for $C_{24}H_{27}N_5O_4$: 450.21; found 450.2.

Reference for preparation of this monomer: Menear, K.; Smith, G. C. M.; Malagu, K.; Duggan, H. M. E.; Martin, N. M. B.; Leroux, F. G. M. 2012. Pyrido-, pyrazo- and pyrimido-pyrimidine derivatives as mTOR inhibitors. U.S. Pat. No. 8,101,602. Kudos Pharmaceuticals, Ltd, which is incorporated by reference in its entirety.

Monomer AM. (1r,4r)-4-[4-amino-5-(7-methoxy-1H-indol-2-yl)imidazo[4,3-f][1,2,4]triazin-7-yl]cyclohexane-1-carboxylic acid

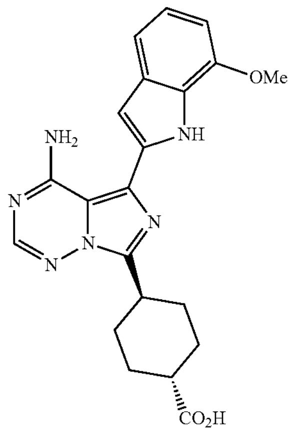 [SMILES: COc1cccc2cc(-c3nc([C@H]4CC[C@H](C(=O)O)CC4)n4ncnc(N)c34)[nH]c12]

This monomer, also known as OSI-027 (CAS #=936890-98-1), is a commercially available compound. At the time this application was prepared, it was available for purchase from several vendors.

Monomer AN. 2-(4-(4-(8-(6-methoxypyridin-3-yl)-3-methyl-2-oxo-2,3-dihydro-1H-imidazo[4,5-c]quinolin-1-yl)-2-(trifluoromethyl)phenyl)piperazin-1-yl)pyrimidine-5-carboxylic acid

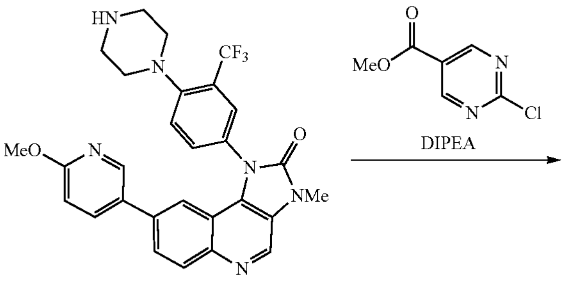

-continued

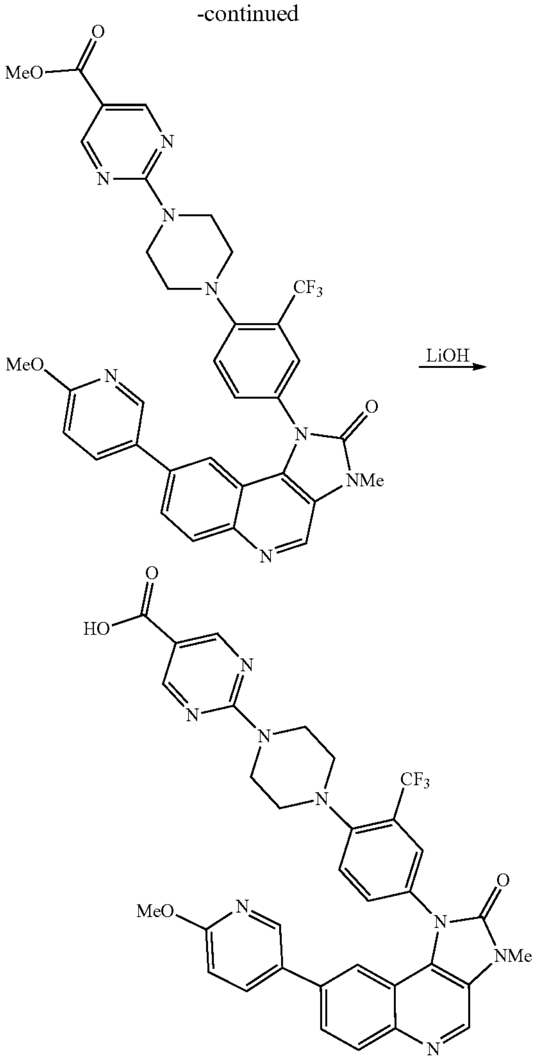

Preparation of this monomer proceeds by reaction of BGT226 with methyl 2-chloropyrimidine-5-carboxylate, followed by ester hydrolysis, to give the titled Monomer.

Monomer AO. 4-amino-5-{1H-pyrrolo[2,3-b]pyridin-5-yl}-5H-pyrimido[5,4-b]indole-8-carboxylic acid

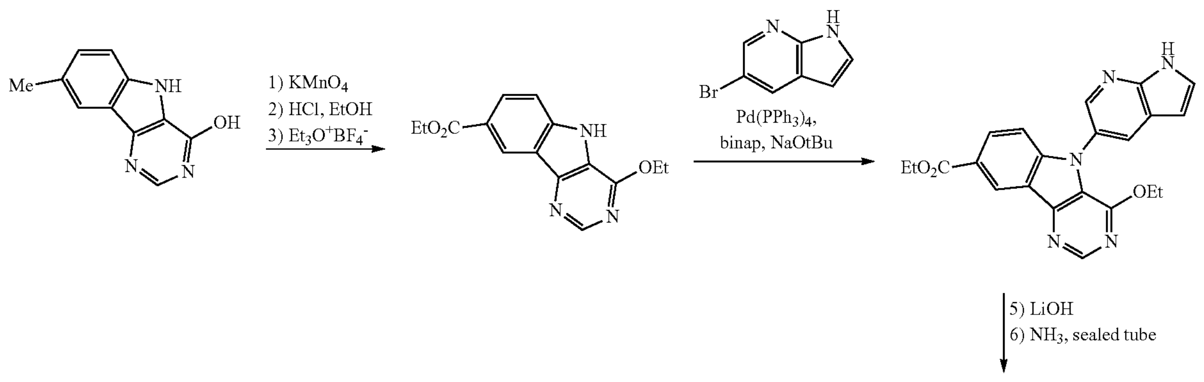

-continued

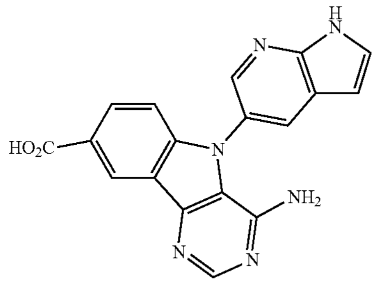

This monomer can be prepared from 7-methyl-5H-pyrimido[5,4-b]indol-4-ol by benzylic oxidation to the carboxylic acid, conversion to the ethyl ester, followed by O-ethylation with triethyloxonium tetrafluoroborate. Palladium-mediated arylation followed by ester hydrolysis and final ammonia-olysis provides the monomer.

Preparation of Pre- and Post-Linkers

Building Block A. tert-butyl N-[(tert-butoxy)carbonyl]-N-{[2-(piperazin-1-yl)pyrimidin-5-yl] methyl}carbamate

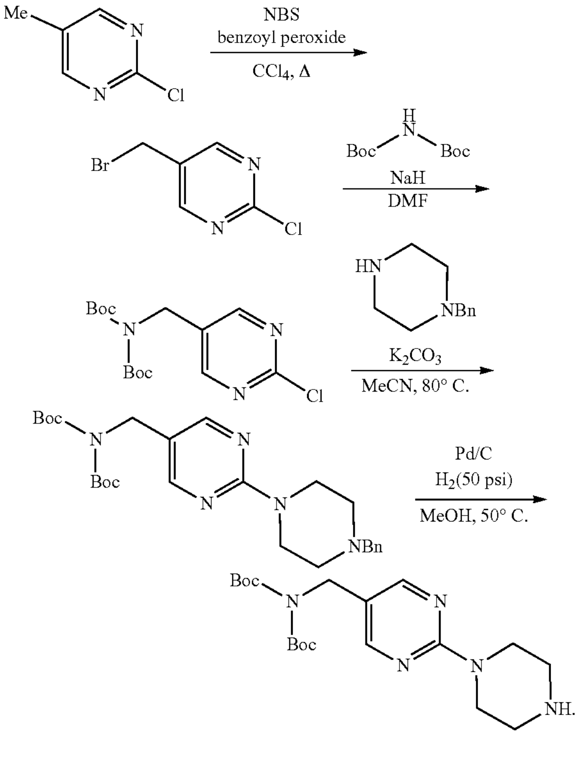

Step 1: Synthesis of 5-(bromomethyl)-2-chloropyrimidine

To a solution of 2-chloro-5-methylpyrimidine (92 g, 715.62 mmol, 1.0 equiv) in $CCl_4$ (1000 mL) was added NBS (178.31 g, 1.00 mol, 1.4 equiv) and benzoyl peroxide (3.47 g, 14.31 mmol, 0.02 equiv). The mixture was stirred at 76° C. for 18 h. The reaction mixture was then cooled to room temperature and concentrated under reduced pressure. The reaction mixture was filtered and the solid cake was washed with DCM (150 mL). The resulting solution was concentrated under reduced pressure to give the crude product. The residue was purified by silica gel chromatography (1/0 to 0/1 petroleum ether/EtOAc) to give the product (70.8 g, 47.7% crude yield) as yellow oil, which was used directly for the next step. LCMS (ESI) m/z: [M+H] calcd for $C_5H_4BrClN_2$: 206.93; found 206.9.

Step 2: Synthesis of tert-butyl N-tert-butoxycarbonyl-N-((2-piperazin-1-ylpyrimidin-5-yl)methyl)carbamate To a solution of tert-butyl N-tert-butoxycarbonylcarbamate (36.89 g, 169.79 mmol, 0.74 equiv) in DMF (750 mL) was added NaH (6.88 g, 172.09 mmol, 60 wt. %, 0.75 equiv) at 0° C. The mixture was stirred at 0° C. for 30 min. Then, 5-(bromomethyl)-2-chloropyrimidine (47.6 g, 229.45 mmol, 1.0 equiv) was added at 0° C. The reaction mixture was stirred at room temperature for 15.5 h. The mixture was then poured into $H_2O$ (1600 mL) and the aqueous phase was extracted with EtOAc (3×300 mL). The combined organic phase was washed with brine (2×200 mL), dried with anhydrous $Na_2SO_4$, filtered and concentrated under reduced pressure. The residue was purified by silica gel chromatography (1/0 to 0/1 petroleum ether/EtOAc) to give the product (70 g, crude) as a yellow solid, which was used to next step directly.

Step 3: Synthesis of tert-butyl N-tert-butoxycarbonyl-N-[(2-piperazin-1-ylpyrimidin-5-yl)methyl]carbamate To a solution of 1-benzylpiperazine (30.44 g, 122.16 mmol, 1.0 equiv, 2HCl) in MeCN (550 mL) was added tert-butyl N-tert-butoxycarbonyl-N-((2-chloropyrimidin-5-yl)methyl)carbamate (42 g, 122.16 mmol, 1.0 equiv) and $K_2CO_3$ (84.42 g, 610.81 mmol, 5.0 equiv). The mixture was stirred at 80° C. for 61 h. The reaction mixture was then diluted with EtOAc (150 mL) and the mixture was filtered. The resulting solution was concentrated under reduced pressure to give the crude product. The residue was purified by silica gel chromatography (1/0 to 0/1 petroleum ether/EtOAc) to give the product (45 g, 74% yield) as a white solid.

Step 4: Synthesis of tert-butyl N-tert-butoxycarbonyl-N-[(2-piperazin-1-ylpyrimidin-5-yl)methyl]carbamate To a solution of tert-butyl N-[[2-(4-benzylpiperazin-1-yl)pyrimidin-5-yl]methyl]-N-tert-butoxycarbonyl-carbamate (24 g, 49.63 mmol, 1.0 equiv) in MeOH (600 mL) was added Pd/C (24 g, 47.56 mmol, 10 wt. %, 1.0 equiv) under argon. The mixture was degassed under reduced pressure and purged with $H_2$ three times. The mixture was stirred under $H_2$ (50 psi) at 50° C. for 19 h. The reaction mixture was cooled to room temperature, filtered, and the filter cake was washed with MeOH (500 mL). The resulting solution was concentrated under reduced pressure. The residue was purified by silica gel chromatography (1/0 to 0/1 EtOAc/MeOH) to give the product (25.5 g, 68% yield) as a white solid.

Building Block B. 2-(4-(5-(((tert-butoxycarbonyl)amino)methyl)pyrimidin-2-yl)piperazin-1-yl)pyrimidine-5-carboxylic acid

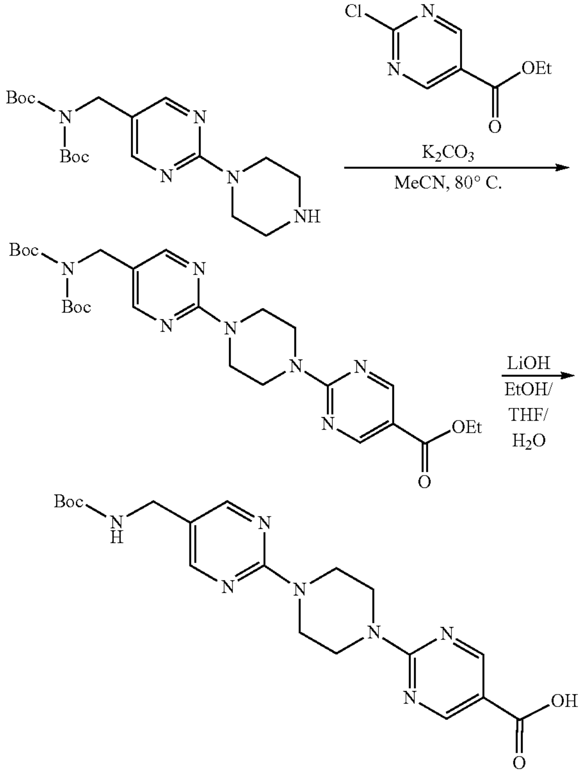

Step 1: Synthesis of ethyl 2-(4-(5-((bis(tert-butoxycarbonyl)amino)methyl)pyrimidin-2-yl)piperazin-1-yl)pyrimidine-5-carboxylate To a solution of ethyl 2-chloropyrimidine-5-carboxylate (2.37 g, 12.71 mmol, 1.0 equiv) and tert-butyl N-tert-butoxycarbonyl-N-((2-piperazin-1-ylpyrimidin-5-yl)methyl)carbamate (5 g, 12.71 mmol, 1.0 equiv) in MeCN (80 mL) was added $K_2CO_3$ (5.27 g, 38.12 mmol, 3.0 equiv). The mixture was stirred at 80° C. for 16 h. The reaction mixture was then poured into $H_2O$ (200 mL) and the suspension was filtered. The filtrate was washed with $H_2O$ (80 mL) and dried under reduced pressure to give the product (6.1 g, 87% yield) as a white solid.

Step 2: Synthesis of 2-(4-(5-(((tert-butoxycarbonyl)amino)methyl)pyrimidin-2-yl)piperazin-1-yl)pyrimidine-5-carboxylic acid To a solution of ethyl 2-(4-(5-((bis(tert-butoxycarbonyl)amino)methyl)pyrimidin-2-yl)piperazin-1-yl)pyrimidine-5-carboxylate (5 g, 9.20 mmol, 1.0 equiv) in $H_2O$ (50 mL), EtOH (15 mL) and THF (50 mL) was added $LiOH{\cdot}H_2O$ (1.54 g, 36.79 mmol, 4.0 equiv). The reaction mixture was stirred at 55° C. for 16 h. The mixture was then concentrated to remove THF and EtOH and then the mixture was diluted with $H_2O$ (55 mL) and was acidified (pH=3) with aqueous HCl (1 N). The mixture was filtered and the filter cake was washed with $H_2O$ (36 mL). The filter cake was dried under reduced pressure to give the product (2.7 g, 69.3%) as a white solid. LCMS (ESI) m/z: [M+H] calcd for $C_{19}H_{25}N_7O_4$: 416.21; found 416.1.

Building Block C. tert-butyl 2-(piperazin-1-yl)-7,8-dihydropyrido[4,3-d]pyrimidine-6(5H)-carboxylate

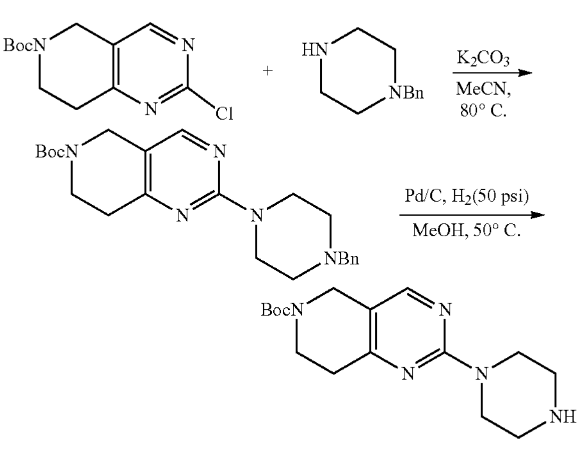

Step 1: Synthesis of tert-butyl 2-(4-benzylpiperazin-1-yl)-7,8-dihydropyrido[4,3-d]pyrimidine-6(5H)-carboxylate To a solution of tert-butyl 2-chloro-7,8-dihydropyrido[4,3-d]pyrimidine-6(5H)-carboxylate (15 g, 55.61 mmol, 1.0 equiv) in MeCN (150 mL) was added 1-benzylpiperazine (11.76 g, 66.73 mmol, 1.2 equiv) and $K_2CO_3$ (46.12 g, 333.67 mmol, 6.0 equiv). The mixture was stirred at 80° C. for 27 h. The reaction mixture was diluted with EtOAc (200 mL), filtered and concentrated under reduced pressure. The crude product was purified by silica gel chromatography (1/0 to 0/1 petroleum ether/EtOAc) to give the product (20.2 g, 80% yield) as a white solid. LCMS (ESI) m/z: [M+H] calcd for $C_{23}H_{31}N_8O_2$: 410.26; found 410.1.

Step 2: Synthesis of tert-butyl 2-(piperazin-1-yl)-7,8-dihydropyrido[4,3-d]pyrimidine-6(5H)-carboxylate To a solution of tert-butyl 2-(4-benzylpiperazin-1-yl)-7,8-dihydropyrido[4,3-d]pyrimidine-6(5H)-carboxylate (8 g, 19.53 mmol, 1.0 equiv) in MeOH (200 mL) was added Pd/C (8 g, 19.53 mmol, 10 wt. %, 1.0 equiv) under argon. The mixture was degassed and purged with $H_2$ three times. The mixture was stirred under $H_2$ (50 psi) at 50° C. for 19 h. The reaction mixture was cooled to room temperature, filtered through a pad of Celite and the filter cake was washed with MeOH (150 mL). The resulting solution was concentrated under reduced pressure. The crude product was washed with petroleum ether (60 mL) to give the product (9.25 g, 72% yield) as a white solid. LCMS (ESI) m/z: [M+H] calcd for $C_{16}H_{25}N_5O_2$: 320.21; found 320.2.

Building Block D. 2-(4-(6-(tert-butoxycarbonyl)-5,6,7,8-tetrahydropyrido[4,3-d]pyrimidin-2-yl)piperazin-1-yl)pyrimidine-5-carboxylic acid

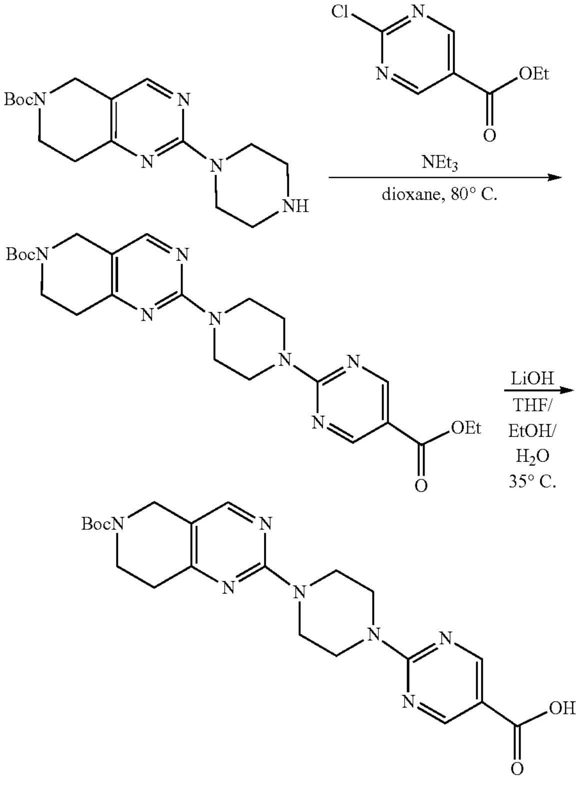

Step 1: Synthesis of tert-butyl 2-(4-(5-(ethoxycarbonyl)pyrimidin-2-yl)piperazin-1-yl)-7,8-dihydropyrido[4,3-d]pyrimidine-6(5H)-carboxylate To a solution of ethyl 2-chloropyrimidine-5-carboxylate (4.09 g, 21.92 mmol, 1.0 equiv) in dioxane (80 mL) was added tert-butyl 2-(piperazin-1-yl)-7,8-dihydropyrido[4,3-d]pyrimidine-6(5H)-carboxylate (7 g, 21.92 mmol, 1.0 equiv) and $Et_3N$ (9.15 mL, 65.75 mmol, 3.0 equiv). The mixture was stirred at 90° C. for 64 h. The solution was poured into $H_2O$ (200 mL) and then the mixture was filtered and the filter cake was washed with $H_2O$ (100 mL) followed by petroleum ether (60 mL). The filter cake was dried under reduced pressure to give the product (10.1 g, 92% yield) as a brown solid. LCMS (ESI) m/z: [M+H] calcd for $C_{23}H_{31}N_7O_4$: 470.25; found 470.4.

Step 2: Synthesis of 2-(4-(6-(tert-butoxycarbonyl)-5,6,7,8-tetrahydropyrido[4,3-d]pyrimidin-2-yl)piperazin-1-yl)pyrimidine-5-carboxylic acid To a solution of tert-butyl 2-(4-(5-(ethoxycarbonyl)pyrimidin-2-yl)piperazin-1-yl)-7,8-dihydropyrido[4,3-d]pyrimidine-6(5H)-carboxylate (6.0 g, 12.78 mmol, 1.0 equiv) in THF (40 mL), EtOH (20 mL) and $H_2O$ (40 mL) was added $LiOH \cdot H_2O$ (1.07 g, 25.56 mmol, 2.0 equiv). The reaction mixture was stirred at 35° C. for 15 h. The mixture was then concentrated under reduced pressure to remove THF and EtOH. The mixture was then diluted with $H_2O$ (500 mL) and was adjusted to pH 3 with aqueous HCl (1 N). The mixture was filtered and the filter cake was washed with $H_2O$ (80 mL) followed by petroleum ether (80 mL). The filter cake was dried under reduced pressure to give the product (3.8 g, 65% yield) as a white solid. LCMS (ESI) m/z: [M+H] calcd for $C_{21}H_{27}N_7O_4$: 442.22; found 442.3.

Building Block E. tert-butyl methyl((2-(piperazin-1-yl)pyrimidin-5-yl)methyl)carbamate

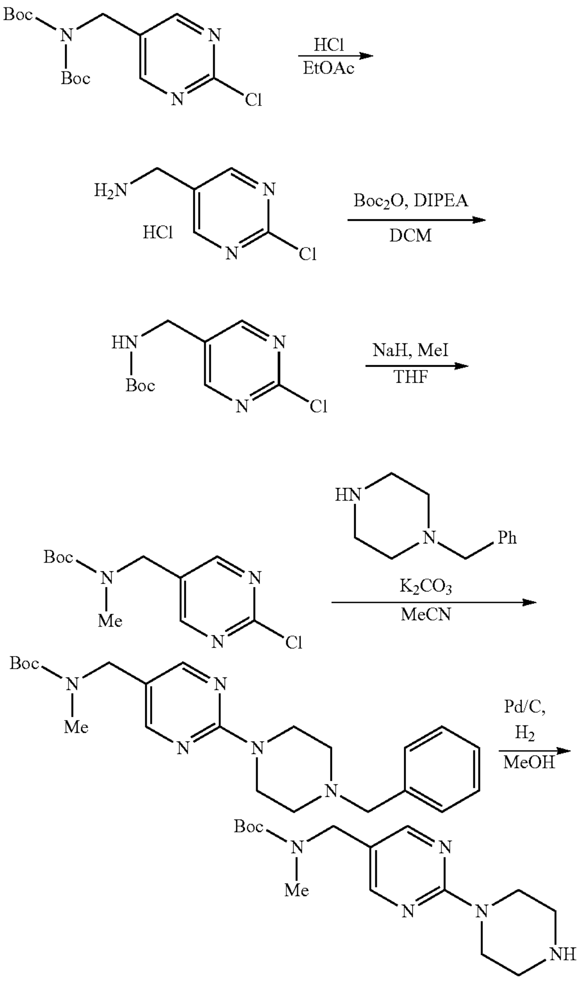

Step 1: Synthesis of (2-chloropyrimidin-5-yl)methanamine

To a solution of tert-butyl N-tert-butoxycarbonyl-N-((2-chloropyrimidin-5-yl)methyl)carbamate (28 g, 81.44 mmol, 1.0 equiv) in EtOAc (30 mL) was added HCl in EtOAc (260 mL). The reaction mixture was stirred at room temperature for 5 h. The reaction mixture was filtered and the filter cake was washed with EtOAc (100 mL). The solid cake was dried under reduced pressure to give the product (14.3 g, 96.6% yield, HCl) as a white solid.

Step 2: Synthesis of tert-butyl ((2-chloropyrimidin-5-yl)methyl)carbamate

To a solution of (2-chloropyrimidin-5-yl)methanamine (13 g, 72.21 mmol, 1.0 equiv, HCl) in DCM (130 mL) was added DIPEA (20.41 mL, 144.42 mmol, 1.8 equiv) and $Boc_2O$ (16.59 mL, 72.21 mmol, 1.0 equiv), then the mixture was stirred at room temperature for 3 h. The reaction mixture was added to $H_2O$ (100 mL) and then the aqueous layer was separated and extracted with DCM (2×100 mL). Then combined organic phase was washed with sat. $NH_4Cl$ (2×200 mL) and brine (2×200 mL), dried with anhydrous $Na_2SO_4$, filtered and concentrated under reduced pressure. The residue was purified by silica gel chromatography (1/0 to 1/1 petroleum ether/EtOAc) to give the product (12 g, 68.2% yield) as a white solid.

Step 3: Synthesis of tert-butyl ((2-chloropyrimidin-5-yl)methyl)(methyl)carbamate To a solution of tert-butyl ((2-chloropyrimidin-5-yl) methyl)carbamate (11 g, 45.14 mmol, 1.0 equiv) and MeI (14.05 mL, 225.70 mmol, 5.0 equiv) in THF (150 mL) was added NaH (1.99 g, 49.65 mmol, 60 wt. %, 1.1 equiv) at 0° C. The mixture was stirred at 0° C. for 3 h and then the reaction was quenched with $H_2O$ (100 mL). The aqueous phase was extracted with EtOAc (3×150 mL) and the combined organic phase was washed with brine (50 mL), dried with anhydrous $Na_2SO_4$, filtered and concentrated under reduced pressure. The residue was purified by silica gel chromatography (1/0 to 3/1 petroleum ether/EtOAc) to give the product (9 g, 77.4% yield) as a white solid.

Step 4: Synthesis of tert-butyl ((2-(4-benzylpiperazin-1-yl)pyrimidin-5-yl)methyl)(methyl)carbamate To a solution of tert-butyl ((2-chloropyrimidin-5-yl) methyl)(methyl)carbamate (9 g, 34.92 mmol, 1.0 equiv) in MeCN (90 mL) was added 1-benzylpiperazine (8.70 g, 34.92 mmol, 1.0 equiv, 2HCl), and $K_2CO_3$ (24.13 g, 174.61 mmol, 5.0 equiv). The reaction mixture was stirred at 80° C. for 20 h. The mixture was then filtered and concentrated under reduced pressure. The residue was purified by silica gel chromatography (1/0 to 1/1 petroleum ether/EtOAc) to give the product (12 g, 86.4% yield) as a yellow oil.

Step 5: Synthesis of tert-butyl methyl((2-(piperazin-1-yl)pyrimidin-5-yl)methyl)carbamate To a solution of tert-butyl ((2-(4-benzylpiperazin-1-yl) pyrimidin-5-yl)methyl)(methyl)carbamate (12 g, 30.19 mmol, 1.0 equiv) in MeOH (120 mL) was added Pd/C (2 g, 10 wt. %). The suspension was degassed and purged with $H_2$ and then the mixture was stirred under $H_2$ (15 psi) at room temperature for 3 h. The reaction mixture was filtered through Celite and the filtrate was concentrated under reduced pressure. The residue was purified by silica gel chromatography 1/0 to 1/1 petroleum ether/EtOAc) to give semi-pure material (9 g) as a yellow oil. Petroleum ether was added to the residue and the solution was stirred at −60° C. until solid appeared. The suspension was filtered and the filtrate was concentrated under reduced pressure to give the product (4.07 g, 55.6% yield) as a yellow oil. LCMS (ESI) m/z: [M+H] calcd for $C_{15}H_{25}N_5O_2$: 308.21; found 308.1.

Building Block F. 2-(4-(5-(((tert-butoxycarbonyl)(methyl)amino)methyl) pyrimidin-2-yl)piperazin-1-yl)pyrimidine-5-carboxylic acid

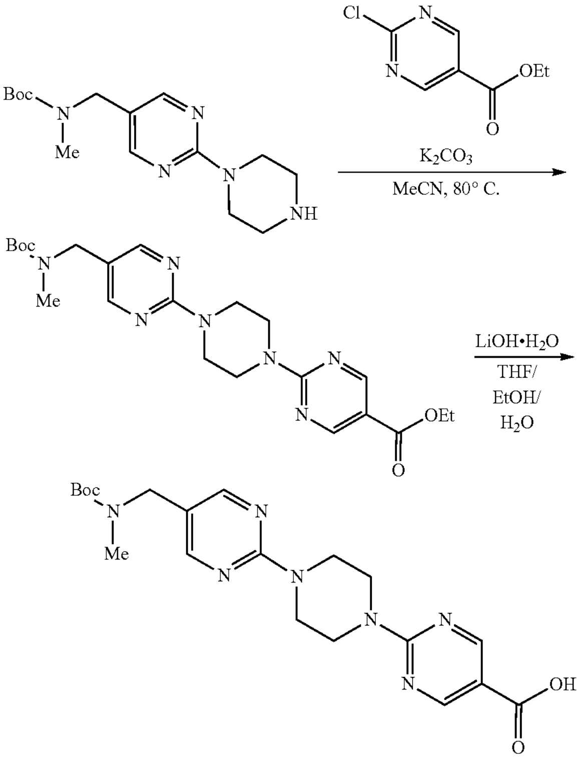

Step 1: Synthesis of ethyl 2-(4-(5-(((tert-butoxycarbonyl)(methyl)amino)methyl) pyrimidin-2-yl)piperazin-1-yl)pyrimidine-5-carboxylate To a mixture of tert-butyl methyl((2-(piperazin-1-yl)pyrimidin-5-yl)methyl)carbamate (4.3 g, 13.99 mmol, 1.0 equiv) and ethyl 2-chloropyrimidine-5-carboxylate (2.87 g, 15.39 mmol, 1.1 equiv) in MeCN (20 mL) was added $K_2CO_3$ (3.87 g, 27.98 mmol, 2.0 equiv). The mixture was stirred at 80° C. for 12 h. The reaction mixture then cooled to room temperature and was filtered. The filtrate was concentrated under reduced pressure and the crude product was purified by silica gel chromatography (1/0 to 1/1 petroleum ether/EtOAc) to give the product (4.7 g, 71.3% yield) as a white solid.

Step 2: Synthesis of 2-(4-(5-(((tert-butoxycarbonyl)(methyl)amino)methyl) pyrimidin-2-yl)piperazin-1-yl)pyrimidine-5-carboxylic acid To a solution of ethyl 2-(4-(5-(((tert-butoxycarbonyl)(methyl)amino)methyl)pyrimidin-2-yl)piperazin-1-yl)pyrimidine-5-carboxylate (6 g, 13.11 mmol, 1.0 equiv) in THF (100 mL), EtOH (30 mL), and $H_2O$ (30 mL) was added $LiOH{\cdot}H_2O$ (1.10 g, 26.23 mmol, 2.0 equiv). The mixture was stirred at room temperature for 16 h. The mixture was then concentrated under reduced pressure to remove THF and EtOH and then neutralized by the addition of 1N HCl. The resulting precipitate was collected by filtration to give the product (5.11 g, 90.1% yield) as a white solid. LCMS (ESI) m/z: [M+H] calcd for $C_{20}H_{27}N_7O_4$: 430.22; found 430.2.

Building Block G. tert-butyl N-tert-butoxycarbonyl-N-((2-(2-((tert-butyl(diphenyl)silyl)oxymethyl)piperazin-1-yl)pyrimidin-5-yl)methyl)carbamate

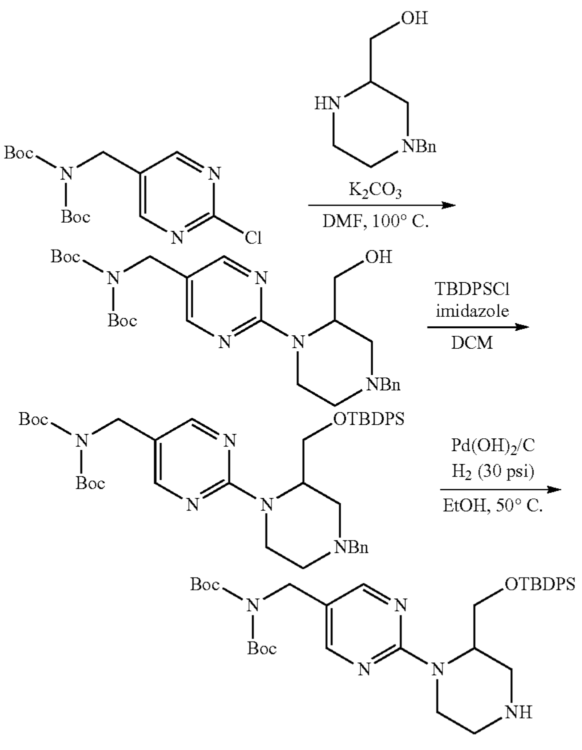

Step 1: Synthesis of tert-butyl N-((2-(4-benzyl-2-(hydroxymethyl)piperazin-1-yl)pyrimidin-5-yl)methyl)-N-tert-butoxy carbonyl-carbamate To a solution of tert-butyl N-tert-butoxycarbonyl-N-((2-chloropyrimidin-5-yl)methyl)carbamate (18.33 g, 53.32 mmol, 1.1 equiv) and (4-benzylpiperazin-2-yl)methanol (10 g, 48.48 mmol, 1.0 equiv) in DMF (100 mL) was added $K_2CO_3$ (13.40 g, 96.95 mmol, 2.0 equiv). The mixture was stirred at 100° C. for 12 h. The reaction mixture was then cooled to room temperature and $H_2O$ (100 mL) was added. The aqueous layer was extracted with EtOAc (2×150 mL) and the combined organic layer was washed with brine (20 mL), dried with $Na_2SO_4$, filtered and the filtrate was concentrated under reduced pressure to give the product (7.3 g, 29.3% yield) as a yellow oil. LCMS (ESI) m/z: [M+H] calcd for $C_{27}H_{39}N_5O_5$: 514.31; found 514.5.

Step 2: Synthesis of tert-butyl N-((2-(4-benzyl-2-((tert-butyl(diphenyl)silyl)oxymethyl)piperazin-1-yl)pyrimidin-5-yl)methyl)-N-tert-butoxycarbonyl-carbamate To a solution of tert-butyl N-((2-(4-benzyl-2-(hydroxymethyl)piperazin-1-yl)pyrimidin-5-yl)methyl)-N-tert-butoxycarbonyl-carbamate (2.3 g, 4.48 mmol, 1.0 equiv) in DCM (30 mL) was added imidazole (609.69 mg, 8.96 mmol, 2.0 equiv) and TBDPSCl (1.73 mL, 6.72 mmol, 1.5 equiv). The reaction mixture was stirred at room temperature for 2 h. The mixture was then washed with $H_2O$ (100 mL) and the aqueous phase extracted with EtOAc (2×60 mL). The combined organic phase was washed with brine (20 mL), dried with $Na_2SO_4$, filtered and concentrated under reduced pressure. The residue was purified by silica gel chromatography (20/1 to 3/1 petroleum ether/EtOAc) to give the product (4 g, 59.4% yield) as a yellow oil. LCMS (ESI) m/z: [M+H] calcd for $C_{43}H_{57}N_5O_5Si$: 752.42; found 752.4.

Step 3: Synthesis of tert-butyl N-tert-butoxycarbonyl-N-((2-(2-((tert-butyl(diphenyl)silyl)oxymethyl)piperazin-1-yl)pyrimidin-5-yl)methyl)carbamate To a solution of tert-butyl N-((2-(4-benzyl-2-((tert-butyl(diphenyl)silyl)oxymethyl)piperazin-1-yl)pyrimidin-5-yl)methyl)-N-tert-butoxycarbonyl-carbamate (3.3 g, 4.39 mmol, 1.0 equiv) in EtOH (10 mL) was added $Pd(OH)_2/C$ (1 g, 10 wt. %). The mixture was heated to 50° C. under $H_2$ (30 psi) for 30 h. The mixture was then cooled to room temperature, filtered through Celite, and concentrated under reduced pressure. The residue was purified by silica gel chromatography (20/1 to 3/1 EtOAc/EtOH) to give the product (1.44 g, 45.6% yield) as a yellow solid. LCMS (ESI) m/z: [M+H] calcd for $C_{36}H_{51}N_5O_5Si$: 662.38; found 662.3.

Building Block H. 2-(4-(5-(((tert-butoxycarbonyl)amino)methyl)pyrimidin-2-yl)-3-(hydroxymethyl)piperazin-1-yl)pyrimidine-5-carboxylic acid

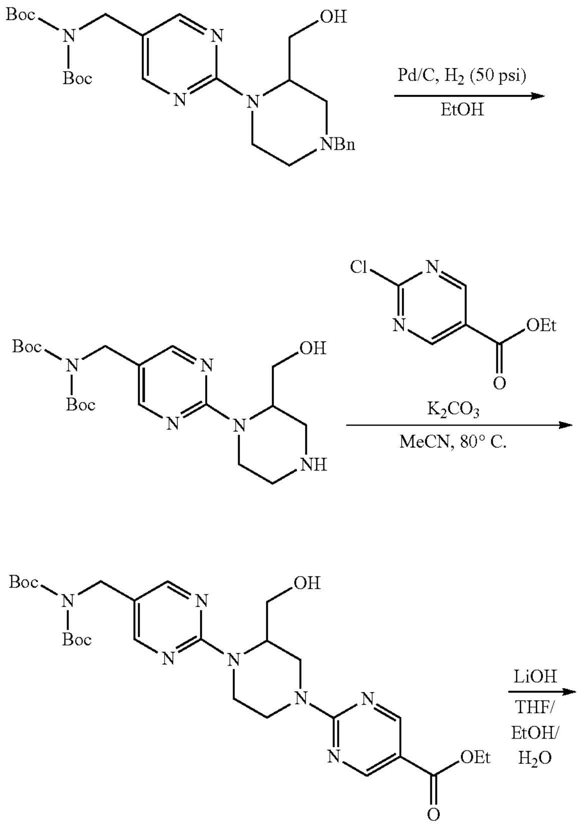

-continued

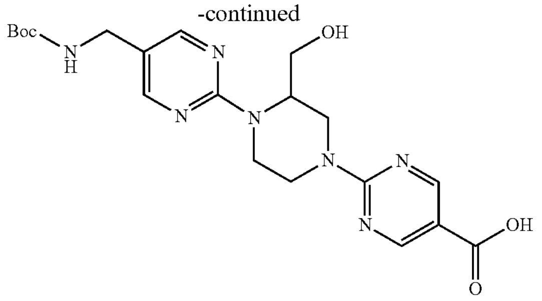

Step 1: Synthesis of tert-butyl N-tert-butoxycarbonyl-N-((2-(2-(hydroxymethyl)piperazin-1-yl)pyrimidin-5-yl)methyl)carbamate To a solution of tert-butyl N-((2-(4-benzyl-2-(hydroxymethyl)piperazin-1-yl)pyrimidin-5-yl)methyl)-N-tert-butoxycarbonyl-carbamate (3 g, 5.84 mmol, 1.0 equiv) in EtOH (40 mL) was added Pd/C (2 g, 10 wt. %). The suspension was degassed and purged with $H_2$, then stirred under $H_2$ (50 psi) at 30° C. for 16 h. The reaction mixture was cooled to room temperature and filtered through Celite and then concentrated under reduced pressure to give the product (1.6 g, crude) as a yellow oil. LCMS (ESI) m/z: [M+H] calcd for $C_{20}H_{33}N_8O_5$: 424.26; found 424.3.

Step 2: Synthesis of ethyl 2-(4-(5-((bis(tert-butoxycarbonyl)amino)methyl)pyrimidin-2-yl)-3-(hydroxymethyl)piperazin-1-yl)pyrimidine-5-carboxylate To a solution of tert-butyl N-tert-butoxycarbonyl-N-((2-(2-(hydroxymethyl)piperazin-1-yl)pyrimidin-5-yl)methyl) carbamate (1.4 g, 3.31 mmol, 1.0 equiv) in MeCN (20 mL) was added $K_2CO_3$ (2.28 g, 16.53 mmol, 5.0 equiv) and ethyl 2-chloropyrimidine-5-carboxylate (616.84 mg, 3.31 mmol, 1.0 equiv). The solution was stirred at 80° C. for 4 h. The mixture was cooled to room temperature and poured into $H_2O$ (30 mL). The aqueous layer was extracted with EtOAc (2×30 mL) and the combined organic layer was washed with brine (20 mL), dried with $Na_2SO_4$, filtered and concentrated under reduced pressure. The mixture was purified by silica gel chromatography (20/1 to 3/1 petroleum ether/EtOAc) to give the product (1.6 g, 66.7% yield) as a light yellow solid. LCMS (ESI) m/z: [M+H] calcd for $C_{27}H_{39}N_7O_7$: 574.30; found 574.4.

Step 3: Synthesis of 2-(4-(5-(((tert-butoxycarbonyl)amino)methyl)pyrimidin-2-yl)-3-(hydroxymethyl)piperazin-1-yl)pyrimidine-5-carboxylic acid To a solution of ethyl 2-(4-(5-((bis(tert-butoxycarbonyl)amino)methyl)pyrimidin-2-yl)-3-(hydroxymethyl)piperazin-1-yl)pyrimidine-5-carboxylate (1.4 g, 2.44 mmol, 1.0 equiv) in THF (6 mL) and EtOH (6 mL) at 0° C. was added a solution of $LiOH \cdot H_2O$ (512.07 mg, 12.20 mmol, 5.0 equiv) in $H_2O$ (3 mL). The reaction mixture was warmed to room temperature and stirred for 2 h. The mixture was then concentrated under reduced pressure to remove THF and EtOH. The aqueous phase was adjusted to pH 3 with 0.1 M HCl and the resulting suspension was filtered. The solid cake was dried under reduced pressure to give the product (613.14 mg, 55.6% yield) as a white solid. LCMS (ESI) m/z: [M+H] calcd for $C_{20}H_{27}N_7O_5$: 446.22; found 446.2.

Building Block I. tert-butyl N-[(tert-butoxy)carbonyl]-N-({2-[(3R)-3-(hydroxymethyl)piperazin-1-yl]pyrimidin-5-yl}methyl)carbamate

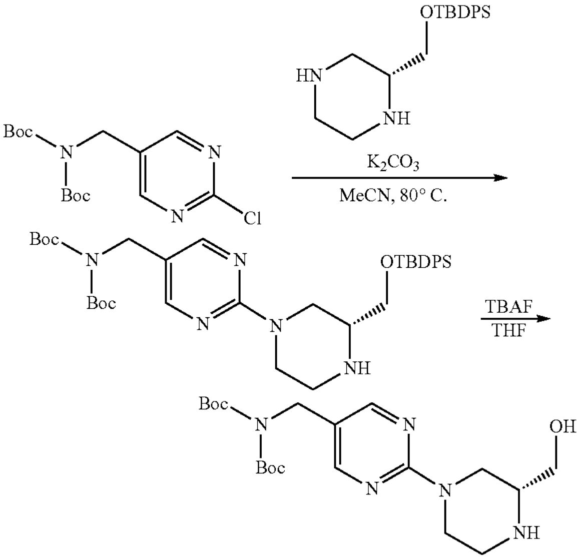

Step 1: Synthesis of (R)-tert-butyl-N-tert-butoxycarbonyl-((2-(3-(((tert-butyldiphenylsilyl)-oxy)methyl)piperazin-1-yl)pyrimidin-5-yl)methyl)carbamate To a solution of tert-butyl-N-tert-butoxycarbonyl-((2-chloropyrimidin-5-yl)methyl)carbamate (24.24 g, 70.51 mmol, 1.0 equiv) in MeCN (300 mL) was added (R)-2-(((tert-butyldiphenylsilyl)oxy)methyl)piperazine (25 g, 70.51 mmol, 1.0 equiv) and $K_2CO_3$ (29.24 g, 211.53 mmol, 3.0 equiv). The mixture was stirred at 80° C. for 16 h. The reaction mixture was then cooled to room temperature, diluted with EtOAc (200 mL), filtered and the filtrate was concentrated under reduced pressure. Purification by silica gel chromatography (0→100% EtOAc/petroleum ether) afforded the desired product (46.5 g, 94% yield) as a white solid.

Step 2: Synthesis of tert-butyl N-[(tert-butoxy)carbonyl]-N-({2-[(3R)-3-(hydroxymethyl)piperazin-1-yl]pyrimidin-5-yl}methyl)carbamate To a solution of (R)-tert-butyl-N-tert-butoxycarbonyl-((2-(3-(((tert-butyldiphenylsilyl)oxy)methyl)piperazin-1-yl)pyrimidin-5-yl)methyl)carbamate (12 g, 18.13 mmol, 1.0 equiv) in THF (120 mL) was added TBAF (1 M, 23.93 mL, 1.3 equiv). The mixture was stirred at room temperature for 2 h. The reaction mixture was then poured into $H_2O$ (300 mL) and the aqueous phase was extracted with EtOAc (3×80 mL). The combined organic phases were combined, washed with brine (80 mL), dried, filtered and the filtrate was concentrated under reduced pressure. Purification by silica gel chromatography (0→20% MeOH/DCM) afforded the desired product (5 g, 64% yield) as a yellow solid.

Building Block J. 2-{4-[5-{[(tert-butoxy)carbonyl] amino}methyl)pyrimidin-2-yl]piperazin-1-yl}pyrimidine-5-carboxylic acid

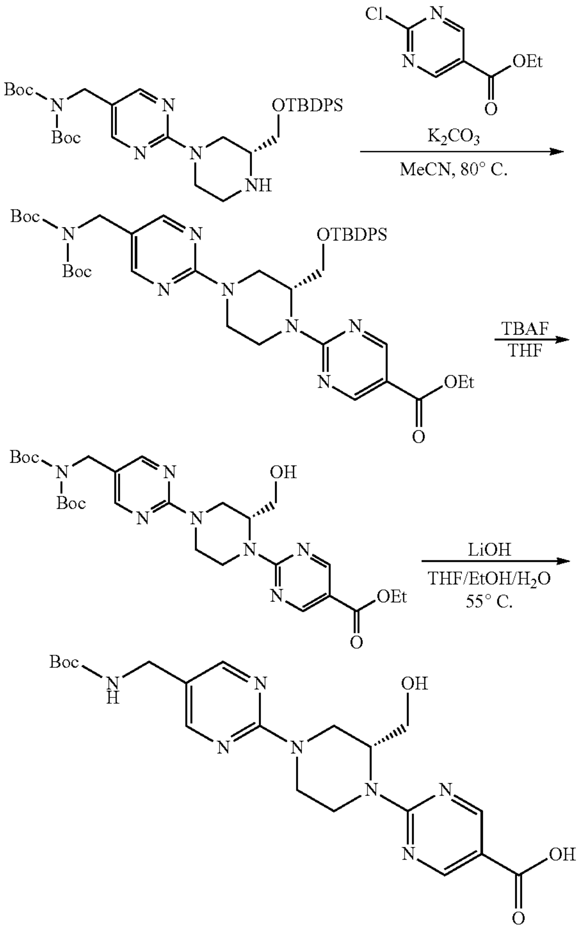

Step 1: Synthesis of (R)-ethyl 2-(4-(5-(((di-tert-butoxycarbonyl)amino)methyl)pyrimidin-2-yl)-2-(((tert-butyldiphenylsilyl)oxy)methyl)piperazin-1-yl) pyrimidine-5-carboxylate To a solution of (R)-tert-butyl-N-tert-butoxycarbonyl-N-((2-(3-(((tert-butyldiphenylsilyl)oxy)methyl)piperazin-1-yl) pyrimidin-5-yl)methyl)carbamate (31.5 g, 45.21 mmol, 1.0 equiv) in MeCN (350 mL) was added ethyl 2-chloropyrimidine-5-carboxylate (8.44 g, 45.21 mmol, 1.0 equiv) and $K_2CO_3$ (18.75 g, 135.63 mmol, 3.0 equiv). The mixture was stirred at 80° C. for 16 h. The reaction mixture was then cooled to room temperature, diluted with EtOAc (150 mL), and filtered to remove inorganic salts. The filtrate was then concentrated under reduced pressure. Purification by silica gel chromatography (0→100% EtOAc/petroleum ether) afforded the desired product (33.5 g, 89% yield).

Step 2: Synthesis of (R)-ethyl 2-(4-(5-(((di-tert-butoxycarbonyl)amino)methyl)pyrimidin-2-yl)-2-(hydroxymethyl)piperazin-1-yl)pyrimidine-5-carboxylate To a solution of (R)-ethyl 2-(4-(5-(((di-tert-butoxycarbonyl)amino)methyl)pyrimidin-2-yl)-2-(((tert-butyldiphenylsilyl)oxy)methyl)piperazin-1-yl)pyrimidine-5-carboxylate (36.5 g, 44.95 mmol, 1.0 equiv) in THF (300 mL) was added TBAF (1 M, 59.33 mL, 1.32 equiv). The mixture was stirred at room temperature for 6 h, at which point the reaction mixture was poured into $H_2O$ (500 mL). The aqueous phase was separated and extracted with EtOAc (3×150 mL) and the combined organic layers were washed with brine (150 mL), dried, filtered, and the filtrate was concentrated under reduced pressure. Purification by silica gel chromatography (0→100% EtOAc/petroleum ether) afforded the desired product (17 g, 64% yield) as a yellow oil.

Step 3: Synthesis of (R)-2-(4-(5-(((tert-butoxycarbonyl)amino)methyl)pyrimidin-2-yl)-2-(hydroxymethyl)piperazin-1-yl)pyrimidine-5-carboxylic acid To a solution of (R)-ethyl 2-(4-(5-(((di-tert-butoxycarbonyl)amino)methyl)pyrimidin-2-yl)-2-(hydroxymethyl)piperazin-1-yl)pyrimidine-5-carboxylate (17 g, 29.64 mmol, 1.0 equiv) in $H_2O$ (160 mL), EtOH (80 mL) and THF (160 mL) was added LiOH·$H_2O$ (4.97 g, 118.54 mmol, 4.0 equiv). The reaction mixture was stirred at 55° C. for 16 h. To the mixture was then added LiOH·$H_2O$ (1.01 g, 24.00 mmol, 0.81 equiv) and the reaction mixture was stirred at 55° C. for an additional 9 h. The mixture was cooled to room temperature, diluted with $H_2O$ (150 mL), and concentrated under reduced pressure to remove THF and EtOH. The mixture was acidified (pH=5) with 1 N HCl, filtered, and the filter cake washed with $H_2O$ (2×30 mL). The filter cake was dried under reduced pressure to afford the desired product (9.2 g, 67% yield) as a white solid. LCMS (ESI) m/z: [M+H] calcd for $C_{20}H_{27}N_7O_5$: 446.22; found 446.1.

Building Block K. tert-butyl N-[(tert-butoxy)carbonyl]-N-({2-[(3S)-3-(hydroxymethyl)piperazin-1-yl] pyrimidin-5-yl}methyl)carbamate

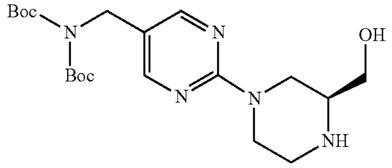 [SMILES: CC(C)(C)OC(=O)N(Cc1cnc(N2CCN[C@H](CO)C2)nc1)C(=O)OC(C)(C)C]

This building block is prepared by a process similar to that for Building Block I by utilizing [(2S)-piperazin-2-yl] methanol.

Building Block L. 2-[(2S)-4-[5-({[(tert-butoxy)carbonyl]amino}methyl)pyrimidin-2-yl]-2-(hydroxymethyl)piperazin-1-yl]pyrimidine-5-carboxylic acid

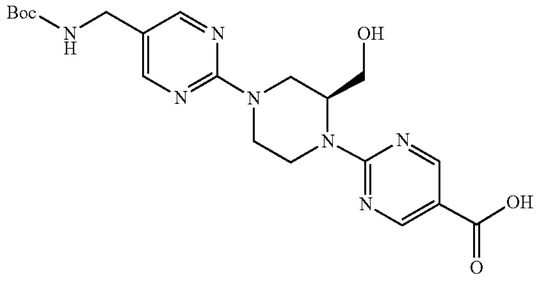 [SMILES: CC(C)(C)OC(=O)NCc1cnc(N2CCN(c3ncc(C(=O)O)cn3)[C@H](CO)C2)nc1]

This building block is prepared from Building Block K by a process similar to that for Building Block J.

Building Block M. tert-butyl 2-[(3R)-3-(hydroxymethyl)piperazin-1-yl]-5H,6H,7H,8H-pyrido[4,3-d]pyrimidine-6-carboxylate

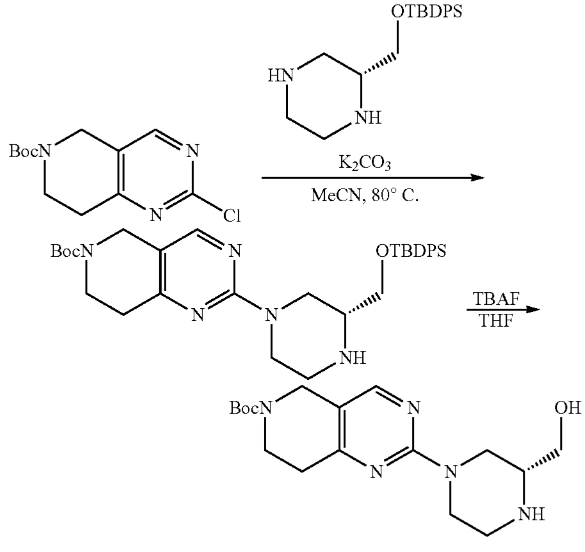

Step 1: Synthesis of (R)-tert-butyl 2-(3-(((tert-butyldiphenylsilyl)oxy)-methyl)piperazin-1-yl)-7,8-dihydropyrido[4,3-d]pyrimidine-6(5H)-carboxylate To a solution of (R)-2-(((tert-butyldiphenylsilyl)oxy)methyl)piperazine (25 g, 70.51 mmol, 1.0 equiv) in MeCN (250 mL) was added $K_2CO_3$ (29.24 g, 211.53 mmol, 3.0 equiv) and tert-butyl 2-chloro-7,8-dihydropyrido[4,3-d]pyrimidine-6(5H)-carboxylate (17.12 g, 63.46 mmol, 0.9 equiv). The mixture was stirred at 80° C. for 17 h. The reaction mixture was then cooled to room temperature, filtered, and the filtrated was concentrated under reduced pressure. Purification by silica gel chromatography (0→100% EtOAc/petroleum ether) afforded the desired product (31 g, 73.5% yield) as a white solid. LCMS (ESI) m/z: [M+H] calcd for $C_{33}H_{45}N_5O_3Si$: 588.34; found 588.2.

Step 2: Synthesis of (R)-tert-butyl 2-(3-(hydroxymethyl)piperazin-1-yl)-7,8-dihydropyrido[4,3-d]pyrimidine-6(5H)-carboxylate To a mixture of (R)-tert-butyl 2-(3-(((tert-butyldiphenylsilyl)oxy)methyl)piperazin-1-yl)-7,8-dihydropyrido[4,3-d]pyrimidine-6(5H)-carboxylate (12 g, 20.41 mmol, 1.0 equiv) in THF (120 mL) was added TBAF (1.0 M, 24.50 mL, 1.2 equiv). The mixture was stirred at room temperature for 5 h. The mixture was poured into $H_2O$ (100 mL), and the aqueous phase was extracted with EtOAc (2×100 mL). The combined organic phases were washed with brine (100 mL), dried, filtered, and the filtrate was concentrated under reduced pressure. Purification by silica gel chromatography (0→10% MeOH/DCM) afforded the desired product (6 g, 84.10% yield) as a white solid. LCMS (ESI) m/z: [M+H] calcd for $C_{17}H_{27}N_5O_3$: 350.22; found 350.2.

Building Block N. 2-[(2R)-4-{6-[(tert-butoxy)carbonyl]-5H,6H,7H,8H-pyrido[4,3-d]pyrimidin-2-yl}-2-(hydroxymethyl)piperazin-1-yl]pyrimidine-5-carboxylic acid

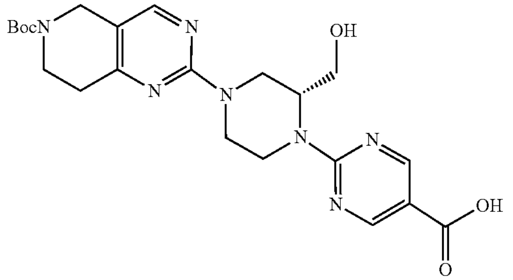 [SMILES: CC(C)(C)OC(=O)N1CCc2nc(N3CCN(c4ncc(C(=O)O)cn4)[C@@H](CO)C3)ncc2C1]

This building block is prepared from Building Block M by a process similar to that for Building Block J.

Building Block O. tert-butyl 2-[(3S)-3-(hydroxymethyl)piperazin-1-yl]-5H,6H,7H,8H-pyrido[4,3-d]pyrimidine-6-carboxylate

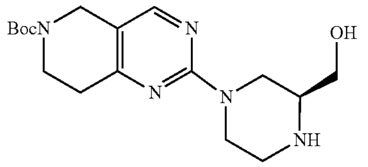 [SMILES: CC(C)(C)OC(=O)N1CCc2nc(N3CCN[C@H](CO)C3)ncc2C1]

This building block is prepared by a process similar to that for Building Block I by utilizing tert-butyl 2-chloro-7,8-dihydropyrido[4,3-d]pyrimidine-6(5H)-carboxylate and [(2S)-piperazin-2-yl]methanol.

Building Block P. 2-[(2S)-4-{6-[(tert-butoxy)carbonyl]-5H,6H,7H,8H-pyrido[4,3-d]pyrimidin-2-yl}-2-(hydroxymethyl)piperazin-1-yl]pyrimidine-5-carboxylic acid

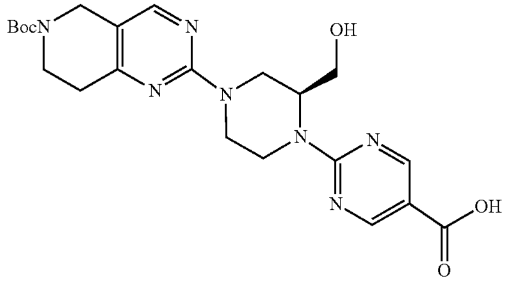 [SMILES: CC(C)(C)OC(=O)N1CCc2nc(N3CCN(c4ncc(C(=O)O)cn4)[C@H](CO)C3)ncc2C1]

This building block is prepared from Building Block O by a process similar to that for Building Block J.

Building Block Q. tert-butyl N-[(tert-butoxy)carbonyl]-N-({2-[(3S)-3-[(dimethylamino)methyl]piperazin-1-yl]pyrimidin-5-yl}methyl)carbamate

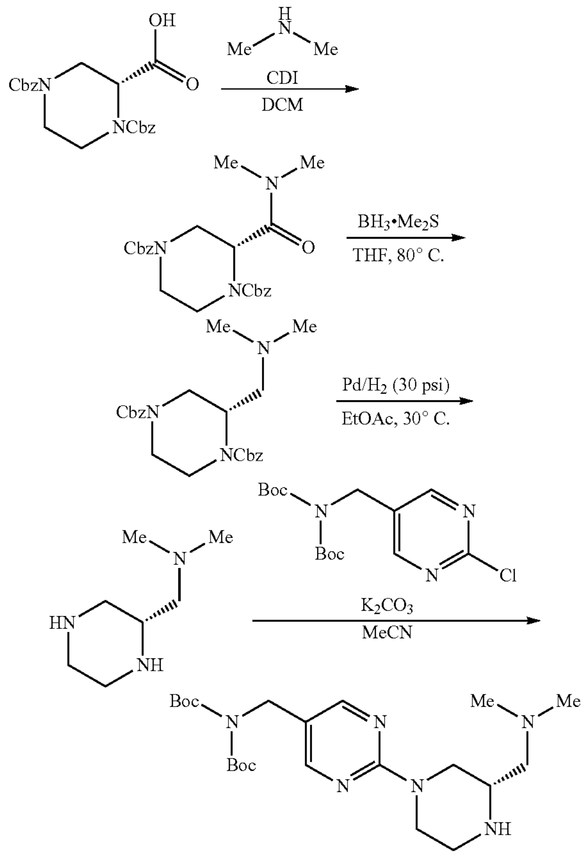

Step 1: Synthesis of (R)-dibenzyl 2-(dimethylcarbamoyl)piperazine-1,4-dicarboxylate To a solution of CDI (12.21 g, 75.30 mmol, 1.2 equiv) in DCM (300 mL) at 0° C. was added (R)-1,4-bis((benzyloxy)carbonyl)piperazine-2-carboxylic acid (25 g, 62.75 mmol, 1.0 equiv). The mixture was stirred at 0° C. for 0.5 h, at which time dimethylamine (8.51 mL, 92.87 mmol, 1.5 equiv, HCl) was added. The reaction mixture was warmed to room temperature and stirred for 12 h. The reaction mixture was then added to $H_2O$ (200 mL), and the aqueous layer was separated and extracted with DCM (2×200 mL). The combined organic phases were washed with brine (2×50 mL), dried, filtered, and the filtrate was concentrated under reduced pressure. Purification by silica gel chromatography (50→100% EtOAc/petroleum ether) afforded the desired product (23.5 g, 88.0% yield) as a yellow oil.

Step 2: Synthesis of (S)-dibenzyl 2-((dimethylamino)methyl)piperazine-1,4-dicarboxylate To a solution of (R)-dibenzyl 2-(dimethylcarbamoyl)piperazine-1,4-dicarboxylate (28 g, 65.81 mmol, 1.0 equiv) in THF (300 mL) at 0° C. was added $BH_3.Me_2S$ (10 M, 13.16 mL, 2.0 equiv). The reaction mixture was then stirred at 80° C. for 3 h. The reaction mixture was cooled to room temperature and then MeOH (50 mL) was added. After stirring for an additional 1 h the mixture was concentrated under reduced pressure. Purification by silica gel chromatography (50→100% EtOAc/petroleum ether) afforded the desired product (18 g, 66.5% yield) as a yellow oil.

Step 3: Synthesis of (R)—N,N-dimethyl-1-(piperazin-2-yl)methanamine

To a solution of (S)-dibenzyl 2-((dimethylamino)methyl) piperazine-1,4-dicarboxylate (18 g, 43.74 mmol, 1.0 equiv) in EtOAc (200 mL) was added Pd/C (1.5 g, 10 wt. %). The suspension was degassed under reduced pressure and purged with $H_2$ three times. The suspension was stirred under $H_2$ (30 psi) at 30° C. for 5 h. The reaction mixture was then filtered through celite and the filtrate was concentrated under reduced pressure to afford the desired product (6 g, 95.8% yield) as a yellow solid.

Step 4: Synthesis of tert-butyl N-tert-butoxycarbonyl-N-((2-((3S)-3-((dimethylamino)methyl)piperazin-1-yl)pyrimidin-5-yl)methyl)carbamate To a solution of (R)—N,N-dimethyl-1-(piperazin-2-yl) methanamine (2.8 g, 19.55 mmol, 1.0 equiv) in MeCN (40 mL) was added tert-butyl N-tert-butoxycarbonyl-N-((2-chloropyrimidin-5-yl)methyl)carbamate (6.72 g, 19.55 mmol, 1.0 equiv) and $K_2CO_3$ (5.40 g, 39.10 mmol, 2.0 equiv). The mixture was stirred at 80° C. for 24 h. The mixture was then cooled to room temperature, filtered, and the filter cake washed with EtOAc (3×10 mL). The filtrate was then concentrated under reduced pressure. Purification by silica gel chromatography (0→100% MeOH/EtOAc) afforded the desired product (5.3 g, 57.8% yield) as a yellow oil. LCMS (ESI) m/z: [M+H] calcd for $C_{22}H_{38}N_6O_4$: 451.31; found 451.2.

Building Block R. 2-[(2S)-4-[5-({[(tert-butoxy)carbonyl]amino}methyl)pyrimidin-2-yl]-2-[(dimethylamino)methyl]piperazin-1-yl]pyrimidine-5-carboxylic acid

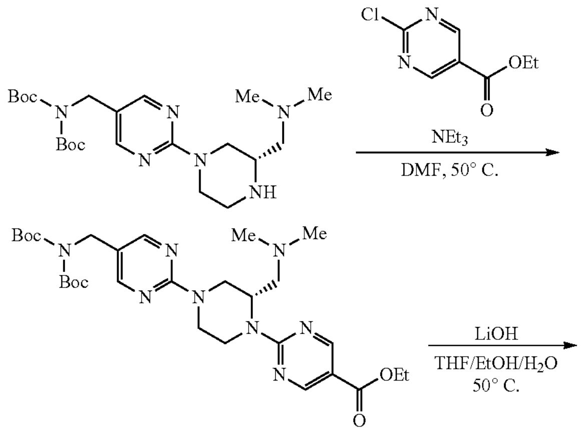

-continued

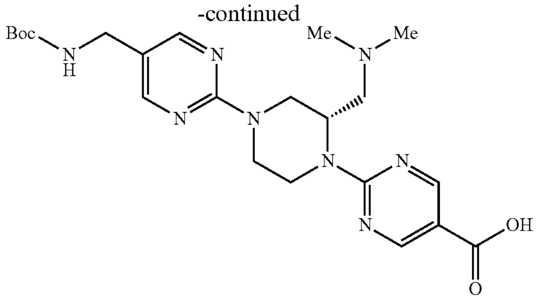

Step 1: Synthesis of (S)-ethyl 2-(4-(5-(((bi-tert-butoxycarbonyl)amino)methyl) pyrimidin-2-yl)-2-((dimethylamino)methyl)piperazin-1-yl)pyrimidine-5-carboxylate To a solution of (S)-tert-butyl-N-tert-butoxycarbonyl ((2-(3-((dimethylamino)methyl) piperazin-1-yl)pyrimidin-5-yl) methyl)carbamate (3.26 g, 7.24 mmol, 1.0 equiv) in DMF (30 mL) was added $Et_3N$ (3.02 mL, 21.71 mmol, 3.0 equiv) and ethyl 2-chloropyrimidine-5-carboxylate (1.47 g, 7.86 mmol, 1.1 equiv). The mixture was stirred at 50° C. for 3 h and then concentrated under reduced pressure to afford the desired product (4.35 g, crude) as a solution in DMF (30 mL), which was used directly in the next step. LCMS (ESI) m/z: [M+H] calcd for $C_{29}H_{44}N_8O_6$: 601.35; found 601.5.

Step 2: Synthesis of (S)-2-(4-(5-(((tert-butoxycarbonyl)amino)methyl)-pyrimidin-2-yl)-2-((dimethylamino)methyl)piperazin-1-yl)pyrimidine-5-carboxylic acid To a solution of (S)-ethyl 2-(4-(5-(((bi-tert-butoxycarbonyl)amino)methyl)-pyrimidin-2-yl)-2-((dimethylamino) methyl)piperazin-1-yl)pyrimidine-5-carboxylate (4.35 g, 7.24 mmol, 1.0 equiv) in DMF (30 mL) was added DMF (50 mL), EtOH (30 mL), and $H_2O$ (30 mL). To the solution was then added $LiOH \cdot H_2O$ (3 g, 71.50 mmol, 9.9 equiv) at 50° C. The reaction was stirred at 50° C. for 36 h. The mixture was then cooled to room temperature, neutralized with 0.5 N HCl, and concentrated under reduced pressure. Purification by reverse phase chromatography (2→30% $MeCN/H_2O$) afforded the desired product (1.15 g, 34% yield) as a white solid. LCMS (ESI) m/z: [M+H] calcd for $C_{22}H_{32}N_8O_4$: 473.26; found 473.3.

Building Block S. tert-butyl N-[(tert-butoxy)carbonyl]-N-({2-[(3R)-3-[(dimethylamino)methyl]piperazin-1-yl]pyrimidin-5-yl}methyl)carbamate

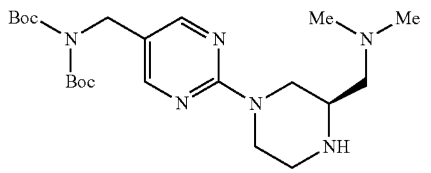 [SMILES: CN(C)C[C@@H]1CN(c2ncc(CN(C(=O)OC(C)(C)C)C(=O)OC(C)(C)C)cn2)CCN1]

This building block is prepared by a process similar to that for Building Block I by utilizing dimethyl({[(2S)-piperazin-2-yl]methyl})amine.

Building Block T. 2-[(2R)-4-[5-({[(tert-butoxy)carbonyl]amino}methyl)pyrimidin-2-yl]-2-[(dimethylamino)methyl]piperazin-1-yl]pyrimidine-5-carboxylic acid

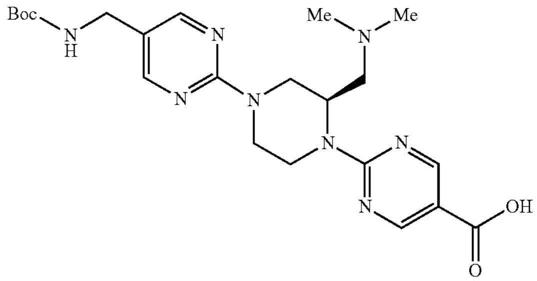 [SMILES: CN(C)C[C@@H]1CN(c2ncc(CNC(=O)OC(C)(C)C)cn2)CCN1c1ncc(C(=O)O)cn1]

This building block is prepared from Building Block S by a process similar to that for Building Block J.

Building Block U. tert-butyl 2-[(3S)-3-[(dimethylamino)methyl]piperazin-1-yl]-5H,6H,7H,8H-pyrido[4,3-d]pyrimidine-6-carboxylate

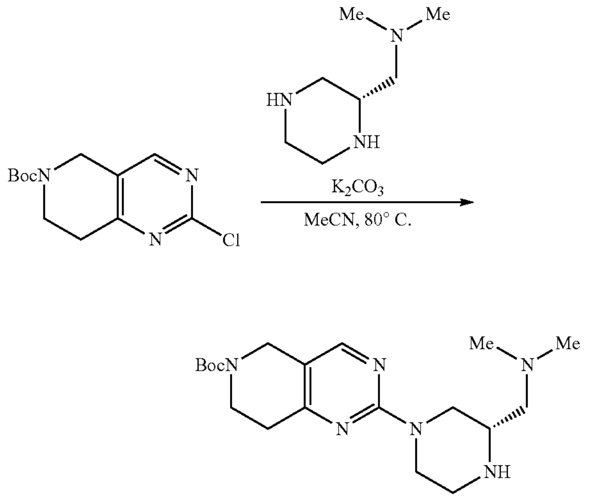

To a solution of tert-butyl 2-chloro-7,8-dihydropyrido[4,3-d]pyrimidine-6(5H)-carboxylate (4.80 g, 17.80 mmol, 1.4 equiv) in MeCN (45 mL) was added $K_2CO_3$ (10.42 g, 75.40 mmol, 3.0 equiv) and (R)—N,N-dimethyl-1-(piperazin-2-yl)methanamine (3.6 g, 25.13 mmol, 1.0 equiv). The mixture was stirred at 80° C. for 8 h. The mixture was then cooled to room temperature, filtered, and the filter cake was washed with EtOAc (50 mL). To the organic phase was added $H_2O$ (50 mL) and the aqueous phase was extracted with EtOAc (3×50 mL). The combined organic phases were washed with brine (5 mL), dried, filtered and concentrated under reduced pressure. Purification by silica gel chromatography (8→67% EtOAc/petroleum ether) afforded the desired product (6.5 g, 63.5% yield) as a yellow oil.

Building Block V. 2-[(2S)-4-{6-[(tert-butoxy)carbonyl]-5H,6H,7H,8H-pyrido[4,3-d]pyrimidin-2-yl}-2-[(dimethylamino)methyl]piperazin-1-yl]pyrimidine-5-carboxylic acid

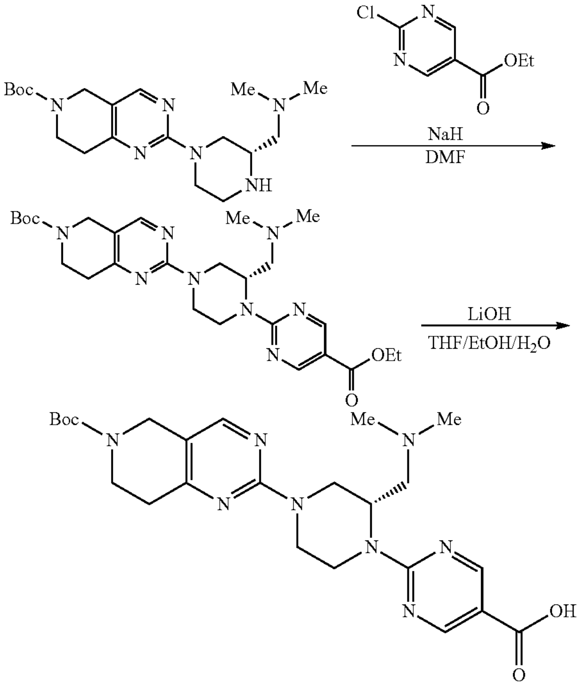

Step 1: Synthesis of (S)-tert-butyl 2-(3-((dimethylamino)methyl)-4-(5-(ethoxycarbonyl)pyrimidin-2-yl)piperazin-1-yl)-7,8-dihydropyrido[4,3-d]pyrimidine-6(5H)-carboxylate To a solution of (S)-tert-butyl 2-(3-((dimethylamino)methyl)piperazin-1-yl)-7,8-dihydropyrido[4,3-d]pyrimidine-6(5H)-carboxylate (3 g, 7.97 mmol, 1.0 equiv) in DMF (70 mL) at 0° C. was added NaH (382.44 mg, 9.56 mmol, 60 wt. %, 1.2 equiv). The suspension was stirred at 0° C. for 0.5 h, then ethyl 2-chloropyrimidine-5-carboxylate (1.49 g, 7.97 mmol, 1 equiv) in DMF (50 mL) was added, dropwise. The mixture was warmed to room temperature and stirred for 5 h. The mixture was then cooled to 0° C. and poured into $H_2O$ (360 mL). The suspension was filtered, and the filter cake washed with $H_2O$ (30 mL) and dried under reduced pressure. Purification by silica gel chromatography (6%→33% EtOAc/petroleum ether) afforded the desired product (1.8 g, 39.6% yield) as a brown oil.

Step 2: Synthesis of (S)-2-(4-(6-(tert-butoxycarbonyl)-5,6,7,8-tetrahydropyrido[4,3-d]pyrimidin-2-yl)-2-((dimethylamino)methyl)piperazin-1-yl)pyrimidine-5-carboxylic acid To a solution of (S)-tert-butyl 2-(3-((dimethylamino)methyl)-4-(5-(ethoxycarbonyl)pyrimidin-2-yl)piperazin-1-yl)-7,8-dihydropyrido[4,3-d]pyrimidine-6(5H)-carboxylate (1.1 g, 2.09 mmol, 1.0 equiv) in THF (5 mL), EtOH (2.5 mL), and $H_2O$ (2.5 mL) was added LiOH·$H_2O$ (175.30 mg, 4.18 mmol, 2.0 equiv). The mixture was stirred at room temperature for 2 h, at which point the pH was adjusted to 7 by the addition of 1 N HCl at 0° C. The mixture was concentrated under reduced pressure to remove THF and MeOH. The resulting suspension was filtered, and the filter cake was washed with $H_2O$ (5 mL) and dried under reduced pressure to afford the desired product (680 mg, 65.3% yield) as a white solid. LCMS (ESI) m/z: [M+H] calcd for $C_{24}H_{34}N_8O_4$: 499.28; found 499.2.

Building Block W. tert-butyl 2-[(3R)-3-[(dimethylamino)methyl]piperazin-1-yl]-5H,6H,7H,8H-pyrido[4,3-d] pyrimidine-6-carboxylate

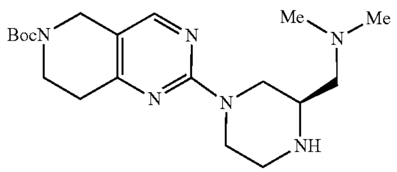 [SMILES: CN(C)C[C@@H]1CN(c2ncc3c(n2)CCN(C(=O)OC(C)(C)C)C3)CCN1]

This building block is prepared by a process similar to that for Building Block I by utilizing tert-butyl 2-chloro-7,8-dihydropyrido[4,3-d]pyrimidine-6(5H)-carboxylate and dimethyl({[(2S)-piperazin-2-yl]methyl})amine.

Building Block X. 2-[(2R)-4-{6-[(tert-butoxy)carbonyl]-5H,6H,7H,8H-pyrido[4,3-d]pyrimidin-2-yl}-2-[(dimethylamino)methyl]piperazin-1-yl]pyrimidine-5-carboxylic acid

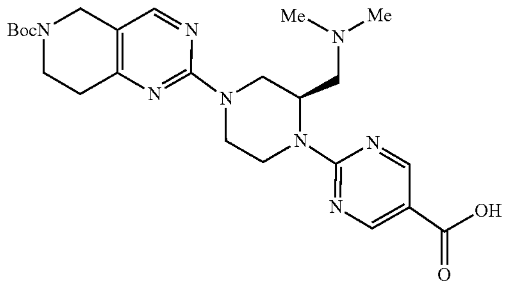 [SMILES: CN(C)C[C@@H]1CN(c2ncc3c(n2)CCN(C(=O)OC(C)(C)C)C3)CCN1c1ncc(C(=O)O)cn1]

This building block is prepared from Building Block W by a process similar to that for Building Block J.

Building Block Y. tert-butyl (2R)-4-{6-[(tert-butoxy)carbonyl]-5H,6H,7H,8H-pyrido[4,3-d]pyrimidin-2-yl}piperazine-2-carboxylate

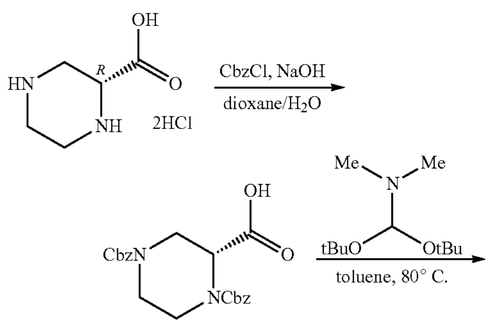

-continued

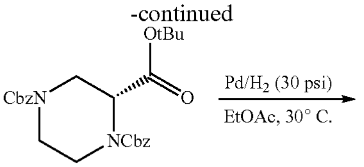

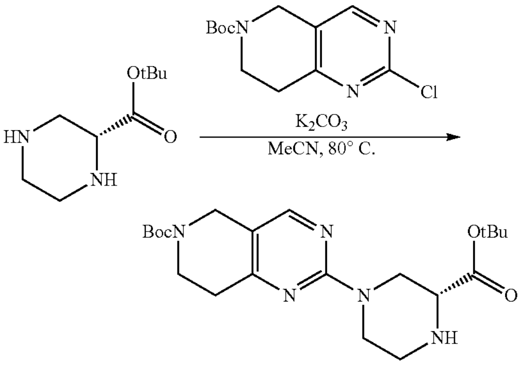

Step 1: Synthesis of (R)-1,4-bis((benzyloxy)carbonyl)piperazine-2-carboxylic acid To a solution of (R)-piperazine-2-carboxylic acid (70 g, 344.71 mmol, 1.0 equiv, 2HCl) in dioxane (1120 mL) and $H_2O$ (700 mL) was added 50% aq. NaOH until the solution was pH=11. Benzyl chloroformate (156.82 mL, 1.10 mol, 3.2 equiv) was added and the reaction mixture was stirred at room temperature for 12 h. To the solution was then added $H_2O$ (1200 mL) and the aqueous layer was washed with MTBE (3x800 mL). The aqueous layer was adjusted to pH=2 with concentrated HCl (12N) and extracted with EtOAc (2x1000 mL). The combined organic extracts were dried, filtered and the filtrate was concentrated under reduced pressure to afford the desired product (137 g, 99.8% yield) as a yellow solid. LCMS (ESI) m/z: [M+H] calcd for $C_{21}H_{22}N_2O_6$: 399.16; found 399.2.

Step 2: Synthesis of (R)-1,4-dibenzyl 2-tert-butyl piperazine-1,2,4-tricarboxylate To a solution of (R)-1,4-bis((benzyloxy)carbonyl)piperazine-2-carboxylic acid (50 g, 125.50 mmol, 1.0 equiv) in toluene (500 mL) at 80° C. was added 1,1-di-tert-butoxy-N,N-dimethylmethanamine (57.17 mL, 238.45 mmol, 1.9 equiv). The solution was stirred at 80° C. for 2 h, at which point the reaction mixture was cooled to room temperature and partitioned between EtOAc (300 mL) and $H_2O$ (500 mL). The aqueous layer was extracted with EtOAc (2x500 mL) and the combined organic layers were dried, filtered and the filtrate was concentrated under reduced pressure. Purification by silica gel chromatography (0%→25% EtOAc/petroleum ether) afforded the desired product (35 g, 61.2% yield) as a white solid. LCMS (ESI) m/z: [M+Na] calcd for $C_{25}H_{30}N_2O_6$: 477.20; found 477.1.

Step 3: Synthesis of (R)-tert-butyl piperazine-2-carboxylate

To a solution of (R)-1,4-dibenzyl 2-tert-butyl piperazine-1,2,4-tricarboxylate (35 g, 77.01 mmol, 1.0 equiv) in EtOAc (350 mL) was added Pd/C (10 g, 10 wt. %). The suspension was degassed under reduced pressure and purged with $H_2$ three times. The mixture was stirred under $H_2$ (30 psi) at 30° C. for 4 h. The reaction mixture was then filtered through celite, the residue was washed with MeOH (5x200 mL), and the filtrate was concentrated under reduced pressure to afford the desired product (14 g, 79.6% yield) as yellow oil. LCMS (ESI) m/z: [M+H] calcd for $C_9H_{18}N_2O_2$: 187.15; found 187.1.

Step 4: Synthesis of (R)-tert-butyl 2-(3-(tert-butoxycarbonyl)piperazin-1-yl)-7,8-dihydropyrido[4,3-d]pyrimidine-6(5H)-carboxylate To a solution of tert-butyl (2R)-piperazine-2-carboxylate (12 g, 64.43 mmol, 1.0 equiv) in MeCN (200 mL) was added $K_2CO_3$ (17.81 g, 128.86 mmol, 2.0 equiv) and tert-butyl 2-chloro-7,8-dihydropyrido[4,3-d]pyrimidine-6(5H)-carboxylate (17.38 g, 64.43 mmol, 1.0 equiv). The reaction mixture was heated to 80° C. and stirred for 12 h. The reaction mixture was then cooled to room temperature and filtered, the residue was washed with EtOAc (3x150 mL), and the filtrate was concentrated under reduced pressure. Purification by silica gel chromatography (0%→100% EtOAc/petroleum ether) afforded the desired product (19 g, 69.2% yield) as a yellow solid. LCMS (ESI) m/z: [M+H] calcd for $C_{21}H_{33}N_5O_4$: 420.26; found 420.2.

Building Block Z. 4-amino-2-[(2R)-2-[(tert-butoxy)carbonyl]-4-{6-[(tert-butoxy)carbonyl]-5H,6H,7H,8H-pyrido[4,3-d]pyrimidin-2-yl}piperazin-1-yl]pyrimidine-5-carboxylic acid

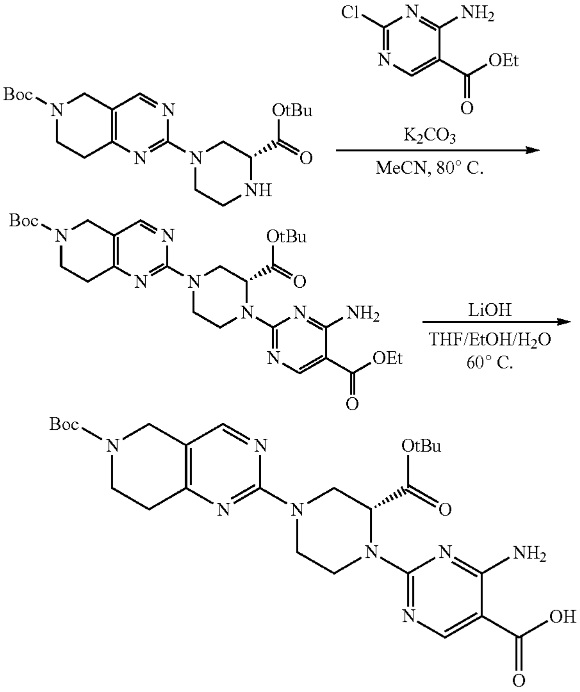

Step 1: Synthesis of (R)-tert-butyl 2-(4-(4-amino-5-(ethoxycarbonyl)pyrimidin-2-yl)-3-(tert-butoxycarbonyl)piperazin-1-yl)-7,8-dihydropyrido[4,3-d]pyrimidine-6(5H)-carboxylate To a stirred solution of (R)-tert-butyl 2-(3-(tert-butoxycarbonyl)piperazin-1-yl)-7,8-dihydropyrido[4,3-d]pyrimidine-6(5H)-carboxylate (12 g, 28.60 mmol, 1.0 equiv) in MeCN (150 mL) was added $K_2CO_3$ (7.91 g, 57.20 mmol, 2.0 equiv) and ethyl 4-amino-2-chloropyrimidine-5-carboxylate (6.92 g, 34.32 mmol, 1.2 equiv). The reaction mixture was stirred at 80° C. for 12 h, at which point the reaction mixture was filtered and the filtrate was concentrated under reduced pressure. Purification by silica gel chromatography (0%→17% EtOAc/petroleum ether) afforded the desired product (16 g, 91.6% yield) as a yellow solid. LCMS (ESI) m/z: [M+H] calcd for $C_{28}H_{40}N_8O_6$: 585.32; found 585.1.

Step 2: Synthesis of (R)-4-amino-2-(2-(tert-butoxycarbonyl)-4-(6-(tert-butoxycarbonyl)-5,6,7,8-tetrahydropyrido[4,3-d]pyrimidin-2-yl)piperazin-1-yl)pyrimidine-5-carboxylic acid To two separate batches run in parallel each containing a solution of (R)-tert-butyl 2-(4-(4-amino-5-(ethoxycarbonyl)pyrimidin-2-yl)-3-(tert-butoxycarbonyl)piperazin-1-yl)-7,8-dihydropyrido[4,3-d]pyrimidine-6(5H)-carboxylate (7 g, 11.97 mmol, 1.0 equiv) in THF (70 mL), EtOH (35 mL) and $H_2O$ (35 mL) was added $LiOH{\cdot}H_2O$ (2.01 g, 47.89 mmol, 4.0 equiv). The mixtures were stirred at 60° C. for 3 h, at which point the two reaction mixtures were combined, and were adjusted to pH=7 with 1 N HCl. The mixture was concentrated under reduced pressure to remove THF and EtOH, filtered, and the residue was dried under reduced pressure. The residue was stirred in MTBE (100 mL) for 10 min, filtered, and the residue was dried under reduced pressure to afford the desired product (8.02 g, 55.1% yield) as a white solid. LCMS (ESI) m/z: [M+H] calcd for $C_{26}H_{36}N_8O_6$:557.29; found 557.3.

Building Block AA. tert-butyl (2S)-4-{6-[(tert-butoxy)carbonyl]-5H,6H,7H,8H-pyrido[4,3-d]pyrimidin-2-yl}piperazine-2-carboxylate

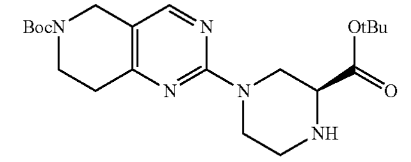 [SMILES: CC(C)(C)OC(=O)[C@@H]1CN(c2ncc3c(n2)CCN(C(=O)OC(C)(C)C)C3)CCN1]

This building block is prepared by a process similar to that for Building Block I by utilizing tert-butyl 2-chloro-7,8-dihydropyrido[4,3-d]pyrimidine-6(5H)-carboxylate and tert-butyl (2S)-piperazine-2-carboxylate.

Building Block AB. 4-amino-2-[(2S)-2-[(tert-butoxy)carbonyl]-4-{6-[(tert-butoxy)carbonyl]-5H,6H,7H,8H-pyrido[4,3-d]pyrimidin-2-yl}piperazin-1-yl]pyrimidine-5-carboxylic acid

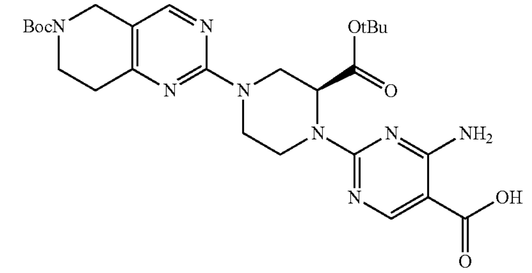 [SMILES: CC(C)(C)OC(=O)[C@@H]1CN(c2ncc3c(n2)CCN(C(=O)OC(C)(C)C)C3)CCN1c1ncc(C(=O)O)c(N)n1]

This building block is prepared from Building Block AA by a process similar to that for Building Block J by utilizing ethyl 4-amino-2-chloropyrimidine-5-carboxylate.

Building Block AC. 4-amino-2-(4-{6-[(tert-butoxy)carbonyl]-5H,6H,7H,8H-pyrido[4,3-d]pyrimidin-2-yl}piperazin-1-yl)pyrimidine-5-carboxylic acid

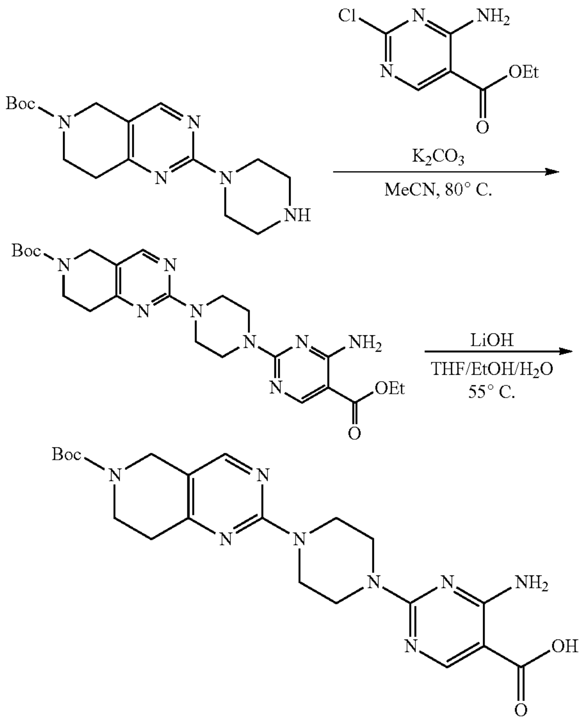

Step 1: Synthesis of tert-butyl 2-(4-(4-amino-5-(ethoxycarbonyl)pyrimidin-2-yl)piperazin-1-yl)-7,8-dihydropyrido[4,3-d]pyrimidine-6(5H)-carboxylate To a solution of tert-butyl 2-(piperazin-1-yl)-7,8-dihydropyrido[4,3-d]pyrimidine-6(5H)-carboxylate (8.3 g, 25.99 mmol, 1.0 equiv) and ethyl 4-amino-2-chloropyrimidine-5-carboxylate (5.24 g, 25.99 mmol, 1.0 equiv) in MeCN (100 mL) was added to $K_2CO_3$ (7.18 g, 51.97 mmol, 2.0 equiv). The reaction was stirred at 80° C. for 12 h. The reaction was then cooled to room temperature, DCM (100 mL) was added, and the reaction mixture was stirred for 30 min. The suspension was filtered, and the filter cake was washed with DCM (6×100 mL). The filtrate was concentrated under reduced pressure and the residue was triturated with EtOAc (30 mL), filtered and then the filter cake was dried under reduced pressure to afford the desired product (8.7 g, 65.9% yield) as light yellow solid.

Step 2: Synthesis of 4-amino-2-(4-(6-(tert-butoxycarbonyl)-5,6,7,8-tetrahydropyrido[4,3-d]pyrimidin-2-yl)piperazin-1-yl)pyrimidine-5-carboxylic acid To a solution of tert-butyl 2-(4-(4-amino-5-(ethoxycarbonyl)pyrimidin-2-yl)piperazin-1-yl)-7,8-dihydropyrido[4,3-d]pyrimidine-6(5H)-carboxylate (8.7 g, 17.95 mmol, 1.0 equiv) in THF (120 mL), EtOH (60 mL), and $H_2O$ (60 mL) was added $LiOH{\cdot}H_2O$ (1.51 g, 35.91 mmol, 2.0 equiv). The mixture was stirred at 55° C. for 12 h. The reaction mixture was then concentrated under reduced pressure to remove EtOH and THF, and the reaction mixture was adjusted to pH=6 by the addition of 1 N HCl. The precipitate was filtered, and the filter cake was washed with $H_2O$ (3×50 mL) and then dried under reduced pressure to afford the desired product (7.3 g, 89.1% yield) as light yellow solid. LCMS (ESI) m/z: [M+H] calcd for $C_{21}H_{28}N_8O_4$: 457.23; found 457.2.

Building Block AD. 4-amino-2-{4-[5-{[(tert-butoxy)carbonyl]amino}methyl)pyrimidin-2-yl]piperazin-1-yl}pyrimidine-5-carboxylic acid

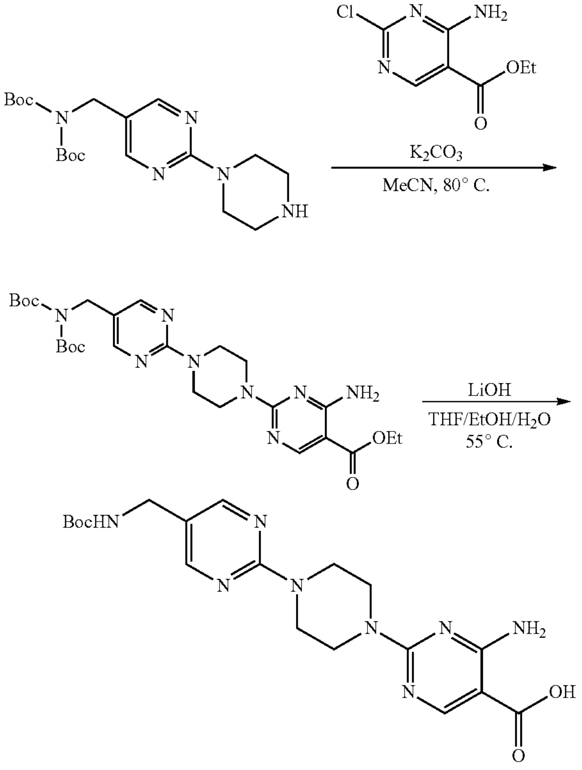

Step 1: Synthesis of ethyl 4-amino-2-(4-(5-(((di-tert-butoxycarbonyl)amino)methyl)pyrimidin-2-yl)piperazin-1-yl)pyrimidine-5-carboxylate To a solution of tert-butyl-N-tert-butoxycarbonyl-N-((2-(piperazin-1-yl)pyrimidin-5-yl)methyl)carbamate (8.3 g, 21.09 mmol, 1.0 equiv) in MeCN (100 mL) was added ethyl 4-amino-2-chloropyrimidine-5-carboxylate (4.04 g, 20.04 mmol, 0.95 equiv) and $K_2CO_3$ (8.75 g, 63.28 mmol, 3.0 equiv). The mixture was stirred at 80° C. for 3 h. The reaction was then cooled to room temperature, DCM (150 mL) was added, and the reaction mixture was stirred for 30 min. The suspension was filtered, the filter cake was washed with DCM (3×100 mL), and the filtrate was concentrated under reduced pressure. Purification by silica gel chromatography (0%→100% EtOAc/petroleum ether) afforded the desired product (8.35 g, 67% yield) as a white solid.

Step 2: Synthesis of 4-amino-2-(4-(5-(((tert-butoxycarbonyl)amino)methyl)pyrimidin-2-yl)piperazin-1-yl)pyrimidine-5-carboxylic acid To a solution of ethyl 4-amino-2-(4-(5-(((di-tert-butoxycarbonyl)amino)methyl)pyrimidin-2-yl)piperazin-1-yl)pyrimidine-5-carboxylate (8.3 g, 14.86 mmol, 1.0 equiv) in $H_2O$ (70 mL), EtOH (36 mL) and THF (80 mL) was added $LiOH{\cdot}H_2O$ (2.49 g, 59.43 mmol, 4.0 equiv). The reaction mixture was stirred at 55° C. for 16 h. The mixture was then concentrated under reduced pressure to remove THF and EtOH. The mixture was diluted with $H_2O$ (55 mL) and was adjusted to pH=6 by the addition of 1 N HCl. The mixture was filtered, and the filter cake was washed with $H_2O$ (2×20 mL). The solid cake was dried under reduced pressure to afford the desired product (5.5 g, 84% yield) as a white solid. LCMS (ESI) m/z: [M+H] calcd for $C_{19}H_{26}N_8O_4$: 431.22; found 431.4.

Building block AE. 4-amino-2-[(2R)-4-{6-[(tert-butoxy)carbonyl]-5H,6H,7H,8H-pyrido[4,3-d]pyrimidin-2-yl}-2-(hydroxymethyl)piperazin-1-yl]pyrimidine-5-carboxylic acid

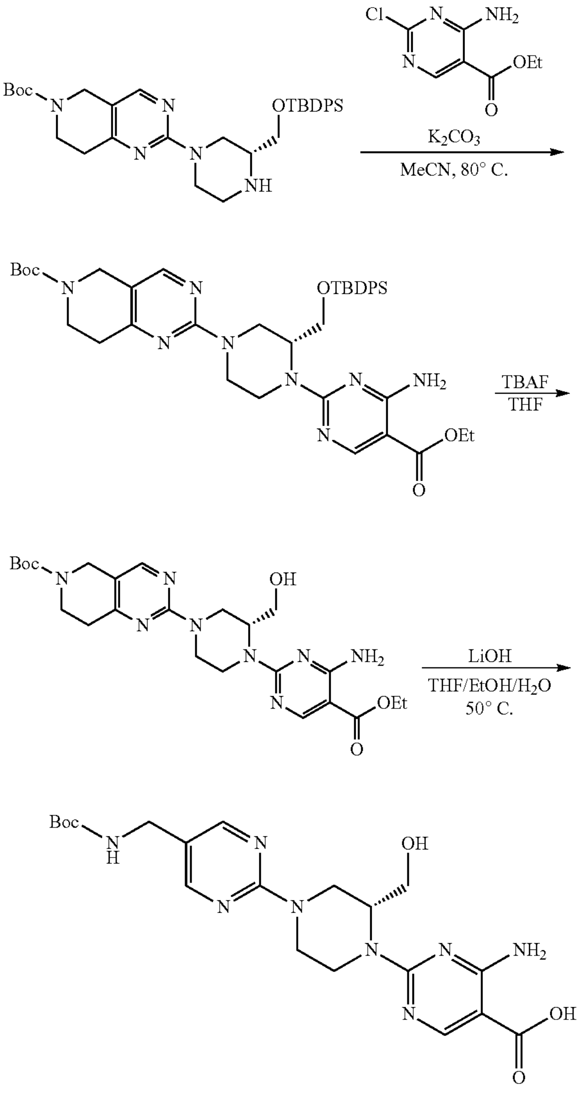

Step 1: Synthesis of (R)-tert-butyl 2-(4-(4-amino-5-(ethoxycarbonyl)pyrimidin-2-yl)-3-(((tert-butyldiphenylsilyl)oxy)methyl)piperazin-1-yl)-7,8-dihydropyrido[4,3-d]pyrimidine-6(5H)-carboxylate To a solution of (R)-tert-butyl 2-(3-(((tert-butyldiphenylsilyl)oxy)methyl) piperazin-1-yl)-7,8-dihydropyrido[4,3-d]pyrimidine-6(5H)-carboxylate (17.2 g, 29.26 mmol, 1.0 equiv) in MeCN (200 mL) was added $K_2CO_3$ (12.13 g, 87.78 mmol, 3.0 equiv) and ethyl 4-amino-2-chloropyrimidine-5-carboxylate (6.37 g, 31.60 mmol, 1.08 equiv). The mixture was stirred at 80° C. for 18 h. The reaction mixture was then cooled to room temperature, filtered and the filtrate was concentrated under reduced pressure. Purification by silica gel chromatography (0%→33% EtOAc/petroleum ether) afforded the desired product (20.3 g, 90.6% yield) as a white solid. LCMS (ESI) m/z: [M+H] calcd for $C_{40}H_{52}N_8O_5Si$: 753.39; found 753.4.

Step 2: Synthesis of (R)-4-amino-2-(4-(6-(tert-butoxycarbonyl)-5,6,7,8-tetrahydropyrido[4,3-d]pyrimidin-2-yl)-2-(hydroxymethyl)piperazin-1-yl)pyrimidine-5-carboxylic acid To a solution of (R)-tert-butyl 2-(4-(4-amino-5-(ethoxycarbonyl)pyrimidin-2-yl)-3-(((tert-butyldiphenylsilyl)oxy)methyl)piperazin-1-yl)-7,8-dihydropyrido[4,3-d]pyrimidine-6(5H)-carboxylate (20.3 g, 26.96 mmol, 1.0 equiv) in THF (200 mL) was added TBAF (1.0 M, 50.75 mL, 1.9 equiv). The reaction mixture was stirred at room temperature for 5 h. The mixture was then poured into $H_2O$ (200 mL) and the aqueous phase was extracted with EtOAc (2×150 mL). The combined organic phases were washed with brine (2×100 mL), dried, filtered and concentrated under reduced pressure. Purification by silica gel chromatography (0%→20% EtOAc/petroleum ether) afforded the desired product (12 g, 85.7% yield) as a white solid. LCMS (ESI) m/z: [M+H] calcd for $C_{24}H_{34}N_8O_5$: 515.28; found 515.4.

Step 3: Synthesis of (R)-4-amino-2-(4-(6-(tert-butoxycarbonyl)-5,6,7,8-tetrahydropyrido[4,3-d]pyrimidin-2-yl)-2-(hydroxymethyl)piperazin-1-yl)pyrimidine-5-carboxylic acid To a solution of (R)-4-amino-2-(4-(6-(tert-butoxycarbonyl)-5,6,7,8-tetrahydropyrido[4,3-d]pyrimidin-2-yl)-2-(hydroxymethyl)piperazin-1-yl)pyrimidine-5-carboxylic acid (12 g, 23.32 mmol, 1.0 equiv) in THF (100 mL), EtOH (30 mL), and $H_2O$ (30 mL) was added $LiOH{\cdot}H_2O$ (5.87 g, 139.92 mmol, 6.0 equiv). The mixture was stirred at 50° C. for 22 h. The mixture was then concentrated under reduced pressure to remove THF and EtOH. The aqueous phase was neutralized with 1 N HCl and the resulting precipitate was filtered. The filter cake was washed with $H_2O$ (50 mL) and dried under reduced pressure. The filtrate was extracted with DCM (8×60 mL) and the combined organic phases were washed with brine (2×50 mL), dried, filtered, and concentrated under reduced pressure. The resulting residue was combined with the initial filter cake and the solid was dissolved in DCM (150 mL) and concentrated under reduced pressure to afford the desired product (9.76 g, 85.2% yield) as a white solid. LCMS (ESI) m/z: [M+H] calcd for $C_{22}H_{30}N_8O_5$: 487.24; found 487.2.

Building block AF. 4-amino-2-[(2S)-4-{6-[(tert-butoxy)carbonyl]-5H,6H,7H,8H-pyrido[4,3-d]pyrimidin-2-yl}-2-(hydroxymethyl)piperazin-1-yl]pyrimidine-5-carboxylic acid

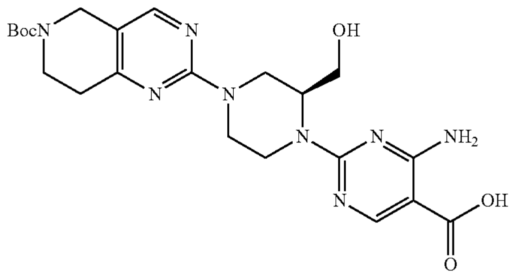 [SMILES: CC(C)(C)OC(=O)N1CCc2nc(N3CCN(c4ncc(C(=O)O)c(N)n4)[C@H](CO)C3)ncc2C1]

This building block is prepared from Building Block O by a process similar to that for Building Block J by utilizing ethyl 4-amino-2-chloropyrimidine-5-carboxylate.

Building Block AG. 2-((2-(4-(5-((di-(tert-butoxycarbonyl)amino)methyl)pyrimidin-2-yl)piperazin-1-yl)-2-oxoethyl)(methyl)amino)acetic acid

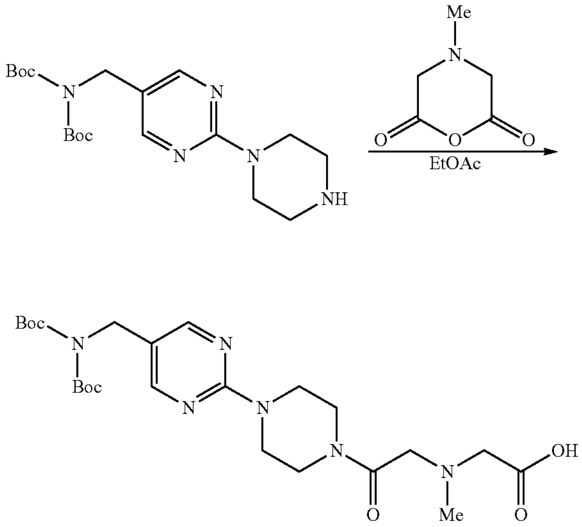

To a solution of tert-butyl N-tert-butoxycarbonyl-N-((2-piperazin-1-ylpyrimidin-5-yl)methyl)carbamate (4.88 g, 12.39 mmol, 1.0 equiv) in EtOAc (40 mL) was added 4-methylmorpholine-2,6-dione (1.6 g, 12.39 mmol, 1.0 equiv). The reaction was stirred at room temperature for 2 h then reaction mixture was concentrated under reduced pressure to give the crude product. The residue was triturated with EtOAc (15 mL) and filtered to give the product (5.65 g, 87.2% yield) as a white solid. LCMS (ESI) m/z: [M+H] calcd for $C_{24}H_{39}N_6O_7$: 523.28; found 523.3.

Building Block AH. tert-butyl N-tert-butoxycarbonyl-N-((2-(4-(3-(2-piperazin-1-ylethoxy)propanoyl)piperazin-1-yl)pyrimidin-5-yl)methyl)carbamate

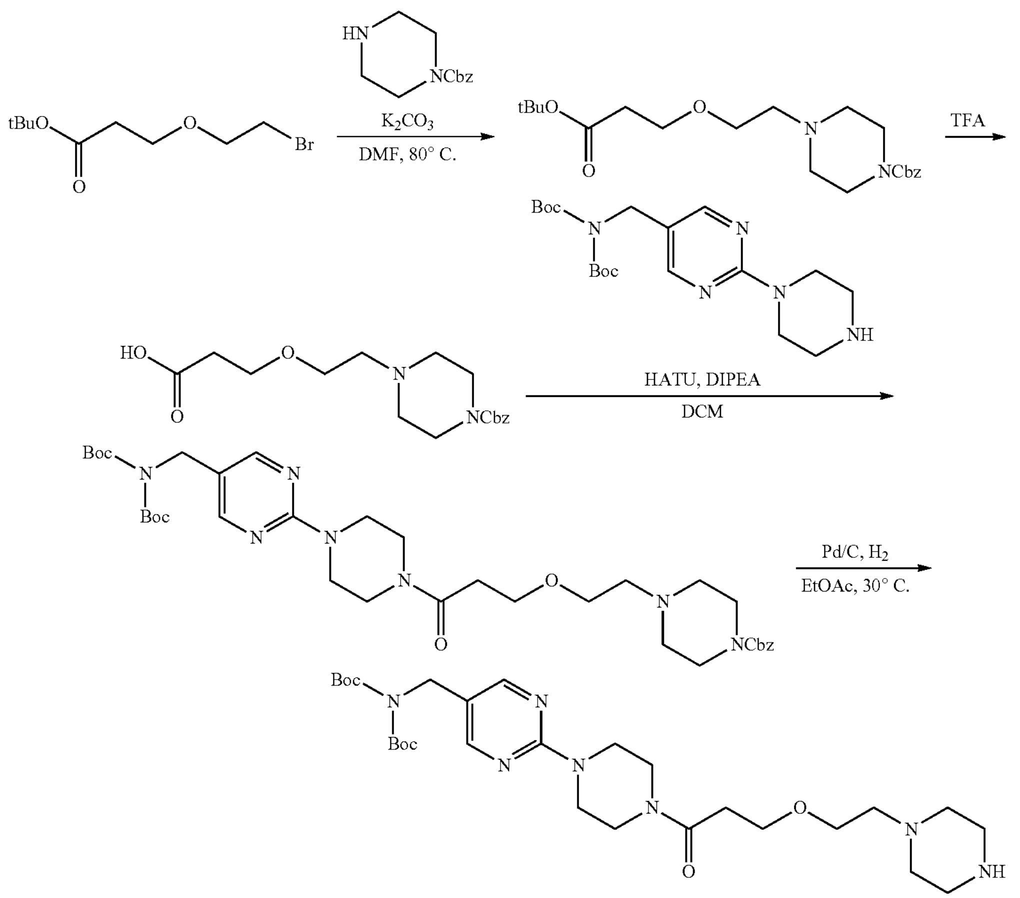

Step 1: Synthesis of benzyl 4-(2-(3-(tert-butoxy)-3-oxopropoxy)ethyl)piperazine-1-carboxylate To a solution of tert-butyl 3-(2-bromoethoxy)propanoate (35 g, 138.27 mmol, 1.0 equiv) and benzyl piperazine-1-carboxylate (31.14 mL, 138.27 mmol, 1.0 equiv, HCl) in MeCN (420 mL) was added $K_2CO_3$ (57.33 g, 414.80 mmol, 3.0 equiv). The reaction was stirred at 80° C. for 20 h. The reaction mixture was cooled to room temperature and the suspension was filtered. The filter cake was washed with EtOAc (3×50 mL) and the combined filtrates were concentrated under reduced pressure to give crude product. The residue was purified by silica gel chromatography (5/1 to 0/1 petroleum ether/EtOAc) to give the product (46 g, 84.8% yield) as a yellow oil.

Step 2: Synthesis of 3-(2-(4-((benzyloxy)carbonyl)piperazin-1-yl)ethoxy)propanoic acid A solution of benzyl 4-(2-(3-(tert-butoxy)-3-oxopropoxy)ethyl)piperazine-1-carboxylate (21 g, 53.50 mmol, 1.0 equiv) in TFA (160 mL) was stirred at room temperature for 2 h and then concentrated under reduced pressure. The residue was purified by silica gel chromatography (1/0 to 4/1 EtOAc/MeOH) to give the product (20.4 g, 84.7% yield) as a yellow oil. LCMS (ESI) m/z: [M+H] calcd for $C_{17}H_{24}N_2O_5$: 337.18; found 337.1.

Step 3: Synthesis of benzyl 4-(2-(3-(4-(5-(((di-tert-butoxycarbonyl)amino)methyl)pyrimidin-2-yl)piperazin-1-yl)-3-oxopropoxy)ethyl)piperazine-1-carboxylate To a solution of 3-(2-(4-((benzyloxy)carbonyl)piperazin-1-yl)ethoxy)propanoic acid (20.2 g, 44.85 mmol, 1.0 equiv, TFA) in DCM (500 mL) was added HATU (25.58 g, 67.27 mmol, 1.5 equiv) and DIPEA (17.39 g, 134.55 mmol, 23.44 mL, 3.0 equiv). The reaction was stirred at room temperature for 30 min, and then tert-butyl N-tert-butoxycarbonyl-N-((2-piperazin-1-ylpyrimidin-5-yl)methyl)carbamate (14.12 g, 35.88 mmol, 0.8 equiv) was added. The reaction mixture was stirred at for 2 h and then quenched with sat. $NH_4Cl$ (500 mL). The aqueous phase was extracted with DCM (3×300 mL) and the combined organic phase was washed with brine (30 mL), dried with anhydrous $Na_2SO_4$, filtered and concentrated under reduced pressure to give crude product. The residue was purified by silica gel chromatography (0/1 petroleum ether/EtOAc to 10/1 DCM/MeOH) to give the product (29 g, 90.8% yield) as a yellow oil. LCMS (ESI) m/z: [M+H] calcd for $C_{36}H_{53}N_7O_8$: 712.41; found 712.4.

Step 4: Synthesis of tert-butyl N-tert-butoxycarbonyl-N-((2-(4-(3-(2-piperazin-1-ylethoxy)propanoyl) piperazin-1-yl)pyrimidin-5-yl)methyl)carbamate To a solution of 4-(2-(3-(4-(5-(((di-tert-butoxycarbonyl) amino)methyl)pyrimidin-2-yl)piperazin-1-yl)-3-oxo-propoxy)ethyl)piperazine-1-carboxylate (5 g, 7.02 mmol, 1.0 equiv) in EtOAc (150 mL) was added Pd/C (2 g, 10 wt. %). The suspension was degassed and purged with $H_2$ and then stirred under $H_2$ (30 psi) at 30° C. for 3 h. The suspension was then cooled to room temperature and filtered through Celite. The filter cake was washed with MeOH (15×100 mL) and the combined filtrates were concentrated under reduced pressure to give the product (12 g, 89.9% yield) as a light yellow oil. LCMS (ESI) m/z: [M+H] calcd for $C_{28}H_{47}N_7O_6$: 578.37; found 578.5.

Building Block AI. ethyl 2-(piperazin-1-yl)pyrimidine-5-carboxylate

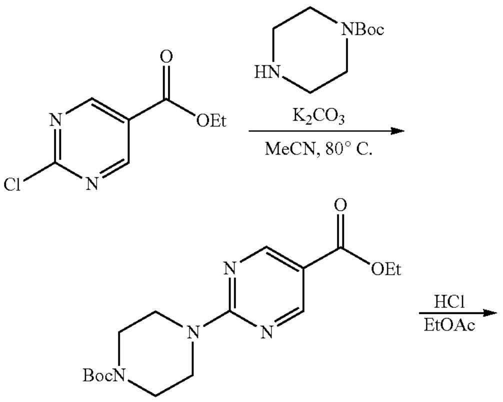

-continued

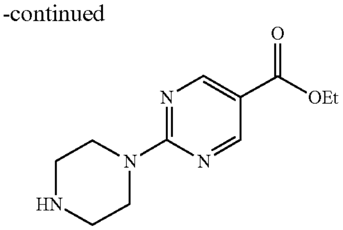

Step 1: Synthesis of ethyl 2-(4-(tert-butoxycarbonyl)piperazin-1-yl)pyrimidine-5-carboxylate To a solution of tert-butyl piperazine-1-carboxylate (11.94 g, 53.59 mmol, 1.0 equiv, HCl) and ethyl 2-chloropyrimidine-5-carboxylate (10 g, 53.59 mmol, 1.0 equiv) in MeCN (100 mL) was added $K_2CO_3$ (7.41 g, 53.59 mmol, 1.0 equiv). The mixture was stirred at 80° C. for 17 h and then poured into $H_2O$ (200 mL). The mixture was filtered and the filter cake was washed with $H_2O$ (80 mL) and dried under reduced pressure to give the product (15.76 g, 82% yield) as a white solid.

Step 2: Synthesis of ethyl 2-(piperazin-1-yl)pyrimidine-5-carboxylate

To a solution of ethyl 2-(4-(tert-butoxycarbonyl)piperazin-1-yl)pyrimidine-5-carboxylate (15.7 g, 46.67 mmol, 1.0 equiv) in EtOAc (150 mL) was added HCl/EtOAc (150 mL) at 0° C. The resulting mixture was stirred at room temperature for 9 h. The reaction mixture was filtered and the filter cake was washed with EtOAc (100 mL). The solid was dried under reduced pressure to give the product (12.55 g, 96% yield, HCl) as a white solid. LCMS (ESI) m/z: [M+H] calcd for $C_{11}H_{16}N_4O_2$: 237.14; found 237.3.

Building Block AJ. 2-(4-(2-(3-(4-(5-(((di-tert-butoxycarbonyl)amino)methyl)pyrimidin-2-yl)piperazin-1-yl)-3-oxopropoxy)ethyl)piperazin-1-yl)pyrimidine-5-carboxylic acid

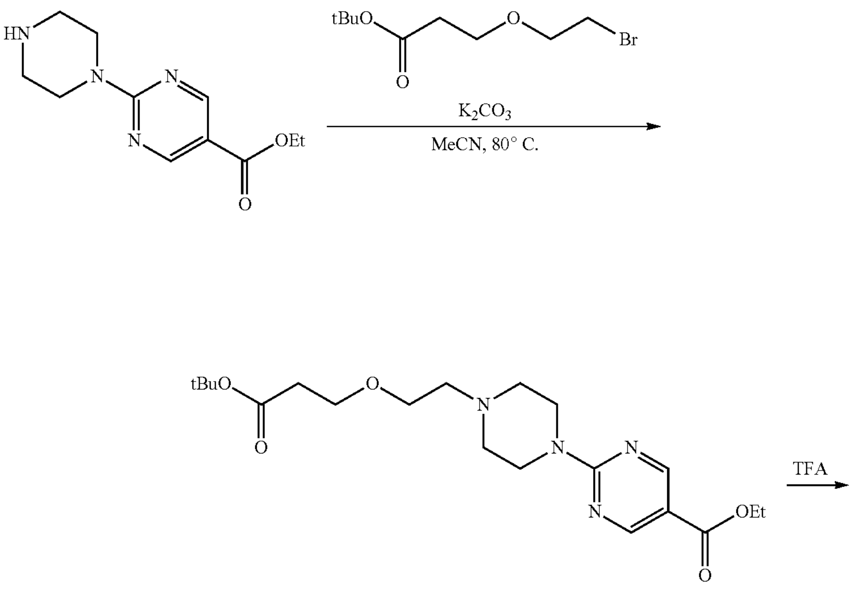

-continued

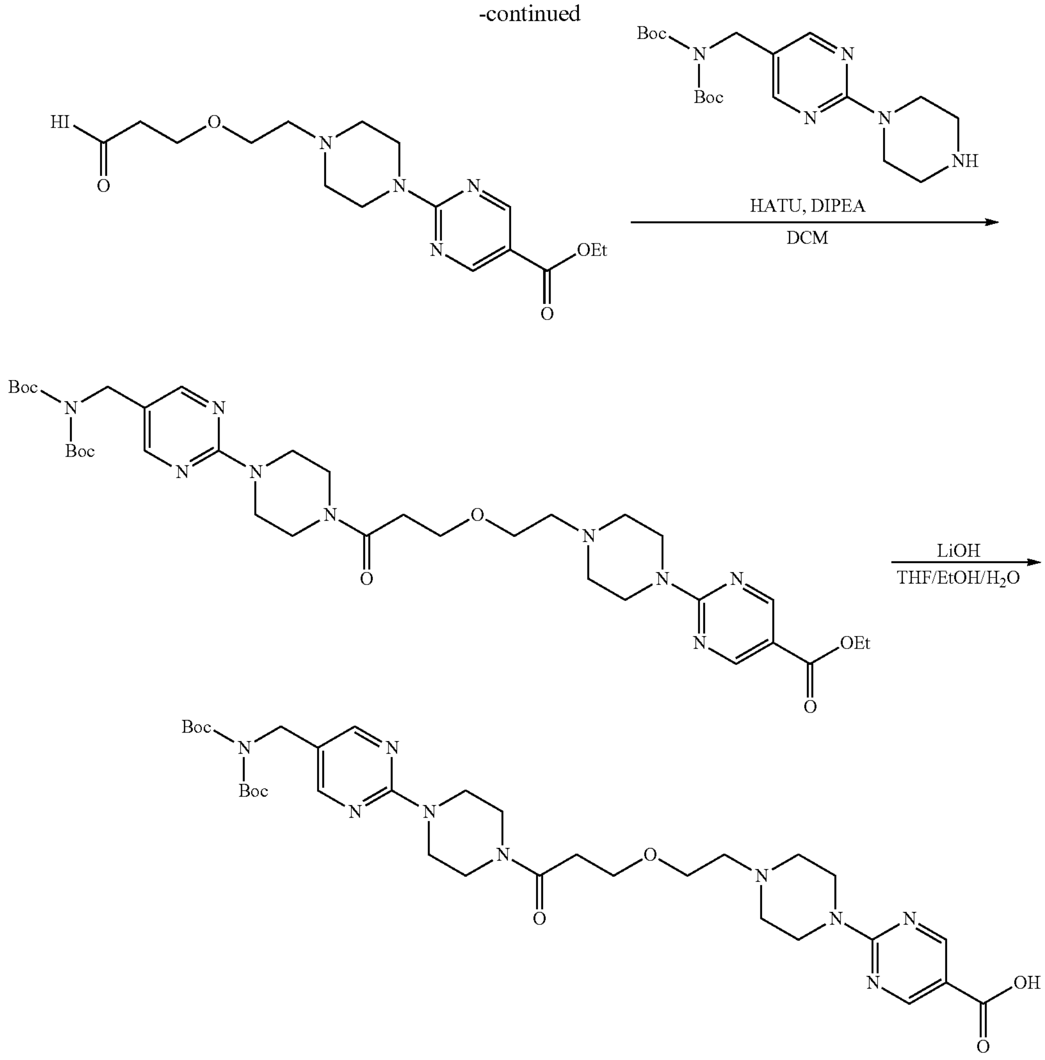

Step 1: Synthesis of ethyl 2-(4-(2-(3-(tert-butoxy)-3-oxopropoxy)ethyl)piperazin-1-yl)pyrimidine-5-carboxylate To a solution of ethyl 2-piperazin-1-ylpyrimidine-5-carboxylate (17.92 g, 75.85 mmol, 1.2 equiv) and tert-butyl 3-(2-bromoethoxy)propanoate (16 g, 63.21 mmol, 1.0 equiv) in MeCN (200 mL) was added $K_2CO_3$ (17.47 g, 126.42 mmol, 2.0 equiv). The reaction was stirred at 80° C. for 12 h and then the reaction mixture was filtered, and the filtrate was concentrated under reduced pressure. The crude product was suspended in petroleum ether (200 mL) and stirred for 20 min at 0° C. and then filtered. The solid was dried under reduced pressure to give the product (19.4 g, 75.1% yield) as a yellow solid.

Step 2: Synthesis of 3-(2-(4-(5-(ethoxycarbonyl)pyrimidin-2-yl)piperazin-1-yl)ethoxy)propanoic acid A solution of ethyl 2-(4-(2-(3-(tert-butoxy)-3-oxopropoxy)ethyl)piperazin-1-yl)pyrimidine-5-carboxylate (19.4 g, 47.49 mmol, 1.0 equiv) in TFA (200 mL) was stirred at room temperature for 30 min. The reaction mixture was then concentrated under reduced pressure and the residue was purified by silica gel chromatography (50/1 to 1/1 EtOAc/MeOH) to give the product (18 g, 81.3% yield) as a yellow oil.

Step 3: Synthesis of ethyl 2-(4-(2-(3-(4-(5-(((di-tert-butoxycarbonyl)amino)methyl)pyrimidin-2-yl)piperazin-1-yl)-3-oxopropoxy)ethyl)piperazin-1-yl)pyrimidine-5-carboxylate To a solution of 3-(2-(4-(5-(ethoxycarbonyl)pyrimidin-2-yl)piperazin-1-yl)ethoxy)propanoic acid (13 g, 27.87 mmol, 1.0 equiv) in DCM (200 mL) was added HATU (15.90 g, 41.81 mmol, 1.5 equiv) and DIPEA (19.42 mL, 111.49 mmol, 4.0 equiv). The reaction was then stirred at room temperature for 30 min and then tert-butyl N-tert-butoxycarbonyl-N-[(2-piperazin-1-ylpyrimidin-5-yl)methyl]carbamate (10.97 g, 27.87 mmol, 1.0 equiv) was added. The mixture was stirred at for 2 h and then poured into a sat. $NH_4Cl$ solution (200 mL). The aqueous phase was extracted with DCM (2×200 mL) and the combined organic phase was washed with brine (2×20 mL), dried with anhydrous $Na_2SO_4$, filtered and concentrated under reduced pressure. The residue was purified by silica gel chromatography (100/1 to 9/1 EtOAc/MeOH) to give the product (17 g, 79.0% yield) as a yellow oil.

Step 4: Synthesis of 2-(4-(2-(3-(4-(5-(((di-tert-butoxycarbonyl)amino)methyl)pyrimidin-2-yl)piperazin-1-yl)-3-oxopropoxy)ethyl)piperazin-1-yl)pyrimidine-5-carboxylic acid To a solution of ethyl 2-(4-(2-(3-(4-(5-(((di-tert-butoxycarbonyl)amino)methyl)pyrimidin-2-yl)piperazin-1-yl)-3-oxopropoxy)ethyl)piperazin-1-yl)pyrimidine-5-carboxylate (11 g, 15.11 mmol, 1.0 equiv) in THF (40 mL), EtOH (10 mL), and $H_2O$ (20 mL) was added $LiOH{\cdot}H_2O$ (1.27 g, 30.23 mmol, 2.0 equiv). The mixture was then stirred at 35° C. for 1.5 h. The reaction mixture was extracted with EtOAc (30 mL) and the aqueous phase was adjusted to pH=7 by addition of HCl (1 N). The mixture was then concentrated under reduced pressure. The crude product was purified by reversed-phase chromatography (20/1 to 3/1 $H_2O$/MeCN) to give the product (6.1 g, 67.3% yield) as a white solid. LCMS (ESI) m/z: [M+H] calcd for $C_{33}H_{49}N_9O_8$: 700.38; found 700.4.

Building Block AK. 2-(4-(2-(3-(4-(5-(((tert-butoxycarbonyl)amino)methyl)pyrimidin-2-yl)piperazin-1-yl)-3-oxopropoxy)ethyl)piperazin-1-yl)pyrimidine-5-carboxylic acid

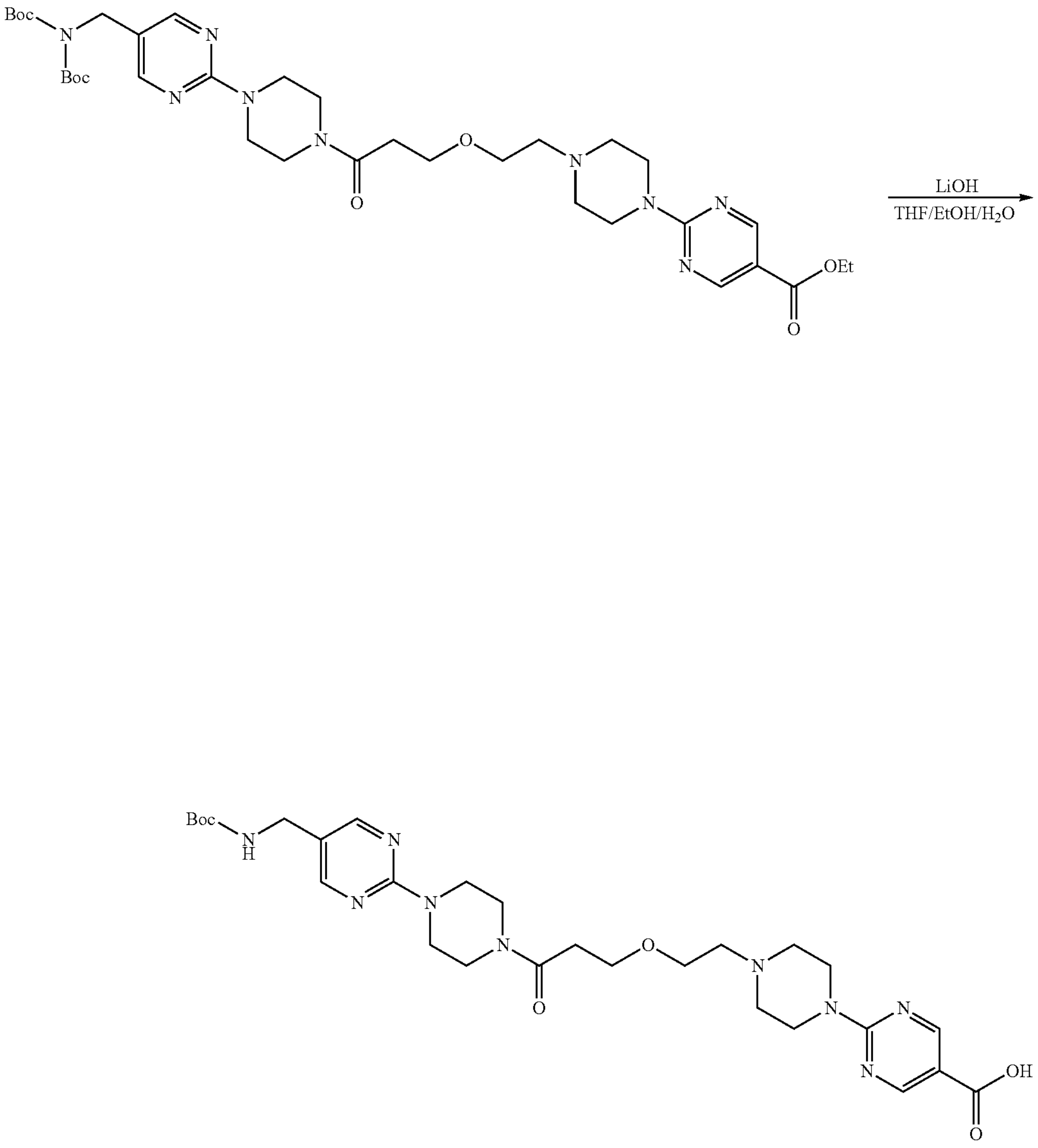

A solution of ethyl 2-(4-(2-(3-(4-(5-(((di-tert-butoxycarbonyl)amino)methyl)pyrimidin-2-yl)piperazin-1-yl)-3-oxopropoxy)ethyl)piperazin-1-yl)pyrimidine-5-carboxylate (5.4 g, 7.42 mmol, 1.0 equiv) in THF (40 mL), EtOH (10 mL), and $H_2O$ (10 mL) was added $LiOH{\cdot}H_2O$ (933.92 mg, 22.26 mmol, 3.0 equiv). The mixture was then stirred at 30° C. for 12 h. The reaction mixture was then extracted with EtOAc (2×50 mL) and the aqueous phase was adjusted to pH=7 by addition of HCl (1 N). The solution was then concentrated under reduced pressure. The crude product was purified by reversed-phase chromatography (20/1 to 3/1 $H_2O$/MeCN) to give the product (1.01 g, 22.5% yield) as a white solid. LCMS (ESI) m/z: [M+H] calcd for $C_{28}H_{41}N_9O_6$: 600.33; found 600.2.

Building Block AL. 4-{4-[2-(3-{4-[5-{[(tert-butoxy)carbonyl]amino}methyl)pyrimidin-2-yl]piperazin-1-yl}-3-oxopropoxy)ethyl]piperazin-1-yl}-4-oxobutanoic acid

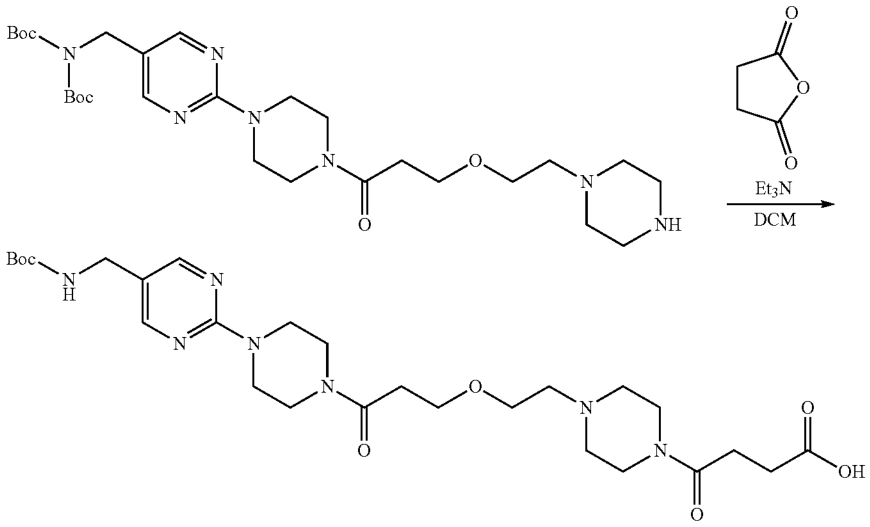

To a solution of tert-butyl N-tert-butoxycarbonyl-N-((2-(4-(3-(2-piperazin-1-ylethoxy)propanoyl)piperazin-1-yl)pyrimidin-5-yl)methyl)carbamate (1.0 equiv) in DCM is added succinic anhydride (1.2 equiv) and $Et_3N$ (2.0 equiv). The reaction is stirred at room temperature until consumption of starting material, as determined by LCMS analysis. The reaction mixture is then concentrated under reduced pressure to give the crude product. The residue is purified by silica gel chromatography to afford the product.

Building Block AM. 2-(4-(4-(4-(5-(((tert-butoxycarbonyl)amino)methyl)pyrimidin-2-yl)piperazin-1-yl)-4-oxobutyl)piperazin-1-yl)pyrimidine-5-carboxylic acid

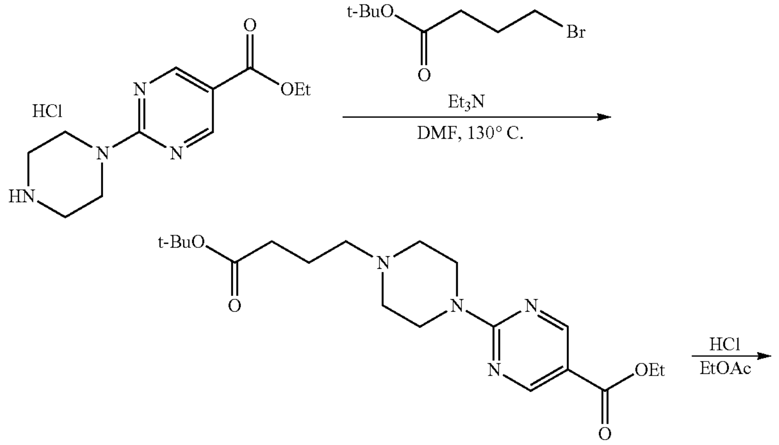

-continued

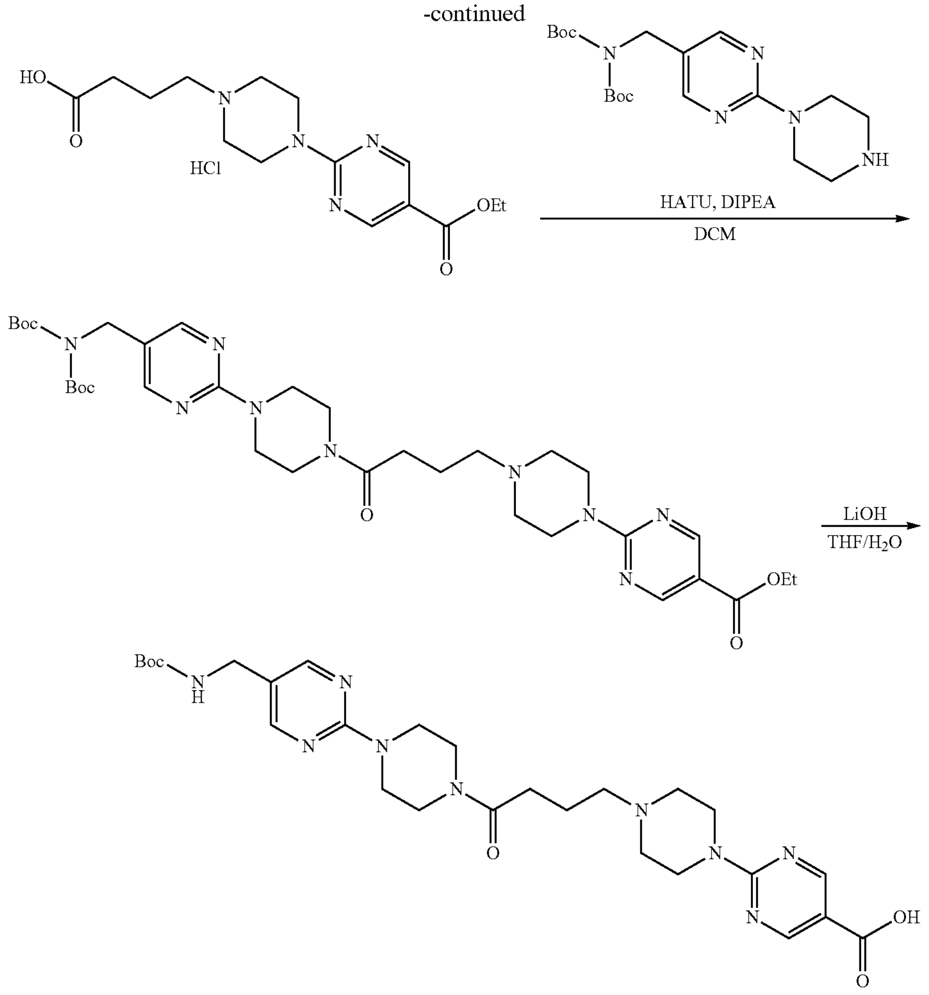

Step 1: Synthesis of ethyl 2-(4-(4-(tert-butoxy)-4-oxobutyl)piperazin-1-yl)pyrimidine-5-carboxylate To a solution of ethyl 2-(piperazin-1-yl)pyrimidine-5-carboxylate hydrochloride (10 g, 36.67 mmol, 1.0 equiv, HCl) and tert-butyl 4-bromobutanoate (8.18 g, 36.67 mmol, 1.0 equiv) in DMF (100 mL) was added $Et_3N$ (15.31 mL, 110.00 mmol, 3.0 equiv). The mixture was stirred at 130° C. for 14 h. The mixture was then poured into $H_2O$ (400 mL) and the solution was extracted with EtOAc (3×150 mL). The combined organic layer was washed with brine (200 mL), dried over $Na_2SO_4$ and concentrated under reduced pressure. The residue was purified by silica gel chromatography (5/1 to 1/1 petroleum ether/EtOAc) to give the product (9.5 g, 68.5% yield) as a yellow solid. LCMS (ESI) m/z: [M+H] calcd for $C_{19}H_{30}N_4O_4$: 379.24; found 379.2, 380.2.

Step 2: Synthesis of 4-(4-(5-(ethoxycarbonyl)pyrimidin-2-yl)piperazin-1-yl)butanoic acid hydrochloride To a solution of ethyl 2-(4-(4-(tert-butoxy)-4-oxobutyl)piperazin-1-yl)pyrimidine-5-carboxylate (9.5 g, 25.10 mmol, 1.0 equiv) in EtOAc (100 mL) was added HCl/EtOAc (500 mL). The mixture was stirred at room temperature for 10 h and then the solution was concentrated under reduced pressure to give the product (9.6 g, 96.8% yield) as a white solid. LCMS (ESI) m/z: [M+H] calcd for $C_{15}H_{22}N_4O_4$: 323.17; found 323.2.

Step 3: Synthesis of ethyl 2-(4-(4-(4-(5-(((di-tert-butoxycarbonyl)amino)methyl)pyrimidin-2-yl)piperazin-1-yl)-4-oxobutyl)piperazin-1-yl)pyrimidine-5-carboxylic acid To a solution of 4-(4-(5-(ethoxycarbonyl)pyrimidin-2-yl)piperazin-1-yl)butanoic acid hydrochloride (5 g, 15.51 mmol, 1.0 equiv) and tert-butyl N-tert-butoxycarbonyl-N-((2-piperazin-1-ylpyrimidin-5-yl)methyl)carbamate (6.10 g, 15.51 mmol, 1.0 equiv) in DMF (150 mL) was added DIPEA (8.11 mL, 46.53 mmol, 3.0 equiv) and HATU (7.08 g, 18.61 mmol, 1.2 equiv). The mixture was stirred at room temperature for 3 h and then the solution was poured into $H_2O$ (600 mL). The aqueous layer was extracted with EtOAc (3×200 mL) and then the combined organic layer was washed with brine (100 mL), dried with $Na_2SO_4$ and concentrated under reduced pressure. The residue was purified by silica gel chromatography (50/1 to 15/1 DCM/MeOH) to give the product (6.3 g, 58.2% yield) as a yellow solid. LCMS (ESI) m/z: [M+H] calcd for $C_{34}H_{51}N_9O_7$: 698.40; found 698.6.

Step 4: Synthesis of 2-(4-(4-(4-(5-(((tert-butoxycarbonyl)amino)methyl)pyrimidin-2-yl)piperazin-1-yl)-4-oxobutyl)piperazin-1-yl)pyrimidine-5-carboxylic acid To a solution of ethyl 2-(4-(4-(4-(5-((bis(tert-butoxycarbonyl)amino)methyl)pyrimidin-2-yl)piperazin-1-yl)-4-oxobutyl)piperazin-1-yl)pyrimidine-5-carboxylate (4.5 g, 6.45 mmol, 1.0 equiv) in EtOH (7 mL) and THF (28 mL) was added a solution of LiOH·$H_2O$ (541.17 mg, 12.90 mmol, 2.0 equiv) in $H_2O$ (7 mL). The mixture was stirred at 30° C. for 8 h, then additional LiOH·$H_2O$ (541 mg, 12.90 mmol, 2.0 equiv) was added. After stirring for an additional 8 h at 30° C., the solution was concentrated under reduced pressure. $H_2O$ (20 mL) was added and solution was adjusted to pH 3 with 1N HCl. The suspension was filtered and the solid dried under reduced pressure to give the product (3.2 g, 79.1% yield) as a white solid. LCMS (ESI) m/z: [M+H] calcd for $C_{27}H_{39}N_9O_5$: 570.32; found 570.3.

Building Block AN. 2-(4-(2-(2-(4-(6-(tert-butoxycarbonyl)-5,6,7,8-tetrahydropyrido[4,3-d]pyrimidin-2-yl)piperazin-1-yl)ethoxy)ethyl)piperazin-1-yl)pyrimidine-5-carboxylic acid

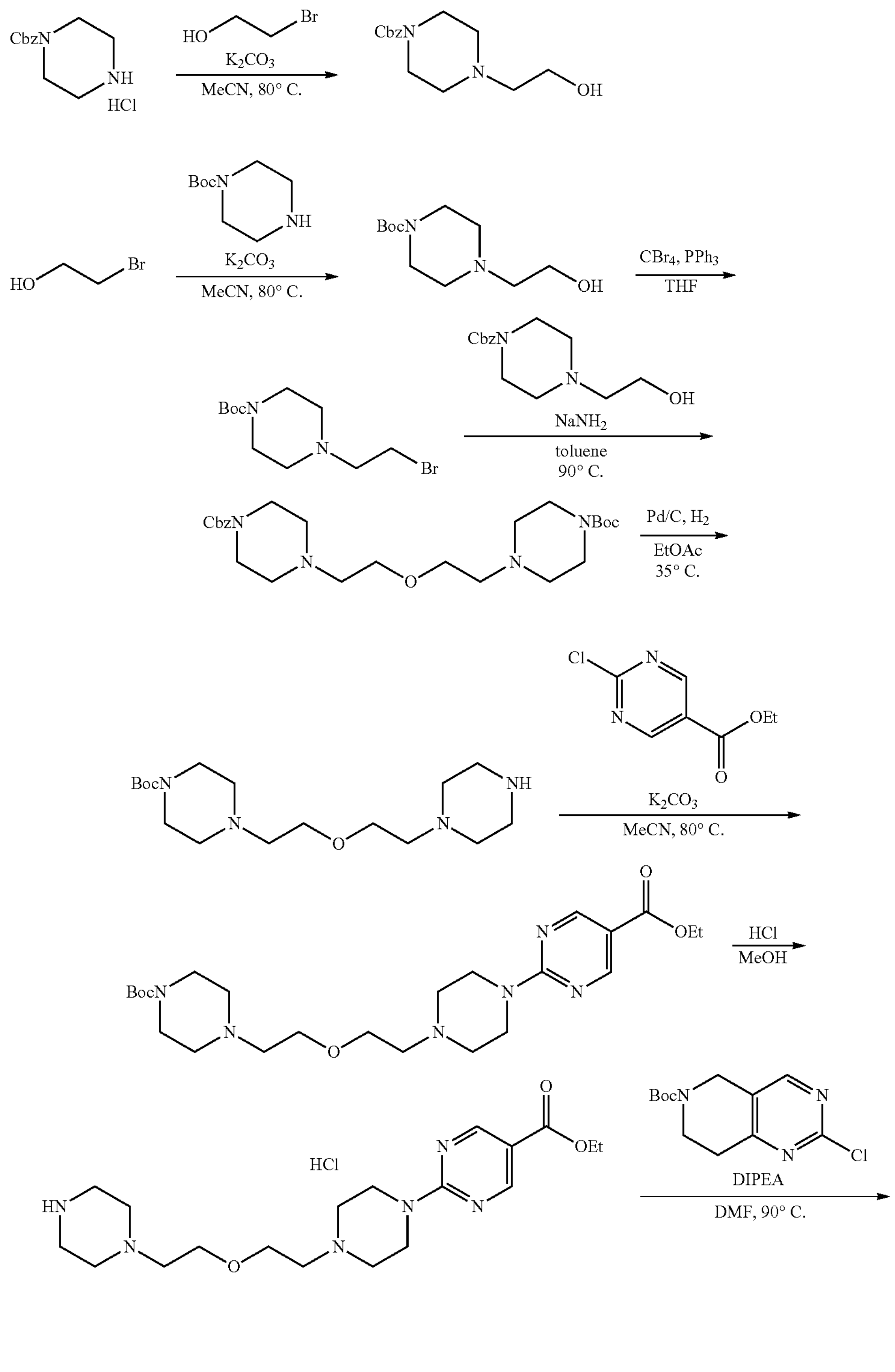

-continued

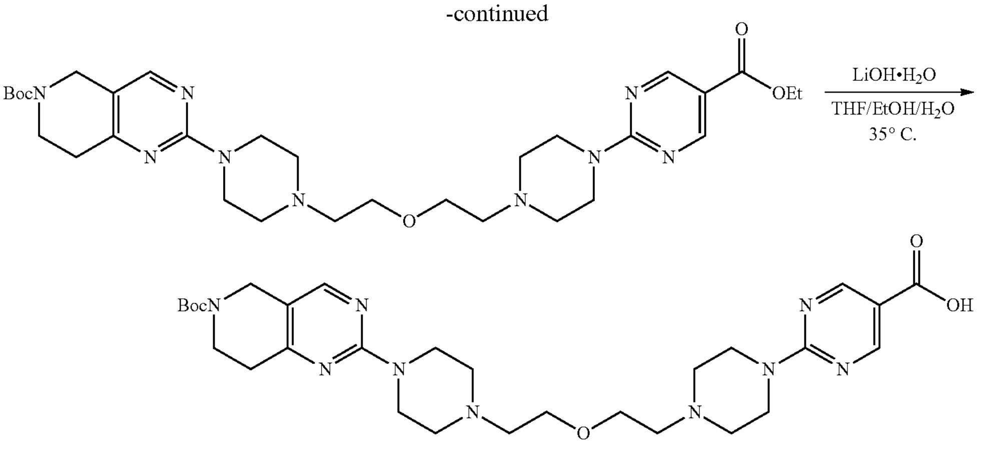

Step 1: Synthesis of benzyl 4-(2-hydroxyethyl)piperazine-1-carboxylate

To a solution of benzyl piperazine-1-carboxylate hydrochloride (41.09 g, 160.04 mmol, 1.0 equiv, HCl) in MeCN (200 mL) was added $K_2CO_3$ (66.36 g, 480.13 mmol, 3.0 equiv) and 2-bromoethanol (20 g, 160.04 mmol, 1.0 equiv). The reaction mixture was stirred at 80° C. for 16 h, at which point it was cooled to room temperature and filtered. The filter cake was washed with EtOAc (100 mL) and the filtrate then washed with $H_2O$ (100 mL). The aqueous phase was extracted with EtOAc (3×50 mL) and the combined organic phases were washed with brine (50 mL), dried, and concentrated under reduced pressure. Purification by silica gel chromatography (5→25% MeOH/EtOAc) afforded the desired product as a yellow solid (20 g, 47% yield). LCMS (ESI) m/z: [M+H] calcd for $C_{14}H_{20}N_2O_3$: 265.16; found 264.9.

Step 2: Synthesis of tert-butyl 4-(2-hydroxyethyl)piperazine-1-carboxylate

To a solution of tert-butyl piperazine-1-carboxylate (198.72 g, 1.07 mol, 1.0 equiv) in MeCN (1500 mL) was added 2-bromoethanol (240 g, 1.92 mol, 1.8 equiv) and $K_2CO_3$ (221.19 g, 1.60 mol, 1.5 equiv). The reaction mixture was stirred at 80° C. for 16 h, at which point the mixture was cooled to room temperature, filtered, and the filtrate was concentrated under reduced pressure. Purification by silica gel chromatography (0→14% MeOH/EtOAc) afforded the desired product as a white solid (146 g, 59% yield).

Step 3: Synthesis of tert-butyl 4-(2-bromoethyl)piperazine-1-carboxylate

To a solution of tert-butyl 4-(2-hydroxyethyl)piperazine-1-carboxylate (45 g, 195.39 mmol, 1.0 equiv) in THF (600 mL) was added triphenylphosphine (97.38 g, 371.25 mmol, 1.9 equiv) and $CBr_4$ (116.64 g, 351.71 mmol, 1.8 equiv). The mixture was stirred at room temperature for 3 h. Two separate batches were combined, and the reaction mixture was filtered, and the filtrate concentrated under reduced pressure. Purification by silica gel chromatography (1-25% EtOAc/petroleum ether) afforded the desired product as a light-yellow solid (31 g, 27% yield).

Step 4: Synthesis of benzyl 4-(2-(2-(4-(tert-butoxycarbonyl)piperazin-1-yl)ethoxy)ethyl)piperazine-1-carboxylate To a solution of benzyl 4-(2-hydroxyethyl)piperazine-1-carboxylate (18 g, 68.10 mmol, 1.0 equiv) in toluene (200 mL) was added $NaNH_2$ (26.57 g, 680.99 mmol, 10.0 equiv). tert-Butyl 4-(2-bromoethyl)piperazine-1-carboxylate (25 g, 85.27 mmol, 1.25 equiv) was added and the mixture was heated to 90° C. for 18 h. The mixture was cooled to room temperature and poured into $H_2O$ (700 mL) at 0° C. The aqueous phase was extracted with EtOAc (3×240 mL) and the combined organic phases were washed successively with $H_2O$ (350 mL) and sat. brine (2×200 mL), dried, filtered, and concentrated under reduced pressure. Purification by silica gel chromatography (0→12% MeOH/EtOAc) afforded the desired product as a light-yellow oil (20 g, 62% yield).

Step 5: Synthesis of tert-butyl 4-(2-(2-(piperazin-1-yl)ethoxy)ethyl)piperazine-1-carboxylate To a solution of benzyl 4-(2-(2-(4-(tert-butoxycarbonyl)piperazin-1-yl)ethoxy)ethyl)piperazine-1-carboxylate (20 g, 41.96 mmol, 1.0 equiv) in EtOAc (180 mL) was added Pd/C (8 g, 10 wt. %). The suspension was degassed under reduced pressure and purged with $H_2$ three times. The mixture was stirred under $H_2$ (30 psi) at 35° C. for 12 h. The reaction mixture was then filtered, and the filtrate was concentrated under reduced pressure. Purification by silica gel chromatography (0→100% MeOH/EtOAc) afforded the desired product as a colorless oil (10.8 g, 75% yield).

Step 6: Synthesis of ethyl 2-(4-(2-(2-(4-(tert-butoxycarbonyl)piperazin-1-yl)ethoxy)-ethyl)piperazin-1-yl)pyrimidine-5-carboxylate To a solution of tert-butyl 4-(2-(2-(piperazin-1-yl)ethoxy)ethyl)piperazine-1-carboxylate (10.8 g, 31.54 mmol, 1.0 equiv) in MeCN (100 mL) was added $K_2CO_3$ (13.08 g, 94.61 mmol, 3.0 equiv) and ethyl 2-chloropyrimidine-5-carboxylate (5.88 g, 31.54 mmol, 1.0 equiv). The mixture was stirred at 80° C. for 12 h, at which point the reaction was cooled to room temperature, filtered, and the filtrate concentrated under reduced pressure. Purification by silica gel chromatography (0→9% MeOH/DCM) afforded the desired product as a white solid (13.6 g, 85% yield).

Step 7: Synthesis of 2-(4-(2-(2-(4-(6-(tert-butoxycarbonyl)-5,6,7,8-tetrahydropyrido-[4,3-d]pyrimidin-2-yl)piperazin-1-yl)ethoxy)ethyl)piperazin-1-yl)pyrimidine-5-carboxylic acid To a solution of ethyl 2-(4-(2-(2-(4-(tert-butoxycarbonyl)piperazin-1-yl)ethoxy)ethyl)piperazin-1-yl)pyrimidine-5-carboxylate (13.6 g, 27.61 mmol, 1.0 equiv) in MeOH (50 mL) was added a solution of HCl in MeOH (4 M, 150 mL, 21.7 equiv). The reaction was stirred at room temperature for 4 h, at which point the mixture was concentrated under reduced pressure to afford the crude desired product as a white solid (13.8 g, 4HCl) that was taken directly onto the next step. LCMS (ESI) m/z: [M+H] calcd for $C_{19}H_{32}N_6O_3$: 393.26; found 393.3.

Step 8: Synthesis of tert-butyl 2-(4-(2-(2-(4-(5-(ethoxycarbonyl)pyrimidin-2-yl)-piperazin-1-yl)ethoxy)ethyl)piperazin-1-yl)-7,8-dihydropyrido[4,3-d]pyrimidine-6(5H)-carboxylate To a stirred solution of 2-(4-(2-(2-(4-(6-(tert-butoxycarbonyl)-5,6,7,8-tetrahydropyrido[4,3-d]pyrimidin-2-yl)piperazin-1-yl)ethoxy)ethyl)piperazin-1-yl)pyrimidine-5-carboxylic acid (10.2 g, 18.95 mmol, 1.0 equiv, 4HCl) and DIPEA (16.50 mL, 94.74 mmol, 5.0 equiv) in DMF (100 mL) was added tert-butyl 2-chloro-7,8-dihydropyrido[4,3-d]pyrimidine-6(5H)-carboxylate (5.11 g, 18.95 mmol, 1.0 equiv). The reaction mixture was stirred at 90° C. for 12 h. The reaction mixture was then cooled to room temperature and added to EtOAc (200 mL) and $H_2O$ (400 mL). The aqueous phase was extracted with EtOAc (2×100 mL) and the combined organic phases were washed with aqueous $NH_4Cl$ (4×100 mL), brine (2×100 mL), dried, filtered and concentrated under reduced pressure. Purification by silica gel chromatography (0→9% MeOH/DCM) afforded the desired product as a white solid (5.4 g, 45% yield). LCMS (ESI) m/z: [M+H] calcd for $C_{31}H_{47}N_9O_5$: 626.38; found 626.3.

Step 9: Synthesis of 2-(4-(2-(2-(4-(6-(tert-butoxycarbonyl)-5,6,7,8-tetrahydropyrido[4,3-d]pyrimidin-2-yl)piperazin-1-yl)ethoxy)ethyl)piperazin-1-yl)pyrimidine-5-carboxylic acid To a solution of tert-butyl 2-(4-(2-(2-(4-(5-(ethoxycarbonyl)pyrimidin-2-yl)piperazin-1-yl)ethoxy)ethyl)piperazin-1-yl)-7,8-dihydropyrido[4,3-d]pyrimidine-6(5H)-carboxylate (5.4 g, 8.63 mmol, 1.0 equiv) in THF (50 mL), EtOH (20 mL), and $H_2O$ (20 mL) was added $LiOH \cdot H_2O$ (1.09 g, 25.89 mmol, 3.0 equiv). The reaction mixture was stirred at 35° C. for 12 h, at which point the mixture was concentrated under reduced pressure to remove THF and EtOH. The aqueous phase was neutralized to pH=7 with 0.5N HCl and concentrated under reduced pressure. Purification by reverse phase chromatography afforded the desired product as a white solid (4.72 g, 92% yield). LCMS (ESI) m/z: [M+H] calcd for $C_{29}H_{43}N_9O_5$: 598.35; found 598.3.

Building Block AO. 1'-[(tert-butoxy)carbonyl]-[1,4'-bipiperidine]-4-carboxylic acid

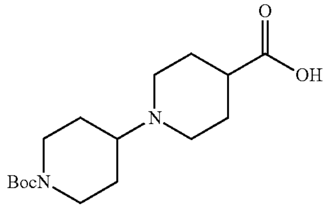 [SMILES: CC(C)(C)OC(=O)N1CCC(N2CCC(C(=O)O)CC2)CC1]

At the time of this application this building block was commercially available (CAS #201810-59-5).

Building Block AP. 2-((2-(piperazin-1-yl)pyrimidin-5-yl)methyl)isoindoline-1,3-dione hydrochloride salt

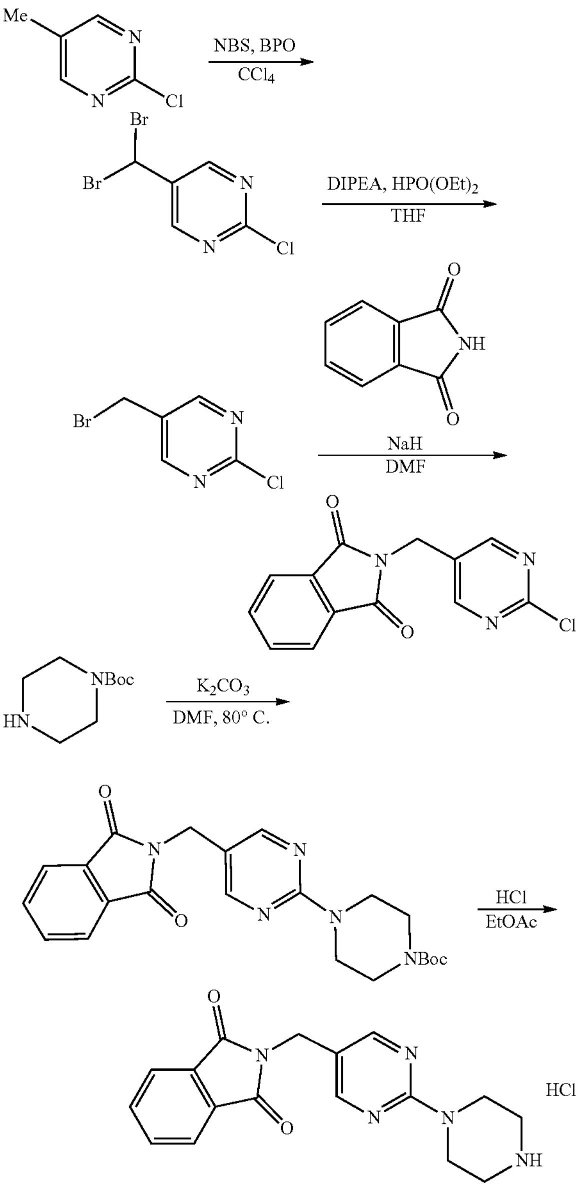

Step 1: Synthesis of 2-chloro-5-(dibromomethyl)pyrimidine

To a solution of 2-chloro-5-methylpyrimidine (100 g, 777.85 mmol, 1.0 equiv) in $CCl_4$ (1200 mL) was added NBS (304.58 g, 1.71 mol, 2.2 equiv) and AIBN (51.09 g, 311.14 mmol, 0.4 equiv). The mixture was stirred at 80° C. for 16 h. The reaction solution was then cooled to room temperature, filtered, and the filtrate was poured into $H_2O$ (1500 mL). The solution was diluted with DCM (3×250 mL) and the organic layer washed with brine (300 mL), dried with anhydrous $Na_2SO_4$, filtered and concentrated under reduced pressure to give the crude product as a brown oil, which was used directly in the next step.

Step 2: Synthesis of 5-(bromomethyl)-2-chloropyrimidine

To a solution of 2-chloro-5-(dibromomethyl)pyrimidine (229 g, 799.72 mmol, 1.0 equiv) in THF (600 mL) was added DIPEA (111.44 mL, 639.77 mmol, 0.8 equiv) and 1-ethoxyphosphonoyloxyethane (82.57 mL, 639.77 mmol, 0.8 equiv). The mixture was stirred at room temperature for 19 h. The mixture was then poured into $H_2O$ (1200 mL) and the aqueous phase was extracted with EtOAc (3×300 mL). The combined organic phase was washed with brine (300 mL), dried with anhydrous $Na_2SO_4$, filtered and concentrated under reduced pressure. The residue was purified by silica gel chromatography (1/0 to 0/1 petroleum ether/EtOAc) to give the product as a brown oil, which was used directly for the next step.

Step 3: Synthesis of 2-((2-chloropyrimidin-5-yl)methyl)isoindoline-1,3-dione

To a mixture of isoindoline-1,3-dione (15 g, 101.95 mmol, 1.0 equiv) in DMF (126 mL) was added NaH (4.89 g, 122.34 mmol, 60 wt. %, 1.2 equiv) at 0° C. The mixture was stirred at 0° C. for 30 min, then a solution of 5-(bromomethyl)-2-chloropyrimidine (30.21 g, 101.95 mmol, 1.0 equiv) in DMF (24 mL) was added dropwise to the above mixture at room temperature. The mixture was stirred at room temperature for 2 h and was then cooled to 0° C. and quenched with sat. $NH_4Cl$ (600 mL). The suspension was filtered and the solid dried under reduced pressure to give the crude product (27.4 g, 98.2% yield) as a grey solid, which was used directly in the next step. LCMS (ESI) m/z: [M+H] calcd for $C_{13}H_8ClN_3O_2$: 274.04; found 274.0.

Step 4: Synthesis of tert-butyl 4-(5-((1,3-dioxoisoindolin-2-yl)methyl)pyrimidin-2-yl)piperazine-1-carboxylate To a solution of 2-((2-chloropyrimidin-5-yl)methyl)isoindoline-1,3-dione (27 g, 98.66 mmol, 1.0 equiv) and tert-butyl piperazine-1-carboxylate (20.21 g, 108.52 mmol, 1.1 equiv) in DMF (270 mL) was added $K_2CO_3$ (34.09 g, 246.64 mmol, 2.5 equiv). The mixture was stirred at 80° C. for 3 h and then the reaction was cooled to room temperature and poured into $H_2O$ (1200 mL). The suspension was filtered and the solid was dried under reduced pressure to give the crude product (35.58 g, 85.2% yield) as a white solid, which was used directly in the next step.

Step 5: Synthesis of 2-((2-(piperazin-1-yl)pyrimidin-5-yl)methyl)isoindoline-1,3-dione A solution of tert-butyl 4-(5-((1,3-dioxoisoindolin-2-yl)methyl)pyrimidin-2-yl)piperazine-1-carboxylate (15 g, 35.42 mmol, 1 equiv) in HCl/EtOAc (150 mL) was stirred at room temperature for 2 h. The mixture was filtered and then the filter cake was washed with EtOAc (20 mL) and dried under reduced pressure to give the product (42.53 g, 92.5% yield) as a white solid.

Building Block AQ. 2-[(2-{4-[2-(3-{4-[5-({bis[(tert-butoxy)carbonyl]amino}methyl)pyrimidin-2-yl]piperazin-1-yl}-3-oxopropoxy)ethyl]piperazin-1-yl}-2-oxoethyl)(methyl)amino]acetic acid

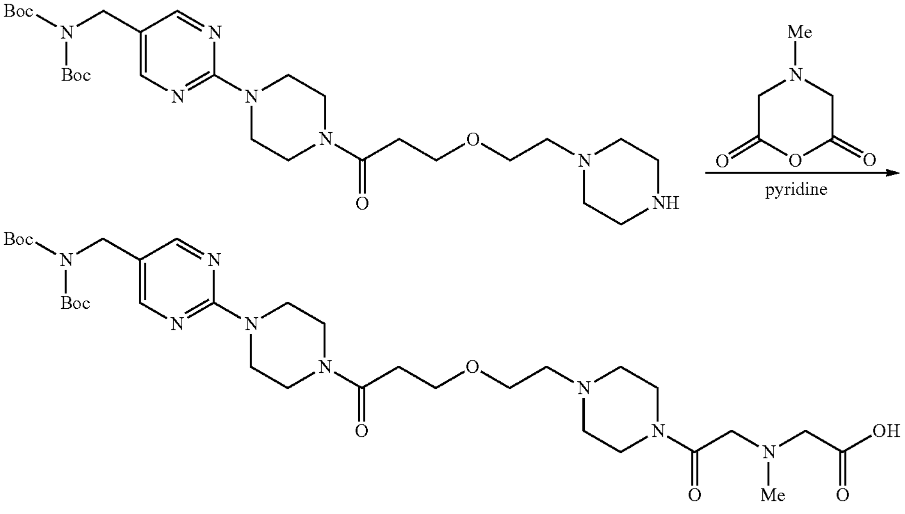

To a solution of tert-butyl N-[(tert-butoxy)carbonyl]-N-{[2-(4-{3-[2-(piperazin-1-yl)ethoxy]propanoyl}piperazin-1-yl)pyrimidin-5-yl]methyl}carbamate (300 mg, 519 μmol, 1.0 equiv) in pyridine (8 mL) at 0° C. was added 4-methylmorpholine-2,6-dione (80.3 mg, 622 μmol, 1.2 equiv). The reaction mixture was stirred at 0° C. for 1 h and then warmed to room temperature and stirred for an additional 12 h. The solvent was concentrated under reduced pressure and the solid was partitioned between DCM and $H_2O$. The organic layer was separated, dried over $MgSO_4$ and the solvent was concentrated under reduced pressure to give the product (23.0 mg, 6.28% yield). LCMS (ESI) m/z: [M+H] calcd for $C_{33}H_{54}N_8O_9$: 707.41; found 707.4.

Building Block AR. 2-(4-(2-(3-(4-(6-(tert-butoxy-carbonyl)-5,6,7,8-tetrahydropyrido[4,3-d]pyrimidin-2-yl)piperazin-1-yl)-3-oxopropoxy)ethyl)piperazin-1-yl)pyrimidine-5-carboxylic acid

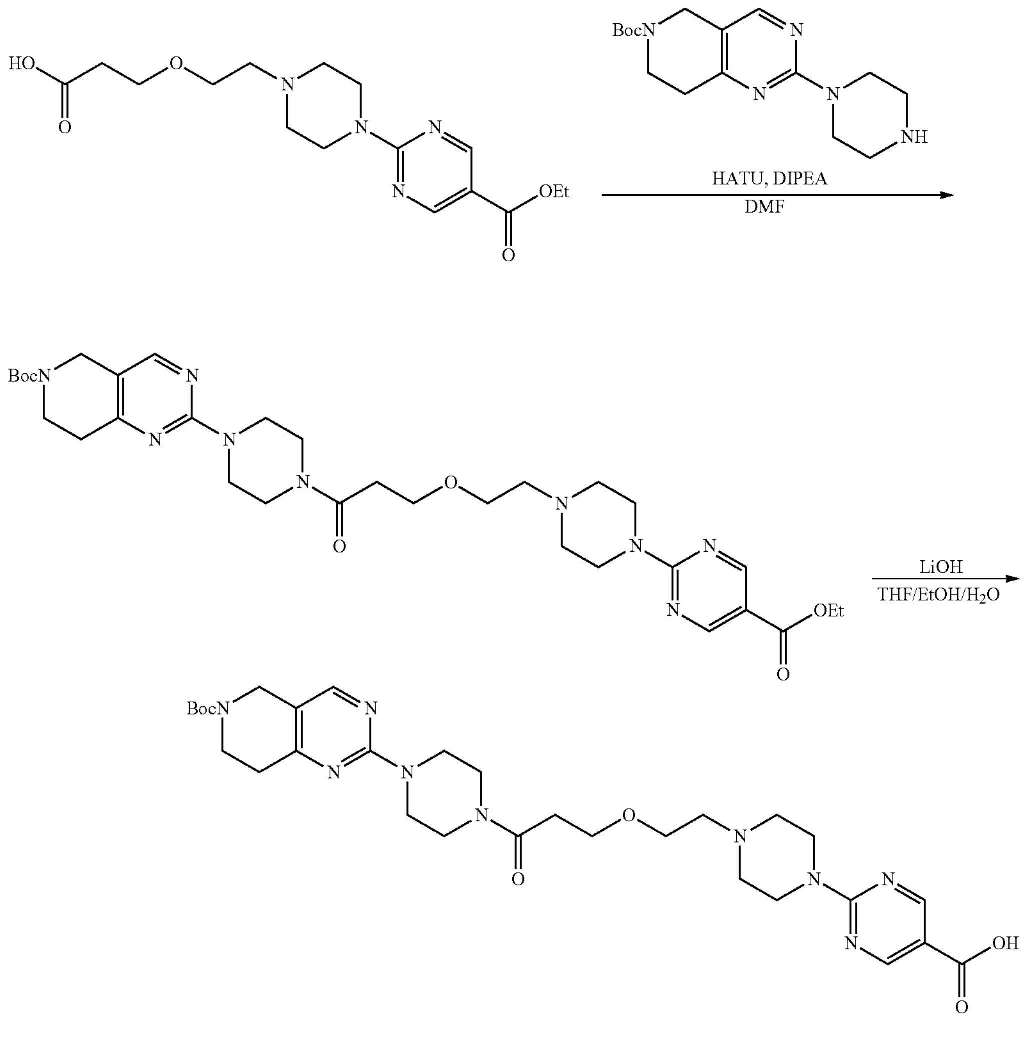

Step 1: Synthesis of tert-butyl 2-(4-(3-(2-(4-(5-(ethoxycarbonyl)pyrimidin-2-yl)piperazin-1-yl)ethoxy)propanoyl)piperazin-1-yl)-7,8-dihydropyrido[4,3-d]pyrimidine-6(5H)-carboxylate To a solution of 3-(2-(4-(5-(ethoxycarbonyl)pyrimidin-2-yl)piperazin-1-yl)ethoxy) propanoic acid (6 g, 12.86 mmol, 1.0 equiv, TFA) in DMF (55 mL) was added HATU (6.36 g, 16.72 mmol, 1.3 equiv) and DIPEA (11.20 mL, 64.32 mmol, 5.0 equiv). After 0.5 h, tert-butyl 2-(piperazin-1-yl)-7,8-dihydropyrido[4,3-d]pyrimidine-6(5H)-carboxylate (4.11 g, 12.86 mmol, 1.0 equiv) was added. The mixture was stirred for 3 h, at which point it was filtered and the solid cake was dried under reduced pressure to afford the desired product as a white solid (7.5 g, 89% yield). LCMS (ESI) m/z: [M+H] calcd for $C_{32}H_{47}N_9O_6$: 654.37; found 654.4.

Step 2: Synthesis of 2-(4-(2-(3-(4-(6-(tert-butoxy-carbonyl)-5,6,7,8-tetrahydropyrido[4,3-d]pyrimidin-2-yl)piperazin-1-yl)-3-oxopropoxy)ethyl)piperazin-1-yl)pyrimidine-5-carboxylic acid To a solution of tert-butyl 2-(4-(3-(2-(4-(5-(ethoxycarbonyl)pyrimidin-2-yl)piperazin-1-yl)ethoxy)propanoyl)piperazin-1-yl)-7,8-dihydropyrido[4,3-d]pyrimidine-6(5H)-carboxylate (7.2 g, 11.01 mmol, 1.0 equiv) in THF (72 mL), EtOH (36 mL) and $H_2O$ (36 mL) was added $LiOH{\cdot}H_2O$ (1.85 g, 44.05 mmol, 4.0 equiv). The reaction mixture was stirred at room temperature for 2.5 h, at which point the mixture was filtered and the filtrate was concentrated under reduced pressure to remove THF and EtOH. The aqueous phase was neutralized to pH=7 with 1N HCl, and then concentrated under reduced pressure. Purification by reverse phase chromatography (30% MeCN/$H_2O$) afforded the desired product as a white solid (3.85 g, 54% yield). LCMS (ESI) m/z: [M+H] calcd for $C_{30}H_{43}N_9O_6$: 626.34; found 626.3.

Building Block AS. 2-(4-(2-(2-(3-(4-(5-((di-tert-butoxycarbonylamino)methyl)pyrimidin-2-yl)piperazin-1-yl)-3-oxo-propoxy)ethoxy)ethyl)piperazin-1-yl)pyrimidine-5-carboxylic acid

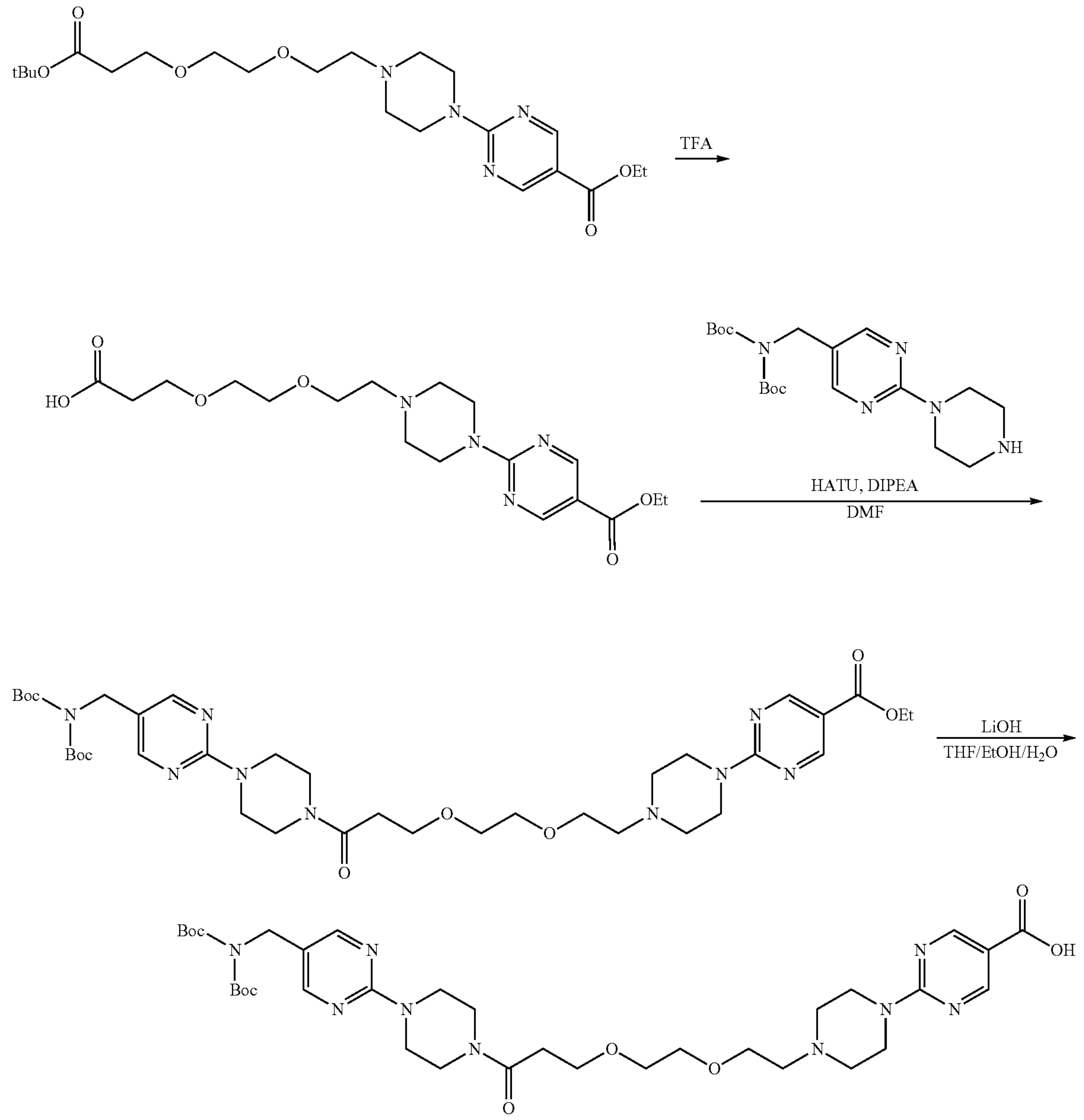

Step 1: Synthesis of 3-(2-(2-(4-(5-(ethoxycarbonyl)pyrimidin-2-yl)piperazin-lyl)ethoxy)ethoxy)propanoic acid A solution of ethyl 2-(4-(2-(2-(3-(tert-butoxy)-3-oxopropoxy)ethoxy)ethyl)piperazin-1-yl)pyrimidine-5-carboxylate (4 g, 8.84 mmol, 1.0 equiv) in TFA (12.29 mL, 166.00 mmol, 18.8 equiv) was stirred at room temperature for 3 h. The reaction mixture was concentrated under reduced pressure. Purification by silica gel chromatography (0→20% MeOH/EtOAc) afforded the desired product as a brown oil (4.35 g, 95% yield, TFA salt).

Step 2: Synthesis of ethyl 2-(4-(2-(2-(3-(4-(5-((bis(tert-butoxycarbonyl)amino)methyl)pyrimidin-2-yl)piperazin-1-yl)-3-oxopropoxy)ethoxy)ethyl)piperazin-1-yl)pyrimidine-5-carboxylate To a solution of 3-(2-(2-(4-(5-ethoxycarbonylpyrimidin-2-yl)piperazin-1-yl)ethoxy)ethoxy)propanoic acid (3.8 g, 7.44 mmol, 1.0 equiv, TFA) in DCM (30 mL) was added HATU (4.25 g, 11.17 mmol, 1.5 equiv) and DIPEA (6.48 mL, 37.22 mmol, 5.0 equiv). The reaction was stirred at room temperature for 30 min, and then tert-butyl N-tert-butoxycarbonyl-N-((2-piperazin-lylpyrimidin-5-yl)methyl)carbamate (2.93 g, 7.44 mmol, 1.0 equiv) was added. The mixture was stirred at room temperature for 3.5 h, at which point the reaction mixture was concentrated under reduced pressure. Purification by silica gel chromatography (0→20% MeOH/EtOAc) afforded the desired product as a brown oil (4.14 g, 70% yield).

Step 3: Synthesis of 2-(4-(2-(2-(3-(4-(5-((di-tert-butoxycarbonylamino)methyl)pyrimidin-2-yl)piperazin-1-yl)-3-oxo-propoxy)ethoxy)ethyl)piperazin-1-yl)pyrimidine-5-carboxylic acid To a solution of ethyl 2-(4-(2-(2-(3-(4-(5-((bis(tert-butoxycarbonyl)amino)methyl)pyrimidin-2-yl)piperazin-1-yl)-3-oxo-propoxy)ethoxy)ethyl)piperazin-1-yl)pyrimidine-5-carboxylate (1.4 g, 1.81 mmol, 1.0 equiv) in THF (28 mL), EtOH (14 mL) and $H_2O$ (14 mL) was added $LiOH{\cdot}H_2O$ (304.44 mg, 7.25 mmol, 4.0 equiv). The mixture was stirred at 40° C. for 30 min, at which point the reaction mixture was concentrated under reduced pressure. Purification by reverse phase chromatography (10→40% $MeCN/H_2O$) afforded the desired product as a yellow solid (500 mg, 43% yield).

Building Block AT. 2-{4-[2-(2-{4-[5-{[(tert-butoxy)carbonyl]amino}methyl)pyrimidin-2-yl]piperazin-1-yl}ethoxy)ethyl]piperazin-1-yl}pyrimidine-5-carboxylic acid

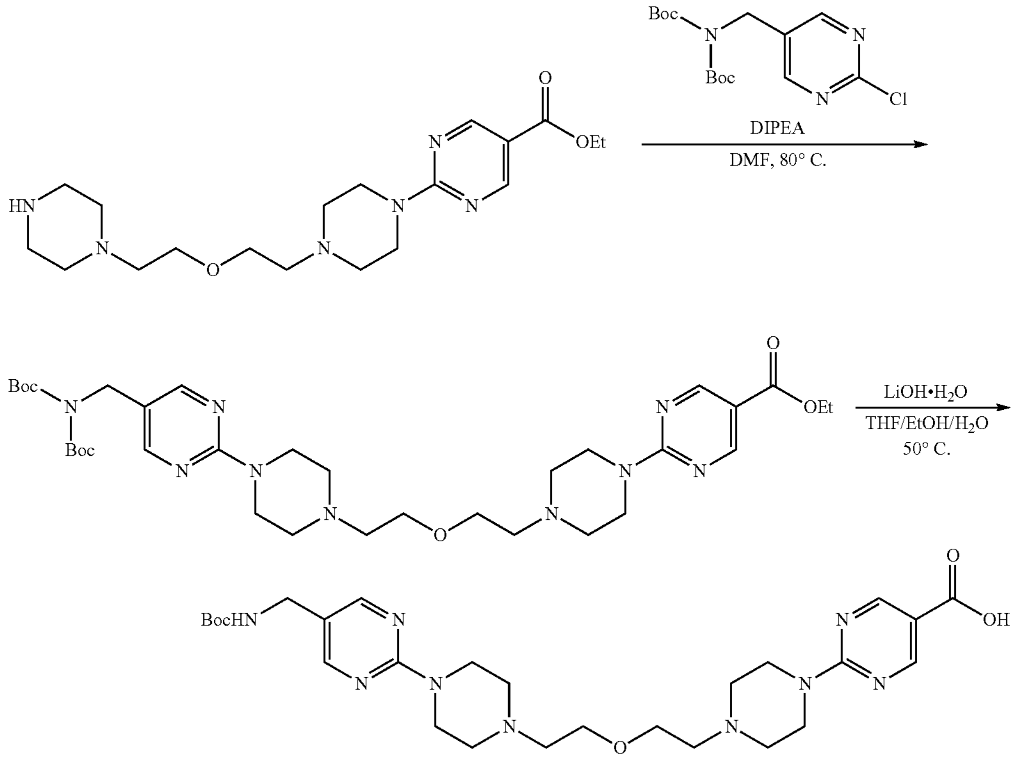

Step 1: Synthesis of ethyl 2-(4-(2-(2-(4-(5-(((di-tert-butoxycarbonyl)amino)methyl)pyrimidin-2-yl)piperazin-1-yl)ethoxy)ethyl)piperazin-1-yl)pyrimidine-5-carboxylate To a solution of ethyl 2-(4-(2-(2-(piperazin-1-yl)ethoxy)ethyl)piperazin-1-yl)pyrimidine-5-carboxylate hydrochloride (7.3 g, 13.56 mmol, 1.0 equiv, 4HCl) in DMF (75 mL) was added DIPEA (14.17 mL, 81.36 mmol, 6.0 equiv) and tert-butyl-N-tert-butoxycarbonyl-N-[(2-chloropyrimidin-5-yl)methyl]carbamate (5.59 g, 16.27 mmol, 1.2 equiv). The mixture was stirred at 80° C. for 12 h. The mixture was then cooled to room temperature and poured into $H_2O$ (300 mL). The aqueous phase was extracted with EtOAc (3×80 mL). The combined organic phases were washed with sat. $NH_4Cl$ (4×80 mL) and brine (150 mL), dried, filtered and the filtrate was concentrated under reduced pressure. Purification by silica gel chromatography (0%→17% MeOH/EtOAc) afforded the desired product (7.7 g, 81.1% yield) as a light yellow oil. LCMS (ESI) m/z: [M+Na] calcd for $C_{34}H_{53}N_9O_7$: 722.40; found 722.4.

Step 2: Synthesis of 2-(4-(2-(2-(4-(5-(((tert-butoxycarbonyl)amino)methyl)pyrimidin-2-yl)piperazin-1-yl)ethoxy)ethyl)piperazin-1-yl)pyrimidine-5-carboxylic acid To a solution of ethyl 2-(4-(2-(2-(4-(5-(((di-tert-butoxycarbonyl)amino)methyl)pyrimidin-2-yl)piperazin-1-yl)ethoxy)ethyl)piperazin-1-yl)pyrimidine-5-carboxylate (7.7 g, 11.00 mmol, 1.0 equiv) in THF (80 mL), EtOH (20 mL), and $H_2O$ (40 mL) was added $LiOH{\cdot}H_2O$ (2.31 g, 55.01 mmol, 5.0 equiv). The mixture was stirred at 50° C. for 26 h. The mixture was then concentrated under reduced pressure to remove THF and EtOH. The aqueous phase was neutralized with 0.5 N HCl, and concentrated under reduced pressure. Purification by reverse phase chromatography afforded the desired product (4.67 g, 74.3% yield) as a white solid. LCMS (ESI) m/z: [M−H] calcd for $C_{27}H_{41}N_9O_5$: 570.31; found 570.3.

Building Block AU. (R)-tert-butyl 4-(5-(((tert-butoxycarbonyl-N-tert-butoxycarbonyl)amino)methyl) pyrimidin-2-yl)piperazine-2-carboxylate

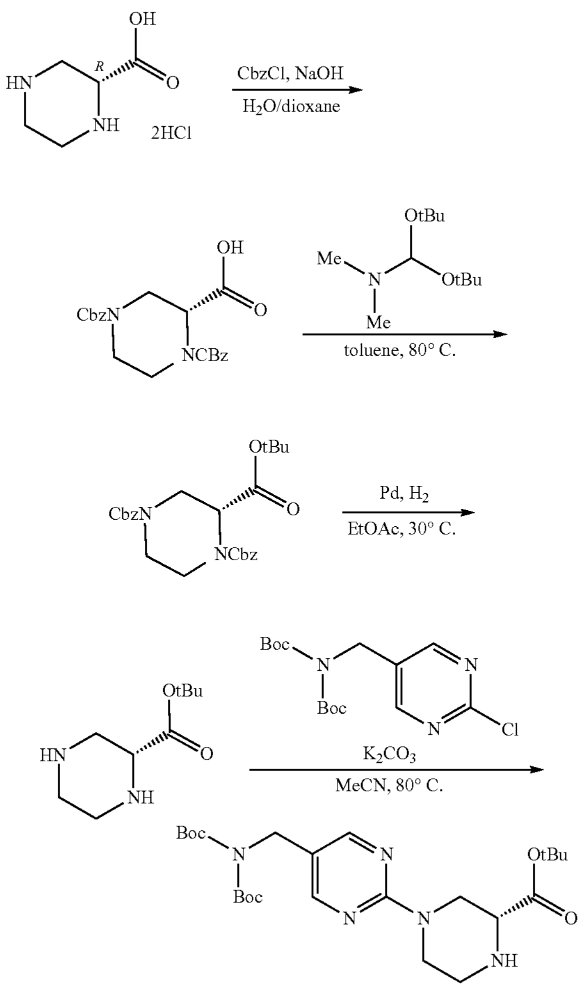

Step 1: Synthesis of (R)-1,4-bis((benzyloxy)carbonyl)piperazine-2-carboxylic acid To two separate batches containing a solution (2R)-piperazine-2-carboxylic acid (70 g, 344.71 mmol, 1 equiv, 2HCl) in $H_2O$ (700 mL) and dioxane (1120 mL) was added 50% aq. NaOH until pH=11. Benzyl chloroformate (156.82 mL, 1.10 mol, 3.2 equiv) was added and the reaction was stirred at room temperature for 12 h. The two reaction mixtures were combined and $H_2O$ (1200 mL) was added. The aqueous layer was extracted with MTBE (3×1000 mL), adjusted to pH=2 with con. HCl, and then extracted with EtOAc (2×1000 mL). The combined organic phases were dried, filtered, and concentrated under reduced pressure to afford the desired product (280 g, 86% yield). LCMS (ESI) m/z: [M+H] calcd for $C_{21}H_{22}N_2O_6$: 399.16; found 399.0.

Step 2: Synthesis of (R)-1,4-dibenzyl 2-tert-butyl piperazine-1,2,4-tricarboxylate To a solution of (R)-1,4-bis((benzyloxy)carbonyl)piperazine-2-carboxylic acid (70 g, 175.70 mmol, 1.0 equiv) in toluene (700 mL) at 80° C. was added 1,1-di-tert-butoxy-N,N-dimethylmethanamine (80.04 mL, 333.83 mmol, 1.9 equiv). The reaction was stirred at 80° C. for 2 h, at which point it was cooled to room temperature and partitioned between EtOAc (300 mL) and $H_2O$ (500 mL). The aqueous layer was extracted with EtOAc (2×500 mL) and the combined organic layers were dried, filtered, and concentrated under reduced pressure. Purification by silica gel chromatography (0→25 EtOAc/petroleum ether) afforded the desired product as a white solid (50 g, 57% yield). LCMS (ESI) m/z: [M+Na] calcd for $C_{25}H_{30}N_2O_6$: 477.20; found 476.9.

Step 3: Synthesis of (R)-tert-butyl piperazine-2-carboxylate

To a solution of (R)-1,4-dibenzyl 2-tert-butyl piperazine-1,2,4-tricarboxylate (50 g, 110.01 mmol, 1 equiv) in EtOAc (20 mL) was added Pd/C (15 g, 10 wt. %). The suspension was degassed under reduced pressure and purged with $H_2$ three times. The suspension was stirred under $H_2$ (30 psi) at 30° C. for 4 h. The reaction mixture was then filtered, the residue was washed with MeOH (5×200 mL), and the filtrate concentrated under reduced pressure to afford the desired product as a yellow oil (17 g, 81% yield). LCMS (ESI) m/z: [M+H] calcd for $C_9H_{18}N_2O_2$: 187.15; found 187.1.

Step 4: Synthesis of (R)-tert-butyl 4-(5-(((tert-butoxycarbonyl-N-tert-butoxycarbonyl)amino)methyl) pyrimidin-2-yl)piperazine-2-carboxylate To a suspension of (R)-tert-butyl piperazine-2-carboxylate (8 g, 23.27 mmol, 1.0 equiv) and tert-butyl-N-tert-butoxycarbonyl ((2-chloropyrimidin-5-yl)methyl)carbamate (5.20 g, 27.92 mmol, 1.2 equiv) in MeCN (100 mL) was added $K_2CO_3$ (6.43 g, 46.54 mmol, 2.0 equiv). The reaction mixture was heated to 80° C. for 12 h, at which point it was cooled to room temperature, filtered, and the filtrate was concentrated under reduced pressure. Purification by silica gel chromatography (0→100% EtOAc/petroleum ether) afforded the desired product as a yellow solid (9.2 g, 73% yield). LCMS (ESI) m/z: [M+H] calcd for $C_{24}H_{39}N_5O_6$: 494.30; found 494.1.

Building Block AV. (S)-tert-butyl 4-(5-(((tert-butoxycarbonyl-N-tert-butoxycarbonyl)amino)methyl) pyrimidin-2-yl)piperazine-2-carboxylate

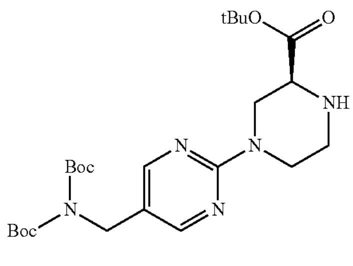 [SMILES: CC(C)(C)OC(=O)[C@@H]1CN(c2ncc(CN(C(=O)OC(C)(C)C)C(=O)OC(C)(C)C)cn2)CCN1]

This building block is prepared by a process similar to that for Building Block AU by utilizing (2S)-piperazine-2-carboxylic acid.

Building Block AW. (R)-2-(4-(2-(3-(2-(tert-butoxy-carbonyl)-4-(5-(((tert-butoxycarbonyl-N-tert-butoxy-carbonyl)amino)methyl)pyrimidin-2-yl)piperazin-1-yl)-3-oxopropoxy)ethyl)piperazin-1-yl)pyrimidine-5-carboxylic acid

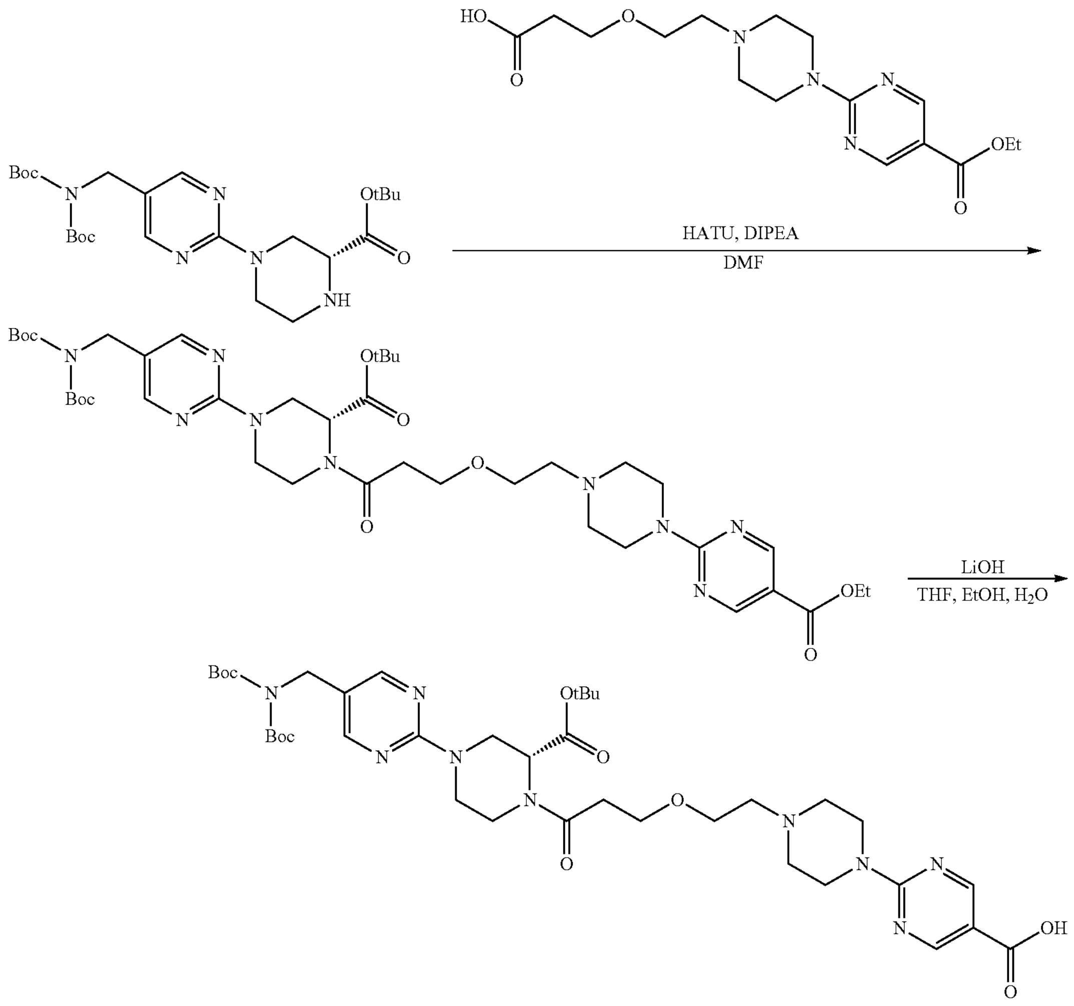

Step 1: Synthesis of (R)-ethyl 2-(4-(2-(3-(2-(tert-butoxycarbonyl)-4-(5-(((tert-butoxycarbonyl-N-tert-butoxycarbonyl)amino)methyl)pyrimidin-2-yl)piperazin-1-yl)-3-oxopropoxy)ethyl)piperazin-1-yl)pyrimidine-5-carboxylate To a solution of (R)-tert-butyl 4-(5-(((tert-butoxycarbonyl-N-tert-butoxycarbonyl)amino)methyl)pyrimidin-2-yl)piperazine-2-carboxylate (5.3 g, 11.36 mmol, 1.0 equiv, TFA) in DCM (80 mL) was added HATU (6.48 g, 17.05 mmol, 1.5 equiv) and DIPEA (7.92 mL, 45.45 mmol, 4.0 equiv). The reaction was stirred at room temperature for 30 min and then tert-butyl (2R)-4-(5-((bis(tert-butoxycarbonyl)amino)methyl)pyrimidin-2-yl)piperazine-2-carboxylate (5.61 g, 11.36 mmol, 1.0 equiv) was added. The mixture was stirred for 1 h, at which point sat. $NH_4Cl$ (80 mL) was added. The organic phase was washed with sat. $NH_4Cl$ (5×80 mL), dried, filtered, and concentrated under reduced pressure. Purification by silica gel chromatography (0-9% MeOH/EtOAc) afforded the desired product as a yellow solid (8.4 g, 85% yield).

Step 2: Synthesis of (R)-2-(4-(2-(3-(2-(tert-butoxy-carbonyl)-4-(5-(((tert-butoxycarbonyl-N-tert-butoxy carbonyl)amino)methyl)pyrimidin-2-yl)piperazin-1-yl)-3-oxopropoxy)ethyl)piperazin-1-yl)pyrimidine-5-carboxylic acid To two separate batches containing a solution a solution of (R)-ethyl 2-(4-(2-(3-(2-(tert-butoxycarbonyl)-4-(5-(((tert-butoxycarbonyl-N-tert-butoxycarbonyl)amino)methyl)pyrimidin-2-yl)piperazin-1-yl)-3-oxopropoxy)ethyl)piperazin-1-yl)pyrimidine-5-carboxylate (3.4 g, 4.11 mmol, 1.0 equiv) in THF (16 mL), EtOH (8 mL) and $H_2O$ (8 mL) was added $LiOH{\cdot}H_2O$ (344.61 mg, 8.21 mmol, 2.0 equiv). The mixture was stirred at room temperature for 2 h. The two reaction mixtures were then combined and were adjusted to pH=7 with 1N HCl. The solution was concentrated under reduced pressure to remove THF and EtOH. The solution was then filtered, and the resulting solid was purified by reverse phase chromatography to afford the desired product as a white solid (4 g, 59% yield). LCMS (ESI) m/z: [M+H] calcd for $C_{38}H_{57}N_9O_{10}$: 800.43; found 800.3.

Building Block AX. (S)-2-(4-(2-(3-(2-(tert-butoxy-carbonyl)-4-(5-(((tert-butoxycarbonyl-N-tert-butoxy-carbonyl)amino)methyl)pyrimidin-2-yl)piperazin-1-yl)-3-oxopropoxy)ethyl)piperazin-1-yl)pyrimidine-5-carboxylic acid

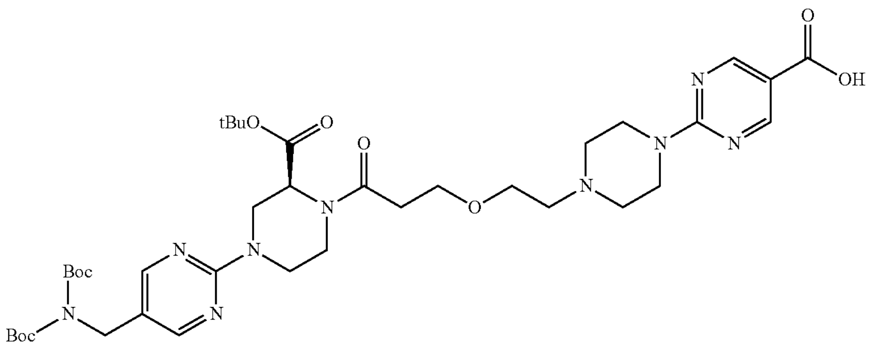 [SMILES: CC(C)(C)OC(=O)[C@@H]1CN(c2ncc(CN(C(=O)OC(C)(C)C)C(=O)OC(C)(C)C)cn2)CCN1C(=O)CCOCCN1CCN(c2ncc(C(=O)O)cn2)CC1]

This building block is prepared from Building Block AV by a process similar to that for Building Block AW.

Building Block AY. 1'-(2-(3-(4-(5-(((tert-butoxycar-bonyl)amino)methyl)pyrimidin-2-yl) piperazin-1-yl)-3-oxopropoxy)ethyl)-[1,4'-bipiperidine]-4-car-boxylic acid

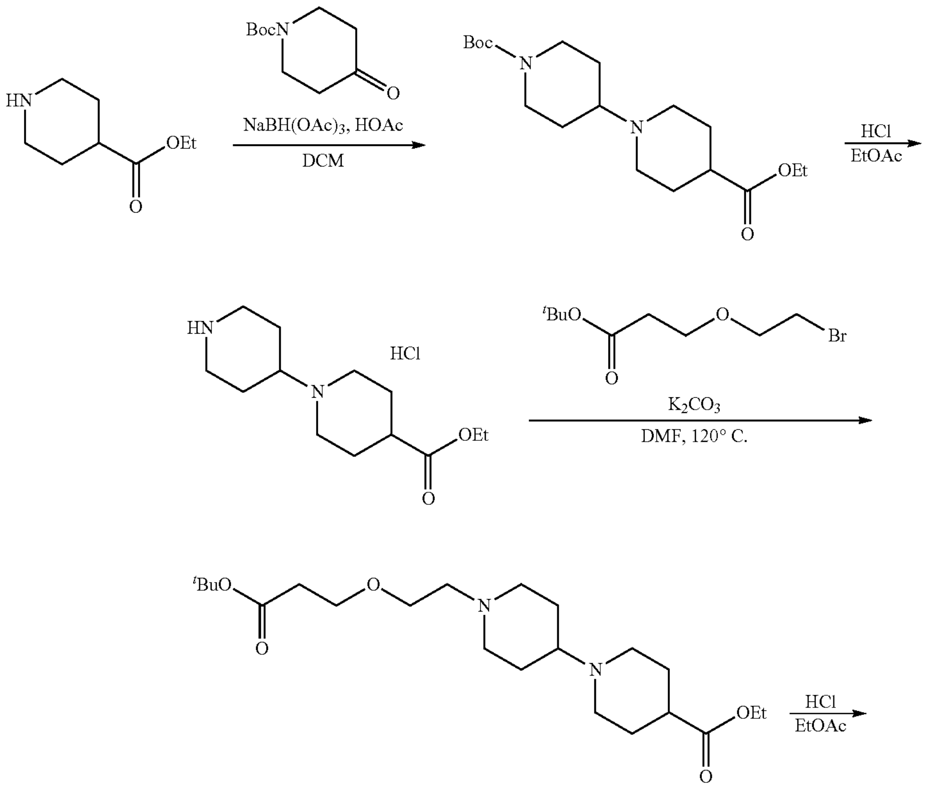

-continued

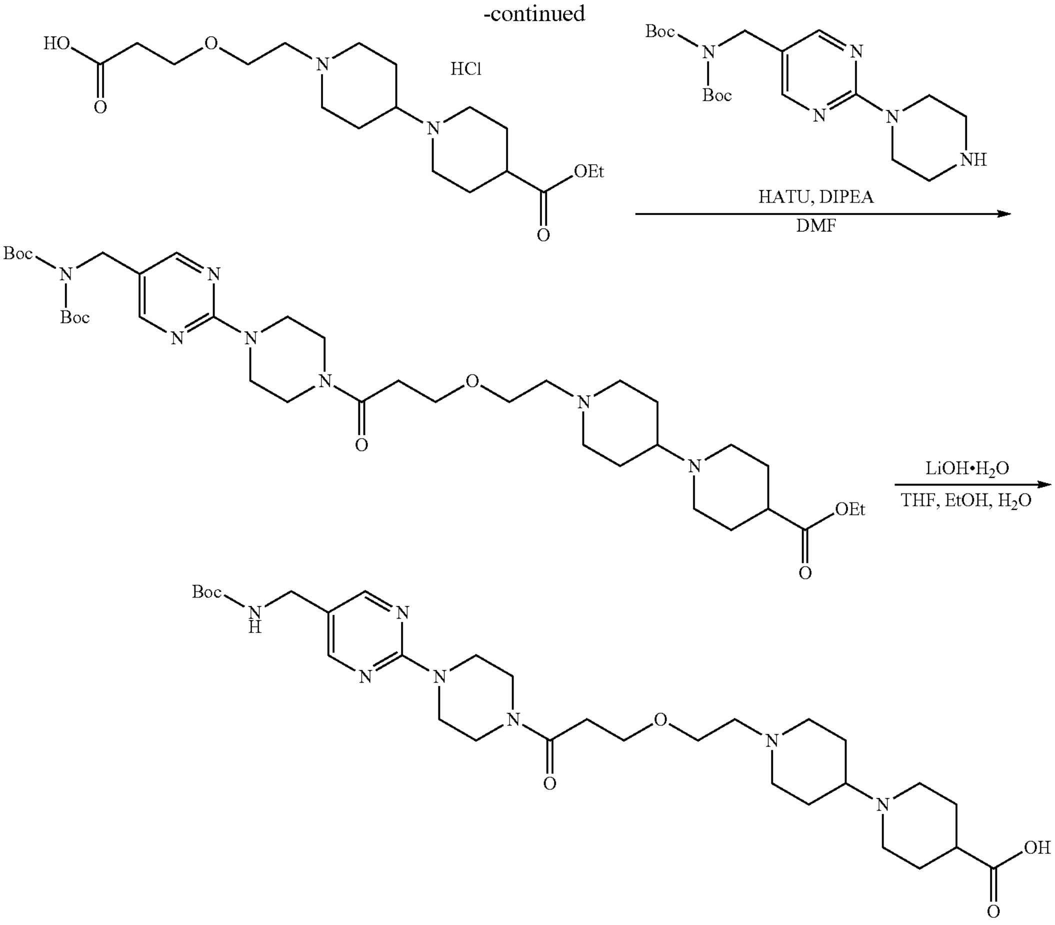

Step 1: Synthesis of 1-tert-butyl 4-ethyl [1,4'-bipiperidine]-1',4-dicarboxylate To a solution of ethyl piperidine-4-carboxylate (30 g, 150.57 mmol, 1.0 equiv) and tert-butyl 4-oxopiperidine-1-carboxylate (23.67 g, 150.57 mmol, 1.0 equiv) in DCM (300 mL) was added HOAc (6.00 mL, 104.95 mmol, 0.7 equiv). The mixture was stirred at room temperature for 30 min, then $NaBH(OAc)_3$ (63.82 g, 301.13 mmol, 2.0 equiv) was added. The mixture was stirred for 16 h, at which point $H_2O$ (50 mL) was added. The aqueous phase was extracted with DCM (3x15 mL) and the combined organic phases were washed with brine (10 mL), dried, filtered, and concentrated under reduced pressure. Purification by silica gel chromatography (8-100 MeOH/EtOAc) afforded the desired product as a yellow oil (30 g, 59% yield).

Step 2: Synthesis of ethyl [1,4'-bipiperidine]-4-carboxylate

To a solution of HCl in EtOAc (200 mL) was added 1'-tert-butyl 4-ethyl [1,4'-bipiperidine]-1',4-dicarboxylate (20 g, 58.74 mmol, 1.0 equiv). The mixture was stirred at room temperature for 3 h. The mixture was then concentrated under reduced pressure to afford the desired crude product as a white solid (15 g, HCl salt).

Step 3: Synthesis of ethyl 1'-(2-(3-(tert-butoxy)-3-oxopropoxy)ethyl)-[1,4'-bipiperidine]-4-carboxylate To a solution of tert-butyl 3-(2-bromoethoxy)propanoate (6.46 g, 25.54 mmol, 1.0 equiv) in DMF (240 mL) was added $K_2CO_3$ (10.59 g, 76.61 mmol, 3.0 equiv) and ethyl [1,4'-bipiperidine]-4-carboxylate (8 g, 25.54 mmol, 1.0 equiv, 2HCl). The mixture was stirred at 120° C. for 12 h, at which point the reaction was cooled to room temperature, filtered, the filter cake washed with $H_2O$ (20 mL), and the filtrate was concentrated under reduced pressure. Purification by silica gel chromatography (0→11% MeOH/EtOAc) afforded the desired product as a yellow oil (6.6 g, 63% yield).

Step 4: Synthesis of 3-(2-(4-(ethoxycarbonyl)-[1,4'-bipiperidin]-1'-yl)ethoxy)propanoic acid To the solution of HCl in EtOAc (70 mL) was added ethyl 1'-(2-(3-(tert-butoxy)-3-oxopropoxy) ethyl)-[1,4'-bipiperidine]-4-carboxylate (6.6 g, 16.00 mmol, 1.0 equiv). The mixture was stirred at room temperature for 3 h, at which point the reaction was concentrated under reduced pressure to afford the desired product as a white solid (6.5 g, 95% yield, 2HCl).

Step 5: Synthesis of ethyl 1'-(2-(3-(4-(5-(((N,N-di-tert-butoxycarbonyl)amino)methyl)pyrimidin-2-yl)piperazin-1-yl)-3-oxopropoxy)ethyl)-[1,4'-bipiperidine]-4-carboxylate To a solution of tert-butyl-tert-butoxycarbonyl((2-(piperazin-1-yl)pyrimidin-5-yl)methyl)carbamate (2.49 g, 6.33 mmol, 1.5 equiv) in DMF (40 mL) was added DIPEA (9.74 mL, 55.89 mmol, 6.0 equiv) and HATU (5.31 g, 13.97 mmol, 1.5 equiv). The mixture was stirred at room temperature for 30 min, and then 3-(2-(4-(ethoxycarbonyl)-[1,4'-bipiperidin]-1'-yl)ethoxy) propanoic acid (4 g, 9.32 mmol, 1.0 equiv, 2HCl) was added. The mixture was stirred at for 1.5 h, at which point $H_2O$ (5 mL) and EtOAc (20 mL) were added. The aqueous phase was extracted with EtOAc (3×10 mL) and the combined organic phases were washed with brine (5 mL), dried, filtered and concentrated under reduced pressure. Purification by reverse phase chromatography afforded the desired product as a brown oil (1.6 g, 23% yield). LCMS (ESI) m/z: [M+H] calcd for $C_{37}H_{61}N_7O_8$: 732.47; found 732.6.

Step 6: Synthesis of 1'-(2-(3-(4-(5-(((tert-butoxycarbonyl)amino)methyl)pyrimidin-2-yl)piperazin-1-yl)-3-oxopropoxy)ethyl)-[1,4'-bipiperidine]-4-carboxylic acid To a solution of ethyl 1'-(2-(3-(4-(5-(((N,N-di-tert-butoxycarbonyl)amino)methyl)pyrimidin-2-yl)piperazin-1-yl)-3-oxopropoxy)ethyl)-[1,4'-bipiperidine]-4-carboxylate (1.4 g, 1.91 mmol, 1.0 equiv) in THF (7.5 mL), EtOH (3.8 mL), and $H_2O$ (3.8 mL) was added LiOH·$H_2O$ (321.07 mg, 7.65 mmol, 4.0 equiv). The mixture was stirred at room temperature for 2 h, at which point the mixture was concentrated under reduced pressure. Purification by reverse phase chromatography (5→38% MeCN/$H_2O$) afforded the desired product as a yellow solid (325 mg, 22% yield). LCMS (ESI) m/z: [M+H] calcd for $C_{30}H_{49}N_7O_6$: 604.38; found 604.3.

Building Block AZ. 1-(4-{2-[2-(2-{[(benzyloxy)carbonyl]amino}ethoxy)ethoxy]ethyl}piperazin-1-yl)-3,6,9,12-tetraoxapentadecan-15-oic acid

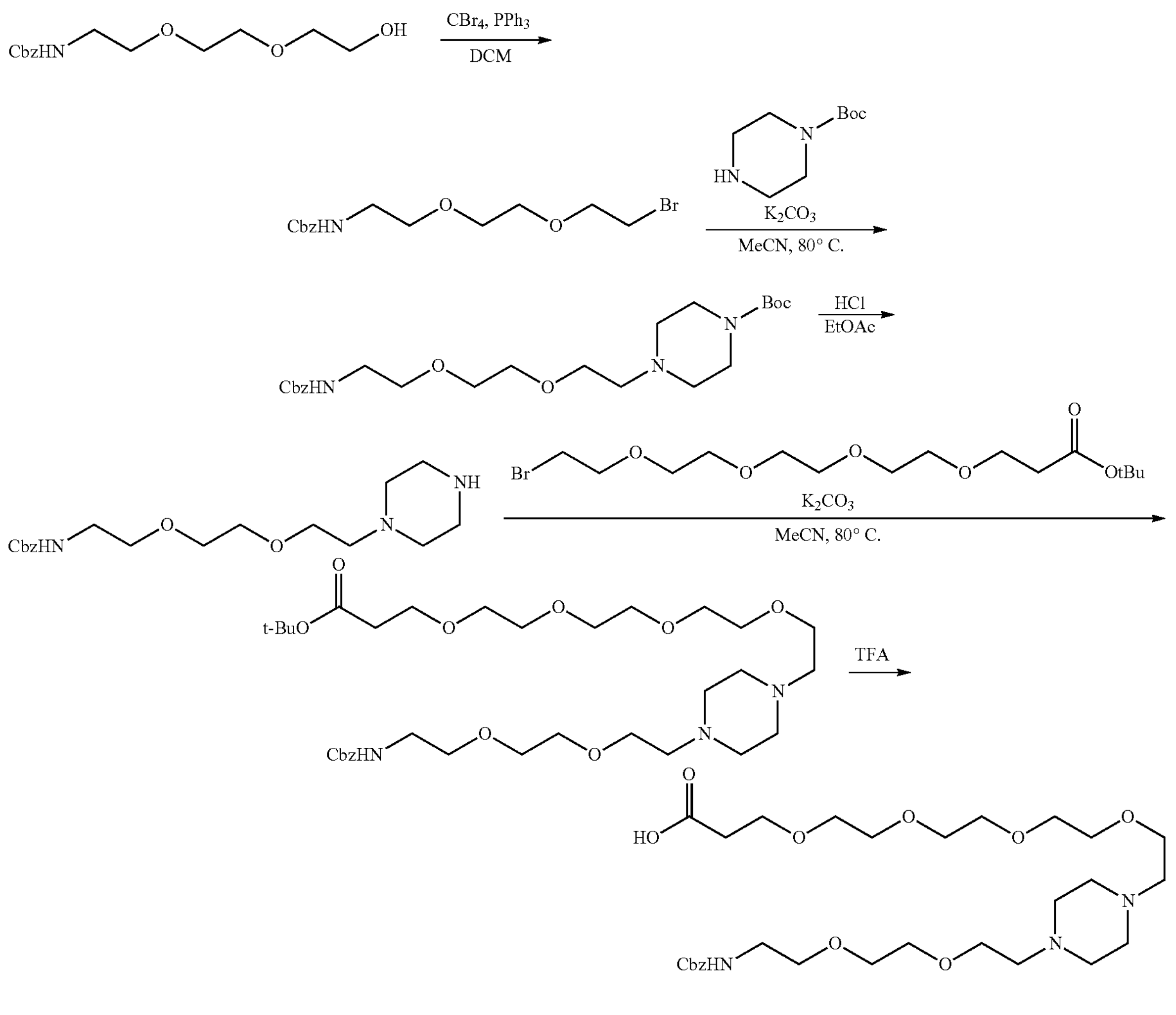

Step 1: Synthesis of benzyl (2-(2-(2-bromoethoxy)ethoxy)ethyl)carbamate

To a solution of benzyl (2-(2-(2-hydroxyethoxy)ethoxy)ethyl)carbamate (10 g, 35.30 mmol, 1.0 equiv) in DCM (300 mL) at 0° C. was added $PPh_3$ (13.79 g, 52.59 mmol, 1.49 equiv) and $CBr_4$ (17.44 g, 52.59 mmol, 1.49 equiv). Then the mixture was warmed to room temperature and stirred for 12 h. The reaction mixture was then filtered, and the filtrate was concentrated under reduced pressure. Purification by silica gel chromatography (1%→25% EtOAc/petroleum ether) afforded the desired product (10.8 g, 88.4% yield) as yellow oil.

Step 2: Synthesis of tert-butyl 4-(3-oxo-1-phenyl-2,7,10-trioxa-4-azadodecan-12-yl)piperazine-1-carboxylate To a solution of benzyl (2-(2-(2-bromoethoxy)ethoxy)ethyl)carbamate (10.8 g, 31.19 mmol, 1.0 equiv) and tert-butyl piperazine-1-carboxylate (5.81 g, 31.19 mmol, 1.0 equiv) in MeCN (100 mL) was added $K_2CO_3$ (4.31 g, 31.19 mmol, 1.0 equiv). The mixture was stirred at 80° C. for 1 h. The reaction mixture was then filtered, and the filtrate was concentrated under reduced pressure. Purification by silica gel chromatography (0%→50% MeOH/EtOAc) afforded the desired product (13.1 g, 93.0% yield) as yellow oil.

Step 3: Synthesis of benzyl (2-(2-(2-(piperazin-1-yl)ethoxy)ethoxy)ethyl)carbamate A solution of tert-butyl 4-(3-oxo-1-phenyl-2,7,10-trioxa-4-azadodecan-12-yl)piperazine-1-carboxylate (5.64 g, 12.49 mmol, 1.0 equiv) in HCl/EtOAc (50 mL, 4 M) was stirred at room temperature for 1 h. The reaction mixture was then concentrated under reduced pressure to afford the desired product (5.23 g, crude, HCl salt) as yellow oil.

Step 4: Synthesis of tert-butyl 1-(4-(3-oxo-1-phenyl-2,7,10-trioxa-4-azadodecan-12-yl)piperazin-1-yl)-3,6,9,12-tetraoxapentadecan-15-oate A solution of benzyl (2-(2-(2-(piperazin-1-yl)ethoxy)ethoxy)ethyl)carbamate (13.3 g, 31.34 mmol, 1.0 equiv, 2HCl) and tert-butyl 1-bromo-3,6,9,12-tetraoxapentadecan-15-oate in MeCN (150 mL) was added $K_2CO_3$ (21.66 g, 156.71 mmol, 5.0 equiv). The mixture was stirred at 80° C. for 12 h. The reaction mixture was then filtered, and the filtrate was concentrated under reduced pressure. Purification by silica gel chromatography (1%→17% MeOH/DCM) afforded the desired product (5.4 g, 26.3% yield) as a yellow oil.

Step 5: Synthesis of 1-(4-(3-oxo-1-phenyl-2,7,10-trioxa-4-azadodecan-12-yl)piperazin-1-yl)-3,6,9,12-tetraoxapentadecan-15-oic acid A solution of tert-butyl 1-(4-(3-oxo-1-phenyl-2,7,10-trioxa-4-azadodecan-12-yl)piperazin-1-yl)-3,6,9,12-tetraoxapentadecan-15-oate (2.4 g, 3.66 mmol, 1.0 equiv) in TFA (20 mL) was stirred at room temperature for 30 min. The reaction mixture was then concentrated under reduced pressure to afford the desired product (3.03 g, TFA salt) as yellow oil.

Building Block BA. (R)-2-(2-(tert-butoxycarbonyl)-4-(6-(tert-butoxycarbonyl)-5,6,7,8-tetrahydropyrido[4,3-d]pyrimidin-2-yl)piperazin-1-yl)pyrimidine-5-carboxylic acid

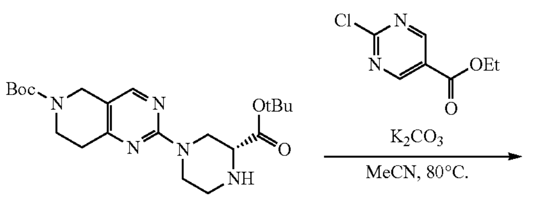

-continued

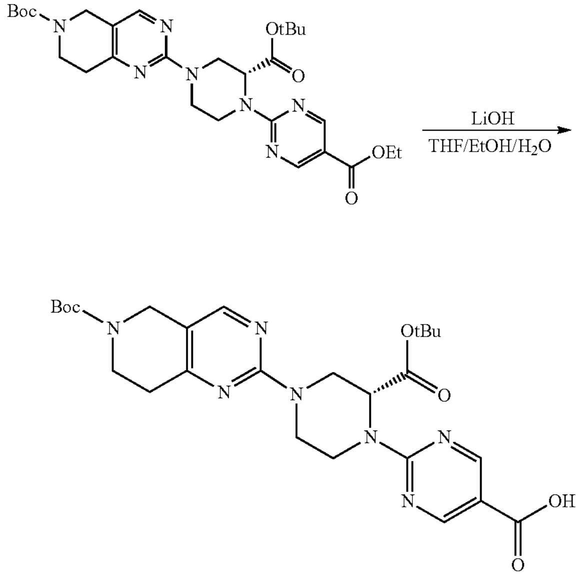

Step 1: Synthesis of (R)-tert-butyl 2-(3-(tert-butoxycarbonyl)-4-(5-(ethoxycarbonyl)pyrimidin-2-yl)piperazin-1-yl)-7,8-dihydropyrido[4,3-d]pyrimidine-6(5H)-carboxylate To two separate batches run in parallel each containing a solution of (R)-tert-butyl 2-(3-(tert-butoxycarbonyl)piperazin-1-yl)-7,8-dihydropyrido[4,3-d]pyrimidine-6(5H)-carboxylate (6 g, 14.30 mmol, 1.0 equiv) and $K_2CO_3$ (3.95 g, 28.60 mmol, 2.0 equiv) in MeCN (80 mL) was added ethyl 2-chloropyrimidine-5-carboxylate (3.20 g, 17.16 mmol, 1.2 equiv). The reaction mixtures were stirred at 80° C. for 12 h. The two reactions mixtures were combined and filtered, the residue was washed with EtOAc (3×50 mL), and the filtrate was concentrated under reduced pressure. Purification by silica gel chromatography (0%→17% MeOH/EtOAc) afforded the desired product (15 g, 91.5% yield) as a yellow solid. LCMS (ESI) m/z: [M+H] calcd for $C_{28}H_{39}N_7O_6$: 570.31; found 570.1.

Step 2: Synthesis of (R)-2-(2-(tert-butoxycarbonyl)-4-(6-(tert-butoxycarbonyl)-5,6,7,8-tetrahydropyrido[4,3-d]pyrimidin-2-yl)piperazin-1-yl)pyrimidine-5-carboxylic acid To a solution of (R)-tert-butyl 2-(3-(tert-butoxycarbonyl)-4-(5-(ethoxycarbonyl)pyrimidin-2-yl)piperazin-1-yl)-7,8-dihydropyrido[4,3-d]pyrimidine-6(5H)-carboxylate (15 g, 26.33 mmol, 1.0 equiv) in THF (80 mL), EtOH (40 mL) and $H_2O$ (40 mL) was added $LiOH \cdot H_2O$ (2.21 g, 52.66 mmol, 2.0 equiv). The mixture was stirred at room temperature for 6 h. The reaction mixture was then adjusted to pH=6 with 1 N HCl. The resulting suspension was filtered, and the solid cake was dried under reduced pressure to afford the desired product (10.87 g, 75.9% yield) as a white solid. LCMS (ESI) m/z: [M+H] calcd for $C_{26}H_{35}N_7O_6$: 542.27; found 542.1.

Building Block BB. (S)-2-(2-(tert-butoxycarbonyl)-4-(6-(tert-butoxycarbonyl)-5,6,7,8-tetrahydropyrido[4,3-d]pyrimidin-2-yl)piperazin-1-yl)pyrimidine-5-carboxylic acid

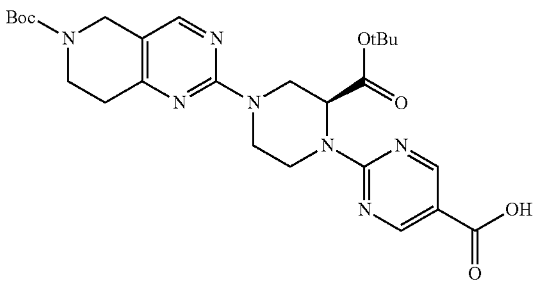 [SMILES: CC(C)(C)OC(=O)[C@@H]1CN(c2ncc3c(n2)CCN(C(=O)OC(C)(C)C)C3)CCN1c1ncc(C(=O)O)cn1]

This building block is prepared from Building Block AA by a process similar to that for Building Block BA.

Building Block BC. 2-[(2R)-2-[(tert-butoxy)carbonyl]-4-[5-({[(tert-butoxy)carbonyl]amino}methyl)pyrimidin-2-yl]piperazin-1-yl]pyrimidine-5-carboxylic acid

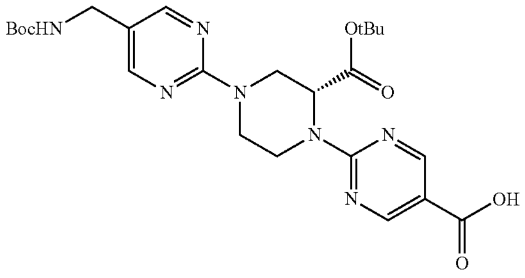 [SMILES: CC(C)(C)OC(=O)NCc1cnc(N2CCN(c3ncc(C(=O)O)cn3)[C@@H](C(=O)OC(C)(C)C)C2)nc1]

This building block is prepared from Building Block AU by a process similar to that for Building Block BA.

Building Block BD. 2-[(2S)-2-[(tert-butoxy)carbonyl]-4-[5-({[(tert-butoxy)carbonyl]amino}methyl)pyrimidin-2-yl]piperazin-1-yl]pyrimidine-5-carboxylic acid

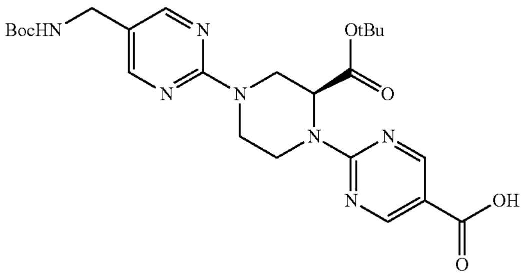 [SMILES: CC(C)(C)OC(=O)NCc1cnc(N2CCN(c3ncc(C(=O)O)cn3)[C@H](C(=O)OC(C)(C)C)C2)nc1]

This building block is prepared from Building Block AV by a process similar to that for Building Block BA.

Building Block BE. 15-(6-((4-amino-3-(2-aminobenzo[d]oxazol-5-yl)-1H-pyrazolo[3,4-d]pyrimidin-1-yl)methyl)-3,4-dihydroisoquinolin-2(1H)-yl)-1-((1S,4S)-5-(2-(2-(2-aminoethoxy)ethoxy)ethyl)-2,5-diazabicyclo[2.2.1]heptan-2-yl)-3,6,9,12-tetraoxapentadecan-15-one

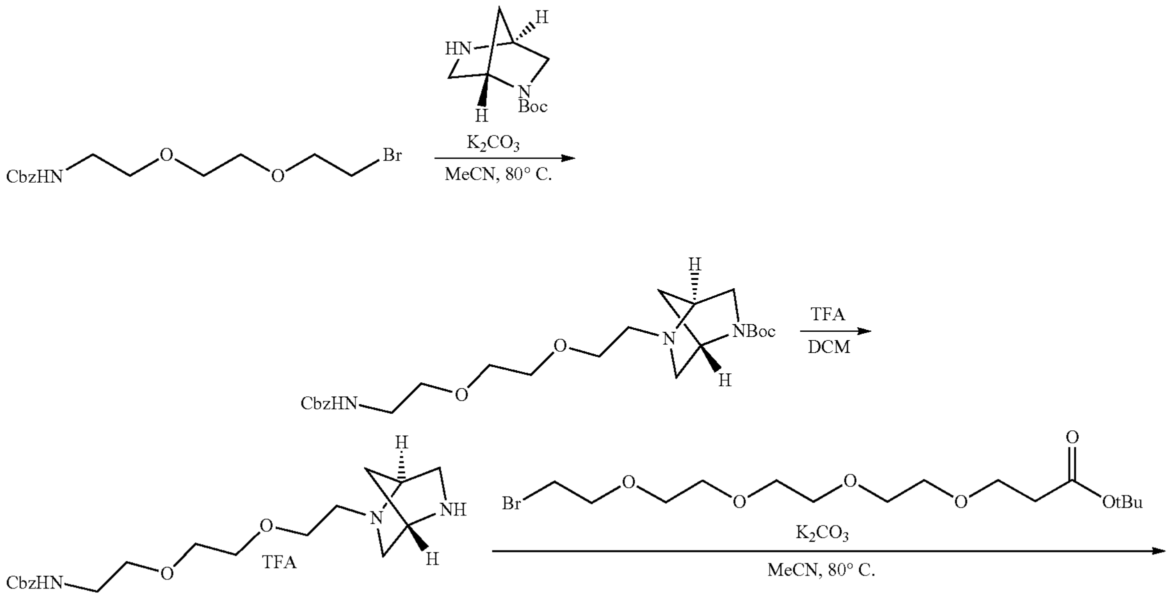

-continued

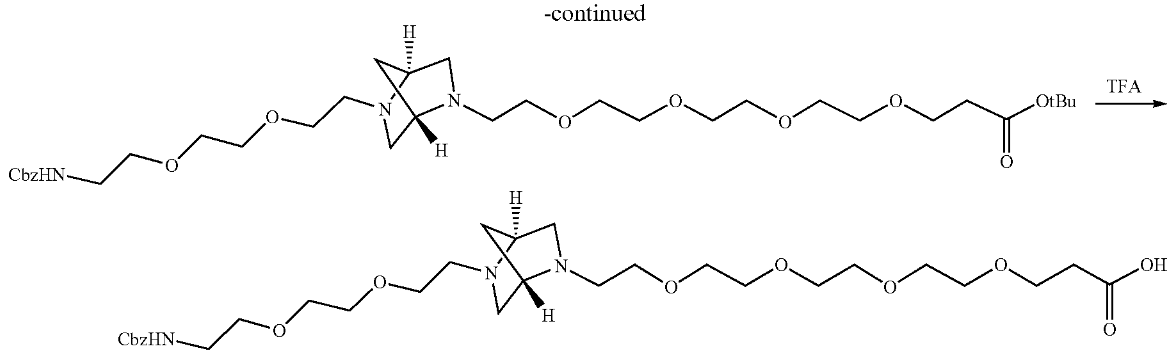

Step 1: Synthesis of (1S,4S)-tert-butyl 5-(3-oxo-1-phenyl-2,7,10-trioxa-4-azadodecan-12-yl)-2,5-diazabicyclo[2.2.1]heptane-2-carboxylate To a solution of (1S,4S)-tert-butyl 2,5-diazabicyclo[2.2.1]heptane-2-carboxylate (2.85 g, 14.37 mmol, 1.0 equiv) in MeCN (50 mL) was added $K_2CO_3$ (3.97 g, 28.75 mmol, 2.0 equiv) and benzyl (2-(2-(2-bromoethoxy)ethoxy)ethyl)carbamate (4.98 g, 14.37 mmol, 1.0 equiv). The mixture was stirred at 80° C. for 24 h. The reaction mixture was then filtered, and the filtrate was concentrated under reduced pressure. Purification by silica gel chromatography (0→10% MeOH/EtOAc) afforded the desired product (6.2 g, 93.0% yield) as colorless oil. LCMS (ESI) m/z: [M+H] calcd for $C_{24}H_{37}N_3O_6$: 464.27; found 464.2.

Step 2: Synthesis of benzyl (2-(2-(2-((1S,4S)-2,5-diazabicyclo[2.2.1]heptan-2-yl)ethoxy)ethoxy)ethyl)carbamate To a solution of (1S,4S)-tert-butyl 5-(3-oxo-1-phenyl-2,7,10-trioxa-4-azadodecan-12-yl)-2,5-diazabicyclo[2.2.1]heptane-2-carboxylate (6.2 g, 13.37 mmol, 1.0 equiv) in DCM (60 mL) was added TFA (20.7 mL, 279.12 mmol, 20.9 equiv). The reaction was stirred for 2 h, at which point the mixture was concentrated under reduced pressure at 45° C. to afford the desired crude product (10.5 g, 4TFA) as light brown oil, which was used the next step directly. LCMS (ESI) m/z: [M+H] calcd for $C_{19}H_{29}N_3O_4$: 364.22; found 364.2.

Step 3: Synthesis of tert-butyl 1-((1S,4S)-5-(3-oxo-1-phenyl-2,7,10-trioxa-4-azadodecan-12-yl)-2,5-diazabicyclo[2.2.1]heptan-2-yl)-3,6,9,12-tetraoxapentadecan-15-oate To a solution of benzyl (2-(2-(2-((1S,4S)-2,5-diazabicyclo[2.2.1]heptan-2-yl)ethoxy) ethoxy)ethyl)carbamate (5 g, 6.10 mmol, 1.0 equiv, 4TFA) in MeCN (80 mL) was added $K_2CO_3$ (5.06 g, 36.61 mmol, 6.0 equiv) and tert-butyl 1-bromo-3,6,9,12-tetraoxapentadecan-15-oate (2.35 g, 6.10 mmol, 1.0 equiv). The reaction mixture was stirred at 80° C. for 12 h. The reaction mixture was then filtered, and the filtrate was concentrated under reduced pressure. Purification by silica gel chromatography (0→15% MeOH/EtOAc) afforded the desired product (5.2 g, 92.8% yield) as light yellow oil. LCMS (ESI) m/z: [M+H] calcd for $C_{34}H_{57}N_3O_{10}$: 668.4; found 668.4.

Step 4: Synthesis of 1-((1S,4S)-5-(3-oxo-1-phenyl-2,7,10-trioxa-4-azadodecan-12-yl)-2,5-diazabicyclo[2.2.1]heptan-2-yl)-3,6,9,12-tetraoxapentadecan-15-oic acid A solution of tert-butyl 1-((1S,4S)-5-(3-oxo-1-phenyl-2,7,10-trioxa-4-azadodecan-12-yl)-2,5-diazabicyclo[2.2.1]heptan-2-yl)-3,6,9,12-tetraoxapentadecan-15-oate (5.2 g, 5.66 mmol, 1.0 equiv) in TFA (47.3 mL, 638.27 mmol, 112.75 equiv) was stirred at room temperature for 30 min. The mixture was then concentrated under reduced pressure at 45° C. Purification by reverse phase chromatography (2→35% $MeCN/H_2O$ (0.05% $NH_4OH$)) afforded the desired product (1.88 g, 54.3% yield) as light brown oil. LCMS (ESI) m/z: [M+H] calcd for $C_{30}H_{49}N_3O_{10}$: 612.34; found 612.3.

Building Block BF. 21-(6-((4-amino-3-(2-aminobenzo[d]oxazol-5-yl)-1H-pyrazolo[3,4-d]pyrimidin-1-yl)methyl)-3,4-dihydroisoquinolin-2(1H)-yl)-1-(piperazin-1-yl)-3,6,9,12,15,18-hexaoxahenicosan-21-one

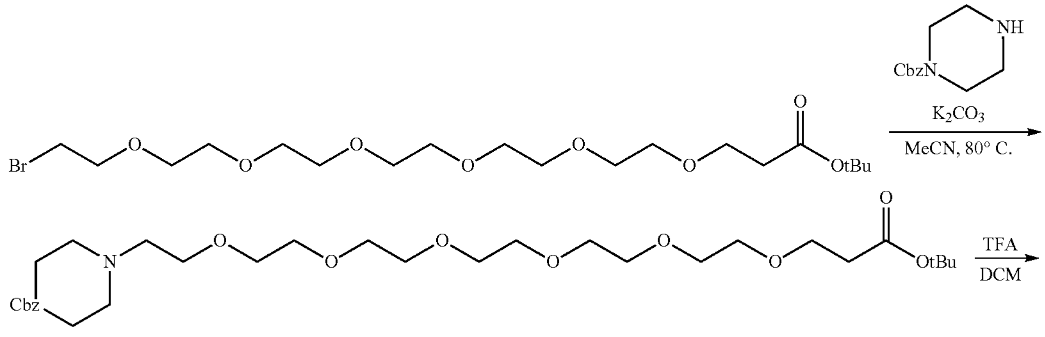

-continued

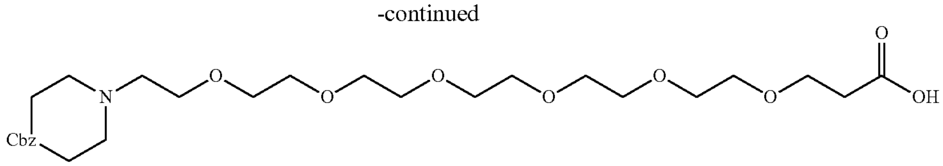

Step 1: Synthesis of benzyl 4-(23,23-dimethyl-21-oxo-3,6,9,12,15,18,22-heptaoxatetracosyl) piperazine-1-carboxylate To a solution of tert-butyl 1-bromo-3,6,9,12,15,18-hexaoxahenicosan-21-oate (5 g, 10.56 mmol, 1.0 equiv) and benzyl piperazine-1-carboxylate (2.62 mL, 11.62 mmol, 1.1 equiv, HCl) in MeCN (50 mL) was added $K_2CO_3$ (4.38 g, 31.69 mmol, 3.0 equiv). The reaction mixture was stirred at 80° C. for 10 h. The mixture was then filtered, the solid cake washed with EtOAc (3x3 mL), and the filtrate concentrated under reduced pressure. Purification by silica gel chromatography (0→10% MeOH/EtOAc) afforded the desired product (4 g, 61.8% yield) as a red liquid.

Step 2: Synthesis of 1-(4-((benzyloxy)carbonyl) piperazin-1-yl)-3,6,9,12,15,18-hexaoxahenicosan-1-oic acid To a solution of benzyl 4-(23,23-dimethyl-21-oxo-3,6,9,12,15,18,22-heptaoxatetracosyl)piperazine-1-carboxylate (1.8 g, 2.94 mmol, 1.0 equiv) in DCM (10 mL) was added TFA (10 mL). The solution was stirred for 0.5 h. The solution was then concentrated under reduced pressure. To the residue was added DCM (30 mL) and then the solution was concentrated under reduced pressure to afford the desired product (1.6 g, 2.87 mmol, TFA) as a red liquid.

Preparation of Rapamycin Monomers.

Monomer 1. 40(R)—O-(4-nitrophenyl)carbonate rapamycin

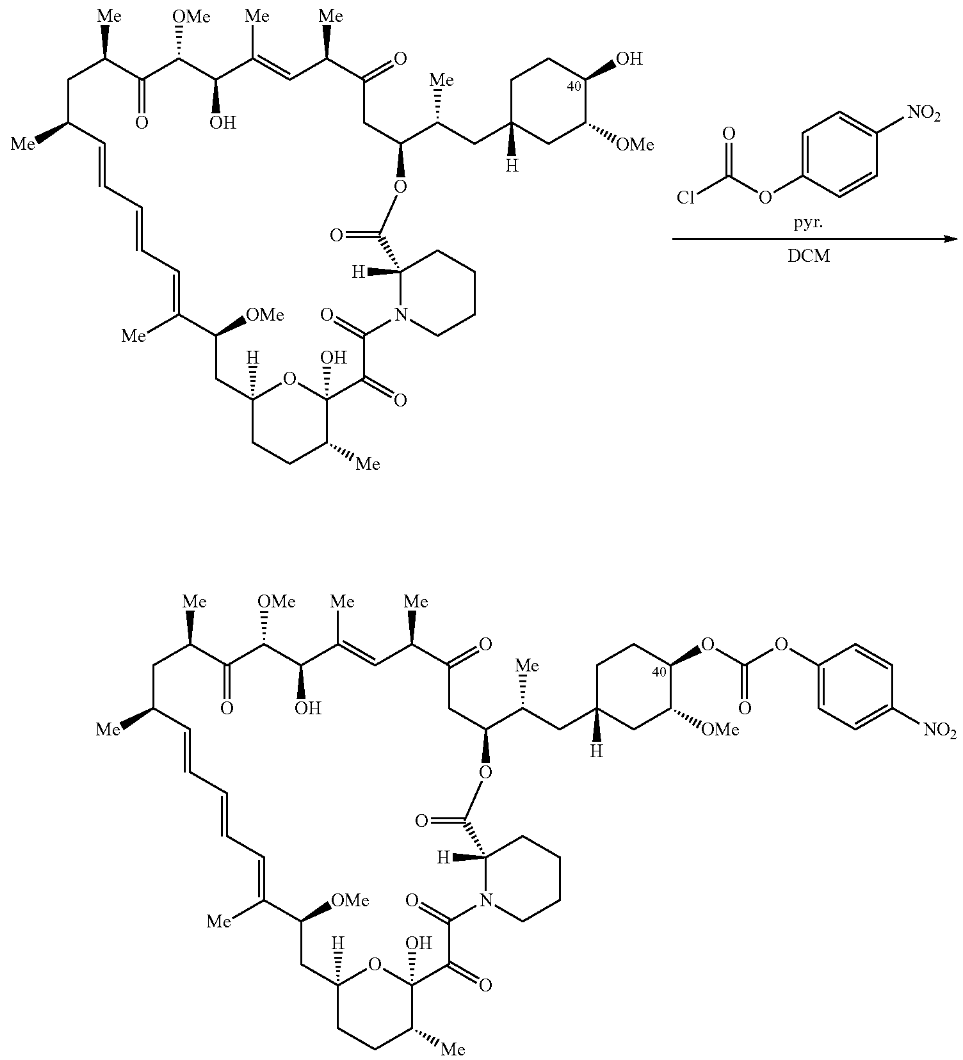

To a solution of rapamycin (30.10 g, 32.92 mmol, 1.0 equiv) in DCM (148.9 mL) was added pyridine (29.6 mL, 367 mmol, 11.1 equiv). The solution was cooled to −78° C. and then p-nitrophenyl chloroformate (12.48 g, 61.92 mmol, 1.9 equiv) was added. The reaction was stirred at −78° C. for 2 h. To the reaction mixture was then added DCM and the solution was then poured into $H_2O$. The aqueous layer was extracted with DCM and the combined organic layers were dried over $MgSO_4$, and concentrated under reduced pressure. The crude material was purified by silica gel chromatography (0→50% EtOAc/hexanes) to provide the product (23.1 g, 59.2% yield) as a white solid. LCMS (ESI) m/z: [M+Na] calcd for $C_{58}H_{82}N_2O_{17}$: 1101.55; found 1101.6.

Monomer 2. 32(R)-hydroxy 40(R)—O-(4-nitrophenyl)carbonate rapamycin

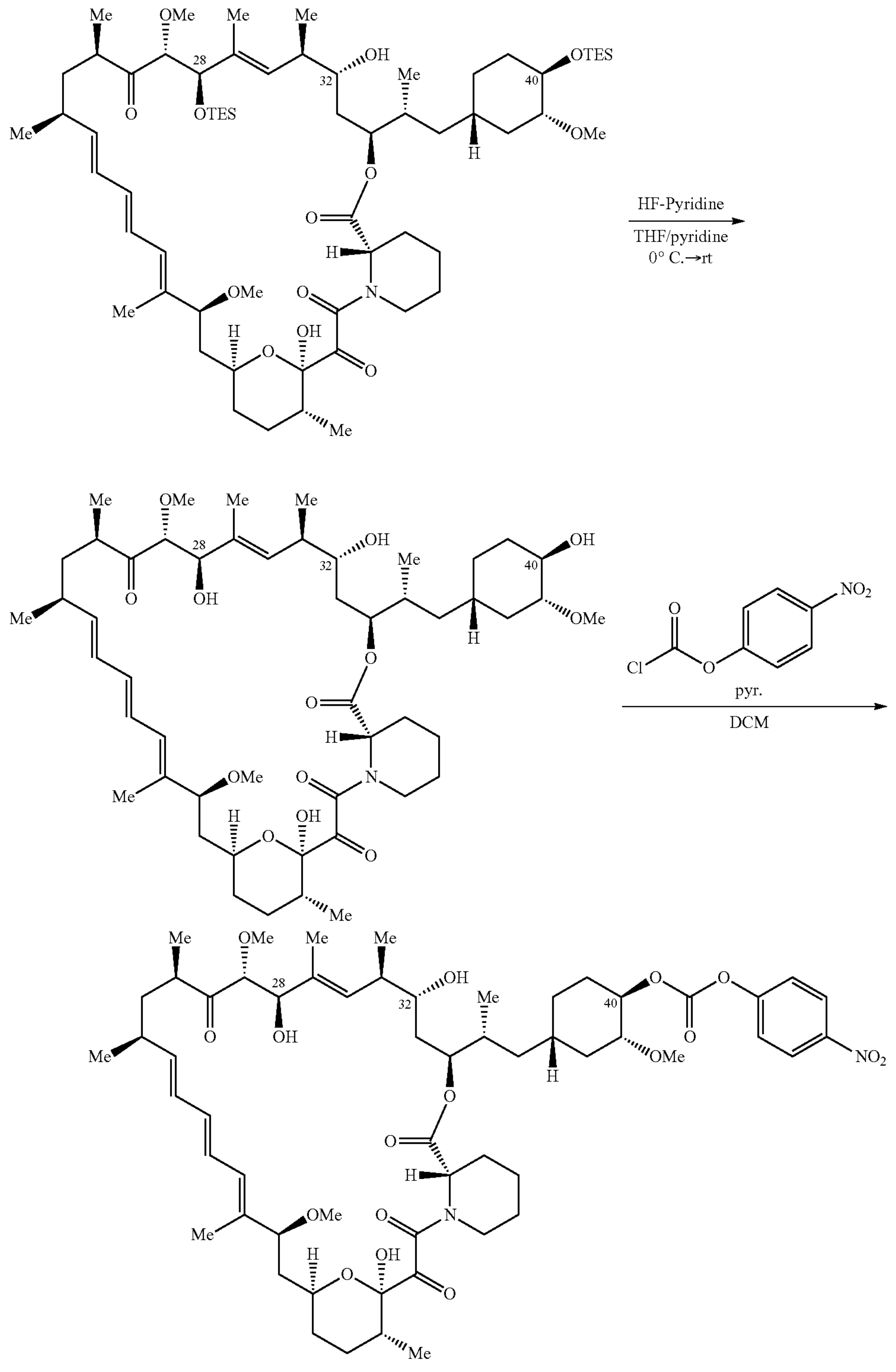

Step 1: Synthesis of 32(R)-hydroxy rapamycin

A solution of 32(R)-hydroxy-28,40-bistriethylsilyl rapamycin (3.64 g, 3.18 mmol, 1 equiv) in THF (41.8 mL) was treated with pyridine (20.8 mL, 258 mmol, 81 equiv) and the reaction mixture was cooled to 0° C. The solution was treated dropwise with 70% HF-pyridine (4.60 mL, 159 mmol, 50 equiv) and the reaction mixture was stirred at 0° C. for 20 min followed by warming to room temperature. After 5 h, the reaction mixture was cooled back to 0° C. and carefully added to ice cold sat. $NaHCO_3$ solution (400 mL). The mixture was extracted with EtOAc (2×100 mL) and the organic phases were washed with 75 mL portions of $H_2O$, sat. $NaHCO_3$ solution and brine. The organic solution was dried over $Na_2SO_4$, filtered and concentrated to yield a light yellow oil that produced a stiff foam under reduced pressure. The crude material was purified by silica gel chromatography (20-40% acetone/hexanes) to yield the desired product as a white amorphous solid (1.66 g, 57% yield). LCMS (ESI) m/z: [M+Na] calcd for $C_{51}H_{81}NO_{13}$: 938.56; found 938.7; m/z: [M−H] calcd for $C_{51}H_{81}NO_{13}$: 914.56; found 914.7.

Step 2: Synthesis of 32(R)-hydroxy 40(R)—O-(4-nitrophenyl)carbonate rapamycin

To a suspension of powdered 4 Å molecular sieves (6.0 g) in DCM (130 mL) was added 32(R)-hydroxy rapamycin (6.00 g, 6.55 mmol, 1.0 equiv). After stirring at room temperature for 45 min, pyridine (5.99 mL, 74.0 mmol, 11.3 equiv) was added. The suspension was cooled to −15° C. and then 4-nitrophenylchloroformate (1.78 g, 8.84 mmol, 1.4 equiv) was then added. The reaction mixture was stirred at −10° C. for 2 h and then filtered, and the filter pad washed with DCM (140 mL). The filtrate was washed with sat. $NaHCO_3$ (130 mL), $H_2O$ (130 mL) and brine (130 mL), dried over $Na_2SO_4$, filtered and concentrated under reduced pressure. The crude material was purified by silica gel chromatography (20→50% EtOAc/hexanes) to give the product (4.44 g, 63% yield) as an off-white stiff foam. LCMS (ESI) m/z: [M+Na] calcd for $C_{58}H_{84}N_2O_{17}$: 1103.57; found 1103.5.

Monomer 3. 32(R)-methoxy 40(R)—O-(4-nitrophenyl)carbonate rapamycin

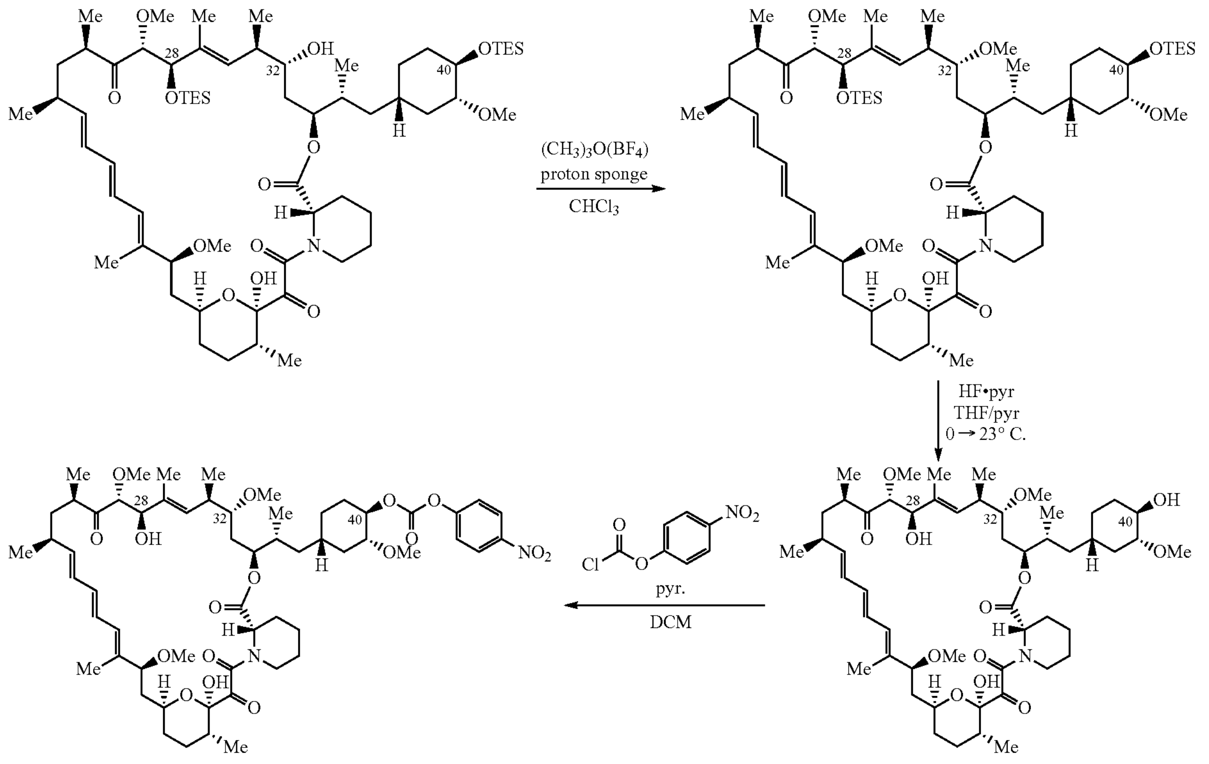

Step 1: Synthesis of 32(R)-methoxy-28,40-bistriethylsilyl rapamycin

To a stirred solution of 32(R)-hydroxy-28,40-bistriethylsilyl rapamycin (3.83 g, 3.34 mmol, 1.0 equiv) in chloroform (95.8 mL) was added Proton Sponge® (7.17 g, 33.5 mmol, 10.0 equiv) along with freshly dried 4 Å molecular sieves (4 g). The solution was stirred for 1 h prior to the addition of trimethyloxonium tetrafluoroborate (4.95 g, 33.5 mmol, 10.0 equiv, dried by heating under reduced pressure at 50° C. for 1 h before use) at room temperature. The reaction mixture was stirred for 18 h, and then the reaction mixture was diluted with DCM and filtered through Celite. The filtrate was washed sequentially with aqueous 1 M HCl (2×), sat. aqueous $NaHCO_3$ solution, then dried and concentrated under reduced pressure. Purification by silica gel chromatography (10→20% EtOAc/hexanes) afforded the desired product as a yellow oil that was contaminated with 3 wt. % Proton Sponge®. The residue was taken up in MTBE and washed with aqueous 1 M HCl, sat. aqueous $NaHCO_3$ solution, dried, and then concentrated under reduced pressure to furnish a yellow foam (3.15 g, 81.2% yield). LCMS (ESI) m/z: [M−TES+$H_2O$] calcd for $C_{64}H_{111}NO_{13}Si_2$: 1061.68; found 1061.9.

Step 2: Synthesis of 32(R)-methoxy rapamycin

To a stirred solution of 32(R)-methoxy-28,40-bistriethylsilyl rapamycin (1.11 g, 0.958 mmol, 1.0 equiv) in THF (12.6 mL) and pyridine (6.30 mL) in a plastic vial was added 70% HF-pyridine (2.22 mL, 76.6 mmol, 80.0 equiv) dropwise at 0° C. The reaction mixture was stirred at 0° C. for 20 min before being warmed to room temperature for 3 h, when HPLC showed complete consumption of starting material. The reaction mixture was cooled to 0° C. and poured slowly into ice cold sat. aqueous $NaHCO_3$ solution (50 mL). The aqueous layer was extracted with EtOAc (3×) and the combined organics were washed with sat. aqueous $NaHCO_3$ solution, brine, dried, and concentrated under reduced pressure. The yellow residue was dissolved in MeOH (5 mL) and added dropwise to $H_2O$ (50 mL) to produce a white precipitate. After stirring for 15 min the slurry was filtered on a medium porosity funnel and the cake washed with $H_2O$ (2×). The solids were then dissolved in MeCN (50 mL) and lyophilized overnight to provide the product as a white solid (780 mg, 87% yield). LCMS (ESI) m/z: [M+Na] calcd for $C_{52}H_{83}NO_{13}$: 952.58; found 952.4.

Step 3: Synthesis of 32(R)-methoxy 40(R)—O-(4-nitrophenyl)carbonate rapamycin

To a solution of 32(R)-methoxy rapamycin (4.50 g, 4.84 mmol, 1.0 equiv) in DCM (180 mL) was added powdered 4 Å molecular sieves (6.0 g). The mixture was stirred at room temperature for 1 h and then pyridine (3.91 mL, 48.4 mmol, 10 equiv) was added. The mixture was cooled to −10° C. and 4-nitrophenylchloroformate (0.990 g, 4.91 mmol, 1.0 equiv) was added in one portion. The reaction was allowed to slowly warm to room temperature and after 3 h the reaction mixture was cooled to 0° C. and 4-nitrophenylchloroformate (250 mg, 1.24 mmol, 0.3 equiv) was added. The mixture was warmed to room temperature and after 1 h the reaction mixture was filtered through a pad of celite and the pad was washed with DCM (140 mL). The filtrate was washed with $H_2O$ (120 mL) and sat $NaHCO_3$ (2×120 mL). The organic phase was dried over $Na_2SO_4$, filtered and concentrated under reduced pressure. The crude material was purified by flash chromatography (20-50% EtOAc/hex) to yield a white stiff foam. The material was taken up in MeCN during which time a white solid formed. The solid was filtered, washed with additional MeCN and allowed to air dry to provide the product (4.51 g, 85% yield). LCMS (ESI) m/z [M+Na] calcd for $C_{59}H_{86}N_2O_{17}$: 1117.58; found 1117.6.

Monomers 4. 32(R)-ethoxy 40(R)—O-(4-nitrophenyl)carbonate rapamycin

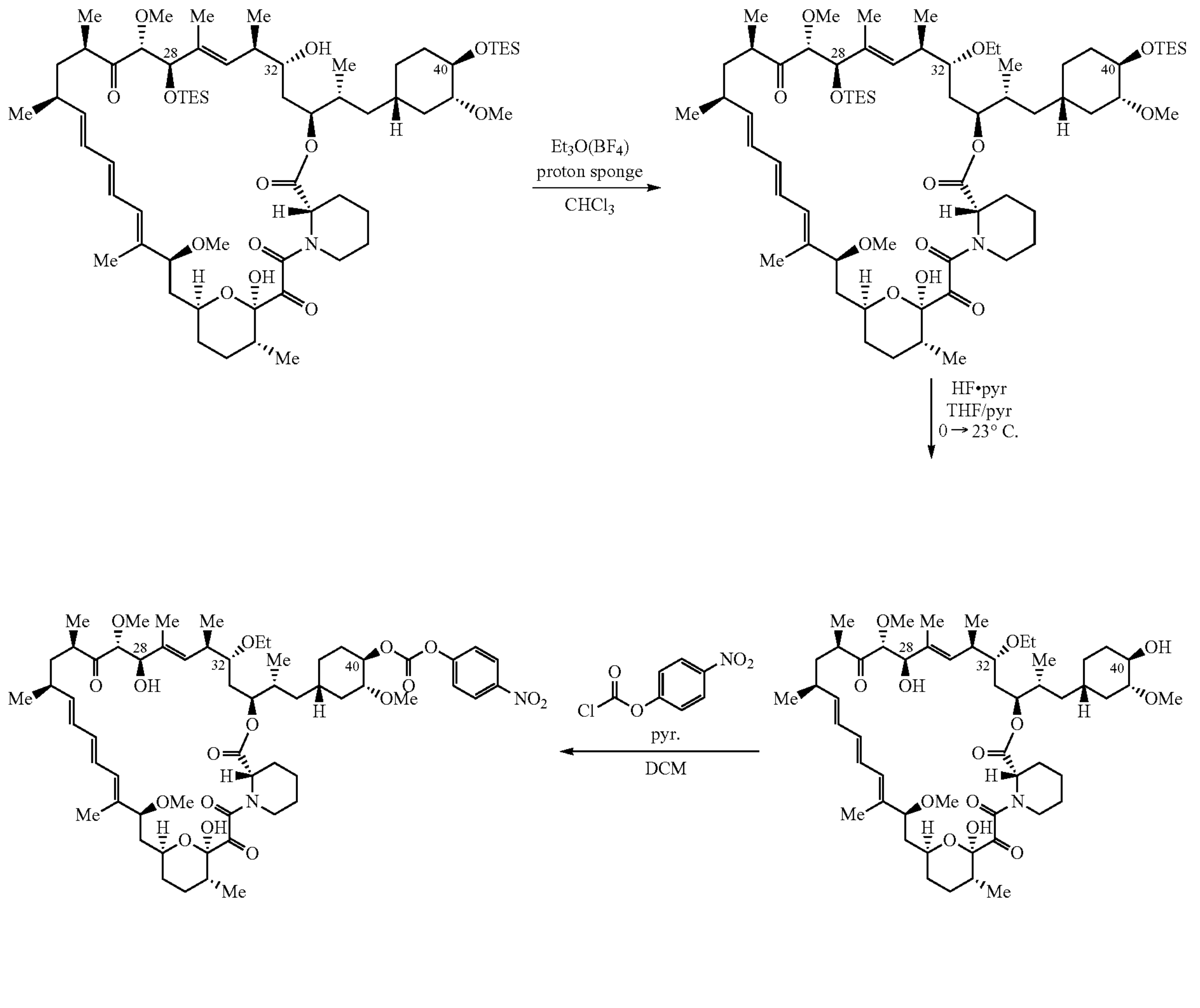

Step 1: Synthesis of 32(R)-ethoxy-28,40-bistriethylsilyl rapamycin

A solution of 32(R)-hydroxy-28,40-bistriethylsilyl rapamycin (773 mg, 0.675 mmol, 1.0 equiv) in chloroform (19 mL) was treated with N,N,N',N'-tetramethyl-1,8-naphthalenediamine (1.85 g, 8.63 mmol, 12.8 equiv) along with freshly dried 4 Å molecular sieves. The mixture was stirred for 1 h at room temperature and treated with triethyloxonium tetrafluoroborate (1.51 g, 7.95 mmol, 11.8 equiv) in one portion at room temperature. The reaction mixture was stirred for 3 h, at which point the reaction mixture was diluted with DCM and filtered through Celite, washing the filter pad with additional DCM. The combined filtrates were washed twice with 1 M HCl, once with saturated $NaHCO_3$ solution, and dried over $Na_2SO_4$. The solution was filtered and concentrated to a residue. The crude residue was treated with MTBE and filtered to remove polar insoluble material. The filtrate was concentrated and purified by silica gel chromatography (5→25% EtOAc/hex) to afford the product as a foam (516 mg, 65% yield). LCMS (ESI) m/z: [M+Na] calcd for $C_{65}H_{113}NO_{13}Si_2$ 1194.77; found 1194.6.

Step 2: Synthesis of 32(R)-ethoxy rapamycin

To a solution of 32(R)-ethoxyethoxy-28,40-bistriethylsilyl rapamycin (131 mg, 0.112 mmol, 1.0 equiv) in THF (1.3 mL) at 0° C. was added pyridine (271 μL, 3.35 mmol, 3.4 equiv) followed by 70% HF-pyridine (51 μL, 1.8 mmol, 1.8 equiv). The reaction flask was capped and stored in the fridge for 3 days, at which point the reaction mixture was poured into cold saturated $NaHCO_3$ (20 mL). The aqueous layer extracted with EtOAc (3×20 mL) and the combined organic layers were washed with 1 M HCl (2×20 mL), saturated $NaHCO_3$ solution (20 mL), and brine. The solution was dried over $Na_2SO_4$, filtered, and concentrated. The residue was taken up in MeOH (1.5 mL) and added dropwise to $H_2O$ (20 mL). The solids were filtered and washed with additional $H_2O$ to provide the product (53 mg, 51% yield) as a white powder. LCMS (ESI) m/z: [M+Na] calcd for $C_{53}H_{85}NO_{13}$: 966.59; found 966.5.

Step 3: Synthesis of 32(R)-ethoxy 40(R)—O-(4-nitrophenyl)carbonate rapamycin

To a 0.03 M solution of 32(R)-ethoxy rapamycin (1.0 equiv) in DCM is added powdered 4 Å molecular sieves. The mixture is stirred at room temperature for 1 h and then pyridine (10 equiv) is added. The mixture is cooled to −10° C. and 4-nitrophenylchloroformate (1.0 equiv) is added in one portion. The reaction is warmed to room temperature and stirred until consumption of 32(R)-ethoxy rapamycin, as determined by LCMS analysis. The mixture is filtered through a pad of celite and the pad washed with DCM. The filtrate is washed with $H_2O$ and sat $NaHCO_3$.The organic phase is then dried over $Na_2SO_4$, filtered and concentrated under reduced pressure. The crude material is purified by flash chromatography (20→50% EtOAc/hex) to provide the product.

Monomer 5. 40(R)—O-(4-nitrophenyl)thiocarbonate rapamycin

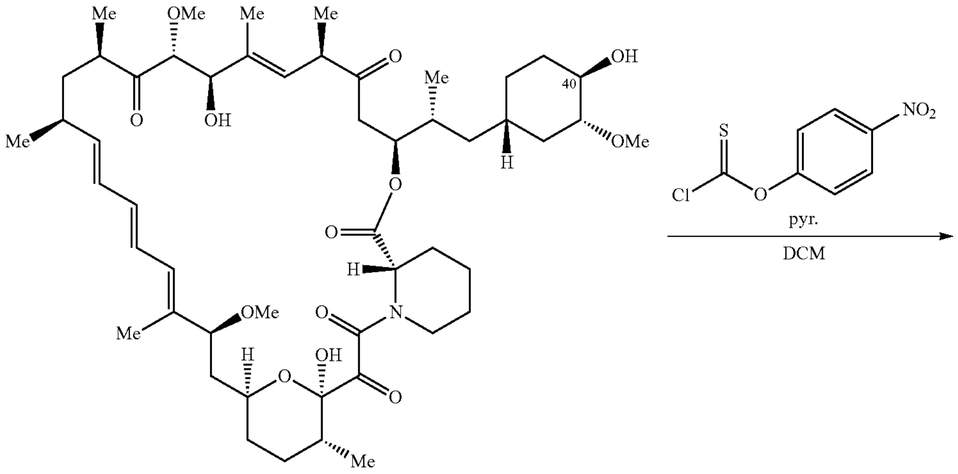

-continued

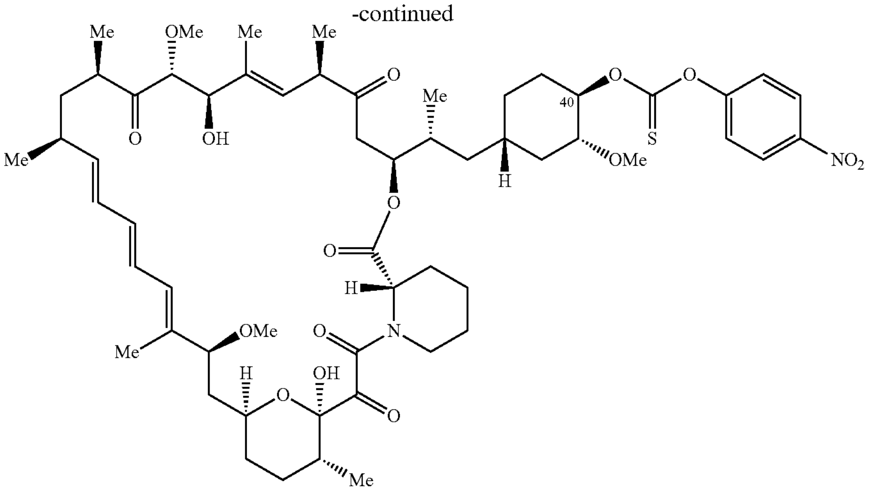

To a solution of rapamycin (4.00 g, 4.38 mmol, 1.0 equiv) in DCM (20 mL) at −78° C. was added pyridine (4.0 mL, 49 mmol, 11.2 equiv), followed by a solution of O-(4-nitrophenyl)chlorothiocarbonate (1.19 g, 5.47 mmol, 1.3 equiv) in DCM (8.0 mL). The reaction mixture was warmed to −20° C. and stirred for 48 h. Hexane (40 mL) was then added and the resulting suspension was purified by silica gel chromatography (15/25/60 EtOAc/DCM/hexane then 20/25/55 EtOAc/DCM/hexane) to provide the product (3.09 g, 64.4% yield) as an off-white solid. LCMS (ESI) m/z: [M+Na] calcd for $C_{58}H_{82}N_2O_{16}S$: 1117.53; found 1117.5.

Monomer 6. 28—O-(4-nitrophenyl)carbonate rapamycin

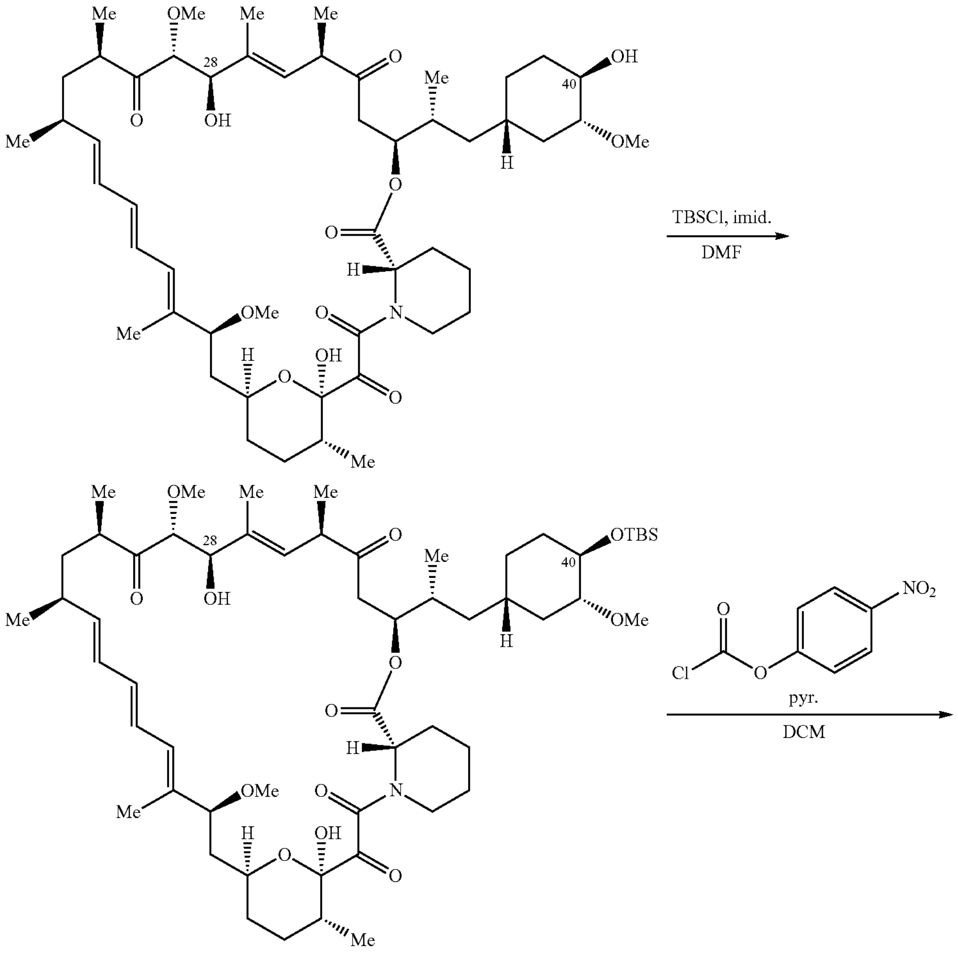

-continued

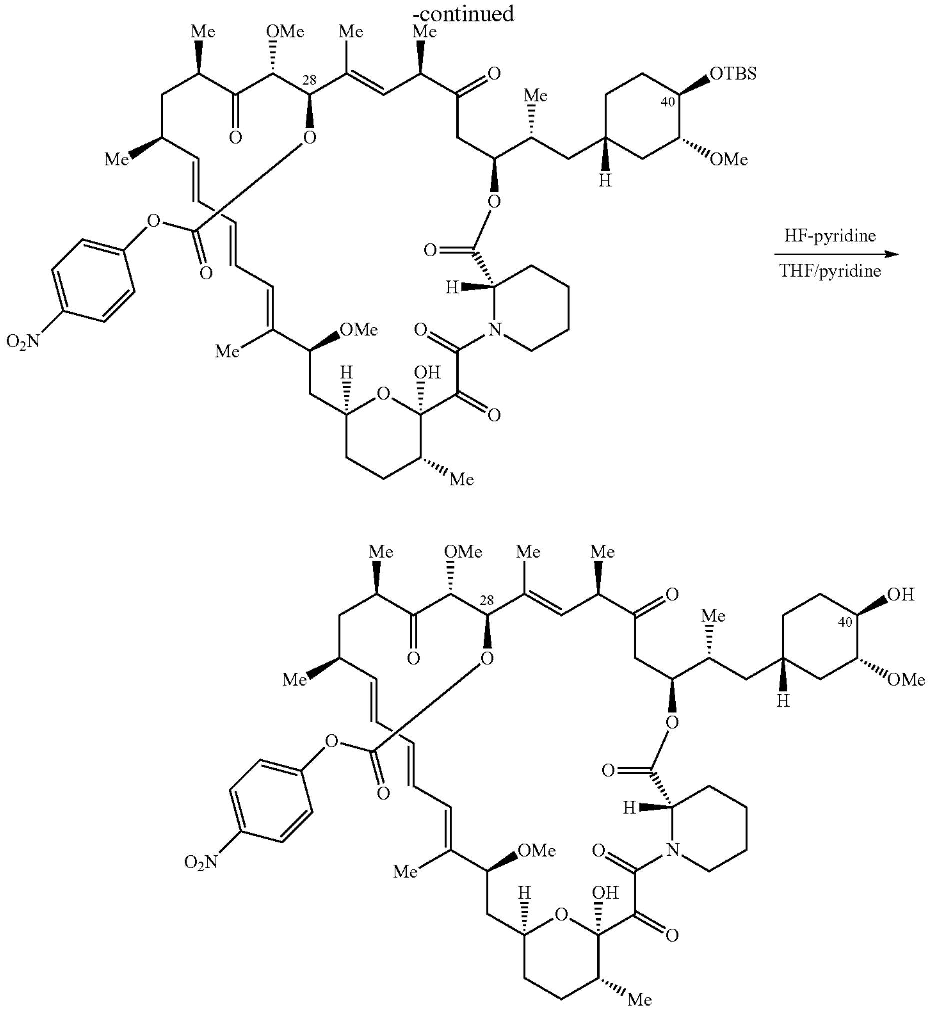

Step 1: Synthesis of 40-O-tert-butyldimethylsilyl rapamycin

To a solution of rapamycin (1.00 g, 1.09 mmol, 1.0 equiv) in DMF (4 mL) at room temperature was added imidazole (0.22 g, 3.2 mmol, 2.9 equiv) followed by tert-butyldimethylsilyl chloride (0.176 g, 1.17 mmol, 1.07 equiv). The reaction mixture was stirred for 18 h. The reaction mixture was then diluted with DCM (100 mL) and washed with 20% aq. LiCl (3x20 mL). The organic layer was dried over $Na_2SO_4$, filtered and concentrated under reduced pressure. The residue was purified by silica gel chromatography (20→40% EtOAc/hexanes) to give the product (950 mg, 75% yield) as a faint yellow glass. LCMS (ESI) m/z: [M+$H_2O$] calcd for $C_{57}H_{93}NO_{13}Si$: 1045.65; found 1045.9.

Step 2: Synthesis of 28-O-(4-nitrophenoxycarbonyl)-40-O-(tert-butyldimethylsilyl) rapamycin To a solution of 40-O-tert-butyldimethylsilyl rapamycin (0.845 g, 0.822 mmol, 1.0 equiv) in DCM (10 mL) at room temperature was added pyridine (0.9 mL, 10 mmol, 12.1 equiv) followed by 4-nitrophenyl chloroformate (0.373 g, 1.85 mmol, 2.25 equiv). The reaction mixture was stirred for 2 h. The reaction mixture was then diluted with DCM (150 mL) and the solution sequentially washed with sat. $NaHCO_3$ (20 mL), 10% citric acid (2x20 mL), and brine (20 mL). The organic layer was dried over $Na_2SO_4$, filtered, and concentrated under reduced pressure. The residue was purified by reverse phase chromatography (30→100% MeCN/$H_2O$) to give the product (930 mg, 95% yield) as a pale yellow foam. LCMS (ESI) m/z: [M+H] calcd for $C_{64}H_{96}N_2O_{17}Si$: 1193.66; found 1193.7.

Step 3: Synthesis of 28-O-(4-nitrophenoxycarbonyl) rapamycin

To a solution of 28-O-(4-nitrophenoxycarbonyl)-40-O-(tert-butyldimethylsilyl)rapamycin (0.930 g, 0.779 mmol, 1.0 equiv) in THF (10.7 mL) was added pyridine (3.78 mL, 46.8 mmol, 60.1 equiv) followed by the dropwise addition of 70% HF-pyridine (0.91 mL, 31.2 mmol, 40.0 equiv). The reaction mixture was stirred at room temperature for 48 h. The mixture was then poured slowly into ice cold sat. aqueous $NaHCO_3$ (20 mL). The aqueous layer was extracted with EtOAc (3x20 mL) and the combined organic layer was washed with sat. $NaHCO_3$ (10 mL) and brine (10 mL), dried over $Na_2SO_4$, filtered, and concentrated under reduced pressure. The residue was purified by reverse phase chromatography (30→100% MeCN/$H_2O$) to give the product (200 mg, 24% yield) as a faint yellow powder. LCMS (ESI) m/z: [M+Na] calcd for $C_{58}H_{82}N_2O_{17}$: 1101.55; found 1101.3.

Monomer 7. 32(R)-hydroxy 40(R)—O-(4-nitrophenyl)thiocarbonate rapamycin

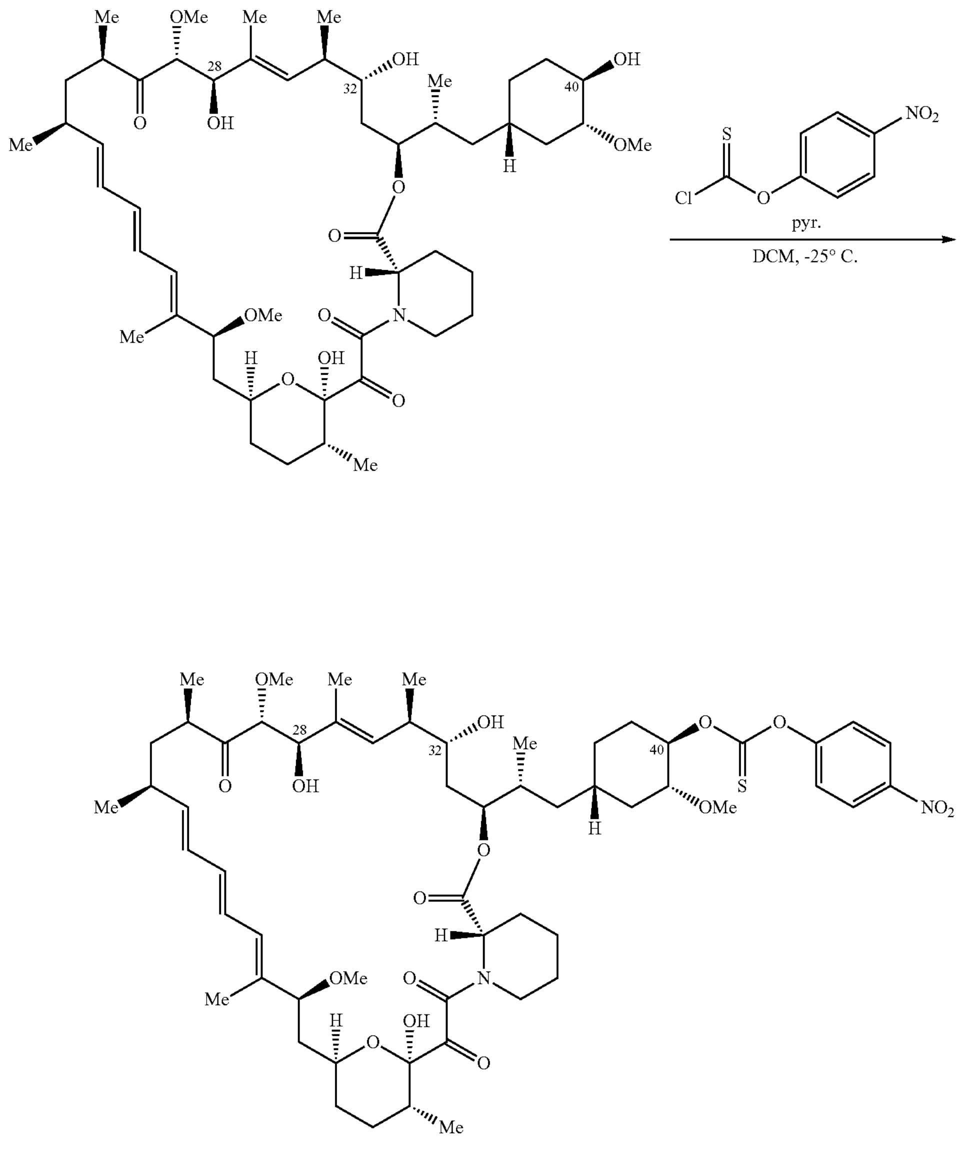

To a solution of 32(R)-hydroxy rapamycin (2.80 g, 3.06 mmol, 1.0 equiv) in DCM (28 mL) was added pyridine (27.6 mL, 34 mmol, 11 equiv) and dried 4 Å molecular sieves (2.8 g). The suspension was stirred at room temperature for 1 h, at which point the mixture was cooled to −25° C. and a solution of O-(4-nitrophenyl)chlorothioformate (0.798 g, 3.67 mmol, 1.2 equiv) in DCM (6 mL) was added. The reaction was warmed to room temperature and after 21 h was filtered through Celite. The filtrate was partitioned between DCM and $H_2O$ and the aqueous layer was extracted with DCM. The combined organic layers were dried and concentrated under reduced pressure. Purification by silica gel chromatography (EtOAc/hexanes) afforded the desired product as a white solid (2.15 g, 64% yield). LCMS (ESI) m/z: [M+Na] calcd for $C_{58}H_{84}N_2O_{16}S$: 1119.54; found 1120.0.

Monomer 8. 32(R)-methoxy 40(R)—O-(4-nitrophenyl)thiocarbonate rapamycin

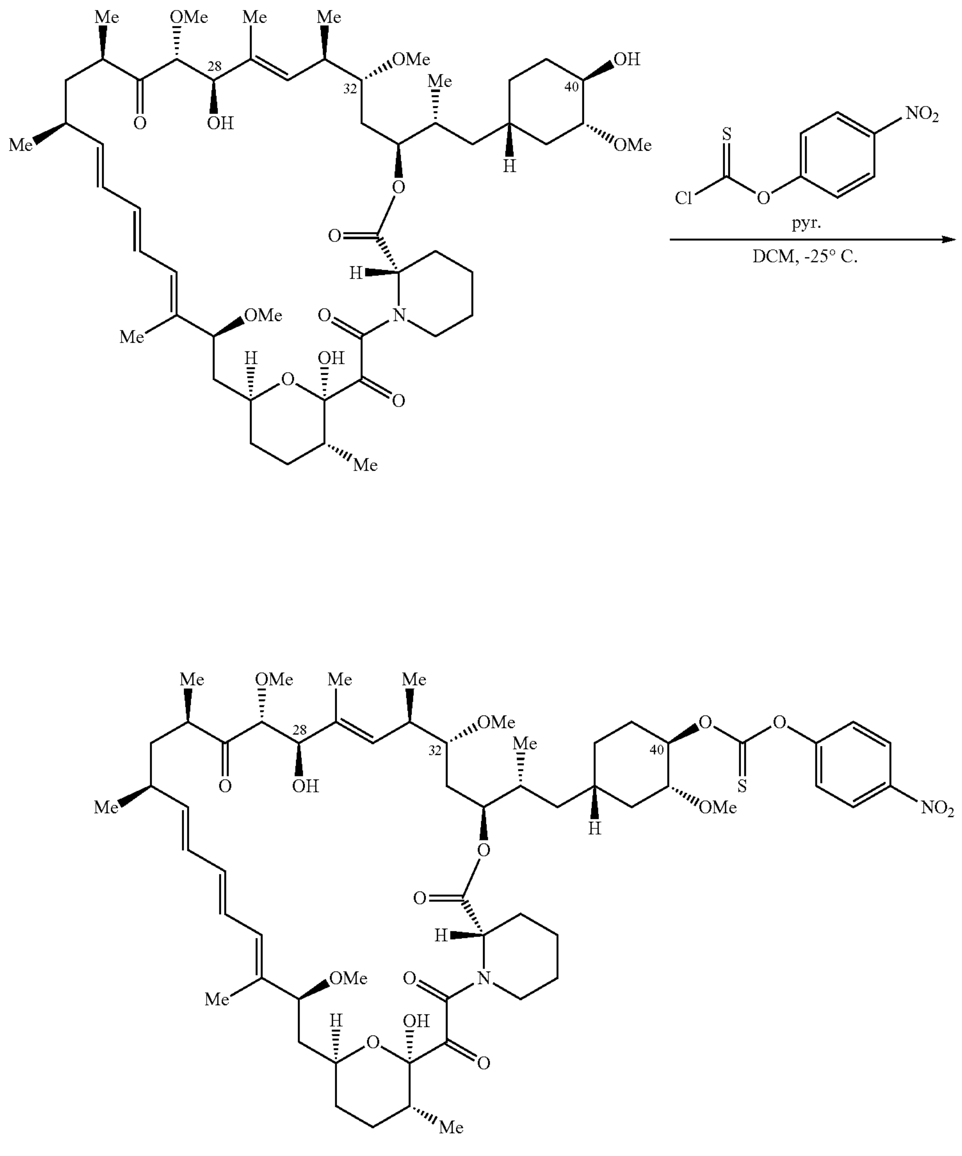

To a solution of 32(R)-methoxy rapamycin (6.69 g, 7.19 mmol, 1.0 equiv) in DCM (67 mL) was added pyridine (6.6 mL, 81 mmol, 11 equiv) and dried 4 Å molecular sieves (6.7 g). The suspension was stirred at room temperature for 1 h, at which point the mixture was cooled to −25° C. and a solution of O-(4-nitrophenyl)chlorothioformate (1.88 g, 8.63 mmol, 1.20 equiv) in DCM (13 mL) was added. The reaction was warmed to room temperature and after 21 h was filtered through Celite. The filtrate was partitioned between DCM and $H_2O$ and the aqueous layer was extracted with DCM. The combined organic layers were dried and concentrated under reduced pressure. Purification by silica gel chromatography (EtOAc/hexanes) afforded the desired product as a white solid (5.1 g, 64% yield). LCMS (ESI) m/z: [M+Na] calcd for $C_{59}H_{86}N_2O_{16}S$: 1133.56; found 1134.1.

Monomer 9. 32-deoxy

40(R)—O-(4-nitrophenyl)carbonate rapamycin

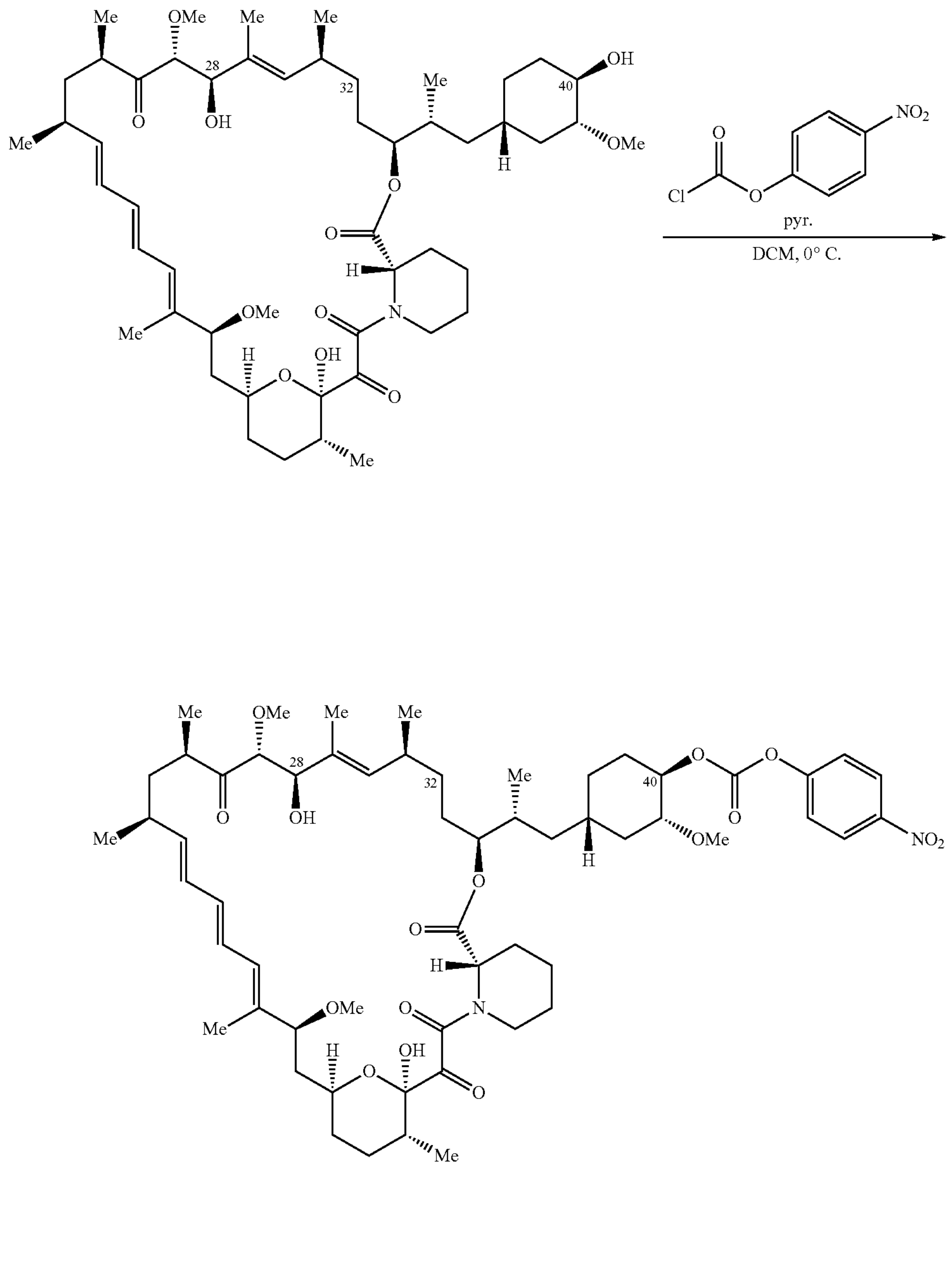

To a solution of 32-deoxy rapamycin (0.623 g, 0.692 mmol, 1.0 equiv) in DCM (24.7 mL) was added 4 Å molecular sieves (600 mg). The suspension was stirred for 1 h and then pyridine (557 μL, 6.92 mmol, 10 equiv) was added. The reaction mixture was cooled to 0° C. and then O-(4-nitrophenyl)chloroformate (175 mg, 1.03 mmol, 1.7 equiv) was added. The reaction warmed to room temperature and stirred for 2 h, at which point the reaction mixture was concentrated under reduced pressure. Purification by silica gel chromatography (0→10% MeOH/DCM) afforded the desired product as a white solid (0.61 g, 82% yield). LCMS (ESI) m/z: [M+Na] calcd for $C_{58}H_{84}N_2O_{16}$: 1087.57; found 1087.6.

Monomer 10. 32-deoxy 40(R)—O-(4-nitrophenyl)thiocarbonate rapamycin

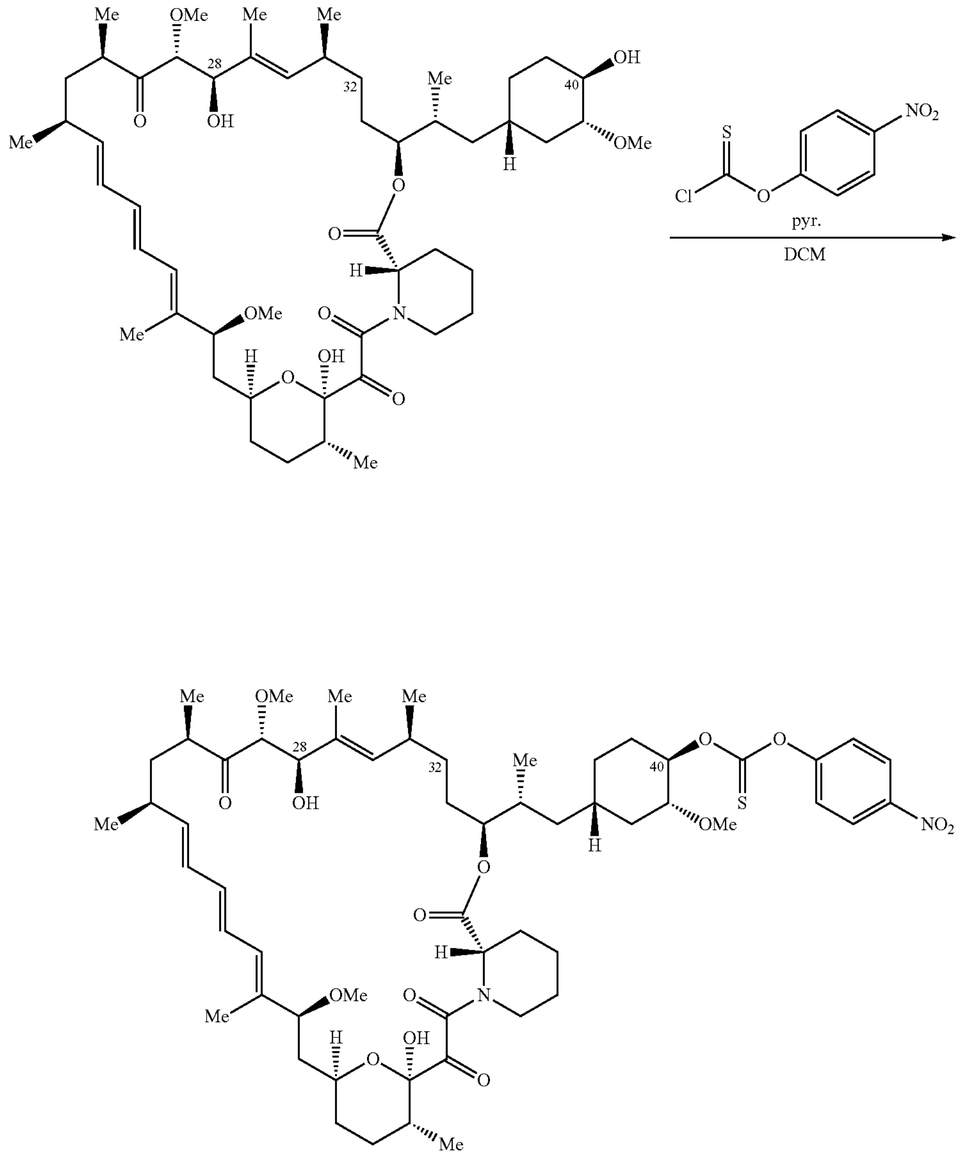

To a 0.2 M solution of 32-deoxy rapamycin (1.0 equiv) in DCM at −78° C. is added pyridine (11.2 equiv), followed by a 0.7 M solution of O-(4-nitrophenyl)chlorothiocarbonate (1.3 equiv) in DCM. The reaction mixture is warmed to −20° C. and stirred until consumption of the starting material, as determined by LCMS analysis. Hexane is then added and the resulting suspension is purified by silica gel chromatography to provide the product.

Monomer 11. 28(R)-methoxy 32(R)-hydroxy 40(R)-(4-nitrophenyl)carbonate rapamycin
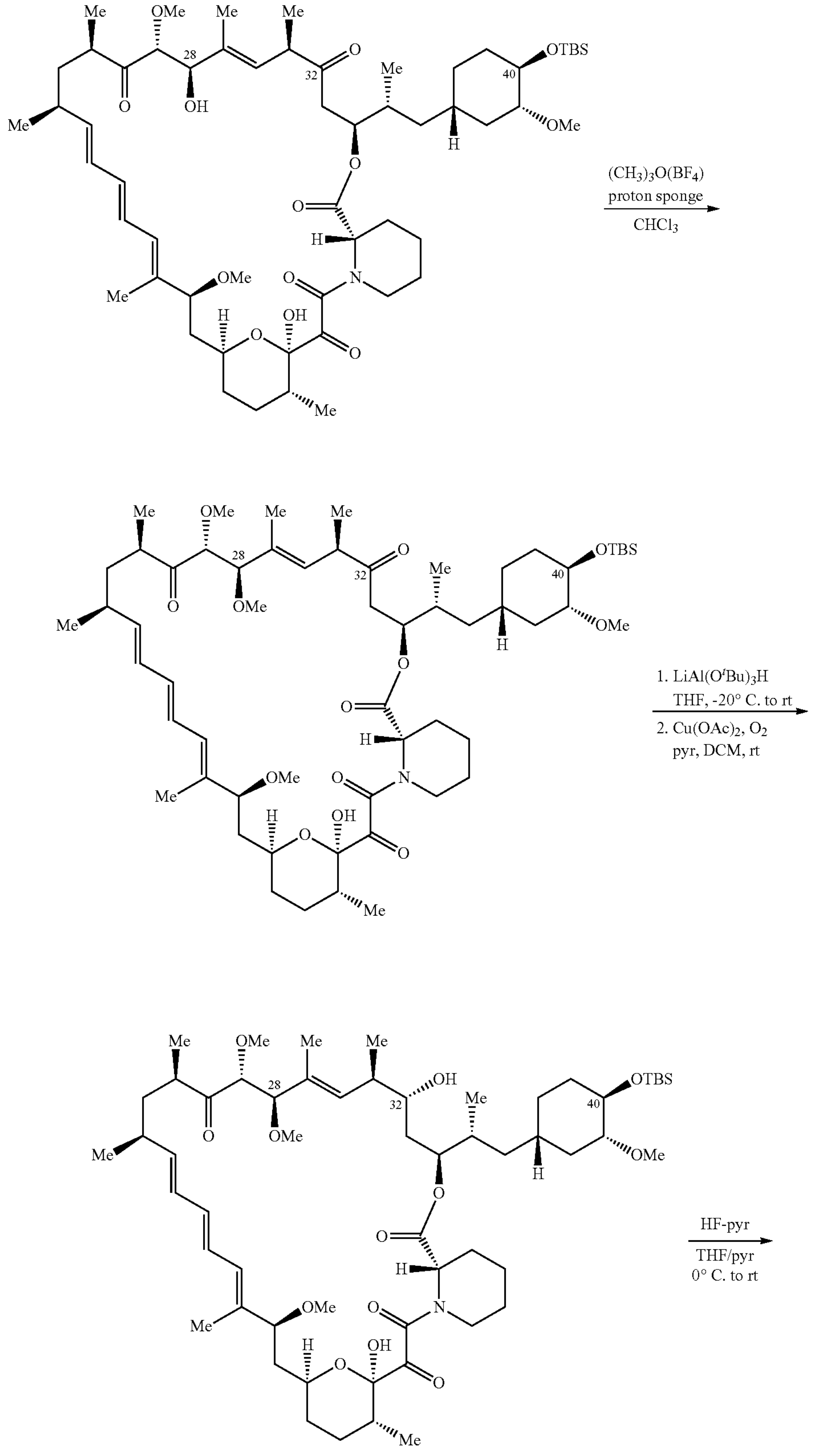

-continued

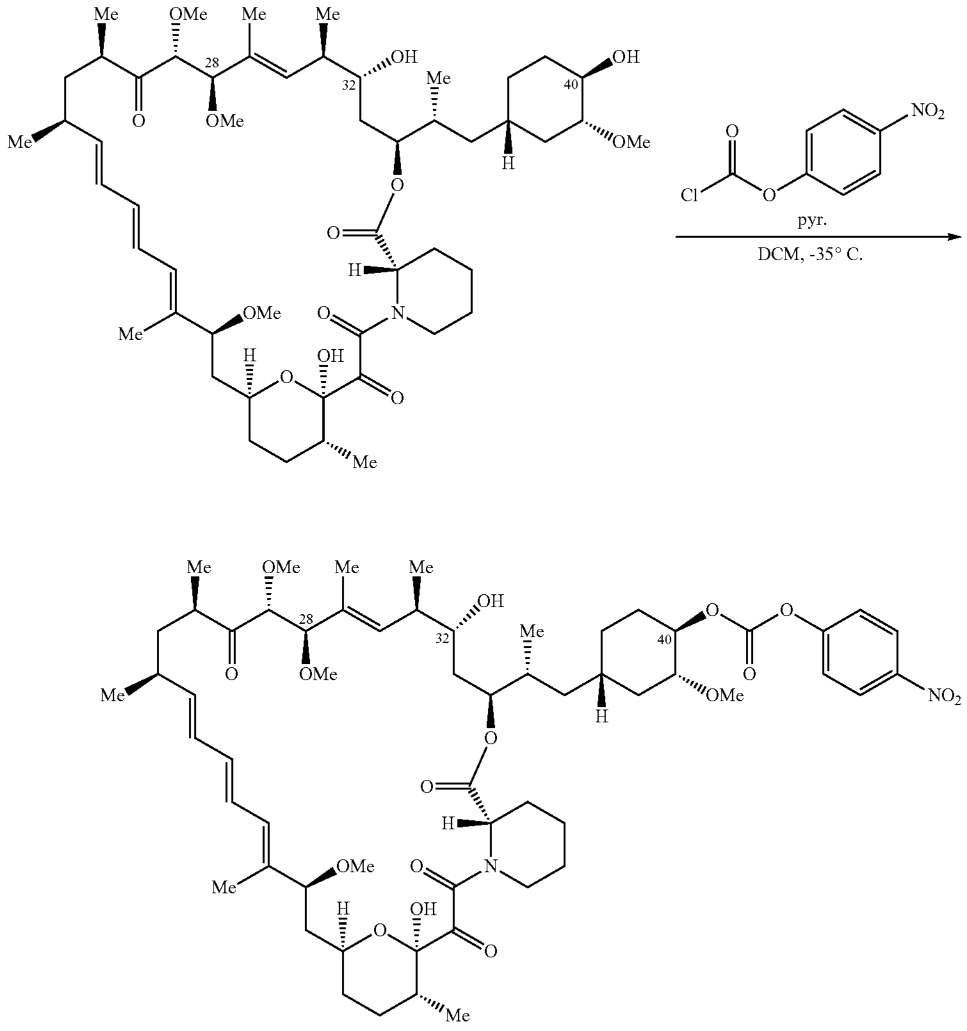

Step 1: Synthesis of 28(R)-methoxy 40(R)—O-tert-butyldimethylsilyl rapamycin

To a solution o 40(R)—O-tert-butyldimethylsilyl rapamycin (4.00 g, 4.89 mmol, 1.0 equiv) in chloroform (67 mL) was added proton sponge (11.2 mL, 52.3 mmol, 13 equiv) and dried 4 Å molecular sieves (5.8 g). The suspension was stirred at room temperature for 1 h, at which point trimethyloxonium tetrafluoroborate (7.21 g, 48.8 mmol, 12.5 equiv) was added. After 4 h the suspension was filtered through Celite. The filtrate was washed sequentially with aqueous 2 N HCl, $H_2O$, sat. aqueous $NaHCO_3$, then dried and concentrated under reduced pressure. Purification by silica gel chromatography (EtOAc/hexane) afforded the desired product as a white solid (2.1 g, 52% yield). LCMS (ESI) m/z: [M+Na] calcd for $C_{58}H_{95}NO_{13}Si$: 1064.65; found 1065.26.

Step 2: Synthesis of 28(R)-methoxy 32(R)-hydroxy 40(R)—O-tert-butyldimethylsilyl rapamycin To a solution of 28(R)-methoxy 40(R)—O-tert-butyldimethylsilyl rapamycin (2.13 g, 2.04 mmol, 1.0 equiv) in THF (31 mL) at −20° C. was added a solution of lithium tri-tert-butoxyaluminum hydride in THF (1 M, 4.09 mL, 4.09 mmol, 2.0 equiv), dropwise. The reaction mixture was warmed to room temperature and after 3 h was added to a solution of $H_2O$ (4 mL), EtOAc (31 mL), and 2 M aqueous citric acid (4 mL) at 0° C. After 5 min the mixture was partitioned, and the aqueous layer was extracted with EtOAc. The combined organic layers were poured into a sat. aqueous $NaHCO_3$ solution (60 mL) at 0° C. The layers were partitioned, and the organic layer was dried and concentrated under reduced pressure to provide a crude white solid (2.32 g). The crude solid was dissolved in DCM (12 mL) and then pyridine (241 μL, 2.98 mmol, 1.5 equiv), dried 4 Å molecular sieves (2.1 g), and cupric acetate (0.27 g, 1.49 mmol, 0.7 equiv) were added. The suspension was stirred at room temperature for 1 h. The suspension was sparged with 02 and then kept under an 02 atmosphere for 30 min. After 2 h the mixture was filtered through Celite and the filtrate was concentrated under reduced pressure. Purification by silica gel chromatography (EtOAc/hexane) afforded the desired product as a white solid (307 mg, 14% yield). LCMS (ESI) m/z: [M+Na] calcd for $C_{58}H_{97}NO_{13}Si$: 1066.66; found 1067.0.

Step 3: Synthesis of 28(R)-methoxy 32(R)-hydroxy rapamycin

To a solution of 28(R)-methoxy 32(R)-hydroxy 40(R)—O-tert-butyldimethylsilyl rapamycin (0.307 g, 0.294 mmol, 1.0 equiv) in THF (4 mL) in a polypropylene vial at 0° C. was added pyridine (1.42 mL, 17.6 mmol, 60.0 equiv) followed by 70% HF-pyridine (0.34 mL, 11.7 mmol, 40 equiv). The solution was warmed to room temperature and stirred for 21 h, at which point the solution was poured into sat. aqueous $NaHCO_3$ at 0° C. The aqueous layer was extracted with EtOAc (2×) and the combined organic layers were washed with sat. aqueous $NaHCO_3$ and brine, then dried and concentrated under reduced pressure. Purification by silica gel chromatography (EtOAc/hexane) afforded the desired product as a white solid (146 mg, 53% yield). LCMS (ESI) m/z: [M+Na] calcd for $C_{52}H_{83}NO_{13}$: 952.58; found 952.8.

Step 4: Synthesis of 28(R)-methoxy 32(R)-hydroxy 40(R)-(4-nitrophenyl)carbonate rapamycin To a solution of 28(R)-methoxy 32(R)-hydroxy rapamycin (0.66 g, 0.71 mmol, 1.0 equiv) in DCM (3 mL) was added pyridine (0.64 mL, 7.9 mmol, 11 equiv) and dried 4 Å molecular sieves (0.66 g). The suspension was stirred at room temperature for 1 h, at which point the mixture was cooled to −35° C. and O-(4-nitrophenyl)chloroformate (0.17 g, 0.85 mmol, 1.2 equiv) was added. After 3 h, DCM (5 mL) was added and the suspension was filtered through Celite. The filtrate was washed with $H_2O$, dried, and concentrated under reduced pressure. Purification by silica gel chromatography (EtOAc/hexanes) afforded the desired product as a white solid (0.44 g, 57% yield). LCMS (ESI) m/z: [M+Na] calcd for $C_{59}H_{86}N_2O_{17}$: 1117.58; found 1118.0.

Monomer 12. 28(R)-methoxy 32(R)-methoxy 40(R)-(4-nitrophenyl)carbonate rapamycin

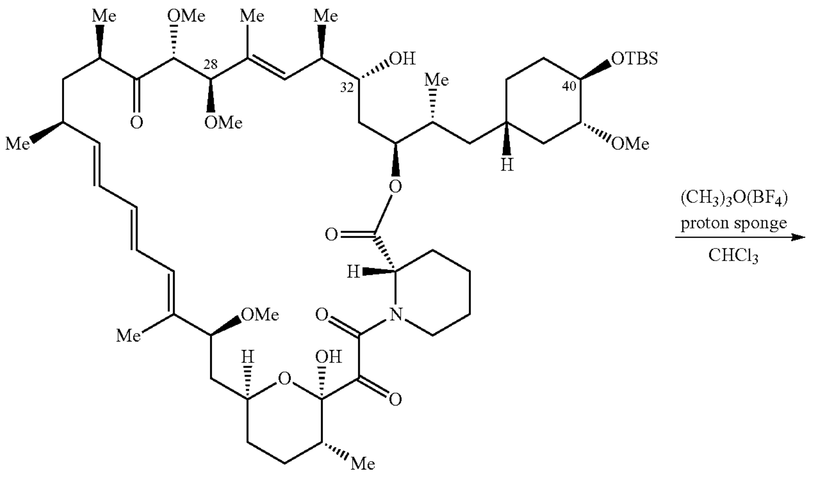

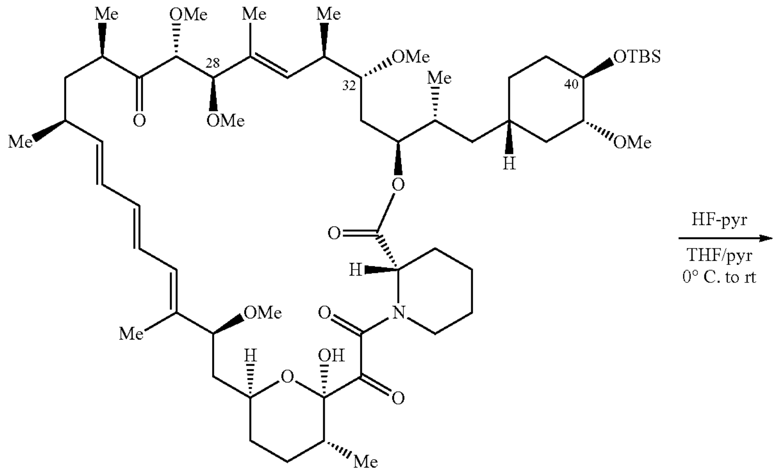

-continued

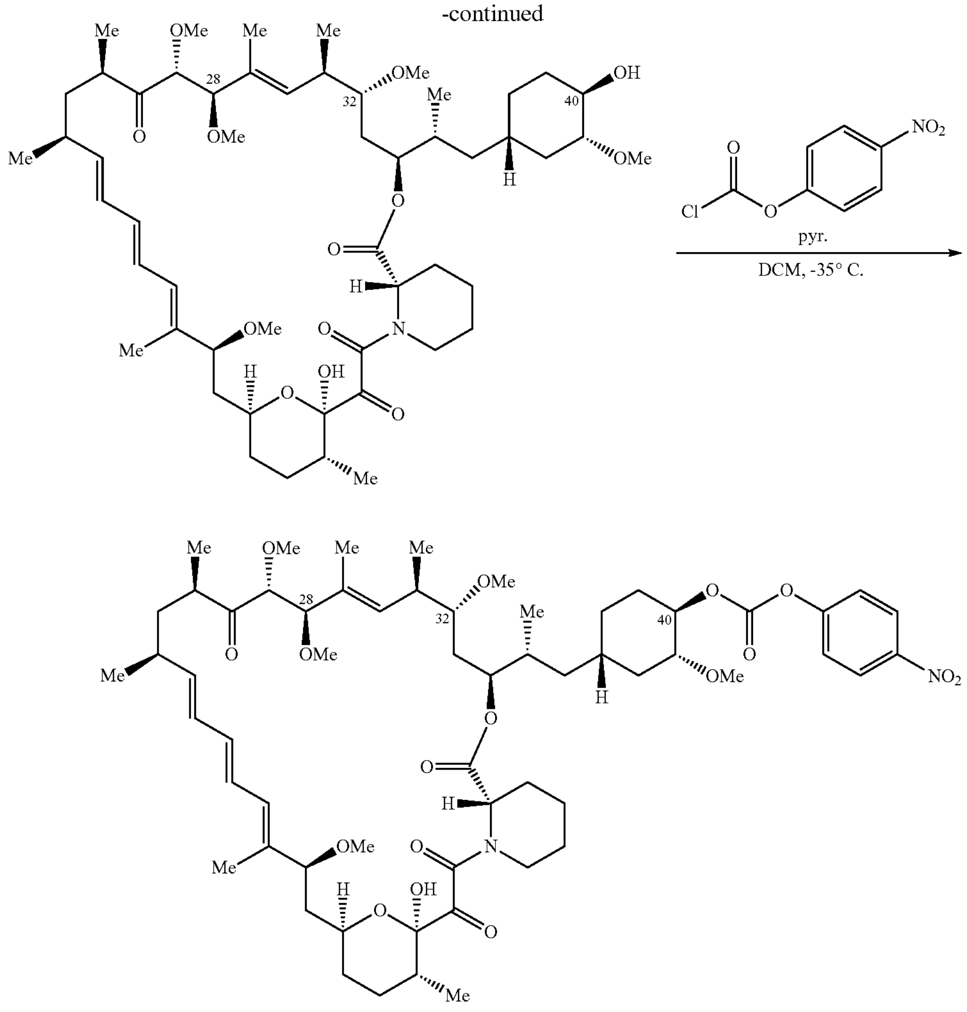

Step 1: Synthesis of 28(R)-methoxy 32(R)-methoxy 40(R)—O-tert-butyldimethylsilyl rapamycin To a solution of 28(R)-methoxy 32(R)-hydroxy 40(R)—O-tert-butyldimethylsilyl rapamycin (1.15 g, 1.10 mmol, 1.0 equiv) in chloroform (19 mL) was added proton sponge (3.22 mL, 15.0 mmol, 14 equiv) and dried 4 Å molecular sieves (2.3 g). The suspension was stirred at room temperature for 1 h, at which point trimethyloxonium tetrafluoroborate (2.07 g, 14.0 mmol, 12.7 equiv) was added. After 4 h the suspension was filtered through Celite and the filtrate was washed with 1N HCl, $H_2O$, and sat. aqueous $NaHCO_3$, dried and concentrated under reduced pressure. Purification by silica gel chromatography (EtOAc/hexane) afforded the desired product as a white solid. LCMS (ESI) m/z: [M+Na] calcd for $C_{59}H_{99}NO_{13}Si$: 1080.68; found 1081.2.

Step 2: Synthesis of 28(R)-methoxy 32(R)-methoxy rapamycin

To a solution of 28(R)-methoxy 32(R)-methoxy 40(R)—O-tert-butyldimethylsilyl rapamycin in THF (4 mL) in a polypropylene vial at 0° C. was added pyridine (1.13 mL, 14.2 mmol, 12.9 equiv) followed by 70% HF-pyridine (0.27 mL, 9.42 mmol, 8.6 equiv). The solution was warmed to room temperature and stirred for 41 h, at which point the solution was poured into sat. aqueous $NaHCO_3$ at 0° C. The aqueous layer was extracted with EtOAc (2×) and the combined organic layers were washed with sat. aqueous $NaHCO_3$ and brine, then dried and concentrated under reduced pressure. Purification by silica gel chromatography (EtOAc/hexane) afforded the desired product as a white solid (516 mg, 49% yield 2-steps). LCMS (ESI) m/z: [M+Na] calcd for $C_{53}H_{85}NO_{13}$: 966.59; found 967.0.

Step 3: Synthesis of 28(R)-methoxy 32(R)-methoxy 40(R)-(4-nitrophenyl)carbonate rapamycin To a solution of 28(R)-methoxy 32(R)-methoxy rapamycin (0.30 g, 0.32 mmol, 1.0 equiv) in DCM (1.4 mL) was added pyridine (0.29 mL, 3.5 mmol, 11 equiv) and dried 4 Å molecular sieves (0.30 g). The suspension was stirred at room temperature for 1 h, at which point it was cooled to −35° C. and O-(4-nitrophenyl)chloroformate (0.08 g, 0.38 mmol, 1.2 equiv) was added. After 3 h, DCM (2 mL) was added and the suspension was filtered through Celite. The filtrate was washed with $H_2O$, dried and concentrated under reduced pressure. Purification by silica gel chromatography (EtOAc/hexanes) afforded the desired product as an off-white solid (0.20 g, 57% yield). LCMS (ESI) m/z: [M+Na] calcd for $C_{60}H_{88}N_2O_{17}$: 1131.60; found 1132.1.

Monomer 13. 32(R)-(4-nitrophenyl)carbonate rapamycin
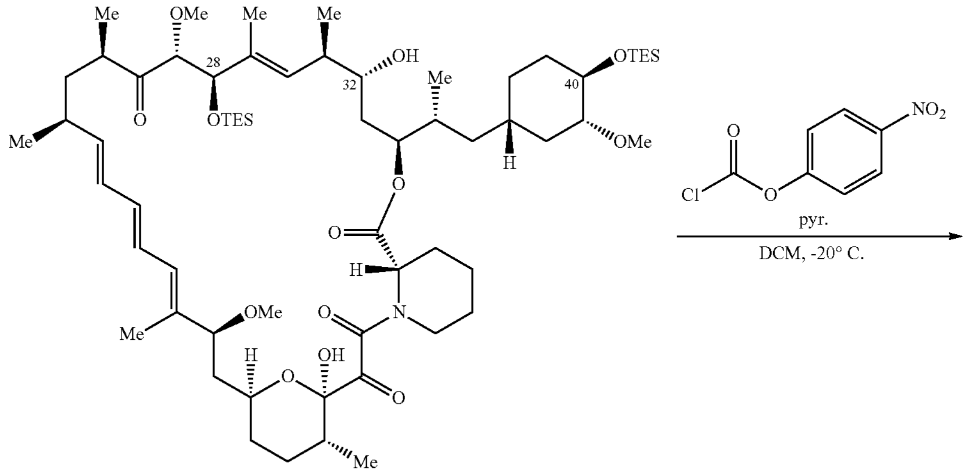
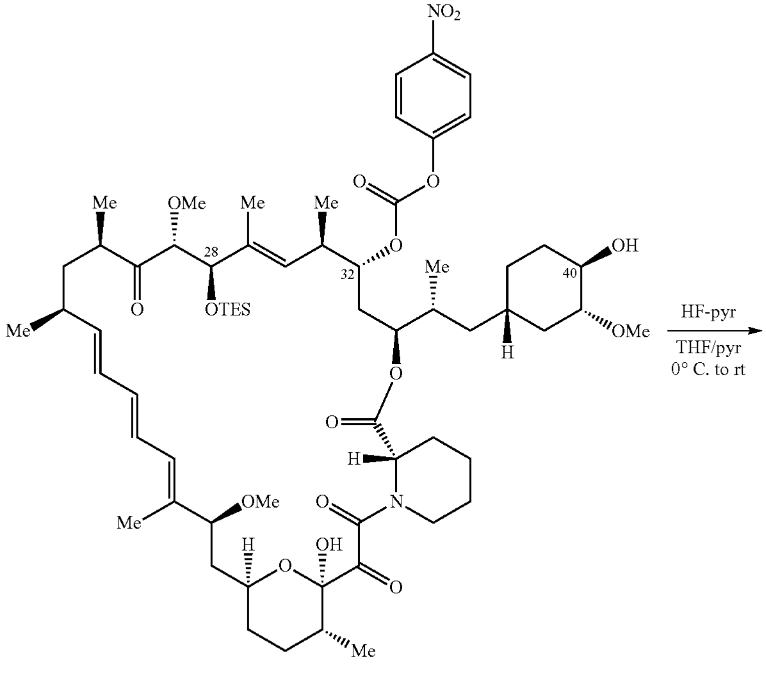

-continued

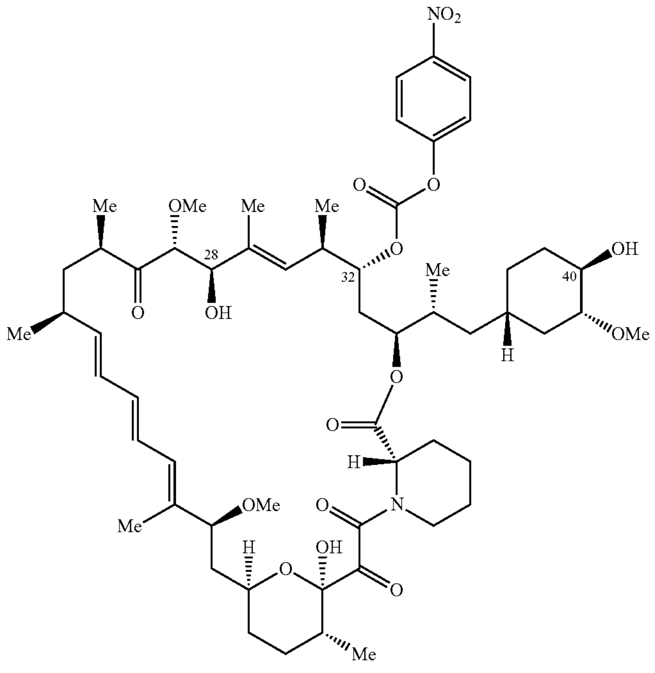

Step 1: Synthesis of 28,40-O-bis(triethylsilyl) 32(R)-(4-nitrophenyl)carbonate rapamycin To a solution of 28,40-O-bis(triethylsilyl) 32(R)-hydroxy rapamycin (0.602 g, 0.526 mmol, 1.0 equiv) in DCM (16 mL) at −20° C. was added pyridine (0.82 mL, 10 mmol, 19 equiv) followed by O-(4-nitrophenyl)chloroformate (0.36 g, 1.8 mmol, 3.4 equiv). The reaction mixture was warmed to room temperature and stirred for 1 h, at which point the solution was diluted with DCM (50 mL) and poured into $H_2O$ (30 mL). The aqueous layer was extracted with DCM (50 mL) and the combined organic layers were washed with brine (20 mL), dried and concentrated under reduced pressure to afford a faint yellow foam that was used directly in the next step.

Step 2: Synthesis of 32(R)-(4-nitrophenyl)carbonate rapamycin

To a solution of 28,40-O-bis(triethylsilyl) 32(R)-(4-nitrophenyl)carbonate rapamycin in THF (10 mL) in a polypropylene vial at 0° C. was added pyridine (1.70 mL, 21.0 mmol, 40.0 equiv) followed by 70% HF-pyridine (0.46 mL, 15.8 mmol, 30.0 equiv). The solution was warmed to room temperature and stirred overnight, at which point the solution was poured into sat. aqueous $NaHCO_3$ at 0° C. The aqueous layer was extracted with EtOAc (3×) and the combined organic layers were washed with sat. aqueous $NaHCO_3$ and brine, then dried and concentrated under reduced pressure. Purification by reverse phase chromatography (20→100% MeCN/$H_2O$) afforded the desired product as an off-white powder (420 mg, 74% yield 2-steps). LCMS (ESI) m/z: [M+Na] calcd for $C_{58}H_{84}N_2O_{17}$: 1103.57; found 1104.0.

Monomer 14. 32(S)-azido 40-(4-nitrophenyl)carbonate rapamycin
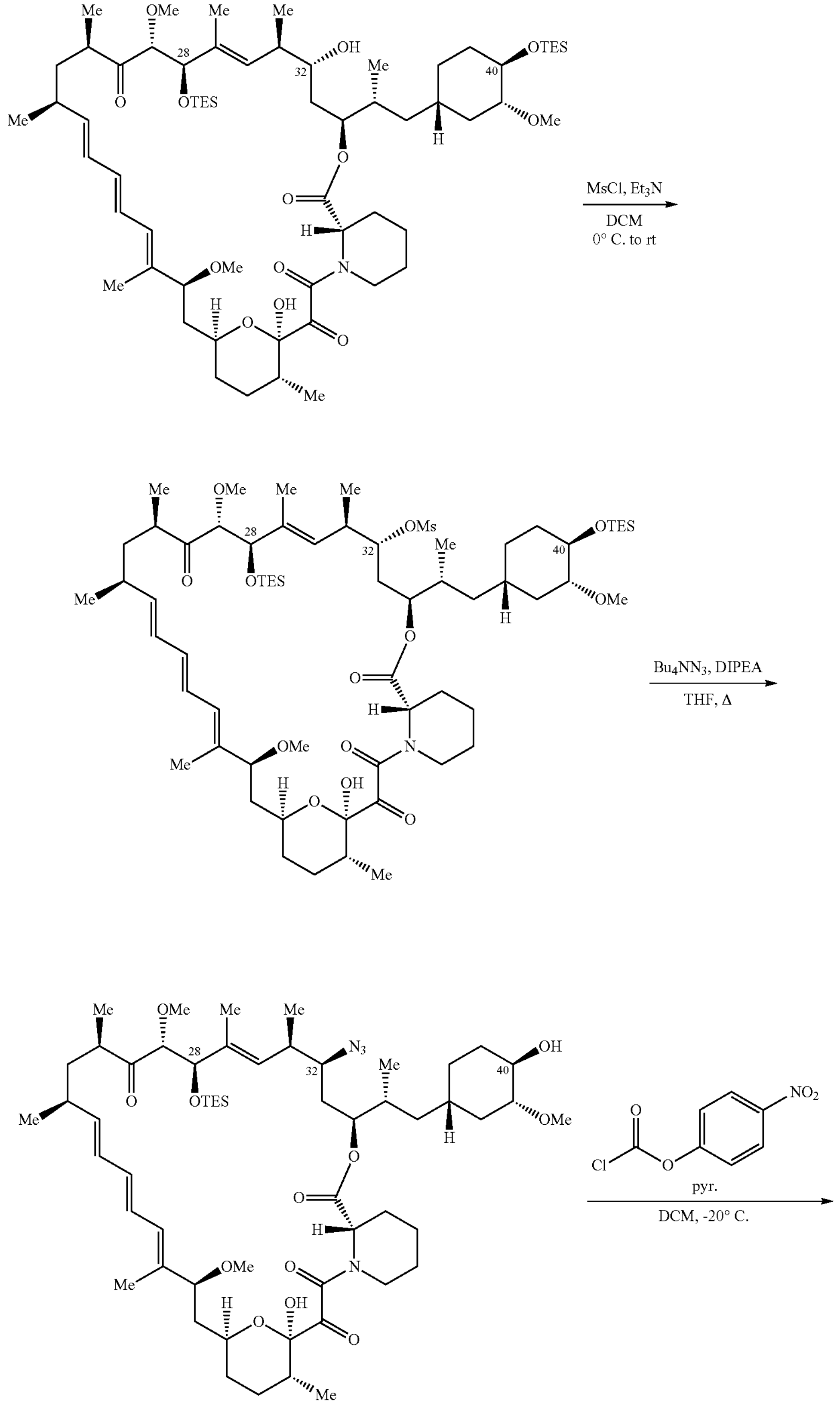

-continued

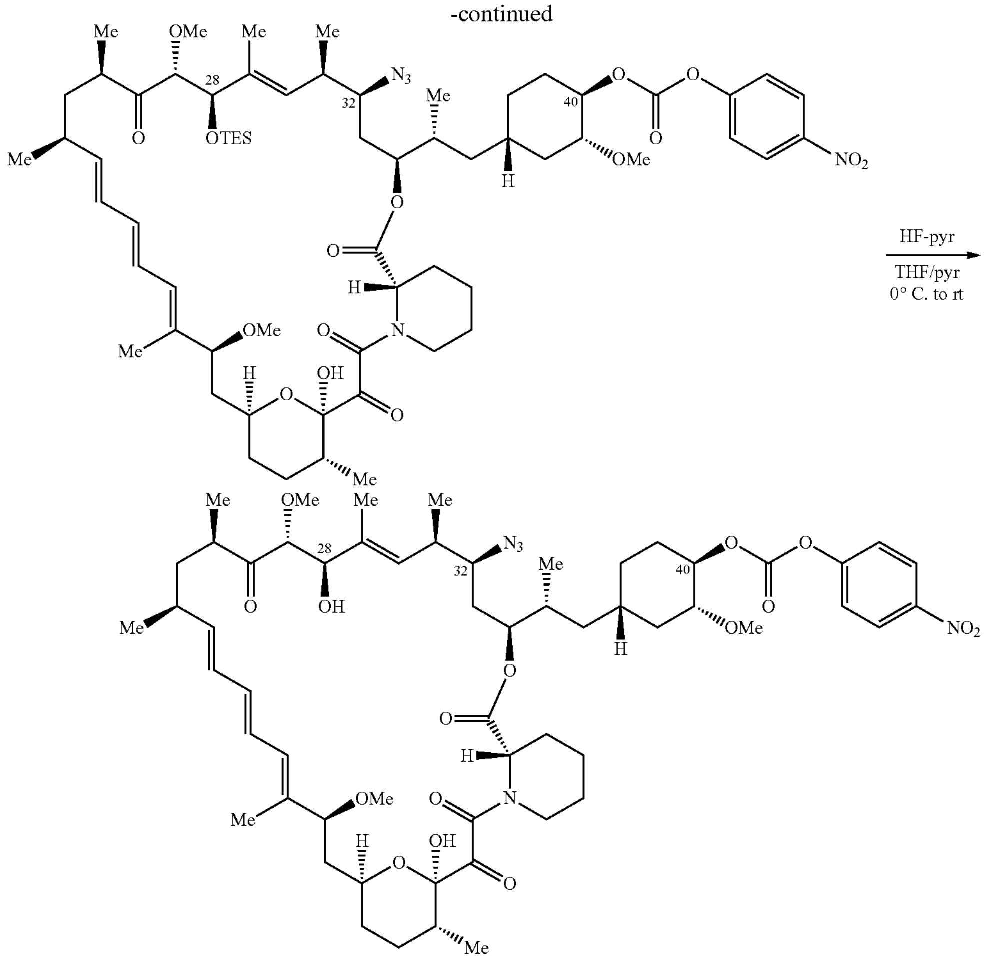

Step 1: Synthesis of 28,40-O-bis(triethylsilyl) 32(R)—O-methanesulfonyl rapamycin To a solution of 28,40-O-bis(triethylsilyl) 32(R)-hydroxy rapamycin (2.50 g, 2.18 mmol, 1.0 equiv) in DCM (25 mL) at 0° C. was added $Et_3N$ (0.912 mL, 6.54 mmol, 3.0 equiv) followed by methanesulfonyl chloride (0.338 mL, 4.36 mmol, 2.0 equiv). The solution was stirred at 0° C. for 3 h, at which point the EtOAc was added and the solution was washed with sat. aqueous $NaHCO_3$. The combined organic layers were washed with brine, dried and concentrated under reduced pressure to give a yellow oil which was used directly in the next step.

Step 2: Synthesis of 28-O-triethylsilyl 32(S)-azido rapamycin

To a solution of 28,40-O-bis(triethylsilyl) 32(R)—O-methanesulfonyl rapamycin in THF (40 mL) was added DIPEA (0.761 mL, 4.37 mmol, 2.0 equiv) and tetrabutylammonium azide (3.72 g, 13.1 mmol, 6.0 equiv). The reaction solution heated to reflux for 5.5 h and then cooled to room temperature. The solution was diluted with EtOAc and washed with sat. aqueous $NaHCO_3$. The combined organic layers were washed with brine, dried and concentrated under reduced pressure. Purification by reverse phase chromatography (30→100% MeCN/$H_2O$) afforded the desired product as a clear glass (746 mg, 33% yield 2-steps). LCMS (ESI) m/z: [M+Na] calcd for $C_{57}H_{94}N_4O_{12}Si$: 1077.65; found 1077.8.

Step 3: Synthesis of 28-O-triethylsilyl 32(S)-azido 40(R)-(4-nitrophenyl)carbonate rapamycin To a solution of 28-O-triethylsilyl 32(S)-azido rapamycin (0.505 g, 0.478 mmol, 1.0 equiv) in DCM (15 mL) was added pyridine (0.75 mL, 9.3 mmol, 19 equiv) and 4 Å molecular sieves. The suspension was cooled to −20° C. and O-(4-nitrophenyl)chloroformate (0.32 g, 1.6 mmol, 3.4 equiv) was added. The suspension was stirred at −20° C. for 2 h, at which point the it was diluted with DCM (50 mL), filtered and poured into $H_2O$ (20 mL). The aqueous layer was extracted with DCM (50 mL) and the combined organic layers were washed with brine (20 mL), dried and concentrated under reduced pressure to give a pale-yellow foam which was used directly in the next step.

Step 4: Synthesis of 32(S)-azido 40-O-(4-nitrophenyl)carbonate rapamycin

To a solution of 28-O-triethylsilyl 32(S)-azido 40(R)-(4-nitrophenyl)carbonate rapamycin in THF (10 mL) in a polypropylene vial at 0° C. was added pyridine (1.55 mL, 19.1 mmol, 40.0 equiv) followed by 70% HF-pyridine (0.42 mL, 14.4 mmol; 30.0 equiv). The solution was warmed to room temperature and stirred overnight, at which point the solution was poured into sat. aqueous $NaHCO_3$ at 0° C. The aqueous layer was extracted with EtOAc (3×) and the combined organic layers were washed with sat. aqueous $NaHCO_3$ and brine, then dried and concentrated under reduced pressure. Purification by reverse phase chromatography (30→100% MeCN/$H_2O$) afforded the desired product as an off-white powder (410 mg, 77% yield 2-steps). LCMS (ESI) m/z: [M+Na] calcd for $C_{58}H_{83}N_5O_{16}$: 1128.57; found 1129.0.

Monomer 15. 28-methoxy-40-O-(4-nitrophenoxy)carbonyl rapamycin

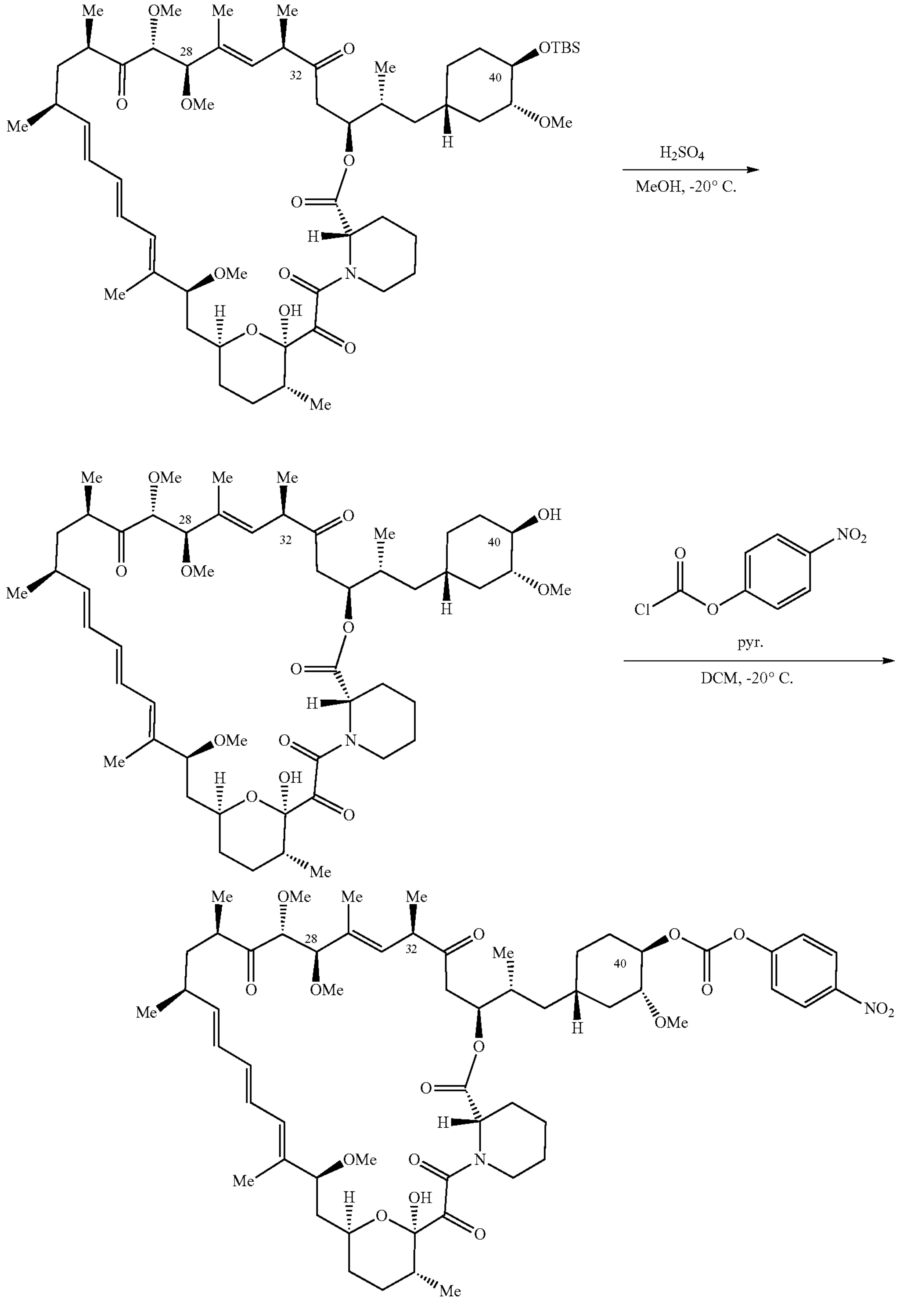

Step 1: Synthesis of 28-methoxy rapamycin

To a solution of 28-methoxy-40-O-(tert-butyldimethyl) silyl rapamycin (0.500 g, 0.480 mmol, 1.0 equiv) in MeOH (1.6 mL) at −20° C. was added $H_2SO_4$ (1.28 μL, 0.024 mmol, 0.05 equiv). The reaction mixture was stirred at −20° C. for 48 h. The reaction mixture was then poured into sat. aqueous $NaHCO_3$ (4 mL)/$H_2O$ (4 mL). The aqueous layer was extracted with MTBE (2×6 mL), and the combined organic phases were dried, filtered, and concentrated under reduced pressure. Purification by reverse phase chromatography (30→100% MeCN/$H_2O$) afforded the desired product as a yellow powder (270 mg, 61% yield). LCMS (ESI) m/z: [M+Na] calcd for $C_{52}H_{81}NO_{13}$: 950.5; found 950.7.

Step 2: Synthesis of 28-methoxy-40-O-(4-nitrophenoxy)carbonyl rapamycin

To a solution of 28-methoxy rapamycin (0.210 g, 0.226 mmol, 1.0 equiv) in DCM (7.1 mL) at −20° C. was added pyridine (0.35 mL, 4.4 mmol, 19 equiv) and then p-nitrophenyl chloroformate (0.15 g, 0.76 mmol, 3.4 equiv). The reaction mixture was stirred at −20° C. for 30 min and then warmed to room temperature. After stirring overnight, p-nitrophenyl chloroformate (0.15 g, 0.76 mmol, 3.4 equiv) was added and the reaction was stirred for an additional 2 h. The reaction mixture was diluted with DCM (20 mL) and poured into $H_2O$ (10 mL). The aqueous layer was extracted with DCM (20 mL), and the combined organic layers were washed with brine (9 mL), dried, filtered and concentrated under reduced pressure. Purification by reverse phase chromatography (50→100% MeCN/$H_2O$) afforded the desired product as a pale yellow powder (200 mg, 81% yield). LCMS (ESI) m/z: [M+Na] calcd for $C_{59}H_{84}N_2O_{17}$: 1115.6; found 1115.8.

Monomer 16. 32(R),40-O,O-bis[(4-nitrophenoxy) carbonyl] rapamycin

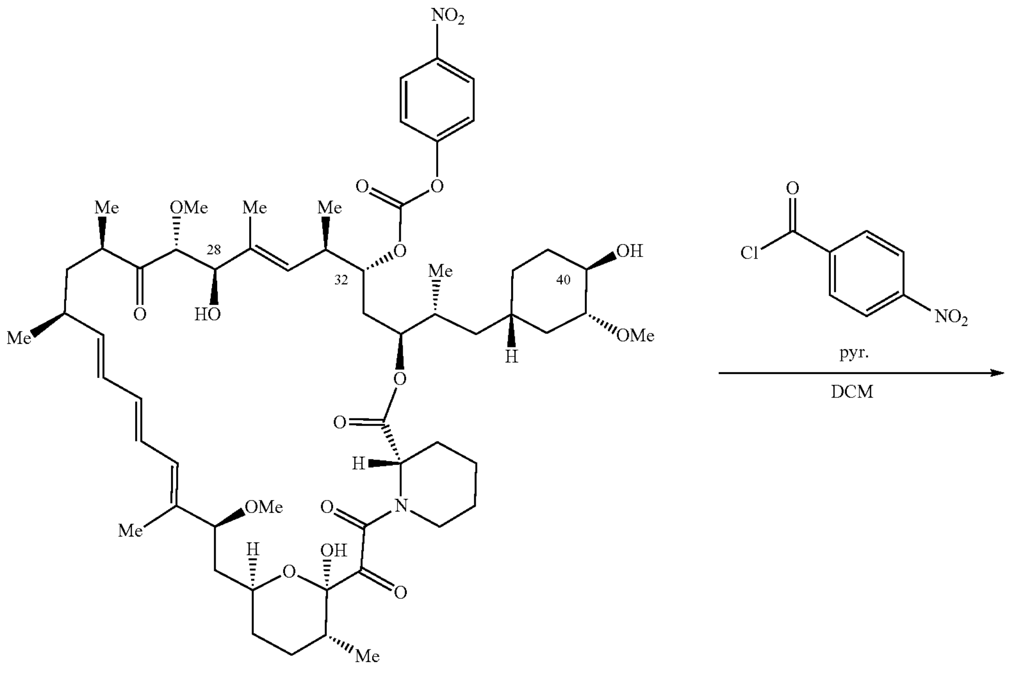

-continued

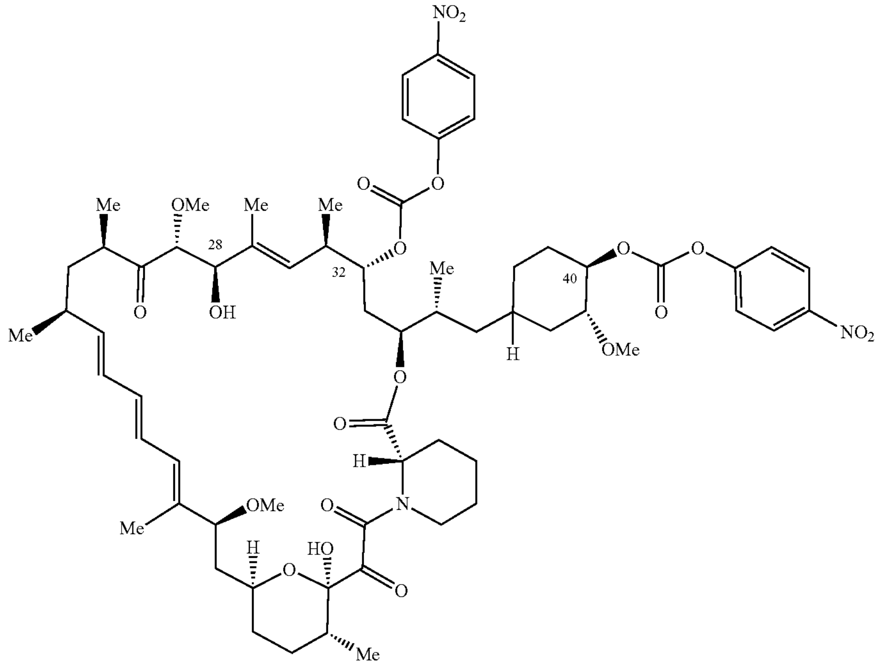

To a solution of 32(R)—O-[(4-nitrophenoxy)carbonyl] rapamycin (675 mg, 0.624 mmol, 1.0 equiv) in DCM (13 mL) was added powdered 4 Å molecular sieves (675 mg). The suspension was stirred for 1 h, at which point pyridine (0.56 mL, 6.90 mmol, 11.1 equiv) was added. The mixture was cooled to −15° C. and then p-nitrophenyl chloroformate (132 mg, 0.655 mmol, 1.05 equiv) was added in one portion. The mixture was warmed to 0° C., stirred for 4 h, and then warmed to room temperature. The reaction mixture was filtered and washed with DCM (25 mL). The filtrate was washed with sat. aqueous $NaHCO_3$ (15 mL), $H_2O$ (15 mL), and brine (10 mL), dried, filtered, and concentrated under reduced pressure. Purification by silica gel chromatography (25→45% EtOAc/hexanes) afforded the desired product as a faint yellow solid (566 mg, 73% yield). LC-MS (ESI) m/z: [M+Na] calcd for $C_{65}H_{87}N_3O_{21}$: 1268.57; found 1269.3.

Monomer 17. 28(R),32(R),40(R)—O,O,O-tris[(4-nitrophenoxy)carbonyl] rapamycin

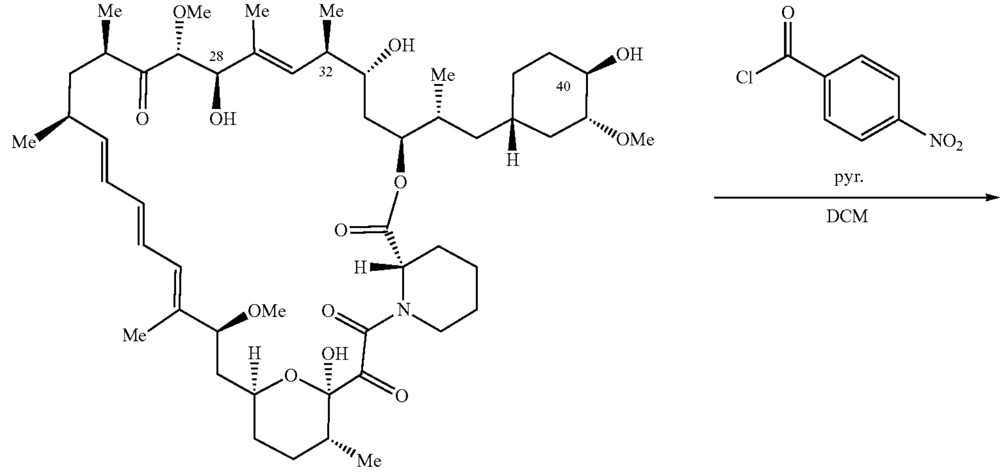

-continued

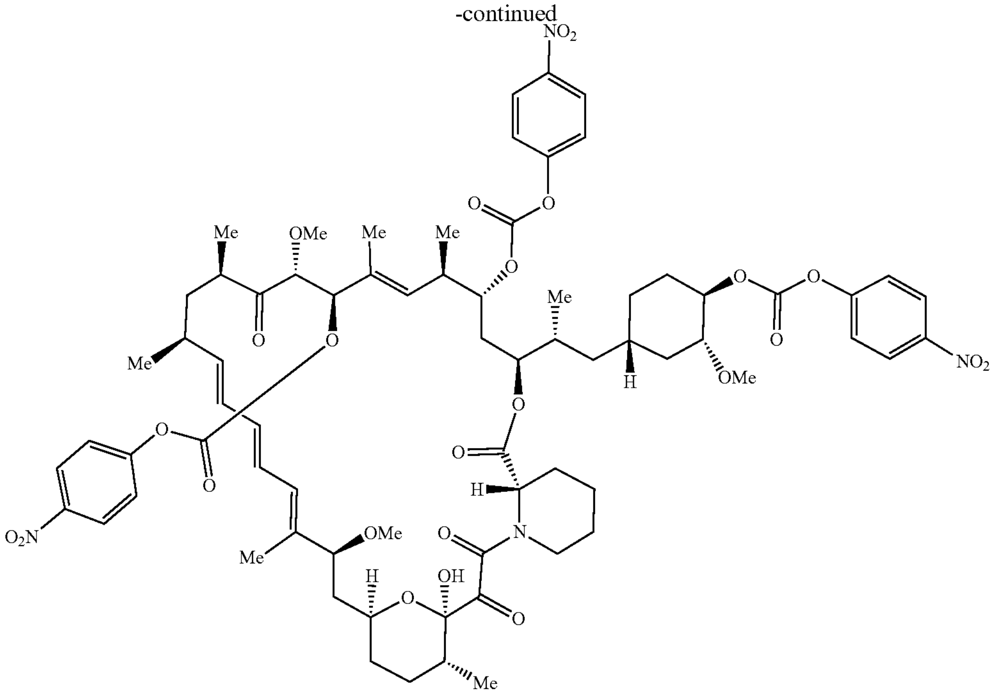

To a solution of 32(R)-hydroxy rapamycin (1.00 g, 1.09 mmol, 1.0 equiv) in DCM (22 mL) was added powdered 4 Å molecular sieves (1.0 g). The suspension was stirred for 45 min, at which point pyridine (0.97 mL, 12.0 mmol, 11.0 equiv) was added. The mixture was cooled to −15° C. and then p-nitrophenyl chloroformate (550 mg, 2.73 mmol, 2.5 equiv) was added in one portion. The mixture was warmed to room temperature over 4 h and stirred overnight. The mixture was cooled to 0° C. and additional p-nitrophenyl chloroformate (220 mg, 1.09 mmol, 1.0 equiv) was added in one portion. The reaction mixture was stirred for 1 h, warmed to room temperature, and then stirred for 2 h. The mixture was once again cooled to 0° C. and additional p-nitrophenyl chloroformate (660 mg, 3.27 mmol, 3.0 equiv) was added. The reaction mixture was stirred for 15 min and then at room temperature for 1 h. The reaction mixture was filtered and washed with DCM (25 mL). The filtrate was washed with sat. aqueous $NaHCO_3$ (20 mL), $H_2O$ (20 mL), and brine (15 mL), dried, filtered, and concentrated under reduced pressure. Purification by silica gel chromatography (5→15% EtOAc/DCM) afforded the desired product as a faint yellow solid (550 mg, 36% yield). LC-MS (ESI) m/z: [M+Na] calcd for $C_{72}H_{90}N_4O_{25}$: 1433.58; found 1434.3.

General Procedures and Specific Examples

General Procedure 1: Coupling of a Carboxylic Acid and an Amine Followed by N-Boc Deprotection.

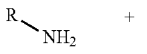

-continued

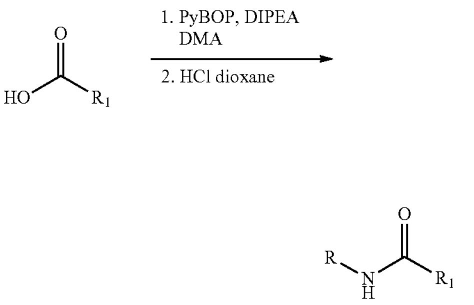

Step 1:

To a 0.1 M solution of carboxylic acid (1.0 equiv) in DMA was added an amine (1.2 equiv), DIPEA (4.0 equiv) and PyBOP (1.3 equiv). The reaction was allowed to stir until consumption of the carboxylic acid, as indicated by LCMS. The reaction mixture was then purified by silica gel chromatography to afford the product.

Step 2:

To a 0.07 M solution of N-Boc protected amine (1.0 equiv) in dioxane was added HCl (4 M in dioxane) (50 equiv). The reaction was allowed to stir until consumption of N-Boc protected amine, as indicated by LCMS. Then the reaction was concentrated to an oil, which was then dissolved in $H_2O$ and lyophilized to afford the product.

Intermediate A1-7. 1-amino-27-(6-{[4-amino-3-(2-amino-1,3-benzoxazol-5-yl)-1H-pyrazolo[3,4-d]pyrimidin-1-yl]methyl}-1,2,3,4-tetrahydroisoquinolin-2-yl)-3,6,9,12,15,18,21,24-octaoxaheptacosan-27-one

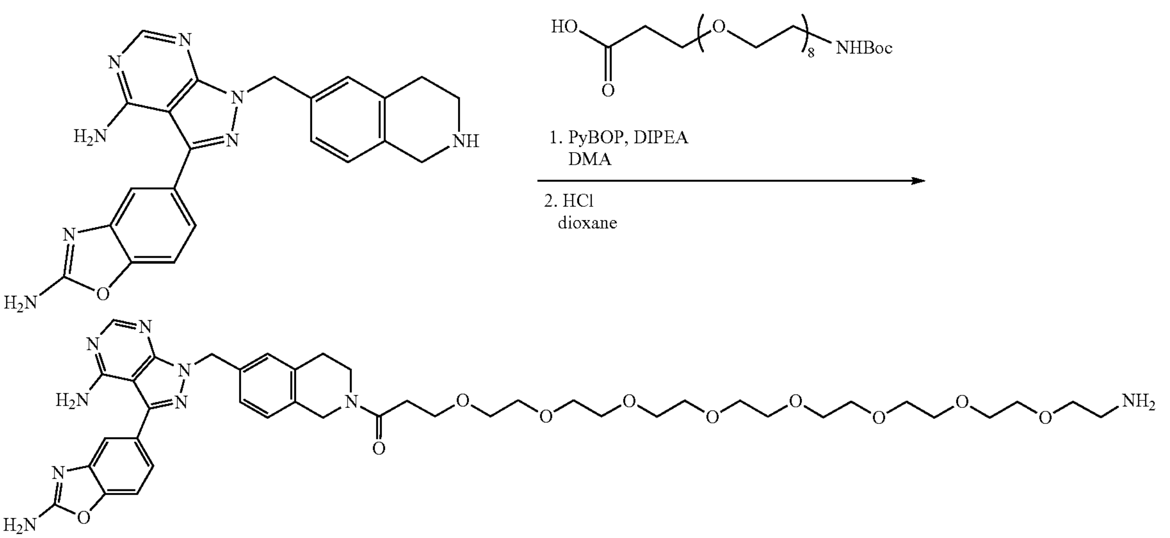

Step 1: Synthesis of tert-butyl N-[27-(6-{[4-amino-3-(2-amino-1,3-benzoxazol-5-yl)-1H-pyrazolo[3,4-d]pyrimidin-1-yl]methyl}-1,2,3,4-tetrahydroisoquinolin-2-yl)-27-oxo-3,6,9,12,15,18,21,24-octaoxaheptacosan-1-yl]carbamatecarbamate To a solution of 1-{[(tert-butoxy)carbonyl]amino}-3,6,9,12,15,18,21,24-octaoxaheptacosan-27-oic acid (102 mg, 189 μmol, 1.0 equiv) and 6-{[4-amino-3-(2-amino-1,3-benzoxazol-5-yl)-1H-pyrazolo[3,4-d]pyrimidin-1-yl]methyl}-1,2,3,4-tetrahydroisoquinolin-2-ium (120 mg, 227 μmol, 1.2 equiv) in DMA (1.88 mL) was added DIPEA (131 μL, 756 μmol, 4.0 equiv) followed by PyBOP (127 mg, 245 μmol, 1.3 equiv). The reaction was stirred at room temperature. After 2 h, the reaction mixture was concentrated under reduced pressure and the crude residue was purified by silica gel chromatography (0→20% MeOH/DCM) to give the product (161.5 mg, 91% yield) as a pale yellow oil. LCMS (ESI) m/z: [M+H] calcd for $C_{46}H_{65}N_9O_{12}$: 936.49; found 936.3.

Step 2: Synthesis of 1-amino-27-(6-{[4-amino-3-(2-amino-1,3-benzoxazol-5-yl)-1H-pyrazolo[3,4-d]pyrimidin-1-yl]methyl}-1,2,3,4-tetrahydroisoquinolin-2-yl)-3,6,9,12,15,18,21,24-octaoxaheptacosan-27-one To a solution of tert-butyl N-[27-(6-{[4-amino-3-(2-amino-1,3-benzoxazol-5-yl)-1H-pyrazolo[3,4-d]pyrimidin-1-yl]methyl}-1,2,3,4-tetrahydroisoquinolin-2-yl)-27-oxo-3,6,9,12,15,18,21,24-octaoxaheptacosan-1-yl]carbamate (0.9 g, 0.9614 mmol, 1.0 equiv) in dioxane (3.20 mL) was added HCl (4 M in dioxane, 2.40 mL, 9.61 mmol, 10.0 equiv). The reaction stirred for 2 h and then was concentrated under reduced pressure to an oil. The oil was azeotroped with DCM (3x15 mL) to provide the product (881 mg, 105% yield, HCl) as a tan solid, which was used directly in the next step. LCMS (ESI) m/z: [M+H] calcd for $C_{41}H_{57}N_9O_{10}$: 836.43; found 836.3.

Following General Procedure 1, but using the appropriate amine-containing active site inhibitor in Table 2 and PEG carboxylic acid, the Intermediates $A^1$ in Table 5 were prepared:

TABLE 5

| Additional amines prepared<br>Structure |
|---|
| 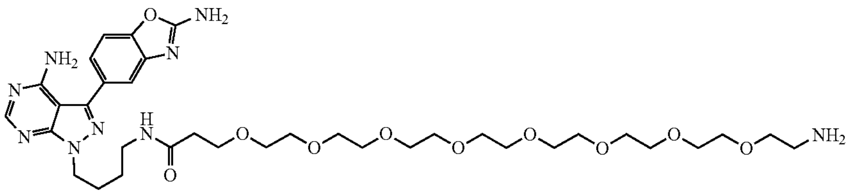 [SMILES: NCCOCCOCCOCCOCCOCCOCCOCCOCCC(=O)NCCCCn1nc(-c2ccc3oc(N)nc3c2)c2c(N)ncnc21]<br>Intermediate A1-1 |

TABLE 5-continued
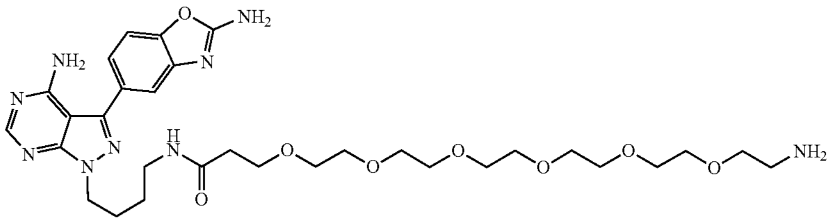 [SMILES: NCCOCCOCCOCCOCCOCCOCCC(=O)NCCCCn1nc(-c2ccc3oc(N)nc3c2)c2c(N)ncnc21]
Intermediate A1-2
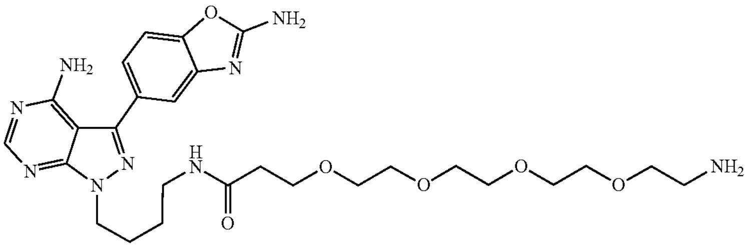 [SMILES: NCCOCCOCCOCCOCCC(=O)NCCCCn1nc(-c2ccc3oc(N)nc3c2)c2c(N)ncnc21]
Intermediate A1-3
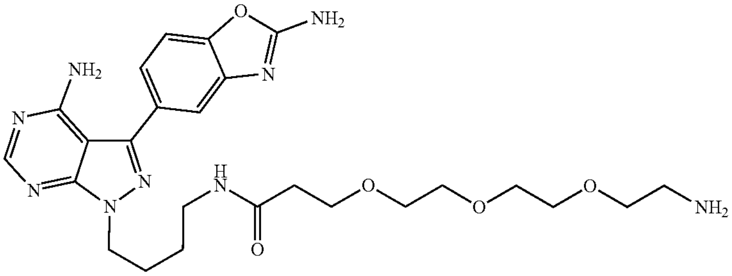 [SMILES: NCCOCCOCCOCCC(=O)NCCCCn1nc(-c2ccc3oc(N)nc3c2)c2c(N)ncnc21]
Intermediate A1-4
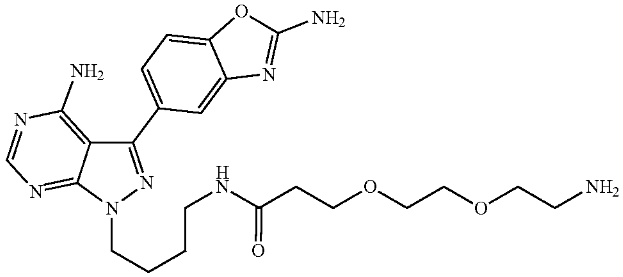 [SMILES: NCCOCCOCCC(=O)NCCCCn1nc(-c2ccc3oc(N)nc3c2)c2c(N)ncnc21]
Intermediate A1-5
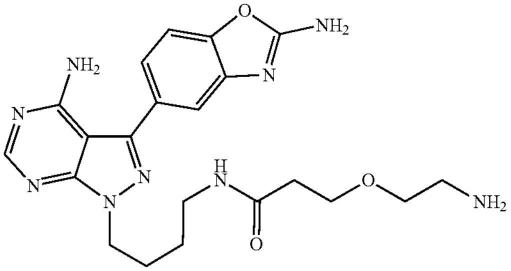 [SMILES: NCCOCCC(=O)NCCCCn1nc(-c2ccc3oc(N)nc3c2)c2c(N)ncnc21]
Intermediate A1-6

TABLE 5-continued
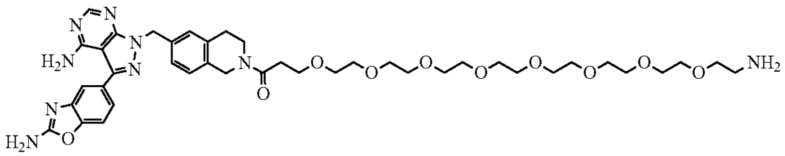 [SMILES: NCCOCCOCCOCCOCCOCCOCCOCCOCCC(=O)N1CCc2cc(Cn3nc(-c4ccc5oc(N)nc5c4)c4c(N)ncnc43)ccc2C1]
Intermediate A1-7
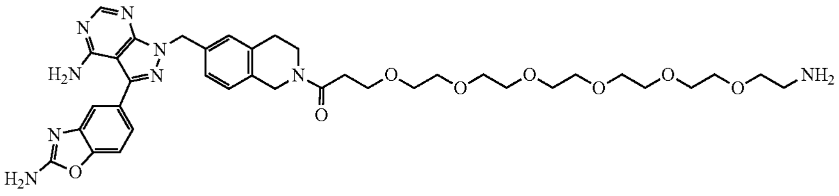 [SMILES: NCCOCCOCCOCCOCCOCCOCCC(=O)N1CCc2cc(Cn3nc(-c4ccc5oc(N)nc5c4)c4c(N)ncnc43)ccc2C1]
Intermediate A1-8
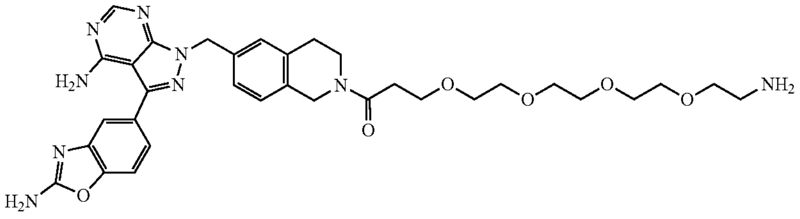 [SMILES: NCCOCCOCCOCCOCCC(=O)N1CCc2cc(Cn3nc(-c4ccc5oc(N)nc5c4)c4c(N)ncnc43)ccc2C1]
Intermediate A1-9
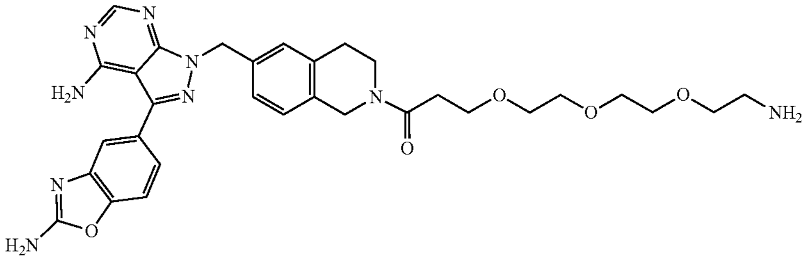 [SMILES: NCCOCCOCCOCCC(=O)N1CCc2cc(Cn3nc(-c4ccc5oc(N)nc5c4)c4c(N)ncnc43)ccc2C1]
Intermediate A1-10
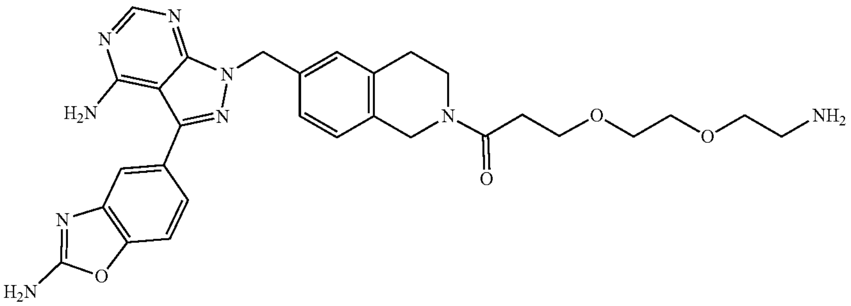 [SMILES: NCCOCCOCCC(=O)N1CCc2cc(Cn3nc(-c4ccc5oc(N)nc5c4)c4c(N)ncnc43)ccc2C1]
Intermediate A1-11

TABLE 5-continued
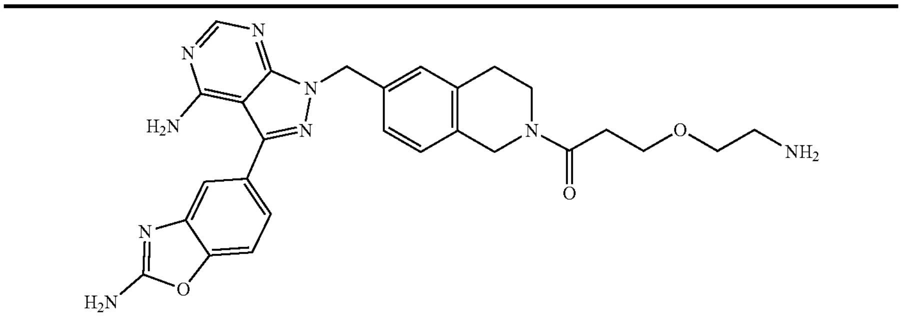
Intermediate A1-12
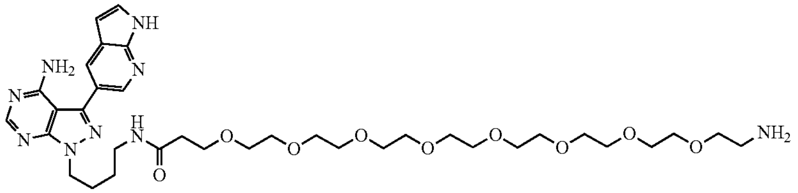 [SMILES: NCCOCCOCCOCCOCCOCCOCCOCCOCCC(=O)NCCCCn1nc(-c2cnc3[nH]ccc3c2)c2c(N)ncnc21]
Intermediate A1-13
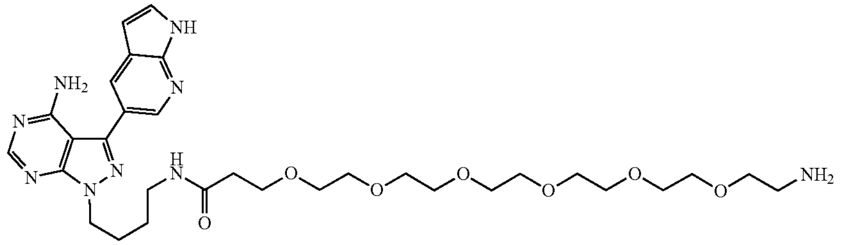 [SMILES: NCCOCCOCCOCCOCCOCCOCCC(=O)NCCCCn1nc(-c2cnc3[nH]ccc3c2)c2c(N)ncnc21]
Intermediate A1-14
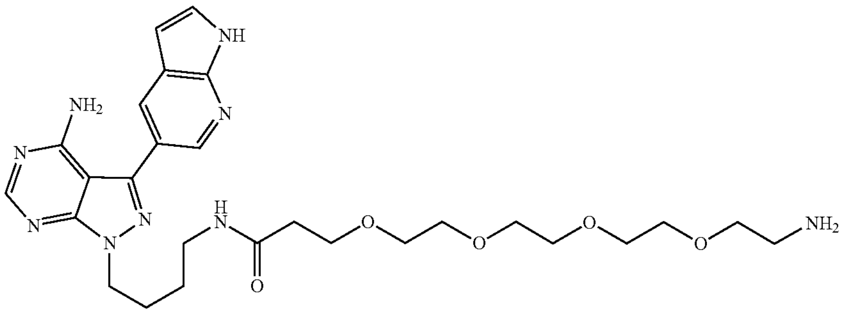 [SMILES: NCCOCCOCCOCCOCCC(=O)NCCCCn1nc(-c2cnc3[nH]ccc3c2)c2c(N)ncnc21]
Intermediate A1-15
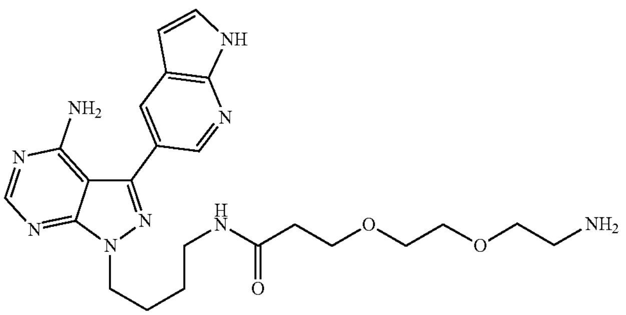 [SMILES: NCCOCCOCCC(=O)NCCCCn1nc(-c2cnc3[nH]ccc3c2)c2c(N)ncnc21]
Intermediate A1-16

TABLE 5-continued
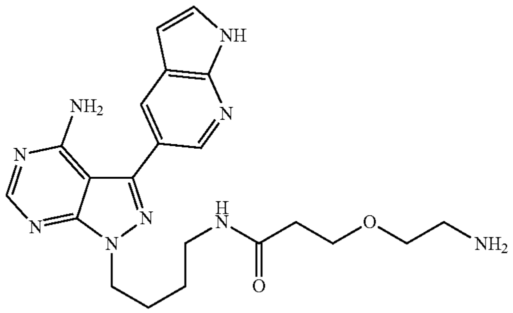 [SMILES: NCCOCCC(=O)NCCCCn1nc(-c2cnc3[nH]ccc3c2)c2c(N)ncnc21]
Intermediate A1-17
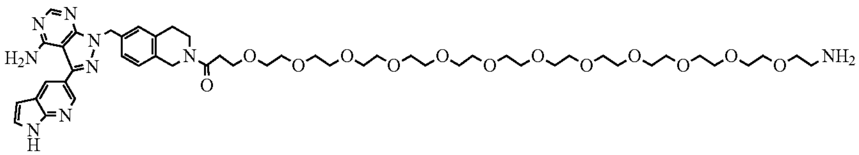 [SMILES: NCCOCCOCCOCCOCCOCCOCCOCCOCCOCCOCCOCCOCCC(=O)N1CCc2cc(Cn3nc(-c4cnc5[nH]ccc5c4)c4c(N)ncnc43)ccc2C1]
Intermediate A1-18
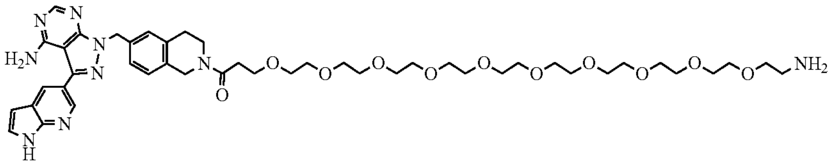 [SMILES: NCCOCCOCCOCCOCCOCCOCCOCCOCCOCCOCCC(=O)N1CCc2cc(Cn3nc(-c4cnc5[nH]ccc5c4)c4c(N)ncnc43)ccc2C1]
Intermediate A1-19
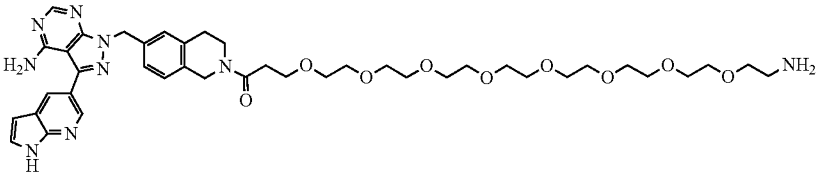 [SMILES: NCCOCCOCCOCCOCCOCCOCCOCCOCCC(=O)N1CCc2cc(Cn3nc(-c4cnc5[nH]ccc5c4)c4c(N)ncnc43)ccc2C1]
Intermediate A1-20
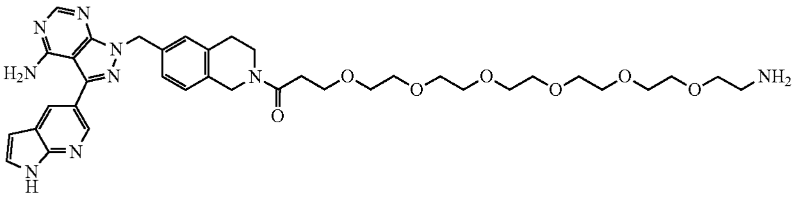 [SMILES: NCCOCCOCCOCCOCCOCCOCCC(=O)N1CCc2cc(Cn3nc(-c4cnc5[nH]ccc5c4)c4c(N)ncnc43)ccc2C1]
Intermediate A1-21
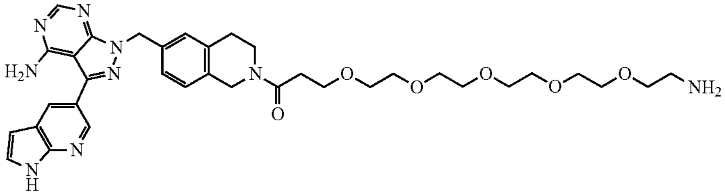 [SMILES: NCCOCCOCCOCCOCCOCCC(=O)N1CCc2cc(Cn3nc(-c4cnc5[nH]ccc5c4)c4c(N)ncnc43)ccc2C1]
Intermediate A1-22

TABLE 5-continued
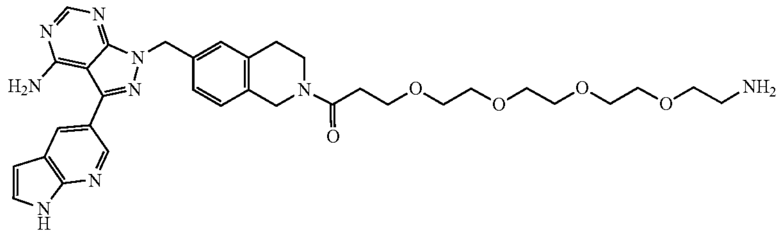 [SMILES: NCCOCCOCCOCCOCCC(=O)N1CCc2cc(Cn3nc(-c4cnc5[nH]ccc5c4)c4c(N)ncnc43)ccc2C1]
Intermediate A1-23
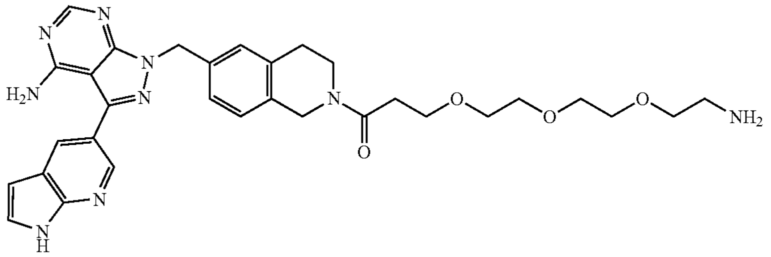 [SMILES: NCCOCCOCCOCCC(=O)N1CCc2cc(Cn3nc(-c4cnc5[nH]ccc5c4)c4c(N)ncnc43)ccc2C1]
Intermediate A1-24
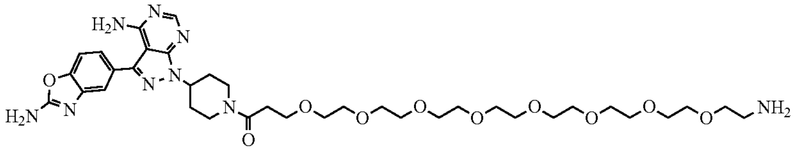 [SMILES: NCCOCCOCCOCCOCCOCCOCCOCCOCCC(=O)N1CCC(n2nc(-c3ccc4oc(N)nc4c3)c3c(N)ncnc32)CC1]
Intermediate A1-25
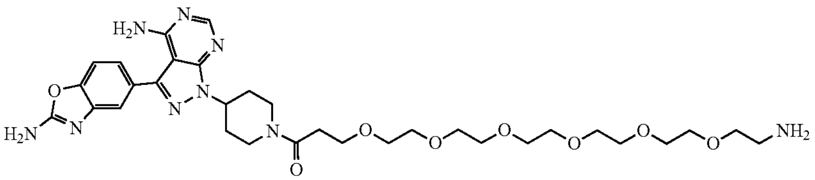 [SMILES: NCCOCCOCCOCCOCCOCCOCCC(=O)N1CCC(n2nc(-c3ccc4oc(N)nc4c3)c3c(N)ncnc32)CC1]
Intermediate A1-26
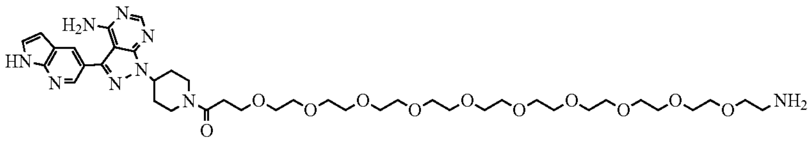
Intermediate A1-27
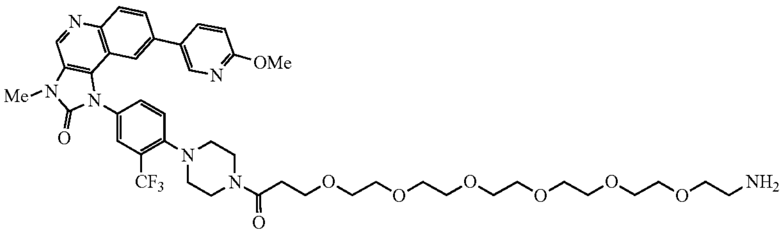 [SMILES: COc1ccc(-c2ccc3ncc4c(c3c2)n(-c2ccc(N3CCN(C(=O)CCOCCOCCOCCOCCOCCOCCN)CC3)c(C(F)(F)F)c2)c(=O)n4C)cn1]
Intermediate A1-28

TABLE 5-continued
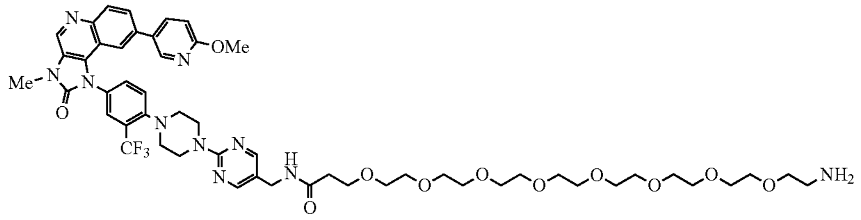 [SMILES: COc1ccc(-c2ccc3ncc4c(c3c2)n(-c2ccc(N3CCN(c5ncc(CNC(=O)CCOCCOCCOCCOCCOCCOCCOCCOCCN)cn5)CC3)c(C(F)(F)F)c2)c(=O)n4C)cn1]
Intermediate A1-29
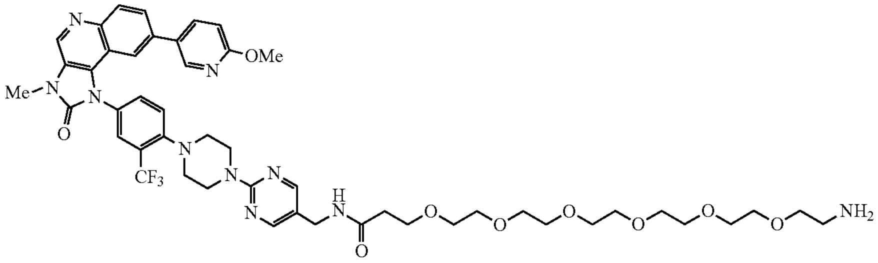 [SMILES: COc1ccc(-c2ccc3ncc4c(c3c2)n(-c2ccc(N3CCN(c5ncc(CNC(=O)CCOCCOCCOCCOCCOCCOCCN)cn5)CC3)c(C(F)(F)F)c2)c(=O)n4C)cn1]
Intermediate A1-30
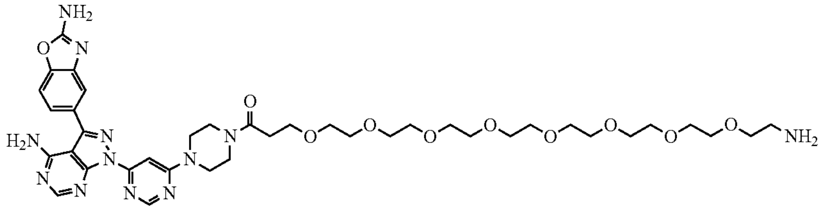 [SMILES: NCCOCCOCCOCCOCCOCCOCCOCCOCCC(=O)N1CCN(c2cc(-n3nc(-c4ccc5oc(N)nc5c4)c4c(N)ncnc43)ncn2)CC1]
Intermediate A1-31
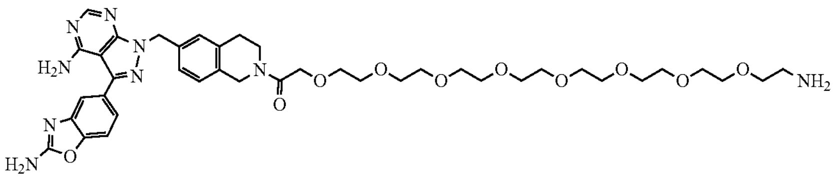 [SMILES: NCCOCCOCCOCCOCCOCCOCCOCCOCC(=O)N1CCc2cc(Cn3nc(-c4ccc5oc(N)nc5c4)c4c(N)ncnc43)ccc2C1]
Intermediate A1-32
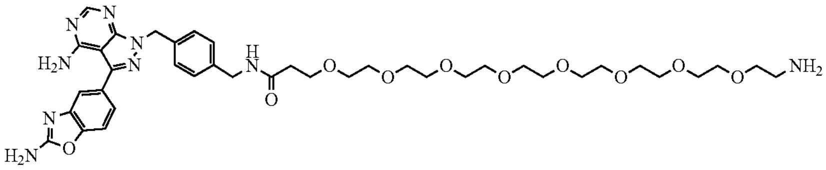 [SMILES: NCCOCCOCCOCCOCCOCCOCCOCCOCCC(=O)NCc1ccc(Cn2nc(-c3ccc4oc(N)nc4c3)c3c(N)ncnc32)cc1]
Intermediate A1-33
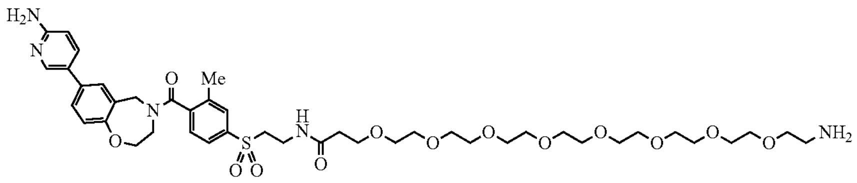 [SMILES: Cc1cc(S(=O)(=O)CCNC(=O)CCOCCOCCOCCOCCOCCOCCOCCOCCN)ccc1C(=O)N1CCOc2ccc(-c3ccc(N)nc3)cc2C1]
Intermediate A1-34

TABLE 5-continued
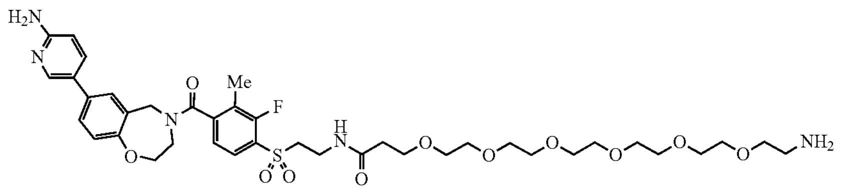 [SMILES: Cc1c(C(=O)N2CCOc3ccc(-c4ccc(N)nc4)cc3C2)ccc(S(=O)(=O)CCNC(=O)CCOCCOCCOCCOCCOCCOCCN)c1F]
Intermediate A1-35
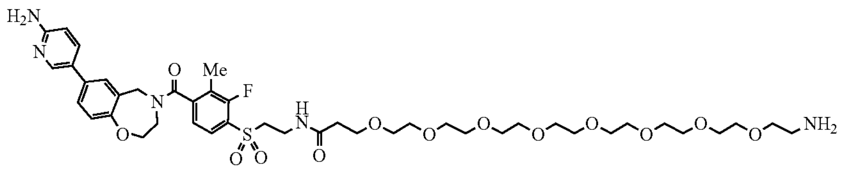 [SMILES: Cc1c(C(=O)N2CCOc3ccc(-c4ccc(N)nc4)cc3C2)ccc(S(=O)(=O)CCNC(=O)CCOCCOCCOCCOCCOCCOCCOCCOCCN)c1F]
Intermediate A1-36
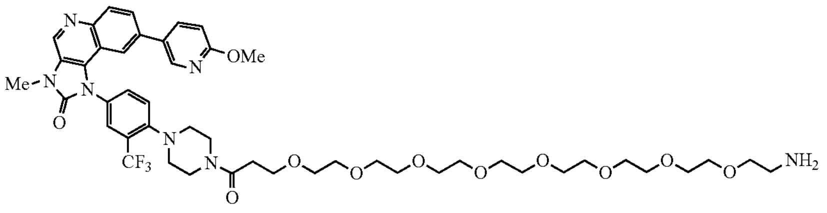 [SMILES: COc1ccc(-c2ccc3ncc4c(c3c2)n(-c2ccc(N3CCN(C(=O)CCOCCOCCOCCOCCOCCOCCOCCOCCN)CC3)c(C(F)(F)F)c2)c(=O)n4C)cn1]
Intermediate A1-37
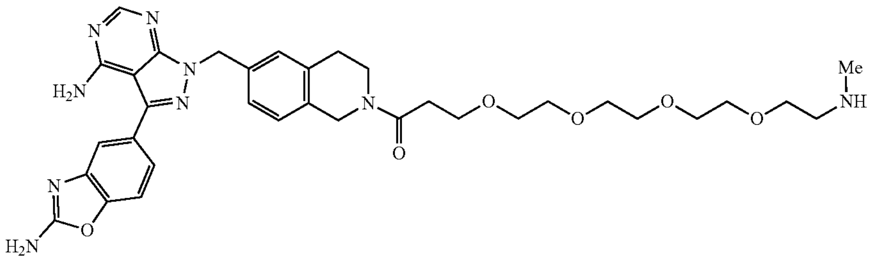 [SMILES: CNCCOCCOCCOCCOCCC(=O)N1CCc2cc(Cn3nc(-c4ccc5oc(N)nc5c4)c4c(N)ncnc43)ccc2C1]
Intermediate A1-38
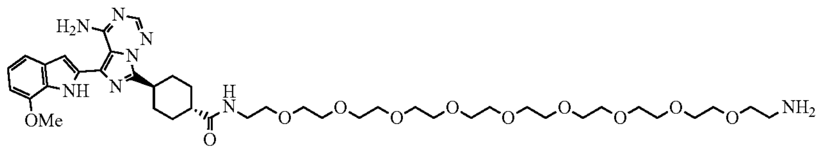 [SMILES: COc1cccc2cc(-c3nc([C@H]4CC[C@H](C(=O)NCCOCCOCCOCCOCCOCCOCCOCCOCCOCCN)CC4)n4ncnc(N)c34)[nH]c12]
Intermediate A1-39
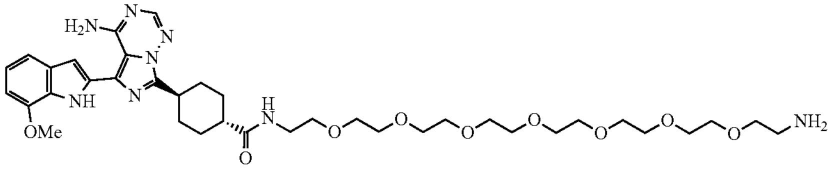 [SMILES: COc1cccc2cc(-c3nc([C@H]4CC[C@H](C(=O)NCCOCCOCCOCCOCCOCCOCCOCCN)CC4)n4ncnc(N)c34)[nH]c12]
Intermediate A1-40

TABLE 5-continued
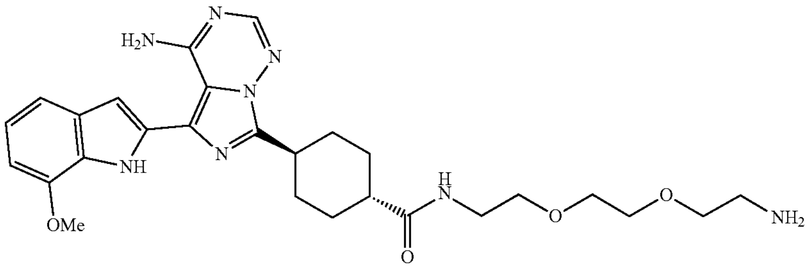 [SMILES: COc1cccc2cc(-c3nc([C@H]4CC[C@H](C(=O)NCCOCCOCCN)CC4)n4ncnc(N)c34)[nH]c12]
Intermediate A1-41
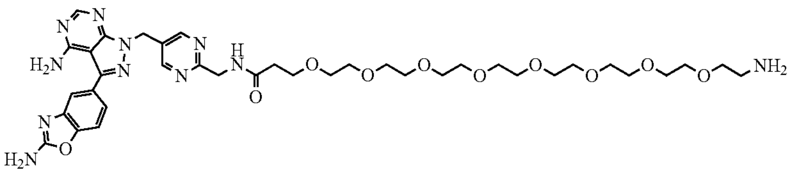 [SMILES: NCCOCCOCCOCCOCCOCCOCCOCCOCCC(=O)NCc1ncc(Cn2nc(-c3ccc4oc(N)nc4c3)c3c(N)ncnc32)cn1]
Intermediate A1-42
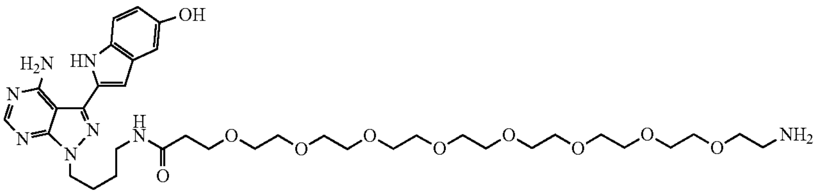 [SMILES: NCCOCCOCCOCCOCCOCCOCCOCCOCCC(=O)NCCCCn1nc(-c2cc3cc(O)ccc3[nH]2)c2c(N)ncnc21]
Intermediate A1-43
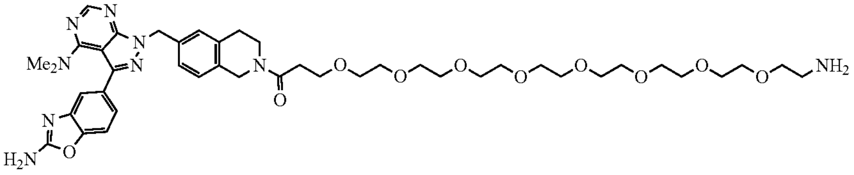 [SMILES: CN(C)c1ncnc2c1c(-c1ccc3oc(N)nc3c1)nn2Cc1ccc2c(c1)CCN(C(=O)CCOCCOCCOCCOCCOCCOCCOCCOCCN)C2]
Intermediate A1-44
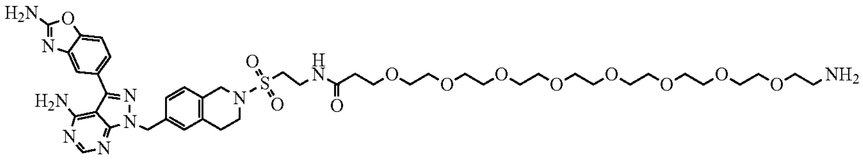 [SMILES: NCCOCCOCCOCCOCCOCCOCCOCCOCCC(=O)NCCS(=O)(=O)N1CCc2cc(Cn3nc(-c4ccc5oc(N)nc5c4)c4c(N)ncnc43)ccc2C1]
Intermediate A1-45
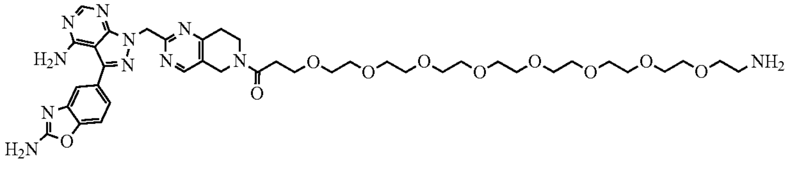 [SMILES: NCCOCCOCCOCCOCCOCCOCCOCCOCCC(=O)N1CCc2nc(Cn3nc(-c4ccc5oc(N)nc5c4)c4c(N)ncnc43)ncc2C1]
Intermediate A1-46
Additional amines prepared
| Structure | Molecular Formula | Calculated MW | Observed MW |
|---|---|---|---|
| Intermediate A1-1 | $C_{35}H_{55}N_9O_{10}$ | [M + H] = 762.42 | [M + H] = 762.3 |
| Intermediate A1-2 | $C_{31}H_{47}N_9O_8$ | [M + H] = 674.36 | [M + H] = 674.3 |
| Intermediate A1-3 | $C_{27}H_{39}N_9O_6$ | [M + H] = 586.31 | [M + H] = 586.6 |

TABLE 5-continued

| | | | |
|---|---|---|---|
| Intermediate A1-4 | $C_{25}H_{35}N_9O_5$ | [M + H] = 542.29 | [M + H] = 542.3 |
| Intermediate A1-5 | $C_{23}H_{31}N_9O_4$ | [M + H] = 498.26 | [M + H] = 498.2 |
| Intermediate A1-6 | $C_{21}H_{27}N_9O_3$ | [M + H] = 454.23 | [M + H] = 454.1 |
| Intermediate A1-7 | $C_{41}H_{57}N_9O_{10}$ | [M + H] = 836.43 | [M + H] = 836.3 |
| Intermediate A1-8 | $C_{37}H_{49}N_9O_8$ | [M + H] = 748.38 | [M + H] = 748.2 |
| Intermediate A1-9 | $C_{33}H_{41}N_9O_6$ | [M + H] = 660.33 | [M + H] = 660.2 |
| Intermediate A1-10 | $C_{31}H_{37}N_9O_5$ | [M + H] = 616.30 | [M + H] = 616.3 |
| Intermediate A1-11 | $C_{29}H_{33}N_9O_4$ | [M + H] = 572.28 | [M + H] = 572.3 |
| Intermediate A1-12 | $C_{27}H_{29}N_9O_3$ | [M + H] = 528.25 | [M + H] = 528.2 |
| Intermediate A1-13 | $C_{35}H_{55}N_9O_9$ | [M + H] = 746.42 | [M + H] = 746.4 |
| Intermediate A1-14 | $C_{31}H_{47}N_9O_7$ | [M + H] = 658.37 | [M + H] = 658.3 |
| Intermediate A1-15 | $C_{27}H_{39}N_9O_5$ | [M + H] = 570.32 | [M + H] = 570.2 |
| Intermediate A1-16 | $C_{23}H_{31}N_9O_3$ | [M + H] = 482.26 | [M + H] = 482.3 |
| Intermediate A1-17 | $C_{21}H_{27}N_9O_2$ | [M + H] = 438.24 | [M + H] = 438.4 |
| Intermediate A1-18 | $C_{49}H_{73}N_9O_{13}$ | [M + H] = 996.54 | [M + H] = 996.4 |
| Intermediate A1-19 | $C_{45}H_{65}N_9O_{11}$ | [M + H] = 908.49 | [M + H] = 908.3 |
| Intermediate A1-20 | $C_{41}H_{57}N_9O_9$ | [M + H] = 820.44 | [M + H] = 820.3 |
| Intermediate A1-21 | $C_{37}H_{49}N_9O_7$ | [M + H] = 732.39 | [M + H] = 732.3 |
| Intermediate A1-22 | $C_{35}H_{45}N_9O_6$ | [M + H] = 688.36 | [M + H] = 688.3 |
| Intermediate A1-23 | $C_{33}H_{41}N_9O_5$ | [M + H] = 644.33 | [M + H] = 644.3 |
| Intermediate A1-24 | $C_{31}H_{37}N_9O_4$ | [M + H] = 600.31 | [M + H] = 600.4 |
| Intermediate A1-25 | $C_{36}H_{55}N_9O_{10}$ | [M + H] = 774.42 | [M + H] = 774.7 |
| Intermediate A1-26 | $C_{32}H_{47}N_9O_8$ | [M + H] = 686.36 | [M + H] = 686.4 |
| Intermediate A1-27 | $C_{40}H_{63}N_9O_{11}$ | [M + H] = 846.47 | [M + H] = 846.8 |
| Intermediate A1-28 | $C_{43}H_{54}F_3N_7O_9$ | [M + H] = 870.40 | [M + H] = 870.4 |
| Intermediate A1-29 | $C_{52}H_{67}F_3N_{10}O_{11}$ | [M + H] = 1065.50 | [M + H] = 1065.4 |
| Intermediate A1-30 | $C_{48}H_{59}F_3N_{10}O_9$ | [M + H] = 977.45 | [M + H] = 977.4 |
| Intermediate A1-31 | $C_{39}H_{57}F_3N_{12}O_{12}$ | [M + H] = 853.43 | [M + H] = 853.4 |
| Intermediate A1-32 | $C_{40}H_{55}N_9O_{10}$ | [M + H] = 822.42 | [M + H] = 822.2 |
| Intermediate A1-33 | $C_{39}H_{55}N_9O_{10}$ | [M + H] = 810.42 | [M + H] = 810.3 |
| Intermediate A1-34 | $C_{43}H_{63}N_5O_{13}S$ | [M + H] = 890.42 | [M + H] = 890.3 |
| Intermediate A1-35 | $C_{39}H_{54}FN_5O_{11}S$ | [M + H] = 820.36 | [M + H] = 820.3 |
| Intermediate A1-36 | $C_{43}H_{62}FN_5O_{13}S$ | [M + H] = 908.41 | [M + H] = 908.3 |
| Intermediate A1-37 | $C_{47}H_{62}F_3N_7O_{11}$ | [M + H] = 958.46 | [M + H] = 958.3 |
| Intermediate A1-38 | $C_{34}H_{43}N_9O_6$ | [M + H] = 674.34 | [M + H] = 674.3 |
| Intermediate A1-39 | $C_{41}H_{64}N_8O_{11}$ | [M + H] = 845.48 | [M + H] = 845.3 |
| Intermediate A1-40 | $C_{37}H_{56}N_8O_9$ | [M + H] = 757.43 | [M + H] = 757.3 |
| Intermediate A1-41 | $C_{27}H_{36}N_8O_4$ | [M + H] = 537.29 | [M + H] = 537.2 |
| Intermediate A1-42 | $C_{37}H_{53}N_{11}O_{10}$ | [M + H] = 812.41 | [M + H] = 812.3 |
| Intermediate A1-43 | $C_{36}H_{56}N_8O_{10}$ | [M + H] = 761.42 | [M + H] = 761.3 |

TABLE 5-continued

| | | | | |
|---|---|---|---|---|
| | Intermediate A1-44 | $C_{43}H_{61}N_9O_{10}$ | [M + H] = 864.46 | [M + H] = 864.4 |
| | Intermediate A1-45 | $C_{43}H_{62}N_{10}O_{12}S$ | [M + H] = 943.44 | [M + H] = 943.3 |
| | Intermediate A1-46 | $C_{39}H_{55}N_{11}O_{10}$ | [M + H] = 838.42 | [M + H] = 838.3 |

Following General Procedure 1, but using the appropriate Intermediate A1 in Table 5 and PEG carboxylic acid, the Intermediates A2 in Table 6 were prepared:

TABLE 6

| Additional amines prepared<br>Structure |
|---|
| 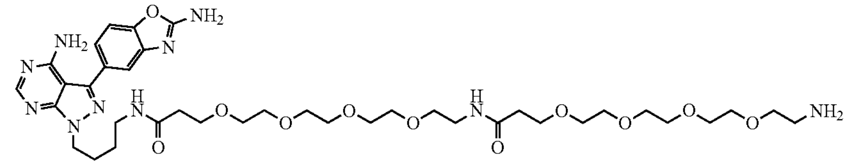 [SMILES: NCCOCCOCCOCCOCCC(=O)NCCOCCOCCOCCOCCC(=O)NCCCCn1nc(-c2ccc3oc(N)nc3c2)c2c(N)ncnc21]<br>Intermediate A2-1 |
| 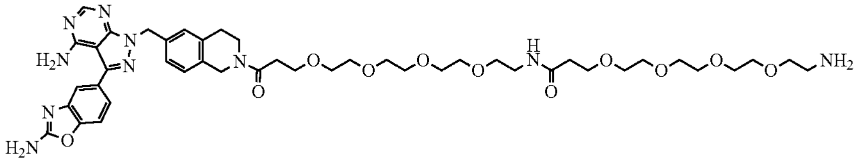 [SMILES: NCCOCCOCCOCCOCCC(=O)NCCOCCOCCOCCOCCC(=O)N1CCc2cc(Cn3nc(-c4ccc5oc(N)nc5c4)c4c(N)ncnc43)ccc2C1]<br>Intermediate A2-2 |
| 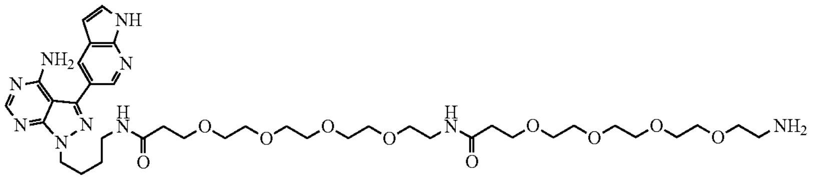 [SMILES: NCCOCCOCCOCCOCCC(=O)NCCOCCOCCOCCOCCC(=O)NCCCCn1nc(-c2cnc3[nH]ccc3c2)c2c(N)ncnc21]<br>Intermediate A2-3 |
| 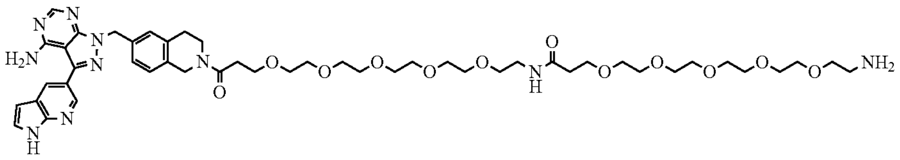 [SMILES: NCCOCCOCCOCCOCCOCCC(=O)NCCOCCOCCOCCOCCOCCC(=O)N1CCc2cc(Cn3nc(-c4cnc5[nH]ccc5c4)c4c(N)ncnc43)ccc2C1]<br>Intermediate A2-4 |
| 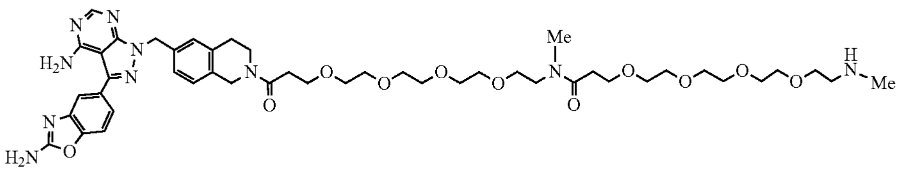 [SMILES: CNCCOCCOCCOCCOCCC(=O)N(C)CCOCCOCCOCCOCCC(=O)N1CCc2cc(Cn3nc(-c4ccc5oc(N)nc5c4)c4c(N)ncnc43)ccc2C1]<br>Intermediate A2-5 |

TABLE 6-continued

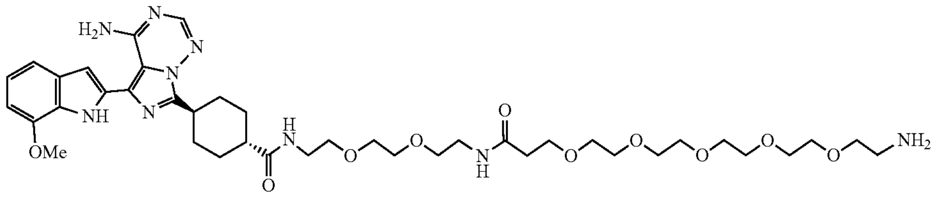 [SMILES: COc1cccc2cc(-c3nc([C@H]4CC[C@H](C(=O)NCCOCCOCCNC(=O)CCOCCOCCOCCOCCOCCN)CC4)n4ncnc(N)c34)[nH]c12]

Intermediate A2-6

Additional amines prepared

| Structure | Molecular Formula | Calculated MW | Observed MW |
|---|---|---|---|
| Intermediate A2-1 | $C_{38}H_{60}N_{10}O_{11}$ | [M + H] = 833.45 | [M + H] = 833.8 |
| Intermediate A2-2 | $C_{44}H_{62}N_{10}O_{11}$ | [M + H] = 907.47 | [M + H] = 908.0 |
| Intermediate A2-3 | $C_{38}H_{60}N_{10}O_{10}$ | [M + H] = 817.46 | [M + H] = 817.4 |
| Intermediate A2-4 | $C_{48}H_{70}N_{10}O_{12}$ | [M + H] = 979.53 | [M + H] = 979.9 |
| Intermediate A2-5 | $C_{46}H_{66}N_{10}O_{11}$ | [M + H] = 935.50 | [M + H] = 935.3 |
| Intermediate A2-6 | $C_{40}H_{61}N_9O_{10}$ | [M + H] = 828.46 | [M + H] = 828.3 |

General Procedure 2: Coupling of a 4-Nitrophenyl Carbonate Containing Rapamycin Monomer and an Active Site Inhibitor Containing Intermediate Having a Primary or Secondary Amine.

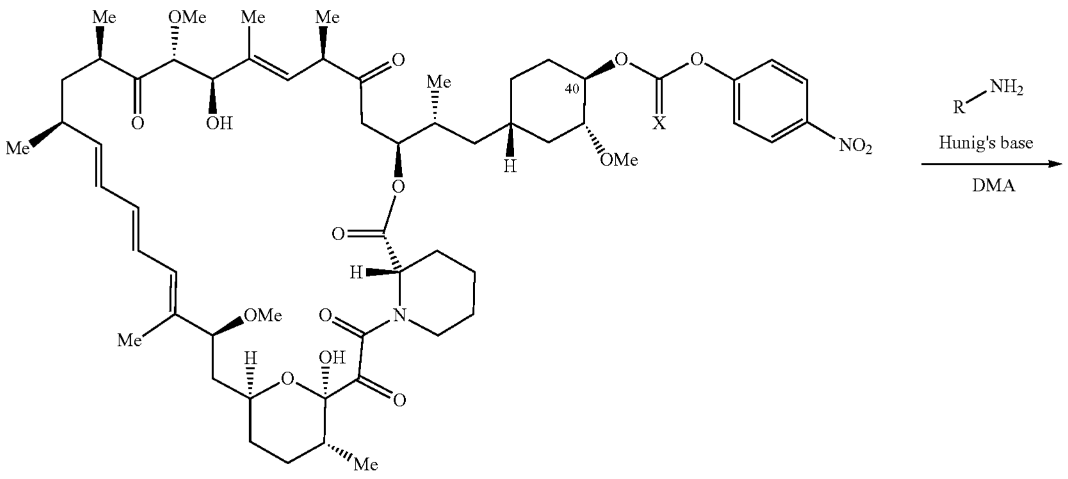

-continued

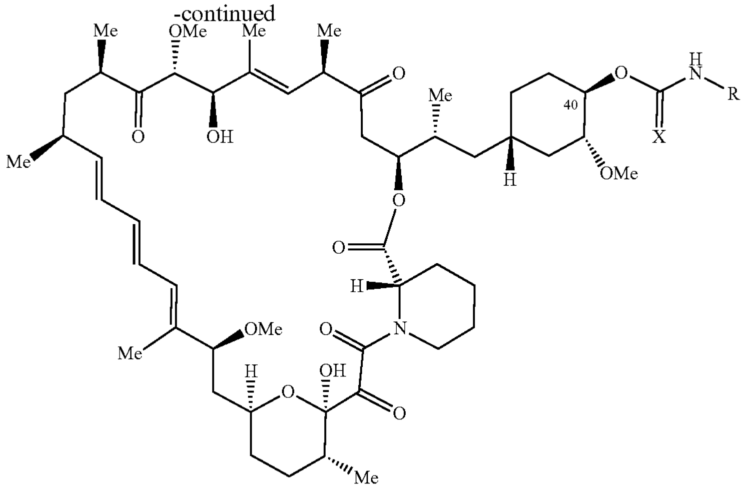

To a 0.02 M solution of 4-nitrophenyl carbonate containing rapamycin monomer (1.0 equiv) and an active site inhibitor containing intermediate (2.0 equiv) in DMA was added DIPEA (4.0 equiv). The resulting solution was stirred at room temperature under nitrogen. Upon completion as determined by LCMS analysis, the crude reaction mixture was purified by preparative HPLC to provide the product.

Example 2: Synthesis of Series 1 Bivalent Rapamycin Compound

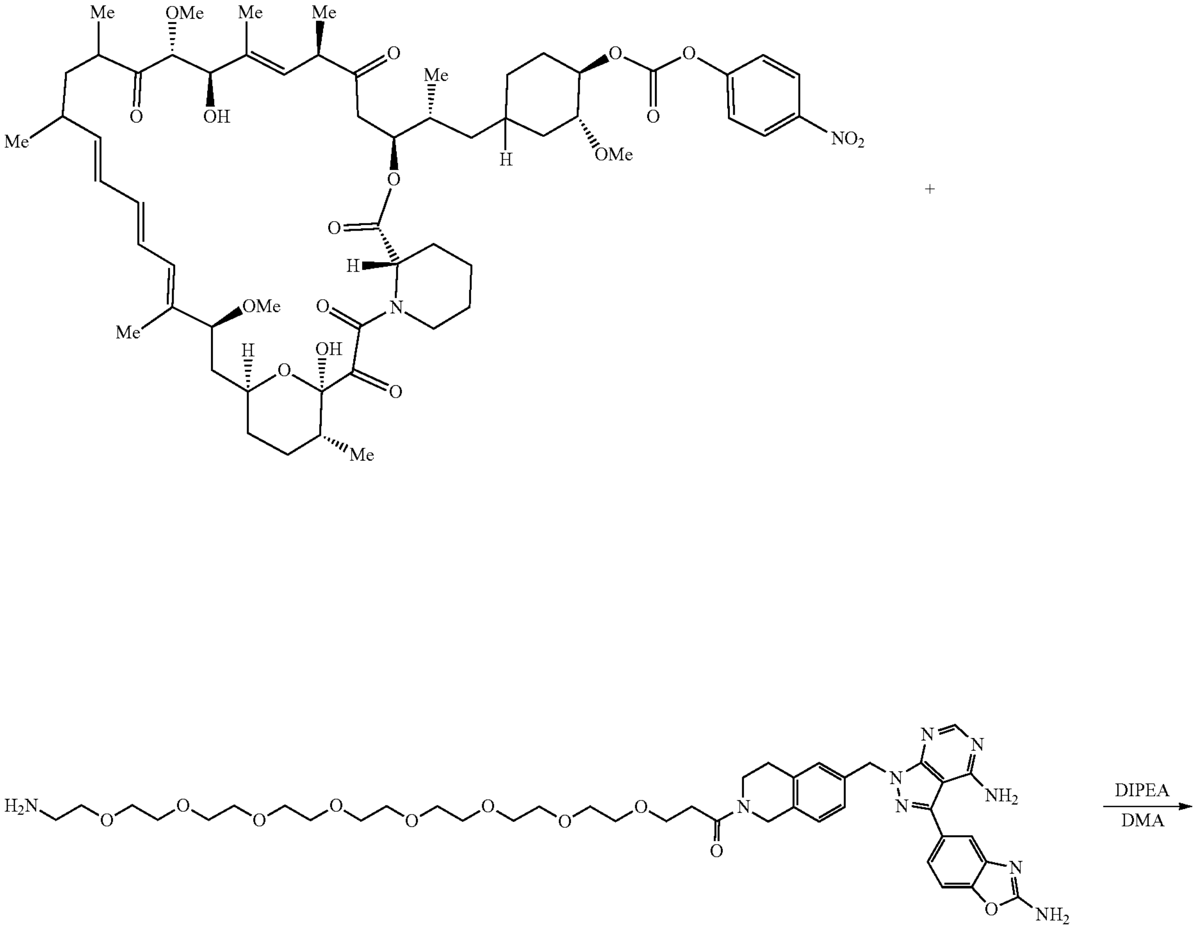

-continued

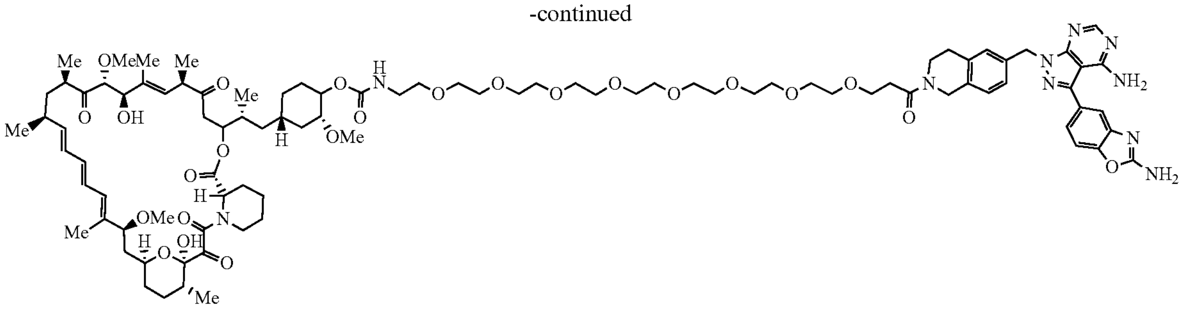

To a solution of 40(R)—O-(4-nitrophenyl carbonate) rapamycin (25 mg, 23.16 μmol, 1.0 equiv) and Intermediate A1-7 (42.0 mg, 46.32 μmol, 2.0 equiv) in DMA (1.15 mL) was added DIPEA (16.0 μL, 92.64 μmol, 4.0 equiv). The reaction was stirred for 18 h, at which point the reaction mixture purified by reverse phase chromatography (10→40→95% MeCN+0.1% formic acid/$H_2O$+0.1% formic acid) to give the product (9.92 mg, 24% yield) as a white solid. LCMS (ESI) m/z: [M+H] calcd for $C_{93}H_{134}N_{10}O_{24}$: 1775.97; found 1775.7.

Following General Procedure 2, but using the appropriate 4-nitrophenyl carbonate containing rapamycin monomer in Table 1 and Intermediates A1 and A2 from Tables 5 and 6, the Series 1 bivalent analogs in Table 7 were synthesized:

TABLE 7

| Series 1 Bivalent Compounds: Structure |
| --- |
| 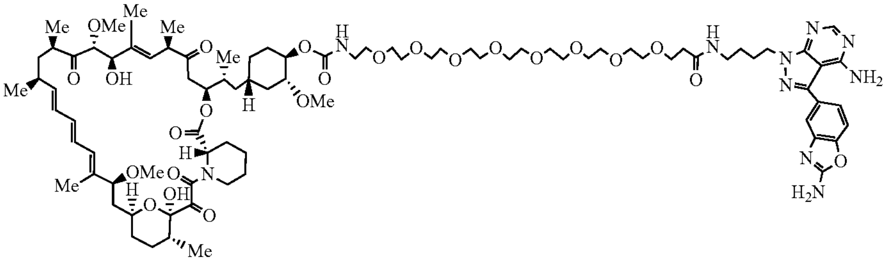 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)NCCCCn3nc(-c4ccc5oc(N)nc5c4)c4c(N)ncnc43)[C@H](OC)C2)CC(=O)[C@H](C)/C=C(\C)[C@@H](O)[C@@H](OC)C(=O)[C@H](C)C[C@H](C)/C=C/C=C/C=C/1C] |
| Example 1 |
| 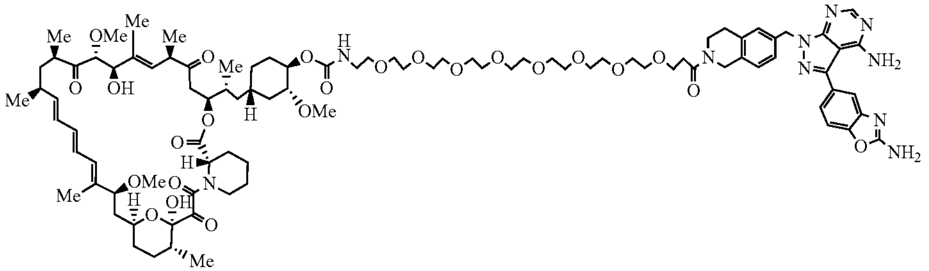 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)N3CCc4cc(Cn5nc(-c6ccc7oc(N)nc7c6)c6c(N)ncnc65)ccc4C3)[C@H](OC)C2)CC(=O)[C@H](C)/C=C(\C)[C@@H](O)[C@@H](OC)C(=O)[C@H](C)C[C@H](C)/C=C/C=C/C=C/1C] |
| Example 2 |
| 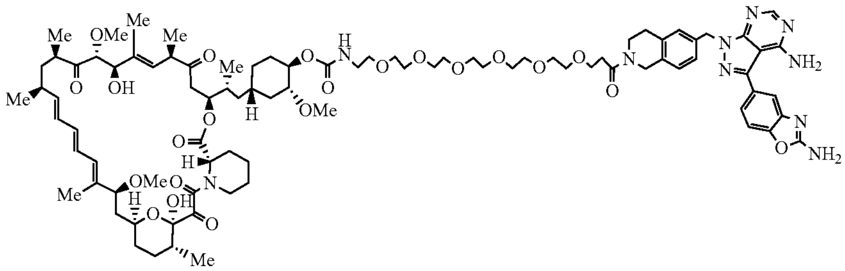 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCC(=O)N3CCc4cc(Cn5nc(-c6ccc7oc(N)nc7c6)c6c(N)ncnc65)ccc4C3)[C@H](OC)C2)CC(=O)[C@H](C)/C=C(\C)[C@@H](O)[C@@H](OC)C(=O)[C@H](C)C[C@H](C)/C=C/C=C/C=C/1C] |
| Example 3 |

TABLE 7-continued
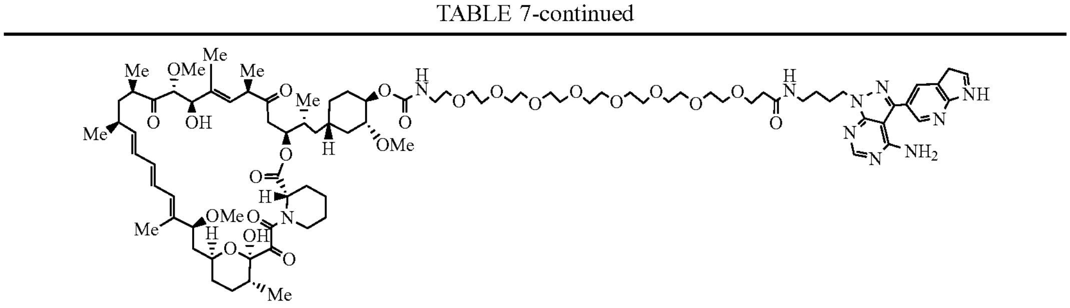
Example 4
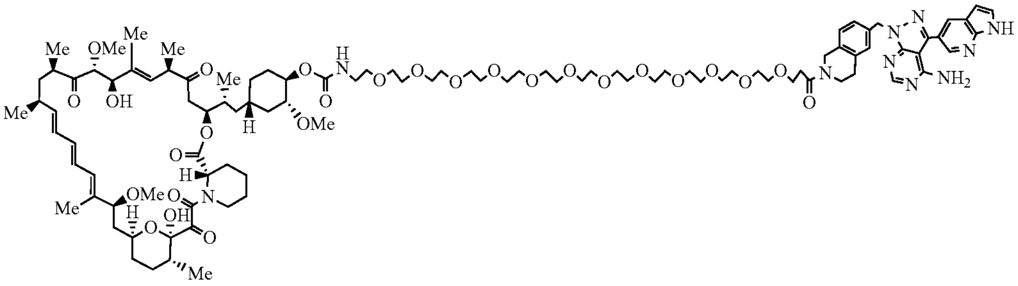 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCOCCOCCOCCOCCC(=O)N3CCc4cc(Cn5nc(-c6cnc7[nH]ccc7c6)c6c(N)ncnc65)ccc4C3)[C@H](OC)C2)CC(=O)[C@H](C)/C=C(\C)[C@@H](O)[C@@H](OC)C(=O)[C@H](C)C[C@H](C)/C=C/C=C/C=C/1C]
Example 5
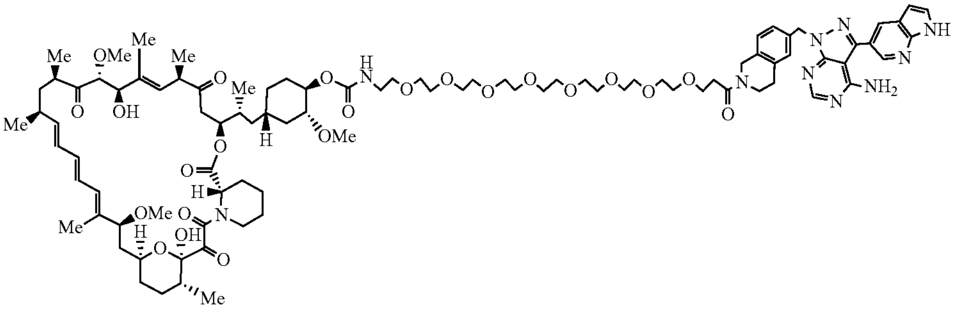 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)N3CCc4cc(Cn5nc(-c6cnc7[nH]ccc7c6)c6c(N)ncnc65)ccc4C3)[C@H](OC)C2)CC(=O)[C@H](C)/C=C(\C)[C@@H](O)[C@@H](OC)C(=O)[C@H](C)C[C@H](C)/C=C/C=C/C=C/1C]
Example 6
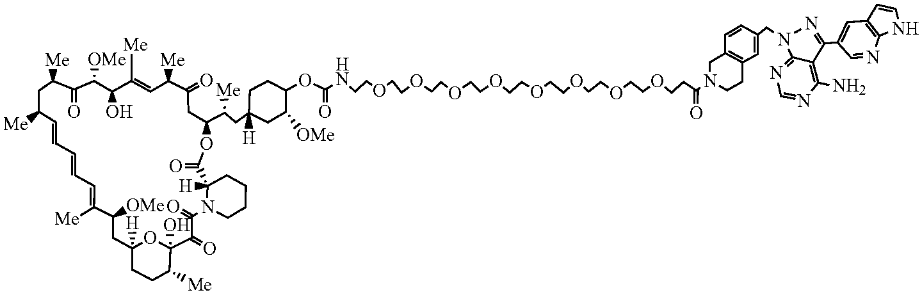 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CCC(OC(=O)NCCOCCOCCOCCOCCOCCOCCOCCOCCC(=O)N3CCc4cc(Cn5nc(-c6cnc7[nH]ccc7c6)c6c(N)ncnc65)ccc4C3)[C@H](OC)C2)CC(=O)[C@H](C)/C=C(\C)[C@@H](O)[C@@H](OC)C(=O)[C@H](C)C[C@H](C)/C=C/C=C/C=C/1C]
Example 7
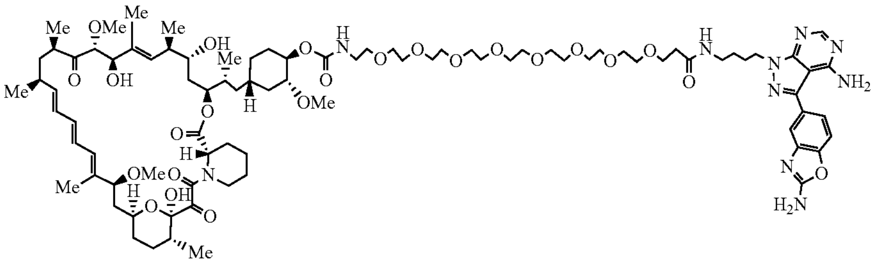 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)NCCCCn3nc(-c4ccc5oc(N)nc5c4)c4c(N)ncnc43)[C@H](OC)C2)C[C@@H](O)[C@H](C)/C=C(\C)[C@@H](O)[C@@H](OC)C(=O)[C@H](C)C[C@H](C)/C=C/C=C/C=C/1C]
Example 8

TABLE 7-continued
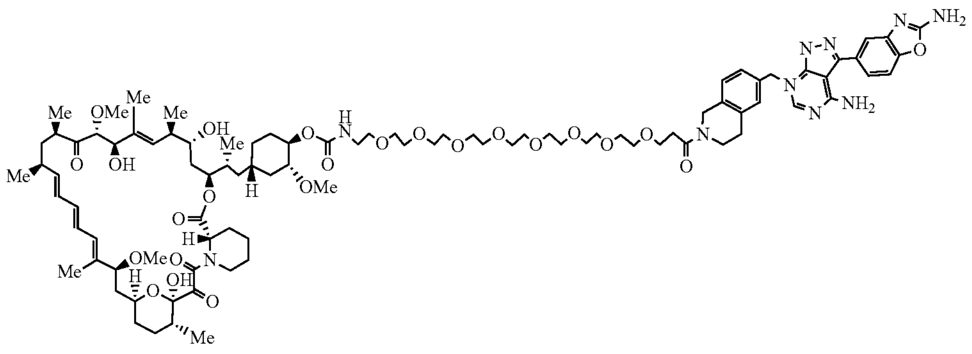
Example 9
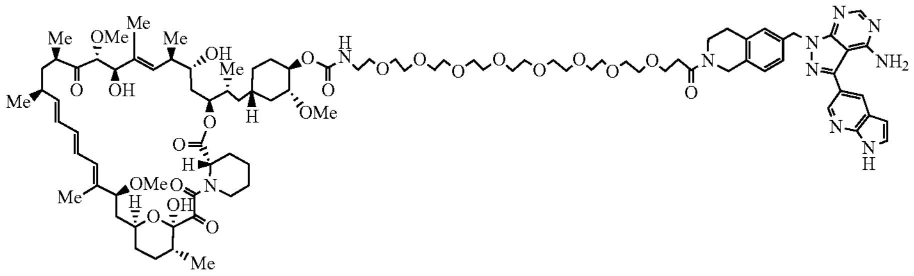 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)N3CCc4cc(Cn5nc(-c6cnc7[nH]ccc7c6)c6c(N)ncnc65)ccc4C3)[C@H](OC)C2)C[C@@H](O)[C@H](C)/C=C(\C)[C@@H](O)[C@@H](OC)C(=O)[C@H](C)C[C@H](C)/C=C/C=C/C=C/1C]
Example 10
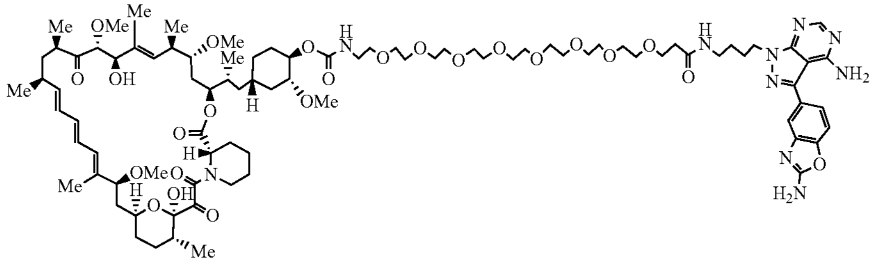 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)NCCCCn3nc(-c4ccc5oc(N)nc5c4)c4c(N)ncnc43)[C@H](OC)C2)C[C@@H](OC)[C@H](C)/C=C(\C)[C@@H](O)[C@@H](OC)C(=O)[C@H](C)C[C@H](C)/C=C/C=C/C=C/1C]
Example 11
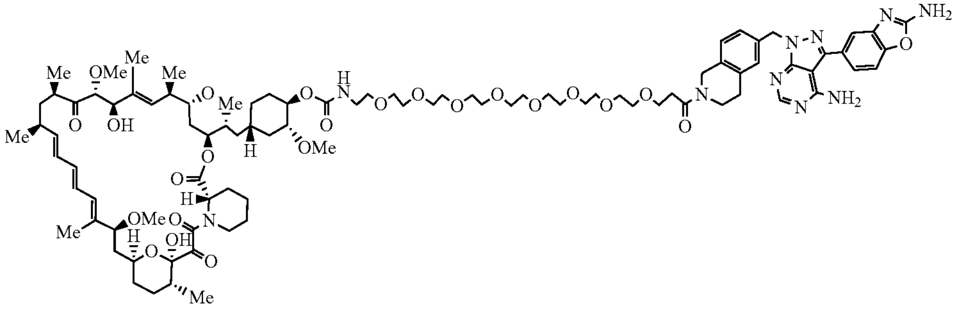 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)N3CCc4cc(Cn5nc(-c6ccc7oc(N)nc7c6)c6c(N)ncnc65)ccc4C3)[C@H](OC)C2)C[C@@H](O)[C@H](C)/C=C(\C)[C@@H](O)[C@@H](OC)C(=O)[C@H](C)C[C@H](C)/C=C/C=C/C=C/1C]
Example 12

TABLE 7-continued
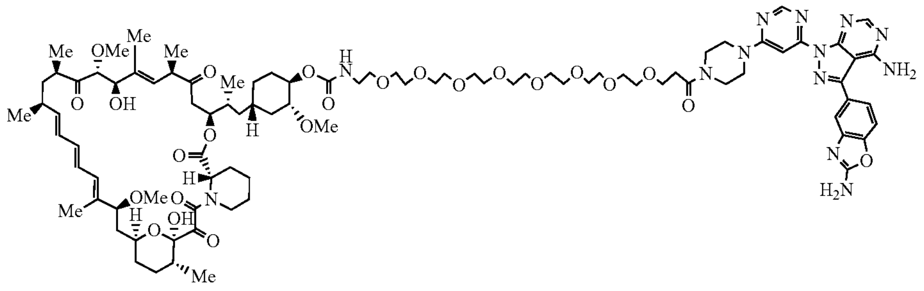 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)N3CCN(c4cc(-n5nc(-c6ccc7oc(N)nc7c6)c6c(N)ncnc65)ncn4)CC3)[C@H](OC)C2)CC(=O)[C@H](C)/C=C(\C)[C@@H](O)[C@@H](OC)C(=O)[C@H](C)C[C@H](C)/C=C/C=C/C=C/1C]
Example 13
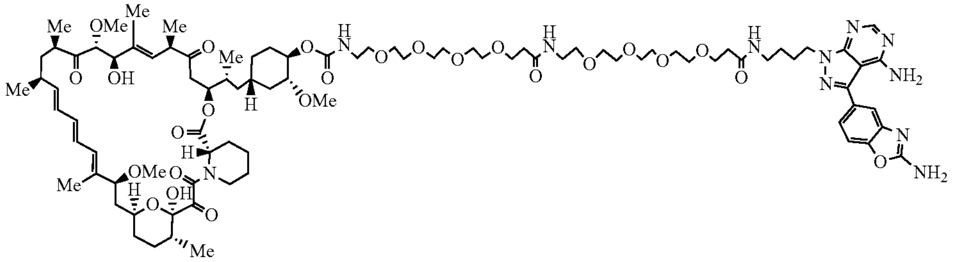 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCC(=O)NCCOCCOCCOCCOCCC(=O)NCCCCn3nc(-c4ccc5oc(N)nc5c4)c4c(N)ncnc43)[C@H](OC)C2)CC(=O)[C@H](C)/C=C(\C)[C@@H](O)[C@@H](OC)C(=O)[C@H](C)C[C@H](C)/C=C/C=C/C=C/1C]
Example 14
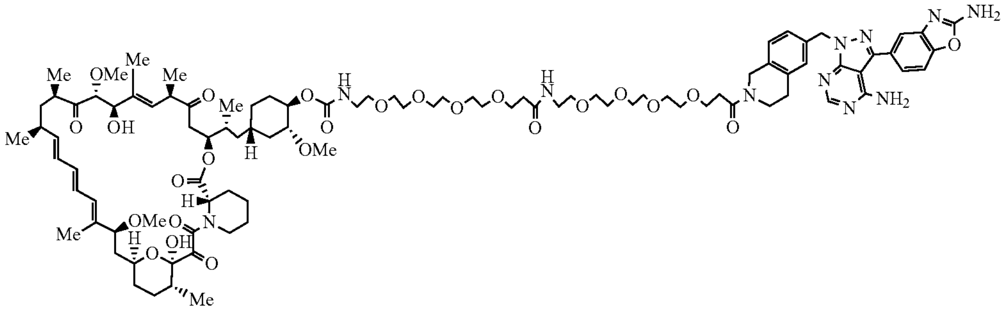 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCC(=O)NCCOCCOCCOCCOCCC(=O)N3CCc4cc(Cn5nc(-c6ccc7oc(N)nc7c6)c6c(N)ncnc65)ccc4C3)[C@H](OC)C2)CC(=O)[C@H](C)/C=C(\C)[C@@H](O)[C@@H](OC)C(=O)[C@H](C)C[C@H](C)/C=C/C=C/C=C/1C]
Example 15
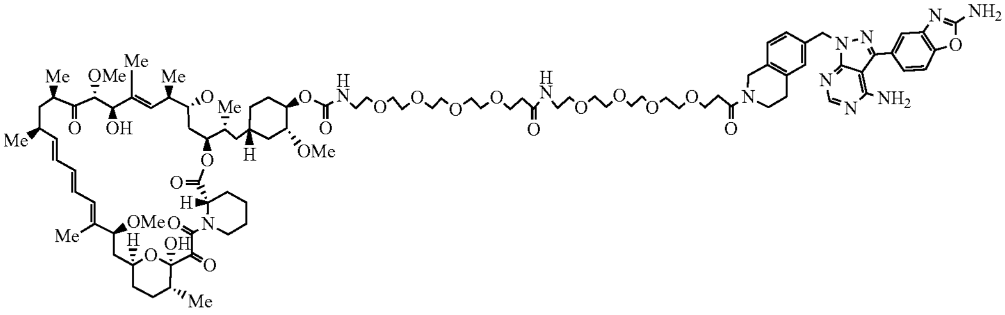 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCC(=O)NCCOCCOCCOCCOCCC(=O)N3CCc4cc(Cn5nc(-c6ccc7oc(N)nc7c6)c6c(N)ncnc65)ccc4C3)[C@H](OC)C2)C[C@@H](O)[C@H](C)/C=C(\C)[C@@H](O)[C@@H](OC)C(=O)[C@H](C)C[C@H](C)/C=C/C=C/C=C/1C]
Example 16

TABLE 7-continued
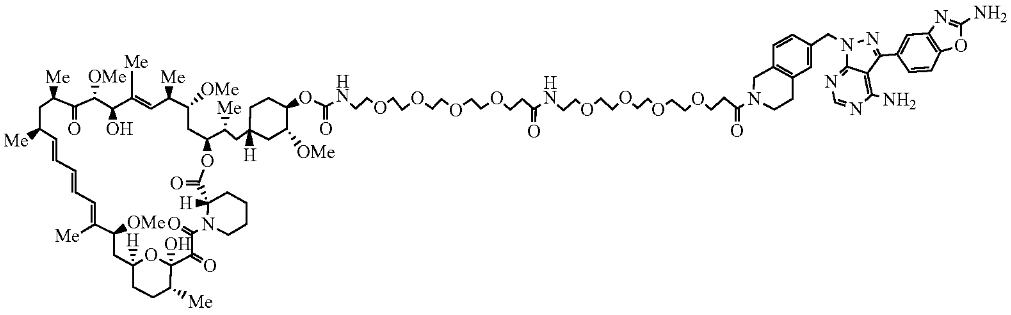 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCC(=O)NCCOCCOCCOCCOCCC(=O)N3CCc4cc(Cn5nc(-c6ccc7oc(N)nc7c6)c6c(N)ncnc65)ccc4C3)[C@H](OC)C2)C[C@@H](OC)[C@H](C)/C=C(\C)[C@@H](O)[C@@H](OC)C(=O)[C@H](C)C[C@H](C)/C=C/C=C/C=C/1C]
Example 17
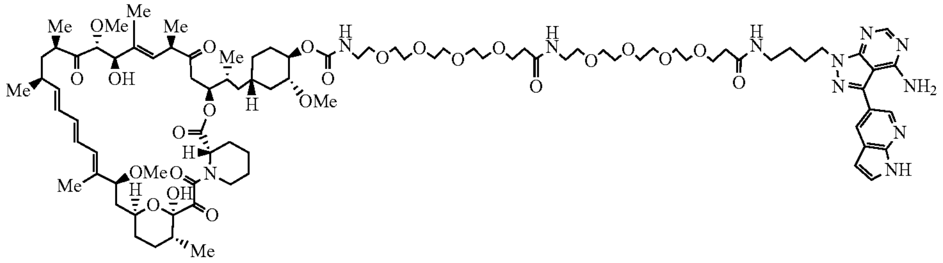 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCC(=O)NCCOCCOCCOCCOCCC(=O)NCCCCn3nc(-c4cnc5[nH]ccc5c4)c4c(N)ncnc43)[C@H](OC)C2)CC(=O)[C@H](C)/C=C(\C)[C@@H](O)[C@@H](OC)C(=O)[C@H](C)C[C@H](C)/C=C/C=C/C=C/1C]
Example 18
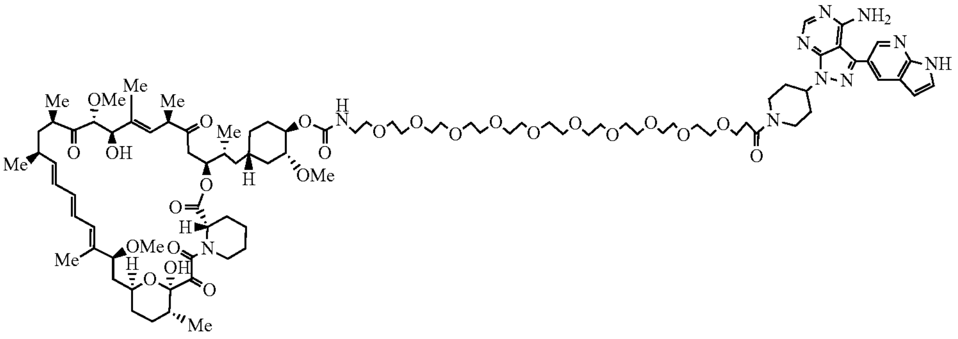 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCOCCOCCC(=O)N3CCC(n4nc(-c5cnc6[nH]ccc6c5)c5c(N)ncnc54)CC3)[C@H](OC)C2)CC(=O)[C@H](C)/C=C(\C)[C@@H](O)[C@@H](OC)C(=O)[C@H](C)C[C@H](C)/C=C/C=C/C=C/1C]
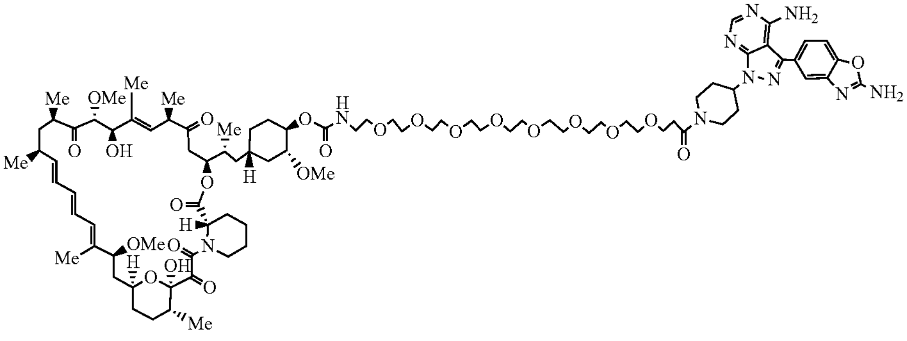 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)N3CCC(n4nc(-c5ccc6oc(N)nc6c5)c5c(N)ncnc54)CC3)[C@H](OC)C2)CC(=O)[C@H](C)/C=C(\C)[C@@H](O)[C@@H](OC)C(=O)[C@H](C)C[C@H](C)/C=C/C=C/C=C/1C]
Example 19

TABLE 7-continued
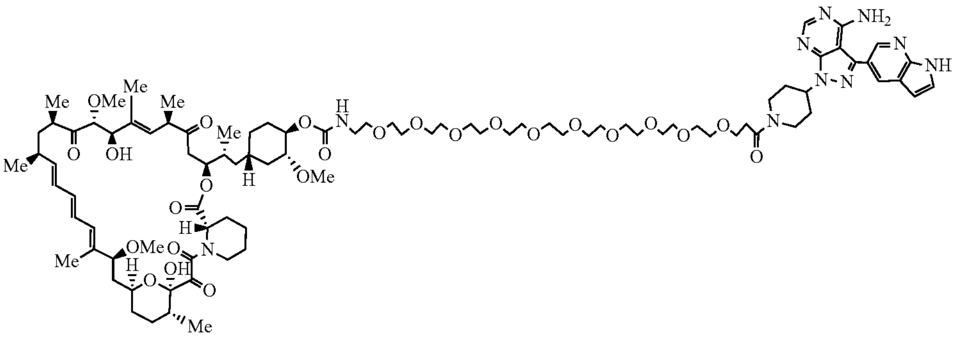 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCOCCOCCC(=O)N3CCC(n4nc(-c5cnc6[nH]ccc6c5)c5c(N)ncnc54)CC3)[C@H](OC)C2)CC(=O)[C@H](C)/C=C(\C)[C@@H](O)[C@@H](OC)C(=O)[C@H](C)C[C@H](C)/C=C/C=C/C=C/1C]
Example 20
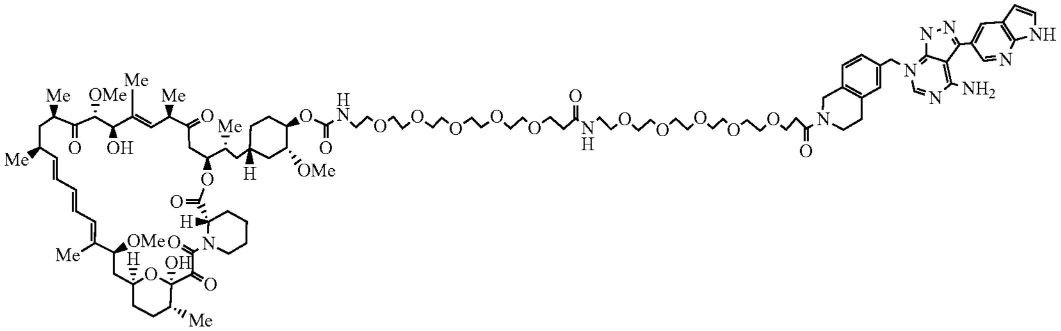
Example 21
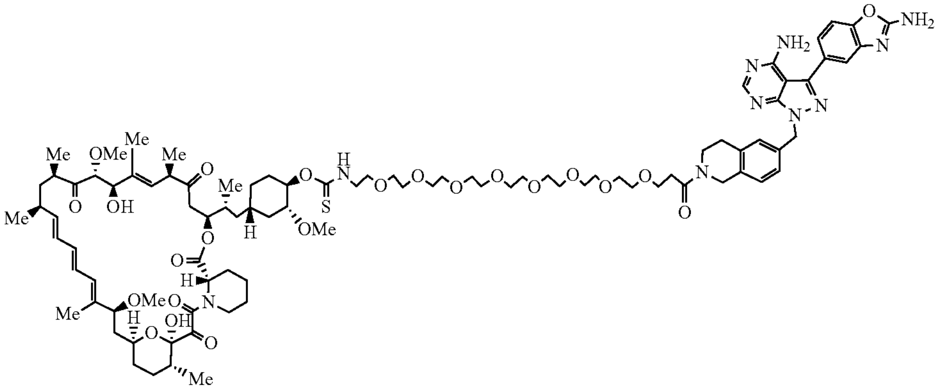 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=S)NCCOCCOCCOCCOCCOCCOCCOCCOCCC(=O)N3CCc4cc(Cn5nc(-c6ccc7oc(N)nc7c6)c6c(N)ncnc65)ccc4C3)[C@H](OC)C2)CC(=O)[C@H](C)/C=C(\C)[C@@H](O)[C@@H](OC)C(=O)[C@H](C)C[C@H](C)/C=C/C=C/C=C/1C]
Example 22
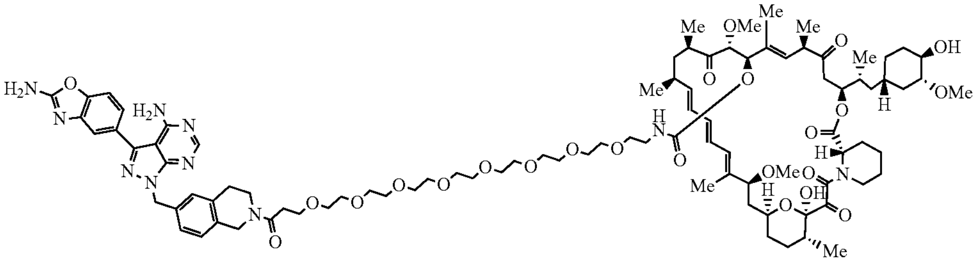 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](OC(=O)NCCOCCOCCOCCOCCOCCOCCOCCOCCC(=O)N2CCc3cc(Cn4nc(-c5ccc6oc(N)nc6c5)c5c(N)ncnc54)ccc3C2)[C@@H](OC)C(=O)[C@H](C)C[C@H](C)/C=C/C=C/C=C/1C]
Example 23

TABLE 7-continued
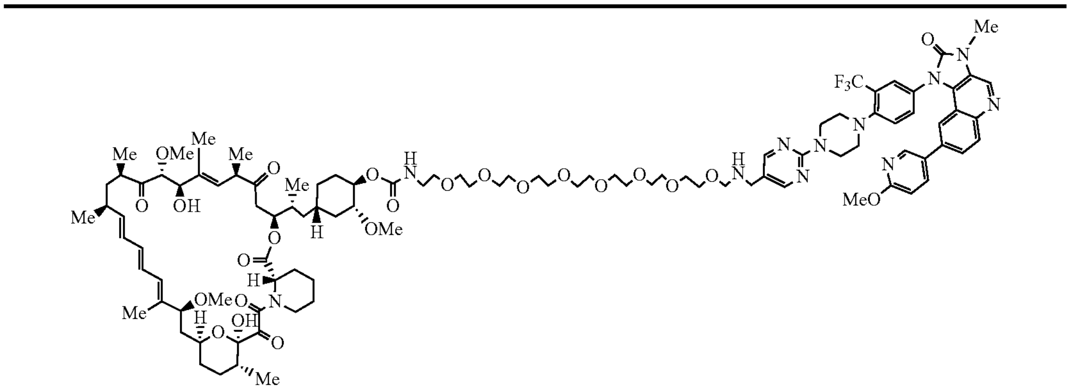
Example 24
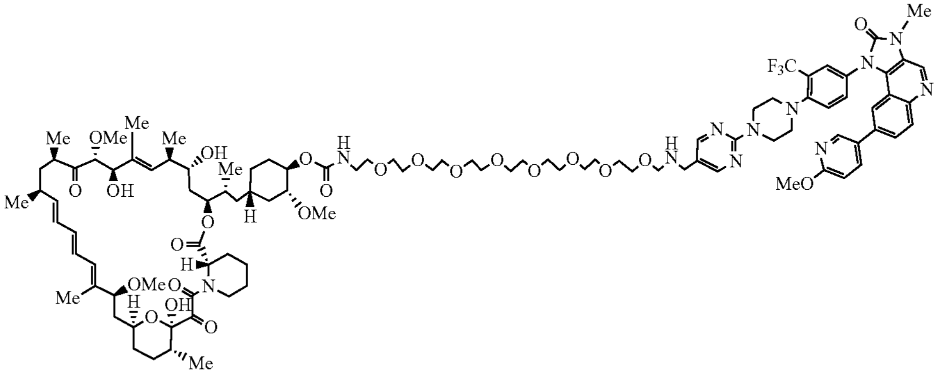 [SMILES: COc1ccc(-c2ccc3ncc4c(c3c2)n(-c2ccc(N3CCN(c5ncc(CNCOCCOCCOCCOCCOCCOCCOCCOCCNC(=O)O[C@@H]6CC[C@@H](C[C@@H](C)[C@@H]7C[C@@H](O)[C@H](C)/C=C(\C)[C@@H](O)[C@@H](OC)C(=O)[C@H](C)C[C@H](C)/C=C/C=C/C=C(\C)[C@@H](OC)C[C@@H]8CC[C@@H](C)[C@@](O)(O8)C(=O)C(=O)N8CCCC[C@H]8C(=O)O7)C[C@H]6OC)cn5)CC3)c(C(F)(F)F)c2)c(=O)n4C)cn1]
Example 25
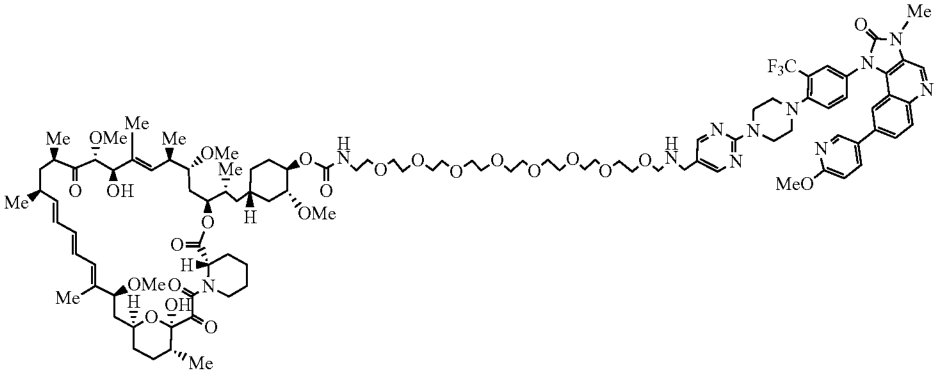 [SMILES: COc1ccc(-c2ccc3ncc4c(c3c2)n(-c2ccc(N3CCN(c5ncc(CNCOCCOCCOCCOCCOCCOCCOCCOCCNC(=O)O[C@@H]6CC[C@@H](C[C@@H](C)[C@@H]7C[C@@H](OC)[C@H](C)/C=C(\C)[C@@H](O)[C@@H](OC)C(=O)[C@H](C)C[C@H](C)/C=C/C=C/C=C(\C)[C@@H](OC)C[C@@H]8CC[C@@H](C)[C@@](O)(O8)C(=O)C(=O)N8CCCC[C@H]8C(=O)O7)C[C@H]6OC)cn5)CC3)c(C(F)(F)F)c2)c(=O)n4C)cn1]
Example 26
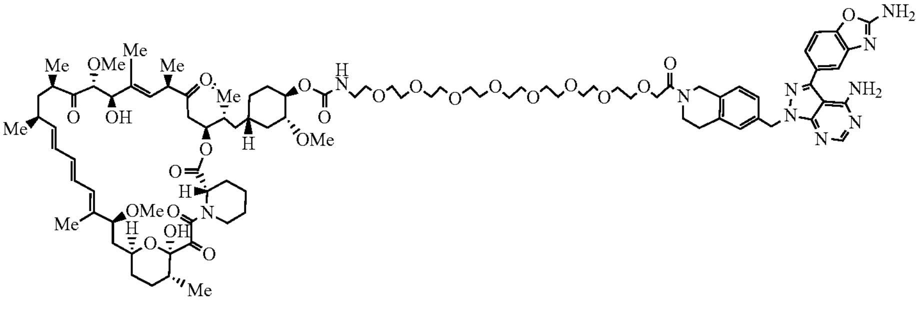 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCC(=O)N3CCc4cc(Cn5nc(-c6ccc7oc(N)nc7c6)c6c(N)ncnc65)ccc4C3)[C@H](OC)C2)CC(=O)[C@H](C)/C=C(\C)[C@@H](O)[C@@H](OC)C(=O)[C@H](C)C[C@H](C)/C=C/C=C/C=C/1C]
Example 71

TABLE 7-continued
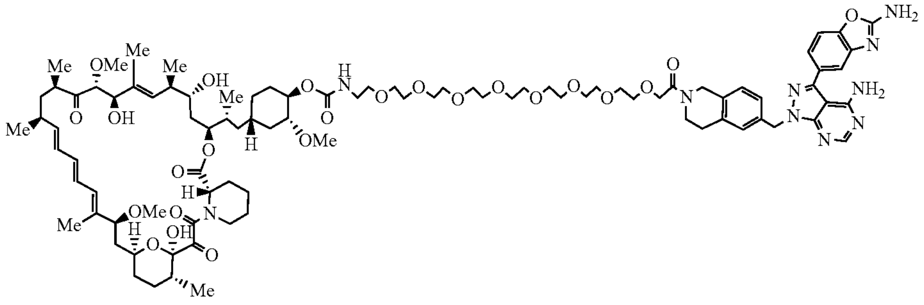 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCC(=O)N3CCc4cc(Cn5nc(-c6ccc7oc(N)nc7c6)c6c(N)ncnc65)ccc4C3)[C@H](OC)C2)C[C@@H](O)[C@H](C)/C=C(\C)[C@@H](O)[C@@H](OC)C(=O)[C@H](C)C[C@H](C)/C=C/C=C/C=C/1C]
Example 72
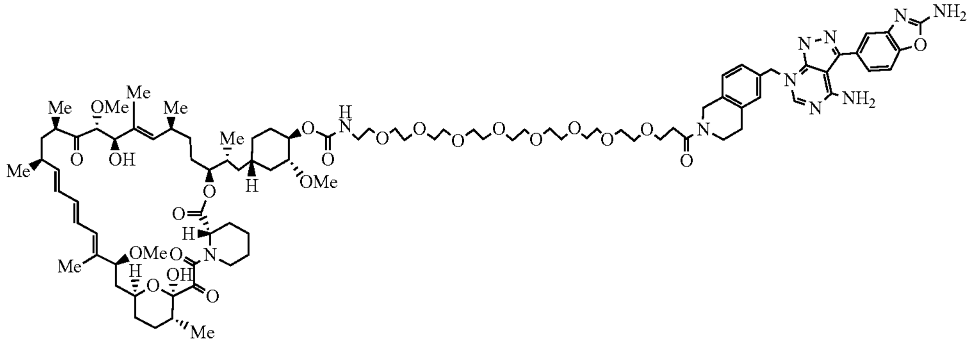
Example 73
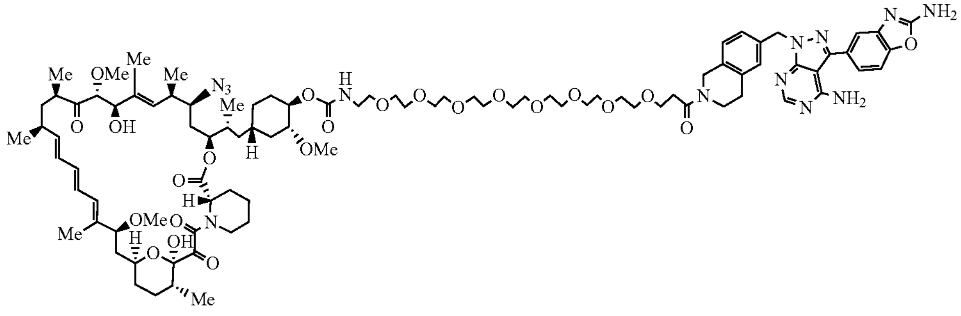 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)N3CCc4cc(Cn5nc(-c6ccc7oc(N)nc7c6)c6c(N)ncnc65)ccc4C3)[C@H](OC)C2)C[C@H](N=[N+]=[N-])[C@H](C)/C=C(\C)[C@@H](O)[C@@H](OC)C(=O)[C@H](C)C[C@H](C)/C=C/C=C/C=C/1C]
Example 74
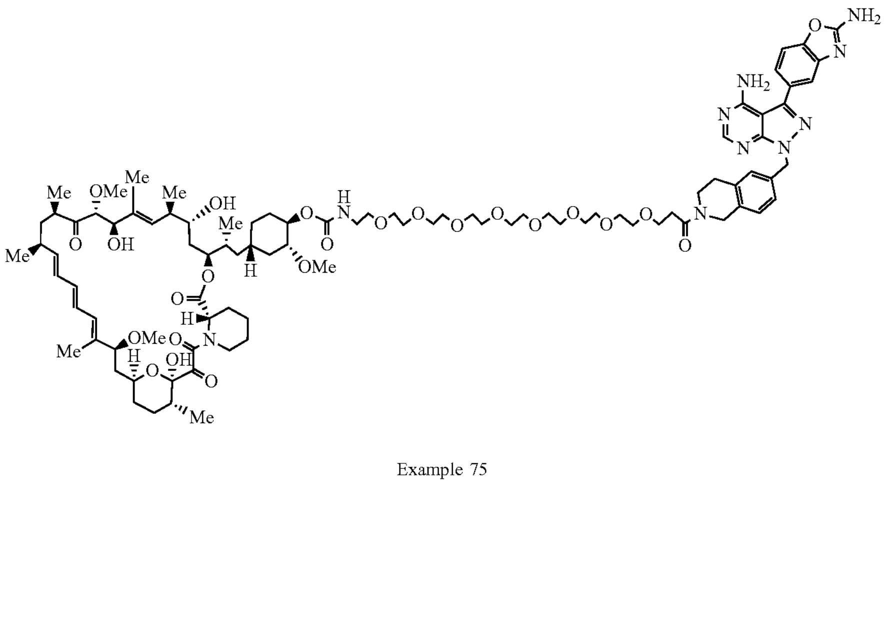
Example 75

TABLE 7-continued
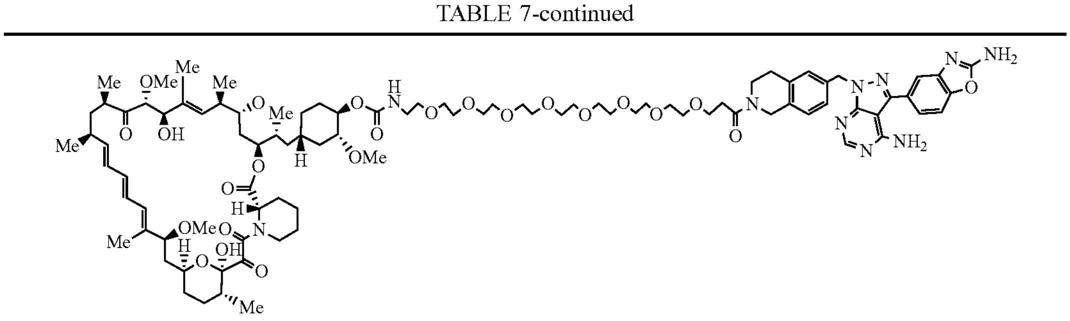
Example 76
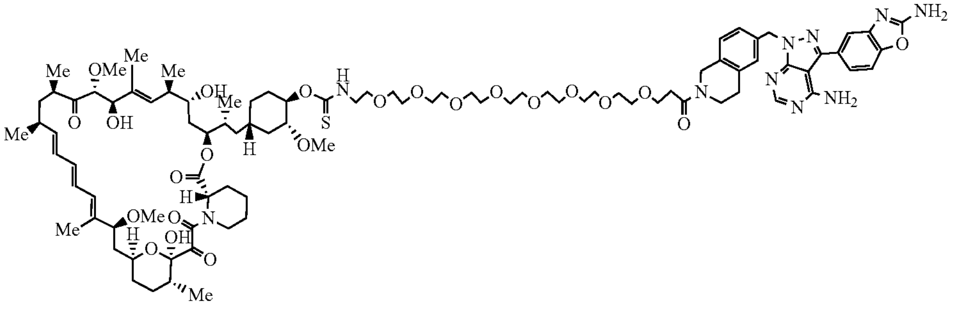 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=S)NCCOCCOCCOCCOCCOCCOCCOCCOCCC(=O)N3CCc4cc(Cn5nc(-c6ccc7oc(N)nc7c6)c6c(N)ncnc65)ccc4C3)[C@H](OC)C2)C[C@@H](O)[C@H](C)/C=C(\C)[C@@H](O)[C@@H](OC)C(=O)[C@H](C)C[C@H](C)/C=C/C=C/C=C/1C]
Example 77
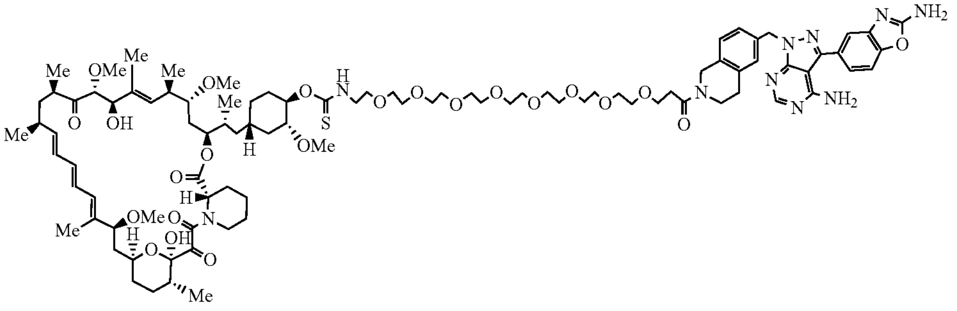 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=S)NCCOCCOCCOCCOCCOCCOCCOCCOCCC(=O)N3CCc4cc(Cn5nc(-c6ccc7oc(N)nc7c6)c6c(N)ncnc65)ccc4C3)[C@H](OC)C2)C[C@@H](OC)[C@H](C)/C=C(\C)[C@@H](O)[C@@H](OC)C(=O)[C@H](C)C[C@H](C)/C=C/C=C/C=C/1C]
Example 78
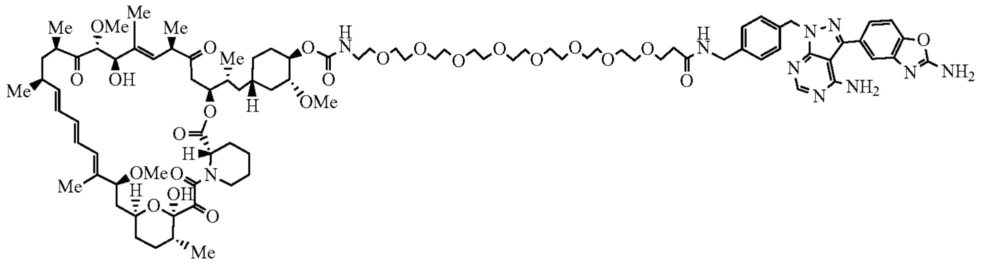 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)NCc3ccc(Cn4nc(-c5ccc6oc(N)nc6c5)c5c(N)ncnc54)cc3)[C@H](OC)C2)CC(=O)[C@H](C)/C=C(\C)[C@@H](O)[C@@H](OC)C(=O)[C@H](C)C[C@H](C)/C=C/C=C/C=C/1C]
Example 79
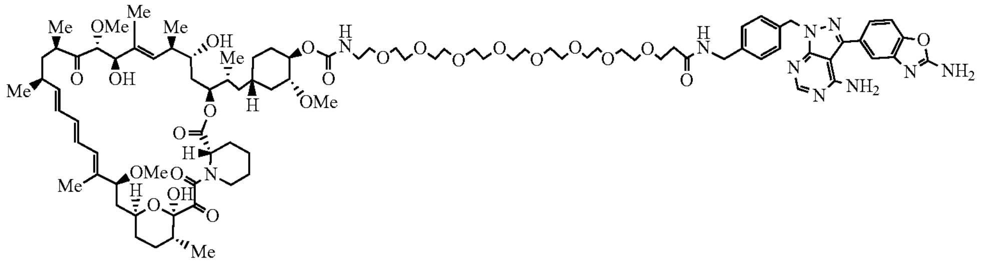 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)NCc3ccc(Cn4nc(-c5ccc6oc(N)nc6c5)c5c(N)ncnc54)cc3)[C@H](OC)C2)C[C@@H](O)[C@H](C)/C=C(\C)[C@@H](O)[C@@H](OC)C(=O)[C@H](C)C[C@H](C)/C=C/C=C/C=C/1C]
Example 80

TABLE 7-continued
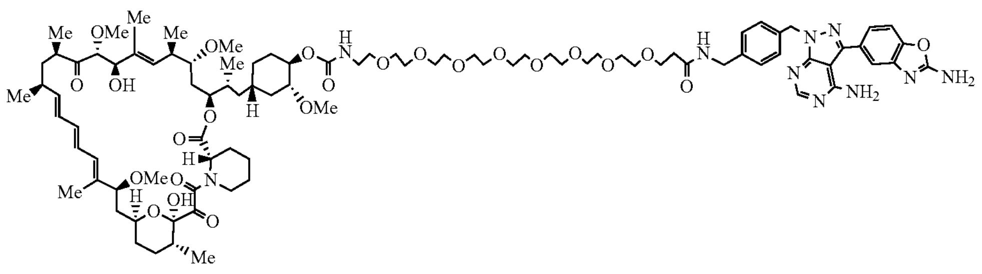 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)NCc3ccc(Cn4nc(-c5ccc6oc(N)nc6c5)c5c(N)ncnc54)cc3)[C@H](OC)C2)C[C@@H](OC)[C@H](C)/C=C(\C)[C@@H](O)[C@@H](OC)C(=O)[C@H](C)C[C@H](C)/C=C/C=C/C=C/1C]
Example 81
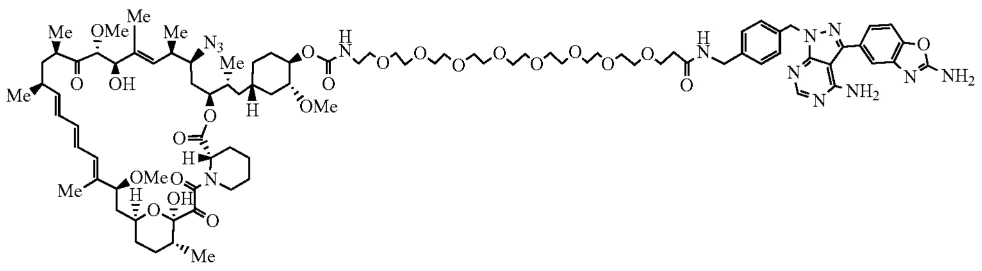 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)NCc3ccc(Cn4nc(-c5ccc6oc(N)nc6c5)c5c(N)ncnc54)cc3)[C@H](OC)C2)C[C@H](N=[N+]=[N-])[C@H](C)/C=C(\C)[C@@H](O)[C@@H](OC)C(=O)[C@H](C)C[C@H](C)/C=C/C=C/C=C/1C]
Example 82
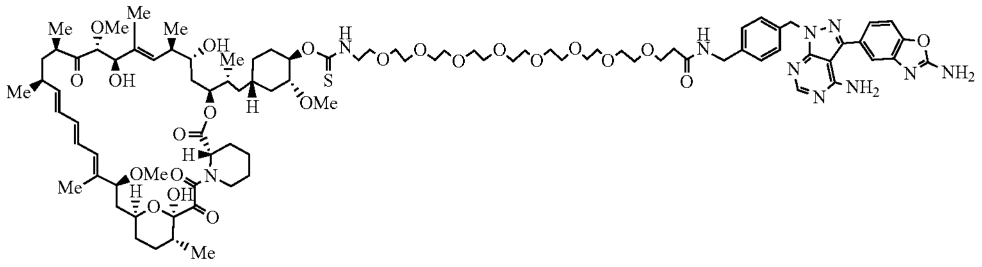 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=S)NCCOCCOCCOCCOCCOCCOCCOCCOCCC(=O)NCc3ccc(Cn4nc(-c5ccc6oc(N)nc6c5)c5c(N)ncnc54)cc3)[C@H](OC)C2)C[C@@H](O)[C@H](C)/C=C(\C)[C@@H](O)[C@@H](OC)C(=O)[C@H](C)C[C@H](C)/C=C/C=C/C=C/1C]
Example 83
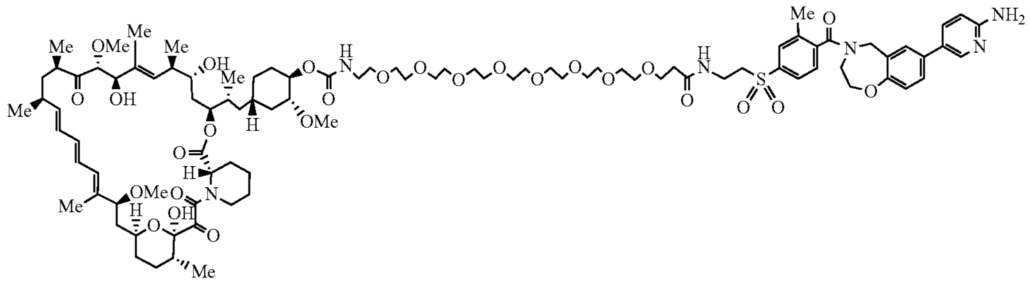 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)NCCS(=O)(=O)c3ccc(C(=O)N4CCOc5ccc(-c6ccc(N)nc6)cc5C4)c(C)c3)[C@H](OC)C2)C[C@@H](O)[C@H](C)/C=C(\C)[C@@H](O)[C@@H](OC)C(=O)[C@H](C)C[C@H](C)/C=C/C=C/C=C/1C]
Example 84
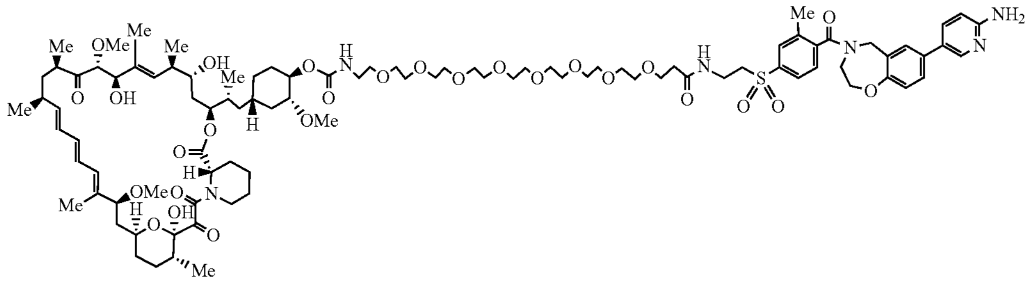 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)NCCS(=O)(=O)c3ccc(C(=O)N4CCOc5ccc(-c6ccc(N)nc6)cc5C4)c(C)c3)[C@H](OC)C2)C[C@@H](O)[C@H](C)/C=C(\C)[C@@H](O)[C@@H](OC)C(=O)[C@H](C)C[C@H](C)/C=C/C=C/C=C/1C]
Example 85

TABLE 7-continued
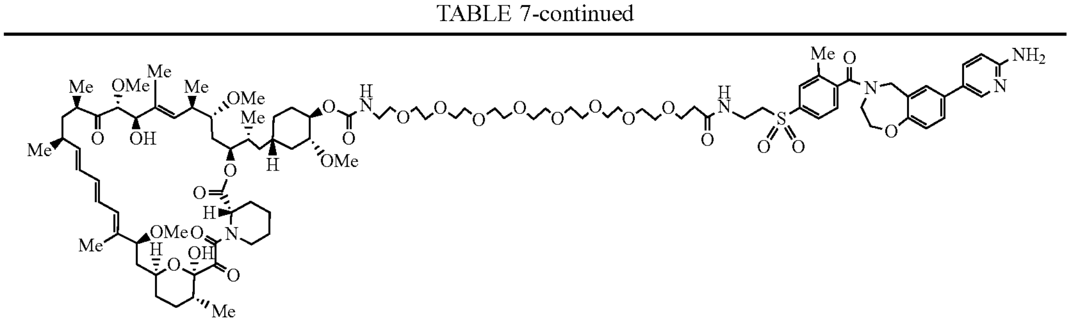
Example 86
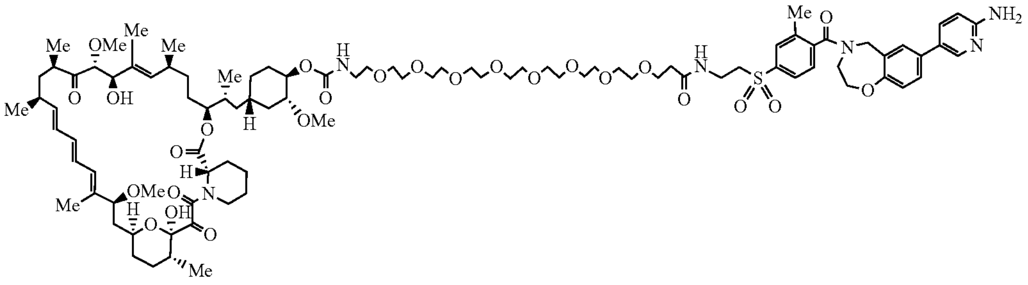 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)NCCS(=O)(=O)c3ccc(C(=O)N4CCOc5ccc(-c6ccc(N)nc6)cc5C4)c(C)c3)[C@H](OC)C2)CC[C@H](C)/C=C(\C)[C@@H](O)[C@@H](OC)C(=O)[C@H](C)C[C@H](C)/C=C/C=C/C=C/1C]
Example 87
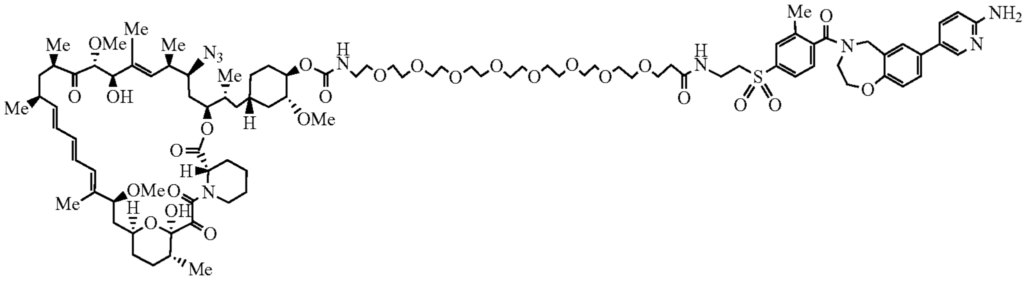 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)NCCS(=O)(=O)c3ccc(C(=O)N4CCOc5ccc(-c6ccc(N)nc6)cc5C4)c(C)c3)[C@H](OC)C2)C[C@H](N=[N+]=[N-])[C@H](C)/C=C(\C)[C@@H](O)[C@@H](OC)C(=O)[C@H](C)C[C@H](C)/C=C/C=C/C=C/1C]
Example 88
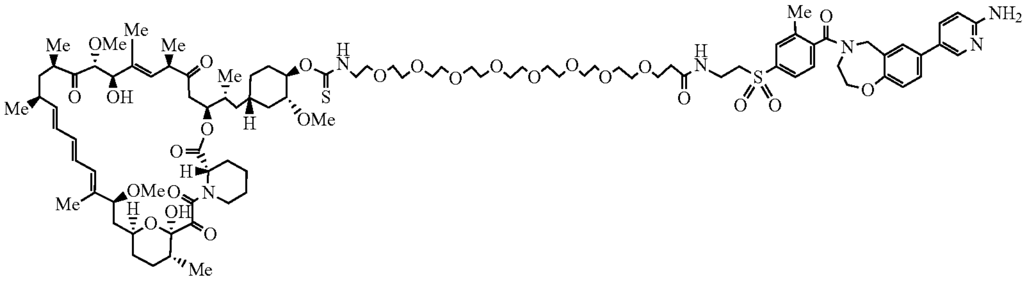 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=S)NCCOCCOCCOCCOCCOCCOCCOCCOCCC(=O)NCCS(=O)(=O)c3ccc(C(=O)N4CCOc5ccc(-c6ccc(N)nc6)cc5C4)c(C)c3)[C@H](OC)C2)CC(=O)[C@H](C)/C=C(\C)[C@@H](O)[C@@H](OC)C(=O)[C@H](C)C[C@H](C)/C=C/C=C/C=C/1C]
Example 89
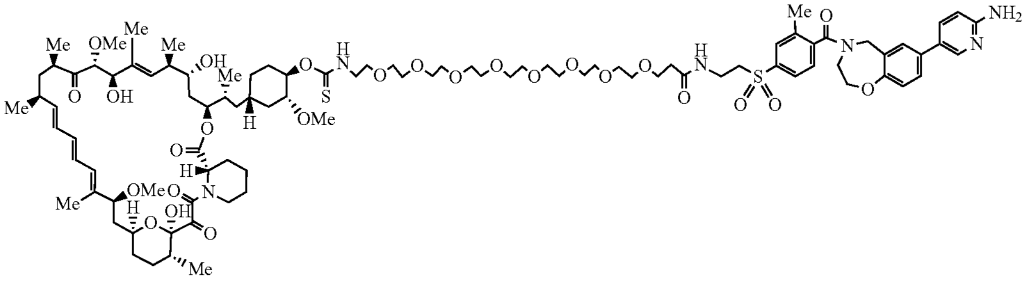
Example 90

TABLE 7-continued
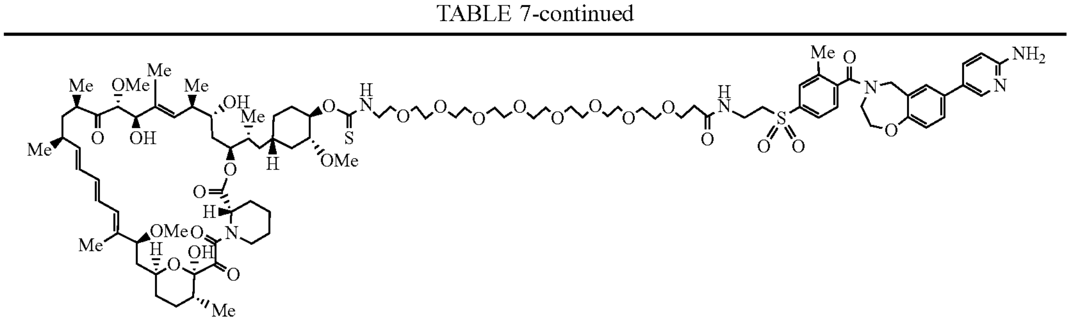
Example 91
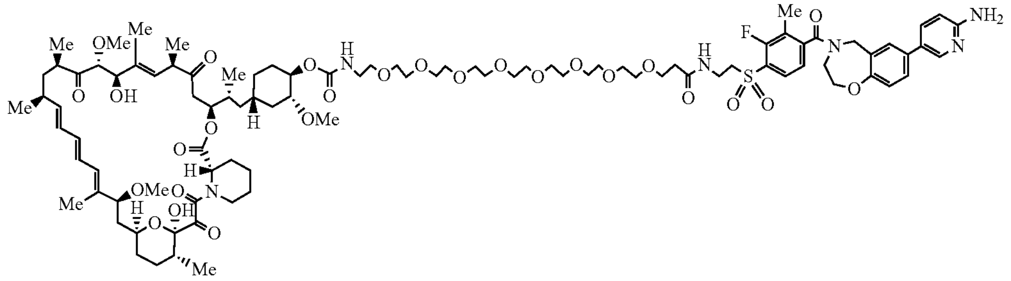 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)NCCS(=O)(=O)c3ccc(C(=O)N4CCOc5ccc(-c6ccc(N)nc6)cc5C4)c(C)c3F)[C@H](OC)C2)CC(=O)[C@H](C)/C=C(\C)[C@@H](O)[C@@H](OC)C(=O)[C@H](C)C[C@H](C)/C=C/C=C/C=C/1C]
Example 92
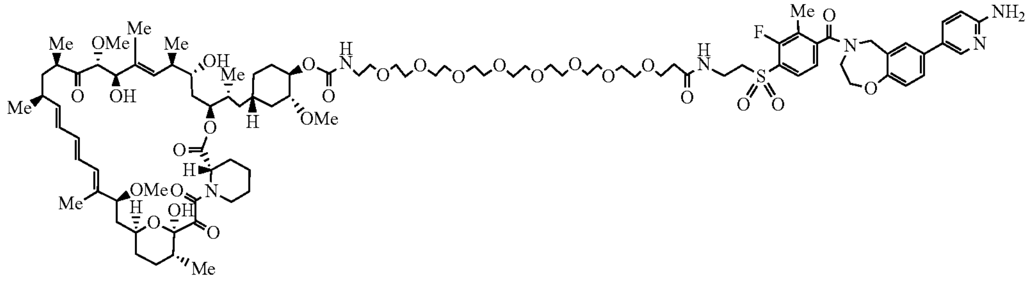
Example 93
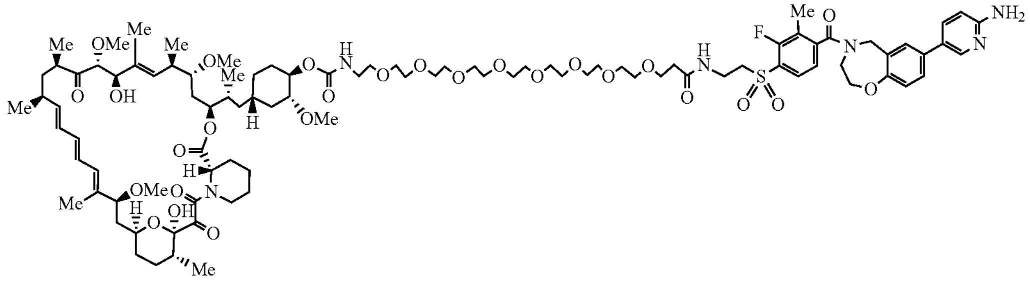
Example 94
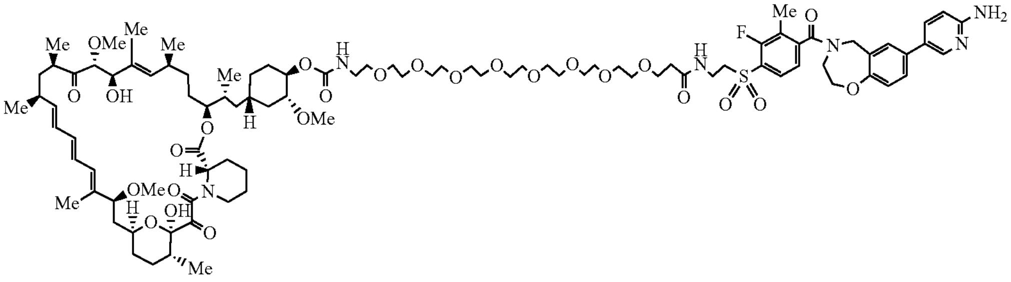 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)NCCS(=O)(=O)c3ccc(C(=O)N4CCOc5ccc(-c6ccc(N)nc6)cc5C4)c(C)c3F)[C@H](OC)C2)CC[C@H](C)/C=C(\C)[C@@H](O)[C@@H](OC)C(=O)[C@H](C)C[C@H](C)/C=C/C=C/C=C/1C]
Example 95

TABLE 7-continued
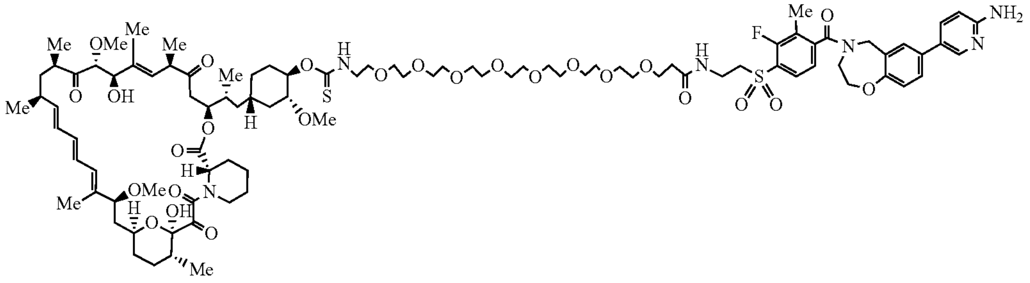 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=S)NCCOCCOCCOCCOCCOCCOCCOCCOCCC(=O)NCCS(=O)(=O)c3ccc(C(=O)N4CCOc5ccc(-c6ccc(N)nc6)cc5C4)c(C)c3F)[C@H](OC)C2)CC(=O)[C@H](C)/C=C(\C)[C@@H](O)[C@@H](OC)C(=O)[C@H](C)C[C@H](C)/C=C/C=C/C=C/1C]
Example 96
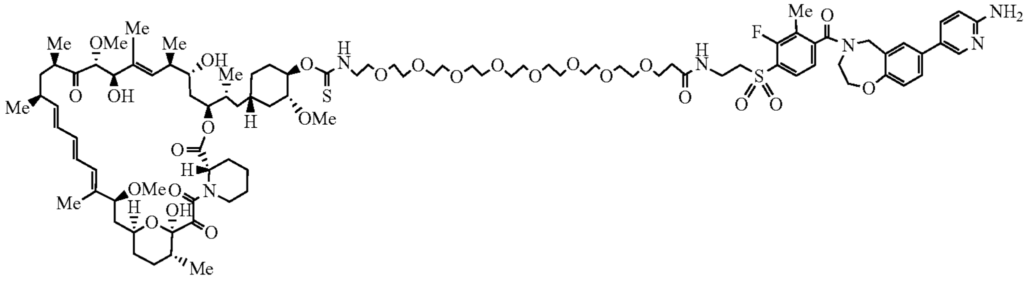 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=S)NCCOCCOCCOCCOCCOCCOCCOCCOCCC(=O)NCCS(=O)(=O)c3ccc(C(=O)N4CCOc5ccc(-c6ccc(N)nc6)cc5C4)c(C)c3F)[C@H](OC)C2)C[C@@H](O)[C@H](C)/C=C(\C)[C@@H](O)[C@@H](OC)C(=O)[C@H](C)C[C@H](C)/C=C/C=C/C=C/1C]
Example 97
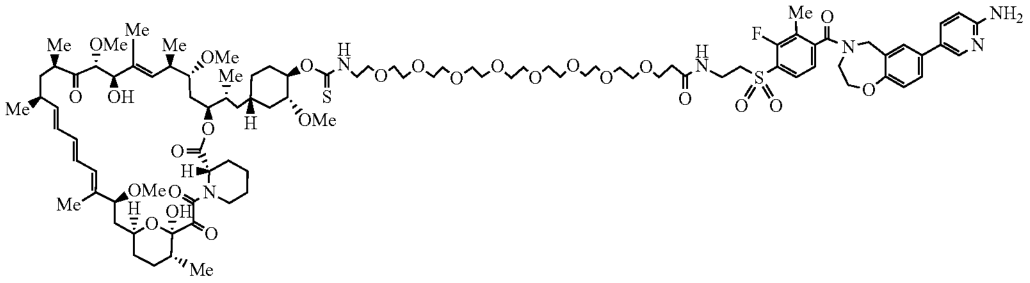 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=S)NCCOCCOCCOCCOCCOCCOCCOCCOCCC(=O)NCCS(=O)(=O)c3ccc(C(=O)N4CCOc5ccc(-c6ccc(N)nc6)cc5C4)c(C)c3F)[C@H](OC)C2)C[C@@H](OC)[C@H](C)/C=C(\C)[C@@H](O)[C@@H](OC)C(=O)[C@H](C)C[C@H](C)/C=C/C=C/C=C/1C]
Example 98
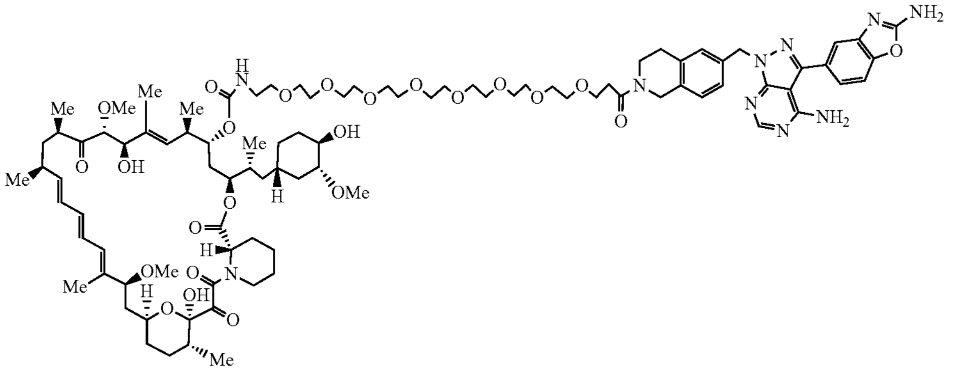
Example 99

TABLE 7-continued
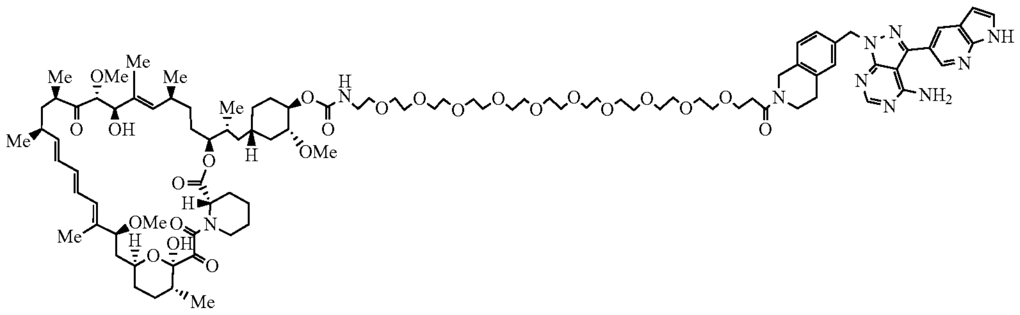 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCOCCOCCC(=O)N3CCc4cc(Cn5nc(-c6cnc7[nH]ccc7c6)c6c(N)ncnc65)ccc4C3)[C@H](OC)C2)CC[C@H](C)/C=C(\C)[C@@H](O)[C@@H](OC)C(=O)[C@H](C)C[C@H](C)/C=C/C=C/C=C/1C]
Example 100
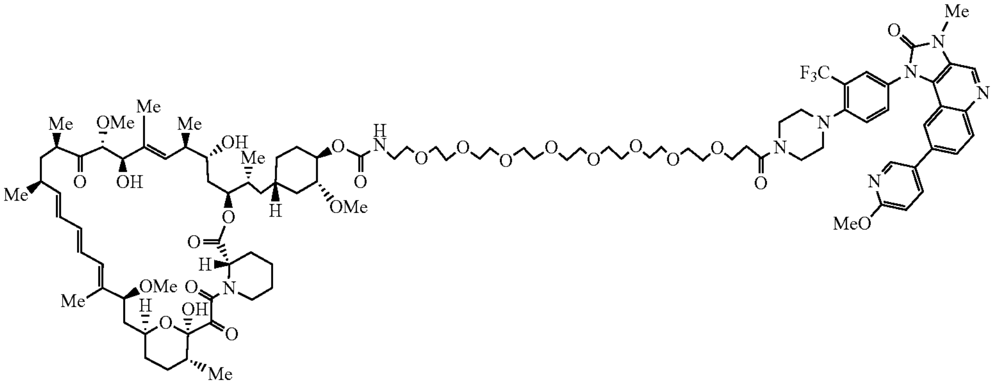 [SMILES: COc1ccc(-c2ccc3ncc4c(c3c2)n(-c2ccc(N3CCN(C(=O)CCOCCOCCOCCOCCOCCOCCOCCOCCNC(=O)O[C@@H]5CC[C@@H](C[C@@H](C)[C@@H]6C[C@@H](O)[C@H](C)/C=C(\C)[C@@H](O)[C@@H](OC)C(=O)[C@H](C)C[C@H](C)/C=C/C=C/C=C(\C)[C@@H](OC)C[C@@H]7CC[C@@H](C)[C@@](O)(O7)C(=O)C(=O)N7CCCC[C@H]7C(=O)O6)C[C@H]5OC)CC3)c(C(F)(F)F)c2)c(=O)n4C)cn1]
Example 101
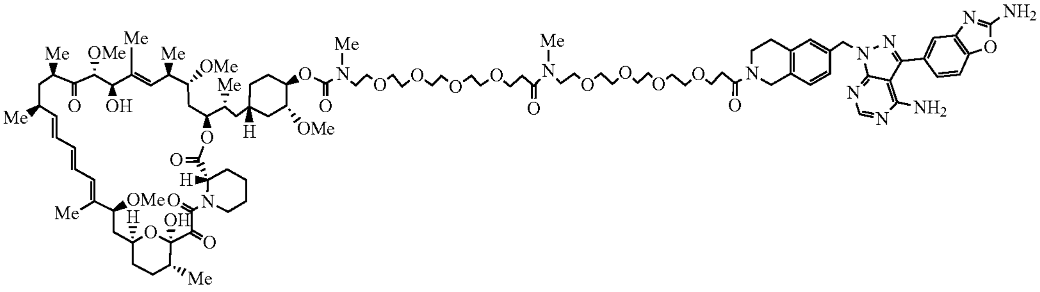 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)N(C)CCOCCOCCOCCOCCC(=O)N(C)CCOCCOCCOCCOCCC(=O)N3CCc4cc(Cn5nc(-c6ccc7oc(N)nc7c6)c6c(N)ncnc65)ccc4C3)[C@H](OC)C2)C[C@@H](OC)[C@H](C)/C=C(\C)[C@@H](O)[C@@H](OC)C(=O)[C@H](C)C[C@H](C)/C=C/C=C/C=C/1C]
Example 102
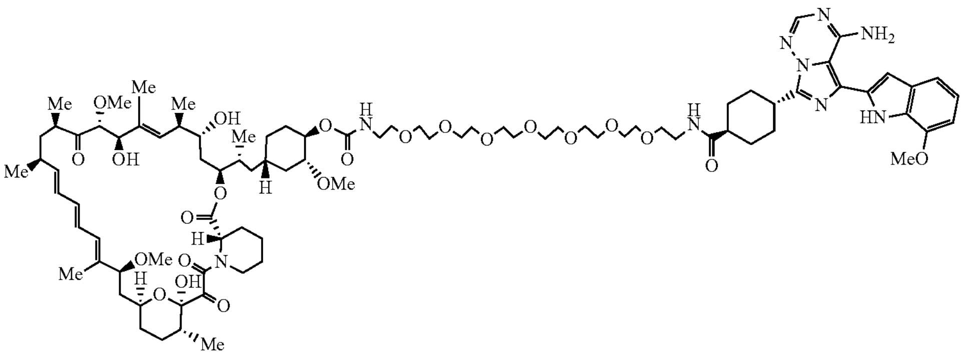 [SMILES: COc1cccc2cc(-c3nc([C@H]4CC[C@H](C(=O)NCCOCCOCCOCCOCCOCCOCCOCCNC(=O)O[C@@H]5CC[C@@H](C[C@@H](C)[C@@H]6C[C@@H](O)[C@H](C)/C=C(\C)[C@@H](O)[C@@H](OC)C(=O)[C@H](C)C[C@H](C)/C=C/C=C/C=C(\C)[C@@H](OC)C[C@@H]7CC[C@@H](C)[C@@](O)(O7)C(=O)C(=O)N7CCCC[C@H]7C(=O)O6)C[C@H]5OC)CC4)n4ncnc(N)c34)[nH]c12]
Example 136

TABLE 7-continued
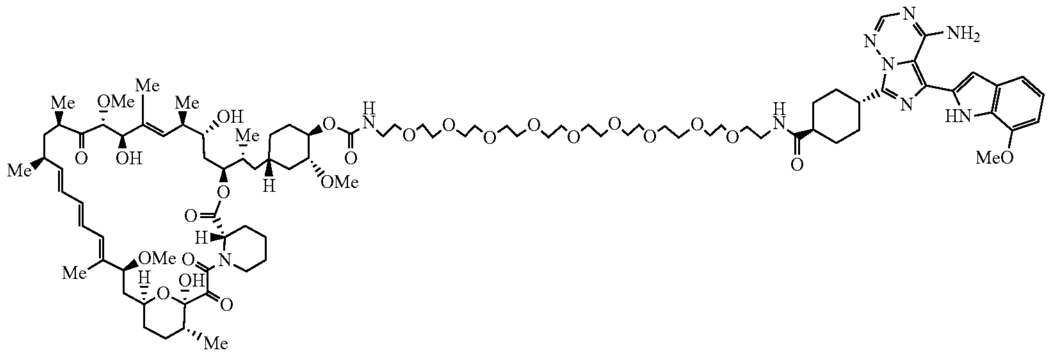 [SMILES: COc1cccc2cc(-c3nc([C@H]4CC[C@H](C(=O)NCCOCCOCCOCCOCCOCCOCCOCCOCCOCCNC(=O)O[C@@H]5CC[C@@H](C[C@@H](C)[C@@H]6C[C@@H](O)[C@H](C)/C=C(\C)[C@@H](O)[C@@H](OC)C(=O)[C@H](C)C[C@H](C)/C=C/C=C/C=C(\C)[C@@H](OC)C[C@@H]7CC[C@@H](C)[C@@](O)(O7)C(=O)C(=O)N7CCCC[C@H]7C(=O)O6)C[C@H]5OC)CC4)n4ncnc(N)c34)[nH]c12]
Example 137
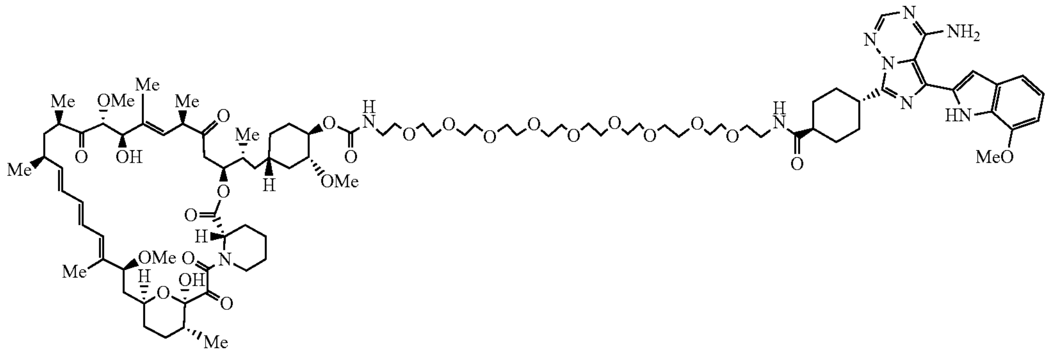 [SMILES: COc1cccc2cc(-c3nc([C@H]4CC[C@H](C(=O)NCCOCCOCCOCCOCCOCCOCCOCCOCCOCCNC(=O)O[C@@H]5CC[C@@H](C[C@@H](C)[C@@H]6CC(=O)[C@H](C)/C=C(\C)[C@@H](O)[C@@H](OC)C(=O)[C@H](C)C[C@H](C)/C=C/C=C/C=C(\C)[C@@H](OC)C[C@@H]7CC[C@@H](C)[C@@](O)(O7)C(=O)C(=O)N7CCCC[C@H]7C(=O)O6)C[C@H]5OC)CC4)n4ncnc(N)c34)[nH]c12]
Example 138
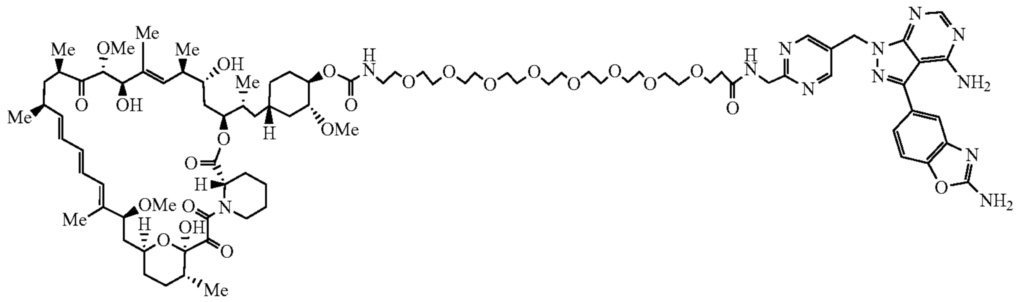 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)NCc3ncc(Cn4nc(-c5ccc6oc(N)nc6c5)c5c(N)ncnc54)cn3)[C@H](OC)C2)C[C@@H](O)[C@H](C)/C=C(\C)[C@@H](O)[C@@H](OC)C(=O)[C@H](C)C[C@H](C)/C=C/C=C/C=C/1C]
Example 139
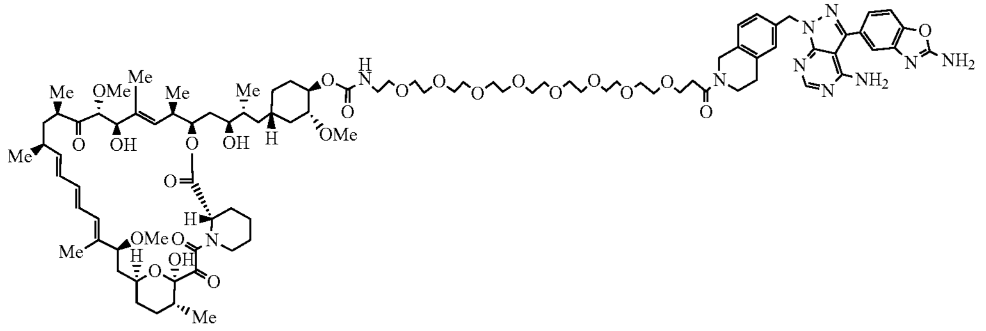 [SMILES: CO[C@H]1C[C@@H]2CC[C@@H](C)[C@@](O)(O2)C(=O)C(=O)N2CCCC[C@H]2C(=O)O[C@H](C[C@H](O)[C@H](C)C[C@@H]2CC[C@@H](OC(=O)NCCOCCOCCOCCOCCOCCOCCOCCOCCC(=O)N3CCc4cc(Cn5nc(-c6ccc7oc(N)nc7c6)c6c(N)ncnc65)ccc4C3)[C@H](OC)C2)[C@H](C)/C=C(\C)[C@@H](O)[C@@H](OC)C(=O)[C@H](C)C[C@H](C)/C=C/C=C/C=C/1C]
Example 140

TABLE 7-continued
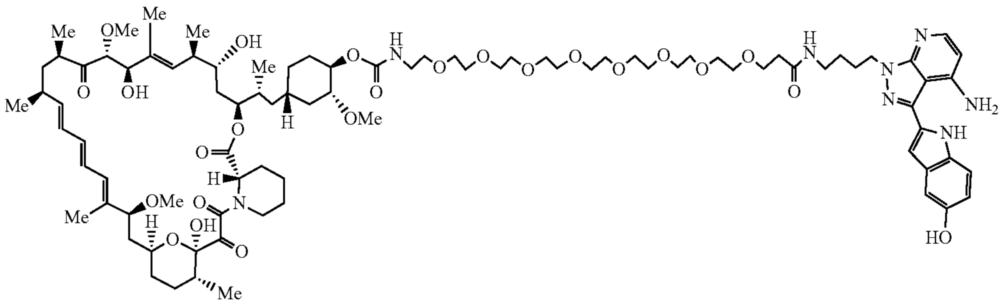 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)NCCCCn3nc(-c4cc5cc(O)ccc5[nH]4)c4c(N)ccnc43)[C@H](OC)C2)C[C@@H](O)[C@H](C)/C=C(\C)[C@@H](O)[C@@H](OC)C(=O)[C@H](C)C[C@H](C)/C=C/C=C/C=C/1C]
Example 141
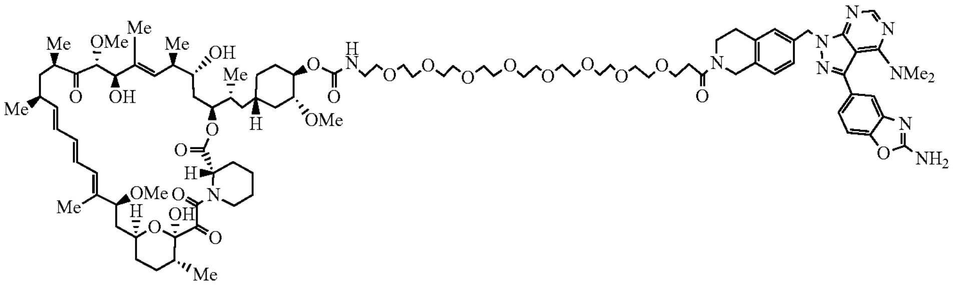 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)N3CCc4cc(Cn5nc(-c6ccc7oc(N)nc7c6)c6c(N(C)C)ncnc65)ccc4C3)[C@H](OC)C2)C[C@@H](O)[C@H](C)/C=C(\C)[C@@H](O)[C@@H](OC)C(=O)[C@H](C)C[C@H](C)/C=C/C=C/C=C/1C]
Example 142
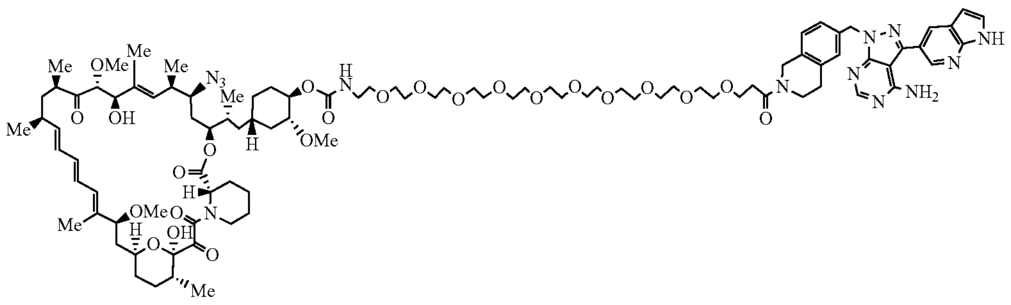 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCOCCOCCC(=O)N3CCc4cc(Cn5nc(-c6cnc7[nH]ccc7c6)c6c(N)ncnc65)ccc4C3)[C@H](OC)C2)C[C@H](N=[N+]=[N-])[C@H](C)/C=C(\C)[C@@H](O)[C@@H](OC)C(=O)[C@H](C)C[C@H](C)/C=C/C=C/C=C/1C]
Example 143
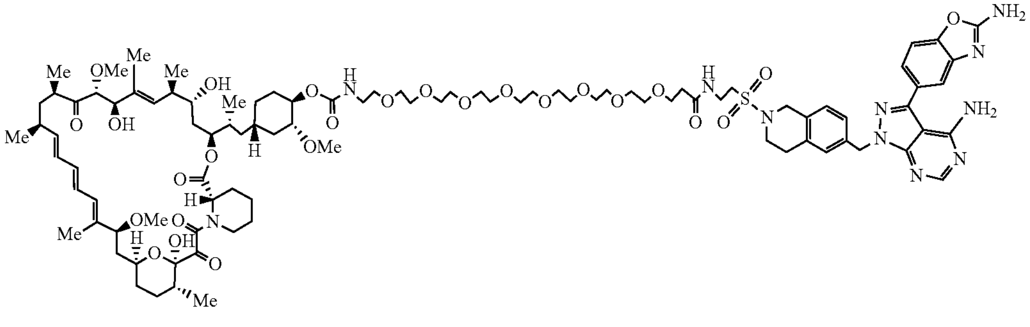 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)NCCS(=O)(=O)N3CCc4cc(Cn5nc(-c6ccc7oc(N)nc7c6)c6c(N)ncnc65)ccc4C3)[C@H](OC)C2)C[C@@H](O)[C@H](C)/C=C(\C)[C@@H](O)[C@@H](OC)C(=O)[C@H](C)C[C@H](C)/C=C/C=C/C=C/1C]
Example 144

TABLE 7-continued
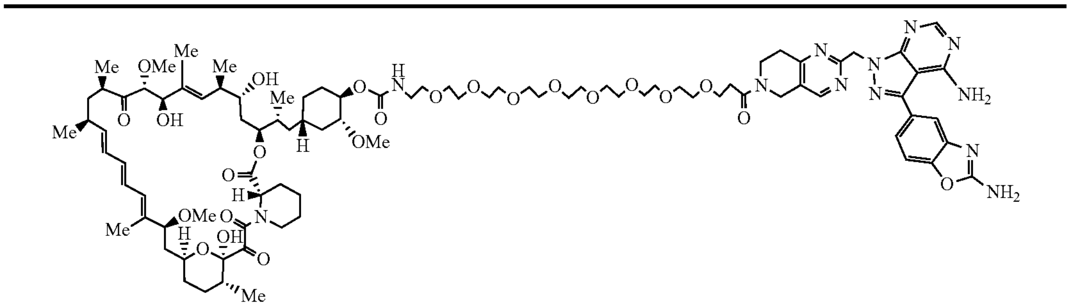
Example 145
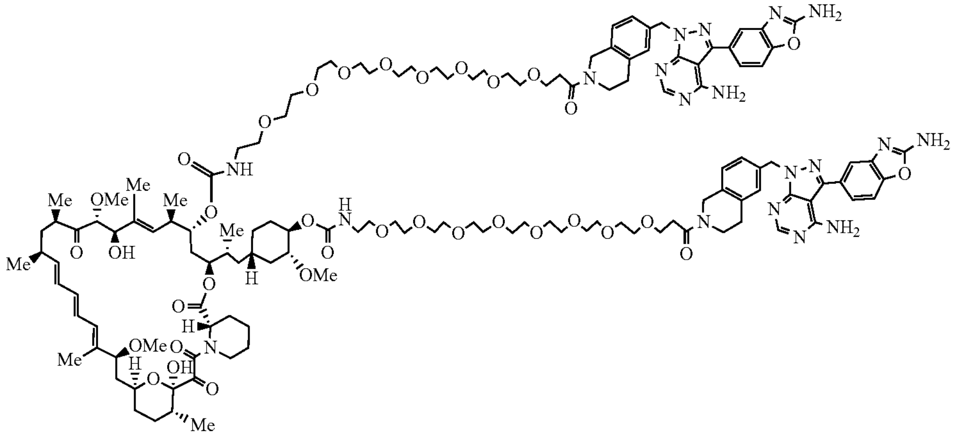 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCOCCOCCC(=O)N3CCc4cc(Cn5nc(-c6ccc7oc(N)nc7c6)c6c(N)ncnc65)ccc4C3)[C@H](OC)C2)C[C@@H](OC(=O)NCCOCCOCCOCCOCCOCCOCCOCCOCCC(=O)N2CCc3cc(Cn4nc(-c5ccc6oc(N)nc6c5)c5c(N)ncnc54)ccc3C2)[C@H](C)/C=C(\C)[C@@H](O)[C@@H](OC)C(=O)[C@H](C)C[C@H](C)/C=C/C=C/C=C/1C]
Example 146
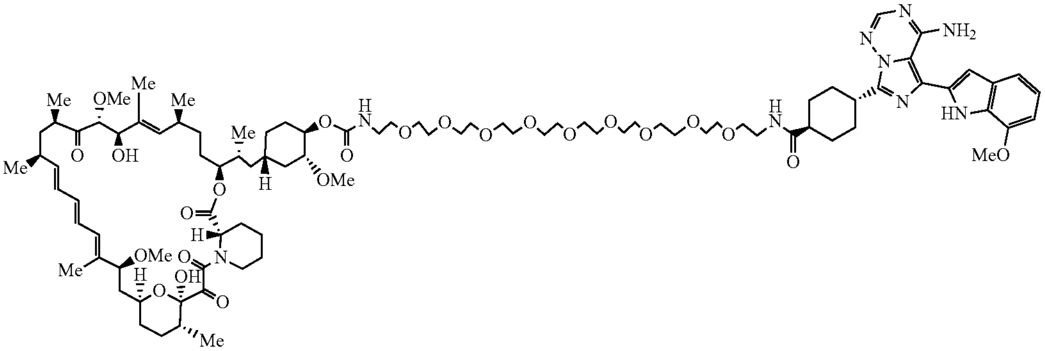 [SMILES: COc1cccc2cc(-c3nc([C@H]4CC[C@H](C(=O)NCCOCCOCCOCCOCCOCCOCCOCCOCCOCCNC(=O)O[C@@H]5CC[C@@H](C[C@@H](C)[C@@H]6CC[C@H](C)/C=C(\C)[C@@H](O)[C@@H](OC)C(=O)[C@H](C)C[C@H](C)/C=C/C=C/C=C(\C)[C@@H](OC)C[C@@H]7CC[C@@H](C)[C@@](O)(O7)C(=O)C(=O)N7CCCC[C@H]7C(=O)O6)C[C@H]5OC)CC4)n4ncnc(N)c34)[nH]c12]
Example 147
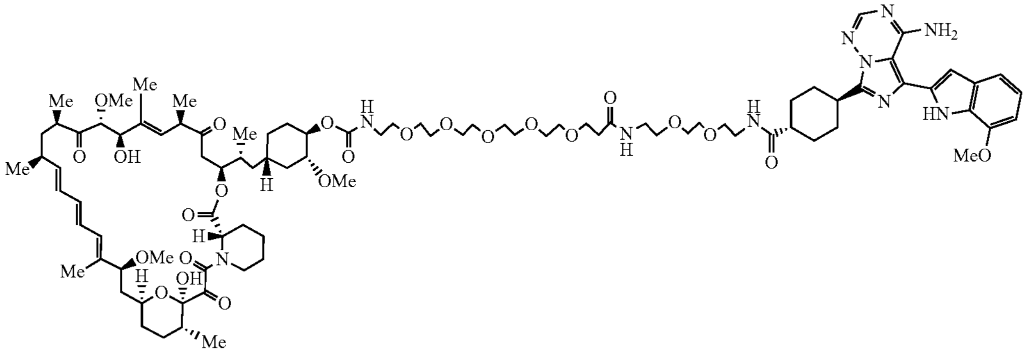 [SMILES: COc1cccc2cc(-c3nc([C@H]4CC[C@H](C(=O)NCCOCCOCCNC(=O)CCOCCOCCOCCOCCOCCNC(=O)O[C@@H]5CC[C@@H](C[C@@H](C)[C@@H]6CC(=O)[C@H](C)/C=C(\C)[C@@H](O)[C@@H](OC)C(=O)[C@H](C)C[C@H](C)/C=C/C=C/C=C(\C)[C@@H](OC)C[C@@H]7CC[C@@H](C)[C@@](O)(O7)C(=O)C(=O)N7CCCC[C@H]7C(=O)O6)C[C@H]5OC)CC4)n4ncnc(N)c34)[nH]c12]
Example 148

TABLE 7-continued

Series 1 Bivalent Compounds:

| Structure | Molecular Formula | Calculated MW | Observed MW |
|---|---|---|---|
| Example 1 | $C_{87}H_{132}N_{10}O_{24}$ | [M + H] = 1701.95 | [M + H] = 1701.8 |
| Example 2 | $C_{93}H_{134}N_{10}O_{24}$ | [M + H] = 1775.97 | [M + H] = 1775.7 |
| Example 3 | $C_{89}H_{126}N_{10}O_{22}$ | [M + H] = 1687.91 | [M + H] = 1687.8 |
| Example 4 | $C_{87}H_{132}N_{10}O_{23}$ | [M + H] = 1684.95 | [M + H] = 1685.1 |
| Example 5 | $C_{101}H_{150}N_{10}O_{27}$ | [M + H] = 1936.08 | [M + H] = 1936.4 |
| Example 6 | $C_{97}H_{142}N_{10}O_{25}$ | [M + H] = 1848.02 | [M + H] = 1848.3 |
| Example 7 | $C_{93}H_{134}N_{10}O_{23}$ | [M + H] = 1759.97 | [M + H] = 1760.1 |
| Example 8 | $C_{87}H_{134}N_{10}O_{24}$ | [M + H] = 1703.97 | [M + H] = 1703.7 |
| Example 9 | $C_{93}H_{136}N_{10}O_{24}$ | [M + H] = 1777.98 | [M + H] = 1777.7 |
| Example 10 | $C_{93}H_{136}N_{10}O_{23}$ | [M + H] = 1761.99 | [M + H] = 1761.7 |
| Example 11 | $C_{88}H_{136}N_{10}O_{24}$ | [M + H] = 1717.98 | [M + H] = 1718.0 |
| Example 12 | $C_{94}H_{138}N_{10}O_{24}$ | [M + H] = 1792.00 | [M + H] = 1791.9 |
| Example 13 | $C_{91}H_{133}N_{13}O_{24}$ | [M + H] = 1792.97 | [M + H] = 1793.0 |
| Example 14 | $C_{90}H_{137}N_{11}O_{25}$ | [M + H] = 1772.99 | [M + H] = 1772.9 |
| Example 15 | $C_{96}H_{139}N_{11}O_{25}$ | [M + H] = 1847.00 | [M + H] = 1847.0 |
| Example 16 | $C_{96}H_{141}N_{11}O_{25}$ | [M + H] = 1849.02 | [M + H] = 1848.9 |
| Example 17 | $C_{97}H_{143}N_{11}O_{25}$ | [M + H] = 1863.04 | [M + H] = 1863.0 |
| Example 18 | $C_{90}H_{137}N_{11}O_{24}$ | [M + H] = 1756.99 | [M + H] = 1756.8 |
| Example 19 | $C_{88}H_{132}N_{10}O_{24}$ | [M + H] = 1713.95 | [M + H] = 1713.9 |
| Example 20 | $C_{92}H_{140}N_{10}O_{25}$ | [M + H] = 1786.01 | [M + H] = 1786.0 |
| Example 21 | $C_{100}H_{147}N_{11}O_{26}$ | [M + H] = 1919.06 | [M + H] = 1919.0 |
| Example 22 | $C_{93}H_{134}N_{10}O_{23}S$ | [M + H] = 1791.94 | [M + H] = 1791.8 |
| Example 23 | $C_{93}H_{134}N_{10}O_{24}$ | [M + H] = 1775.97 | [M + H] = 1775.9 |
| Example 24 | $C_{104}H_{144}F_3N_{11}O_{25}$ | [M + 2H]/2 = 1003.03 | [M + 2H]/2 = 1003.5 |
| Example 25 | $C_{104}H_{146}F_3N_{11}O_{25}$ | [M + 2H]/2 = 1004.03 | [M + 2H]/2 = 1004.5 |
| Example 26 | $C_{105}H_{148}F_3N_{11}O_{25}$ | [M + 2H]/2 = 1011.04 | [M + 2H]/2 = 1011.5 |
| Example 71 | $C_{92}H_{132}N_{10}O_{24}$ | [M + H] = 1761.95 | [M + H] = 1761.8 |
| Example 72 | $C_{92}H_{134}N_{10}O_{24}$ | [M + H] = 1763.97 | [M + H] = 1763.8 |
| Example 73 | $C_{93}H_{136}N_{10}O_{23}$ | [M + H] = 1761.99 | [M + H] = 1762.0 |
| Example 74 | $C_{93}H_{135}N_{13}O_{23}$ | [M + H] = 1802.99 | [M + H] = 1802.9 |
| Example 75 | $C_{94}H_{138}N_{10}O_{24}$ | [M + H] = 1792.00 | [M + H] = 1791.7 |
| Example 76 | $C_{95}H_{140}N_{10}O_{24}$ | [M + H] = 1806.01 | [M + H] = 1805.8 |
| Example 77 | $C_{93}H_{136}N_{10}O_{23}S$ | [M + H] = 1793.96 | [M + H] = 1793.9 |
| Example 78 | $C_{94}H_{138}N_{10}O_{23}S$ | [M + H] = 1807.97 | [M + H] = 1807.9 |
| Example 79 | $C_{91}H_{132}N_{10}O_{24}$ | [M + H] = 1749.95 | [M + H] = 1749.9 |
| Example 80 | $C_{91}H_{134}N_{10}O_{24}$ | [M + H] = 1751.97 | [M + H] = 1751.9 |

TABLE 7-continued

| | | | |
|---|---|---|---|
| Example 81 | $C_{92}H_{136}N_{10}O_{24}$ | [M + H] = 1765.98 | [M + H] = 1765.8 |
| Example 82 | $C_{91}H_{133}N_{13}O_{23}$ | [M + H] = 1776.97 | [M + H] = 1776.9 |
| Example 83 | $C_{91}H_{133}N_{10}O_{23}S$ | [M + H] = 1766.93 | [M + H] = 1766.8 |
| Example 84 | $C_{95}H_{140}N_{6}O_{27}S$ | [M + H] = 1829.96 | [M + H] = 1830.0 |
| Example 85 | $C_{95}H_{142}N_{6}O_{27}S$ | [M + H] = 1831.97 | [M + H] = 1831.9 |
| Example 86 | $C_{96}H_{144}N_{6}O_{27}S$ | [M + H] = 1845.99 | [M + H] = 1846.0 |
| Example 87 | $C_{95}H_{142}N_{6}O_{26}S$ | [M + H] = 1815.98 | [M + H] = 1815.8 |
| Example 88 | $C_{95}H_{141}N_{9}O_{26}S$ | [M + H] = 1856.98 | [M + H] = 1856.8 |
| Example 89 | $C_{95}H_{140}N_{6}O_{26}S_{2}$ | [M + H] = 1845.93 | [M + H] = 1846.0 |
| Example 90 | $C_{95}H_{142}N_{6}O_{26}S_{2}$ | [M + H] = 1847.95 | [M + H] = 1847.9 |
| Example 91 | $C_{96}H_{144}N_{6}O_{26}S_{2}$ | [M + H] = 1861.96 | [M + H] = 1861.7 |
| Example 92 | $C_{95}H_{139}FN_{6}O_{27}S$ | [M + H] = 1847.95 | [M + H] = 1848.0 |
| Example 93 | $C_{95}H_{141}FN_{6}O_{27}S$ | [M + H] = 1849.96 | [M + H] = 1850.0 |
| Example 94 | $C_{96}H_{143}FN_{6}O_{27}S$ | [M + H] = 1863.98 | [M + H] = 1864.0 |
| Example 95 | $C_{96}H_{143}FN_{6}O_{26}S$ | [M + H] = 1833.97 | [M + H] = 1833.9 |
| Example 96 | $C_{95}H_{139}FN_{6}O_{26}S_{2}$ | [M + H] = 1863.92 | [M + H] = 1863.8 |
| Example 97 | $C_{95}H_{141}FN_{6}O_{26}S_{2}$ | [M + H] = 1865.94 | [M + H] = 1865.8 |
| Example 98 | $C_{96}H_{143}FN_{6}O_{26}S_{2}$ | [M + H] = 1879.96 | [M + H] = 1879.9 |
| Example 99 | $C_{93}H_{136}N_{10}O_{24}$ | [M + H] = 1777.98 | [M + H] = 1777.8 |
| Example 100 | $C_{97}H_{144}N_{10}O_{24}$ | [M + H] = 1834.04 | [M + H] = 1833.8 |
| Example 101 | $C_{99}H_{141}F_{3}N_{8}O_{25}$ | [M + H] = 1900.00 | [M + H] = 1899.9 |
| Example 102 | $C_{99}H_{147}N_{11}O_{25}$ | [M + H] = 1891.06 | [M + H] = 1890.9 |
| Example 136 | $C_{89}H_{135}N_{9}O_{23}$ | [M + H] = 1698.97 | [M + H] = 1698.8 |
| Example 137 | $C_{93}H_{143}N_{9}O_{25}$ | [M + H] = 1787.03 | [M + H] = 1786.7 |
| Example 138 | $C_{93}H_{141}N_{9}O_{25}$ | [M + H] = 1785.01 | [M + H] = 1784.9 |
| Example 139 | $C_{89}H_{132}N_{12}O_{24}$ | [M + H] = 1753.96 | [M + H] = 1753.7 |
| Example 140 | $C_{93}H_{136}N_{10}O_{24}$ | [M + H] = 1777.98 | [M + H] = 1777.7 |
| Example 141 | $C_{88}H_{135}N_{9}O_{24}$ | [M + H] = 1702.97 | [M + H] = 1702.9 |
| Example 142 | $C_{95}H_{140}N_{10}O_{24}$ | [M + H] = 1806.01 | [M + H] = 1805.8 |
| Example 143 | $C_{97}H_{143}N_{13}O_{24}$ | [M + H] = 1875.04 | [M + H] = 1874.9 |
| Example 144 | $C_{95}H_{141}N_{11}O_{26}S$ | [M + H] = 1884.98 | [M + H] = 1884.9 |
| Example 145 | $C_{91}H_{134}N_{12}O_{24}$ | [M + H] = 1779.97 | [M + H] = 1779.8 |
| Example 146 | $C_{135}H_{191}N_{19}O_{35}$ | [M + 2H]/2 = 1320.19 | [M + 2H]/2 = 1320.8 |
| Example 147 | $C_{93}H_{143}N_{9}O_{24}$ | [M + H] = 1771.03 | [M + H] = 1770.8 |
| Example 148 | $C_{92}H_{138}N_{10}O_{24}$ | [M + H] = 1768.00 | [M + H] = 1767.8 |

General Procedure 3: Coupling of a Halide Containing PEG Ester and an Amine Containing Pre-Linker Followed by Ester Deprotection.

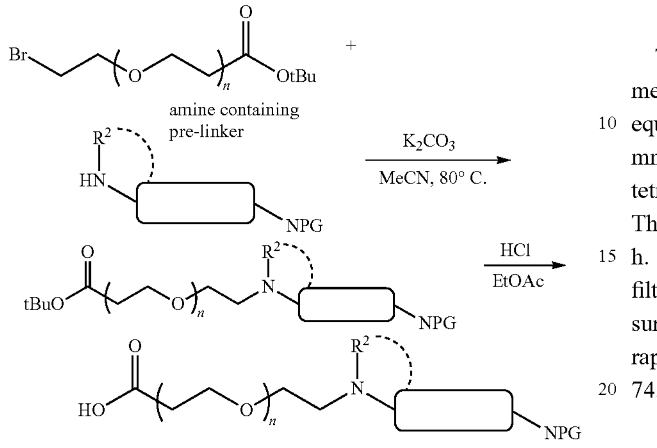

Step 1:

To a 0.1 M solution of amine containing pre-linker (1.0 equiv) in MeCN was added $K_2CO_3$ (2.0 equiv) followed by halide containing PEG ester (1.0 equiv). The reaction was stirred at 80° C. until consumption of amine containing pre-linker, as indicated by LCMS analysis. The reaction was then purified by silica gel chromatography to afford the product.

Step 2:

To a 0.1 M solution of PEG tert-butyl ester (1.0 equiv) in EtOAc was added a solution of HCl in EtOAc. The resulting suspension was stirred at room temperature until consumption of the PEG ester, as indicated by LCMS analysis. The reaction was then concentrated under reduced pressure to afford the product.

Intermediate B1-1. 1-(4-(5-((1,3-dioxoisoindolin-2-yl)methyl)pyrimidin-2-yl)piperazin-1-yl)-3,6,9,12-tetraoxapentadecan-15-oic acid Step 1: Synthesis of tert-butyl 1-(4-(5-((1,3-dioxoisoindolin-2-yl)methyl)pyrimidin-2-yl)piperazin-1-yl)-3,6,9,12-tetraoxapentadecan-15-oate To a mixture of 2-((2-(piperazin-1-yl)pyrimidin-5-yl)methyl)isoindoline-1,3-dione (7.97 g, 24.66 mmol, 1.0 equiv) in MeCN (200 mL) was added $K_2CO_3$ (6.82 g, 49.31 mmol, 2.0 equiv) followed by tert-butyl 1-bromo-3,6,9,12-tetraoxapentadecan-15-oate (9.5 g, 24.66 mmol, 1.0 equiv). The reaction mixture was heated to 85° C. and stirred for 15 h. The mixture was then cooled to room temperature and filtered. The filtrate was concentrated under reduced pressure and the residue was purified by silica gel chromatography (0-20% EtOAc/MeOH) to give the product (11.5 g, 74.3% yield) a light yellow liquid.

Step 2: Synthesis of 1-(4-(5-((1,3-dioxoisoindolin-2-yl)methyl)pyrimidin-2-yl)piperazin-1-yl)-3,6,9,12-tetraoxapentadecan-15-oic acid To a solution of tert-butyl 1-(4-(5-((1,3-dioxoisoindolin-2-yl)methyl)pyrimidin-2-yl)piperazin-1-yl)-3,6,9,12-tetraoxapentadecan-15-oate (3.5 g, 5.58 mmol, 1.0 equiv) in EtOAc (50 mL) was added a solution of HCl in EtOAc (500 mL). The mixture was stirred at room temperature for 3 h. The mixture was then concentrated under reduced pressure to give the product (5.3 g, 78.2% yield, HCl) as a white solid. LCMS (ESI) m/z: [M+H] calcd for $C_{28}H_{37}N_5O_8$: 572.27; found 572.4.

Following General Procedure 3, but using the appropriate halide containing PEG and amine containing pre-linkers in Table 4, the Intermediates B1 in Table 8 were prepared:

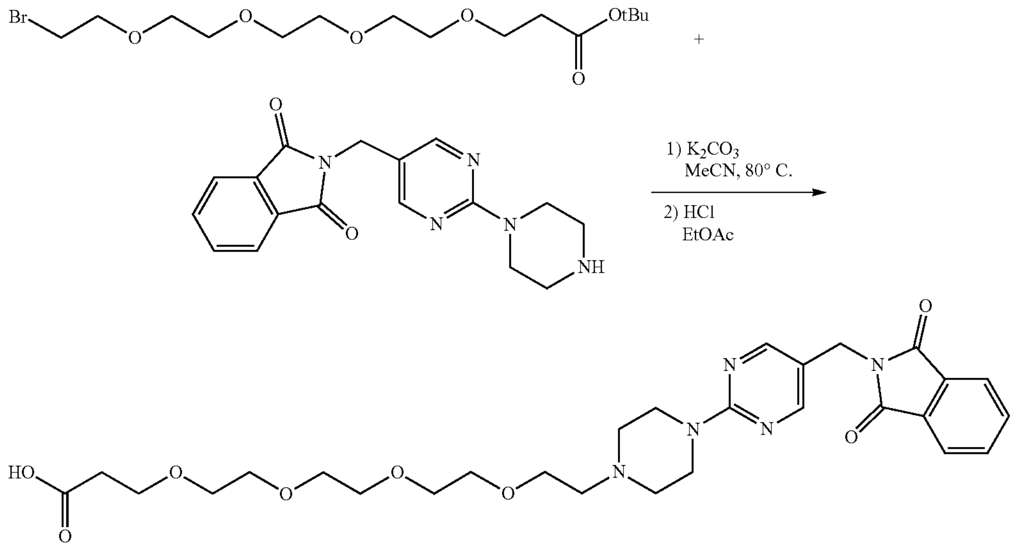

TABLE 8

Additional protected amines prepared

| Structure | Molecular Formula | Calculated MW | Observed MW |
|---|---|---|---|
| 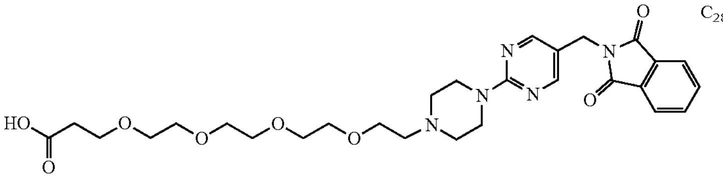 Intermediate B1-1 | $C_{28}H_{37}N_5O_8$ | [M + H] = 572.27 | [M + H] = 572.4 |

General Procedure 4: Coupling of a PEG Carboxylic Acid and an Amine Containing Active Site Inhibitor Followed by Amine Deprotection.

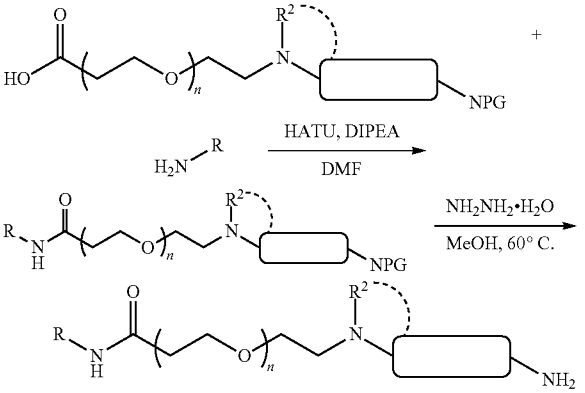

Step 1:

To a 0.15 M solution of PEG carboxylic acid (1.0 equiv) in DMF was added HATU (1.3 equiv) and DIPEA (5.0 equiv). After stirring for 30 min, the amine containing active site inhibitor (1.2 equiv) was added. The reaction was stirred at room temperature until consumption of PEG carboxylic acid, as indicated by LCMS. The reaction was then purified by reverse phase chromatography to afford the product.

Step 2:

To a 0.1 M solution of phthalimide protected amine (1.0 equiv) in MeOH at 0° C. was added $NH_2NH_2H_2O$ (4.0 equiv). The resulting mixture was stirred at 60° C. until consumption of the phthalimide protected amine, as indicated by LCMS analysis. The reaction was then purified by reverse phase chromatography to afford the product.

Intermediate B2-1. N-(4-(4-amino-3-(2-aminobenzo[d]oxazol-5-yl)-1H-pyrazolo[3,4-d]pyrimidin-1-yl)butyl)-1-(4-(5-(aminomethyl)pyrimidin-2-yl)piperazin-1-yl)-3,6,9,12-tetraoxapentadecan-15-amide

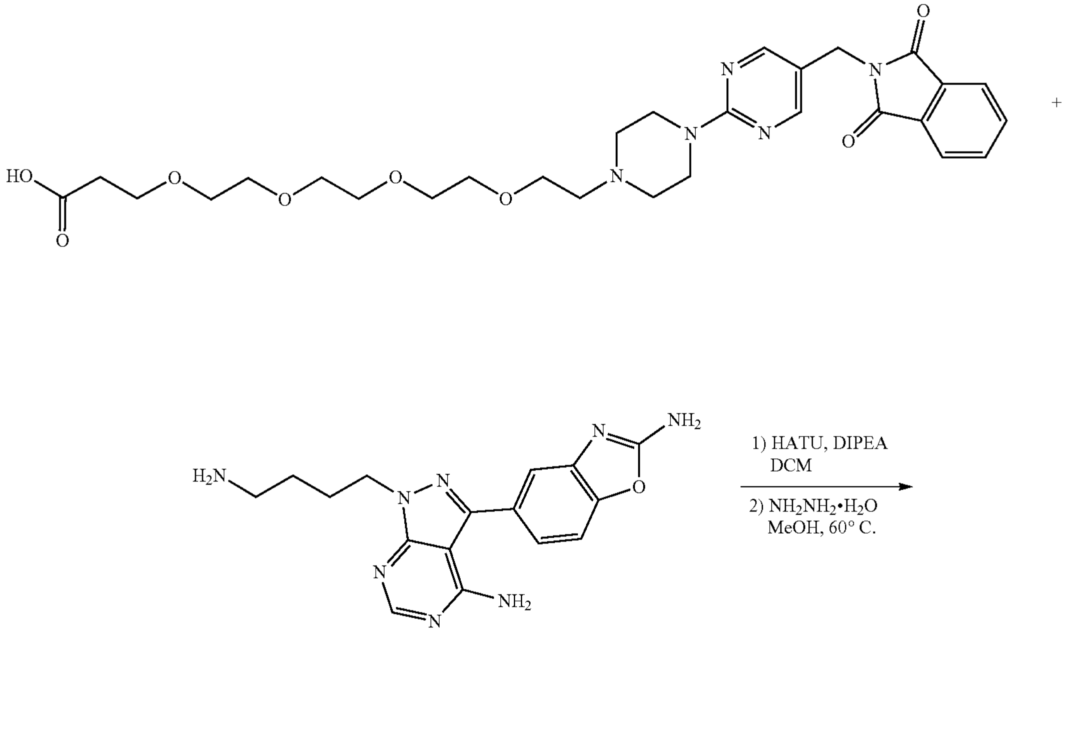

-continued

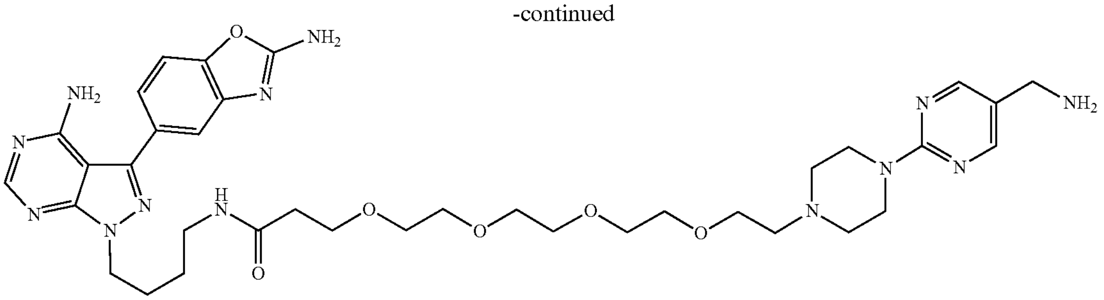

Step 1: Synthesis of N-(4-(4-amino-3-(2-aminobenzo[d]oxazol-5-yl)-1H-pyrazolo[3,4-d]pyrimidin-1-yl)butyl)-1-(4-(5-((1,3-dioxoisoindolin-2-yl)methyl)pyrimidin-2-yl)piperazin-1-yl)-3,6,9,12-tetraoxapentadecan-15-amide To a mixture of 1-(4-(5-((1,3-dioxoisoindolin-2-yl)methyl)pyrimidin-2-yl)piperazin-1-yl)-3,6,9,12-tetraoxapentadecan-15-oic acid (3 g, 4.93 mmol, 1.0 equiv, HCl) in DMF (30 mL) was added HATU (12.11 μL, 6.41 mmol, 1.3 equiv) and DIPEA (4.30 mL, 24.67 mmol, 5.0 equiv). After 30 min, 5-(4-amino-1-(4-aminobutyl)-1H-pyrazolo[3,4-d]pyrimidin-3-yl)benzo[d]oxazol-2-amine (4.03 g, 5.92 mmol, 1.2 equiv, 3TFA) was added. The mixture was stirred at room temperature for 3 h. The reaction mixture was then purified by prep-HPLC ($MeCN/H_2O$) to give the product (5.4 g, 81.2% yield, 4TFA) as a light red solid. LCMS (ESI) m/z: [M+2H]/2 calcd for $C_{44}H_{53}N_{13}O_8$: 446.71; found 447.0.

Step 2: Synthesis of N-(4-(4-amino-3-(2-aminobenzo[d]oxazol-5-yl)-1H-pyrazolo[3,4-d]pyrimidin-1-yl)butyl)-1-(4-(5-(aminomethyl)pyrimidin-2-yl)piperazin-1-yl)-3,6,9,12-tetraoxapentadecan-15-amide To a mixture of N-(4-(4-amino-3-(2-aminobenzo[d]oxazol-5-yl)-1H-pyrazolo[3,4-d]pyrimidin-1-yl)butyl)-1-(4-(5-((1,3-dioxoisoindolin-2-yl)methyl)pyrimidin-2-yl)piperazin-1-yl)-3,6,9,12-tetraoxapentadecan-15-amide (4 g, 2.97 mmol, 1.0 equiv, 4TFA) in MeOH (25 mL) at 0° C. was added $NH_2NH_2 \cdot H_2O$ (588.63 μL, 11.87 mmol, 4.0 equiv). The mixture was stirred at 60° C. for 2 h. The mixture was then cooled to room temperature and filtered, and the filter cake was washed with MeOH (5 mL). The filtrate was concentrated under reduced pressure and the residue was purified by prep-HPLC ($MeCN/H_2O$) to give the product (700 mg, 24.5% yield, TFA) as a white solid. LCMS (ESI) m/z: [M+2H]/2 calcd for $C_{36}H_{51}N_{13}O_6$: 381.71; found 381.8.

Following General Procedure 4, but using the appropriate Intermediate B1 in Table 8 and amine containing active site inhibitors in Table 2, the Intermediates B2 in Table 9 were prepared:

TABLE 9

Additional amines prepared

| Structure | Molecular Formula | Calculated MW | Observed MW |
|---|---|---|---|
| 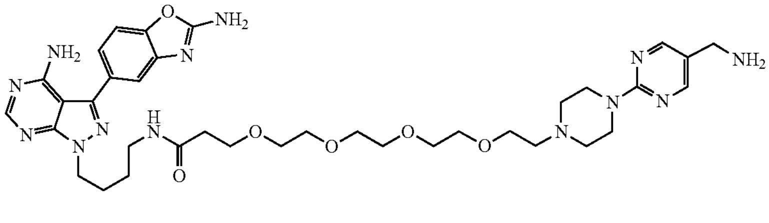 [SMILES: NCc1cnc(N2CCN(CCOCCOCCOCCOCCC(=O)NCCCCn3nc(-c4ccc5oc(N)nc5c4)c4c(N)ncnc43)CC2)nc1] Intermediate B2-1 | $C_{36}H_{51}N_{13}O_6$ | [M + 2H]/2 = 381.71 | [M + 2H]/2 = 381.8 |
| 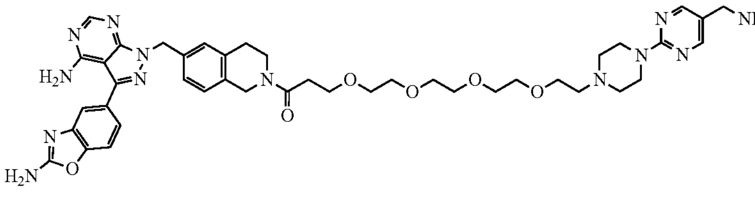 Intermediate B2-2 | $C_{42}H_{53}N_{13}O_6$ | [M + H] = 836.43 | [M + H] = 836.4 |

TABLE 9-continued

| Additional amines prepared | | | |
|---|---|---|---|
| Structure | Molecular Formula | Calculated MW | Observed MW |
| 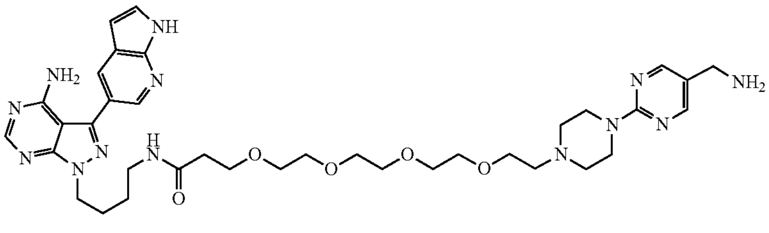 [SMILES: NCc1cnc(N2CCN(CCOCCOCCOCCOCCC(=O)NCCCCn3nc(-c4cnc5[nH]ccc5c4)c4c(N)ncnc43)CC2)nc1] Intermediate B2-3 | $C_{36}H_{51}N_{13}O_5$ | [M + 2H]/2 = 373.72 | [M + 2H]/2 = 737.7 |

General Procedure 5: Coupling of a Halide Containing PEG Carboxylic Acid and an Amine Containing Active Site Inhibitor.

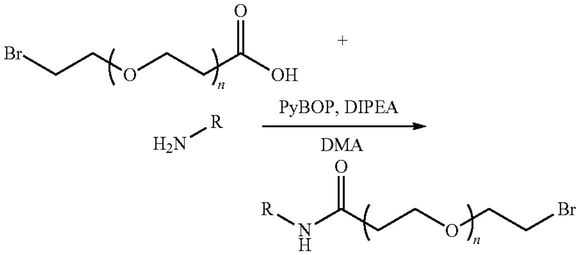

To a 0.1 M solution of amine containing active site inhibitor (1.0 equiv) and PEG containing carboxylic acid (1.2 equiv) in DMA was added DIPEA (4.0 equiv) followed by PyBOP (1.3 equiv). The reaction was stirred until consumption of amine containing active site inhibitor, as indicated by LCMS. The reaction was then purified by reverse phase HPLC to afford the product.

Intermediate B3-1. 18-{6-[(4-amino-3-{1H-pyrrolo[2,3-b]pyridin-5-yl}-1H-pyrazolo[3,4-d]pyrimidin-1-yl)methyl]-1,2,3,4-tetrahydroisoquinolin-2-yl}-1-bromo-3,6,9,12,15-pentaoxaoctadecan-18-one

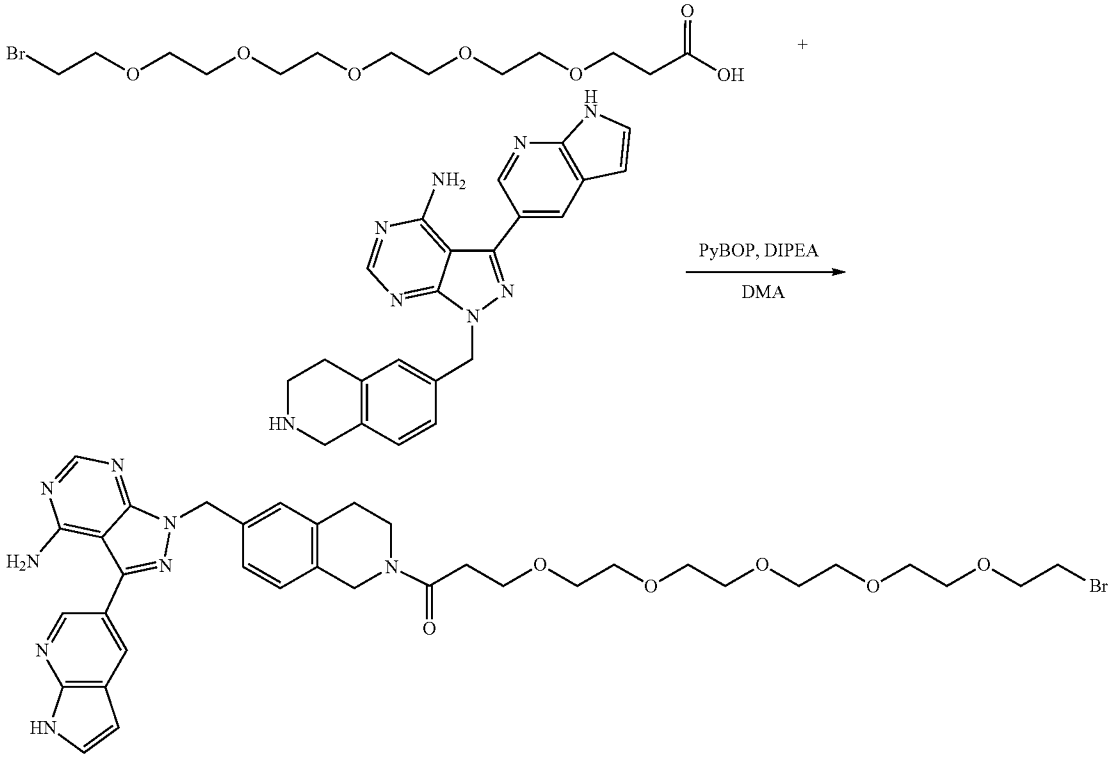

To a solution of 1-bromo-3,6,9,12,15-pentaoxaoctadecan-18-oic acid (105 mg, 282 μmol, 1.2 equiv) and 3-{1H-pyrrolo[2,3-b]pyridin-5-yl}-1-[(1,2,3,4-tetrahydroisoquinolin-6-yl)methyl]-1H-pyrazolo[3,4-d]pyrimidin-4-amine (120 mg, 235 μmol, 1.0 equiv) in DMA (2.34 mL) was added DIPEA (163 μL, 940 μmol, 4.0 equiv) followed by PyBOP (158 mg, 305 μmol, 1.3 equiv). The resulting solution was stirred at room temperature for 3 h then purified by reverse phase HPLC (10→98% MeCN+0.1% formic acid/$H_2O$+ 0.1% formic acid) to afford the product (82.7 mg, 47% yield). LCMS (ESI) m/z: [M+H] calcd for $C_{35}H_{43}BrN_8O_6$: 751.26; found 751.2.

Following General Procedure 5, but using the appropriate halide containing PEG carboxylic acid and amine containing active site inhibitors in Table 2, the Intermediates B3 in Table 10 were prepared:

-continued

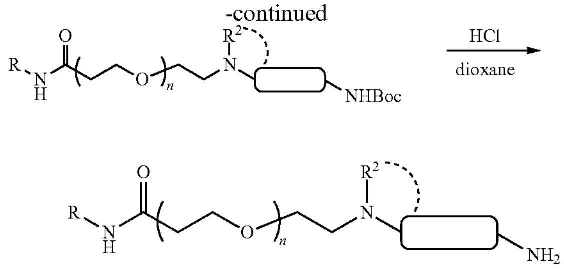

Step 1:

To a 0.1 M solution of halide containing PEG (1.0 equiv) in MeCN was added $K_2CO_3$ (3.0 equiv) followed by amine

TABLE 10

Additional PEG halides prepared

| Structure | Molecular Formula | Calculated MW | Observed MW |
|---|---|---|---|
| 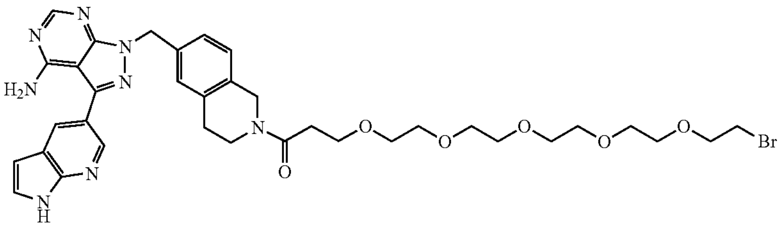 [SMILES: Nc1ncnc2c1c(-c1cnc3[nH]ccc3c1)nn2Cc1ccc2c(c1)CCN(C(=O)CCOCCOCCOCCOCCOCCBr)C2] Intermediate B3-1 | $C_{35}H_{43}BrN_8O_6$ | [M + H] = 751.26 | [M + H] = 751.2 |
| 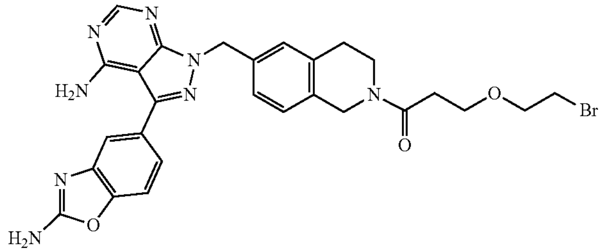 [SMILES: Nc1nc2cc(-c3nn(Cc4ccc5c(c4)CCN(C(=O)CCOCCBr)C5)c4ncnc(N)c34)ccc2o1] Intermediate B3-2 | $C_{27}H_{27}BrN_8O_3$ | [M + H] = 591.15 | [M + H] = 591.2 |

General Procedure 6: Displacement of a PEG Halide with an Amine Containing Post Linker and Deprotection of the Amine.

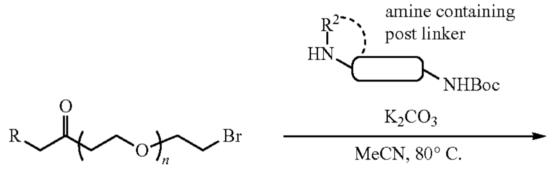

containing post linker (1.2 equiv). The resulting suspension was heated to 80° C. and stirred until consumption of the PEG halide, as indicated by LCMS analysis. The reaction was cooled to room temperature and then purified by silica gel chromatography to afford the product.

Step 2:

To a 0.07 M solution of N-Boc protected amine (1.0 equiv) in dioxane was added HCl (4 M in dioxane, 10.0 equiv). The reaction was stirred until consumption of N-Boc protected amine, as indicated by LCMS analysis. The reaction was then concentrated under reduced pressure to afford the product.

Intermediate B2-4. 18-{6-[(4-amino-3-{1H-pyrrolo[2,3-b]pyridin-5-yl}-1H-pyrazolo[3,4-d]pyrimidin-1-yl)methyl]-1,2,3,4-tetrahydroisoquinolin-2-yl}-1-(4-{5H,6H,7H,8H-pyrido[4,3-d]pyrimidin-2-yl}piperazin-1-yl)-3,6,9,12,15-pentaoxaoctadecan-18-one

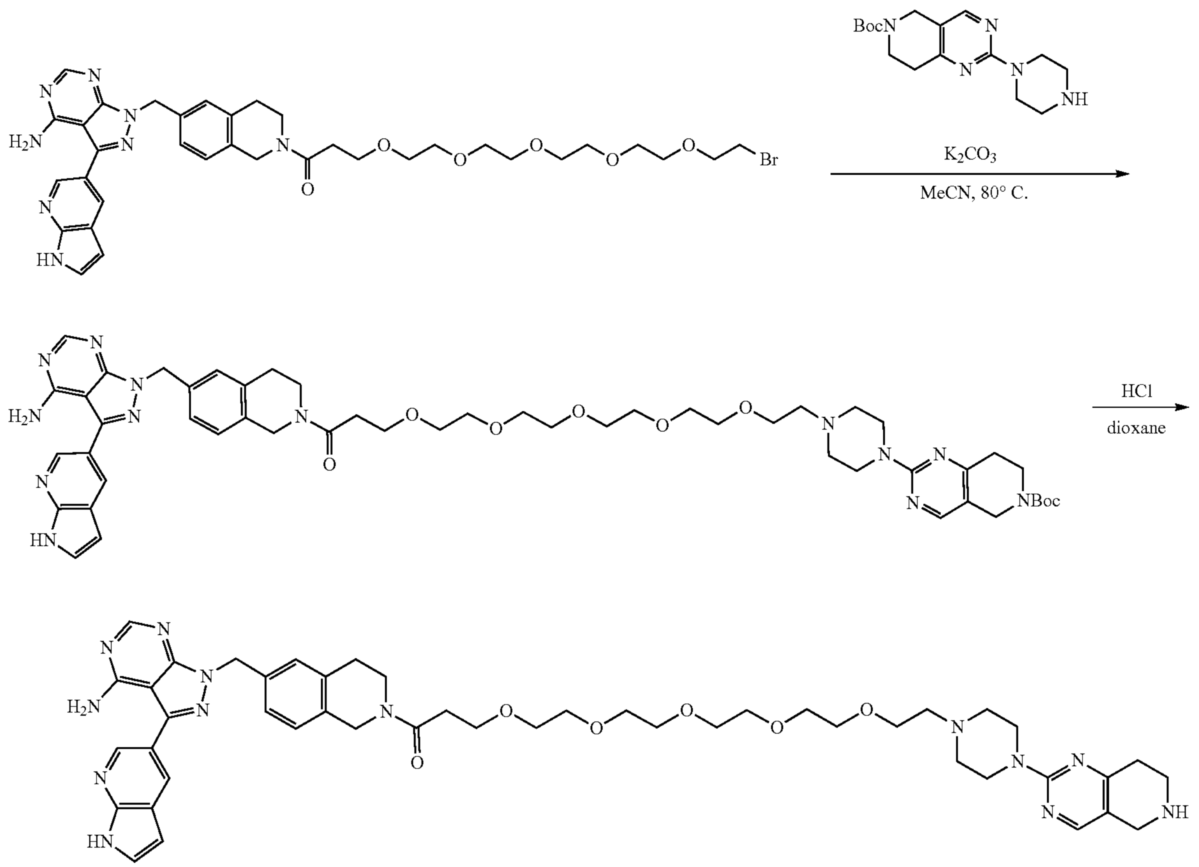

Step 1: Synthesis of tert-butyl 2-[4-(18-{6-[(4-amino-3-{1H-pyrrolo[2,3-b]pyridin-5-yl}-1H-pyrazolo[3,4-d]pyrimidin-1-yl)methyl]-1,2,3,4-tetrahydroisoquinolin-2-yl}-18-oxo-3,6,9,12,15-pentaoxaoctadecan-1-yl)piperazin-1-yl]-5H,6H,7H,8H-pyrido[4,3-d]pyrimidine-6-carboxylate To a suspension of 18-{6-[(4-amino-3-{1H-pyrrolo[2,3-b]pyridin-5-yl}-1H-pyrazolo[3,4-d]pyrimidin-1-yl)methyl]-1,2,3,4-tetrahydroisoquinolin-2-yl}-1-bromo-3,6,9,12,15-pentaoxaoctadecan-18-one (82.7 mg, 110 μmol, 1.0 equiv) in MeCN (1.09 mL) was added $K_2CO_3$ (45.6 mg, 330 μmol, 3.0 equiv) followed by tert-butyl 2-(piperazin-1-yl)-5H,6H,7H,8H-pyrido[4,3-d]pyrimidine-6-carboxylate (42.1 mg, 132 μmol, 1.2 equiv). The resulting suspension was heated to 80° C. for 8 h, then purified by silica gel chromatography (0→20% MeOH/DCM) to afford the product (75.1 mg, 70% yield). LCMS (ESI) m/z: [M+H] calcd for $C_{51}H_{67}N_{13}O_8$: 990.53; found 990.5.

Step 2: Synthesis of 18-{6-[(4-amino-3-{1H-pyrrolo[2,3-b]pyridin-5-yl}-1H-pyrazolo[3,4-d]pyrimidin-1-yl)methyl]-1,2,3,4-tetrahydroisoquinolin-2-yl}-1-(4-{5H,6H,7H,8H-pyrido[4,3-d]pyrimidin-2-yl}piperazin-1-yl)-3,6,9,12,15-pentaoxaoctadecan-18-one To a solution of tert-butyl 2-[4-(18-{6-[(4-amino-3-{1H-pyrrolo[2,3-b]pyridin-5-yl}-1H-pyrazolo[3,4-d]pyrimidin-1-yl)methyl]-1,2,3,4-tetrahydroisoquinolin-2-yl}-18-oxo-3,6,9,12,15-pentaoxaoctadecan-1-yl)piperazin-1-yl]-5H,6H,7H,8H-pyrido[4,3-d]pyrimidine-6-carboxylate (75.1 mg, 75.8 μmol, 1.0 equiv) in dioxane (1 mL) was added HCl (4 M in dioxane, 472 μL, 1.89 mmol, 10.0 equiv). The solution was stirred at room temperature for 45 min, then concentrated under reduced pressure to afford the product. LCMS (ESI) m/z: [M+Na] calcd for $C_{46}H_{59}N_{13}O_6$: 912.46; found 912.5.

Following General Procedure 6, but using the appropriate PEG carboxylic acid and amine containing active site inhibitors in Table 2, the Intermediates B2 in Table 11 were prepared:

TABLE 11

| Additional amines prepared | | | |
|---|---|---|---|
| Structure | Molecular Formula | Calculated MW | Observed MW |
| 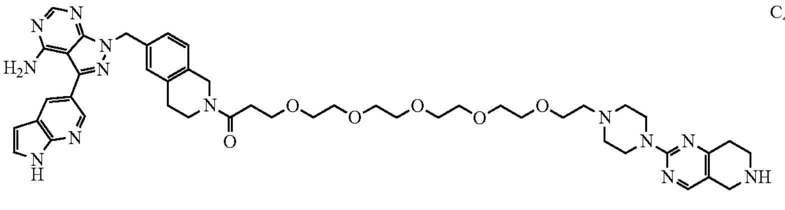 Intermediate B2-4 | $C_{46}H_{59}N_{13}O_6$ | [M + H] = 890.48 | [M + H] = 890.5 |

Following General Procedure 1, but using the appropriate carboxylic acid PEG tert-butyl ester and amine containing active site inhibitors in Table 2, the Intermediates B4 in Table 12 were prepared:

TABLE 12

| Additional amines prepared | | | |
|---|---|---|---|
| Structure | Molecular Formula | Calculated MW | Observed MW |
| 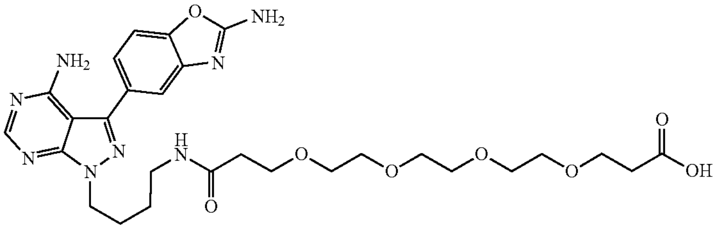 [SMILES: Nc1nc2cc(-c3nn(CCCCNC(=O)CCOCCOCCOCCOCCC(=O)O)c4ncnc(N)c34)ccc2o1] Intermediate B4-1 | $C_{28}H_{38}N_8O_8$ | [M + H] = 615.29 | [M + H] = 615.1 |

Following General Procedure 1, but using the appropriate Intermediates B4 in Table 12 and amine containing pre-linkers in Table 4, the Intermediates B2 in Table 13 were

TABLE 13

| Additional amines prepared | | | |
|---|---|---|---|
| Structure | Molecular Formula | Calculated MW | Observed MW |
| 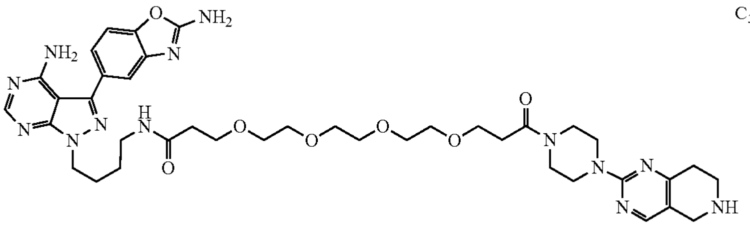 Intermediate B2-5 | $C_{39}H_{53}N_{13}O_7$ | [M + H] = 816.43 | [M + H] = 816.4 |

Following General Procedure 1, but using the appropriate Intermediates A1 and amine containing pre-linkers in Table 4, the Intermediates B2 in Table 14 were prepared:

TABLE 14

| Additional amines prepared | | | |
|---|---|---|---|
| Structure | Molecular Formula | Calculated MW | Observed MW |
| 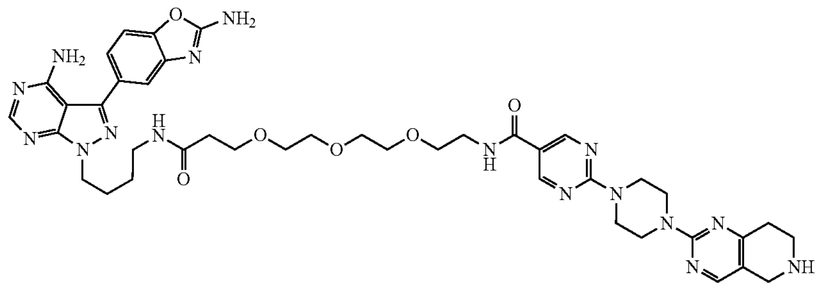 [SMILES: Nc1nc2cc(-c3nn(CCCCNC(=O)CCOCCOCCOCCNC(=O)c4cnc(N5CCN(c6ncc7c(n6)CCNC7)CC5)nc4)c4ncnc(N)c34)ccc2o1] Intermediate B2-6 | $C_{41}H_{52}N_{16}O_6$ | [M + H] = 865.44 | [M + H] = 865.2 |
| 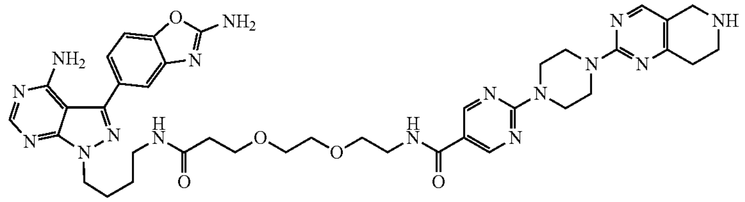 [SMILES: Nc1nc2cc(-c3nn(CCCCNC(=O)CCOCCOCCNC(=O)c4cnc(N5CCN(c6ncc7c(n6)CCNC7)CC5)nc4)c4ncnc(N)c34)ccc2o1] Intermediate B2-7 | $C_{39}H_{48}N_{16}O_5$ | [M + H] = 821.41 | [M + H] = 821.2 |
| 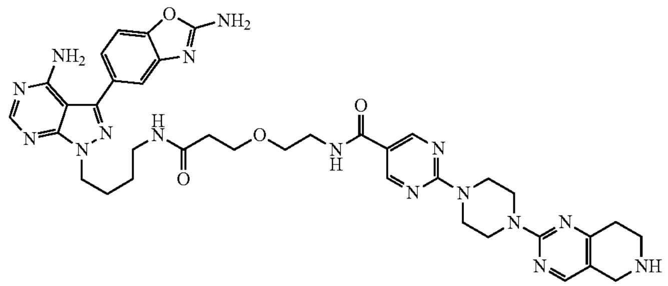 [SMILES: Nc1nc2cc(-c3nn(CCCCNC(=O)CCOCCNC(=O)c4cnc(N5CCN(c6ncc7c(n6)CCNC7)CC5)nc4)c4ncnc(N)c34)ccc2o1] Intermediate B2-8 | $C_{37}H_{44}N_{16}O_4$ | [M + H] = 777.38 | [M + H] = 777.3 |
| 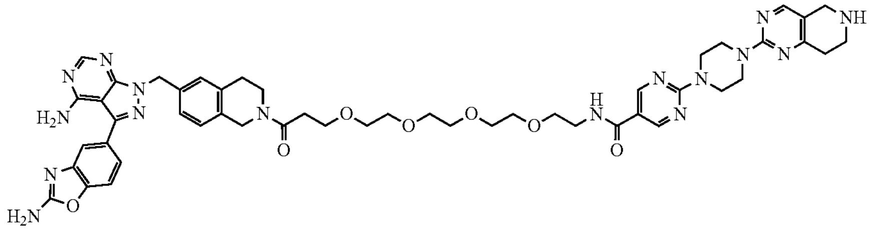 [SMILES: Nc1nc2cc(-c3nn(Cc4ccc5c(c4)CCN(C(=O)CCOCCOCCOCCOCCNC(=O)c4cnc(N6CCN(c7ncc8c(n7)CCNC8)CC6)nc4)C5)c4ncnc(N)c34)ccc2o1] Intermediate B2-9 | $C_{49}H_{58}N_{16}O_7$ | [M + H] = 983.48 | [M + H] = 983.4 |
| 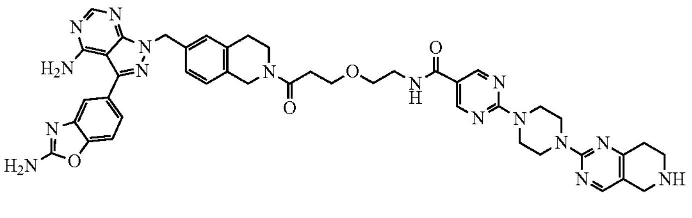 [SMILES: Nc1nc2cc(-c3nn(Cc4ccc5c(c4)CCN(C(=O)CCOCCNC(=O)c4cnc(N6CCN(c7ncc8c(n7)CCNC8)CC6)nc4)C5)c4ncnc(N)c34)ccc2o1] Intermediate B2-10 | $C_{43}H_{46}N_{16}O_4$ | [M + H] = 851.40 | [M + H] = 851.4 |

TABLE 14-continued
Additional amines prepared
| Structure | Molecular Formula | Calculated MW | Observed MW |
|---|---|---|---|
| 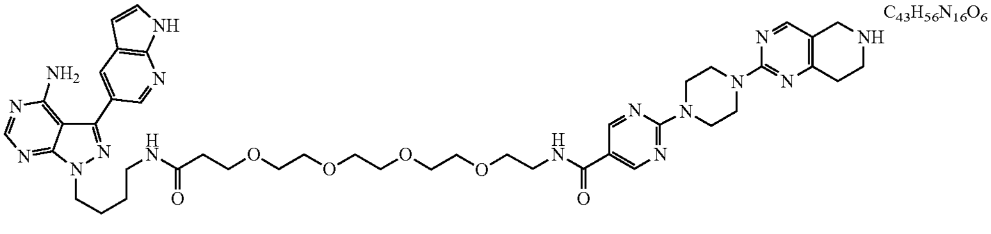 Intermediate B2-11 | $C_{43}H_{56}N_{16}O_6$ | [M + H] = 893.47 | [M + H] = 893.3 |
| 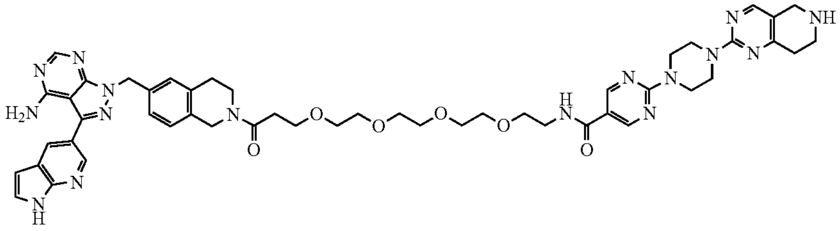 [SMILES: Nc1ncnc2c1c(-c1cnc3[nH]ccc3c1)nn2Cc1ccc2c(c1)CCN(C(=O)CCOCCOCCOCCOCCNC(=O)c1cnc(N3CCN(c4ncc5c(n4)CCNC5)CC3)nc1)C2] Intermediate B2-12 | $C_{49}H_{58}N_{16}O_6$ | [M + Na] = 989.46 | [M + Na] = 989.4 |
| 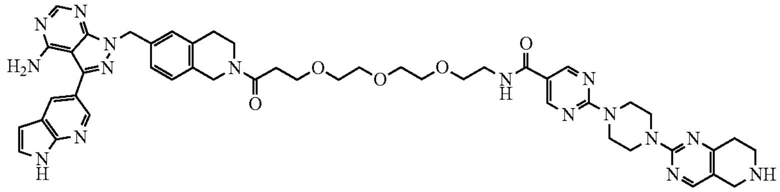 [SMILES: Nc1ncnc2c1c(-c1cnc3[nH]ccc3c1)nn2Cc1ccc2c(c1)CCN(C(=O)CCOCCOCCOCCNC(=O)c1cnc(N3CCN(c4ncc5c(n4)CCNC5)CC3)nc1)C2] Intermediate B2-13 | $C_{47}H_{54}N_{16}O_5$ | [M + H] = 923.46 | [M + H] = 923.4 |
| 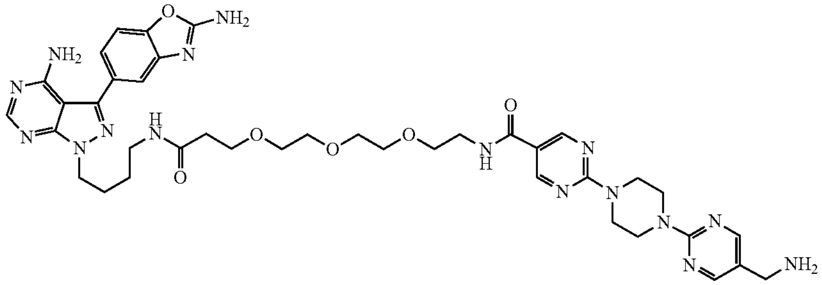 [SMILES: NCc1cnc(N2CCN(c3ncc(C(=O)NCCOCCOCCOCCC(=O)NCCCCn4nc(-c5ccc6oc(N)nc6c5)c5c(N)ncnc54)cn3)CC2)nc1] Intermediate B2-14 | $C_{39}H_{50}N_{16}O_6$ | [M + H] = 839.42 | [M + H] = 893.3 |
| 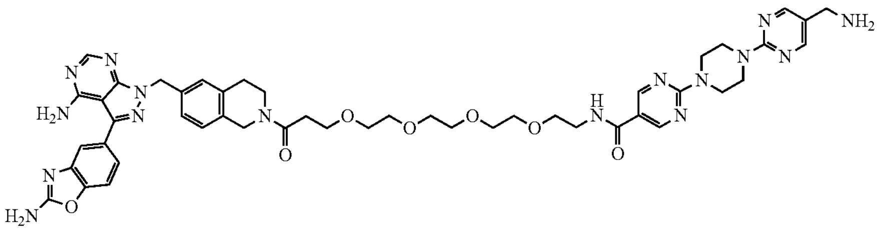 [SMILES: NCc1cnc(N2CCN(c3ncc(C(=O)NCCOCCOCCOCCOCCC(=O)N4CCc5cc(Cn6nc(-c7ccc8oc(N)nc8c7)c7c(N)ncnc76)ccc5C4)cn3)CC2)nc1] Intermediate B2-15 | $C_{47}H_{56}N_{16}O_7$ | [M + H] = 957.46 | [M + H] = 957.7 |

TABLE 14-continued
| Additional amines prepared | | | |
|---|---|---|---|
| Structure | Molecular Formula | Calculated MW | Observed MW |
| 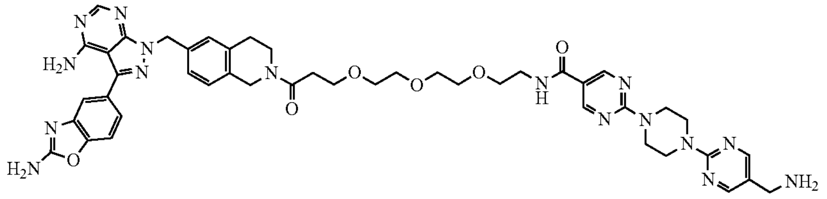 [SMILES: NCc1cnc(N2CCN(c3ncc(C(=O)NCCOCCOCCOCCC(=O)N4CCc5cc(Cn6nc(-c7ccc8oc(N)nc8c7)c7c(N)ncnc76)ccc5C4)cn3)CC2)nc1]<br>Intermediate B2-16 | $C_{45}H_{52}N_{16}O_6$ | [M + Na] = 935.42 | [M + Na] = 935.3 |
| 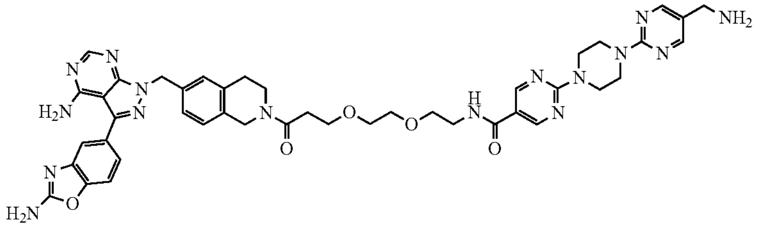 [SMILES: NCc1cnc(N2CCN(c3ncc(C(=O)NCCOCCOCCC(=O)N4CCc5cc(Cn6nc(-c7ccc8oc(N)nc8c7)c7c(N)ncnc76)ccc5C4)cn3)CC2)nc1]<br>Intermediate B2-17 | $C_{43}H_{48}N_{16}O_5$ | [M + Na] = 891.39 | [M + Na] = 891.4 |
| 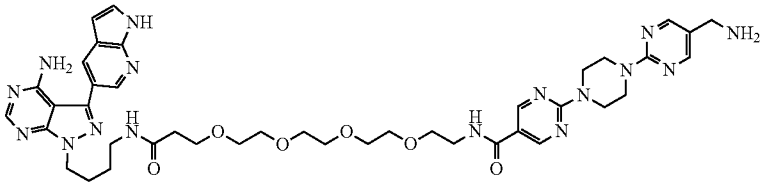 [SMILES: NCc1cnc(N2CCN(c3ncc(C(=O)NCCOCCOCCOCCOCCC(=O)NCCCCn4nc(-c5cnc6[nH]ccc6c5)c5c(N)ncnc54)cn3)CC2)nc1]<br>Intermediate B2-18 | $C_{41}H_{54}N_{16}O_6$ | [M + H] = 867.45 | [M + H] = 867.3 |
| 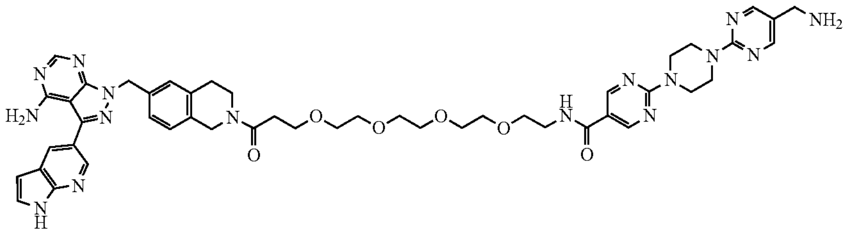 [SMILES: NCc1cnc(N2CCN(c3ncc(C(=O)NCCOCCOCCOCCOCCC(=O)N4CCc5cc(Cn6nc(-c7cnc8[nH]ccc8c7)c7c(N)ncnc76)ccc5C4)cn3)CC2)nc1]<br>Intermediate B2-19 | $C_{47}H_{56}N_{16}O_6$ | [M + H] = 941.47 | [M + H] = 941.2 |
| 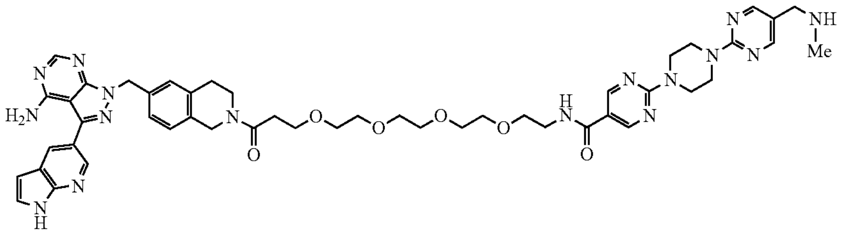 [SMILES: CNCc1cnc(N2CCN(c3ncc(C(=O)NCCOCCOCCOCCOCCC(=O)N4CCc5cc(Cn6nc(-c7cnc8[nH]ccc8c7)c7c(N)ncnc76)ccc5C4)cn3)CC2)nc1]<br>Intermediate B2-20 | $C_{48}H_{58}N_{16}O_6$ | [M + H] = 955.48 | [M + H] = 955.2 |

TABLE 14-continued
| Additional amines prepared | | | |
|---|---|---|---|
| Structure | Molecular Formula | Calculated MW | Observed MW |
| 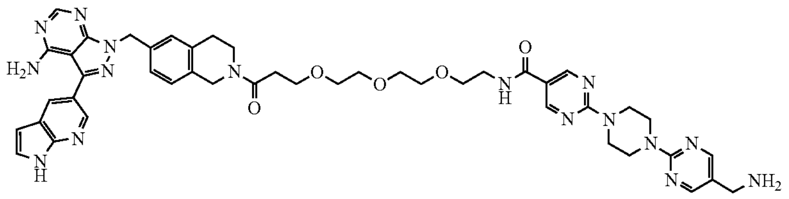 [SMILES: NCc1cnc(N2CCN(c3ncc(C(=O)NCCOCCOCCOCCC(=O)N4CCc5cc(Cn6nc(-c7cnc8[nH]ccc8c7)c7c(N)ncnc76)ccc5C4)cn3)CC2)nc1] Intermediate B2-21 | $C_{45}H_{52}N_{16}O_5$ | [M + H] = 897.44 | [M + H] = 897.3 |
| 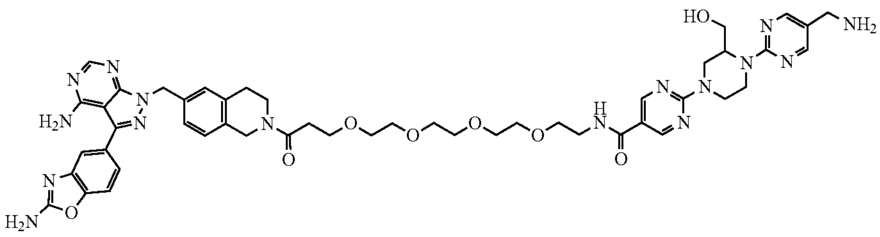 [SMILES: NCc1cnc(N2CCN(c3ncc(C(=O)NCCOCCOCCOCCOCCC(=O)N4CCc5cc(Cn6nc(-c7ccc8oc(N)nc8c7)c7c(N)ncnc76)ccc5C4)cn3)CC2CO)nc1] Intermediate B2-22 | $C_{48}H_{58}N_{16}O_8$ | [M + H] = 987.47 | [M + H] = 987.42 |
| 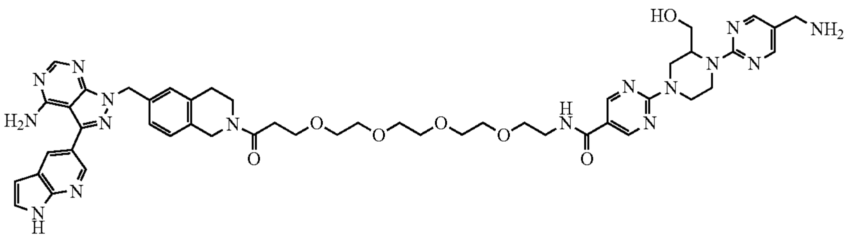 [SMILES: NCc1cnc(N2CCN(c3ncc(C(=O)NCCOCCOCCOCCOCCC(=O)N4CCc5cc(Cn6nc(-c7cnc8[nH]ccc8c7)c7c(N)ncnc76)ccc5C4)cn3)CC2CO)nc1] Intermediate B2-23 | $C_{48}H_{58}N_{16}O_7$ | [M + H] = 971.48 | [M + H] = 971.31 |
| 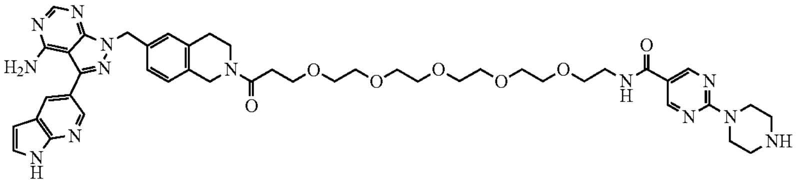 [SMILES: Nc1ncnc2c1c(-c1cnc3[nH]ccc3c1)nn2Cc1ccc2c(c1)CCN(C(=O)CCOCCOCCOCCOCCOCCNC(=O)c1cnc(N3CCNCC3)nc1)C2] Intermediate B2-24 | $C_{44}H_{55}N_{13}O_7$ | [M + H] = 878.44 | [M + H] = 878.5 |
| 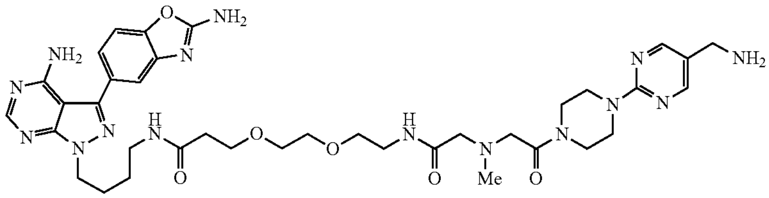 [SMILES: CN(CC(=O)NCCOCCOCCC(=O)NCCCCn1nc(-c2ccc3oc(N)nc3c2)c2c(N)ncnc21)CC(=O)N1CCN(c2ncc(CN)cn2)CC1] Intermediate B2-25 | $C_{37}H_{51}N_{15}O_6$ | [M + H] = 802.42 | [M + H] = 802.4 |

TABLE 14-continued
Additional amines prepared
| Structure | Molecular Formula | Calculated MW | Observed MW |
|---|---|---|---|
| 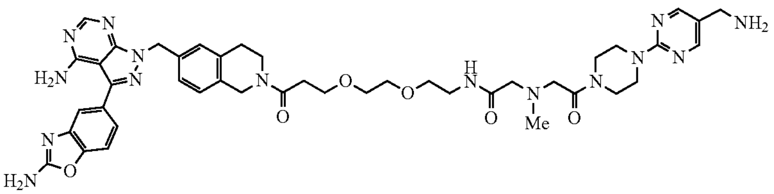 [SMILES: CN(CC(=O)NCCOCCOCCC(=O)N1CCc2cc(Cn3nc(-c4ccc5oc(N)nc5c4)c4c(N)ncnc43)ccc2C1)CC(=O)N1CCN(c2ncc(CN)cn2)CC1] Intermediate B2-26 | $C_{43}H_{53}N_{15}O_6$ | [M + H] = 876.44 | [M + H] = 876.4 |
| 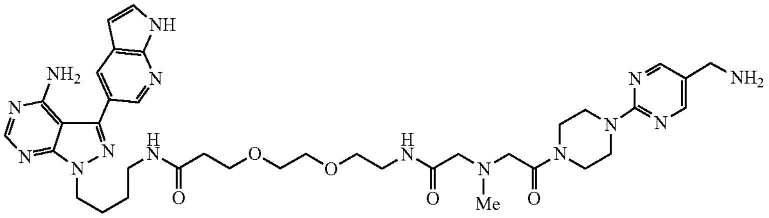 [SMILES: CN(CC(=O)NCCOCCOCCC(=O)NCCCCn1nc(-c2cnc3[nH]ccc3c2)c2c(N)ncnc21)CC(=O)N1CCN(c2ncc(CN)cn2)CC1] Intermediate B2-27 | $C_{37}H_{51}N_{15}O_5$ | [M + H] = 786.43 | [M + H] = 786.5 |
| 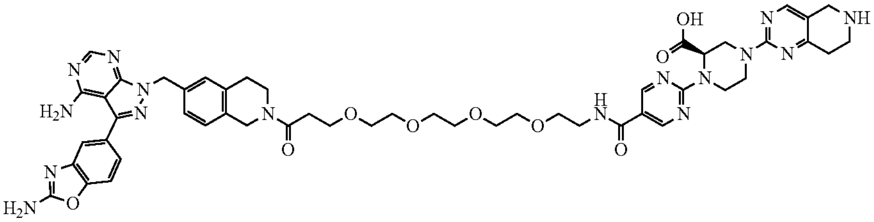 [SMILES: Nc1nc2cc(-c3nn(Cc4ccc5c(c4)CCN(C(=O)CCOCCOCCOCCOCCNC(=O)c4cnc(N6CCN(c7ncc8c(n7)CCNC8)C[C@@H]6C(=O)O)nc4)C5)c4ncnc(N)c34)ccc2o1] Intermediate B2-28 | $C_{50}H_{58}N_{16}O_9$ | [M + H] = 1027.47 | [M + H] = 1027.1 |
| 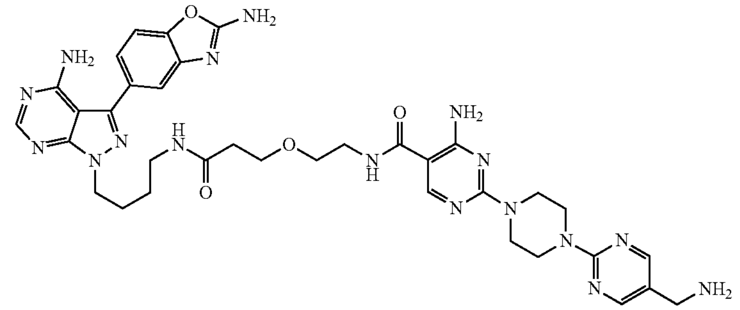 [SMILES: NCc1cnc(N2CCN(c3ncc(C(=O)NCCOCCC(=O)NCCCCn4nc(-c5ccc6oc(N)nc6c5)c5c(N)ncnc54)c(N)n3)CC2)nc1] Intermediate B2-29 | $C_{35}H_{43}N_{17}O_4$ | [M + H] = 766.38 | [M + H] = 766.3 |
| 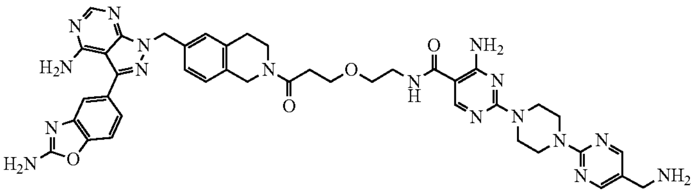 [SMILES: NCc1cnc(N2CCN(c3ncc(C(=O)NCCOCCC(=O)N4CCc5cc(Cn6nc(-c7ccc8oc(N)nc8c7)c7c(N)ncnc76)ccc5C4)c(N)n3)CC2)nc1] Intermediate B2-30 | $C_{41}H_{45}N_{17}O_4$ | [M + H] = 840.39 | [M + H] = 840.4 |

TABLE 14-continued
| Structure | Molecular Formula | Calculated MW | Observed MW |
|---|---|---|---|
| Additional amines prepared | | | |
| 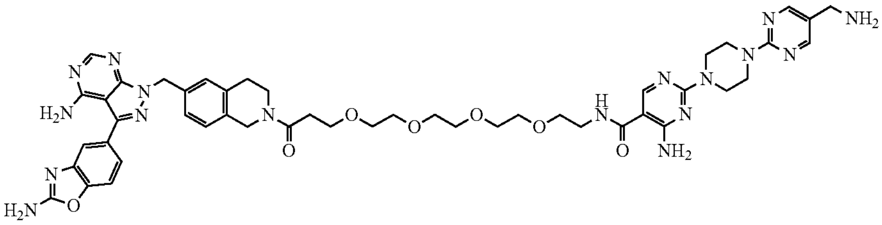 [SMILES: NCc1cnc(N2CCN(c3ncc(C(=O)NCCOCCOCCOCCOCCC(=O)N4CCc5cc(Cn6nc(-c7ccc8oc(N)nc8c7)c7c(N)ncnc76)ccc5C4)c(N)n3)CC2)nc1] Intermediate B2-31 | $C_{47}H_{57}N_{17}O_7$ | [M + H] = 972.47 | [M + H] = 972.5 |
| 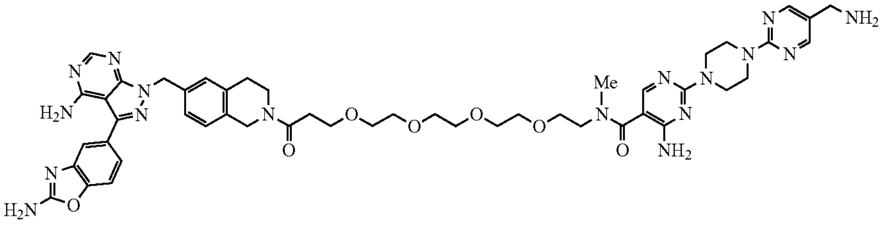 [SMILES: CN(CCOCCOCCOCCOCCC(=O)N1CCc2cc(Cn3nc(-c4ccc5oc(N)nc5c4)c4c(N)ncnc43)ccc2C1)C(=O)c1cnc(N2CCN(c3ncc(CN)cn3)CC2)nc1N] Intermediate B2-32 | $C_{48}H_{59}N_{17}O_7$ | [M + H] = 986.49 | [M + H] = 986.4 |
| 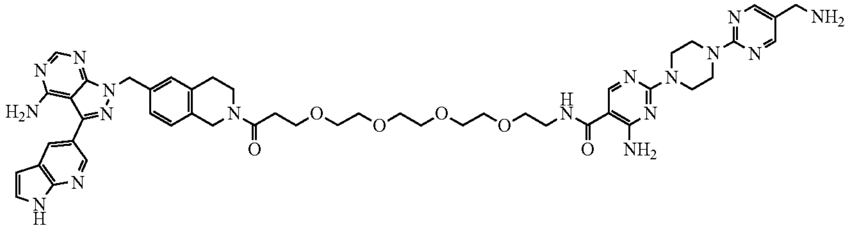 [SMILES: NCc1cnc(N2CCN(c3ncc(C(=O)NCCOCCOCCOCCOCCC(=O)N4CCc5cc(Cn6nc(-c7cnc8[nH]ccc8c7)c7c(N)ncnc76)ccc5C4)c(N)n3)CC2)nc1] Intermediate B2-33 | $C_{47}H_{57}N_{17}O_6$ | [M + H] = 956.48 | [M + H] = 956.3 |
| 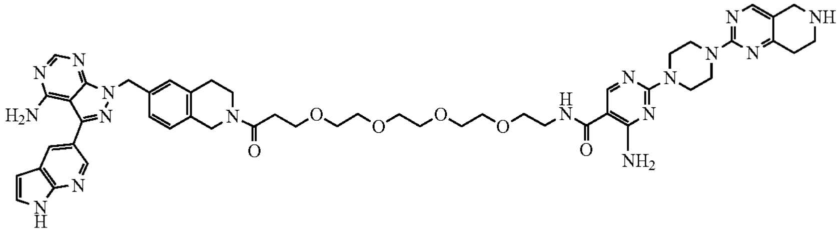 [SMILES: Nc1nc(N2CCN(c3ncc4c(n3)CCNC4)CC2)ncc1C(=O)NCCOCCOCCOCCOCCC(=O)N1CCc2cc(Cn3nc(-c4cnc5[nH]ccc5c4)c4c(N)ncnc43)ccc2C1] Intermediate B2-34 | $C_{49}H_{59}N_{17}O_6$ | [M + H] = 982.49 | [M + H] = 982.2 |
| 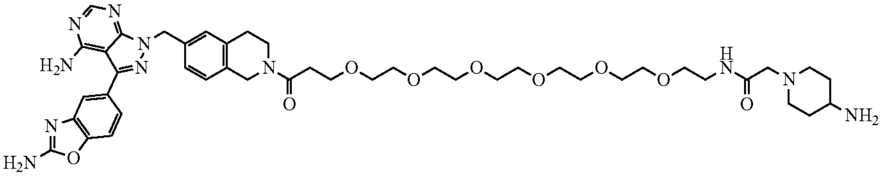 [SMILES: Nc1nc2cc(-c3nn(Cc4ccc5c(c4)CCN(C(=O)CCOCCOCCOCCOCCOCCOCCNC(=O)CN4CCC(N)CC4)C5)c4ncnc(N)c34)ccc2o1] Intermediate B2-35 | $C_{44}H_{61}N_{11}O_9$ | [M + H] = 888.48 | [M + H] = 888.3 |

TABLE 14-continued
| Additional amines prepared | | | |
|---|---|---|---|
| Structure | Molecular Formula | Calculated MW | Observed MW |
| 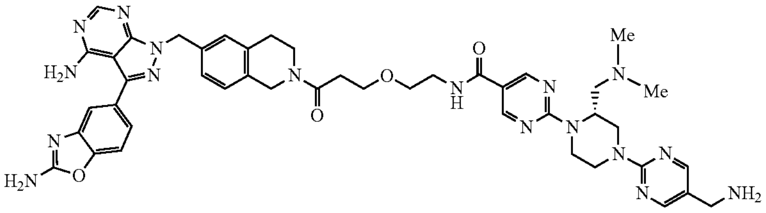 [SMILES: CN(C)C[C@@H]1CN(c2ncc(CN)cn2)CCN1c1ncc(C(=O)NCCOCCC(=O)N2CCc3cc(Cn4nc(-c5ccc6oc(N)nc6c5)c5c(N)ncnc54)ccc3C2)cn1] Intermediate B2-36 | $C_{44}H_{51}N_{17}O_4$ | [M + H] = 882.44 | [M + H] = 882.4 |
| 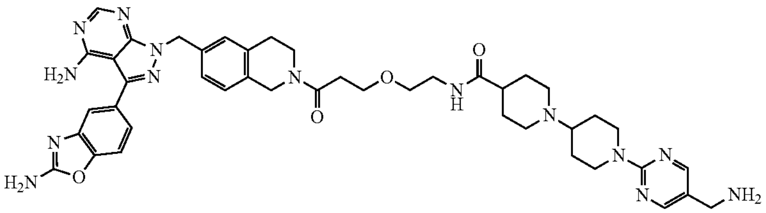 [SMILES: NCc1cnc(N2CCC(N3CCC(C(=O)NCCOCCC(=O)N4CCc5cc(Cn6nc(-c7ccc8oc(N)nc8c7)c7c(N)ncnc76)ccc5C4)CC3)CC2)nc1] Intermediate B2-37 | $C_{43}H_{52}N_{14}O_4$ | [M + H] = 829.44 | [M + H] = 829.3 |
| 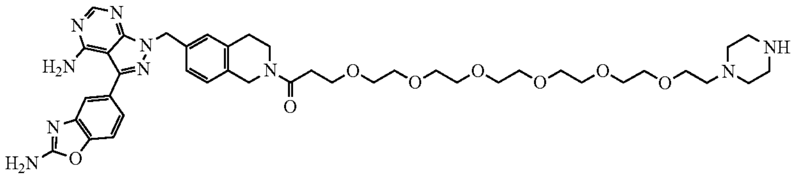 [SMILES: Nc1nc2cc(-c3nn(Cc4ccc5c(c4)CCN(C(=O)CCOCCOCCOCCOCCOCCOCCN4CCNCC4)C5)c4ncnc(N)c34)ccc2o1] Intermediate B2-38 | $C_{41}H_{56}N_{10}O_8$ | [M + H] = 817.44 | [M + H] = 817.2 |
| 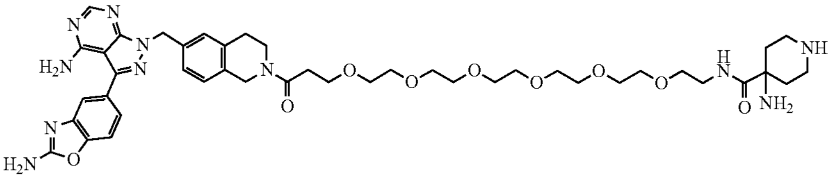 [SMILES: Nc1nc2cc(-c3nn(Cc4ccc5c(c4)CCN(C(=O)CCOCCOCCOCCOCCOCCOCCNC(=O)C4(N)CCNCC4)C5)c4ncnc(N)c34)ccc2o1] Intermediate B2-39 | $C_{43}H_{59}N_{11}O_9$ | [M + H] = 874.46 | [M + H] = 874.3 |

Following General Procedure 2, but using the appropriate 4-nitrophenyl carbonate containing rapamycin monomer in Table 1 and Intermediates B2 from Tables 9, 11, and 13 and 14, the Series 2 bivalent analogs in Table 15 were synthesized:
TABLE 15
Series 2 Bivalent Compounds:
| Structure | Molecular Formula | Calculated MW | Observed MW |
|---|---|---|---|
| 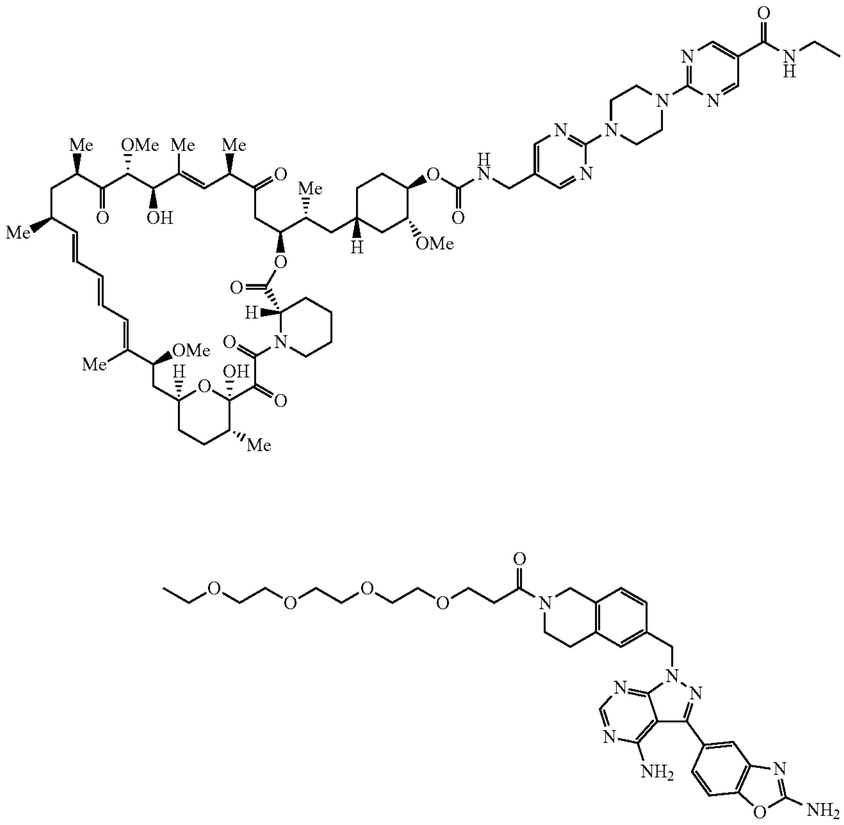<br>Example 27 | $C_{99}H_{1333}N_{17}O_{21}$ | [M + H] = 1896.99 | [M + H] = 1896.7 |
| 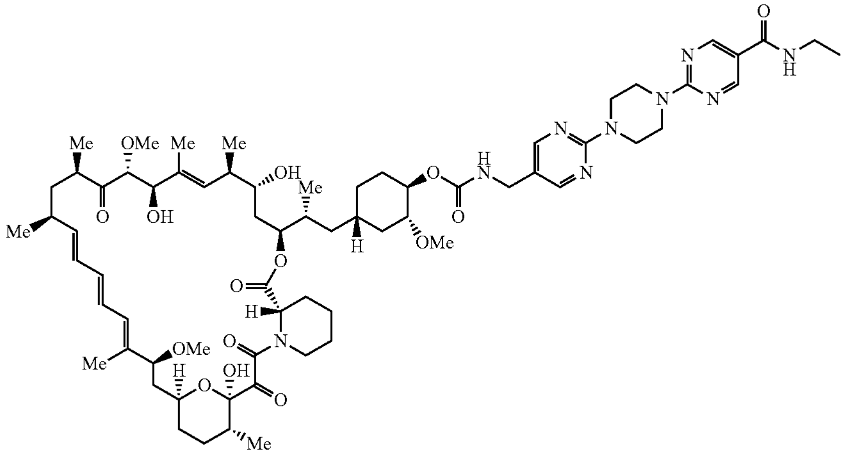 | $C_{99}H_{135}N_{17}O_{21}$ | [M + H] = 1899.01 | [M + H] = 1899.1 |

TABLE 15-continued
Series 2 Bivalent Compounds:
| Structure | Molecular Formula | Calculated MW | Observed MW |
|---|---|---|---|
| 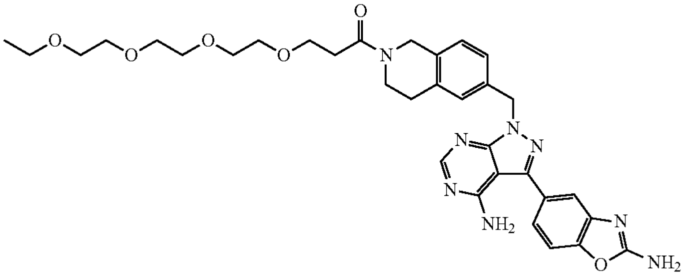 | | | |
| Example 28 | | | |
| 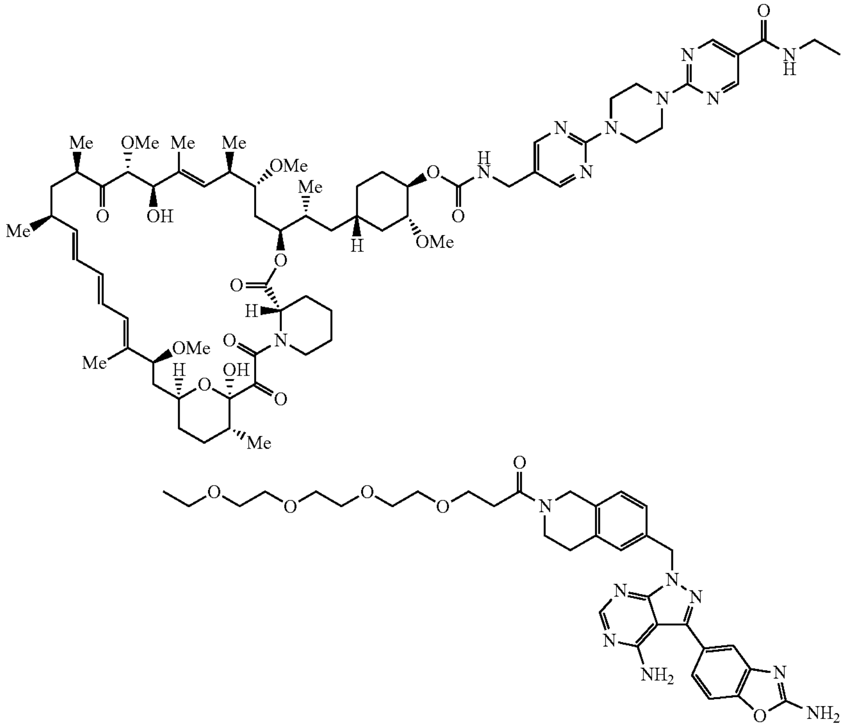 | $C_{100}H_{137}N_{17}O_{21}$ | [M + H] = 1913.03 | [M + H] = 1913.0 |
| Example 29 | | | |
| 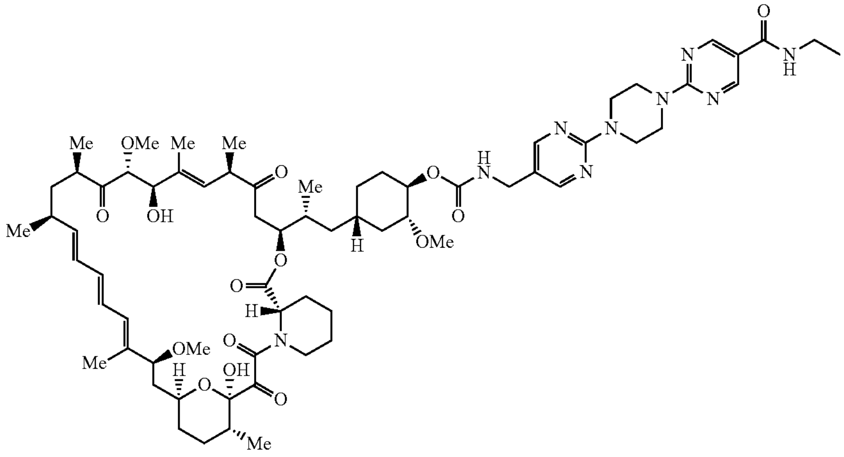 | $C_{97}H_{129}N_{17}O_{20}$ | [M + H] = 1852.97 | [M + H] = 1852.9 |

TABLE 15-continued
| Series 2 Bivalent Compounds: | | | |
|---|---|---|---|
| Structure | Molecular Formula | Calculated MW | Observed MW |
| 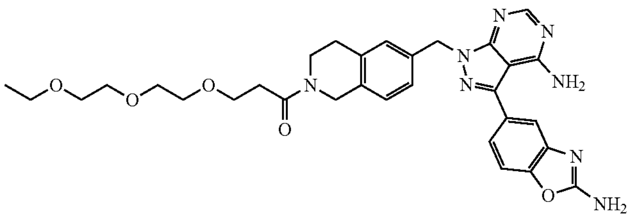 | | | |
| Example 30 | | | |
| 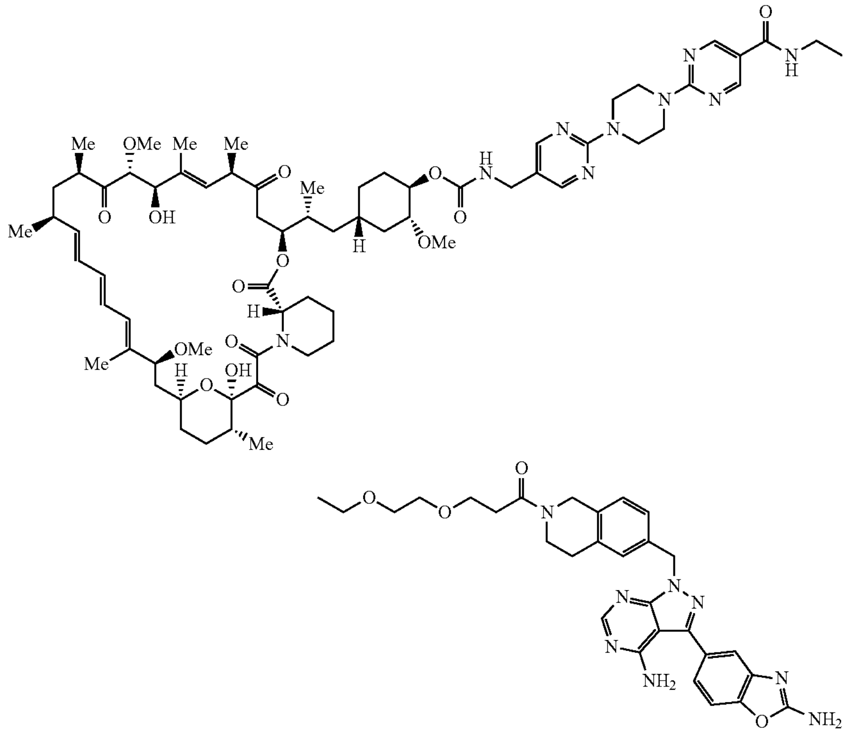 | $C_{95}H_{125}N_{17}O_{19}$ | [M + H] = 1808.94 | [M + H] = 1809.0 |
| Example 31 | | | |
| 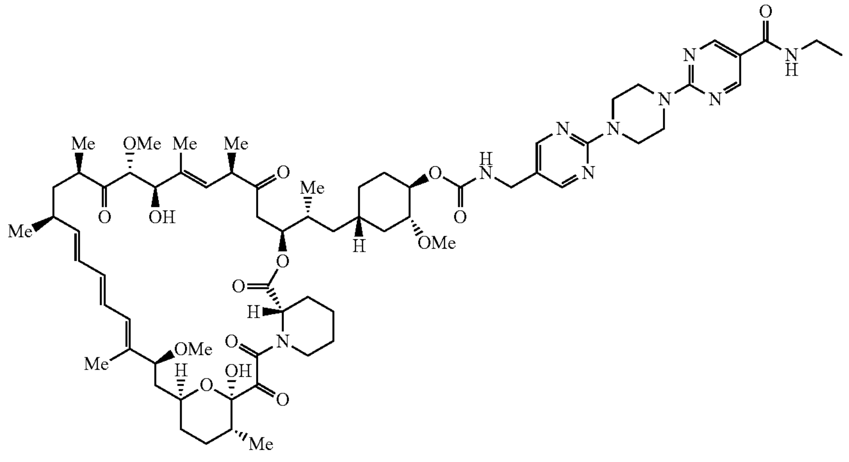 | $C_{93}H_{131}N_{17}O_{20}$ | [M + H] = 1806.98 | [M + H] = 1806.7 |

TABLE 15-continued
| Series 2 Bivalent Compounds: | | | |
|---|---|---|---|
| Structure | Molecular Formula | Calculated MW | Observed MW |
| 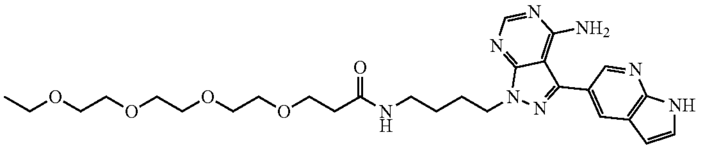<br>Example 32 | | | |
| 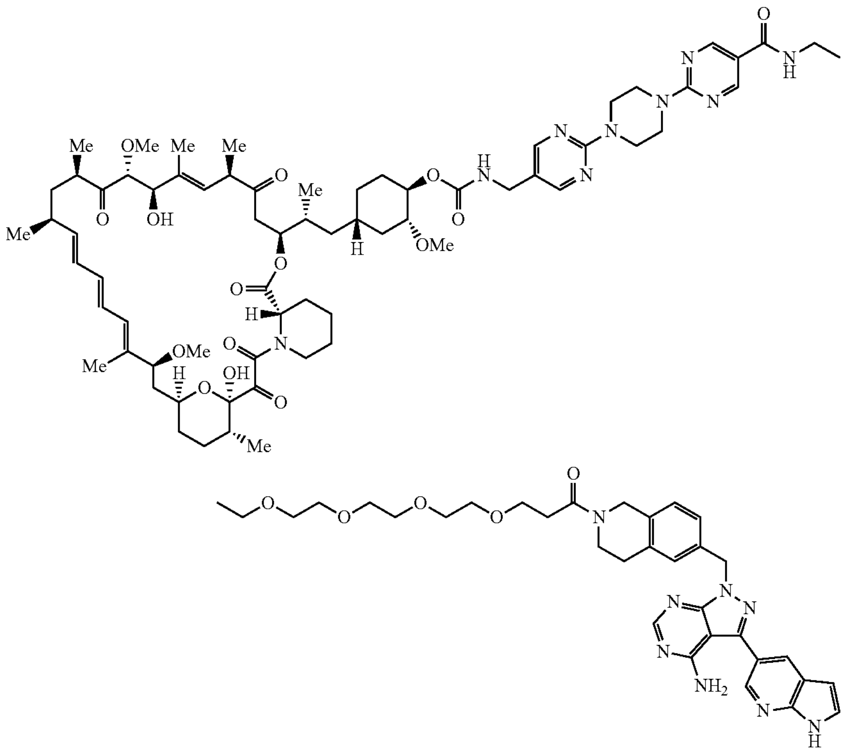<br>Example 33 | $C_{99}H_{133}N_{17}O_{20}$ | [M + H] = 1881.00 | [M + H] = 1881.0 |
| 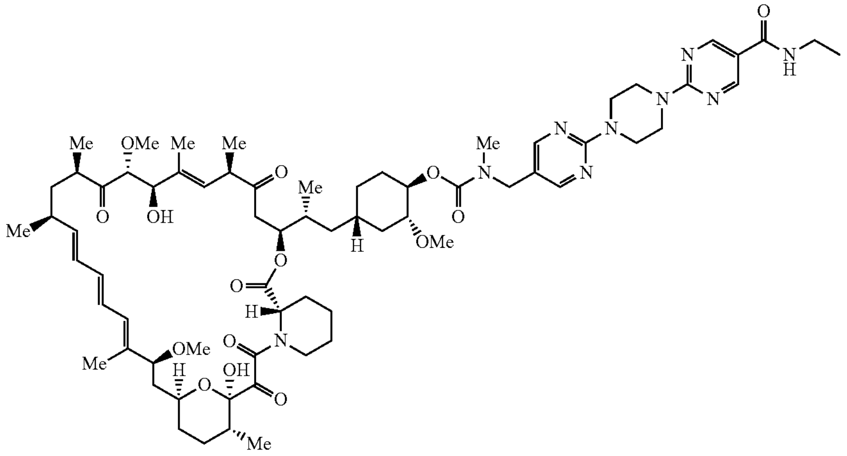 | $C_{100}H_{135}N_{17}O_{20}$ | [M + H] = 1895.01 | [M + H] = 1895.1 |

TABLE 15-continued
| Series 2 Bivalent Compounds: | | | |
|---|---|---|---|
| Structure | Molecular Formula | Calculated MW | Observed MW |
| 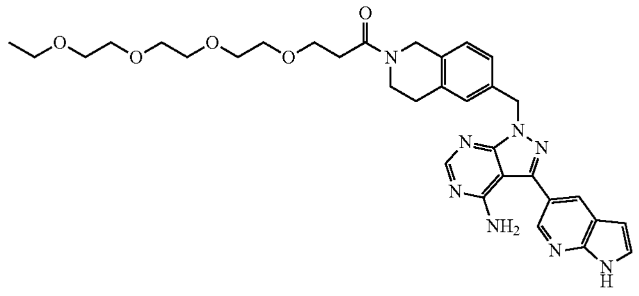 | | | |
| Example 34 | | | |
| 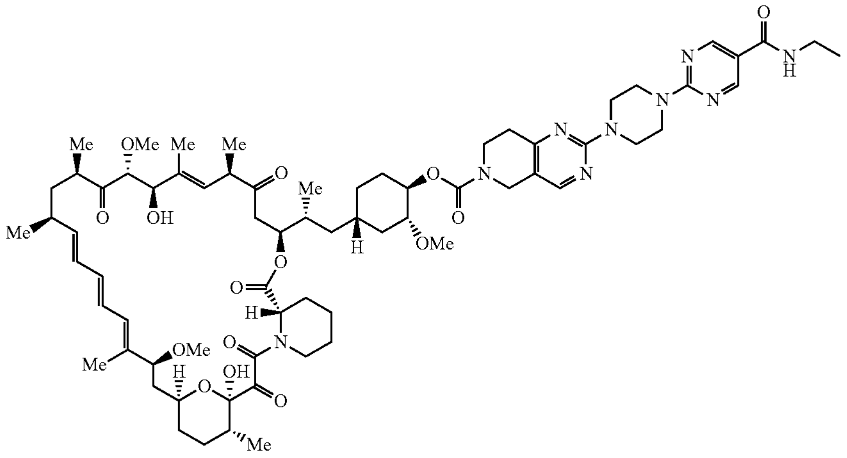 | $C_{95}H_{133}N_{17}O_{20}$ | [M + H] = 1833.00 | [M + H] = 1832.9 |
| 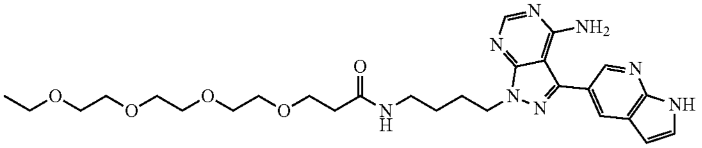 | | | |
| Example 35 | | | |
| 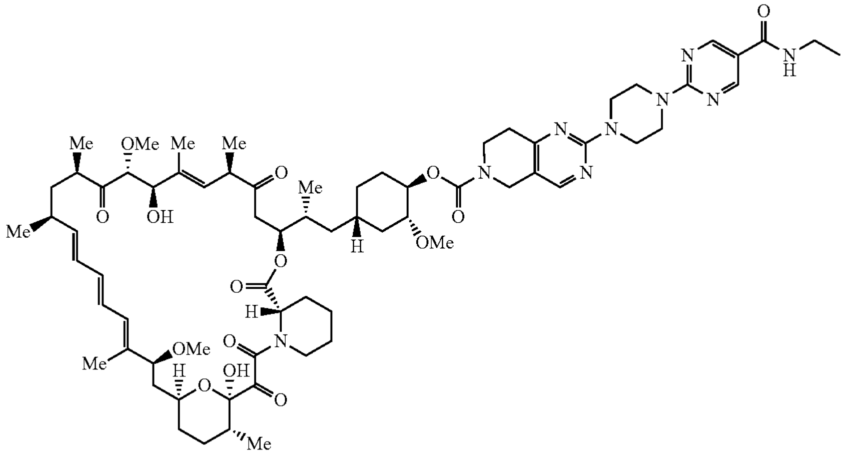 | $C_{101}H_{135}N_{17}O_{20}$ | [M + H] = 1907.01 | [M + H] = 1907.0 |

TABLE 15-continued
Series 2 Bivalent Compounds:
| Structure | Molecular Formula | Calculated MW | Observed MW |
|---|---|---|---|
| 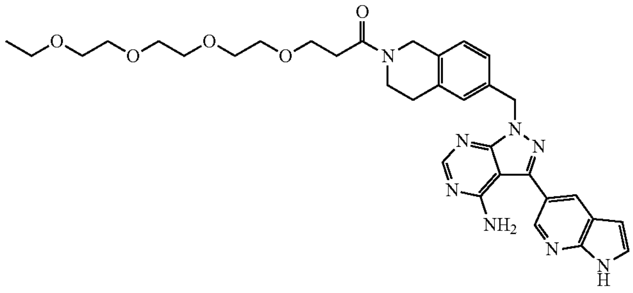 | | | |
| Example 36 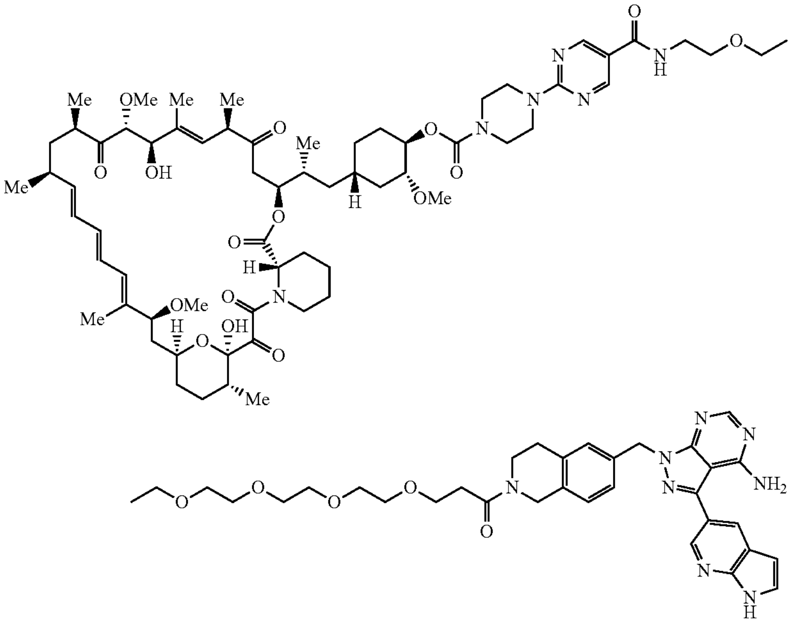 | $C_{96}H_{132}N_{14}O_{21}$ | [M + H] = 1817.98 | [M + H] = 1817.9 |
| Example 37 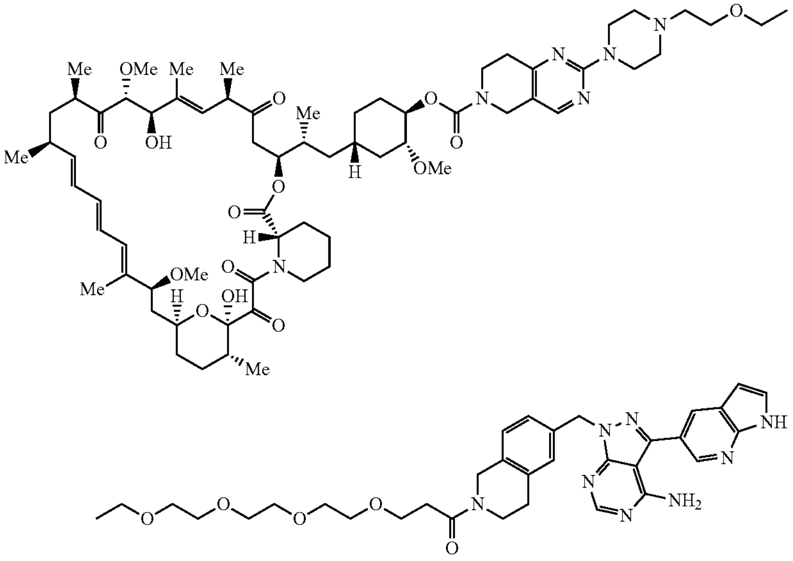 | $C_{98}H_{136}N_{14}O_{20}$ | [M + H] = 1830.01 | [M + H] = 1830.1 |

TABLE 15-continued
| Structure | Molecular Formula | Calculated MW | Observed MW |
|---|---|---|---|
| Series 2 Bivalent Compounds: | | | |
| Example 38<br>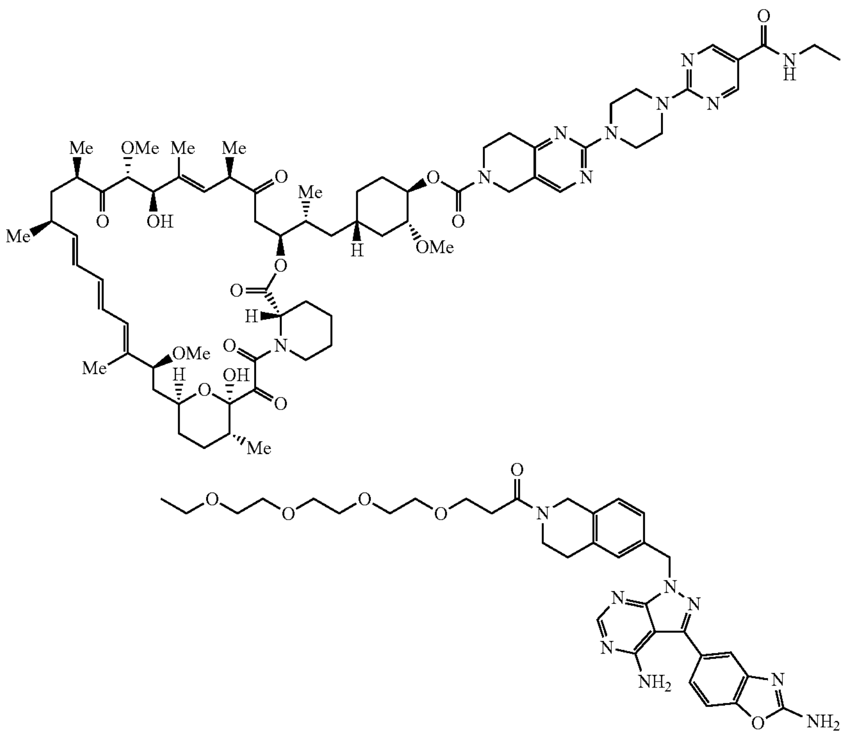 | $C_{101}H_{135}N_{17}O_{21}$ | [M + H] = 1923.01 | [M + H] = 1923.1 |
| Example 39<br>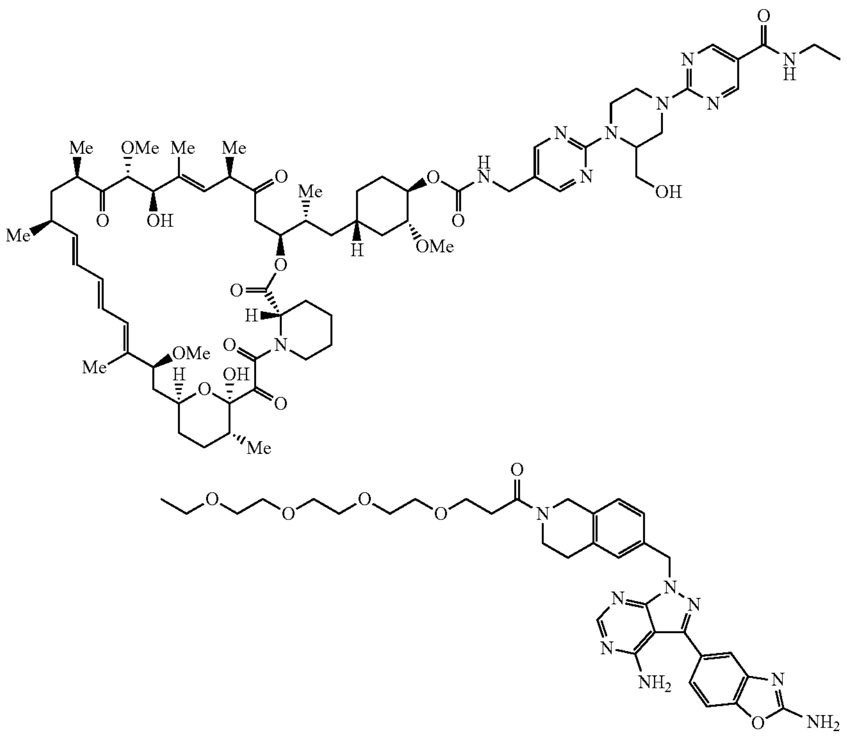 | $C_{100}H_{135}N_{17}O_{22}$ | [M + H] = 1927.01 | [M + H] = 1927.0 |

TABLE 15-continued
Series 2 Bivalent Compounds:
| Structure | Molecular Formula | Calculated MW | Observed MW |
|---|---|---|---|
| Example 40 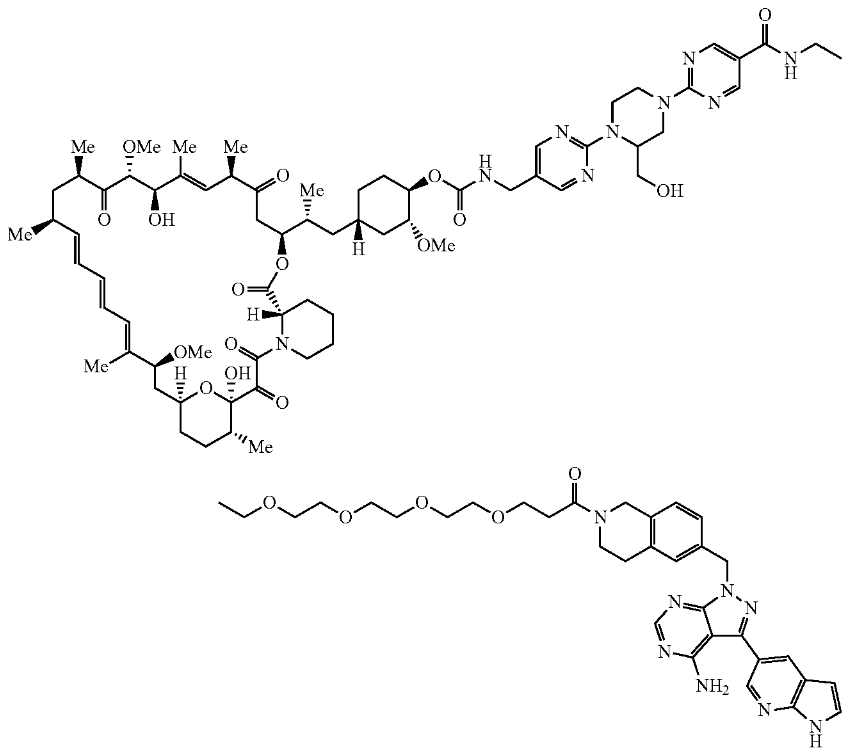 | $C_{100}H_{135}N_{17}O_{21}$ | [M + H] = 1911.01 | [M + H] = 1911.0 |
| Example 41 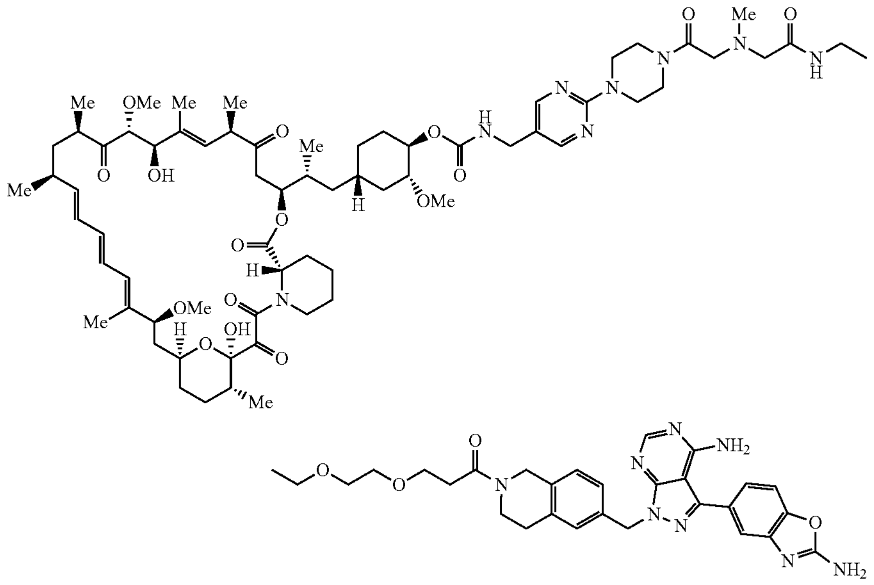 | $C_{95}H_{130}N_{16}O_{20}$ | [M + H] = 1815.97 | [M + H] = 1816.0 |
| Example 42 | | | |

TABLE 15-continued
| Series 2 Bivalent Compounds: | | | |
|---|---|---|---|
| Structure | Molecular Formula | Calculated MW | Observed MW |
| 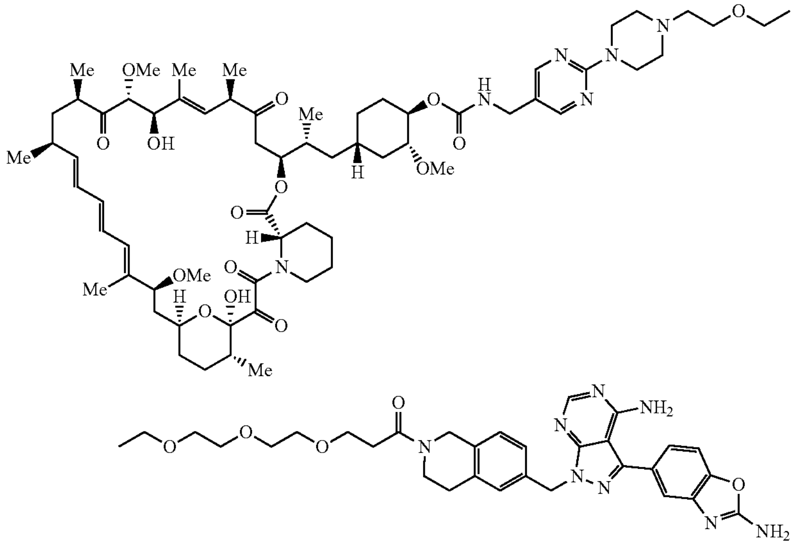 Example 43 | $C_{94}H_{130}N_{14}O_{20}$ | [M + H] = 1775.97 | [M + H] = 1775.9 |
| 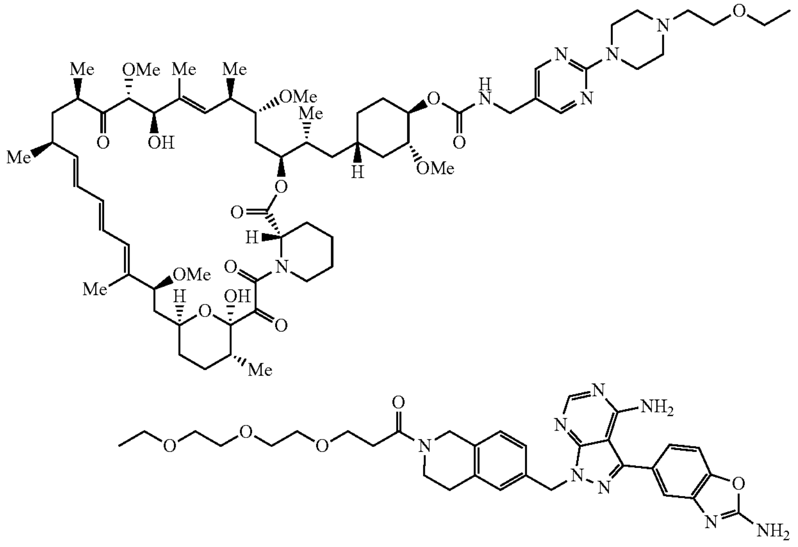 Example 44 | $C_{95}H_{134}N_{14}O_{20}$ | [M + H] = 1791.99 | [M + H] = 1791.8 |
| 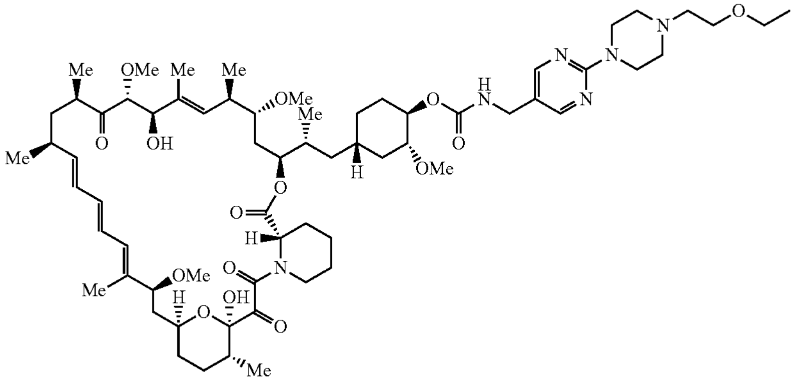 | $C_{89}H_{132}N_{14}O_{20}$ | [M + H] = 1717.98 | [M + H] = 1717.9 |

TABLE 15-continued
| Series 2 Bivalent Compounds: | | | |
| --- | --- | --- | --- |
| Structure | Molecular Formula | Calculated MW | Observed MW |
| 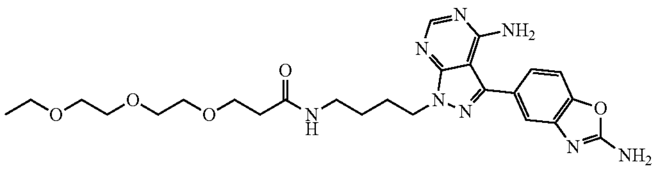 Example 45 | | | |
| 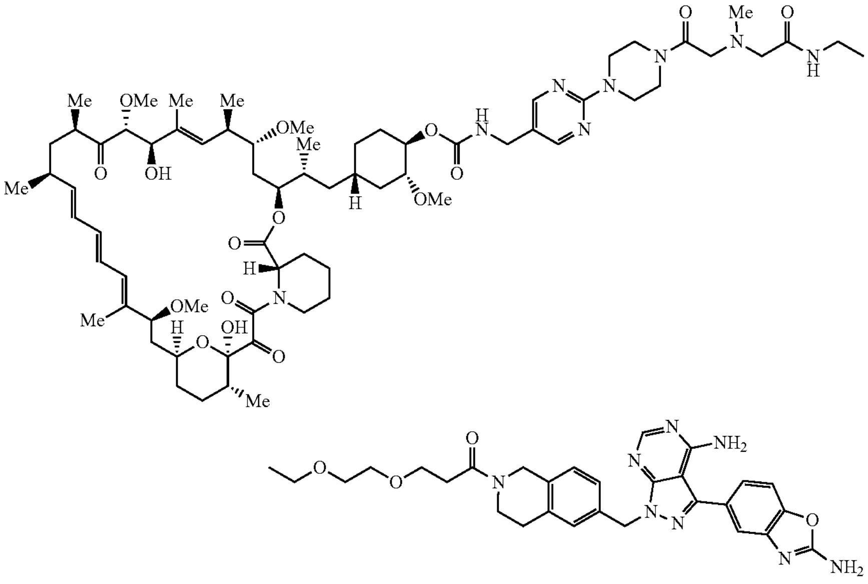 Example 103 | $C_{96}H_{134}N_{16}O_{20}$ | [M + H] = 1832.00 | [M + H] = 1832.0 |
| 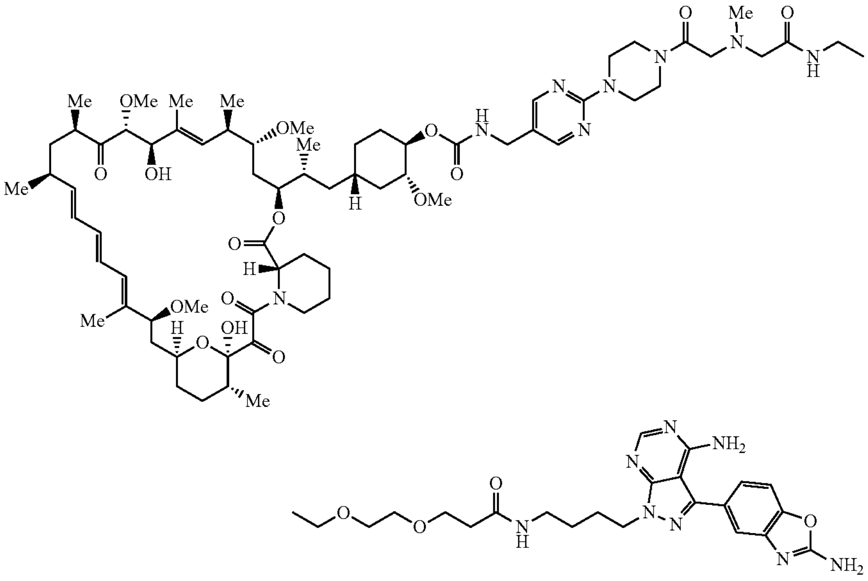 Example 104 | $C_{90}H_{132}N_{16}O_{20}$ | [M + H] = 1757.99 | [M + H] = 1757.9 |

TABLE 15-continued
| Series 2 Bivalent Compounds: | | | |
|---|---|---|---|
| Structure | Molecular Formula | Calculated MW | Observed MW |
| 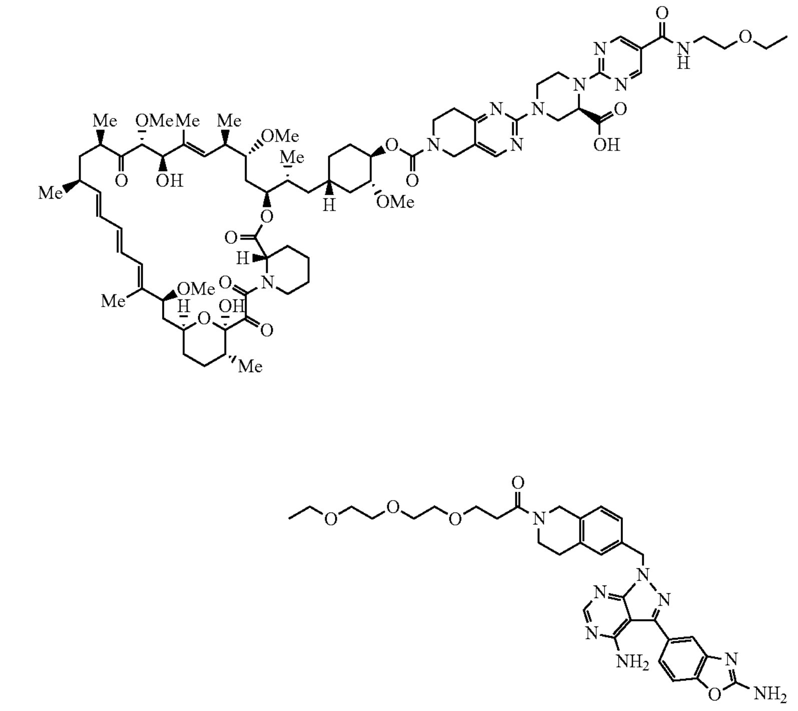 Example 105 | $C_{103}H_{139}N_{17}O_{23}$ | [M + H] = 1983.03 | [M + H] = 1983.0 |
| 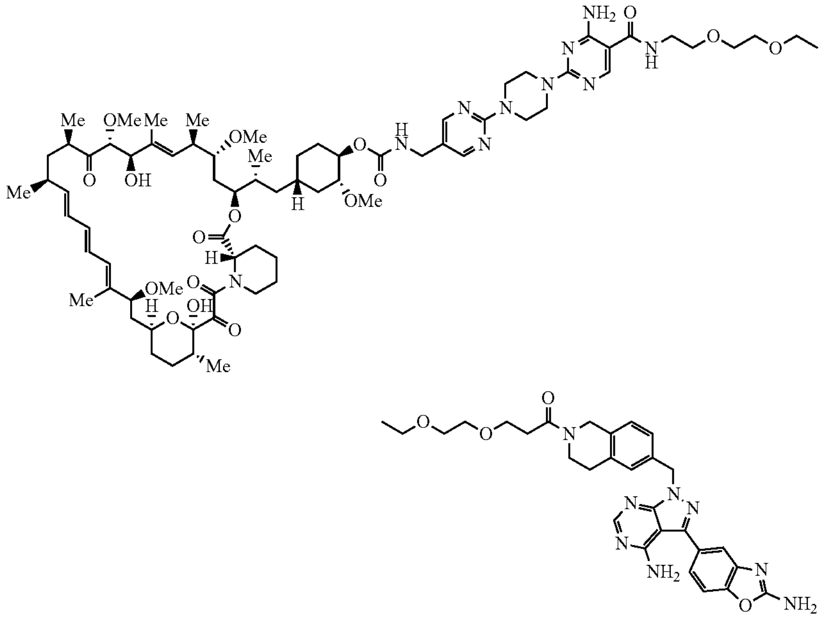 Example 106 | $C_{100}H_{138}N_{18}O_{21}$ | [M + H] = 1928.04 | [M + H] = 1927.9 |

TABLE 15-continued
| Series 2 Bivalent Compounds: | | | |
|---|---|---|---|
| Structure | Molecular Formula | Calculated MW | Observed MW |
| 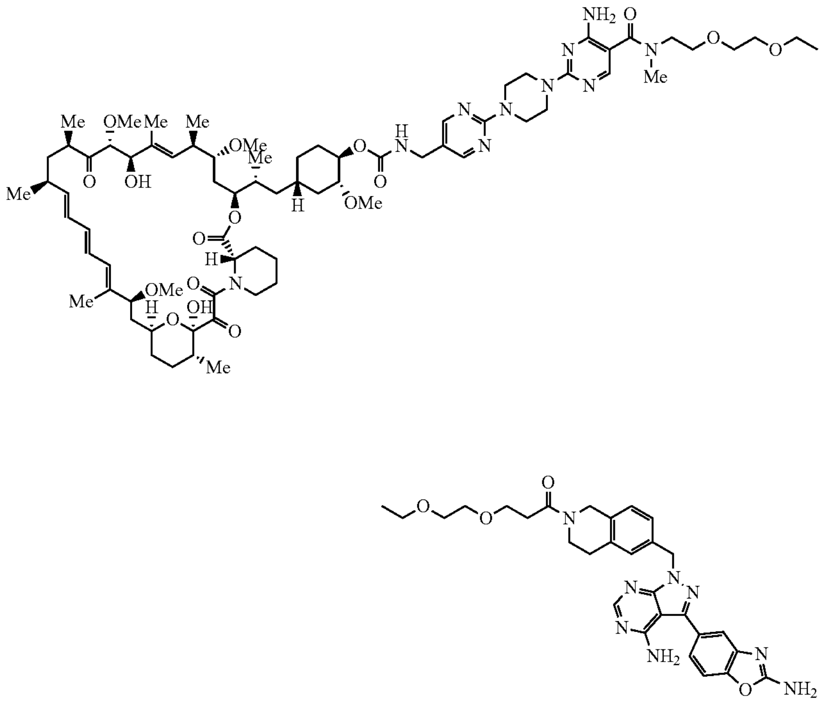 Example 107 | $C_{101}H_{140}N_{18}O_{21}$ | [M + H] = 1942.05 | [M + H] = 1942.1 |
| 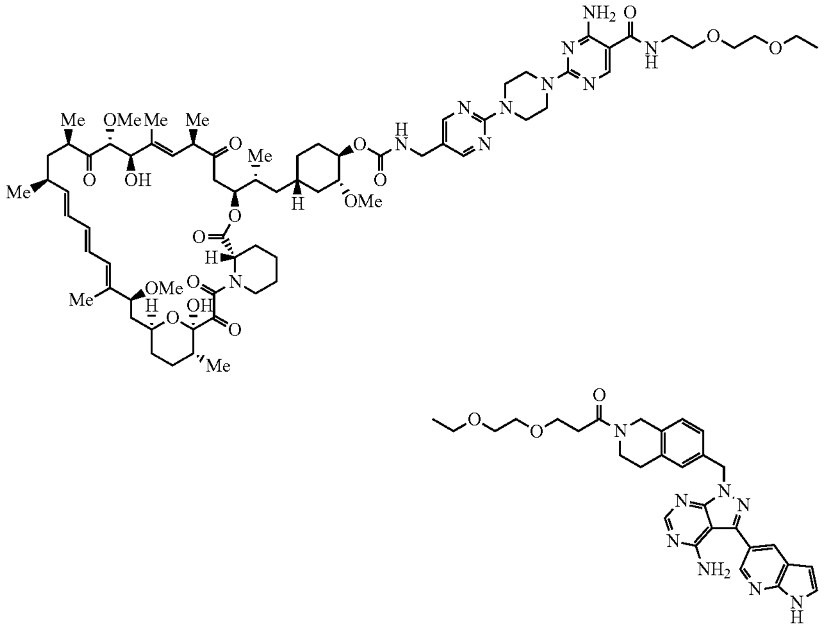 Example 108 | $C_{99}H_{134}N_{18}O_{20}$ | [M + H] = 1896.01 | [M + H] = 1896.0 |

TABLE 15-continued
| Series 2 Bivalent Compounds: | | | |
|---|---|---|---|
| Structure | Molecular Formula | Calculated MW | Observed MW |
| 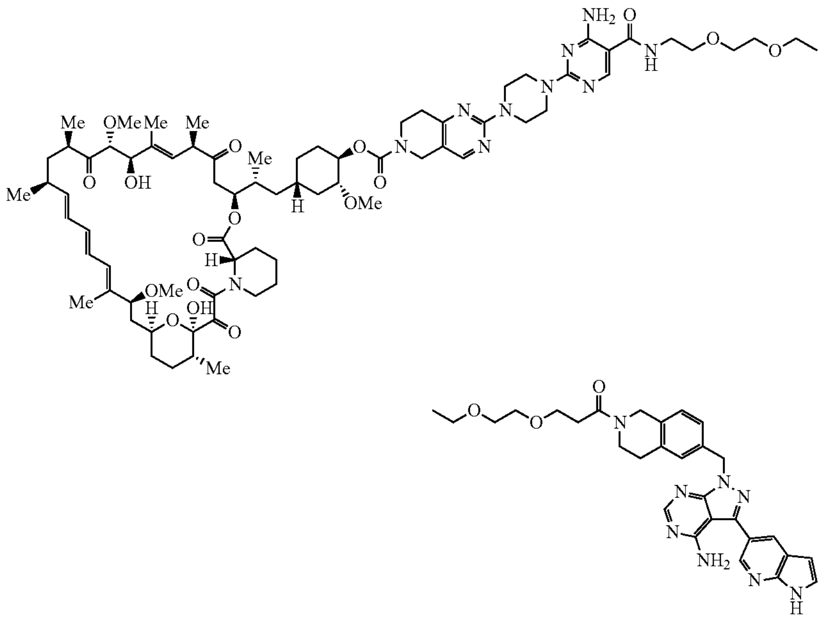 Example 109 | $C_{101}H_{136}N_{18}O_{20}$ | [M + H] = 1922.03 | [M + H] = 1922.1 |
| 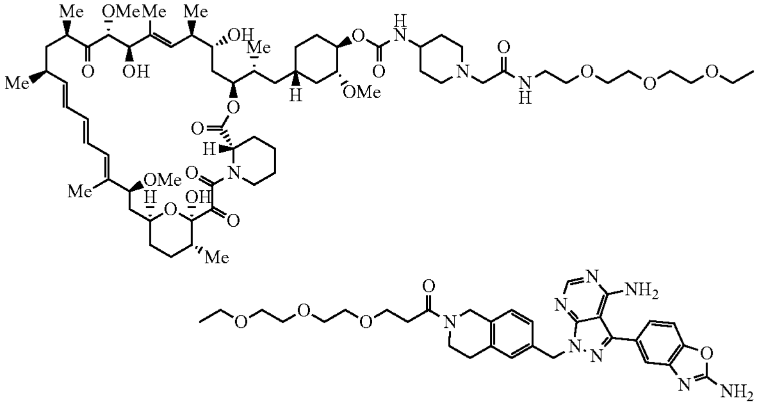 Example 110 | $C_{96}H_{140}N_{12}O_{23}$ | [M + H] = 1830.02 | [M + H] = 1829.9 |
| 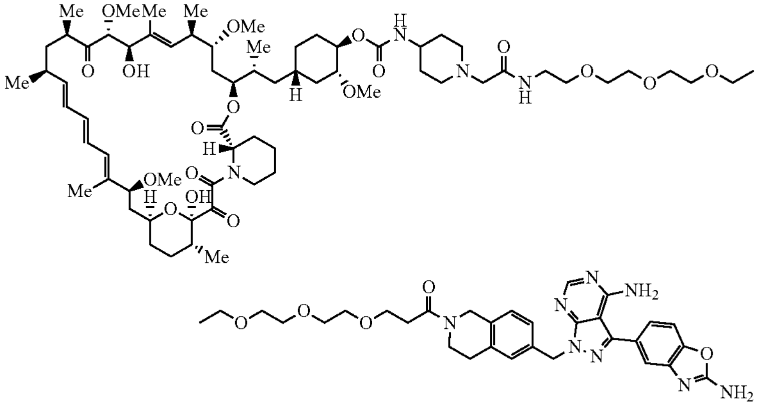 Example 111 | $C_{97}H_{142}N_{12}O_{23}$ | [M + H] = 1844.04 | [M + H] = 1843.9 |

TABLE 15-continued
| Series 2 Bivalent Compounds: | | | |
|---|---|---|---|
| Structure | Molecular Formula | Calculated MW | Observed MW |
| 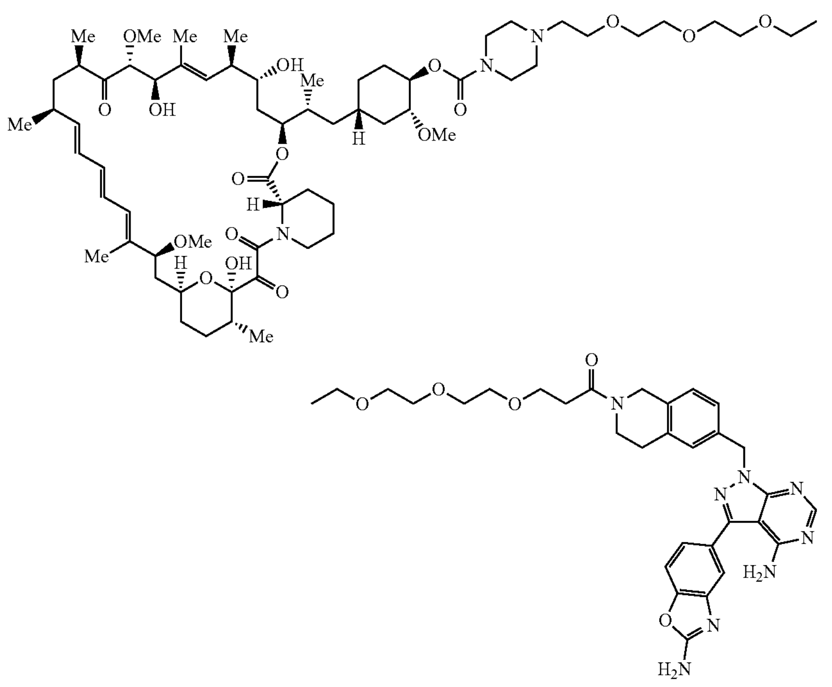<br>Example 149 | $C_{93}H_{135}N_{11}O_{22}$ | [M + H] = 1758.99 | [M + H] = 1758.9 |
| 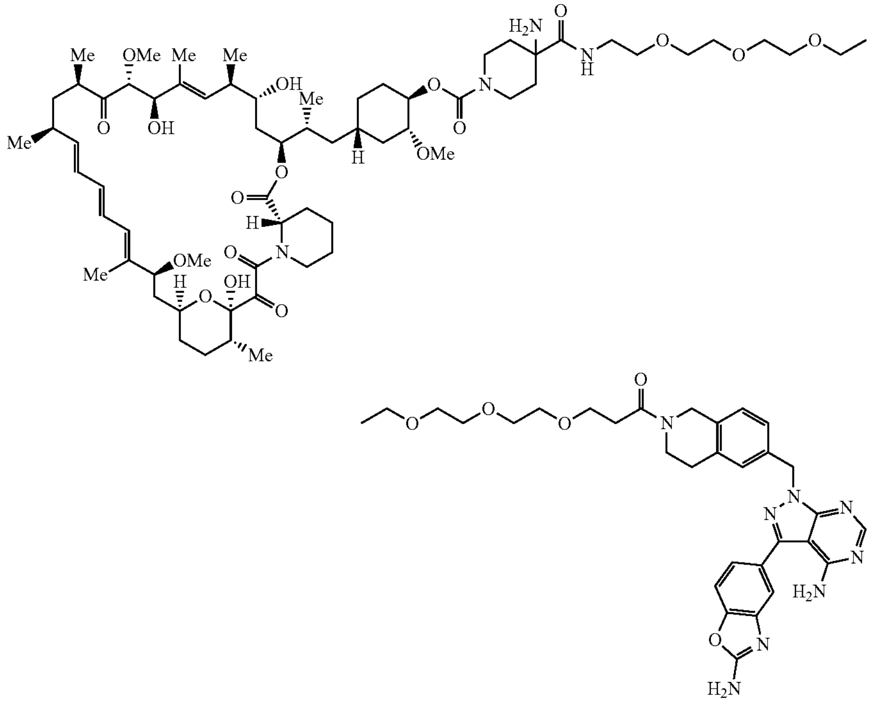<br>Example 150 | $C_{95}H_{138}N_{12}O_{23}$ | [M + H] = 1816.01 | [M + H] = 1815.9 |

Following General Procedure 1, but using the appropriate amine containing active site inhibitors in Table 2 and amine containing pre-linkers in Table 4, the Intermediates C1 in Table 16 were prepared:

TABLE 16

Additional amines prepared

| Structure | Molecular Formula | Calculated MW | Observed MW |
|---|---|---|---|
| 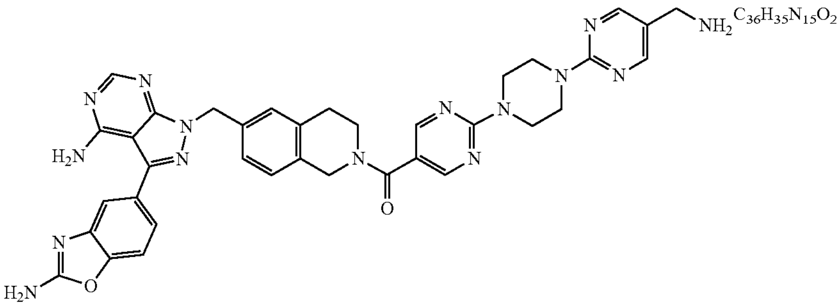 Intermediate C1-1 | $C_{36}H_{35}N_{15}O_2$ | [M + H] = 710.32 | [M + H] = 710.2 |
| 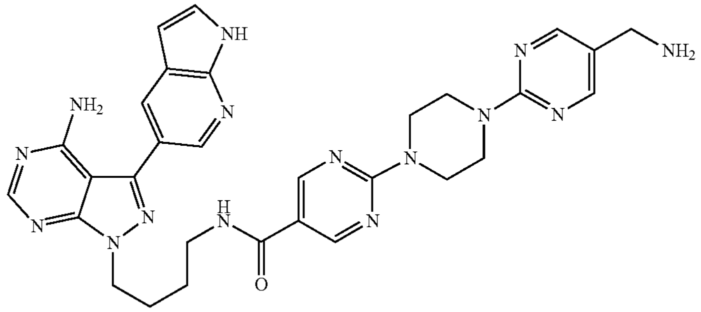 [SMILES: NCc1cnc(N2CCN(c3ncc(C(=O)NCCCCn4nc(-c5cnc6[nH]ccc6c5)c5c(N)ncnc54)cn3)CC2)nc1] Intermediate C1-2 | $C_{30}H_{33}N_{15}O$ | [M + H] = 620.31 | [M + H] = 620.2 |
| 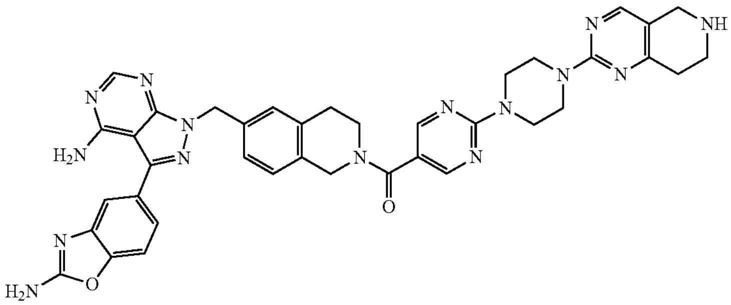 [SMILES: Nc1nc2cc(-c3nn(Cc4ccc5c(c4)CCN(C(=O)c4cnc(N6CCN(c7ncc8c(n7)CCNC8)CC6)nc4)C5)c4ncnc(N)c34)ccc2o1] Intermediate C1-3 | $C_{38}H_{37}N_{15}O_2$ | [M + H] = 736.34 | [M + H] = 736.2 |
| 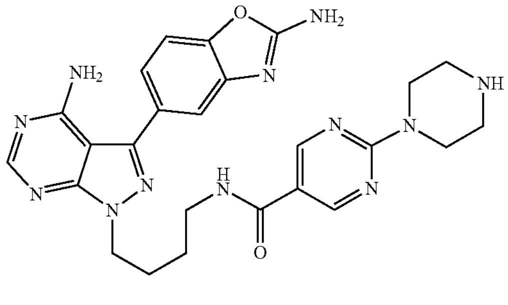 [SMILES: Nc1nc2cc(-c3nn(CCCCNC(=O)c4cnc(N5CCNCC5)nc4)c4ncnc(N)c34)ccc2o1] Intermediate C1-4 | $C_{25}H_{28}N_{12}O_2$ | [M + H] = 529.26 | [M + H] = 529.5 |

TABLE 16-continued
Additional amines prepared
| Structure | Molecular Formula | Calculated MW | Observed MW |
| --- | --- | --- | --- |
| 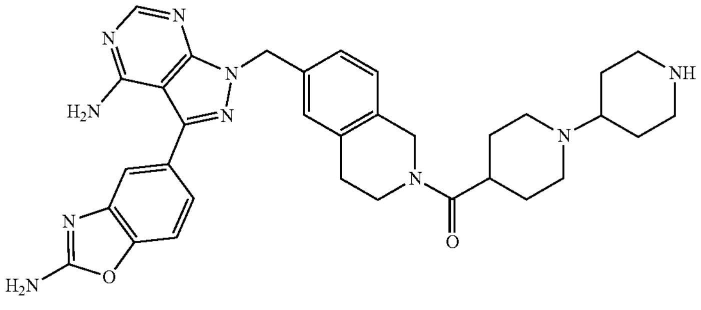 [SMILES: Nc1nc2cc(-c3nn(Cc4ccc5c(c4)CCN(C(=O)C4CCN(C6CCNCC6)CC4)C5)c4ncnc(N)c34)ccc2o1] Intermediate C1-5 | $C_{33}H_3N_{10}O_2$ | [M + H] = 607.33 | [M + H] = 607.3 |
| 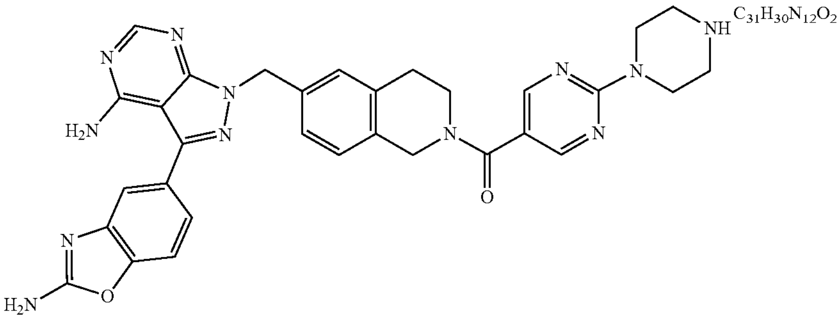 Intermediate C1-6 | $C_{31}H_{30}N_{12}O_2$ | [M + H] = 603.27 | [M + H] = 603.3 |
| 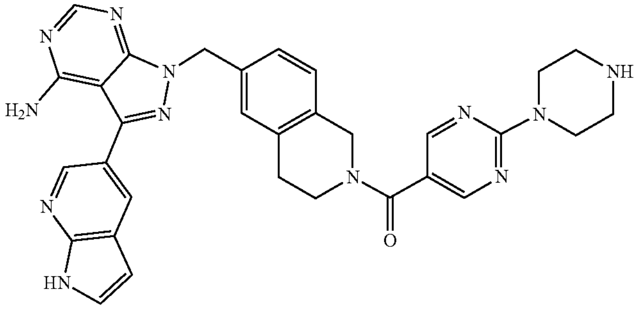 [SMILES: Nc1ncnc2c1c(-c1cnc3[nH]ccc3c1)nn2Cc1ccc2c(c1)CCN(C(=O)c1cnc(N3CCNCC3)nc1)C2] Intermediate C1-7 | $C_{31}H_{30}N_{12}O$ | [M + H] = 587.28 | [M + H] = 587.3 |
| 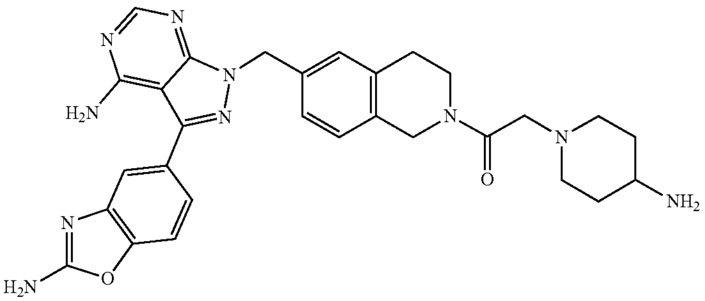 [SMILES: Nc1nc2cc(-c3nn(Cc4ccc5c(c4)CCN(C(=O)CN4CCC(N)CC4)C5)c4ncnc(N)c34)ccc2o1] Intermediate C1-8 | $C_{29}H_{32}N_{10}O_2$ | [M + H] = 553.28 | [M + H] = |

Following General Procedure 1, but using the PEG carboxylic acids and Intermediates C1 in Table 16, the Intermediates C2 in Table 17 were prepared:

TABLE 17

Additional amines prepared

| Structure | Molecular Formula | Calculated MW | Observed MW |
|---|---|---|---|
| 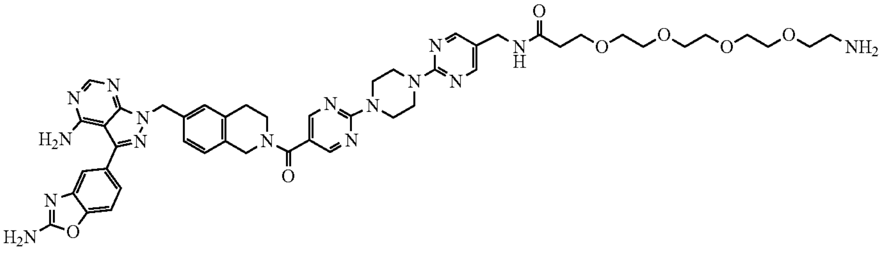 [SMILES: NCCOCCOCCOCCOCCC(=O)NCc1cnc(N2CCN(c3ncc(C(=O)N4CCc5cc(Cn6nc(-c7ccc8oc(N)nc8c7)c7c(N)ncnc76)ccc5C4)cn3)CC2)nc1] Intermediate C2-1 | $C_{47}H_{56}N_{16}O_7$ | [M + H] = 957.46 | [M + H] = 957.7 |
| 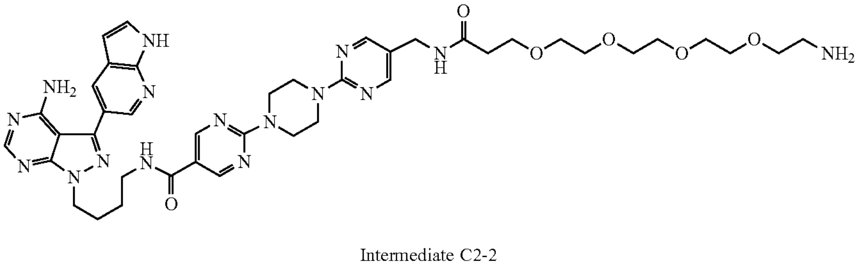 Intermediate C2-2 | $C_{41}H_{54}N_{16}O_6$ | [M + H] = 867.45 | [M + H] = 867.2 |
| 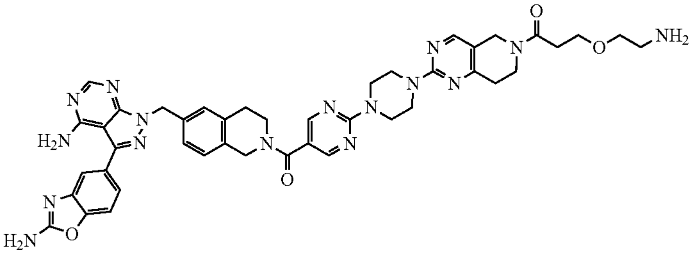 [SMILES: NCCOCCC(=O)N1CCc2nc(N3CCN(c4ncc(C(=O)N5CCc6cc(Cn7nc(-c8ccc9oc(N)nc9c8)c8c(N)ncnc87)ccc6C5)cn4)CC3)ncc2C1] Intermediate C2-3 | $C_{43}H_{46}N_{16}O_4$ | [M + H] = 851.40 | [M + H] = 851.2 |
| 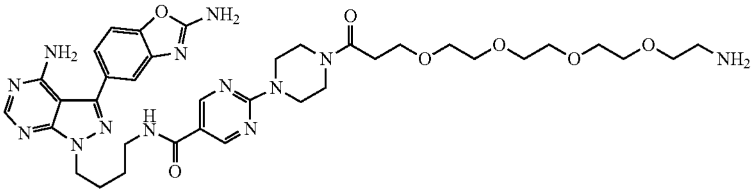 [SMILES: NCCOCCOCCOCCOCCC(=O)N1CCN(c2ncc(C(=O)NCCCCn3nc(-c4ccc5oc(N)nc5c4)c4c(N)ncnc43)cn2)CC1] Intermediate C2-4 | $C_{36}H_{49}N_{13}O_7$ | [M + H] = 776.40 | [M + H] = 776.3 |
| 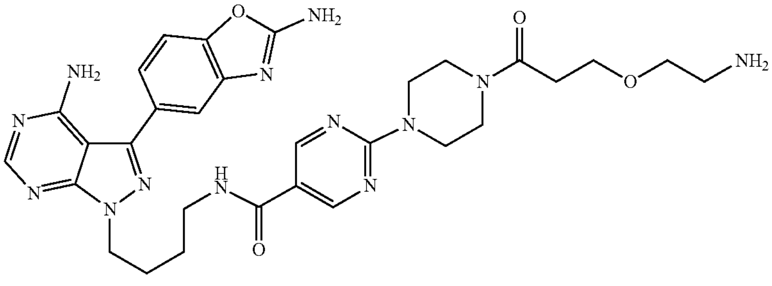 [SMILES: NCCOCCC(=O)N1CCN(c2ncc(C(=O)NCCCCn3nc(-c4ccc5oc(N)nc5c4)c4c(N)ncnc43)cn2)CC1] Intermediate C2-5 | $C_{30}H_{37}N_{13}O_4$ | [M + H] = 644.32 | [M + H] = 644.3 |

TABLE 17-continued

| Additional amines prepared | | | |
|---|---|---|---|
| Structure | Molecular Formula | Calculated MW | Observed MW |
| 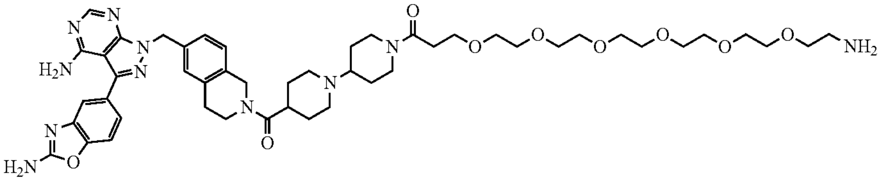 [SMILES: NCCOCCOCCOCCOCCOCCOCCC(=O)N1CCC(N2CCC(C(=O)N3CCc4cc(Cn5nc(-c6ccc7oc(N)nc7c6)c6c(N)ncnc65)ccc4C3)CC2)CC1] Intermediate C2-6 | $C_{48}H_{67}N_{11}O_9$ | [M + H] = 942.52 | [M + H] = 943.2 |
| 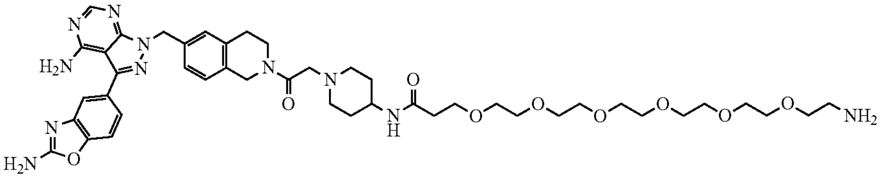 [SMILES: NCCOCCOCCOCCOCCOCCOCCC(=O)NC1CCN(CC(=O)N2CCc3cc(Cn4nc(-c5ccc6oc(N)nc6c5)c5c(N)ncnc54)ccc3C2)CC1] Intermediate C2-7 | $C_{44}H_{61}N_{11}O_9$ | [M + H] = 888.48 | [M + H] = 888.3 |

Following General Procedure 2, but using the appropriate 4-nitrophenyl carbonate containing rapamycin monomer in Table 1 and Intermediates C2 from Table 17, the Series 3 bivalent analogs in Table 18 were synthesized:

TABLE 18
| Series 3 Bivalent Compounds | | | |
|---|---|---|---|
| Structure | Molecular Formula | Calculated MW | Observed MW |
| 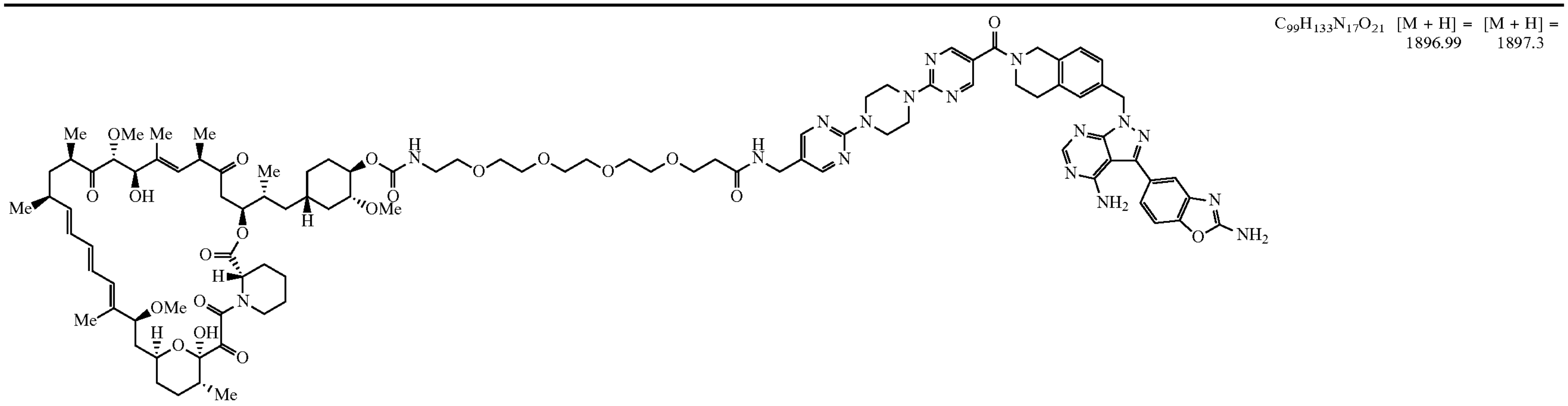<br>Example 46 | $C_{99}H_{133}N_{17}O_{21}$ | [M + H] = 1896.99 | [M + H] = 1897.3 |

TABLE 18-continued
| Structure | Molecular Formula | Calculated MW | Observed MW |
| --- | --- | --- | --- |
| Series 3 Bivalent Compounds | | | |
| 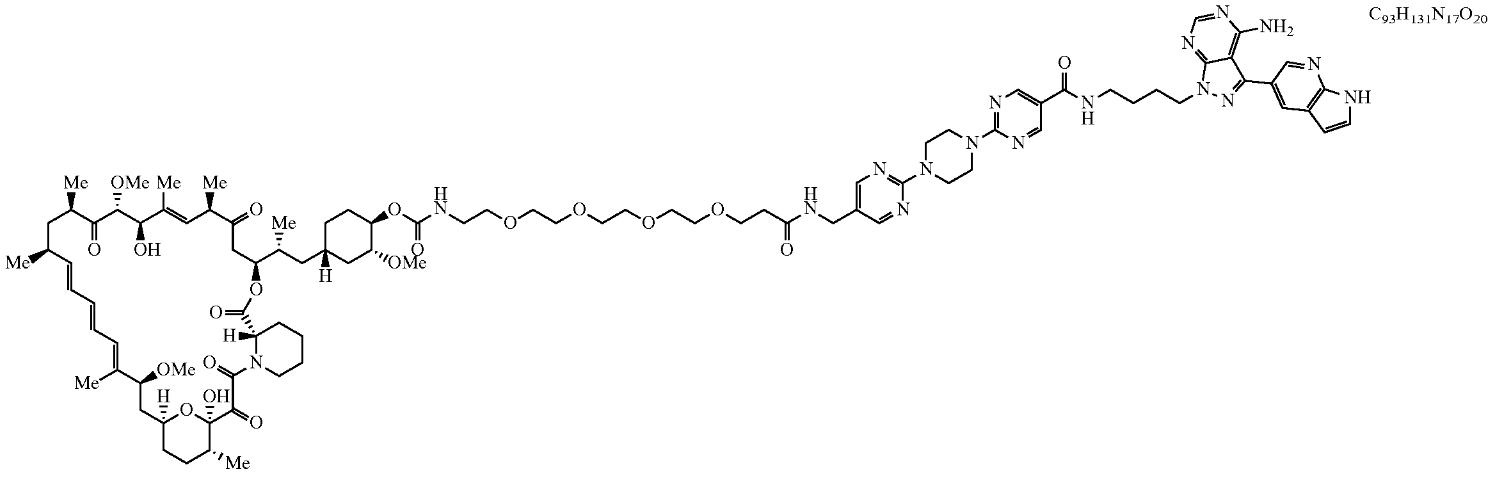 Example 47 | $C_{93}H_{131}N_{17}O_{20}$ | [M + H] = 1806.98 | [M + H] = 1806.8 |
| 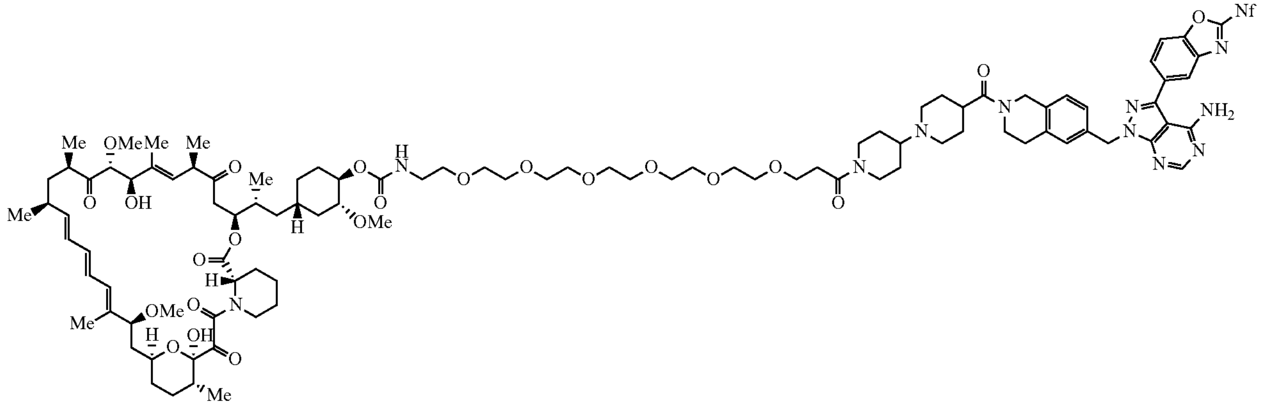 Example 48 | $C_{100}H_{144}N_{12}O_{23}$ | [M + H] = 1882.06 | [M + H] = 1882.1 |

TABLE 18-continued
| Series 3 Bivalent Compounds | | | |
|---|---|---|---|
| Structure | Molecular Formula | Calculated MW | Observed MW |
| 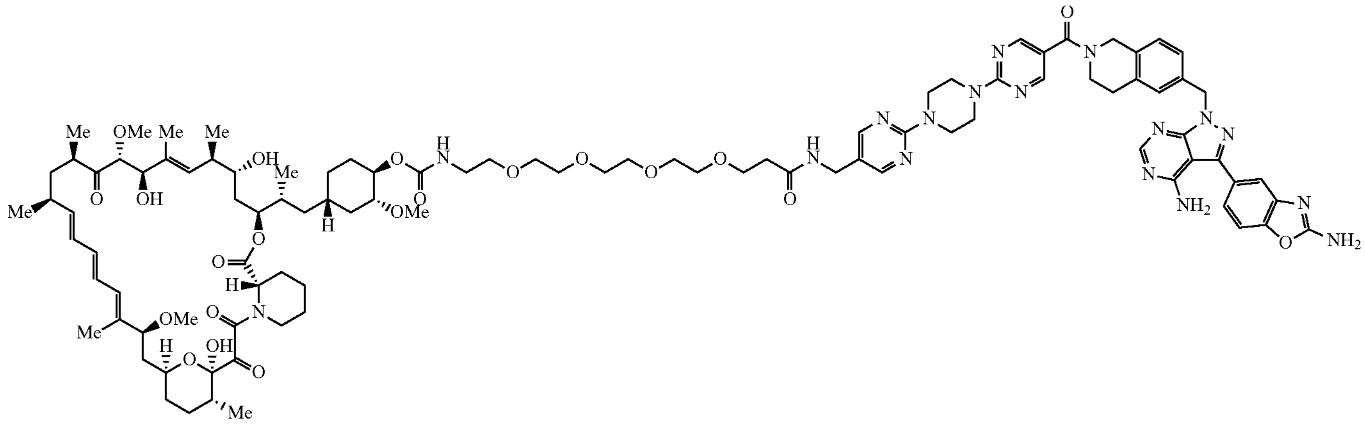 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCC(=O)NCc3cnc(N4CCN(c5ncc(C(=O)N6CCc7cc(Cn8nc(-c9ccc%10oc(N)nc%10c9)c9c(N)ncnc98)ccc7C6)cn5)CC4)nc3)[C@H](OC)C2)C[C@@H](O)[C@H](C)/C=C(\C)[C@@H](O)[C@@H](OC)C(=O)[C@H](C)C[C@H](C)/C=C/C=C/C=C/1C] Example 49 | $C_{99}H_{135}N_{17}O_{21}$ | [M + H] = 1899.01 | [M + H] = 1899.1 |
| 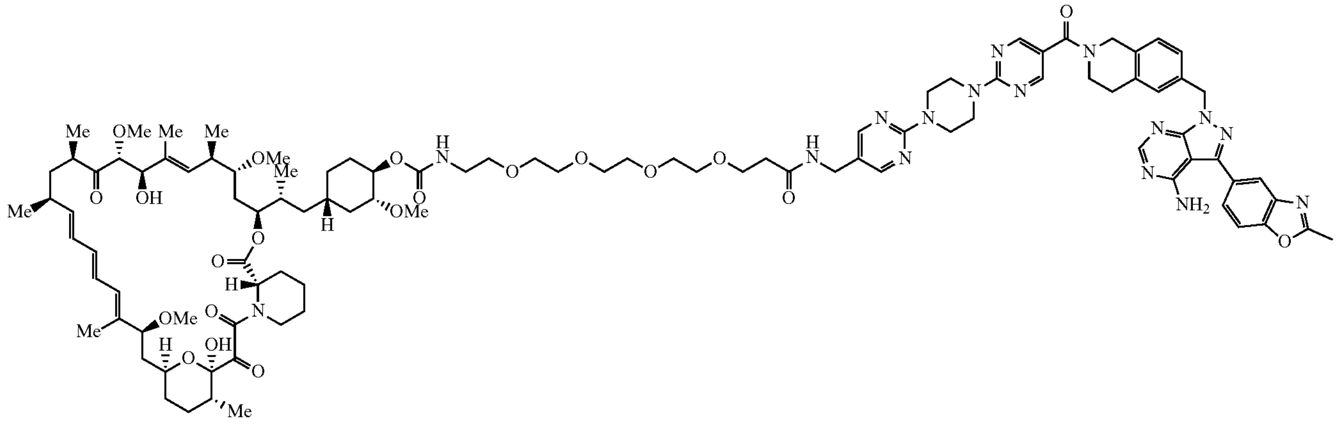 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCC(=O)NCc3cnc(N4CCN(c5ncc(C(=O)N6CCc7cc(Cn8nc(-c9ccc%10oc(C)nc%10c9)c9c(N)ncnc98)ccc7C6)cn5)CC4)nc3)[C@H](OC)C2)C[C@@H](OC)[C@H](C)/C=C(\C)[C@@H](O)[C@@H](OC)C(=O)[C@H](C)C[C@H](C)/C=C/C=C/C=C/1C] Example 50 | $C_{100}H_{137}N_{17}O_{21}$ | [M + H] = 1913.03 | [M + H] = 1913.1 |

TABLE 18-continued
| Series 3 Bivalent Compounds | | | |
|---|---|---|---|
| Structure | Molecular Formula | Calculated MW | Observed MW |
| 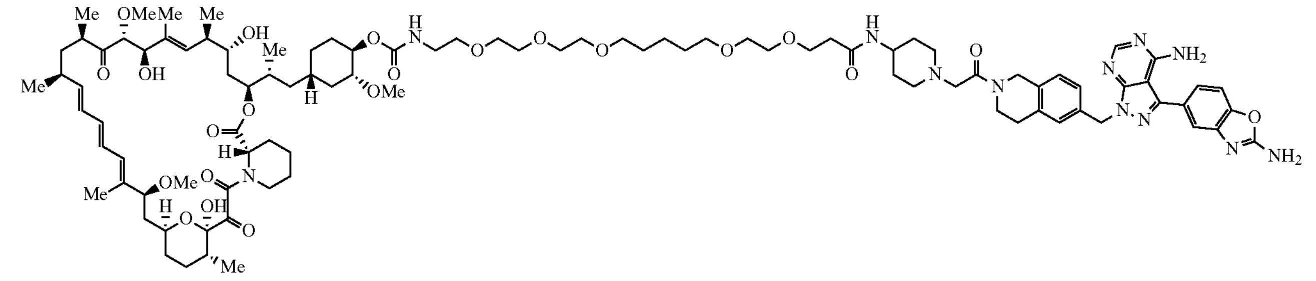 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCCCCOCCOCCC(=O)NC3CCN(CC(=O)N4CCc5cc(Cn6nc(-c7ccc8oc(N)nc8c7)c7c(N)ncnc76)ccc5C4)CC3)[C@H](OC)C2)C[C@@H](O)[C@H](C)/C=C(\C)[C@@H](O)[C@@H](OC)C(=O)[C@H](C)C[C@H](C)/C=C/C=C/C=C/1C] Example 112 | $C_{96}H_{140}N_{12}O_{23}$ | [M + H] = 1830.02 | [M + H] = 1829.9 |
| 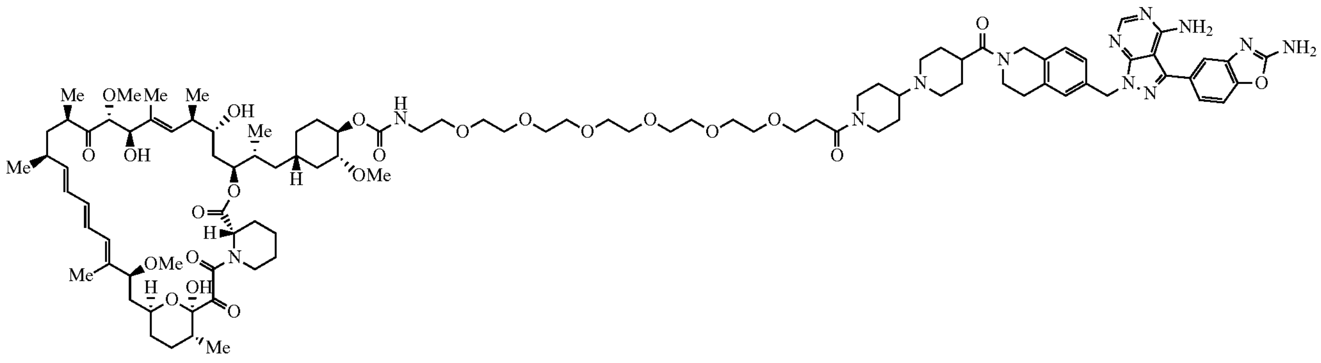 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCOCCOCCOCCOCCC(=O)N3CCC(N4CCC(C(=O)N5CCc6cc(Cn7nc(-c8ccc9oc(N)nc9c8)c8c(N)ncnc87)ccc6C5)CC4)CC3)[C@H](OC)C2)C[C@@H](O)[C@H](C)/C=C(\C)[C@@H](O)[C@@H](OC)C(=O)[C@H](C)C[C@H](C)/C=C/C=C/C=C/1C] Example 113 | $C_{100}H_{146}N_{12}O_{23}$ | [M + H] = 1884.07 | [M + H] = 1883.7 |

Following General Procedure 1, but using the appropriate Intermediates C2 in Table 17 and amine containing pre-linkers in Table 4, the Intermediates D1 in Table 19 were prepared:

TABLE 19

Additional amines prepared

| Structure | Molecular Formula | Calculated MW | Observed MW |
| --- | --- | --- | --- |
| 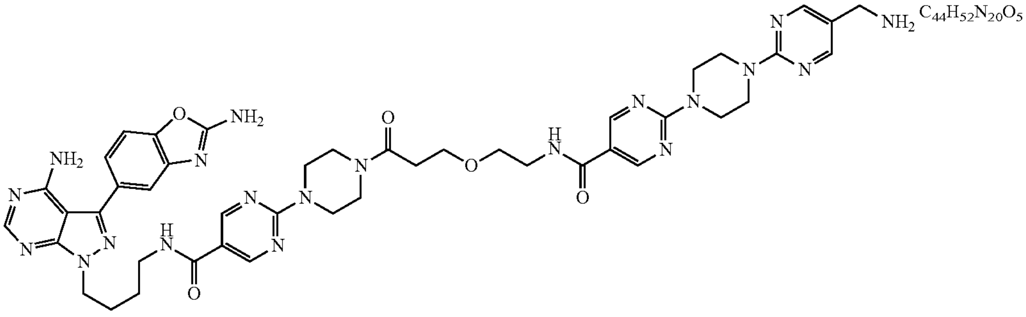 Intermediate D1-1 | $C_{44}H_{52}N_{20}O_5$ | [M + H] = 941.45 | [M + H] = 941.5 |

Following General Procedure 1, but using the appropriate amine containing active site inhibitors in Table 2 and amine containing pre-linkers in Table 4, the Intermediates D1 in Table 20 were prepared:

TABLE 20
Additional amines prepared
| Structure | Molecular Formula | Calculated MW | Observed MW |
| --- | --- | --- | --- |
| 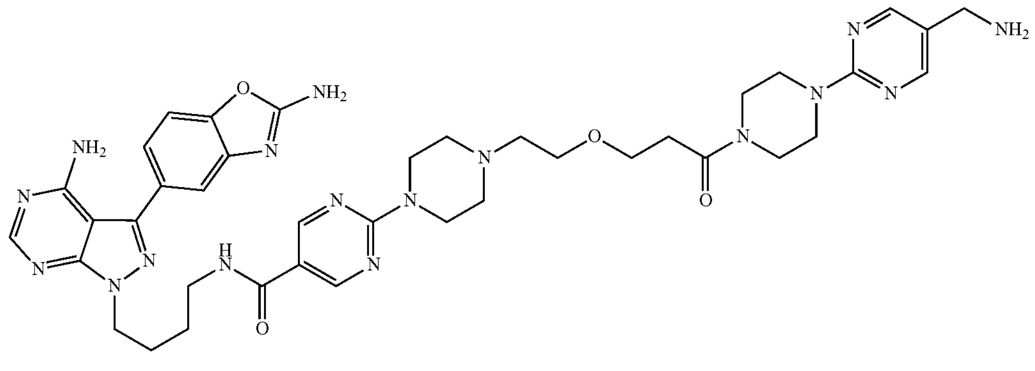 [SMILES: NCc1cnc(N2CCN(C(=O)CCOCCN3CCN(c4ncc(C(=O)NCCCCn5nc(-c6ccc7oc(N)nc7c6)c6c(N)ncnc65)cn4)CC3)CC2)nc1] Intermediate D1-2 | $C_{39}H_{49}N_{17}O_4$ | [M + H] = 820.43 | [M + H] = 820.4 |
| 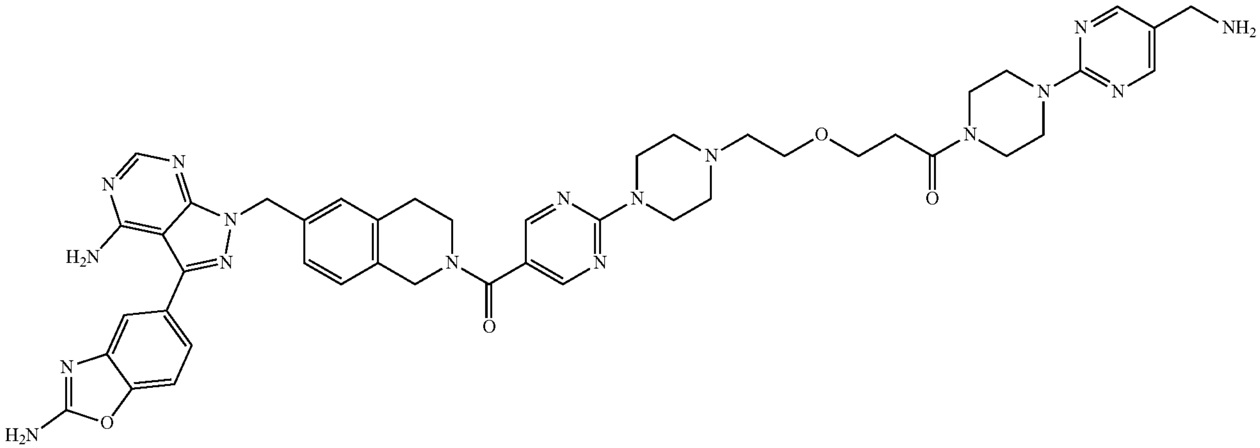 [SMILES: NCc1cnc(N2CCN(C(=O)CCOCCN3CCN(c4ncc(C(=O)N5CCc6cc(Cn7nc(-c8ccc9oc(N)nc9c8)c8c(N)ncnc87)ccc6C5)cn4)CC3)CC2)nc1] Intermediate D1-3 | $C_{45}H_{51}N_{17}O_4$ | [M + H] = 894.44 | [M + H] = 894.4 |

TABLE 20-continued
Additional amines prepared
| Structure | Molecular Formula | Calculated MW | Observed MW |
|---|---|---|---|
| 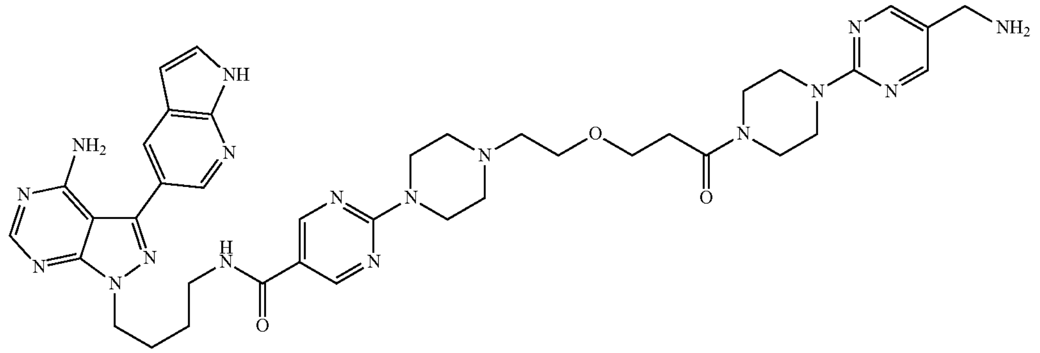 [SMILES: NCc1cnc(N2CCN(C(=O)CCOCCN3CCN(c4ncc(C(=O)NCCCCn5nc(-c6cnc7[nH]ccc7c6)c6c(N)ncnc65)cn4)CC3)CC2)nc1] Intermediate D1-4 | $C_{39}H_{49}N_{17}O_3$ | [M + H] = 804.43 | [M + H] = 804.4 |
| 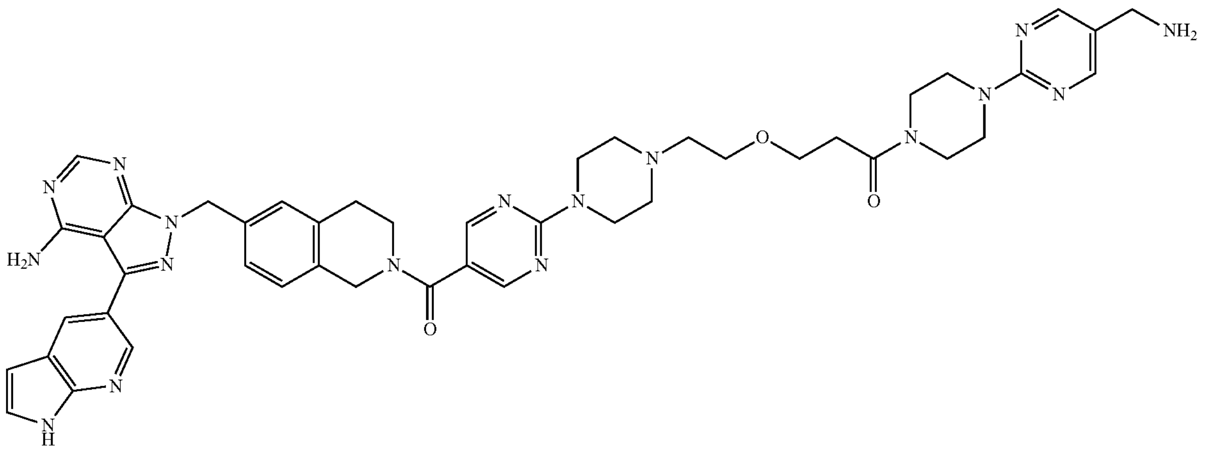 [SMILES: NCc1cnc(N2CCN(C(=O)CCOCCN3CCN(c4ncc(C(=O)N5CCc6cc(Cn7nc(-c8cnc9[nH]ccc9c8)c8c(N)ncnc87)ccc6C5)cn4)CC3)CC2)nc1] Intermediate D1-5 | $C_{45}H_{51}N_{17}O_3$ | [M + H] = 878.45 | [M + H] = 878.4 |

TABLE 20-continued
| Additional amines prepared | | | |
|---|---|---|---|
| Structure | Molecular Formula | Calculated MW | Observed MW |
| 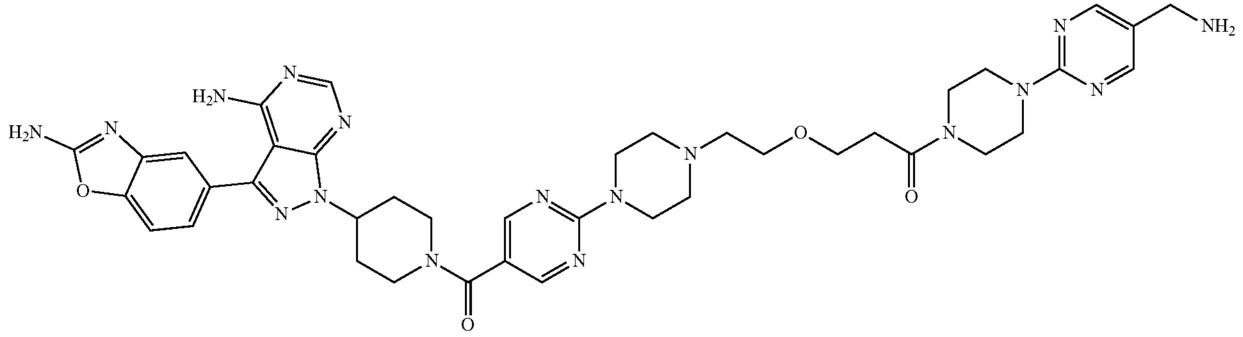 [SMILES: NCc1cnc(N2CCN(C(=O)CCOCCN3CCN(c4ncc(C(=O)N5CCC(n6nc(-c7ccc8oc(N)nc8c7)c7c(N)ncnc76)CC5)cn4)CC3)CC2)nc1]<br>Intermediate D1-6 | $C_{40}H_{49}N_{17}O_4$ | [M + H] = 832.43 | [M + H] = 832.4 |
| 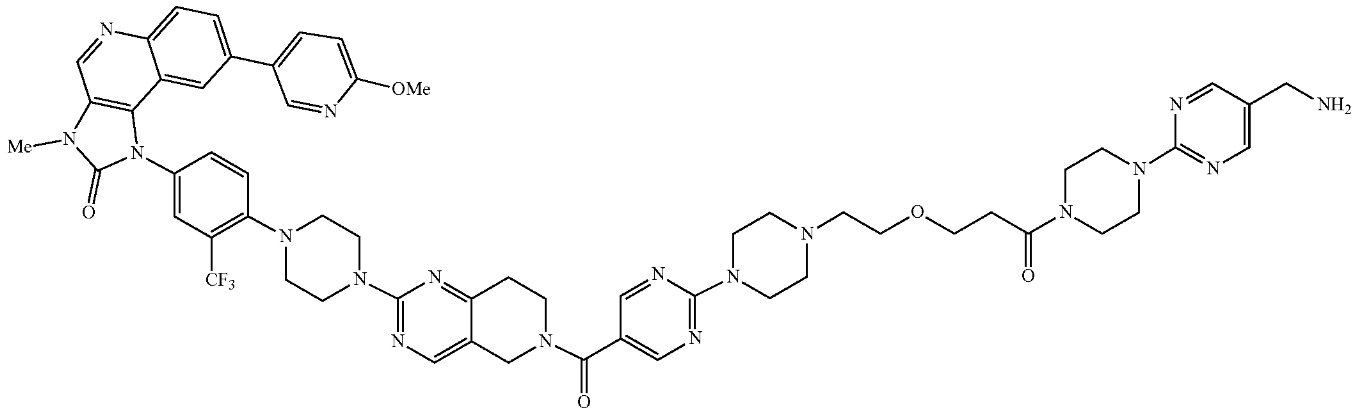 [SMILES: COc1ccc(-c2ccc3ncc4c(c3c2)n(-c2ccc(N3CCN(c5ncc6c(n5)CCN(C(=O)c5cnc(N7CCN(CCOCCC(=O)N8CCN(c9ncc(CN)cn9)CC8)CC7)nc5)C6)CC3)c(C(F)(F)F)c2)c(=O)n4C)cn1]<br>Intermediate D1-7 | $C_{58}H_{63}F_3N_{18}O_5$ | [M + H] = 1149.53 | [M + H] = 1149.4 |

TABLE 20-continued
Additional amines prepared
| Structure | Molecular Formula | Calculated MW | Observed MW |
| --- | --- | --- | --- |
| 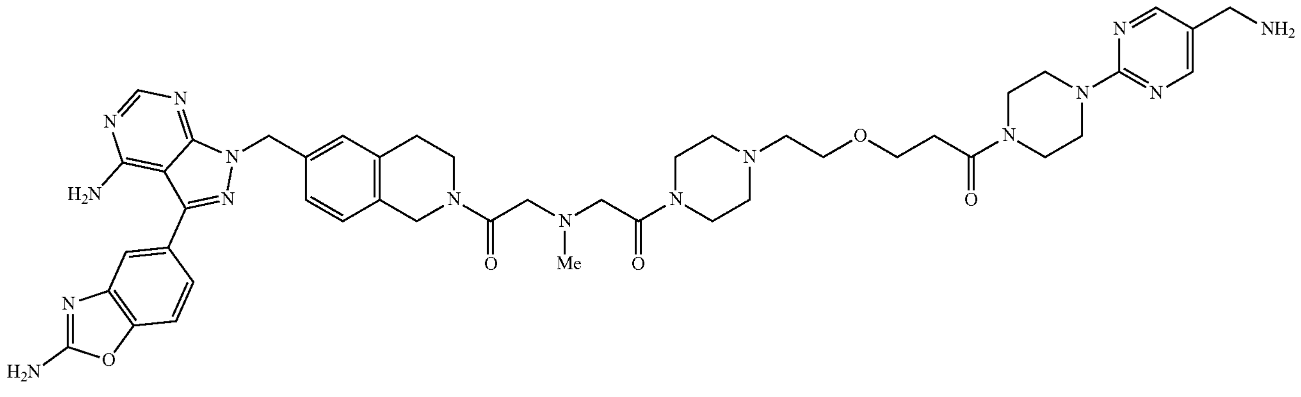 [SMILES: CN(CC(=O)N1CCN(CCOCCC(=O)N2CCN(c3ncc(CN)cn3)CC2)CC1)CC(=O)N1CCc2cc(Cn3nc(-c4ccc5oc(N)nc5c4)c4c(N)ncnc43)ccc2C1] Intermediate D1-8 | $C_{45}H_{56}N_{16}O_5$ | [M + H] = 901.47 | [M + H] = 901.4 |
| 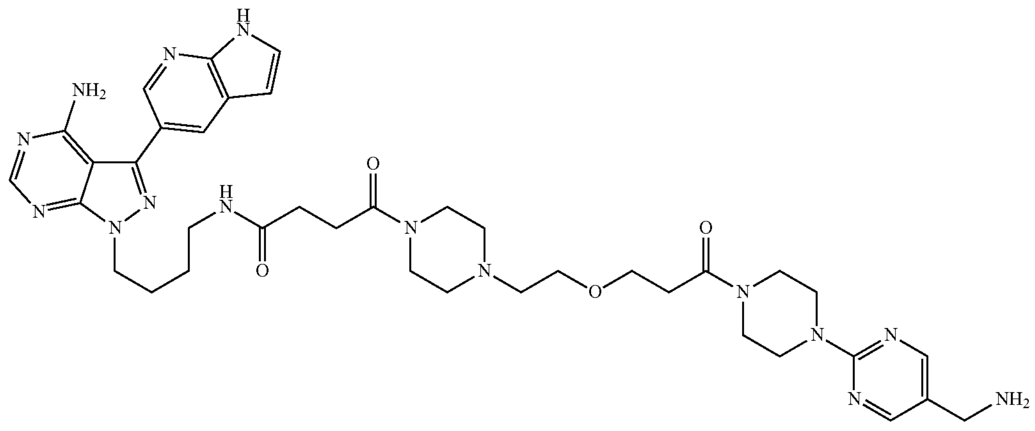 [SMILES: NCc1cnc(N2CCN(C(=O)CCOCCN3CCN(C(=O)CCC(=O)NCCCCn4nc(-c5cnc6[nH]ccc6c5)c5c(N)ncnc54)CC3)CC2)nc1] Intermediate D1-9 | $C_{38}H_{51}N_{15}O_4$ | [M + H] = 782.43 | [M + H] = 782.4 |

TABLE 20-continued
| Additional amines prepared | | | |
|---|---|---|---|
| Structure | Molecular Formula | Calculated MW | Observed MW |
| 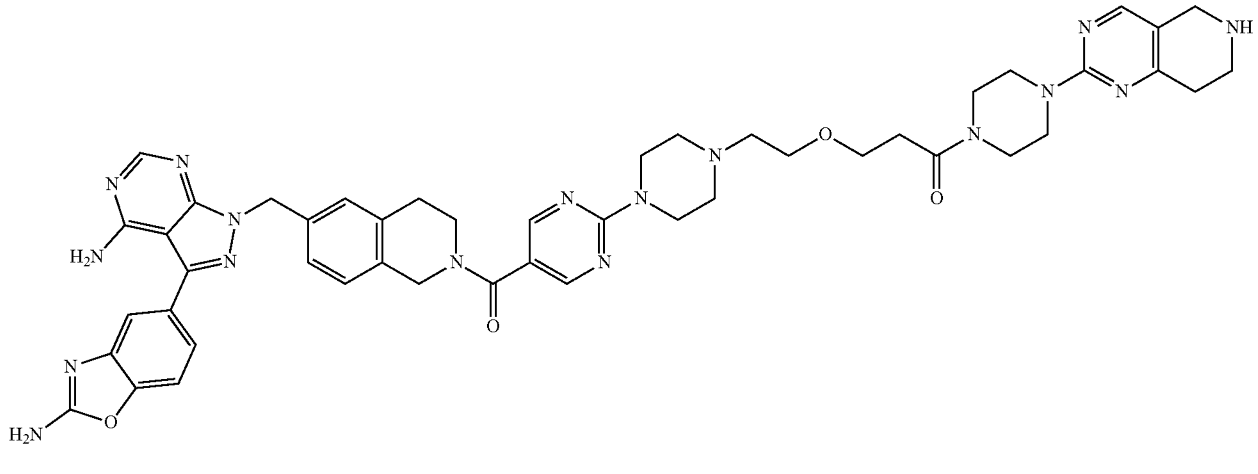 [SMILES: Nc1nc2cc(-c3nn(Cc4ccc5c(c4)CCN(C(=O)c4cnc(N6CCN(CCOCCC(=O)N7CCN(c8ncc9c(n8)CCNC9)CC7)CC6)nc4)C5)c4ncnc(N)c34)ccc2o1] Intermediate D1-10 | $C_{47}H_{53}N_{17}O_4$ | [M + H] = 920.46 | [M + H] = 920.4 |
| 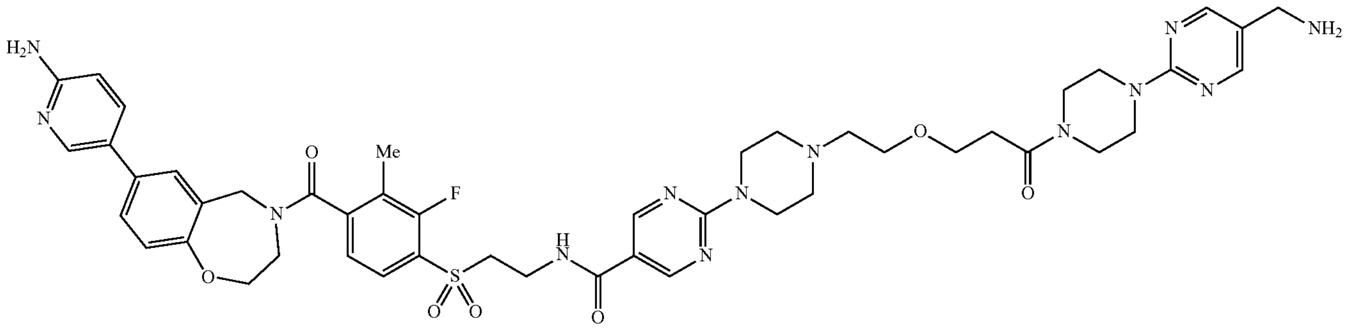 [SMILES: Cc1c(C(=O)N2CCOc3ccc(-c4ccc(N)nc4)cc3C2)ccc(S(=O)(=O)CCNC(=O)c2cnc(N3CCN(CCOCCC(=O)N4CCN(c5ncc(CN)cn5)CC4)CC3)nc2)c1F] Intermediate D1-11 | $C_{47}H_{56}FN_{13}O_7S$ | [M + H] = 966.42 | [M + H] = 966.3 |

TABLE 20-continued
| Additional amines prepared | | | |
|---|---|---|---|
| Structure | Molecular Formula | Calculated MW | Observed MW |
| 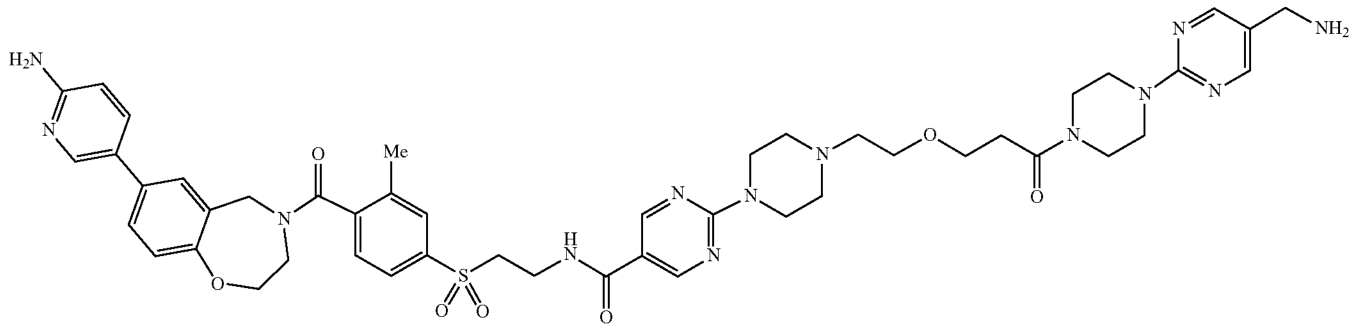 [SMILES: Cc1cc(S(=O)(=O)CCNC(=O)c2cnc(N3CCN(CCOCCC(=O)N4CCN(c5ncc(CN)cn5)CC4)CC3)nc2)ccc1C(=O)N1CCOc2ccc(-c3ccc(N)nc3)cc2C1] Intermediate D1-12 | $C_{47}H_{57}N_{13}O_7S$ | [M + H] = 948.43 | [M + H] = 948.4 |
| 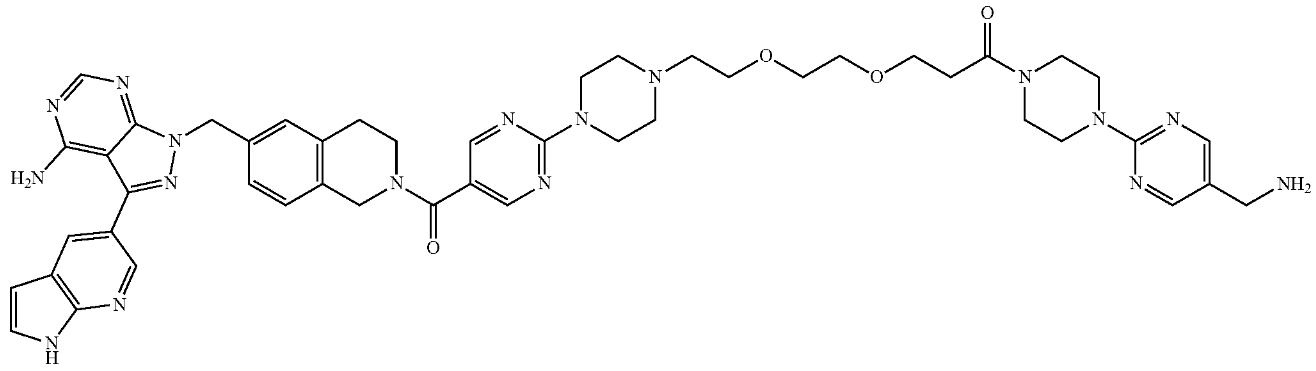 [SMILES: NCc1cnc(N2CCN(C(=O)CCOCCOCCN3CCN(c4ncc(C(=O)N5CCc6cc(Cn7nc(-c8cnc9[nH]ccc9c8)c8c(N)ncnc87)ccc6C5)cn4)CC3)CC2)nc1] Intermediate D1-13 | $C_{47}H_{55}N_{17}O_4$ | [M + H] = 922.47 | [M + H] = 922.4 |

TABLE 20-continued
| Additional amines prepared | | | |
|---|---|---|---|
| Structure | Molecular Formula | Calculated MW | Observed MW |
| 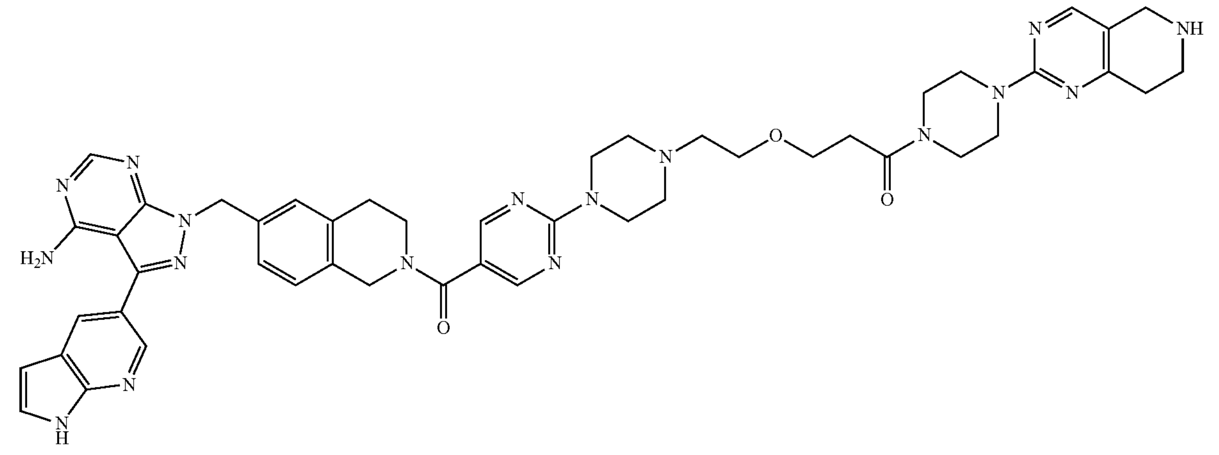 [SMILES: Nc1ncnc2c1c(-c1cnc3[nH]ccc3c1)nn2Cc1ccc2c(c1)CCN(C(=O)c1cnc(N3CCN(CCOCCC(=O)N4CCN(c5ncc6c(n5)CCNC6)CC4)CC3)nc1)C2]<br>Intermediate D1-14 | $C_{47}H_{53}N_{17}O_3$ | [M + H] = 904.46 | [M + H] = 904.4 |
| 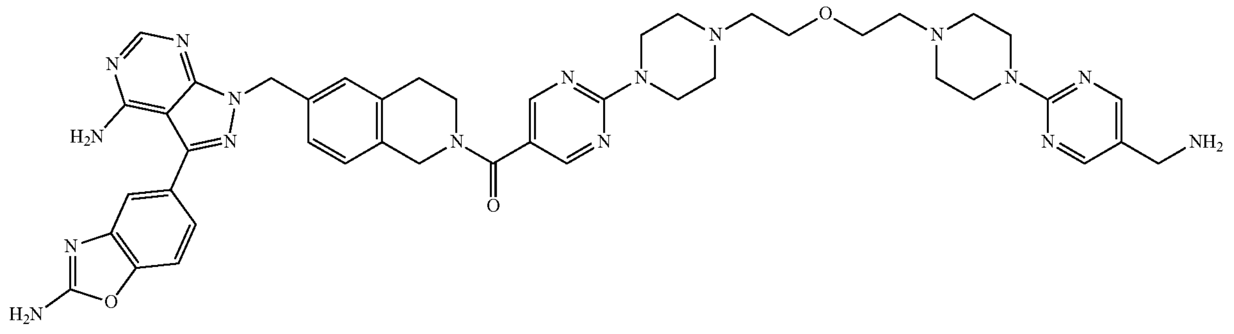 [SMILES: NCc1cnc(N2CCN(CCOCCN3CCN(c4ncc(C(=O)N5CCc6cc(Cn7nc(-c8ccc9oc(N)nc9c8)c8c(N)ncnc87)ccc6C5)cn4)CC3)CC2)nc1]<br>Intermediate D1-15 | $C_{44}H_{51}N_{17}O_3$ | [M + H] = 866.45 | [M + H] = 866.3 |

TABLE 20-continued
| Additional amines prepared | | | |
|---|---|---|---|
| Structure | Molecular Formula | Calculated MW | Observed MW |
| 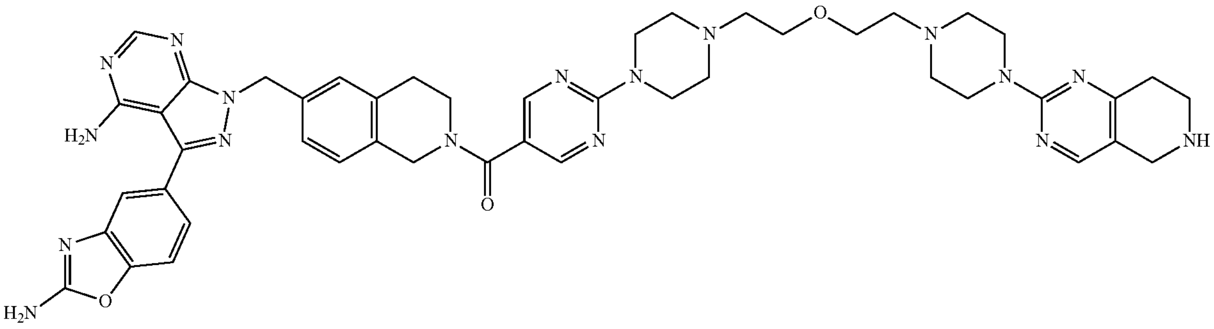 [SMILES: Nc1nc2cc(-c3nn(Cc4ccc5c(c4)CCN(C(=O)c4cnc(N6CCN(CCOCCN7CCN(c8ncc9c(n8)CCNC9)CC7)CC6)nc4)C5)c4ncnc(N)c34)ccc2o1] Intermediate D1-16 | $C_{46}H_{53}N_{17}O_3$ | [M + H] = 892.46 | [M + H] = 892.3 |
| 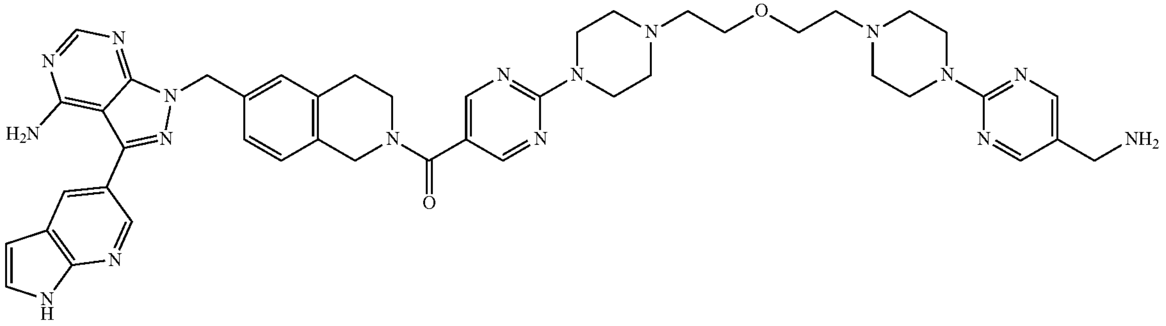 [SMILES: NCc1cnc(N2CCN(CCOCCN3CCN(c4ncc(C(=O)N5CCc6cc(Cn7nc(-c8cnc9[nH]ccc9c8)c8c(N)ncnc87)ccc6C5)cn4)CC3)CC2)nc1] Intermediate D1-17 | $C_{44}H_{51}N_{17}O_2$ | [M + H] = 850.45 | [M + H] = 850.3 |

TABLE 20-continued
| Additional amines prepared | | | |
|---|---|---|---|
| Structure | Molecular Formula | Calculated MW | Observed MW |
| 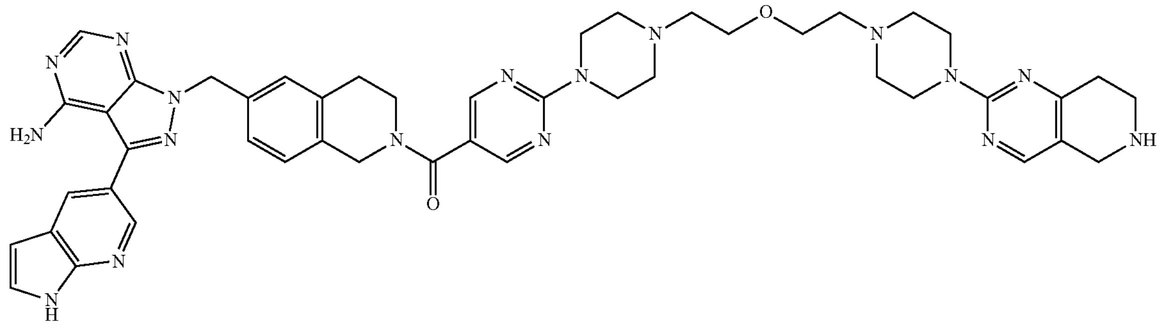 [SMILES: Nc1ncnc2c1c(-c1cnc3[nH]ccc3c1)nn2Cc1ccc2c(c1)CCN(C(=O)c1cnc(N3CCN(CCOCCN4CCN(c5ncc6c(n5)CCNC6)CC4)CC3)nc1)C2]<br>Intermediate D1-18 | $C_{46}H_{53}N_{17}O_2$ | [M + H] = 876.47 | [M + H] = 876.3 |
| 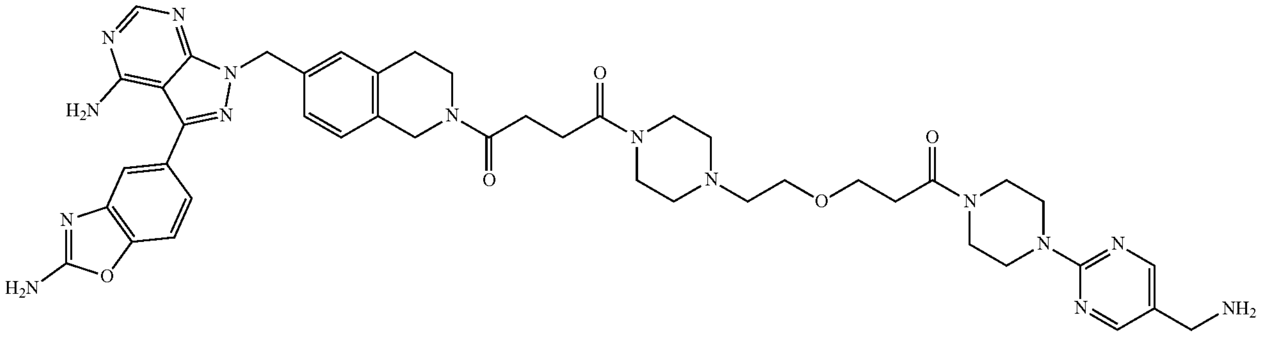 [SMILES: NCc1cnc(N2CCN(C(=O)CCOCCN3CCN(C(=O)CCC(=O)N4CCc5cc(Cn6nc(-c7ccc8oc(N)nc8c7)c7c(N)ncnc76)ccc5C4)CC3)CC2)nc1]<br>Intermediate D1-19 | $C_{44}H_{53}N_{15}O_5$ | [M + H] = 872.45 | [M + H] = 872.3 |

TABLE 20-continued
| Additional amines prepared | | | |
|---|---|---|---|
| Structure | Molecular Formula | Calculated MW | Observed MW |
| 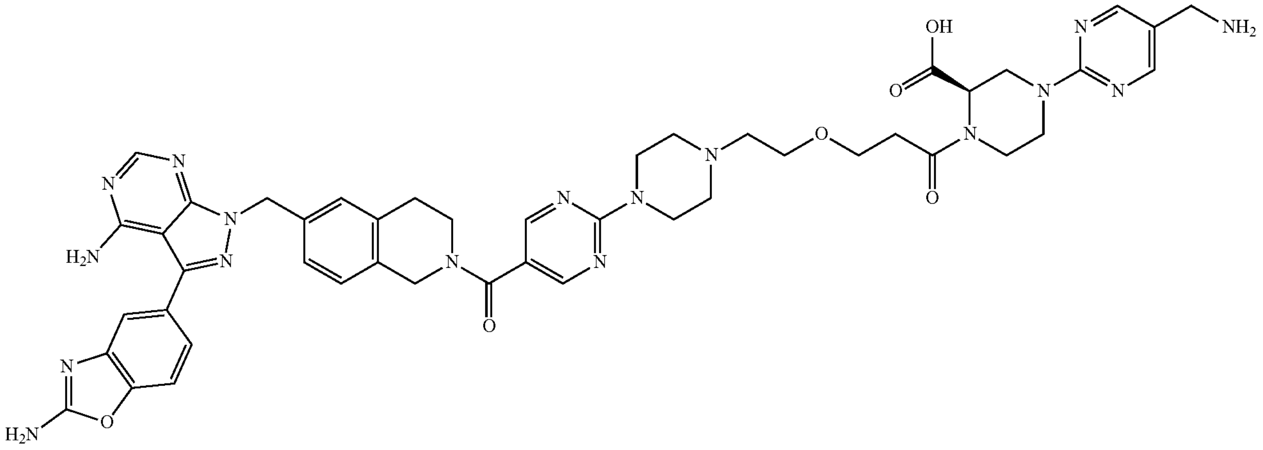 [SMILES: NCc1cnc(N2CCN(C(=O)CCOCCN3CCN(c4ncc(C(=O)N5CCc6cc(Cn7nc(-c8ccc9oc(N)nc9c8)c8c(N)ncnc87)ccc6C5)cn4)CC3)[C@@H](C(=O)O)C2)nc1] Intermediate D1-20 | $C_{46}H_{51}N_{17}O_6$ | [M + H] = 938.61 | [M + H] = 938.3 |
| 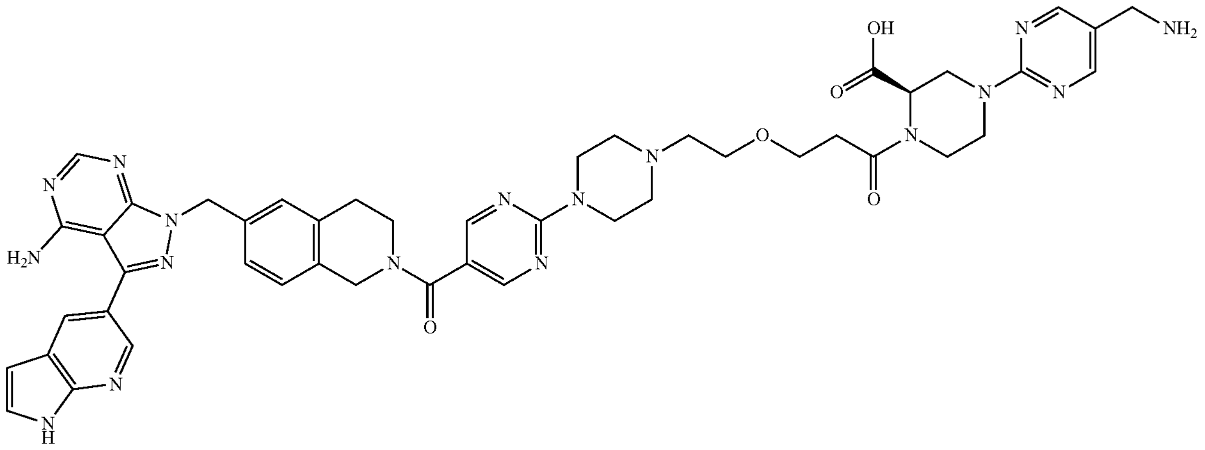 [SMILES: NCc1cnc(N2CCN(C(=O)CCOCCN3CCN(c4ncc(C(=O)N5CCc6cc(Cn7nc(-c8cnc9[nH]ccc9c8)c8c(N)ncnc87)ccc6C5)cn4)CC3)[C@@H](C(=O)O)C2)nc1] Intermediate D1-21 | $C_{46}H_{51}N_{17}O_5$ | [M + H] = 922.44 | [M + H] = 922.3 |

TABLE 20-continued
| Additional amines prepared | | | |
|---|---|---|---|
| Structure | Molecular Formula | Calculated MW | Observed MW |
| 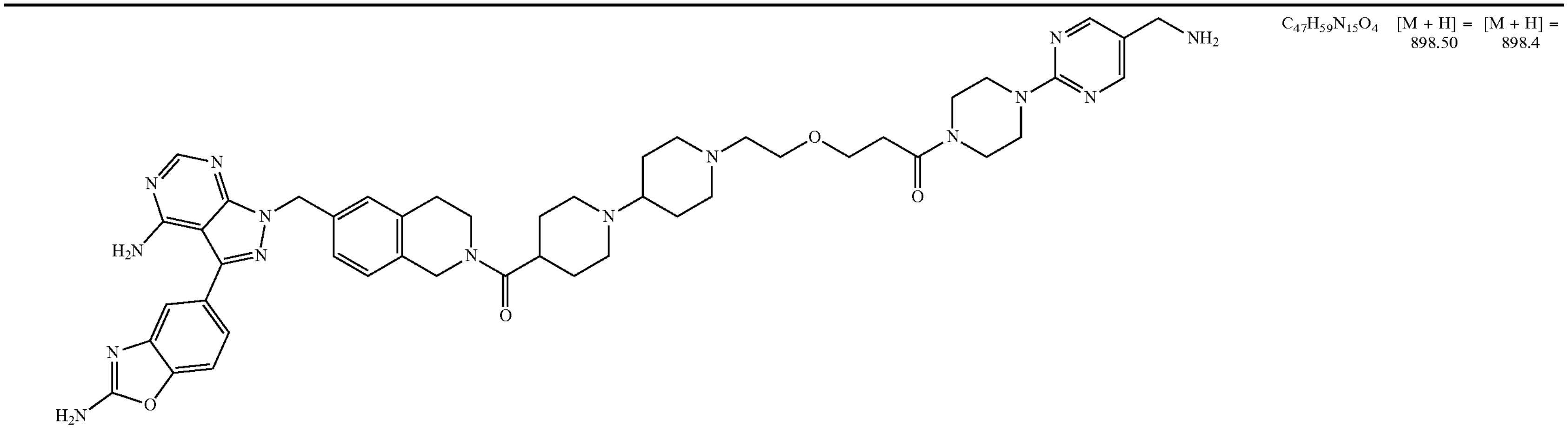 Intermediate D1-22 | $C_{47}H_{59}N_{15}O_4$ | [M + H] = 898.50 | [M + H] = 898.4 |

Following General Procedure 2, but using the appropriate 4-nitrophenyl carbonate containing rapamycin monomer in Table 1 and Intermediates D1 from Tables 19 and 20, the Series 4 bivalent analogs in Table 21 were synthesized:

TABLE 21
| Series 4 Bivalent Compounds | | | |
|---|---|---|---|
| Structure | Molecular Formula | Calculated MW | Observed MW |
| 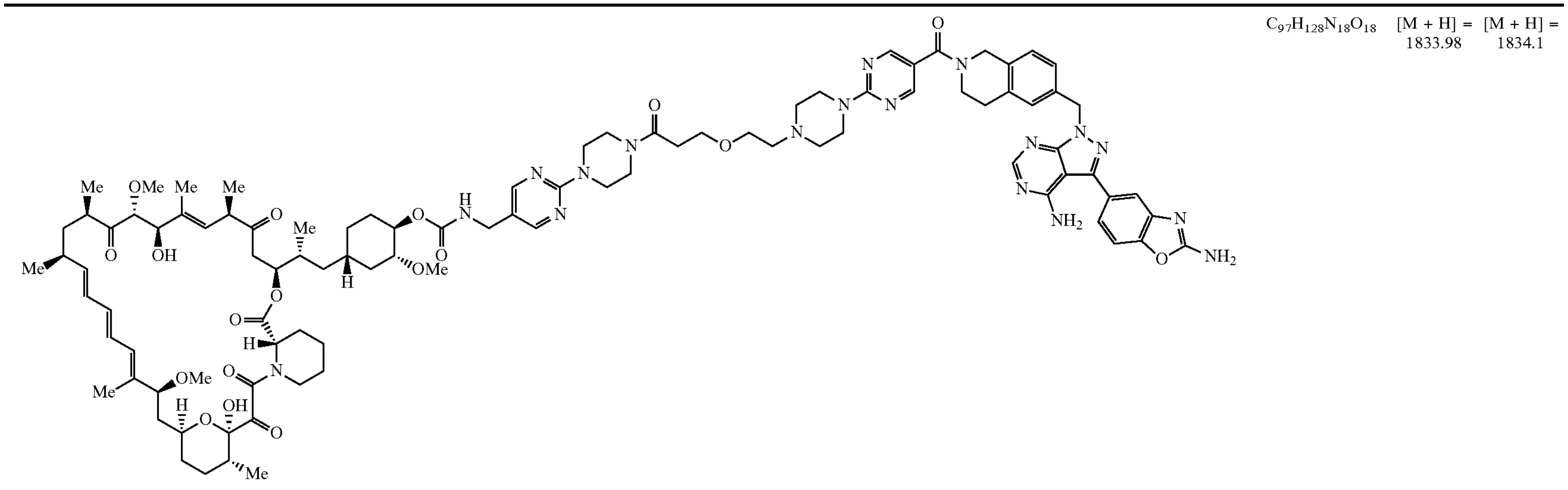 Example 51 | $C_{97}H_{128}N_{18}O_{18}$ | [M + H] = 1833.98 | [M + H] = 1834.1 |

TABLE 21-continued
| Series 4 Bivalent Compounds | | | |
|---|---|---|---|
| Structure | Molecular Formula | Calculated MW | Observed MW |
| 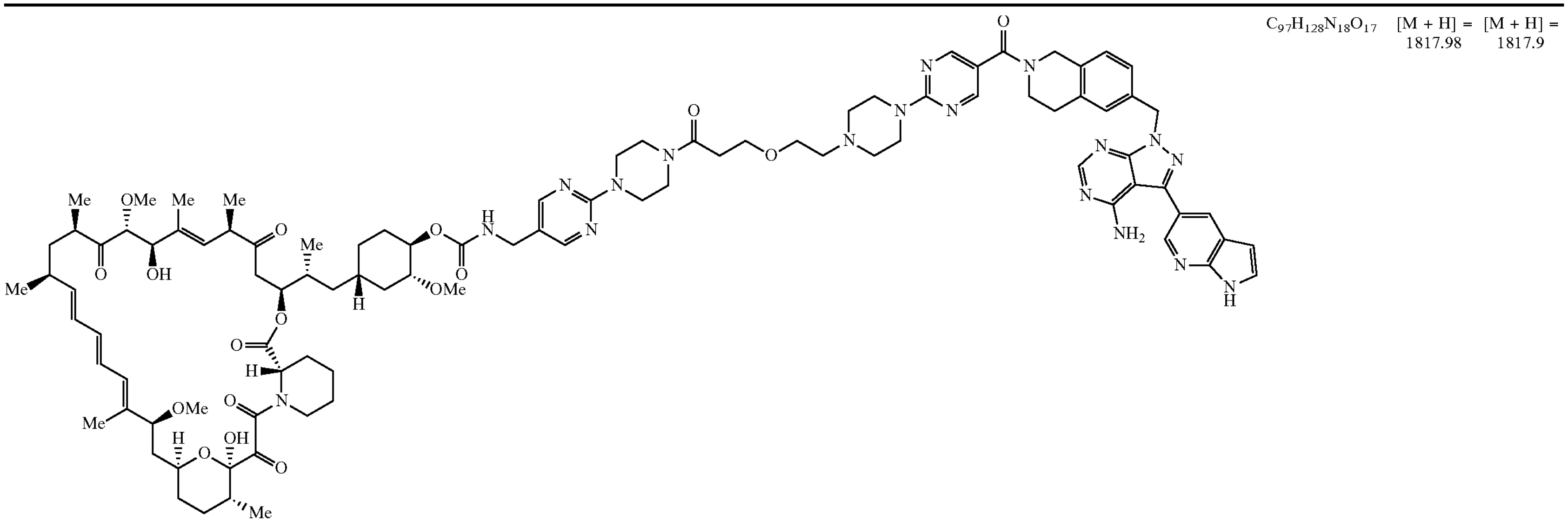<br>Example 52 | $C_{97}H_{128}N_{18}O_{17}$ | [M + H] = 1817.98 | [M + H] = 1817.9 |

TABLE 21-continued
Series 4 Bivalent Compounds
| Structure | Molecular Formula | Calculated MW | Observed MW |
| --- | --- | --- | --- |
| 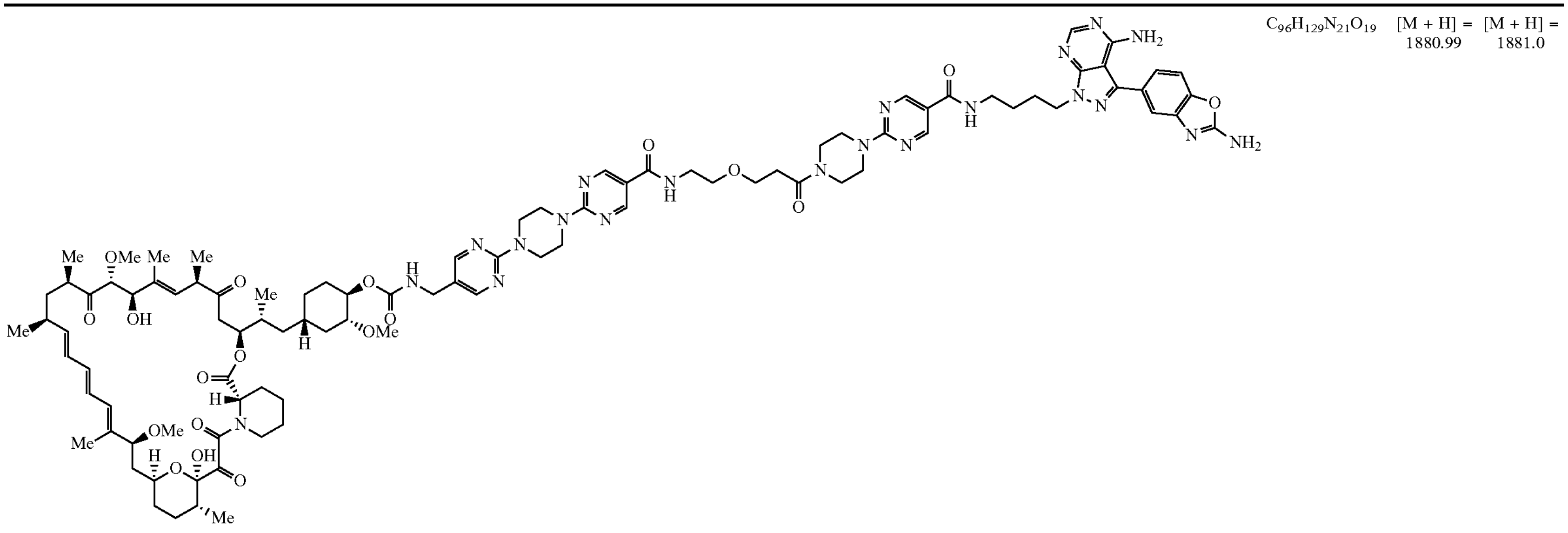 Example 53 | $C_{96}H_{129}N_{21}O_{19}$ | [M + H] = 1880.99 | [M + H] = 1881.0 |

TABLE 21-continued
| Series 4 Bivalent Compounds | | | |
|---|---|---|---|
| Structure | Molecular Formula | Calculated MW | Observed MW |
| 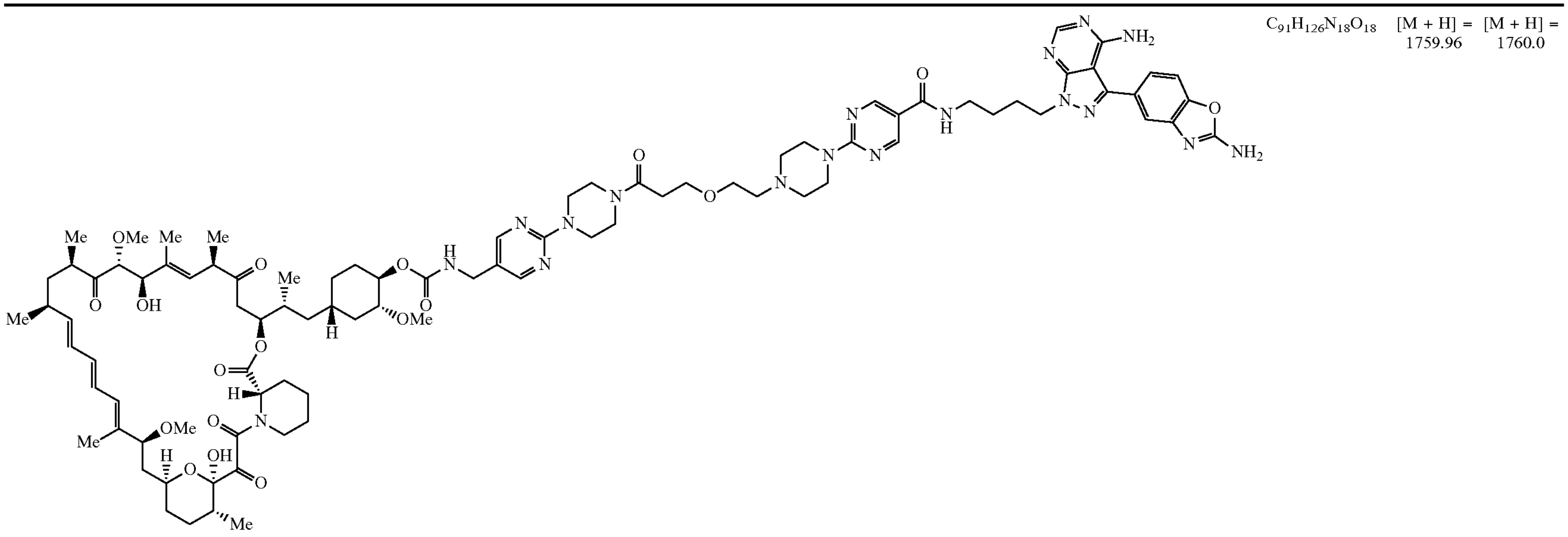 Example 54 | $C_{91}H_{126}N_{18}O_{18}$ | [M + H] = 1759.96 | [M + H] = 1760.0 |

TABLE 21-continued
| Series 4 Bivalent Compounds | | | |
|---|---|---|---|
| Structure | Molecular Formula | Calculated MW | Observed MW |
| 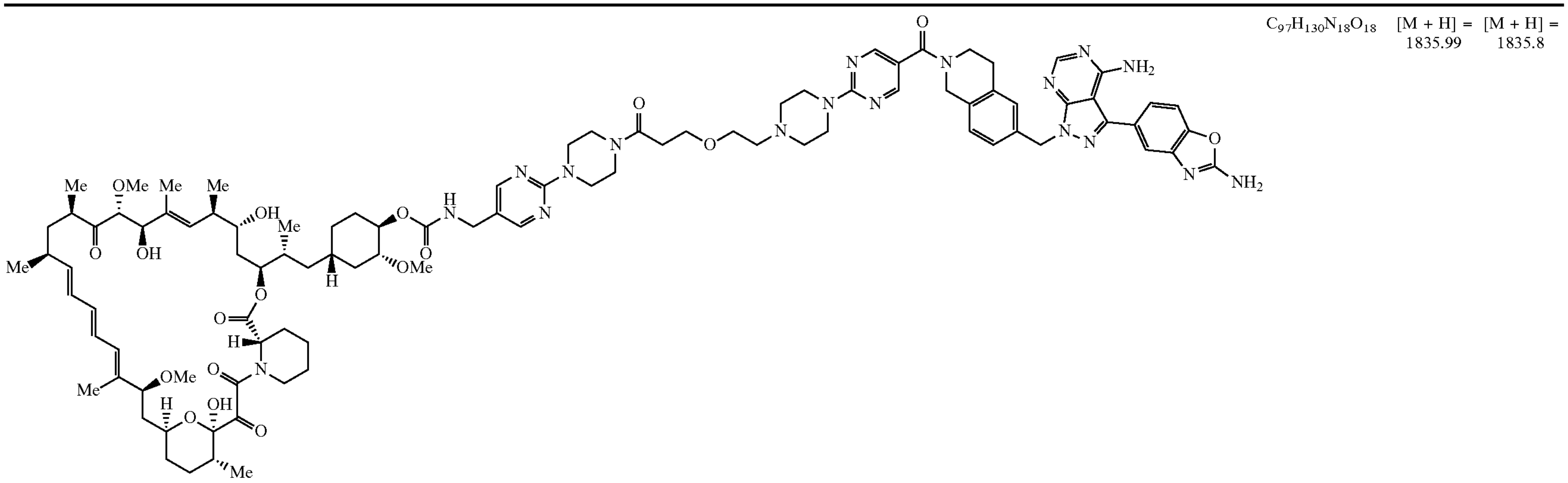<br>Example 55 | $C_{97}H_{130}N_{18}O_{18}$ | [M + H] = 1835.99 | [M + H] = 1835.8 |

TABLE 21-continued
| Series 4 Bivalent Compounds | | | |
|---|---|---|---|
| Structure | Molecular Formula | Calculated MW | Observed MW |
| 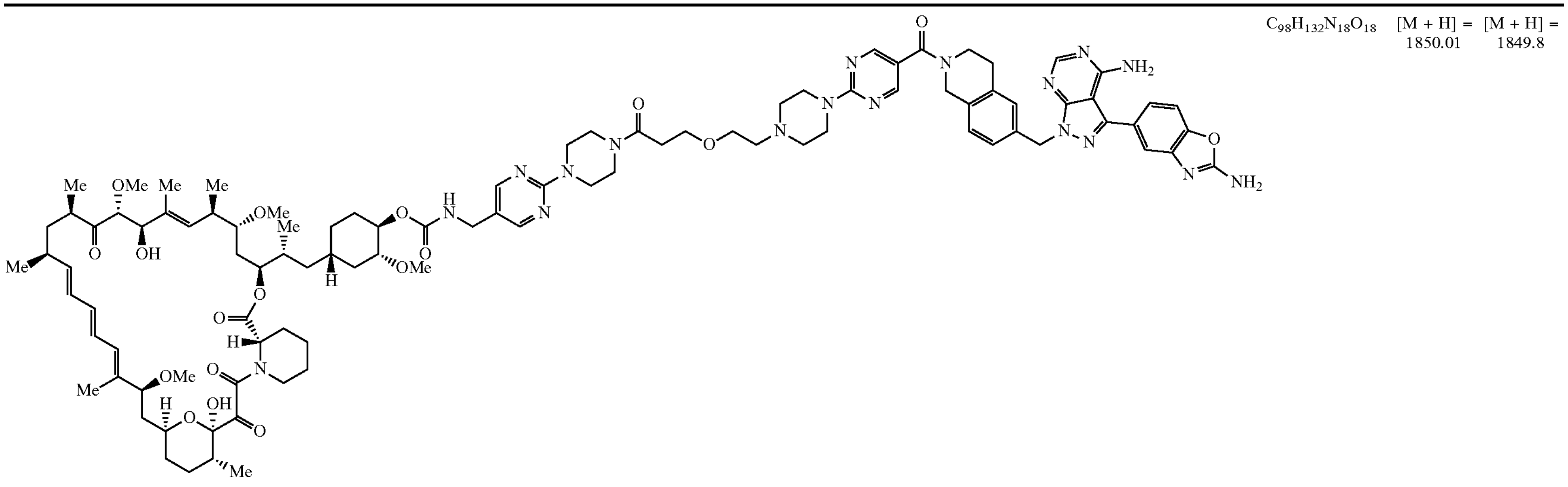<br>Example 56 | $C_{98}H_{132}N_{18}O_{18}$ | [M + H] = 1850.01 | [M + H] = 1849.8 |

TABLE 21-continued
| Series 4 Bivalent Compounds | | | |
|---|---|---|---|
| Structure | Molecular Formula | Calculated MW | Observed MW |
| 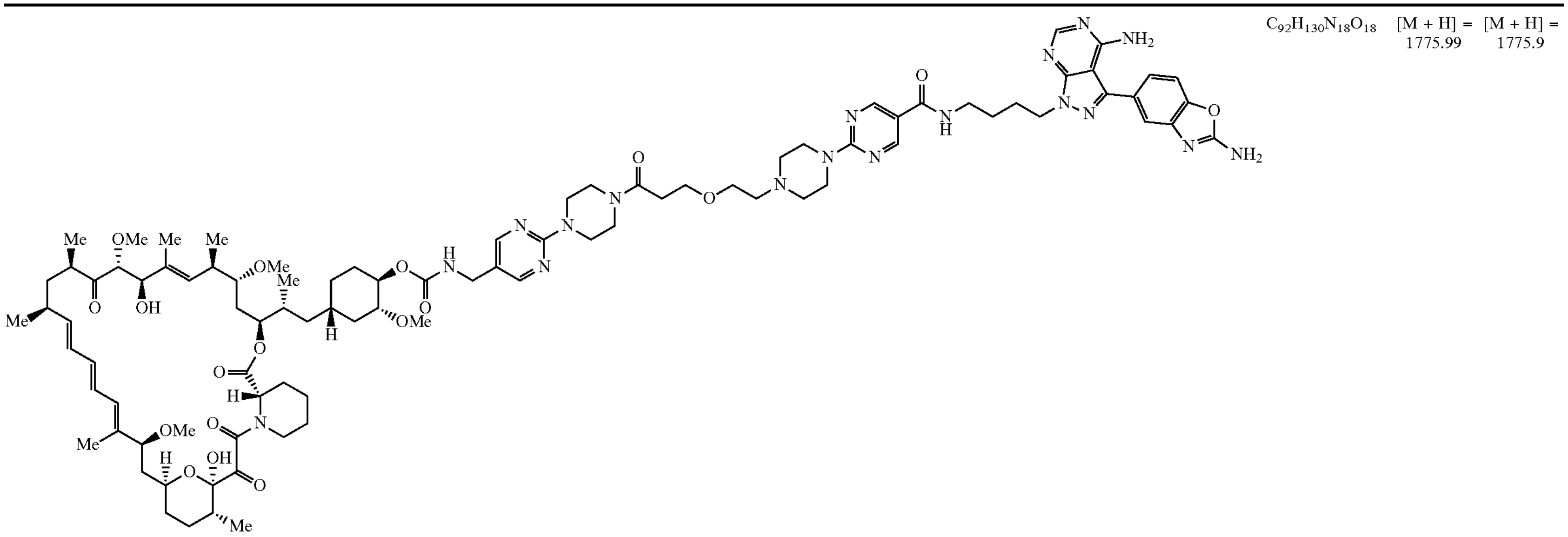<br>Example 57 | $C_{92}H_{130}N_{18}O_{18}$ | [M + H] = 1775.99 | [M + H] = 1775.9 |

TABLE 21-continued
| Series 4 Bivalent Compounds | | | |
|---|---|---|---|
| Structure | Molecular Formula | Calculated MW | Observed MW |
| 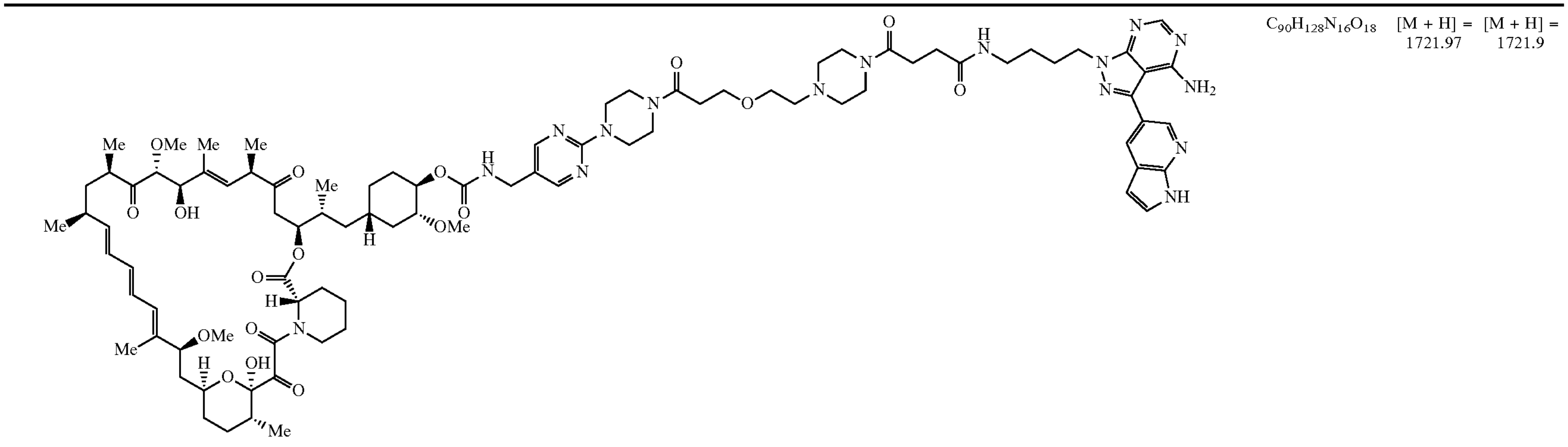 Example 58 | $C_{90}H_{128}N_{16}O_{18}$ | [M + H] = 1721.97 | [M + H] = 1721.9 |

TABLE 21-continued
| Series 4 Bivalent Compounds | | | |
|---|---|---|---|
| Structure | Molecular Formula | Calculated MW | Observed MW |
| 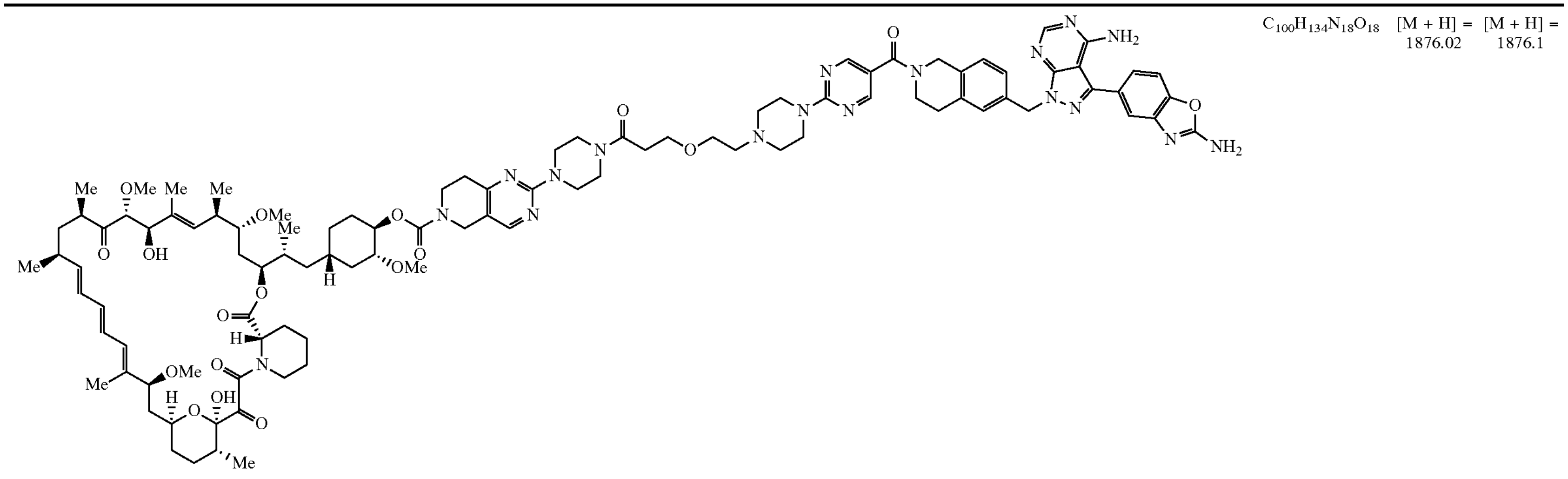<br>Example 114 | $C_{100}H_{134}N_{18}O_{18}$ | [M + H] = 1876.02 | [M + H] = 1876.1 |

TABLE 21-continued
| Series 4 Bivalent Compounds | | | |
|---|---|---|---|
| Structure | Molecular Formula | Calculated MW | Observed MW |
| 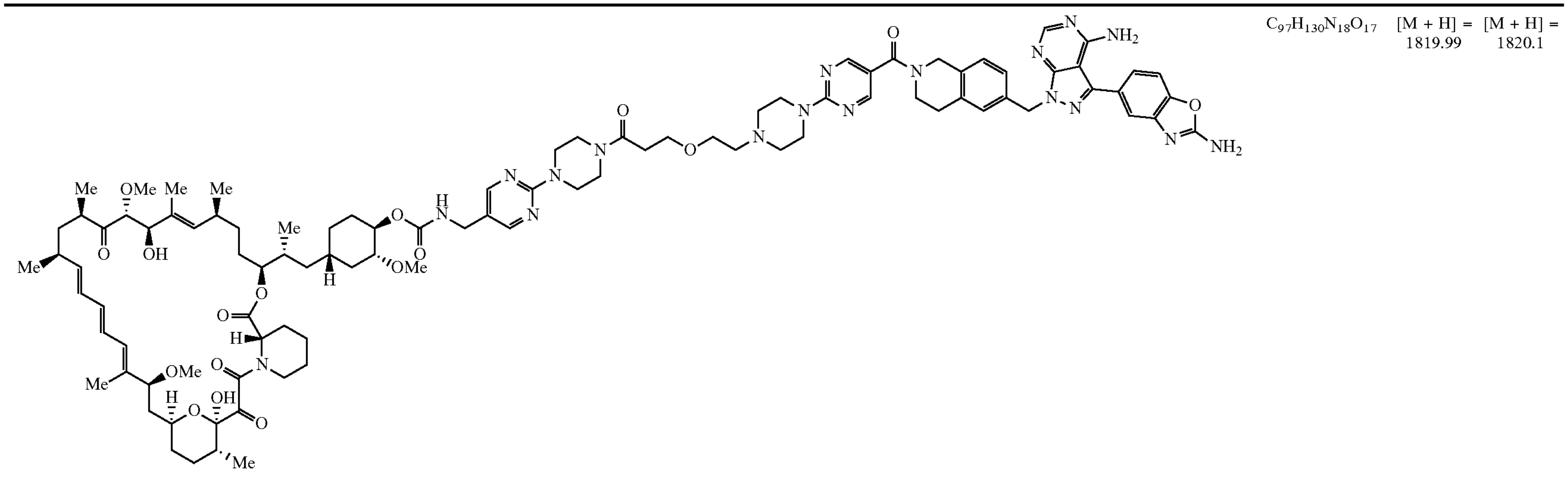<br>Example 115 | $C_{97}H_{130}N_{18}O_{17}$ | [M + H] = 1819.99 | [M + H] = 1820.1 |

TABLE 21-continued
| Series 4 Bivalent Compounds | | | |
|---|---|---|---|
| Structure | Molecular Formula | Calculated MW | Observed MW |
| 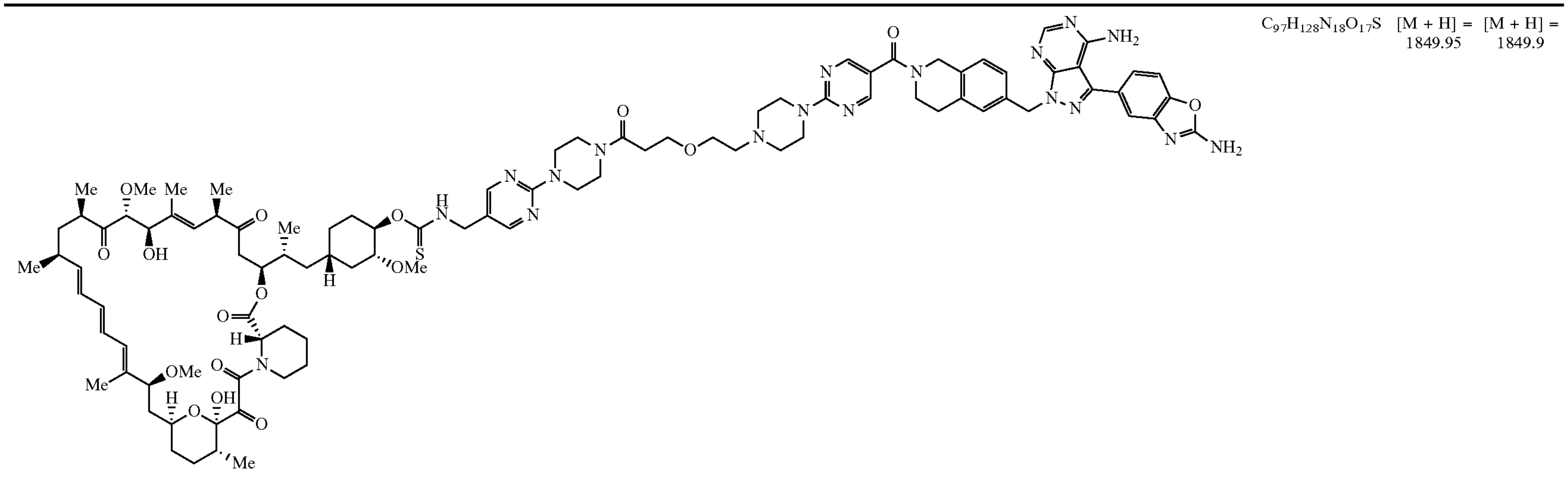 Example 116 | $C_{97}H_{128}N_{18}O_{17}S$ | [M + H] = 1849.95 | [M + H] = 1849.9 |

TABLE 21-continued
| Series 4 Bivalent Compounds | | | |
|---|---|---|---|
| Structure | Molecular Formula | Calculated MW | Observed MW |
| 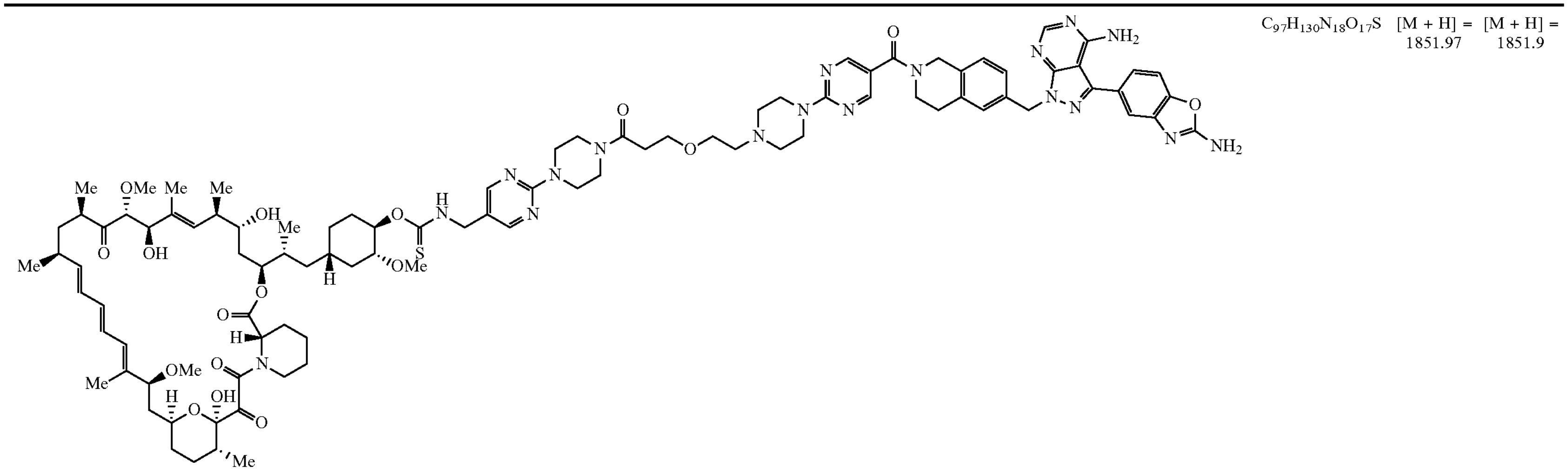 Example 117 | $C_{97}H_{130}N_{18}O_{17}S$ | [M + H] = 1851.97 | [M + H] = 1851.9 |

TABLE 21-continued
| Series 4 Bivalent Compounds | | | |
|---|---|---|---|
| Structure | Molecular Formula | Calculated MW | Observed MW |
| 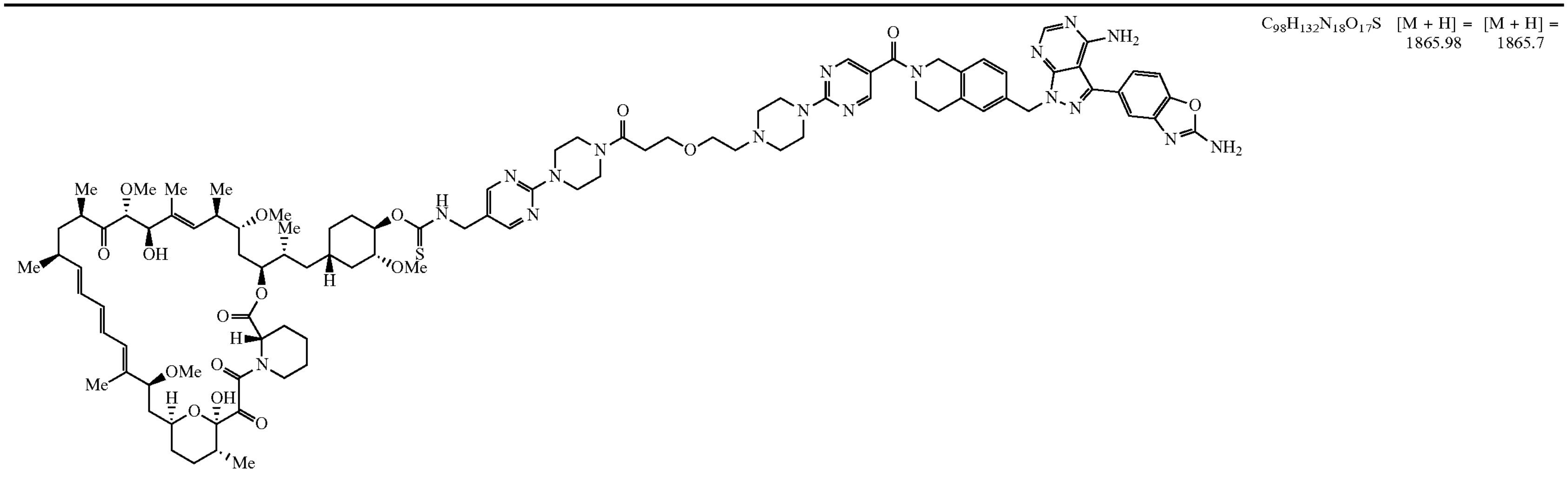 Example 118 | $C_{98}H_{132}N_{18}O_{17}S$ | [M + H] = 1865.98 | [M + H] = 1865.7 |

TABLE 21-continued
| Series 4 Bivalent Compounds | | | |
|---|---|---|---|
| Structure | Molecular Formula | Calculated MW | Observed MW |
| 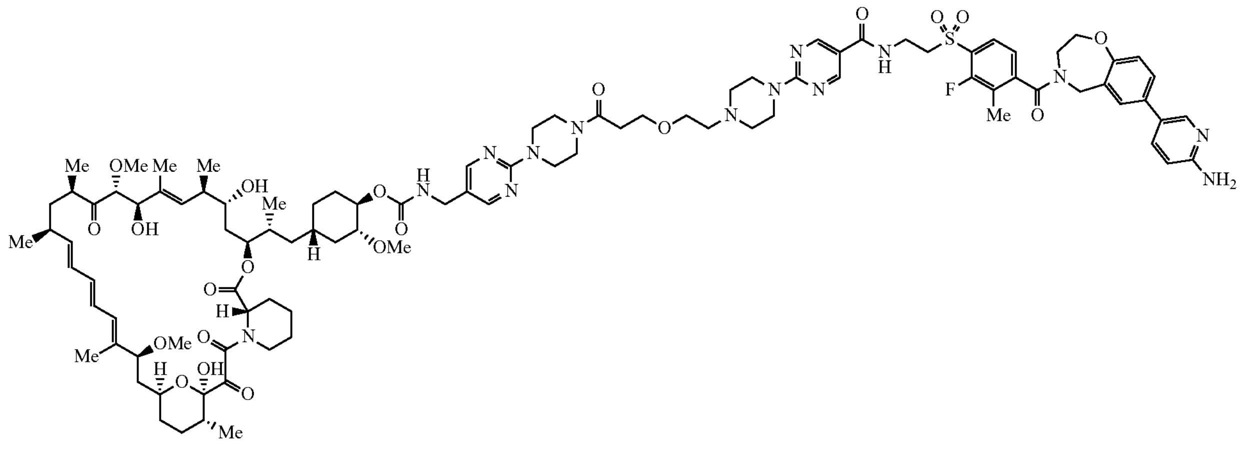 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCc3cnc(N4CCN(C(=O)CCOCCN5CCN(c6ncc(C(=O)NCCS(=O)(=O)c7ccc(C(=O)N8CCOc9ccc(-c%10ccc(N)nc%10)cc9C8)c(C)c7F)cn6)CC5)CC4)nc3)[C@H](OC)C2)C[C@@H](O)[C@H](C)/C=C(\C)[C@@H](O)[C@@H](OC)C(=O)[C@H](C)C[C@H](C)/C=C/C=C/C=C/1C] Example 119 | $C_{99}H_{135}FN_{14}O_{21}S$ | [M + H] = 1907.97 | [M + H] = 1908.0 |
| 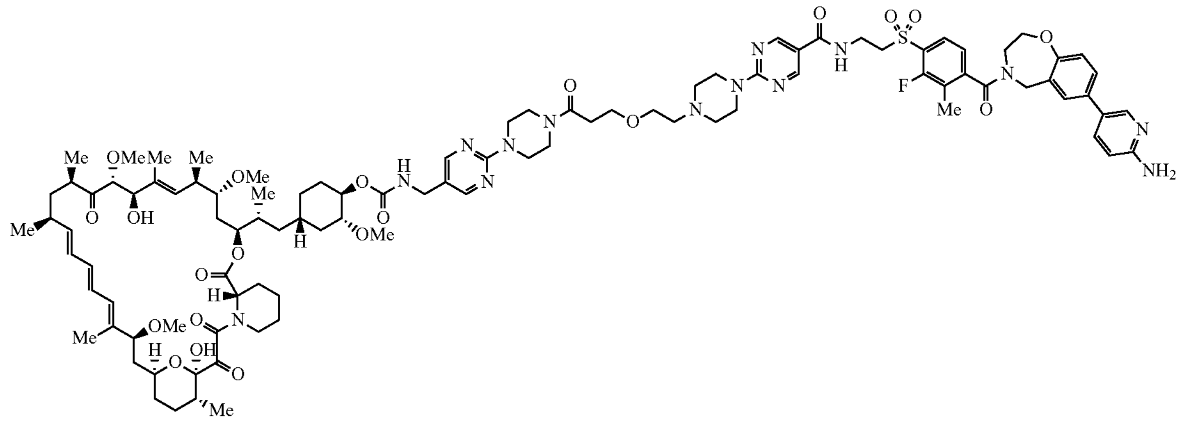 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCc3cnc(N4CCN(C(=O)CCOCCN5CCN(c6ncc(C(=O)NCCS(=O)(=O)c7ccc(C(=O)N8CCOc9ccc(-c%10ccc(N)nc%10)cc9C8)c(C)c7F)cn6)CC5)CC4)nc3)[C@H](OC)C2)C[C@@H](OC)[C@H](C)/C=C(\C)[C@@H](O)[C@@H](OC)C(=O)[C@H](C)C[C@H](C)/C=C/C=C/C=C/1C] Example 120 | $C_{100}H_{137}FN_{14}O_{21}S$ | [M + H] = 1921.99 | [M + H] = 1922.0 |

TABLE 21-continued
| Series 4 Bivalent Compounds | | | |
|---|---|---|---|
| Structure | Molecular Formula | Calculated MW | Observed MW |
| 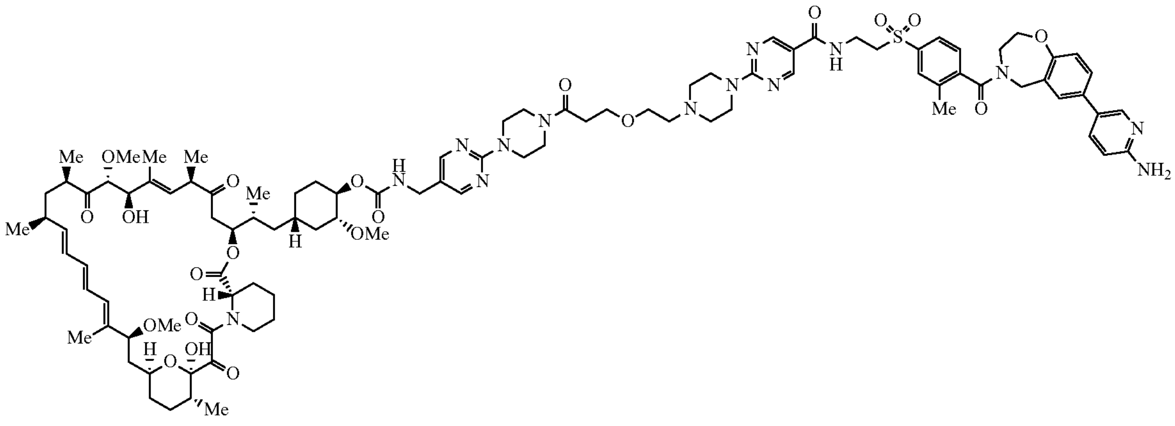 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCc3cnc(N4CCN(C(=O)CCOCCN5CCN(c6ncc(C(=O)NCCS(=O)(=O)c7ccc(C(=O)N8CCOc9ccc(-c%10ccc(N)nc%10)cc9C8)c(C)c7)cn6)CC5)CC4)nc3)[C@H](OC)C2)CC(=O)[C@H](C)/C=C(\C)[C@@H](O)[C@@H](OC)C(=O)[C@H](C)C[C@H](C)/C=C/C=C/C=C/1C] Example 121 | $C_{99}H_{134}N_{14}O_{21}S$ | [M + H] = 1887.96 | [M + H] = 1888.0 |
| 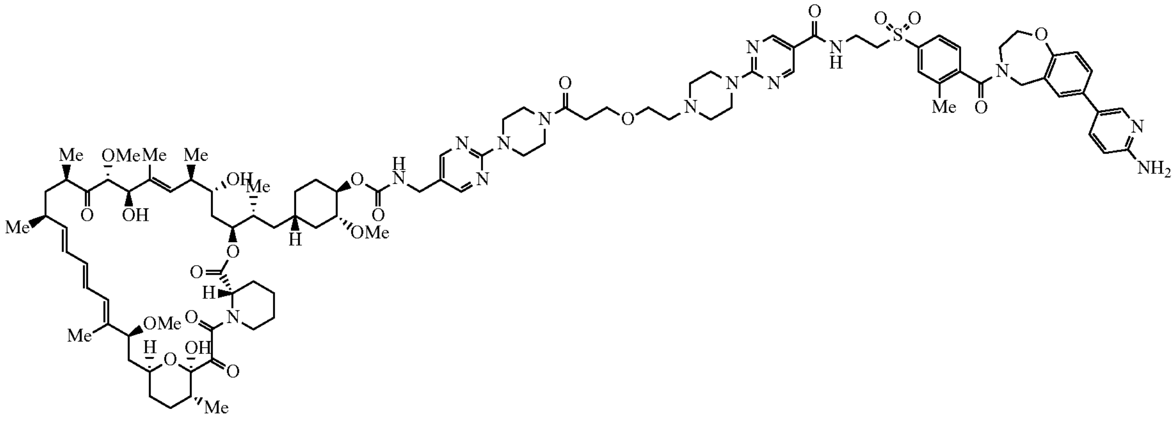 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCc3cnc(N4CCN(C(=O)CCOCCN5CCN(c6ncc(C(=O)NCCS(=O)(=O)c7ccc(C(=O)N8CCOc9ccc(-c%10ccc(N)nc%10)cc9C8)c(C)c7)cn6)CC5)CC4)nc3)[C@H](OC)C2)C[C@@H](O)[C@H](C)/C=C(\C)[C@@H](O)[C@@H](OC)C(=O)[C@H](C)C[C@H](C)/C=C/C=C/C=C/1C] Example 122 | $C_{99}H_{136}N_{14}O_{21}S$ | [M + H] = 1889.98 | [M + H] = 1890.0 |

TABLE 21-continued
Series 4 Bivalent Compounds
| Structure | Molecular Formula | Calculated MW | Observed MW |
| --- | --- | --- | --- |
| 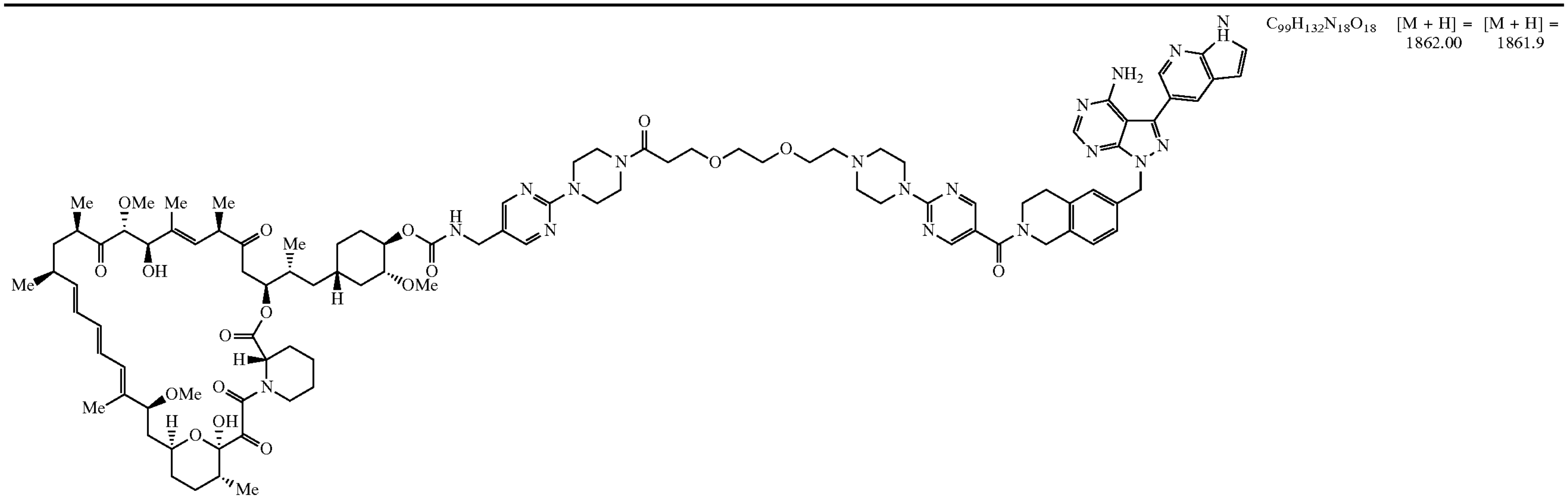 Example 123 | $C_{99}H_{132}N_{18}O_{18}$ | [M + H] = 1862.00 | [M + H] = 1861.9 |

TABLE 21-continued
| Series 4 Bivalent Compounds | | | |
|---|---|---|---|
| Structure | Molecular Formula | Calculated MW | Observed MW |
| 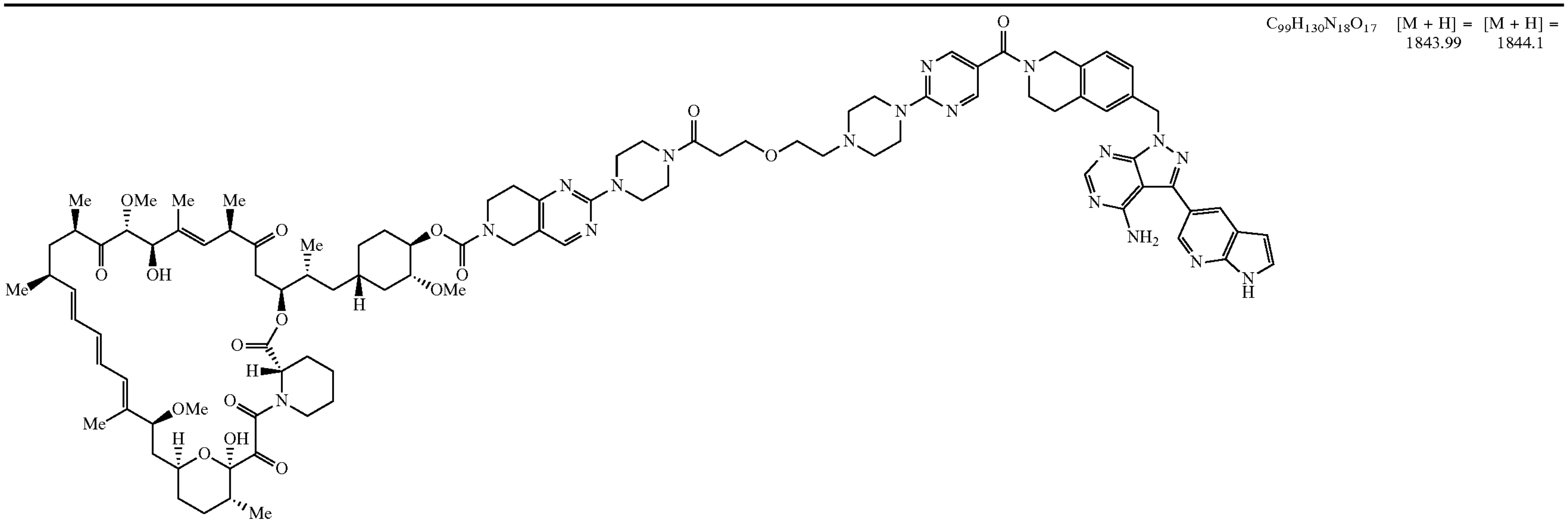<br>Example 124 | $C_{99}H_{130}N_{18}O_{17}$ | [M + H] = 1843.99 | [M + H] = 1844.1 |

TABLE 21-continued
| Series 4 Bivalent Compounds | | | |
|---|---|---|---|
| Structure | Molecular Formula | Calculated MW | Observed MW |
| 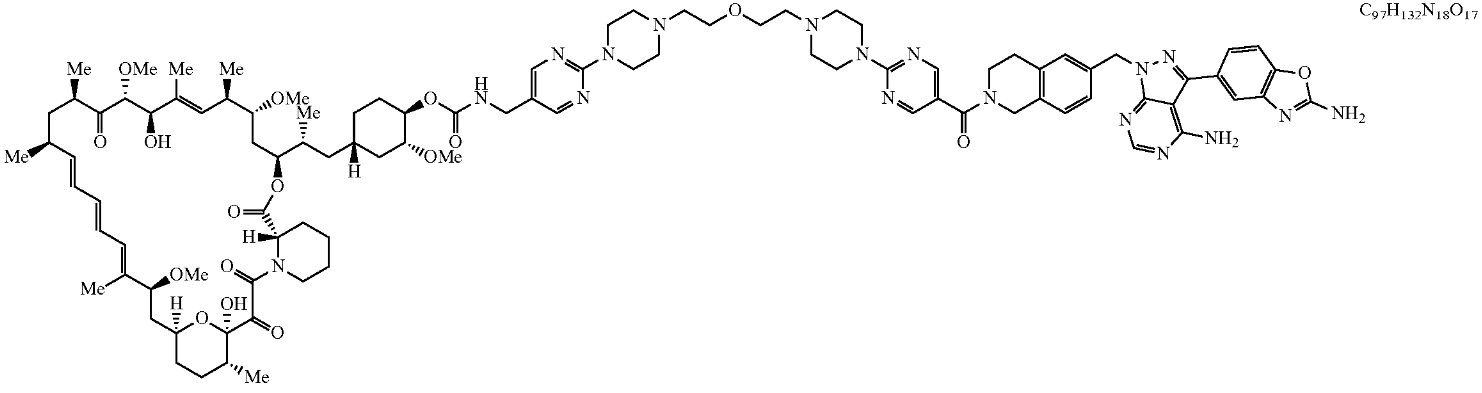 Example 125 | $C_{97}H_{132}N_{18}O_{17}$ | [M + H] = 1822.01 | [M + H] = 1822.0 |
| 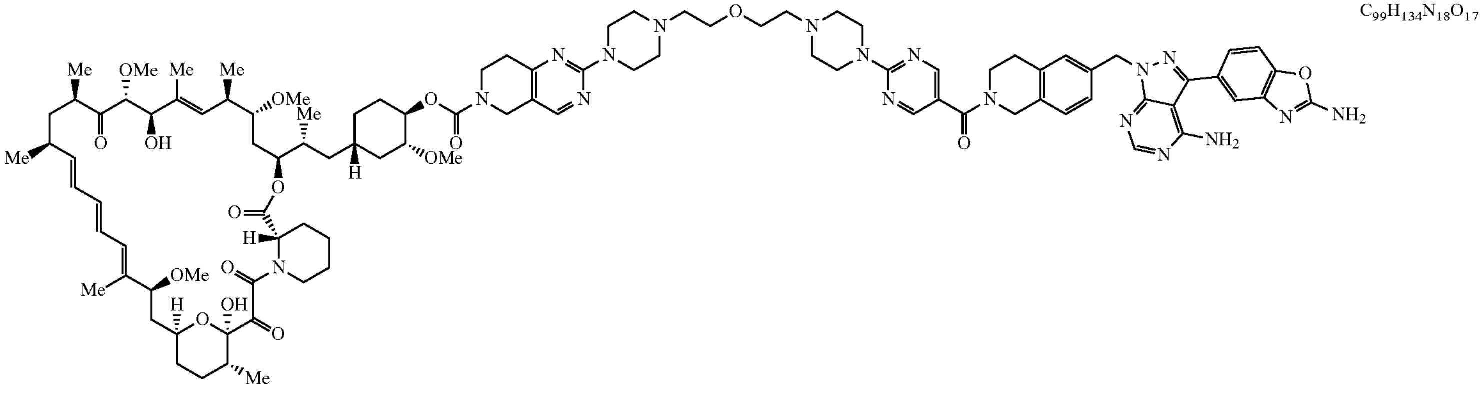 Example 126 | $C_{99}H_{134}N_{18}O_{17}$ | [M + H] = 1848.03 | [M + H] = 1848.0 |

TABLE 21-continued
| Series 4 Bivalent Compounds | | | |
|---|---|---|---|
| Structure | Molecular Formula | Calculated MW | Observed MW |
| 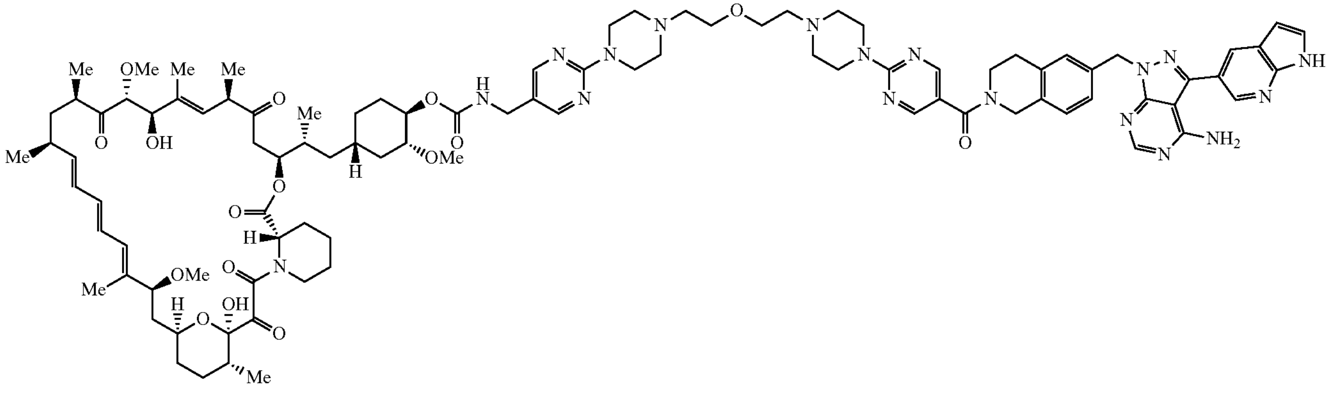 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCc3cnc(N4CCN(CCOCCN5CCN(c6ncc(C(=O)N7CCc8cc(Cn9nc(-c%10cnc%11[nH]ccc%11c%10)c%10c(N)ncnc%109)ccc8C7)cn6)CC5)CC4)nc3)[C@H](OC)C2)CC(=O)[C@H](C)/C=C(\C)[C@@H](O)[C@@H](OC)C(=O)[C@H](C)C[C@H](C)/C=C/C=C/C=C/1C] Example 127 | $C_{96}H_{128}N_{18}O_{16}$ | [M + H] = 1789.98 | [M + H] = 1789.9 |
| 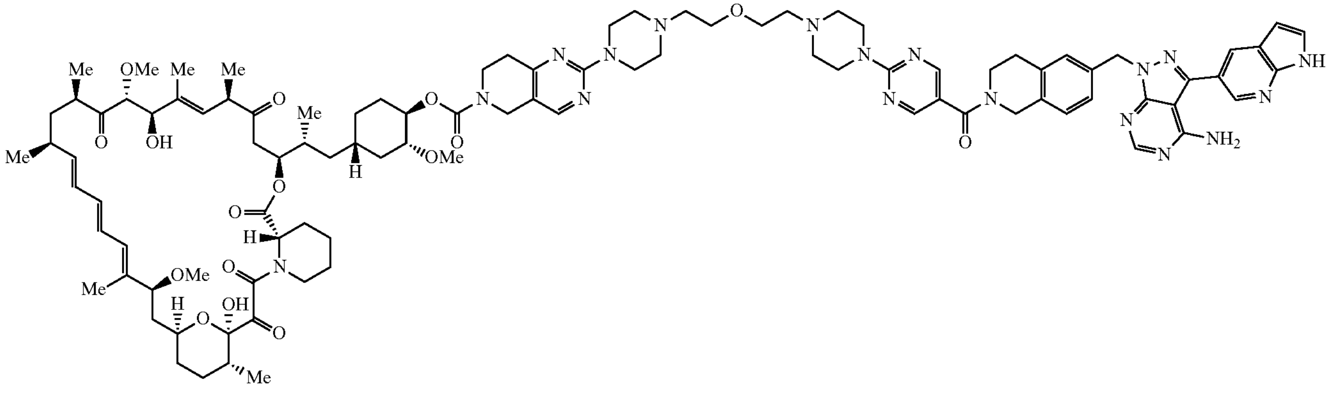 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)N3CCc4nc(N5CCN(CCOCCN6CCN(c7ncc(C(=O)N8CCc9cc(Cn%10nc(-c%11cnc%12[nH]ccc%12c%11)c%11c(N)ncnc%11%10)ccc9C8)cn7)CC6)CC5)ncc4C3)[C@H](OC)C2)CC(=O)[C@H](C)/C=C(\C)[C@@H](O)[C@@H](OC)C(=O)[C@H](C)C[C@H](C)/C=C/C=C/C=C/1C] Example 128 | $C_{98}H_{130}N_{18}O_{16}$ | [M + H] = 1816.00 | [M + H] = 1815.9 |

TABLE 21-continued
| Series 4 Bivalent Compounds | | | |
|---|---|---|---|
| Structure | Molecular Formula | Calculated MW | Observed MW |
| 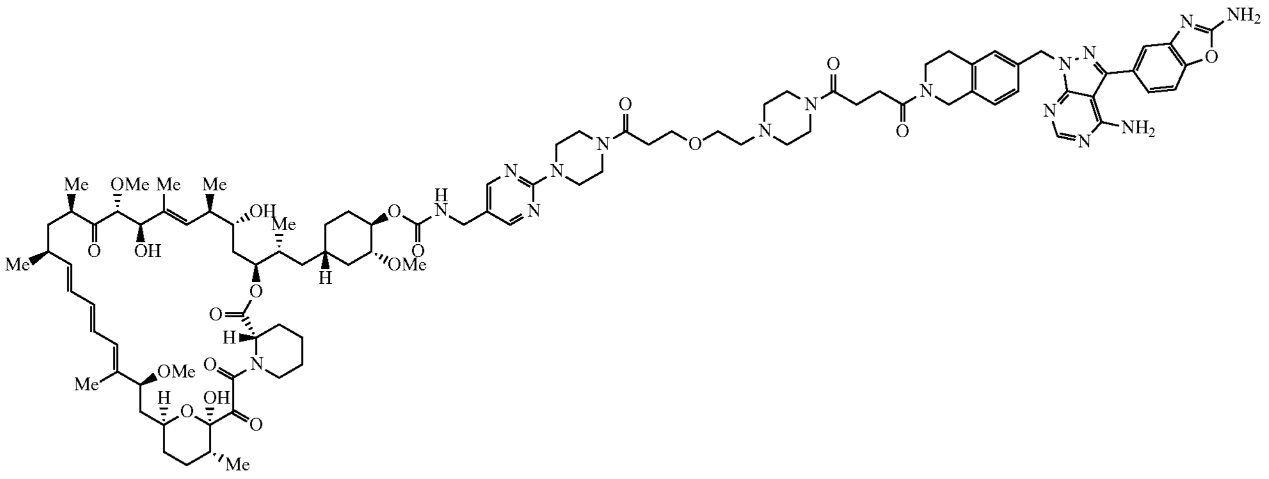 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCc3cnc(N4CCN(C(=O)CCOCCN5CCN(C(=O)CCC(=O)N6CCc7cc(Cn8nc(-c9ccc%10oc(N)nc%10c9)c9c(N)ncnc98)ccc7C6)CC5)CC4)nc3)[C@H](OC)C2)C[C@@H](OC)[C@H](C)/C=C(\C)[C@@H](O)[C@@H](OC)C(=O)[C@H](C)C[C@H](C)/C=C/C=C/C=C/1C]<br>Example 129 | $C_{96}H_{132}N_{16}O_{19}$ | [M + H] = 1813.99 | [M + H] = 1814.0 |

TABLE 21-continued
| Series 4 Bivalent Compounds | | | |
|---|---|---|---|
| Structure | Molecular Formula | Calculated MW | Observed MW |
| 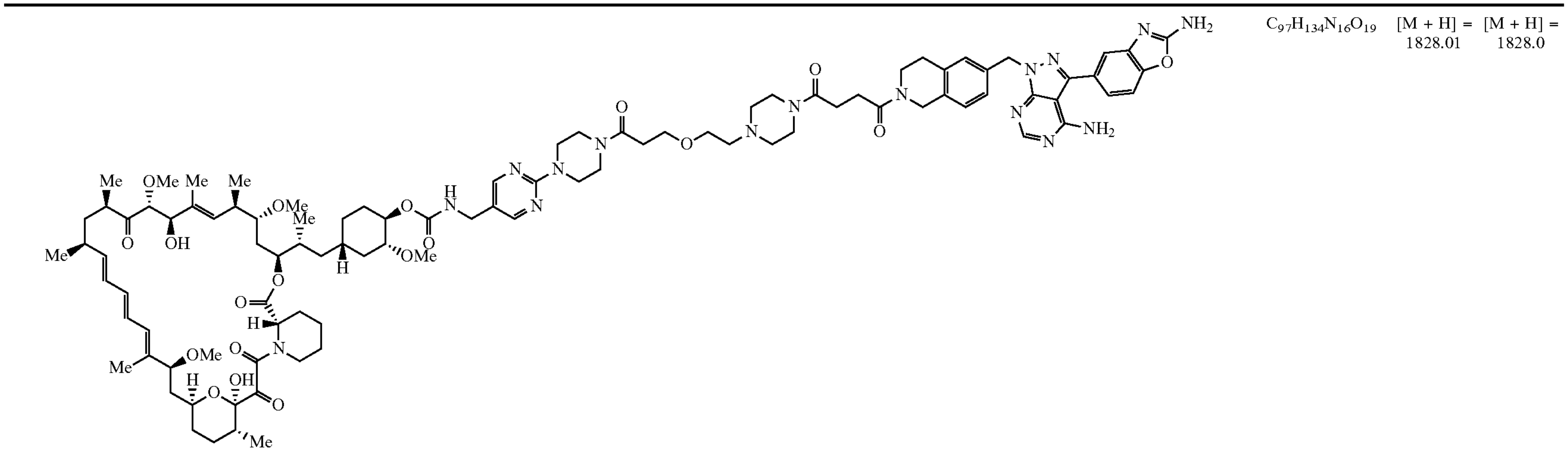<br>Example 130 | $C_{97}H_{134}N_{16}O_{19}$ | [M + H] = 1828.01 | [M + H] = 1828.0 |

TABLE 21-continued
| Series 4 Bivalent Compounds | | | |
|---|---|---|---|
| Structure | Molecular Formula | Calculated MW | Observed MW |
| 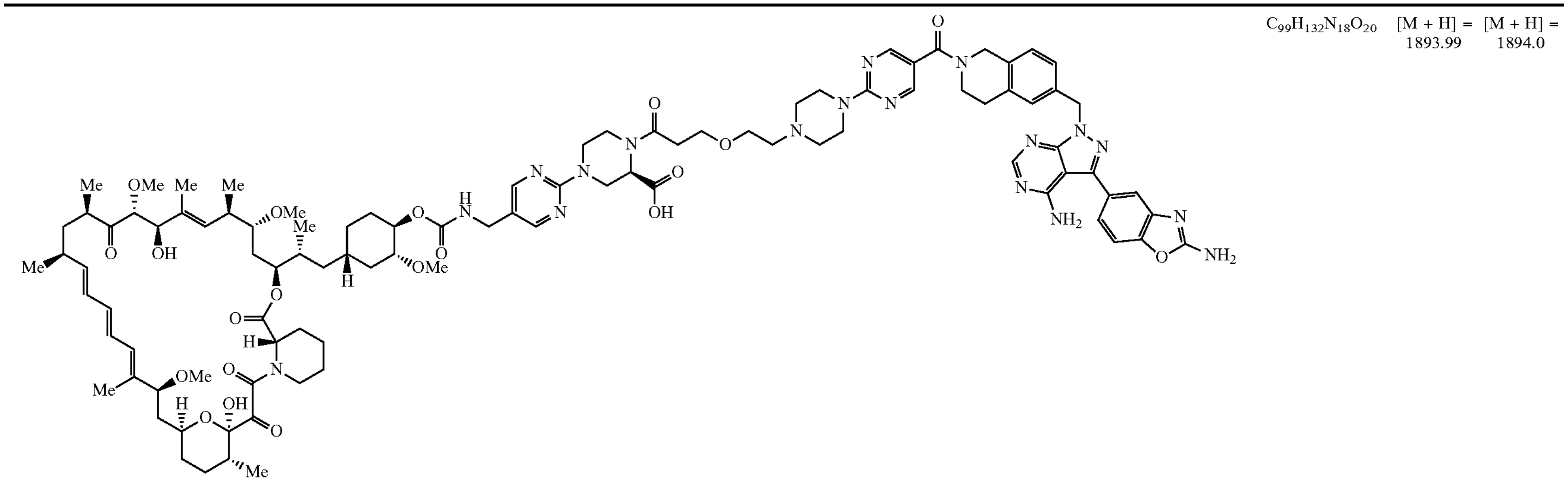<br>Example 131 | $C_{99}H_{132}N_{18}O_{20}$ | [M + H] = 1893.99 | [M + H] = 1894.0 |

TABLE 21-continued
| Series 4 Bivalent Compounds | | | |
| --- | --- | --- | --- |
| Structure | Molecular Formula | Calculated MW | Observed MW |
| 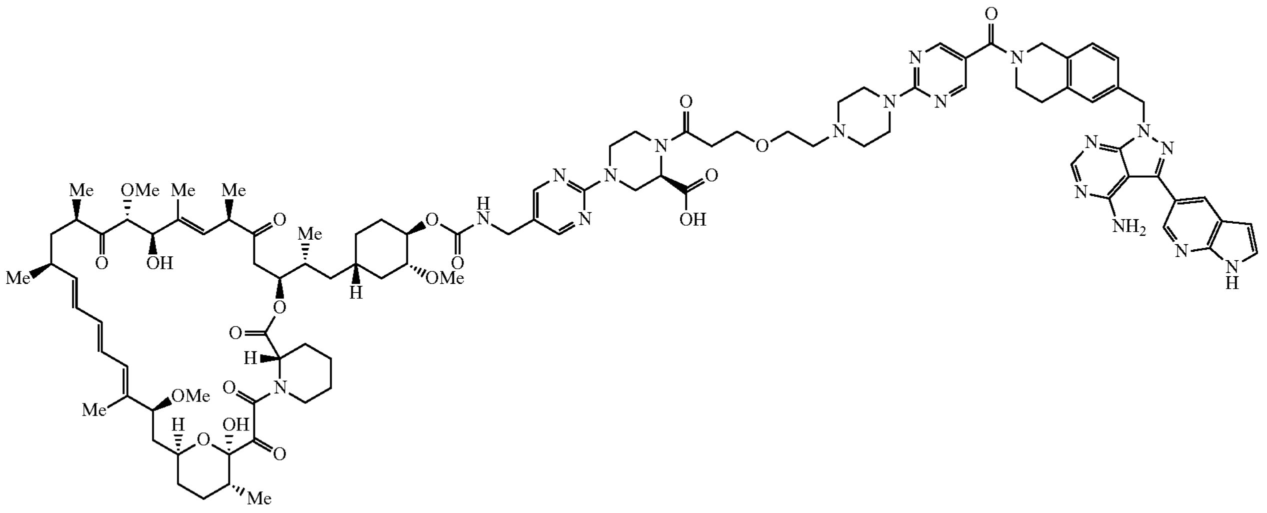 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCc3cnc(N4CCN(C(=O)CCOCCN5CCN(c6ncc(C(=O)N7CCc8cc(Cn9nc(-c%10cnc%11[nH]ccc%11c%10)c%10c(N)ncnc%109)ccc8C7)cn6)CC5)[C@@H](C(=O)O)C4)nc3)[C@H](OC)C2)CC(=O)[C@H](C)/C=C(\C)[C@@H](O)[C@@H](OC)C(=O)[C@H](C)C[C@H](C)/C=C/C=C/C=C/1C]<br>Example 132 | $C_{98}H_{128}N_{18}O_{19}$ | [M + H] = 1861.97 | [M + H] = 1861.9 |
| 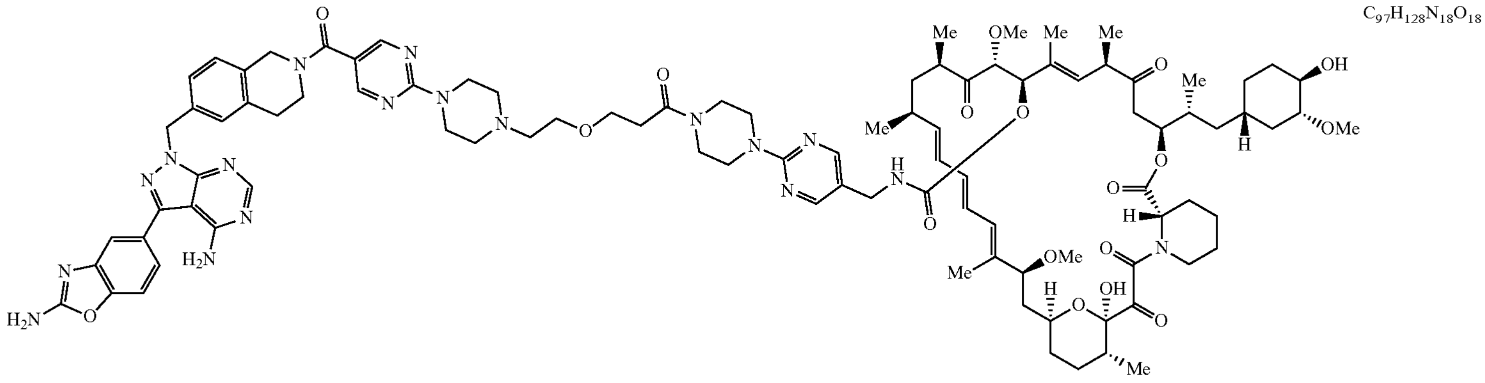<br>Example 133 | $C_{97}H_{128}N_{18}O_{18}$ | [M + H] = 1833.97 | [M + H] = 1833.9 |

TABLE 21-continued
| Series 4 Bivalent Compounds | | | |
|---|---|---|---|
| Structure | Molecular Formula | Calculated MW | Observed MW |
| 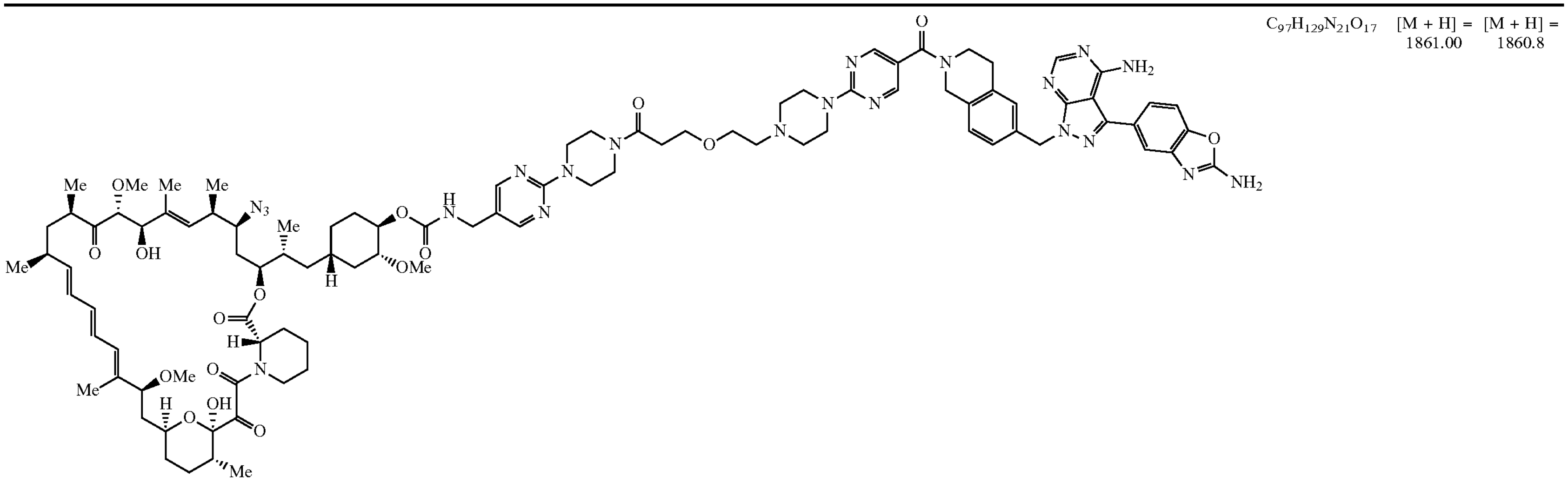 Example 151 | $C_{97}H_{129}N_{21}O_{17}$ | [M + H] = 1861.00 | [M + H] = 1860.8 |

Following General Procedure 1, but using the appropriate Intermediates C1 in Table 16 and amine containing pre-linkers in Table 4, the Intermediates E1 in Table 22 were prepared:

TABLE 22

| Additional amines prepared | | | |
|---|---|---|---|
| Structure | Molecular Formula | Calculated MW | Observed MW |
| 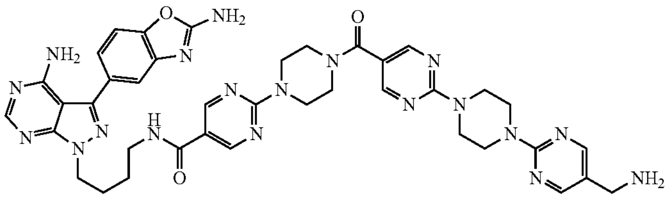 [SMILES: NCc1cnc(N2CCN(c3ncc(C(=O)N4CCN(c5ncc(C(=O)NCCCCn6nc(-c7ccc8oc(N)nc8c7)c7c(N)ncnc76)cn5)CC4)cn3)CC2)nc1] Intermediate E1-1 | $C_{39}H_{43}N_{19}O_3$ | [M + H] = 826.39 | [M + H] = 826.5 |
| 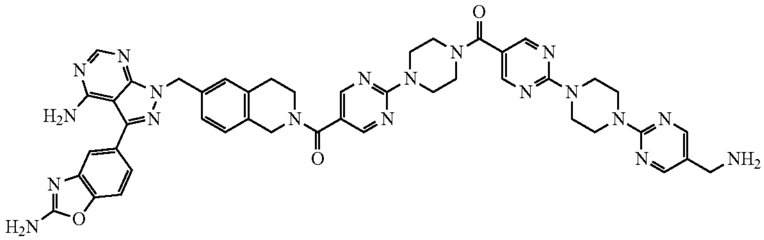 [SMILES: NCc1cnc(N2CCN(c3ncc(C(=O)N4CCN(c5ncc(C(=O)N6CCc7cc(Cn8nc(-c9ccc%10oc(N)nc%10c9)c9c(N)ncnc98)ccc7C6)cn5)CC4)cn3)CC2)nc1] Intermediate E1-2 | $C_{45}H_{45}N_{19}O_3$ | [M + H] = 900.41 | [M + H] = 900.2 |
| 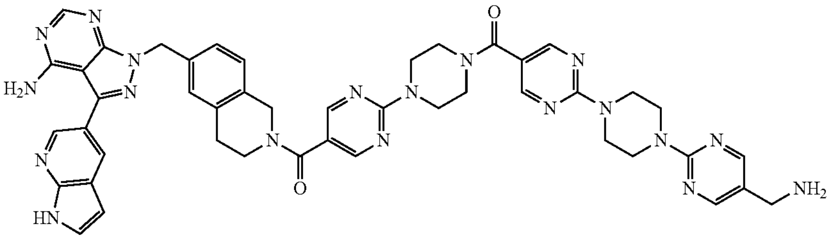 [SMILES: NCc1cnc(N2CCN(c3ncc(C(=O)N4CCN(c5ncc(C(=O)N6CCc7cc(Cn8nc(-c9cnc%10[nH]ccc%10c9)c9c(N)ncnc98)ccc7C6)cn5)CC4)cn3)CC2)nc1] Intermediate E1-3 | $C_{45}H_{45}N_{19}O_2$ | [M + H] = 884.41 | [M + H] = 884.4 |
| 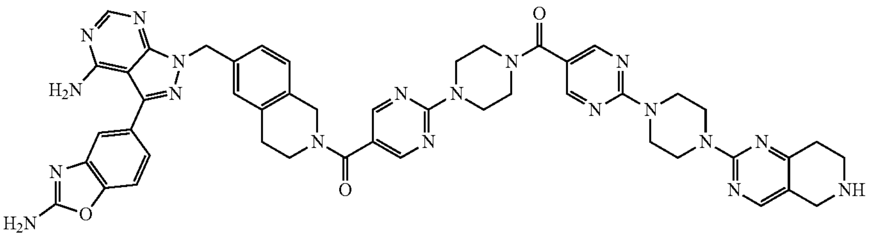 [SMILES: Nc1nc2cc(-c3nn(Cc4ccc5c(c4)CCN(C(=O)c4cnc(N6CCN(C(=O)c7cnc(N8CCN(c9ncc%10c(n9)CCNC%10)CC8)nc7)CC6)nc4)C5)c4ncnc(N)c34)ccc2o1] Intermediate E1-4 | $C_{47}H_{47}N_{19}O_3$ | [M + H] = 926.42 | [M + H] = 926.6 |
| 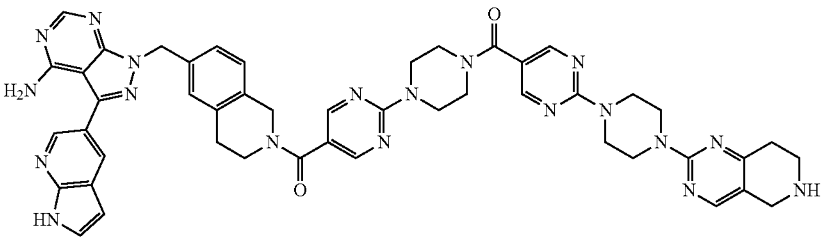 [SMILES: Nc1ncnc2c1c(-c1cnc3[nH]ccc3c1)nn2Cc1ccc2c(c1)CCN(C(=O)c1cnc(N3CCN(C(=O)c4cnc(N5CCN(c6ncc7c(n6)CCNC7)CC5)nc4)CC3)nc1)C2] Intermediate E1-5 | $C_{47}H_{47}N_{19}O_2$ | [M + H] = 910.43 | [M + H] = 910.2 |

TABLE 22-continued

| Additional amines prepared | | | |
|---|---|---|---|
| Structure | Molecular Formula | Calculated MW | Observed MW |
| 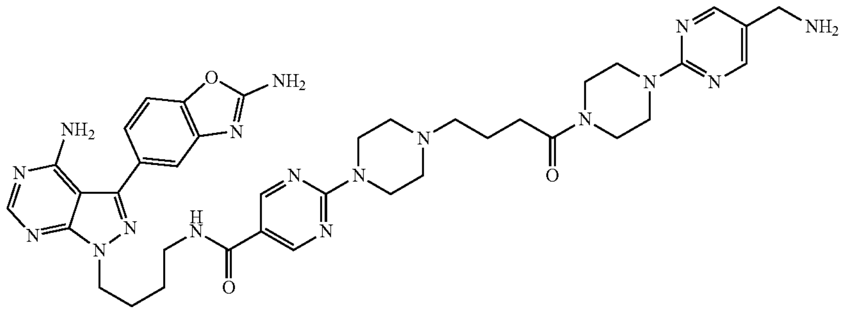 [SMILES: NCc1cnc(N2CCN(C(=O)CCCN3CCN(c4ncc(C(=O)NCCCCn5nc(-c6ccc7oc(N)nc7c6)c6c(N)ncnc65)cn4)CC3)CC2)nc1] Intermediate E1-6 | $C_{38}H_{47}N_{17}O_3$ | [M + H] = 790.41 | [M + H] = 790.4 |
| 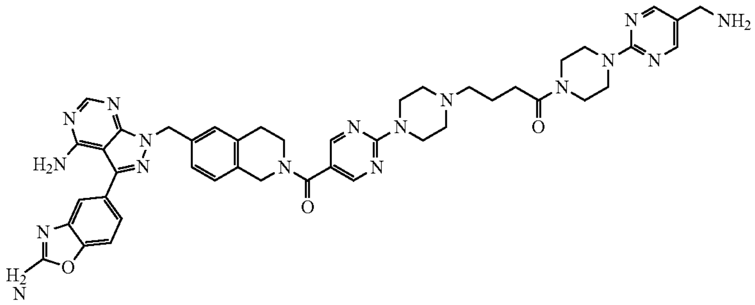 [SMILES: NCc1cnc(N2CCN(C(=O)CCCN3CCN(c4ncc(C(=O)N5CCc6cc(Cn7nc(-c8ccc9oc(N)nc9c8)c8c(N)ncnc87)ccc6C5)cn4)CC3)CC2)nc1] Intermediate E1-7 | $C_{44}H_{49}N_{17}O_3$ | [M + H] = 864.43 | [M + H] = 864.3 |
| 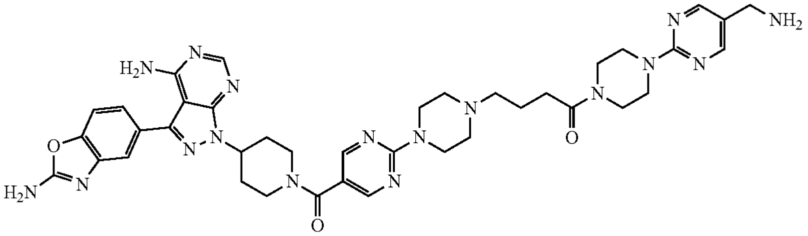 [SMILES: NCc1cnc(N2CCN(C(=O)CCCN3CCN(c4ncc(C(=O)N5CCC(n6nc(-c7ccc8oc(N)nc8c7)c7c(N)ncnc76)CC5)cn4)CC3)CC2)nc1] Intermediate E1-8 | $C_{39}H_{47}N_{17}O_3$ | [M + H] = 802.41 | [M + H] = 802.3 |

Following General Procedure 2, but using the appropriate 4-nitrophenyl carbonate containing rapamycin monomer in Table 1 and Intermediates E1 from Table 22, the Series 5 bivalent analogs in Table 23 were synthesized:

TABLE 23
| Series 5 Bivalent Compounds | | | |
|---|---|---|---|
| Structure | Molecular Formula | Calculated MW | Observed MW |
| 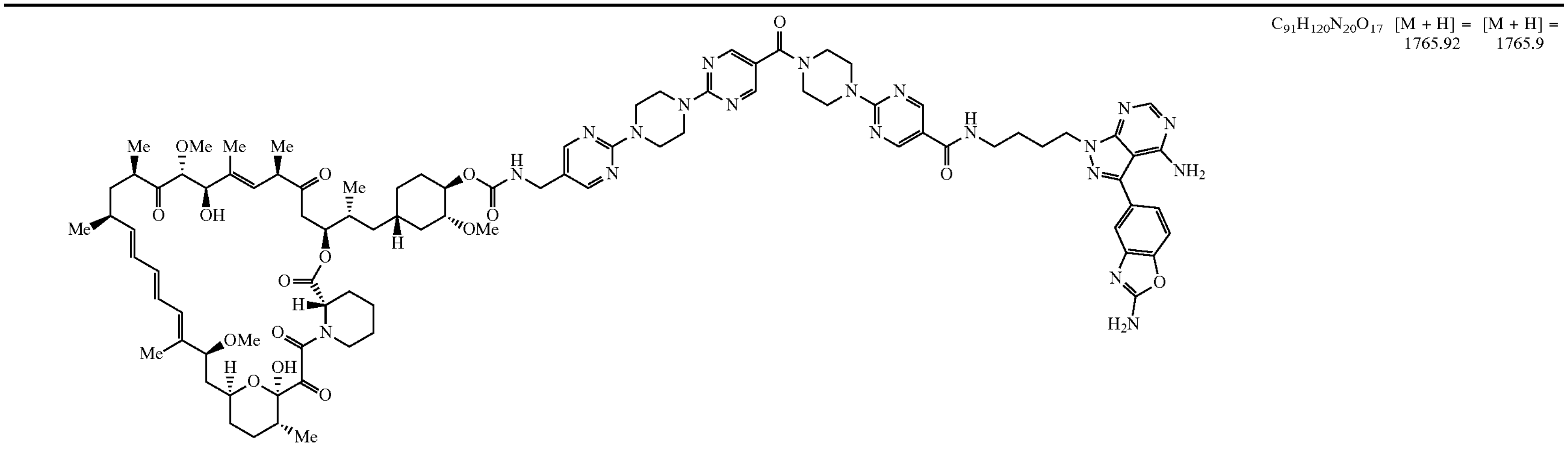<br>Example 59 | $C_{91}H_{120}N_{20}O_{17}$ | [M + H] = 1765.92 | [M + H] = 1765.9 |

TABLE 23-continued
| Series 5 Bivalent Compounds | | | |
|---|---|---|---|
| Structure | Molecular Formula | Calculated MW | Observed MW |
| 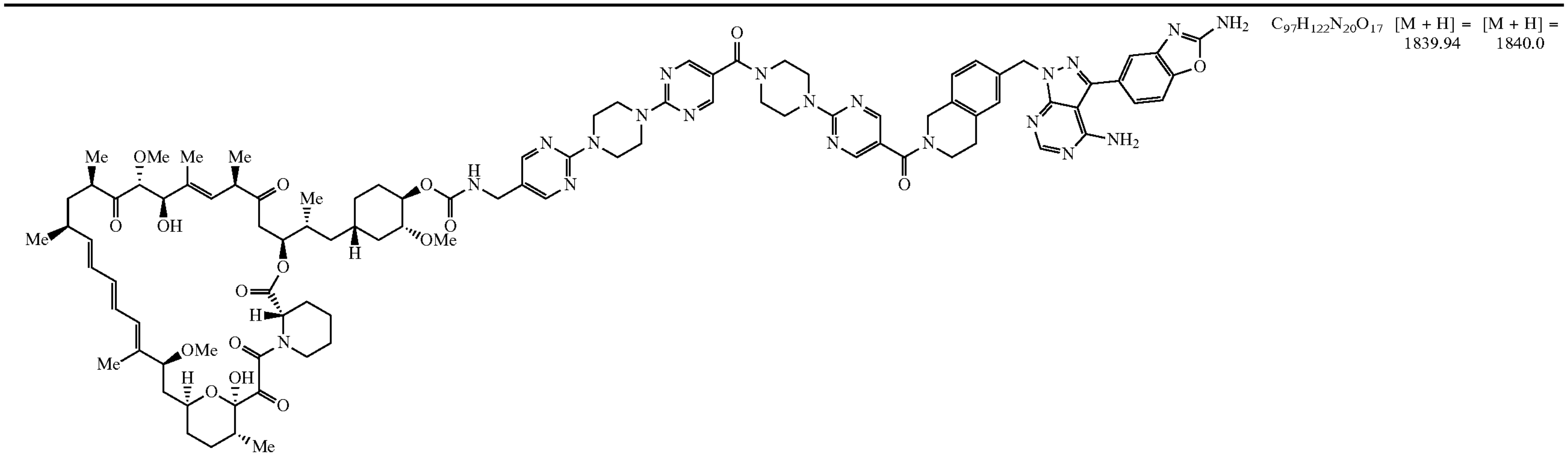 Example 60 | $C_{97}H_{122}N_{20}O_{17}$ | [M + H] = 1839.94 | [M + H] = 1840.0 |

TABLE 23-continued
| Series 5 Bivalent Compounds | | | |
|---|---|---|---|
| Structure | Molecular Formula | Calculated MW | Observed MW |
| 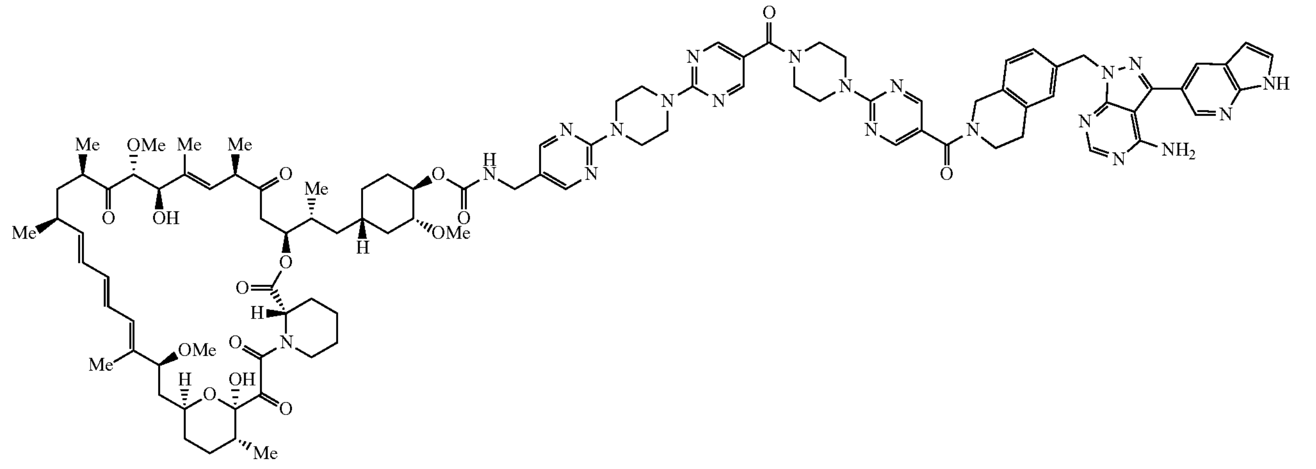 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCc3cnc(N4CCN(c5ncc(C(=O)N6CCN(c7ncc(C(=O)N8CCc9cc(Cn%10nc(-c%11cnc%12[nH]ccc%12c%11)c%11c(N)ncnc%11%10)ccc9C8)cn7)CC6)cn5)CC4)nc3)[C@H](OC)C2)CC(=O)[C@H](C)/C=C(\C)[C@@H](O)[C@@H](OC)C(=O)[C@H](C)C[C@H](C)/C=C/C=C/C=C/1C] Example 61 | $C_{97}H_{122}N_{20}O_{16}$ | [M + H] = 1823.94 | [M + H] = 1823.9 |
| 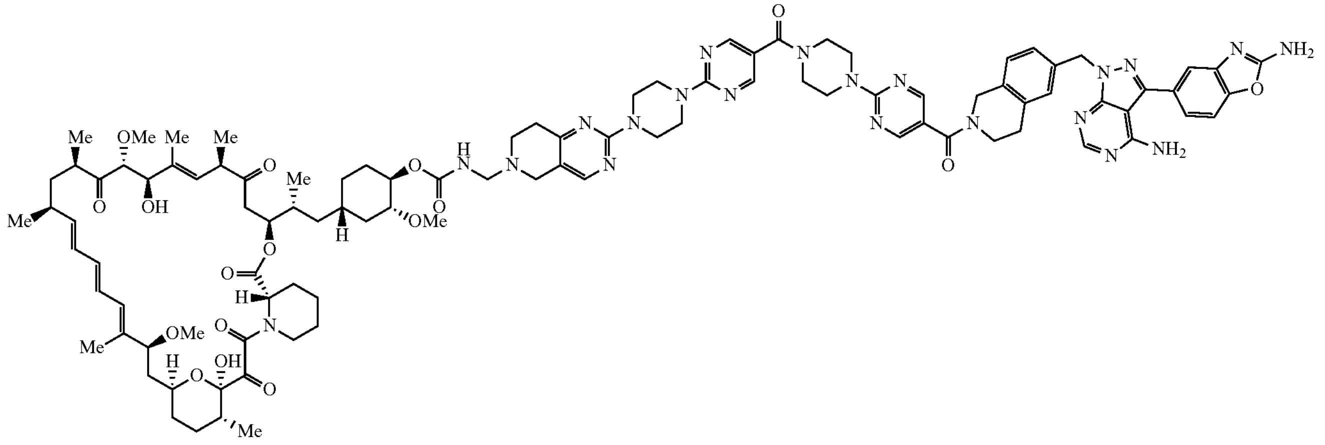 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCN3CCc4nc(N5CCN(c6ncc(C(=O)N7CCN(c8ncc(C(=O)N9CCc%10cc(Cn%11nc(-c%12ccc%13oc(N)nc%13c%12)c%12c(N)ncnc%12%11)ccc%10C9)cn8)CC7)cn6)CC5)ncc4C3)[C@H](OC)C2)CC(=O)[C@H](C)/C=C(\C)[C@@H](O)[C@@H](OC)C(=O)[C@H](C)C[C@H](C)/C=C/C=C/C=C/1C] Example 62 | $C_{99}H_{124}N_{20}O_{17}$ | [M + H] = 1865.95 | [M + H] = 1865.8 |

TABLE 23-continued
| Series 5 Bivalent Compounds | | | |
|---|---|---|---|
| Structure | Molecular Formula | Calculated MW | Observed MW |
| 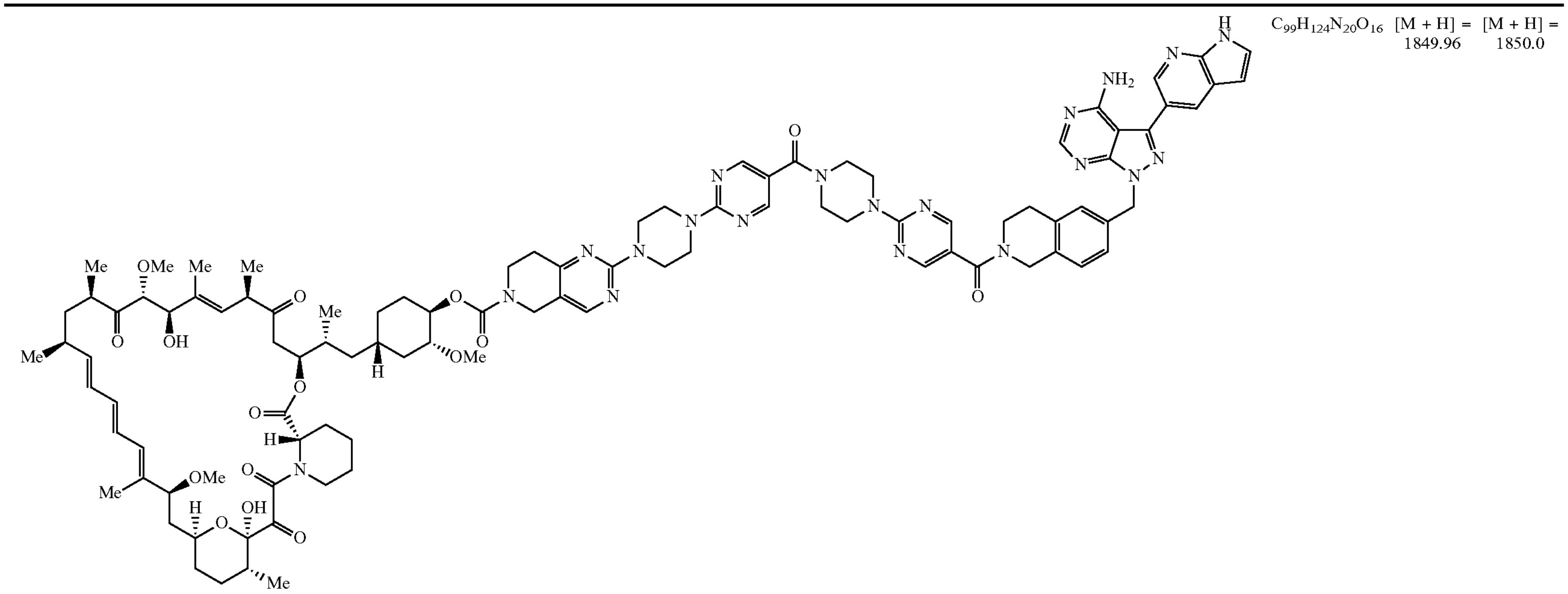<br>Example 134 | $C_{99}H_{124}N_{20}O_{16}$ | [M + H] = 1849.96 | [M + H] = 1850.0 |

TABLE 24
Additional amines prepared
| Structure | Molecular Formula | Calculated MW | Observed MW |
|---|---|---|---|
| 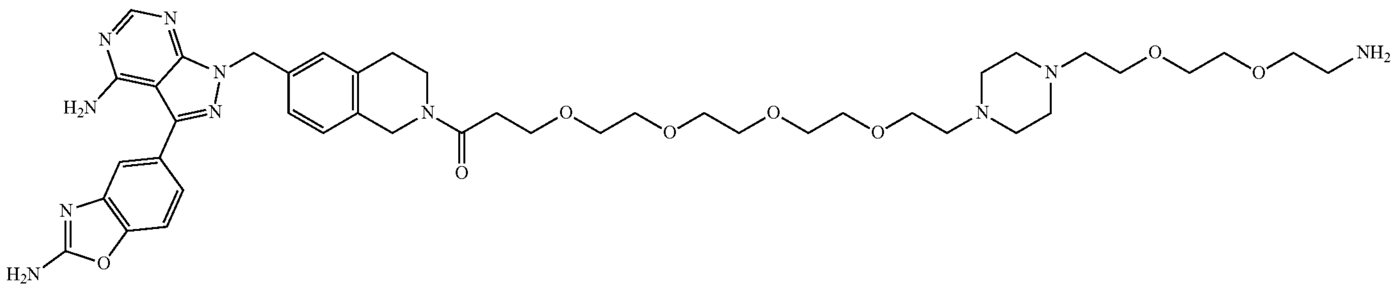 [SMILES: NCCOCCOCCN1CCN(CCOCCOCCOCCOCCC(=O)N2CCc3cc(Cn4nc(-c5ccc6oc(N)nc6c5)c5c(N)ncnc54)ccc3C2)CC1] Intermediate F1-1 | $C_{43}H_{61}N_{11}O_8$ | [M + H] = 860.48 | [M + H] = 860.4 |
| 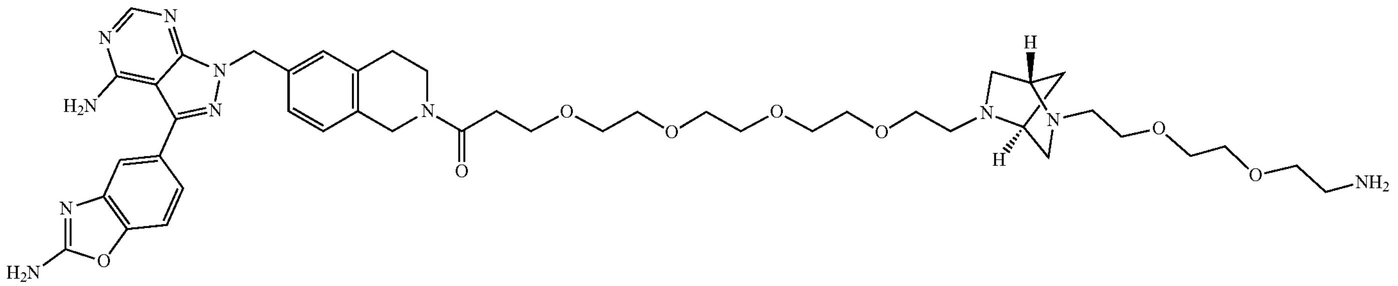 Intermediate F1-2 | $C_{44}H_{61}N_{11}O_8$ | [M + H] = 872.48 | [M + H] = 872.2 |

Following General Procedure 2, but using the appropriate 4-nitrophenyl carbonate containing rapamycin monomer in Table 1 and Intermediates F1 from Table 24, the Series 6 bivalent analogs in Table 25 were synthesized:

TABLE 25
| Structure | Molecular Formula | Calculated MW | Observed MW |
|---|---|---|---|
| Series 6 Bivalent Compounds | | | |
| 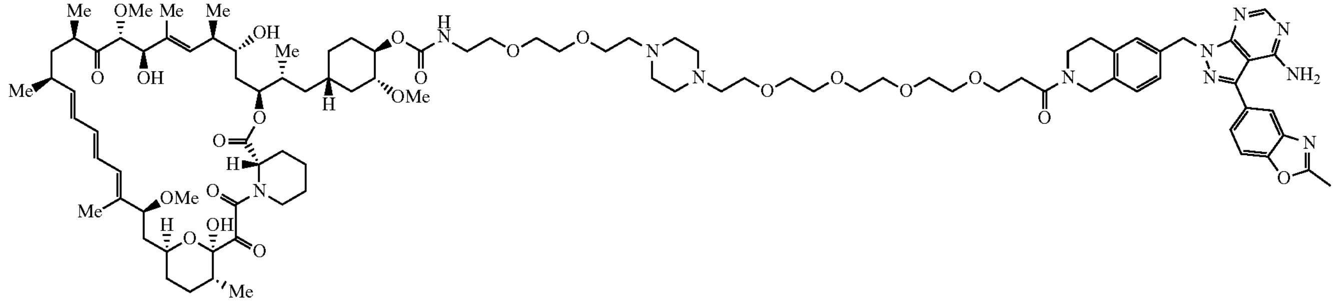 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCOCCN3CCN(CCOCCOCCOCCOCCC(=O)N4CCc5cc(Cn6nc(-c7ccc8oc(C)nc8c7)c7c(N)ncnc76)ccc5C4)CC3)[C@H](OC)C2)C[C@@H](O)[C@H](C)/C=C(\C)[C@@H](O)[C@@H](OC)C(=O)[C@H](C)C[C@H](C)/C=C/C=C/C=C/1C] Example 135 | $C_{95}H_{140}N_{12}O_{22}$ | [M + H] = 1802.03 | [M + H] = 1802.5 |
| 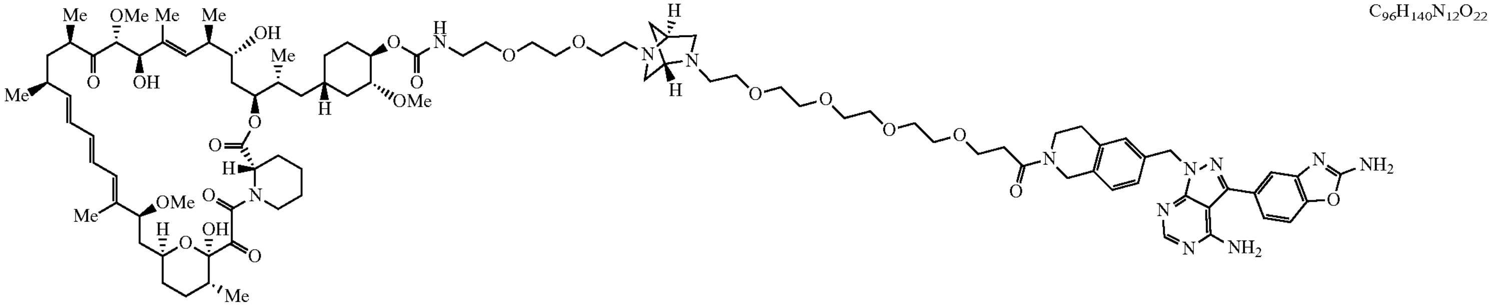 Example 152 | $C_{96}H_{140}N_{12}O_{22}$ | [M + H] = 1814.03 | [M + H] = 1813.9 |

Following General Procedure 1, but using the appropriate Intermediates A1 in Table 5 and amine containing pre-linkers in Table 4, the Intermediates G1 in Table 26 were prepared:

TABLE 26
| Additional amines prepared | | | |
|---|---|---|---|
| Structure | Molecular Formula | Calculated MW | Observed MW |
| 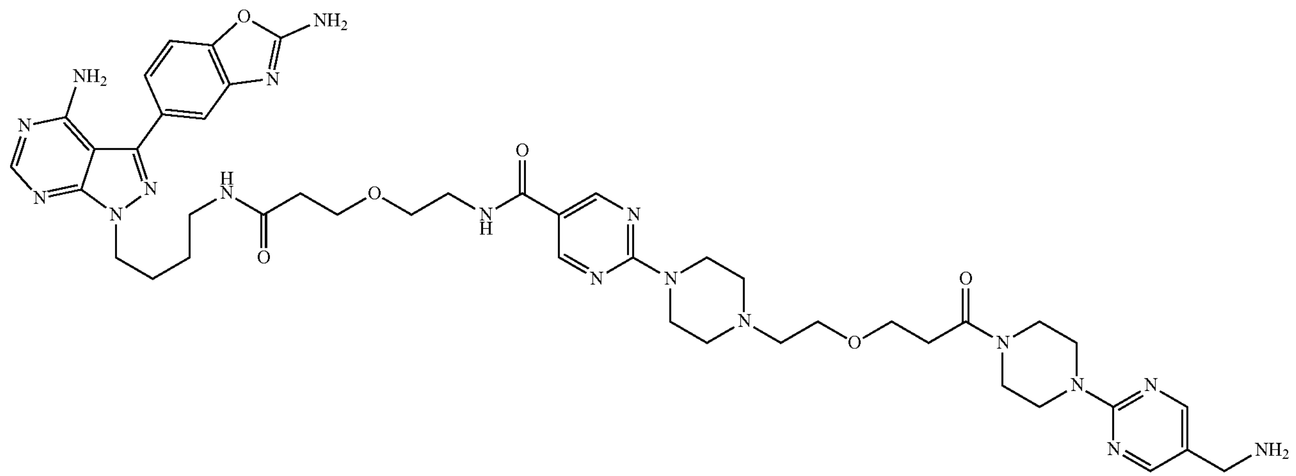 [SMILES: NCc1cnc(N2CCN(C(=O)CCOCCN3CCN(c4ncc(C(=O)NCCOCCC(=O)NCCCCn5nc(-c6ccc7oc(N)nc7c6)c6c(N)ncnc65)cn4)CC3)CC2)nc1] Intermediate G1-1 | $C_{44}H_{58}N_{18}O_6$ | [M + H] = 935.49 | [M + H] = 935.5 |
| 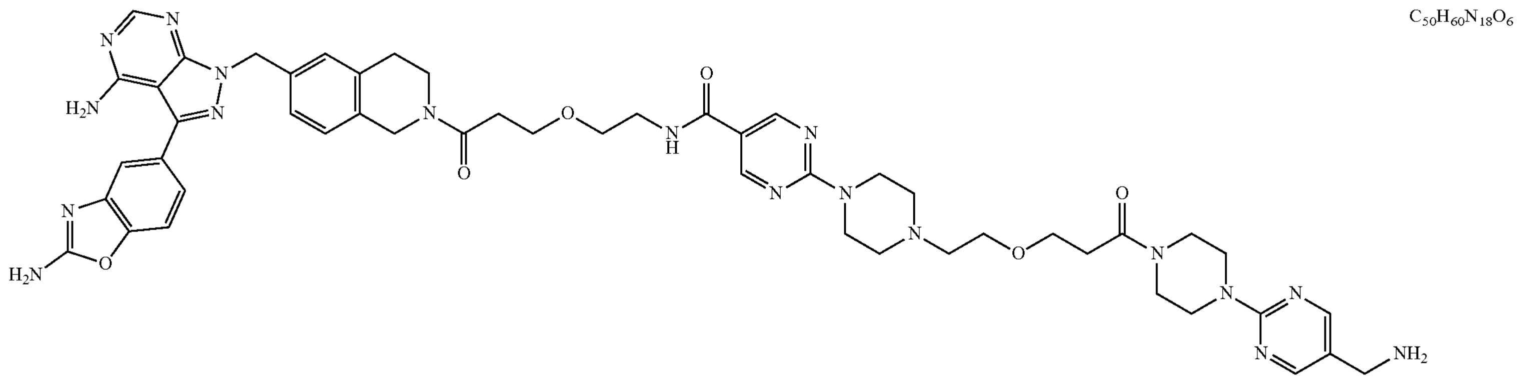 Intermediate G1-2 | $C_{50}H_{60}N_{18}O_6$ | [M + H] = 1009.50 | [M + H] = 1009.5 |

TABLE 26-continued
| Additional amines prepared | | | |
|---|---|---|---|
| Structure | Molecular Formula | Calculated MW | Observed MW |
| 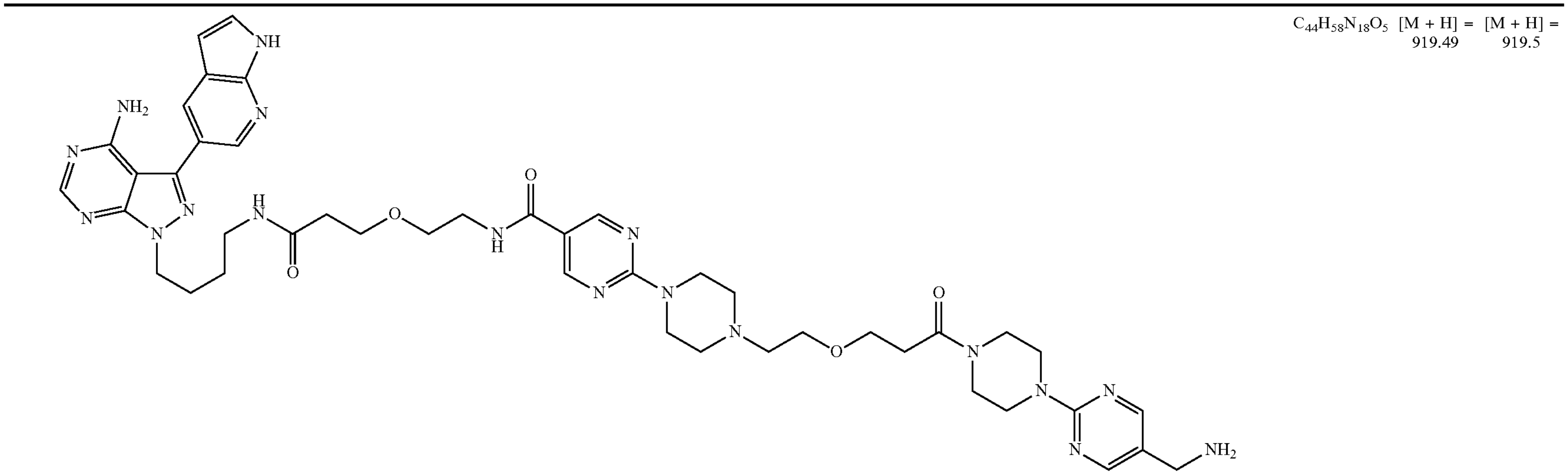 Intermediate G1-3 | $C_{44}H_{58}N_{18}O_5$ | [M + H] = 919.49 | [M + H] = 919.5 |

Following General Procedure 6, but using the appropriate Intermediates B3 in Table 10 and amine containing pre-linkers in Table 4, the Intermediates G1 in Table 27 were prepared:

TABLE 27

| Additional amines prepared | | | |
|---|---|---|---|
| Structure | Molecular Formula | Calculated MW | Observed MW |
| 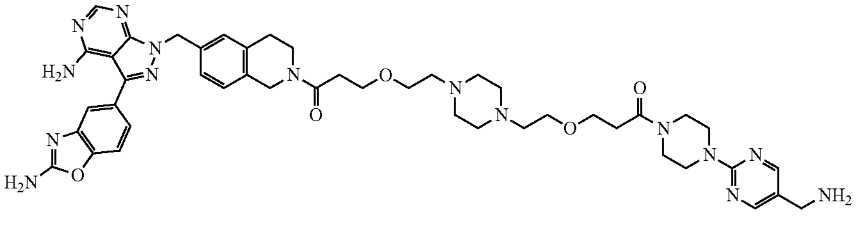 [SMILES: NCc1cnc(N2CCN(C(=O)CCOCCN3CCN(CCOCCC(=O)N4CCc5cc(Cn6nc(-c7ccc8oc(N)nc8c7)c7c(N)ncnc76)ccc5C4)CC3)CC2)nc1] Intermediate G1-4 | $C_{45}H_{57}N_{15}O_5$ | [M + H] = 888.48 | [M + H] = 888.4 |

Following General Procedure 2, but using the appropriate 4-nitrophenyl carbonate containing rapamycin monomer in Table 1 and Intermediates G1 from Tables 26 and 27, the Series 7 bivalent analogs in Table 28 were synthesized:

TABLE 28
Series 7 Bivalent Compounds
| Structure | Molecular Formula | Calculated MW | Observed MW |
|---|---|---|---|
| 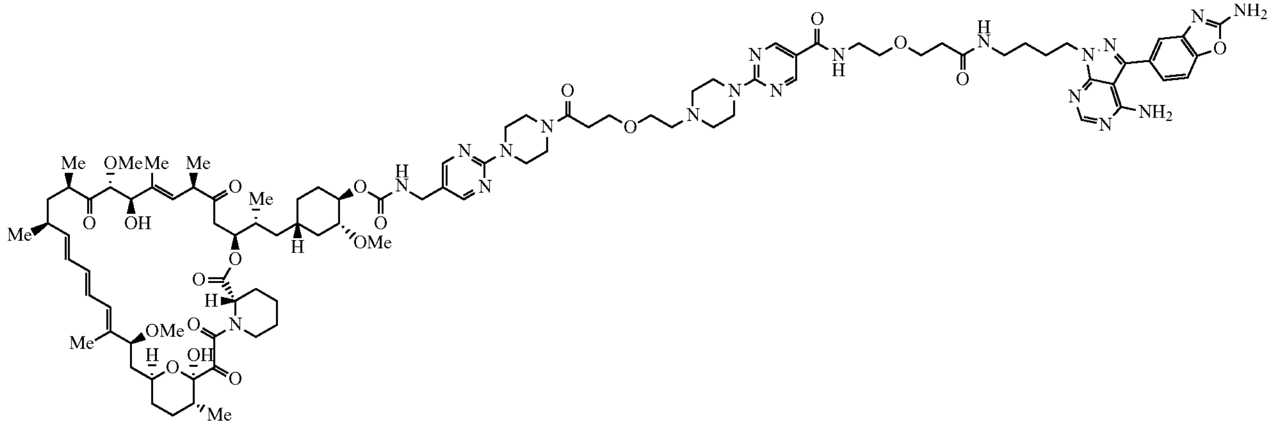 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCc3cnc(N4CCN(C(=O)CCOCCN5CCN(c6ncc(C(=O)NCCOCCC(=O)NCCCCn7nc(-c8ccc9oc(N)nc9c8)c8c(N)ncnc87)cn6)CC5)CC4)nc3)[C@H](OC)C2)CC(=O)[C@H](C)/C=C(\C)[C@@H](O)[C@@H](OC)C(=O)[C@H](C)C[C@H](C)/C=C/C=C/C=C/1C] Example 63 | $C_{96}H_{135}N_{19}O_{20}$ | [M + H] = 1875.02 | [M + H] = 1874.9 |

TABLE 28-continued
| Series 7 Bivalent Compounds | | | |
|---|---|---|---|
| Structure | Molecular Formula | Calculated MW | Observed MW |
| 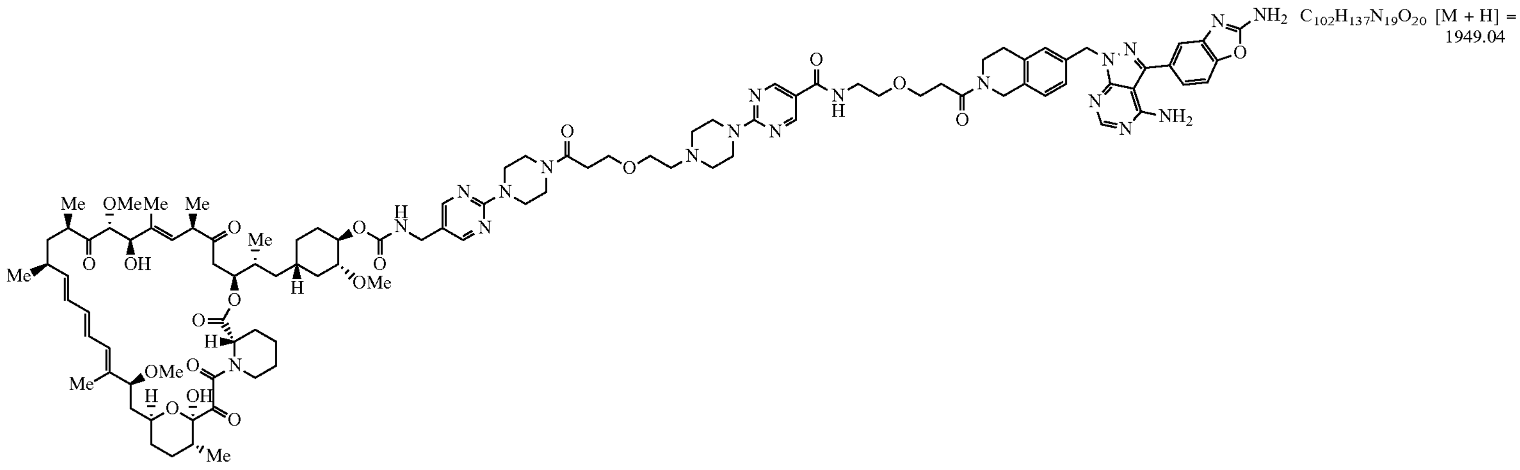<br>Example 64 | $C_{102}H_{137}N_{19}O_{20}$ | [M + H] = 1949.04 | [M + H] = 1949.0 |

TABLE 28-continued
Series 7 Bivalent Compounds
| Structure | Molecular Formula | Calculated MW | Observed MW |
| --- | --- | --- | --- |
| 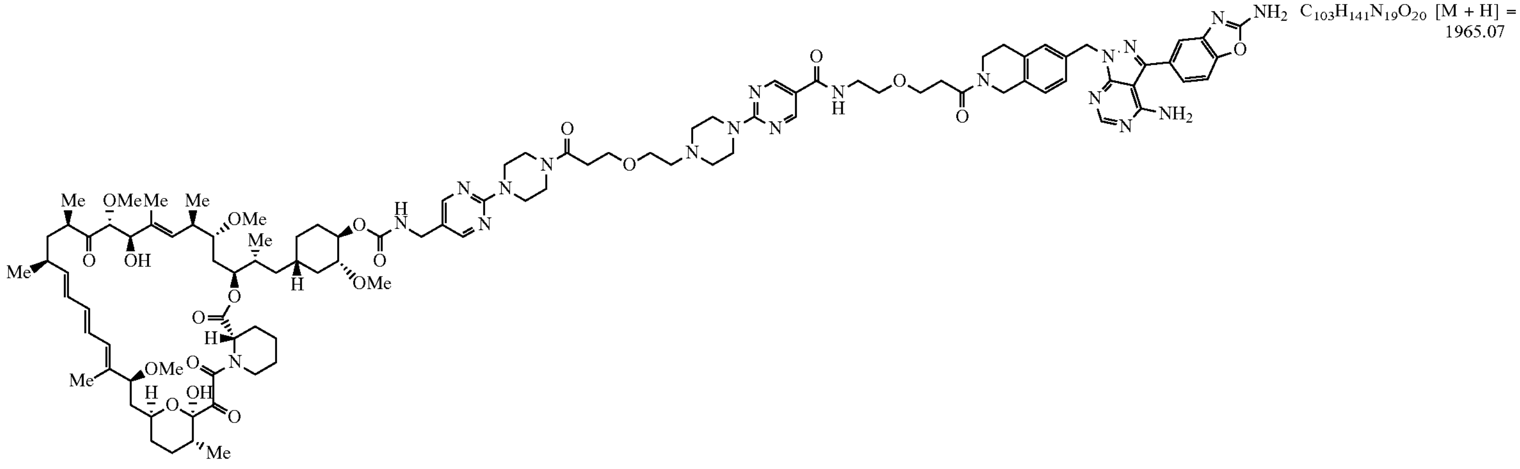 Example 65 | $C_{103}H_{141}N_{19}O_{20}$ | [M + H] = 1965.07 | [M + H] = 1965.0 |

TABLE 28-continued
| Series 7 Bivalent Compounds | | | |
|---|---|---|---|
| Structure | Molecular Formula | Calculated MW | Observed MW |
| 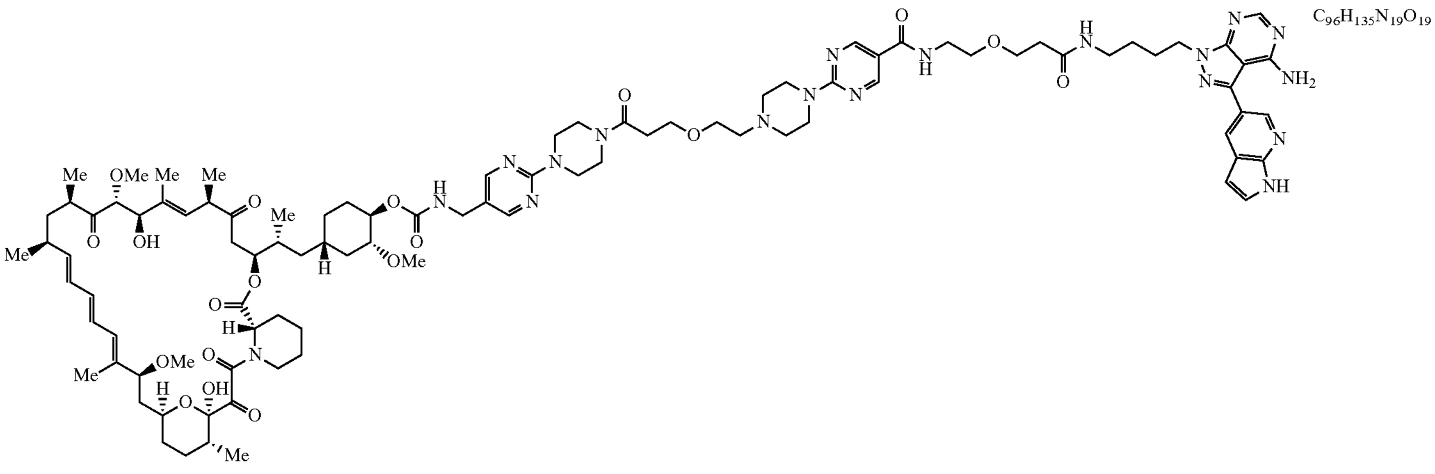 Example 66 | $C_{96}H_{135}N_{19}O_{19}$ | [M + H] = 1859.03 | [M + H] = 1859.0 |

Following General Procedure 1, but using the appropriate Intermediates D1 in Tables 19 and 20 and PEG carboxylic acids, the Intermediates H1 in Table 29 were prepared:

TABLE 29
| Additional amines prepared | | | |
|---|---|---|---|
| Structure | Molecular Formula | Calculated MW | Observed MW |
| 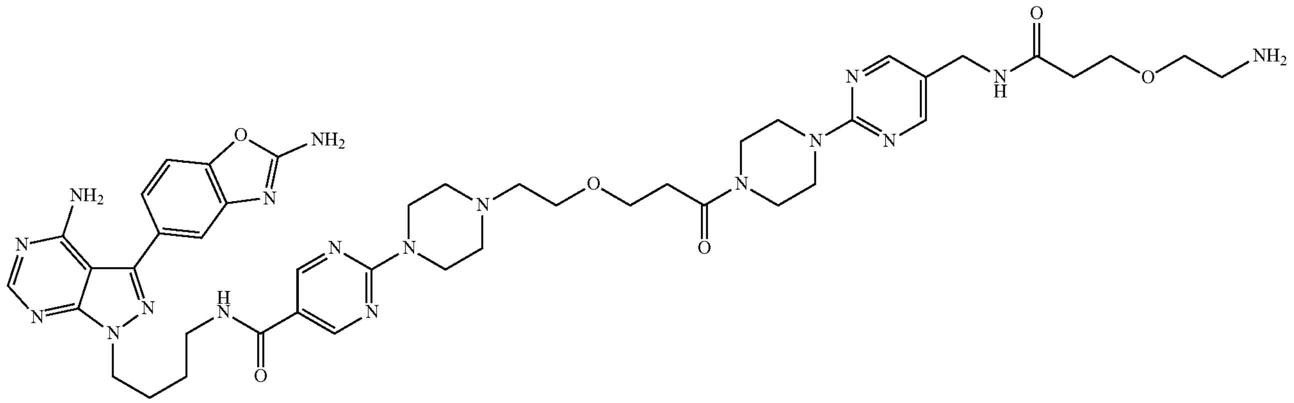 [SMILES: NCCOCCC(=O)NCc1cnc(N2CCN(C(=O)CCOCCN3CCN(c4ncc(C(=O)NCCCCn5nc(-c6ccc7oc(N)nc7c6)c6c(N)ncnc65)cn4)CC3)CC2)nc1]<br>Intermediate H1-1 | $C_{44}H_{58}N_{18}O_6$ | [M + H] = 935.49 | [M + H] = 935.5 |
| 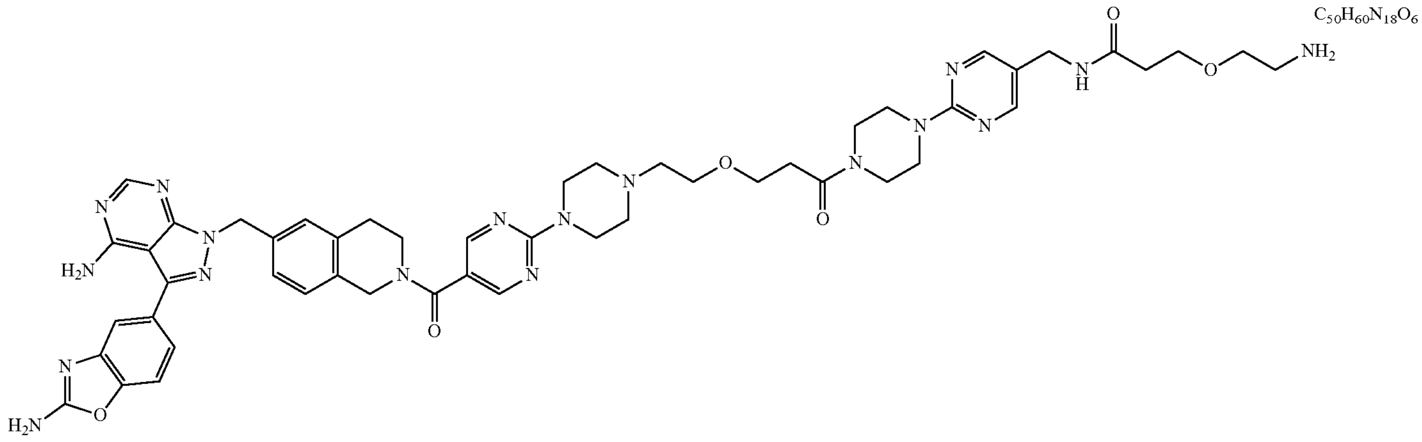<br>Intermediate H1-2 | $C_{50}H_{60}N_{18}O_6$ | [M + H] = 505.23 | [M + H] = 505.4 |

TABLE 29-continued
| Additional amines prepared | | | |
|---|---|---|---|
| Structure | Molecular Formula | Calculated MW | Observed MW |
| 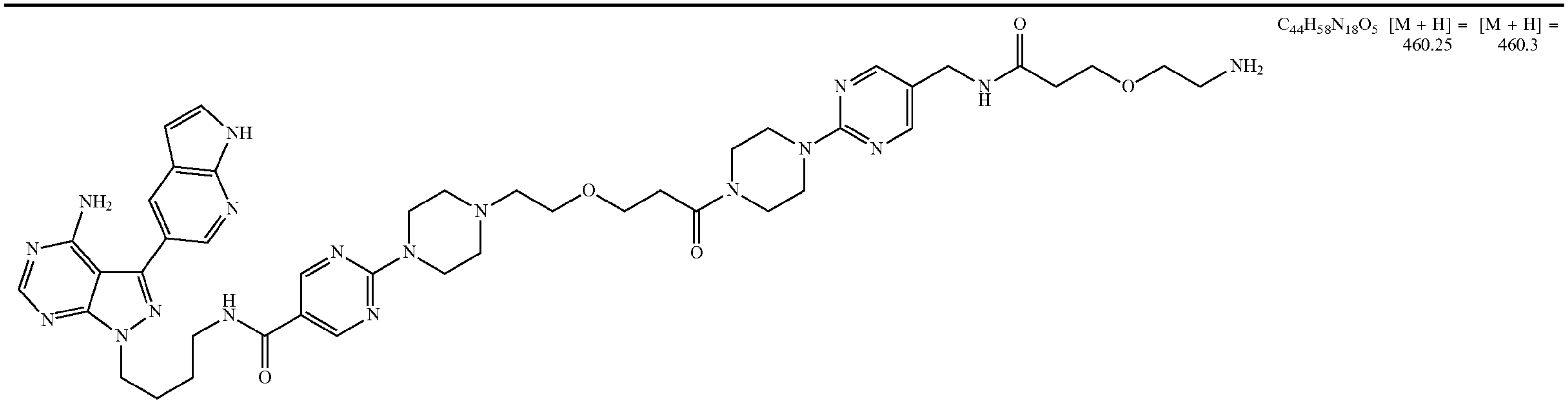<br>Intermediate H1-3 | $C_{44}H_{58}N_{18}O_5$ | [M + H] = 460.25 | [M + H] = 460.3 |

Following General Procedure 2, but using the appropriate 4-nitrophenyl carbonate containing rapamycin monomer in Table 1 and Intermediates H1 from Table 29, the Series 8 bivalent analogs in Table 30 were synthesized:

TABLE 30
Series 8 Bivalent Compounds:
| Structure | Molecular Formula | Calculated MW | Observed MW |
|---|---|---|---|
| 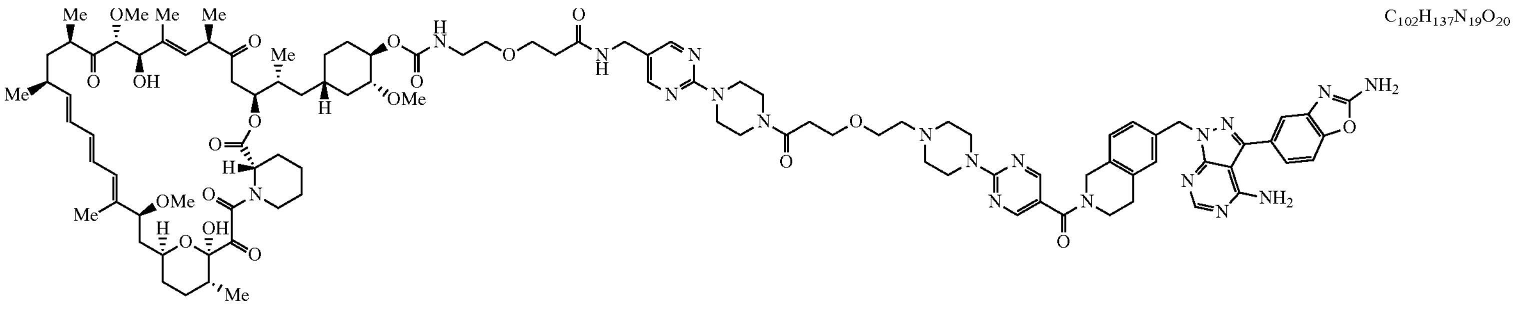 Example 67 | $C_{102}H_{137}N_{19}O_{20}$ | [M + H] = 1949.04 | [M + H] = 1949.0 |
| 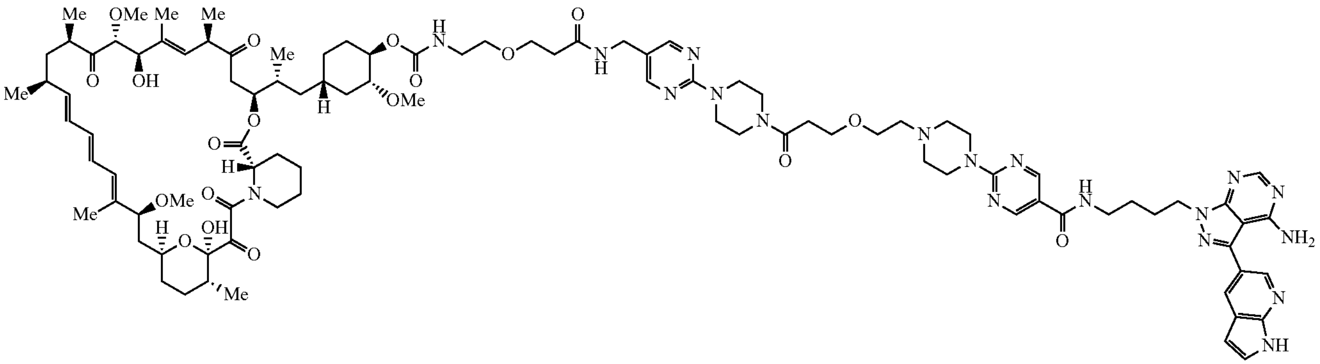 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)NCCOCCC(=O)NCc3cnc(N4CCN(C(=O)CCOCCN5CCN(c6ncc(C(=O)NCCCCn7nc(-c8cnc9[nH]ccc9c8)c8c(N)ncnc87)cn6)CC5)CC4)nc3)[C@H](OC)C2)CC(=O)[C@H](C)/C=C(\C)[C@@H](O)[C@@H](OC)C(=O)[C@H](C)C[C@H](C)/C=C/C=C/C=C/1C] Example 68 | $C_{96}H_{135}N_{19}O_{19}$ | [M + H] = 1859.03 | [M + H] = 1859.0 |

TABLE 30-continued
| Series 8 Bivalent Compounds: | | | |
|---|---|---|---|
| Structure | Molecular Formula | Calculated MW | Observed MW |
| 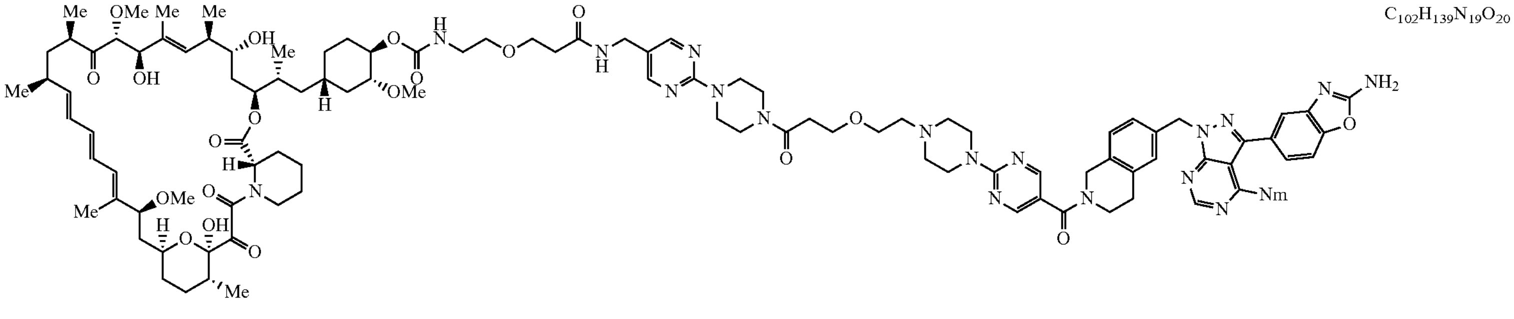 Example 69 | $C_{102}H_{139}N_{19}O_{20}$ | [M + H] = 1951.05 | [M + H] = 1951.1 |
| 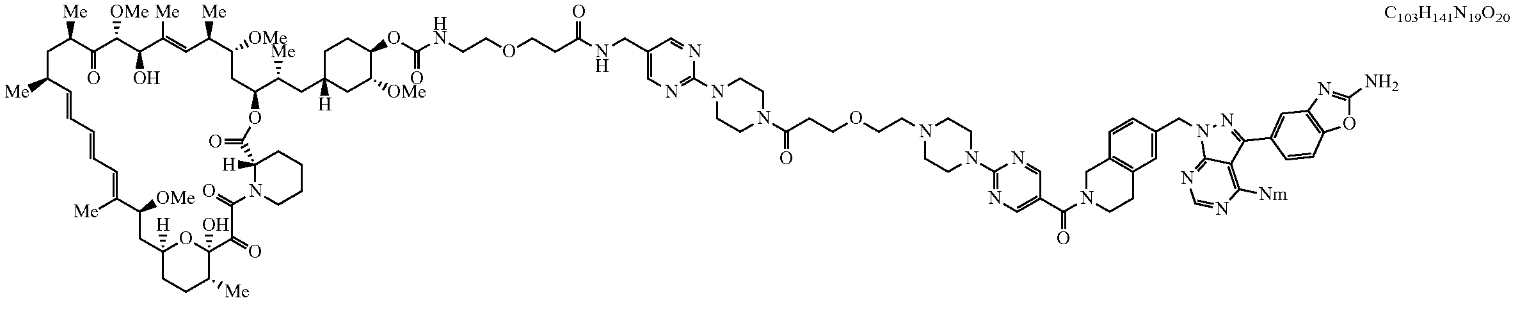 Example 70 | $C_{103}H_{141}N_{19}O_{20}$ | [M + H] = 1965.07 | [M + H] = 1965.1 |

BIOLOGICAL EXAMPLES

Cell Based AlphaLISA Assays for Determining IC50 for Inhibition of P-Akt (S473), P-4E-BP1 (T37/46), and P-P70S6K (T389) in MDA-MB-468 Cells mTOR Kinase Cellular Assay To measure functional activity of mTORC1 and mTORC2 in cells the phosphorylation of 4EBP1 (Thr37/46) and P70S6K (Thr389), and AKT1/2/3 (Ser473) was monitored using AlphaLisa SureFire Ultra Kits (Perkin Elmer). MDA-MB-468 cells (ATCC® HTB-132) were cultured in 96-well tissue culture plates and treated with compounds in the disclosure at concentrations varying from 0.017-1,000 nM for two to four hours at 37° C. Incubations were terminated by removal of the assay buffer and addition of lysis buffer provided with the assay kit. Samples were processed according to the manufacturer's instructions. The Alpha signal from the respective phosphoproteins was measured in duplicate using a microplate reader (Envision, Perkin-Elmer or Spectramax M5, Molecular Devices). Inhibitor concentration response curves were analyzed using normalized $IC_{50}$ regression curve fitting with control based normalization.

As an example, measured $IC_{50}$ values for selected compounds are reported below:

| | $IC_{50}$ for Inhibition of mTORC1 and mTORC2 Substrate Phosphorylation (nM) | | |
|---|---|---|---|
| Compound | p-P70S6K-(T389) | p-4E-BP1-(T37/46) | p-AKT1/2/3-(S473) |
| MLN-128 | 1.4 | 16 | 3.7 |
| Rapamycin | 0.2 | >1,000 | >1,000 |

As an example, measured $pIC_{50}$ values for selected compounds are reported below:

| | $pIC_{50}$ for Inhibition of mTORC1 and mTORC2 Substrate Phosphorylation | | |
|---|---|---|---|
| Example | p-P70S6K-(T389) | P-4E-BP1-(T37/46) | p-AKT1/2/3-(S473) |
| 1 | +++ | +++ | ++ |
| 2 | +++ | +++ | ++ |
| 3 | +++ | +++ | ++ |
| 4 | +++ | +++ | ++ |
| 5 | +++ | +++ | + |
| 6 | +++ | +++ | ++ |
| 7 | +++ | +++ | ++ |
| 8 | +++ | +++ | ++ |
| 9 | +++ | +++ | ++ |
| 10 | +++ | − | − |
| 11 | +++ | +++ | ++ |
| 12 | +++ | +++ | + |
| 13 | +++ | +++ | ++ |
| 14 | ++ | +++ | ++ |
| 15 | +++ | +++ | ++ |
| 16 | +++ | +++ | +++ |
| 17 | +++ | +++ | ++ |
| 18 | +++ | ++ | + |
| 19 | +++ | +++ | +++ |
| 20 | +++ | +++ | +++ |
| 21 | +++ | +++ | + |
| 27 | +++ | +++ | ++ |
| 28 | +++ | +++ | − |
| 29 | +++ | +++ | − |
| 30 | +++ | +++ | ++ |
| 31 | +++ | +++ | ++ |
| 32 | +++ | +++ | ++ |
| 33 | +++ | +++ | − |
| 34 | +++ | − | − |
| 35 | +++ | +++ | ++ |

-continued

| | $pIC_{50}$ for Inhibition of mTORC1 and mTORC2 Substrate Phosphorylation | | |
|---|---|---|---|
| Example | p-P70S6K-(T389) | P-4E-BP1-(T37/46) | p-AKT1/2/3-(S473) |
| 36 | +++ | +++ | − |
| 37 | +++ | +++ | − |
| 38 | +++ | − | − |
| 39 | +++ | +++ | +++ |
| 40 | +++ | +++ | ++ |
| 41 | +++ | +++ | − |
| 42 | +++ | +++ | ++ |
| 43 | +++ | +++ | ++ |
| 46 | +++ | +++ | ++ |
| 47 | +++ | +++ | ++ |
| 48 | +++ | +++ | ++ |
| 49 | +++ | +++ | ++ |
| 50 | +++ | +++ | + |
| 51 | +++ | +++ | +++ |
| 52 | +++ | +++ | − |
| 53 | +++ | +++ | ++ |
| 54 | +++ | +++ | +++ |
| 55 | +++ | +++ | ++ |
| 56 | +++ | +++ | − |
| 59 | +++ | +++ | +++ |
| 60 | +++ | ++ | + |
| 61 | +++ | − | − |
| 62 | ++ | − | − |
| 63 | +++ | +++ | +++ |
| 64 | +++ | +++ | ++ |
| 65 | +++ | +++ | + |
| 66 | +++ | +++ | ++ |
| 67 | + | + | + |
| 68 | + | + | − |
| 69 | +++ | +++ | ++ |
| 70 | +++ | +++ | + |
| 71 | +++ | +++ | ++ |
| 72 | +++ | +++ | +++ |
| 73 | +++ | +++ | + |
| 74 | +++ | +++ | + |
| 75 | +++ | +++ | ++ |
| 76 | +++ | +++ | ++ |
| 77 | +++ | ++ | + |
| 78 | +++ | +++ | +++ |
| 79 | +++ | +++ | + |
| 80 | +++ | +++ | +++ |
| 81 | +++ | ++ | − |
| 82 | +++ | +++ | − |
| 83 | +++ | +++ | ++ |
| 84 | +++ | +++ | ++ |
| 85 | +++ | +++ | ++ |
| 86 | +++ | +++ | ++ |
| 87 | +++ | +++ | ++ |
| 88 | +++ | +++ | ++ |
| 89 | +++ | +++ | − |
| 90 | +++ | − | − |
| 91 | +++ | +++ | ++ |
| 92 | +++ | +++ | ++ |
| 93 | +++ | +++ | ++ |
| 94 | +++ | +++ | +++ |
| 95 | +++ | +++ | ++ |
| 96 | +++ | +++ | + |
| 97 | +++ | +++ | ++ |
| 98 | +++ | +++ | ++ |
| 99 | +++ | +++ | − |
| 100 | +++ | +++ | ++ |
| 101 | +++ | +++ | ++ |
| 102 | +++ | +++ | ++ |
| 103 | +++ | − | − |
| 104 | +++ | +++ | − |
| 105 | +++ | ++ | − |
| 106 | +++ | ++ | − |
| 107 | +++ | − | − |
| 108 | ++ | − | − |
| 109 | + | − | − |
| 110 | ++ | − | − |
| 111 | +++ | +++ | − |
| 112 | +++ | − | − |

-continued

| | pIC$_{50}$ for Inhibition of mTORC1 and mTORC2 Substrate Phosphorylation | | |
|---|---|---|---|
| Example | p-P70S6K-(T389) | P-4E-BP1-(T37/46) | p-AKT1/2/3-(S473) |
| 113 | +++ | +++ | ++ |
| 114 | +++ | +++ | – |
| 115 | +++ | +++ | +++ |
| 116 | +++ | +++ | – |
| 117 | +++ | +++ | ++ |
| 118 | +++ | +++ | ++ |
| 119 | +++ | +++ | ++ |
| 120 | +++ | +++ | ++ |
| 121 | +++ | +++ | – |
| 122 | +++ | +++ | ++ |
| 123 | +++ | +++ | + |
| 124 | +++ | +++ | ++ |
| 125 | +++ | +++ | ++ |
| 126 | +++ | ++ | – |
| 127 | +++ | ++ | – |
| 128 | +++ | ++ | + |
| 129 | +++ | +++ | – |
| 130 | +++ | +++ | – |
| 131 | +++ | +++ | ++ |
| 132 | +++ | +++ | ++ |
| 133 | +++ | +++ | ++ |
| 134 | +++ | +++ | – |
| 135 | +++ | – | – |
| 136 | +++ | ++ | ++ |
| 137 | +++ | +++ | ++ |
| 138 | +++ | +++ | +++ |
| 139 | +++ | +++ | + |
| 140 | + | + | – |
| 141 | +++ | +++ | + |
| 142 | ++ | – | – |
| 143 | +++ | ++ | – |

-continued

| | pIC$_{50}$ for Inhibition of mTORC1 and mTORC2 Substrate Phosphorylation | | |
|---|---|---|---|
| Example | p-P70S6K-(T389) | P-4E-BP1-(T37/46) | p-AKT1/2/3-(S473) |
| 144 | +++ | +++ | ++ |
| 145 | +++ | ++ | + |
| 146 | – | – | – |
| 147 | +++ | +++ | ++ |
| 148 | +++ | +++ | ++ |
| 149 | +++ | +++ | ++ |
| 150 | +++ | +++ | + |
| 151 | +++ | ++ | – |
| 152 | +++ | +++ | + |

Note:

| | |
|---|---|
| pIC50 (p-P70S6K-(T389)) | |
| ≥9 | +++ |
| 9 > pIC50 ≥ 8 | ++ |
| 8 > pIC50 ≥ 6 | + |
| <6 | – |
| pIC50 (p-4E-BP1-(T37/46) or p-AKT1/2/3-(S473)) | |
| ≥8.5 | +++ |
| 8.5 > pIC50 ≥ 7.5 | ++ |
| 7.5 > pIC50 ≥ 6.0 | + |
| <6 | – |

EQUIVALENTS

While the present disclosure has been described in conjunction with the specific embodiments set forth above, many alternatives, modifications and other variations thereof will be apparent to those of ordinary skill in the art. All such alternatives, modifications and variations are intended to fall within the spirit and scope of the present disclosure.

The invention claimed is:

1. A method of treating a cancer selected from the group consisting of head and neck cancers, lung cancer, liver cancer, ovarian cancer, prostate cancer, pancreatic cancers, endometrial cancer, vulva cancer, intestinal or rectal cancer, bile duct cancer, and thyroid cancer in a subject in need thereof, comprising administering to the subject a therapeutically effective amount of either a compound or a composition selected from the group consisting of (1) a compound having the formula

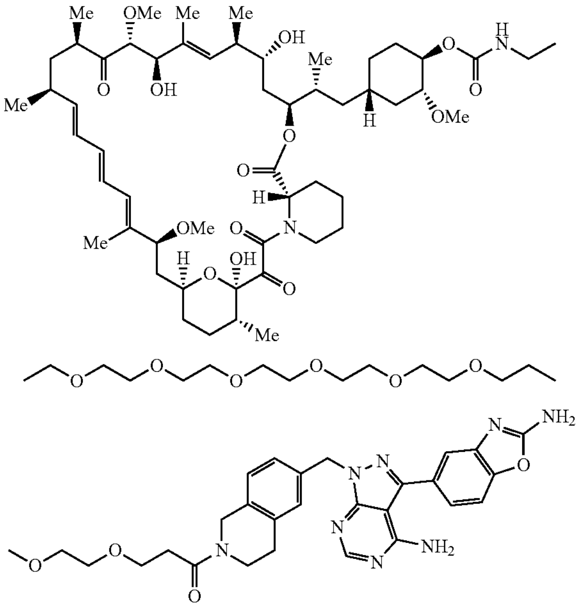

or a stereoisomer thereof;

(2) a compound having the formula

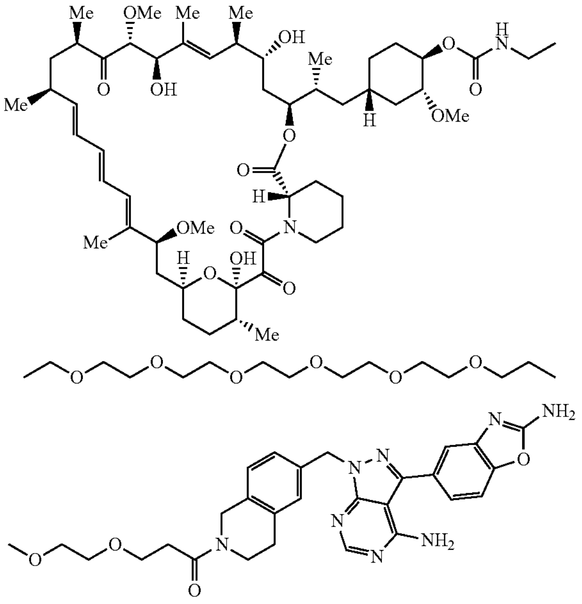

or a tautomer thereof;

(3) a compound having the formula

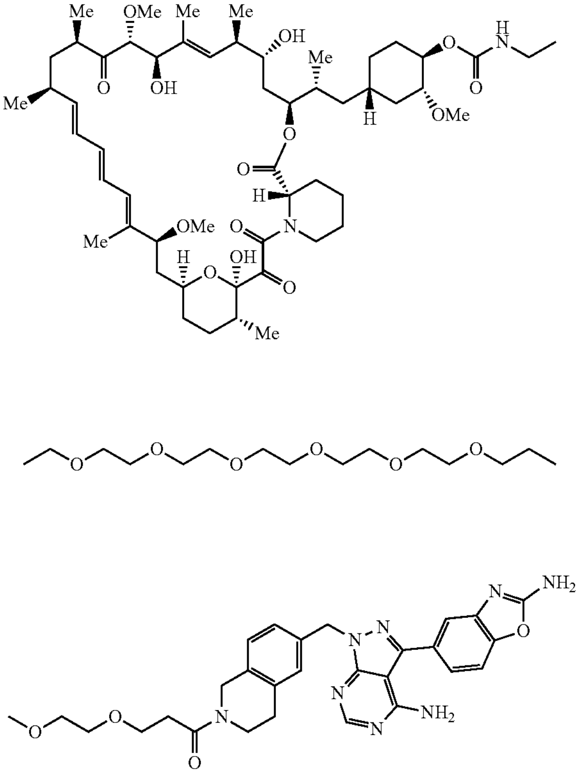

or an oxepane isomer thereof;

(4) a compound having the formula

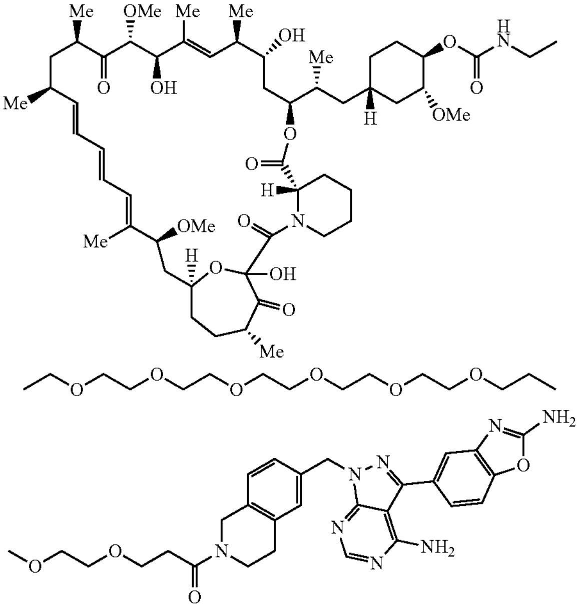

or a stereoisomer thereof;
(5) a compound having the formula
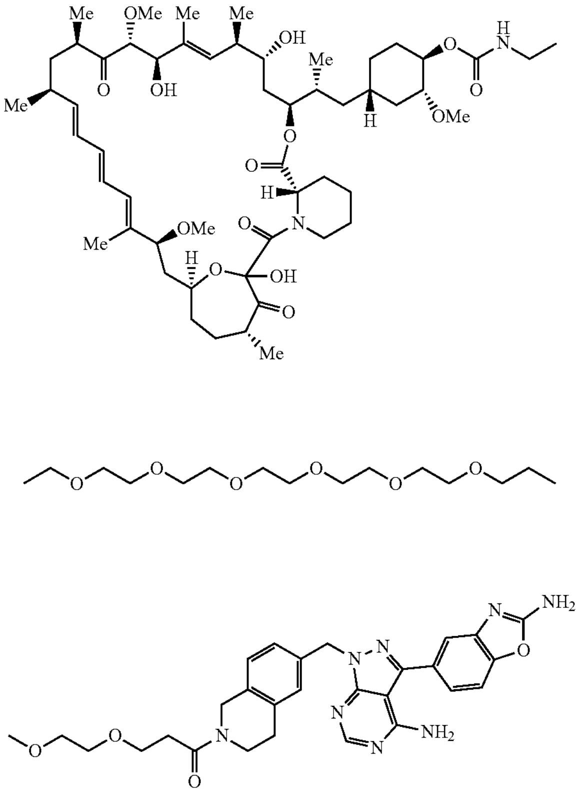
or a tautomer thereof;
(6) a compound having the formula
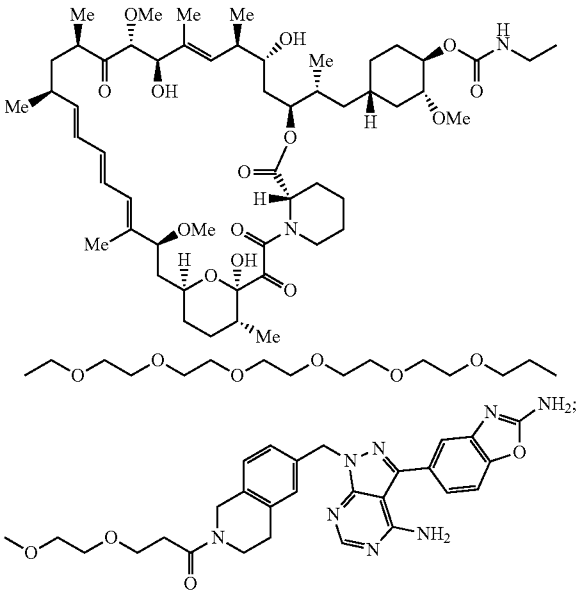
(7) a compound having the formula
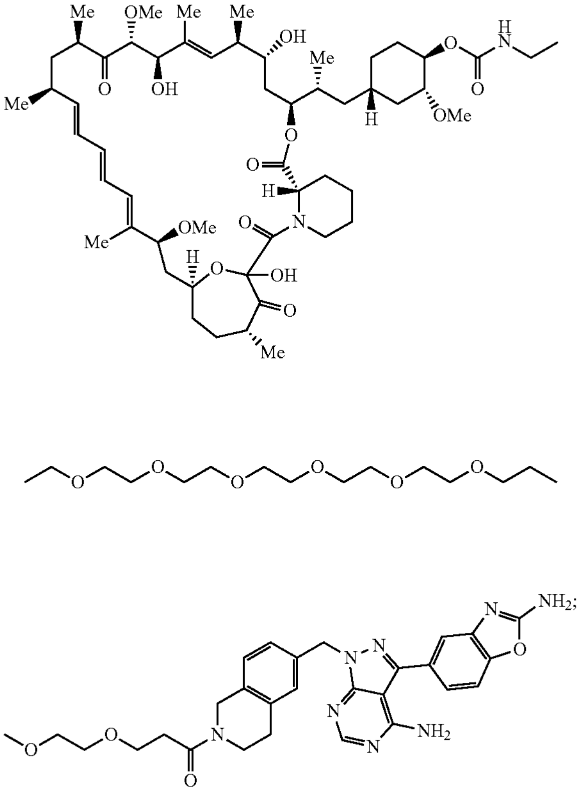
(8) a composition comprising a mixture of
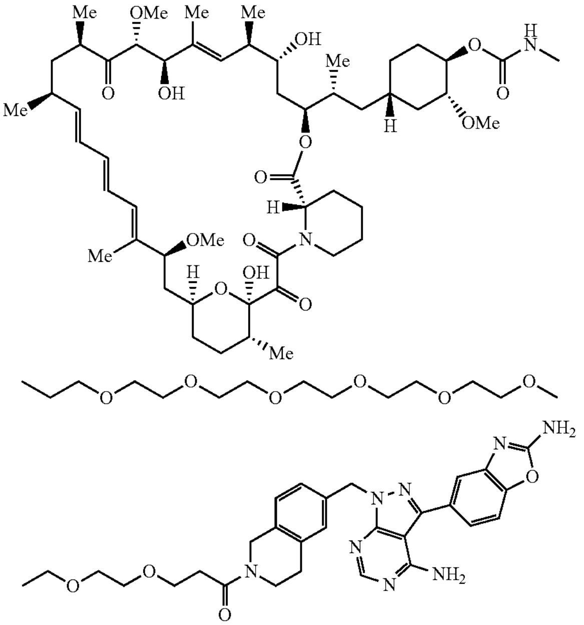

or a stereoisomer or tautomer thereof and
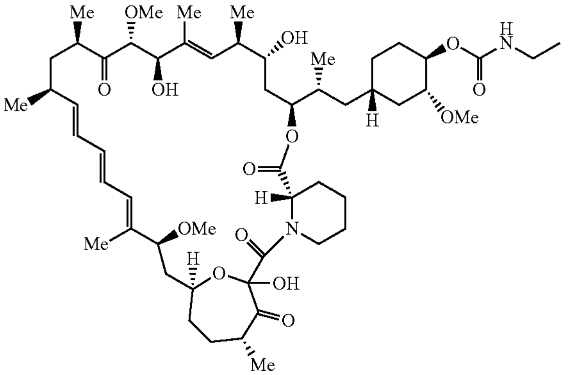
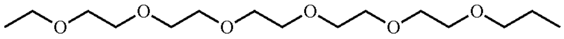
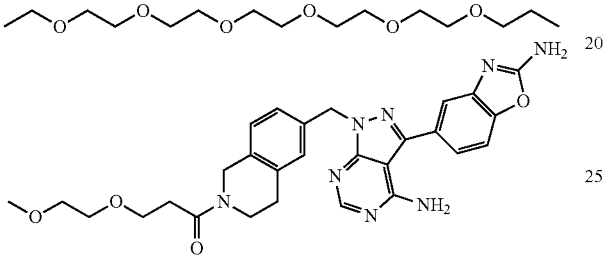
or a stereoisomer or tautomer thereof; and
(9) a composition comprising a mixture of
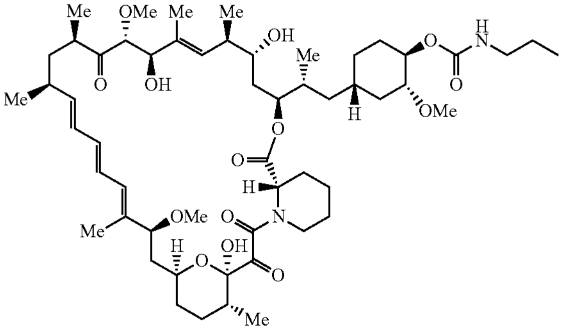
-continued
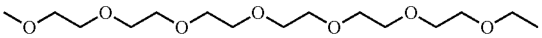
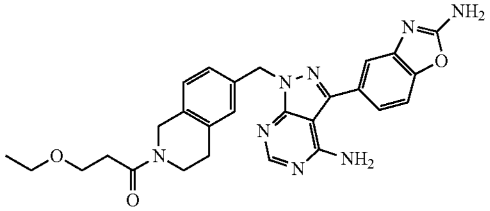
and
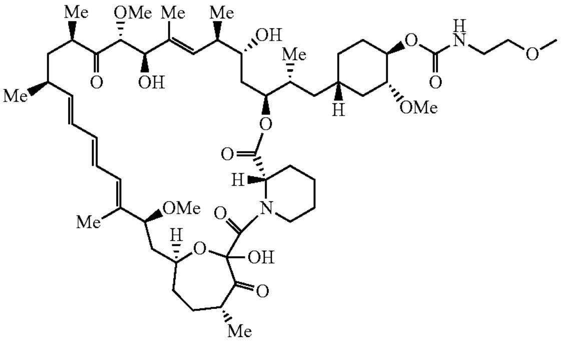
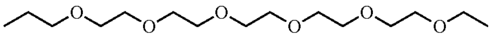
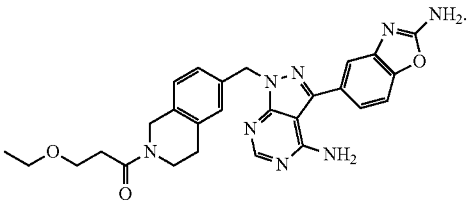
2. The method of claim 1, wherein the compound is
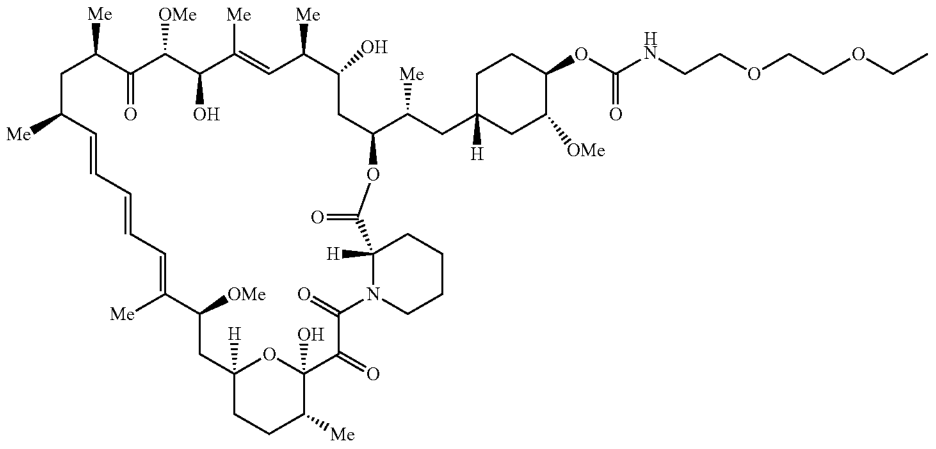

-continued
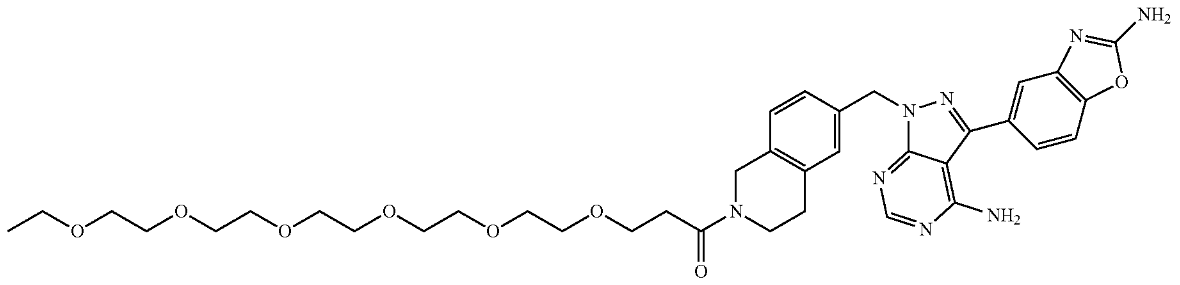
or a stereoisomer thereof.
3. The method of claim 1, wherein the compound is
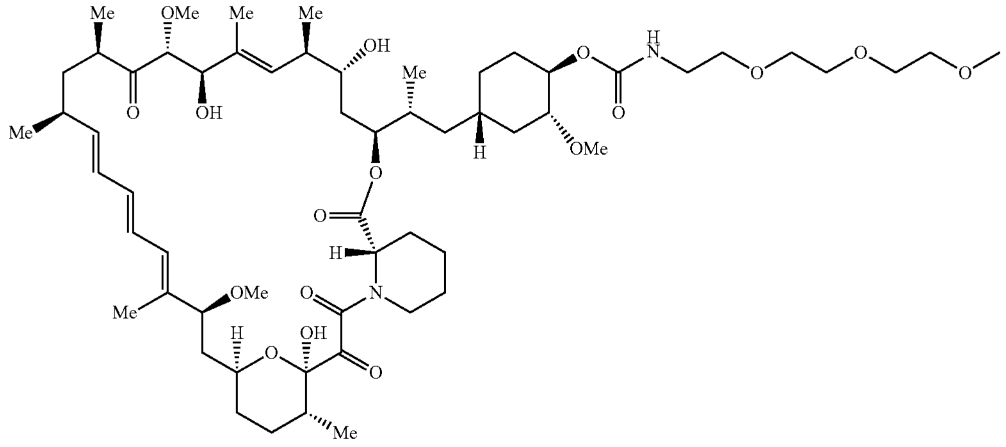
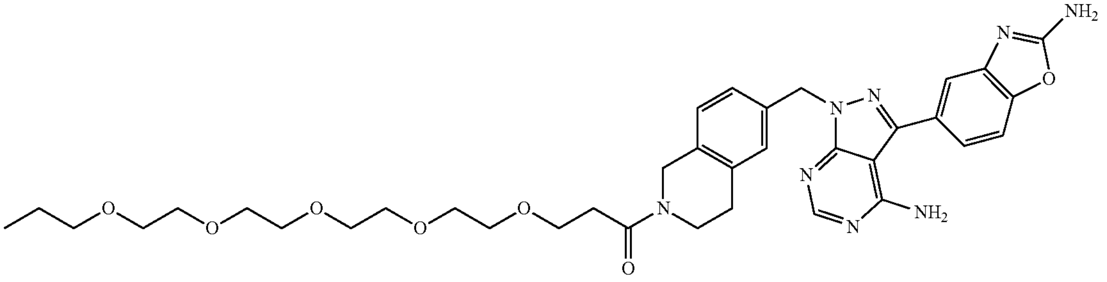

or a tautomer thereof.
4. The method of claim 1, wherein the compound is
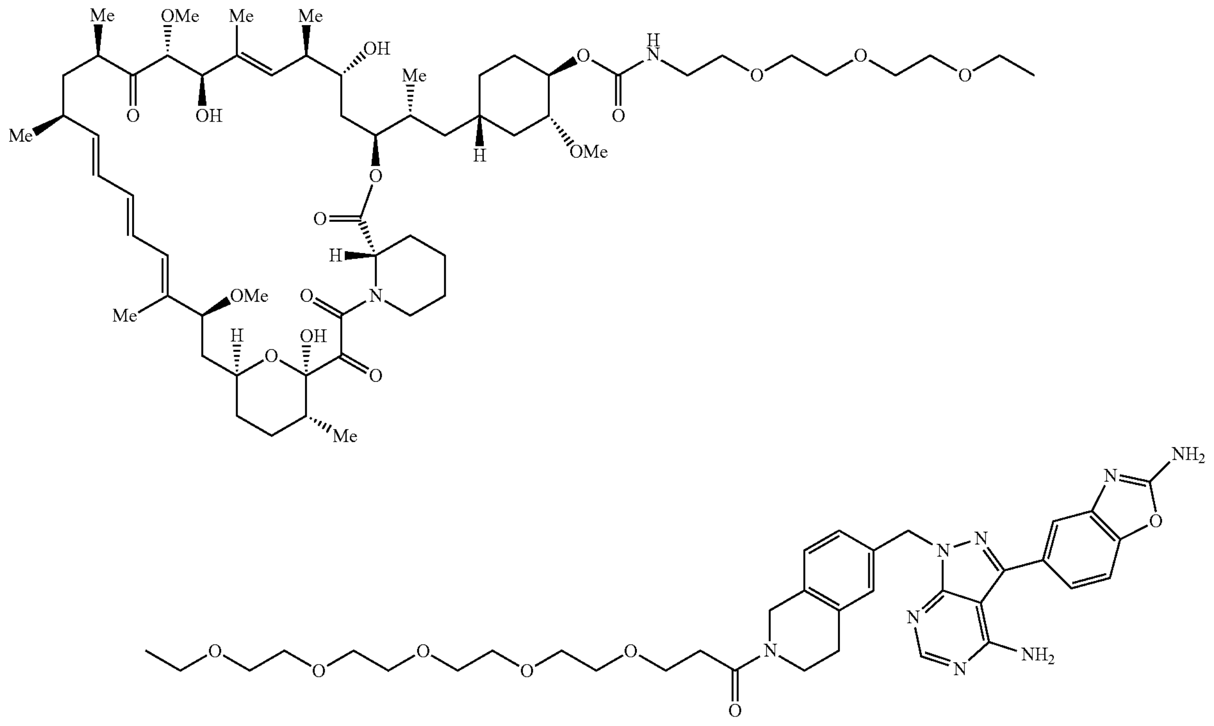
or an oxepane isomer thereof.
5. The method of claim 1, wherein the compound is
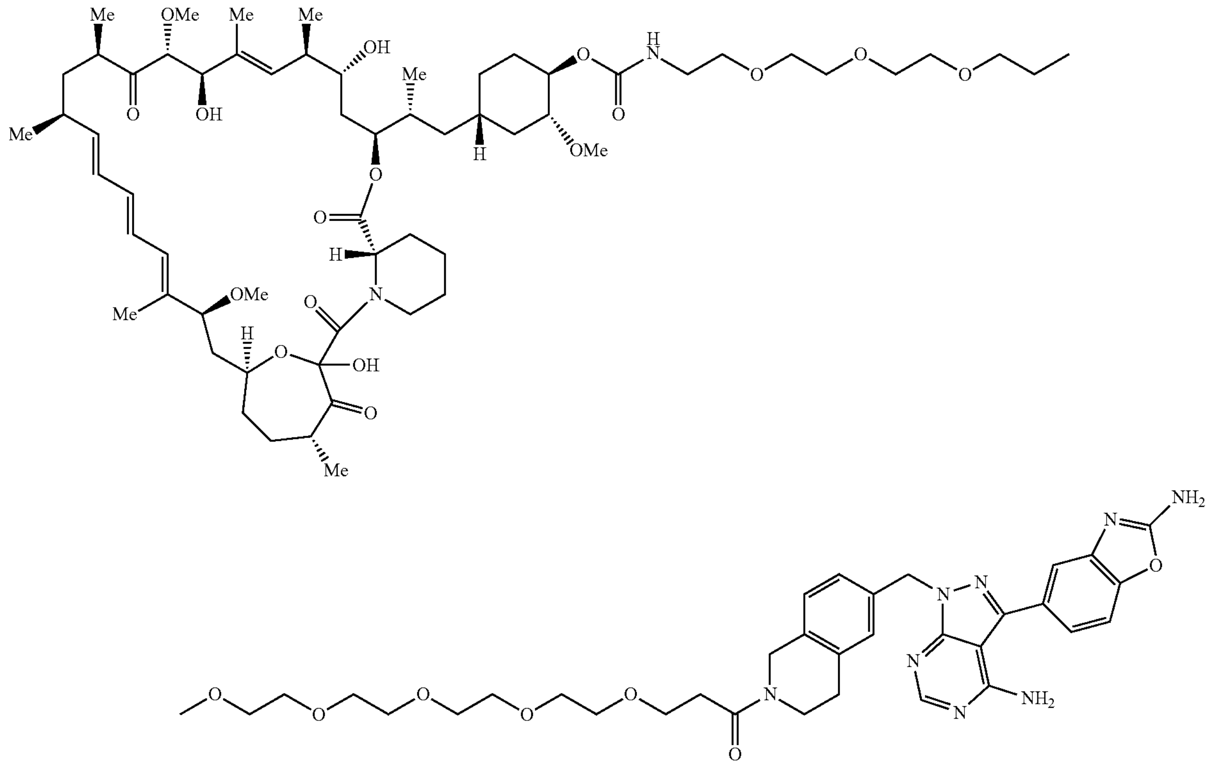

or a stereoisomer thereof.
6. The method of claim 1, wherein the compound is
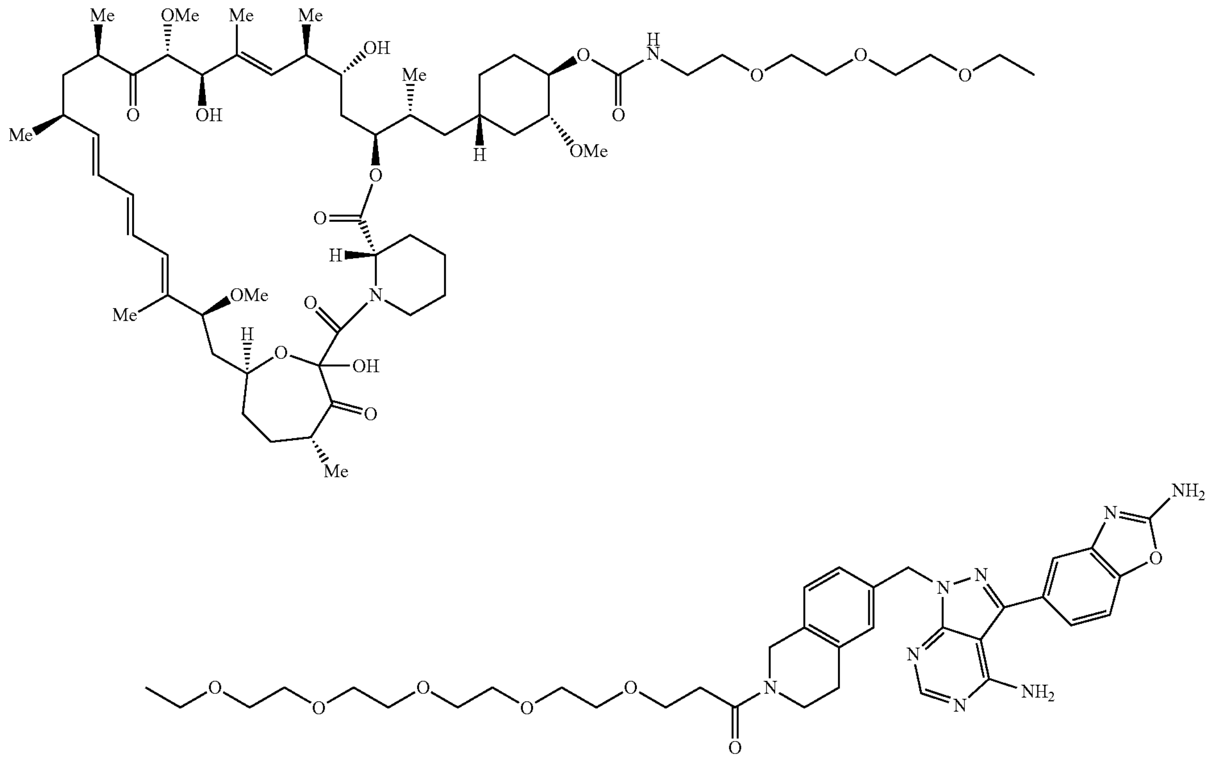
or a tautomer thereof.
7. The method of claim 1, wherein the compound is
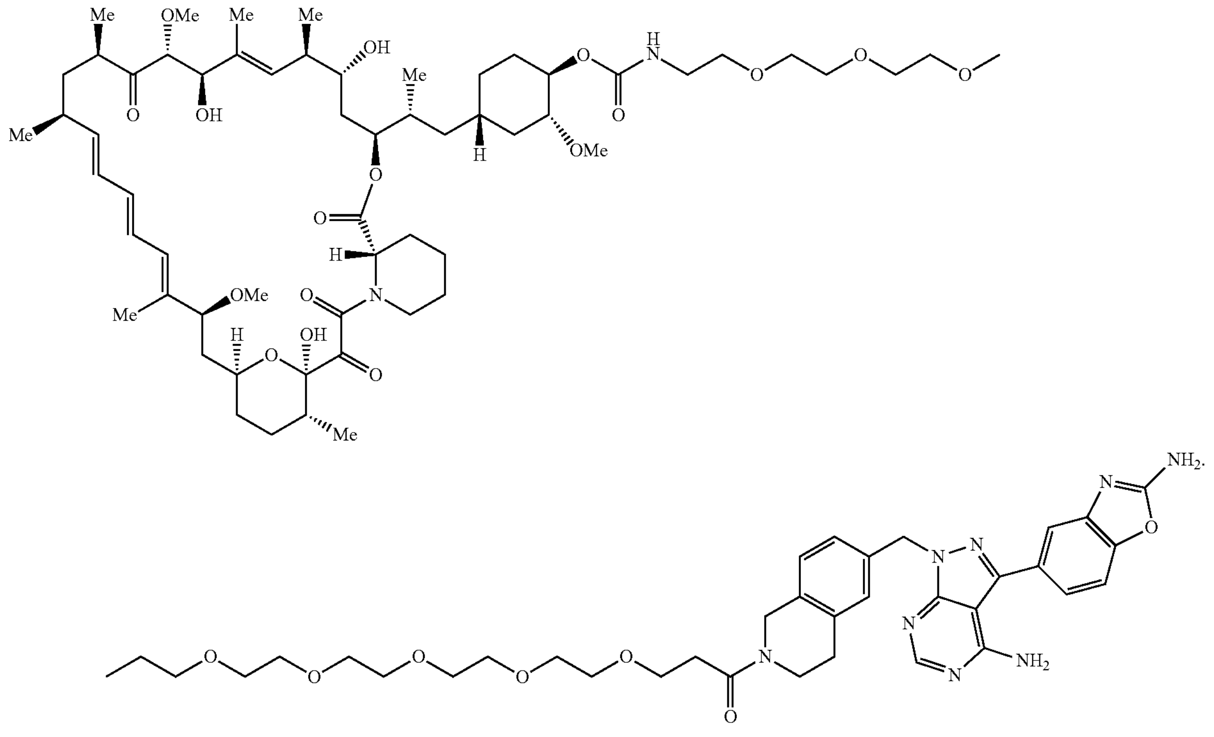

8. The method of claim 1, wherein the compound is
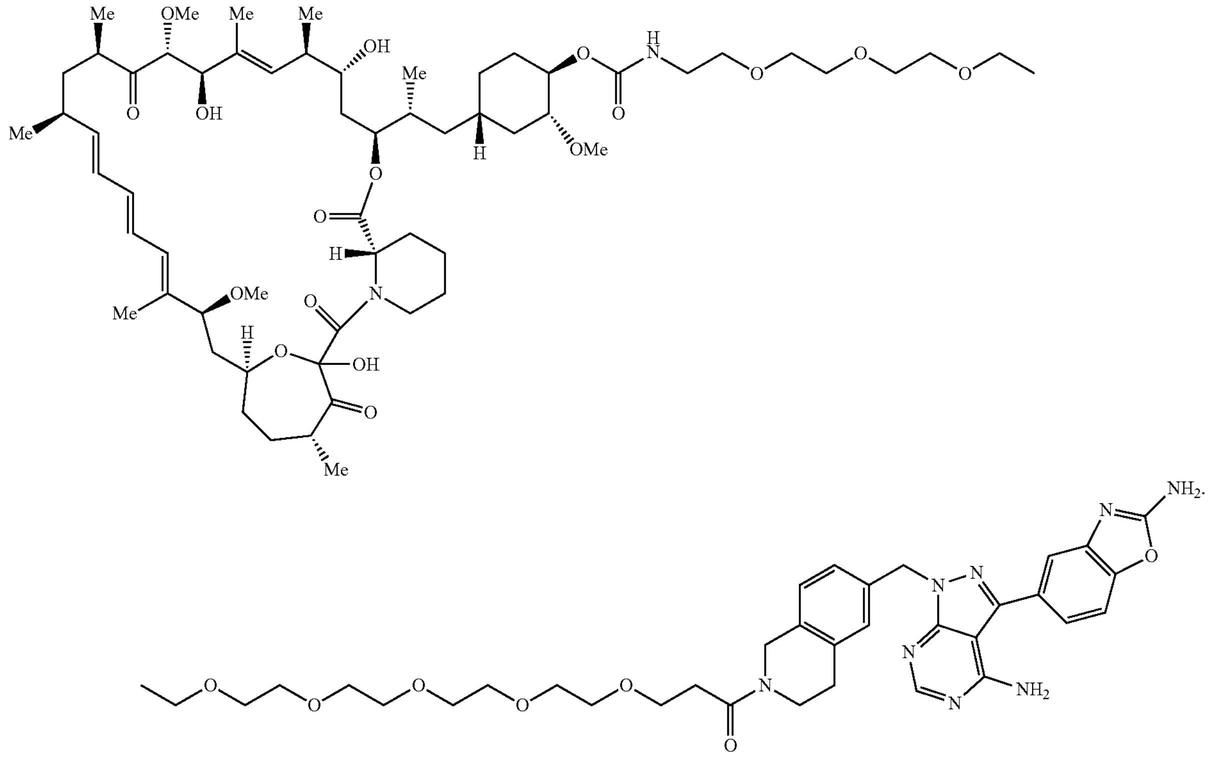
9. The method of claim 1, wherein the composition comprises a mixture of
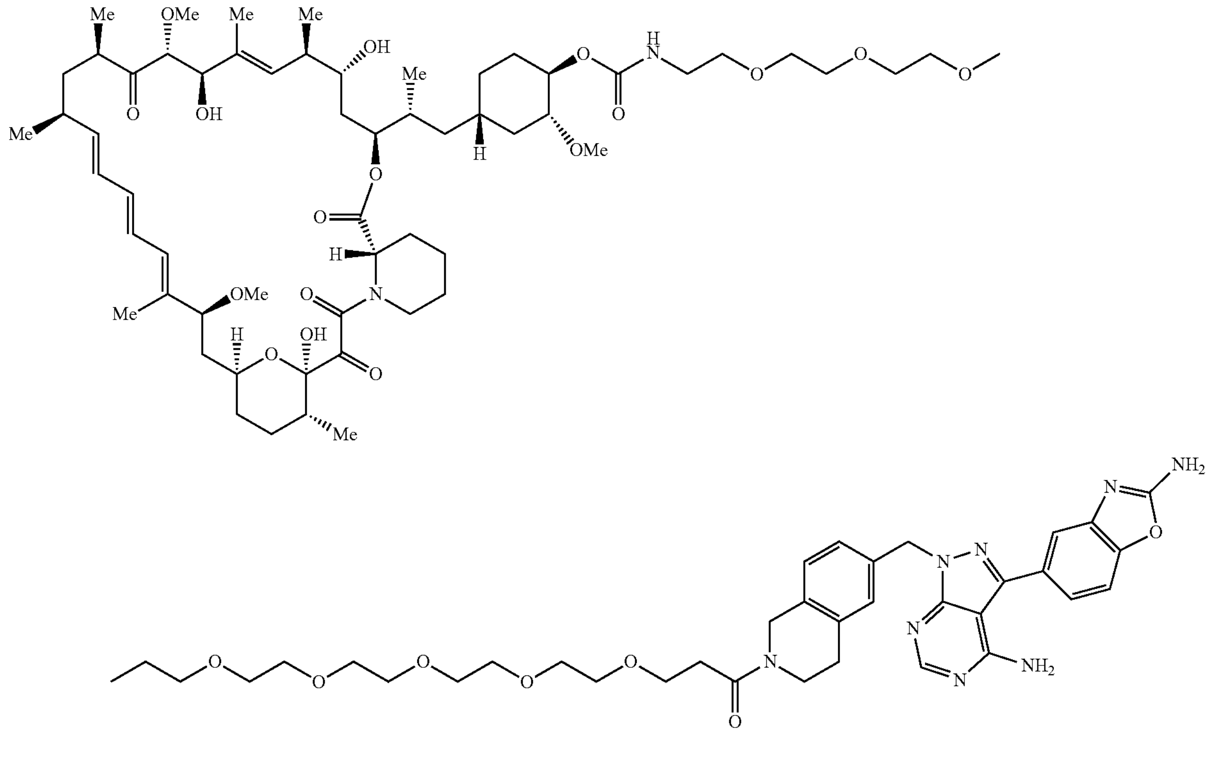

or a stereoisomer or tautomer thereof and
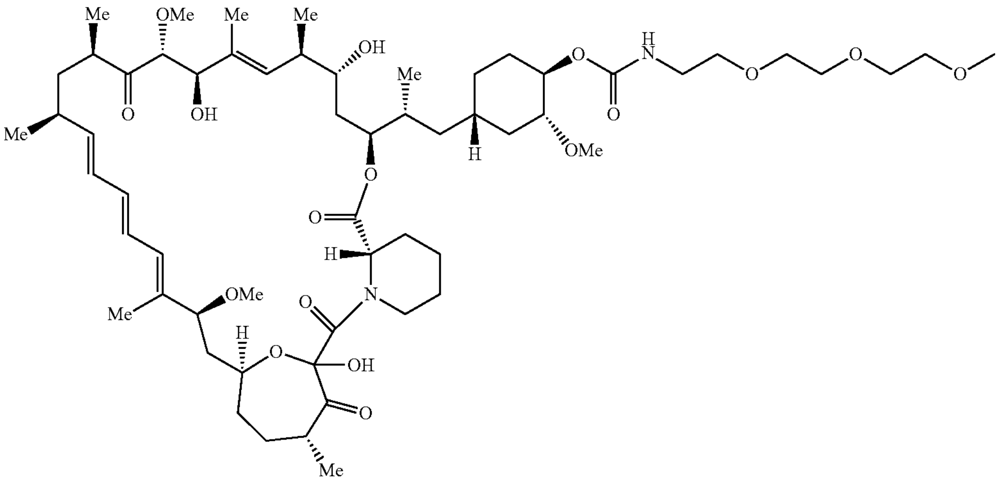
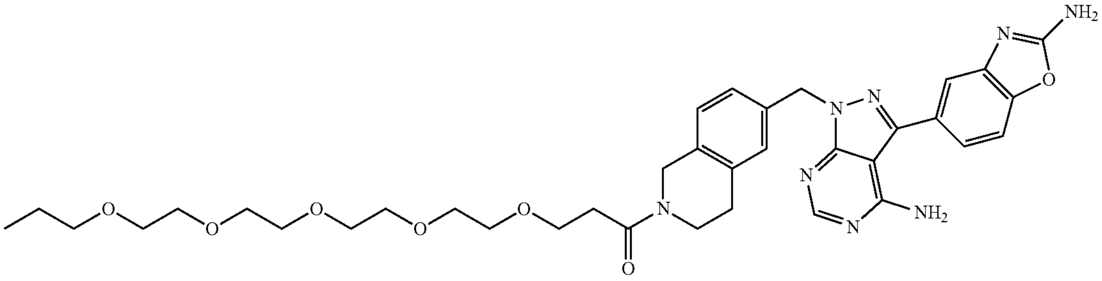
or a stereoisomer or tautomer thereof.
10. The method of claim 1, wherein the composition comprises a mixture of
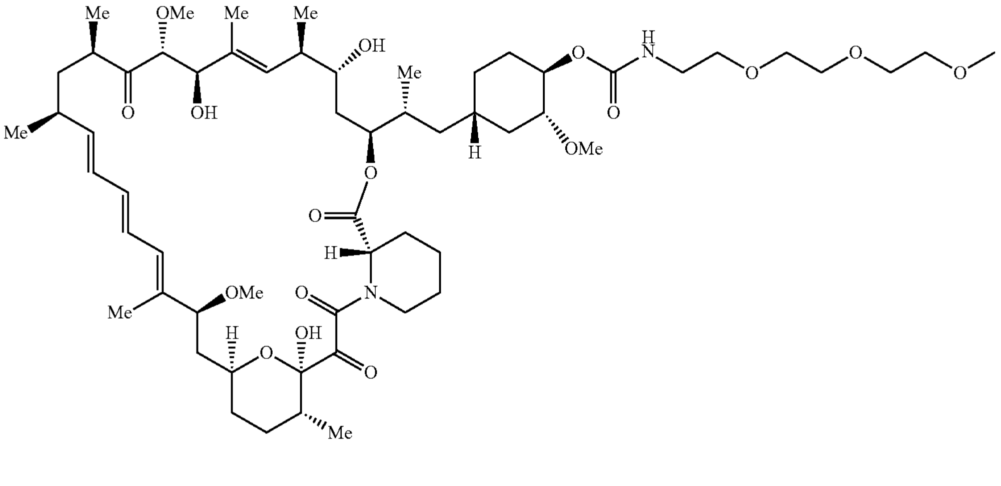
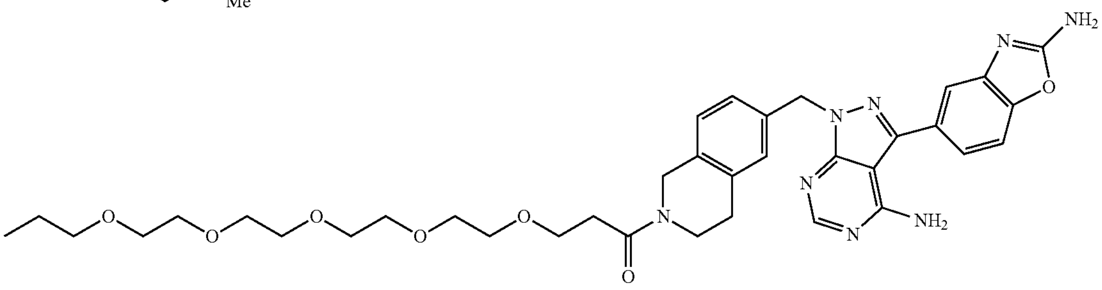

and
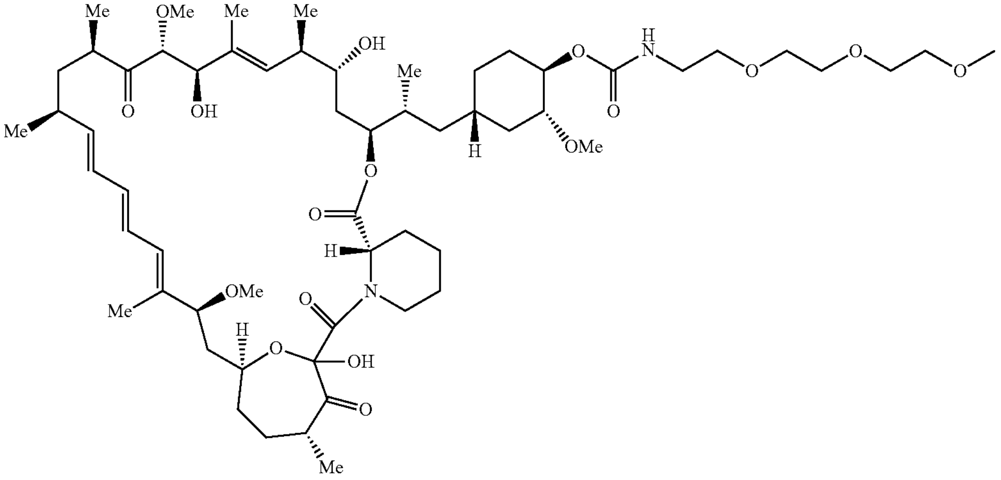
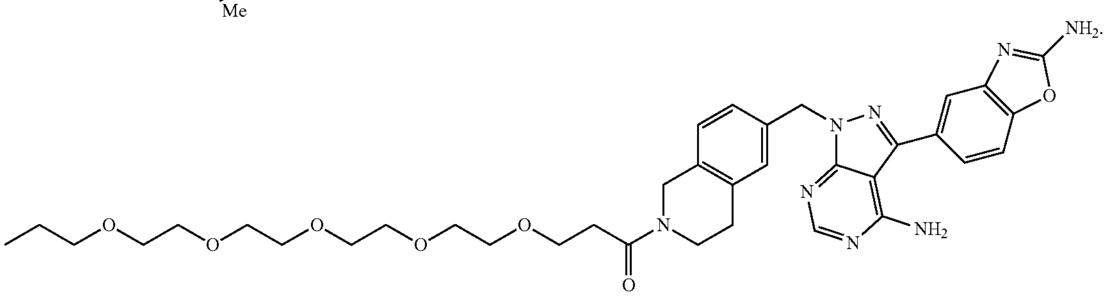
* * * * *